US012049464B2

(12) United States Patent
Nasveschuk et al.

(10) Patent No.: US 12,049,464 B2
(45) Date of Patent: *Jul. 30, 2024

(54) COMPOUNDS FOR TARGETED DEGRADATION OF BRD9

(71) Applicant: C4 Therapeutics, Inc., Watertown, MA (US)

(72) Inventors: Christopher G. Nasveschuk, Stoneham, MA (US); Rhamy Zeid, Arlington, MA (US); Ning Yin, Lexington, MA (US); Katrina L. Jackson, Weston, MA (US); Gesine Kerstin Veits, Sommerville, MA (US); Moses Moustakim, Brighton, MA (US); Jeremy L. Yap, Sudbury, MA (US)

(73) Assignee: C4 Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/901,775

(22) Filed: Sep. 1, 2022

(65) Prior Publication Data
US 2023/0060334 A1 Mar. 2, 2023

Related U.S. Application Data

(63) Continuation of application No. 17/541,035, filed on Dec. 2, 2021, which is a continuation of application No. PCT/US2021/021240, filed on Mar. 5, 2021.

(60) Provisional application No. 63/061,659, filed on Aug. 5, 2020, provisional application No. 62/985,774, filed on Mar. 5, 2020.

(51) Int. Cl.
C07D 471/04 (2006.01)
A61P 35/00 (2006.01)
C07D 401/14 (2006.01)

(52) U.S. Cl.
CPC ............ C07D 471/04 (2013.01); A61P 35/00 (2018.01); C07D 401/14 (2013.01)

(58) Field of Classification Search
None
See application file for complete search history.

(56) References Cited

U.S. PATENT DOCUMENTS

| | | | |
|---|---|---|---|
| 5,635,517 A | 6/1997 | Muller et al. | |
| 6,306,663 B1 | 10/2001 | Kenten et al. | |
| 10,646,575 B2 | 5/2020 | Phillips et al. | |
| 10,660,968 B2 | 5/2020 | Phillips et al. | |
| 10,849,982 B2 | 12/2020 | Phillips et al. | |
| 10,905,768 B1 | 2/2021 | Phillips et al. | |
| 11,185,592 B2 | 11/2021 | Phillips et al. | |
| 11,254,672 B2 | 2/2022 | Norcross et al. | |
| 11,319,318 B2 | 5/2022 | Martin et al. | |
| 11,401,256 B2 | 8/2022 | Norcross et al. | |
| 11,407,732 B1 | 8/2022 | Henderson et al. | |
| 11,414,416 B1 | 8/2022 | Ruppel et al. | |
| 11,459,335 B2 | 10/2022 | Phillips et al. | |
| 11,524,949 B2 | 12/2022 | Phillips et al. | |
| 11,584,748 B2 | 2/2023 | Nasveschuk et al. | |
| 11,623,929 B2 | 4/2023 | Nasveschuk et al. | |
| 11,673,902 B2 | 6/2023 | Nasveschuk et al. | |
| 11,691,972 B2 * | 7/2023 | Nasveschuk ......... | C07D 401/14 514/210.21 |
| 11,753,197 B2 | 9/2023 | Henderson et al. | |
| 11,787,802 B2 | 10/2023 | Norcross et al. | |
| 11,802,131 B2 | 10/2023 | Norcross et al. | |
| 2014/0302523 A1 | 10/2014 | Crews et al. | |
| 2014/0356322 A1 | 12/2014 | Crews et al. | |
| 2015/0291562 A1 | 10/2015 | Crew et al. | |
| 2016/0022642 A1 | 1/2016 | Crews et al. | |
| 2016/0045607 A1 | 2/2016 | Crew et al. | |
| 2016/0046661 A1 | 2/2016 | Gray et al. | |
| 2016/0058872 A1 | 3/2016 | Crew et al. | |
| 2016/0176916 A1 | 6/2016 | Bradner et al. | |
| 2016/0272639 A1 | 9/2016 | Crew et al. | |
| 2018/0085465 A1 | 3/2018 | Bradner et al. | |
| 2019/0247509 A1 | 8/2019 | Buckley et al. | |
| 2020/0207733 A1 | 7/2020 | Norcross et al. | |
| 2020/0207783 A1 | 7/2020 | Norcross et al. | |
| 2021/0009559 A1 | 1/2021 | Henderson et al. | |
| 2021/0032245 A1 | 2/2021 | Nasveschuk et al. | |
| 2021/0070763 A1 | 3/2021 | Nasveschuk et al. | |
| 2021/0198256 A1 | 7/2021 | Nasveschuk et al. | |
| 2022/0098194 A1 | 3/2022 | Nasveschuk et al. | |

(Continued)

FOREIGN PATENT DOCUMENTS

WO WO 2013/097052 A1 7/2013
WO WO 2016/065139 A1 4/2016

(Continued)

OTHER PUBLICATIONS

Bartlett, et al. "The evolution of thalidomide and its IMiD derivatives as anticancer agents," Nat Rev Cancer, Apr. 2004, 4(4):314-322.
Berndsen et al. "New insights into ubiquitin E3 ligase mechanism," Nat. Struct. Mol. Biol. Nature America, Inc. Apr. 2014, 21:4, 301-307.
Bondeson et al. "Catalytic in vivo protein knockdown by small-molecule PROTACs" Nature Chemical Biology Jun. 10, 2015, 11:611-617.
Brien, G. L. et al. Targeted degradation of BRD9 reverses oncogenic gene expression in synovial sarcoma, Elife e41305, Biochemistry and Chemical Biology, pp. 1-26 (2018).
Clark Peter G. K., et al., "LP99: Discovery and Synthesis of the First Selective BRD7/9 Bromodomain Inhibitor," Angewandte Chemie Int. Ed. Weinheim Bergstr Ger. 2015, 54, 6217-6221.

(Continued)

*Primary Examiner* — Amy C Bonaparte
*Assistant Examiner* — Lauren Wells
(74) *Attorney, Agent, or Firm* — Knowles Intellectual Property Strategies, LLC

(57) ABSTRACT

BRD9 protein degradation compounds or pharmaceutically acceptable salts thereof are provided for the treatment of disorders mediated by BRD9, including but not limited to abnormal cellular proliferation.

11 Claims, 19 Drawing Sheets

(56) References Cited

U.S. PATENT DOCUMENTS

| | | |
|---|---|---|
| 2022/0251061 A1 | 8/2022 | Phillips et al. |
| 2022/0289738 A1 | 9/2022 | Norcross et al. |
| 2022/0313826 A1 | 10/2022 | Phillips et al. |
| 2022/0313827 A1 | 10/2022 | Phillips et al. |
| 2022/0372016 A1 | 11/2022 | Phillips et al. |
| 2023/0014124 A1 | 1/2023 | Phillips et al. |
| 2023/0019060 A1 | 1/2023 | Nasveschuk et al. |
| 2023/0082430 A1 | 3/2023 | Henderson et al. |
| 2023/0095223 A1 | 3/2023 | Phillips et al. |
| 2023/0145336 A1 | 5/2023 | Nasveschuk et al. |
| 2023/0190760 A1 | 6/2023 | Proia et al. |
| 2023/0192643 A1 | 6/2023 | Norcross et al. |
| 2023/0233692 A1 | 7/2023 | Henderson et al. |
| 2023/0279023 A1 | 9/2023 | Phillips et al. |

FOREIGN PATENT DOCUMENTS

| | | |
|---|---|---|
| WO | WO 2016/105518 A1 | 6/2016 |
| WO | WO 2016/197032 A1 | 12/2016 |
| WO | WO 2017/024317 A1 | 2/2017 |
| WO | WO 2017/079267 A1 | 5/2017 |
| WO | WO 2017/161119 A1 | 9/2017 |
| WO | WO 2017/180417 A1 | 10/2017 |
| WO | WO 2017/197046 A1 | 11/2017 |
| WO | WO 2017/201069 A1 | 11/2017 |
| WO | WO 2017/223452 A1 | 12/2017 |
| WO | WO 2018/052945 A1 | 3/2018 |
| WO | WO 2018/052949 A1 | 3/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/144649 A1 | 8/2018 |
| WO | WO 2019/060742 A1 | 3/2019 |
| WO | WO 2019/152440 A1 | 8/2019 |
| WO | WO 2019/246423 A1 | 12/2019 |
| WO | WO 2019/246430 A1 | 12/2019 |
| WO | WO 2020/051235 A1 | 3/2020 |
| WO | WO 2020/106915 A1 | 5/2020 |
| WO | WO 2020/160192 A1 | 8/2020 |
| WO | WO 2020/160193 A1 | 8/2020 |
| WO | WO 2020/160196 A1 | 8/2020 |
| WO | WO 2020/172655 A1 | 8/2020 |
| WO | WO 2021/022163 A1 | 2/2021 |
| WO | WO 2021/053495 A1 | 3/2021 |
| WO | WO 2021/055295 A1 | 3/2021 |
| WO | WO 2021/155100 A1 | 8/2021 |

OTHER PUBLICATIONS

C4 Therapeutics Presentation Phillips—"Small Molecule Driven Targeted Protein Degradation", ChemBio in the Hub 47, Cambridge, MA, 47 pages (Oct. 22, 2018).

C4 Therapeutics Presentation Fisher—"Targeted Protein Degradation", Targeted Protein Degradation Summit, Boston, MA, 39 pages, Oct. 24-25, 2018.

C4 Therapeutics Presentation Fisher—"Degrader Drugs: From cellular activity to in vivo pharmacology Discovery on Target," Boston, MA, 21 pages, Sep. 18, 2019.

C4 Therapeutics Presentation Nasveschuk—"Degrader Drug Space: What Rules?" HT-ADME Conference Cambridge, MA, Jun. 20, 2019; 20 pages.

Chamberlain et al. "Structure of the human cereblon-DDB1-lenalidomide complex reveals basis for responsiveness to thalidomide analogs" Nature Structural and Molecule Biology, Nature American, Inc., Sep. 2014, 21(9):803-809.

Corson et al. "Design and applications of bifunctional small molecules: Why two heads are better than one" ACS Chemical Biology Nov. 21, 2008, 3(11): 677-692.

Fischer et al. "Structure of the DDB1-CRBN E3 ubiquitin ligase in complex with thalidomide" Nature Aug. 7, 2014, Macmillan Publisher Limited, 512:49-53.

Fischer et al. "The Molecular Basis of CRL4$^{DDB2/CSA}$ Ubiquitin Ligase Architecture, Targeting, and Activation," Cell Nov. 23, 2011, 147:1024-1039.

International Application No. PCT/US21/21240, filed Mar. 5, 2021; International Search Report and Written Opinion dated Jul. 27, 2021, 10 pages.

Karim, Rezaul Md.; et al., "Structural Basis of Inhibitor Selectivity in the BRD7/9 Subfamily of Bromodomains," Journal of Medicinal Chemistry (2020), 63(6), 3227-3237.

Lu et al. "Hijacking the E3 Ubiquitin Ligase Cereblon to Efficiently Target BRD4" Chemistry and Biology 2015, 22(6):755-763.

Martin, Laetitia J.; et al., Structure-Based Design of an in Vivo Active Selective BRD9 Inhibitor, Journal of Medicinal Chemistry (2016), 59(10), 4462-4475, Language: English, Database: CAplus and Medline, ACS Publications.

McDaniel, Keith F. et al. Discovery of N-(4-(2,4-Difluorophenoxy)-3-(6-methyl-7-oxo-6,7-dihydro-1H-pyrrolo[2,3-c]pyridin-4-yl)phenyl)ethanesulfonamide (ABBV-075/Mivebresib), a Potent and Orally Available Bromodomain and Extraterminal Domain (BET) Family Bromodomain Inhibitor, Journal of Medicinal Chemistry, Sep. 26, 2017, 60, 20, 8369-8384.

Michel, B. C., et al., A noncanonical SWI/SNF complex is a synthetic lethal target in cancers driven by BAF complex perturbation, Nat Cell Biol 20, 1-11 (2018).

Pérez-Salvia M. et al., "Bromodomain inhibitors and cancer therapy: From structures to applications" Epigenetics. 2017; 12(5): 323-339.

Pubchem, SID 386724358, Available Date Nov. 2, 2019 [retrieved on Jul. 7, 2021] Retrieved from the Internet: <URL: https://pubchem.ncbi.nim.nih.gov/substance/386724358>.

Zengerle et al. "Selective Small Molecule Induced Degradation of the BET Bromodomain Protein BRD4" ACS Chem. Biol. 2015, 10:1770-1777.

Zoppi, Vittoria; et al., "Iterative Design and Optimization of Initially Inactive Proteolysis Targeting Chimeras (PROTACs) Identify VZ185 as a Potent, Fast, and Selective von Hippel-Lindau (VHL) Based Dual Degrader Probe of BRD9 and BRD7," Journal of Medicinal Chemistry (2019), 62(2), 699-726.

U.S. Appl. No. 17/164,446, filed Feb. 1, 2021, Phillips et al.
U.S. Appl. No. 17/723,199, filed Apr. 18, 2022, Henderson et al.
U.S. Appl. No. 17/843,769, filed Jun. 17, 2022, Nasveschuk et al.
U.S. Appl. No. 17/351,935, filed Jun. 18, 2021, Phillips et al.
U.S. Appl. No. 17/878,753, filed Aug. 1, 2022, Norcross et al.
U.S. Appl. No. 17/465,583, filed Sep. 2, 2021, Nasveschuk et al.
U.S. Appl. No. 17/524,558, filed Nov. 11, 2021, Phillips et al.
U.S. Appl. No. 17/959,144, filed Oct. 3, 2022, Phillips et al.
U.S. Appl. No. 18/240,231, filed Aug. 30, 2023, Henderson et al.
U.S. Appl. No. 18/100,992, filed Jan. 24, 2023, Nasveschuk et al.
U.S. Appl. No. 18/117,978, filed Mar. 6, 2023, Nasveschuk et al.
U.S. Appl. No. 18/134,985, filed Apr. 14, 2023, Nasveschuk et al.
U.S. Appl. No. 18/134,990, filed Apr. 14, 2023, Nasveschuk et al.
U.S. Appl. No. 18/144,800, filed May 8, 2023, Nasveschuk et al.
U.S. Appl. No. 17/965,569, filed Oct. 13, 2022, Nasveschuk et al.
U.S. Appl. No. 18/079,815, filed Dec. 12, 2022, Phillips et al.
U.S. Appl. No. 18/370,186, filed Sep. 19, 2023, Norcross et al.
U.S. Appl. No. 18/385,277, filed Oct. 30, 2023, Norcross et al.
U.S. Appl. No. 18/516,589, filed Nov. 21, 2023, Nasveschuk et al.
U.S. Appl. No. 18/534,395, filed Dec. 8, 2023, Nasveschuk et al.

C4 Therapeutics Press Release—Reports Third Quarter 2023 Financial Results and Recent Business Highlights; 2023, Nov. 1, 2023.

C4 Therapeutics CFT8634: An Oral BRD9 BiDAC™ Degrader, TPD Summit slides, Oct. 31, 2023.

C4 Therapeutics Agulnik, Mark et al. "Initial Results From a Phase 1 Study of CFT8634, a Novel Bifunctional Degradation Activating Compound (or BIDAC™ Degrader) of BRD9, in Synovial Sarcoma and SMARCB1-Null Tumors" CTOS poster, Nov. 1, 2023.

* cited by examiner

COMPOUNDS FOR TARGETED DEGRADATION OF BRD9

CROSS-REFERENCE TO RELATED APPLICATIONS

This application is a continuation of U.S. patent application Ser. No. 17/541,035, filed Dec. 2, 2021, which is a continuation of International Patent Application Number PCT/US21/21240, filed with the PCT Receiving Office on Mar. 5, 2021, which claims priority to U.S. Provisional Application 62/985,774 filed on Mar. 5, 2020, and U.S. Provisional Application 63/061,659 filed on Aug. 5, 2020. The entirety of each of these applications is hereby incorporated by reference for all purposes.

FIELD OF THE INVENTION

This invention provides BRD9 degrading compounds for therapeutic applications as described further herein.

BACKGROUND

Bromodomain containing proteins (BRD) such as BRD9 are proteins that recognize acetylated lysine residues such as those on the N-terminals of histones. BRDs are evolutionarily conserved and present in diverse nuclear proteins comprising HATs (GCN5, PCAF), ATP-dependent chromatin-remodeling complexes (BAZ1B), helicases (SMARCA), methyltransferases (MLL, ASH1L), transcriptional coactivators (TRIM/TIF1, TAFs) transcriptional mediators (TAF1), nuclear-scaffolding proteins (PB1), and the BET family. (Muller S, Filippakopoulos P, Knapp S., Bromodomains as therapeutic targets, Expert Rev Mol Med. 2011, 13(29)). Bromodomain containing proteins have a number of functions that relate to transcription mediation and coactivation, therefore, they are involved in cellular proliferation.

Studies have also shown that BRD9 is preferentially used by cancers that harbor SMARCB1 abnormalities such as malignant rhabdoid tumors and several specific types of sarcoma. BRD9-containing complexes bind to both active promoters and enhancers, where they contribute to gene expression. Loss of BRD9 results in gene expression changes related to apoptosis regulation, translation, and development regulation. BRD9 is essential for the proliferation of SMARCB1-deficient cancer cell lines, suggesting it is a therapeutic target for these lethal cancers. (Xiaofeng Wang et. al., "BRD9 defines a SWI/SNF sub-complex and constitutes a specific vulnerability in malignant rhabdoid tumors," Nature Communications, 2019, 10 (1881)). BRD9 is also a critical target required in acute myeloid leukemia, "Nature Chemical Biology, 2016, 101038/nchembio.2115." In addition to the role of BRD9 as a functional dependency in certain cancers, BRD9 also plays a pivotal role in immune cells as a regulator of regulatory T cells (Tregs) via transcriptional control of Foxp3 target genes, "BioRxiv, 10.1101/2020.02.26.964981.

Studies have also shown that the newly identified noncanonical BAF (ncBAF) complex is a distinct entity made up of a unique combination of sub-units as compared to the canonical BAF (cBAF) and polybromo (pBAF) complexes. (Alpsoy, A. & Dykhuizen, E. C. Glioma tumor suppressor candidate region gene 1 (GLTSCR1) and its paralog GLTSCR1-like form SWI/SNF chromatin remodeling subcomplexes. *J Biol Chem* 293, 3892-3903 (2018)). Notably, BRD9 incorporates selectively into the noncanonical BAF (ncBAF) complex while SMARCB1 is absent. In a SMARCB1 perturbed setting (cBAF complex eviction, deletion, truncation, inactivation), the cBAF complex function is compromised leading to a unique so-called synthetic lethal dependency on ncBAF complex function. In turn, BRD9 is essential for ncBAF complex function and thus BRD9 is a unique dependency in SMARCB1 perturbed cancers (Michel, B. C. et al. A non-canonical SWI/SNF complex is a synthetic lethal target in cancers driven by BAF complex perturbation. *Nat Cell Biol* 20, 1-11 (2018) and Brien, G. L. et al. Targeted degradation of BRD9 reverses oncogenic gene expression in synovial sarcoma. Elife 7, e41305 (2018)).

Bromodomain-containing protein 7 (BRD7) is also a subunit of PBAF SWI/SNF. Publications describing BRD7 and ligands to BRD7 and BRD9 include: a paper by Pérez-Salvia M. et al, titled "Bromodomain inhibitors and cancer therapy: From structures to applications" Epigenetics. 2017; 12(5): 323-339; 99; and a paper by Clark P. G. K., et al., titled "Discovery and Synthesis of the First Selective BRD7/9 Bromodomain Inhibitor" Angew Chem Weinheim Bergstr Ger. 2015, 127(21): 6315-6319.

Because of BRD9's role in cancer proliferation there has been interest in the development of BRD9 inhibitors for the treatment of cancers including those described in: WO 2014/114721, WO 2016/077375, WO 2016/077378, WO 2016/139361, WO 2019/152440, a paper by Martin L. J. et. al., (*Journal of Medicinal Chemistry* 2016, 59, 4462-4475) titled "Structure-Based Design of an in Vivo Active Selective BRD9 Inhibitor"; a paper by Theodoulou N. H. et. al., (*Journal of Medicinal Chemistry* 2015, 59, 1425-1439) titled "Discovery of I-BRD9, a selective Cell Active Chemical Probe for Bromodomain Containing Protein 9 Inhibition"; and a paper by Clack P. et. al., (*Angewandte Chemie*, 2015, 127, 6315-6319).

Research has also been reported on protein degrading compounds that have an E3 ligase binding portion and a BRD9 binding portion wherein the BRD9 binding ligand binds to BRD9 and brings it to the ligase for ultimate degradation by the proteasome. See, for example, WO 2017/223452, WO 2019/152440, WO 2019/246423, WO 2019/246430, WO 2020/051235, WO 2020/106915, WO 2020/160192, WO 2020/160193, WO 2020/160196, and WO 2021/022163.

Patent applications filed by C4 Therapeutics, Inc., that describe compounds capable of binding to an E3 ubiquitin ligase and a target protein for degradation include: WO/2020/132561 titled "Targeted Protein Degradation"; WO/2019/204354 titled "Spirocyclic Compounds"; WO/2019/099868 titled "Degraders and Degrons for Targeted Protein Degradation"; WO/2018/237026 titled "N/O-Linked Degrons and Degronimers for Protein Degradation"; WO 2017/197051 titled "Amine-Linked C3-Glutarimide Degronimers for Target Protein Degradation"; WO 2017/197055 titled "Heterocyclic Degronimers for Target Protein Degradation"; WO 2017/197036 titled "Spirocyclic Degronimers for Target Protein Degradation"; WO 2017/197046 titled "C3-Carbon Linked Glutarimide Degronimers for Target Protein Degradation"; and WO 2017/197056 titled "Bromodomain Targeting Degronimers for Target Protein Degradation."

Other patent applications that describe protein degrading compounds include: WO 2015/160845; WO 2016/105518; WO 2016/118666; WO 2016/149668; WO 2016/197032; WO 2016/197114; WO 2017/007612; WO 2017/011371; WO 2017/011590; WO 2017/030814; WO 2017/046036; WO 2017/176708; WO 2017/176957; WO 2017/180417; WO 2018/053354; WO 2018/071606; WO 2018/102067;

WO 2018/102725; WO 2018/118598; WO 2018/119357; WO 2018/119441; WO 2018/119448; WO 2018/140809; WO2018/144649; WO 2018/119448; WO 2018/226542; WO 2019/023553, WO/2019/195201, WO2019/199816, and WO/2019/099926.

Due to the important role BRD9 plays in cancer, there remains a need for new compounds and methods that treat disorders mediated by BRD9.

SUMMARY OF THE INVENTION

Compounds and their uses and manufacture are provided that degrade bromodomain containing protein 9 (BRD9) via the ubiquitin proteasome pathway (UPP). The present invention provides a compound of Formula I, Formula II, Formula III, Formula IV, Formula V, or Formula VI, that includes a "Targeting Ligand" that binds to BRD9, an E3 Ligase binding portion (typically via a cereblon subunit), and a Linker that covalently links the Targeting Ligand to the E3 Ligase binding portion. In certain embodiments the Targeting Ligand is a moiety of B of the Formulas described below, the Linker is a moiety L, and the remainder of the molecule is the E3 Ligase binding portion.

By degrading BRD9 the compounds of the present invention can inhibit the formation of the BRD9 containing BAF complex and as a result reduce cellular proliferation. Some cancers rely on the BRD9 containing BAF complex more than healthy cells so these cancers, for example acute myeloid leukemia, rhabdoid tumors, synovial sarcoma, and multiple myeloma, can be effectively treated with compounds of the present invention.

The compound of the present invention provided herein or its pharmaceutically acceptable salt and/or its pharmaceutically acceptable composition can be used to treat a disorder which is mediated by the selected Target Protein, for example BRD9 or alternatively BRD7 or another BRD containing protein, that binds to the Targeting Ligand.

In some embodiments a method to treat a patient with a disorder mediated by BRD9 is provided that includes administering an effective amount of one or more compounds as described herein, or a pharmaceutically acceptable salt thereof, to the patient, typically a human, optionally in a pharmaceutically acceptable composition.

In one aspect, the present invention provides a compound of Formula I, Formula II, Formula III, Formula IV, Formula V, or Formula VI:

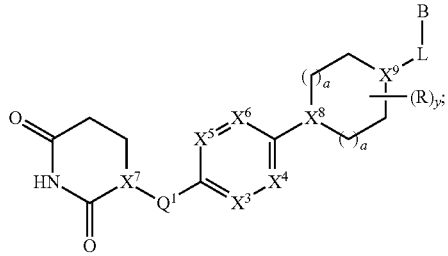

(I)

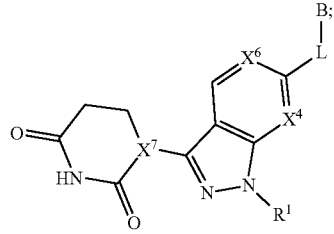

(II)

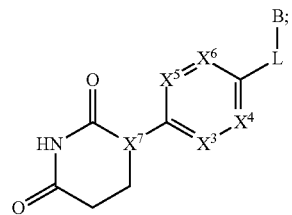

(III)

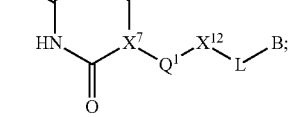

(IV)

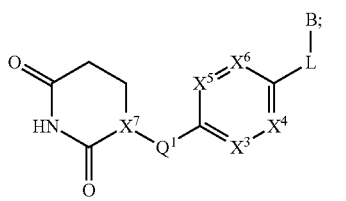

(V)

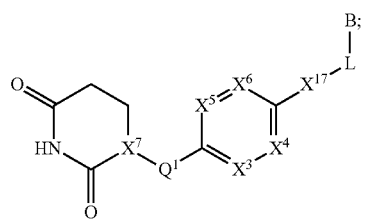

(VI)

or a pharmaceutically acceptable salt thereof;
wherein
  each a is independently 0, 1, or 2;
  each y is independently 0, 1, or 2;
  $X^3$, $X^4$, $X^5$, and $X^6$, are selected from the group consisting of N, CH and $CR^3$, wherein no more than 3 of $X^3$, $X^4$, $X^5$, and $X^6$ are N;
  $X^7$ is N or CH;
  $X^8$ and $X^9$ are each independently at each occurrence selected from the group consisting of N and CH; wherein at least one of $X^8$ or $X^9$ is CH;
  or $X^8$ and $X^9$ are each independently at each occurrence selected from the group consisting of N, CH, or C—O—$R^7$; wherein at least one of $X^8$ or $X^9$ is CH or C—O—$R^7$;
  $X^{12}$ is a 5-membered heteroaryl group with 1, 2, or 3 atoms independently selected from N, O, and S, wherein $X^{12}$ is optionally substituted with 1, 2, or 3 groups independently selected from $R^3$;
  $X^{17}$ is aryl, heteroaryl, bicycle, or cycloalkyl, each of which is optionally substituted with 1, 2, 3, or 4 substituents independently selected from $R^3$;
  $Q^1$ is independently at each occurrence selected from the group consisting of NH, N(alkyl), N(haloalkyl), $CH_2$, O, and S; wherein if $X^7$ is N, then $Q^1$ is $CH_2$;
  R is independently at each occurrence selected from the group consisting of hydrogen, $C_1$-$C_4$haloalkyl, $C_1$-$C_4$alkyl, fluorine, chlorine, bromine, iodine, $CH_2F$, $CHF_2$, $CF_3$, $CH_2Cl$, $CHCl_2$, $CCl_3$, $CH_2Br$, $CHBr_2$, and $CBr_3$;
  $R^1$ is hydrogen, C1-$C_4$alkyl, C1-$C_4$haloalkyl, or cycloalkyl;

$R^3$ is independently at each occurrence selected from the group consisting of hydrogen, hydroxyl, alkoxy, $C_1$-$C_4$alkyl, $C_1$-$C_4$haloalkyl, cycloalkyl, fluorine, chlorine, bromine, and iodine;

B is selected from $B^1$ and $B^2$;

$B^1$ is selected from the group consisting of:

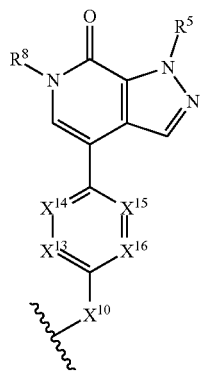
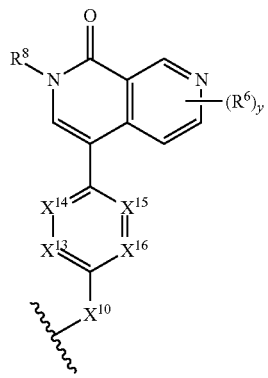

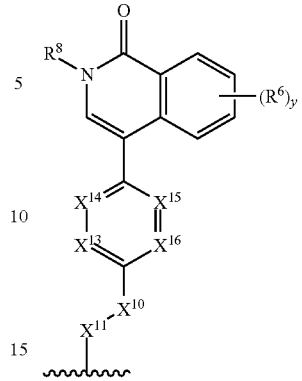 and 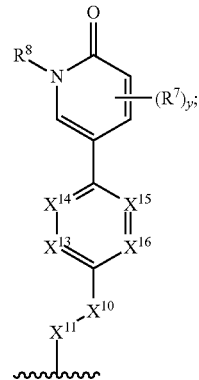

$X^{10}$ is $C(R^7)_2$, $C(O)$, or $O$;

$X^{11}$ is heterocycle, heteroaryl, aryl, cycloalkyl, or a bicycle, each of which $X^{11}$ groups is optionally substituted with 1, 2, 3, or 4 groups independently selected from $R^3$;

or $X^{10}$ and $X^{11}$ are taken together to form

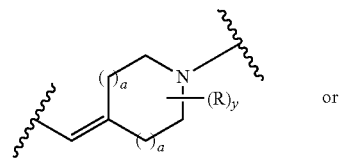 or

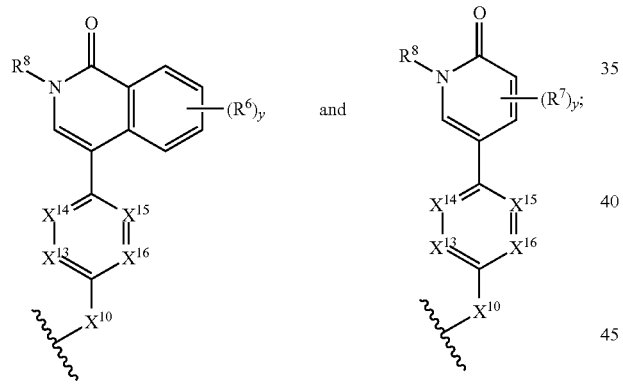

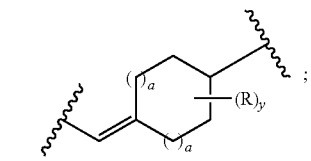

$B^2$ is selected from the group consisting of:

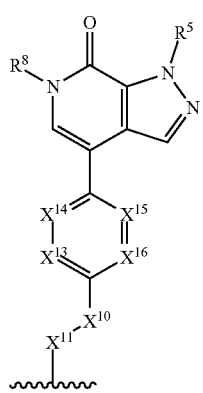
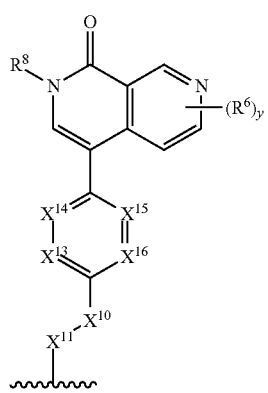

$X^{13}$, $X^{14}$, $X^{15}$, and $X^{16}$, are independently selected from the group consisting of N, CH and $CR^4$, wherein no more than 3 of $X^{13}$, $X^{14}$, $X^{15}$, and $X^{16}$ are N;

each $R^4$ is independently selected from hydrogen, aryl, heteroaryl, C1-$C_4$alkoxy, $C_1$-$C_4$haloalkyl, $C_1$-$C_4$haloalkoxy, C1-$C_4$alkyl, fluorine, chlorine, bromine, and iodine;

wherein two $R^4$ groups on adjacent carbon atoms may optionally combine to form a fused cycle, wherein the fused cycle is optionally substituted with 1, 2, or 3 R substituents, thus, non-limiting examples of

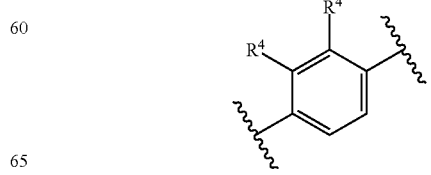

include

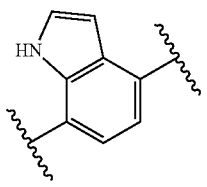 [SMILES: *c1ccc(*)c2[nH]ccc12]

and

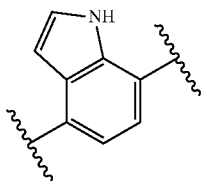 [SMILES: *c1ccc(*)c2[nH]ccc12]

wherein two R⁴ groups combined to form a pyrrole;
R⁵ is hydrogen, $C_1$-$C_4$alkyl, allyl, crotyl, alkenyl, alkynyl, haloalkyl, or cycloalkyl;
each R⁶ is independently selected from hydrogen, $C_1$-$C_4$alkoxy, $C_1$-$C_4$alkyl, $C_1$-$C_4$haloalkyl, fluorine, chlorine, bromine, and iodine;
each R⁷ is independently hydrogen or $C_1$-$C_4$alkyl;
R⁸ is hydrogen, $C_1$-$C_4$alkyl, allyl, crotyl, alkenyl, alkynyl, haloalkyl, or cycloalkyl; and
L is a bivalent linking group, for example a bivalent linking group of Formula LI.

Every combination of variables, substituents, embodiments and the compounds that result from these combinations, is deemed specifically and individually disclosed, as such depiction is for convenience of space only and not intended to describe only a genus or even a subgenus of compounds.

In certain embodiments L is a linker of formula:

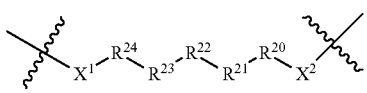

(LI)

wherein,
X¹ and X² are independently at each occurrence selected from bond, heterocycle, NR², C(R²)₂, O, C(O), and S;
R² is independently at each occurrence selected from the group consisting of hydrogen, alkyl, aliphatic, heteroaliphatic, heterocycle, aryl, heteroaryl, —C(O)H, —C(O)OH, —C(O)alkyl, —C(O)Oalkyl, —C(O)(aliphatic, aryl, heteroaliphatic or heteroaryl), —C(O)O (aliphatic, aryl, heteroaliphatic, or heteroaryl), alkene, and alkyne;
R²⁰, R²¹, R²², R²³, and R²⁴ are independently at each occurrence selected from the group consisting of a bond, alkyl, —C(O)—, —C(O)O—, —OC(O)—, —SO₂—, —S(O)—, —C(S)—, —C(O)NR²—, —NR²C(O)—, —O—, —S—, —NR²—, —C(R⁴⁰R⁴⁰)—, —P(O)(OR²⁶)O—, —P(O)(OR²⁶)—, bicycle, alkene, alkyne, haloalkyl, alkoxy, aryl, heterocycle, aliphatic, heteroaliphatic, heteroaryl, lactic acid, glycolic acid, and carbocycle; each of which is optionally substituted with 1, 2, 3, or 4 substituents independently selected from R⁴⁰;

R²⁶ is independently at each occurrence selected from the group consisting of hydrogen, alkyl, arylalkyl, heteroarylalkyl, alkene, alkyne, aryl, heteroaryl, heterocycle, aliphatic and heteroaliphatic; and
R⁴⁰ is independently at each occurrence selected from the group consisting of hydrogen, alkyl, alkene, alkyne, fluoro, bromo, chloro, hydroxyl, alkoxy, azide, amino, cyano, —NH(aliphatic, including alkyl), —N(aliphatic, including alkyl)₂, —NHSO₂(aliphatic, including alkyl), —N(aliphatic, including alkyl)SO₂alkyl, —NHSO₂(aryl, heteroaryl or heterocycle), —N(alkyl)SO₂(aryl, heteroaryl or heterocycle), —NHSO₂alkenyl, —N(alkyl)SO₂alkenyl, —NHSO₂alkynyl, —N(alkyl)SO₂alkynyl, haloalkyl, aliphatic, heteroaliphatic, aryl, heteroaryl, heterocycle, and cycloalkyl.

In one aspect, the compounds of Formula I, Formula II, Formula III, Formula IV, Formula V, or Formula VI are compounds with an E3 Ubiquitin Ligase targeting ligand linked to a BRD9 targeting ligand, which function to recruit a Target Protein, typically via a cereblon-containing E3 Ubiquitin Ligase for degradation.

In certain embodiments, a method of treatment is provided comprising administering an effective amount of a compound of Formula I, Formula II, Formula III, Formula IV, Formula V, or Formula VI to a patient in need thereof, for example a human, optionally in a pharmaceutically acceptable carrier. For example, in one embodiment, a compound of Formula I, Formula II, Formula III, Formula IV, Formula V, or Formula VI is administered to a human to treat a cancer, for example synovial sarcoma. In one embodiment a compound of the present invention is administered to a patient to treat synovial sarcoma. In one embodiment a compound of the present invention is administered to a patient with a SS18-SSX translocation cancer. In one embodiment a compound of the present invention is administered to a patient with metastatic synovial sarcoma. In one embodiment a compound of the present invention is administered to a patient with a malignant rhabdoid tumor. In one embodiment a compound of the present invention is administered to a patient with epithelioid sarcoma.

In certain embodiments, the Targeting Ligand (B moiety) binds BRD9 and is used in the treatment of BRD9 mediated disorders. In other embodiments the Targeting Ligand (B moiety) binds a different bromodomain containing protein and is used in the treatment of a BRD mediated disorder. In an alternative embodiment the compound of the present invention is used in the treatment of non-BRD mediated disorder.

In certain embodiments, the compound of the present invention provides multiple advantages over traditional treatment with a BRD9 ligand, for example the BRD9 degrading compound of the present invention may a) overcome resistance in certain cases; b) prolong the kinetics of drug effect by destroying the protein, thus requiring resynthesis of the protein even after the compound has been metabolized; c) target all functions of a protein at once rather than a specific catalytic activity or binding event; d) expand the number of drug targets by including all proteins that a ligand can be developed for, rather than proteins whose activity can be affected by a small molecule inhibitor, antagonist or agonist; and/or e) have increased potency compared to inhibitors due to the possibility of the small molecule acting catalytically.

In certain embodiment, the compound of the present invention inhibits the growth of cells or decreases the viability of cells at a GI50 value that is lower than the GI50 of the Targeting Ligand, when the Targeting Ligand is administered alone.

In certain embodiments, the compound of the present invention provides an improved efficacy and/or safety profile relative to known BRD9 inhibitors.

In certain embodiments, the compound of the present invention is more efficacious in the treatment of a BRD9 mediated disorders than the targeting ligand portion alone.

In certain embodiments, less concentration of the compounds described herein is needed for the treatment of BRD9 mediated disorders, than the targeting ligand portion alone.

In certain embodiments, the compound of the present invention has less side-effects in the treatment of BRD9 mediated disorders, than the targeting ligand portion alone.

In certain embodiments, less frequent dose regimen of the compounds described herein is needed for the treatment of BRD9 mediated disorders, than the targeting ligand portion alone.

Another aspect of the present invention provides a compound as described herein, or an enantiomer, diastereomer, or stereoisomer thereof, or pharmaceutically acceptable salt, hydrate, or solvate thereof, or a pharmaceutical composition, for use in the manufacture of a medicament for inhibiting or preventing a disorder mediated by a bromodomain protein or for modulating or decreasing the amount of a bromodomain containing protein.

Another aspect of the present invention provides a compound as described herein, or an enantiomer, diastereomer, or stereoisomer thereof, or pharmaceutically acceptable salt, hydrate, or solvate thereof, or a pharmaceutical composition, for use in the manufacture of a medicament for treating or preventing a disease in which BRD9 plays a role.

In certain embodiments, the compound as described herein is useful to treat a disorder comprising an abnormal cellular proliferation, such as a tumor or cancer, wherein BRD9 is an oncogenic protein or a signaling mediator of an abnormal cellular proliferative pathway and its degradation decreases abnormal cell growth.

In certain embodiments, the compounds as described herein are useful as therapeutic agents when administered in an effective amount to a patient, for the treatment of a medical disorder that can be treated with thalidomide, pomalidomide, or lenalidomide.

In certain embodiments, the compound of Formula I, Formula II, Formula III, Formula IV, Formula V, or Formula VI has at least one desired isotopic substitution of an atom, at an amount above the natural abundance of the isotope, i.e., enriched.

In one embodiment, the compound of Formula I, Formula II, Formula III, Formula IV, Formula V, or Formula VI includes a deuterium or multiple deuterium atoms.

Other features and advantages of the present application will be apparent from the following detailed description.

The present invention thus includes at least the following features:

(a) A compound of Formula I, Formula II, Formula III, Formula IV, Formula V, or Formula VI, as described herein, or a pharmaceutically acceptable salt or isotopic derivative (including a deuterated derivative) thereof;

(b) A method for treating a BRD9 mediated disorder, comprising administering an effective amount of a compound of Formula I, Formula II, Formula III, Formula IV, Formula V, or Formula VI, or pharmaceutically acceptable salt thereof, as described herein, to a patient in need thereof;

(c) A compound of Formula I, Formula II, Formula III, Formula IV, Formula V, or Formula VI, or a pharmaceutically acceptable salt, orisotopic derivative (including a deuterated derivative) thereof for use in the treatment of a disorder that is mediated by BRD9, for example an abnormal cellular proliferation such as a tumor or cancer;

(d) Use of a compound of Formula I, Formula II, Formula III, Formula IV, Formula V, or Formula VI, or a pharmaceutically acceptable salt thereof, in an effective amount in the treatment of a patient in need thereof, typically a human, with BRD9 mediated disorder, for example an abnormal cellular proliferation such as a tumor or cancer;

(e) Use of a compound of Formula I, Formula II, Formula III, Formula IV, Formula V, or Formula VI, or a pharmaceutically acceptable salt or isotopic derivative (including a deuterated derivative) thereof in the manufacture of a medicament for the treatment of a BRD9 mediated disorder, for example an abnormal cellular proliferation such as a tumor or cancer;

(f) A pharmaceutical composition comprising an effective patient-treating amount of a compound of Formula I, Formula II, Formula III, Formula IV, Formula V, or Formula VI, or a pharmaceutically acceptable salt, isotopic derivative thereof, and optionally a pharmaceutically acceptable carrier or diluent;

(g) A compound of Formula I, Formula II, Formula III, Formula IV, Formula V, or Formula VI, as described herein as a mixture of enantiomers or diastereomers (as relevant), including as a racemate;

(h) A compound of Formula I, Formula II, Formula III, Formula IV, Formula V, or Formula VI, as described herein in enantiomerically or diastereomerically (as relevant) enriched form, including an isolated enantiomer or diastereomer (i.e., greater than 85, 90, 95, 97, or 99% pure); and (i) A process for the preparation of therapeutic products that contain an effective amount of a compound of Formula I, Formula II, Formula III, Formula IV, Formula V, or Formula VI, or a pharmaceutically acceptable salt thereof, as described herein.

DETAILED DESCRIPTION OF THE INVENTION

I. Definitions

Figure 1:
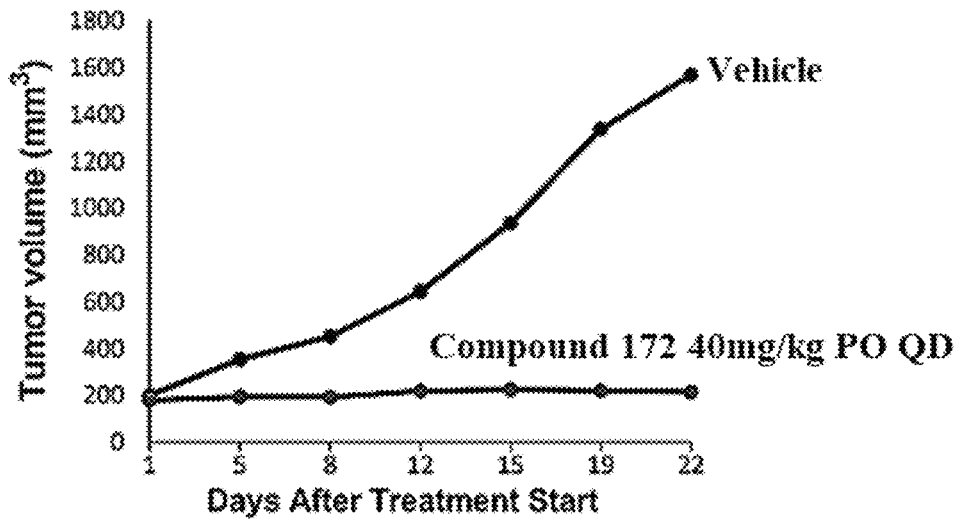
FIG. 1 is a graph of tumor volume after treatment with Compound 172 demonstrating strong effect in a synovial sarcoma xenograft model. The x-axis is time after start of treatment measured in days and the y-axis is tumor volume measured in $mm^3$.

Compounds are described using standard nomenclature. Unless defined otherwise, all technical and scientific terms used herein have the same meaning as is commonly understood by one of skill in the art to which this invention belongs.

The compounds in any of the Formulas described herein may be in the form of a racemate, enantiomer, mixture of enantiomers, diastereomer, mixture of diastereomers, tautomer, N-oxide, isomer; such as rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds of Formula I, Formula II, Formula III, Formula IV, Formula V, or Formula VI, with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^2$H, $^3$H, $^{11}$C, $^{13}$C, $^{14}$C, $^{15}$N, $^{17}$O, $^{18}$O, $^{18}$F $^{31}$P, $^{32}$P, $^{35}$S, $^{36}$Cl, and $^{125}$I respectively. In one non-limiting embodiment, isotopically labelled compounds can be used in metabolic studies (with, for example $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound of Formula I, Formula II, Formula III, Formula IV, Formula V, or Formula VI. In one non-limiting embodiment, the substitution of a hydrogen atom for a deuterium atom occurs within one or more groups selected from any of R's or variables described herein, Linker, and Targeting Ligand. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compound of the present invention may form a solvate with a solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO (dimethyl sulfoxide). A solvate can be in a liquid or solid form.

A dash ("—") that is not between two letters or symbols is used to indicate a point of attachment for a substituent. For example, —(C═O)NH$_2$ is attached through carbon of the carbonyl (C═O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species and therefore each subset is considered separately disclosed. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "alkyl" also encompasses cycloalkyl or carbocyclic groups. For example, when a term is used that includes "alk" then "cycloalkyl" or "carbocyclic" can be considered part of the definition, unless unambiguously excluded by the context. For example, and without limitation, the terms alkyl, alkoxy, haloalkyl, etc., can all be considered to include the cyclic forms of alkyl, unless unambiguously excluded by context.

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In an alternative embodiment "alkyl" is "optionally substituted" with 1, 2, 3, or 4 substituents.

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.
In one embodiment "cycloalkyl" has four carbons.
In one embodiment "cycloalkyl" has five carbons.
In one embodiment "cycloalkyl" has six carbons.

In one embodiment "cycloalkyl" has seven carbons.
In one embodiment "cycloalkyl" has eight carbons.
In one embodiment "cycloalkyl" has nine carbons.
In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Additional non-limiting examples of "cycloalkyl" include dihydro-indene and tetrahydronaphthalene wherein the point of attachment for each group is on the cycloalkyl ring.

For example:

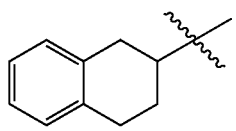 [SMILES: *C1CCc2ccccc2C1]

is an "cycloalkyl" group.

However,

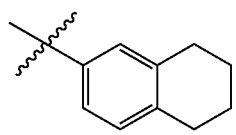 [SMILES: *c1ccc2c(c1)CCCC2]

is an "aryl" group.

In an alternative embodiment "cycloalkyl" is a "optionally substituted" with 1, 2, 3, or 4 substituents.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or cycloalkyl groups possessing at least one point of unsaturation. In an alternative embodiment "alkenyl" is "optionally substituted" with 1, 2, 3, or 4 substituents.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or cycloalkyl groups possessing at least one triple bond. In an alternative embodiment "alkynyl" is "optionally substituted" with 1, 2, 3, or 4 substituents.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_5$alkylene, or $C_1$-$C_6$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, a 2 to 6 carbon moiety, or an indicated number of carbon atoms, for example $C_2$-$C_4$alkynylene.

"Halo" and "Halogen" refers independently to fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.
In one embodiment "haloalkyl" has one carbon and one halogen.
In one embodiment "haloalkyl" has one carbon and two halogens.
In one embodiment "haloalkyl" has one carbon and three halogens.
In one embodiment "haloalkyl" has two carbons.
In one embodiment "haloalkyl" has three carbons.
In one embodiment "haloalkyl" has four carbons.
In one embodiment "haloalkyl" has five carbons.
In one embodiment "haloalkyl" has six carbons.

Non-limiting examples of "haloalkyl" include:

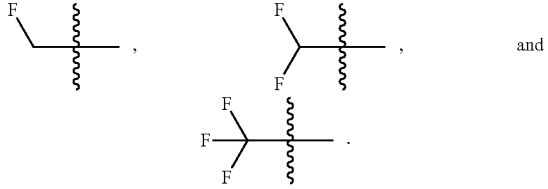

Additional non-limiting examples of "haloalkyl" include:

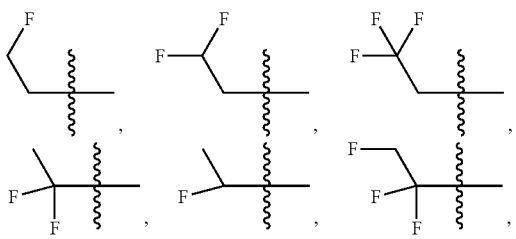

-continued

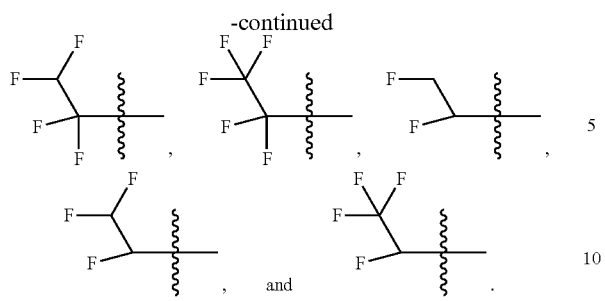

Additional non-limiting examples of "haloalkyl" include:

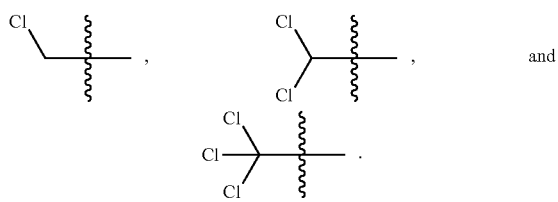

Additional non-limiting examples of "haloalkyl" include:

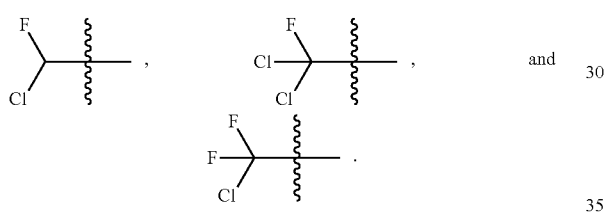

"Chain" indicates a linear chain to which all other chains, long or short or both, may be regarded as being pendant. Where two or more chains could equally be considered to be the main chain, "chain" refers to the one which leads to the simplest representation of the molecule.

"Haloalkoxy" indicates a haloalkyl group as described herein attached through an oxygen bridge (oxygen of an alcohol radical).

"Heterocycloalkyl" is an alkyl group as described herein substituted with a heterocyclo group as described herein.

"Arylalkyl" is an alkyl group as described herein substituted with an aryl group as described herein.

Non-limiting examples of "arylalkyl" include:

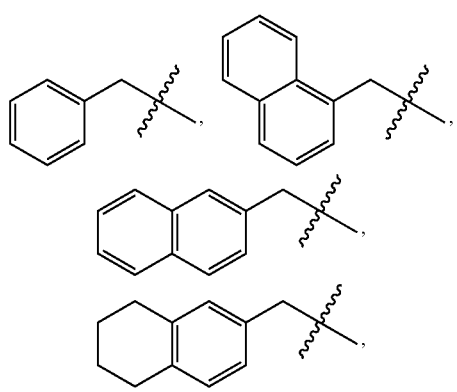

-continued

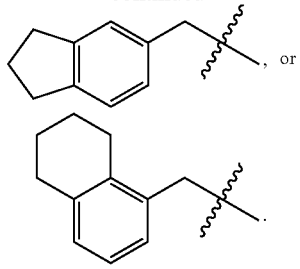

In one embodiment "arylalkyl" is

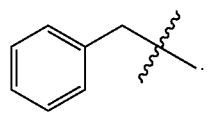 [SMILES: *Cc1ccccc1]

In one embodiment the "arylalkyl" refers to a 2 carbon alkyl group substituted with an aryl group.

Non-limiting examples of "arylalkyl" include:

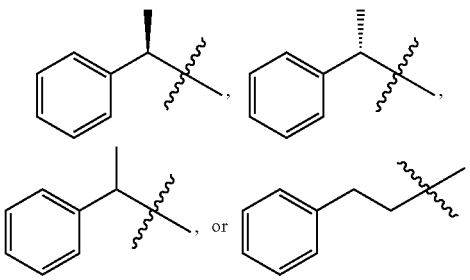

In one embodiment the "arylalkyl" refers to a 3 carbon alkyl group substituted with an aryl group.

"Heteroarylalkyl" is an alkyl group as described herein substituted with a heteroaryl group as described herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocycle groups wherein the radical or point of attachment is on the aryl ring, and in such instances, the number of carbon atoms continue to designate the number of carbon atoms in the aryl ring system. The one or more fused carbocyclyl or heterocycle groups can be 4 to 7 or 5 to 7-membered saturated or partially unsaturated carbocyclyl or heterocycle groups that optionally contain 1, 2, or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_{6-14}$ aryl. In certain embodiments, the aryl group is a substituted $C_{6-14}$ aryl. An aryl group may be optionally substituted with one or more functional groups that include but are not limited to, halo, hydroxy, nitro, amino, cyano, haloalkyl, aryl, heteroaryl, and heterocyclo.

In one embodiment "aryl" is a 6 carbon aromatic group (phenyl).

In one embodiment "aryl" is a 10 carbon aromatic group (napthyl).

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example,

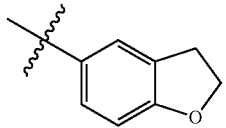 [SMILES: *c1ccc2c(c1)CCO2]

is an "aryl" group.

However,

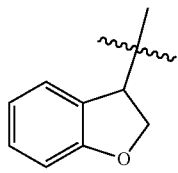 [SMILES: *C1COc2ccccc21]

is a "heterocycle" group.

In one embodiment "aryl" is a 6 carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

For example,

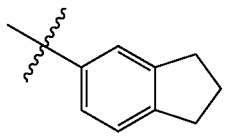

is an "aryl" group.

However,

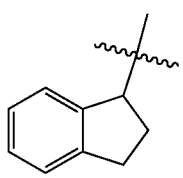 [SMILES: *C1CCc2ccccc21]

is a "cycloalkyl" group.

In an alternative embodiment "aryl" is "optionally substituted" with 1, 2, 3, or 4 substitutents.

The term "heterocyclyl", "heterocycle", and "heterocyclo" includes saturated, and partially saturated heteroatom-containing ring radicals, where the heteroatoms may be selected from nitrogen, sulfur and oxygen. Heterocyclic rings comprise monocyclic 3, 4, 5, 6, 7, 8, 9, or 10 membered rings, as well as 5, 6, 7, 8, 9, 10, 11, 12, 13, 14, 15, or 16 membered bicyclic ring systems (which can include bridged fused and spiro-fused bicyclic ring systems). It does not include rings containing —O—O—, —O—S— or —S—S— portions. Said "heterocycle" group may be optionally substituted, for example, with 1, 2, 3, 4 or more substituents that include but are not limited to, hydroxyl, Boc, halo, haloalkyl, cyano, alkyl, aralkyl, oxo, alkoxy, and amino. Examples of saturated heterocyclo groups include saturated 3, 4, 5, or 6-membered heteromonocyclic groups containing 1, 2, 3, or 4 nitrogen atoms [e.g. pyrrolidinyl, imidazolidinyl, piperidinyl, pyrrolinyl, piperazinyl]; saturated 3, 4, 5, or 6-membered heteromonocyclic group containing 1 or 2 oxygen atoms and 1, 2, or 3 nitrogen atoms [e.g. morpholinyl]; saturated 3, 4, 5, or 6-membered heteromonocyclic group containing 1 or 2 sulfur atoms and 1, 2, or 3 nitrogen atoms [e.g., thiazolidinyl]. Examples of partially saturated heterocycle radicals include, but are not limited to, dihydrothienyl, dihydropyranyl, dihydrofuryl, and dihydrothiazolyl. Examples of partially saturated and saturated heterocyclo groups include, but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl, isoquinolin-1(2H)-onyl, benzo[d]oxazol-2(3H)-onyl, 1,3-dihydro-2H-benzo[d]midazol-2-onyl, benzo[d]thiazole-2(3H)-onyl, 1,2-dihydro-3H-pyrazol-3-onyl, 2(1H)-pyridinonyl, 2-piperazinonyl, indolinyl, and dihydrothiazolyl.

The term "heterocyclyl", "heterocycle", and "heterocyclo" groups also include moieties where heterocycle radicals are fused/condensed with aryl or heteroaryl radicals: such as unsaturated condensed heterocycle group containing 1, 2, 3, 4, or 5 nitrogen atoms, for example, indoline, isoindoline, unsaturated condensed heterocycle group containing 1 or 2 oxygen atoms and 1, 2, or 3 nitrogen atoms, unsaturated condensed heterocycle group containing 1 or 2 sulfur atoms and 1, 2, or 3 nitrogen atoms, and saturated, partially unsaturated and unsaturated condensed heterocycle group containing 1 or 2 oxygen or sulfur atoms.

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocycle ring.

For example,

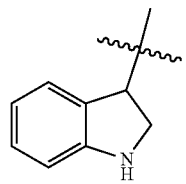 [SMILES: *C1CNc2ccccc21]

is a "heterocycle" group.

However,

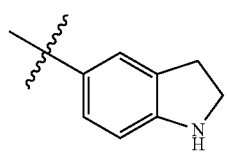 [SMILES: *c1ccc2c(c1)CCN2]

is an "aryl" group.

Non-limiting examples of "heterocycle" also include:

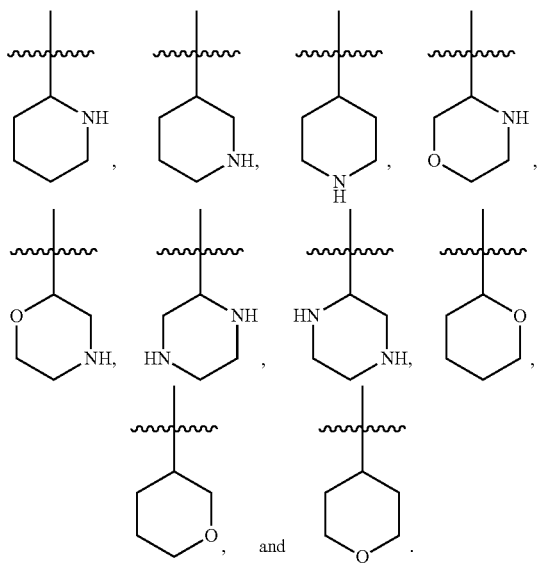

Additional non-limiting examples of "heterocycle" include:

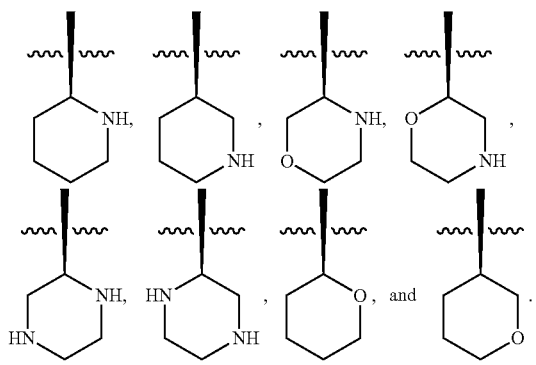

Additional non-limiting examples of "heterocycle" include:

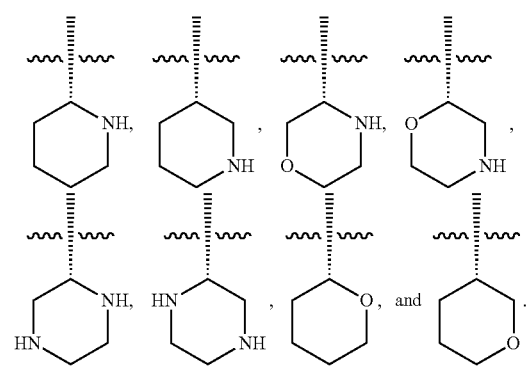

Non-limiting examples of "heterocycle" also include:

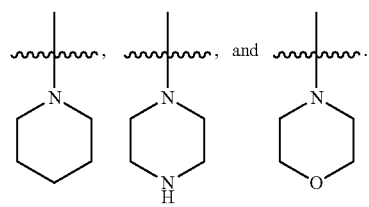

Non-limiting examples of "heterocycle" also include:

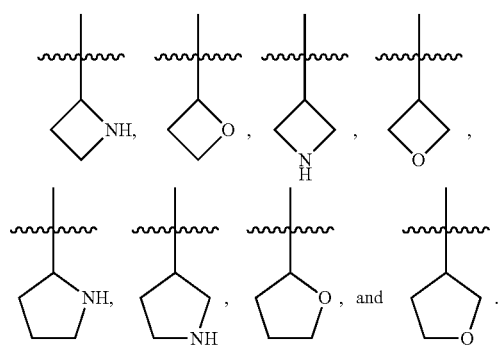

Additional non-limiting examples of "heterocycle" include:

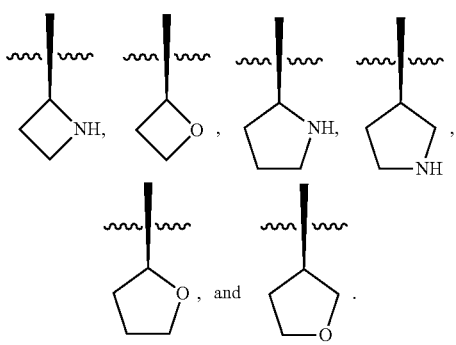

Additional non-limiting examples of "heterocycle" include:

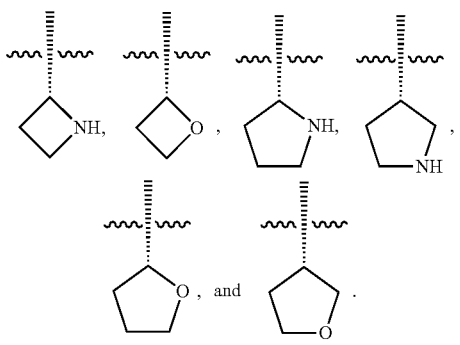

In an alternative embodiment "heterocycle" is "optionally substituted" with 1, 2, 3, or 4 substituents.

The term "heteroaryl" denotes a monocyclic or polycyclic (e.g., bicyclic or tricyclic) 4n+2 aromatic ring system (e.g., having 6, 10, or 14 π electrons shared in a cyclic array) and 1, 2, 3, 4, 5, or 6, heteroatoms independently selected from O, N, and S, wherein the ring nitrogen and sulfur atom(s) are optionally oxidized, and nitrogen atom(s) are optionally quarternized. Examples include, but are not limited to, unsaturated 5 to 6 membered heteromonocyclyl groups containing 1, 2, 3, or 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- or 6-membered heteromonocyclic groups containing an oxygen atom, for example, pyranyl, 2-furyl, 3-furyl, etc.; unsaturated 5- or 6-membered heteromonocyclic groups containing a sulfur atom, for example, 2-thienyl, 3-thienyl, etc.; unsaturated 5- or 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 or 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. Additional examples include 8-, 9-, or 10-membered heteroaryl bicyclic groups such as indazolyl, indolyl, imidazo[1,5-a]pyridinyl, benzimidazolyl, 4(3H)-quinazolinonyl, quinolinyl, isoquinolinyl, isoindolyl, thienothienyl, indolizinyl, benzofuranyl, isobenzofuranyl, benzothienyl, isobenzothienyl, benzoxazolyl, benzothiazolyl, purinyl, coumarinyl, cinnolinyl, and triazolopyridinyl.

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

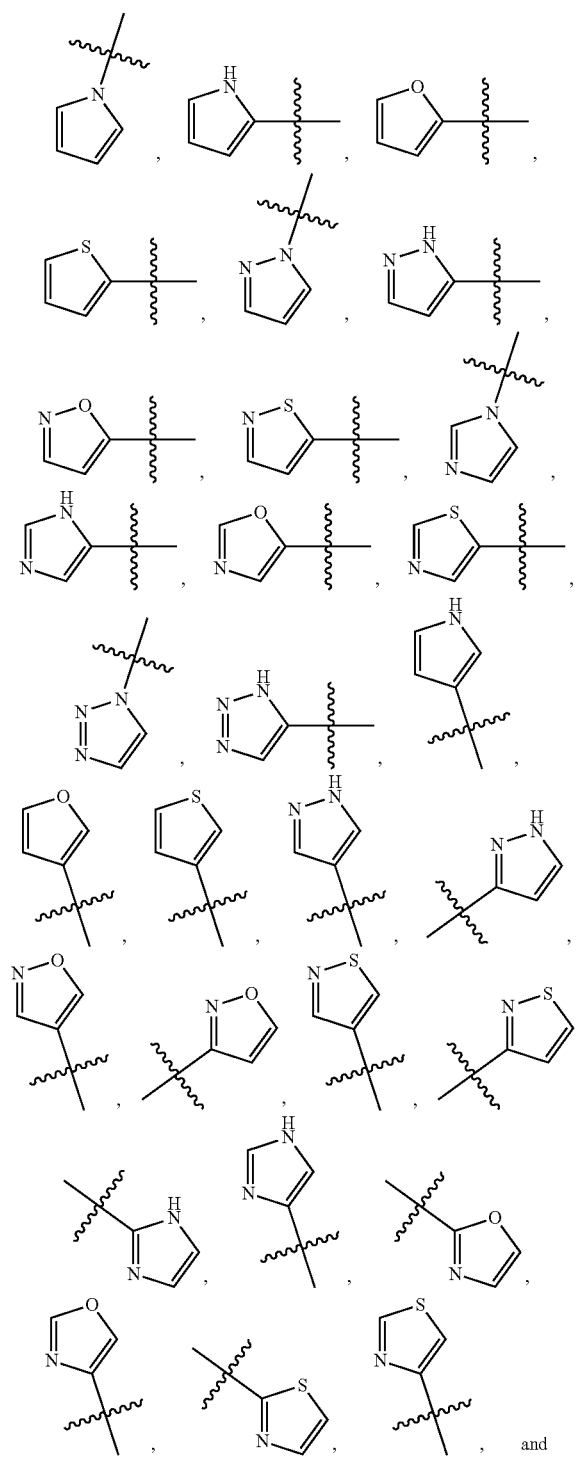

-continued

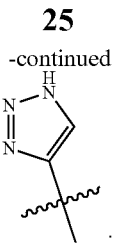

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

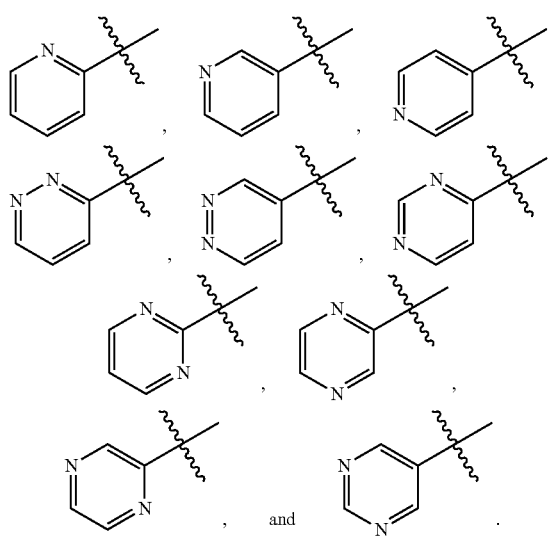

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

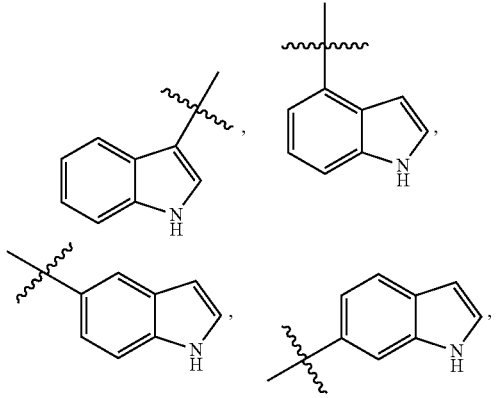

-continued

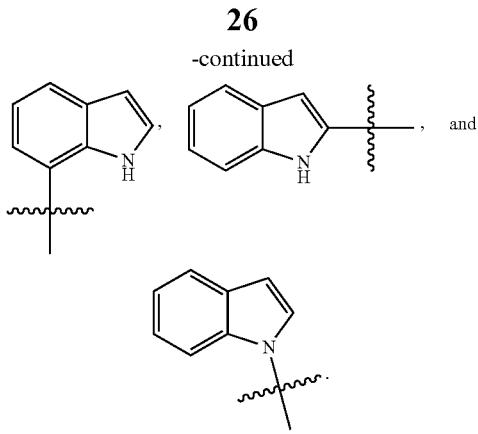

Additional non-limiting examples of "heteroaryl" groups that are bicyclic include:

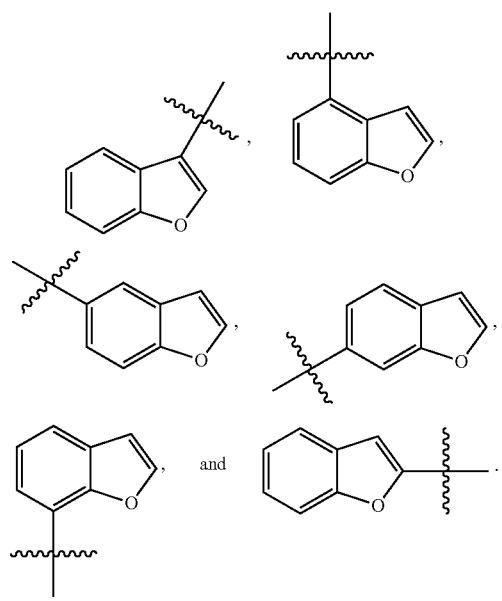

Additional non-limiting examples of "heteroaryl" groups that are bicyclic include:

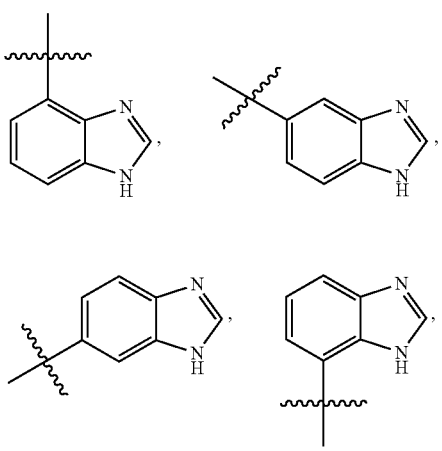

-continued

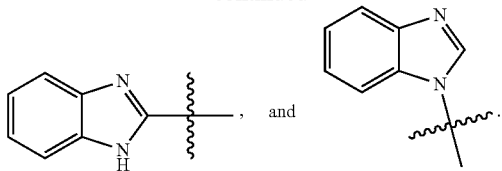, and 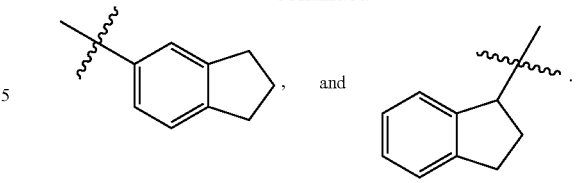

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

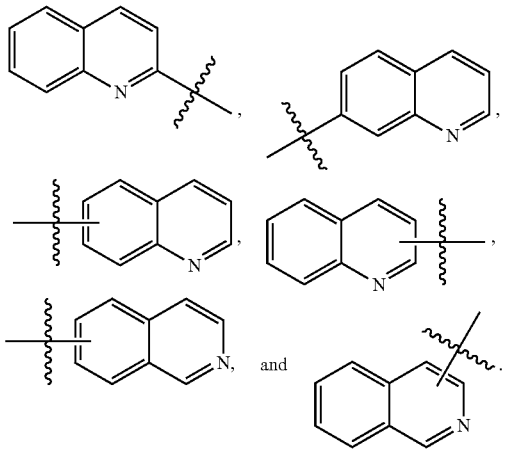

In an alternative embodiment "heteroaryl" is "optionally substituted" with 1, 2, 3, or 4 substituents.

The term "bicycle" refers to a ring system wherein two rings are fused together and each ring is independently selected from carbocycle, heterocycle, aryl, and heteroaryl. Non-limiting examples of bicycle groups include:

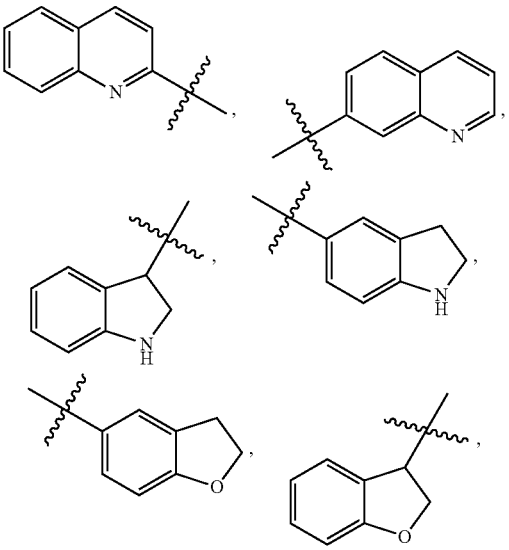

When the term "bicycle" is used in the context of a bivalent residue such as Linker or $X^{11}$ the attachment points can be on separate rings or on the same ring. In certain embodiments both attachment points are on the same ring. In certain embodiments both attachment points are on different rings. Non-limiting examples of bivalent bicycle groups include:

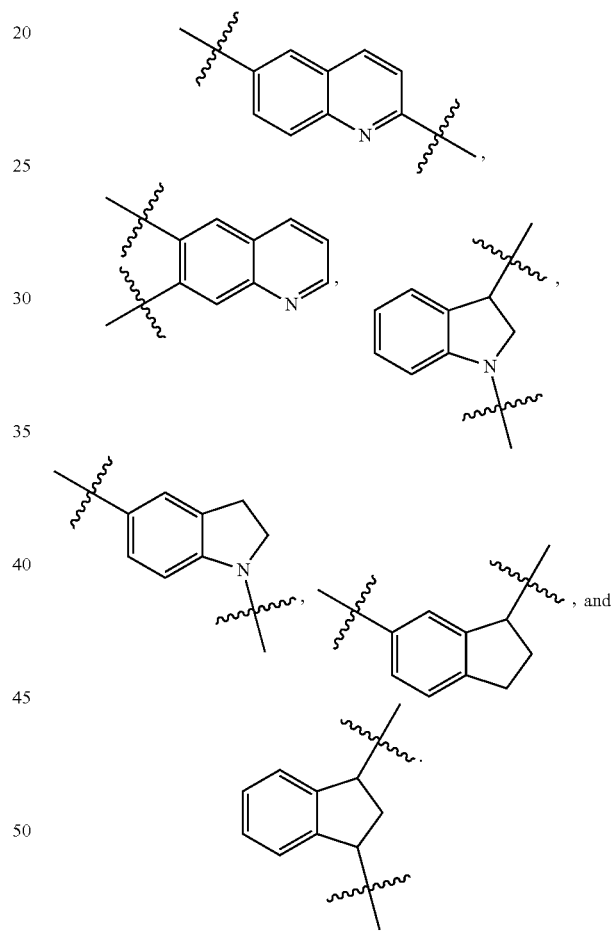

In an alternative embodiment "bicycle" is "optionally substituted" with 1, 2, 3, or 4 substituents.

The term "optionally substituted" denotes the substitution of a group herein by a moiety including, but not limited to, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, $C_1$-$C_{12}$ heterocycloalkyl, $C_3$-$C_{12}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{10}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, azido, acyl, thioacyl, acyloxy, carboxyl, and carboxylic ester.

In one alternative embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino.

In certain embodiments "optionally substituted" includes one or more substituents independently selected from halogen, hydroxyl, amino, cyano, —CHO, —COOH, —CONH$_2$, alkyl including $C_1$-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, C1-$C_6$alkylester, (mono- and di-$C_1$-$C_6$alkylamino)$C_0$-$C_2$alkyl, haloalkyl including $C_1$-$C_6$haloalkyl, hydroxy$C_1$-$C_6$alkyl, ester, carbamate, urea, sulfonamide, —$C_1$-$C_6$alkyl (heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), B(OH)$_2$, phosphate, phosphonate and haloalkoxy including $C_1$-$C_6$haloalkoxy.

In some embodiments, the suitable group present on a "substituted" or "optionally substituted" is divalent including, but not limited to, oxo (=O), =S, =CH$_2$, etc. The suitable group on a "substituted" or "optional substituted" position may be monovalent, divalent, or trivalent such that it forms a stable molecule and meets the desired purpose of the invention.

In one embodiment a group described herein that can be substituted with 1, 2, 3, or 4 substituents is substituted with one substituent.

In one embodiment a group described herein that can be substituted with 1, 2, 3, or 4 substituents is substituted with two substituents.

In one embodiment a group described herein that can be substituted with 1, 2, 3, or 4 substituents is substituted with three substituents.

In one embodiment a group described herein that can be substituted with 1, 2, 3, or 4 substituents is substituted with four substituents.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein, means an amount which provides a therapeutic or prophylactic benefit.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a patient compared with the level of a response in the patient in the absence of a treatment or compound, and/or compared with the level of a response in an otherwise identical but untreated patient. The term encompasses perturbing and/or affecting a native signal or response thereby mediating a beneficial therapeutic response in a patient, preferably, a human.

"Parenteral" administration of a pharmaceutical composition includes, e.g., subcutaneous (s.c.), intravenous (i.v.), intramuscular (i.m.), intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and the maximum number of amino acids present within the protein or peptide's sequence is typically comparable to up to that found in nature. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

To "treat" a disease as the term is used herein, means to reduce the frequency or severity of at least one sign or symptom of a disease or disorder experienced by a patient (i.e. palliative treatment) or to decrease a cause or effect of the disease or disorder (i.e. disease-modifying treatment).

Throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, "pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable carrier" means a carrier or excipient that is useful in preparing a pharmaceutical composition/combination that is generally safe, non-toxic and neither biologically nor otherwise inappropriate for administration to a patient, typically a human. In one embodiment, an excipient is used that is acceptable for veterinary use.

A "patient" or "subject" is a human or non-human animal in need of treatment or prevention of any of the disorders as specifically described herein, for example that is modulated by a natural (wild-type) or modified (non-wild type) protein that can be degraded according to the present invention, resulting in a therapeutic effect. As described further herein, the word patient or subject typically refers to a human patient or subject unless it is clear from the context or wording that the disclosure is meant to include a non-human animal. Typically, the patient is a human. In an alternative embodiment, the patient or subject is a non-human animal in need of such therapy and responsive thereto.

A "therapeutically effective amount" of a pharmaceutical composition/combination of this invention means an amount effective, when administered to a patient, typically a human patient, to provide a therapeutic benefit such as an amelioration of symptoms or reduction or diminution of the disease itself.

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

II. Compounds of Formula I, Formula II, Formula III, Formula IV Formula V, and Formula VI In certain embodiments, the structure of the compound is typically selected such that it is sufficiently stable to sustain a shelf life of at least two, three, four, or five months under ambient conditions. To accomplish this, each of the R groups described herein must be sufficiently stable to sustain the corresponding desired shelf life of at least two, three, four, or five months under ambient conditions. One of ordinary skill in the art is well aware of the stability of chemical moieties and can avoid those that are not stable or are too reactive under appropriate conditions.

In certain alternative embodiments, the compound of the present invention including any of the "R" groups described herein, may be optionally substituted as described below in Section I. Definitions, if desired to achieve the target effect, results in a stable R moiety and final compound that makes chemical sense to the routineer, and if a final compound for therapy, is pharmaceutically acceptable. Also, all R groups, with or without optional substituents, should be interpreted in a manner that does not include redundancy (i.e., as known in the art, alkyl substituted with alkyl is redundant; however, for example, alkoxy substituted with alkoxy is not redundant).

In one aspect, the present invention provides a compound of Formula I, Formula II, Formula III, Formula IV, Formula V, or Formula VI:

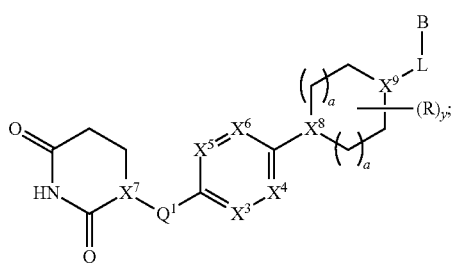

(I)

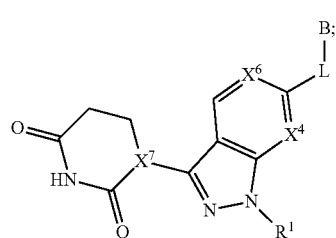

(II)

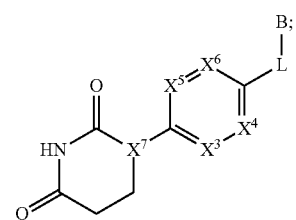

(III)

-continued

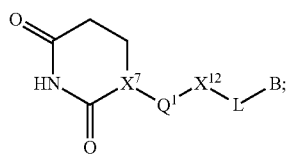

(IV)

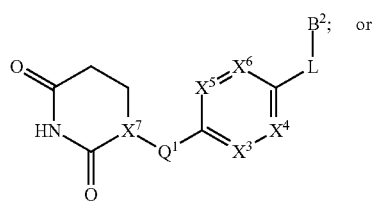

(V)

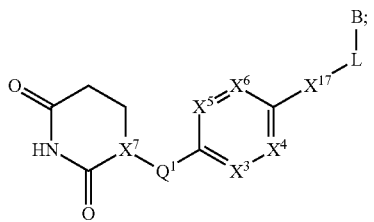

(VI)

or a pharmaceutically acceptable salt thereof;
wherein all variables are defined as above.
In certain embodiments the compound of the present invention is selected from:

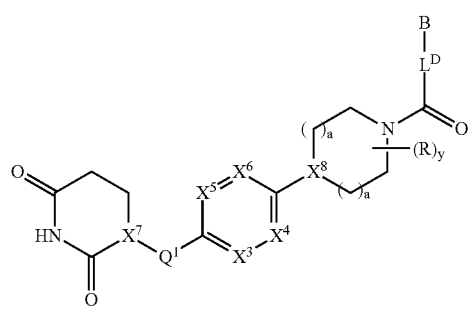

(Ia)

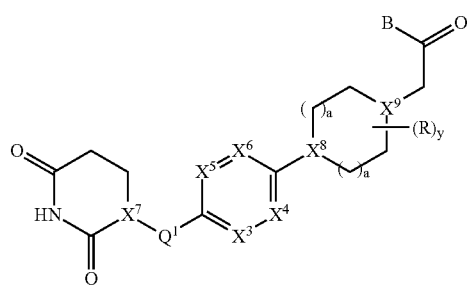

(Ib)

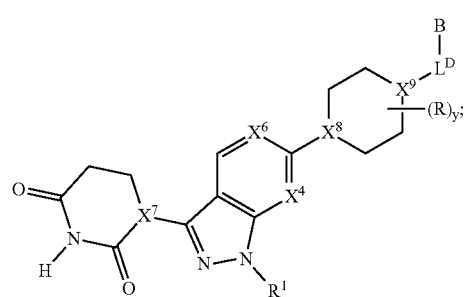
(IIa)

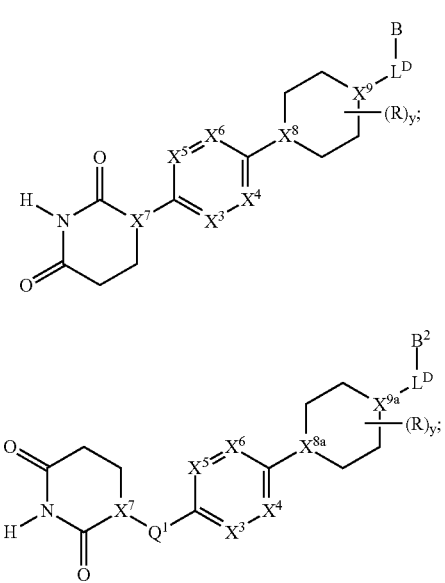
(IIIa)

(Va)

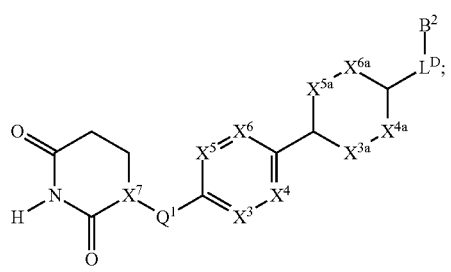
(Vb)

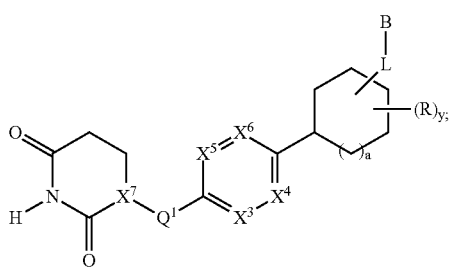
(VIa)

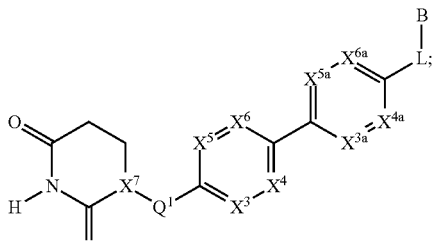
(VIb)

or a pharmaceutically acceptable salt thereof.
wherein
$L^D$ is a bivalent linking group, for example a bivalent linking group of Formula LDI;
$X^{3a}$, $X^{4a}$, $X^{5a}$, and $X^{6a}$, are selected from the group consisting of N, CH and $CR^3$, wherein no more than 3 of $X^3b$, $X^4b$, $X^5b$, and $X^6b$ are N;
and wherein all other variables are as described herein.

In certain embodiments at most two of $X^3$, $X^4$, $X^5$ and $X^6$ is N.

In certain embodiments all of $X^3$, $X^4$, $X^5$ and $X^6$ are CH.

In certain embodiments one of $X^3$, $X^4$, $X^5$ and $X^6$ is $CR^3$; wherein $R^3$ is selected from the group consisting of fluoro, chloro, and bromo. In certain embodiments $R^3$ is $C_1$-$C_4$haloalkyl. In certain embodiments $R^3$ is $C_1$-$C_4$alkyl.

In certain embodiments one of $X^3$, $X^4$, $X^5$ and $X^6$ is $CR^3$, wherein $R^3$ is $C_1$-$C_4$alkyl.

In certain embodiments $X^4$ or $X^6$ is N. In certain embodiments $X^4$ and $X^6$ are both N. In certain embodiments $X^4$ or $X^6$ is CH. In certain embodiments $X^4$ and $X^6$ are both CH.

In certain embodiments $X^4$ or $X^6$ is $CR^3$; wherein $R^3$ is selected from the group consisting of fluoro, chloro, and bromo.

In certain embodiments $X^4$ or $X^6$ is $CR^3$, wherein $R^3$ is selected from the group consisting of $C_1$-$C_4$haloalkyl, $CH_2F$, $CHF_2$, $CF_3$, $CH_2Cl$, $CHCl_2$, $CCl_3$, $CH_2Br$, $CHBr_2$, and $CBr_3$.

In certain embodiments $X^4$ or $X^6$ is $CR^3$; wherein $R^3$ is $C_1$-$C_4$alkyl.

In certain embodiments, $X^7$ is N and $Q^1$ is $CH_2$. In certain embodiments, $X^7$ is CH. In certain embodiments, $X^7$ is $C_1$-$C_4$alkyl. In certain embodiments, $X^7$ is $C_1$-$C_4$haloalkyl.

In certain embodiments at least one of $X^8$ and $X^9$ is CH.

In certain embodiments $X^8$ is N.

In certain embodiments $X^9$ is N.

In certain embodiments each of $X^8$ and $X^9$ is CH.

In certain embodiments, $X^{10}$ is $CH_2$. In certain embodiments, $X^{10}$ is C(O). In certain embodiments, $X^{10}$ is O.

In certain embodiments, $X^{11}$ is heterocycle containing at least one N, O or S. In certain embodiments, $X^{11}$ is heterocycle, is a $C_3$-$C_9$ heterocycle containing at least one N, O or S.

In certain embodiments, $X^{11}$ is a bicyclic heterocycle, containing at least one N, O or S. In certain embodiments, the bicyclic heterocycle is fused. In certain embodiments, the bicyclic heterocycle is bridged. In certain embodiments, the bicyclic heterocycle is spirocyclic.

In certain embodiments, $X^{11}$ is heteroaryl containing at least one N, O or S.

In certain embodiments, $X^{11}$ is aryl.

In certain embodiments, $X^{11}$ is cycloalkyl.

In certain embodiments, $X^{12}$ is a substituted 5 membered heteroaryl containing at least one N, O or S atom.

In certain embodiments, $X^{12}$ is a substituted 5 membered heteroaryl containing at least one N atom.

In certain embodiments, $X^{12}$ is a substituted 5 membered heteroaryl containing at least two N atoms.

In certain embodiments, $X^{12}$ is an unsubstituted 5 membered heteroaryl containing at least one N, O or S atom.

In certain embodiments, $X^{12}$ is an unsubstituted 5 membered heteroaryl containing at least one N atom.

In certain embodiments, $X^{12}$ is an unsubstituted 5 membered heteroaryl containing at least two N atoms.

In certain embodiments, $Q^1$ is NH. In certain embodiments, $Q^1$ is O. In certain embodiments, $Q^1$ is S. In certain embodiments, $Q^1$ is $CH_2$. In certain embodiments, $Q^1$ is N(alkyl) wherein the alkyl is a $C_1$-$C_4$alkyl, or $C_1$-$C_4$haloalkyl. In certain embodiments, $Q^1$ is N(haloalkyl) wherein the haloalkyl is a $C_1$-$C_4$haloalkyl.

In certain embodiments, R is hydrogen. In certain embodiments R is selected from the group consisting of fluoro, chloro, and bromo. In certain embodiments, R is $C_1$-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments, R is $C_1$-$C_4$alkyl.

In certain embodiments, $R^1$ is hydrogen. In certain embodiments $R^1$ is selected from the group consisting of fluoro, chloro, and bromo. In certain embodiments $R^1$ is $C_1$-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^1$ is cycloalkyl.

In certain embodiments, $R^3$ is hydrogen. In certain embodiments $R^3$ is selected from the group consisting of fluoro, chloro, and bromo. In certain embodiments $R^3$ is a C1-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^3$ is $C_1$-$C_4$alkoxy. In certain embodiments, $R^4$ is C1-$C_4$alkyl. In certain embodiments $R^3$ is cycloalkyl.

In certain embodiments, $R^4$ is hydrogen. In certain embodiments $R^4$ is selected from the group consisting of fluoro, chloro, and bromo. In certain embodiments $R^4$ is a C1-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^4$ is $C_1$-$C_4$alkoxy. In certain embodiments, $R^4$ is C1-$C_4$alkyl. In certain embodiments, $R^4$ is $C_1$-$C_4$haloalkoxy.

In an alternative embodiment $R^4$ is selected from hydrogen, aryl, heteroaryl, C1-$C_4$alkoxy, $C_1$-$C_4$haloalkyl, $C_1$-$C_4$haloalkoxy, $C_1$-$C_4$alkyl, hydroxyl, amino, fluorine, chlorine, bromine, and iodine.

In certain embodiments, $R^5$ is hydrogen. In certain embodiments $R^5$ is a C1-$C_4$alkyl. In certain embodiments, $R^5$ is allyl. In certain embodiments, $R^5$ is crotyl. In certain embodiments, $R^5$ is alkenyl. In certain embodiments, $R^5$ is alkynyl. In certain embodiments, $R^5$ is haloalkyl. In certain embodiments, $R^5$ is cycloalkyl.

In certain embodiments, $R^6$ is hydrogen. In certain embodiments $R^6$ is selected from the group consisting of fluoro, chloro, and bromo. In certain embodiments $R^6$ is C1-$C_4$haloalkyl, $CH_2F$, $CHF_2$, $CF_3$, $CH_2Cl$, $CHCl_2$, $CCl_3$, $CH_2Br$, $CHBr_2$, or $CBr_3$. In certain embodiments $R^6$ is $C_1$-$C_4$alkyl.

In certain embodiments, $R^7$ is hydrogen. In certain embodiments $R^7$ is a C1-$C_4$alkyl.

In certain embodiments, $R^8$ is hydrogen. In certain embodiments $R^8$ is a $C_1$-$C_4$alkyl. In certain embodiments, $R^8$ is allyl. In certain embodiments, $R^8$ is crotyl. In certain embodiments, $R^8$ is alkenyl. In certain embodiments, $R^8$ is alkynyl. In certain embodiments, $R^8$ is haloalkyl. In certain embodiments, $R^8$ is cycloalkyl.

In an alternative embodiment $X^{11}$ is heterocycle optionally substituted with 1, 2, 3, or 4 substituents independently selected from $R^3$. Non-limiting examples of $X^{17}$ heterocycle groups include pyrrolidine, piperidine, morpholine, thiomorpholine, azepane, tetrahydrofuran, tetrahydropyran, dioxane, thiane, oxepane, azocane, thioane, and azonane.

In certain embodiments

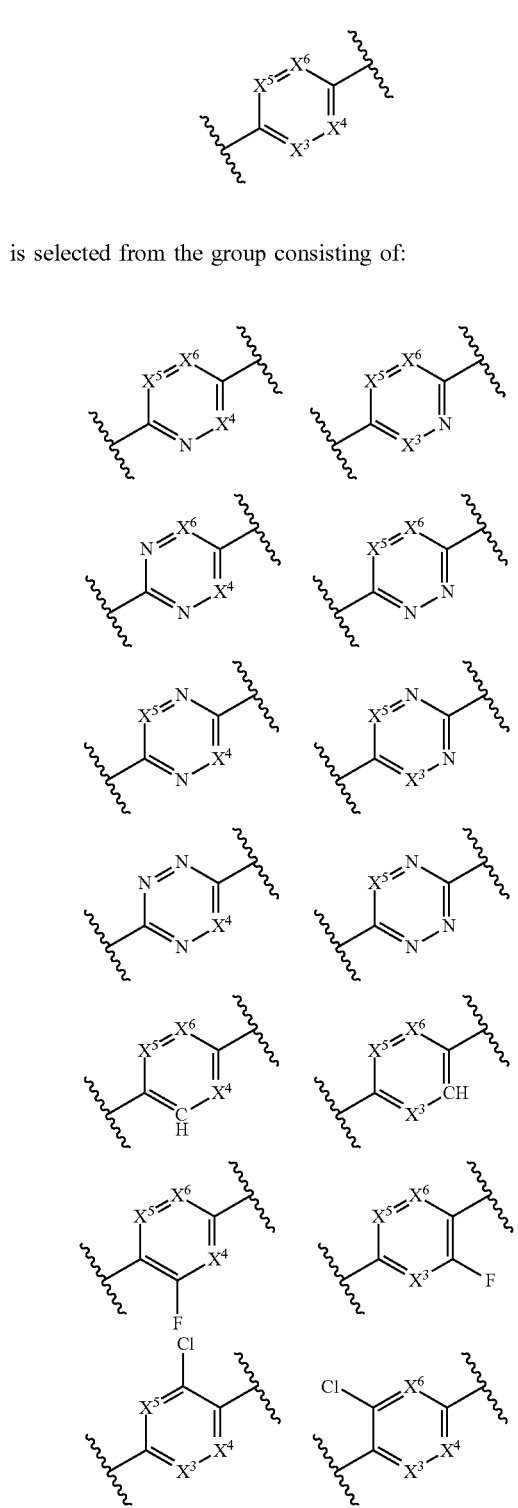

is selected from the group consisting of:

-continued
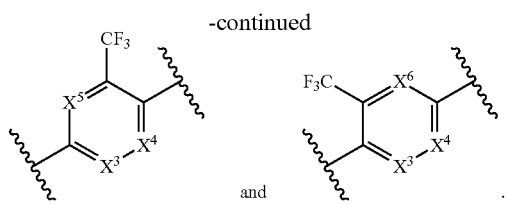
and
In certain embodiments
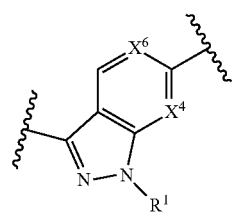
is selected from the group consisting of:
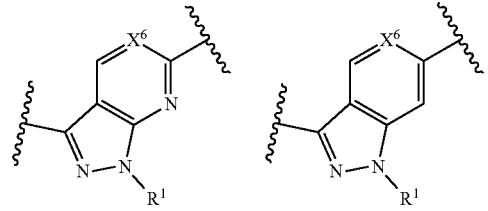
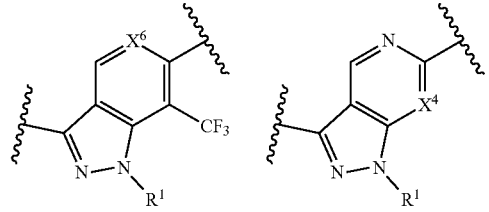
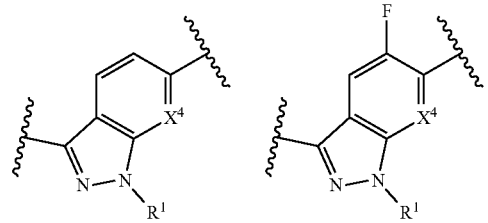
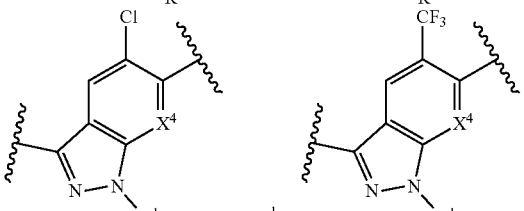
and
In certain embodiments
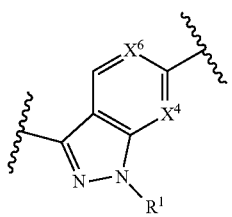
is selected from the group consisting of:
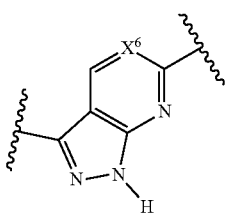 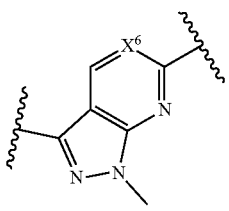
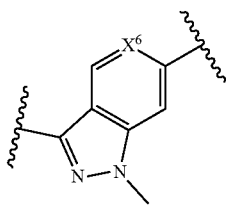 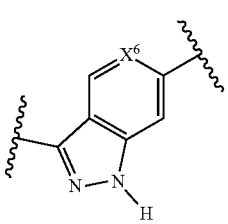
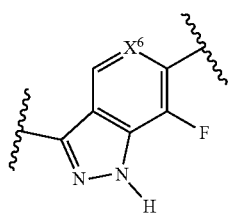 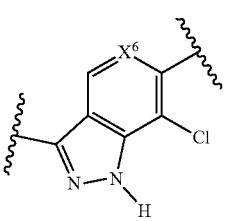
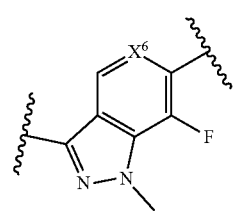 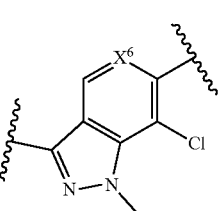
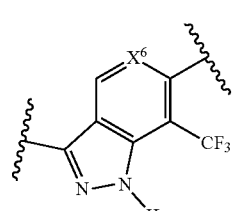 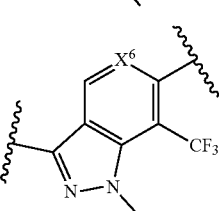
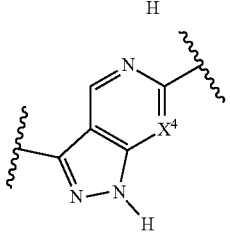 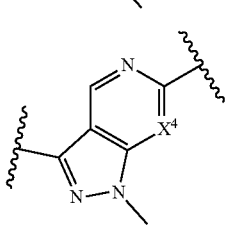

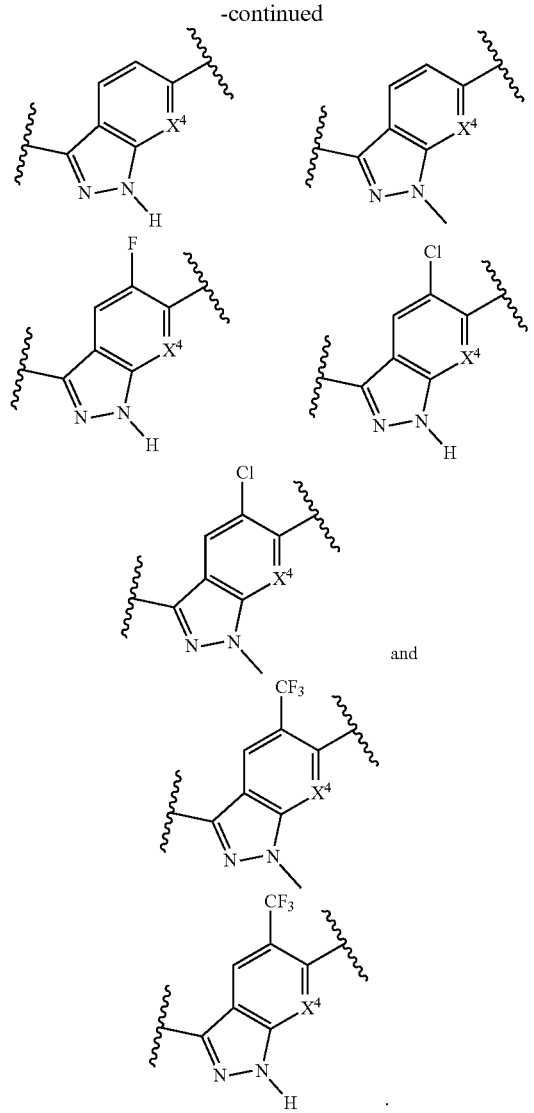
In certain embodiments
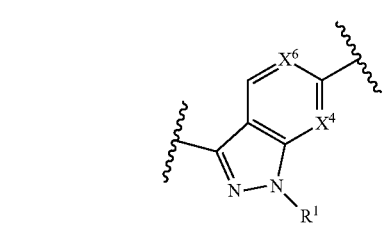
is selected from the group consisting of:
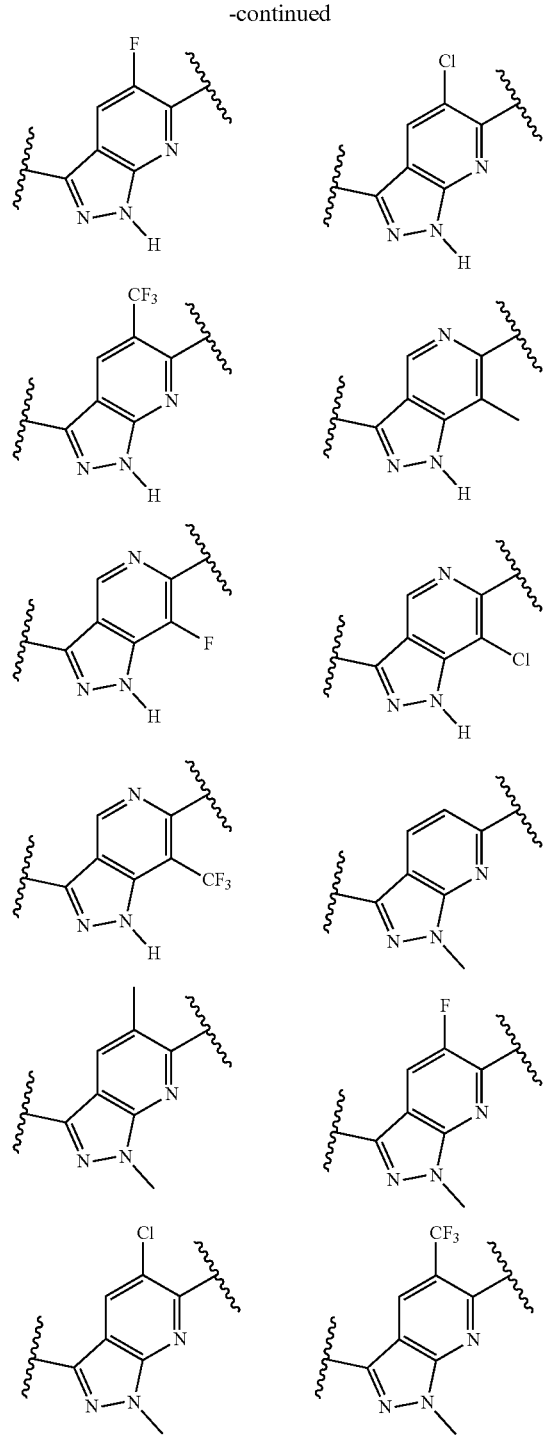
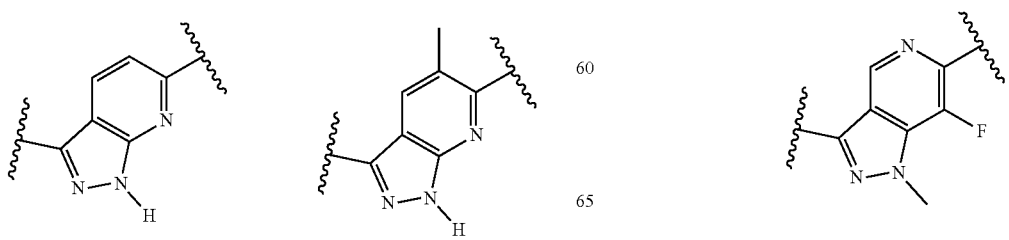

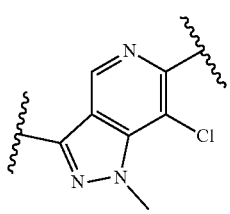
and
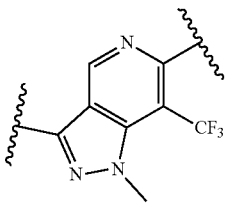
In certain embodiments
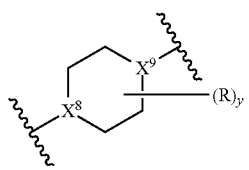
is selected from the group consisting of:
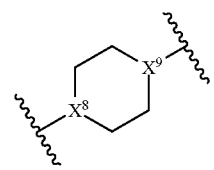 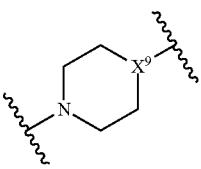
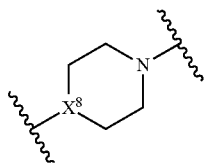 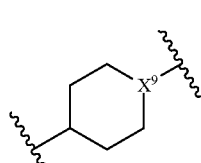
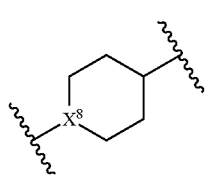 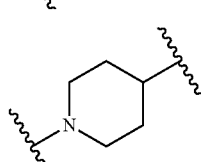
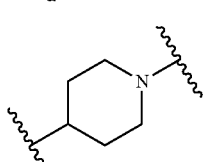 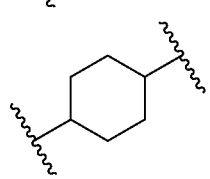
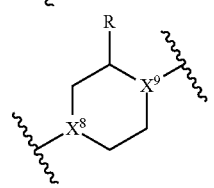 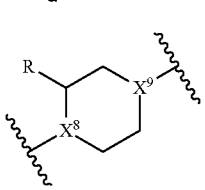
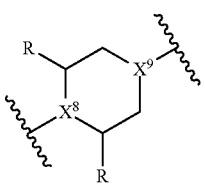
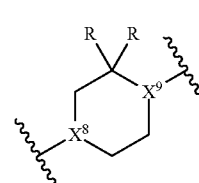
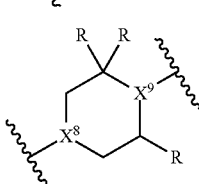
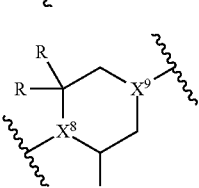
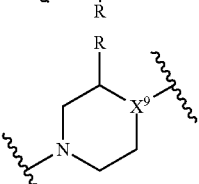
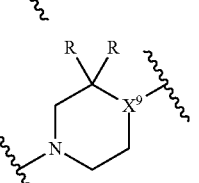
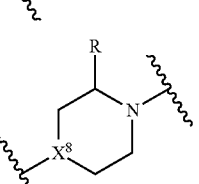
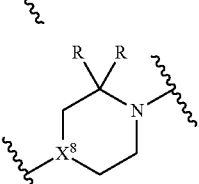
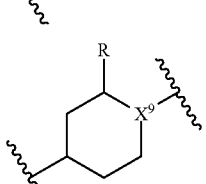
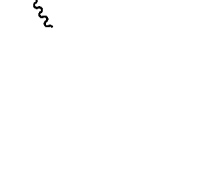

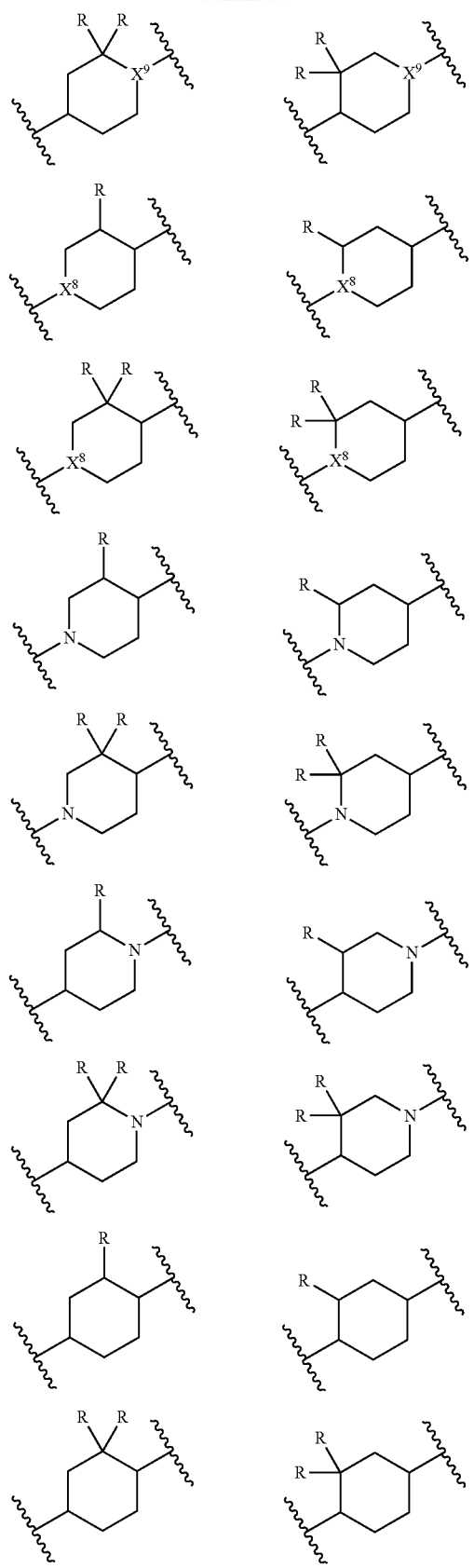
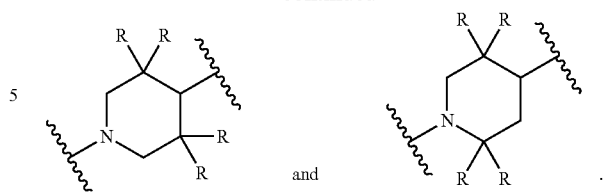
In certain embodiments $X^1$ is selected from the group consisting of:
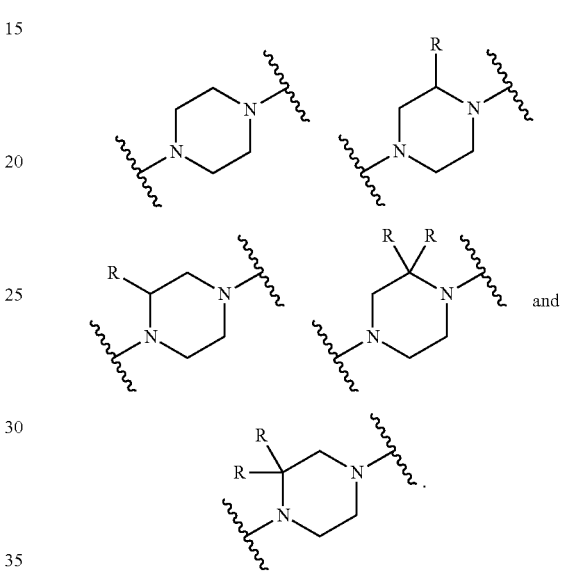
In certain embodiments $X^{12}$-L-B is selected from the group consisting of:
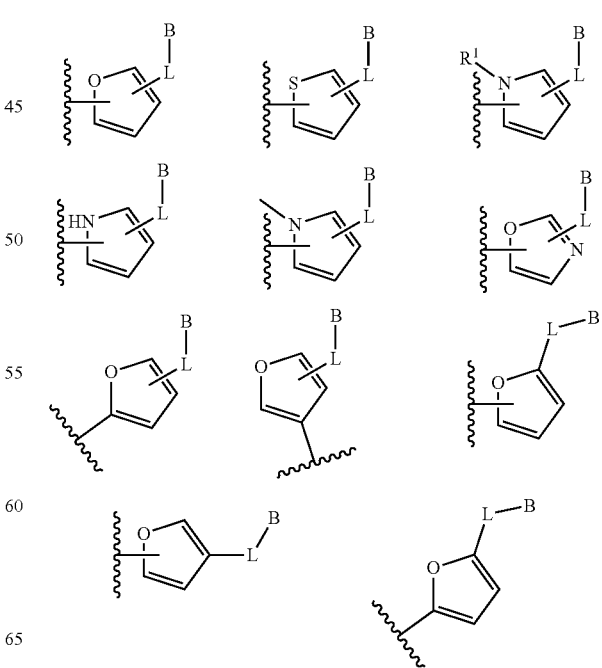

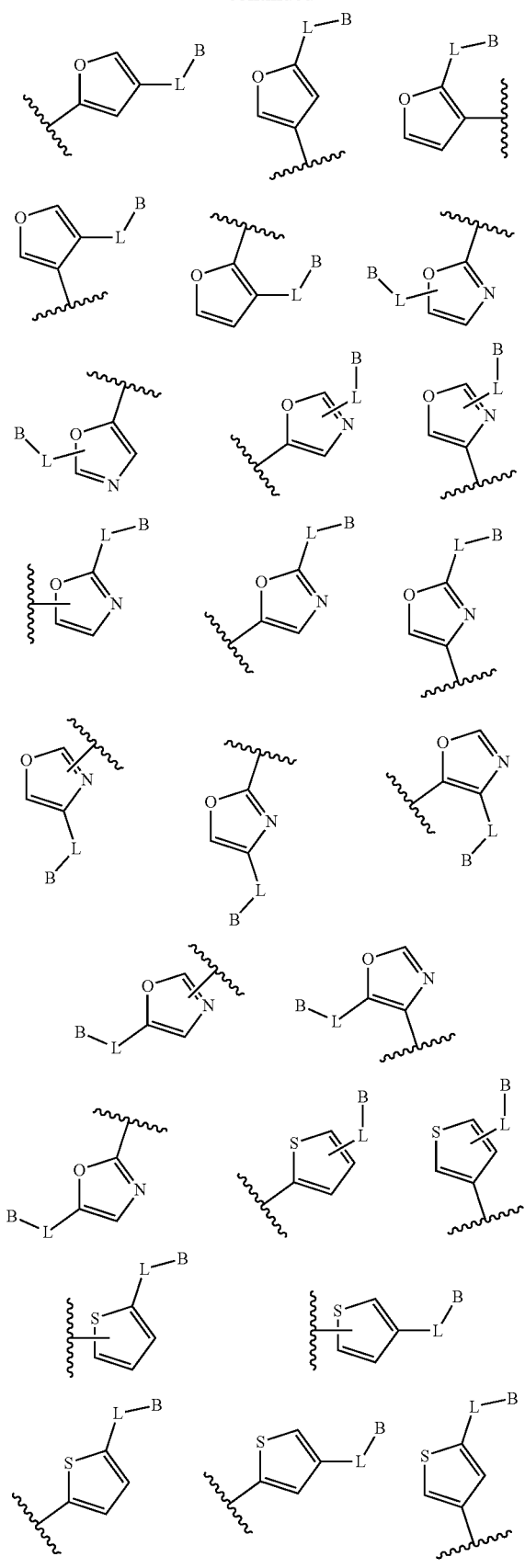
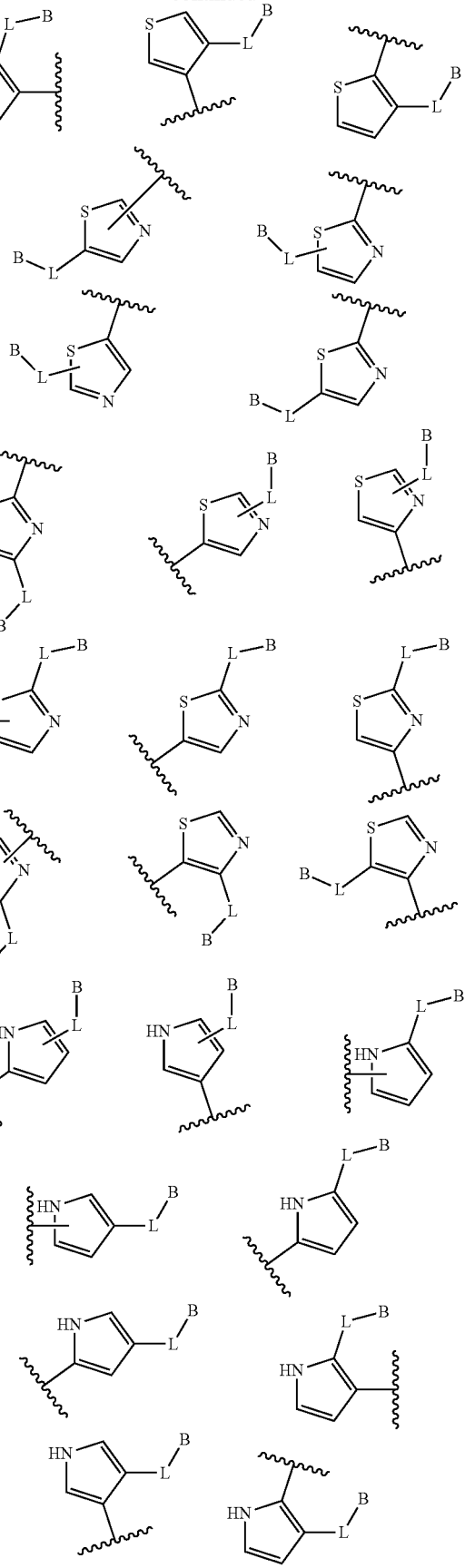

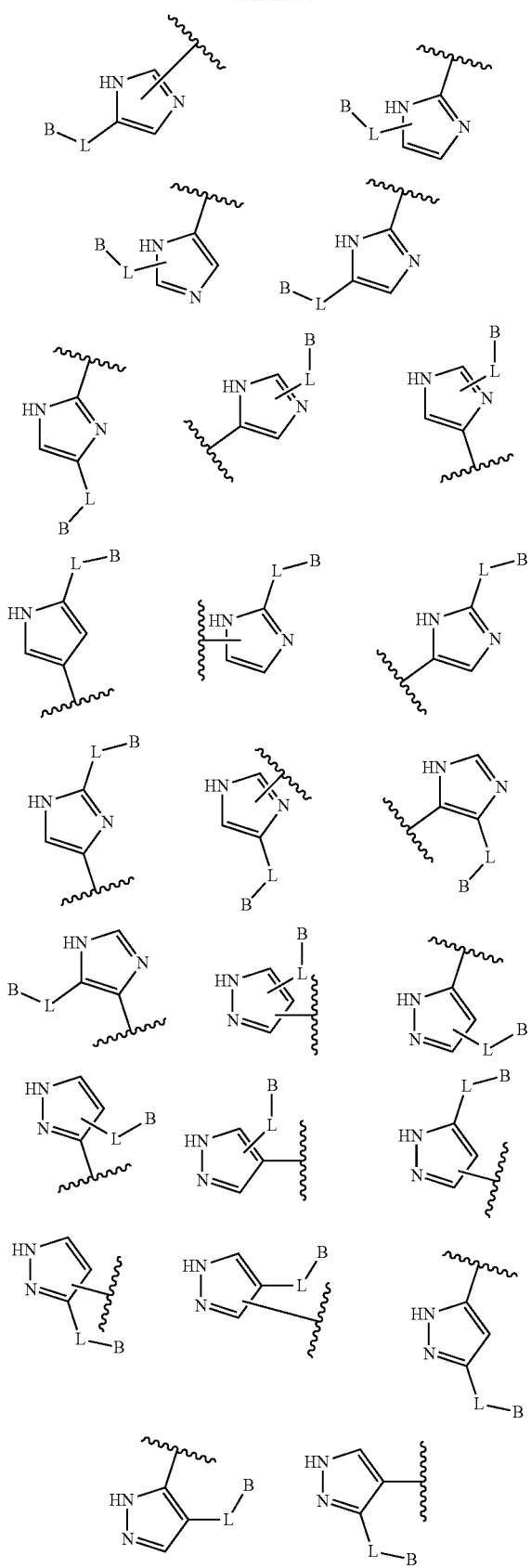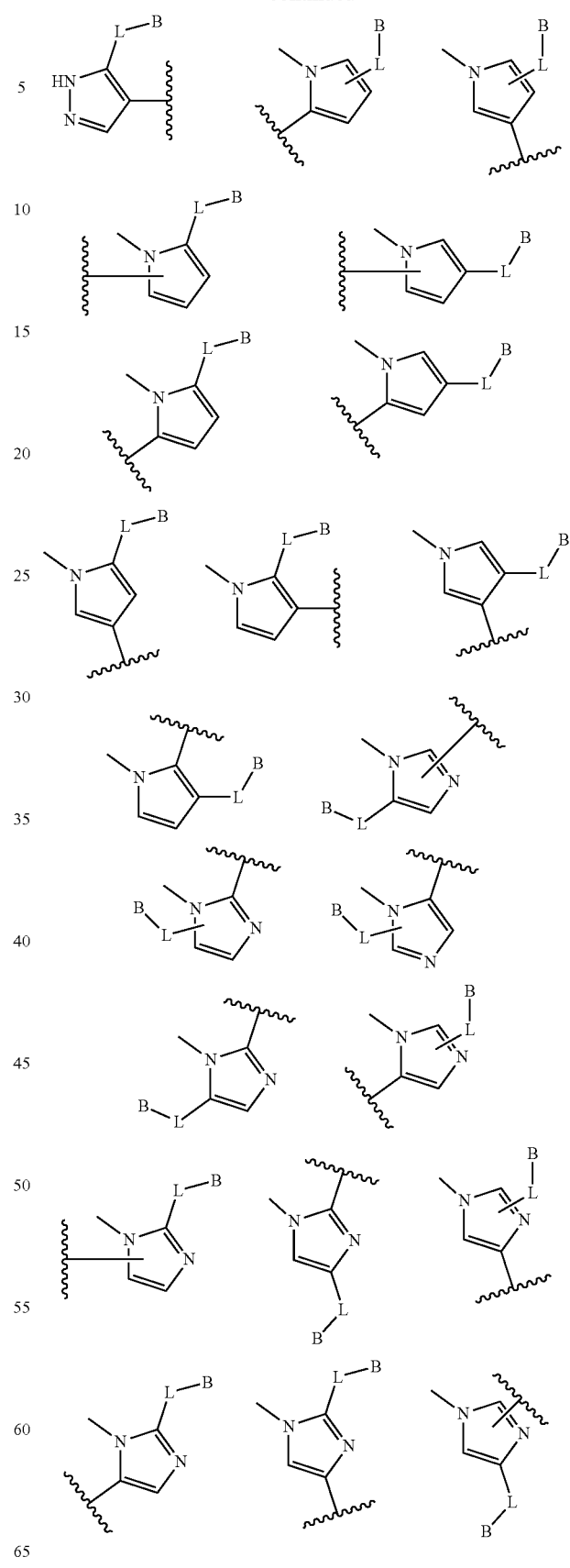

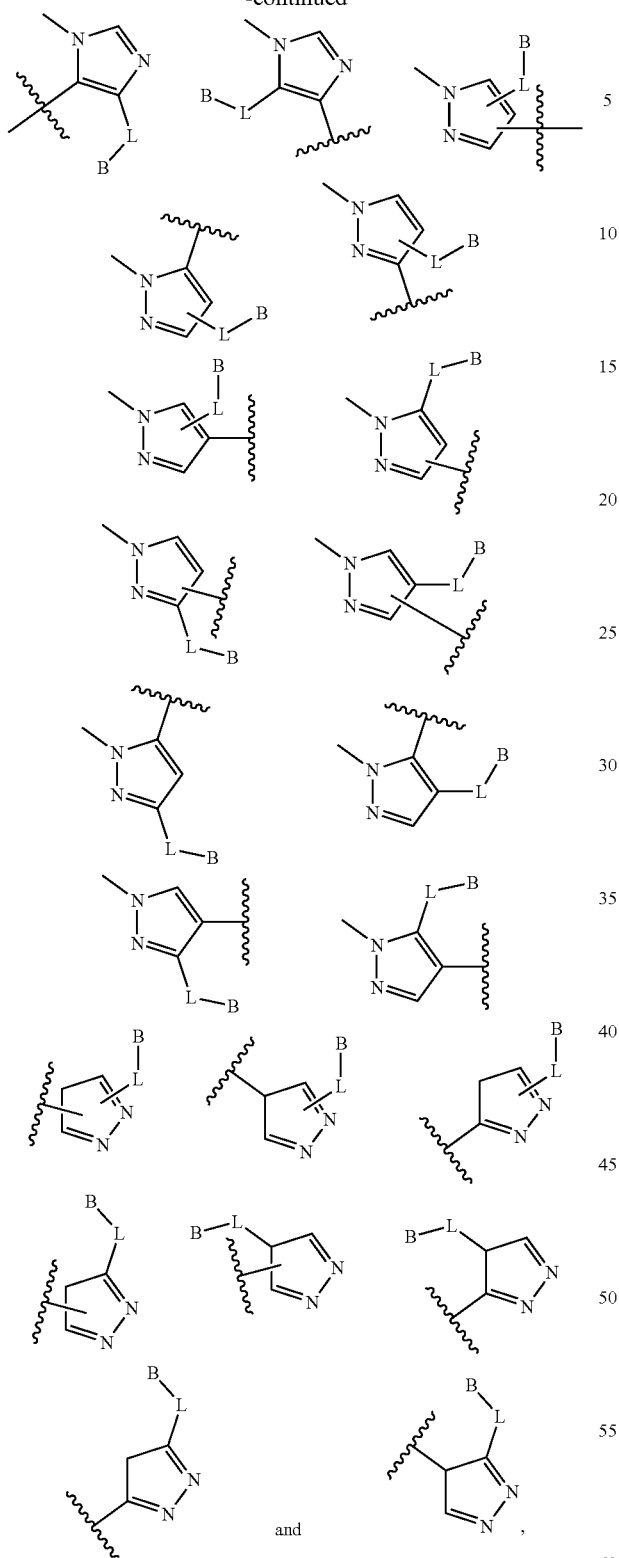
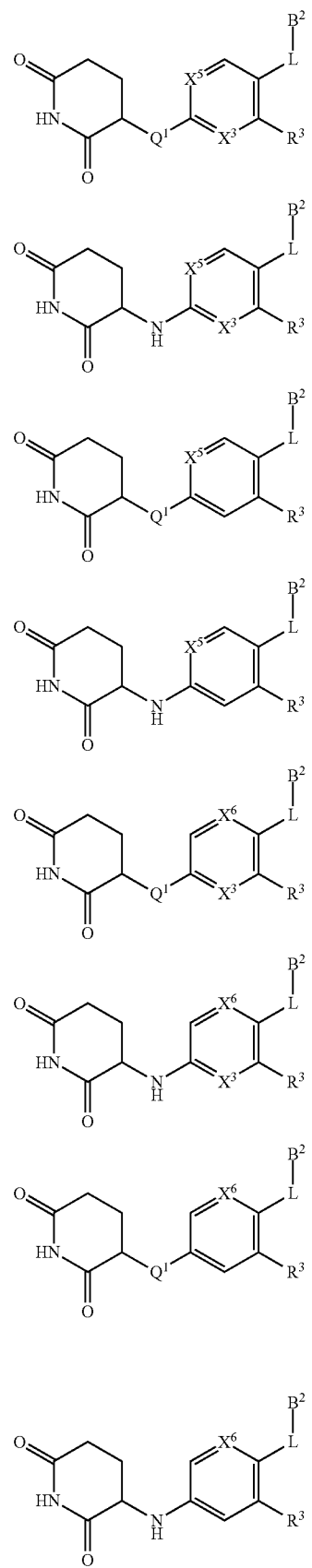
wherein each of the above X¹² moieties is optionally substituted with 1 or 2 substituents independently selected from $R^3$.
In one embodiment the compound of the present invention is selected from:

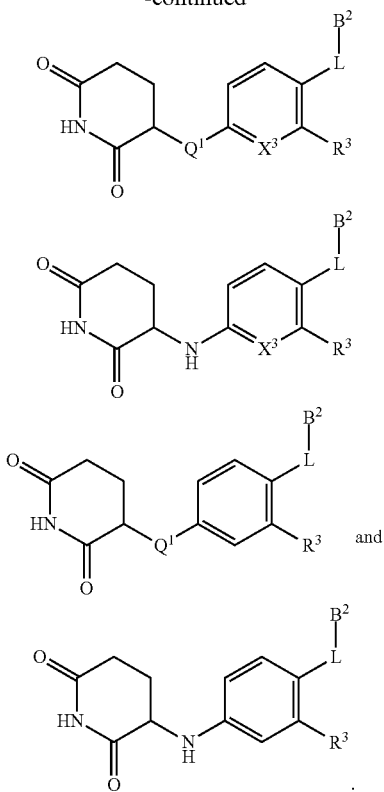
In one embodiment the compound of the present invention is selected from:
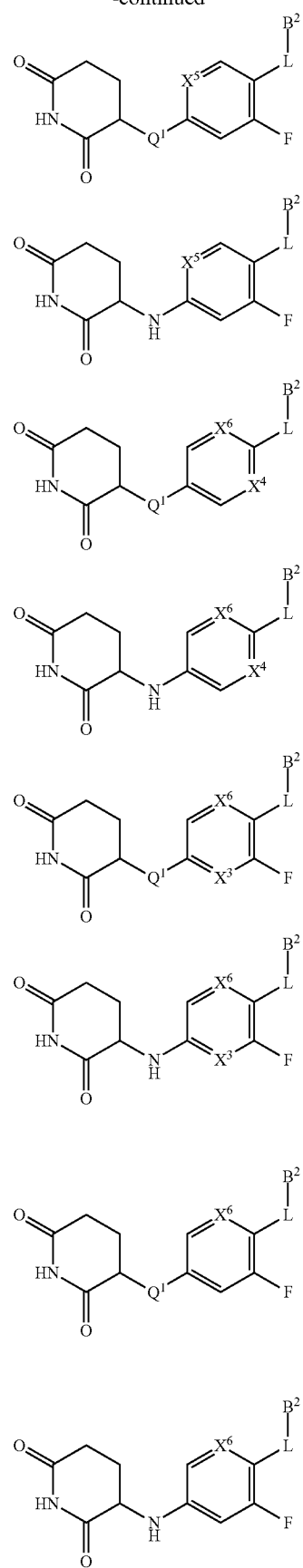

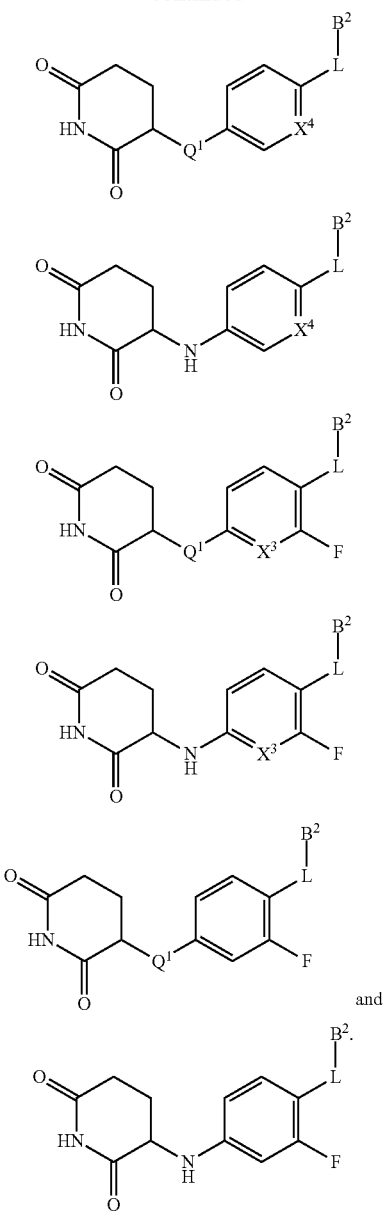
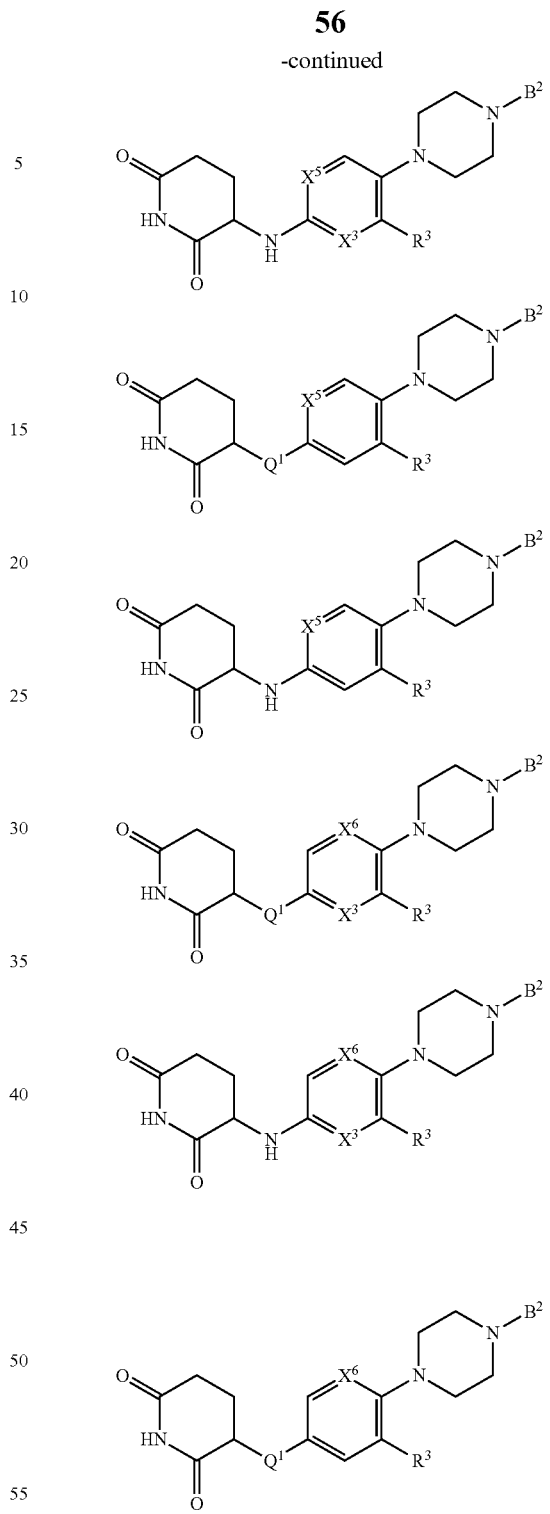
In one embodiment the compound of the present invention is selected from:
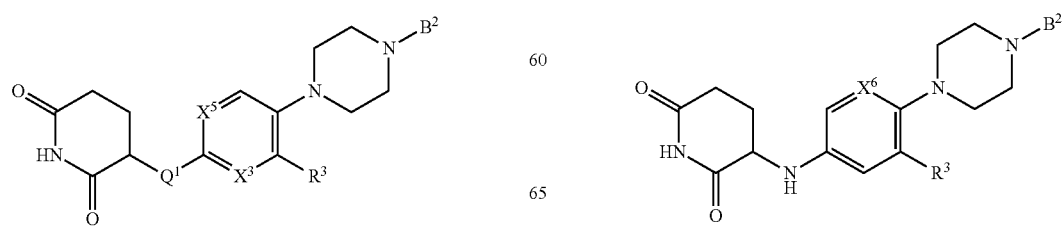

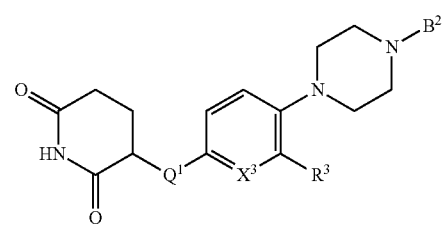
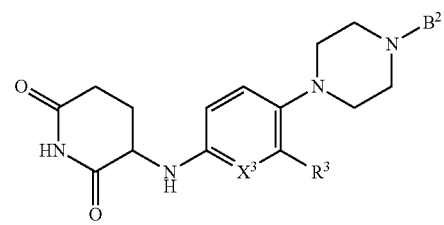
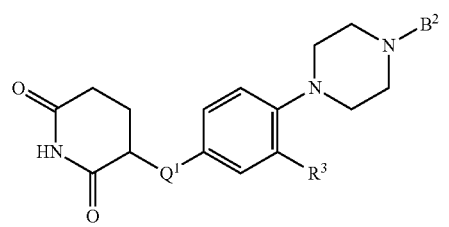
and
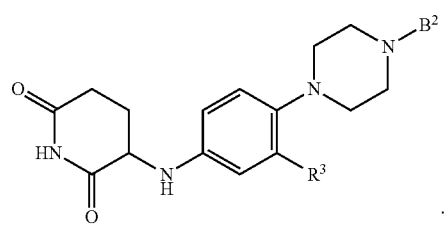
In one embodiment the compound of the present invention is selected from:
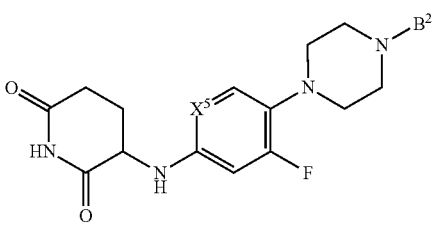
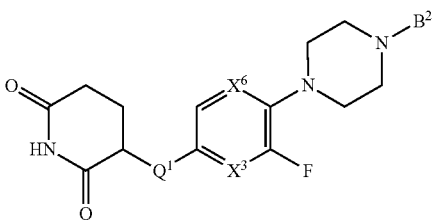
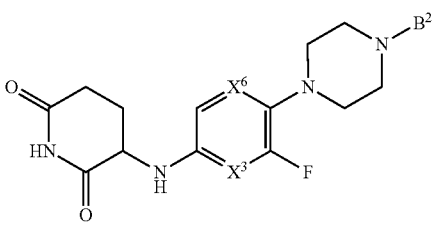
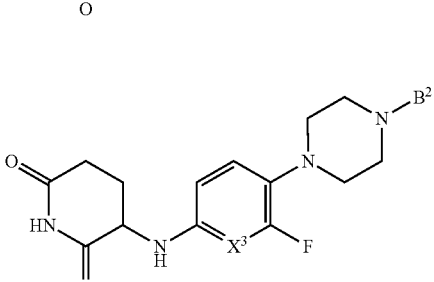

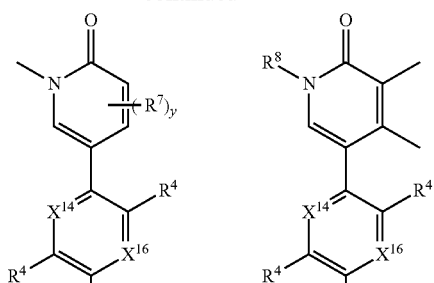
and
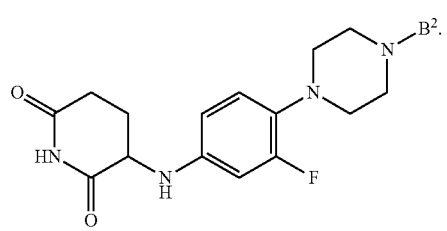
In certain embodiments the compound of the present invention is selected from:
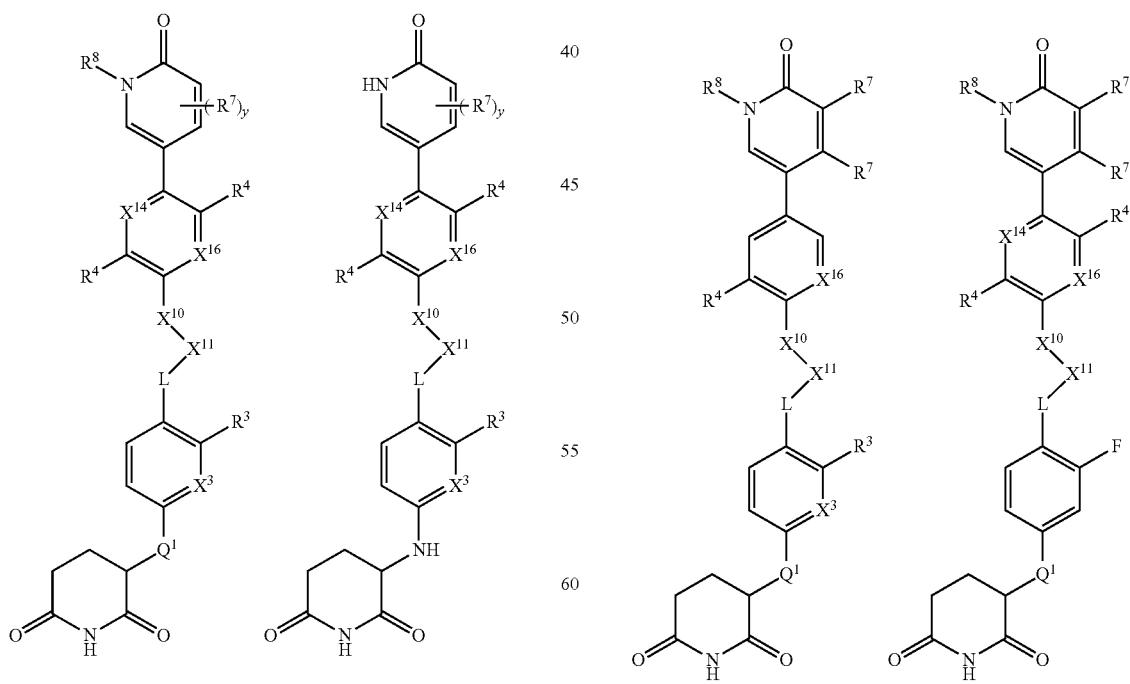

61
-continued
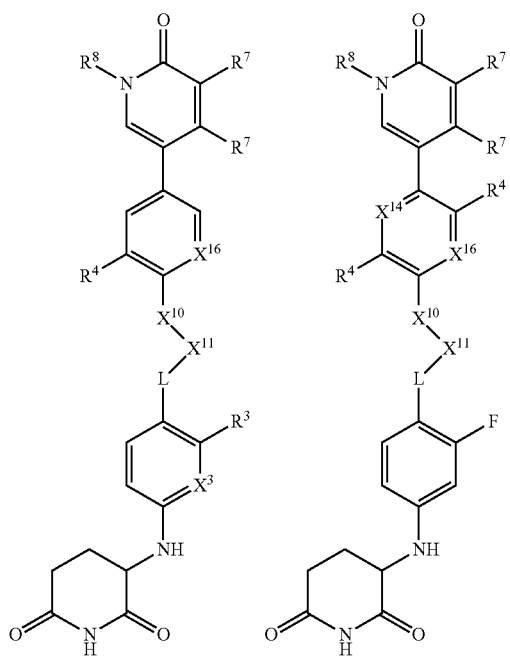
62
-continued
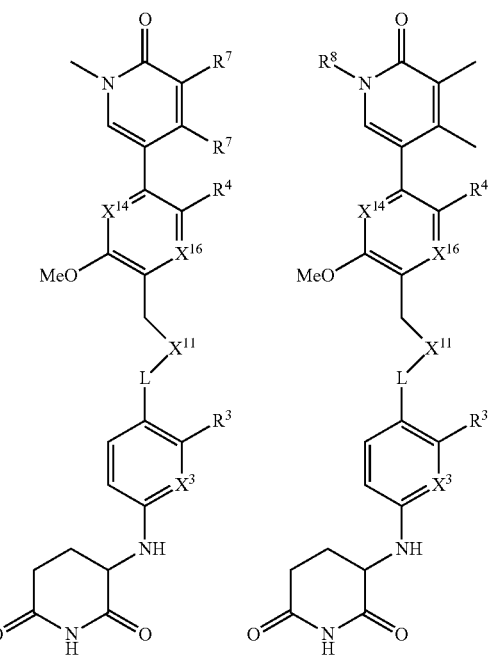
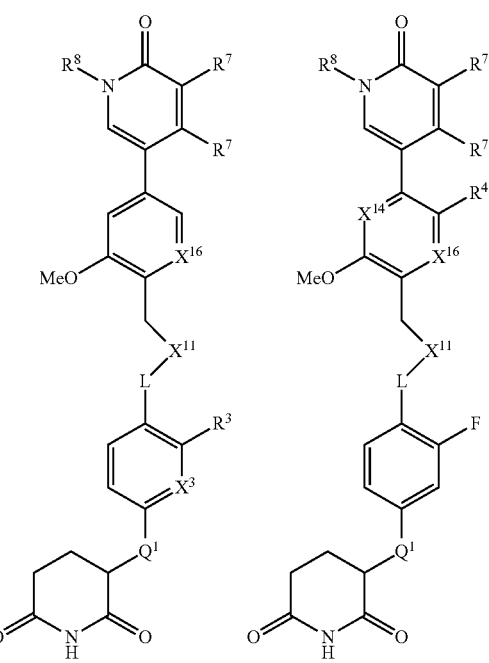

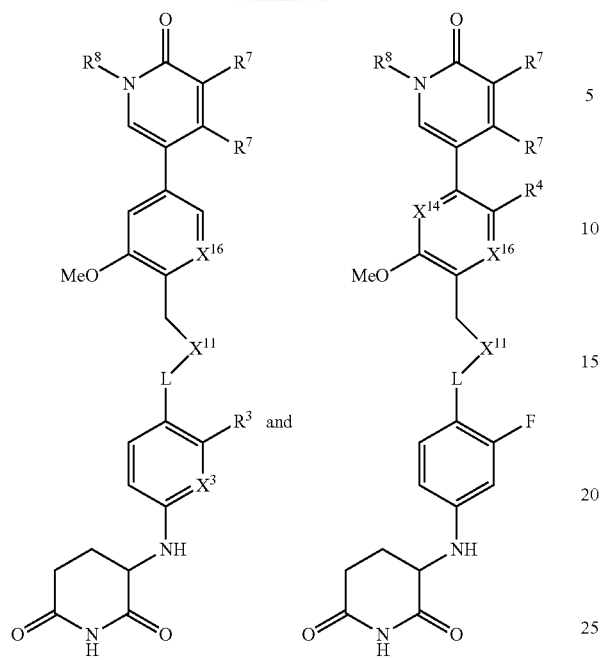
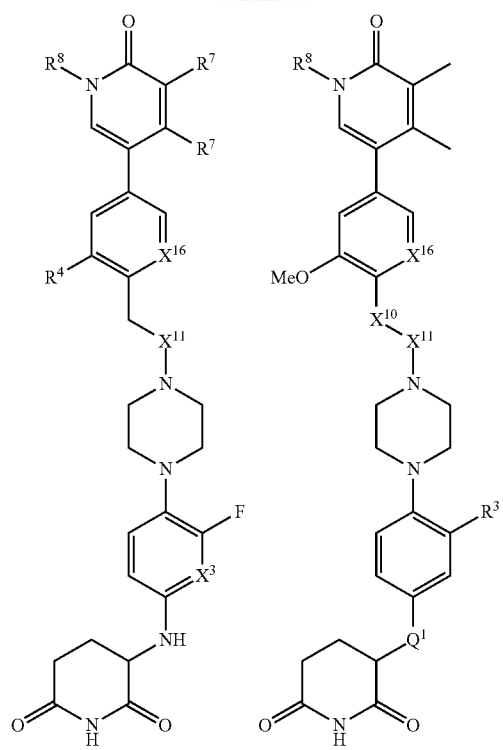
or a pharmaceutically acceptable salt thereof.
In one embodiment the compound of the present invention is selected from:
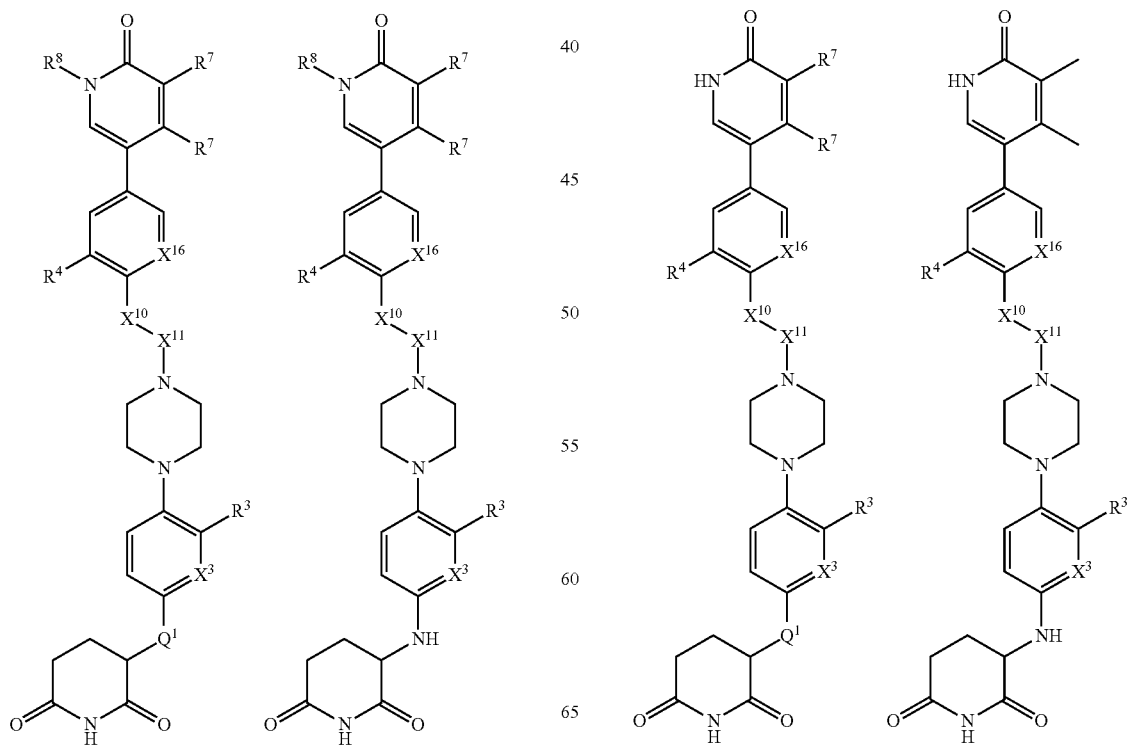

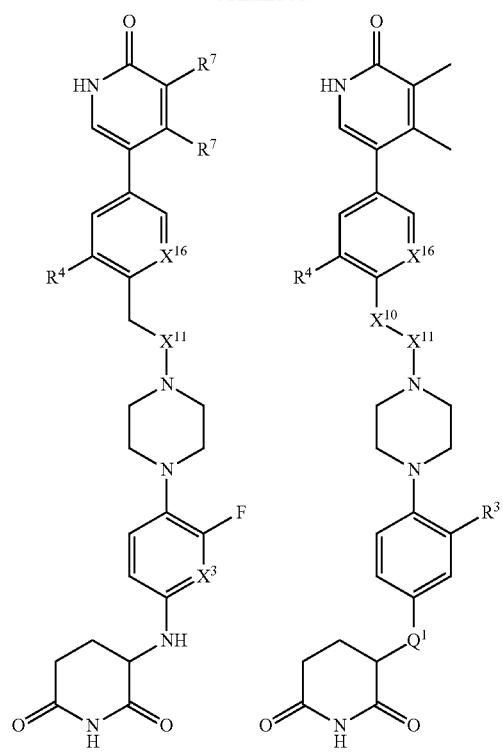
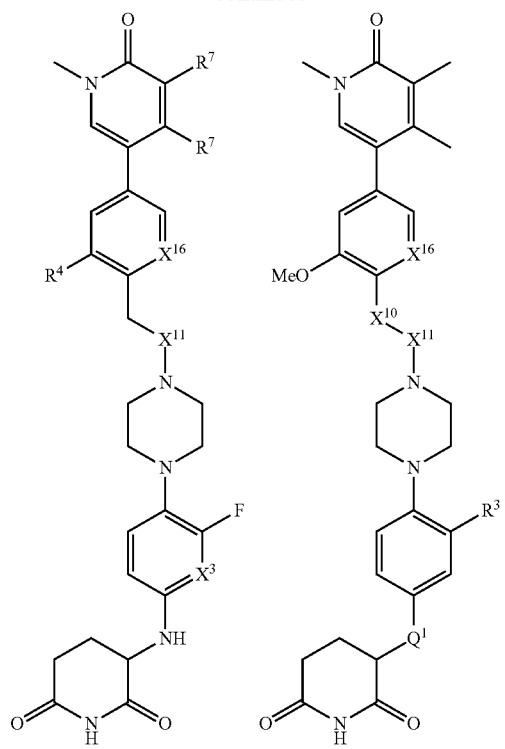
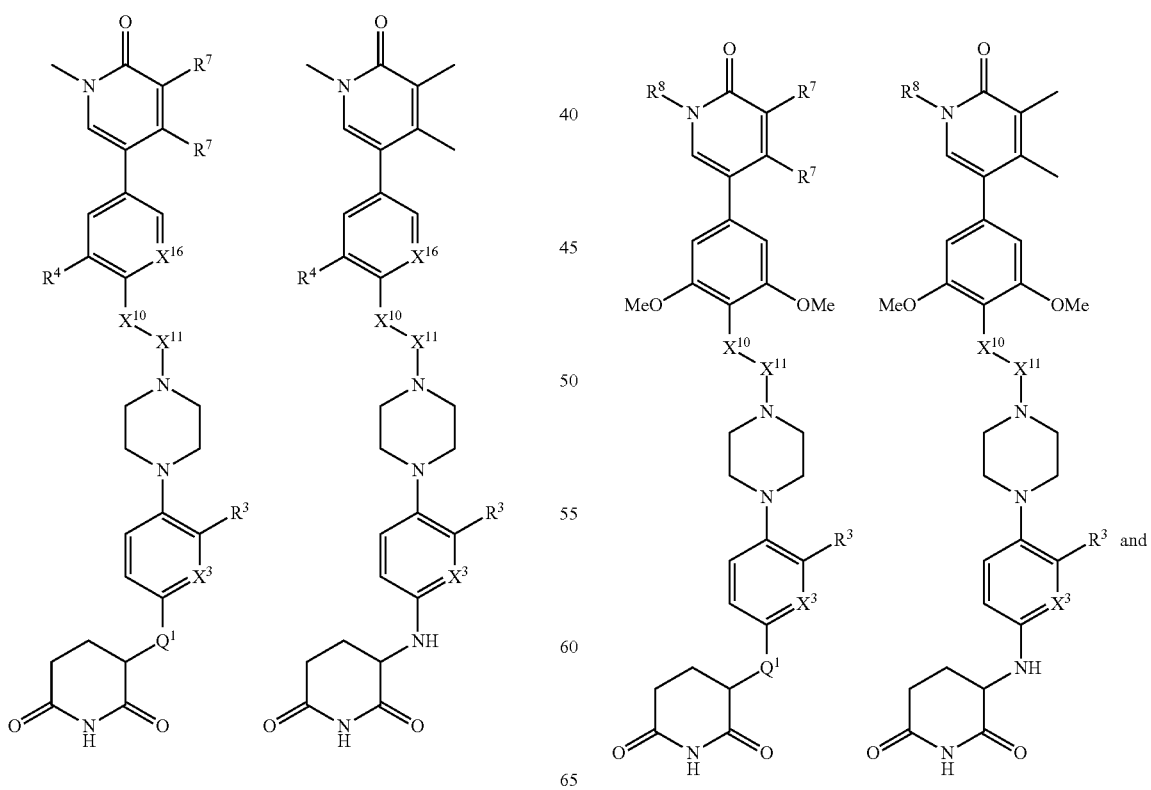

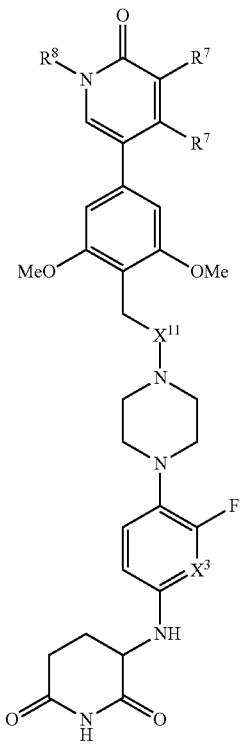
or a pharmaceutically acceptable salt thereof.
In one embodiment the compound of the present invention is selected from:
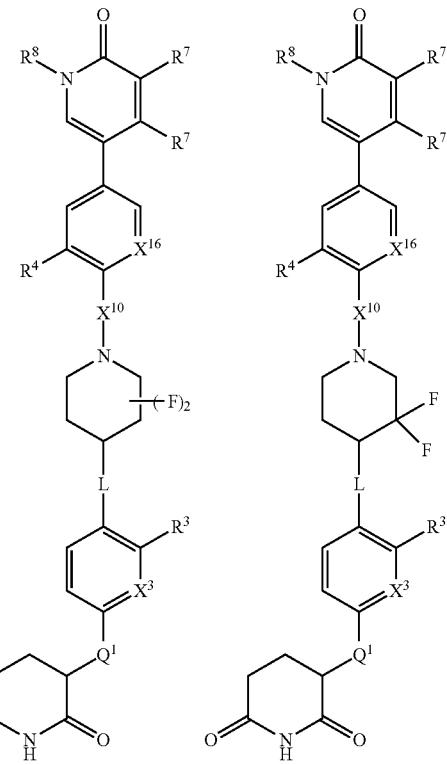
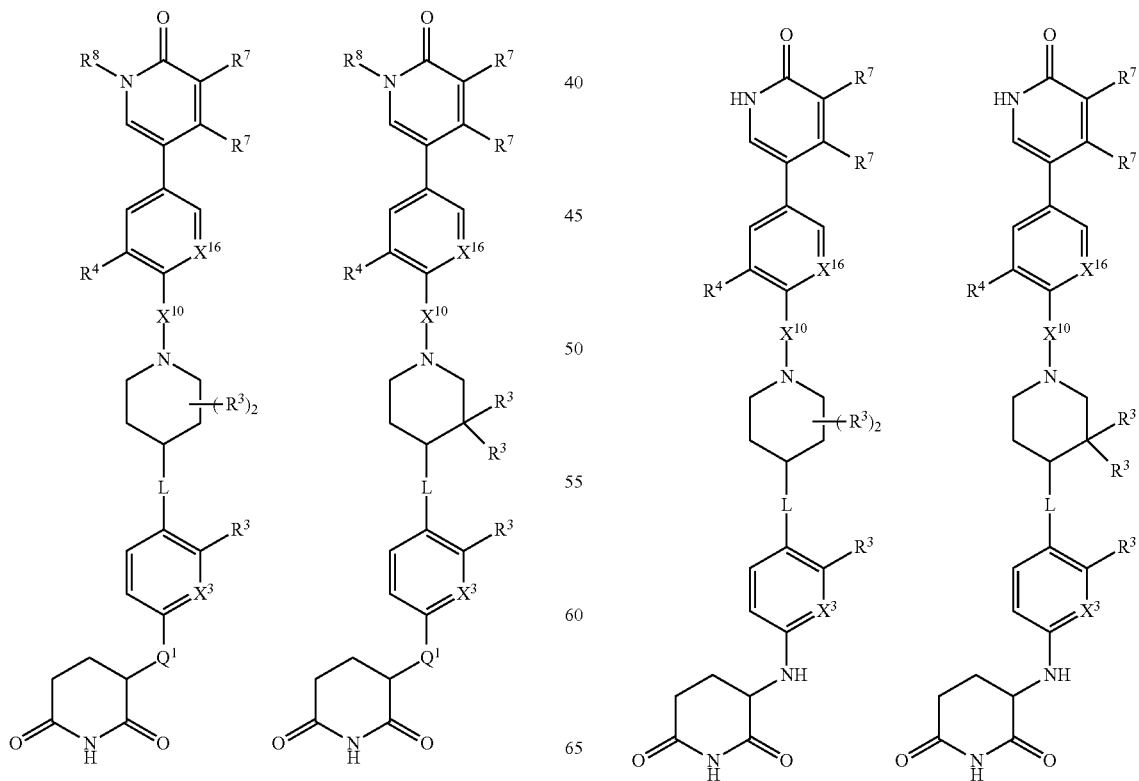

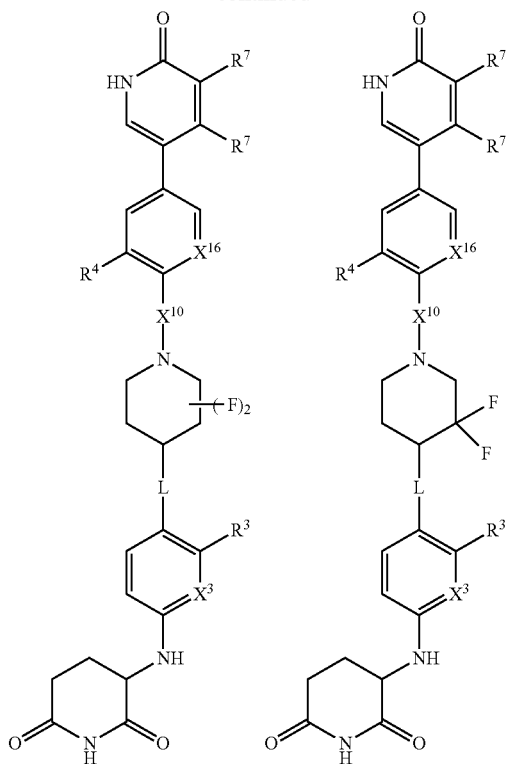
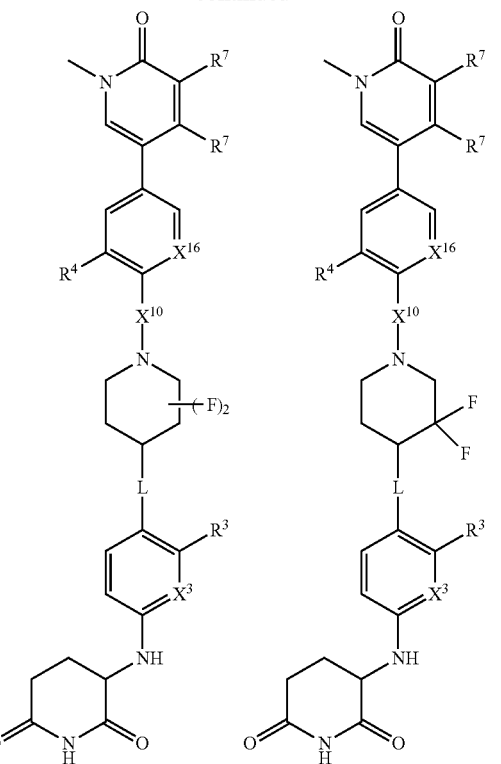
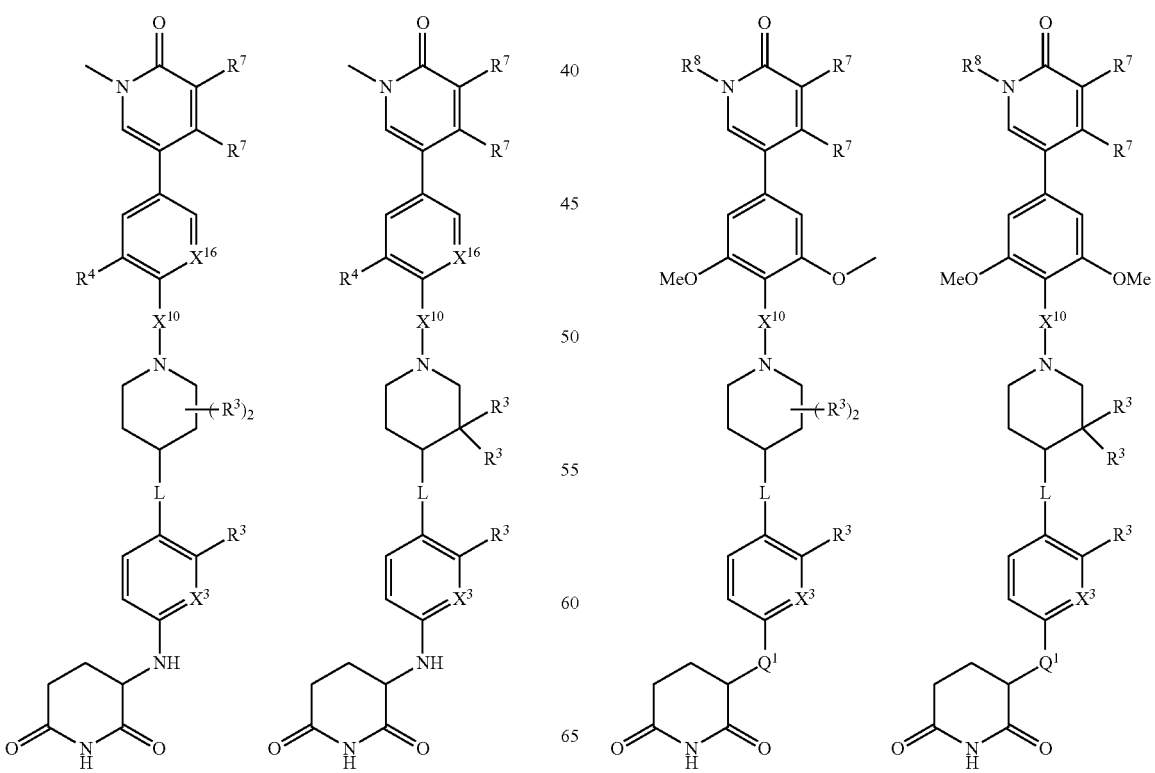

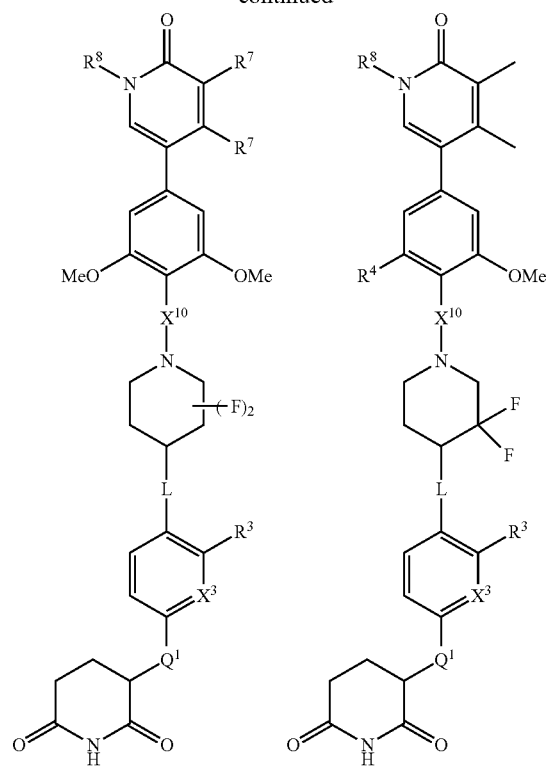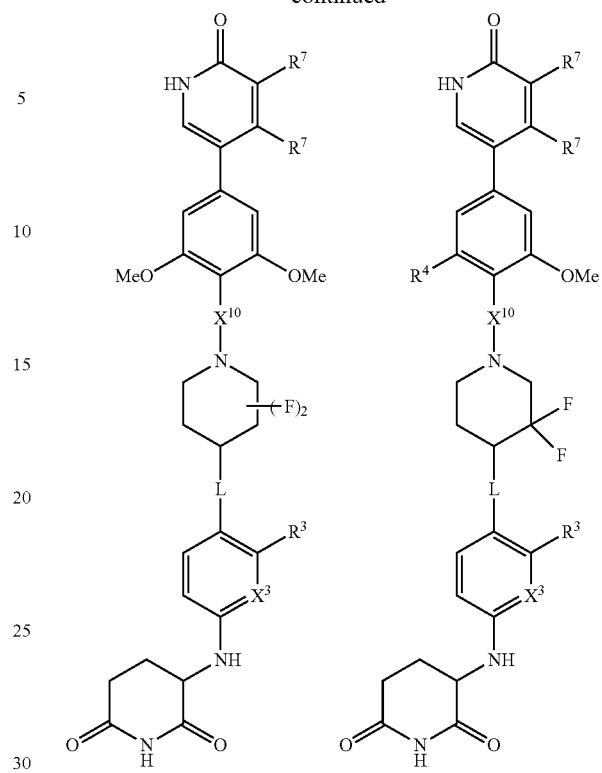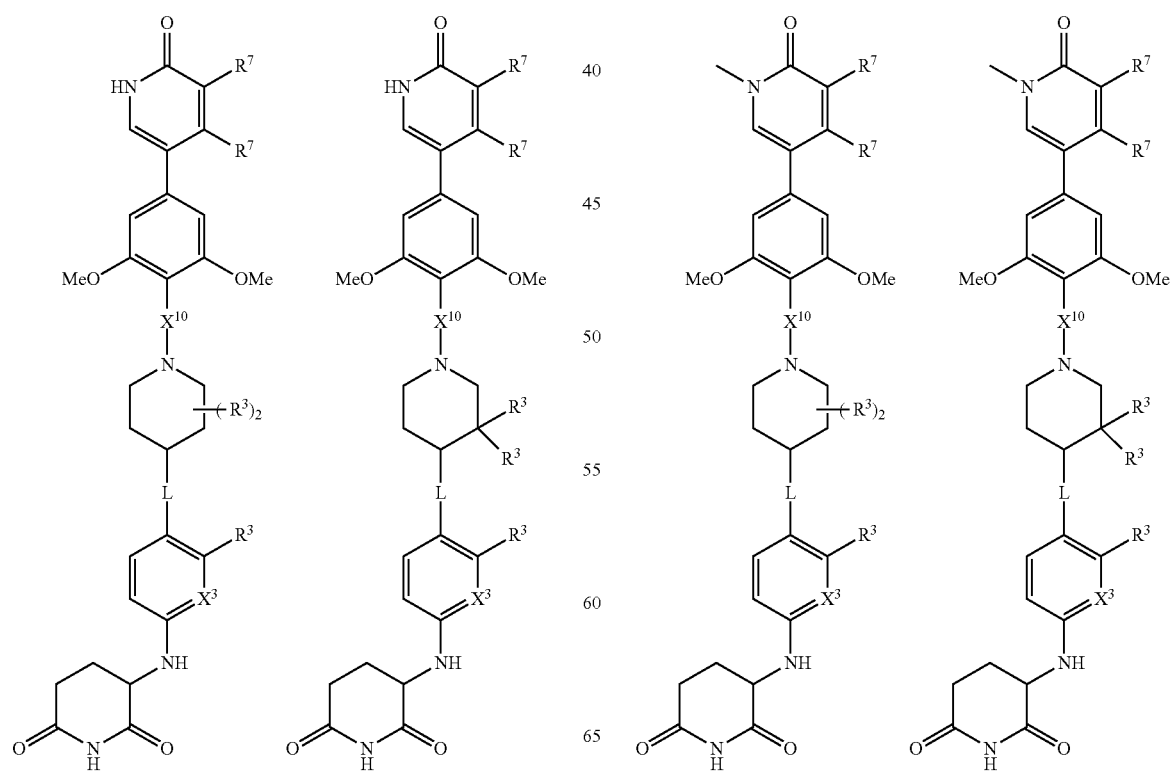

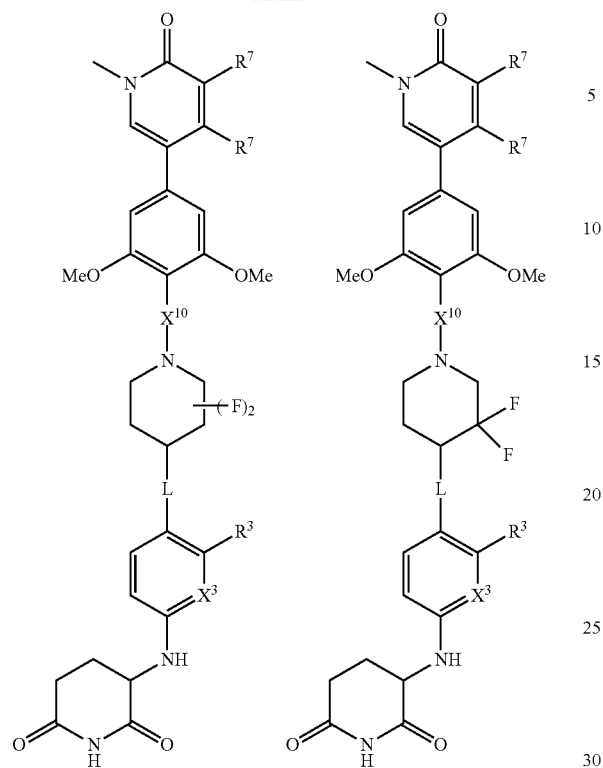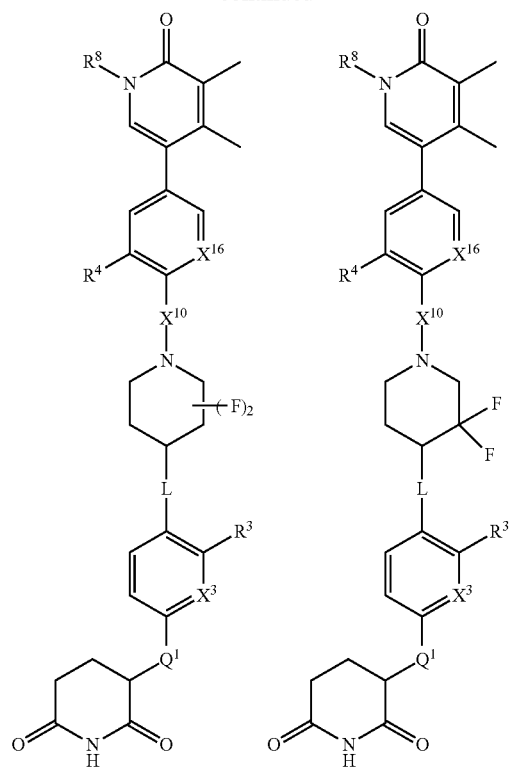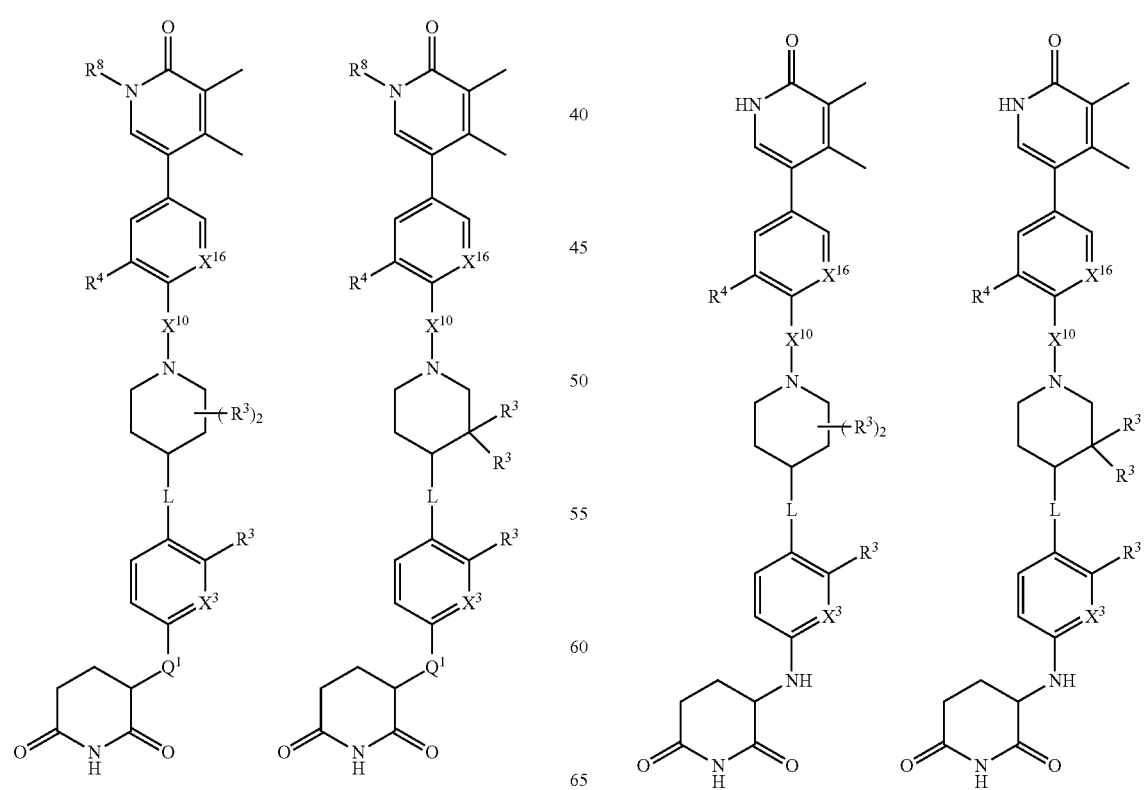

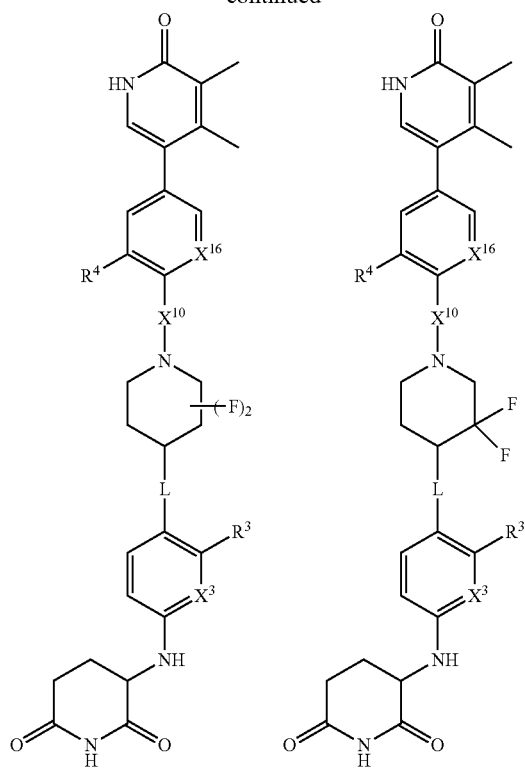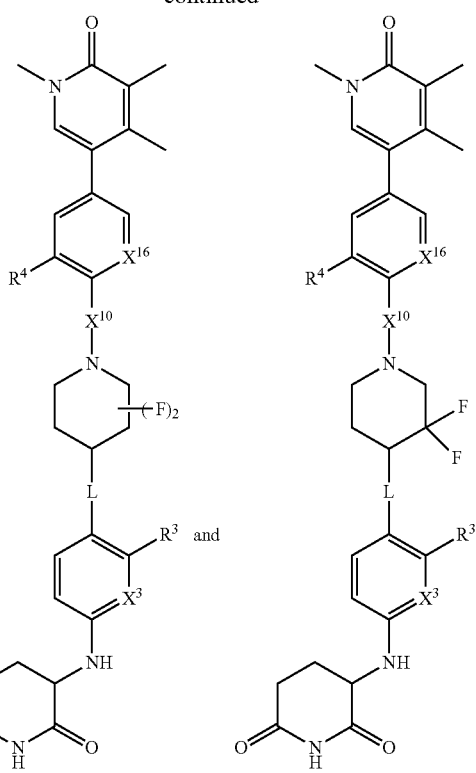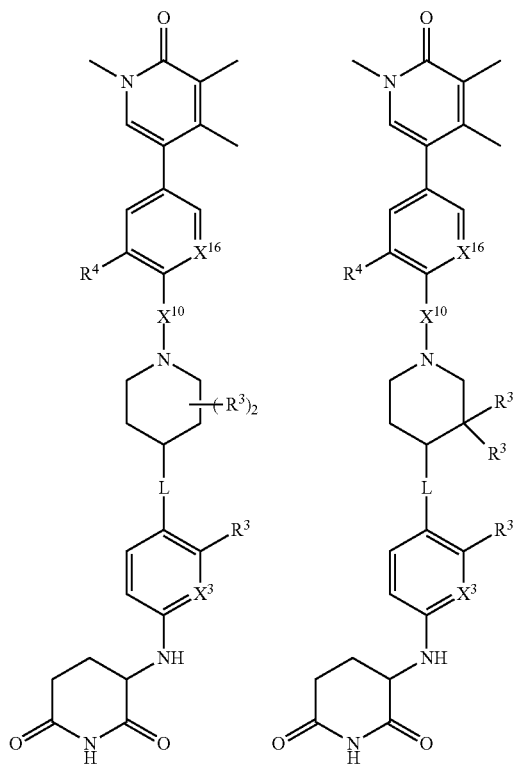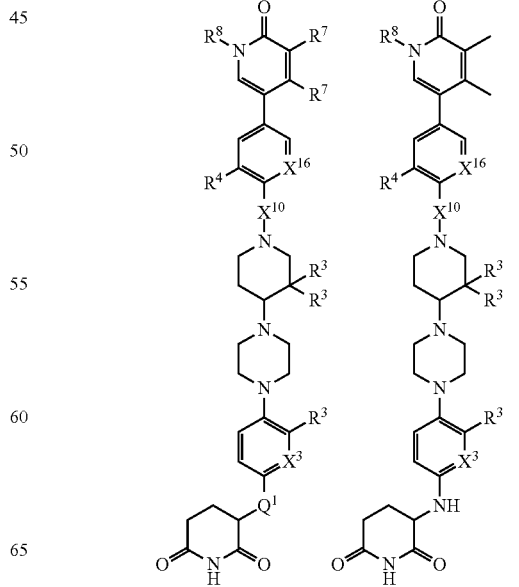
or a pharmaceutically acceptable salt thereof.
In one embodiment the compound of the present invention is selected from:

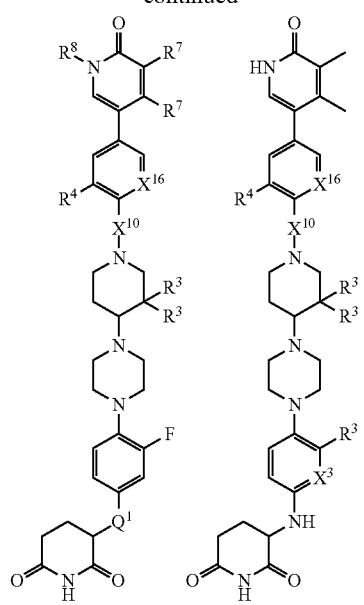
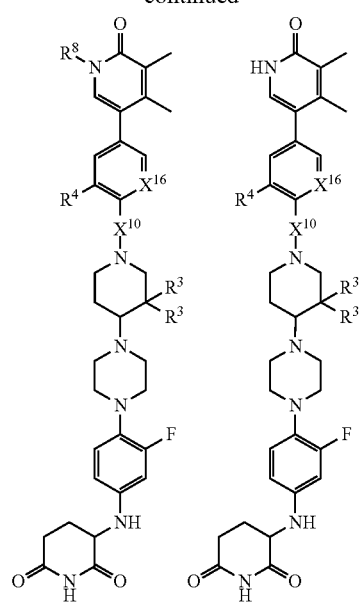
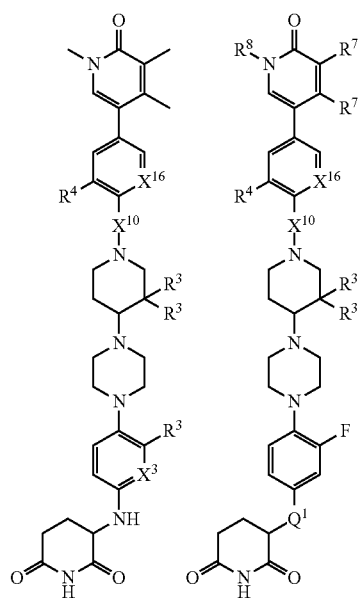
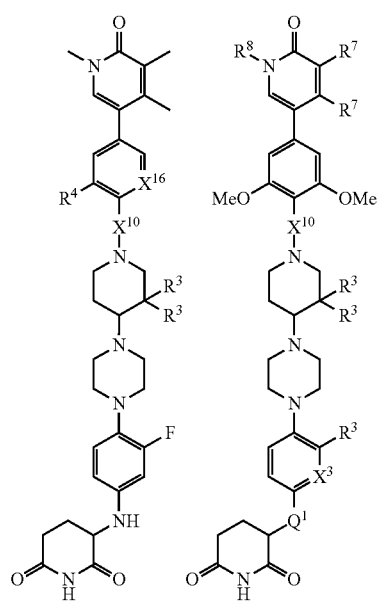

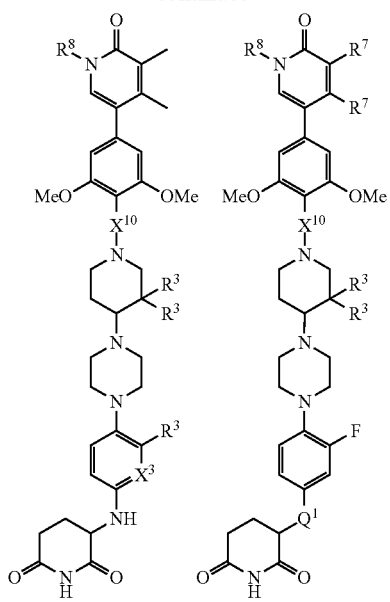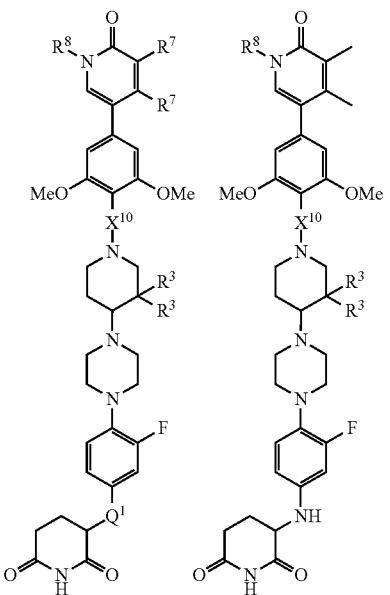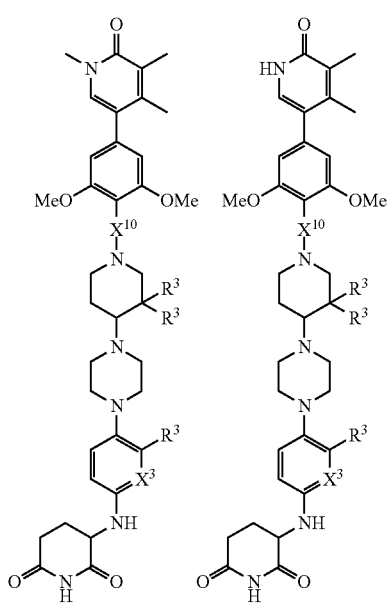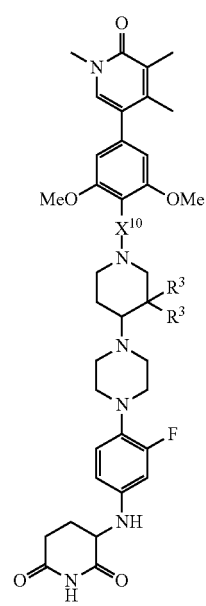

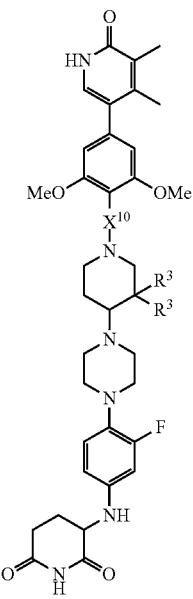
or a pharmaceutically acceptable salt thereof.
In one embodiment the compound of the present invention is selected from:
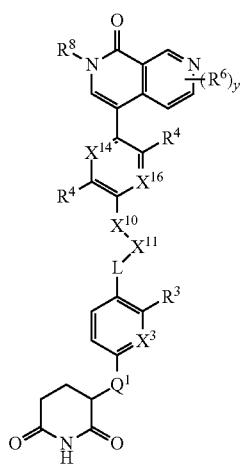
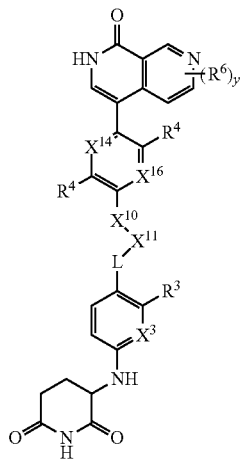
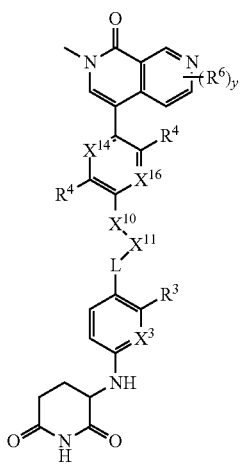
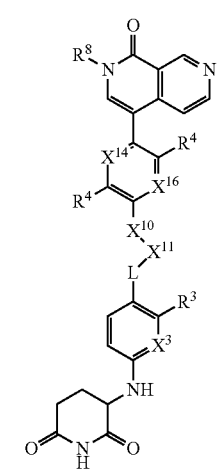
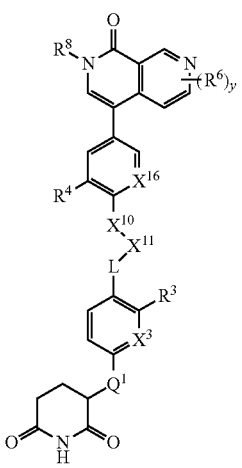

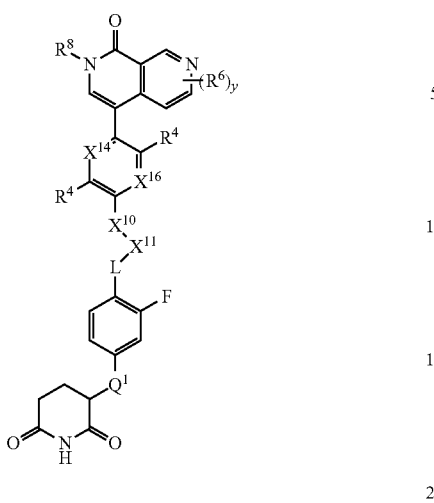
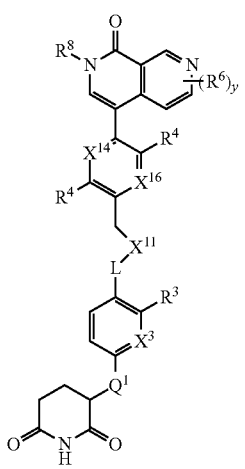
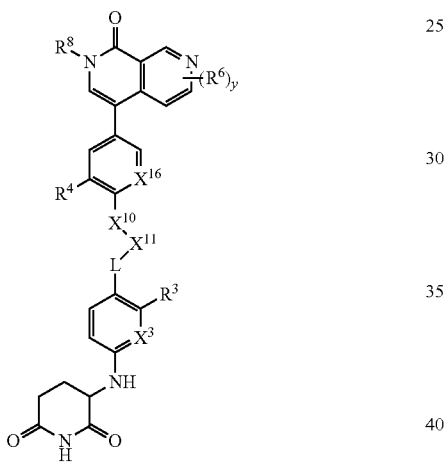
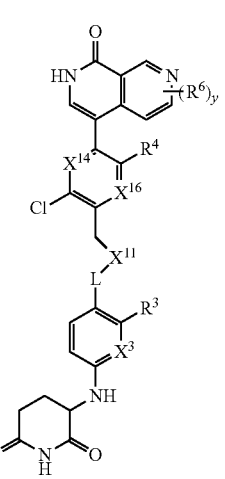
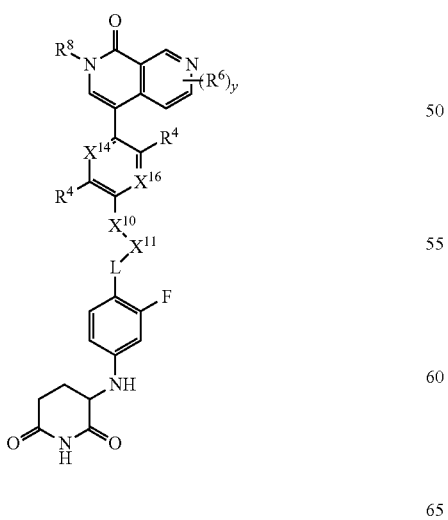
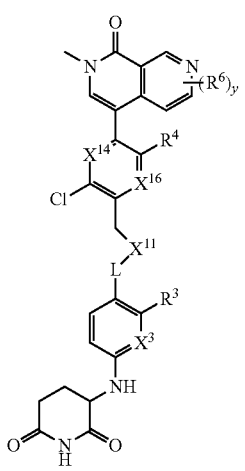

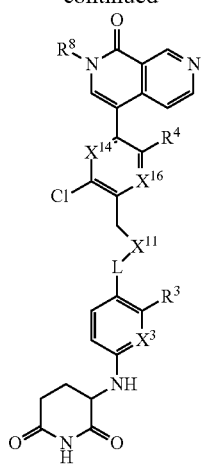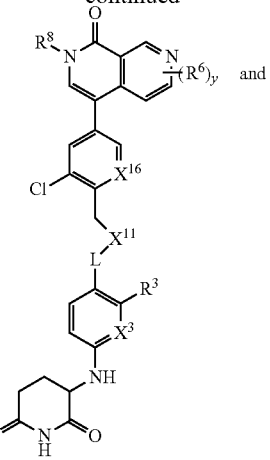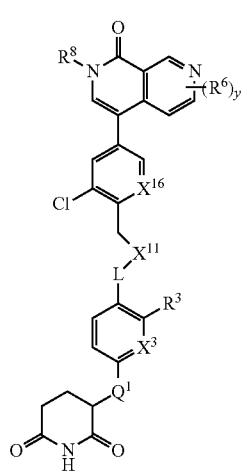
In one embodiment the compound of the present invention is selected from:

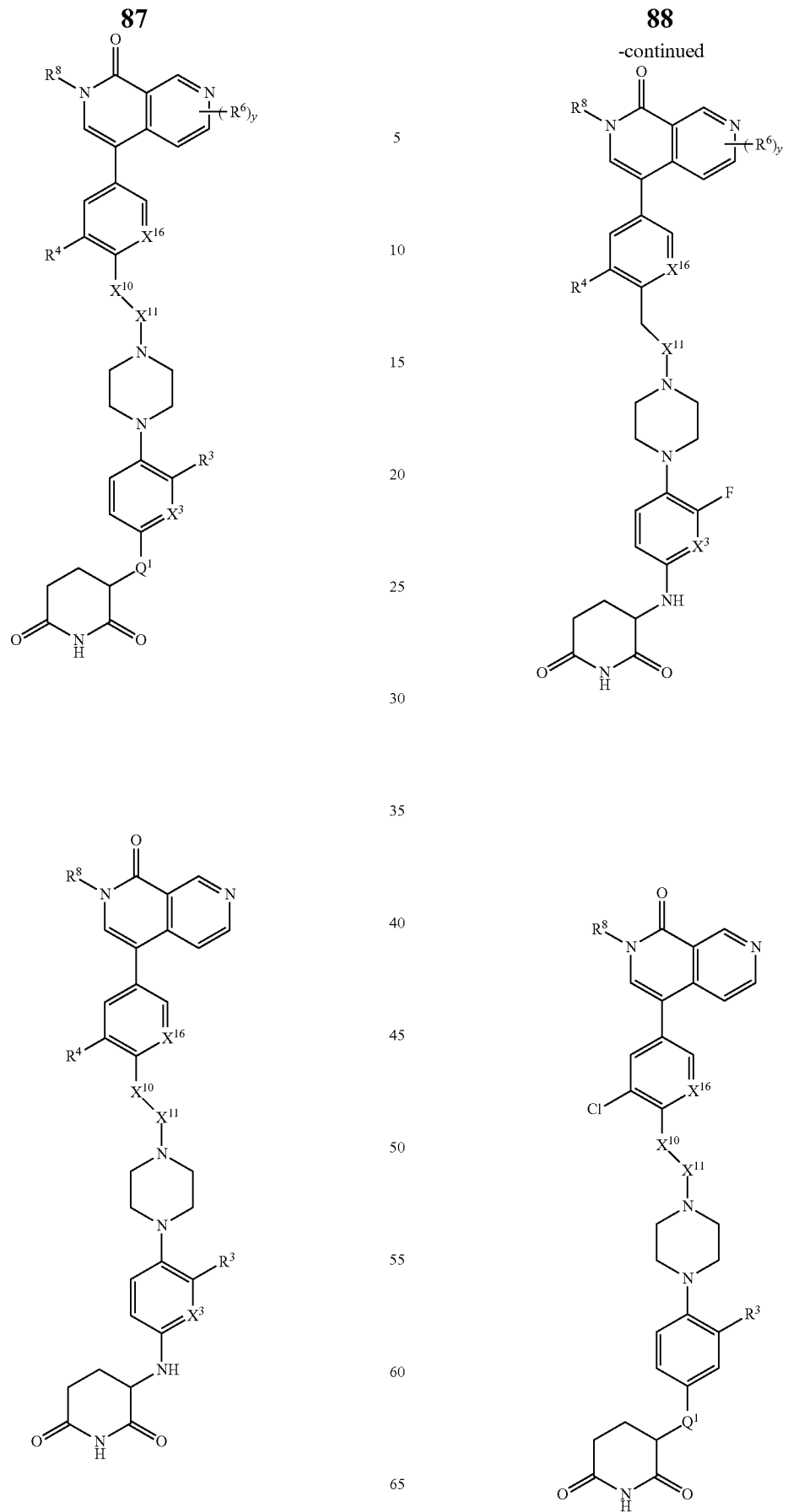

89
-continued
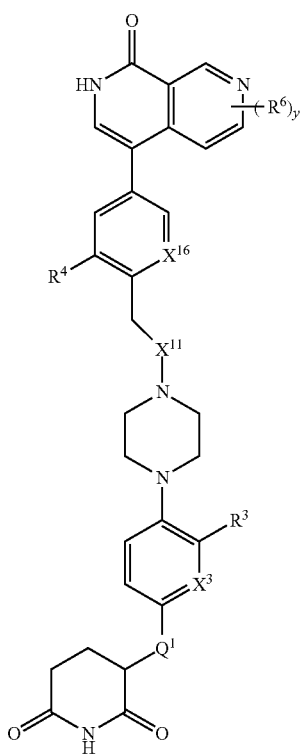
90
-continued
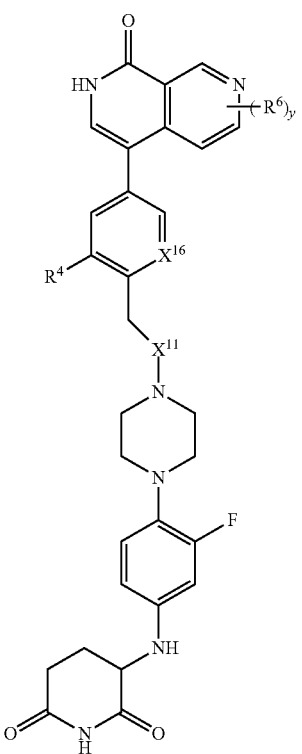
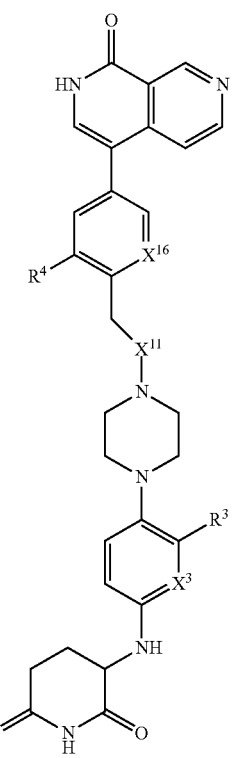
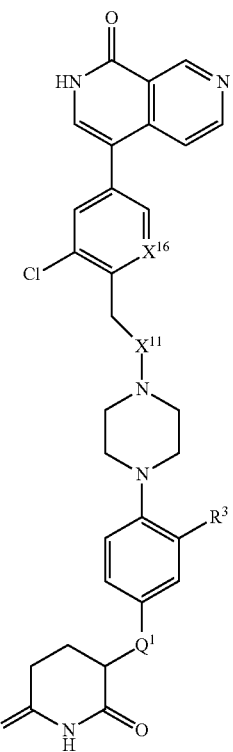

91
-continued
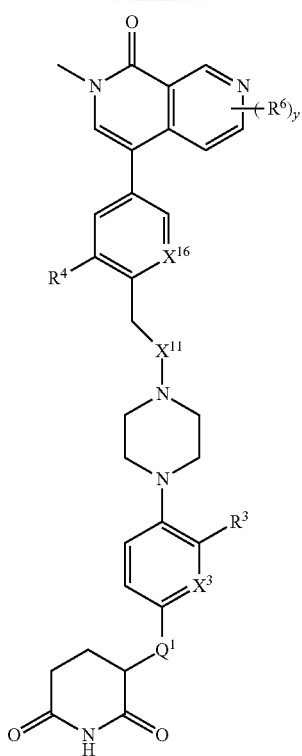
92
-continued
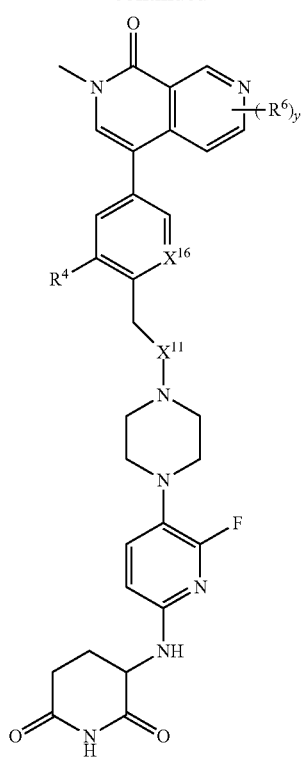

93
-continued
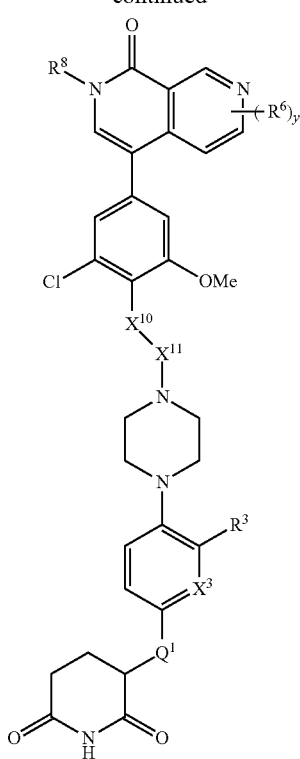
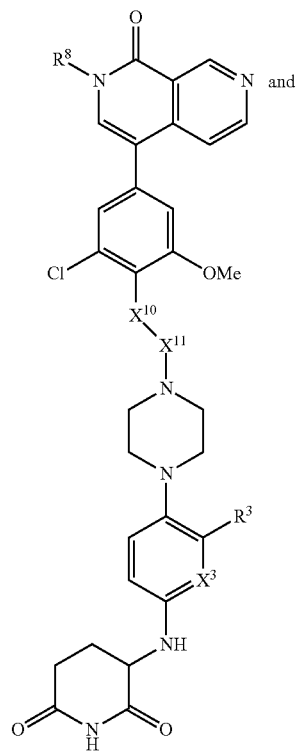
94
-continued
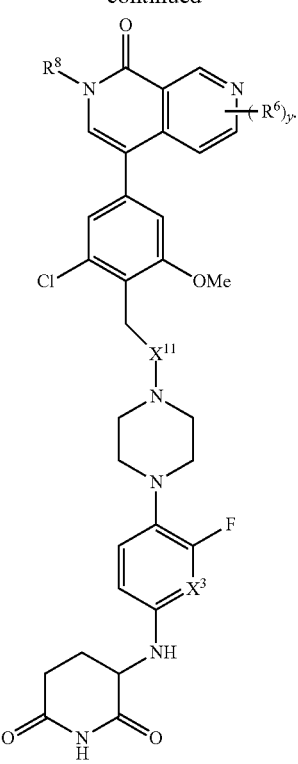
In one embodiment the compound of the present invention is selected from:
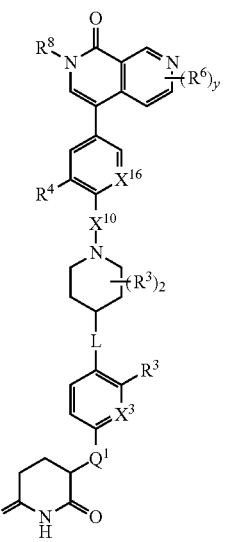

-continued
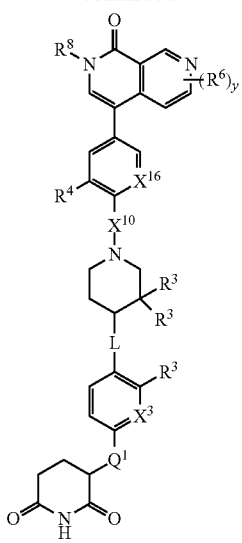
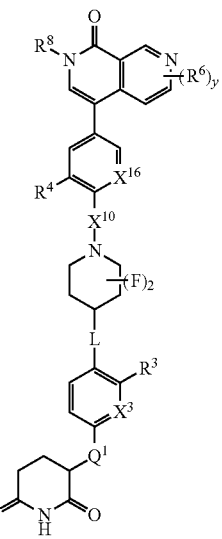
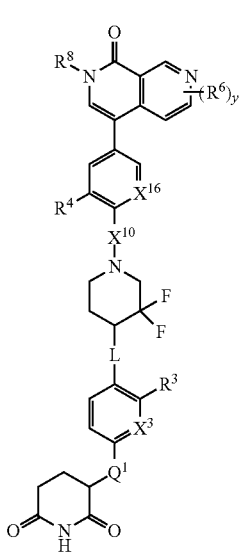
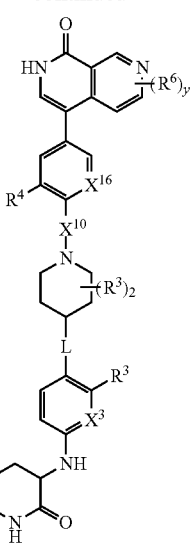
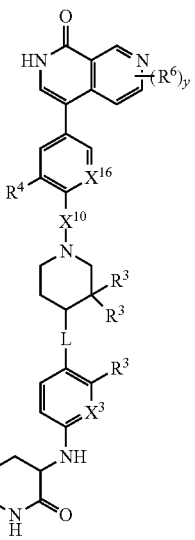
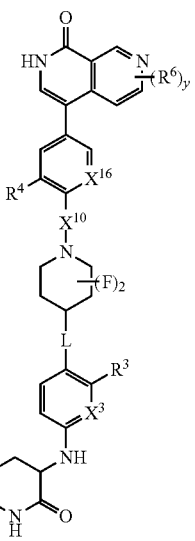

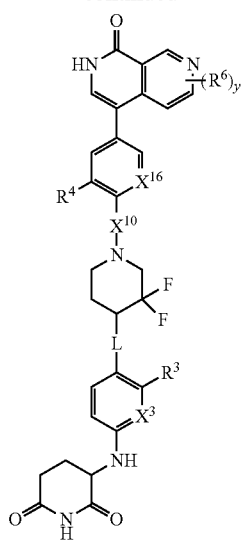
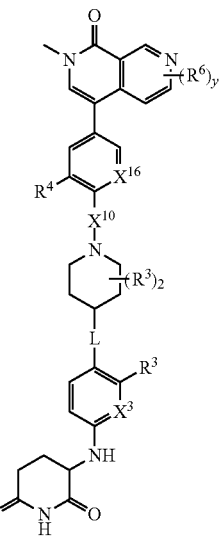

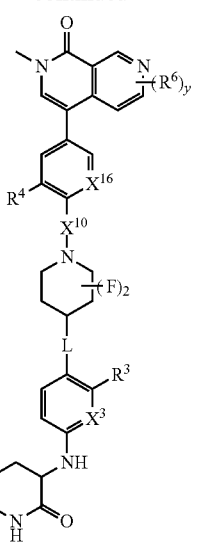
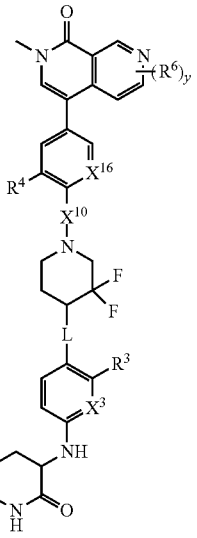
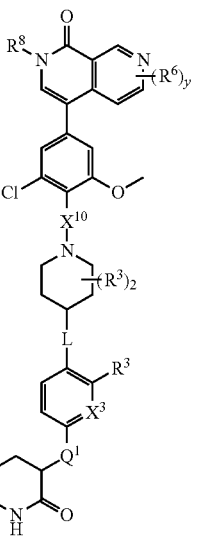

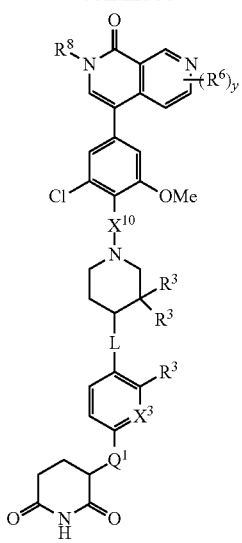
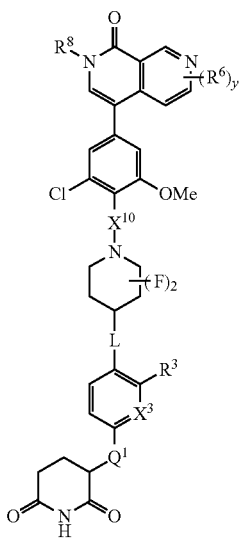
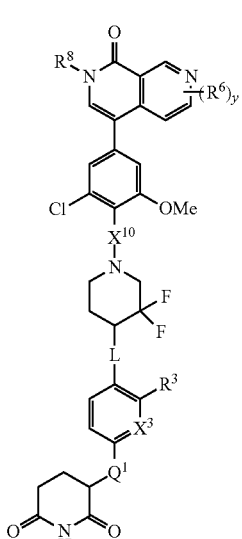
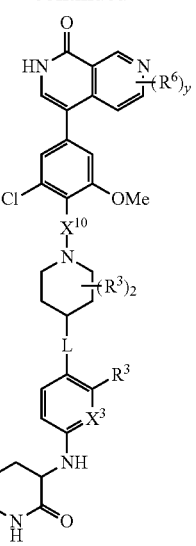
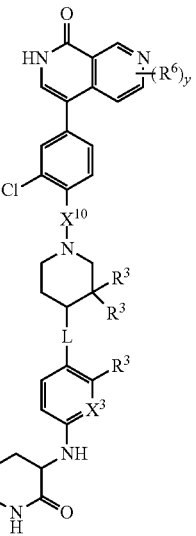
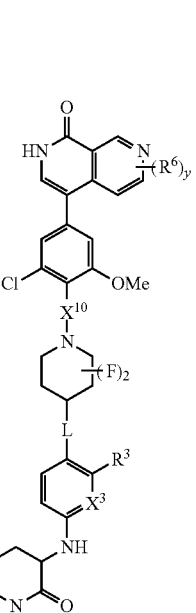

-continued
101
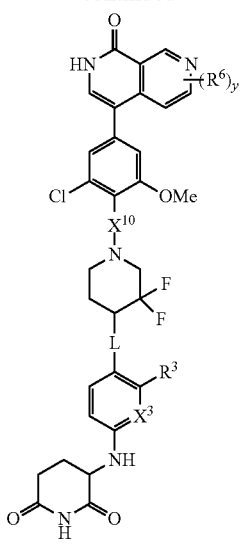
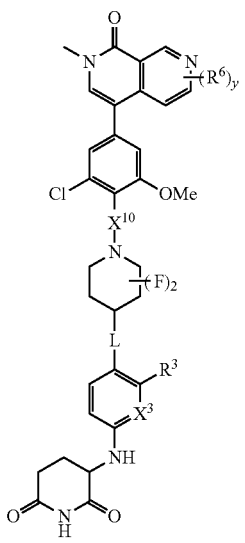
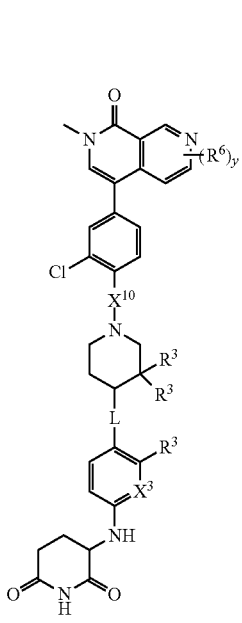
-continued
102
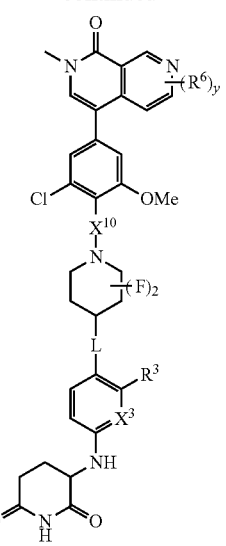
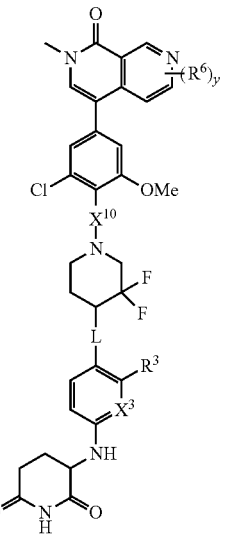
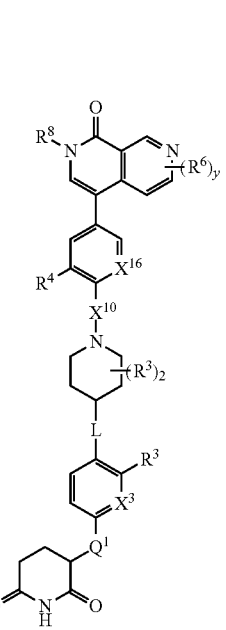

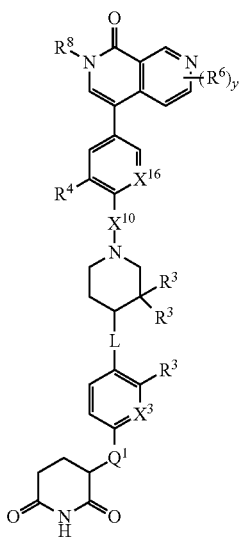
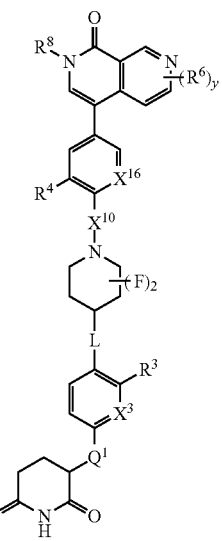
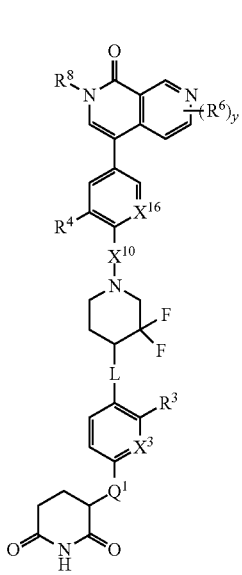
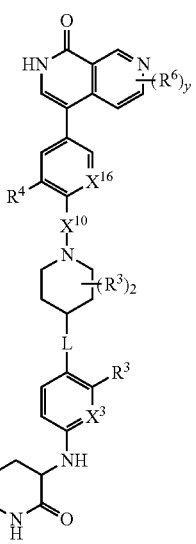
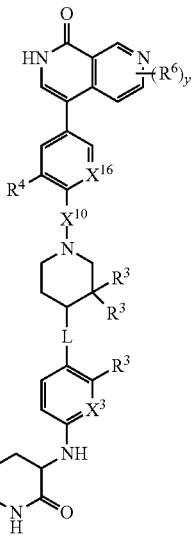
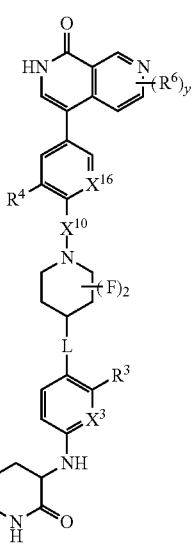

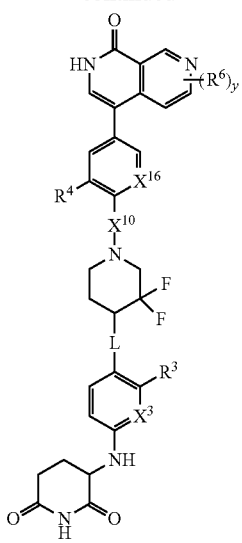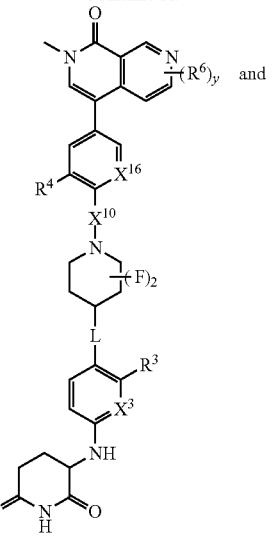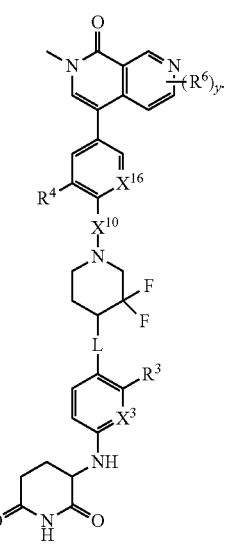
In one embodiment the compound of the present invention is selected from:

107
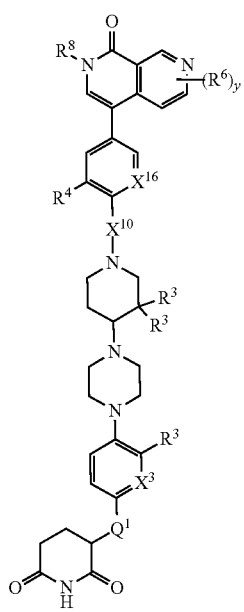
108
-continued
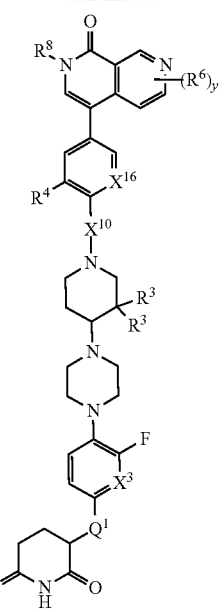
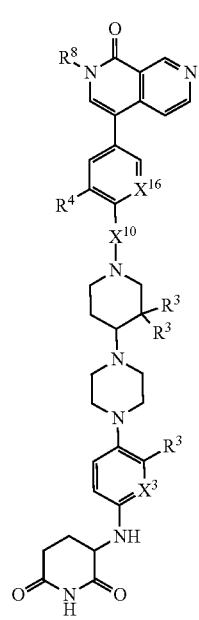
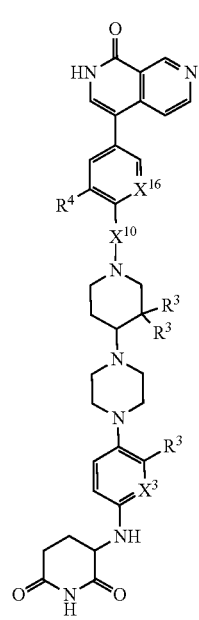

109
-continued
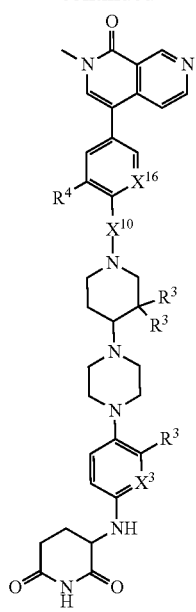
110
-continued
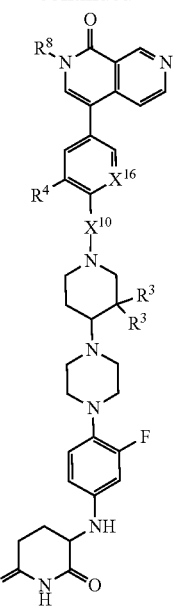
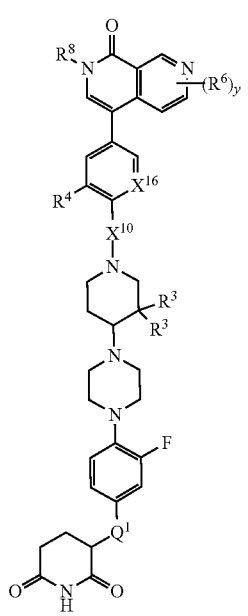
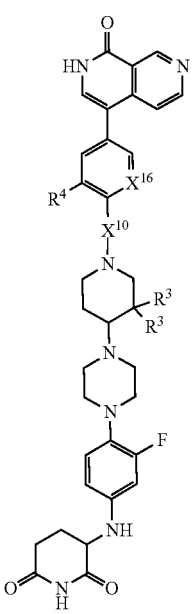

111
-continued
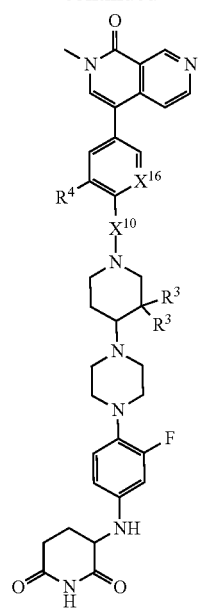
112
-continued
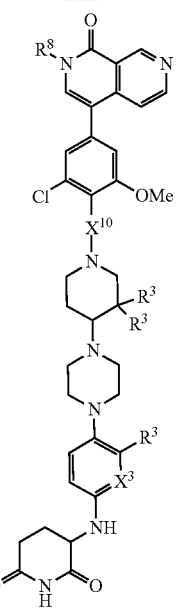
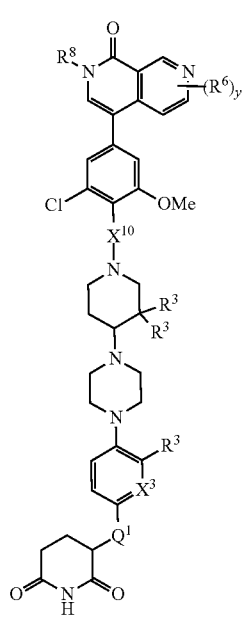
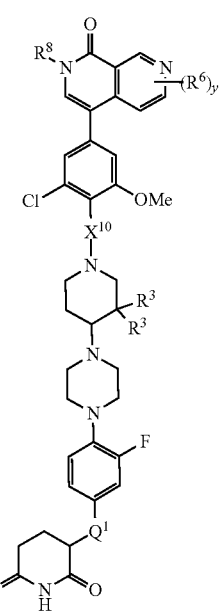

113
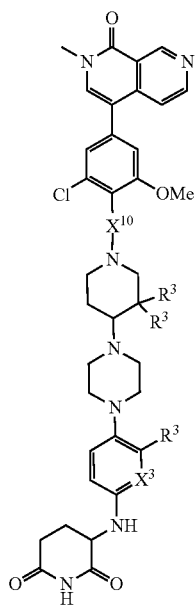
114
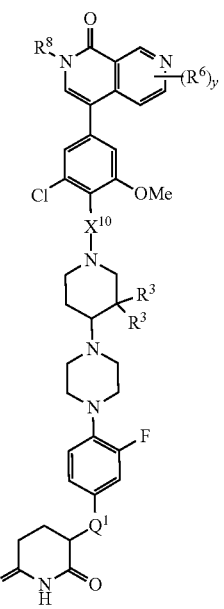

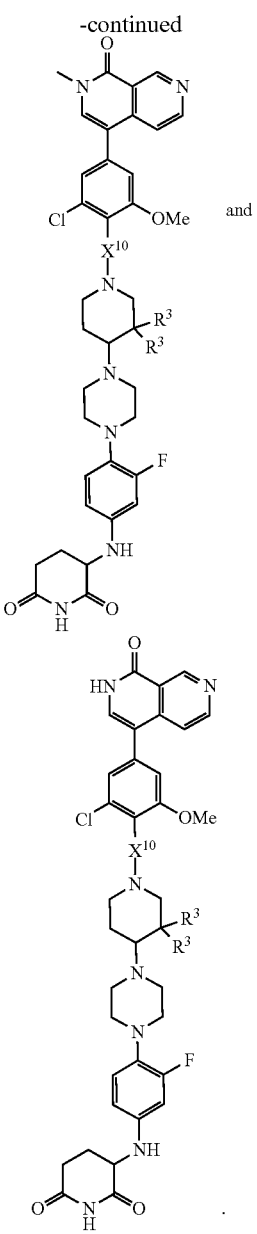
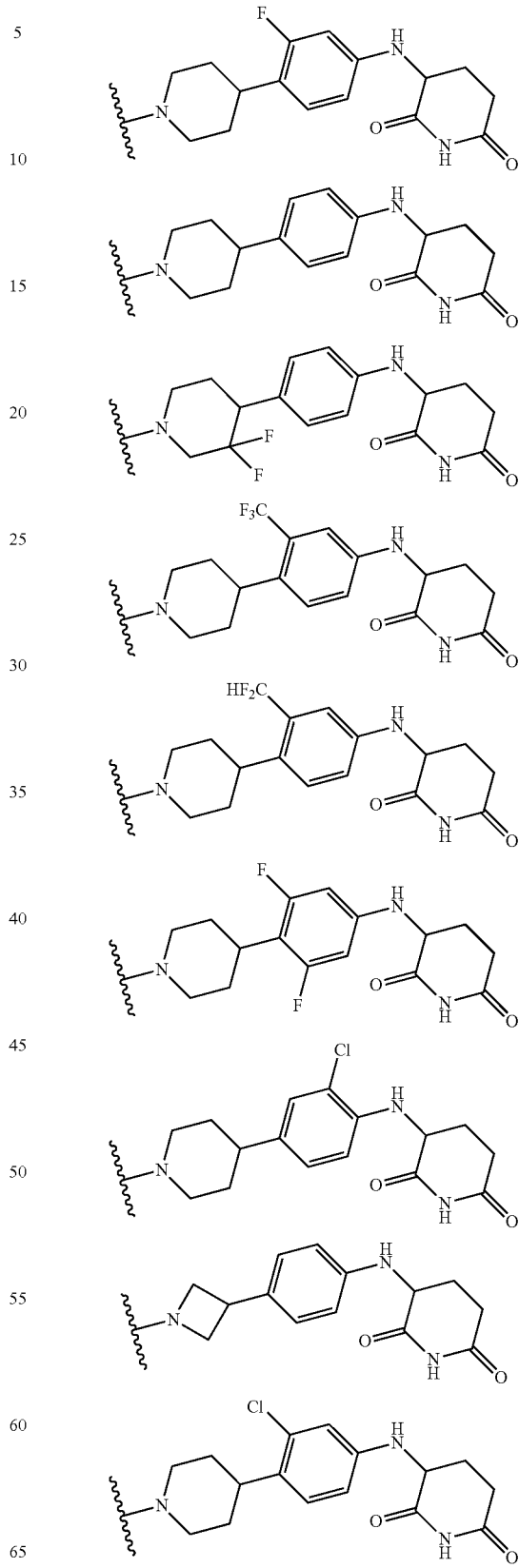
In certain embodiments
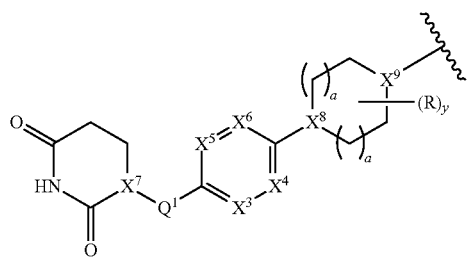
is selected from:

-continued
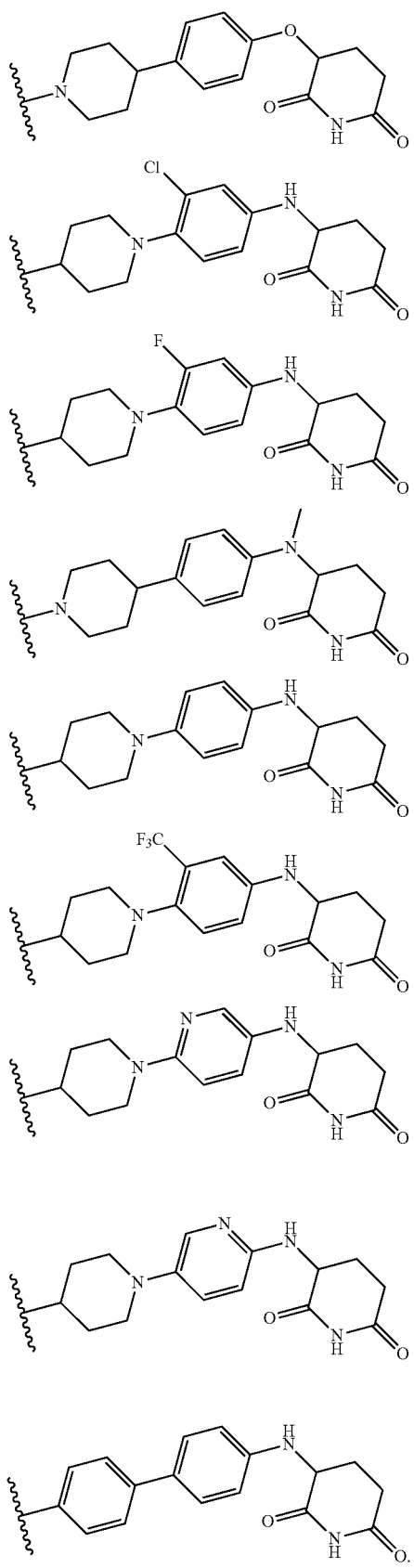
In certain embodiments
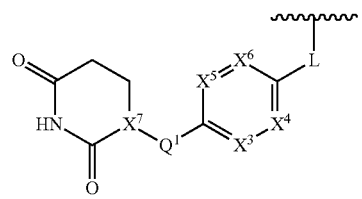
is selected from:
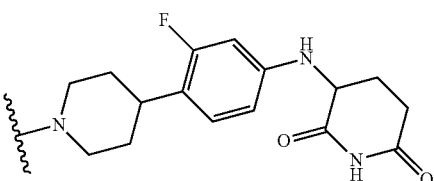
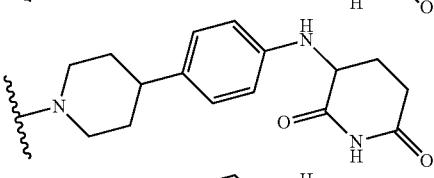
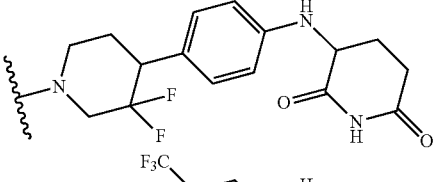
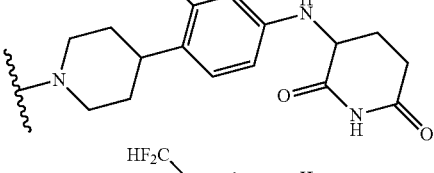
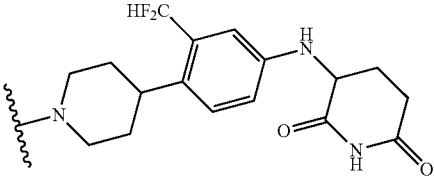
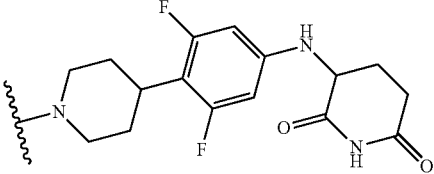
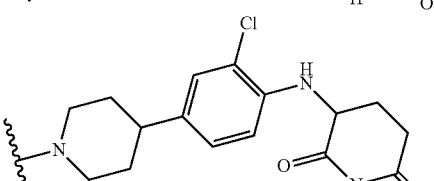
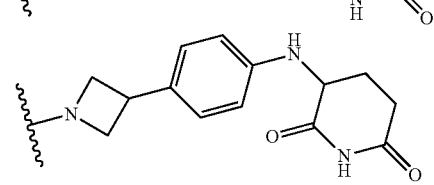

-continued
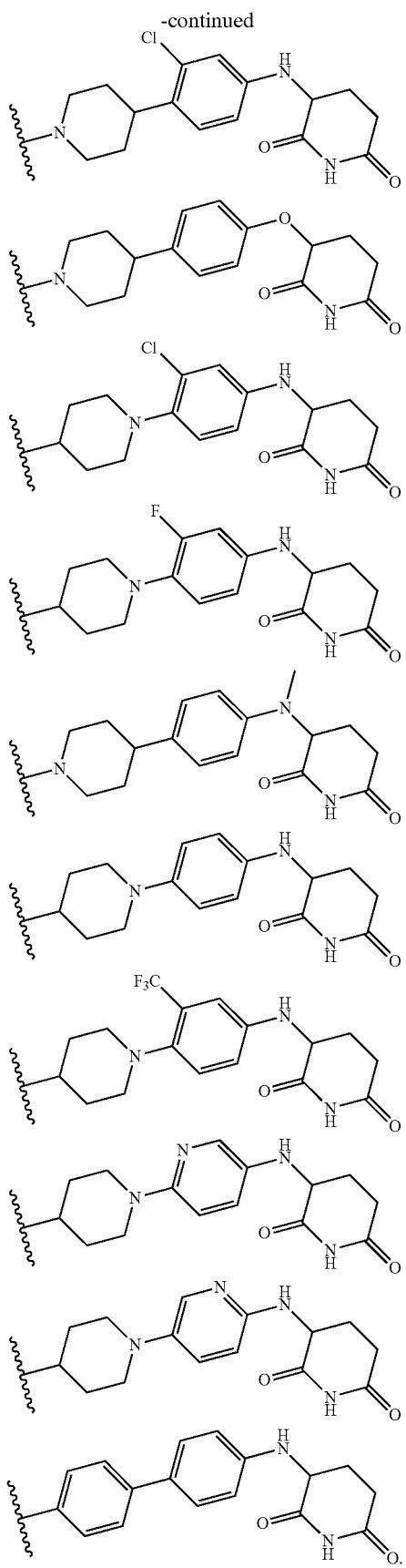
In certain embodiments
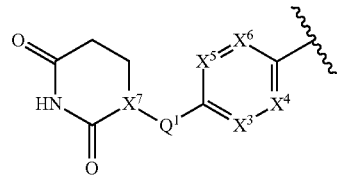
is selected from:
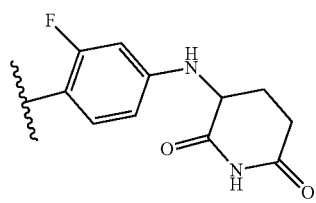
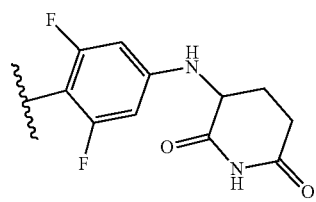
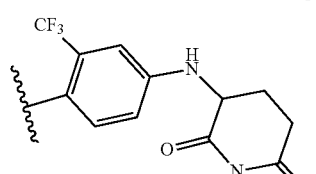
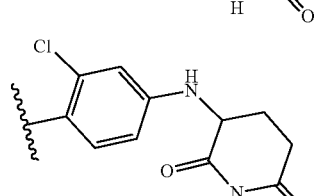
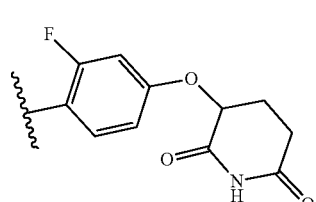
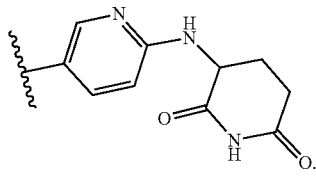

In certain embodiments
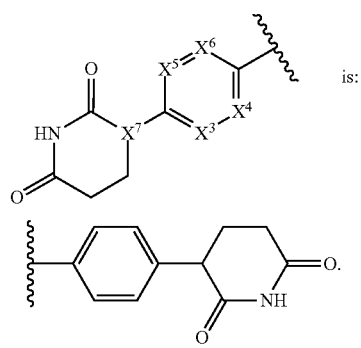
is:
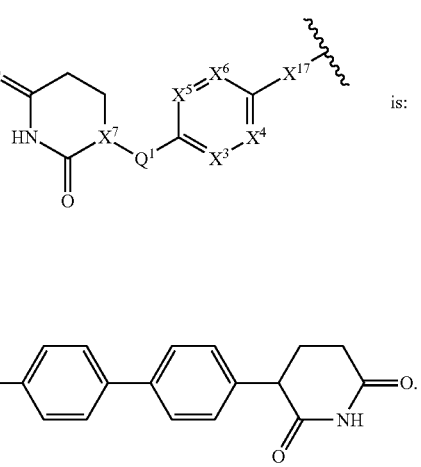
In certain embodiments
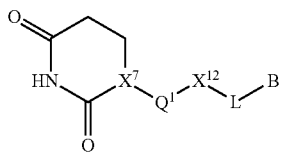
is selected from:
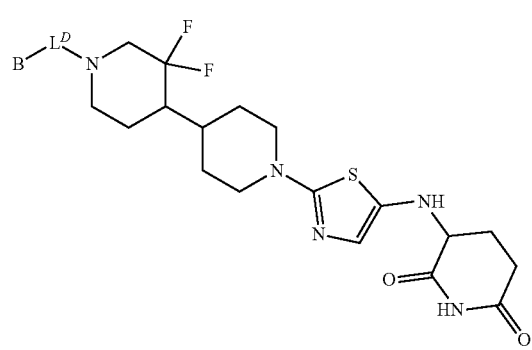
-continued
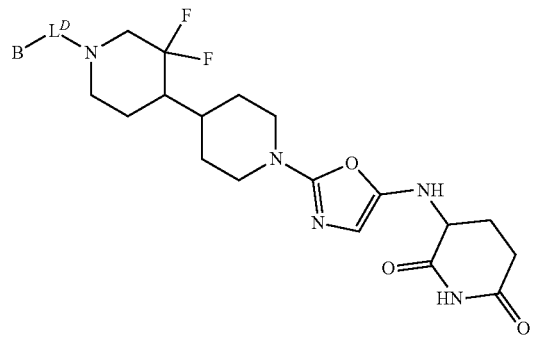

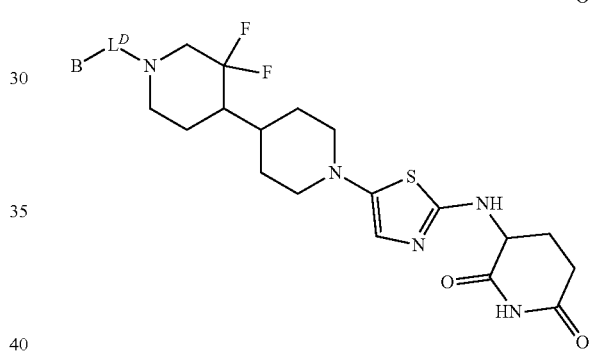
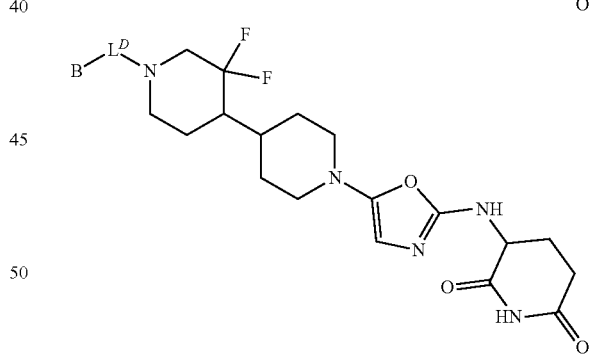
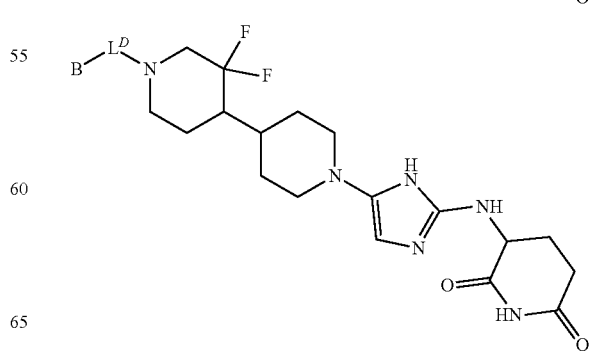

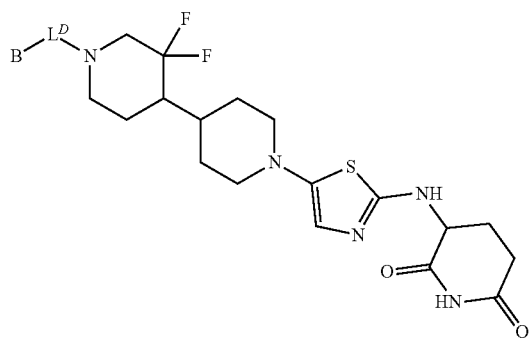
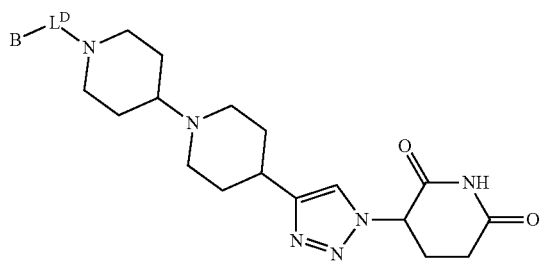
In certain embodiments
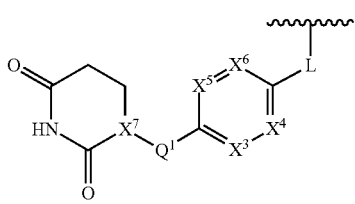

is selected from:
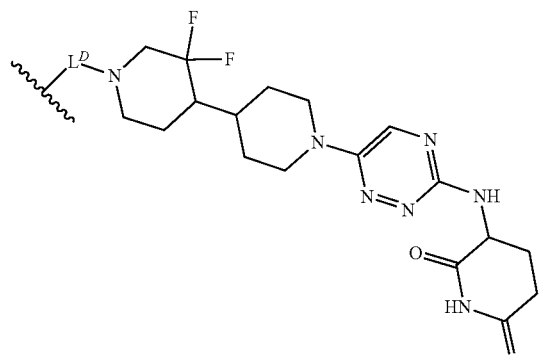
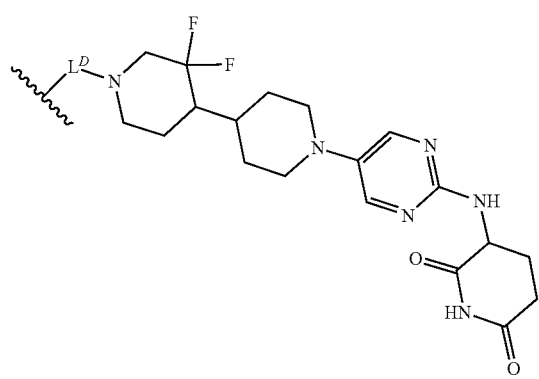
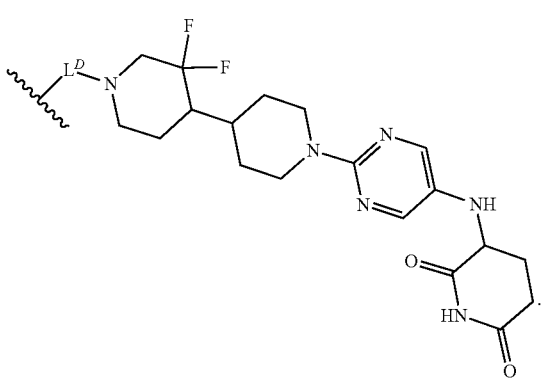
In certain embodiments
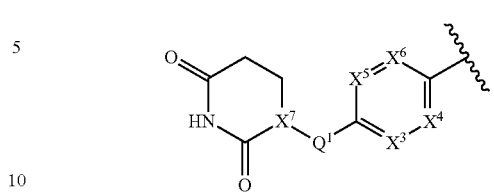
is selected from:
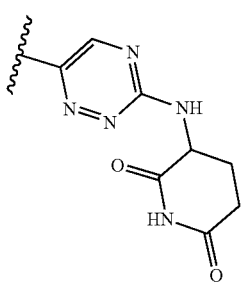 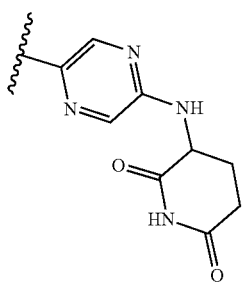
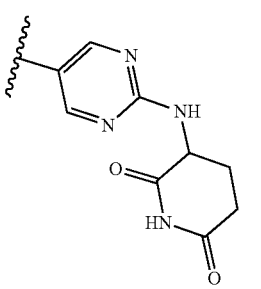 and 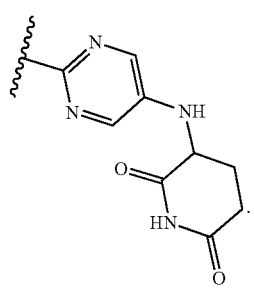.
In certain embodiments
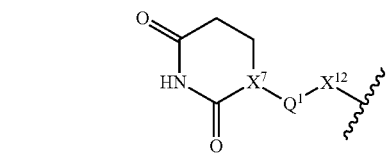
is selected from:
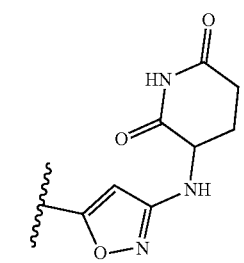 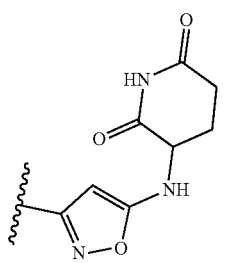

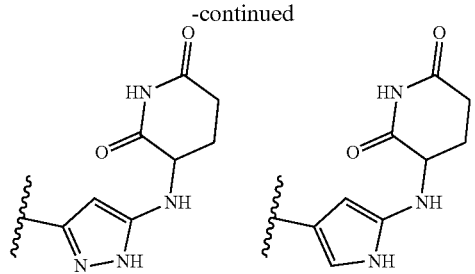
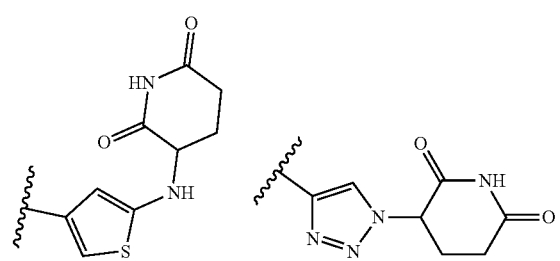
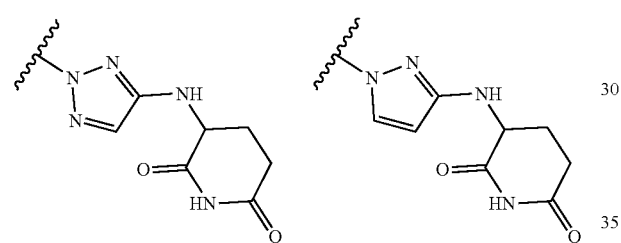
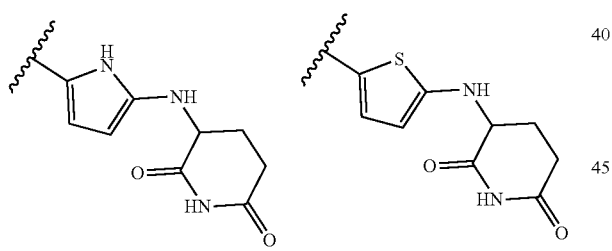
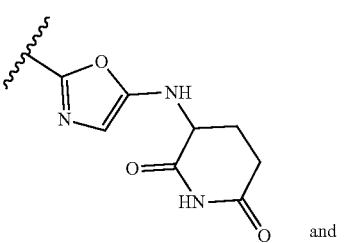
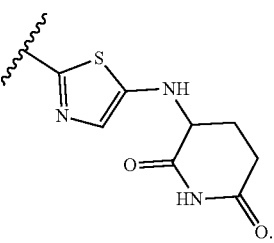 and
In certain embodiments Compound 172 is
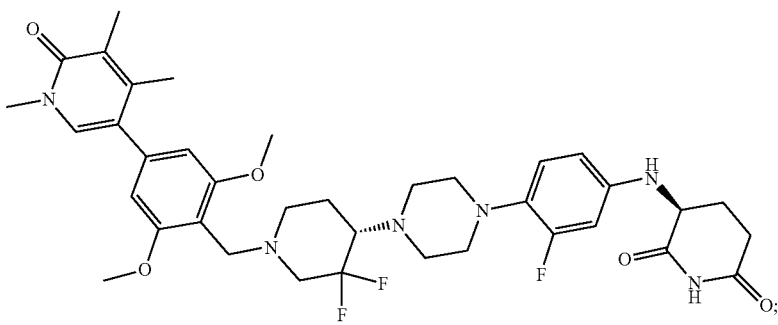 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]
or a pharmaceutically acceptable salt thereof.

Additional Embodiments of the Present Invention

001. In certain embodiments the compound of the present invention is of Formula:

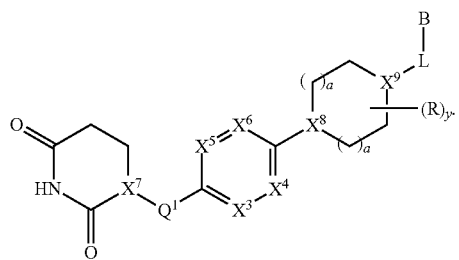

002. The compound of embodiment 1, wherein $X^8$ is N and $X^9$ is CH.

003. The compound of embodiment 1, wherein $X^8$ is CH and $X^9$ is N.

004. The compound of embodiment 1, wherein $X^8$ is CH and $X^9$ is CH.

005. The compound of any one of embodiments 1-4, wherein

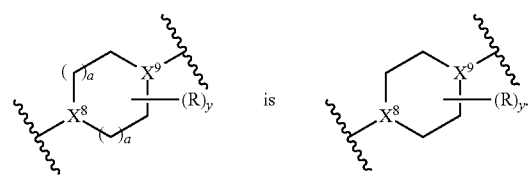

006. The compound of any one of embodiments 1-4, wherein

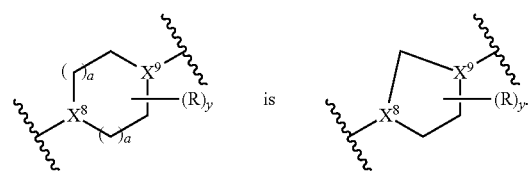

007. The compound of any one of embodiments 1-4, wherein

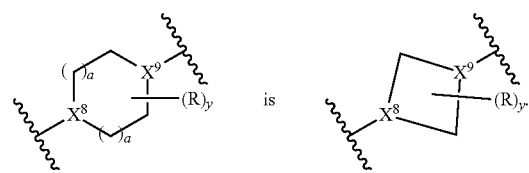

008. The compound of any one of embodiments 1-7, wherein

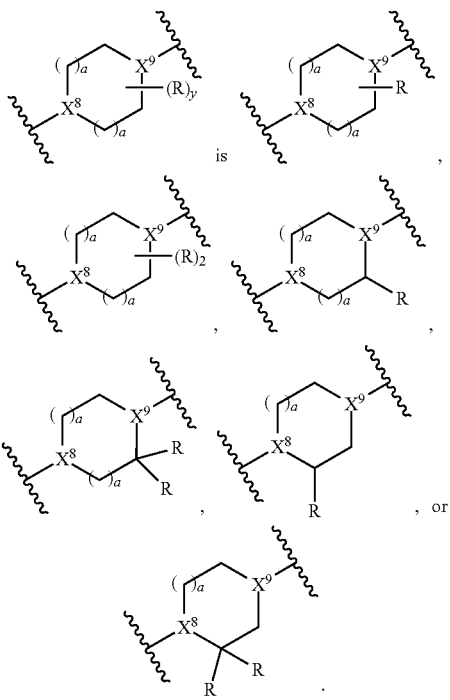

009. The compound of any one of embodiments 1-8, wherein R is $C_1$-$C_4$haloalkyl, $C_1$-$C_4$alkyl, fluorine, chlorine, or bromine.

010. The compound of any one of embodiments 1-8, wherein R is fluorine.

011. In certain embodiments the compound of the present invention is of Formula:

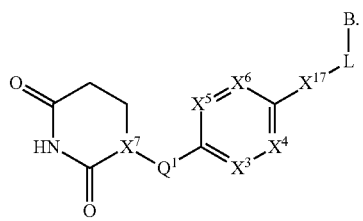

012. The compound of embodiment 11, wherein $X^{17}$ is an aryl group optionally substituted with 1, 2, 3, or 4 substituents independently selected from $R^3$.

013. The compound of embodiment 12, wherein $X^{11}$ is phenyl.

014. The compound of embodiment 11, wherein $X^{17}$ is a heteroaryl group or cycloalkyl group; each of which is optionally substituted with 1, 2, 3, or 4 substituents independently selected from $R^3$.

015. The compound of any one of embodiments 1-14, wherein $Q^1$ is NH and $X^7$ is CH.

016. The compound of any one of embodiments 1-14, wherein $Q^1$ is O and $X^7$ is CH.

017. The compound of any one of embodiments 1-14, wherein $Q^1$ is $N(CH_3)$ and $X^7$ is CH.

018. In certain embodiments the compound of the present invention is of Formula:

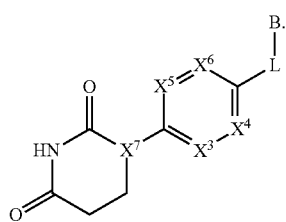

019. The compound of any one of embodiments 1-18, wherein $X^3$ is $CR^3$.
020. The compound of any one of embodiments 1-18, wherein $X^3$ is N.
021. The compound of any one of embodiments 1-18, wherein $X^3$ is CH.
022. The compound of any one of embodiments 1-18, wherein $X^3$ is CF.
023. The compound of any one of embodiments 1-18, wherein $X^3$ is $C(CF_3)$.
024. The compound of any one of embodiments 1-18, wherein $X^3$ is C(Cl).
025. The compound of any one of embodiments 1-24, wherein $X^5$ is $CR^3$.
026. The compound of any one of embodiments 1-24, wherein $X^5$ is N.
027. The compound of any one of embodiments 1-24, wherein $X^5$ is CH.
028. The compound of any one of embodiments 1-24, wherein $X^5$ is CF.
029. The compound of any one of embodiments 1-24, wherein $X^5$ is $C(CF_3)$.
030. The compound of any one of embodiments 1-24, wherein $X^5$ is C(Cl).
031. In certain embodiments the compound of the present invention is of Formula:

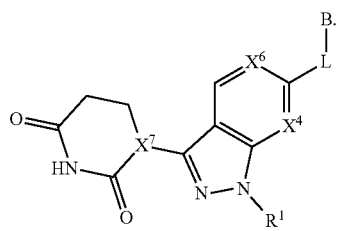

032. The compound of embodiment 31, wherein $R^1$ is hydrogen.
033. The compound of embodiment 31, wherein $R^1$ is $CH_3$.
034. The compound of any one of embodiments 1-33, wherein $X^4$ is $CR^3$.
035. The compound of any one of embodiments 1-33, wherein $X^4$ is N.
036. The compound of any one of embodiments 1-33, wherein $X^4$ is CH.
037. The compound of any one of embodiments 1-33, wherein $X^4$ is CF.
038. The compound of any one of embodiments 1-33, wherein $X^4$ is $C(CF_3)$.
039. The compound of any one of embodiments 1-33, wherein $X^4$ is C(Cl).
040. The compound of any one of embodiments 1-39, wherein $X^6$ is $CR^3$.
041. The compound of any one of embodiments 1-39, wherein $X^6$ is CH.
042. The compound of any one of embodiments 1-39, wherein $X^6$ is CF.
043. The compound of any one of embodiments 1-39, wherein $X^6$ is $C(CF_3)$.
044. The compound of any one of embodiments 1-39, wherein $X^6$ is C(Cl).
045. In certain embodiments the compound of the present invention is of Formula:

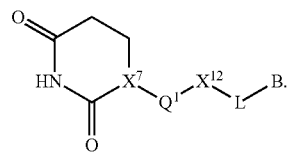

046. The compound of embodiment 45, wherein $Q^1$ is NH and $X^7$ is CH.
047. The compound of embodiment 45, wherein $Q^1$ is O and $X^7$ is CH.
048. The compound of embodiment 45, wherein $Q^1$ is $N(CH_3)$ and $X^7$ is CH.
049. The compound of any one of embodiments 45-48, wherein $X^{11}$ is a 5-membered heteroaryl group with 1, 2, or 3 atoms independently selected from N, wherein $X^{12}$ is optionally substituted with 1, 2, or 3 groups independently selected from $R^3$.
050. The compound of any one of embodiments 45-48, wherein $X^{12}$ furan, wherein $X^{12}$ is optionally substituted with 1, 2, or 3 groups independently selected from $R^3$;
051. The compound of any one of embodiments 1-50, wherein B is $B^1$.
052. The compound of embodiment 51, wherein $B^1$ is

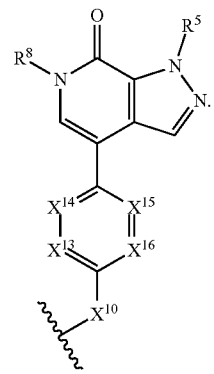

053. The compound of embodiment 52, wherein $R^5$ is hydrogen.
054. The compound of embodiment 52, wherein $R^5$ is methyl.

055. The compound of embodiment 51, wherein B¹ is

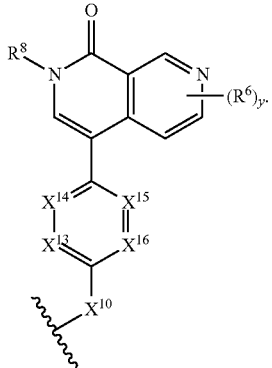

056. The compound of embodiment 51, wherein B¹ is

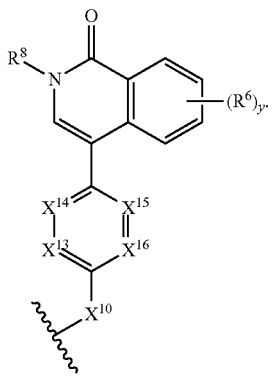

057. The compound of embodiment 51, wherein B¹ is

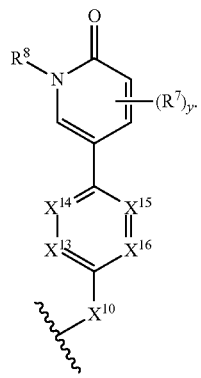

058. The compound of any one of embodiments 1-50, wherein B is B².

059. In certain embodiments the compound of the present invention is of Formula:

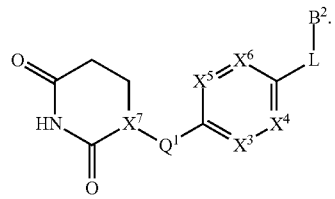

060. The compound of embodiment 59, wherein $Q^1$ is NH and $X^7$ is CH.

061. The compound of embodiment 59, wherein $Q^1$ is O and $X^7$ is CH.

062. The compound of embodiment 59, wherein $Q^1$ is $N(CH_3)$ and $X^7$ is CH.

063. The compound of any one of embodiments 59-62, wherein $X^3$ is $CR^3$.

064. The compound of any one of embodiments 59-62, wherein $X^3$ is N.

065. The compound of any one of embodiments 59-62, wherein $X^3$ is CH.

066. The compound of any one of embodiments 59-62, wherein $X^3$ is CF.

067. The compound of any one of embodiments 59-62, wherein $X^3$ is $C(CF_3)$.

068. The compound of any one of embodiments 59-62, wherein $X^3$ is C(Cl).

069. The compound of any one of embodiments 59-68, wherein $X^5$ is $CR^3$.

070. The compound of any one of embodiments 59-68, wherein $X^5$ is N.

071. The compound of any one of embodiments 59-68, wherein $X^5$ is CH.

072. The compound of any one of embodiments 59-68, wherein $X^5$ is CF.

073. The compound of any one of embodiments 59-68, wherein $X^5$ is $C(CF_3)$.

074. The compound of any one of embodiments 59-68, wherein $X^5$ is C(Cl).

075. The compound of any one of embodiments 59-74, wherein $X^4$ is $CR^3$.

076. The compound of any one of embodiments 59-74, wherein $X^4$ is N.

077. The compound of any one of embodiments 59-74, wherein $X^4$ is CH.

078. The compound of any one of embodiments 59-74, wherein $X^4$ is CF.

079. The compound of any one of embodiments 59-74, wherein $X^4$ is $C(CF_3)$.

080. The compound of any one of embodiments 59-74, wherein $X^4$ is C(Cl).

081. The compound of any one of embodiments 59-80, wherein $X^6$ is $CR^3$.

082. The compound of any one of embodiments 59-80, wherein $X^6$ is CH.

083. The compound of any one of embodiments 59-80, wherein $X^6$ is CF.

084. The compound of any one of embodiments 59-80, wherein $X^6$ is $C(CF_3)$.

085. The compound of any one of embodiments 59-80, wherein $X^6$ is C(Cl).

086. The compound of any one of embodiments 58-85, wherein B² is

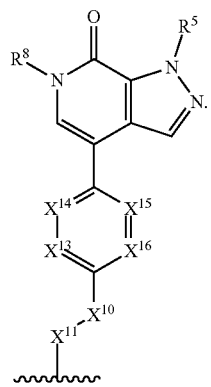

087. The compound of embodiment 86, wherein $R^5$ is hydrogen.

088. The compound of embodiment 86, wherein $R^5$ is methyl.

089. The compound of any one of embodiments 58-85, wherein $B^2$ is

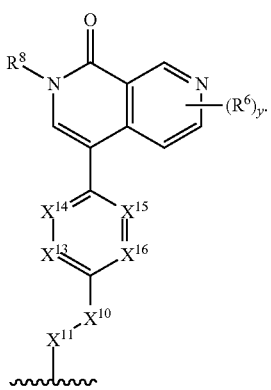

090. The compound of any one of embodiments 58-85, wherein $B^2$ is

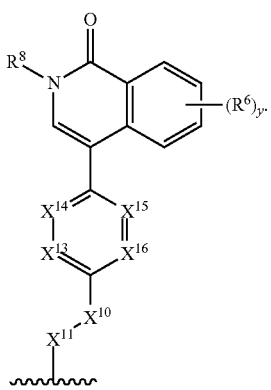

091. The compound of any one of embodiments 58-85, wherein $B^2$ is

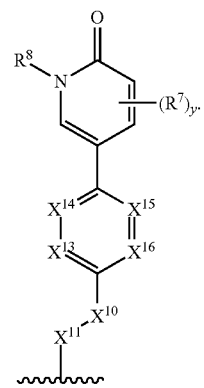

092. The compound of any one of embodiments 58-91, wherein $X^{11}$ is heterocycle, each of which $X^{11}$ groups is optionally substituted with 1, 2, 3, or 4 groups independently selected from $R^3$.

093. The compound of any one of embodiments 58-91, wherein $X^{11}$ is bicycle, each of which $X^{11}$ groups is optionally substituted with 1, 2, 3, or 4 groups independently selected from $R^3$.

094. The compound of any one of embodiments 58-91, wherein $X^{11}$ is heteroaryl, aryl, or cycloalkyl, each of which $X^{11}$ groups is optionally substituted with 1, 2, 3, or 4 groups independently selected from $R^3$.

095. The compound of any one of embodiments 58-91, wherein $X^{11}$ is selected from:

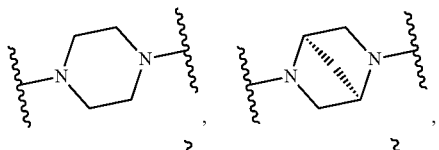

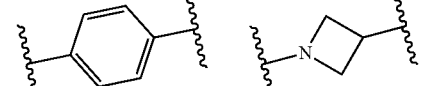

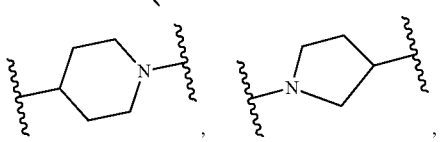

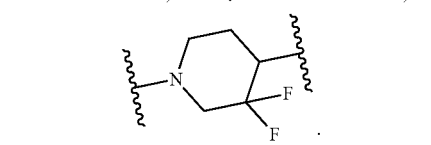

, and

096. The compound of any one of embodiments 58-91, wherein $X^{11}$ is selected from:

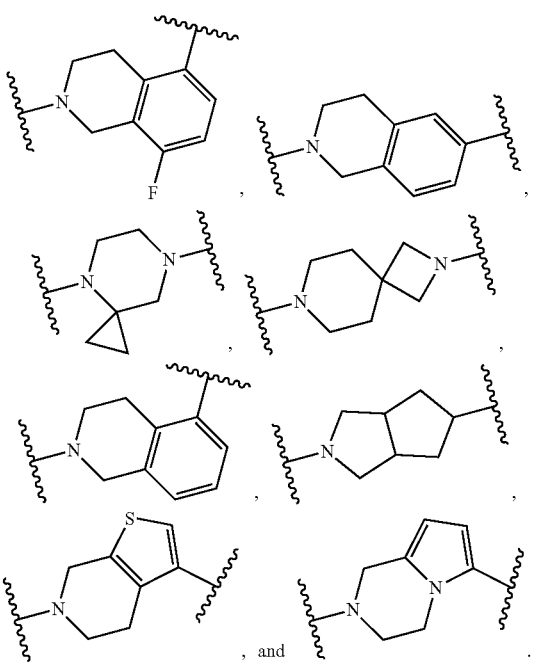

097. The compound of any one of embodiments 58-91, wherein $X^{10}$ and $X^{11}$ are taken together to form

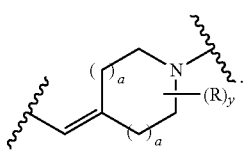

098. The compound of any one of embodiments 58-91, wherein $X^{10}$ and $X^{11}$ are taken together to form

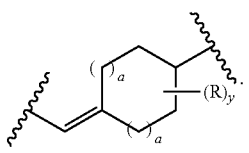

099. The compound of any one of embodiments 1-96, wherein $X^{10}$ is $C(R^7)_2$.
100. The compound of any one of embodiments 1-96, wherein $X^{10}$ is $CH_2$.
101. The compound of any one of embodiments 1-96, wherein $X^{10}$ is $C(O)$.
102. The compound of any one of embodiments 1-96, wherein $X^{10}$ is O.
103. The compound of any one of embodiments 1-102, wherein $X^{13}$ is $CR^3$.
104. The compound of any one of embodiments 1-102, wherein $X^{13}$ is N.
105. The compound of any one of embodiments 1-102, wherein $X^{13}$ is CH.
106. The compound of any one of embodiments 1-102, wherein $X^{13}$ is CF.
107. The compound of any one of embodiments 1-102, wherein $X^{13}$ is $C(CF_3)$.
108. The compound of any one of embodiments 1-102, wherein $X^{13}$ is C(Cl).
109. The compound of any one of embodiments 1-108, wherein $X^{14}$ is $CR^3$.
110. The compound of any one of embodiments 1-108, wherein $X^{14}$ is N.
111. The compound of any one of embodiments 1-108, wherein $X^{14}$ is CH.
112. The compound of any one of embodiments 1-108, wherein $X^{14}$ is CF.
113. The compound of any one of embodiments 1-108, wherein $X^{14}$ is $C(CF_3)$.
114. The compound of any one of embodiments 1-108, wherein $X^{14}$ is C(Cl).
115. The compound of any one of embodiments 1-114, wherein $X^{15}$ is $CR^3$.
116. The compound of any one of embodiments 1-114, wherein $X^{15}$ is N.
117. The compound of any one of embodiments 1-114, wherein $X^{15}$ is CH.
118. The compound of any one of embodiments 1-114, wherein $X^{15}$ is CF.
119. The compound of any one of embodiments 1-114, wherein $X^{15}$ is $C(CF_3)$.
120. The compound of any one of embodiments 1-114, wherein $X^{15}$ is C(Cl).
121. The compound of any one of embodiments 1-120, wherein $X^{16}$ is $CR^3$.
122. The compound of any one of embodiments 1-120, wherein $X^{16}$ is CH.
123. The compound of any one of embodiments 1-120, wherein $X^{16}$ is CF.
124. The compound of any one of embodiments 1-120, wherein $X^{16}$ is $C(CF_3)$.
125. The compound of any one of embodiments 1-120, wherein $X^{16}$ is C(Cl).
126. The compound of any one of embodiments 1-125, wherein $R^8$ is hydrogen.
127. The compound of any one of embodiments 1-125, wherein $R^8$ is methyl.
128. The compound of any one of embodiments 1-127, wherein L is a linker of formula:

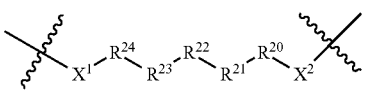

(LI)

wherein, $X^1$ and $X^2$ are independently at each occurrence selected from bond, heterocycle, $NR^2$, $C(R^2)_2$, O, C(O), and S;

$R^2$ is independently at each occurrence selected from the group consisting of hydrogen, alkyl, aliphatic, heteroaliphatic, heterocycle, aryl, heteroaryl, —C(O)H, —C(O)OH, —C(O)alkyl, —C(O)Oalkyl, —C(O)(aliphatic, aryl, heteroaliphatic or heteroaryl), —C(O)O(aliphatic, aryl, heteroaliphatic, or heteroaryl), alkene, and alkyne;

$R^{20}$, $R^{21}$, $R^{22}$, $R^{23}$, and $R^{24}$ are independently at each occurrence selected from the group consisting of a bond, alkyl, —C(O)—, —C(O)O—, —OC(O)—, —SO$_2$—, —S(O)—, —C(S)—, —C(O)NR$^2$—, —NR$^2$C(O)—, —O—, —S—, —NR$^2$—, —C(R$^{40}$R$^{40}$)—, —P(O)(OR$^{26}$)O—, —P(O)(OR$^{26}$)—, alkene, alkyne, haloalkyl, alkoxy, aryl, heterocycle, aliphatic, heteroaliphatic, heteroaryl, lactic acid, glycolic acid, and carbocycle; each of which is optionally substituted with 1, 2, 3, or 4 substituents independently selected from $R^{40}$;

$R^{26}$ is independently at each occurrence selected from the group consisting of hydrogen, alkyl, arylalkyl, heteroarylalkyl, alkene, alkyne, aryl, heteroaryl, heterocycle, aliphatic and heteroaliphatic; and $R^{40}$ is independently at each occurrence selected from the group consisting of hydrogen, alkyl, alkene, alkyne, fluoro, bromo, chloro, hydroxyl, alkoxy, azide, amino, cyano, —NH(aliphatic, including alkyl), —N(aliphatic, including alkyl)$_2$, —NHSO$_2$(aliphatic, including alkyl), —N(aliphatic, including alkyl)SO$_2$alkyl, —NHSO$_2$(aryl, heteroaryl or heterocycle), —N(alkyl)SO$_2$(aryl, heteroaryl or heterocycle), —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, aryl, heteroaryl, heterocycle, and cycloalkyl.

129. The compound of embodiment 128, wherein L is a linker of formula:

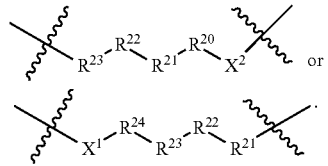

130. The compound of embodiment 128 or 129, wherein $X^1$ is bond.
131. The compound of embodiment 128 or 129, wherein $X^1$ is heterocycle.
132. The compound of embodiment 128 or 129, wherein $X^1$ is $NR^2$.
133. The compound of embodiment 128 or 129, wherein $X^1$ is C(O).
134. The compound of any one of embodiments 128-133, wherein $X^2$ is bond.
135. The compound of any one of embodiments 128-133, wherein $X^2$ is heterocycle.
136. The compound of any one of embodiments 128-133, wherein $X^2$ is $NR^2$.
137. The compound of any one of embodiments 128-133, wherein $X^2$ is C(O).
138. The compound of any one of embodiments 128-137, wherein $R^{20}$ is bond.
139. The compound of any one of embodiments 128-137, wherein $R^{20}$ is CH$_2$.
140. The compound of any one of embodiments 128-137, wherein $R^{20}$ is heterocycle.
141. The compound of any one of embodiments 128-137, wherein $R^{20}$ is aryl.
142. The compound of any one of embodiments 128-137, wherein $R^{20}$ is phenyl.
143. The compound of any one of embodiments 128-137, wherein $R^{20}$ is bicycle.
144. The compound of any one of embodiments 128-143, wherein $R^{21}$ is bond.
145. The compound of any one of embodiments 128-143, wherein $R^{21}$ is CH$_2$.
146. The compound of any one of embodiments 128-143, wherein $R^{21}$ is heterocycle.
147. The compound of any one of embodiments 128-143, wherein $R^{21}$ is aryl.
148. The compound of any one of embodiments 128-143, wherein $R^{21}$ is phenyl.
149. The compound of any one of embodiments 128-143, wherein $R^{21}$ is bicycle.
150. The compound of embodiment 128, wherein L is a linker of formula:

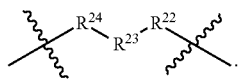

151. The compound of any one of embodiments 128-150, wherein $R^{22}$ is bond.
152. The compound of any one of embodiments 128-150, wherein $R^{22}$ is CH$_2$.
153. The compound of any one of embodiments 128-150, wherein $R^{22}$ is heterocycle.
154. The compound of any one of embodiments 128-150, wherein $R^{22}$ is aryl.
155. The compound of any one of embodiments 128-150, wherein $R^{22}$ is phenyl.
156. The compound of any one of embodiments 128-150, wherein $R^{22}$ is bicycle.
157. The compound of embodiment 128, wherein L is a linker of formula:

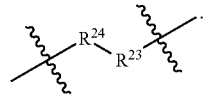

158. The compound of any one of embodiments 128-157, wherein $R^{23}$ is bond.
159. The compound of any one of embodiments 128-157, wherein $R^{23}$ is CH$_2$.
160. The compound of any one of embodiments 128-157, wherein $R^{23}$ is heterocycle.
161. The compound of any one of embodiments 128-157, wherein $R^{23}$ is aryl.
162. The compound of any one of embodiments 128-157, wherein $R^{23}$ is phenyl.
163. The compound of any one of embodiments 128-157, wherein $R^{23}$ is bicycle.
164. The compound of embodiment 128, wherein L is a linker of formula:

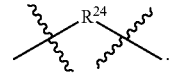

165. The compound of any one of embodiments 128-164, wherein $R^{24}$ is bond.
166. The compound of any one of embodiments 128-164, wherein $R^{24}$ is CH$_2$.
167. The compound of any one of embodiments 128-164, wherein $R^{24}$ is heterocycle.
168. The compound of any one of embodiments 128-164, wherein $R^{24}$ is aryl.
169. The compound of any one of embodiments 128-164, wherein $R^{24}$ is phenyl.
170. The compound of any one of embodiments 128-164, wherein $R^{24}$ is bicycle.
171. The compound of any one of embodiments 128-164, wherein $R^{24}$ is C(O).

172. The compound of any one of embodiments 1-171, wherein L is selected from:
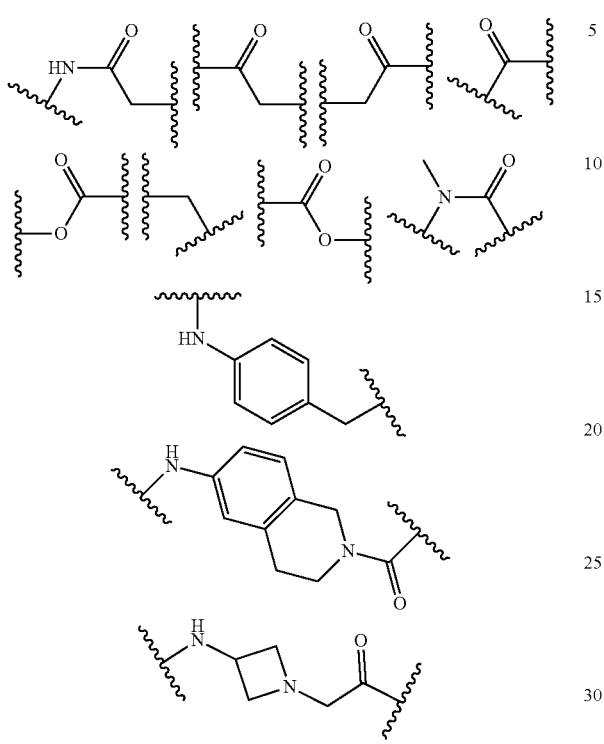
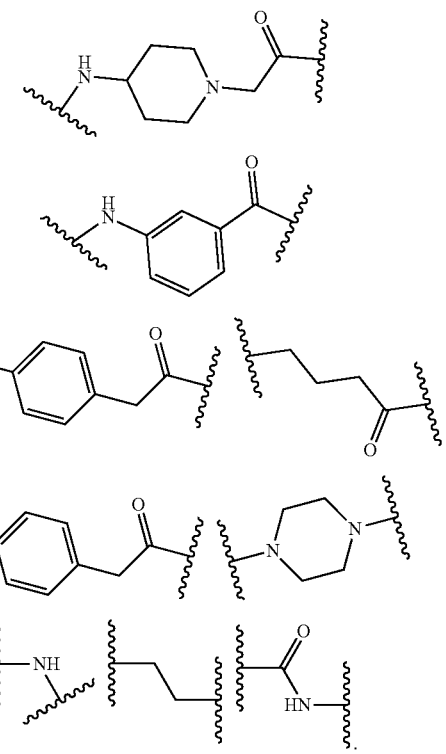
In certain embodiments Compound 172 is
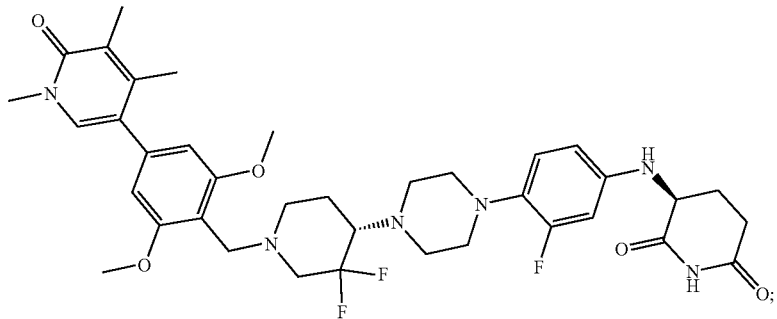 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]
or a pharmaceutically acceptable salt thereof.
In certain embodiments Compound 172 is
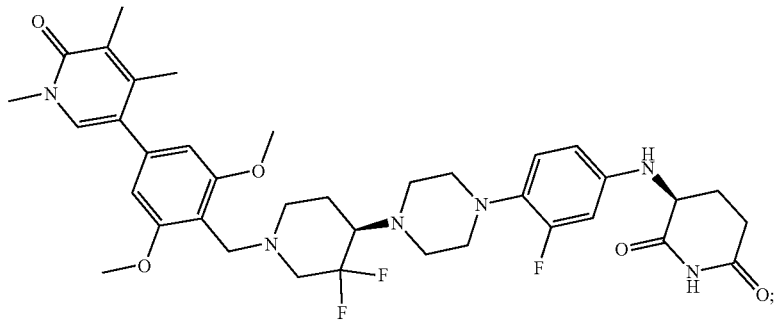 [SMILES: COc1cc(-c2cn(C)c(=O)c(C)c2C)cc(OC)c1CN1CC[C@@H](N2CCN(c3ccc(N[C@H]4CCC(=O)NC4=O)cc3F)CC2)C(F)(F)C1]
or a pharmaceutically acceptable salt thereof.

In certain embodiments Compound 172 is

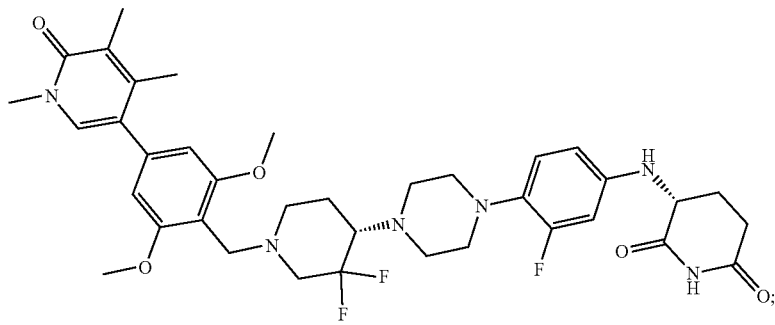 [SMILES: COc1cc(-c2cn(C)c(=O)c(C)c2C)cc(OC)c1CN1CC[C@H](N2CCN(c3ccc(N[C@@H]4CCC(=O)NC4=O)cc3F)CC2)C(F)(F)C1]

or a pharmaceutically acceptable salt thereof.

In certain embodiments Compound 172 is

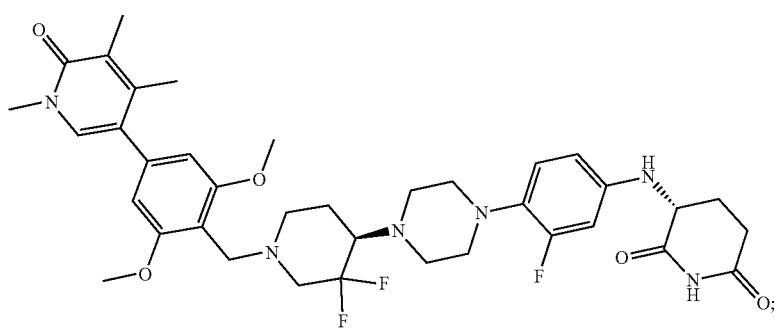 [SMILES: COc1cc(-c2cn(C)c(=O)c(C)c2C)cc(OC)c1CN1CC[C@@H](N2CCN(c3ccc(N[C@@H]4CCC(=O)NC4=O)cc3F)CC2)C(F)(F)C1]

or a pharmaceutically acceptable salt thereof.

III. Targeting Ligands

Bromodomains (BRDs) are protein interaction modules that exclusively recognize acetylation motifs. BRDs are evolutionarily conserved and present in diverse nuclear proteins comprising HATs (GCN5, PCAF), ATP-dependent chromatin-remodeling complexes (BAZ1B), helicases (SMARCA), methyltransferases (MLL, ASH1L), transcriptional coactivators (TRIM/TIF1, TAFs) transcriptional mediators (TAF1), nuclear-scaffolding proteins (PB1), and the BET family. (Muller S, Filippakopoulos P, Knapp S., Bromodomains as therapeutic targets, Expert Rev Mol Med. 2011, 13(29).)

Bromodomain-containing protein 7 (BRD7) is similar to BRD9 and is a subunit of PBAF SWI/SNF. (Pérez-Salvia M., Estellera M., Bromodomain inhibitors and cancer therapy: From structures to applications, Epigenetics. 2017; 12(5): 323-339; P99: Clark P. G. K., et al., Discovery and Synthesis of the First Selective BRD7/9 Bromodomain Inhibitor, Angew Chem Weinheim Bergstr Ger. 2015, 127 (21): 6315-6319).

In certain embodiments moiety B is a targeting ligand for a disorder mediated by one or more bromodomain containing protein.

In certain embodiments moiety B is a targeting ligand for BRD9 mediated disorders.

In certain embodiments moiety B is a targeting ligand for BRD7 mediated disorders.

In certain embodiments B is B1.

In certain embodiments B is B2.

In certain embodiments B2 is selected from the group consisting of:

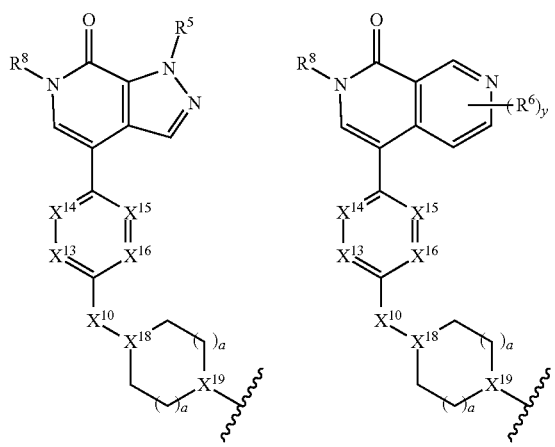

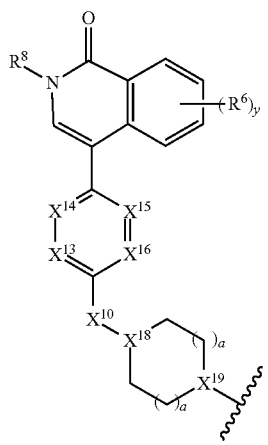
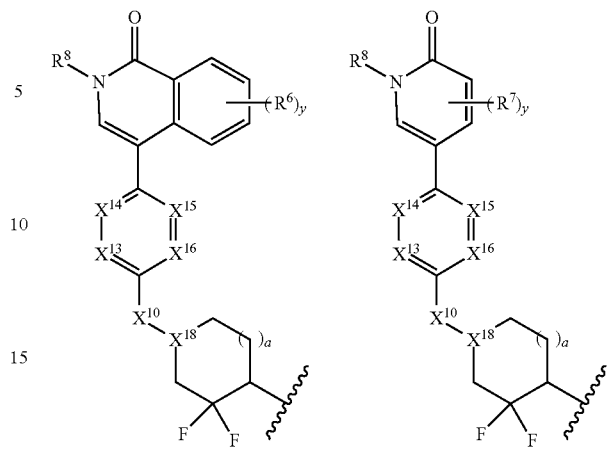
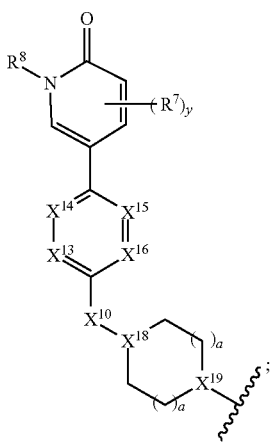
wherein $X^{18}$ and $X^{19}$ are independently selected from —N— and —CH—, and wherein all other variables are as defined herein.
In certain embodiments B2 is selected from the group consisting of:
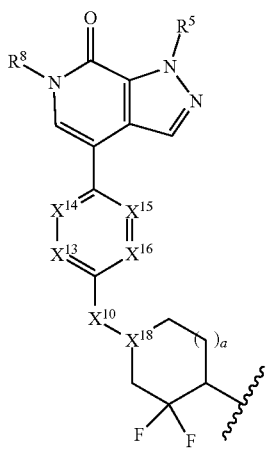
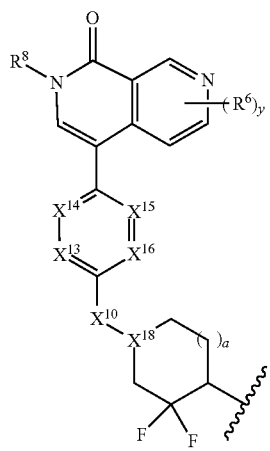
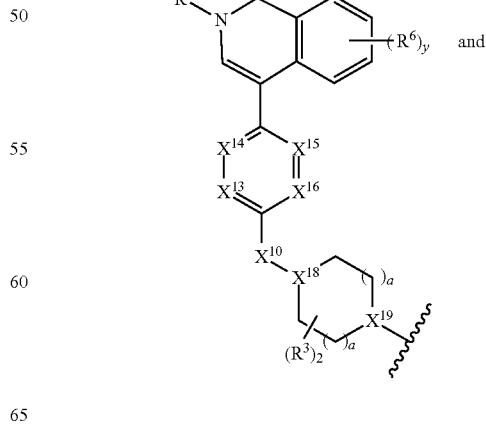

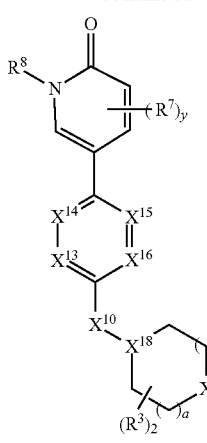

wherein $X^{18}$ and $X^{19}$ are independently selected from —N— and —CH—, and wherein all other variables are as defined herein.

In certain embodiments B2 is selected from the group consisting of:

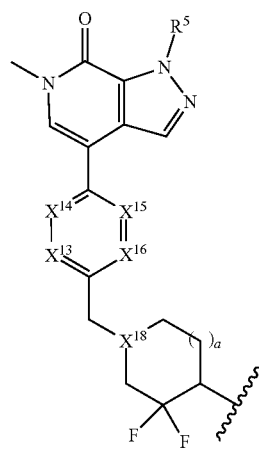 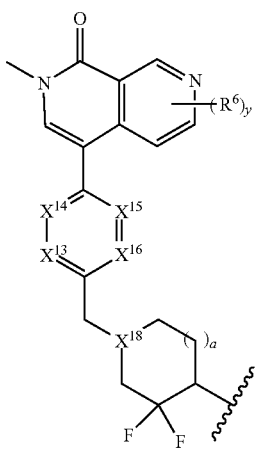

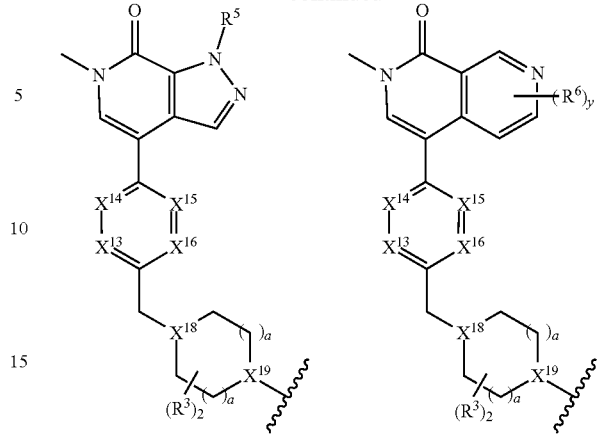

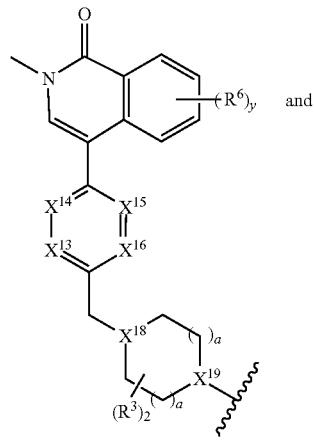 and

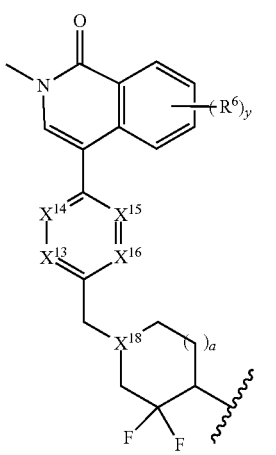 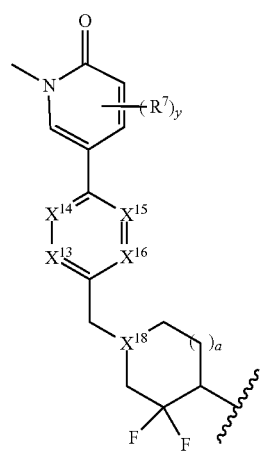

wherein $X^{18}$ and $X^{19}$ are independently selected from —N— and —CH—, and wherein all other variables are as defined herein.

In certain embodiments B2 is selected from the group consisting of:

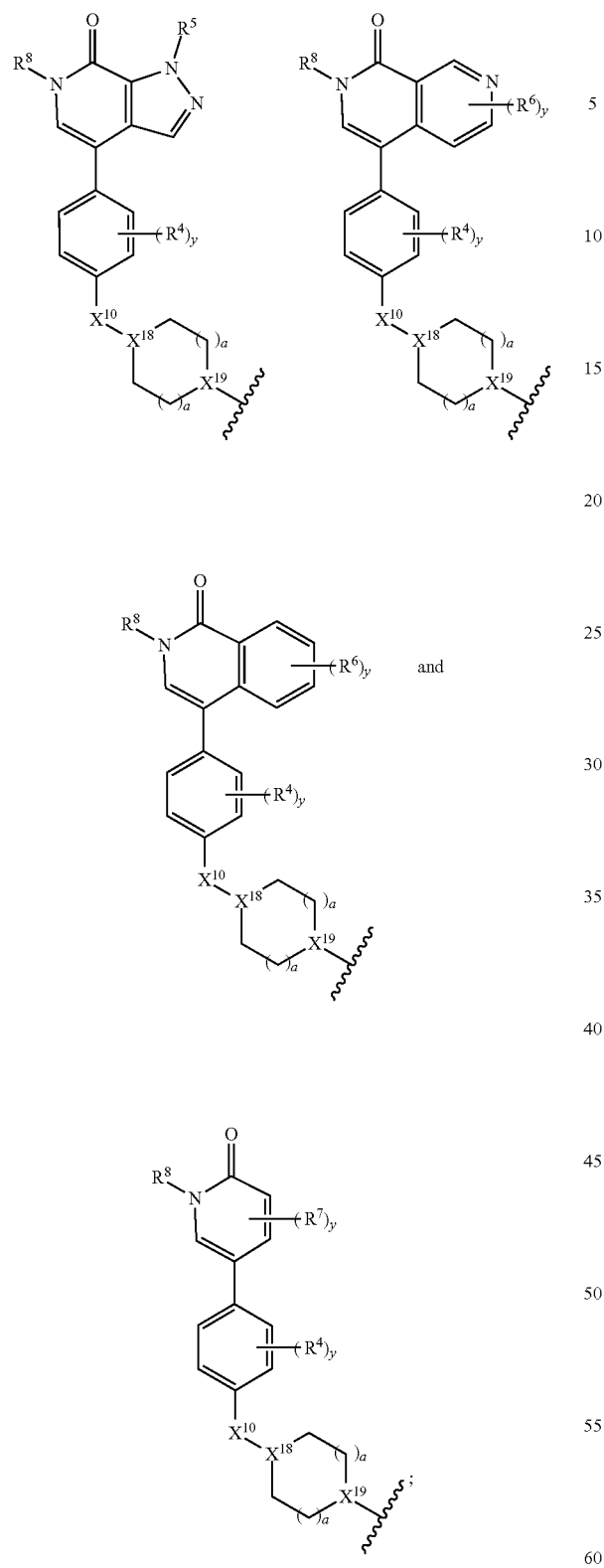
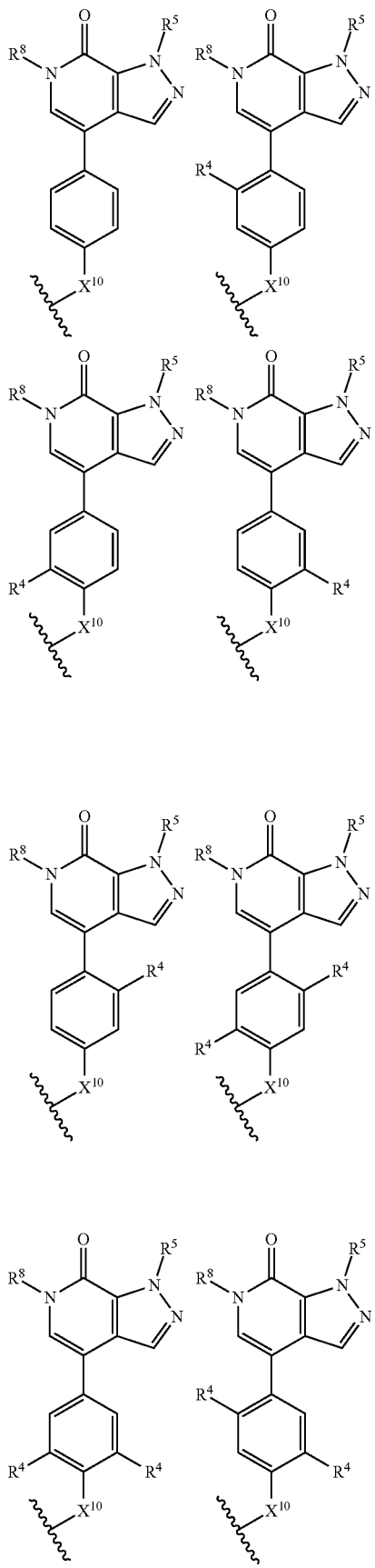
wherein $X^{18}$ and $X^{19}$ are independently selected from —N— and —CH—, and wherein all other variables are as defined herein.
In certain embodiments, B1 is selected from the group consisting of:

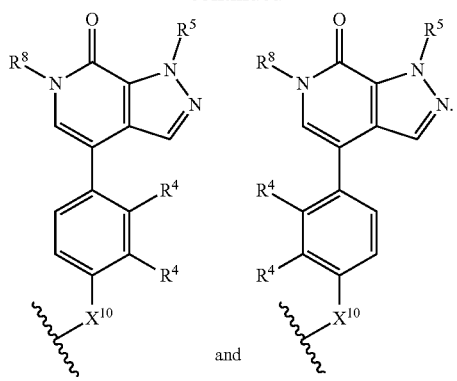
and
In certain embodiments, B1 is selected from the group consisting of:
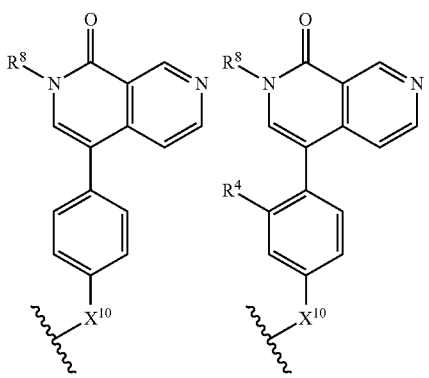
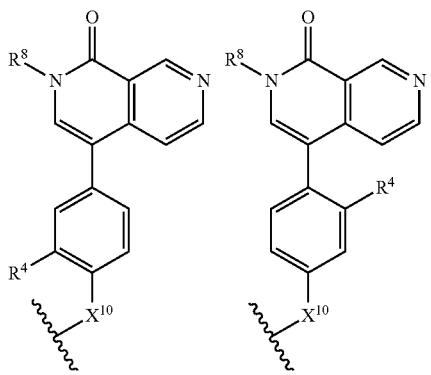
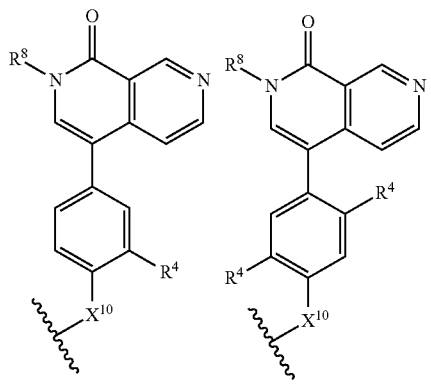
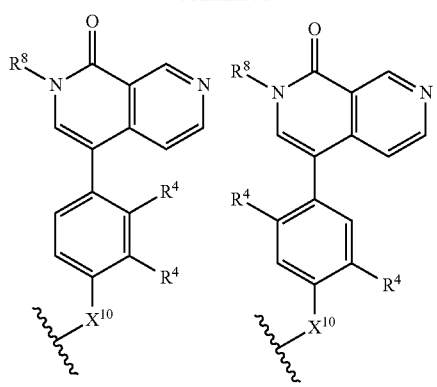
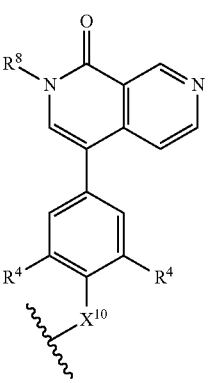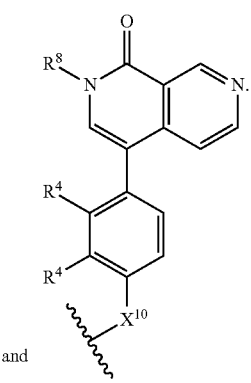
and
In certain embodiments B1 is selected from the group consisting of:
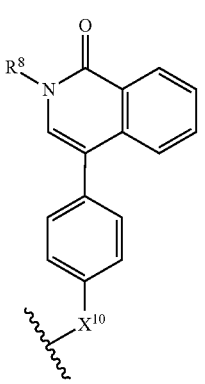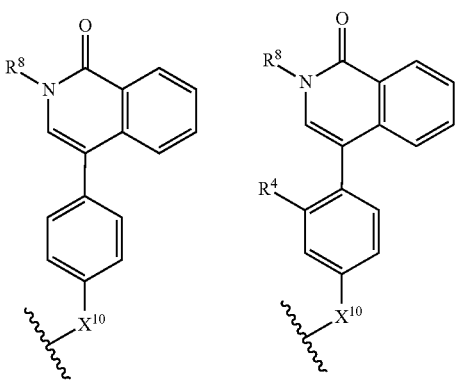
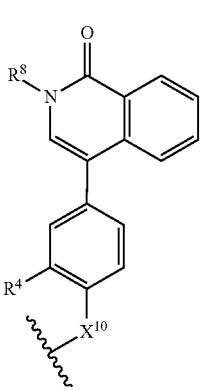

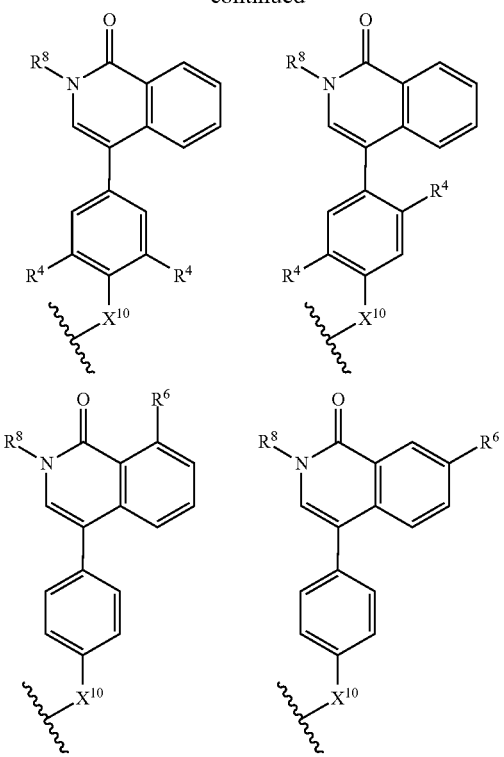
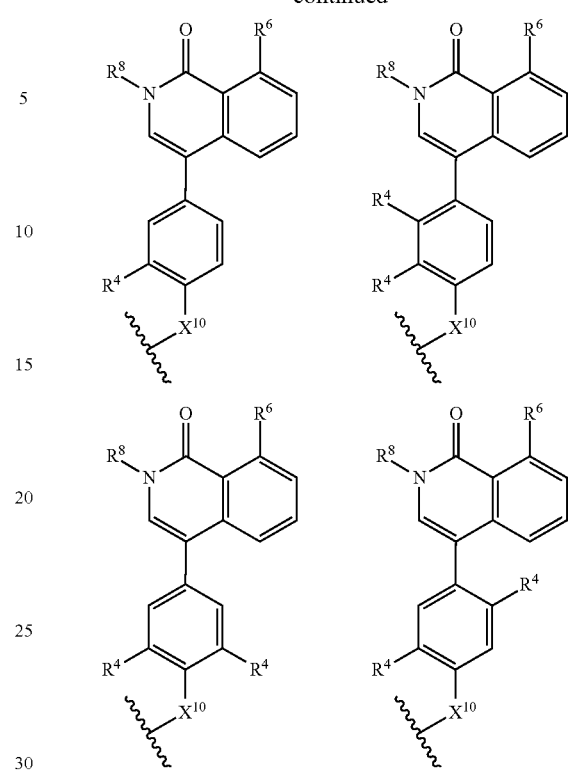
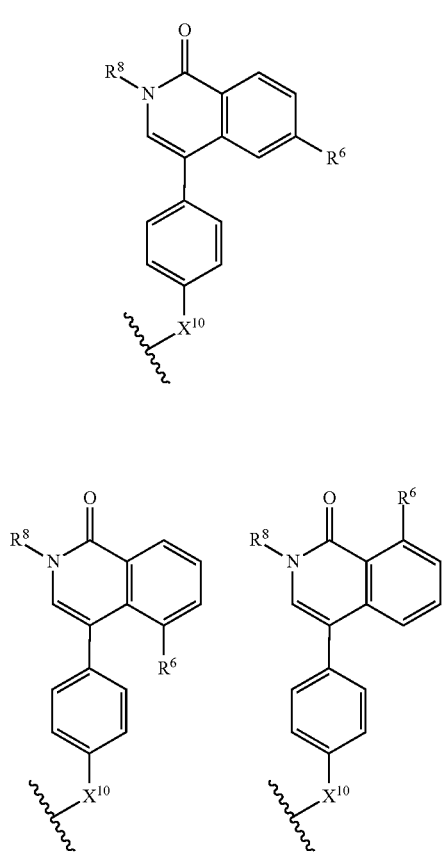

-continued
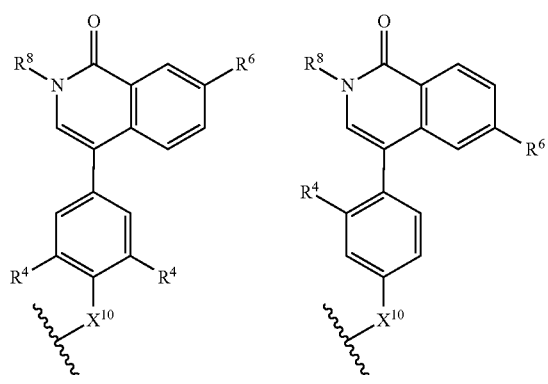
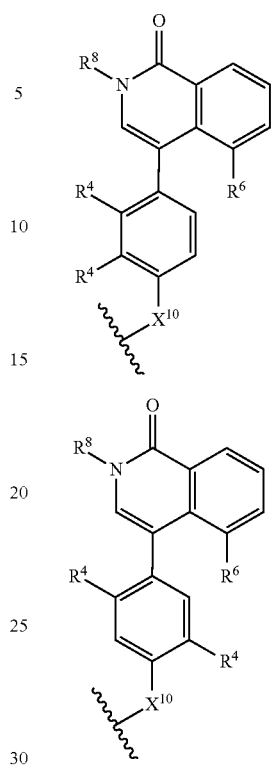
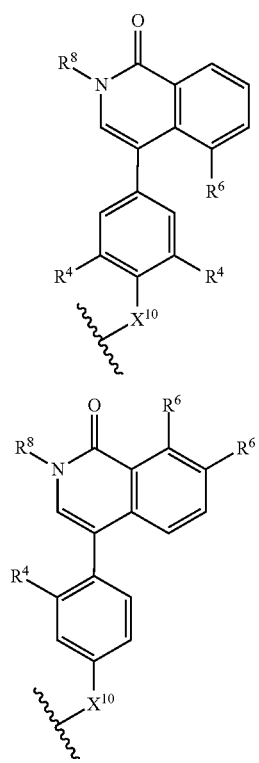
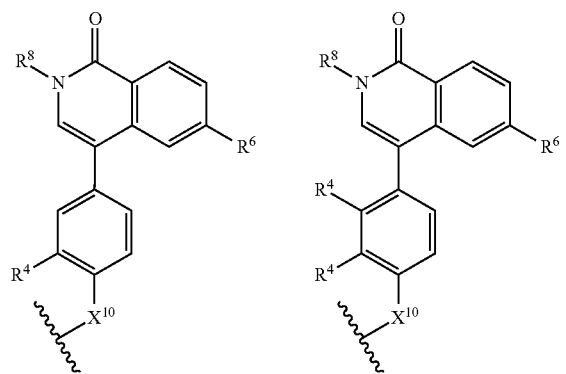
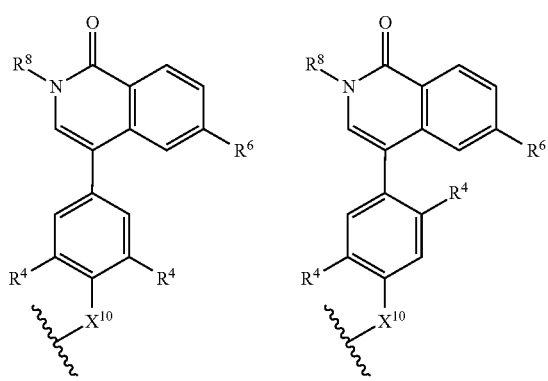
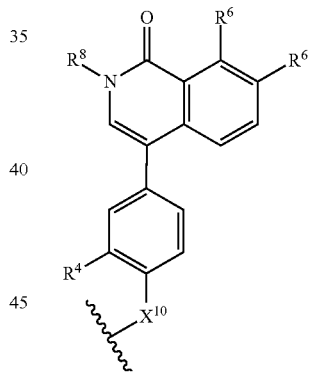
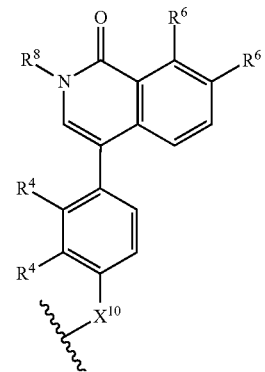
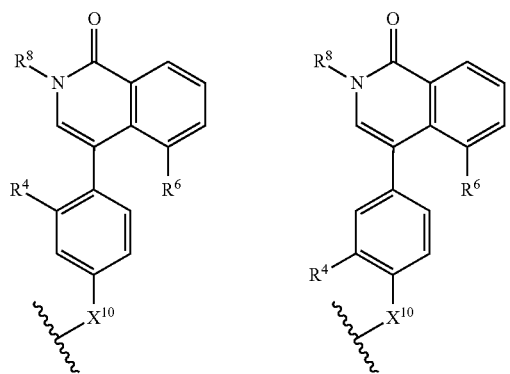
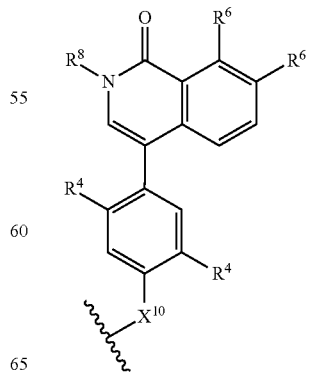
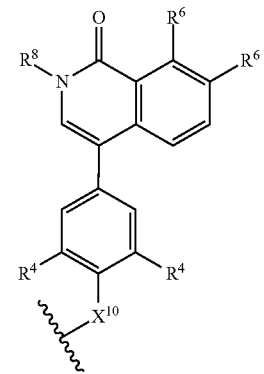

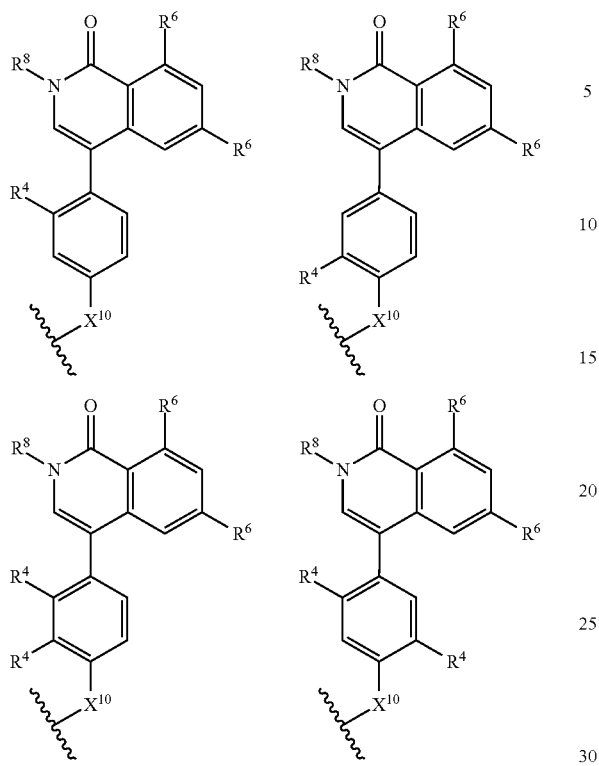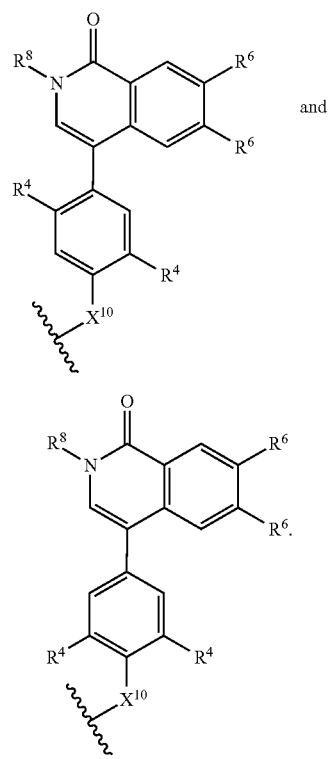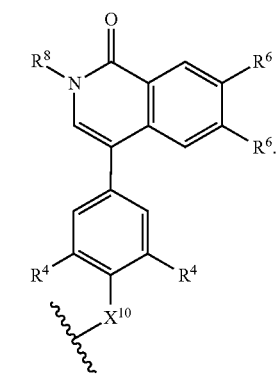
In certain embodiments, B1 is selected from the group consisting of:
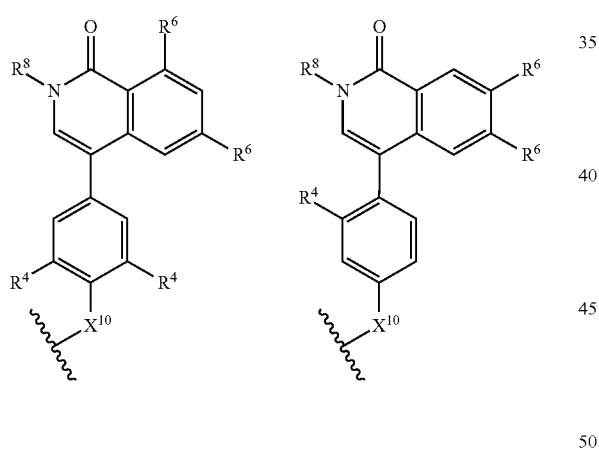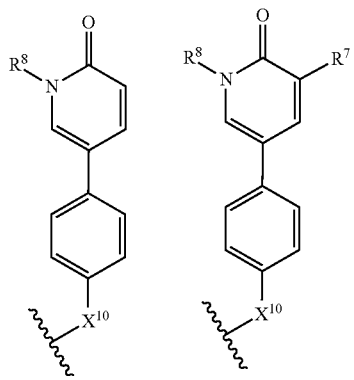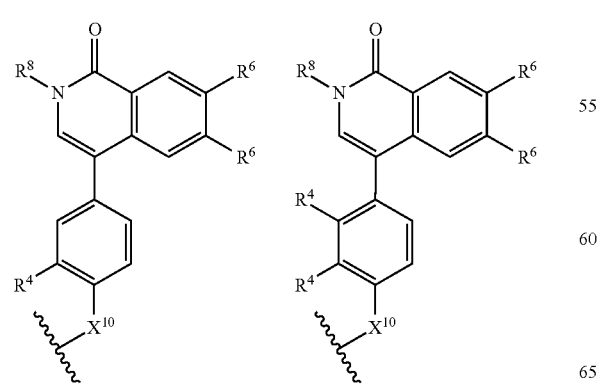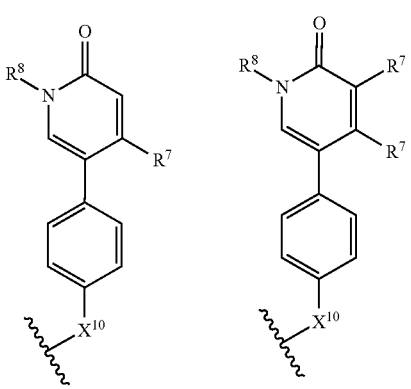

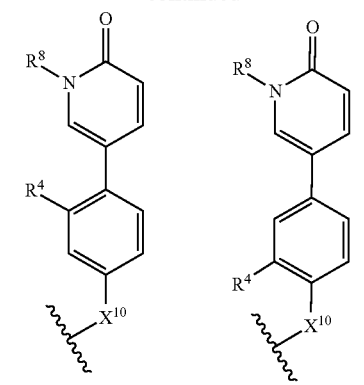
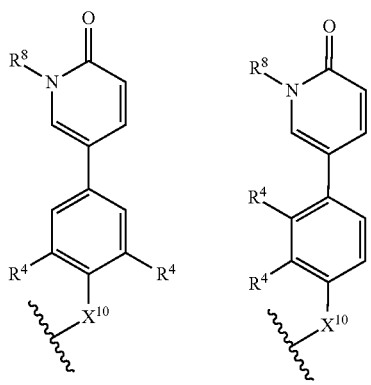
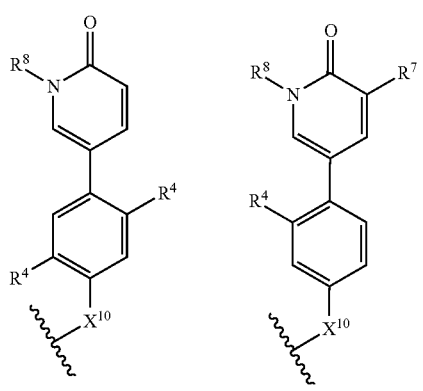
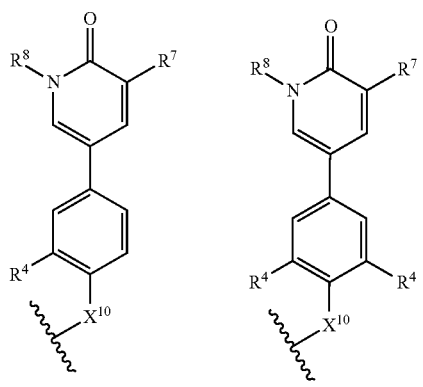
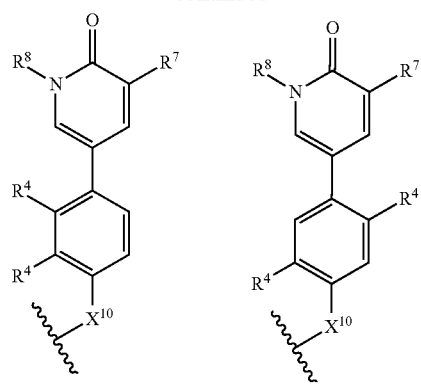
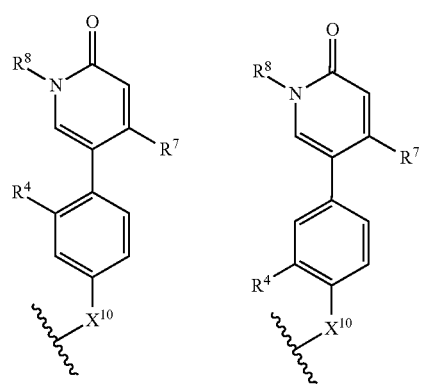
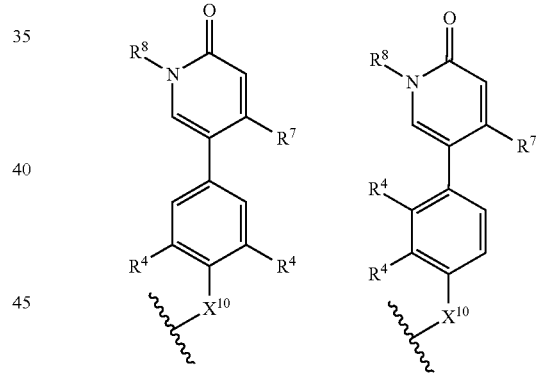

-continued
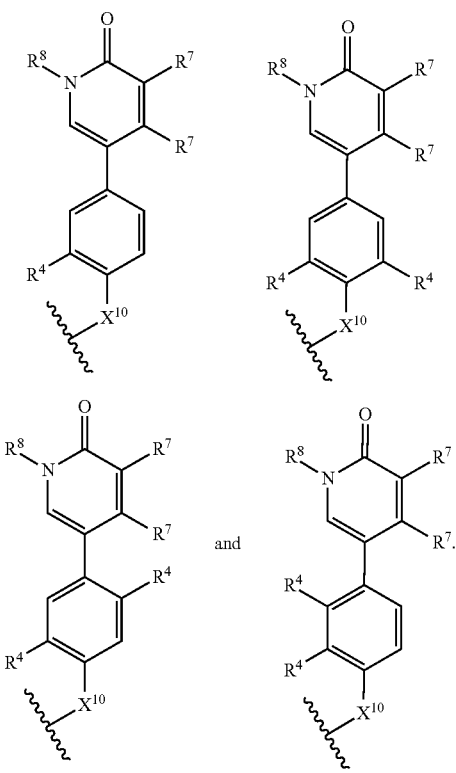
In certain embodiments B² is selected from the group consisting of:
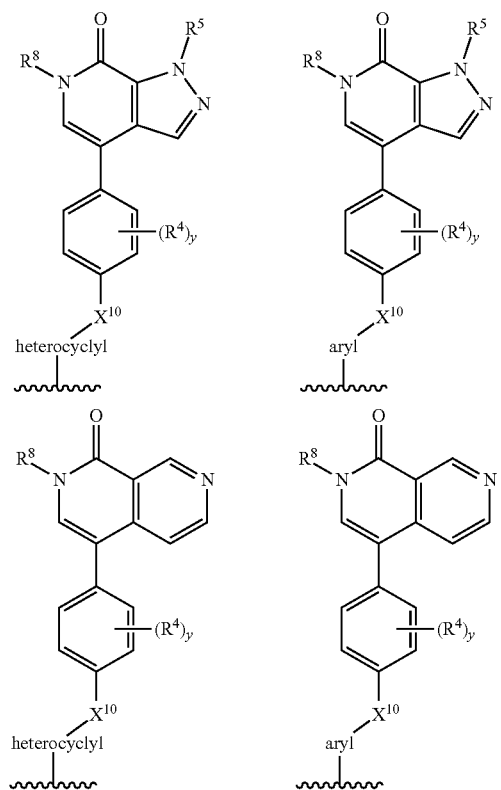
-continued
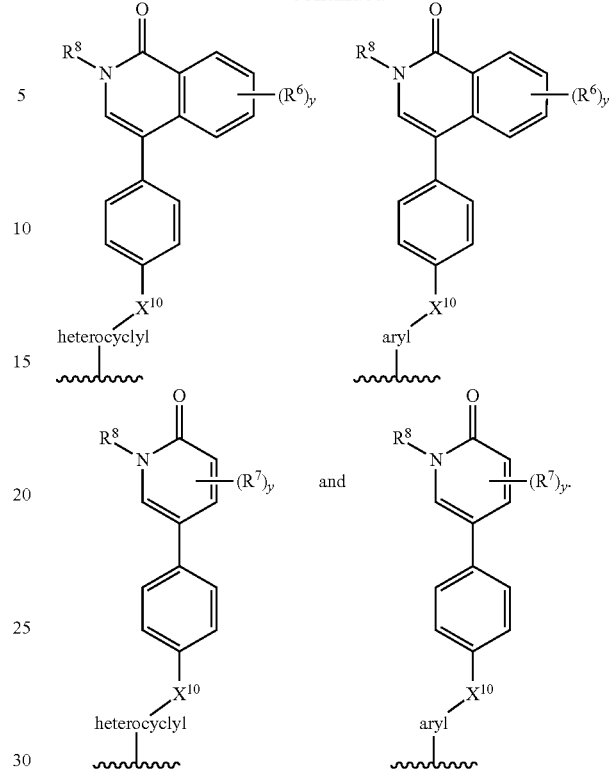
In certain embodiments B² is selected from the group consisting of:
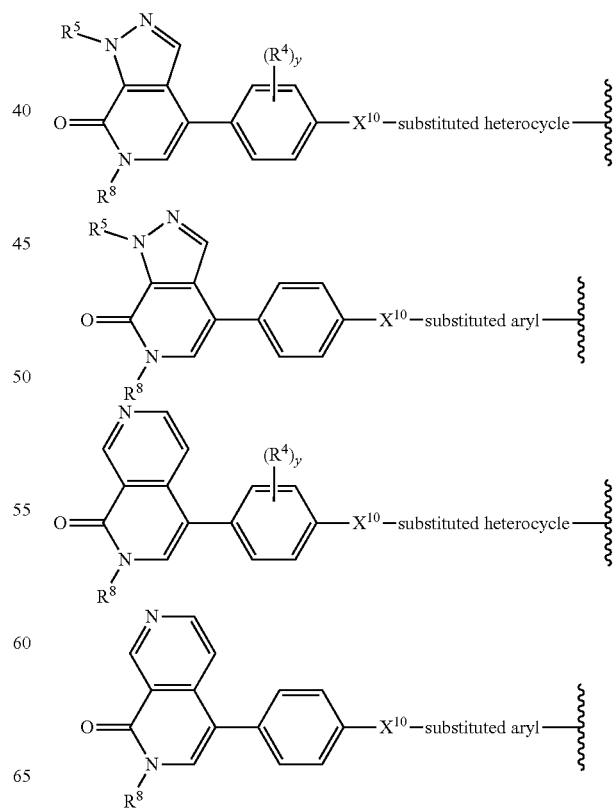

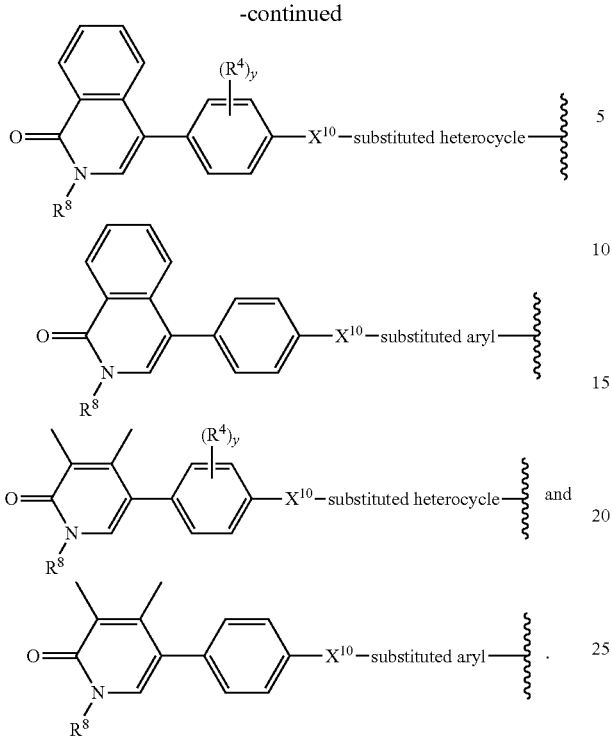
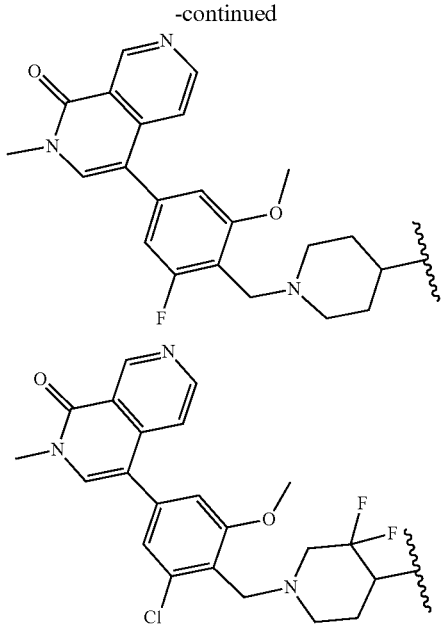
In certain embodiments B2 is selected from:
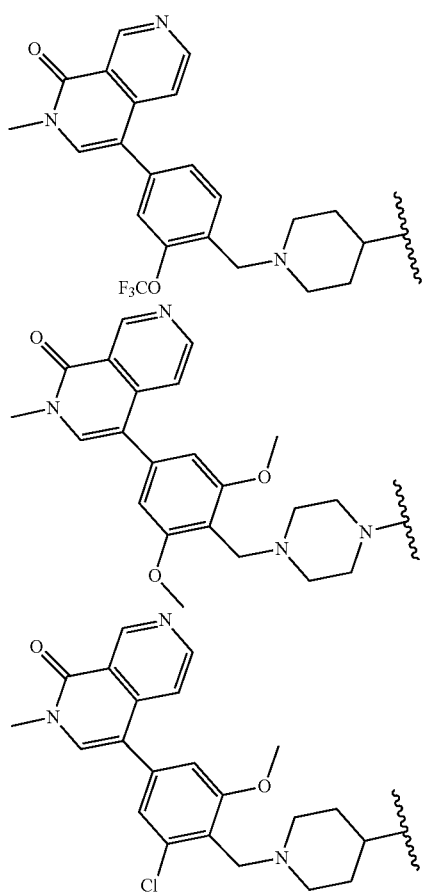
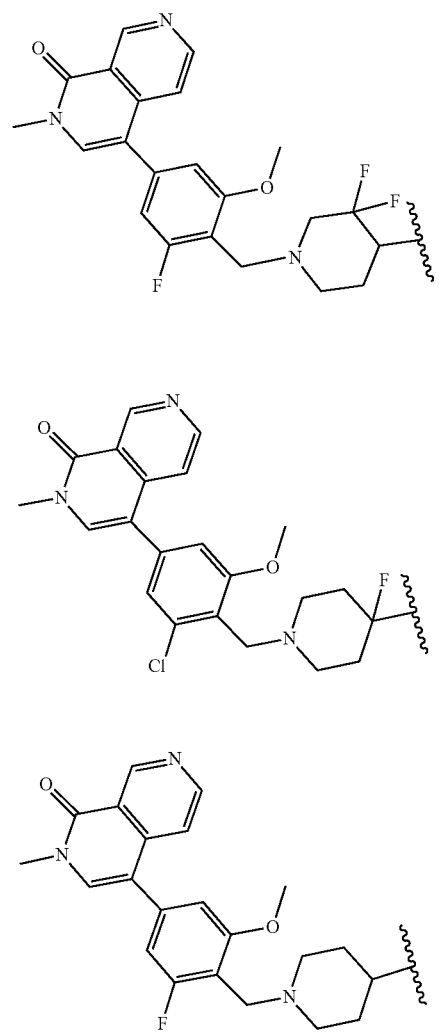

-continued
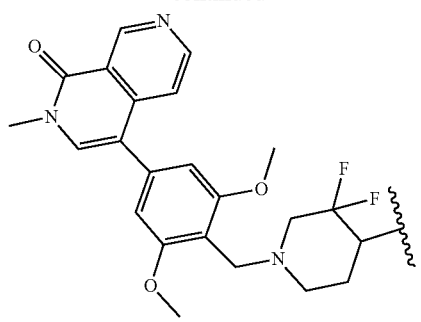
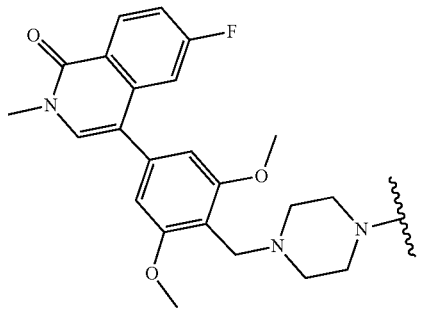
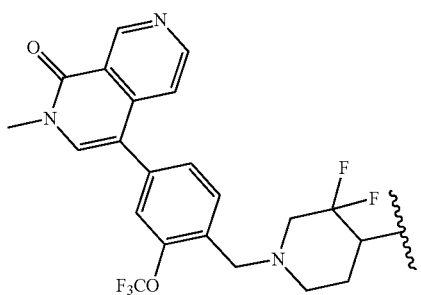
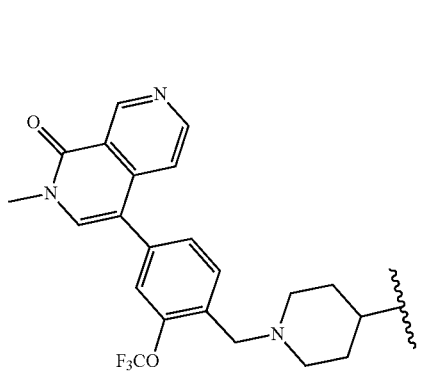
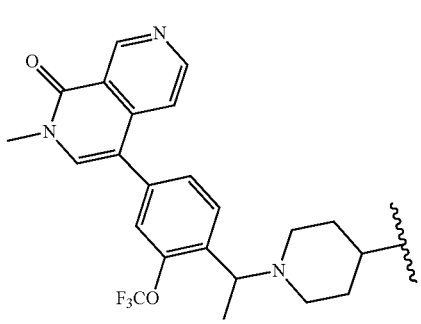
-continued
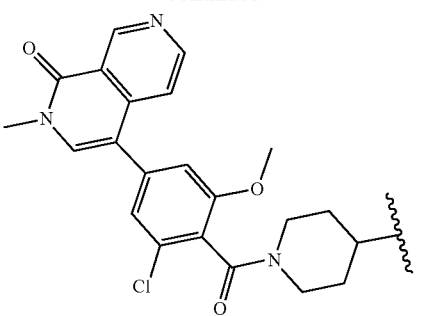
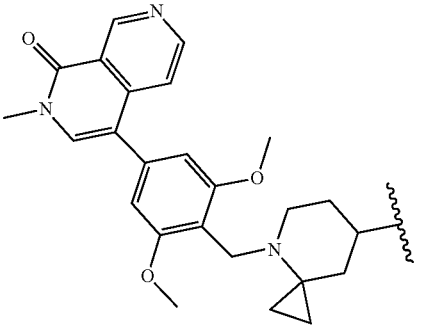
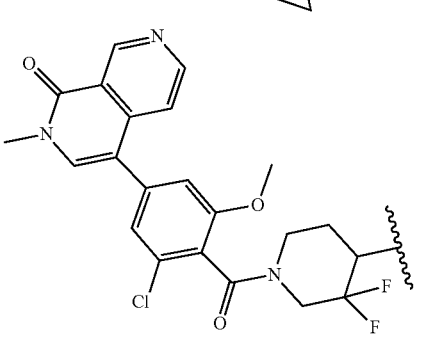
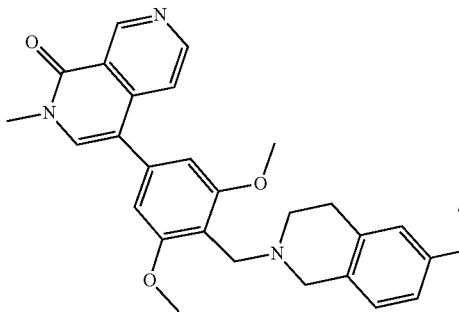
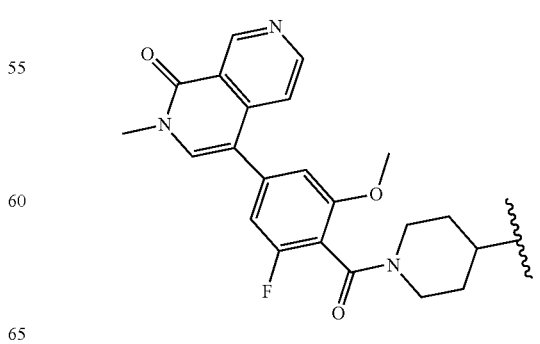

167
-continued
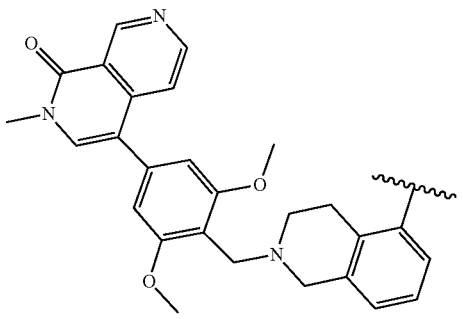
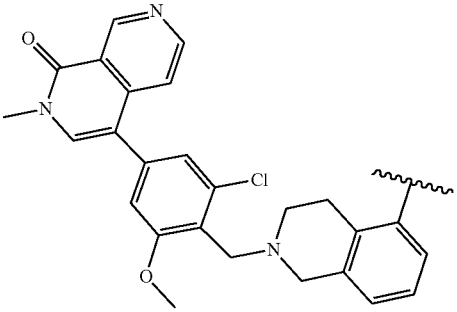
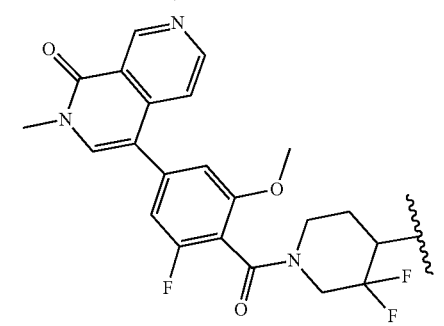
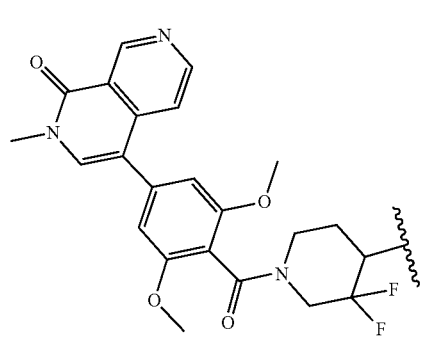
168
-continued
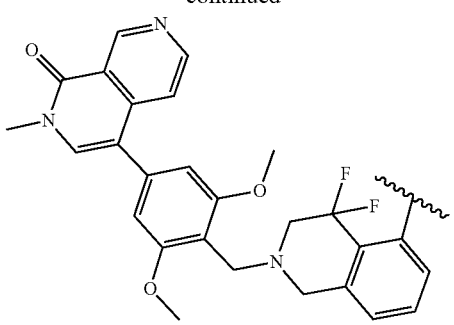
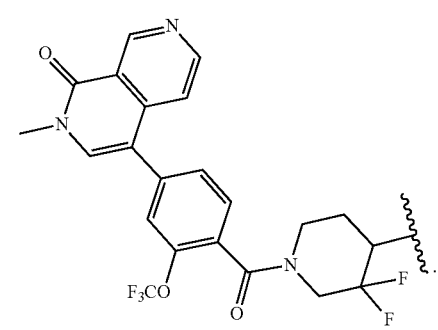
In certain embodiments B2 is selected from:
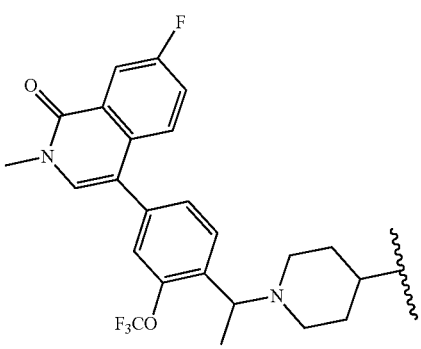
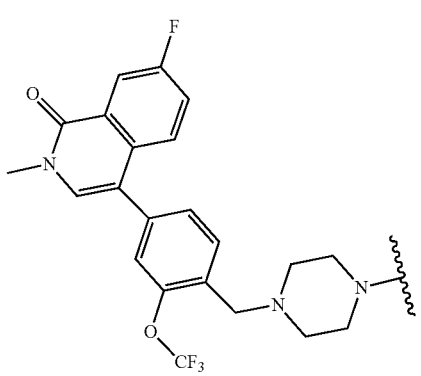

169
-continued
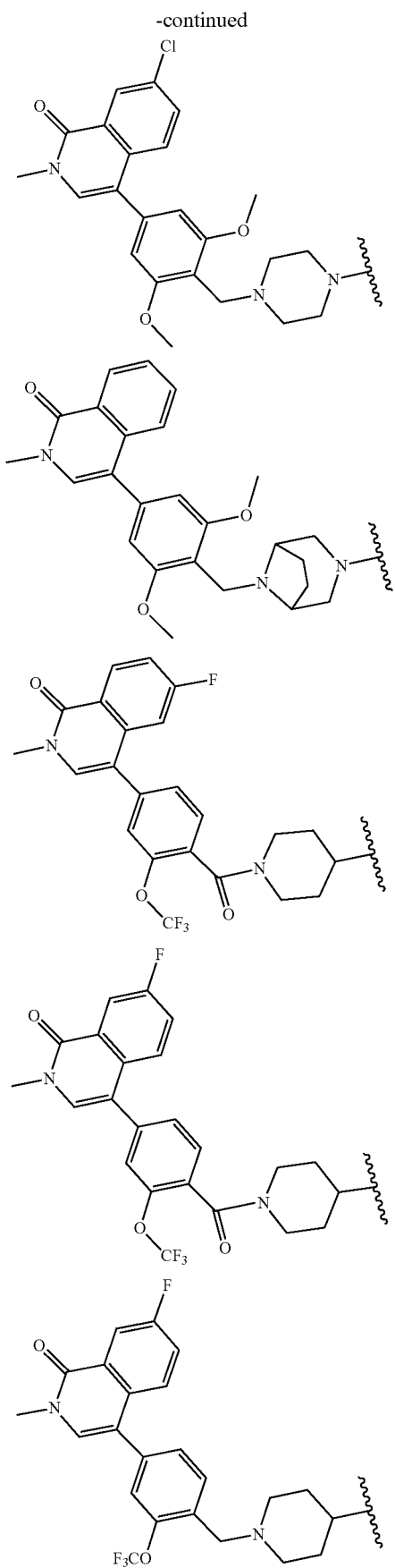
170
-continued
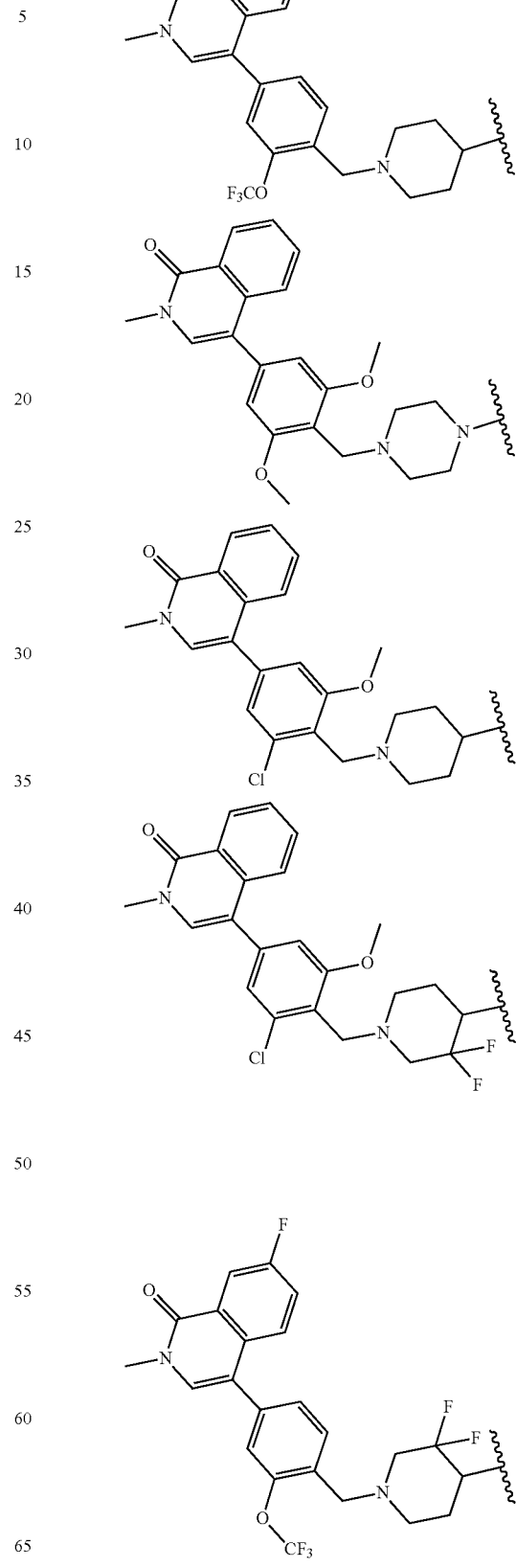

-continued
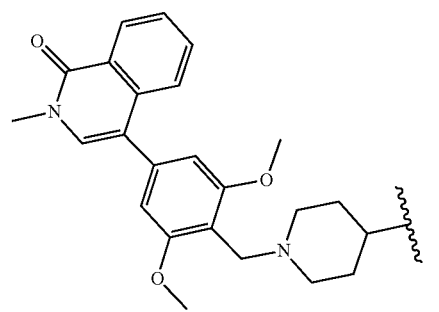
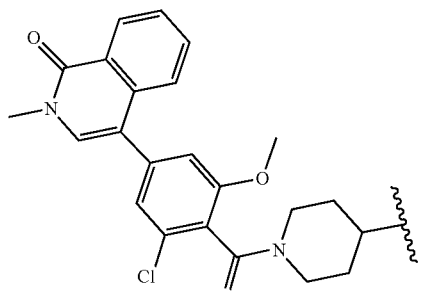
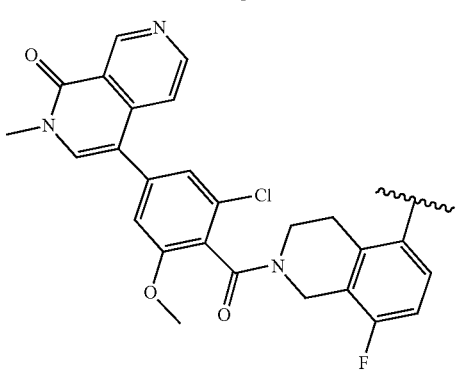
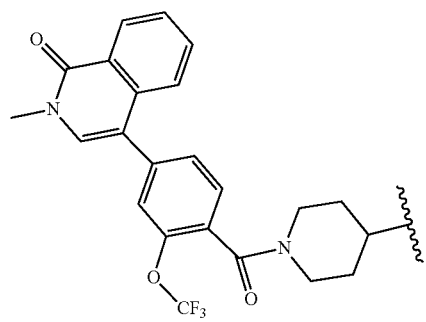
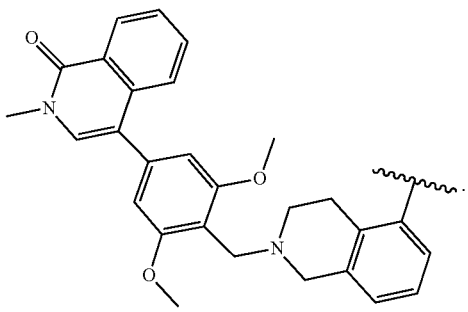
In certain embodiments B2 is selected from:
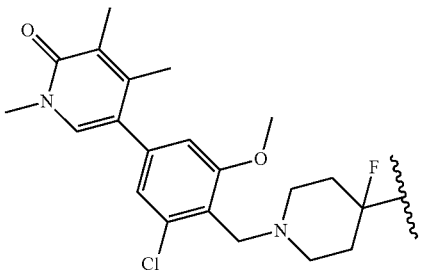
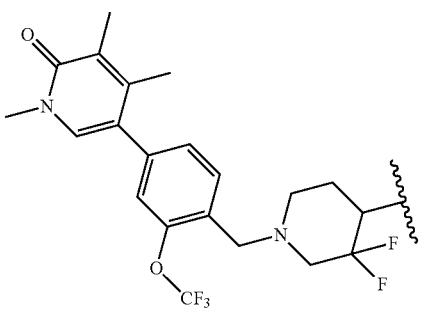
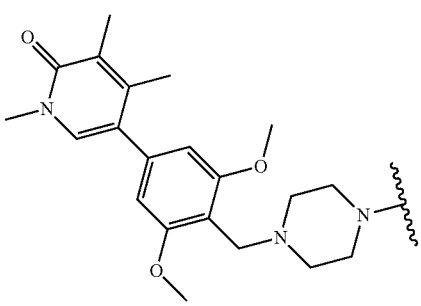
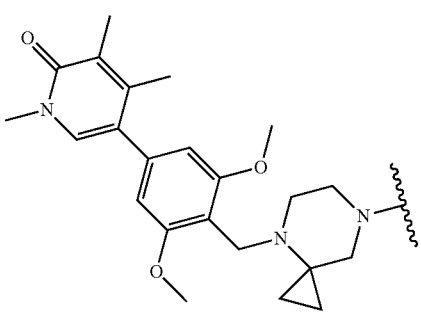
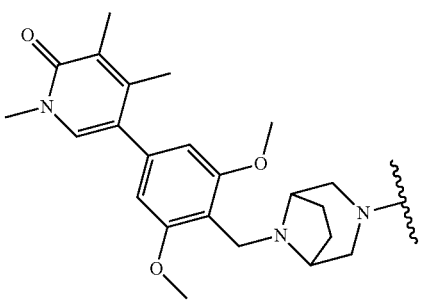

173
-continued
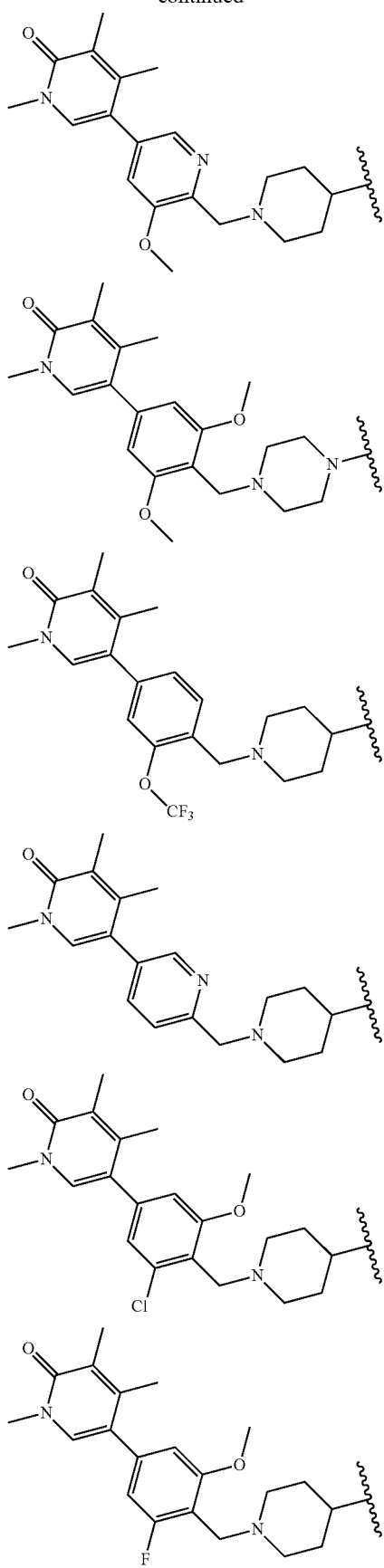
174
-continued
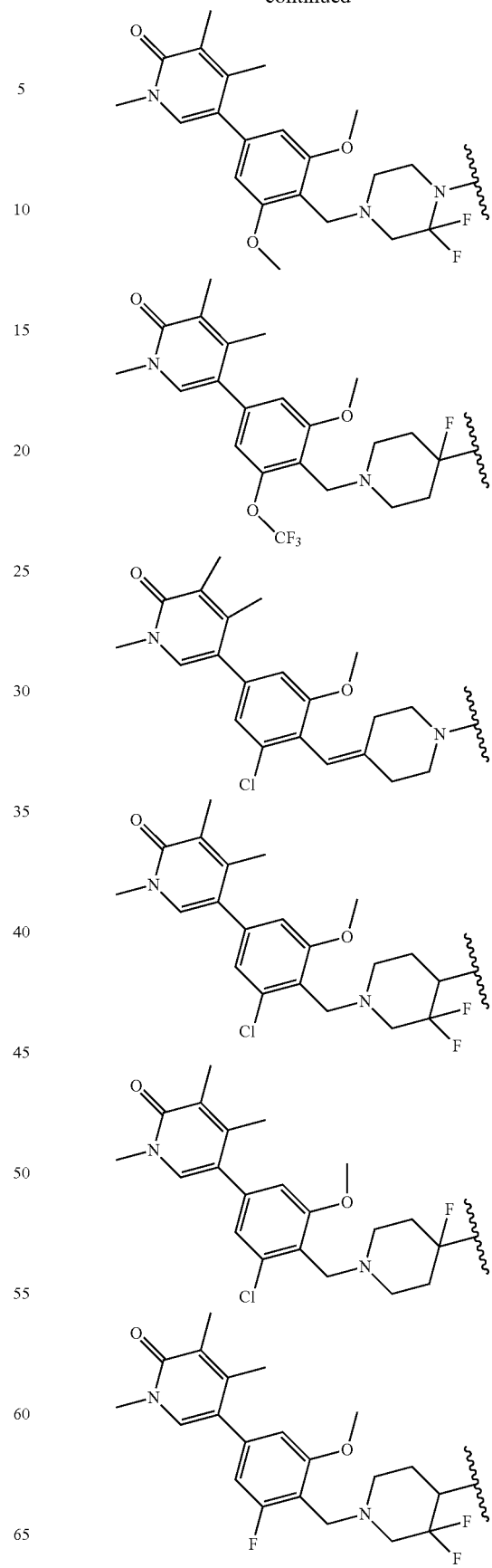

175
-continued
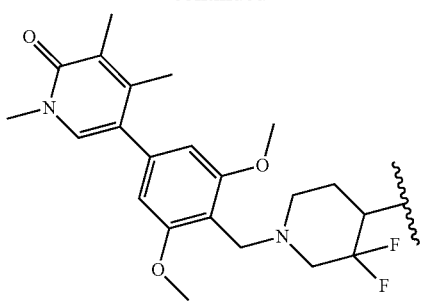
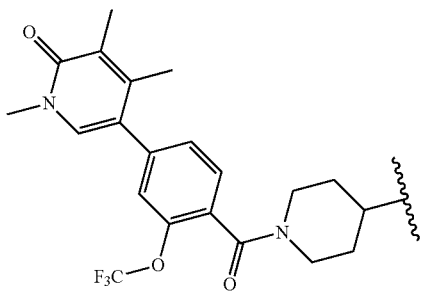
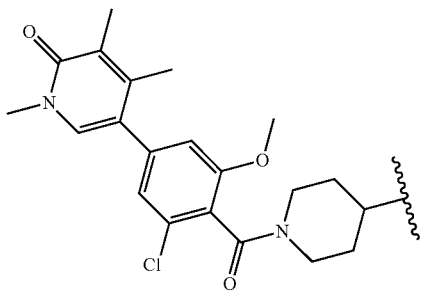
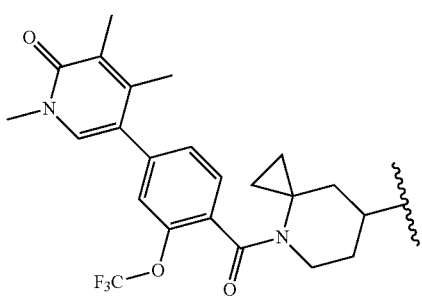
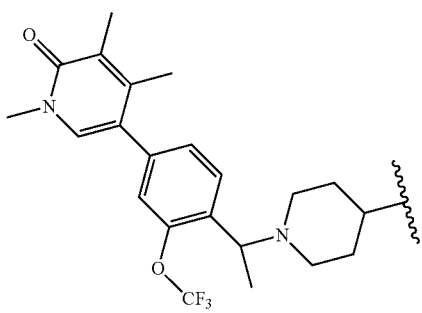
176
-continued
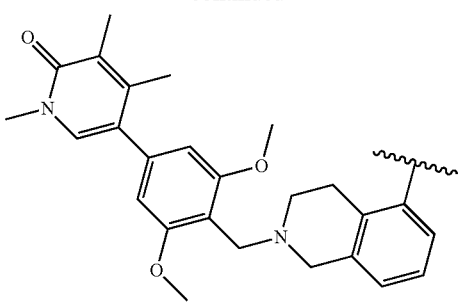
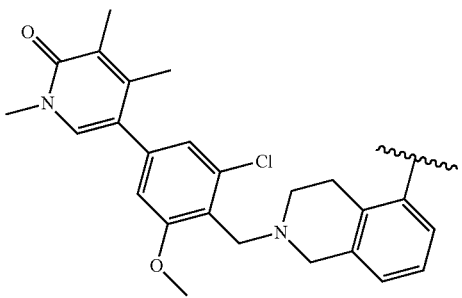
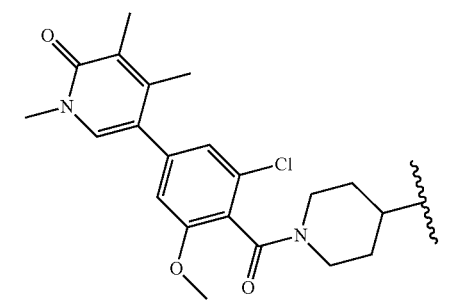
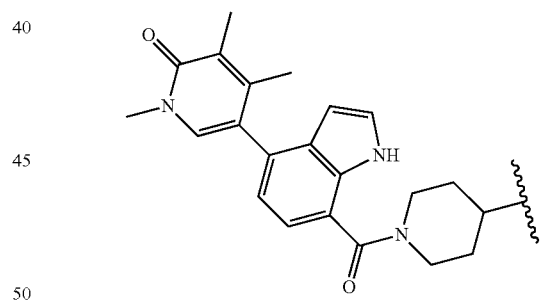
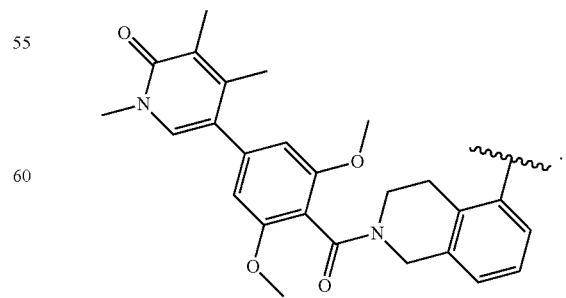

In certain embodiments B2 is selected from:
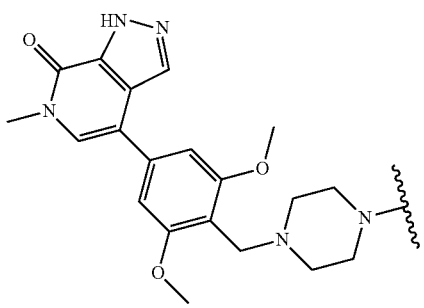
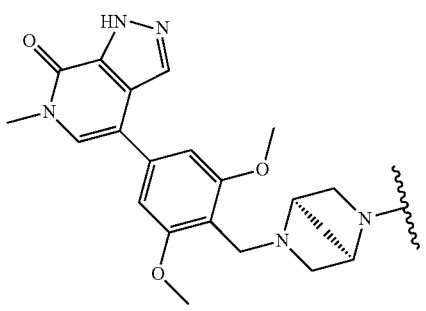
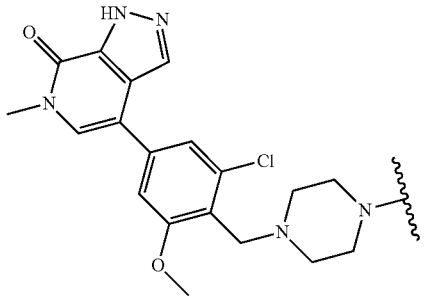
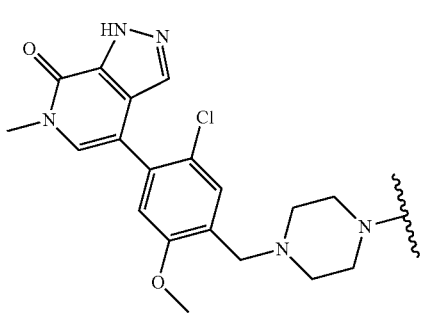
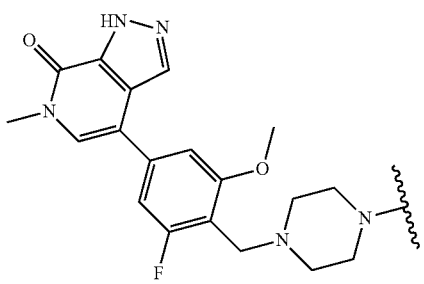
-continued
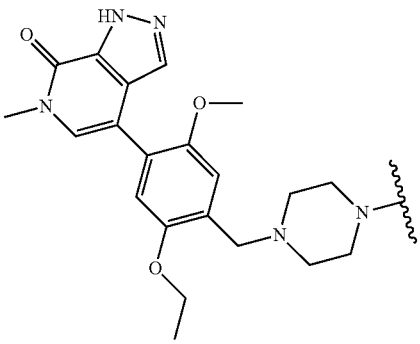
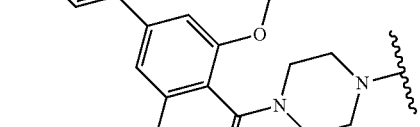
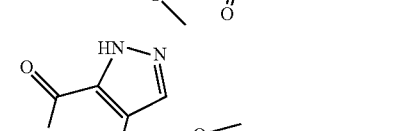

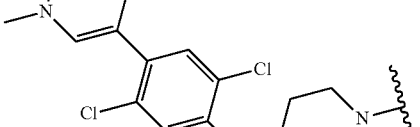

179
-continued
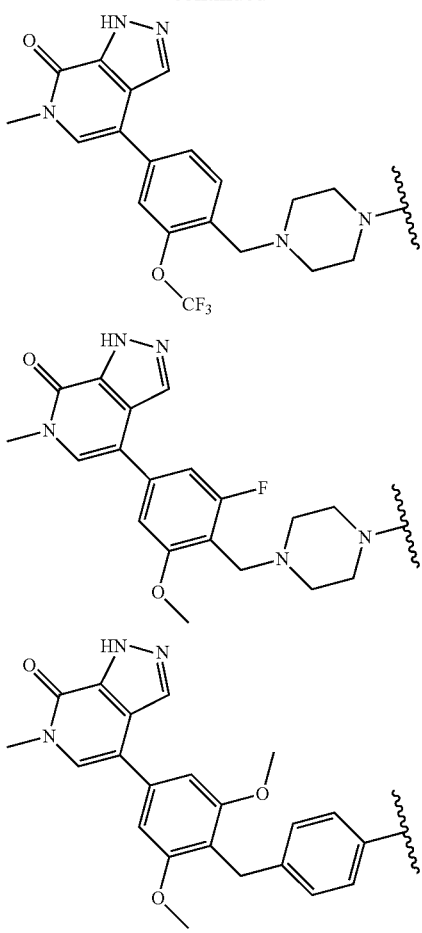
180
-continued
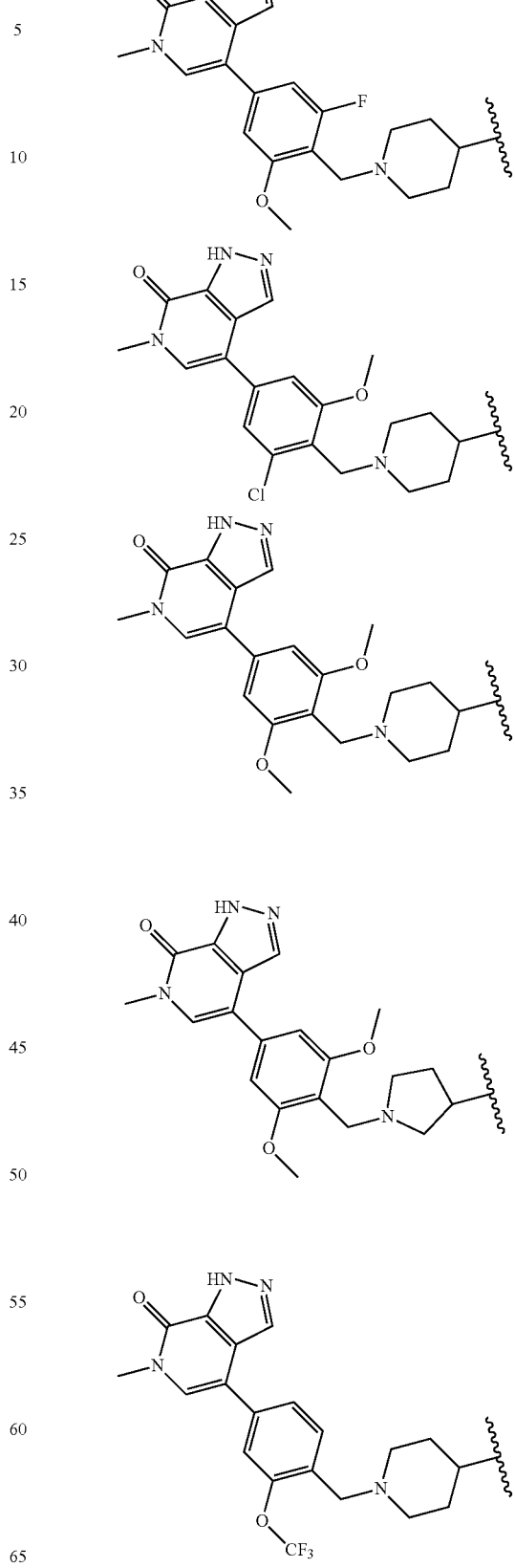

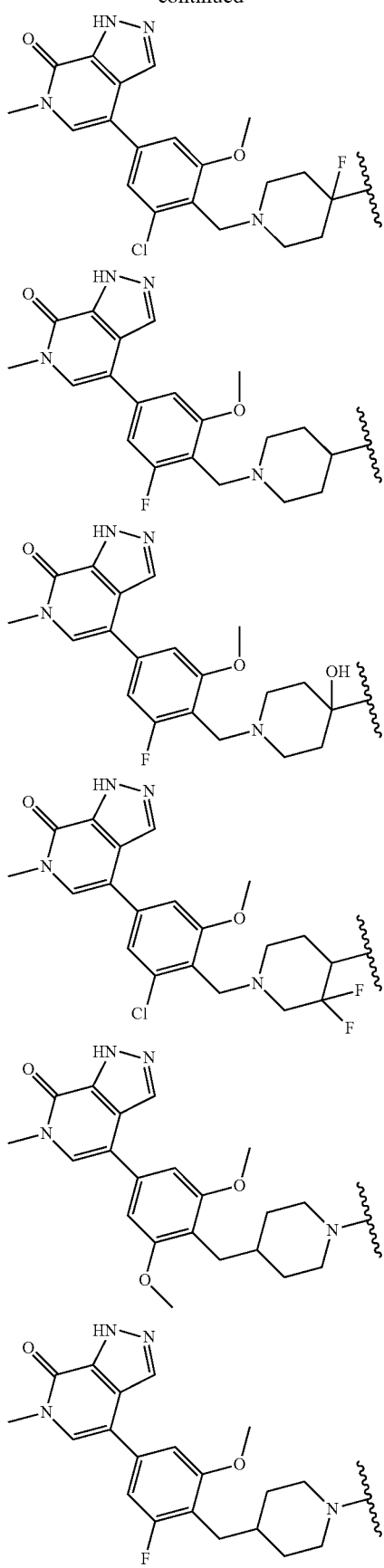
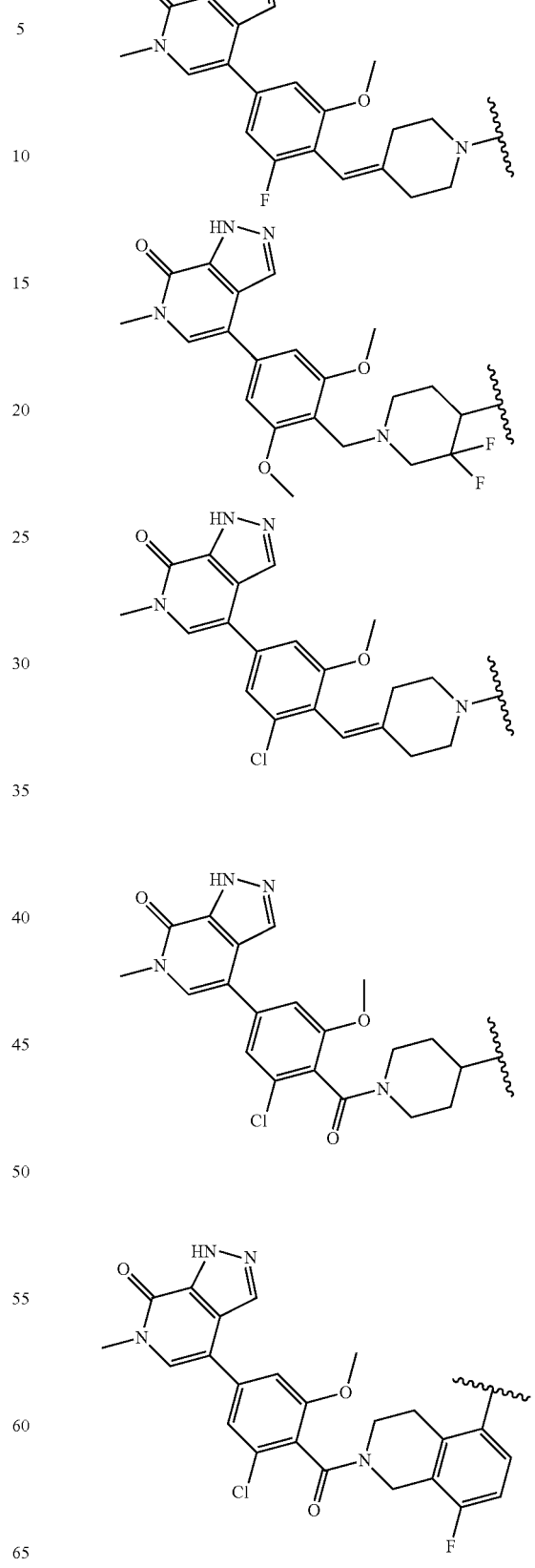

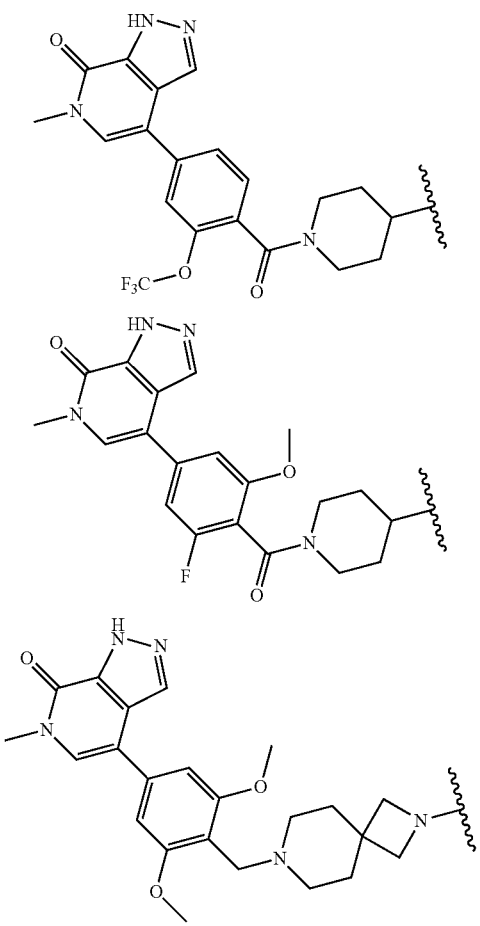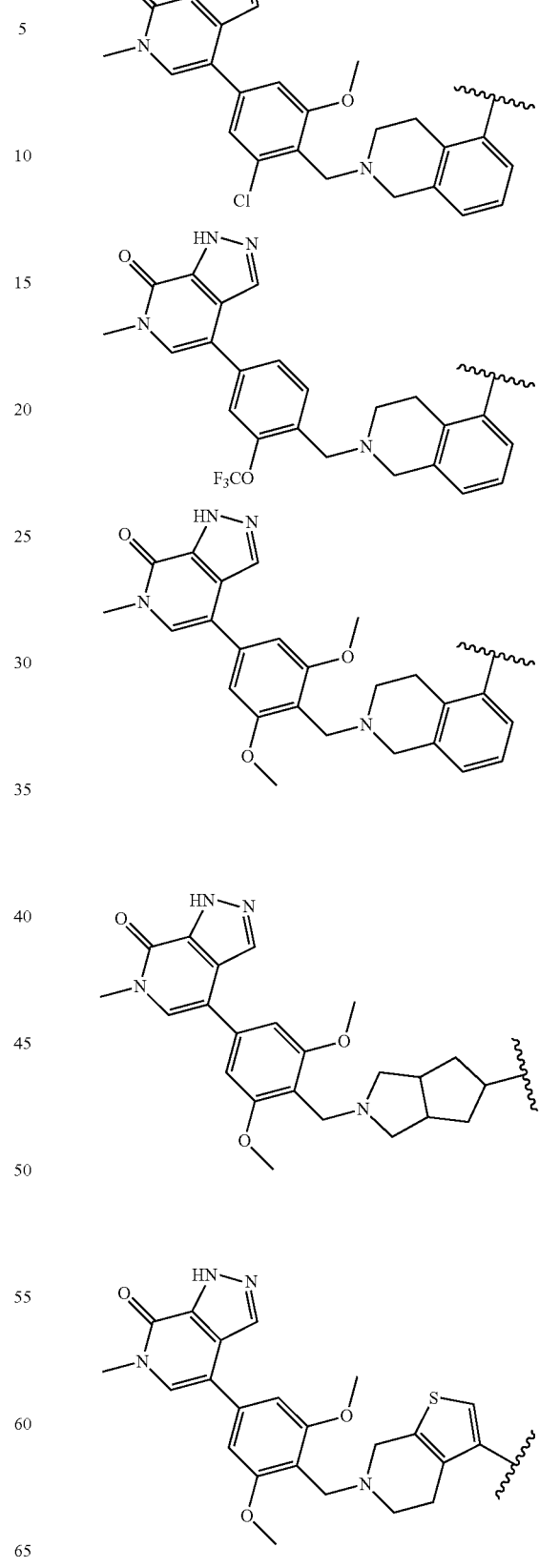

-continued
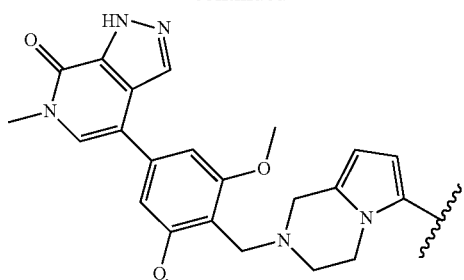
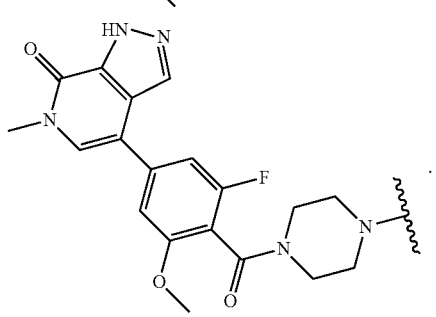
In certain embodiments B1 is
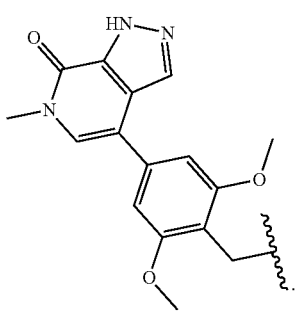 [SMILES: *Cc1c(OC)cc(-c2cn(C)c(=O)c3[nH]ncc23)cc1OC]
In certain embodiments $X^{11}$ is selected from the group consisting of:
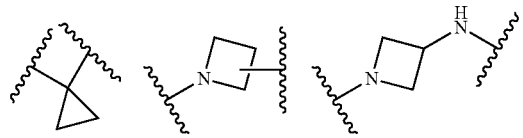
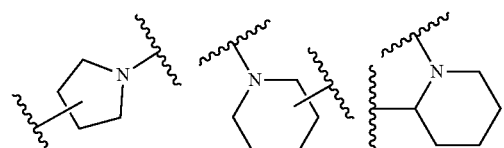
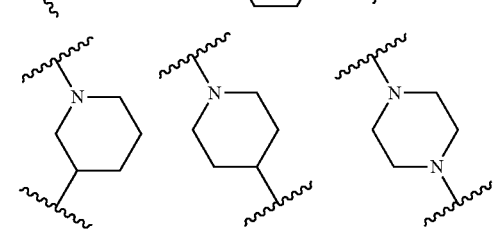
-continued
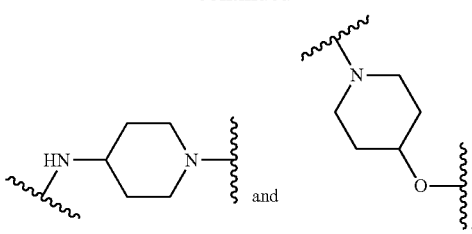
and
In certain embodiments $X^{11}$ is selected from the group consisting of:
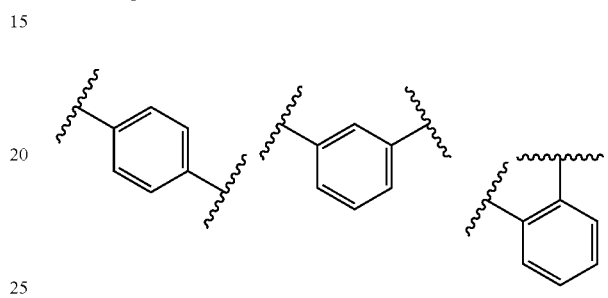
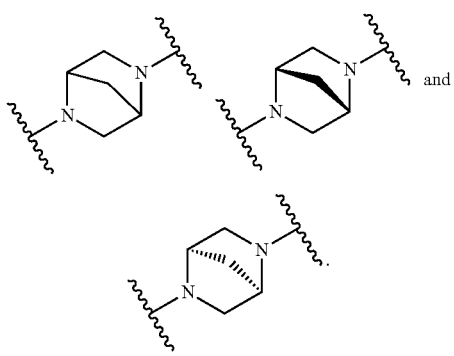
In certain embodiments, $X^{11}$ is selected from the group consisting of:
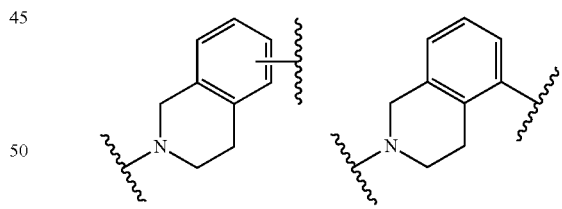
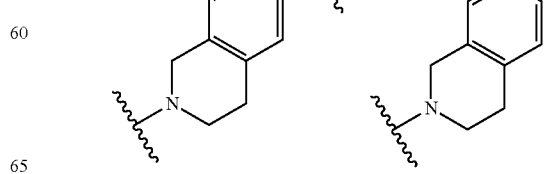

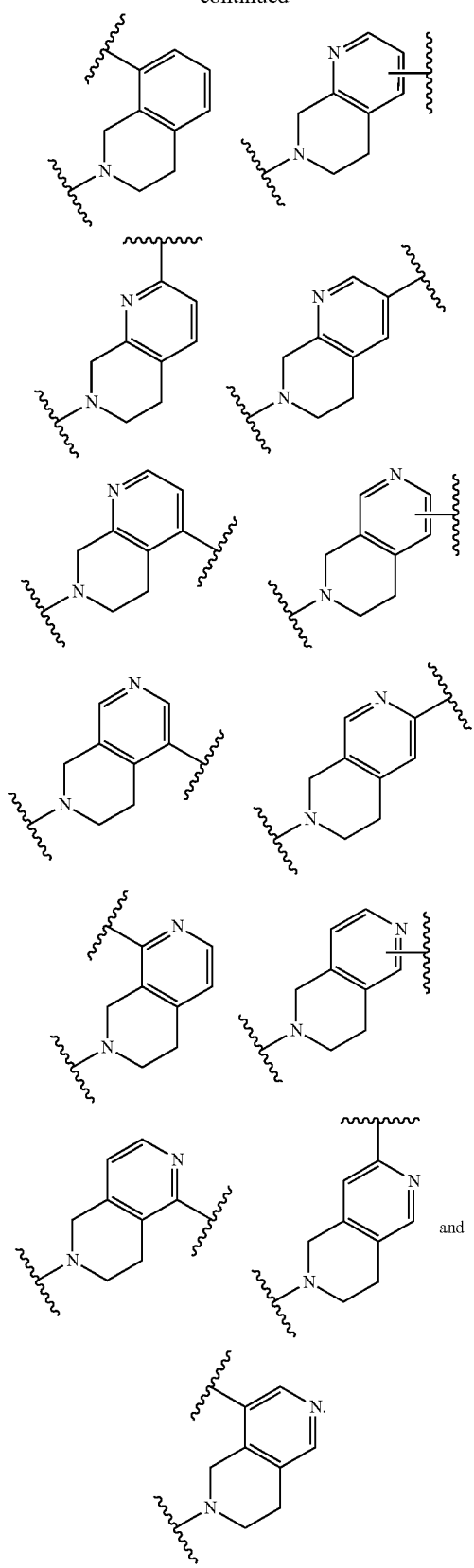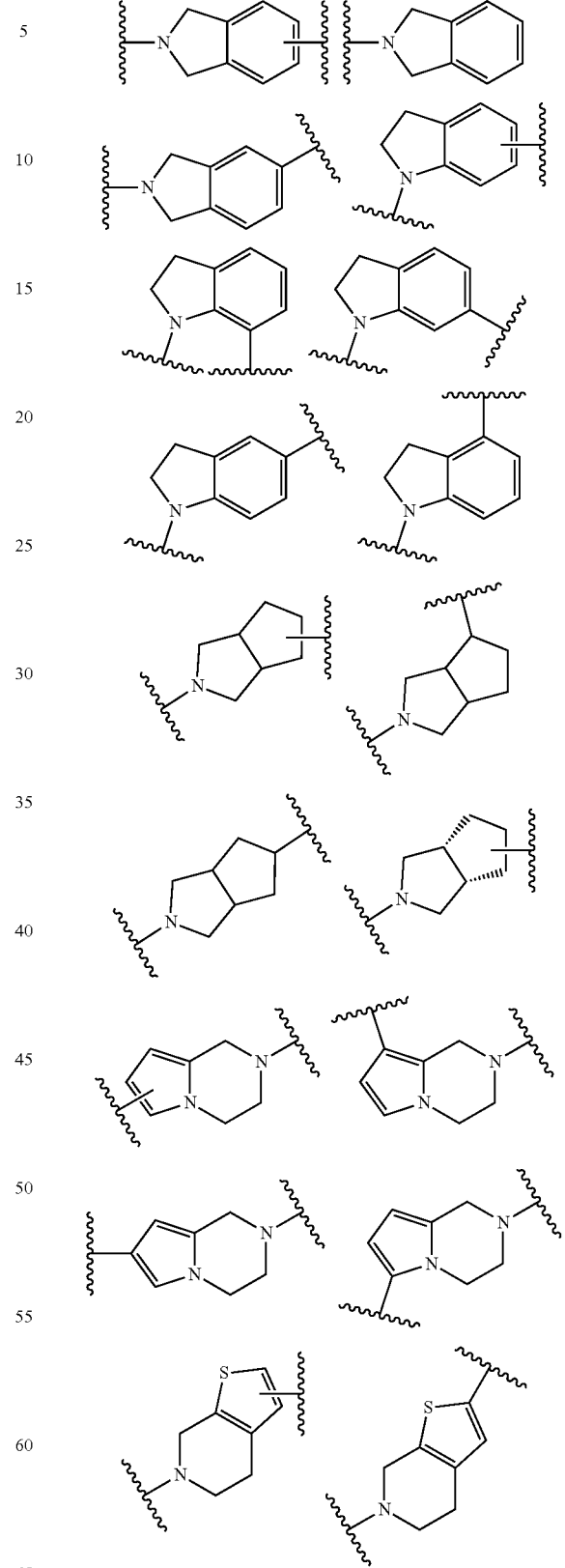
In certain embodiments $X^{11}$ is selected from the group consisting of:

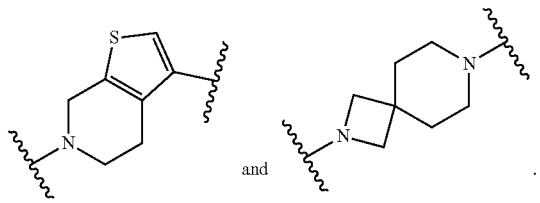 [SMILES: *c1csc2c1CCN(*)C2 ; *N1CCC2(CC1)CN(*)C2]

and

IV. Linkers

A Linker is included in the compounds of Formula I, Formula II, Formula III, Formula IV, Formula V, or Formula VI, or a pharmaceutically acceptable salt thereof as described herein. Linker (L or $L^D$) is a chemically stable bivalent group that attaches an E3 Ligase binding portion to a Targeting Ligand. According to the invention, any desired linker, as described herein, can be used as long as the resulting compound has a stable shelf life for at least 2 months, 3 months, 6 months or 1 year as part of a pharmaceutically acceptable dosage form, and itself is pharmaceutically acceptable.

Linker as described herein can be used in either direction, i.e., either the left end is linked to the E3 Ligase Binding portion and the right end to the Target Linker, or the left end is linked to the Target Linker and the right end is linked to the E3 Ligase Binding portion.

In certain embodiments Linker is a bond.

In certain embodiments, the Linker has a chain of 2 to 14, 15, 16, 17, 18 or 20 or more carbon atoms of which one or more carbons can be replaced by a heteroatom such as O, N, S, or P.

In certain embodiments the chain has 2, 3, 4, 5, 6, 7, 8, 9, 10, 11, 12, 13, 14, 15, 16, 17, 18, 19 or 20 contiguous atoms in the chain. For example, the chain may include 1 or more ethylene glycol units that can be contiguous, partially contiguous or non-contiguous (for example, 2, 3, 4, 5, 6, 7, 8, 9, 10, 11 or 12 ethylene glycol units).

In certain embodiments the chain has at least 1, 2, 3, 4, 5, 6, 7, or 8 contiguous chains which can have branches which can be independently alkyl, aryl, heteroaryl, alkenyl, or alkynyl, aliphatic, heteroaliphatic, cycloalkyl or heterocycle substituents.

In other embodiments, the linker can include or be comprised of one or more of ethylene glycol, propylene glycol, lactic acid and/or glycolic acid. In general, propylene glycol adds hydrophobicity, while propylene glycol adds hydrophilicity. Lactic acid segments tend to have a longer half-life than glycolic acid segments. Block and random lactic acid-co-glycolic acid moieties, as well as ethylene glycol and propylene glycol, are known in the art to be pharmaceutically acceptable and can be modified or arranged to obtain the desired half-life and hydrophilicity. In certain aspects, these units can be flanked or interspersed with other moieties, such as aliphatic, including alkyl, heteroaliphatic, aryl, heteroaryl, heterocycle, cycloalkyl, etc., as desired to achieve the appropriate drug properties.

In certain embodiments, L is a linker selected from:

(LI)

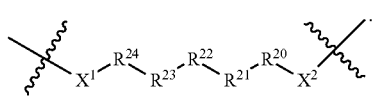

In one aspect, Linker (L) is selected from the group consisting of a moiety of Formula LI, Formula LII, Formula LIII, Formula LIV, Formula LV, Formula LVI, Formula LVII Formula LVIII, Formula IX and Formula LX:

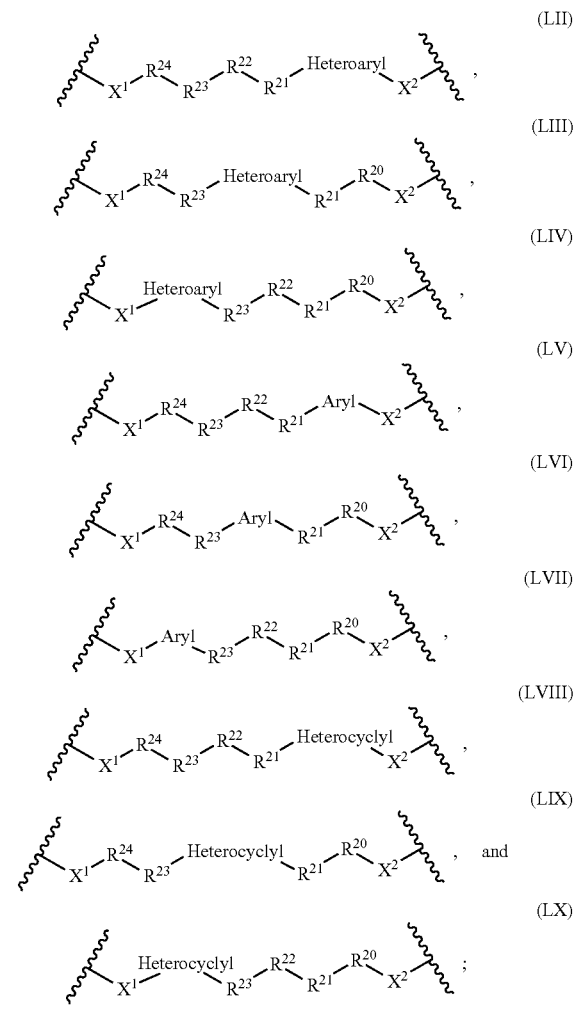

wherein, $X^1$ and $X^2$ are independently at each occurrence selected from bond, heterocycle, $NR^2$, $C(R^2)_2$, O, C(O), and S;

$R^2$ is independently at each occurrence selected from the group consisting of hydrogen, alkyl, aliphatic, heteroaliphatic, heterocycle, aryl, heteroaryl, —C(O)H, —C(O)OH, —C(O)alkyl, —C(O)Oalkyl, —C(O)(aliphatic, aryl, heteroaliphatic or heteroaryl), —C(O)O(aliphatic, aryl, heteroaliphatic, or heteroaryl), alkene, and alkyne;

$R^{20}$, $R^{21}$, $R^{22}$, $R^{23}$, and $R^{24}$ are independently at each occurrence selected from the group consisting of a bond, alkyl, —C(O)—, —C(O)O—, —OC(O)—, —SO$_2$—, —S(O)—, —C(S)—, —C(O)NR$^2$—, —NR$^2$C(O)—, —O—, —S—, —NR$^2$—, —C(R$^{40}$R$^{40}$)—, —P(O)(OR$^{26}$)O—, —P(O)(OR$^{26}$)—, alkene, alkyne, haloalkyl, alkoxy, aryl, heterocycle, aliphatic, heteroaliphatic, heteroaryl, lactic acid, glycolic acid, and carbocycle; each of which is optionally substituted with 1, 2, 3, or 4 substituents independently selected from R$^{40}$;

$R^{26}$ is independently at each occurrence selected from the group consisting of hydrogen, alkyl, arylalkyl, heteroarylalkyl, alkene, alkyne, aryl, heteroaryl, heterocycle, aliphatic and heteroaliphatic; and $R^{40}$ is independently at each occurrence selected from the group consisting of hydrogen, alkyl, alkene, alkyne, fluoro, bromo, chloro, hydroxyl, alkoxy, azide, amino, cyano, —NH(aliphatic, including alkyl), —N(aliphatic, including alkyl)$_2$, —NHSO$_2$(aliphatic, including alkyl), —N(aliphatic, including alkyl)SO$_2$alkyl, —NHSO$_2$(aryl, heteroaryl or heterocycle), —N(alkyl)SO$_2$(aryl, heteroaryl or heterocycle), —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, aryl, heteroaryl, heterocycle, and cycloalkyl.

In certain embodiments, $L^D$ is a linker selected from:

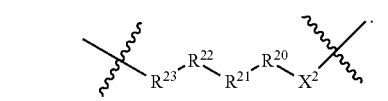

In one aspect, Linker ($L^D$) is selected from the group consisting of a moiety of Formula LDI, Formula LDII, Formula LDIII, Formula LDIV, Formula LDV, Formula LDVI, and Formula LDVII:

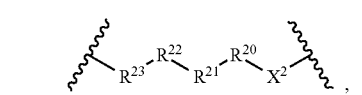 (LDI)

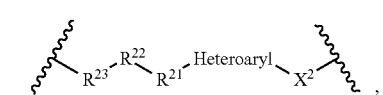 (LDII)

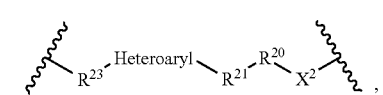 (LDIII)

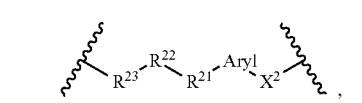 (LDIV)

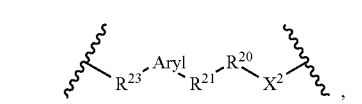 (LDV)

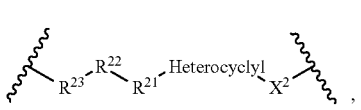 (LDVI), and

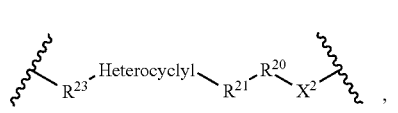 (LDVII)

wherein all variables are described herein.

The following are non-limiting examples of Linkers (L or $L^D$) that can be used in this invention. Based on this elaboration, those of skill in the art will understand how to use the full breadth of Linkers that will accomplish the goal of the invention.

Non-limiting examples of Formula LI, Formula LII, Formula LIII, Formula LIV, Formula LV, Formula LVI, or Formula LVII include:

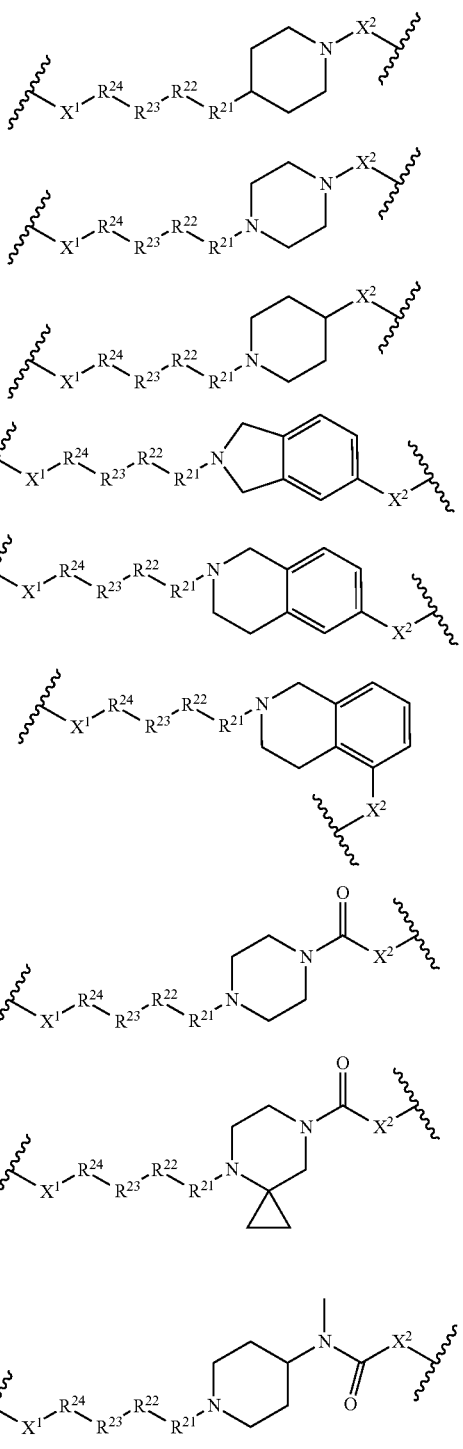

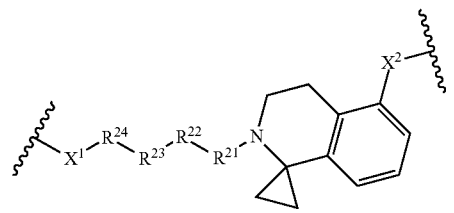

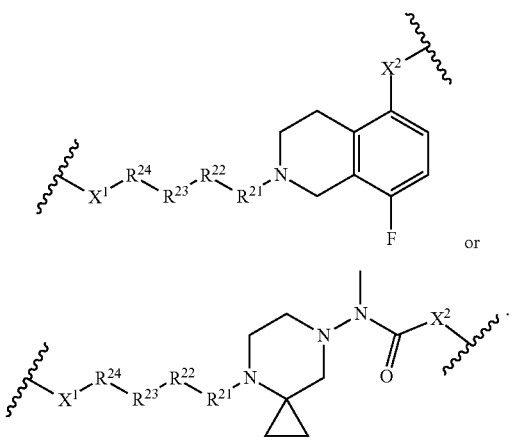
Non-limiting examples of Formula LDI, Formula LDII, Formula LDIII, Formula LDIV, Formula LDV, Formula LDVI, or Formula LDVII: include:
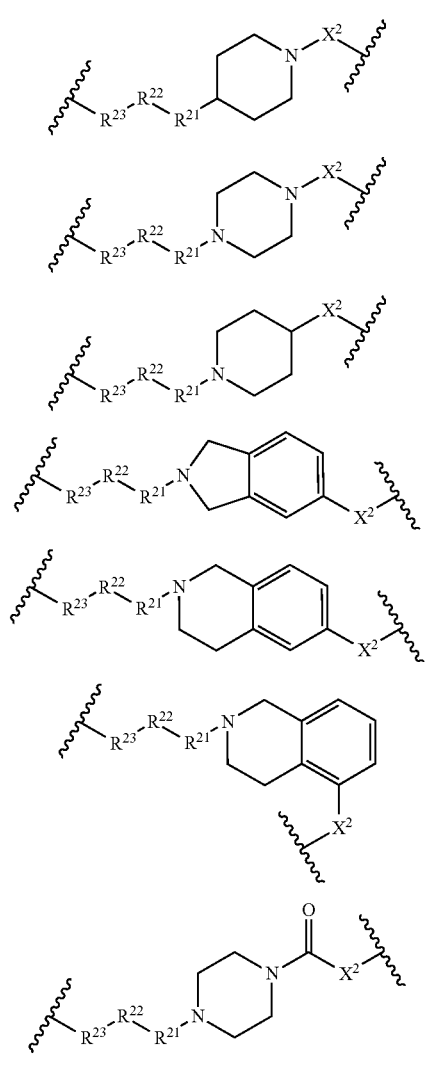
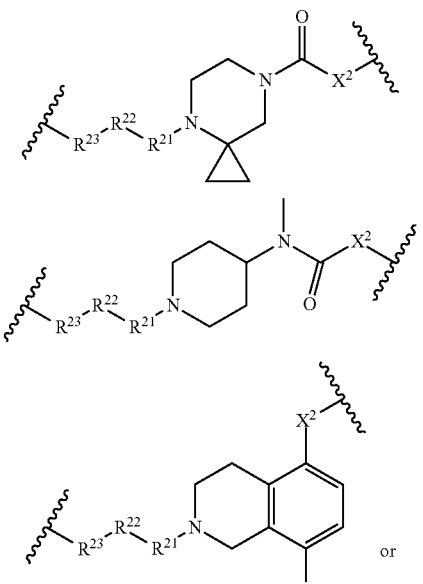
In one embodiment $X^1$ is attached to the B. In another embodiment $X^2$ is attached to the B.
Non-limiting examples of moieties of $R^{20}$, $R^{21}$, $R^{22}$, $R^{23}$, and $R^{24}$ include:
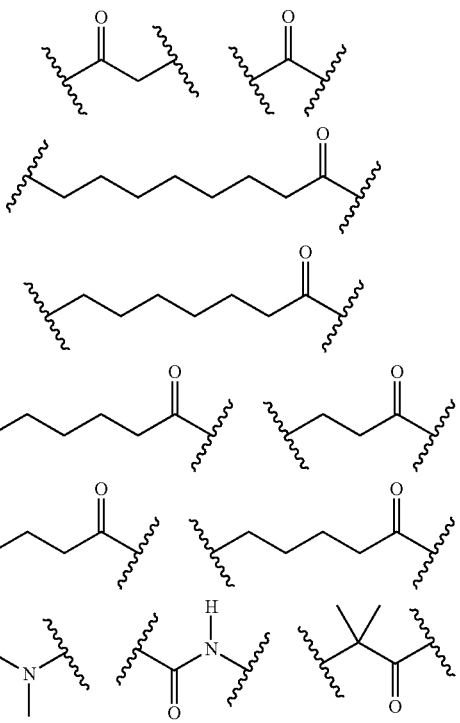

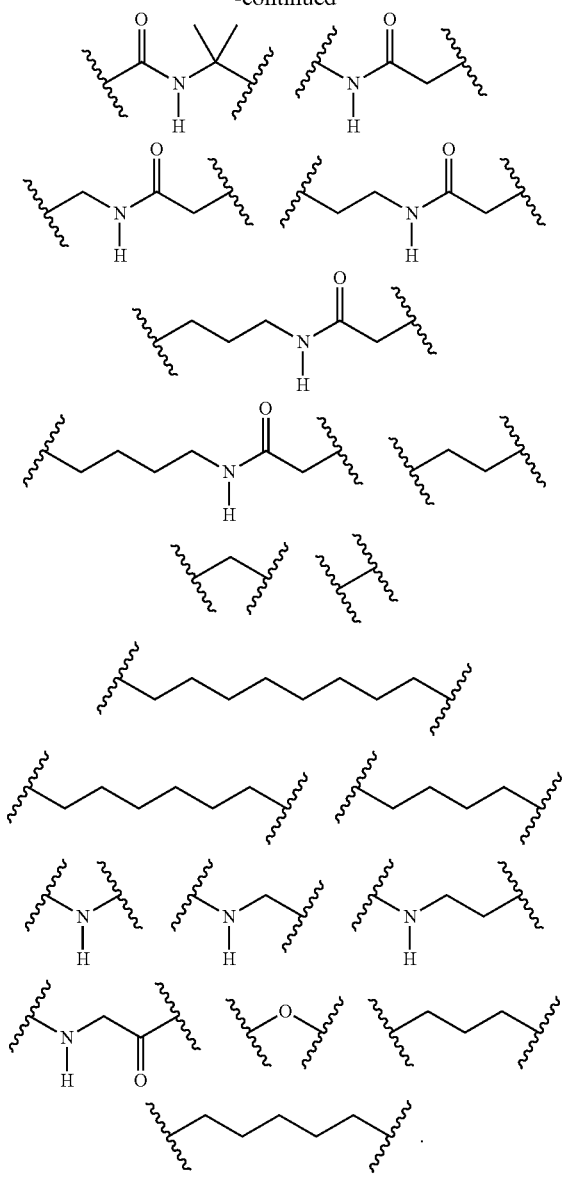
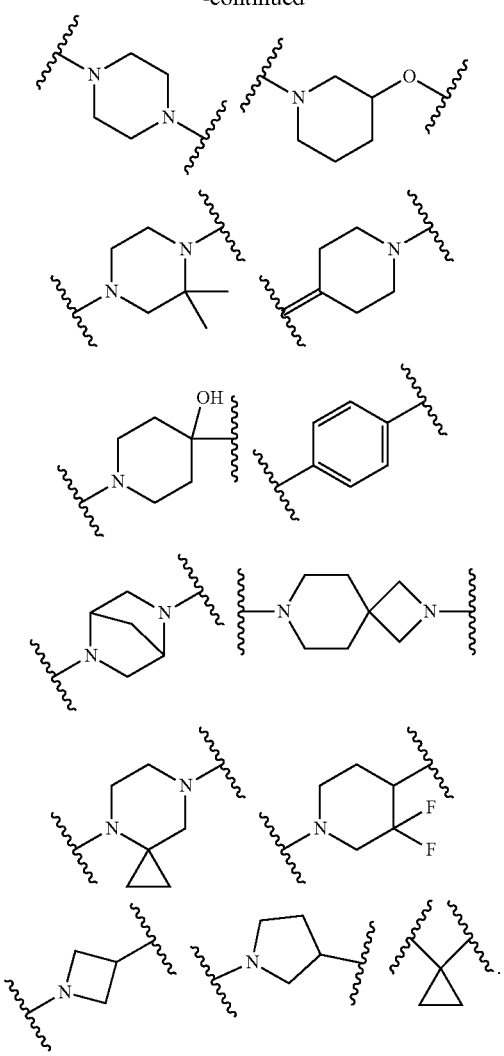
Additional non-limiting examples of moieties of $R^{20}$, $R^{21}$, $R^{22}$, $R^{23}$, and $R^{24}$ include:
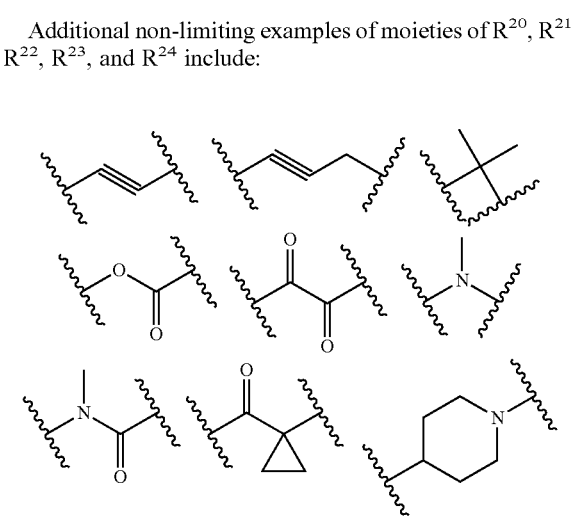
Additional non-limiting examples of moieties of $R^{20}$, $R^{21}$, $R^{22}$, $R^{23}$, and $R^{24}$ include:
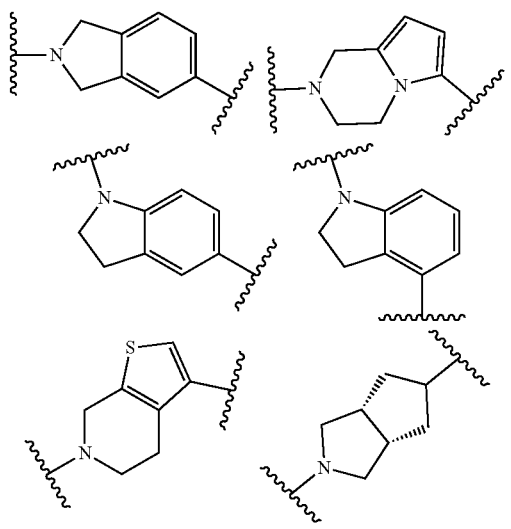

-continued

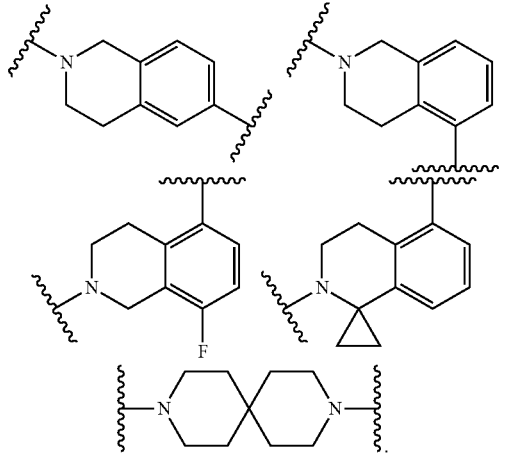

In additional embodiments, the Linker moiety is an optionally substituted (poly)ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms.

In certain embodiments, the Linker is flanked, substituted, or interspersed with an aryl, phenyl, benzyl, alkyl, alkylene, or heterocycle group.

In certain embodiments, the Linker may be asymmetric or symmetrical.

In certain embodiments, Linker can be a nonlinear chain, and can be, or include, aliphatic or aromatic or heteroaromatic cyclic moieties.

In any of the embodiments of the compounds described herein, the Linker group may be any suitable moiety as described herein.

In certain embodiments, the Linker is selected from the group consisting of:

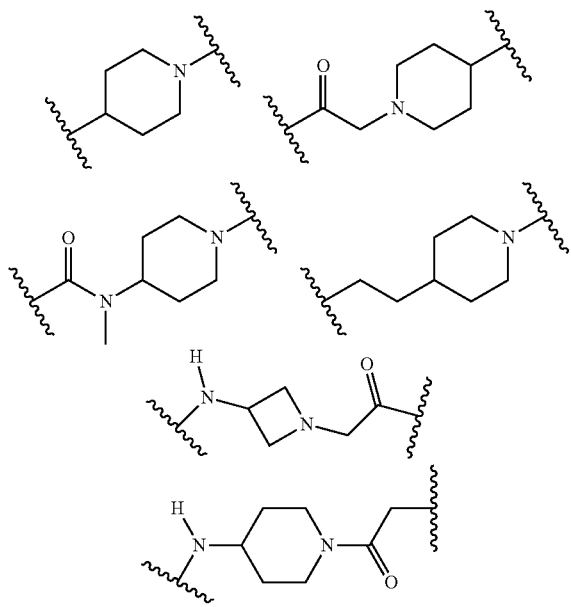

-continued


In certain embodiments, the linker (L or L$^D$) is selected from the group consisting of:

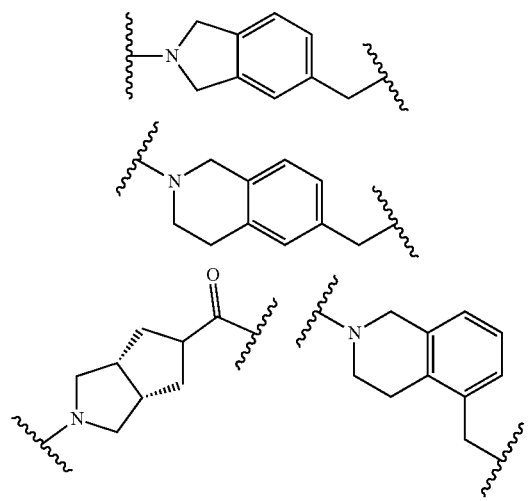

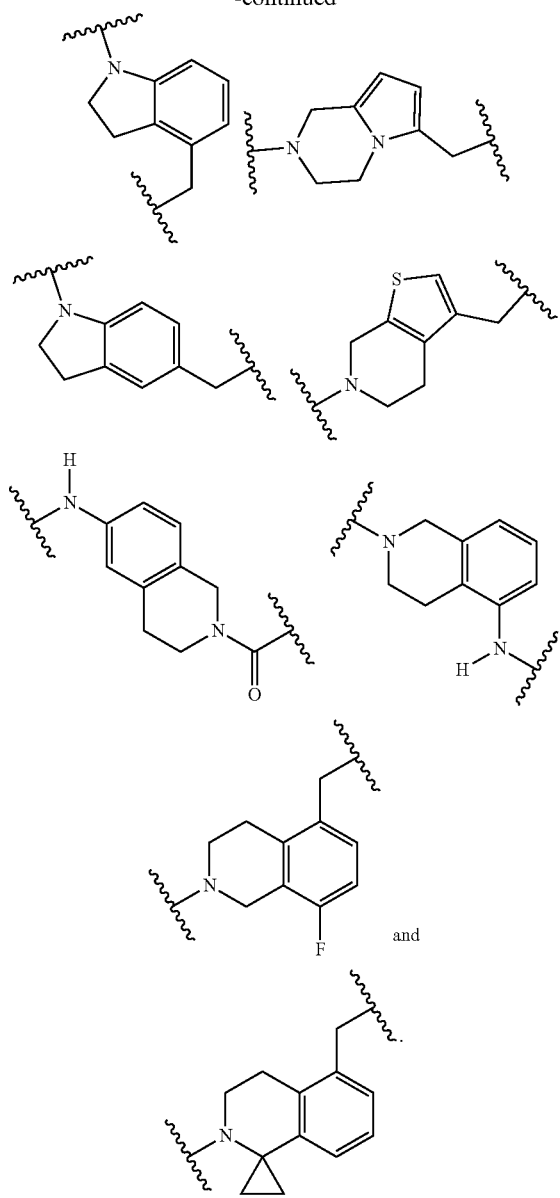
In certain embodiments, the linker (L or $L^D$) is selected from the group consisting of:
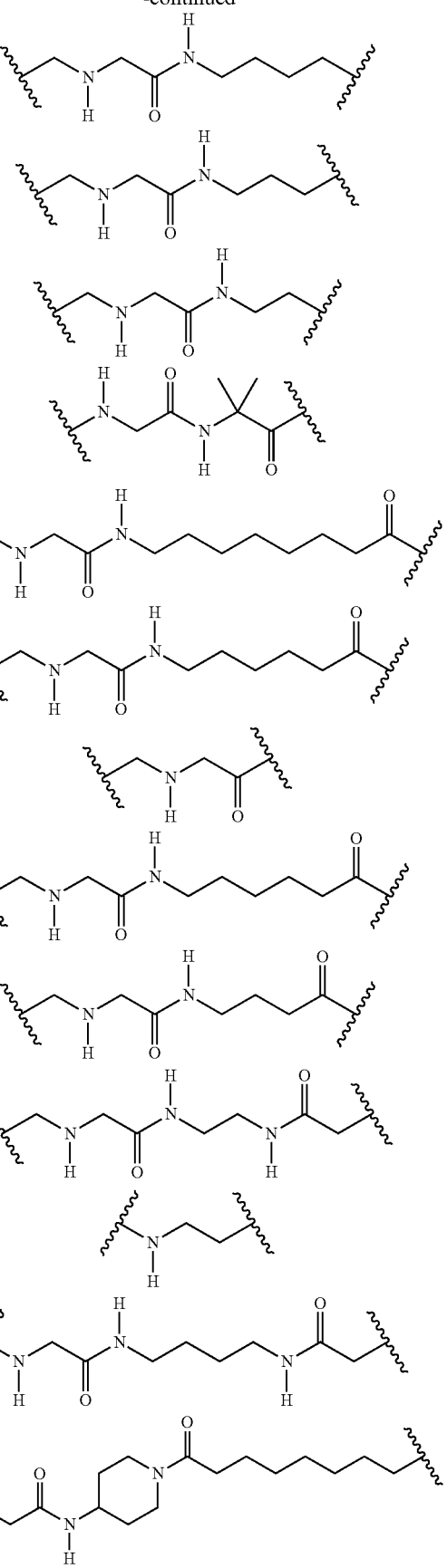

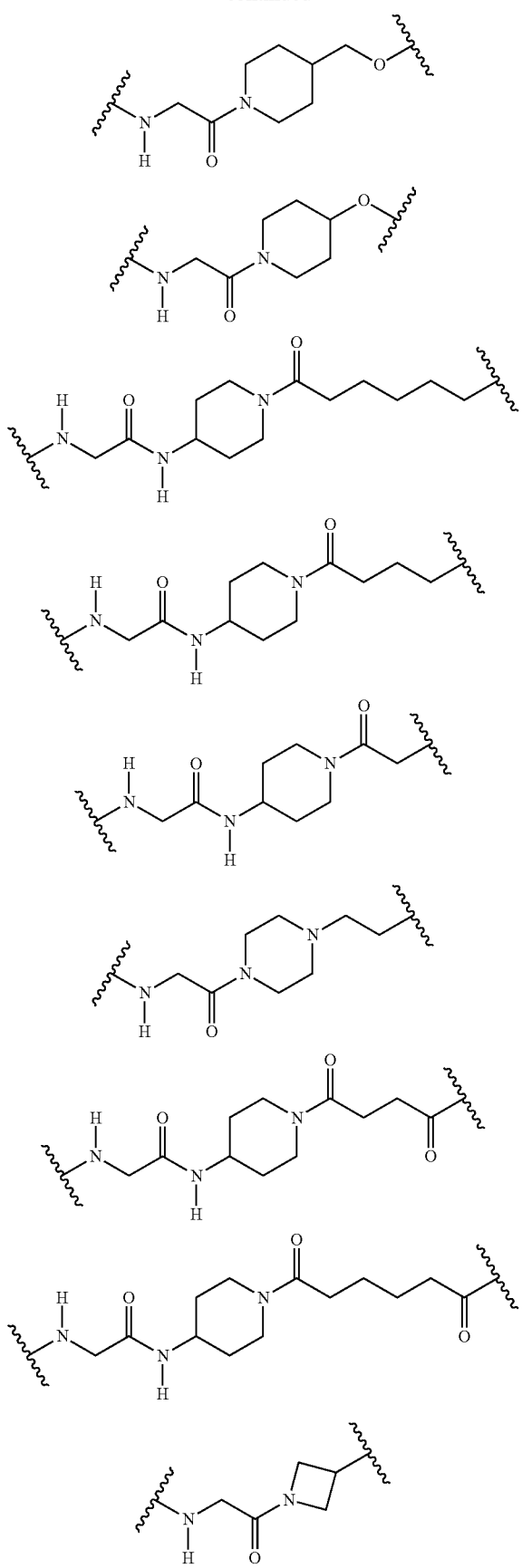
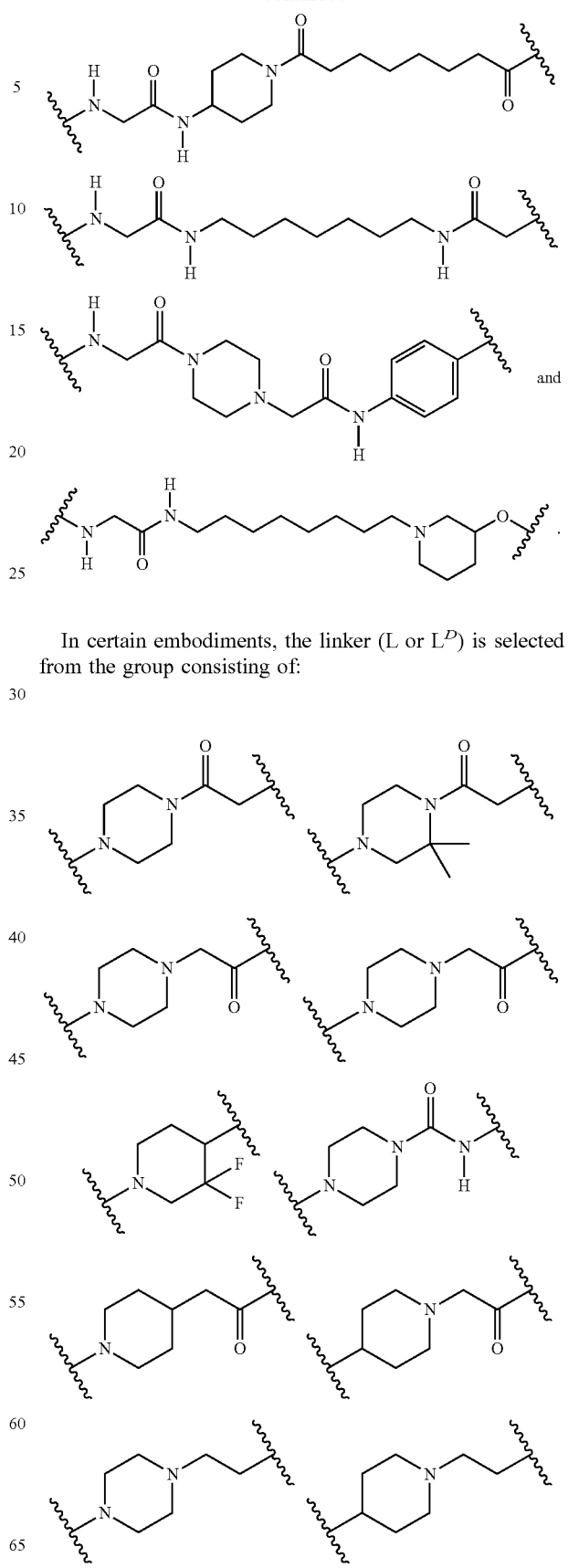
In certain embodiments, the linker (L or $L^D$) is selected from the group consisting of:

-continued
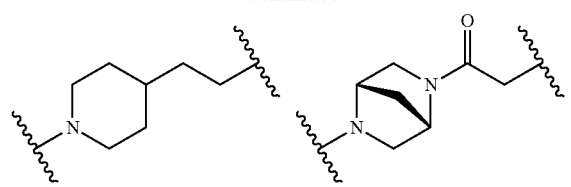
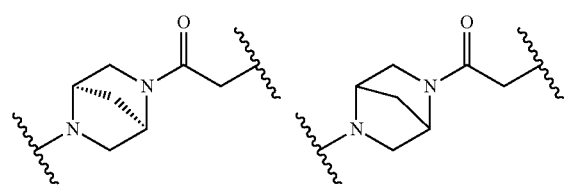
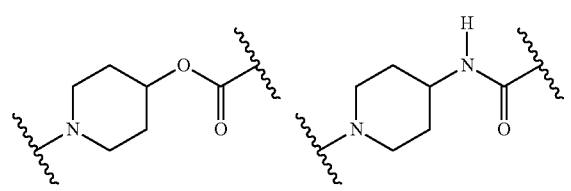
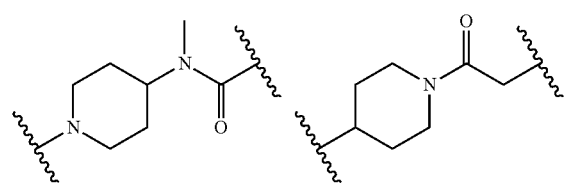
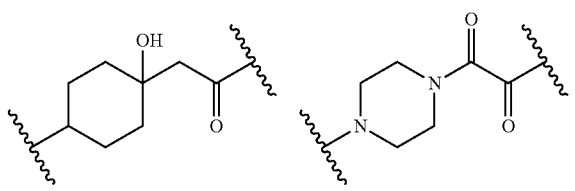
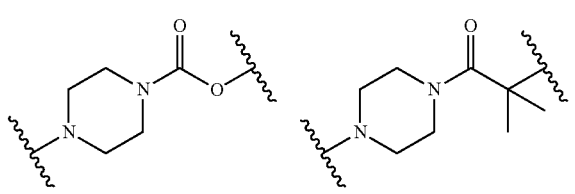
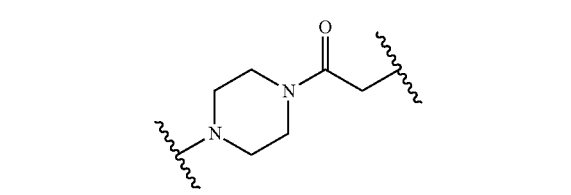
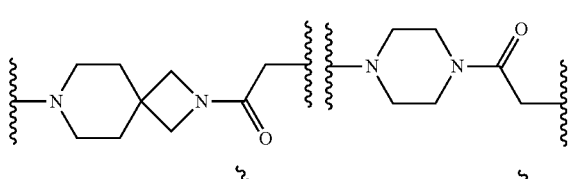
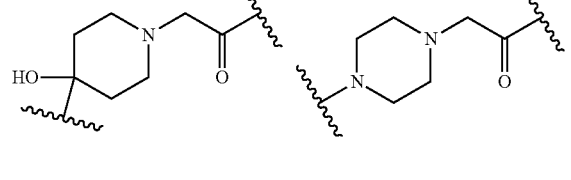
-continued
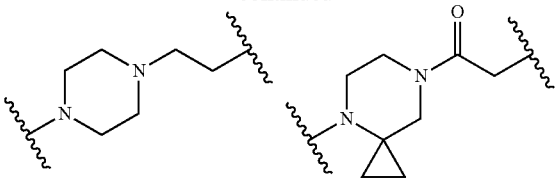
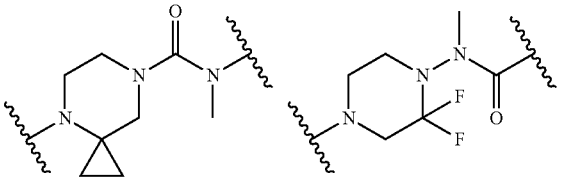
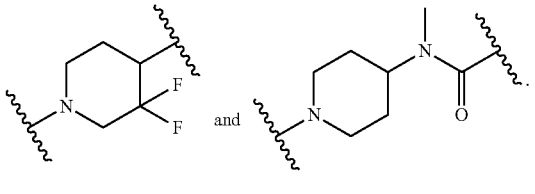
and
In certain embodiments, the linker (L or $L^D$) is selected from the group consisting of:
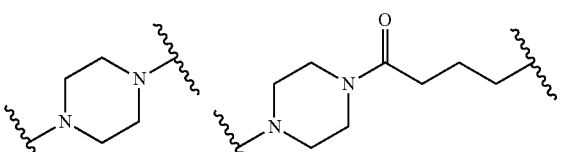
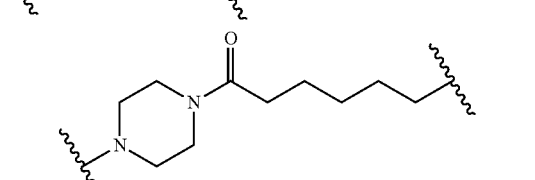
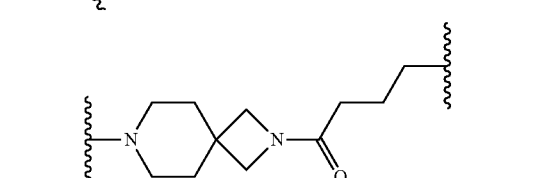
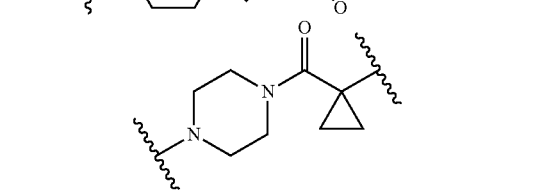
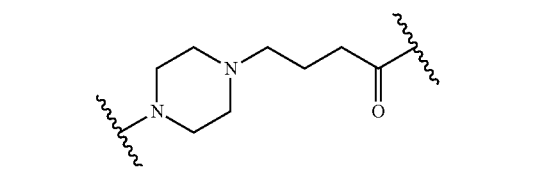
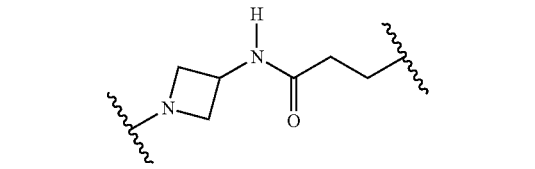

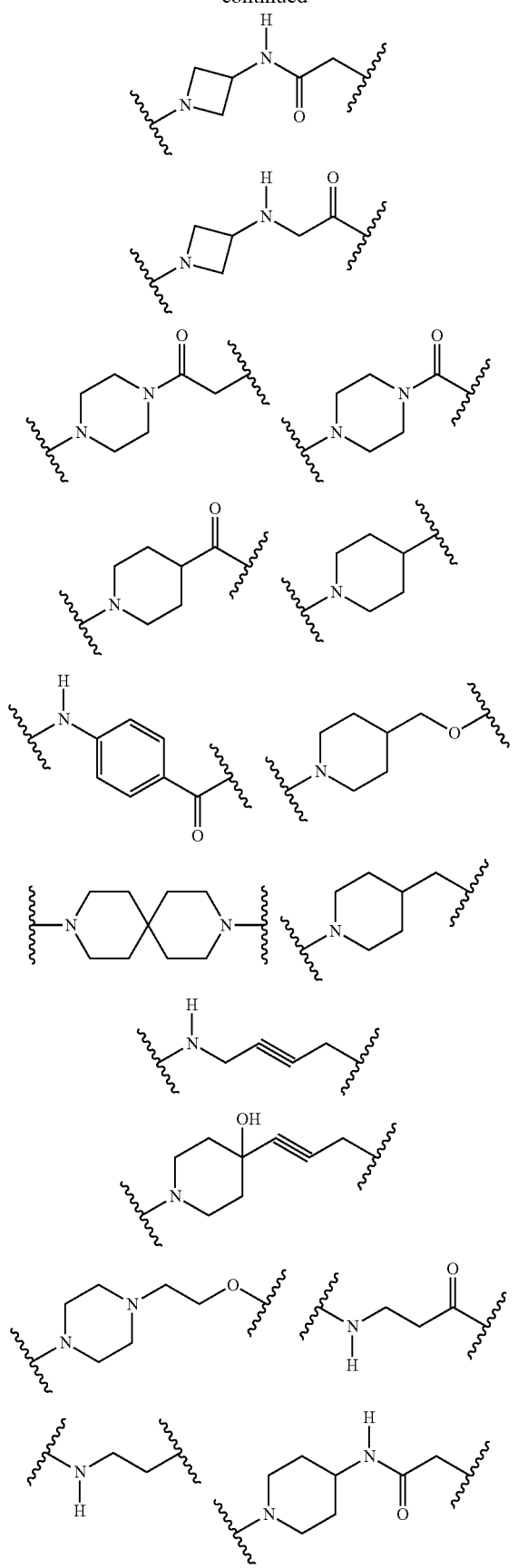
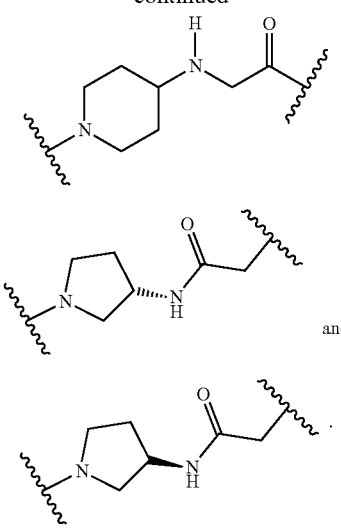
and
In certain embodiments linker (L or $L^D$) is selected from:
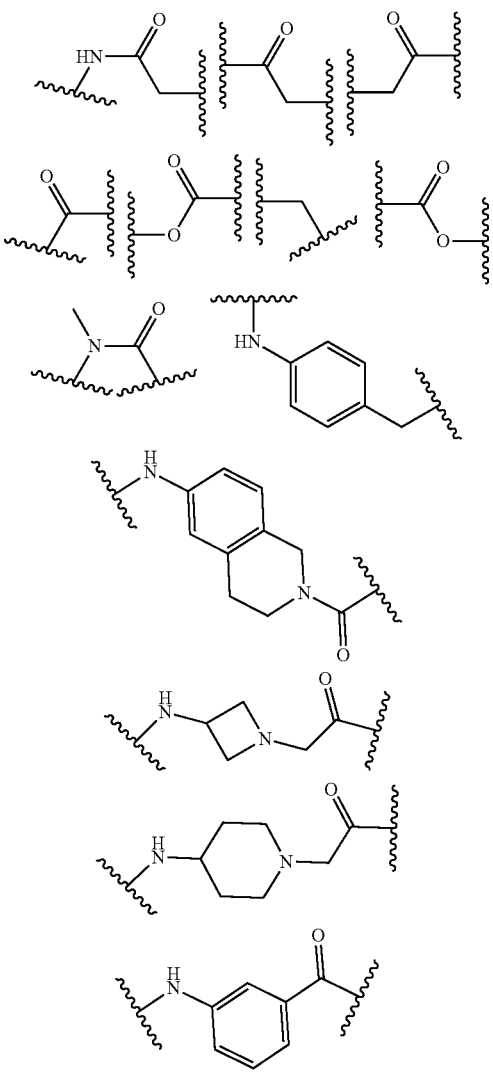

207

-continued

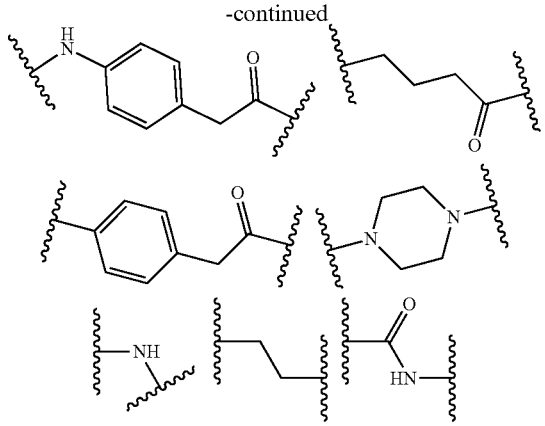

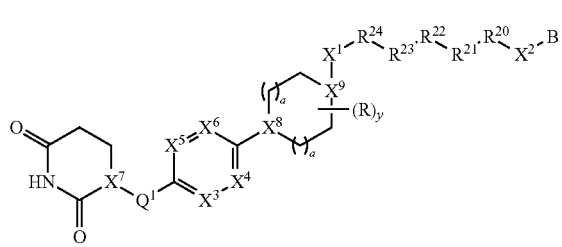

In certain embodiments the linker drawn above is attached on the left side to the B group. In other embodiments the linker drawn above is attached on the right side to the B group.

In certain embodiments, the compound of the present invention is selected from:

208

-continued

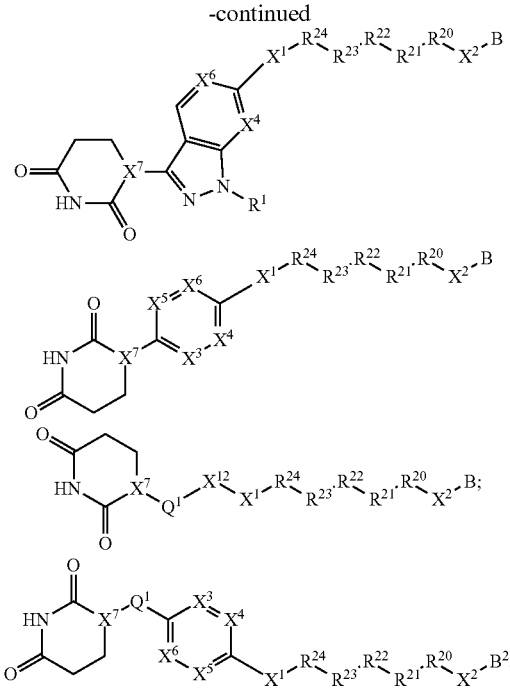

or a pharmaceutically acceptable salt thereof.

V. Additional Non-Limiting Examples of Compounds of Tile Present Invention

In certain embodiments the compound of the present invention is selected from:

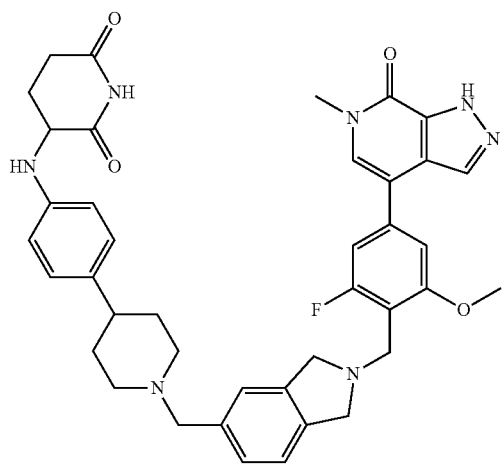

209
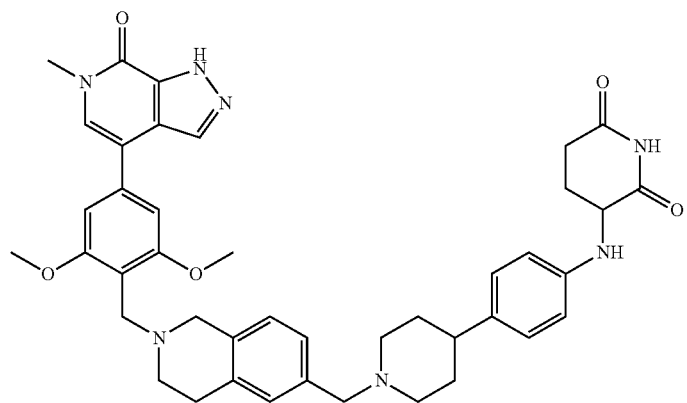
210
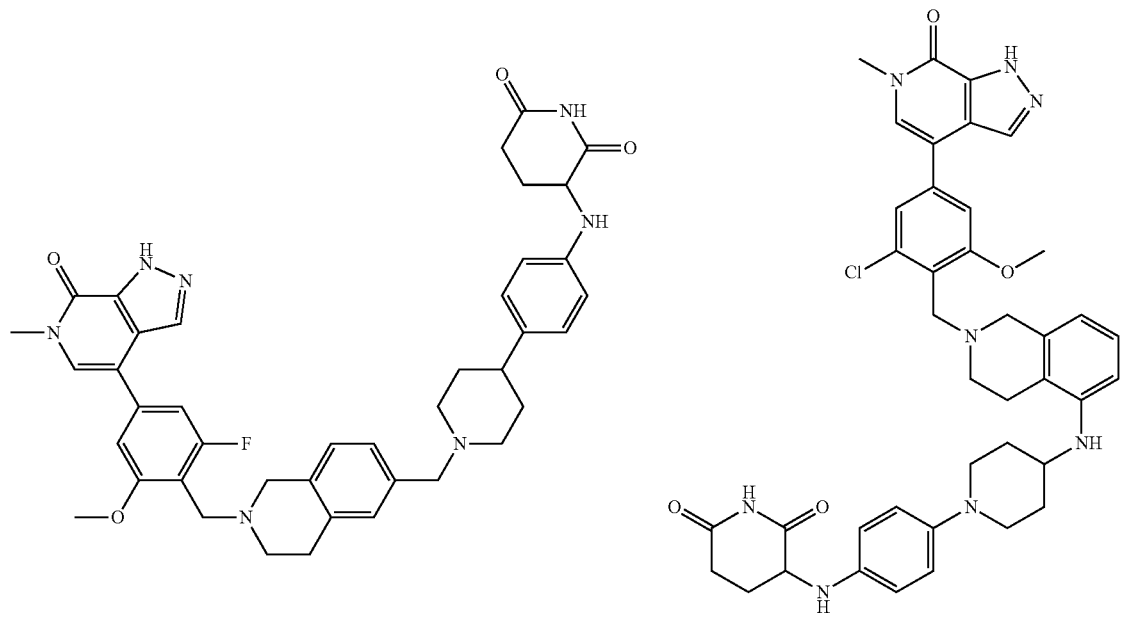
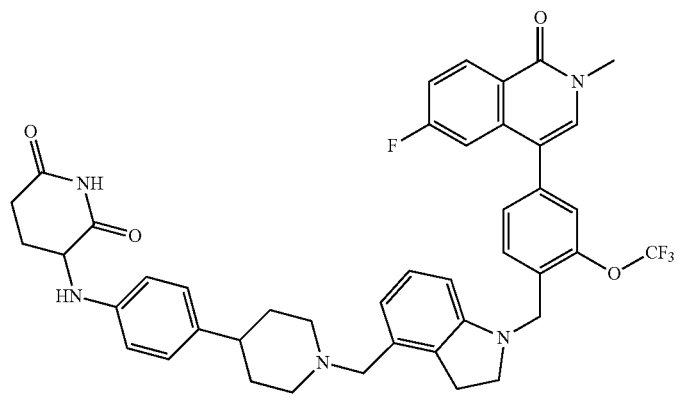

211 212
-continued
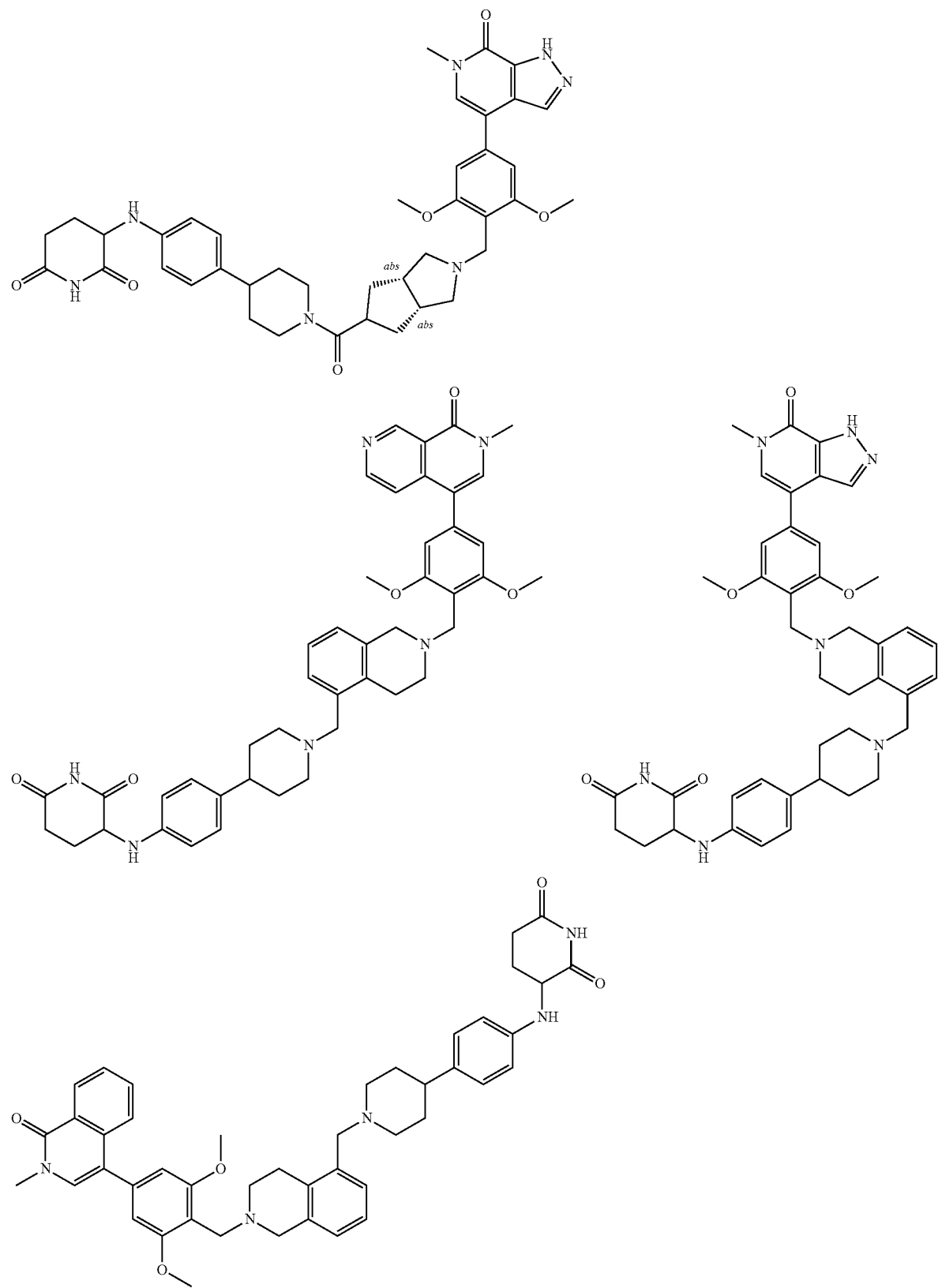

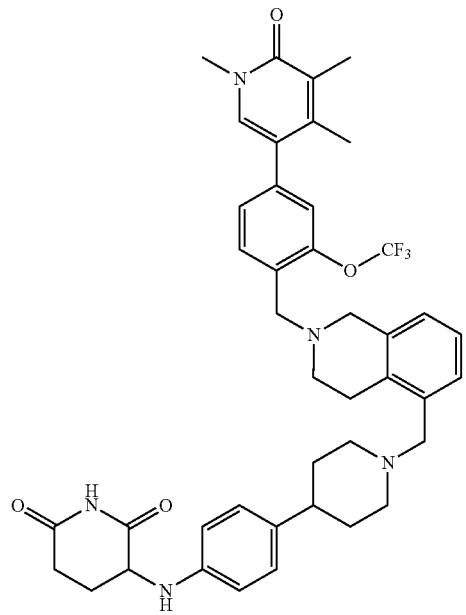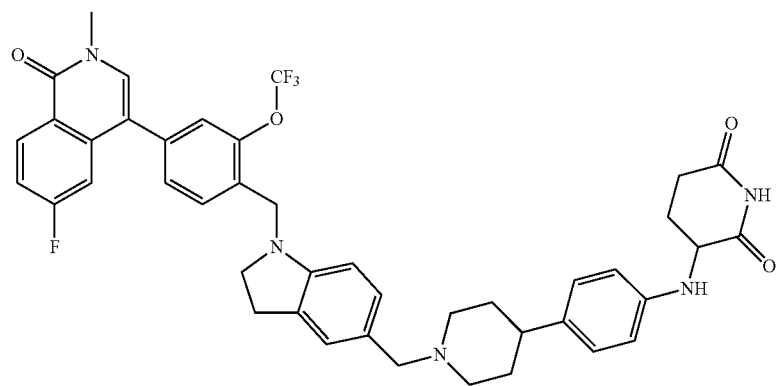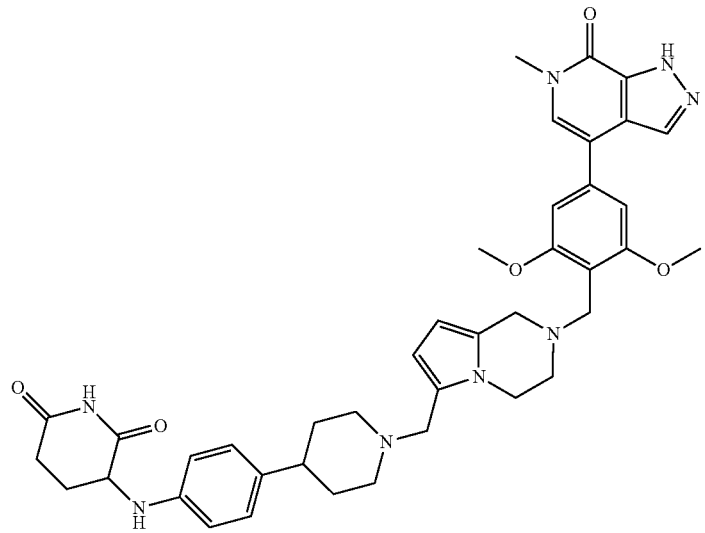

-continued
215
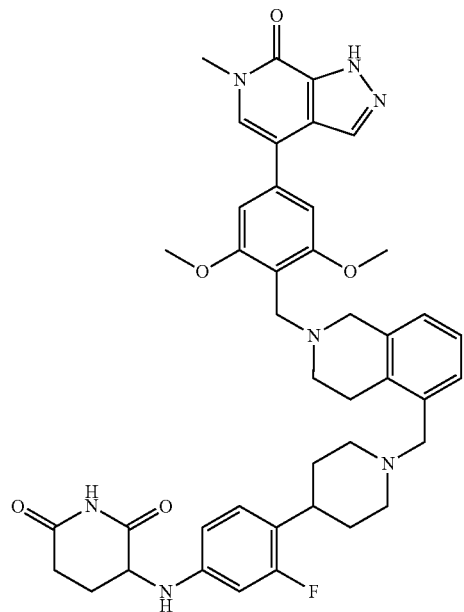
216
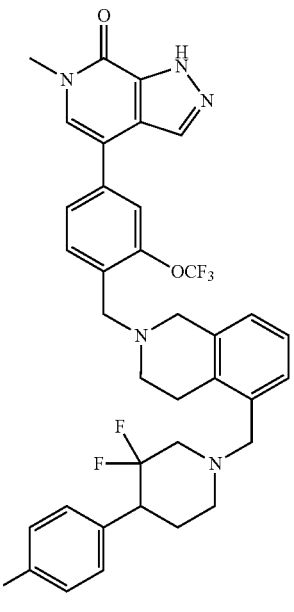
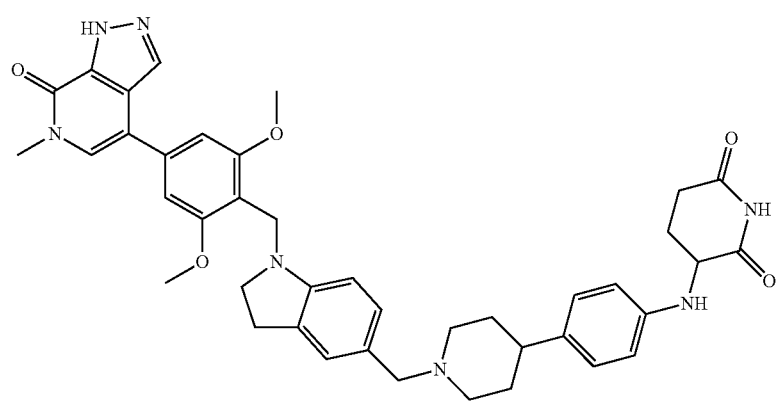
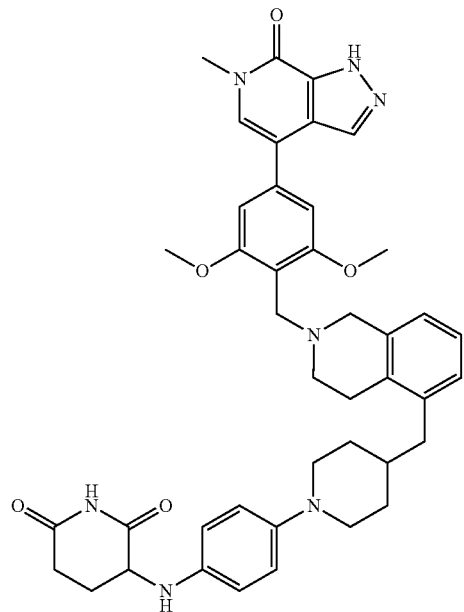

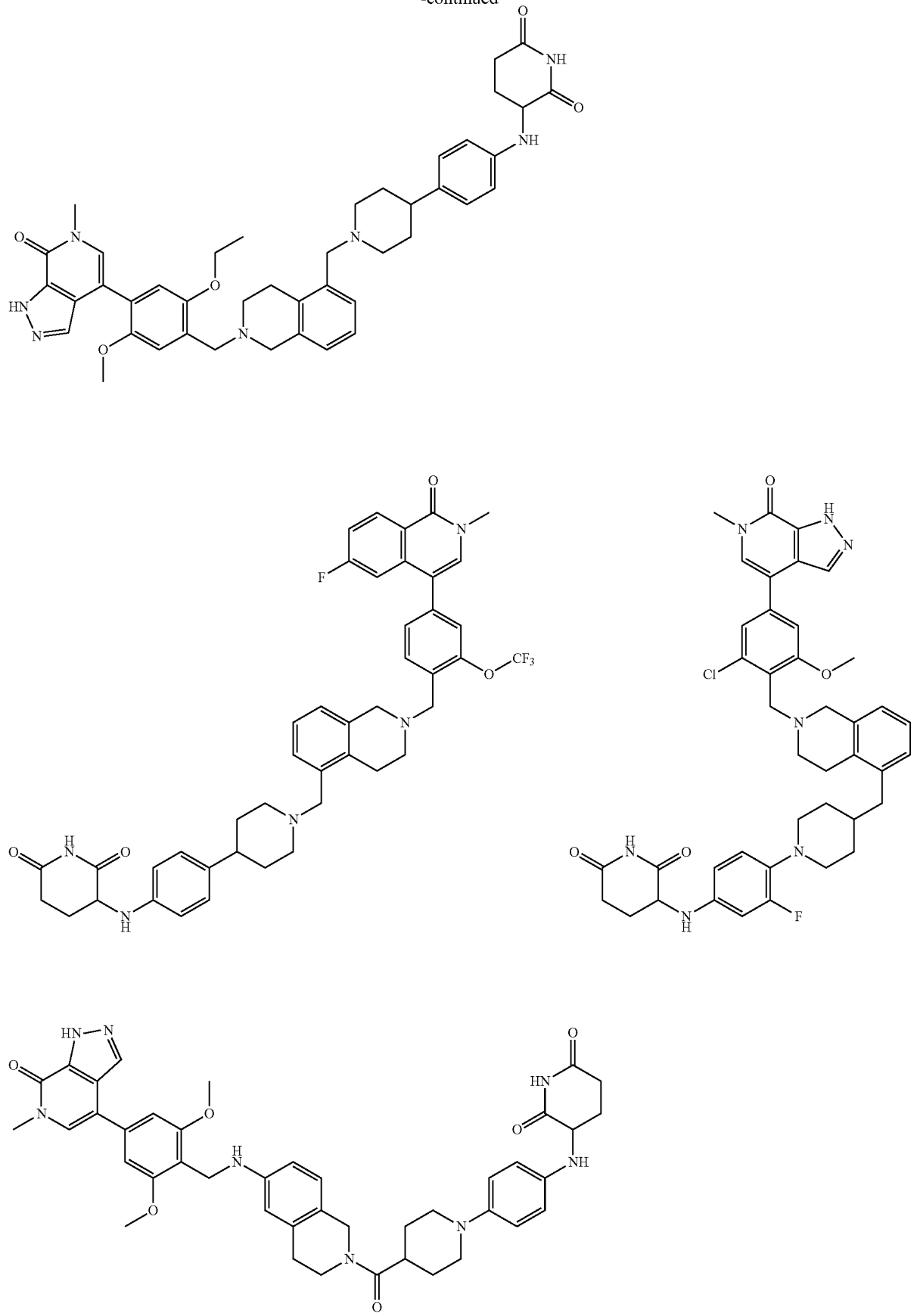

-continued
219
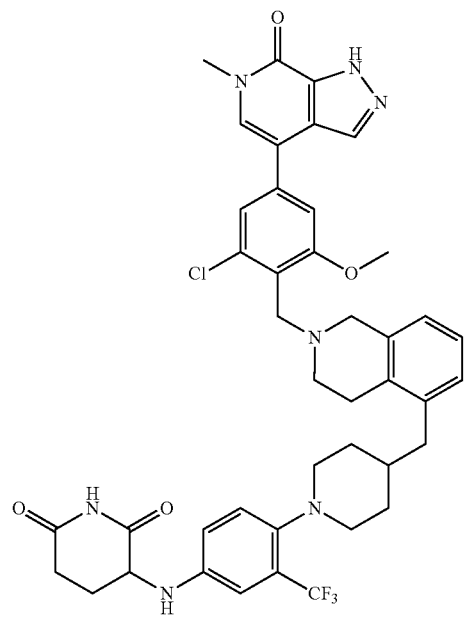
220
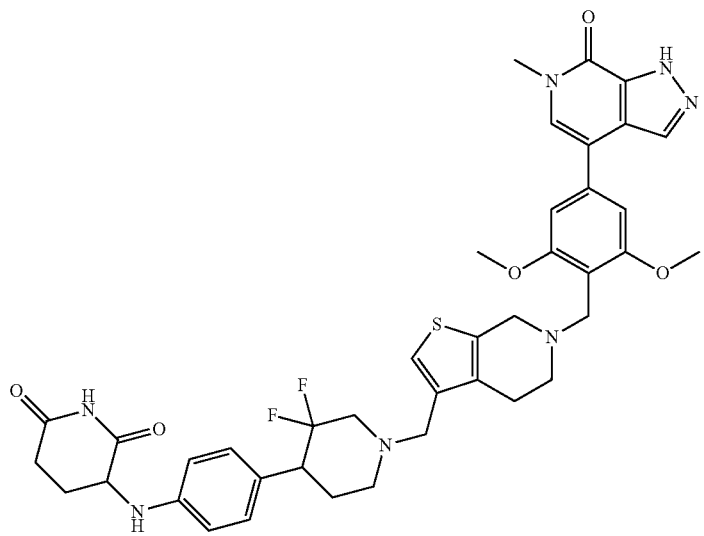
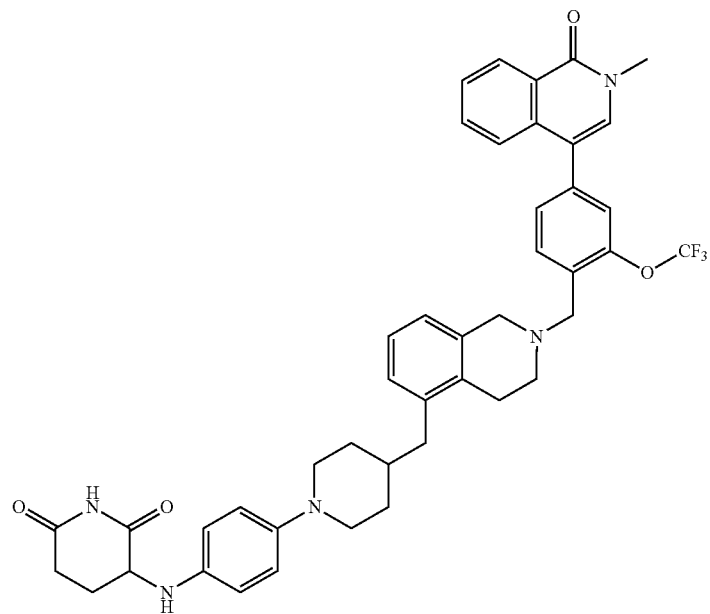
and

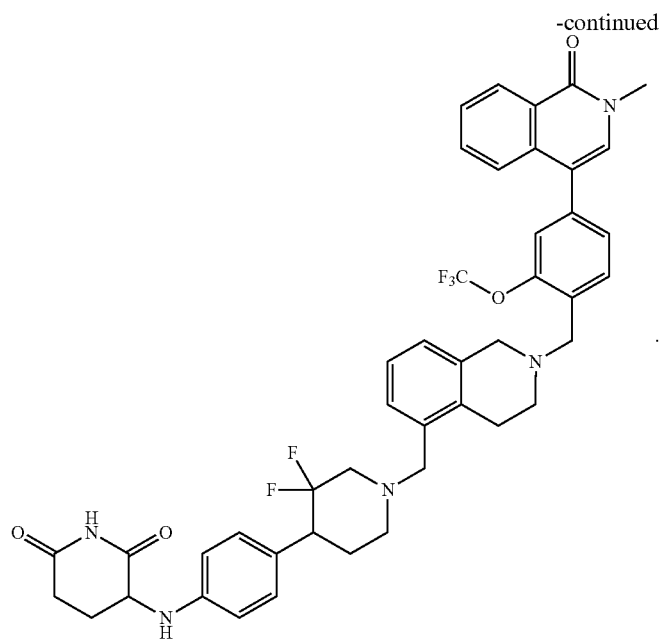
In certain embodiments the compound of the present invention is selected from:
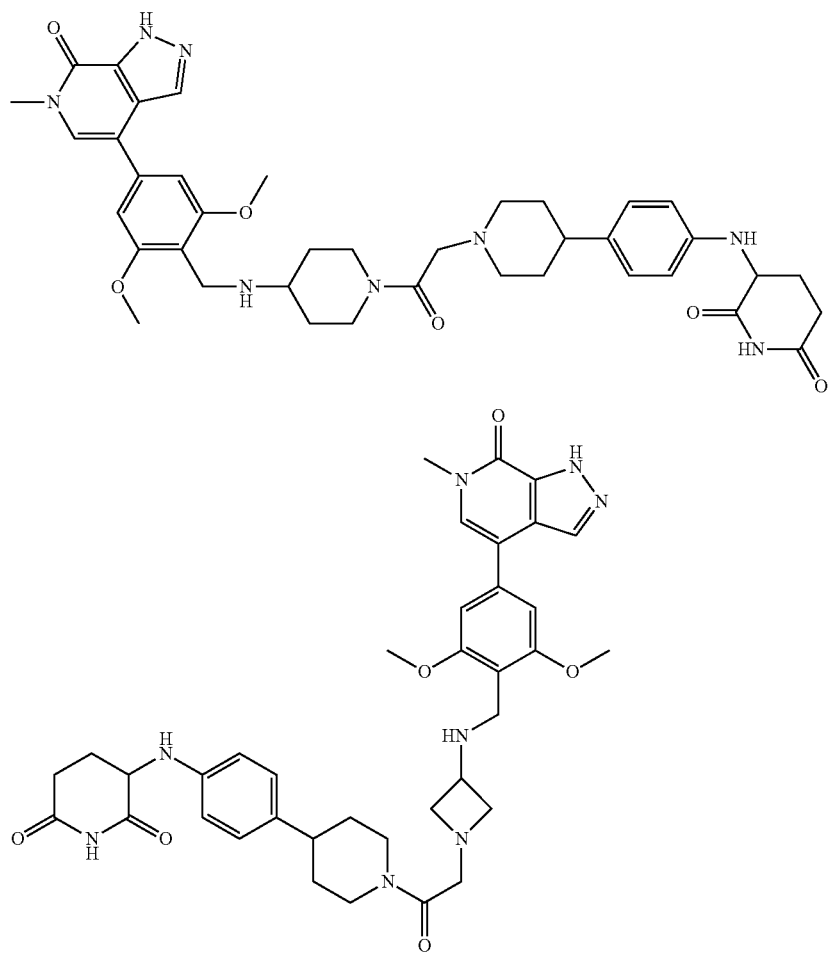

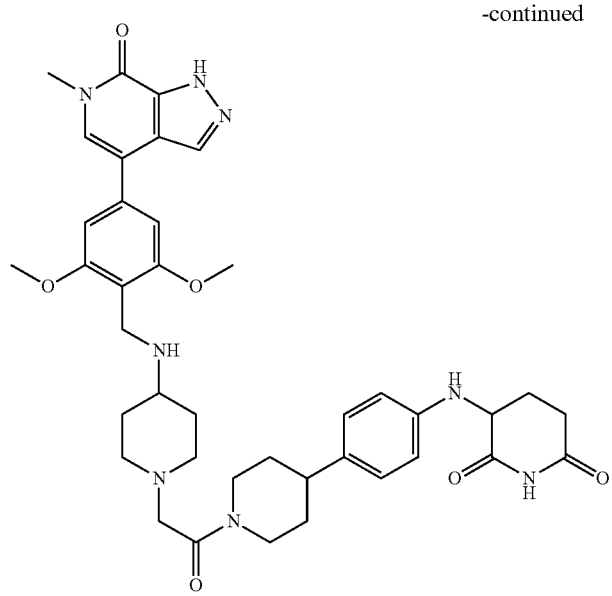
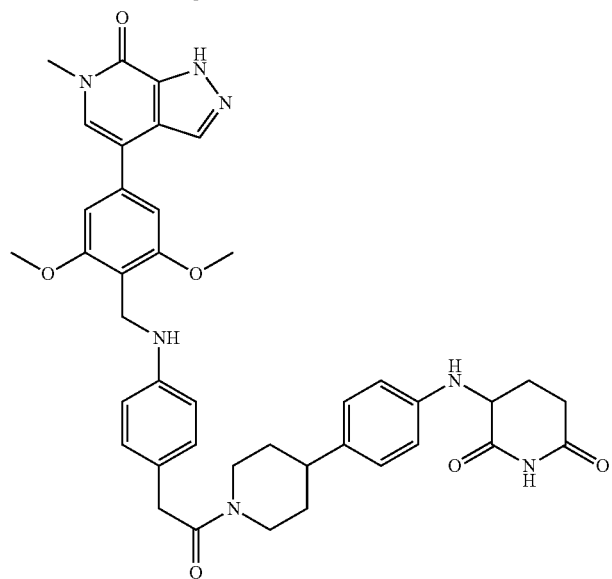
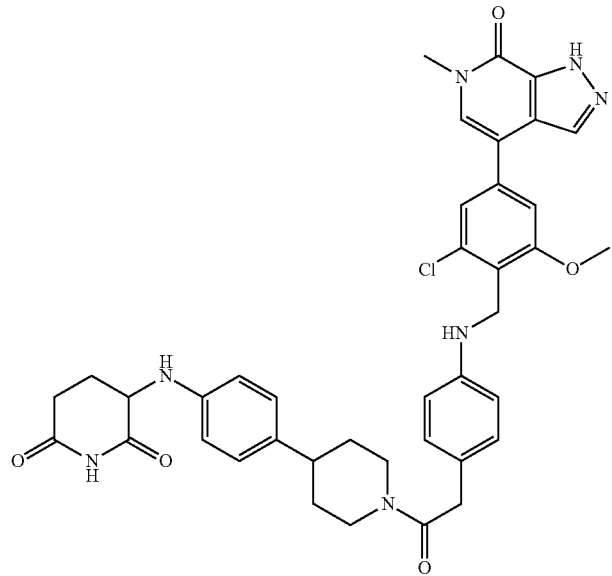

225
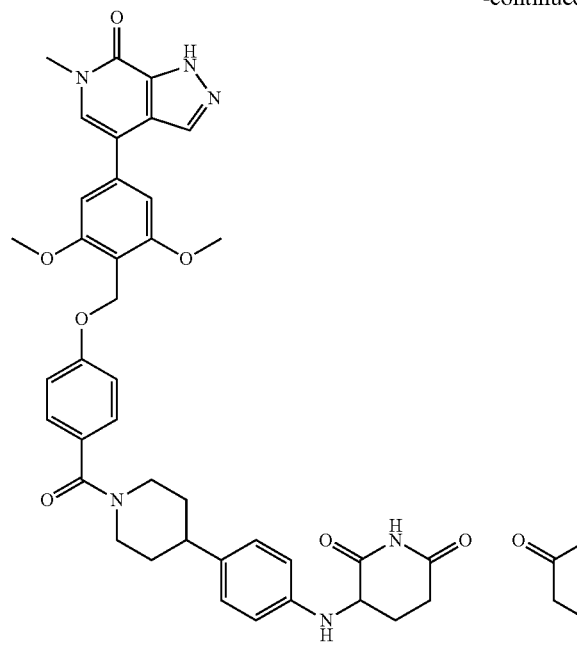
226
-continued
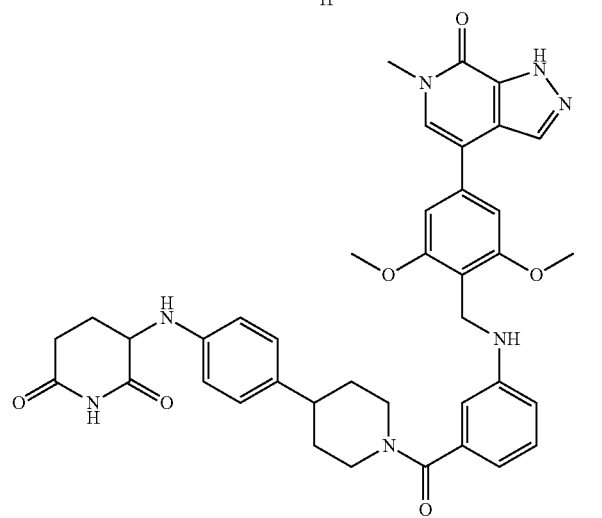
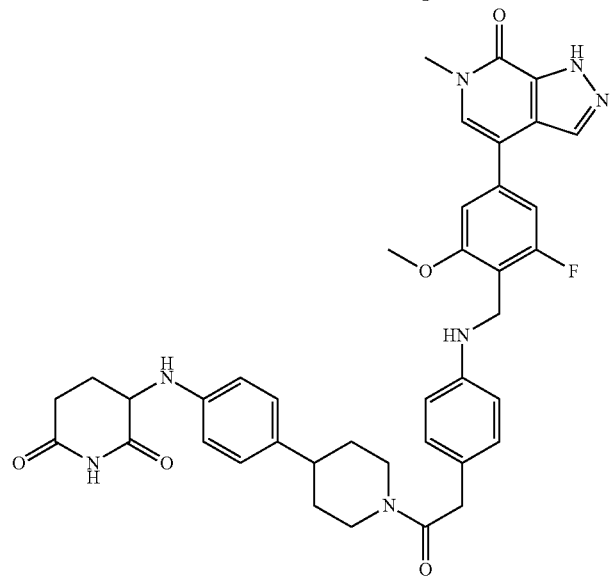
and

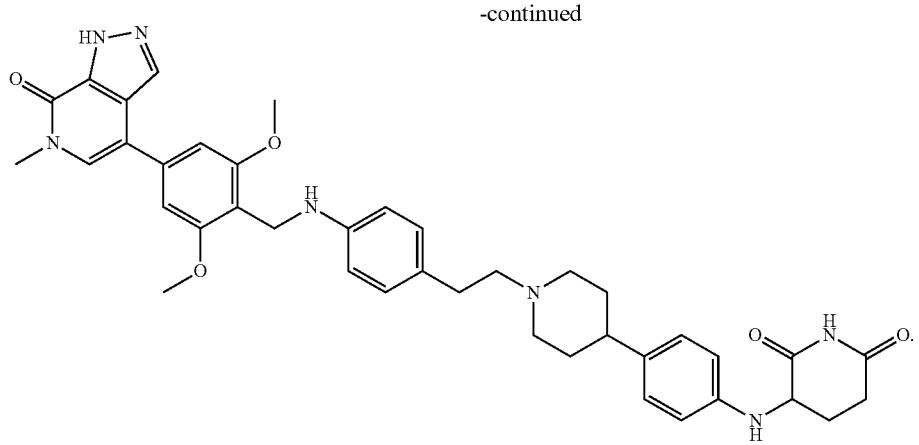
In certain embodiments a compound of the present invention is selected from:
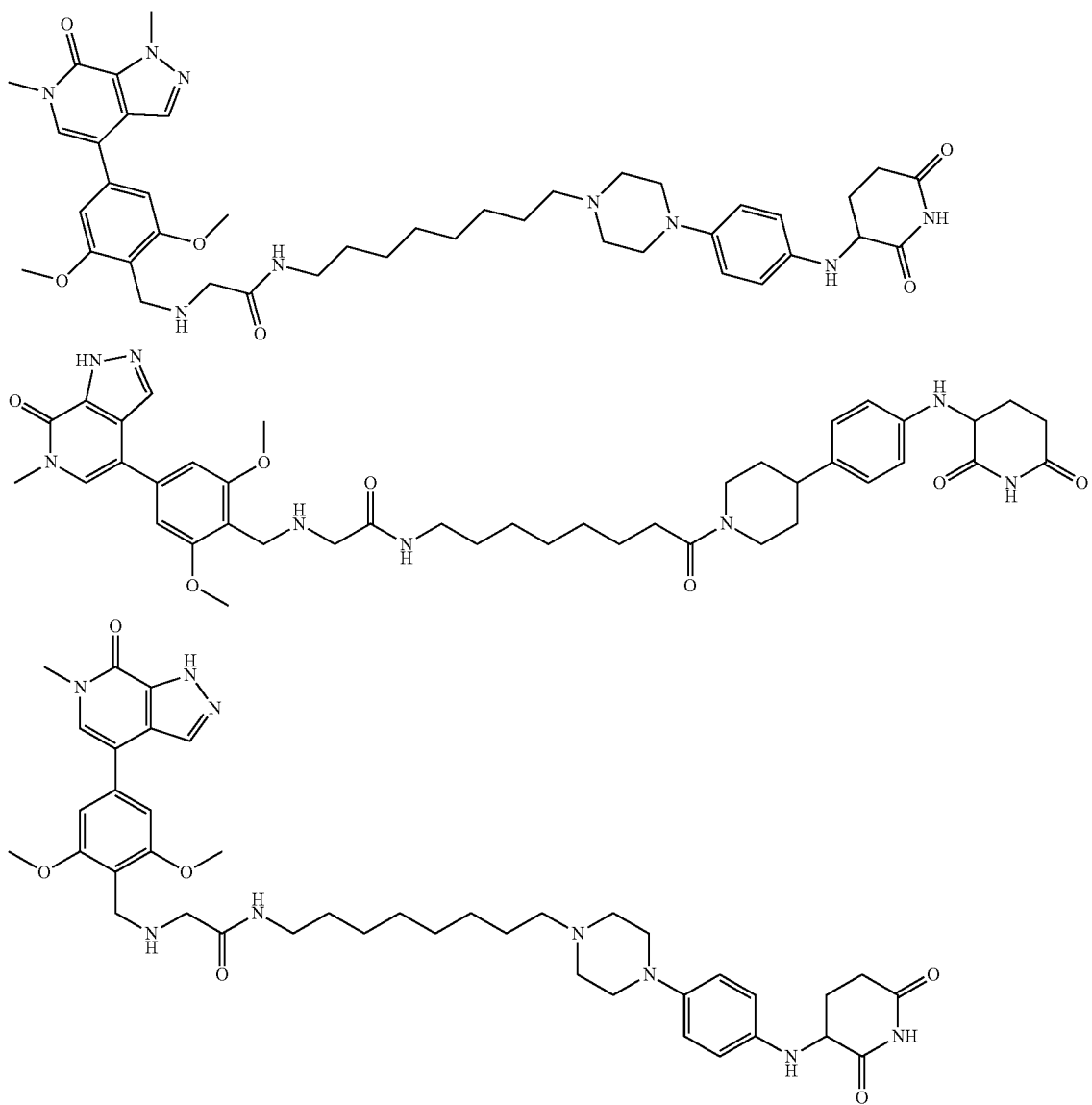

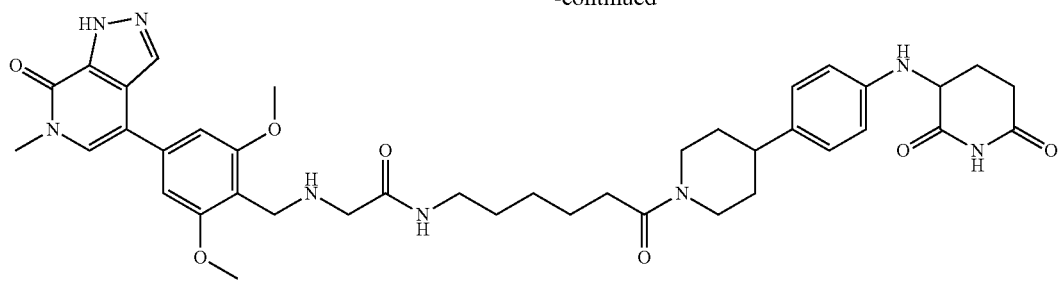
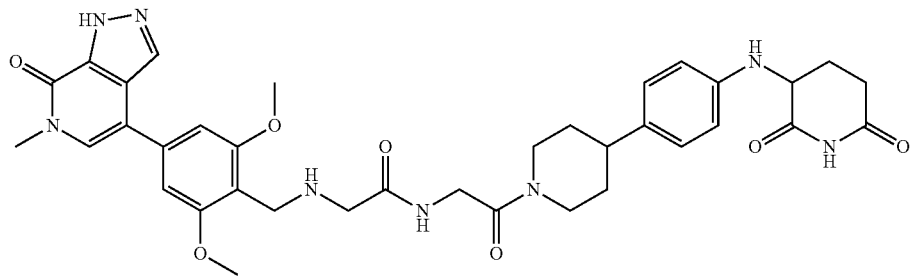
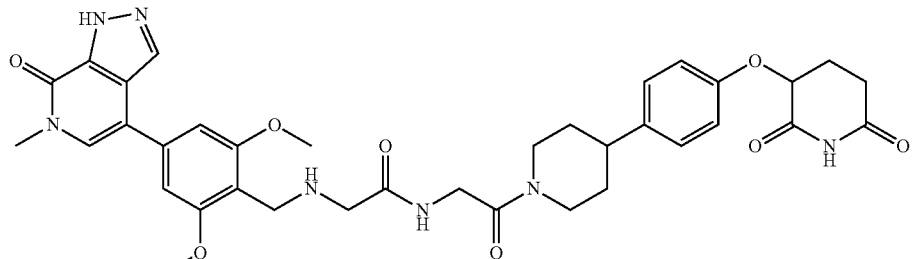
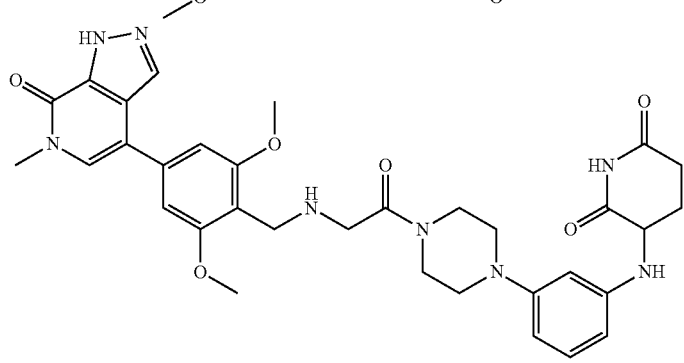
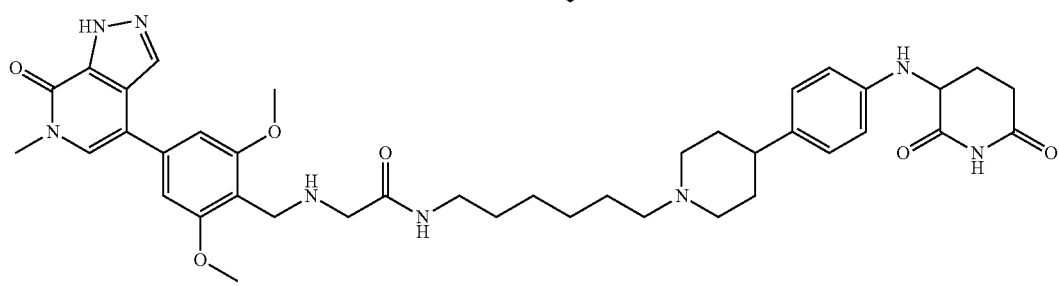
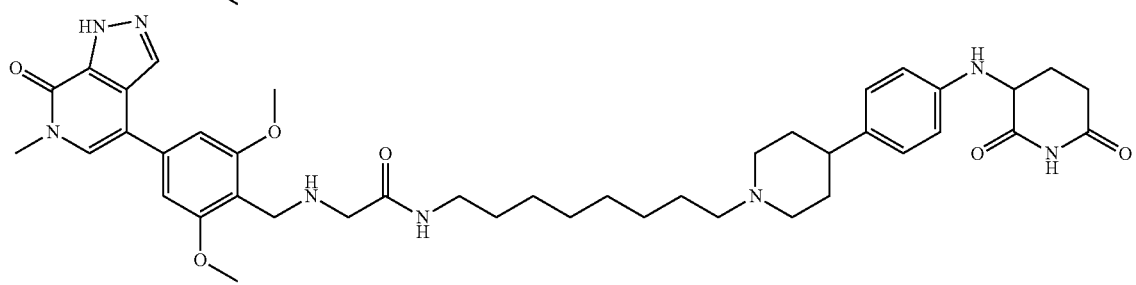

-continued
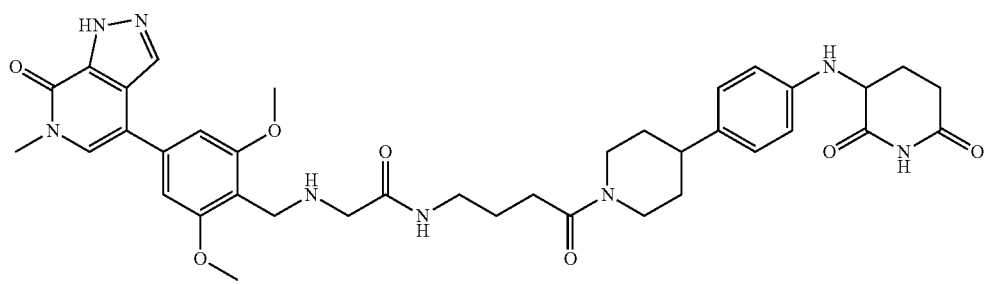
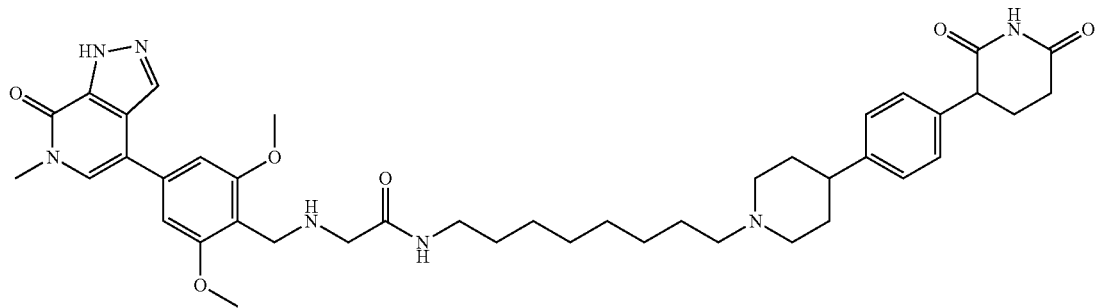
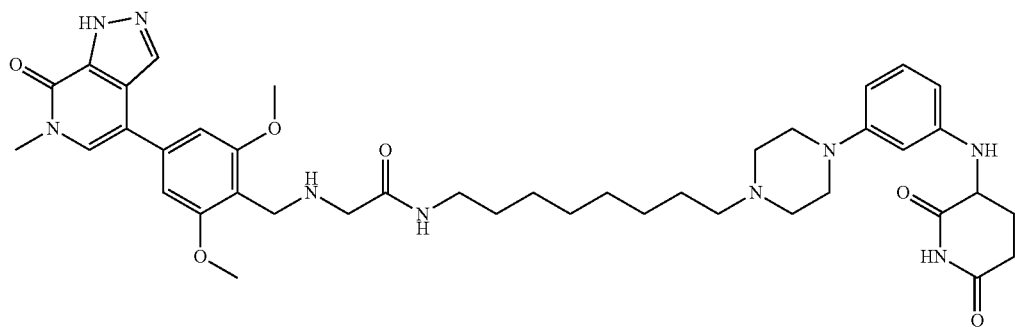
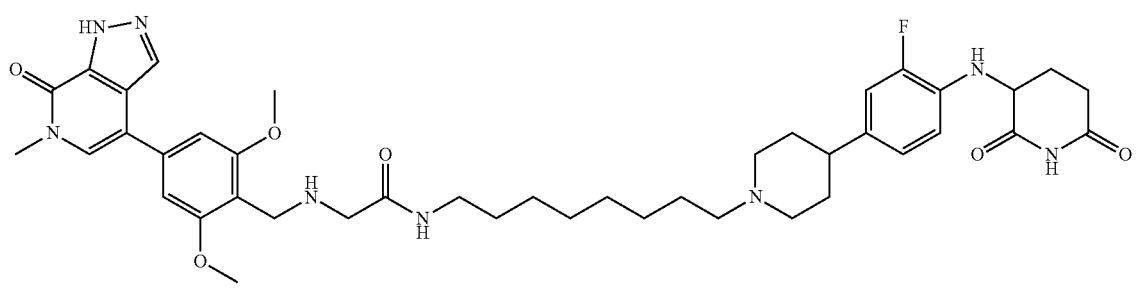
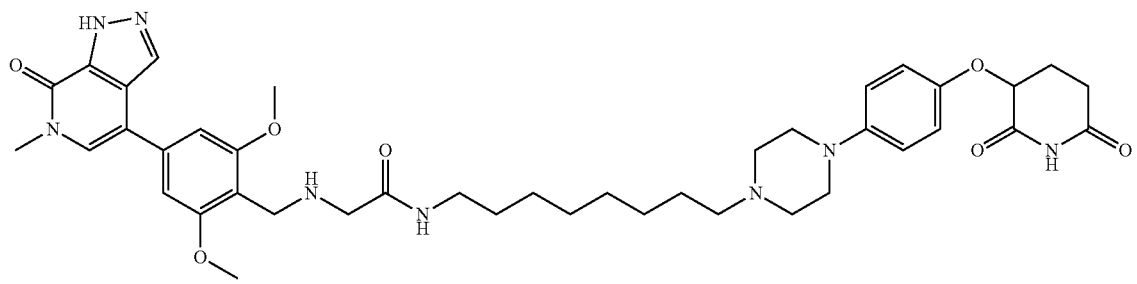

233
234
-continued
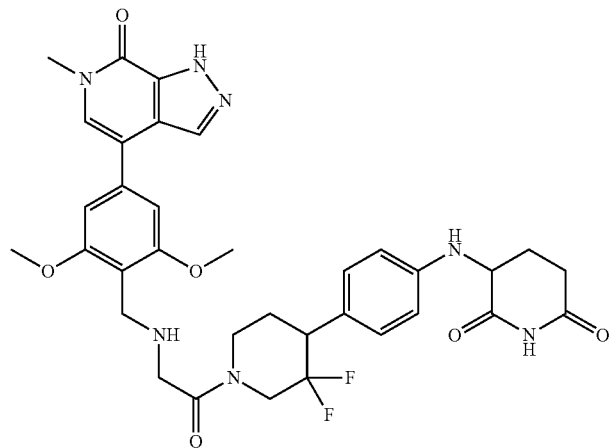
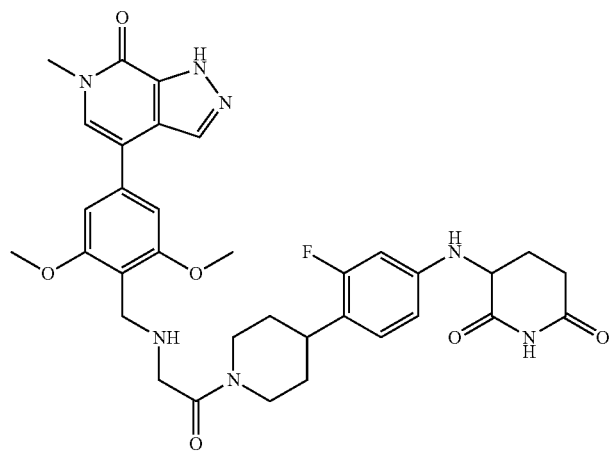
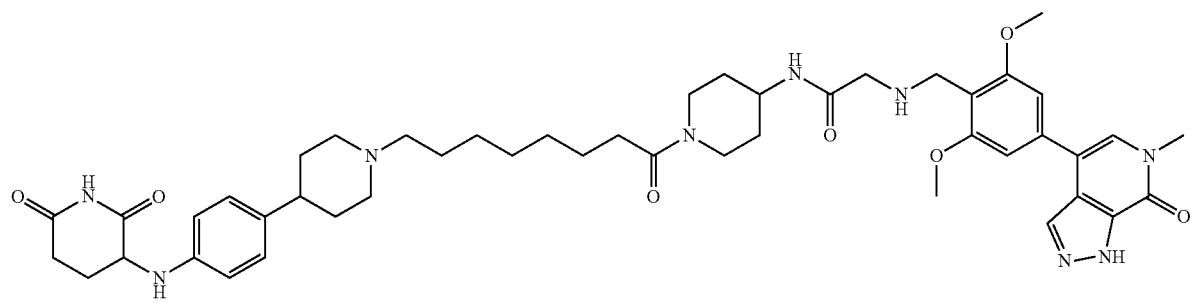
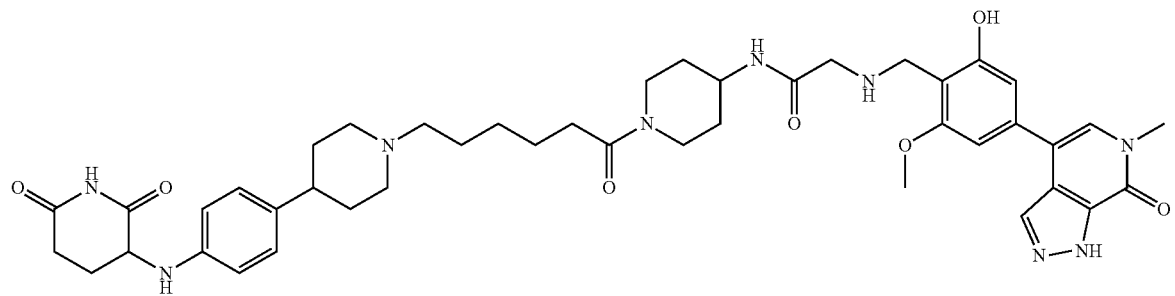

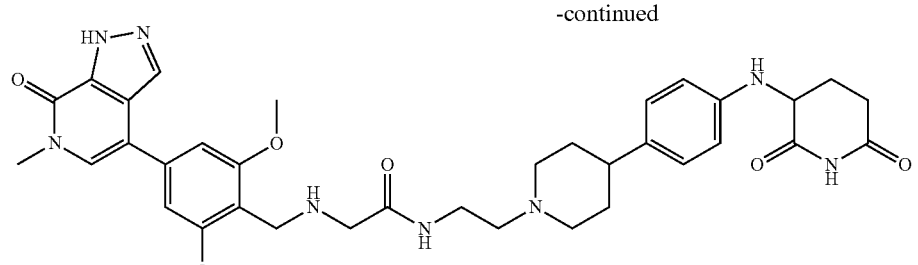
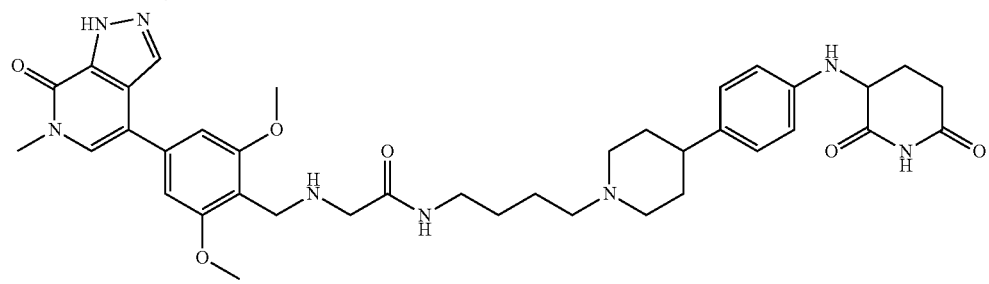
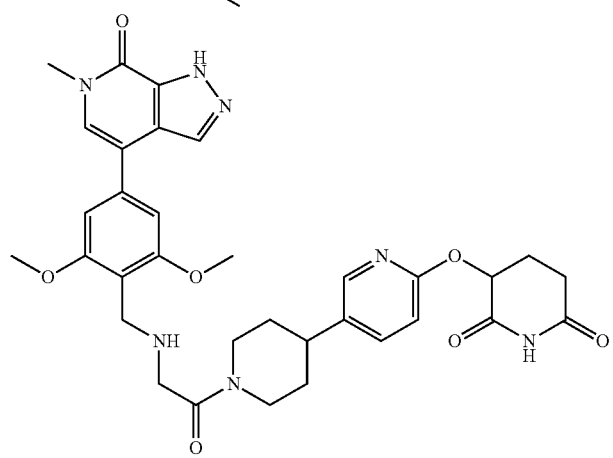
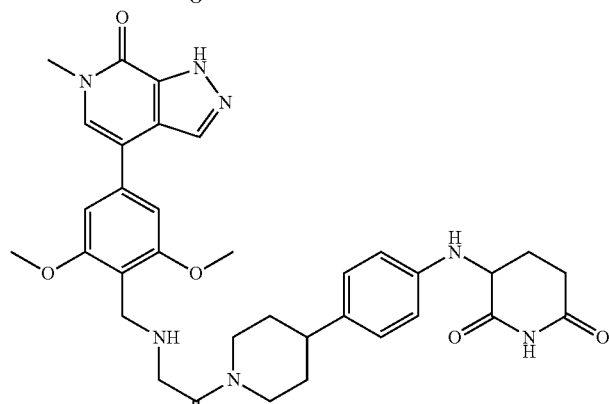
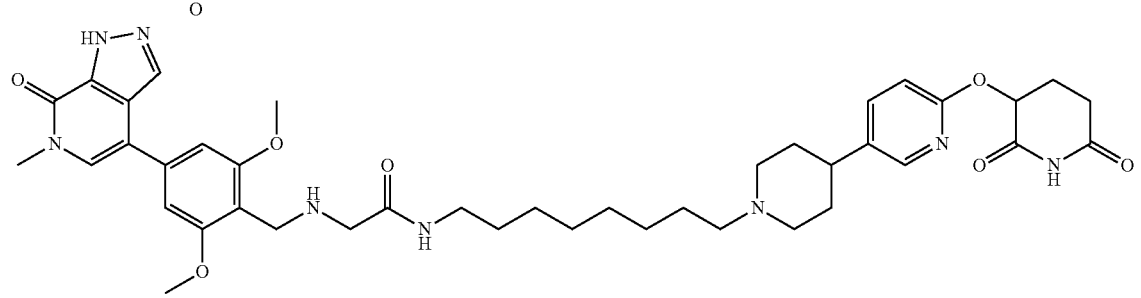

-continued
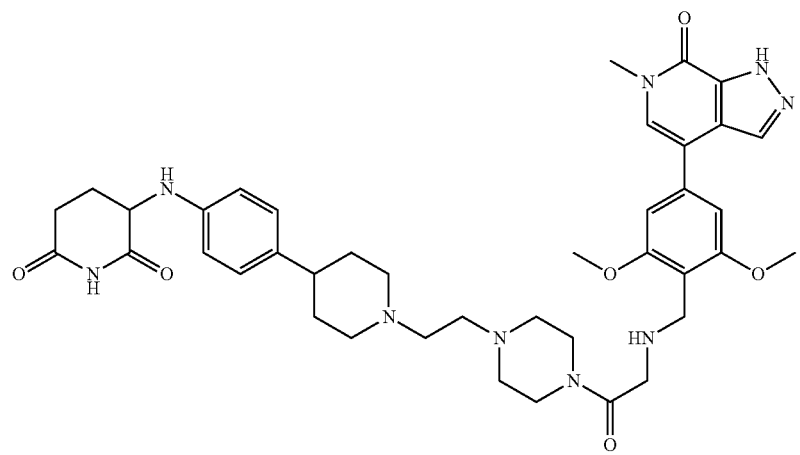
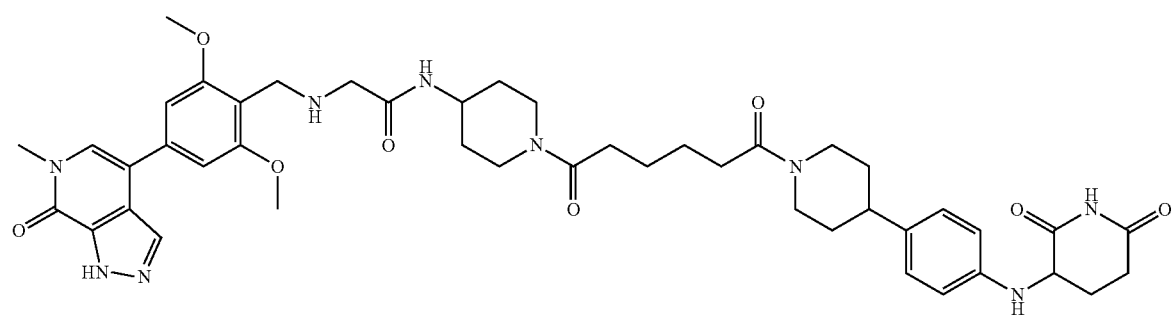
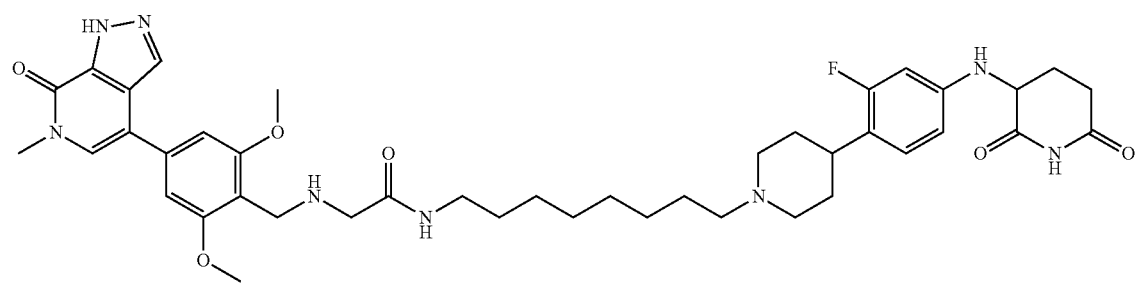
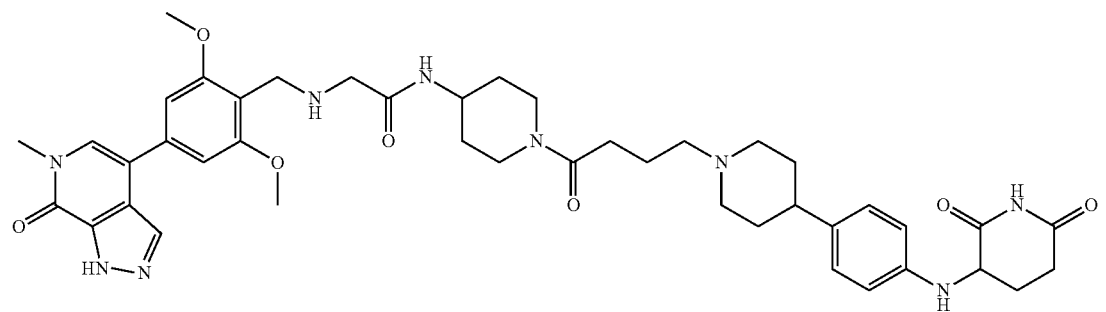

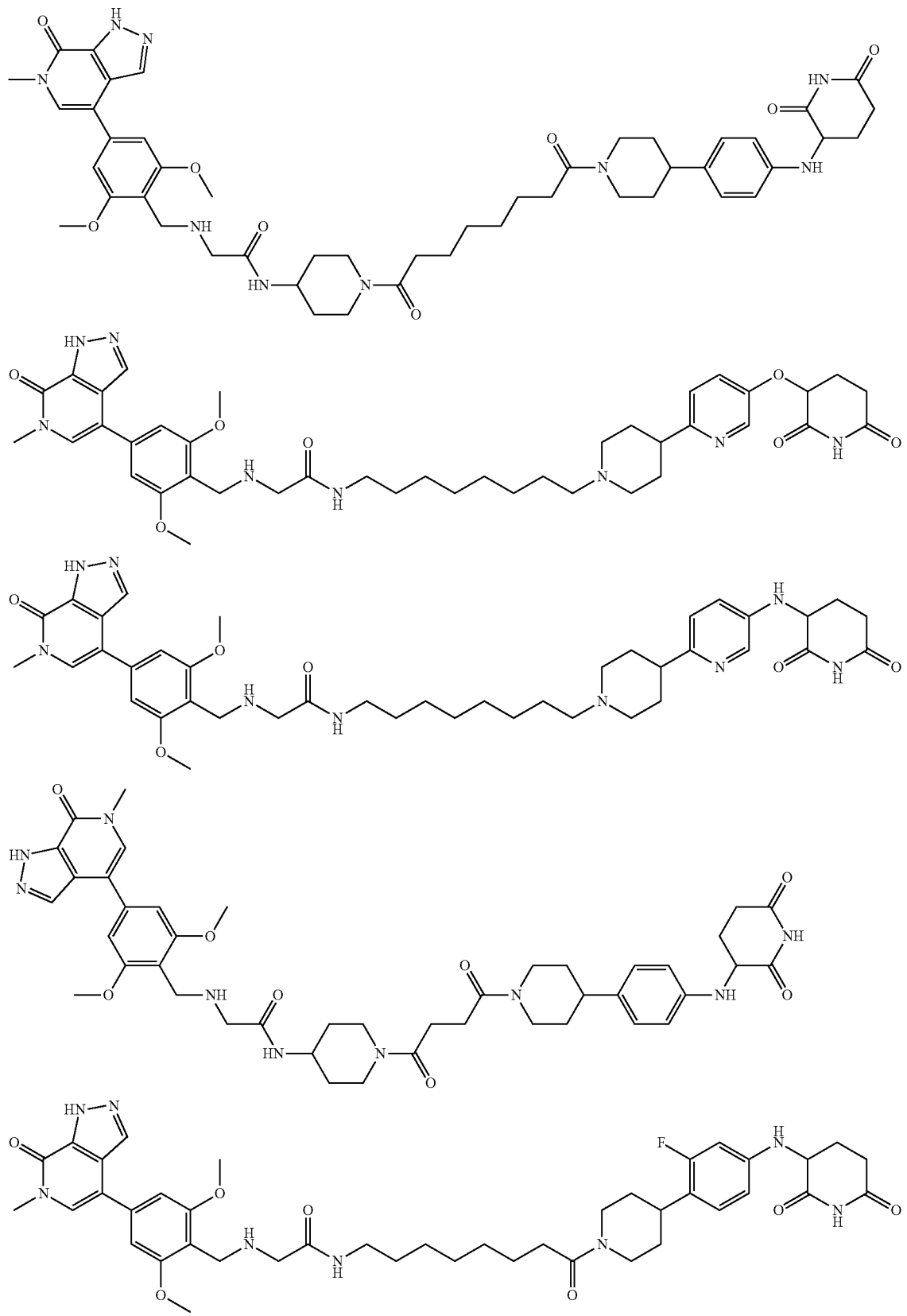

241
242
-continued
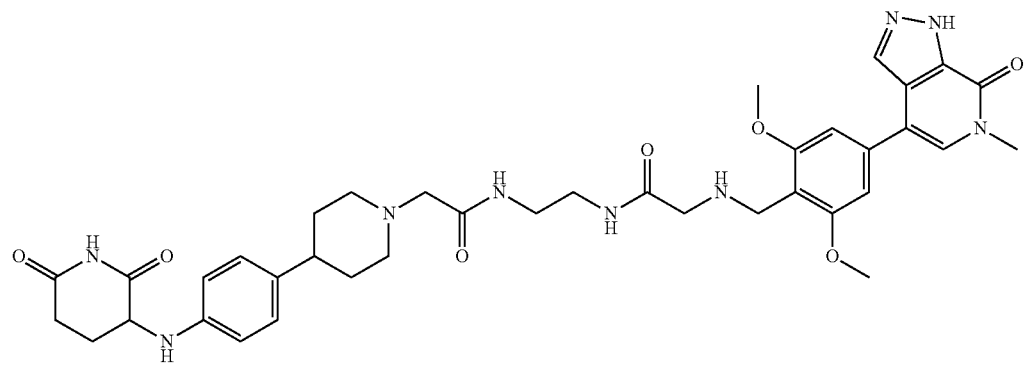
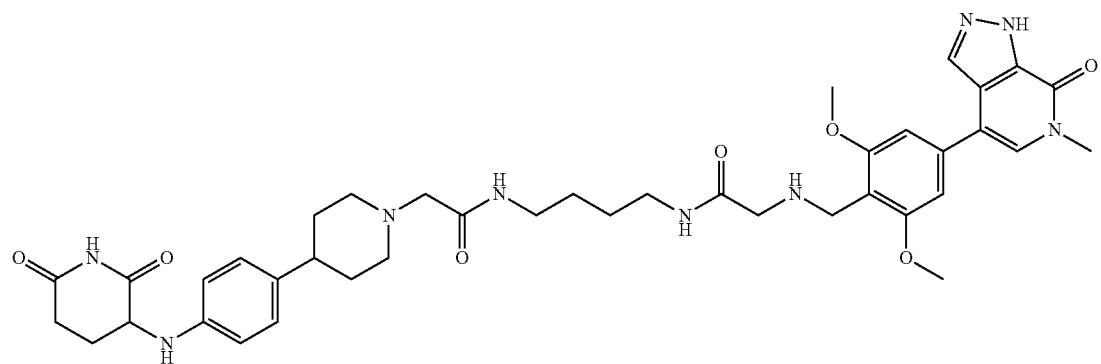
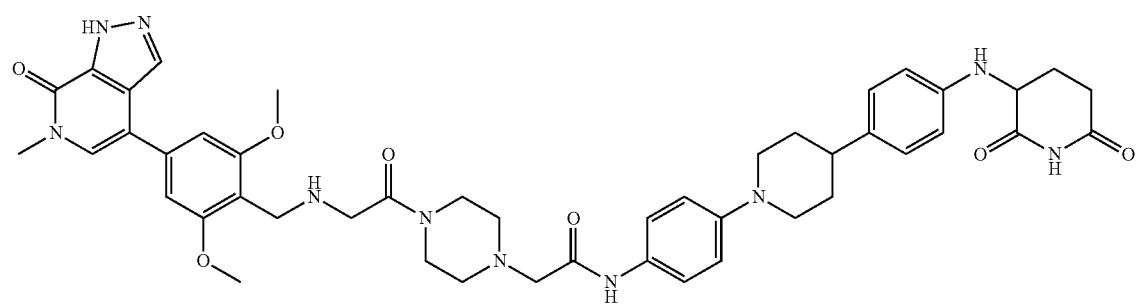
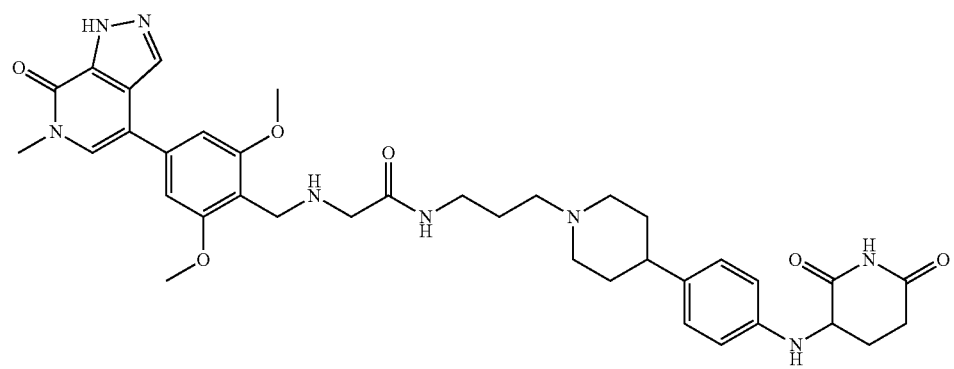

-continued
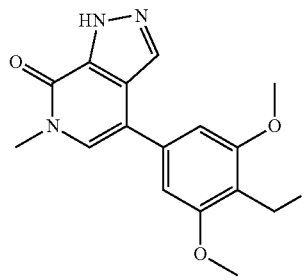

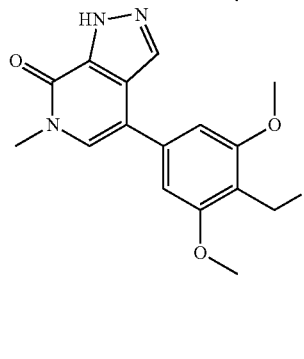
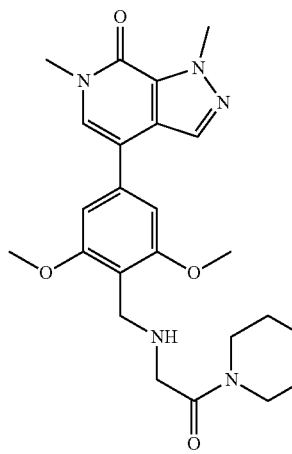
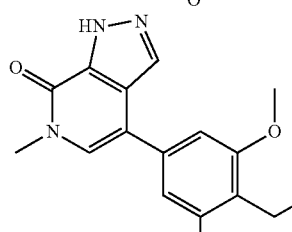
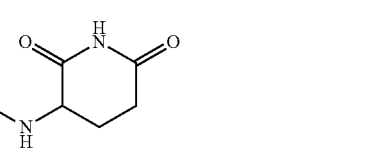
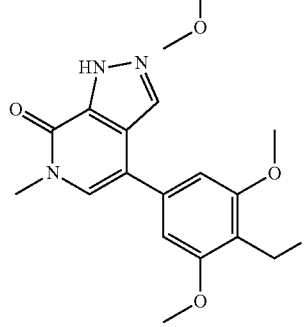

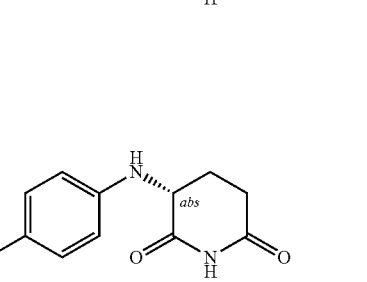

-continued
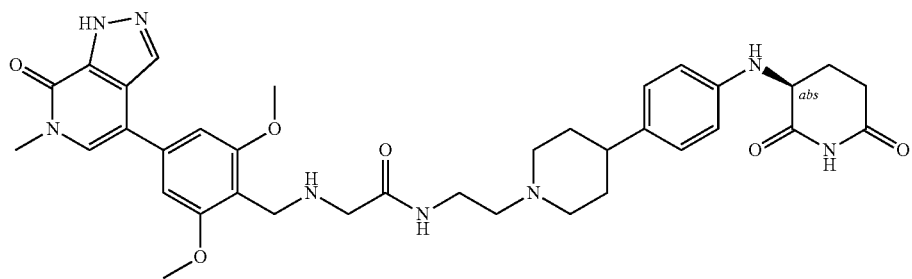
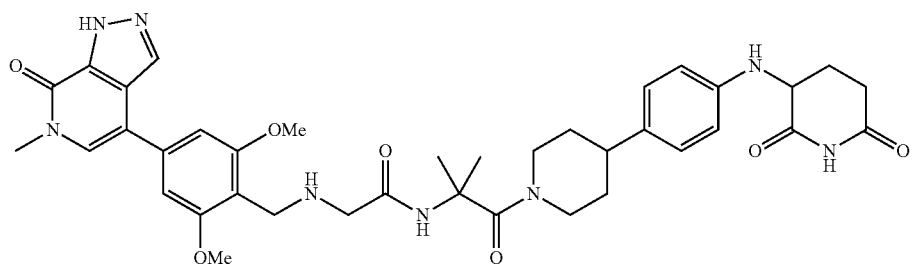
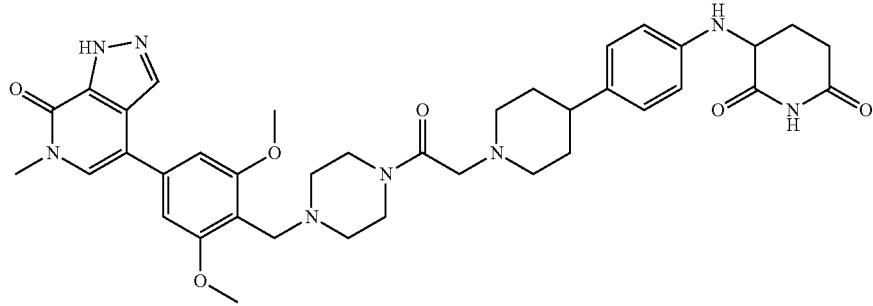
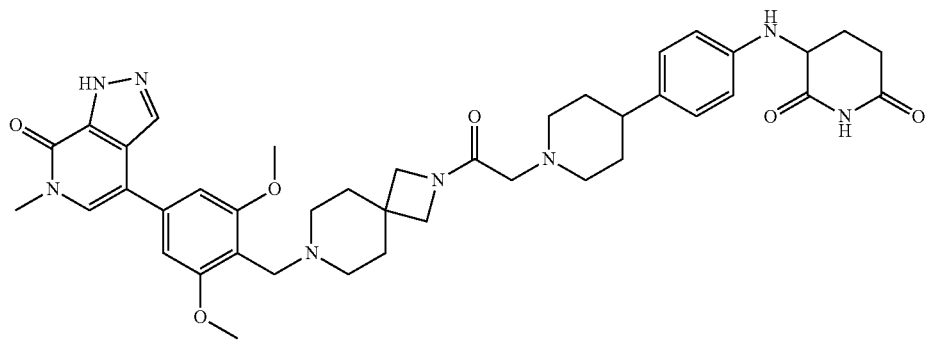
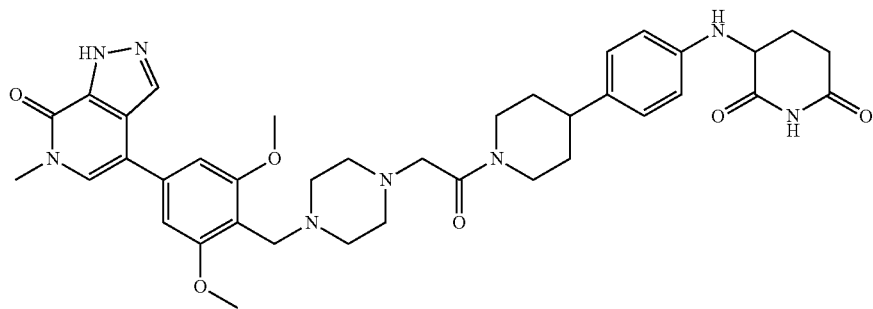

-continued
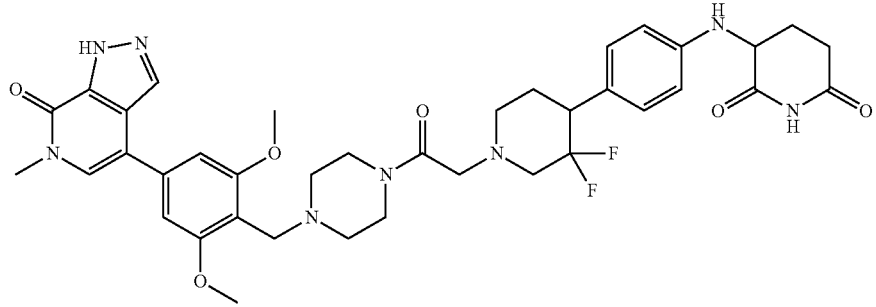
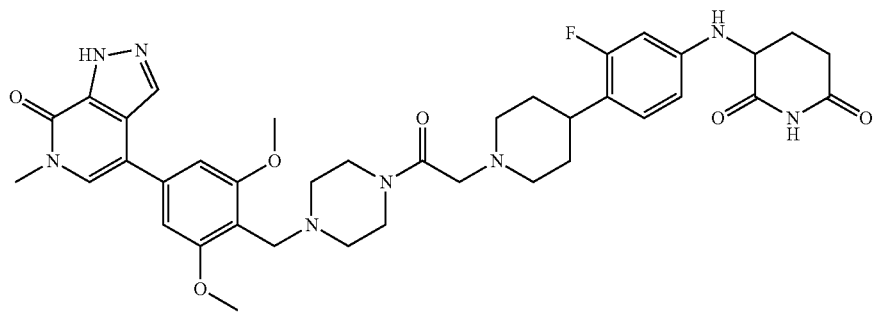
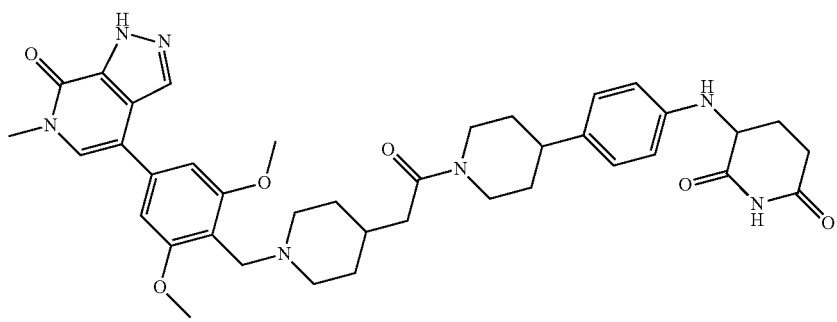
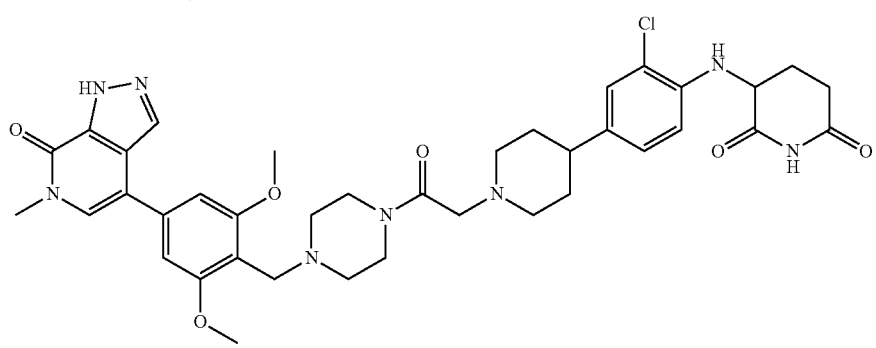
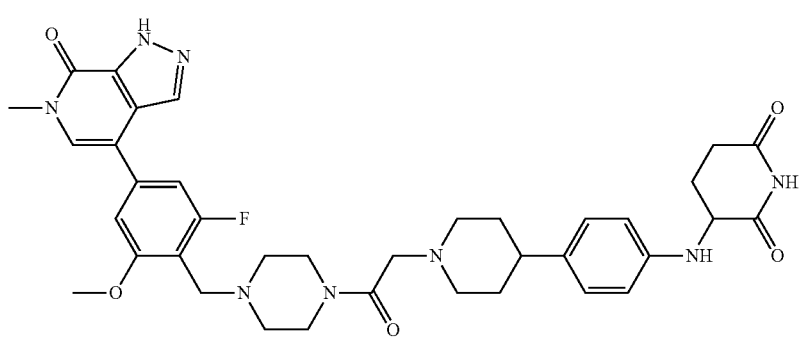

-continued
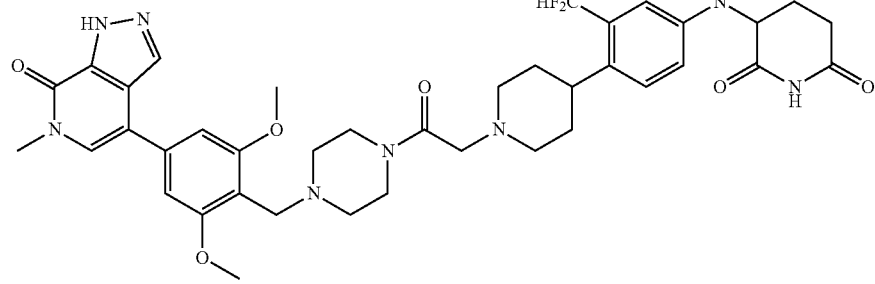
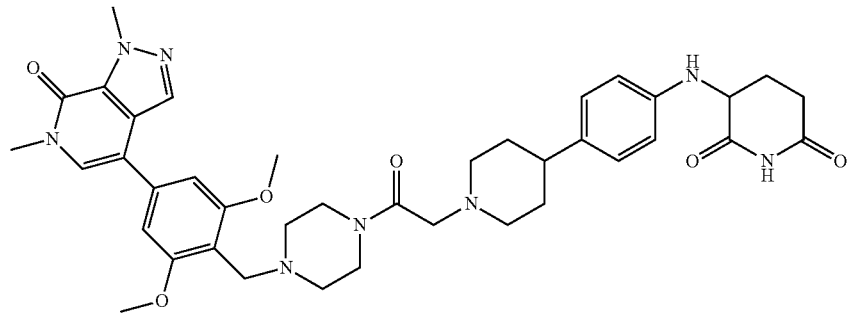
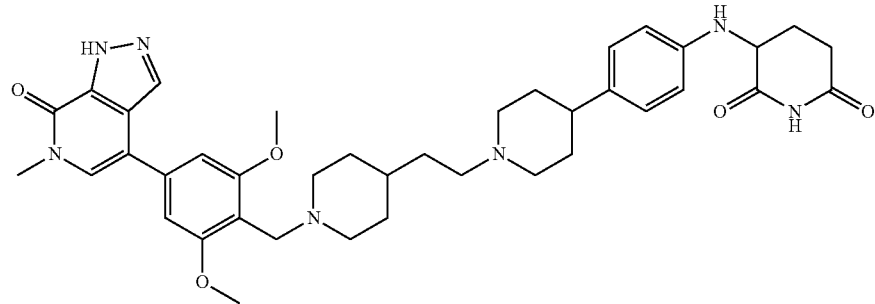
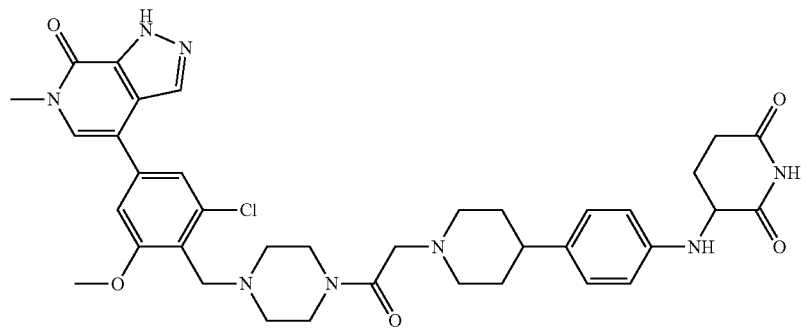
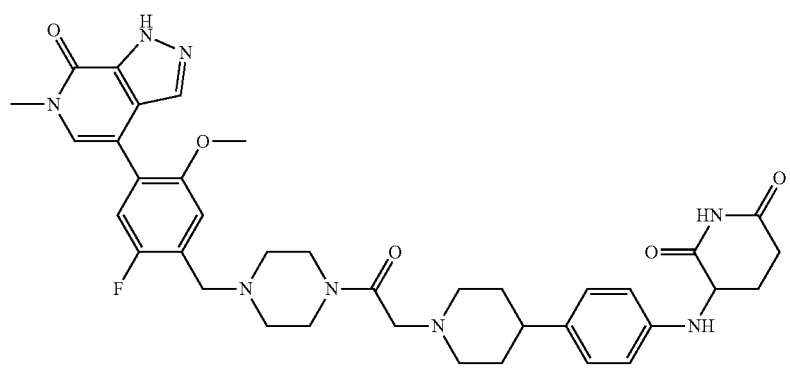

-continued
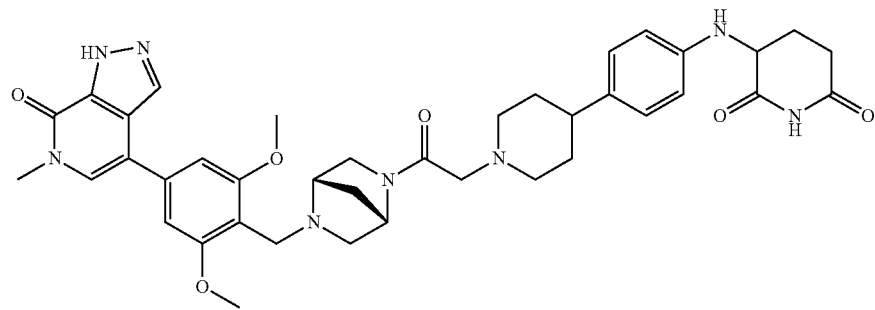
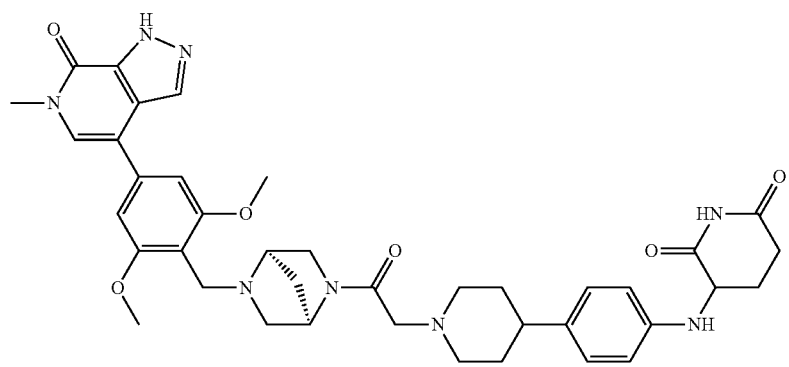
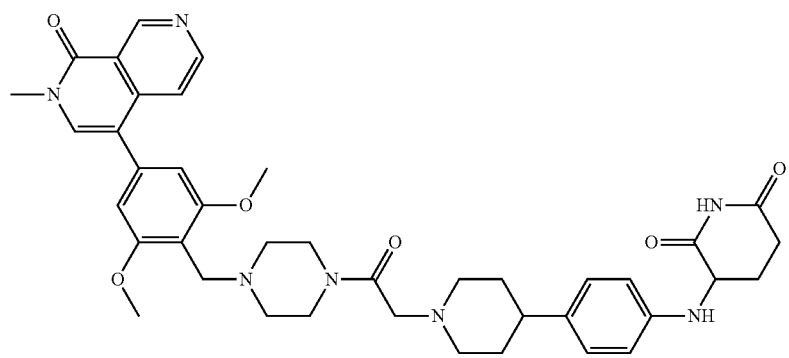
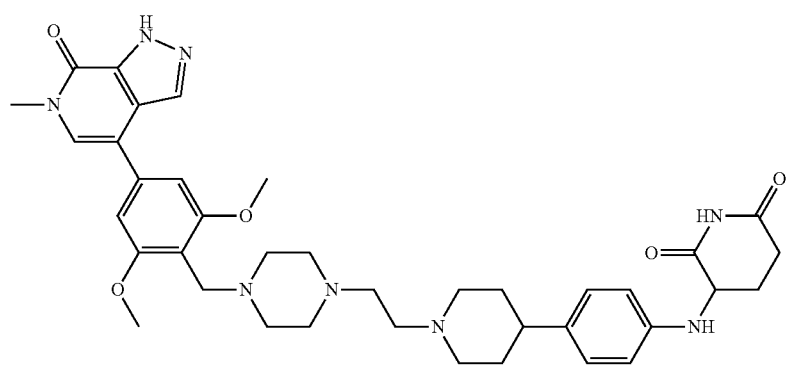

-continued
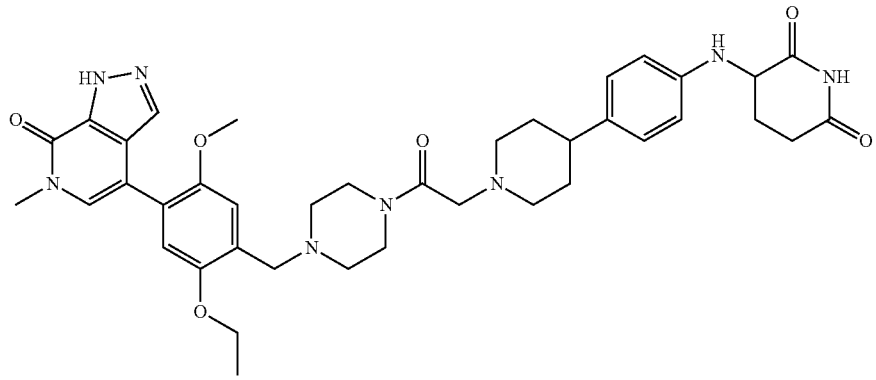
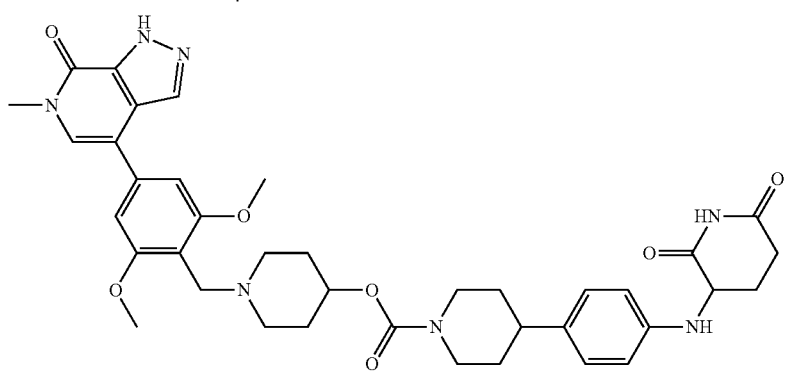
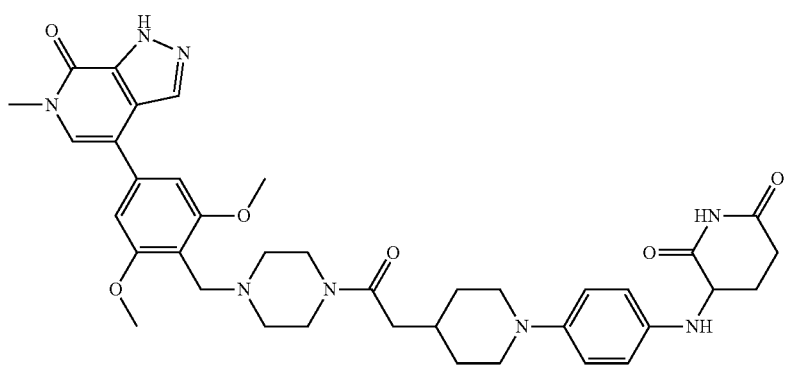
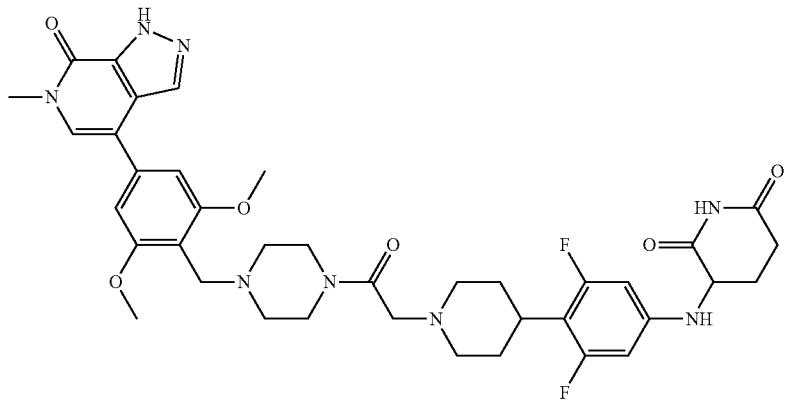

-continued
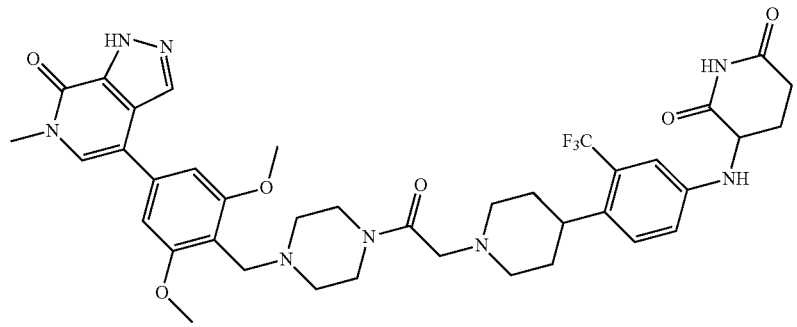
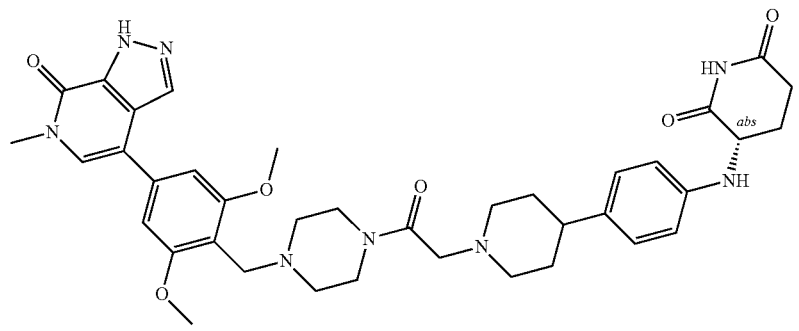
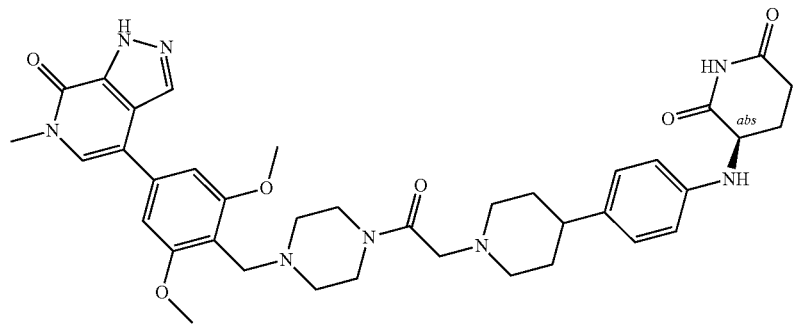
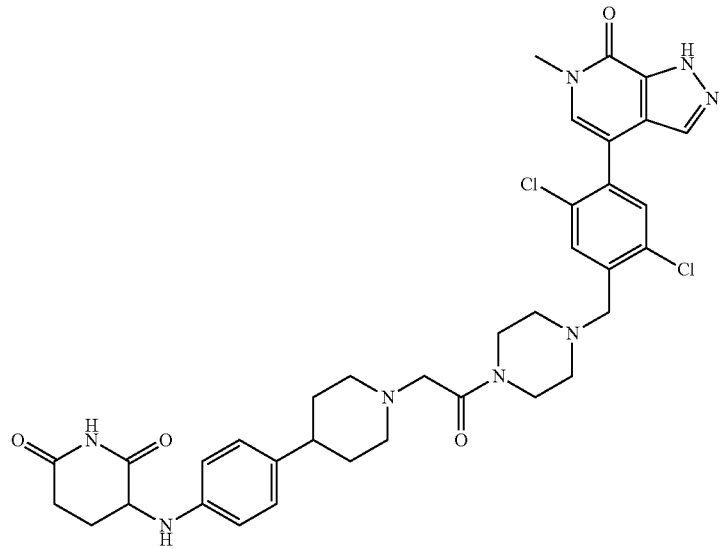

-continued
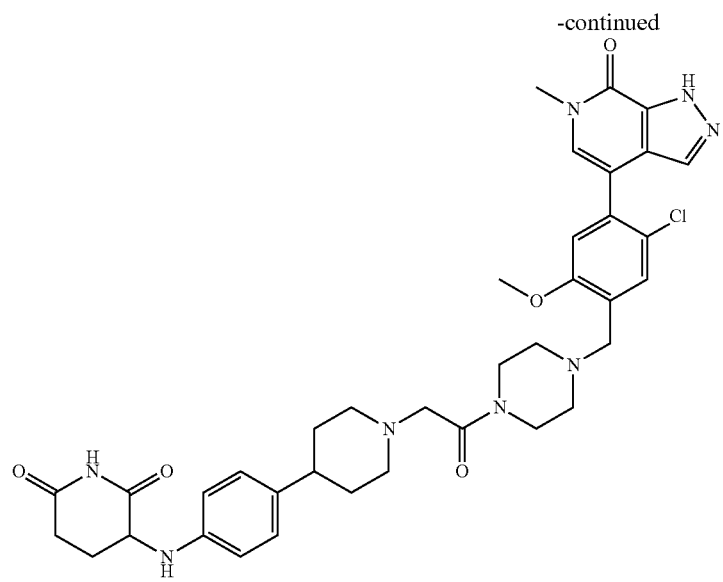
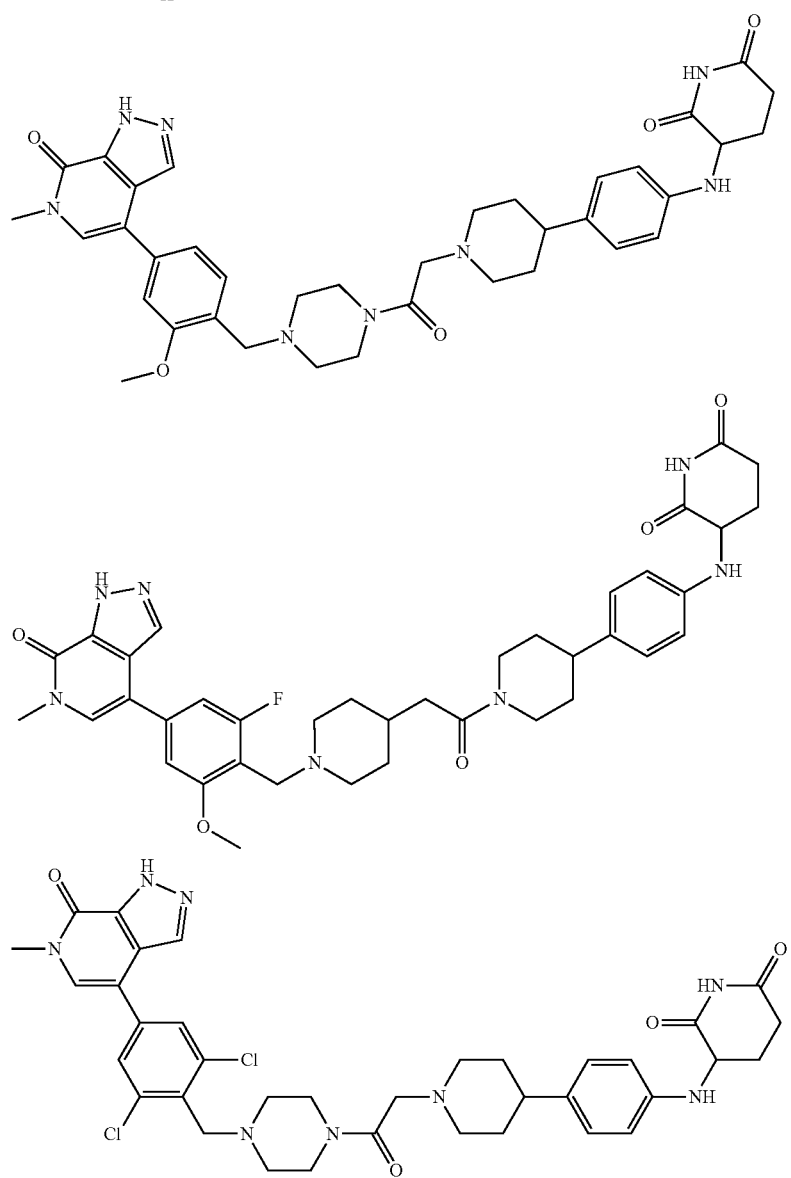

-continued
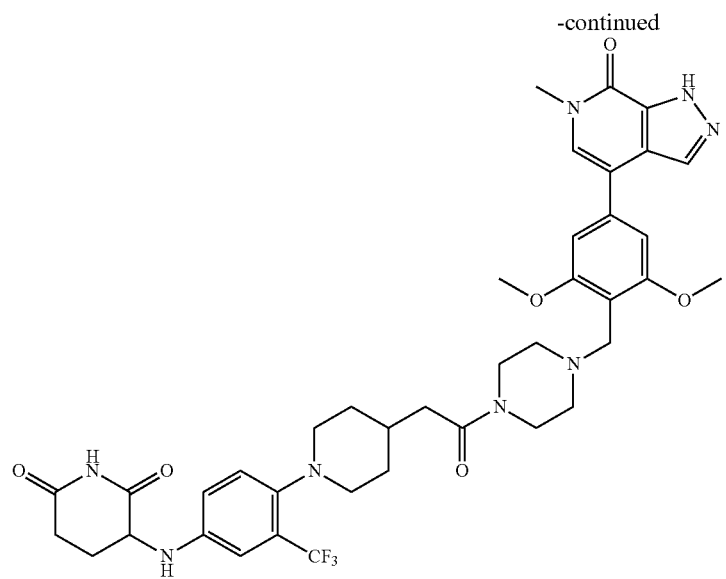
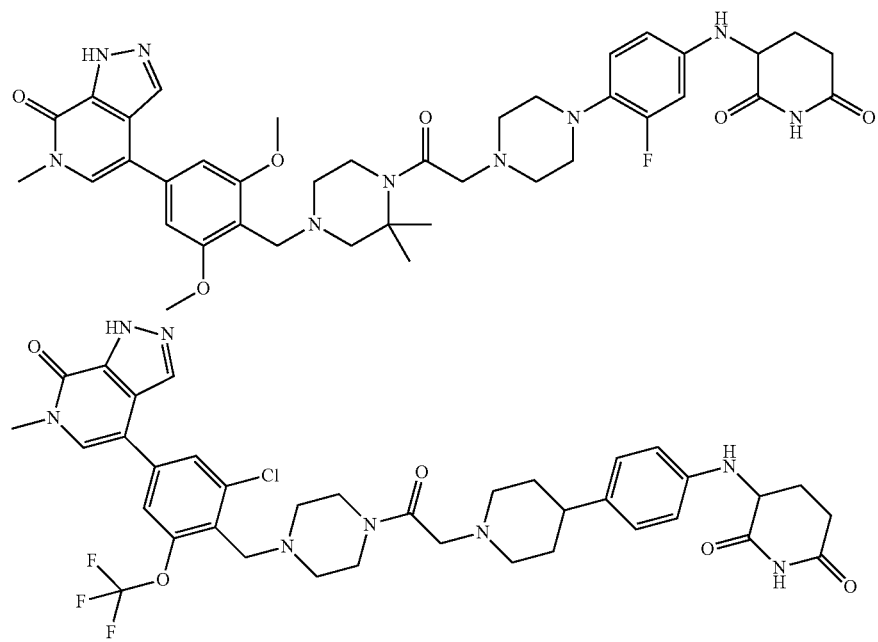
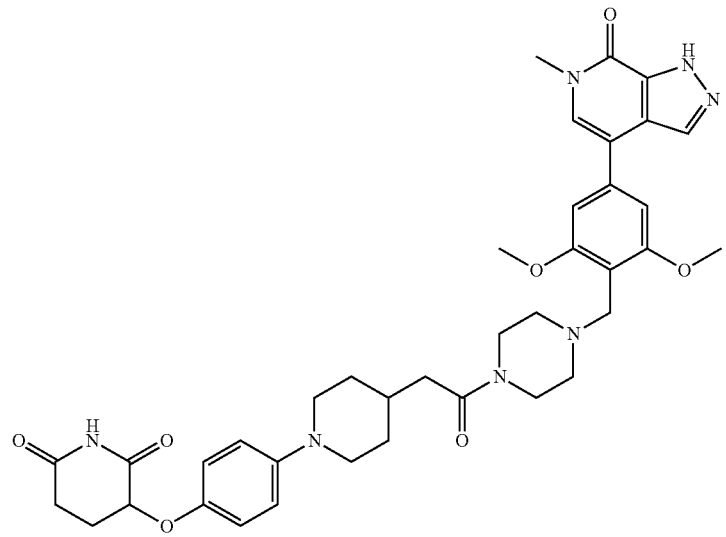

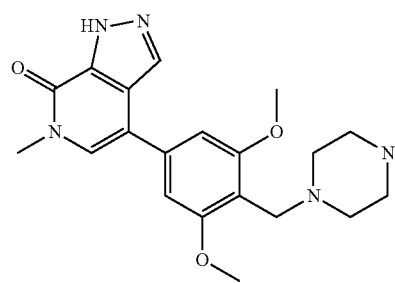
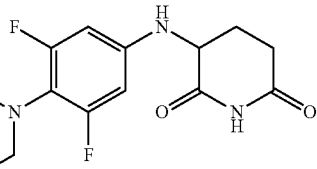
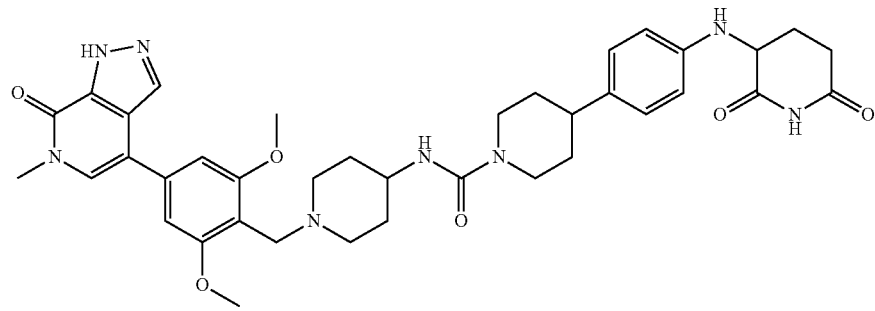
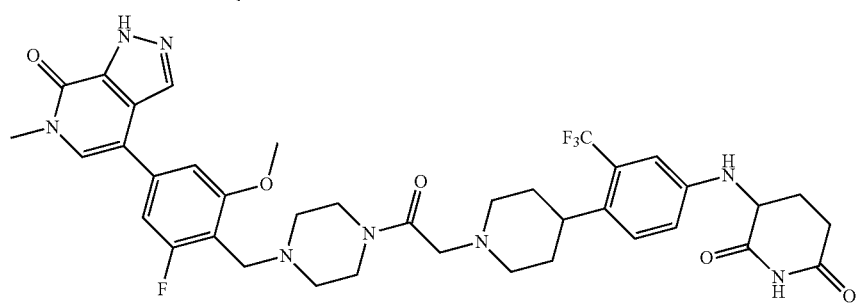
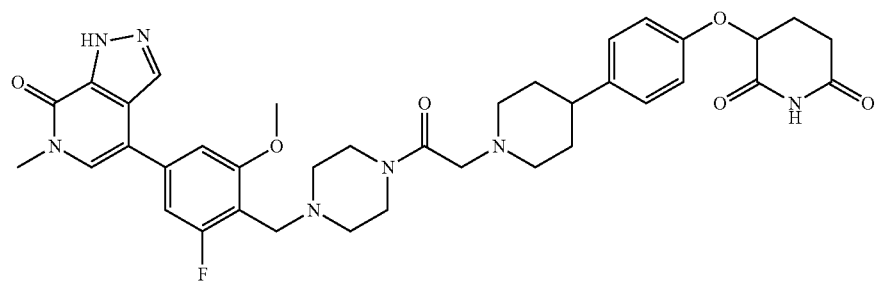
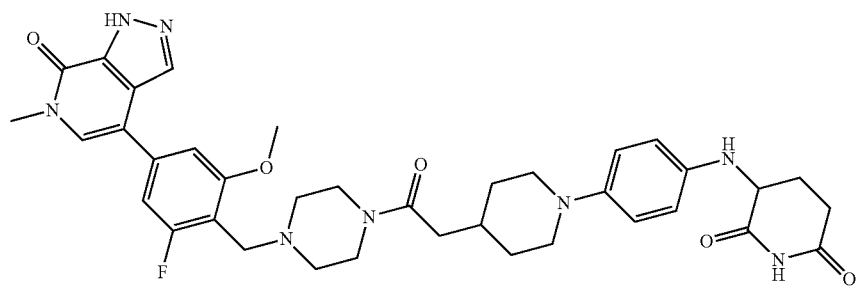

-continued
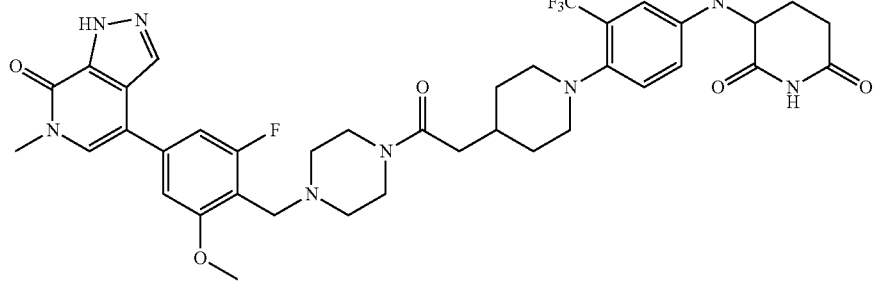
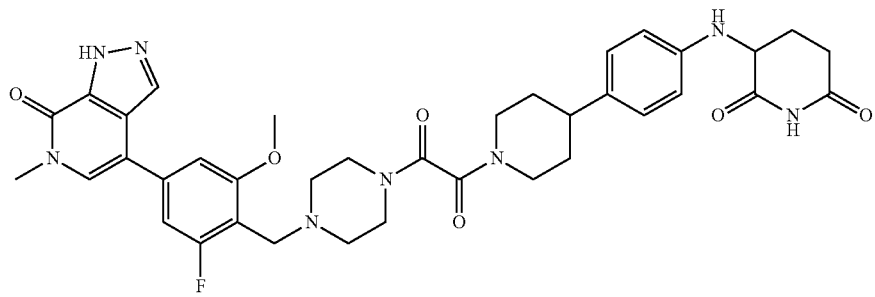
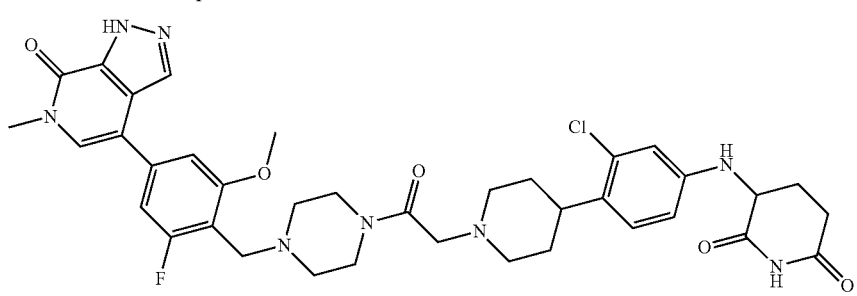
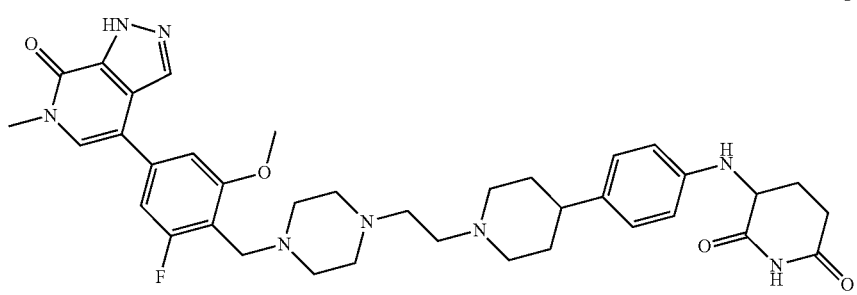
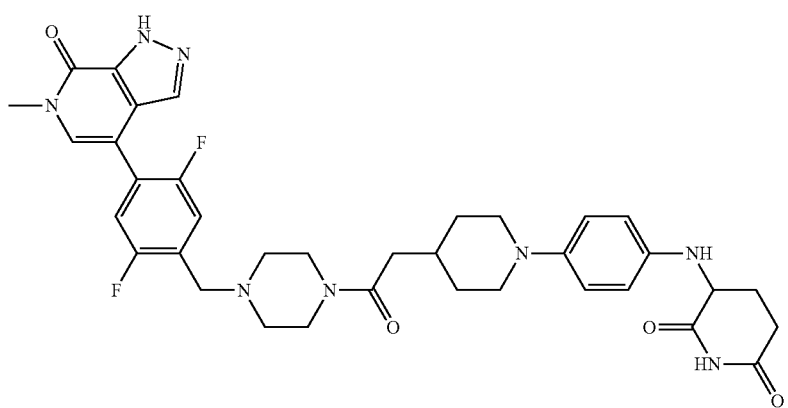

-continued
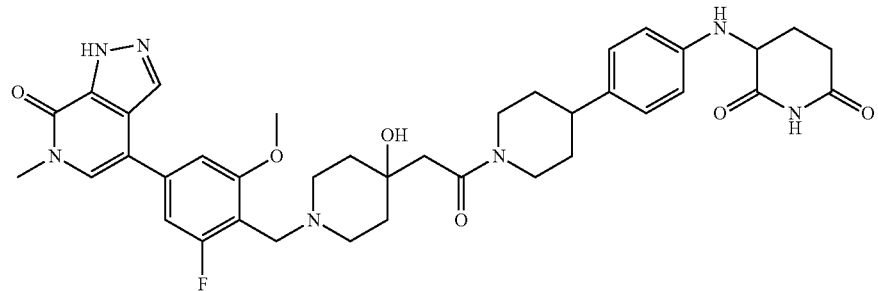
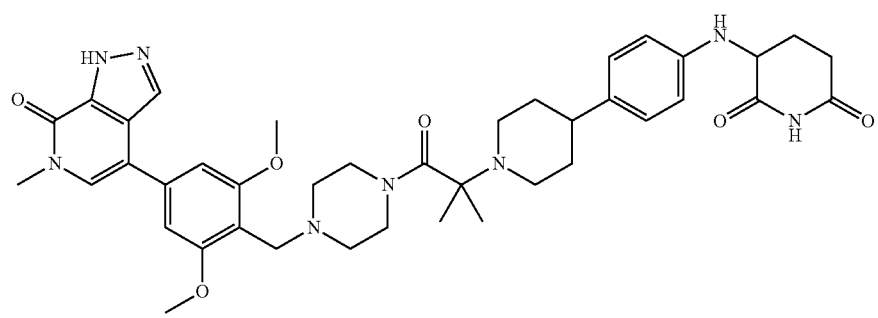
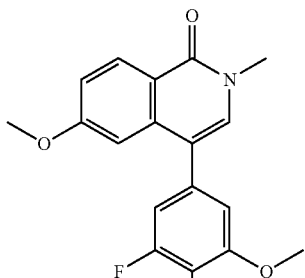
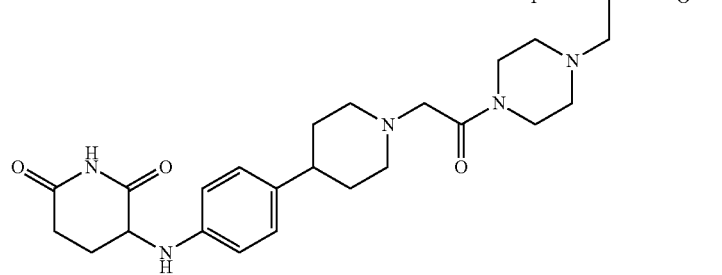
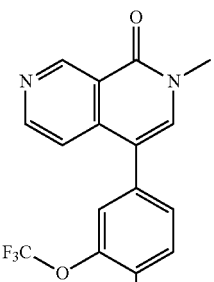
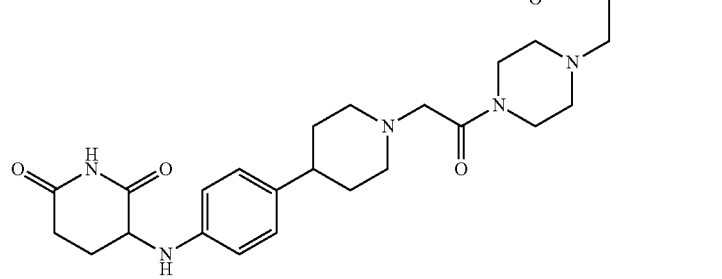

-continued
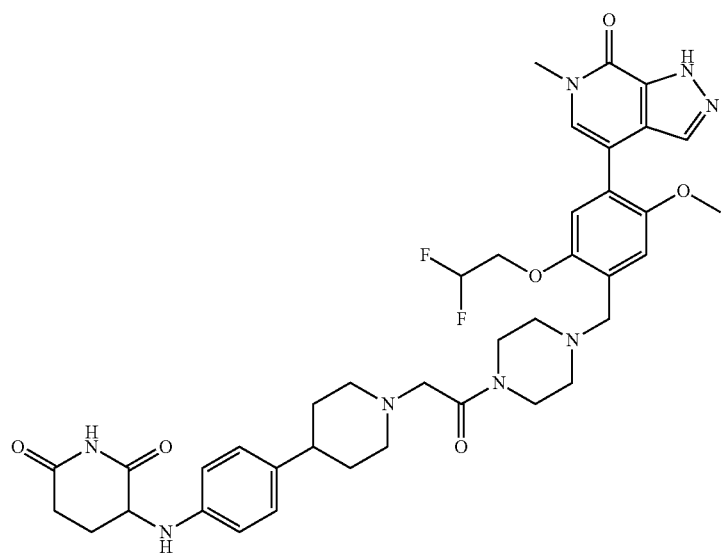
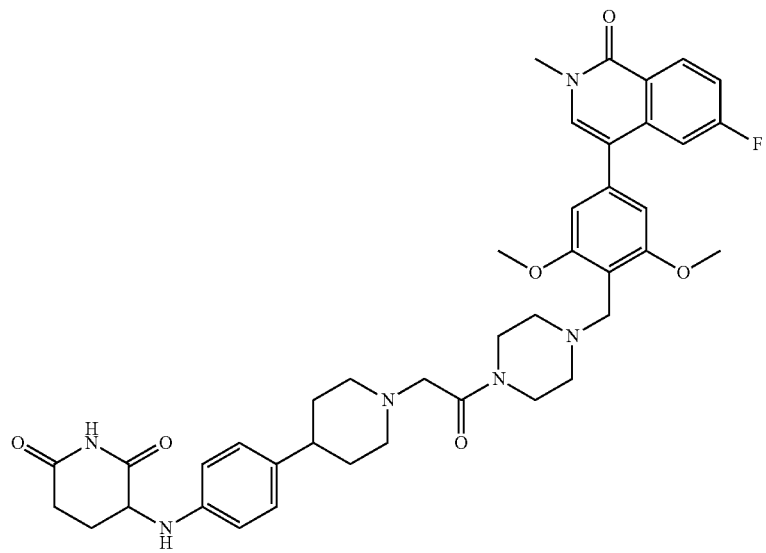
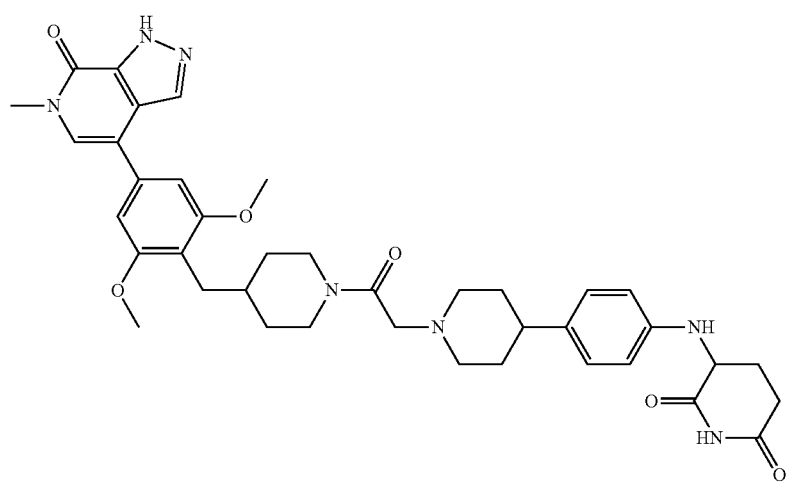

-continued
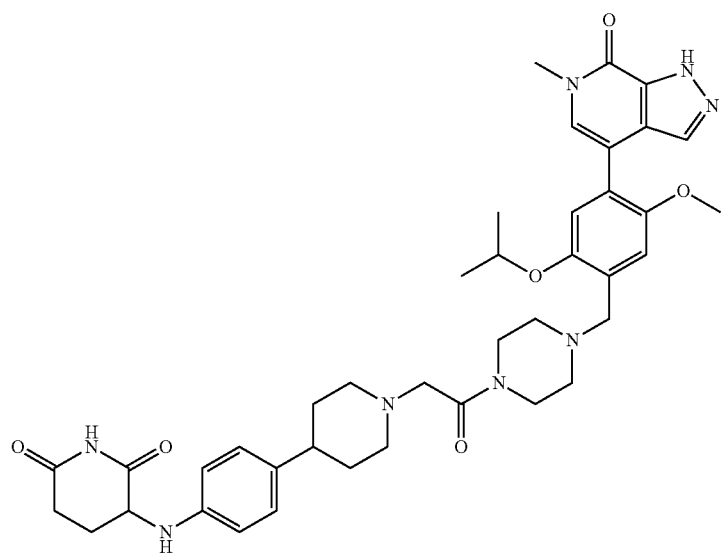
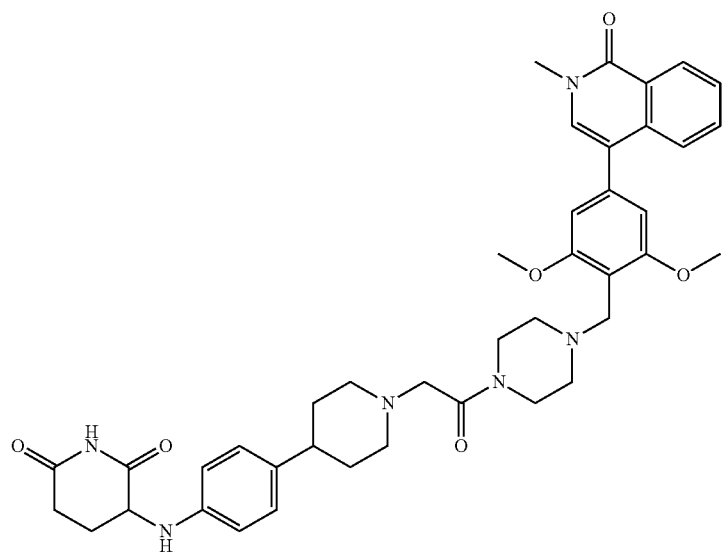
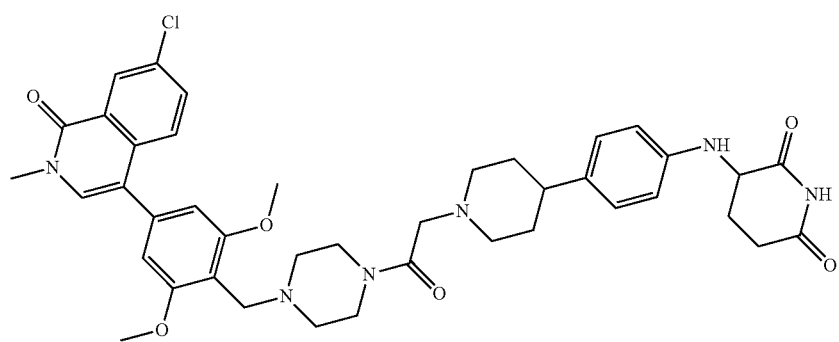

-continued
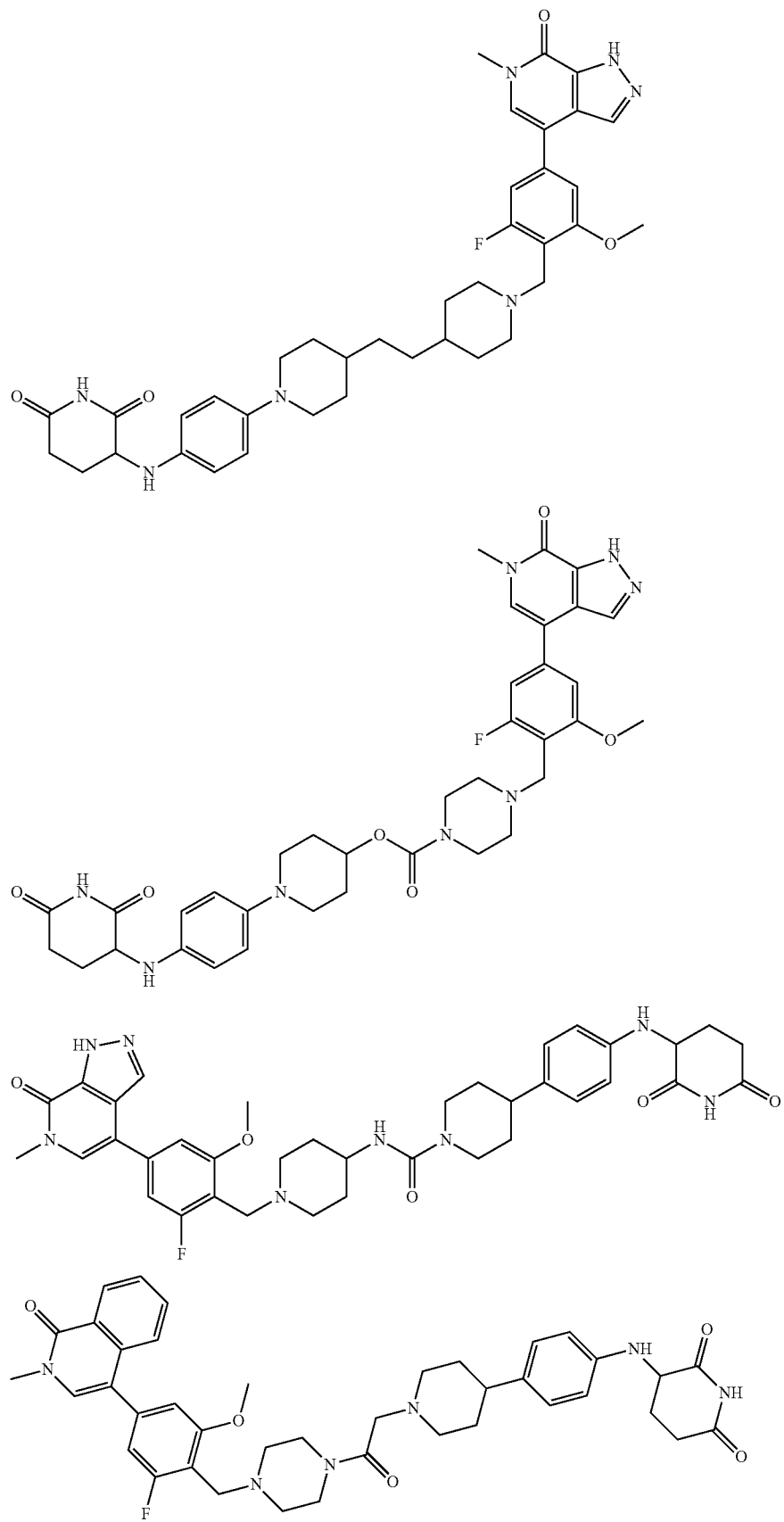

-continued
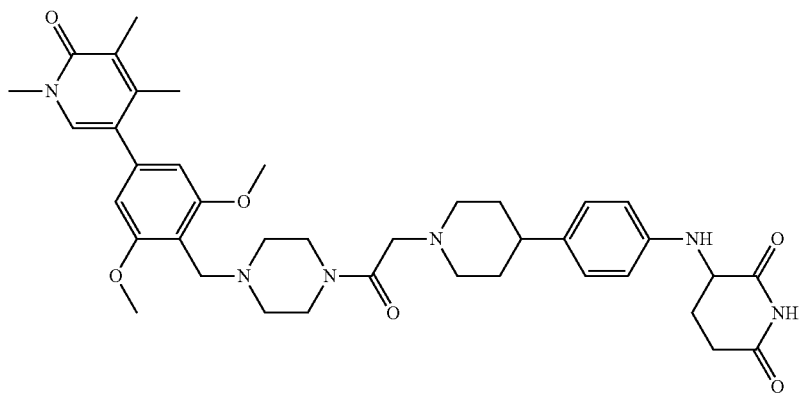
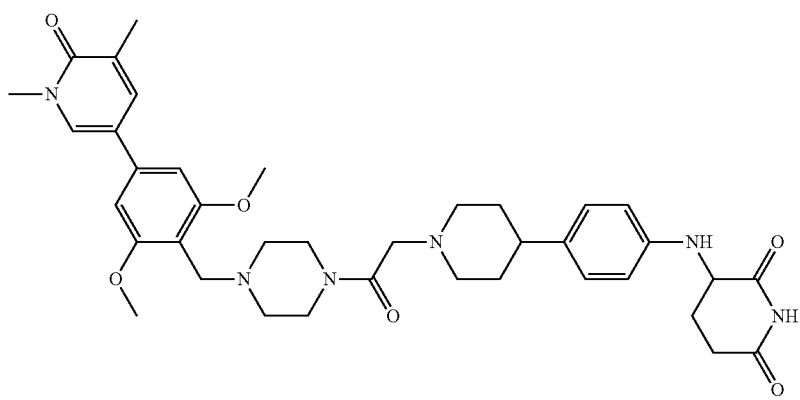
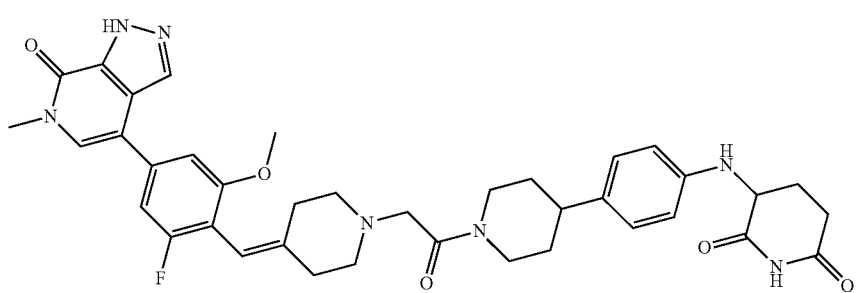
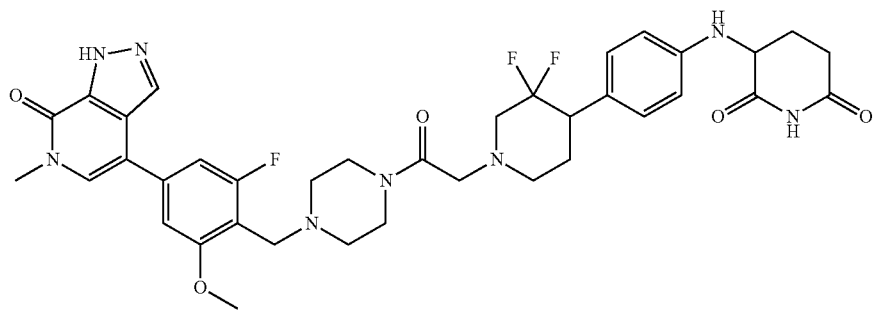
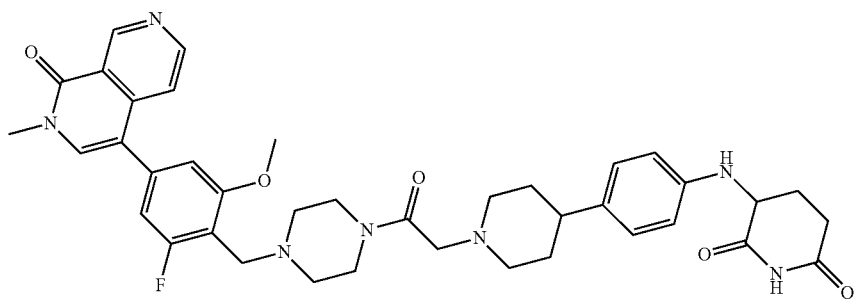

-continued
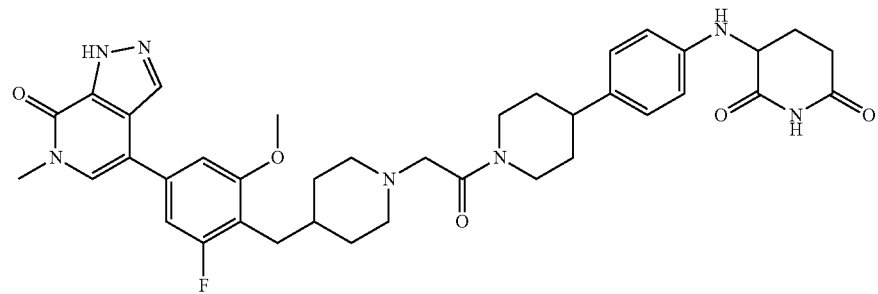
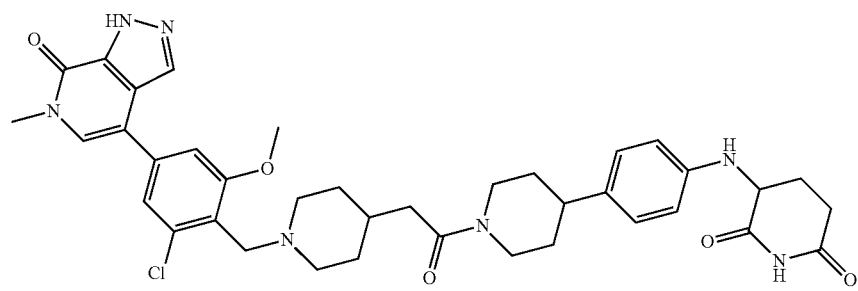
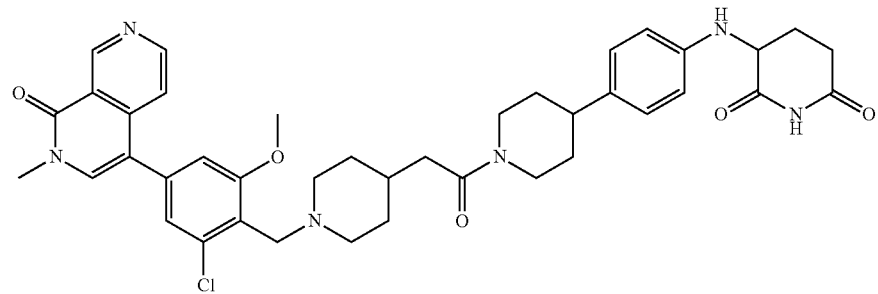
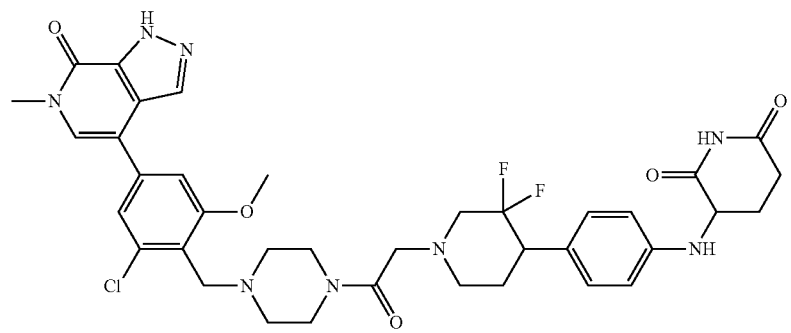
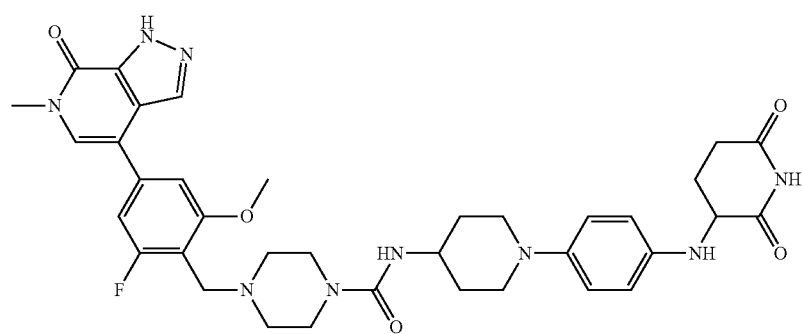

-continued
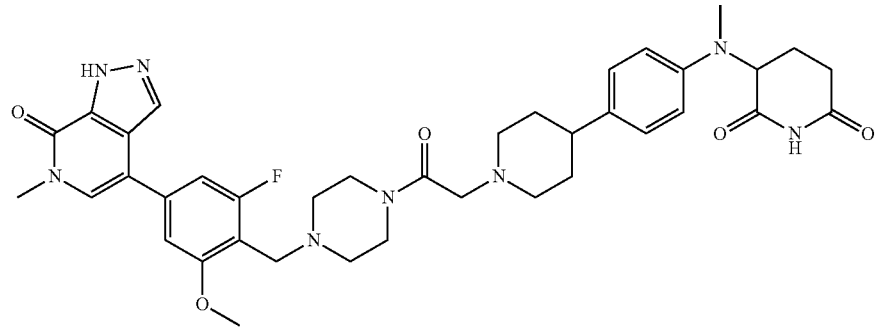
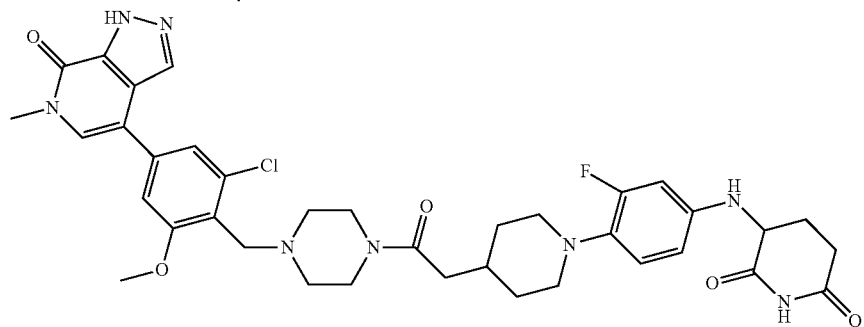
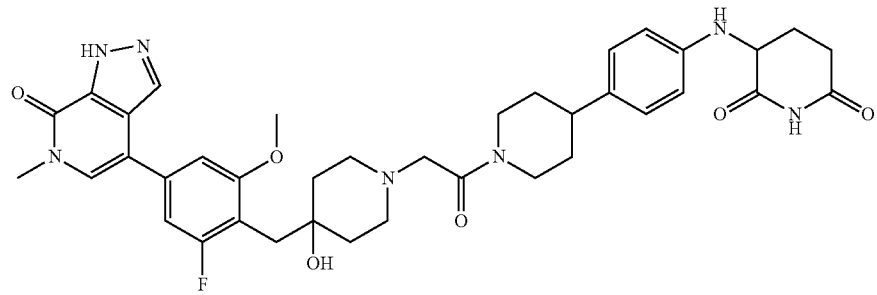
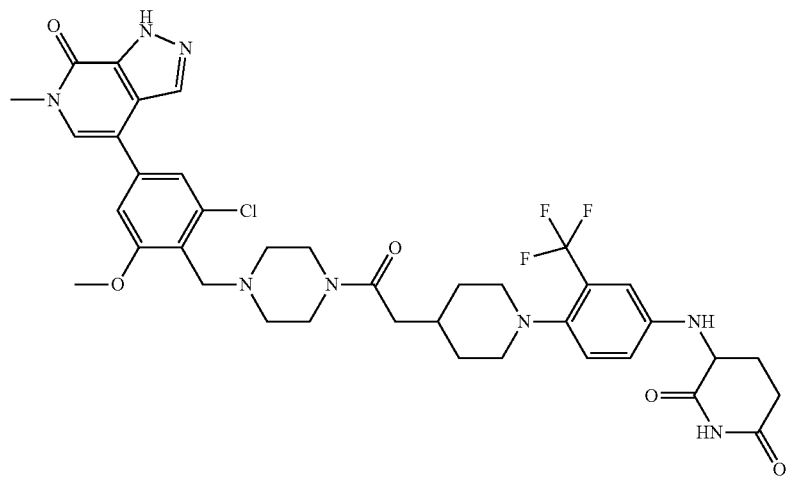

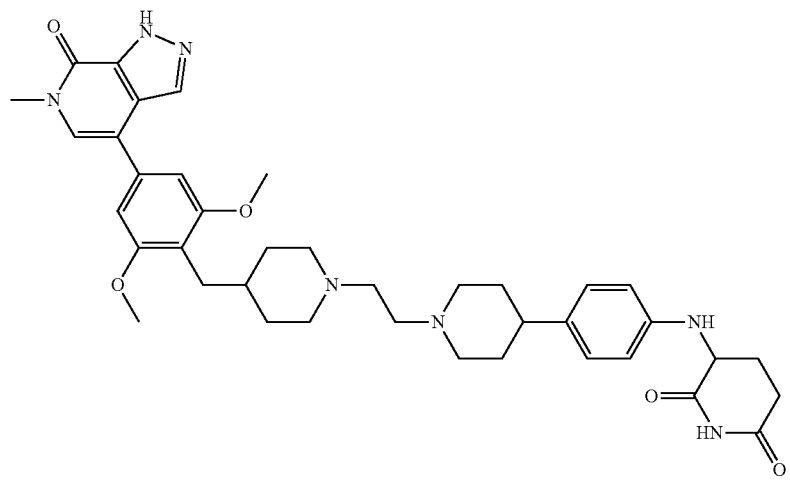
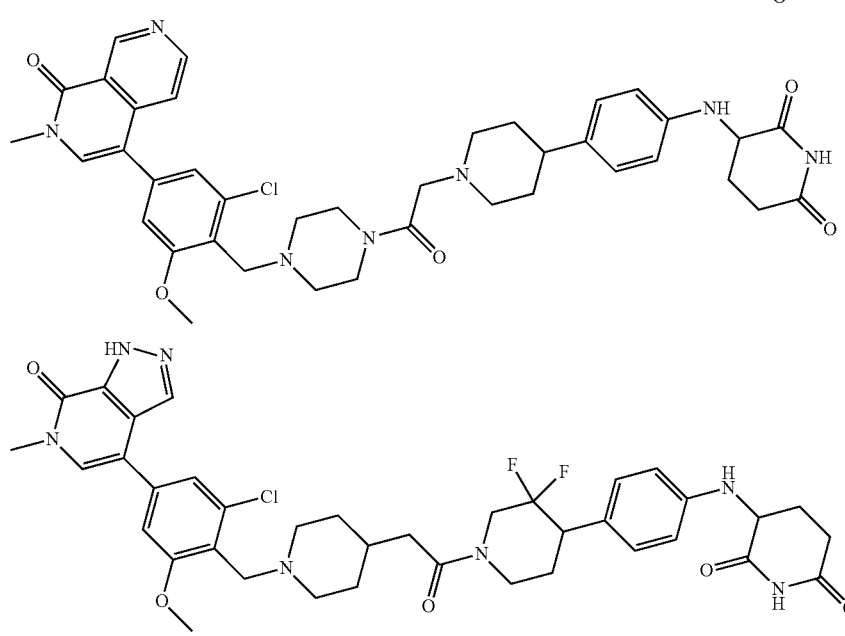
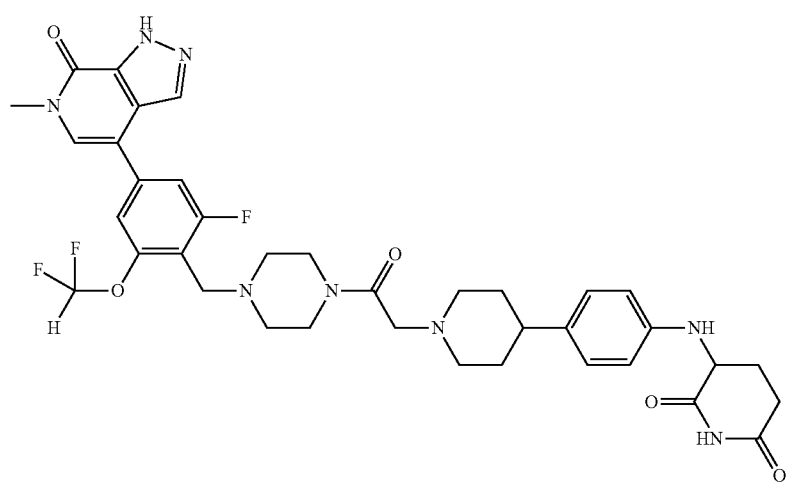

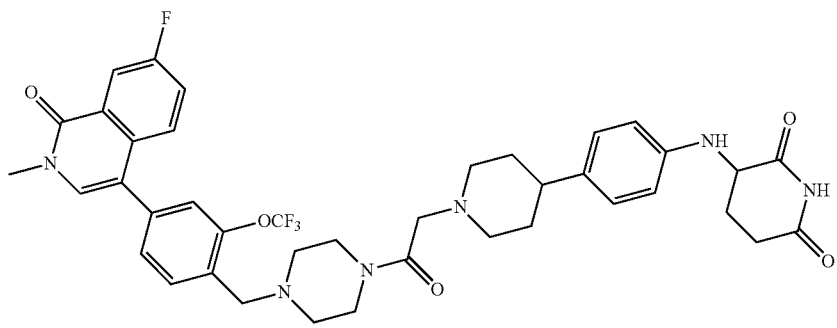
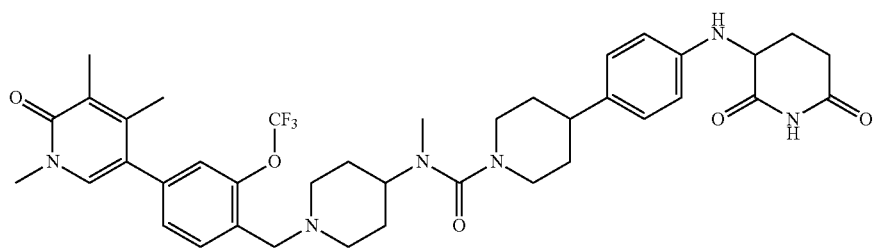
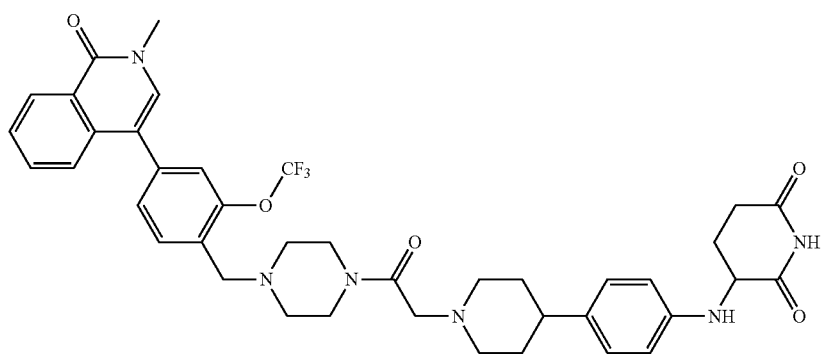
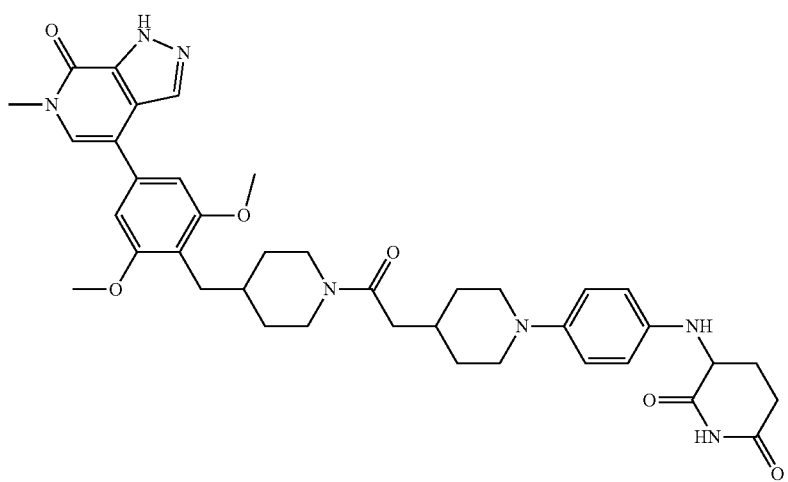

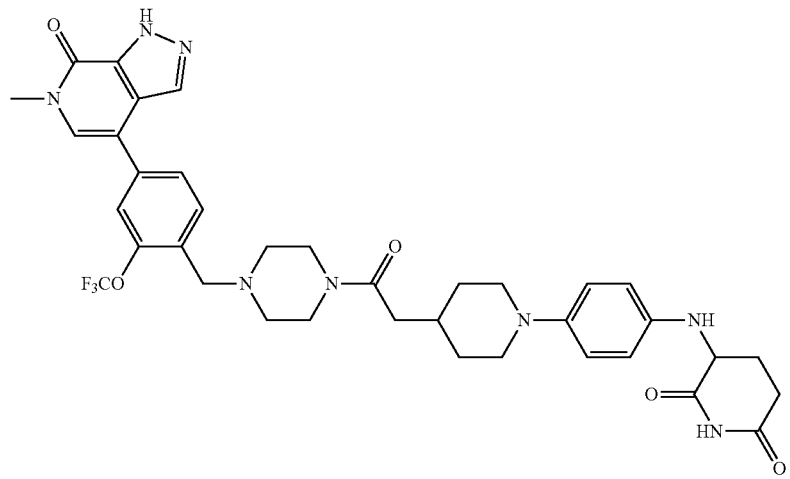
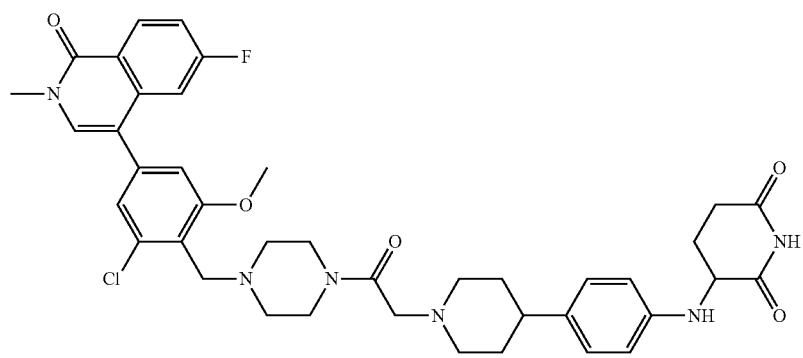
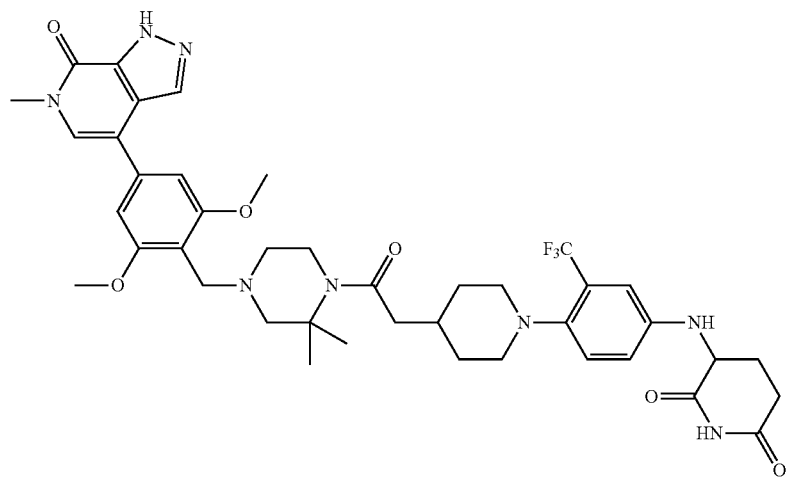

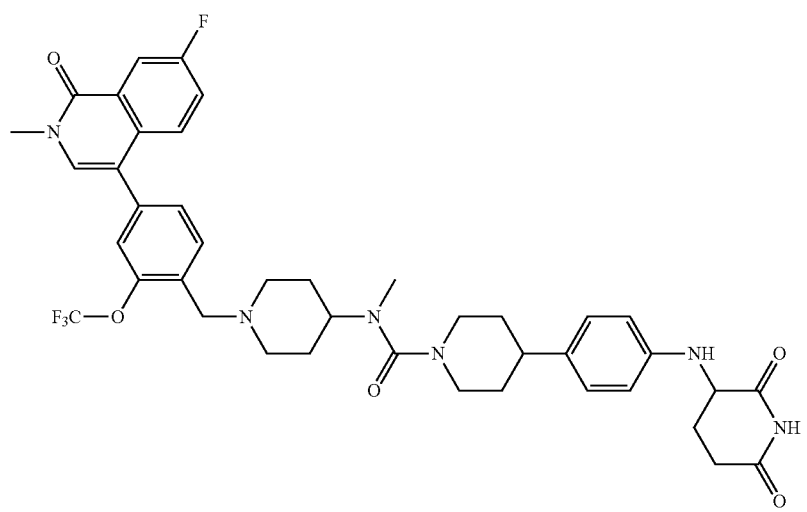
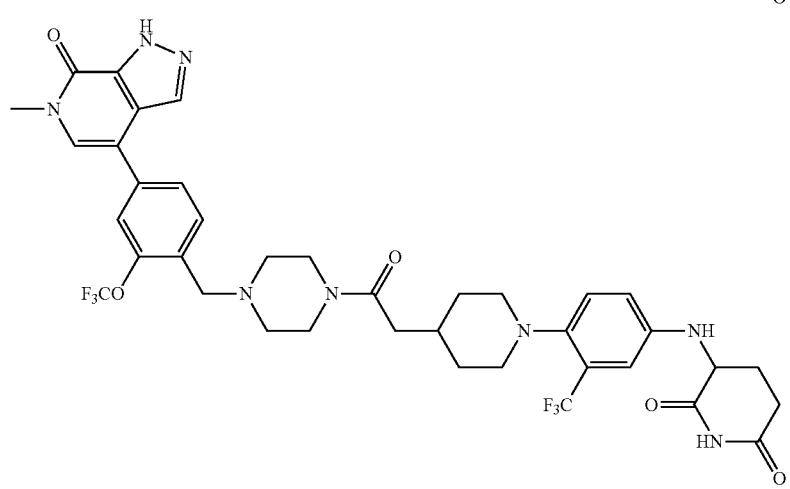
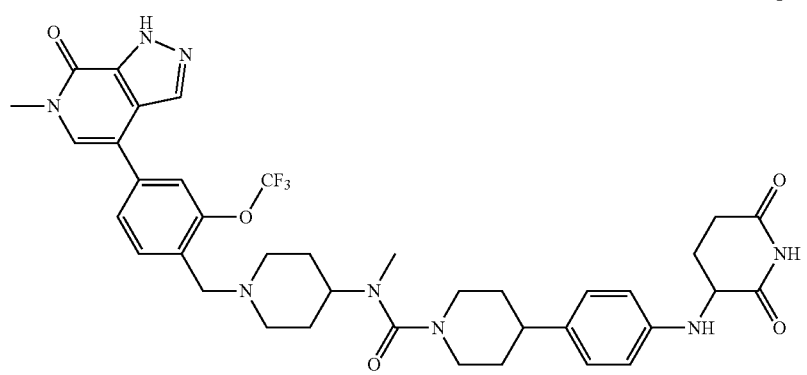

-continued
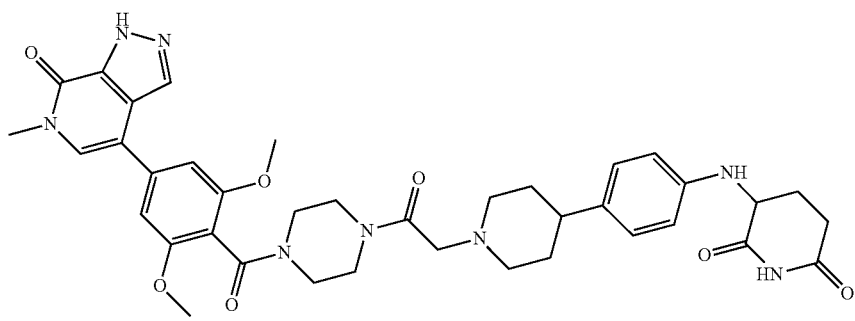
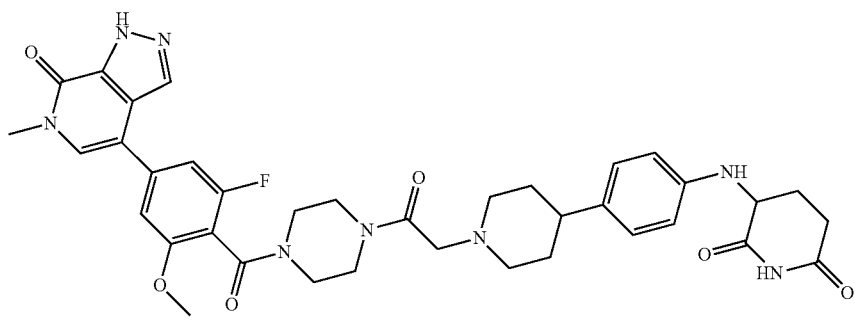
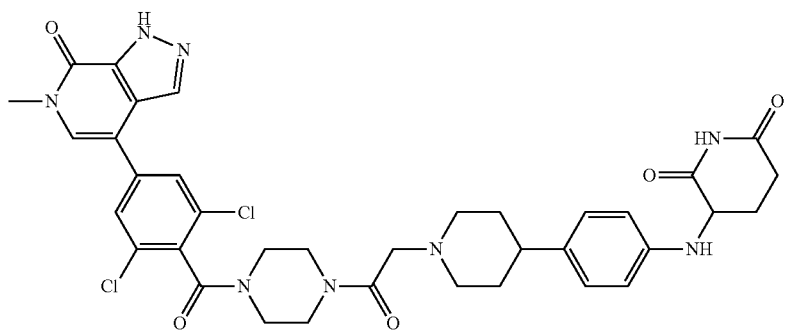
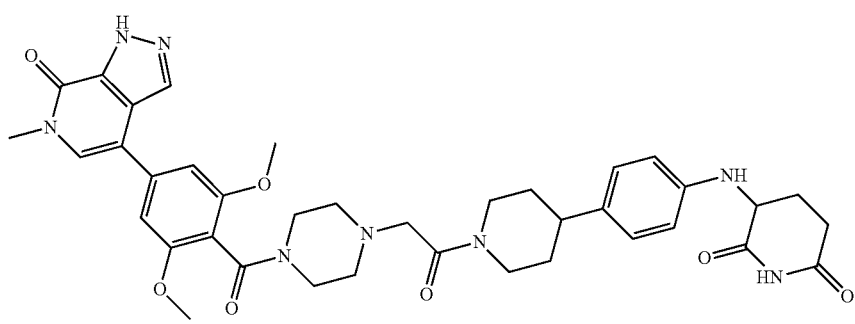
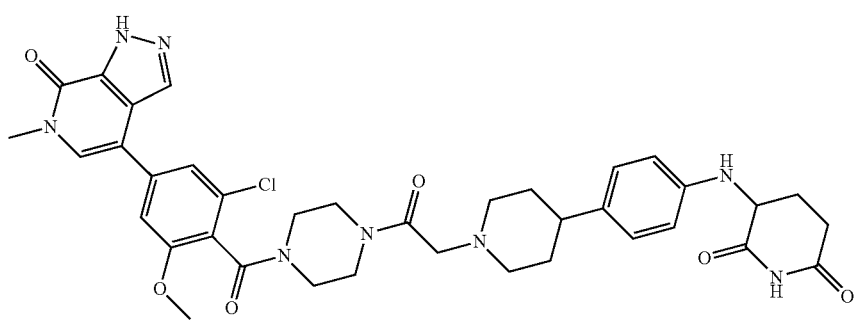

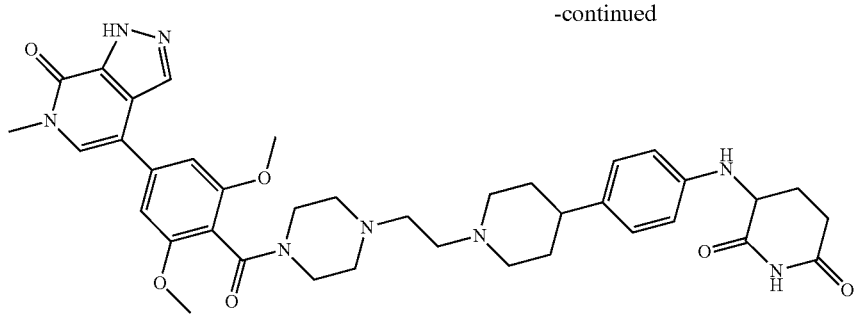
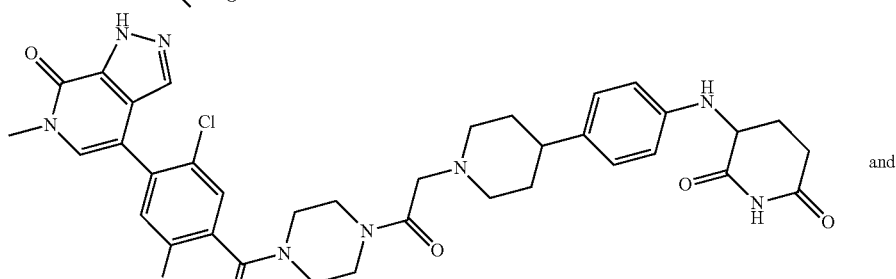
and
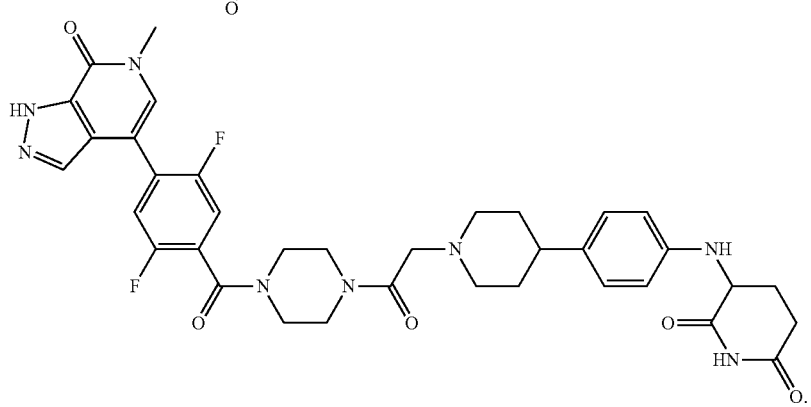
In certain embodiments a compound of the present invention is selected from:
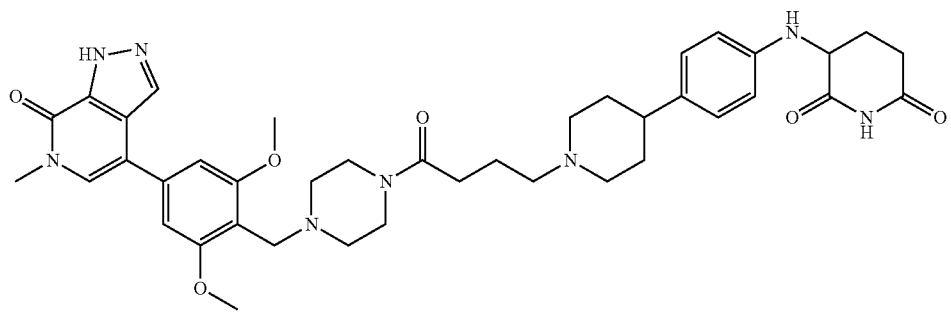

-continued
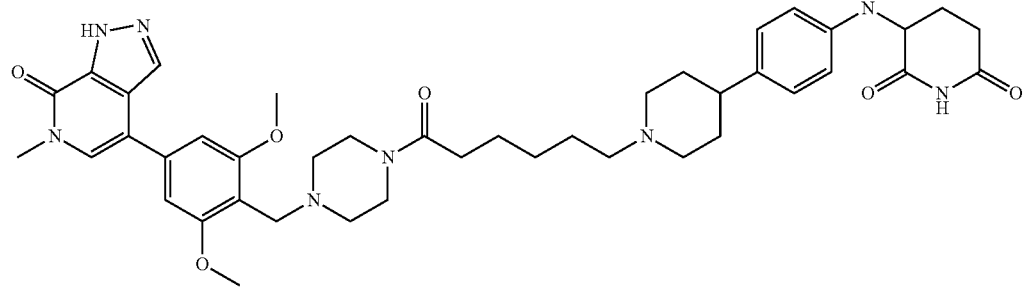
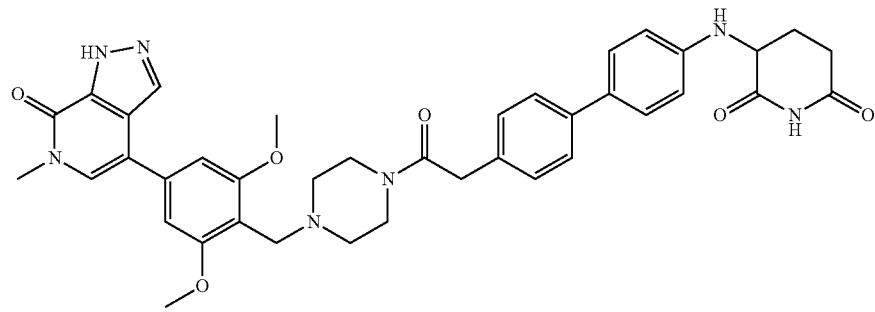
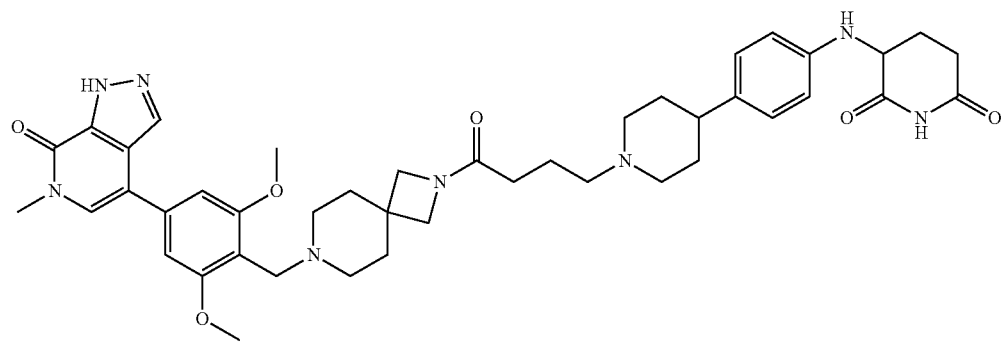
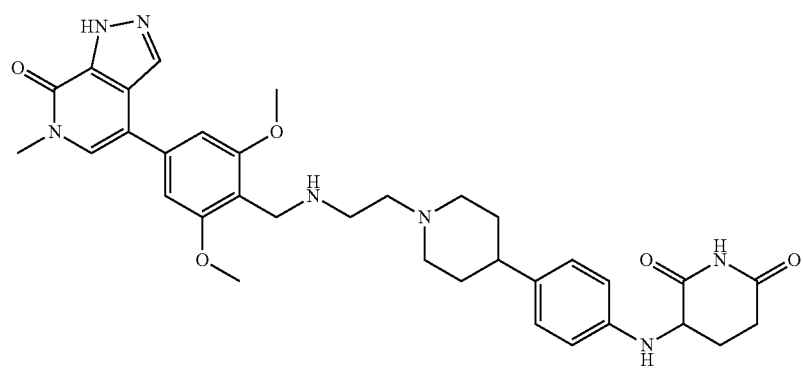
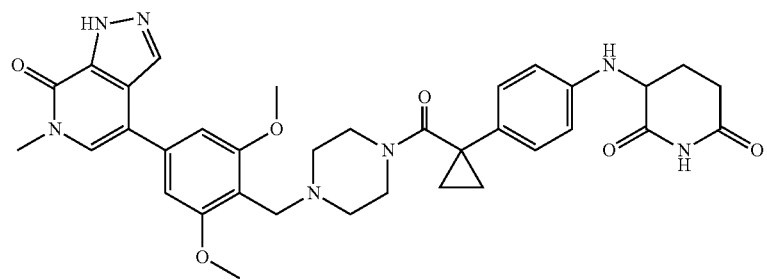

-continued
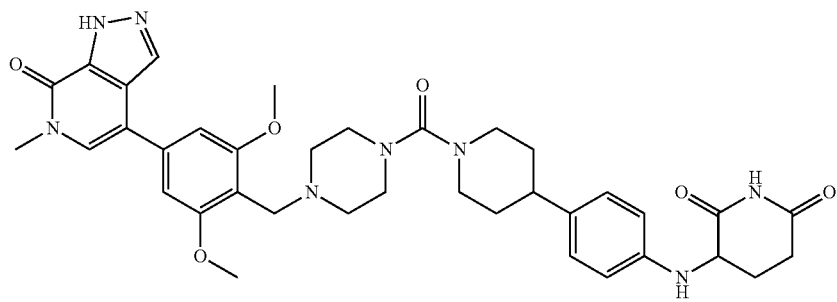
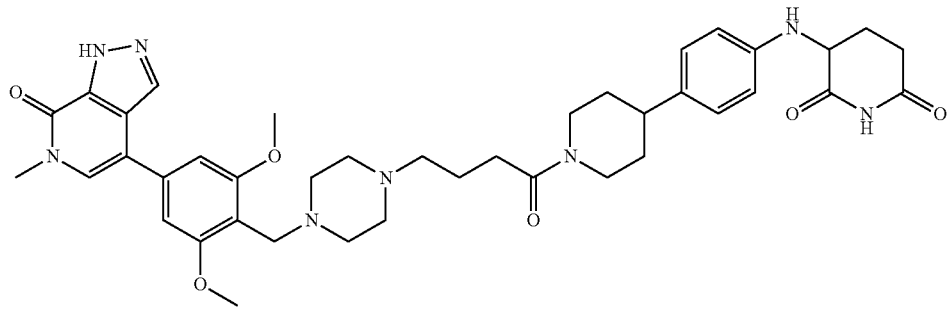
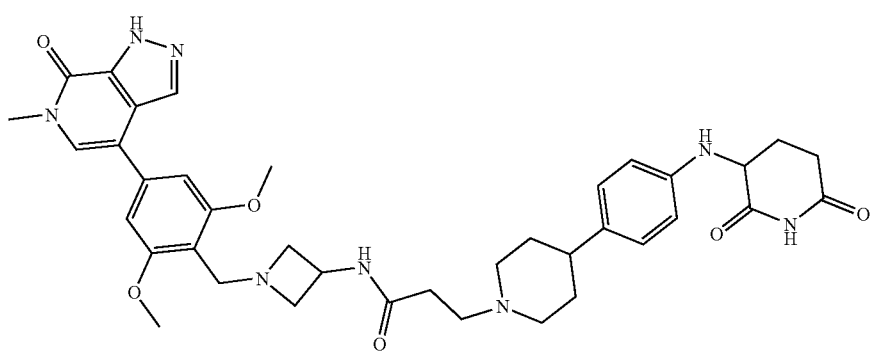
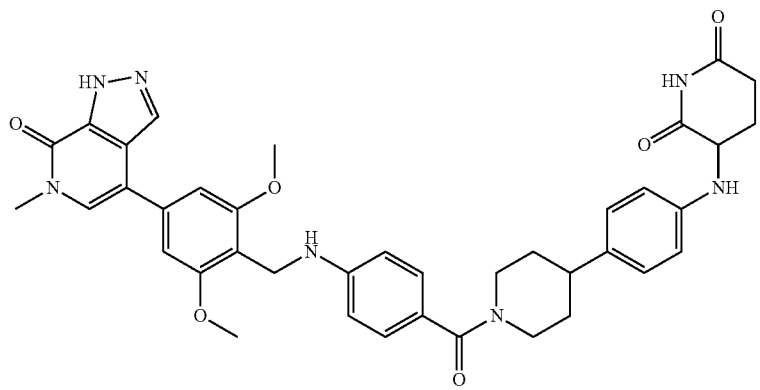
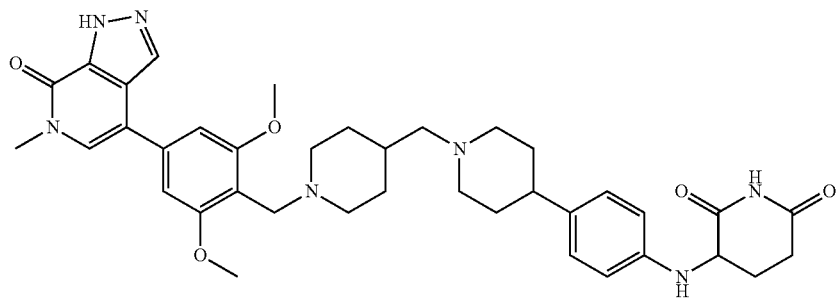

-continued
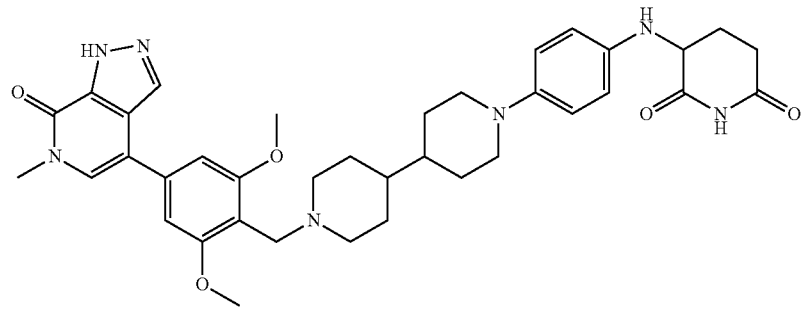
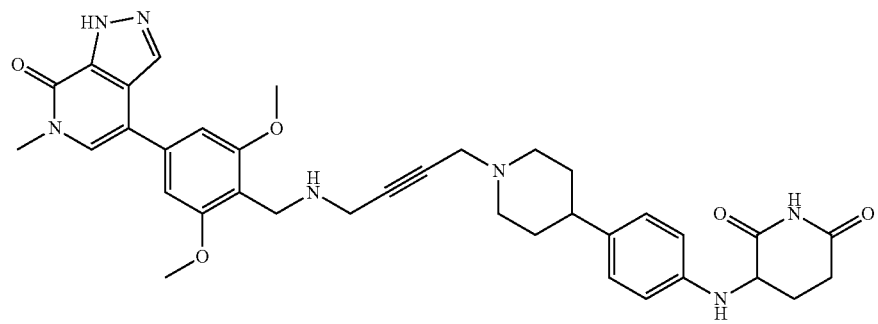
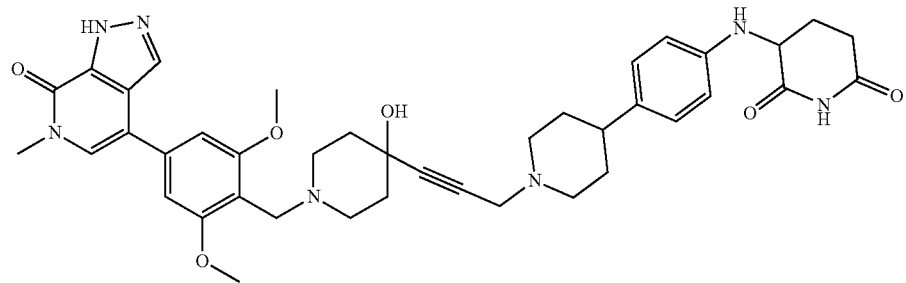
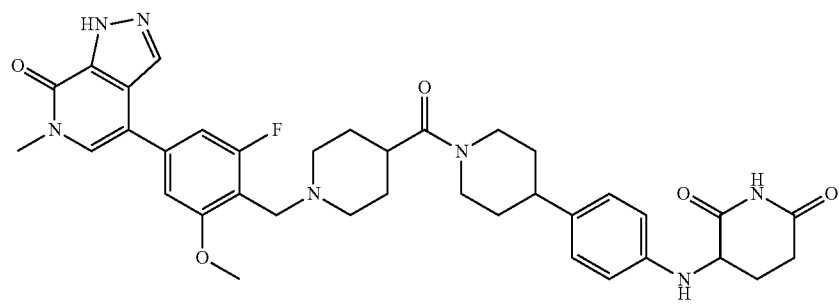
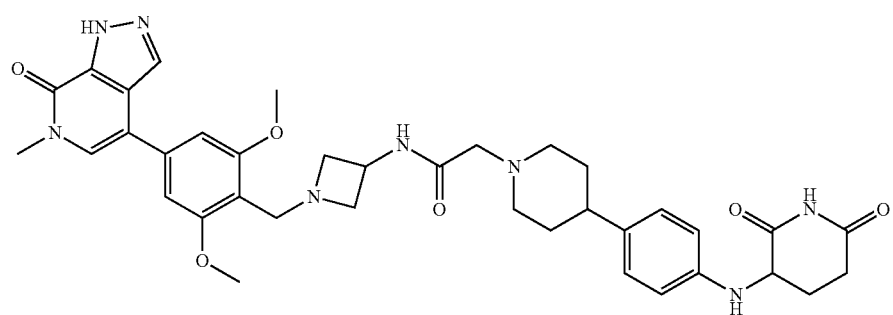

-continued
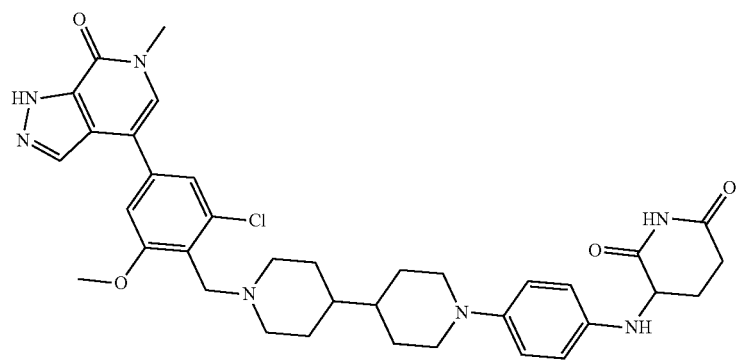
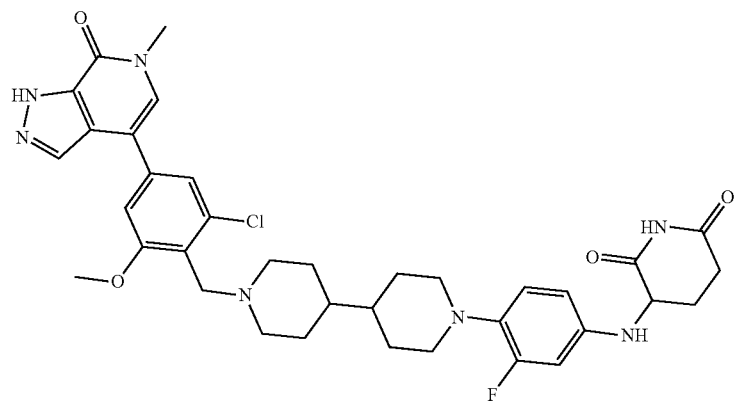
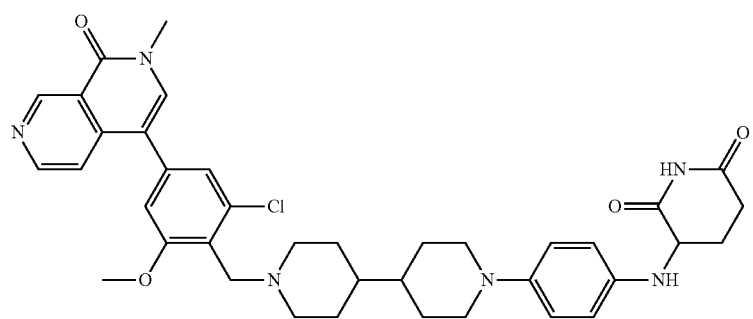
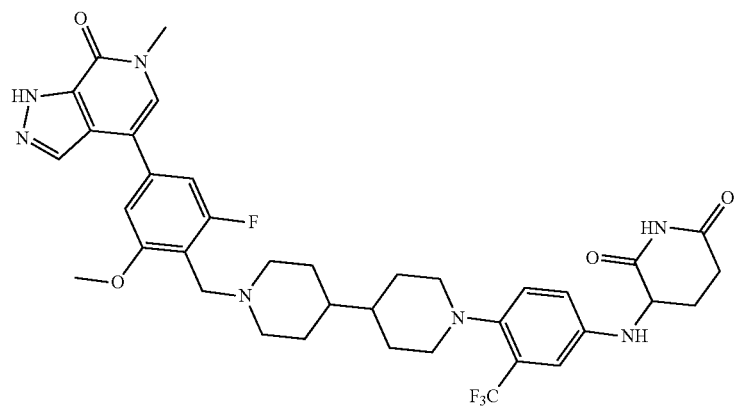

-continued
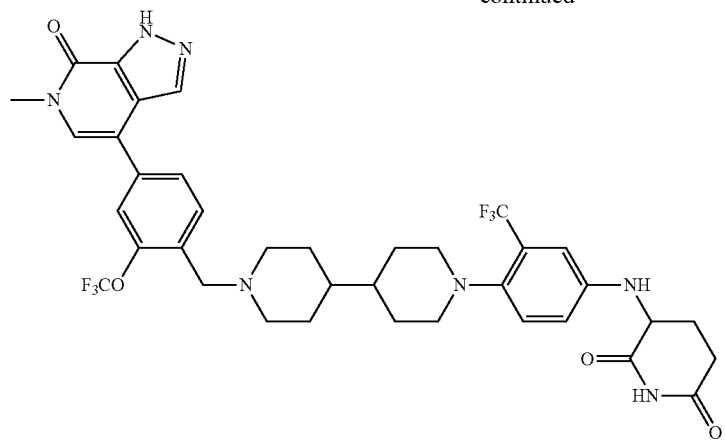
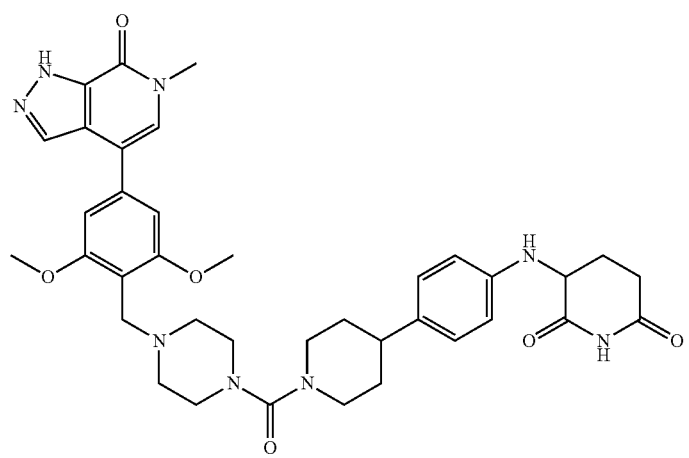
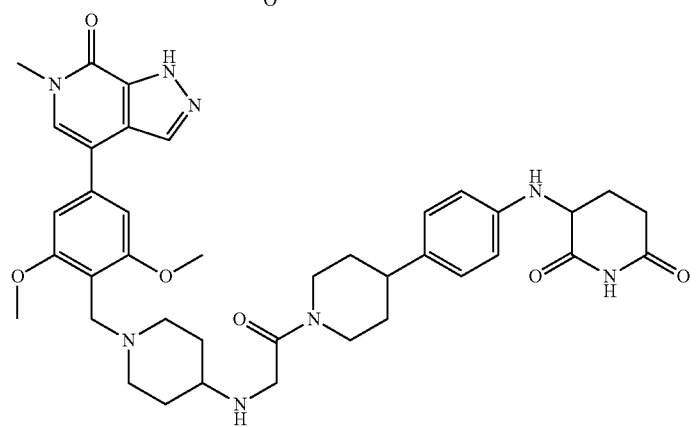
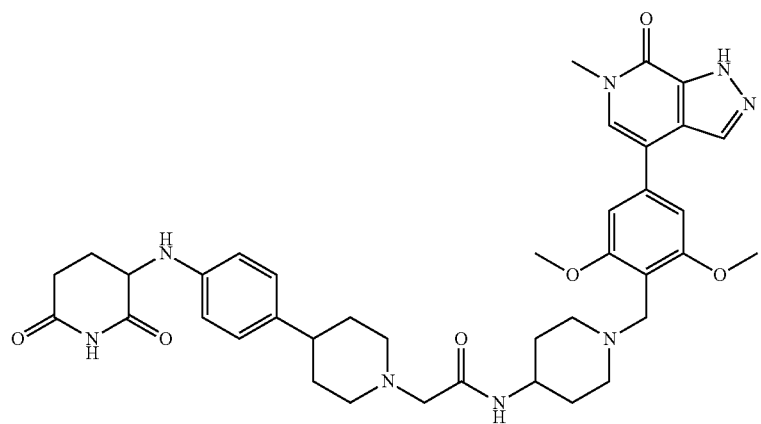

-continued
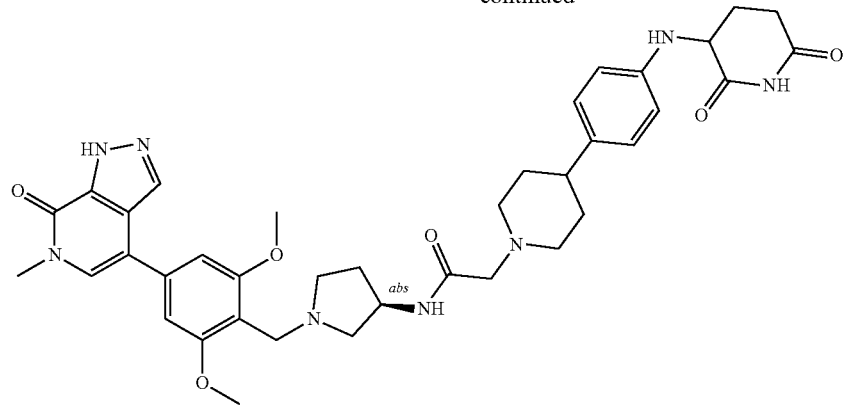
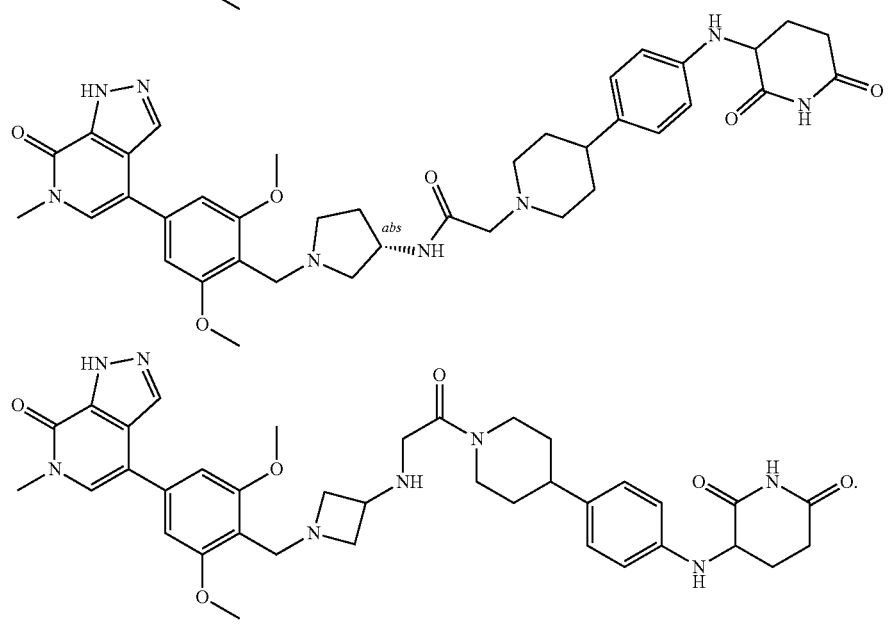
and
In certain embodiments a compound of the present invention is selected from:
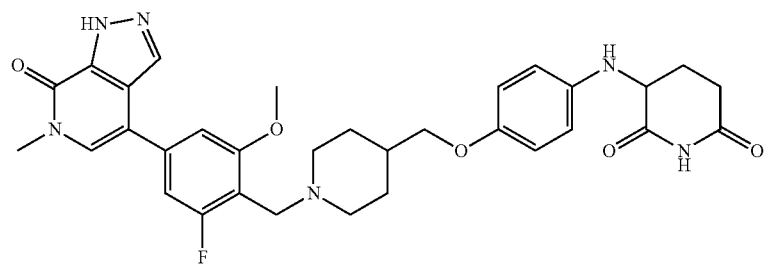
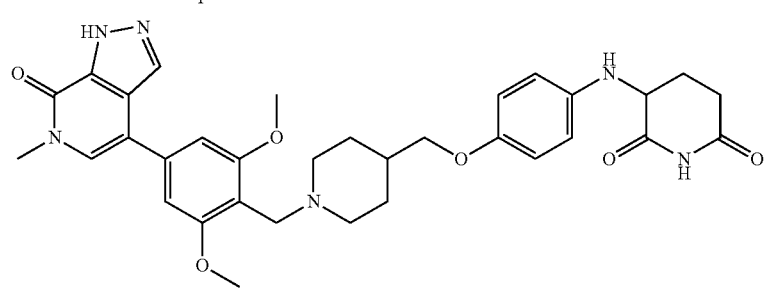

-continued
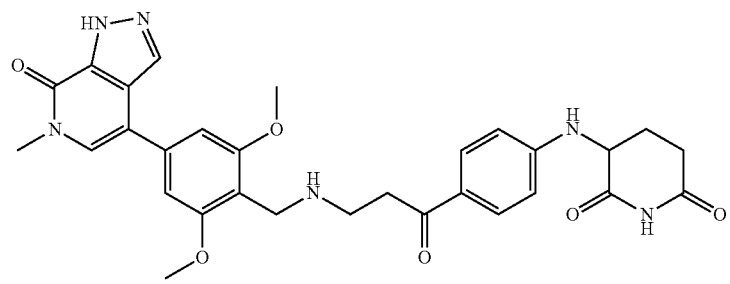
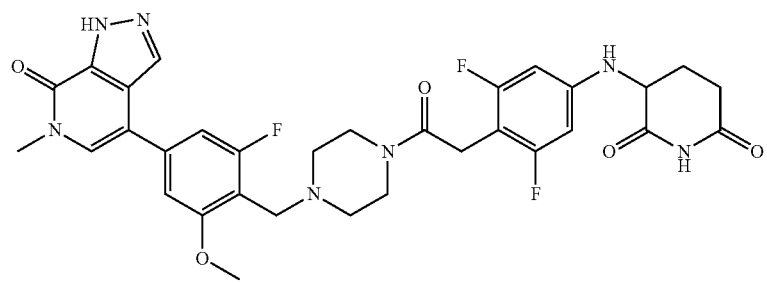
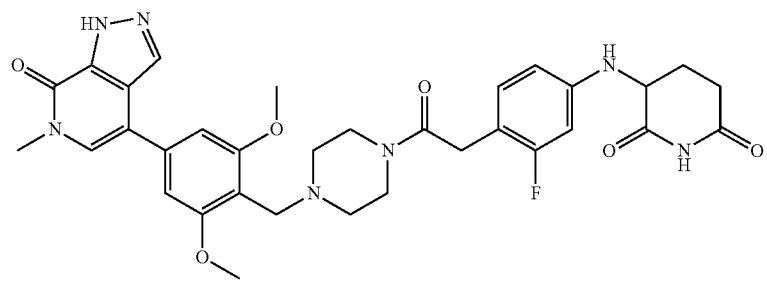
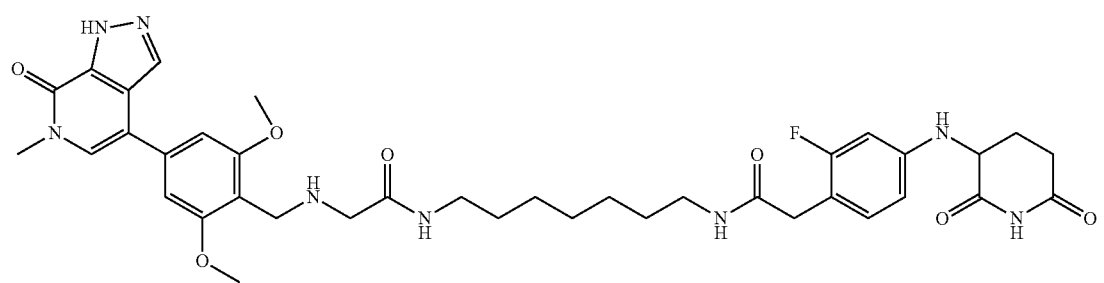
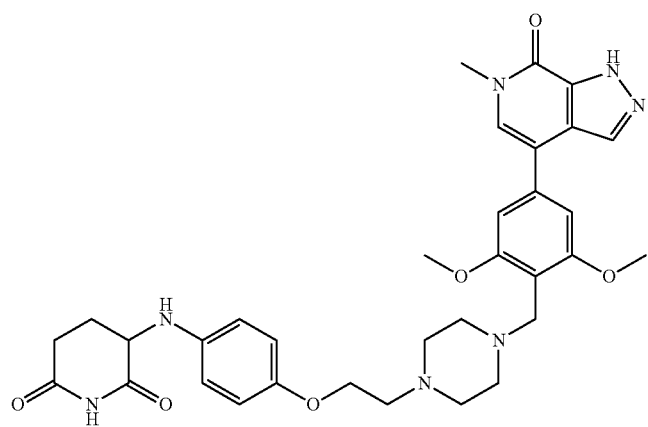

-continued
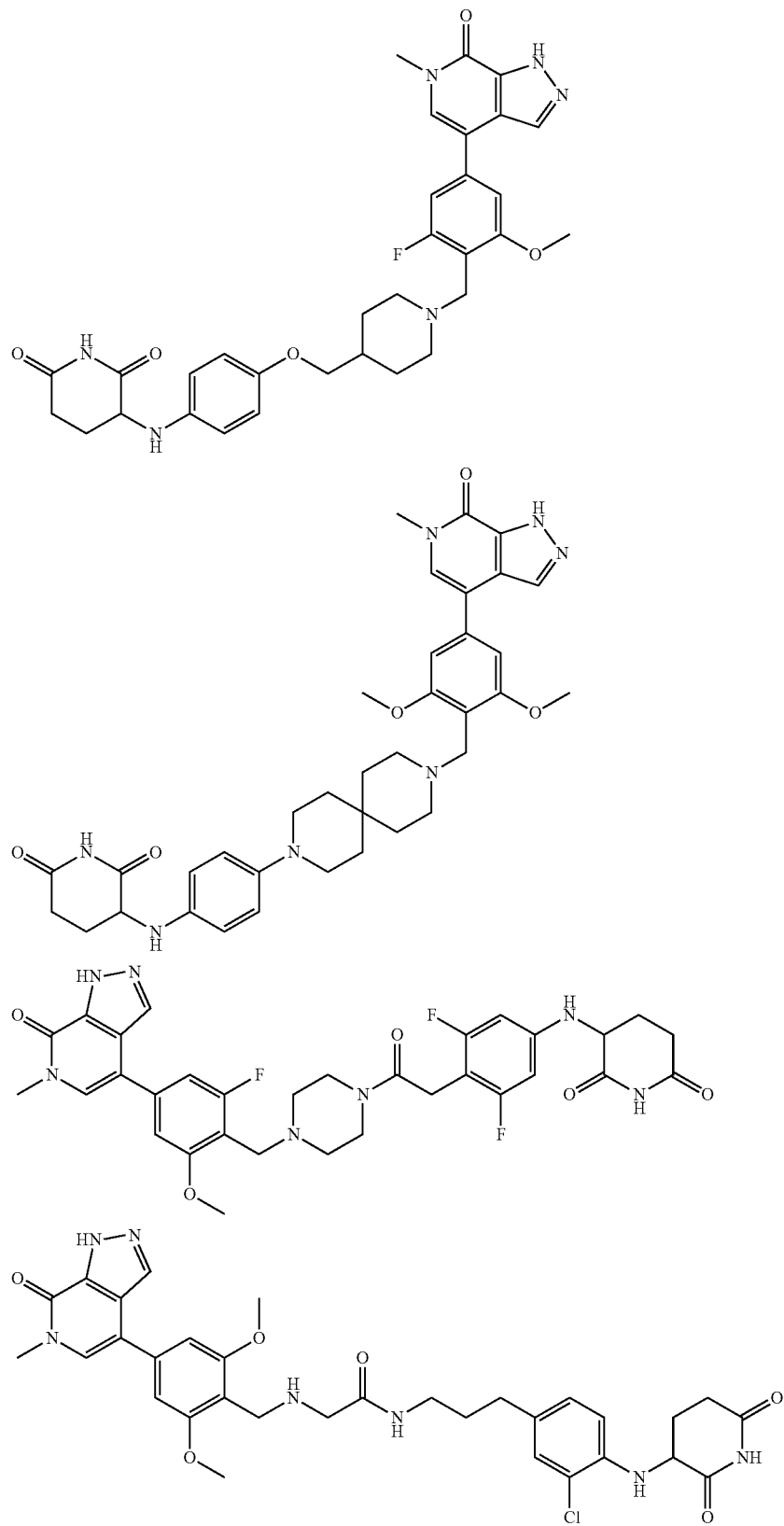

-continued
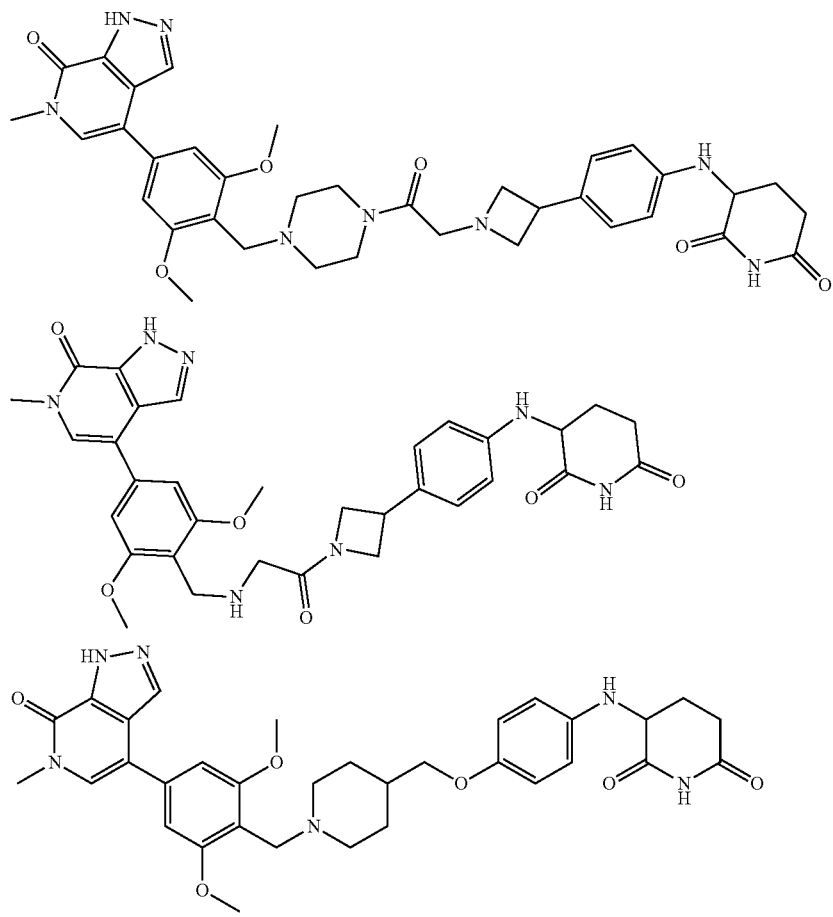
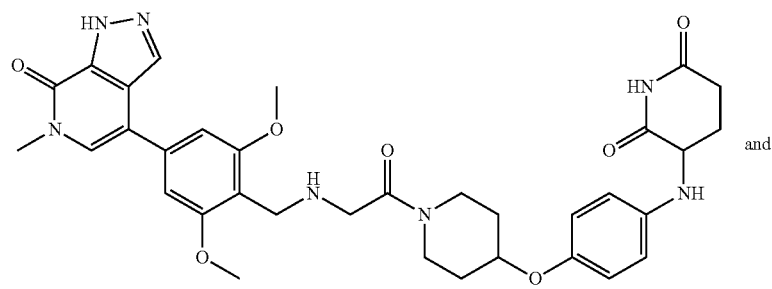
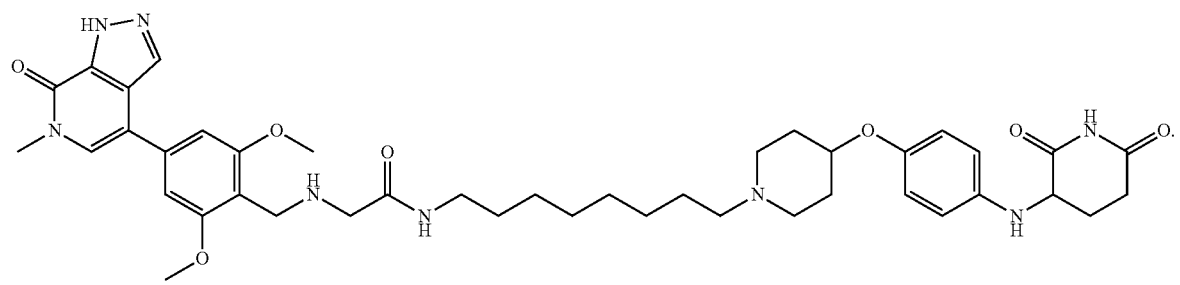

In certain embodiments a compound of the present invention is selected from:
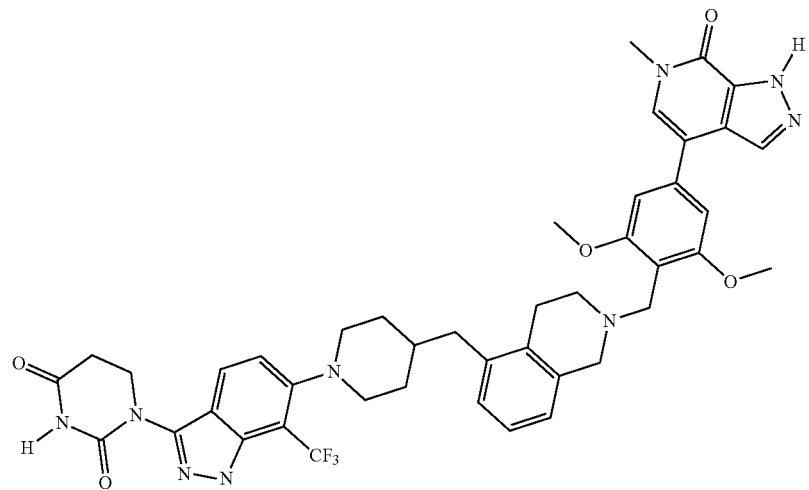
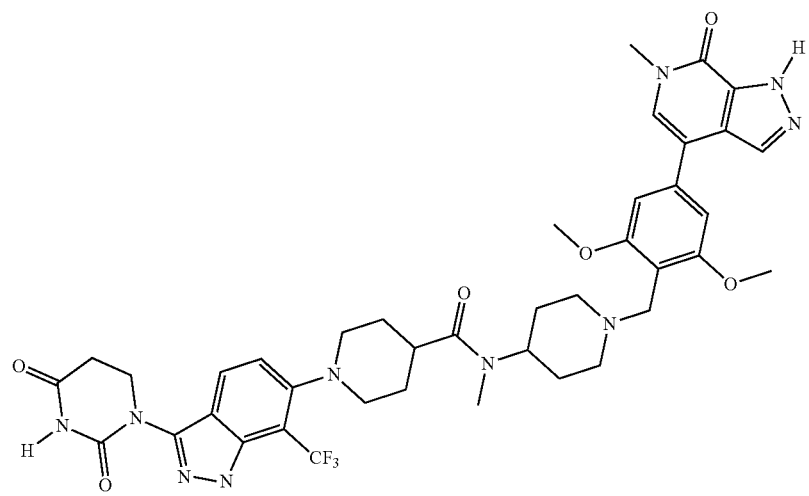
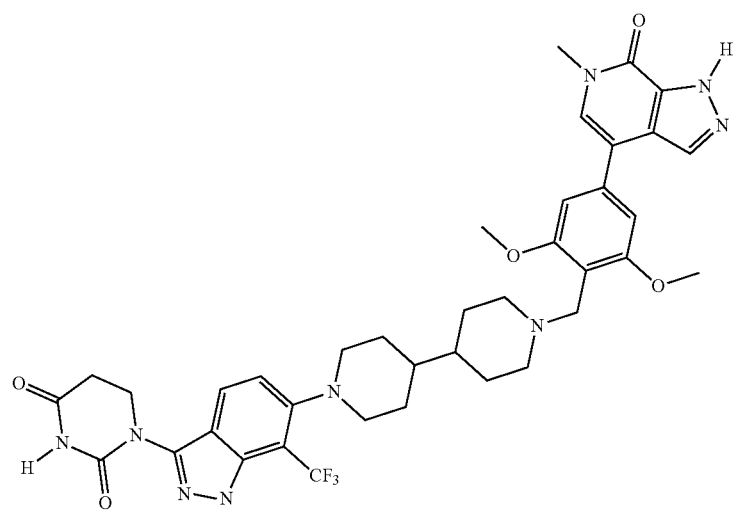

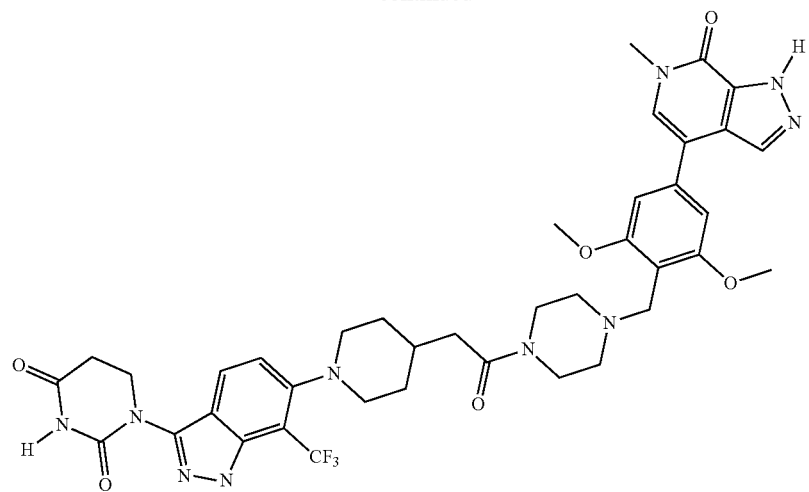
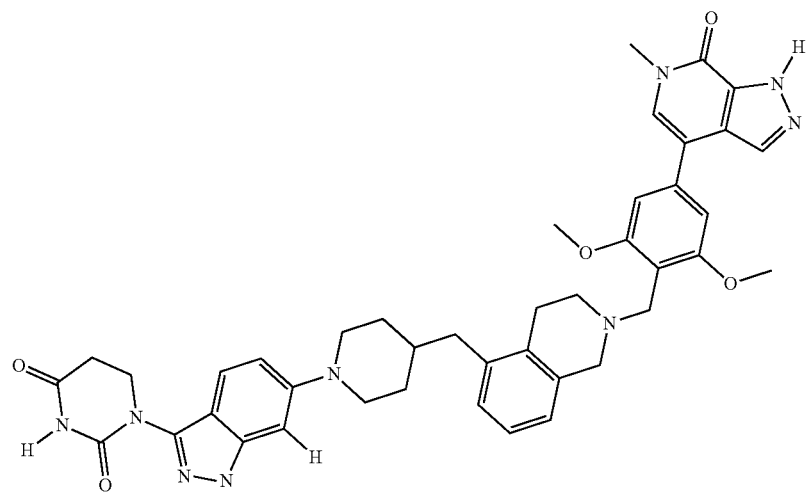
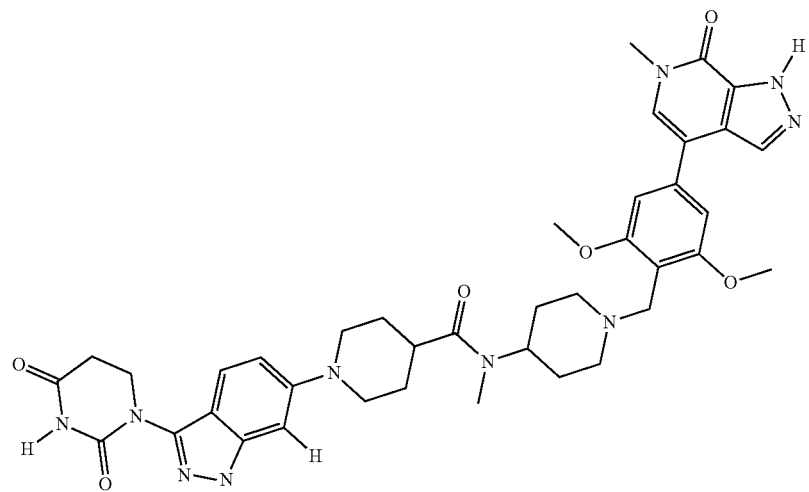

-continued
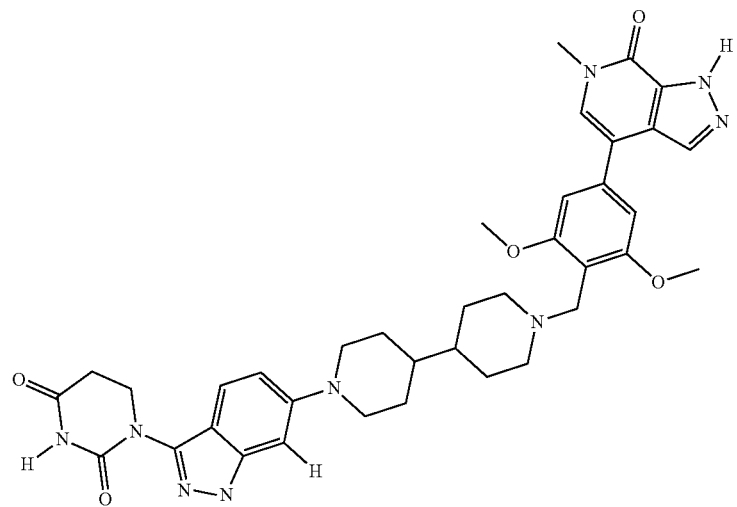
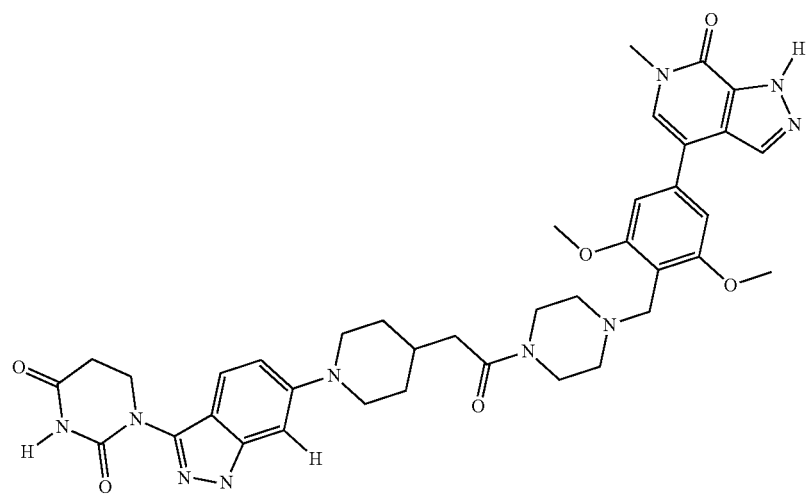
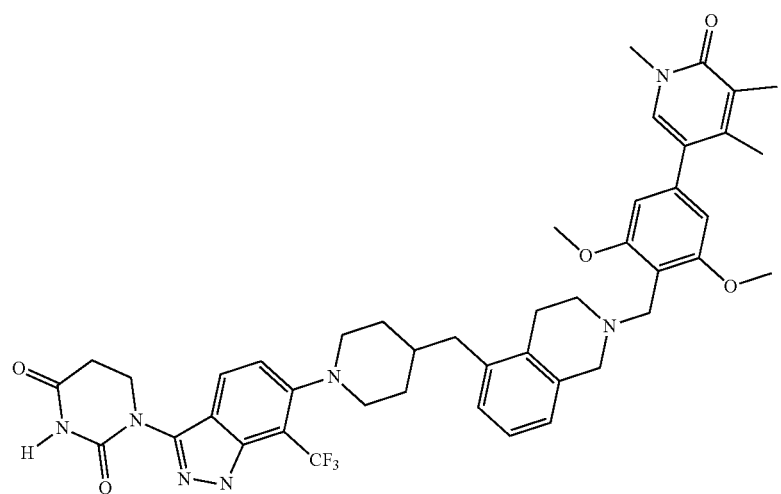

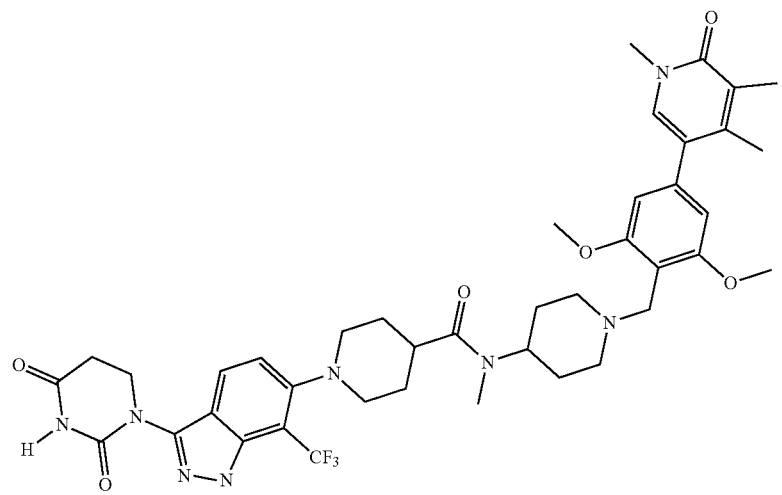
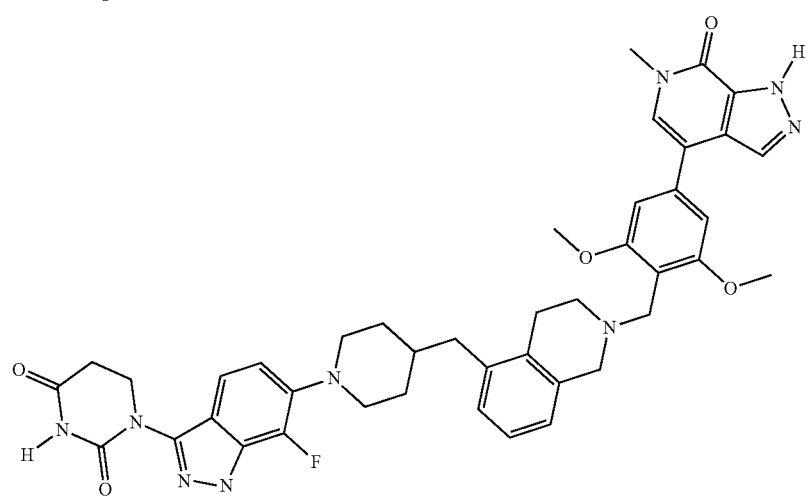
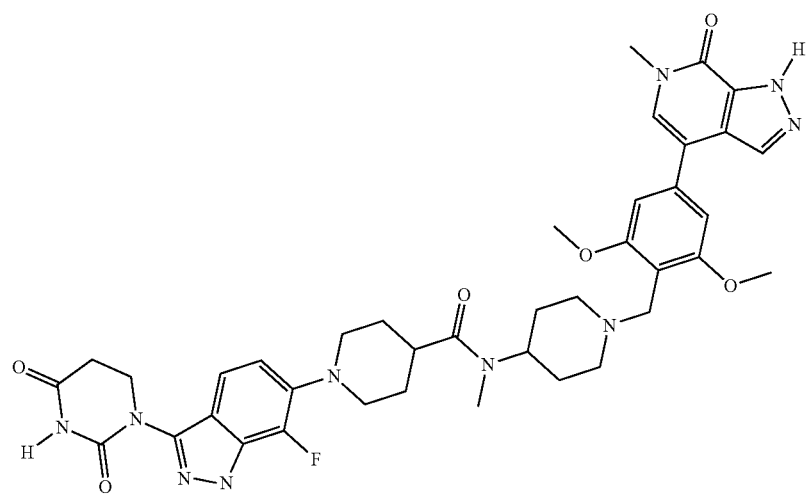

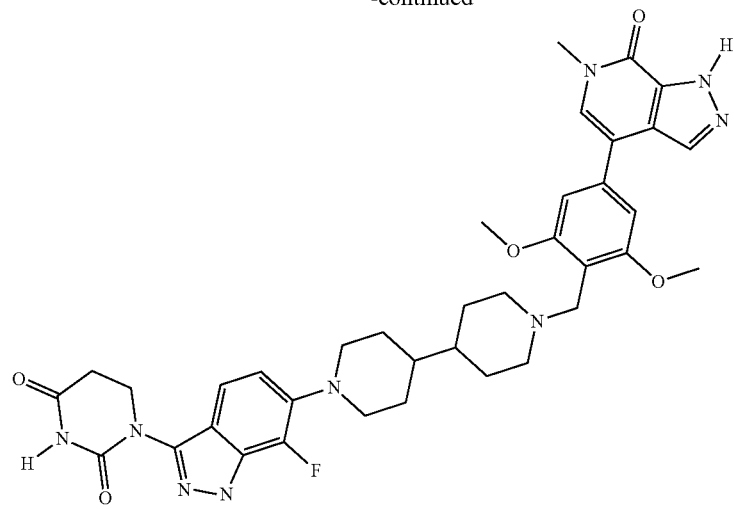
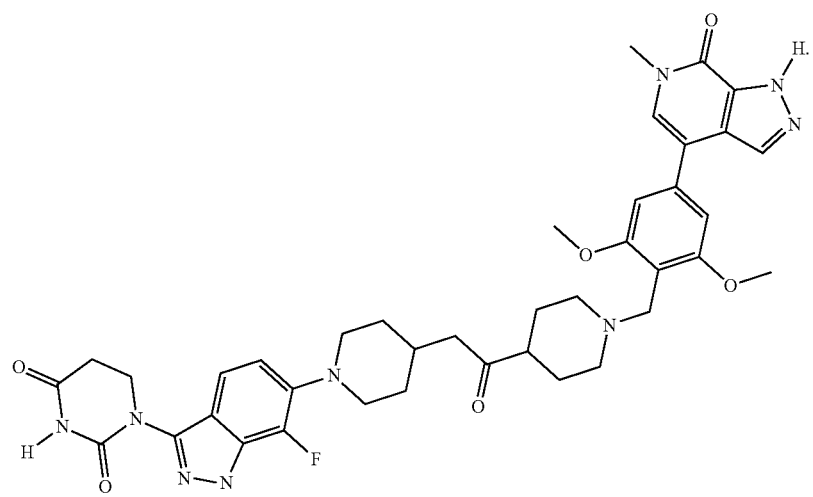
In certain embodiments a compound of the present invention is selected from:
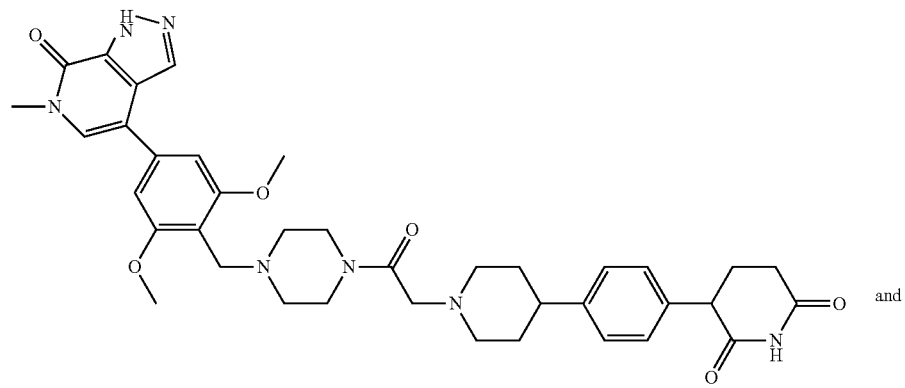
and -continued
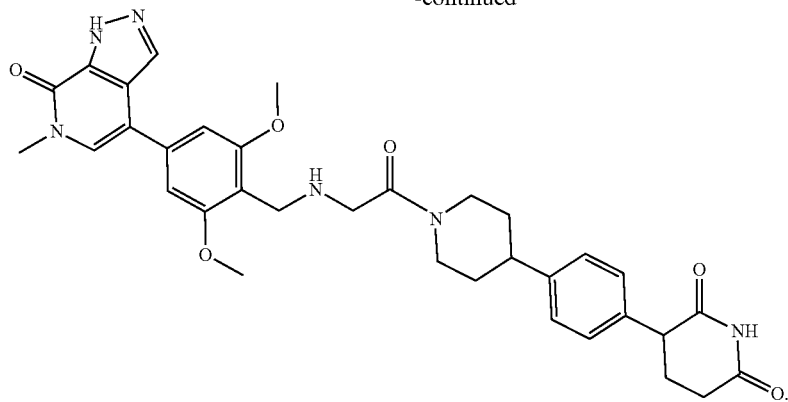
In certain embodiments a compound of the present invention is selected from:
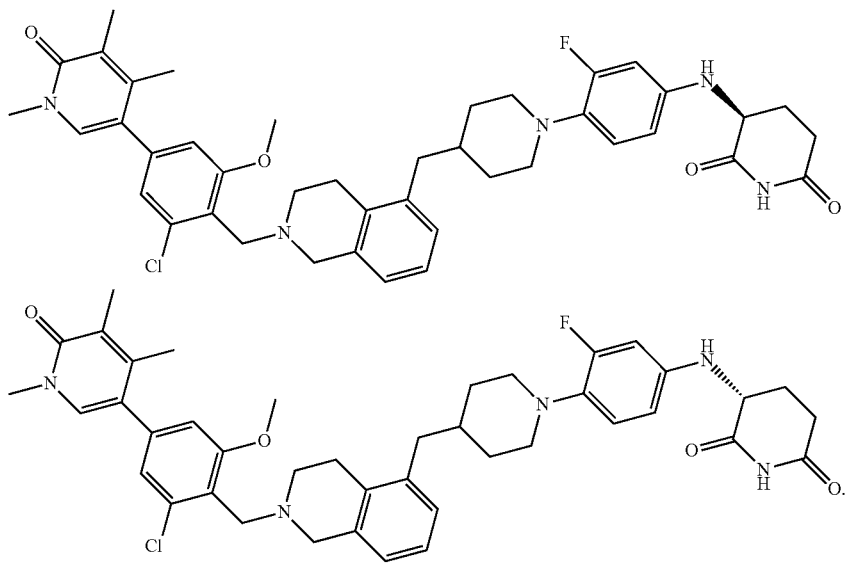
In certain embodiments a compound of the present invention is selected from:
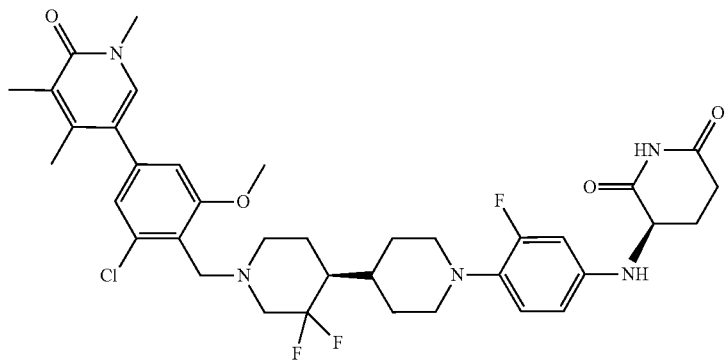

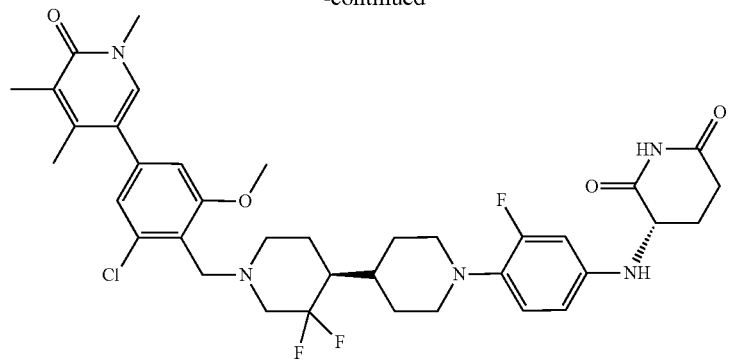
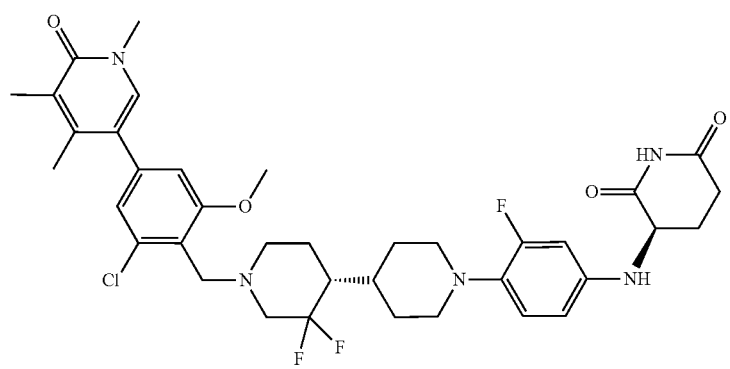
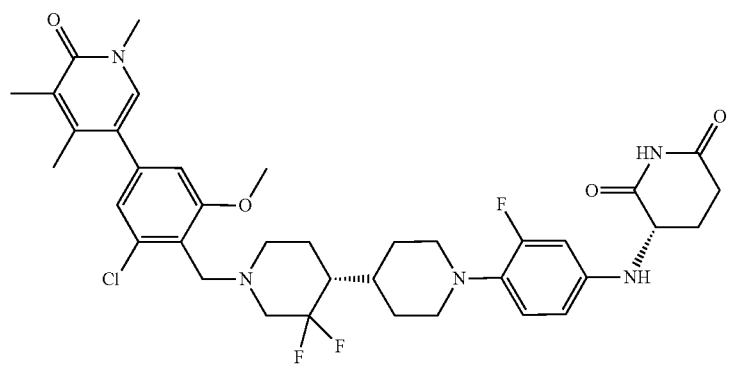
In certain embodiments a compound of the present invention is selected from:
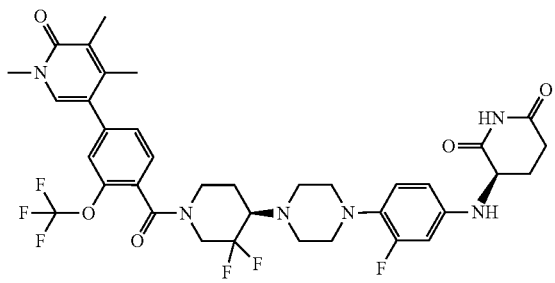

323
-continued
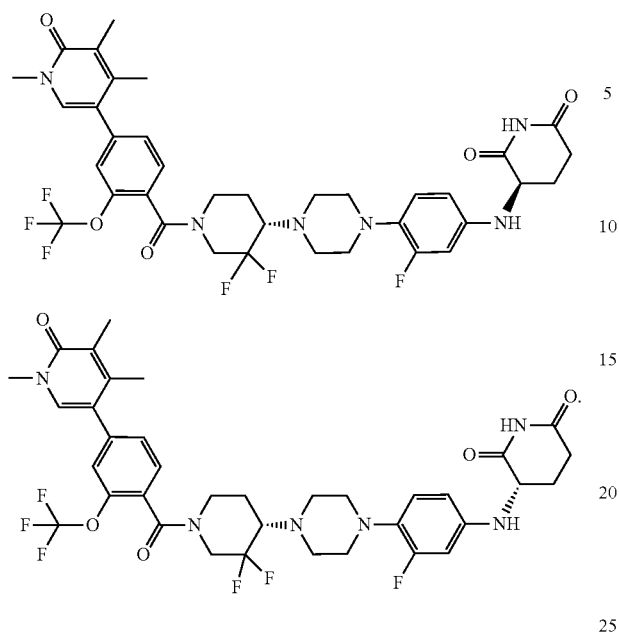
Nonlimiting examples of compounds of the present invention include:
324
-continued
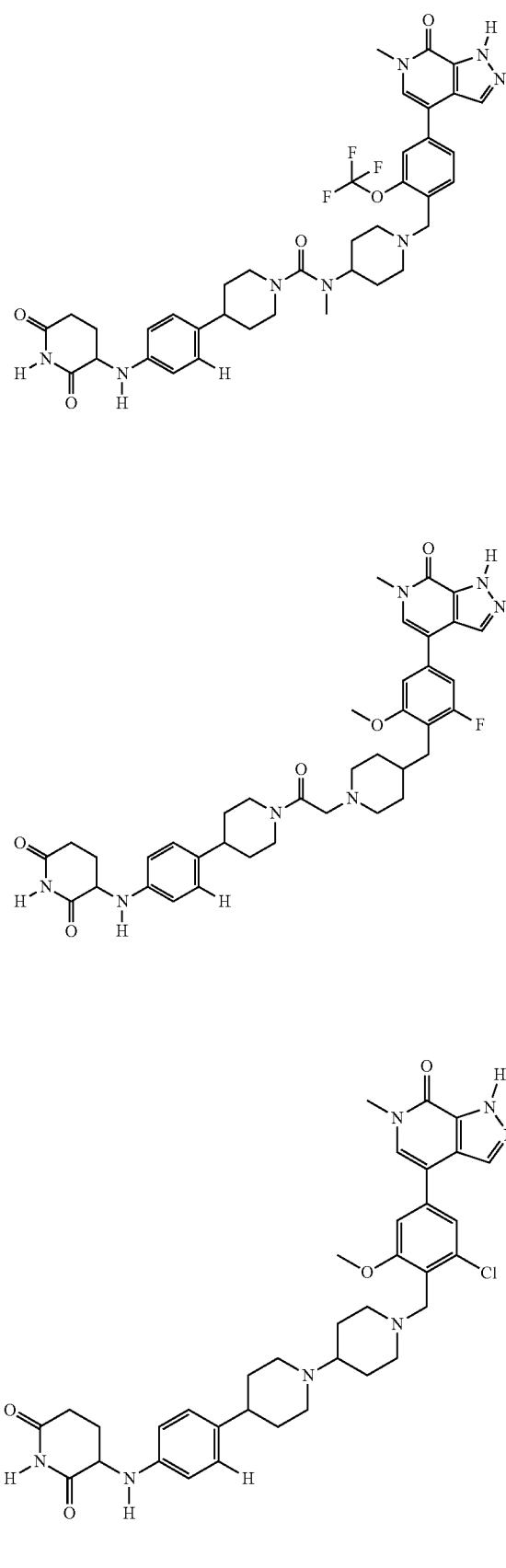

325
-continued
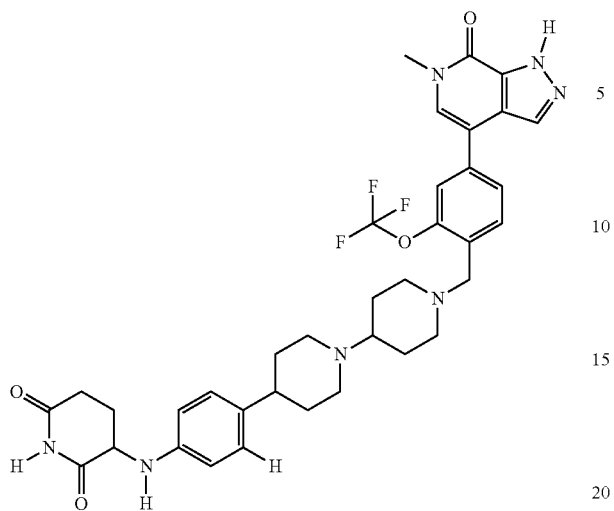
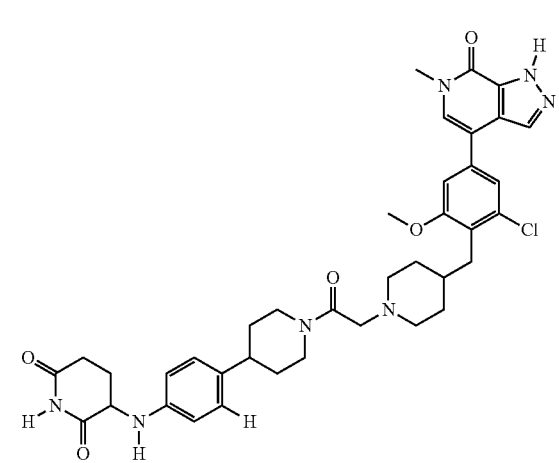
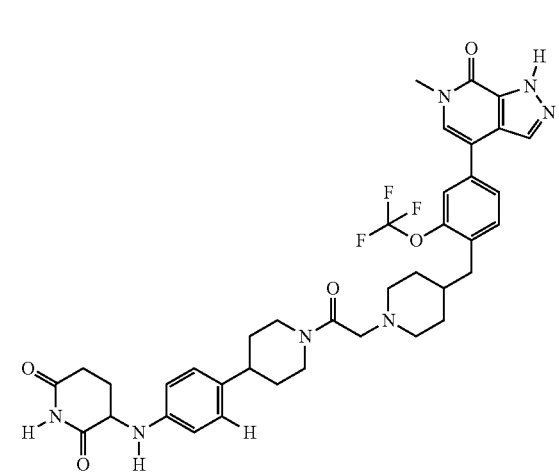
326
-continued
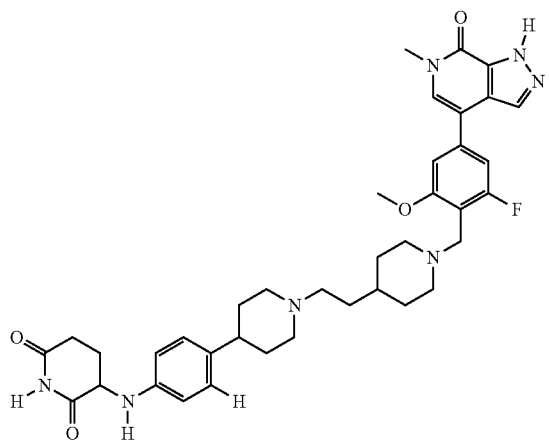
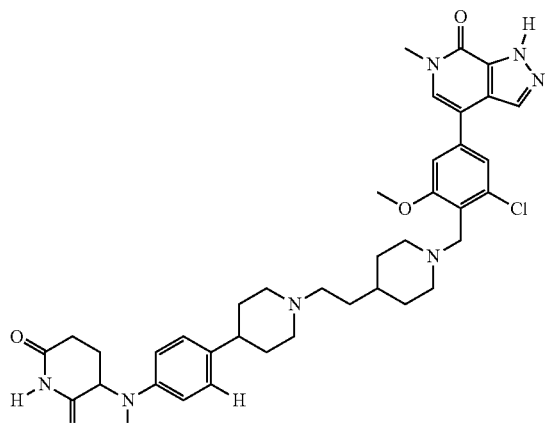
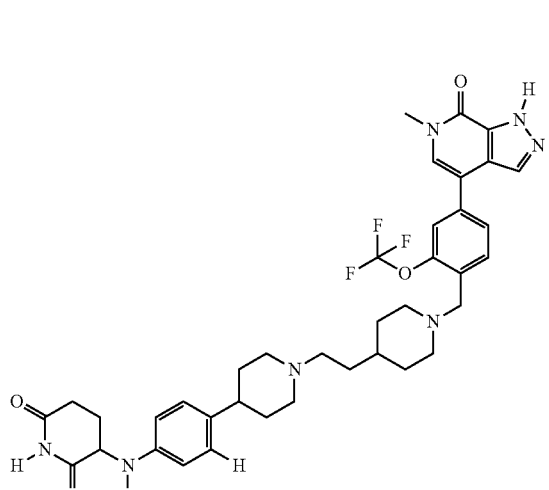

327
-continued
328
-continued
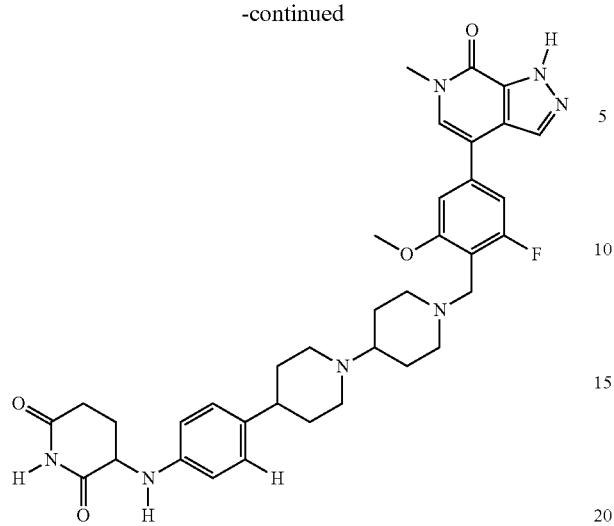
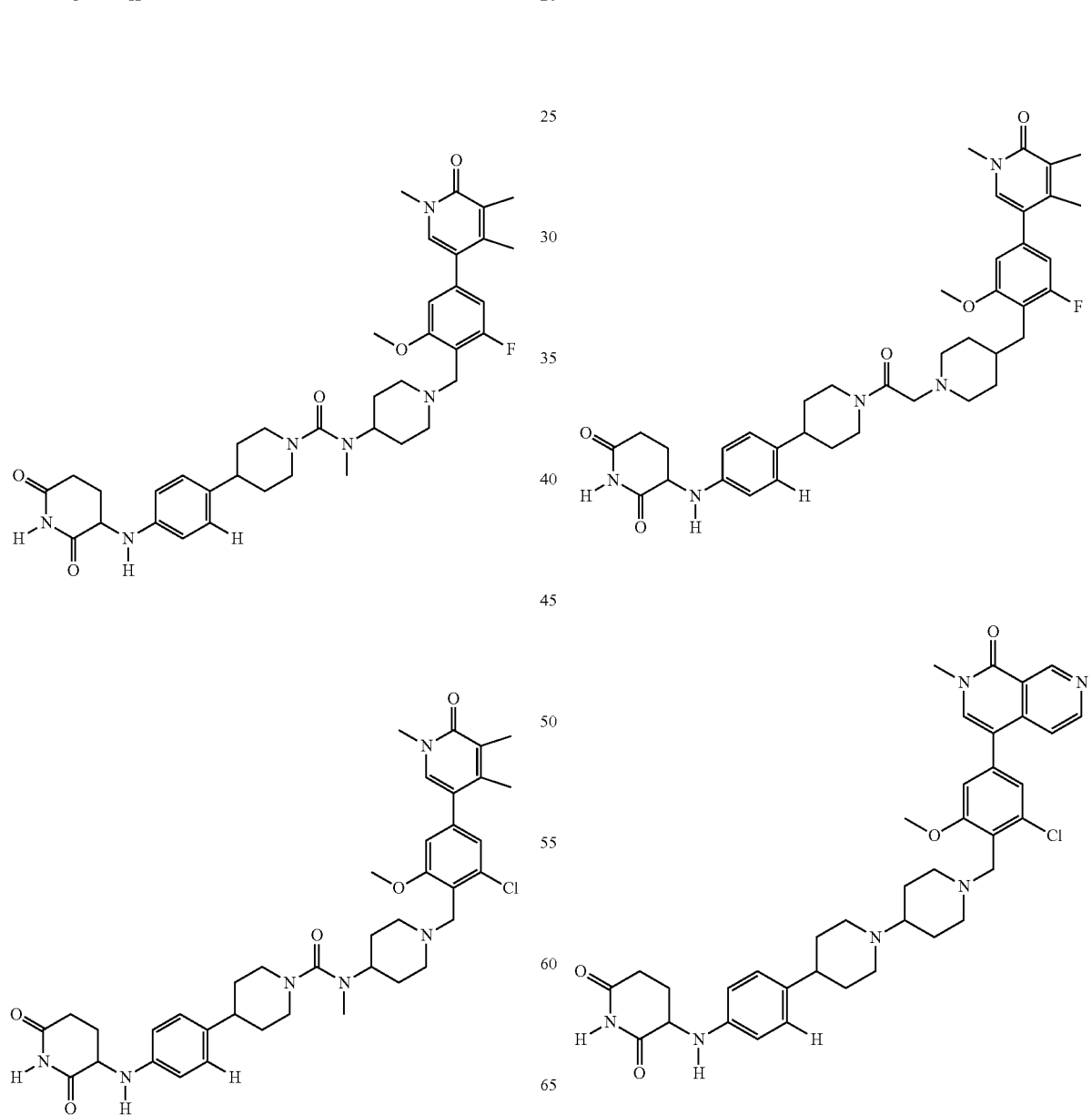

329
-continued
330
-continued
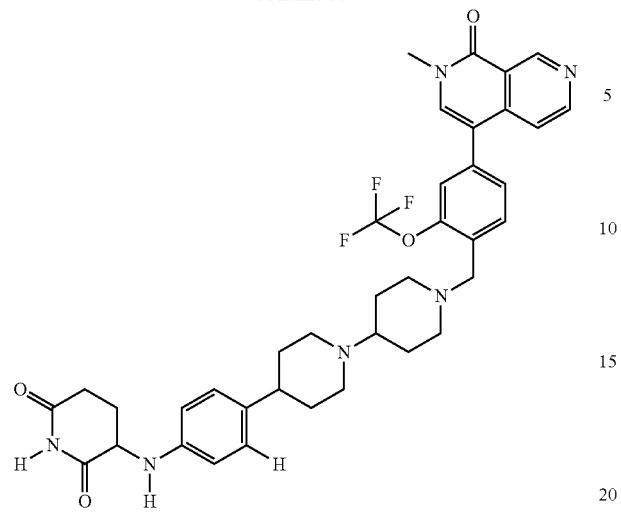
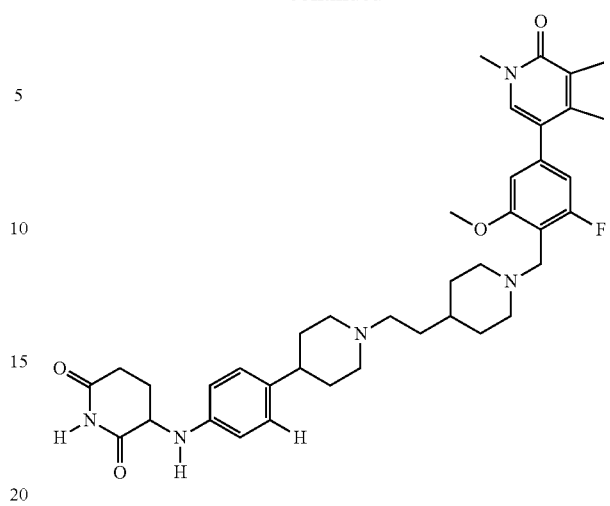
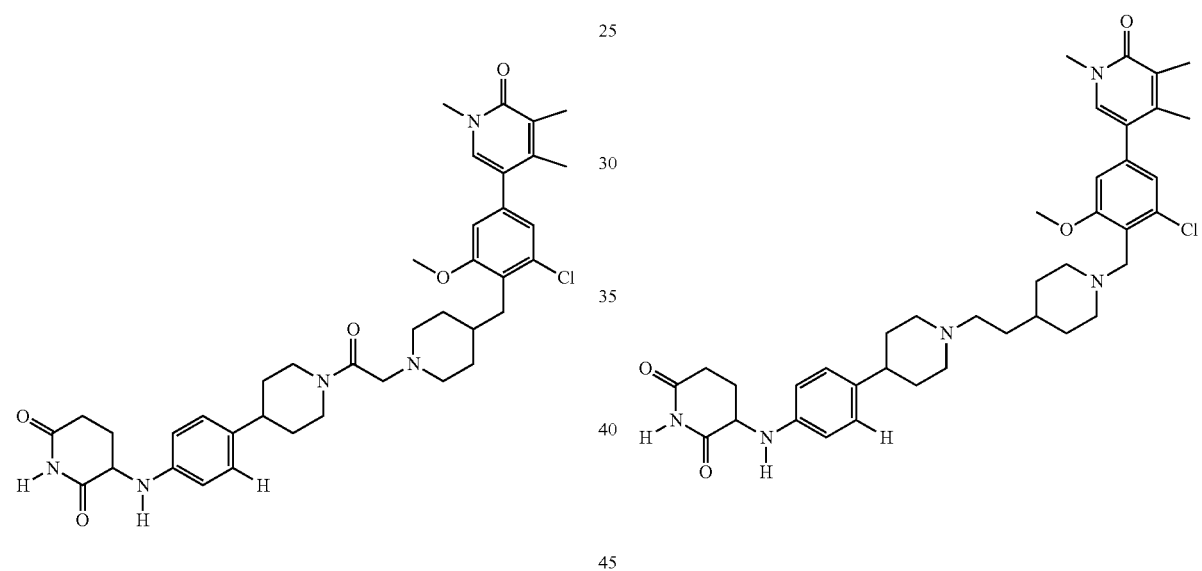
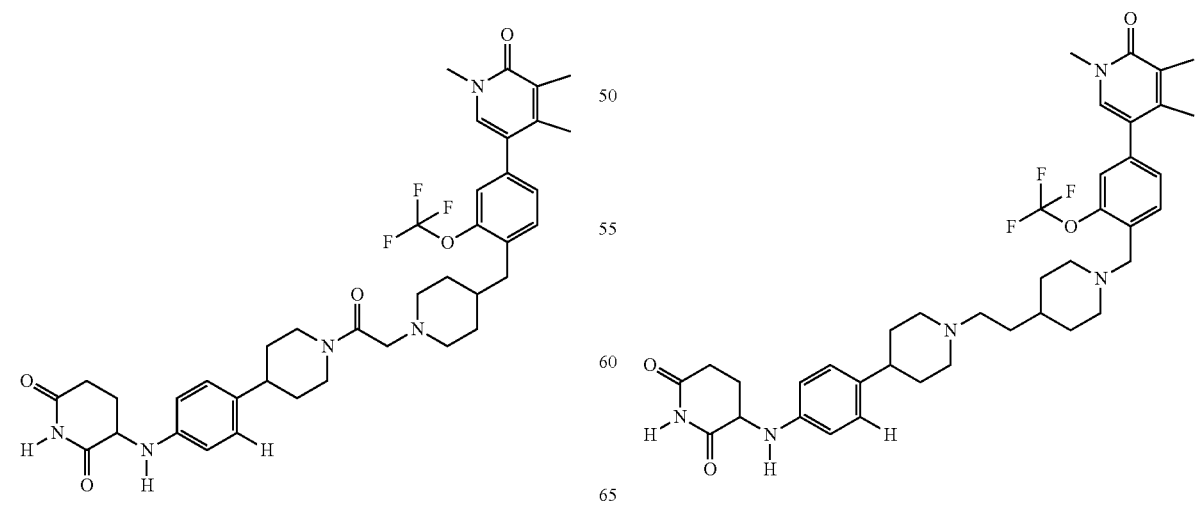

331
-continued
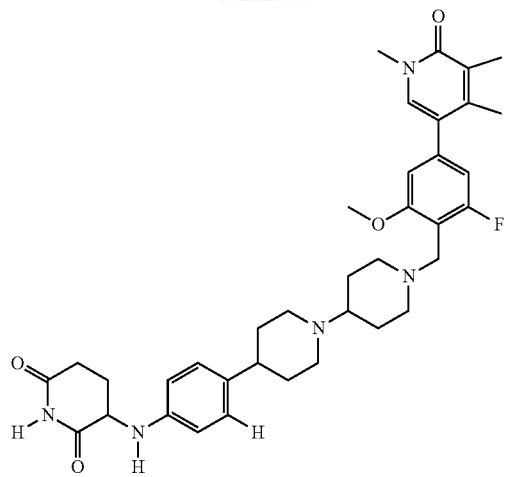
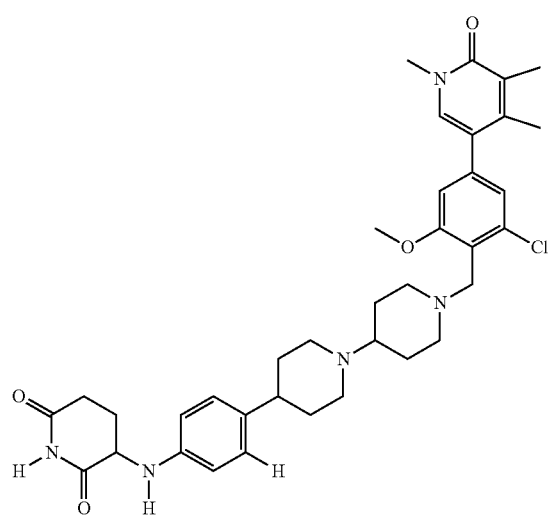
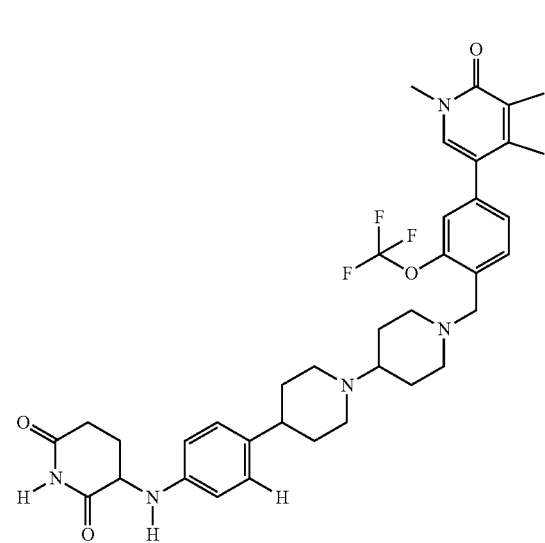
332
-continued
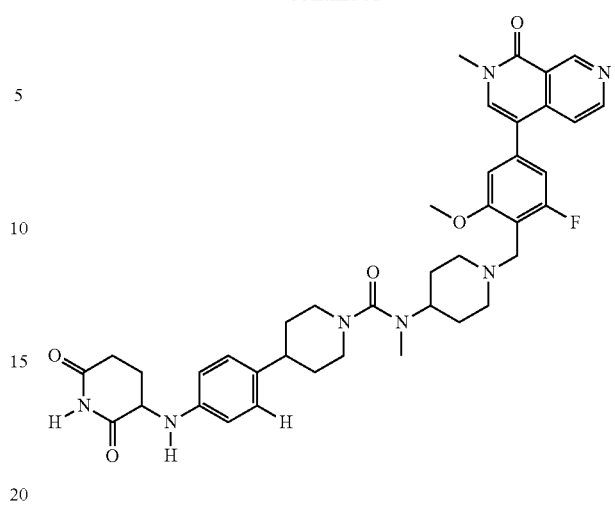
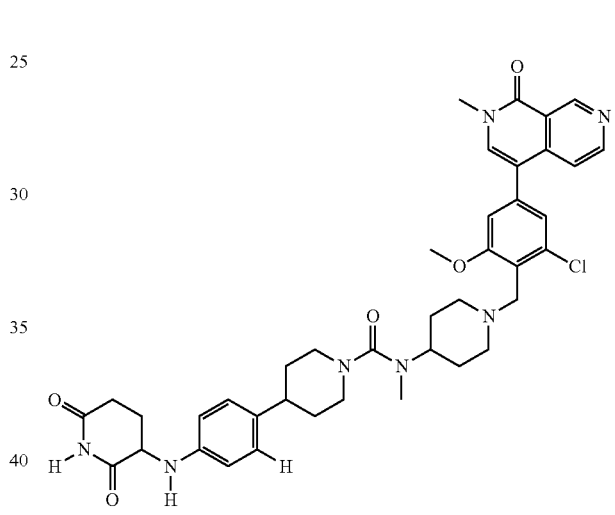
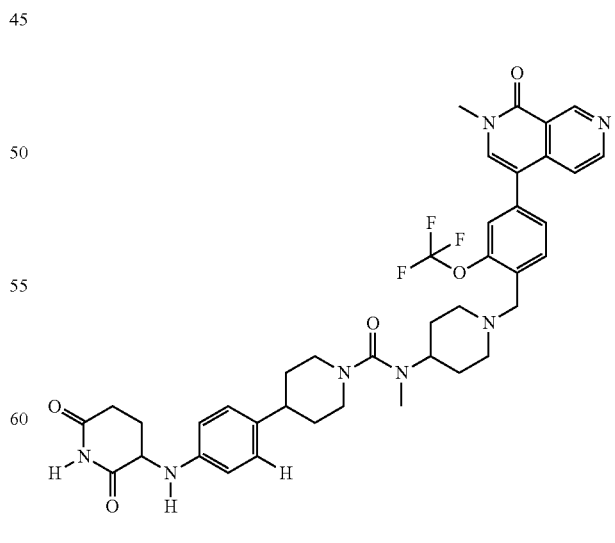

333
-continued
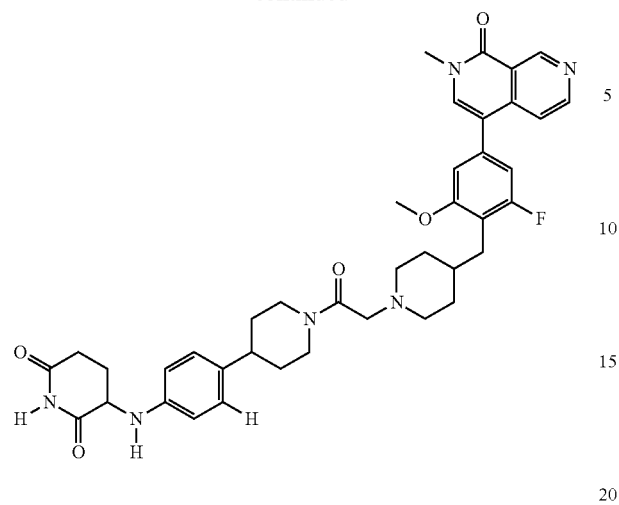
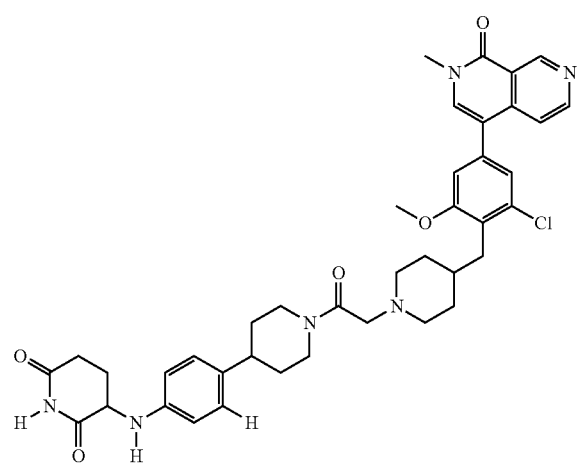
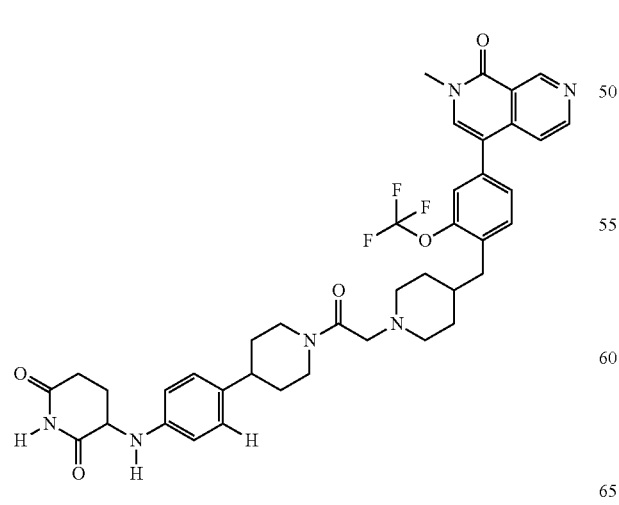
334
-continued
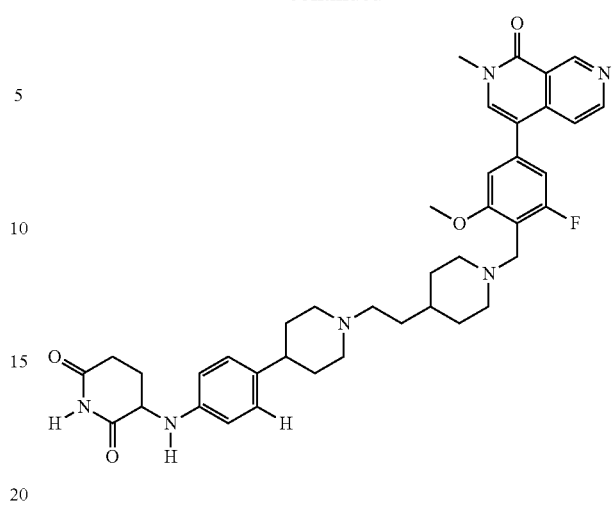
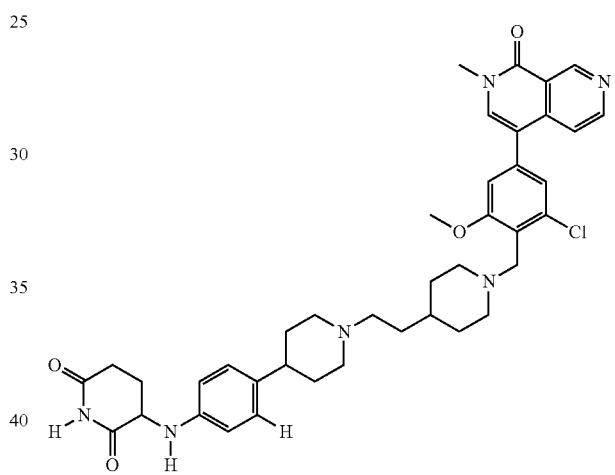
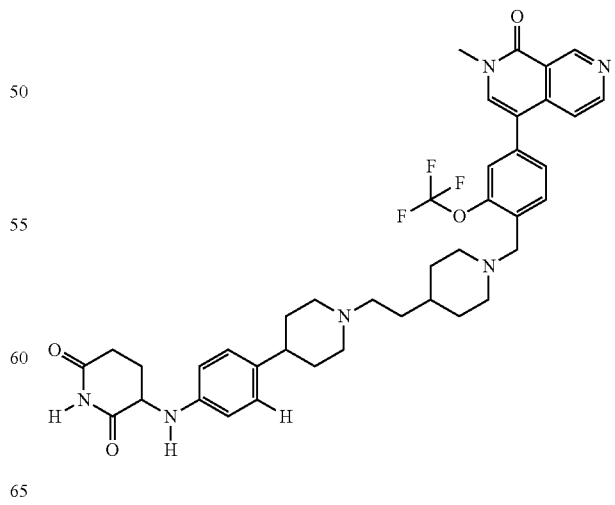

335
-continued
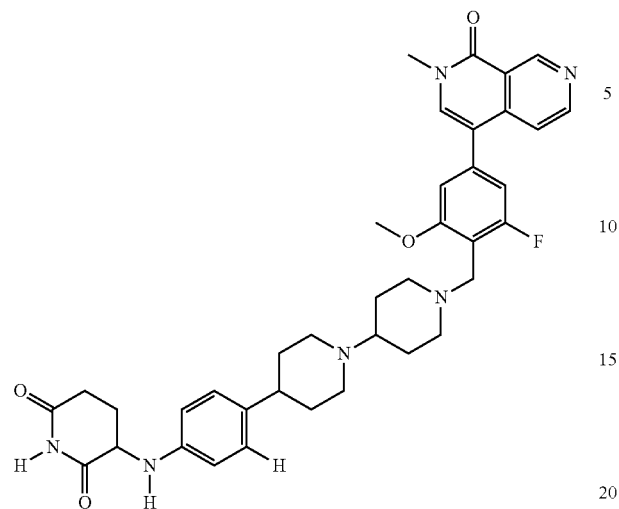
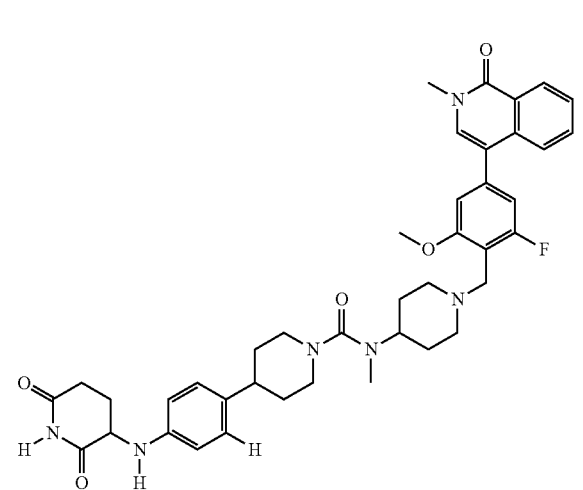
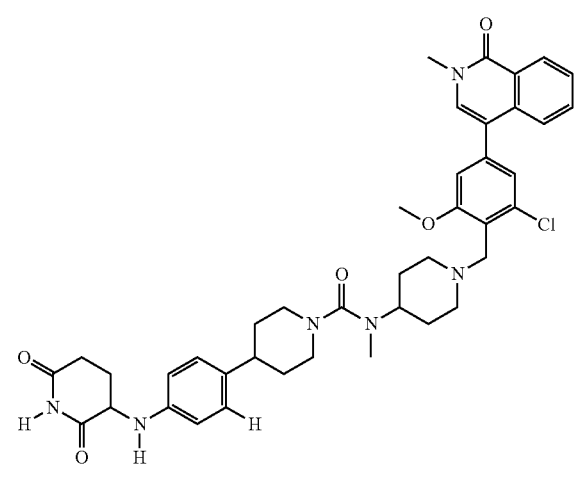
336
-continued
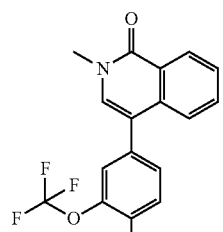
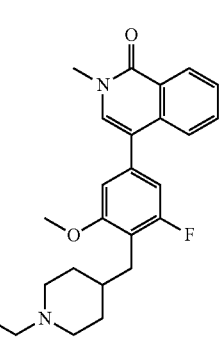
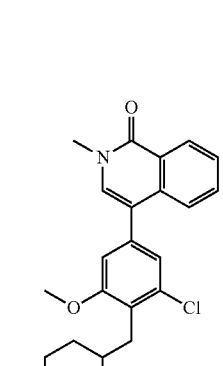
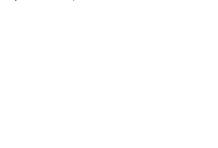

337
-continued
338
-continued
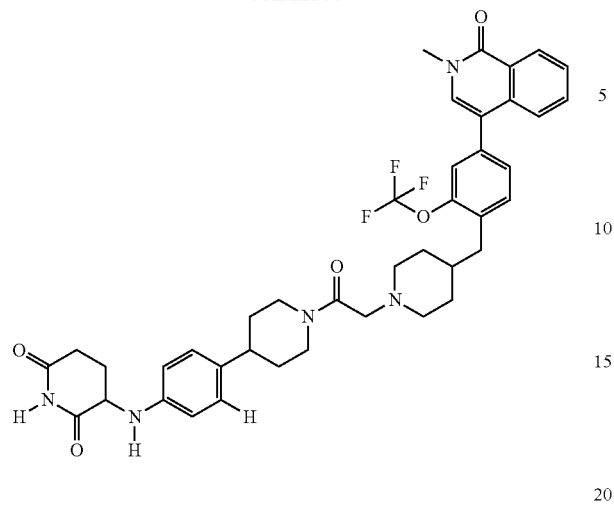
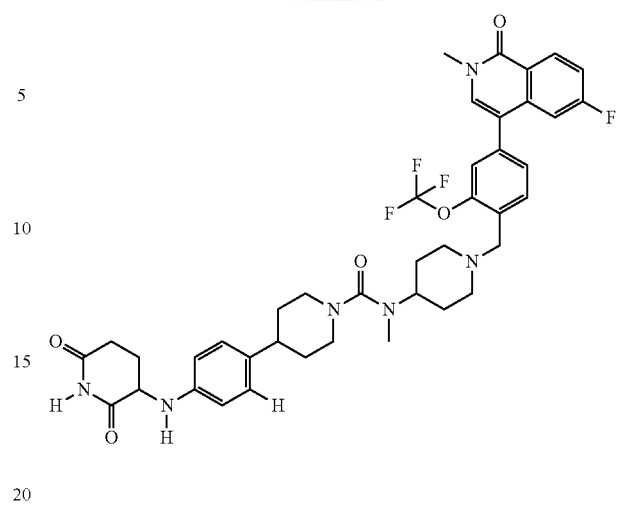
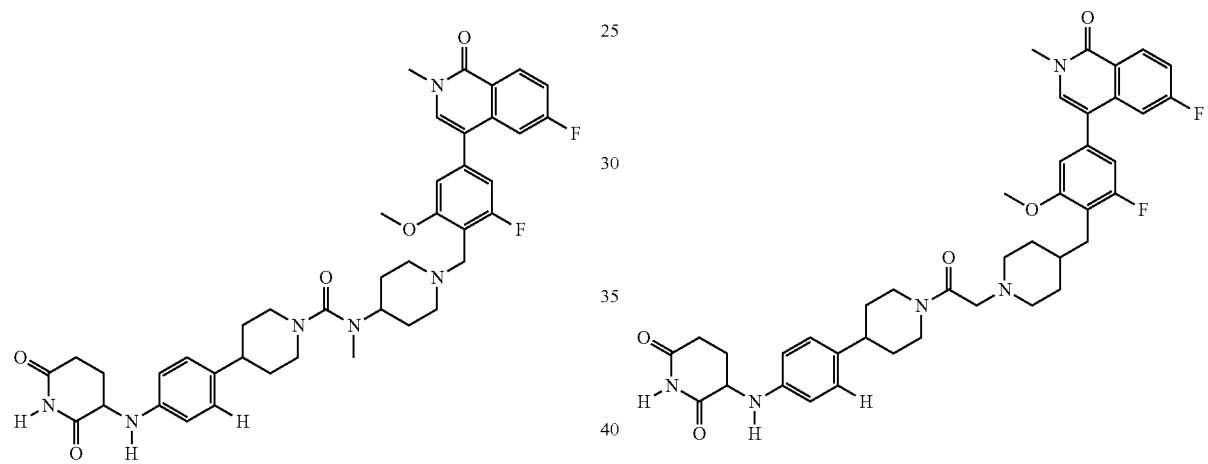
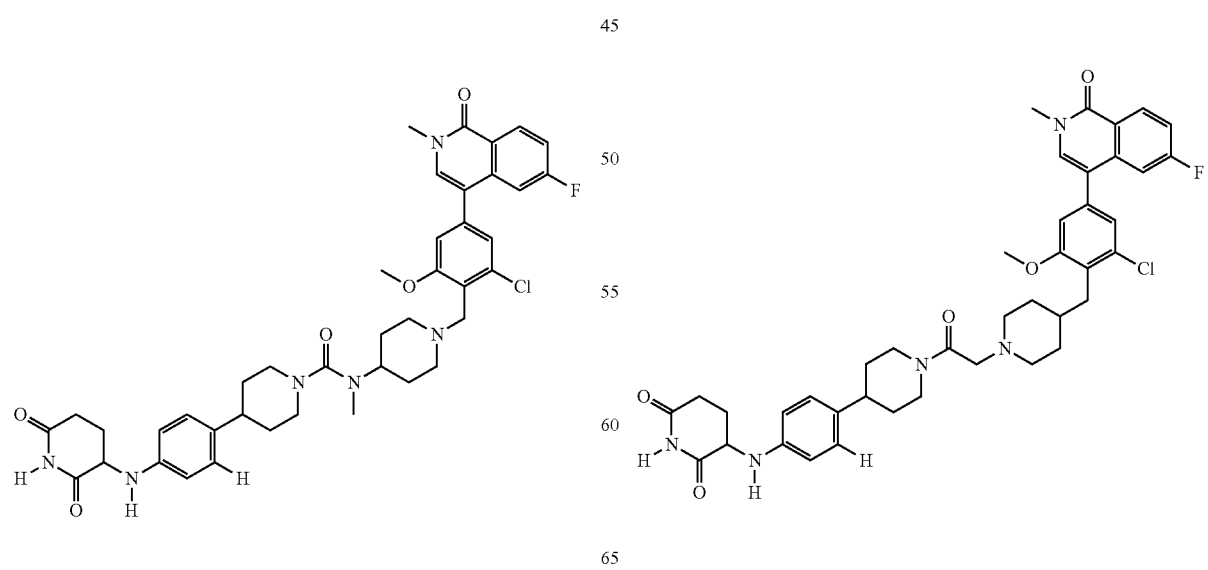

339
-continued
340
-continued
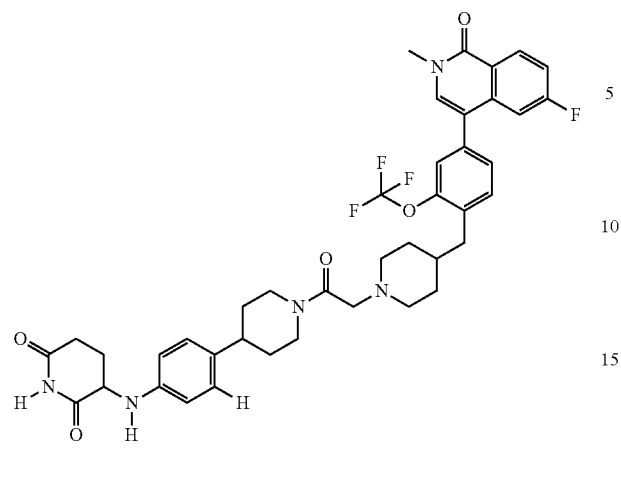
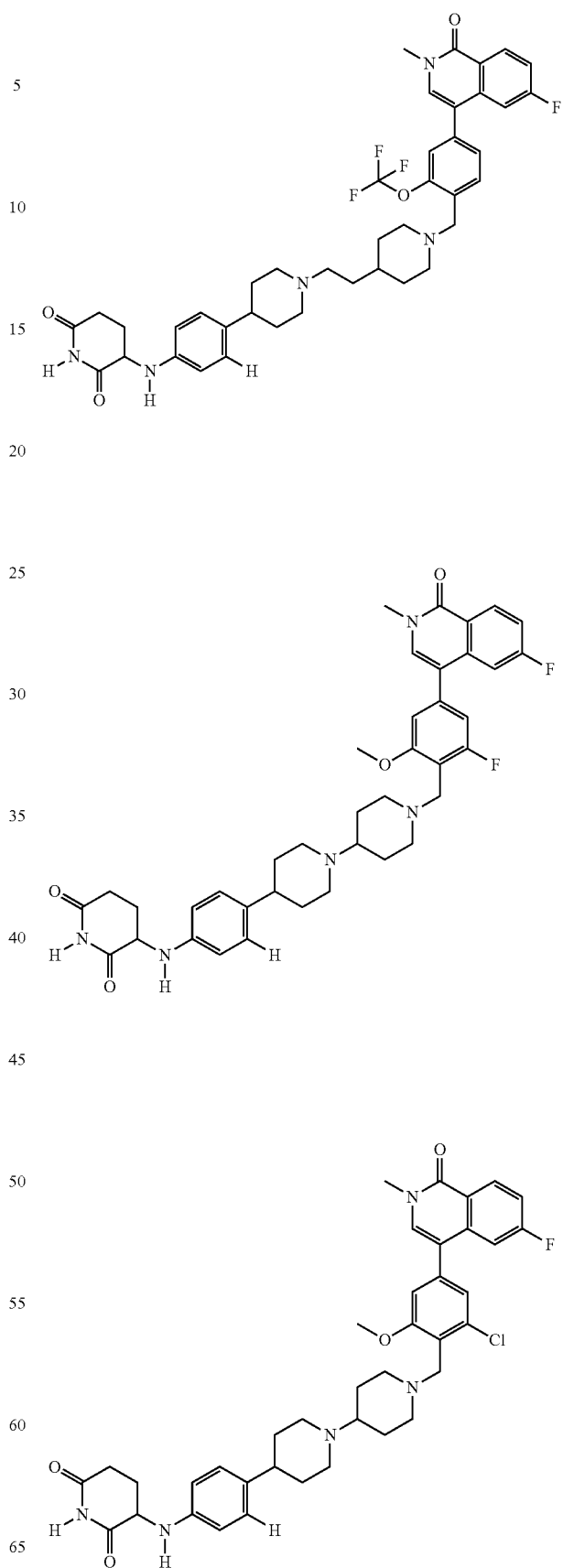

341
-continued
342
-continued
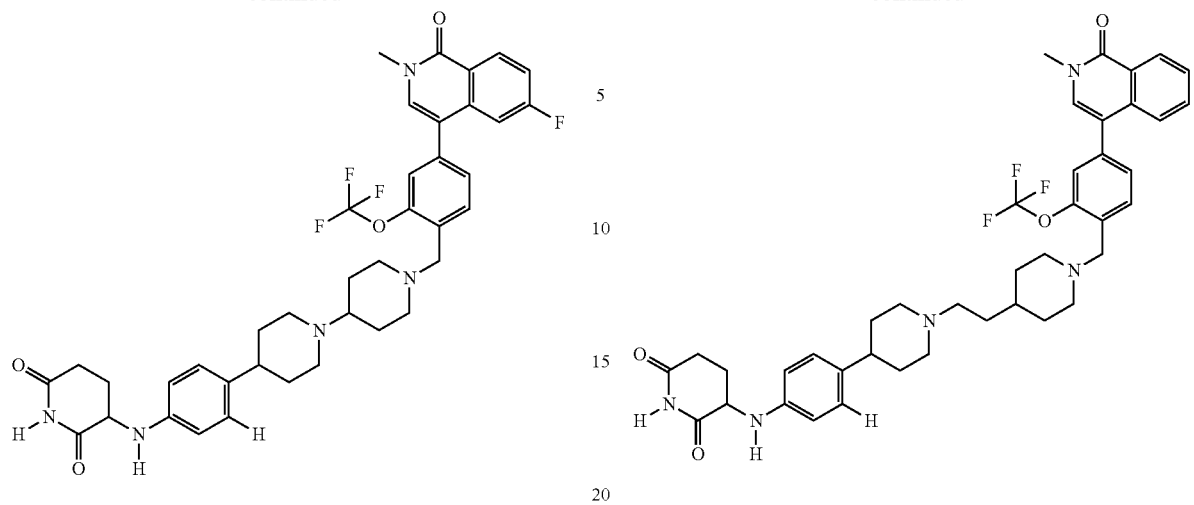
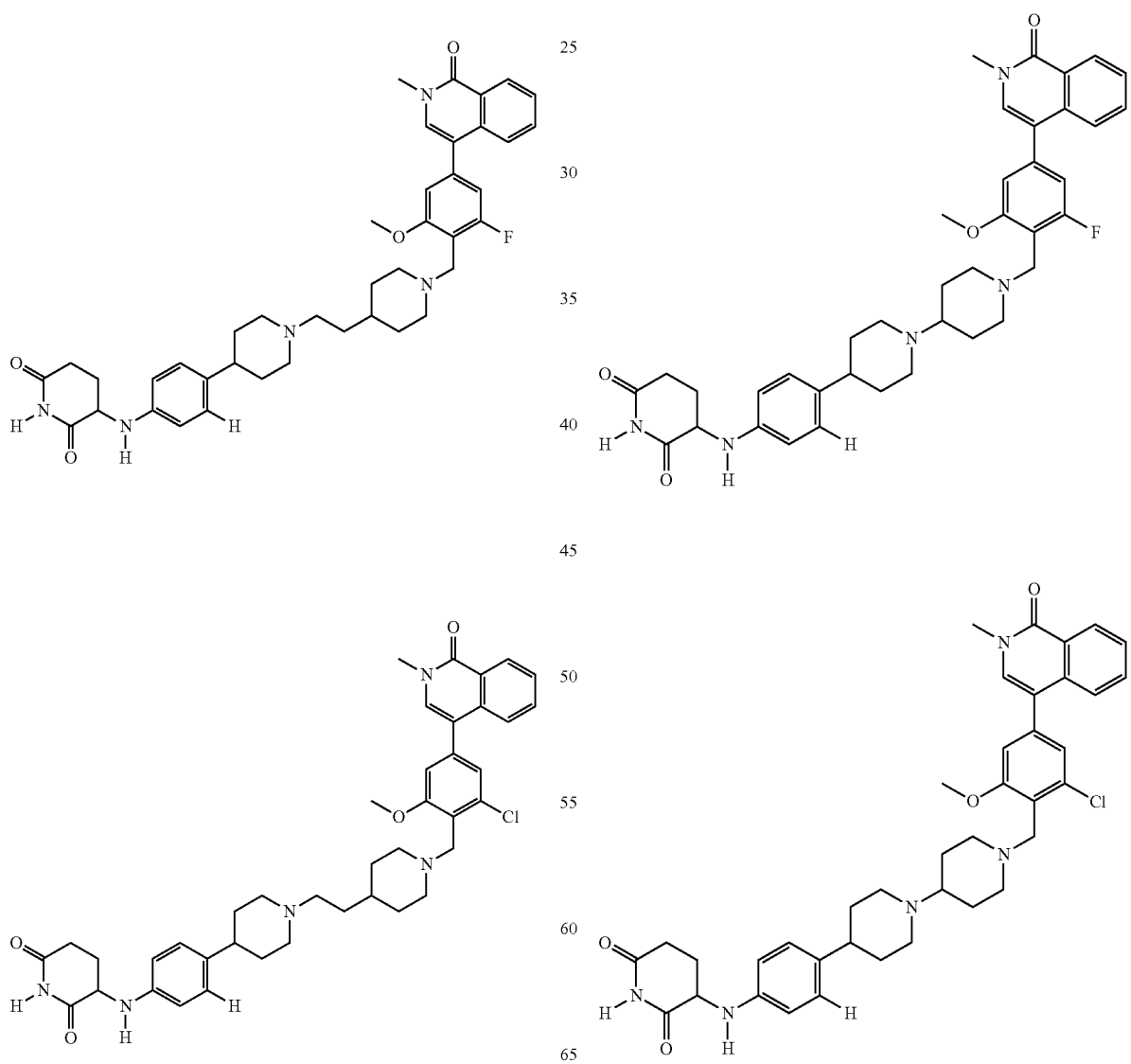

343
-continued
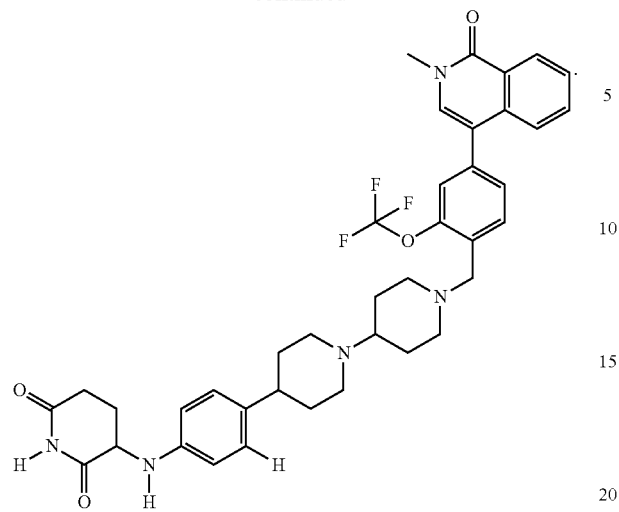
Nonlimiting examples of compounds of the present invention include:
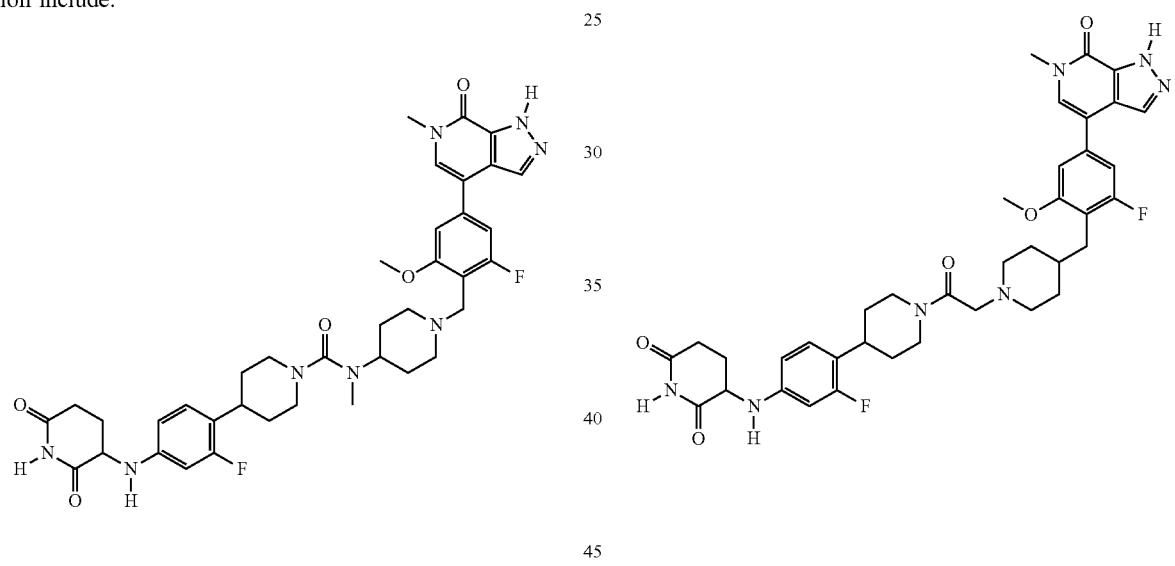
344
-continued
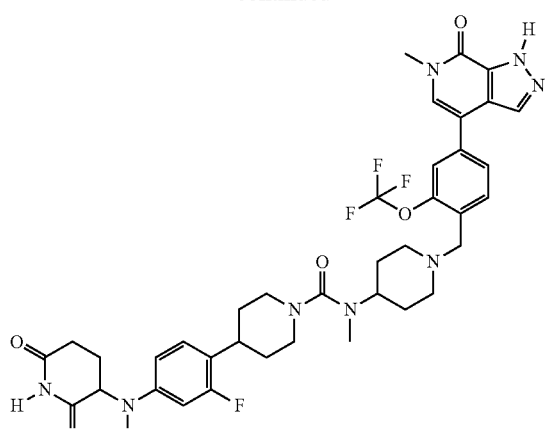
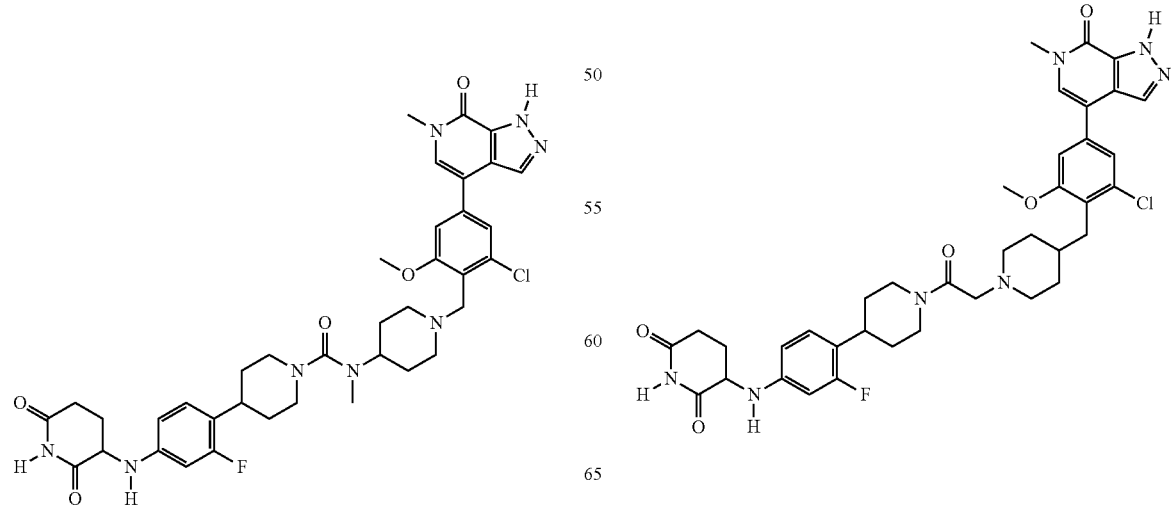

345
-continued
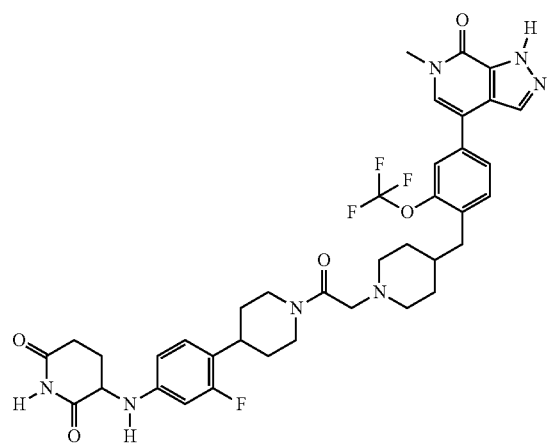
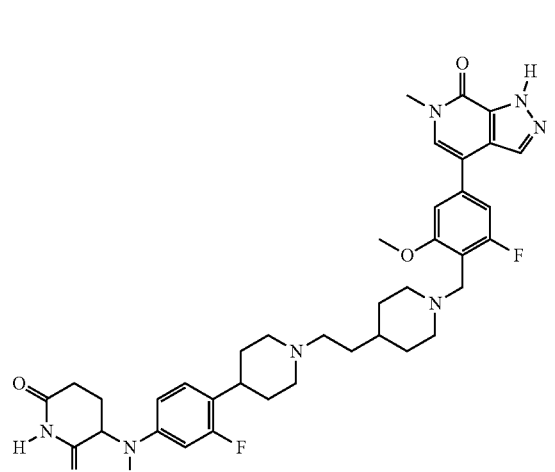
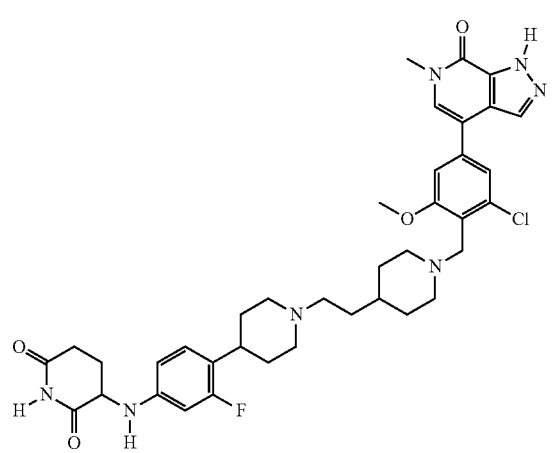
346
-continued
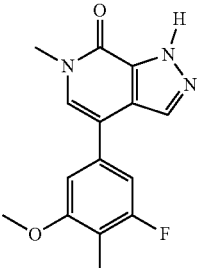
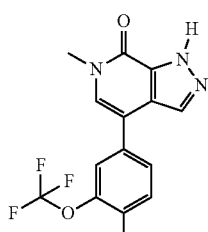
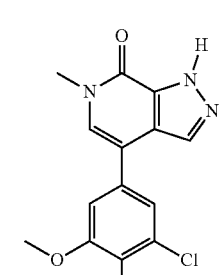

347
-continued
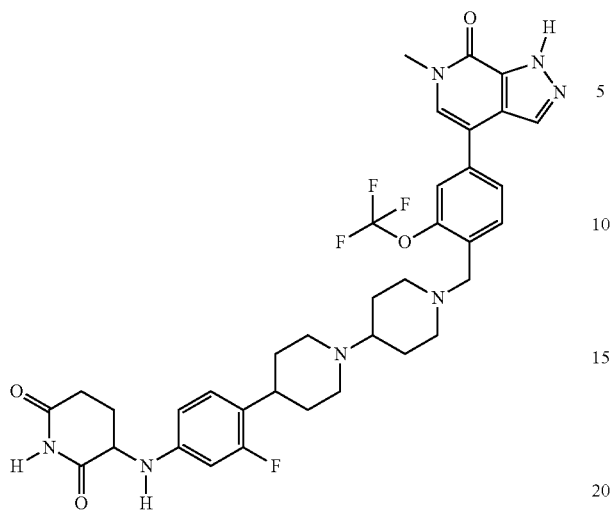
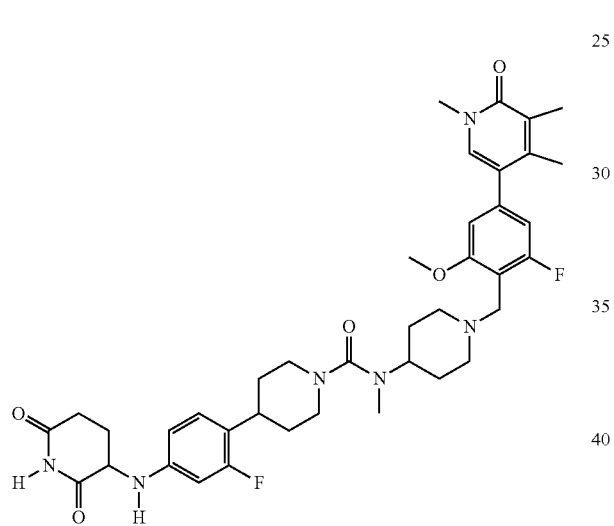
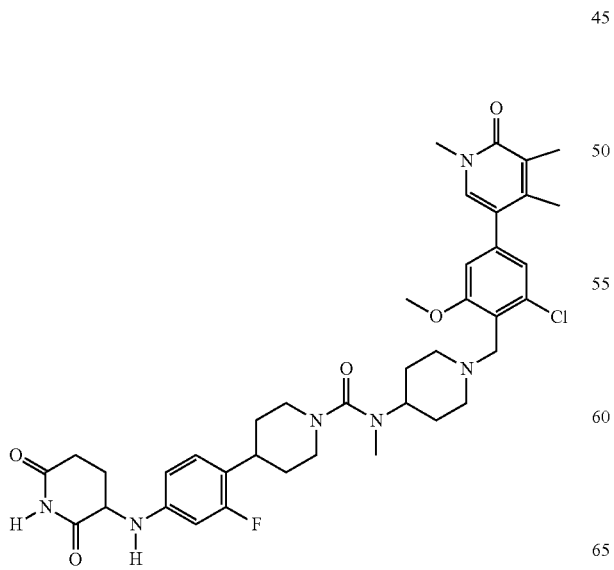
348
-continued
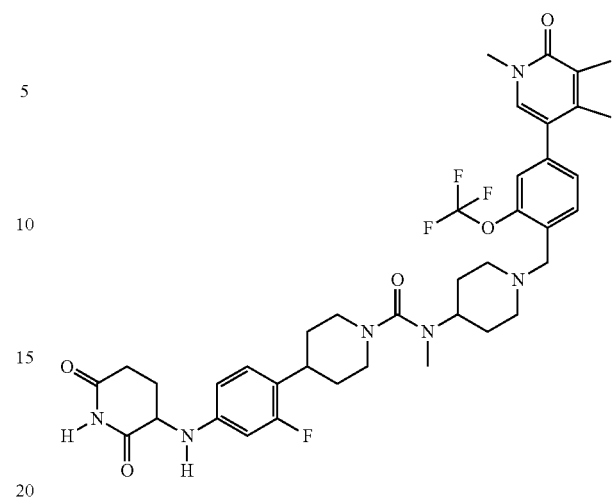
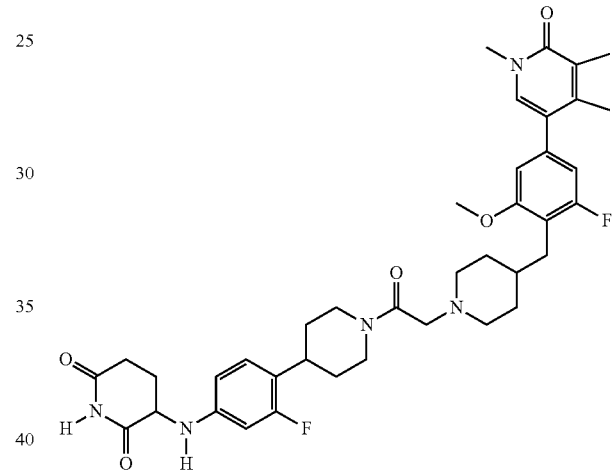
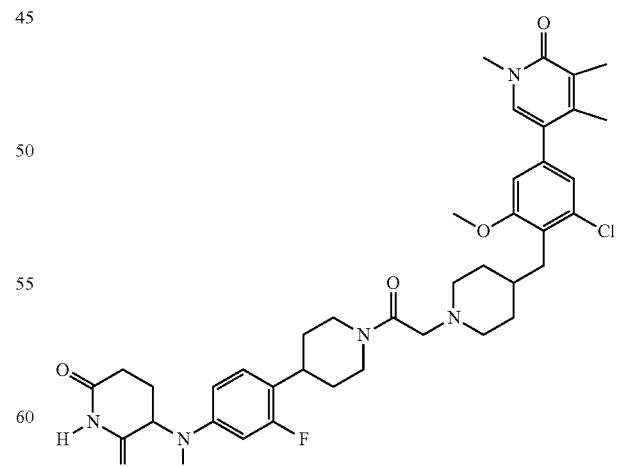

349
-continued
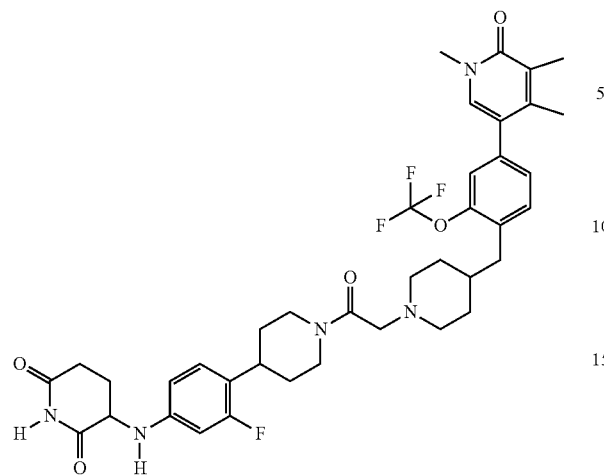
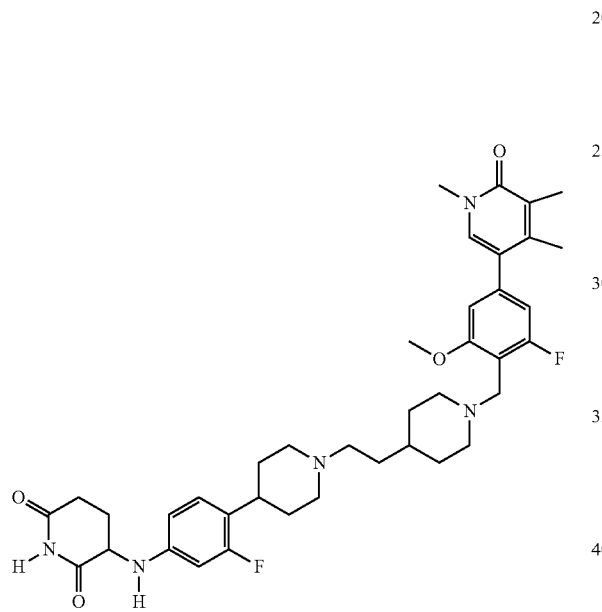
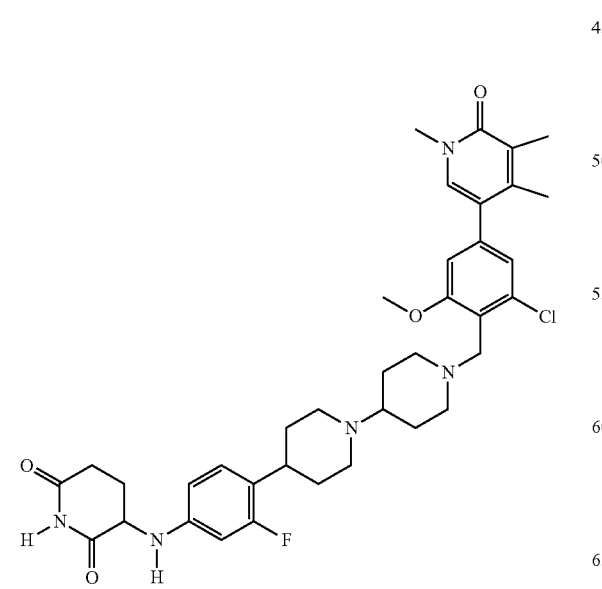
350
-continued
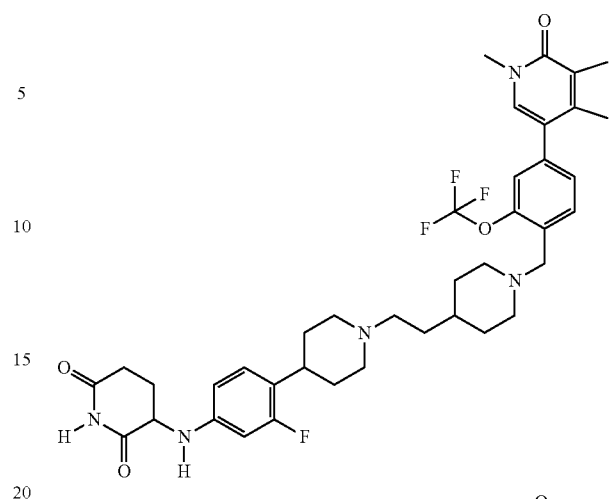
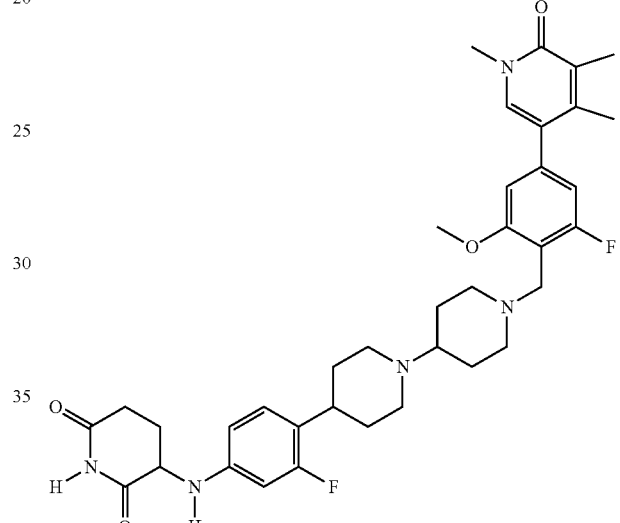
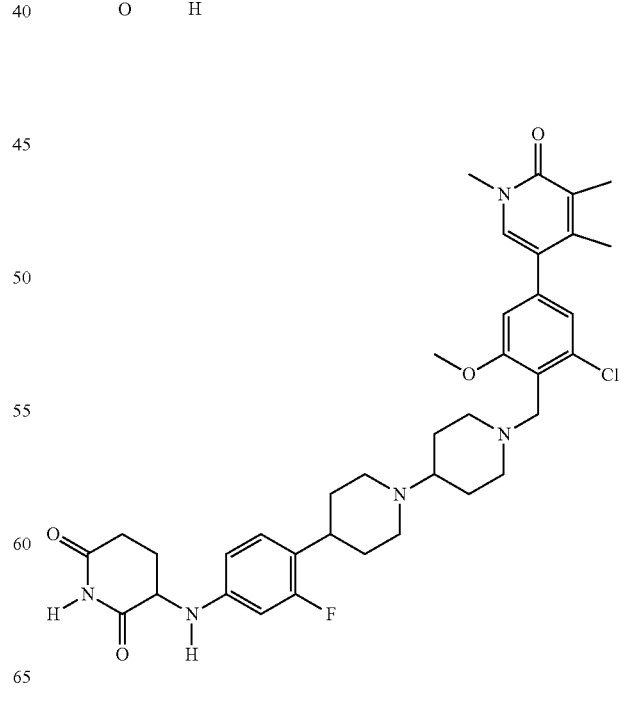

351
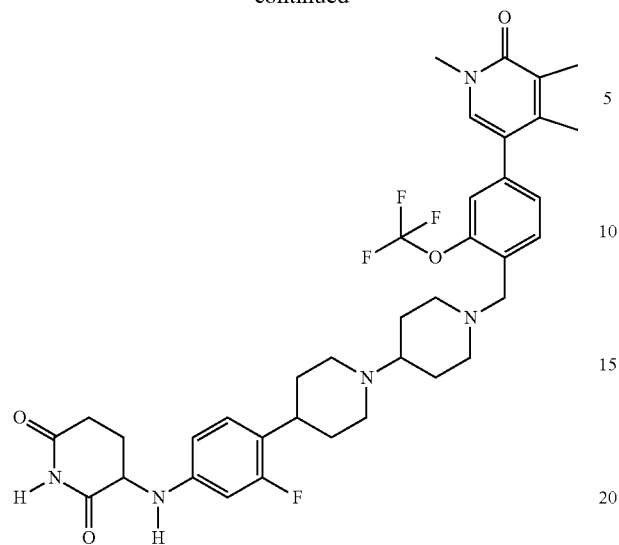
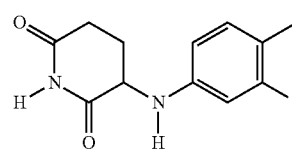
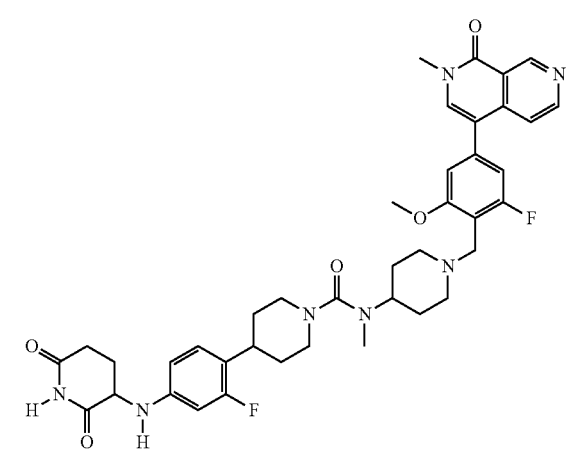
352
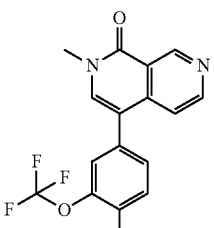
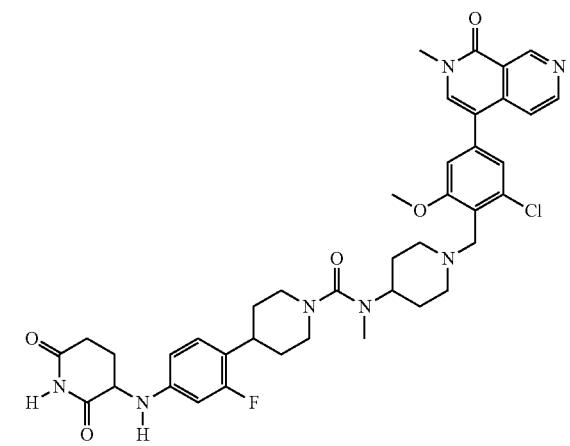
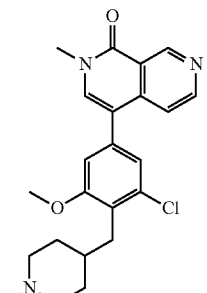

353
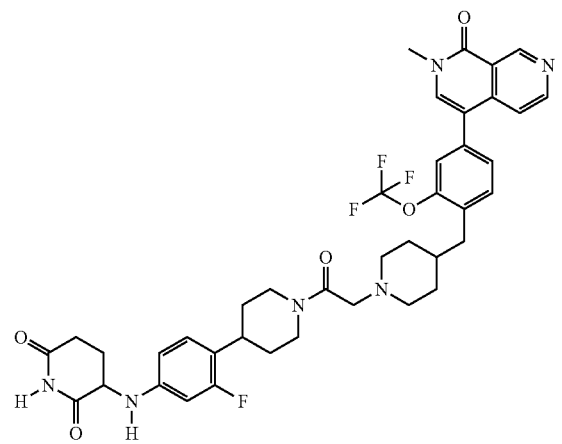
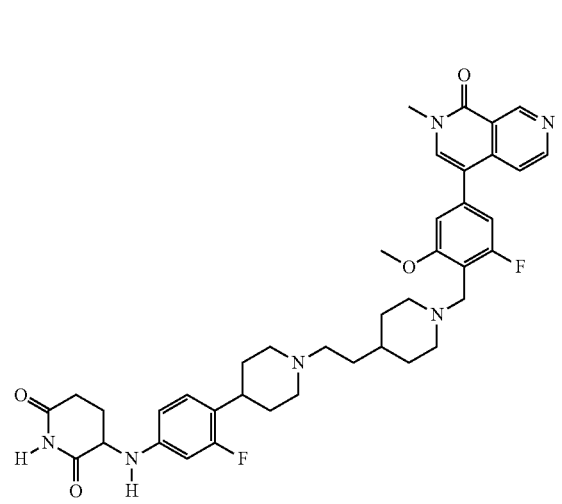
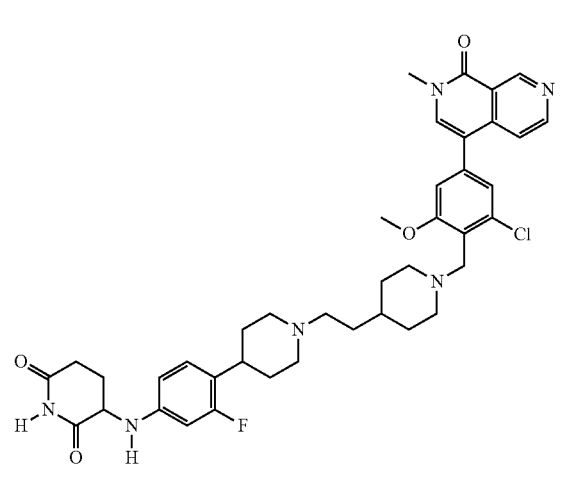
354
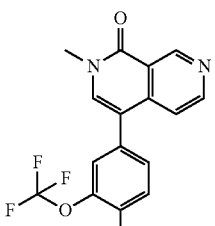

355
-continued
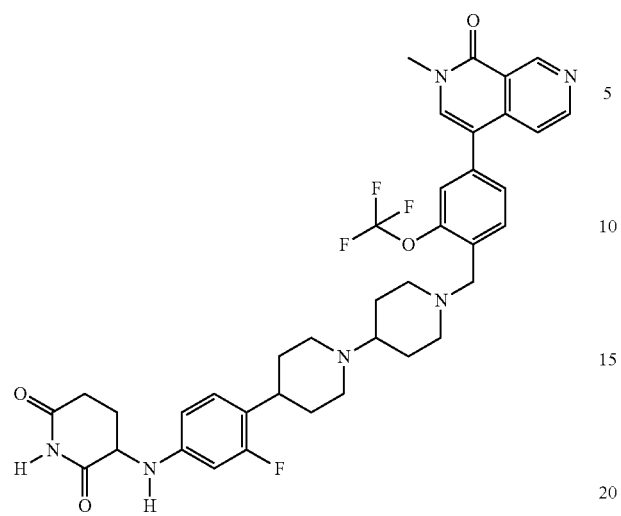
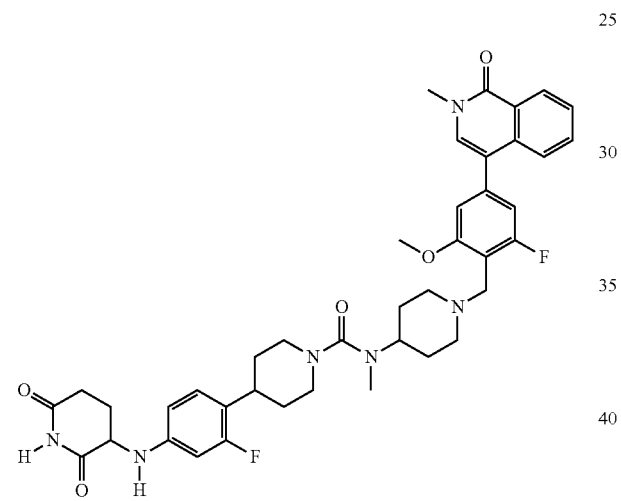
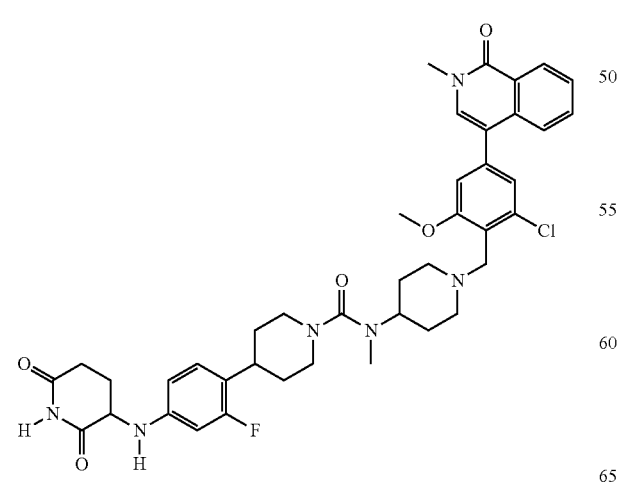
356
-continued

357
-continued
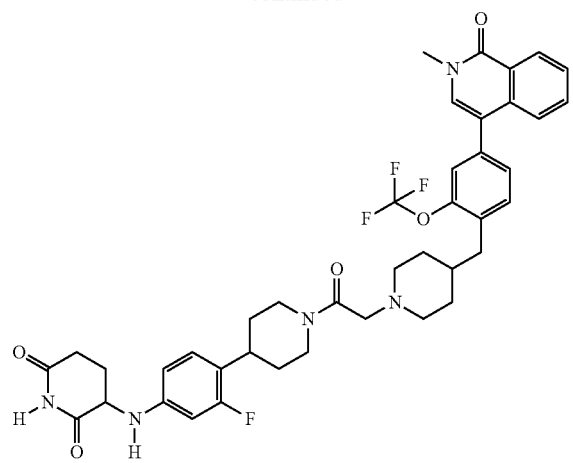
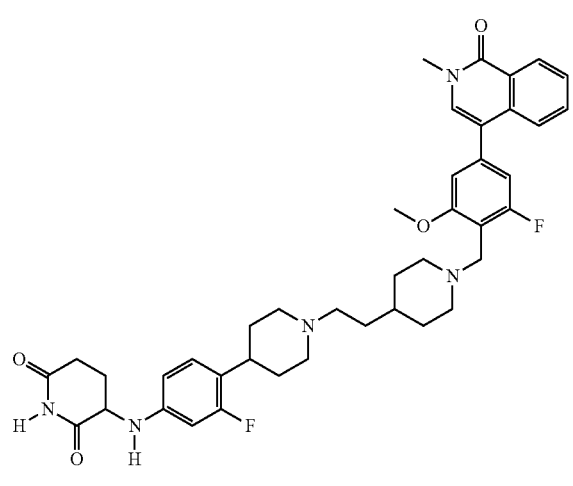
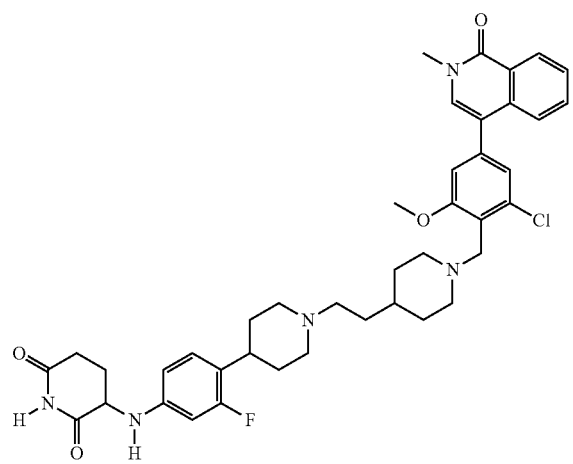
358
-continued
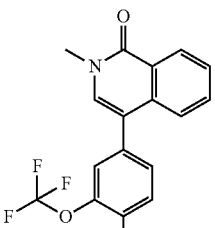
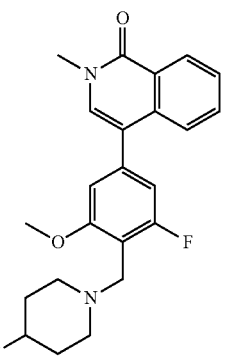
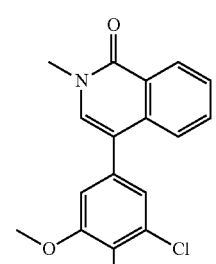

359
-continued
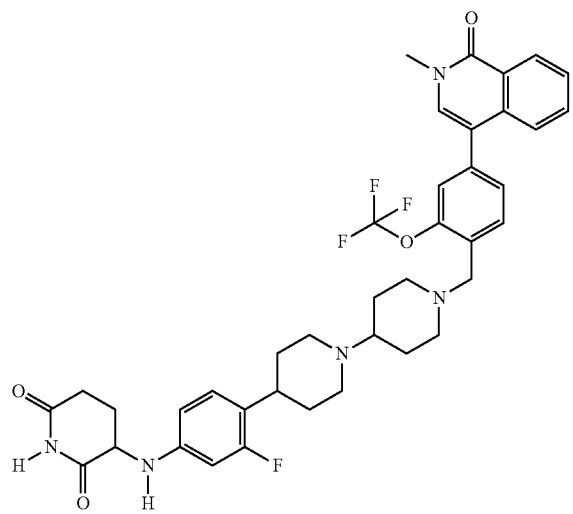
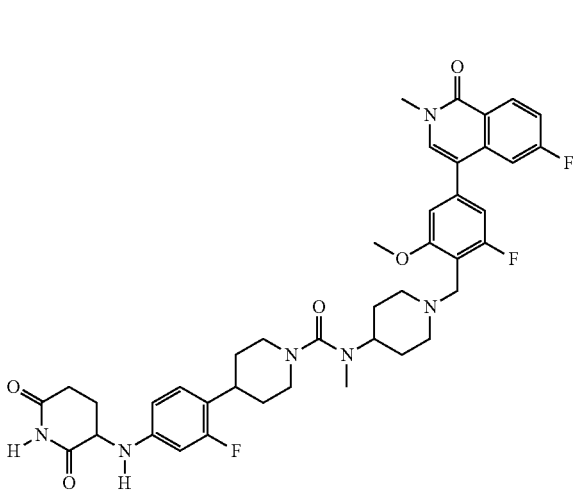
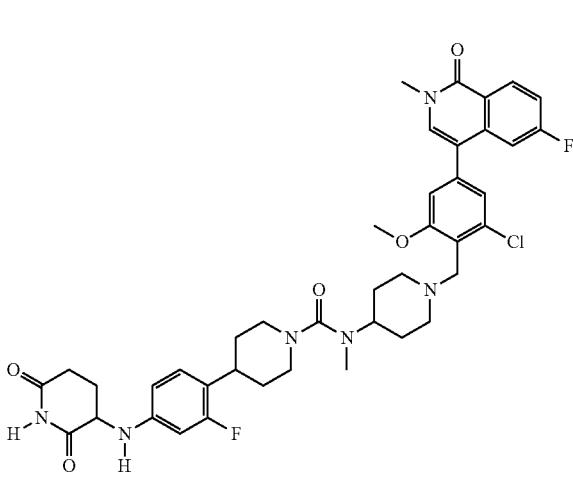
360
-continued
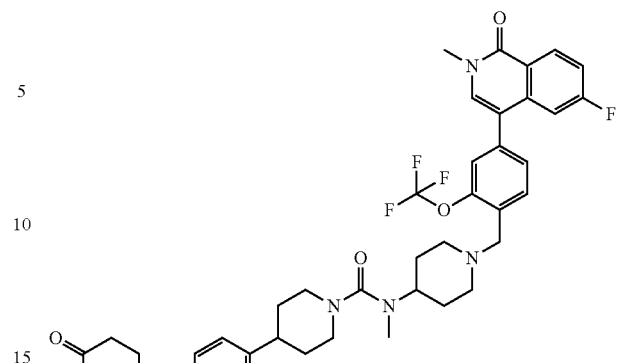
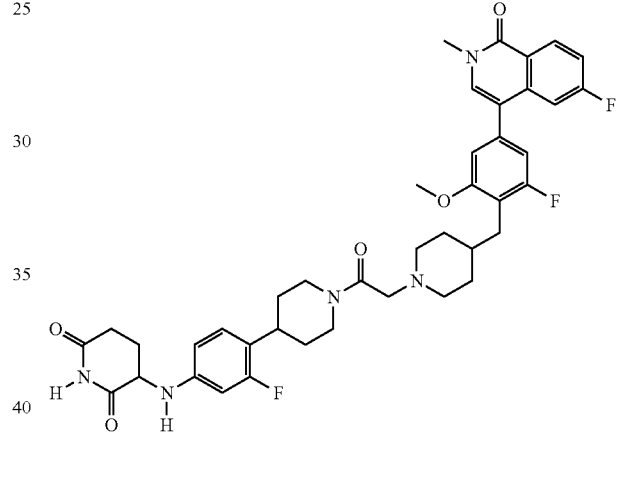
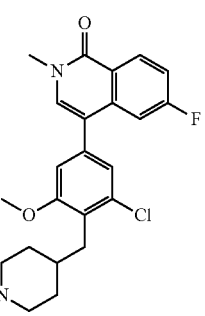

361
-continued
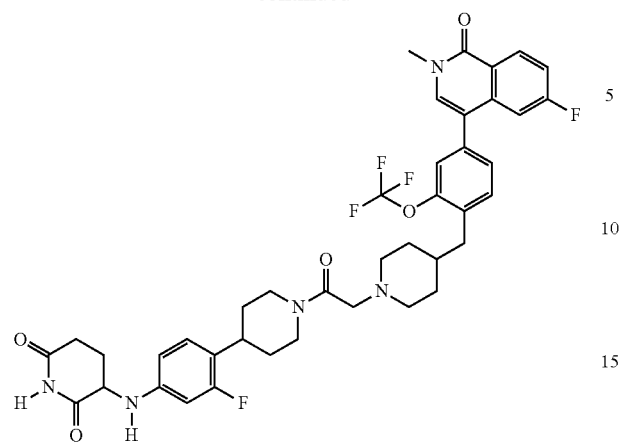
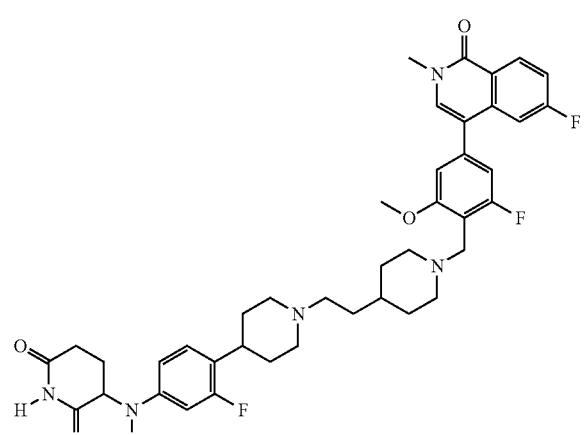
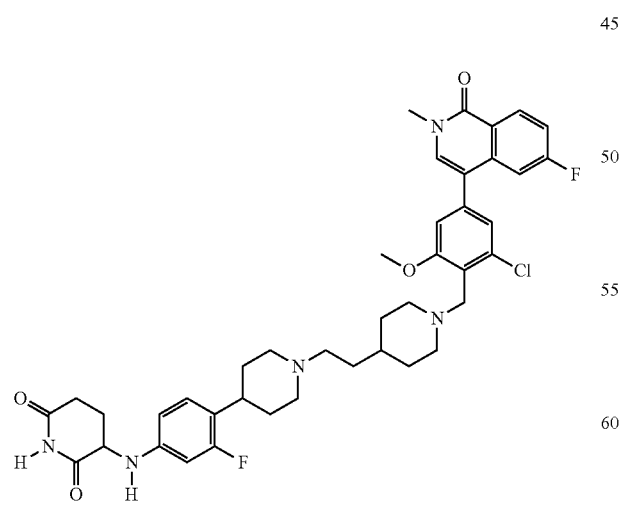
362
-continued
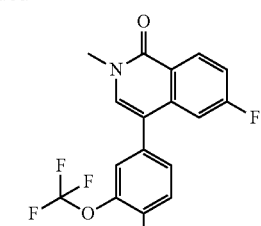
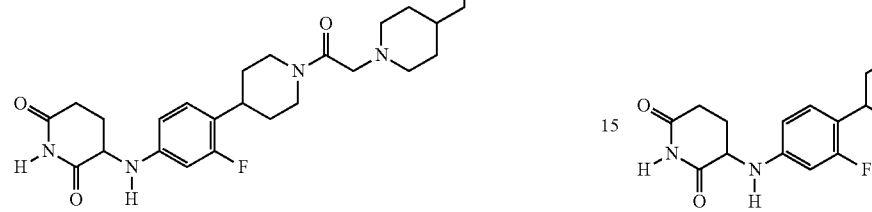
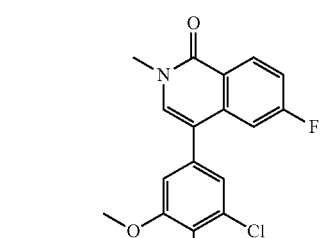
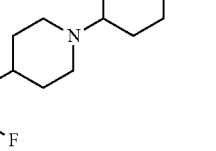

363
-continued
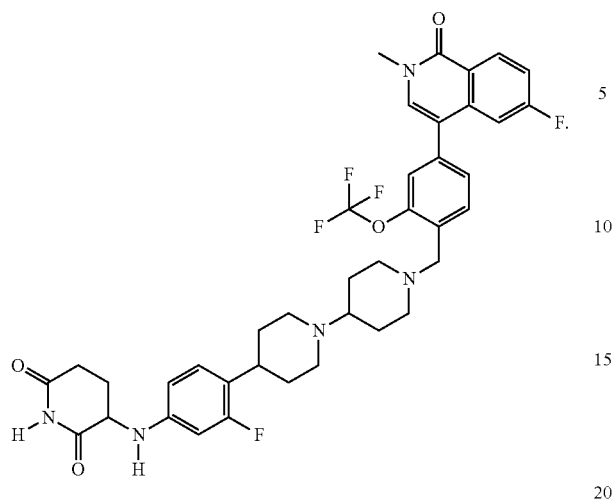
Nonlimiting examples of compounds of the present invention include:
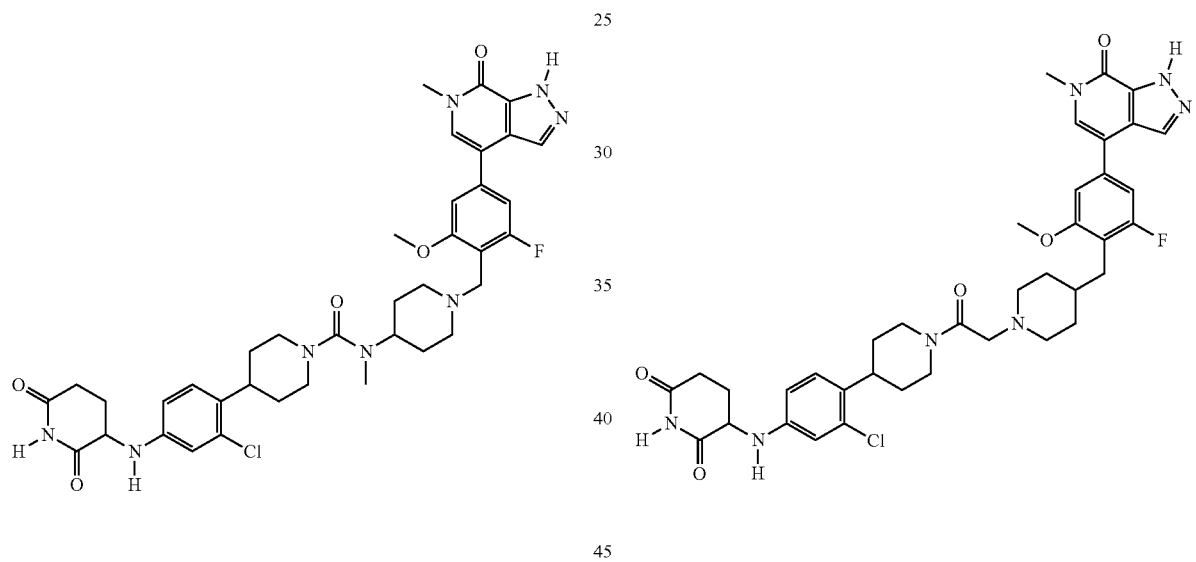
364
-continued
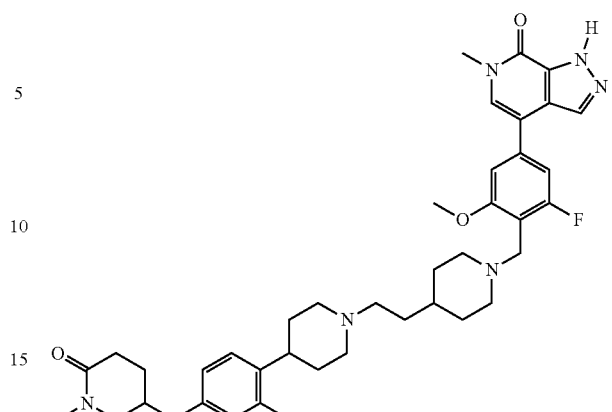
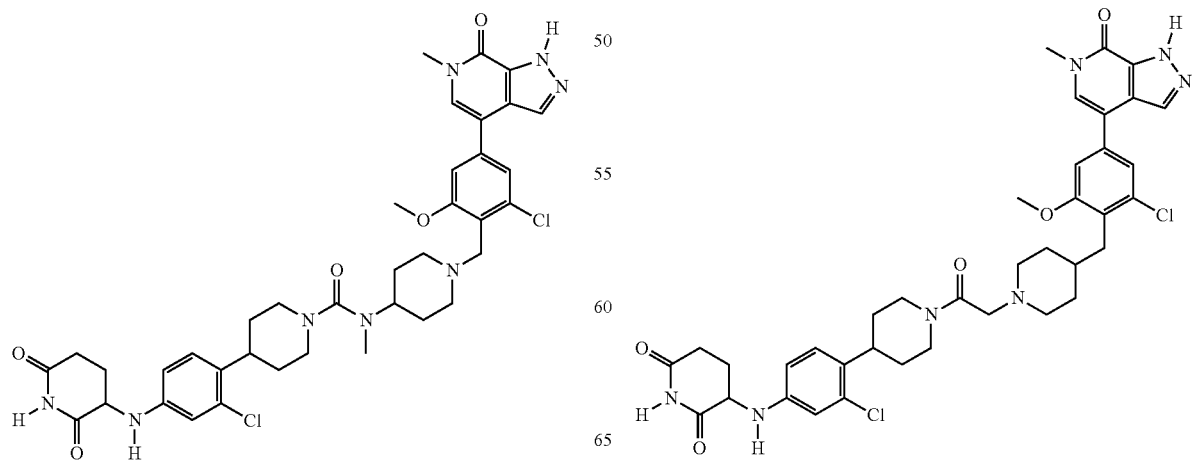

365
-continued
366
-continued
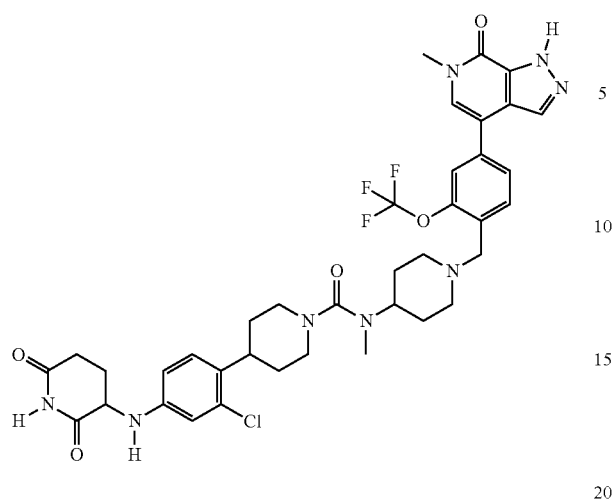
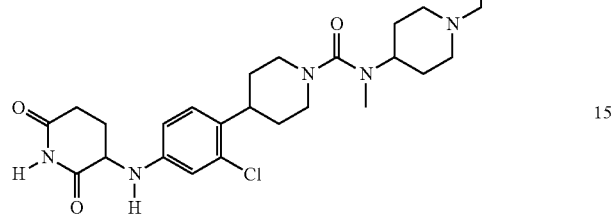
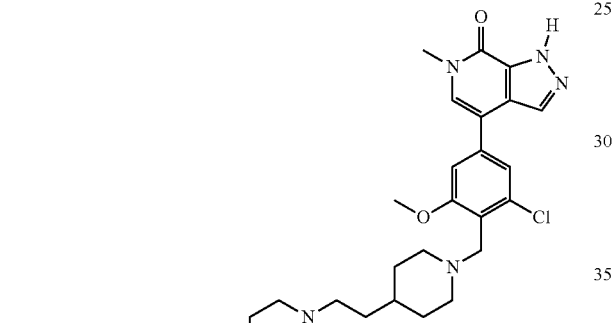
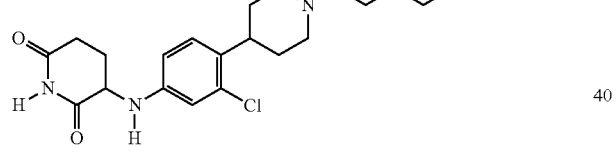
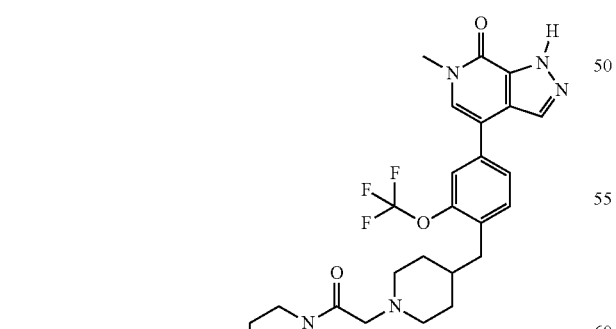
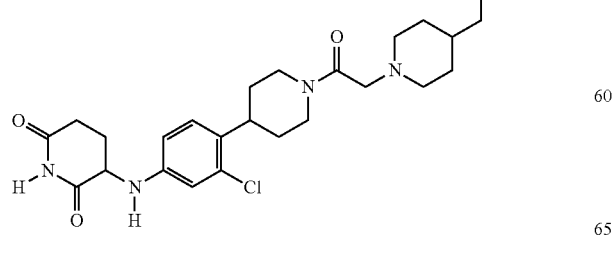

367
-continued
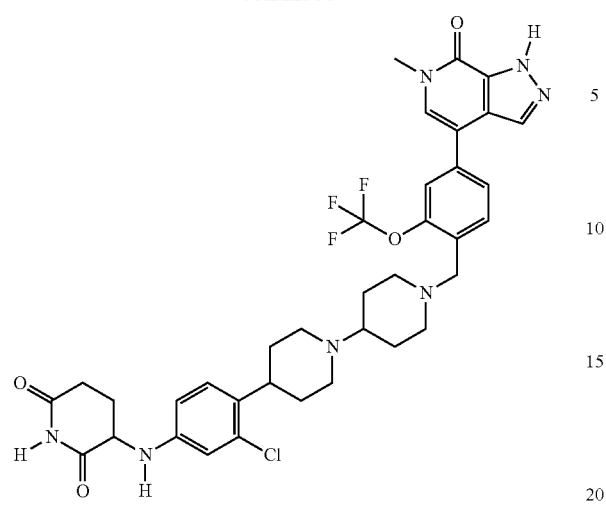
368
-continued
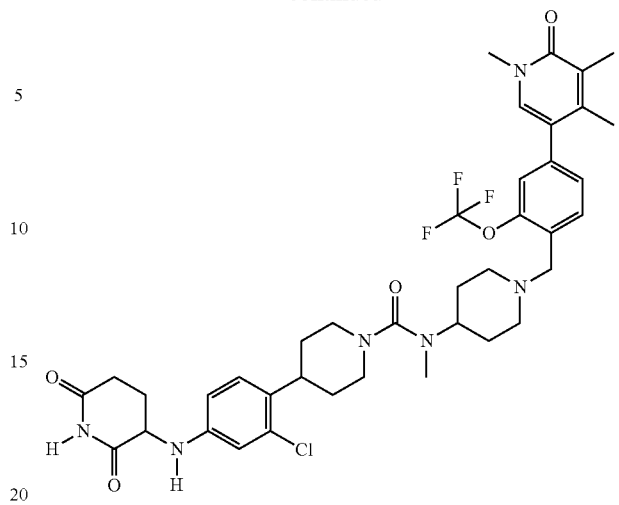
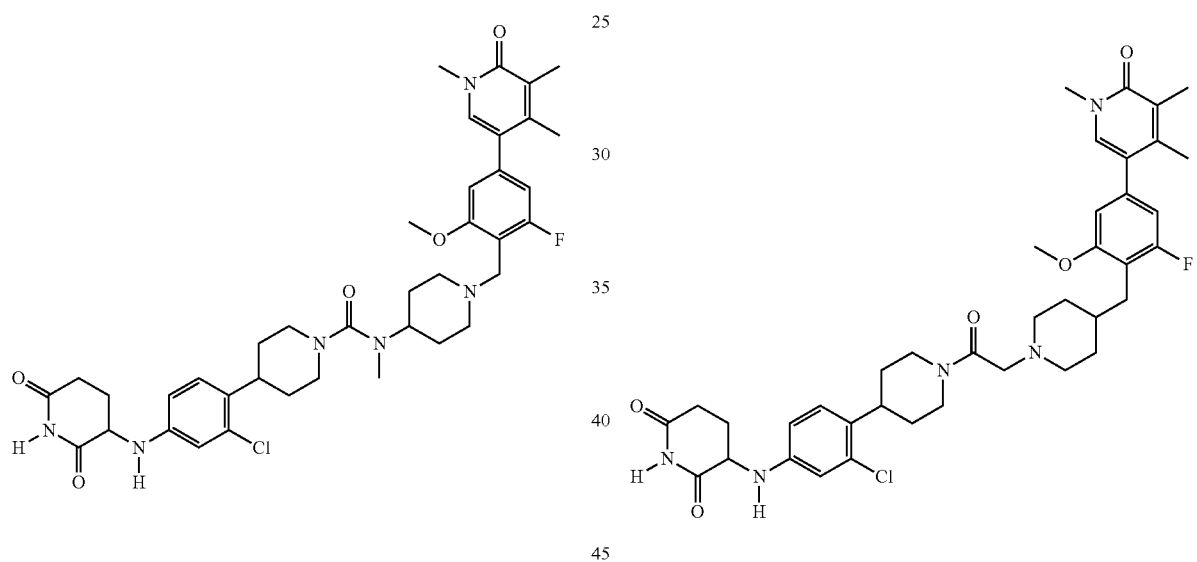
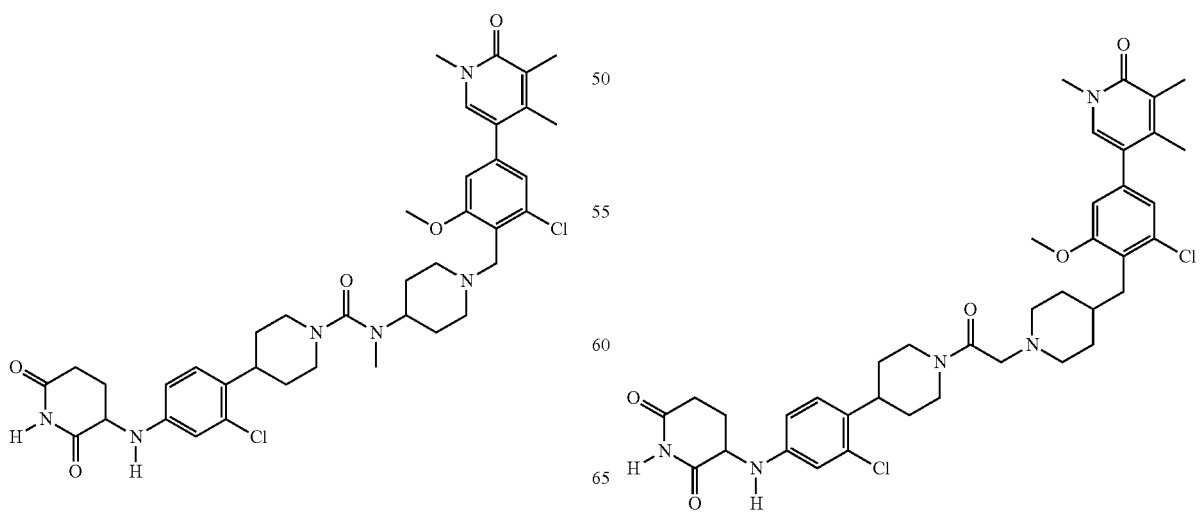

369
-continued
370
-continued
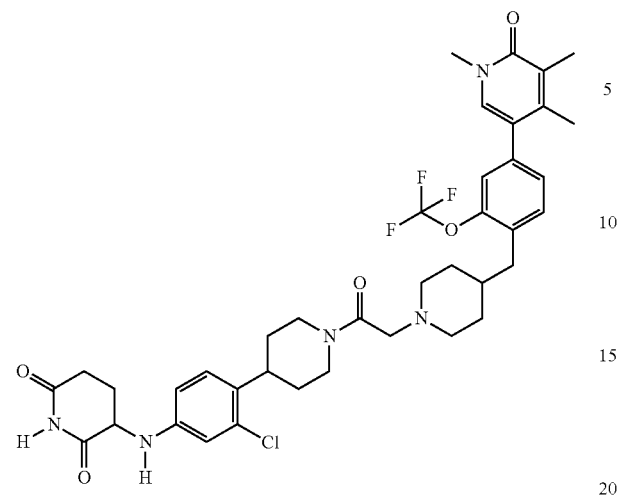
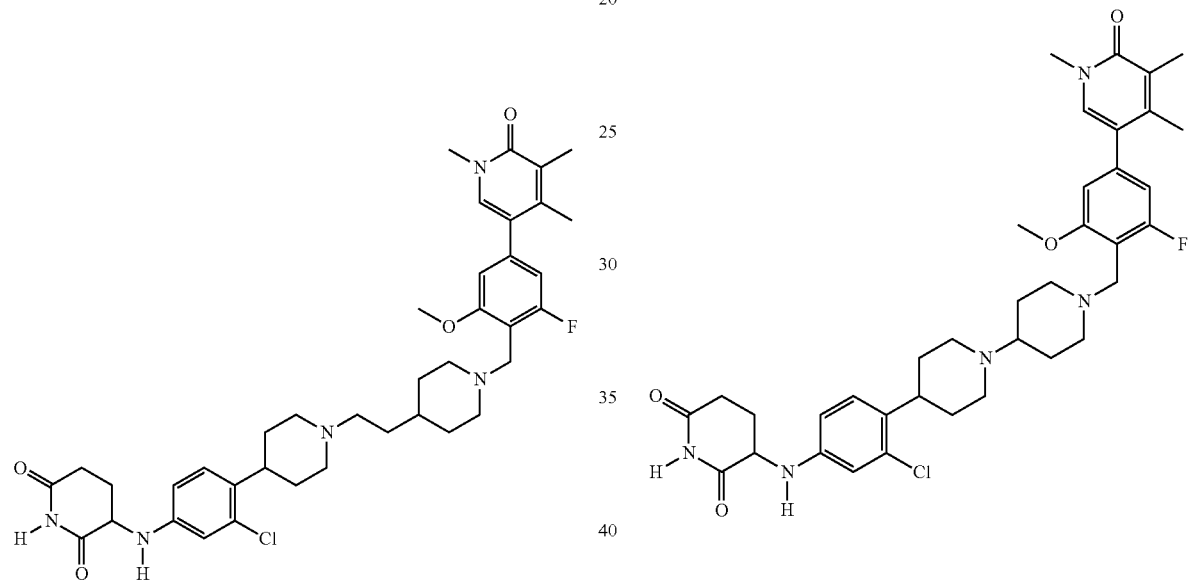
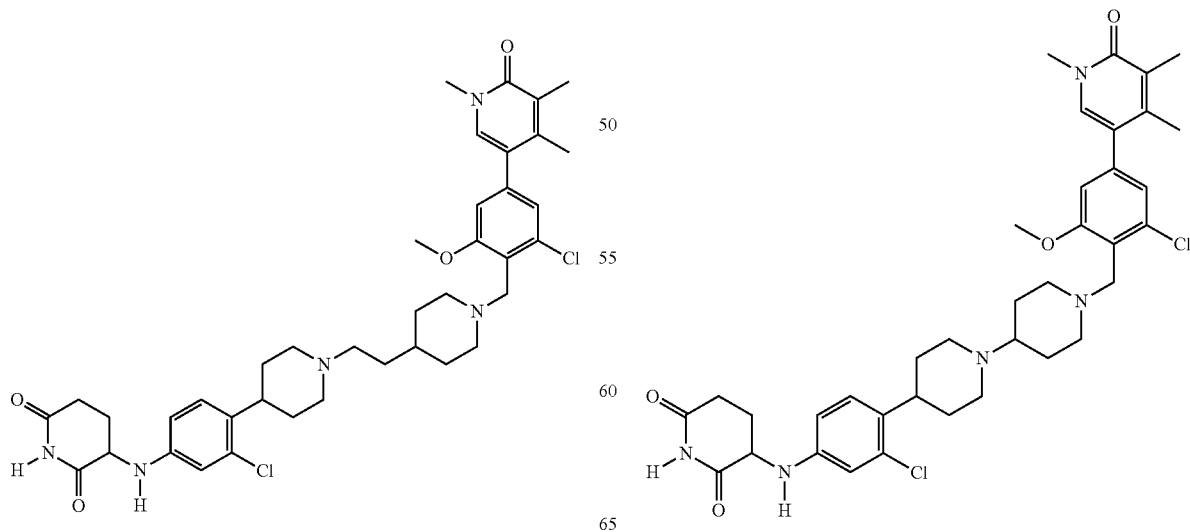

371
-continued
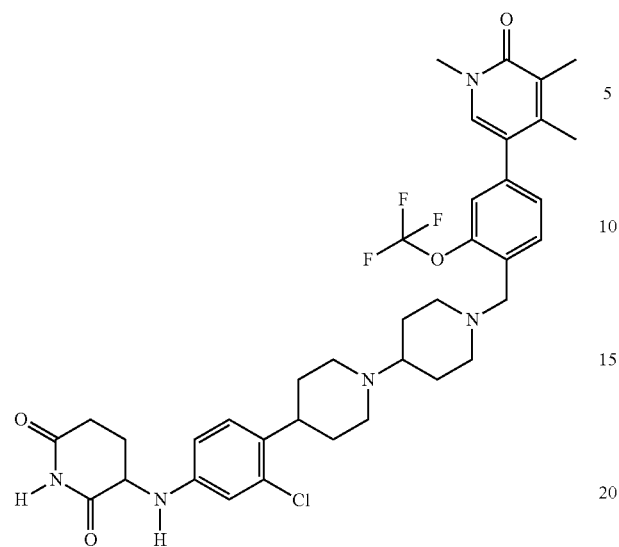
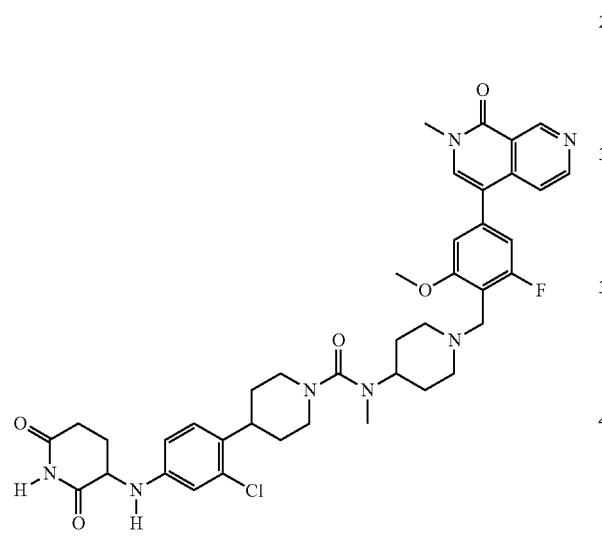
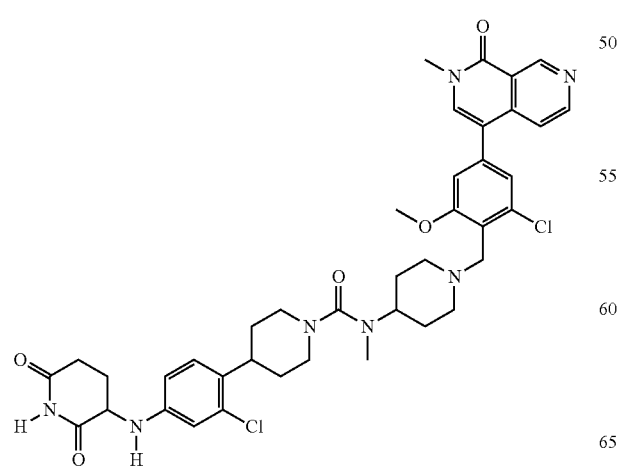
372
-continued
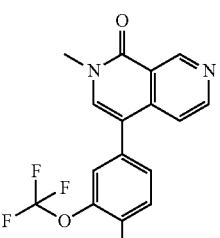
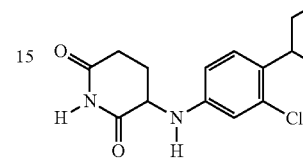
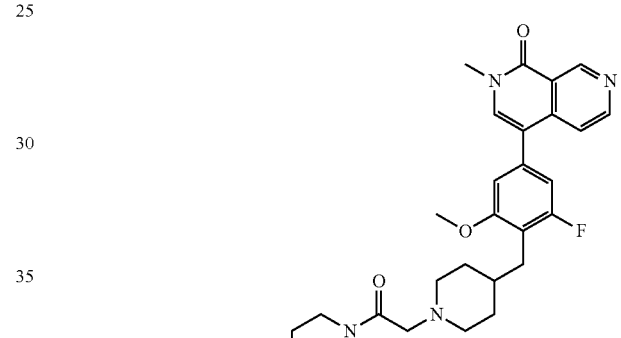
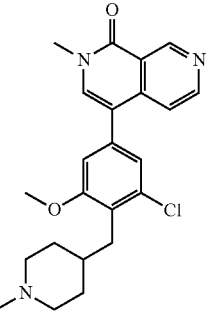

373
-continued
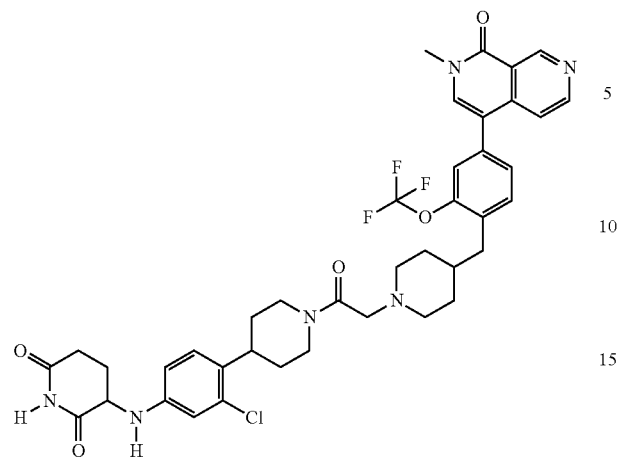
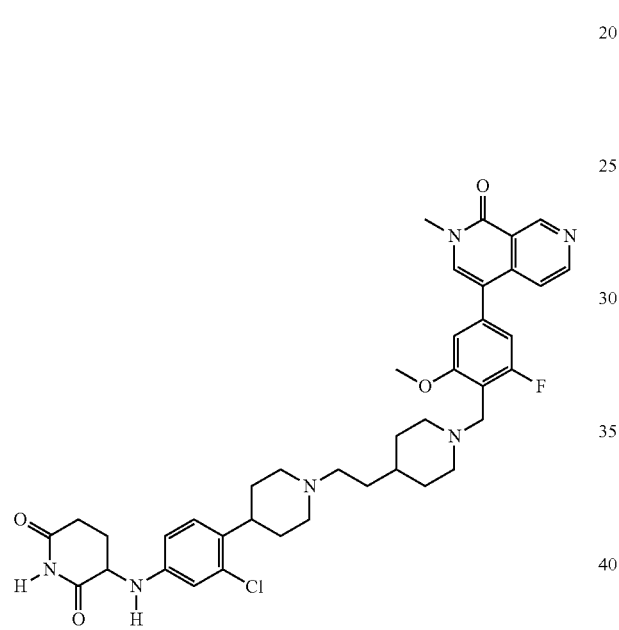
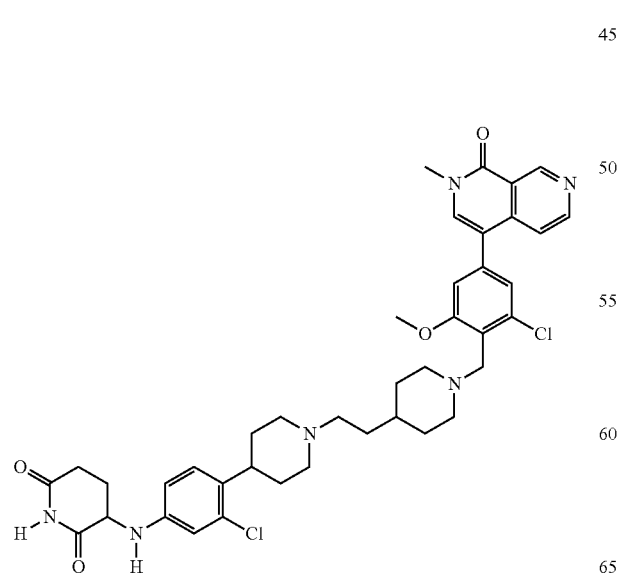
374
-continued
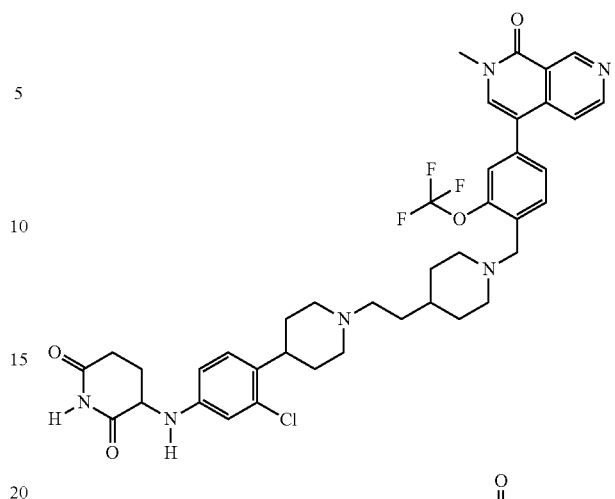
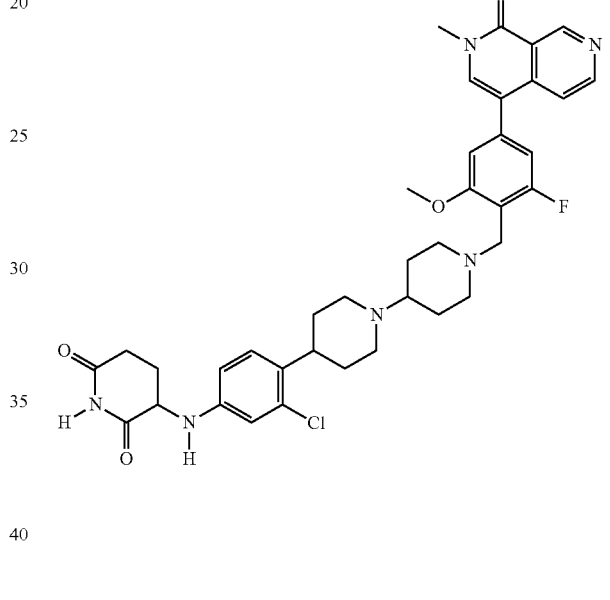
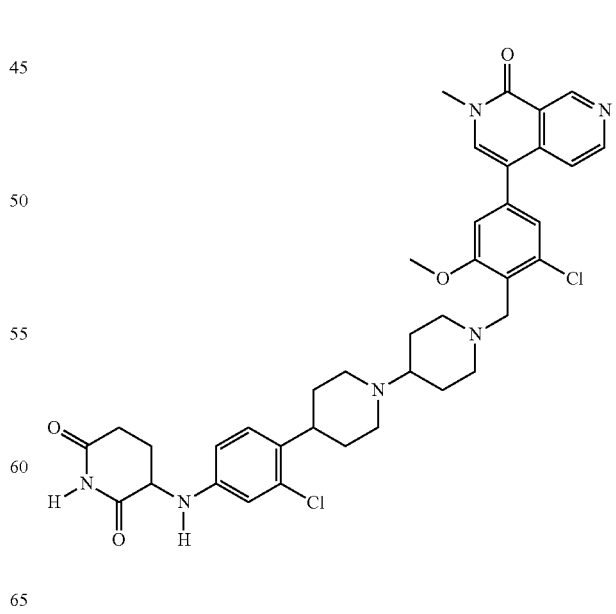

375
-continued
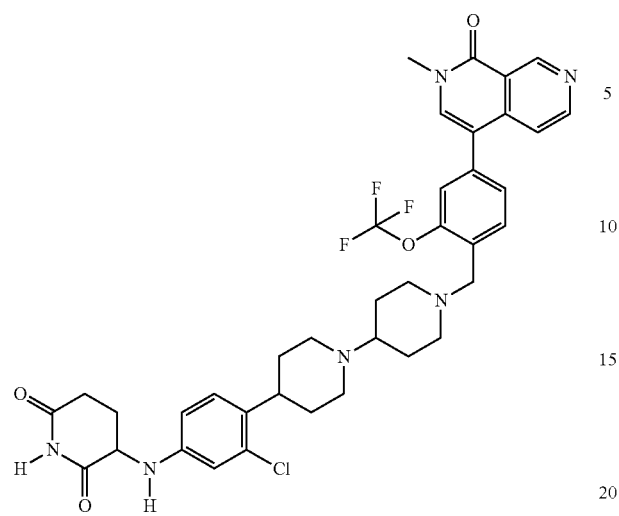
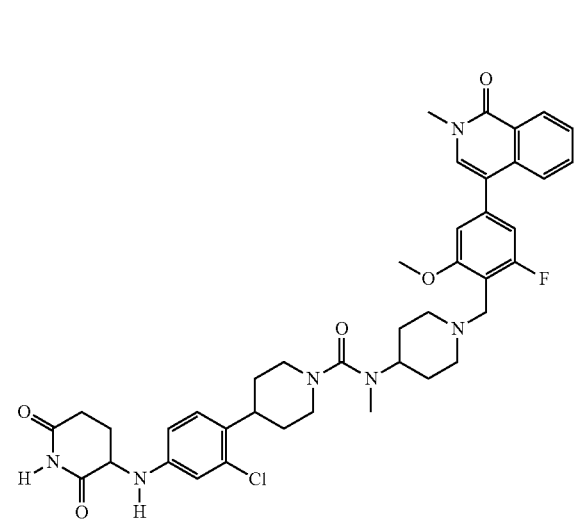
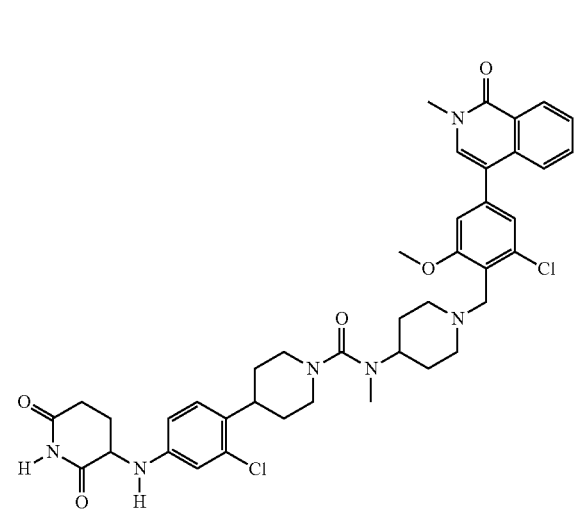
376
-continued
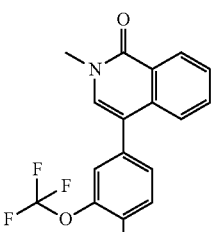
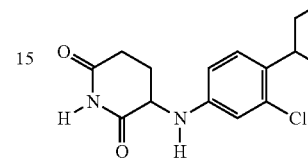
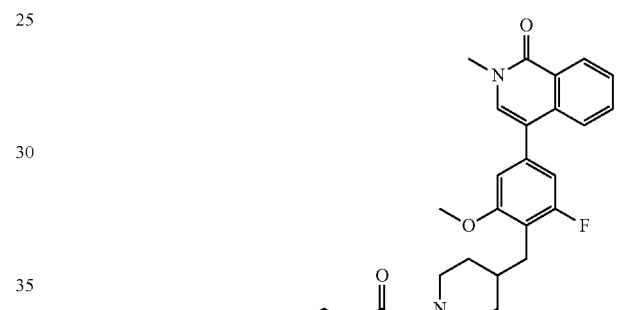
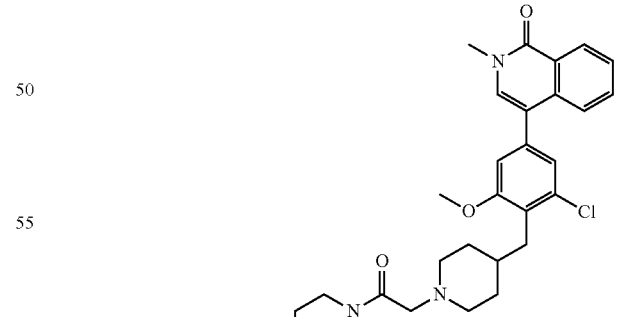

377
-continued
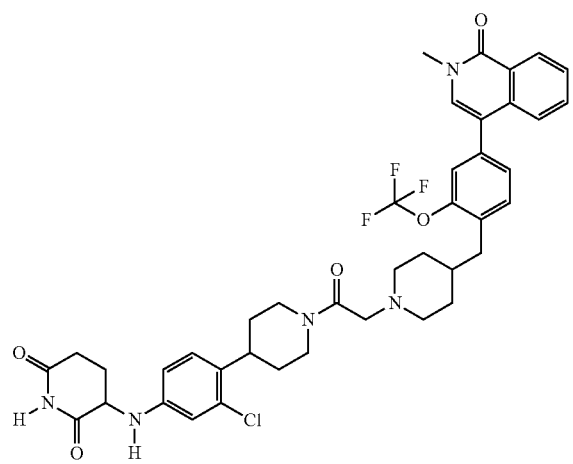
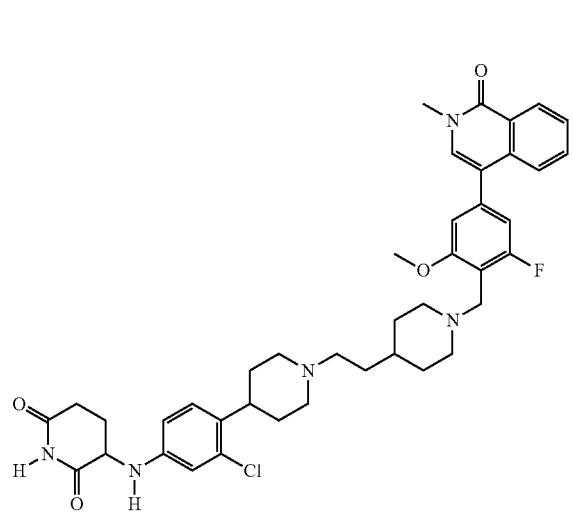
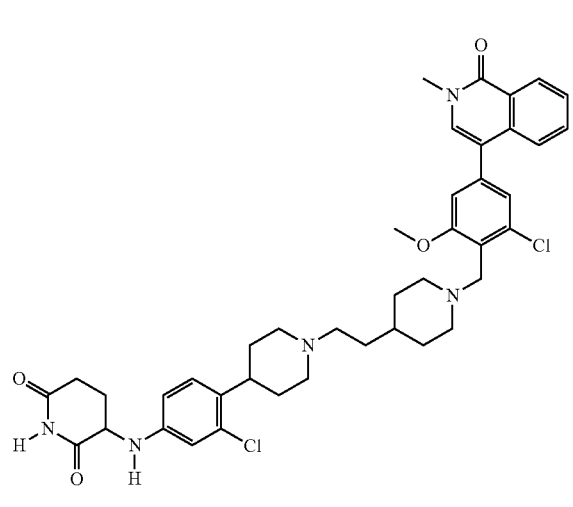
378
-continued
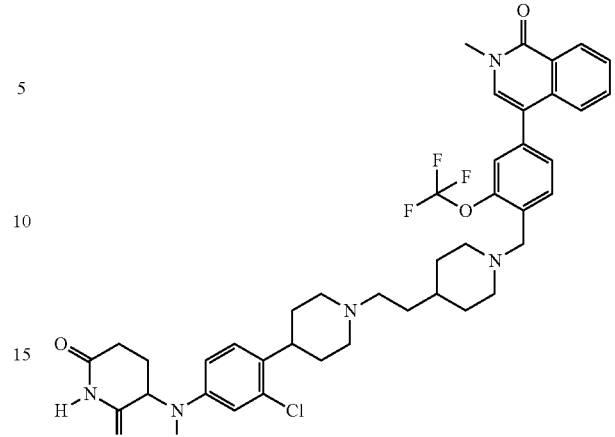
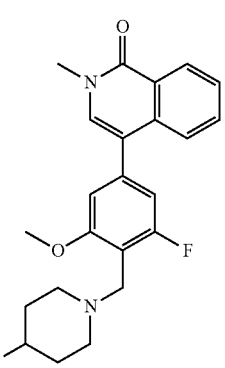
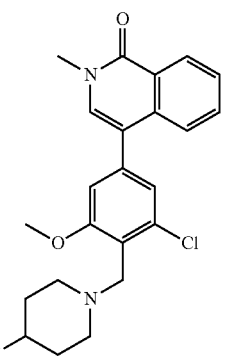

379
-continued
380
-continued
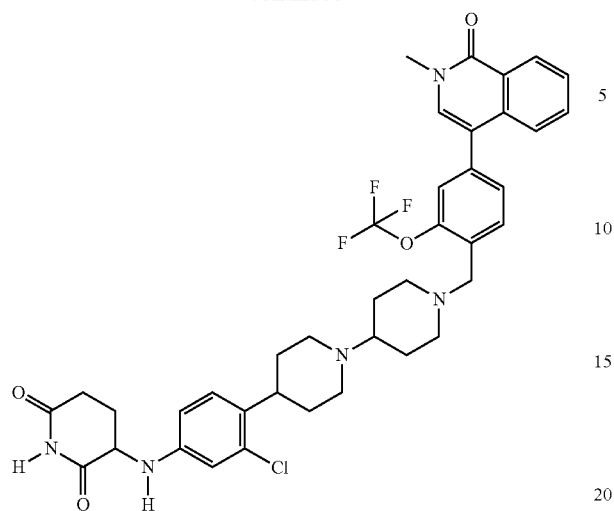
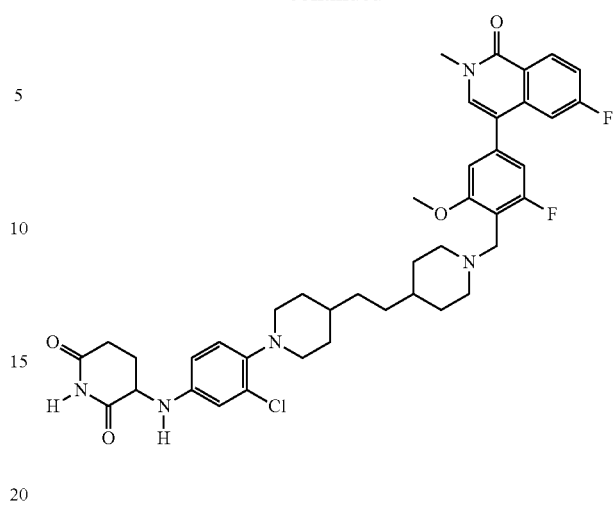

381
-continued
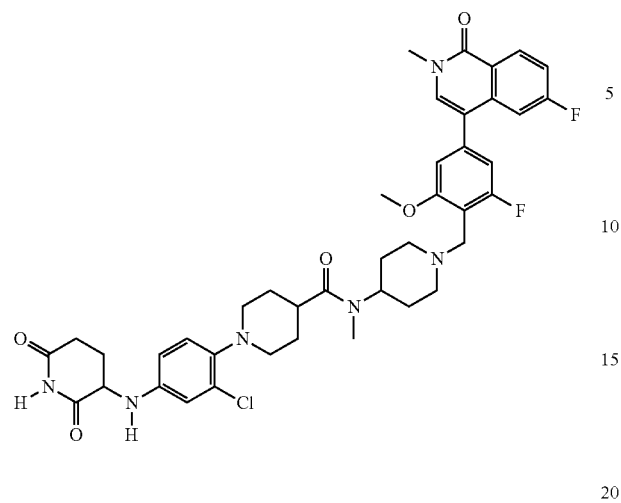
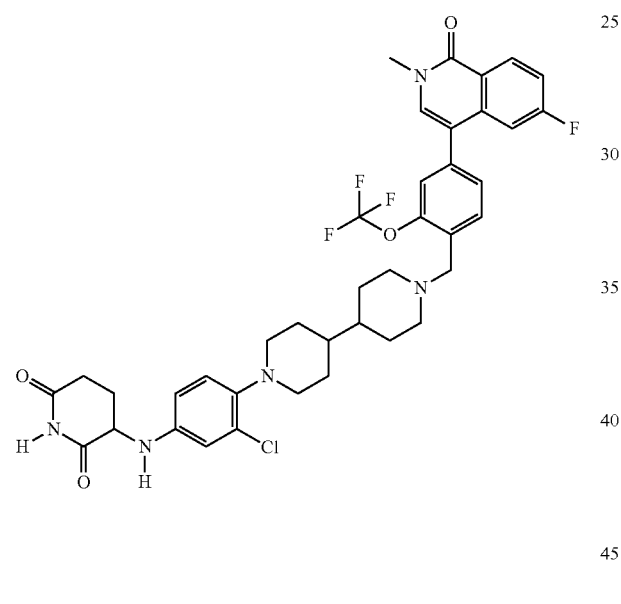
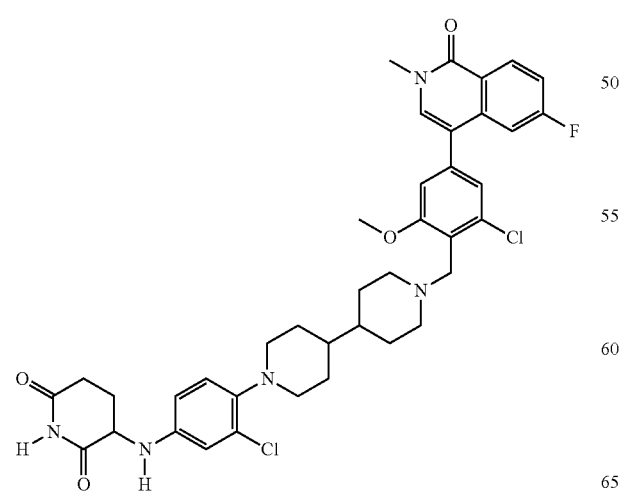
382
-continued
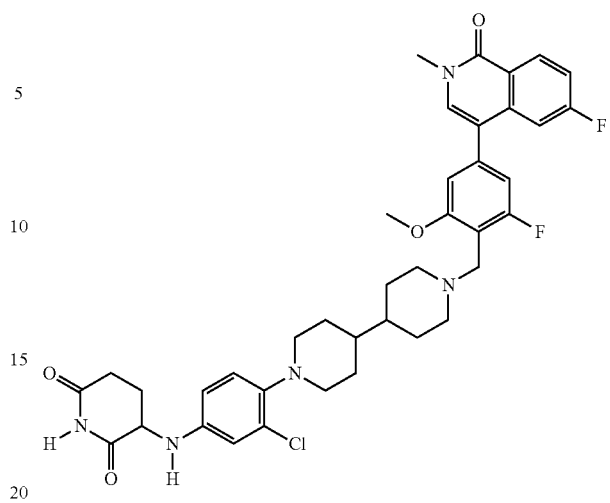
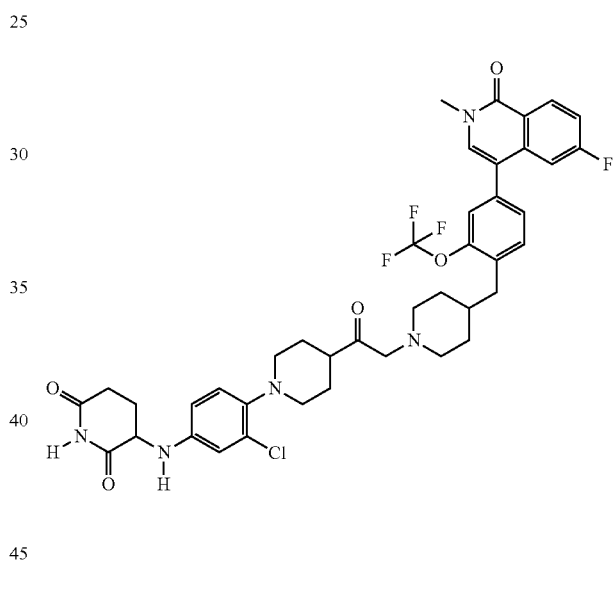
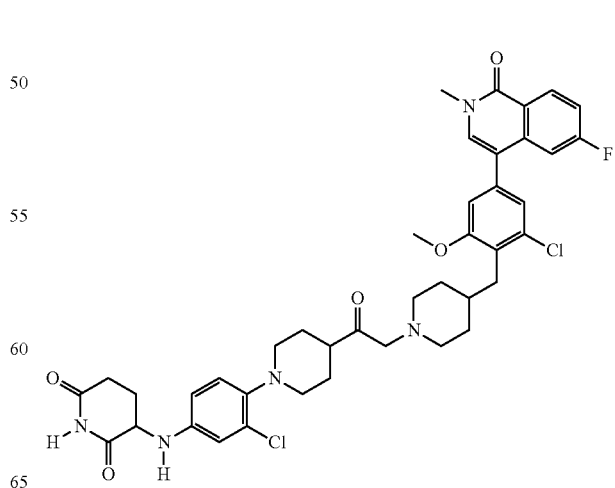

383
-continued
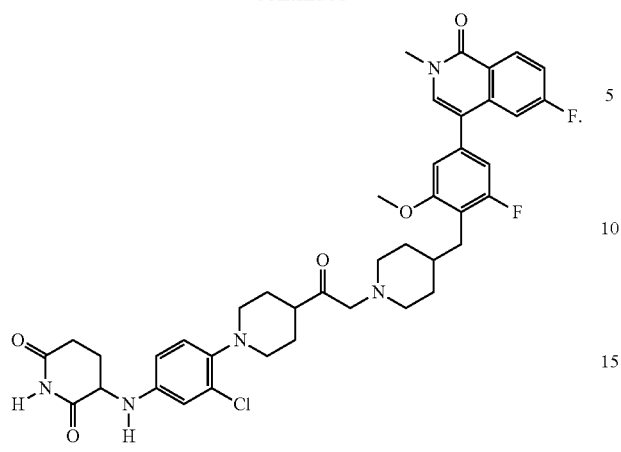
Nonlimiting examples of compounds of the present invention include:
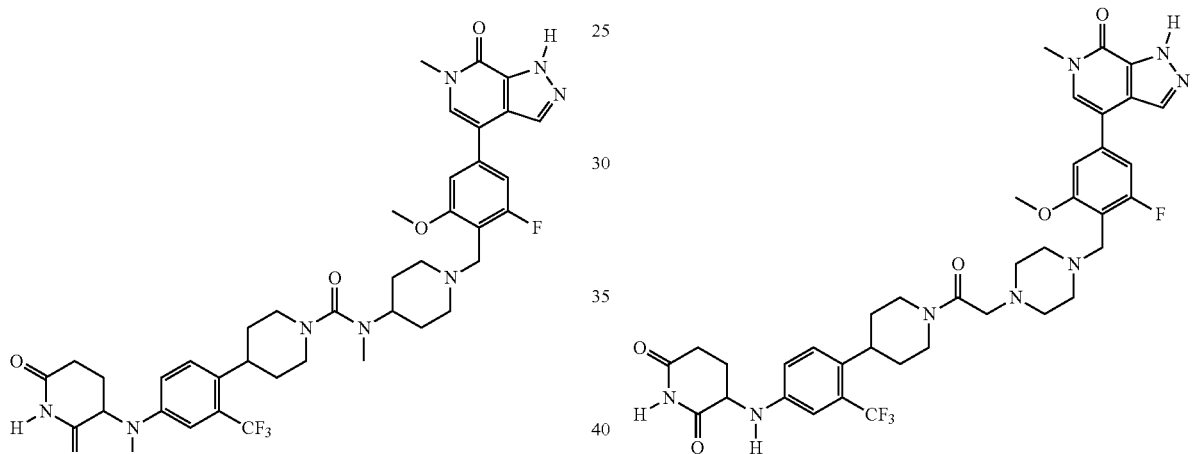
384
-continued
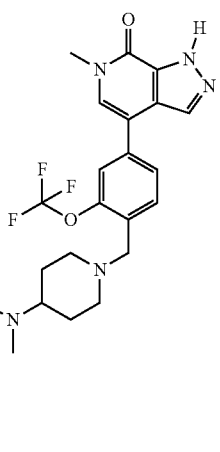
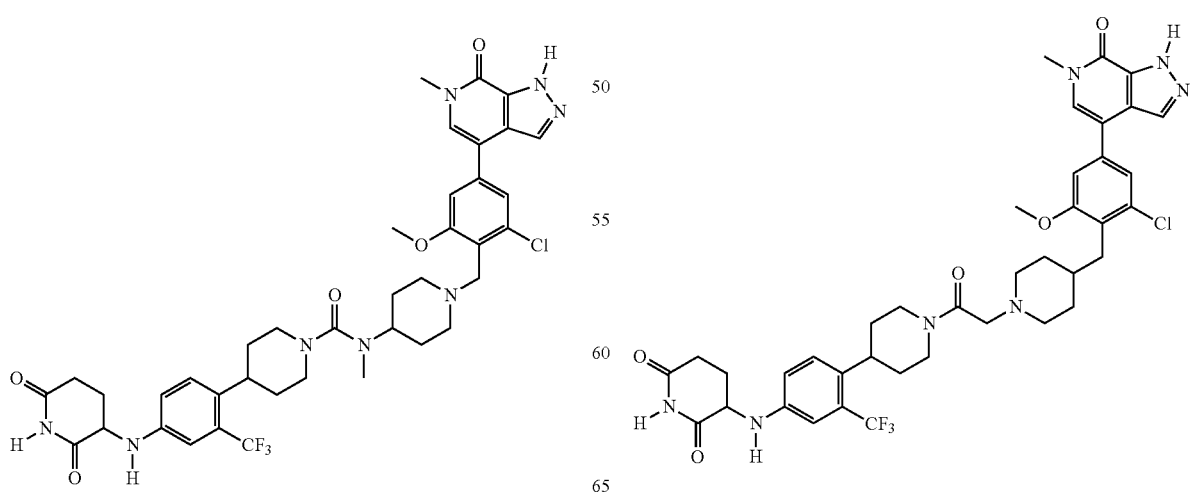

385
-continued
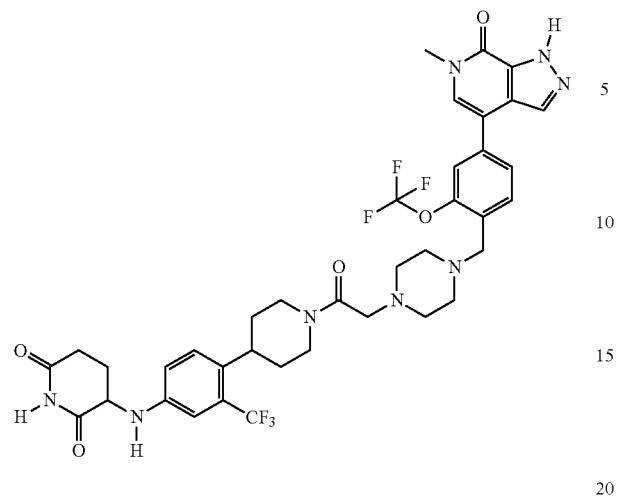
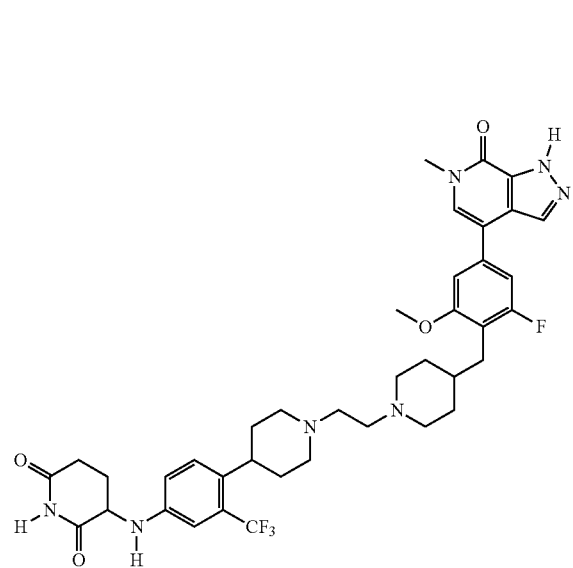
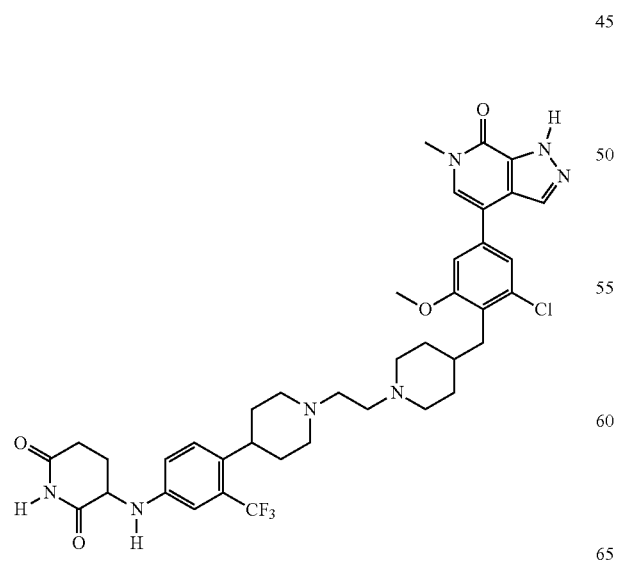
386
-continued
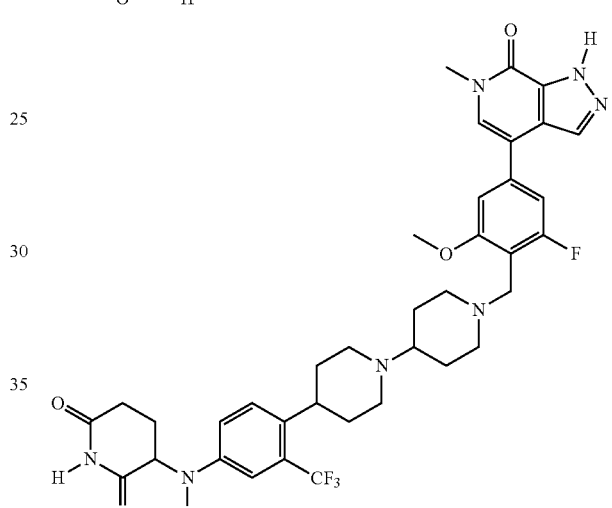
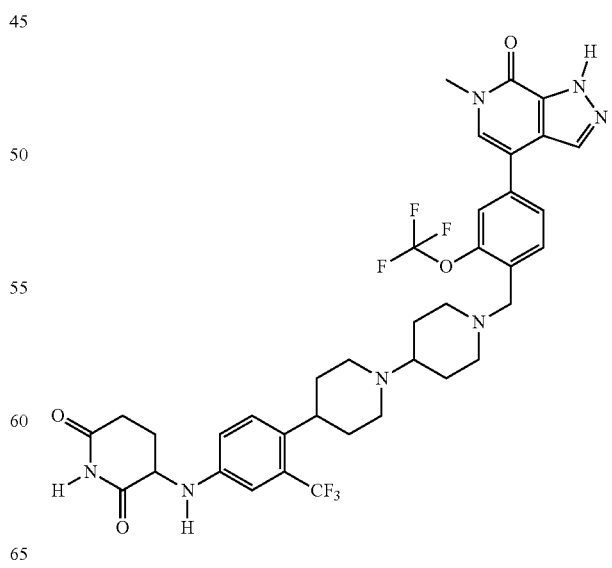

387
-continued
388
-continued
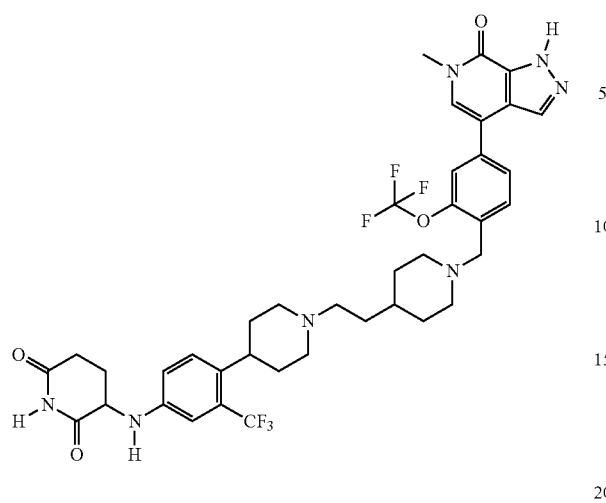
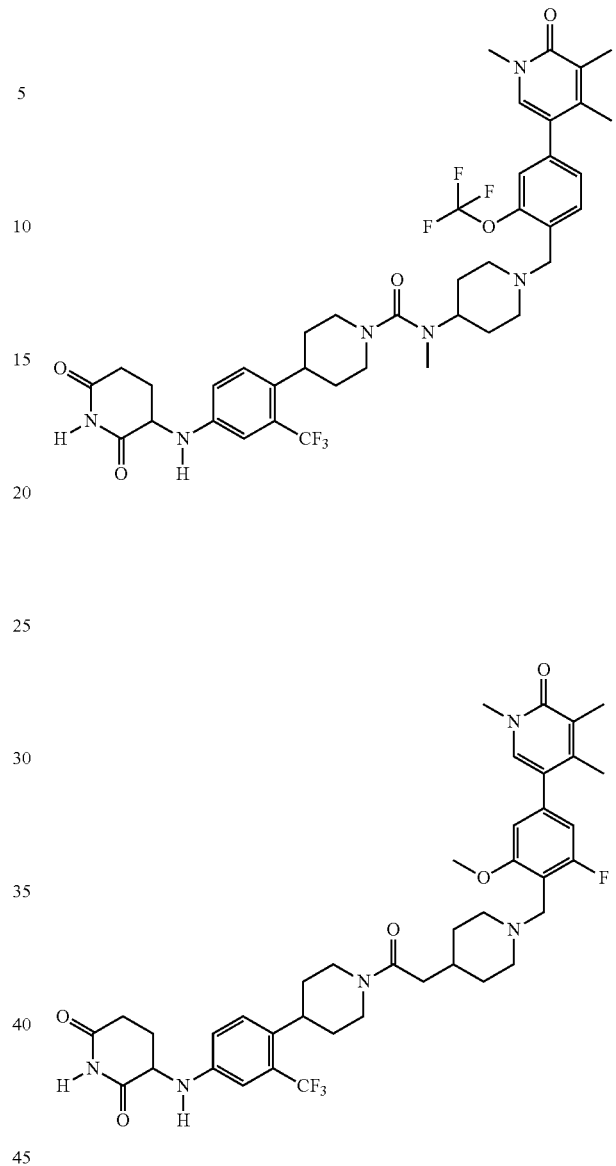
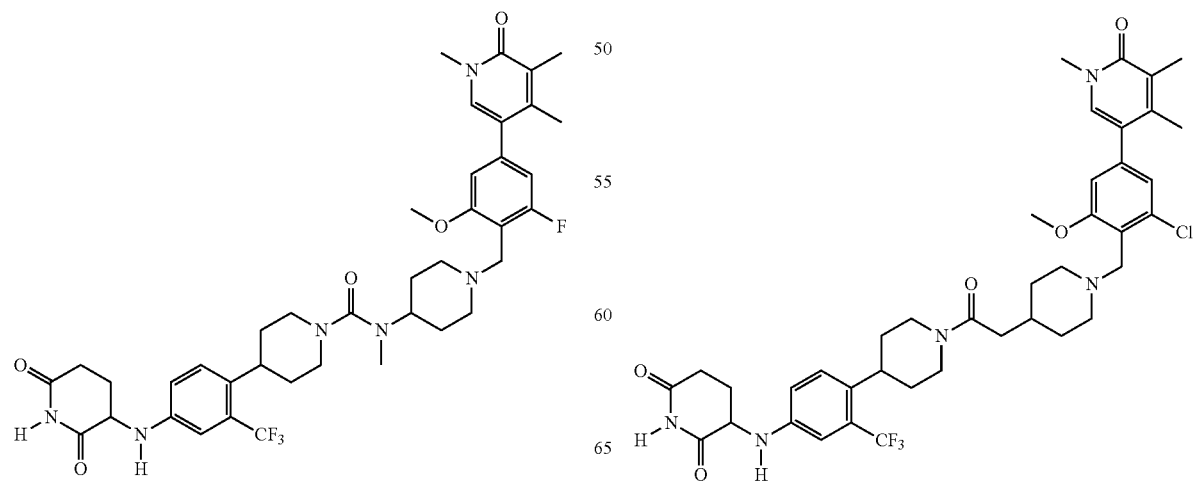

389
-continued
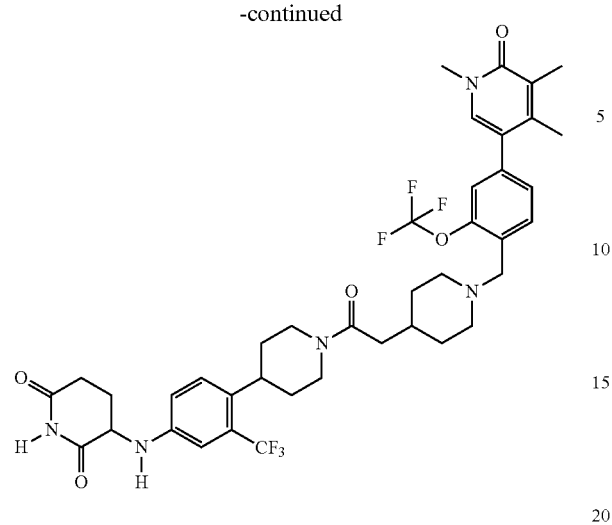
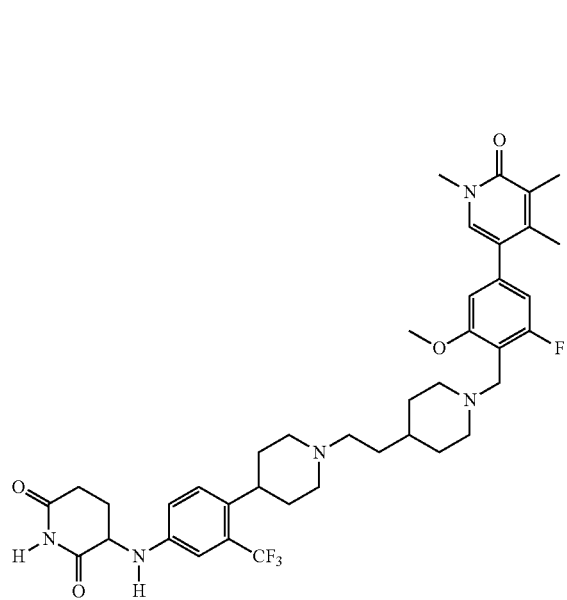
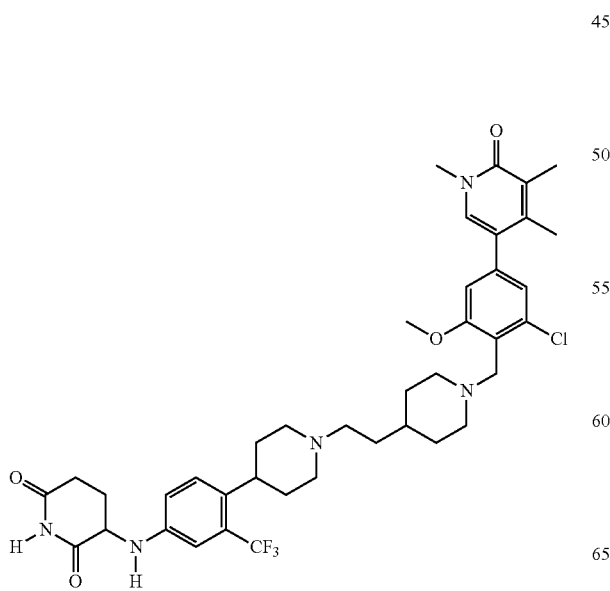
390
-continued
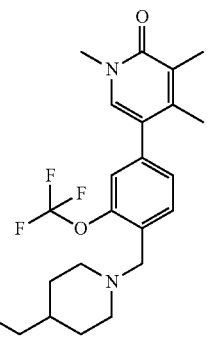
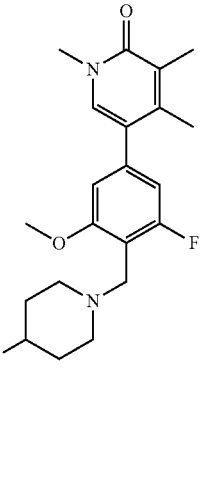
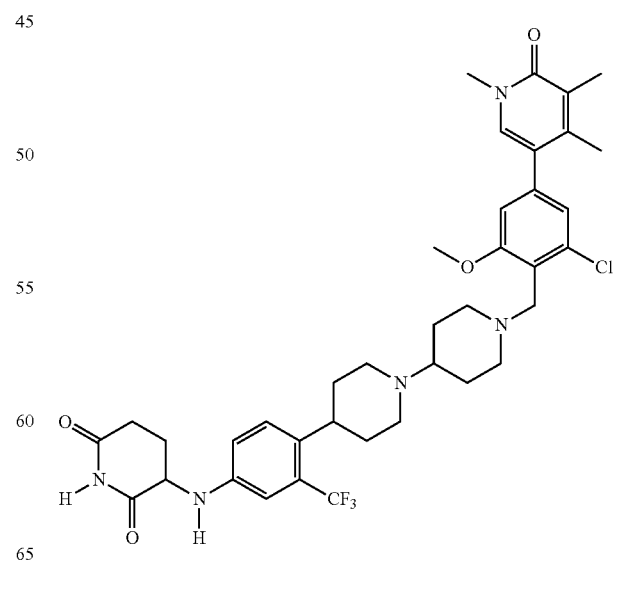

391
-continued
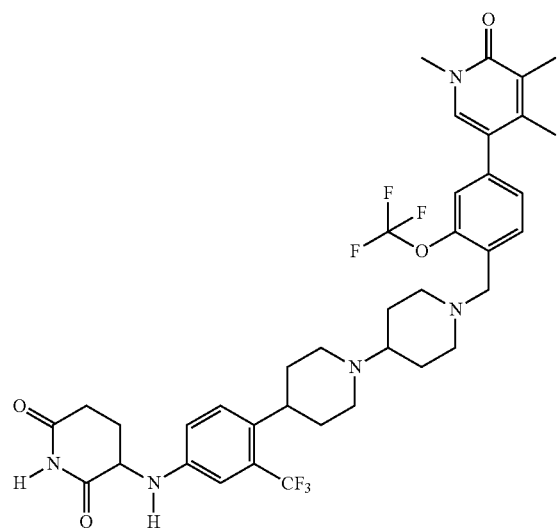
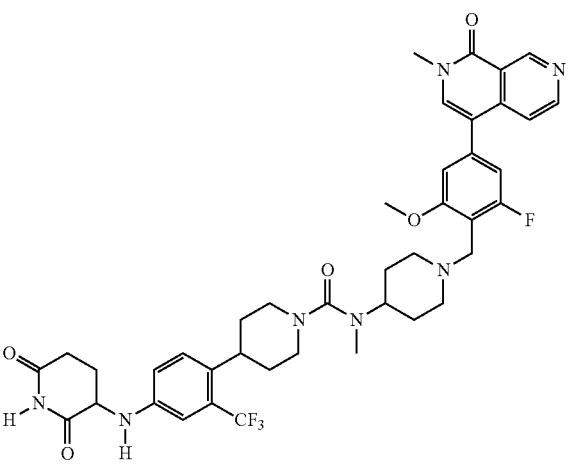
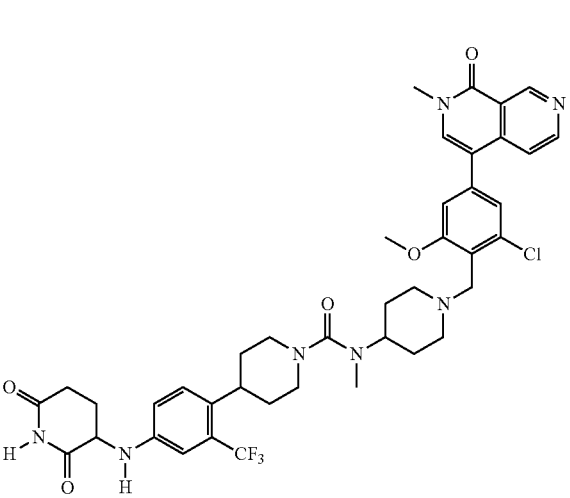
392
-continued
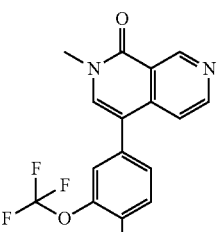
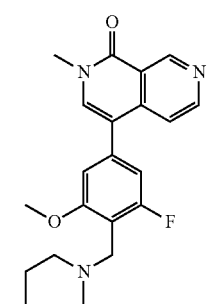
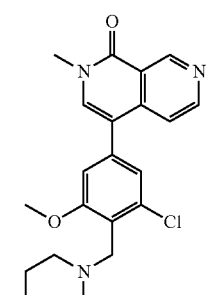

393
-continued
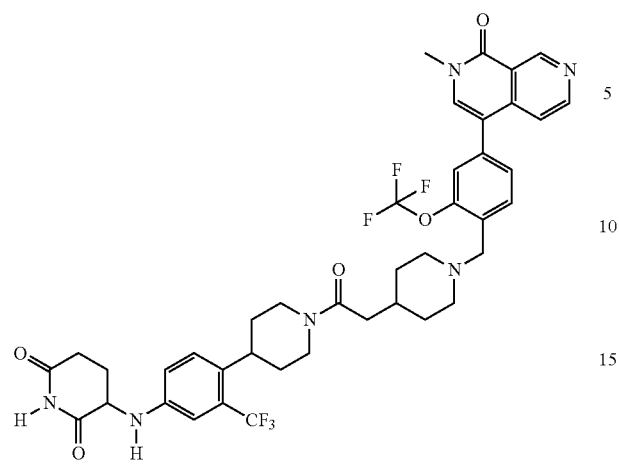
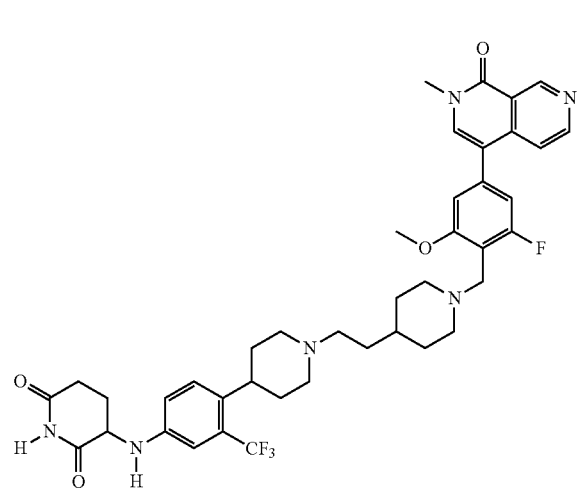
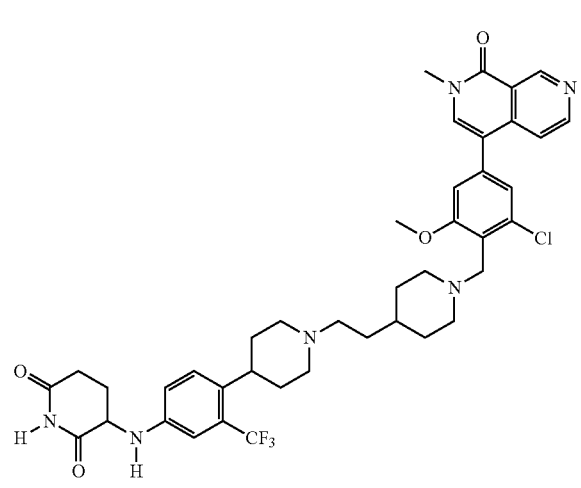
394
-continued
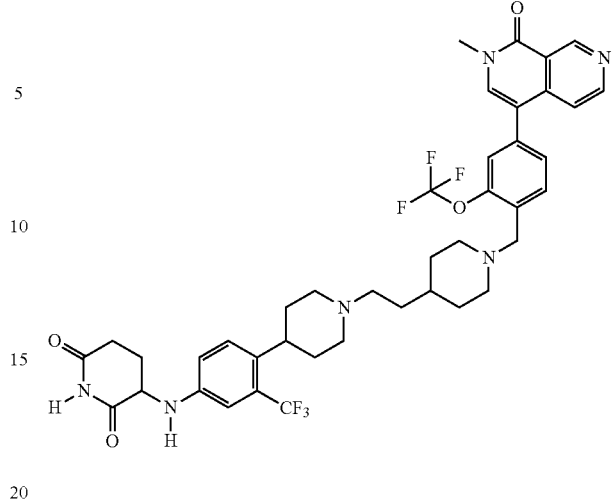
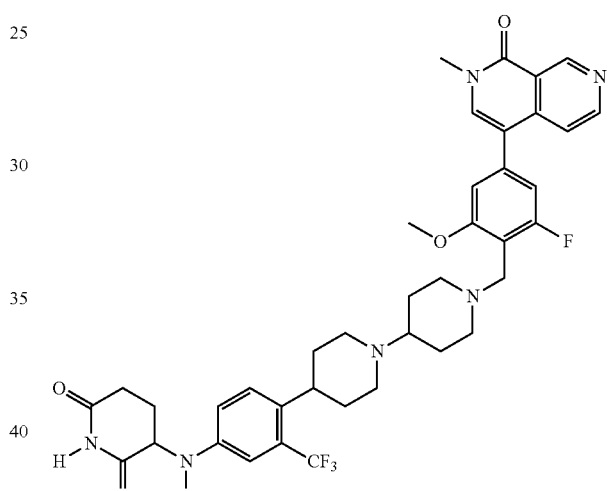
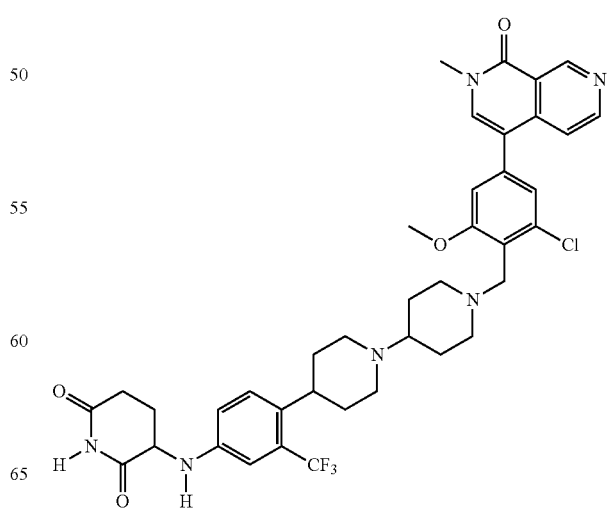

395
-continued
396
-continued
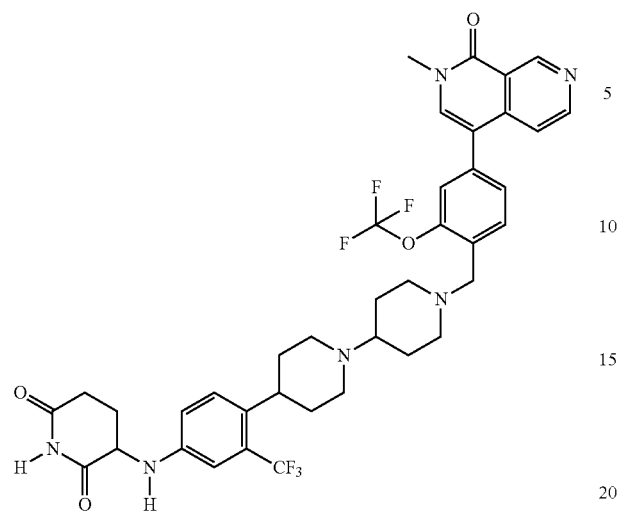
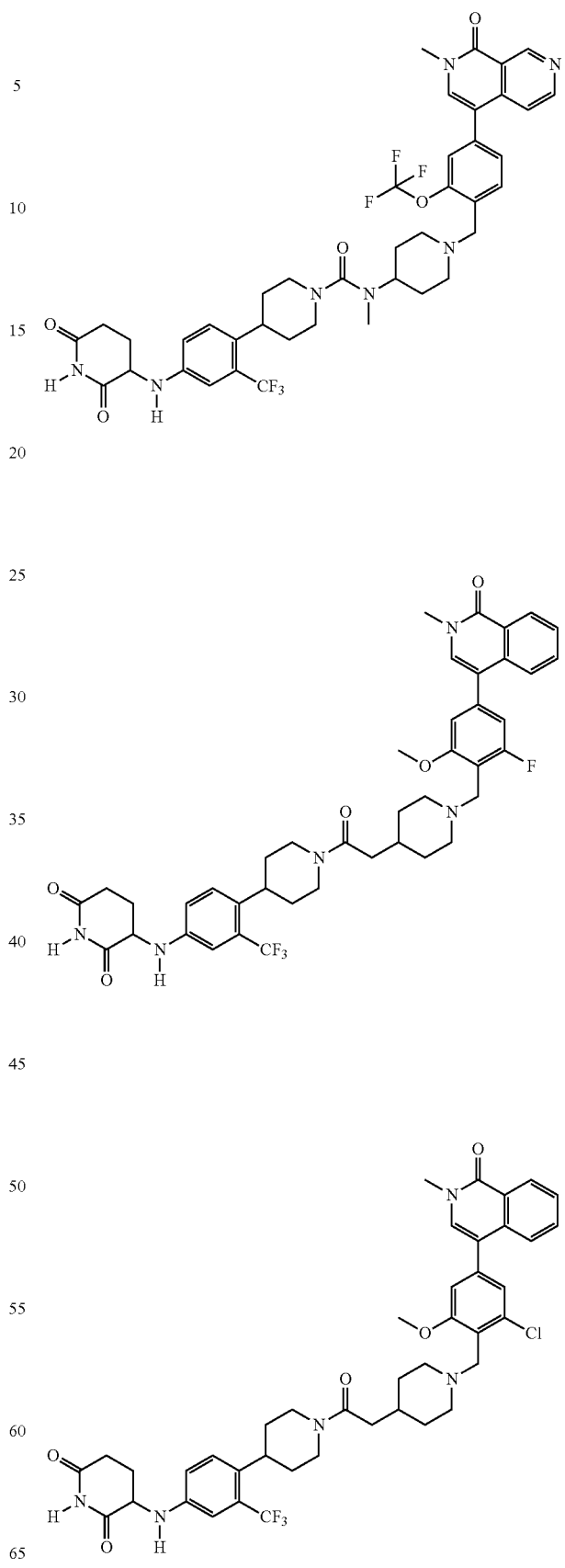

397
-continued
398
-continued
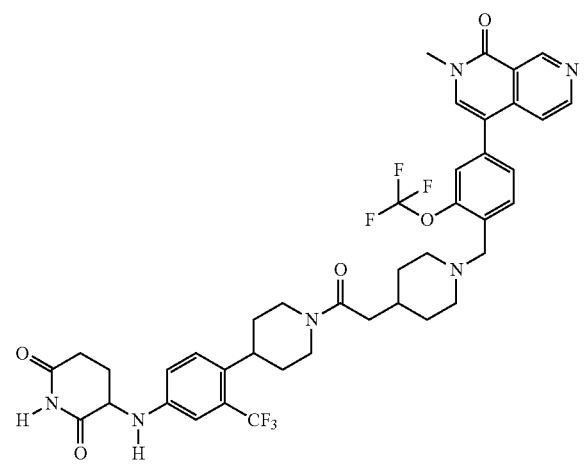
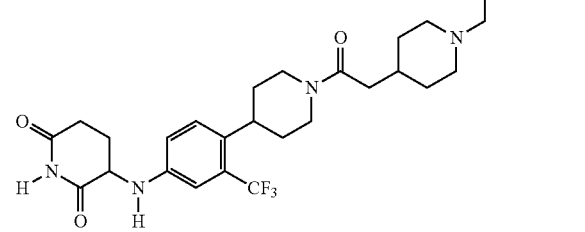

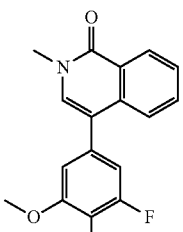
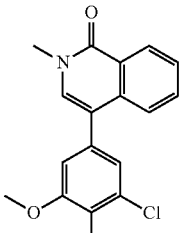

399
-continued
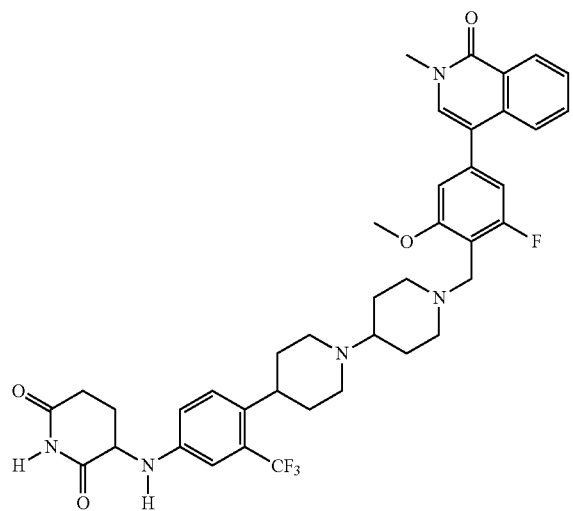
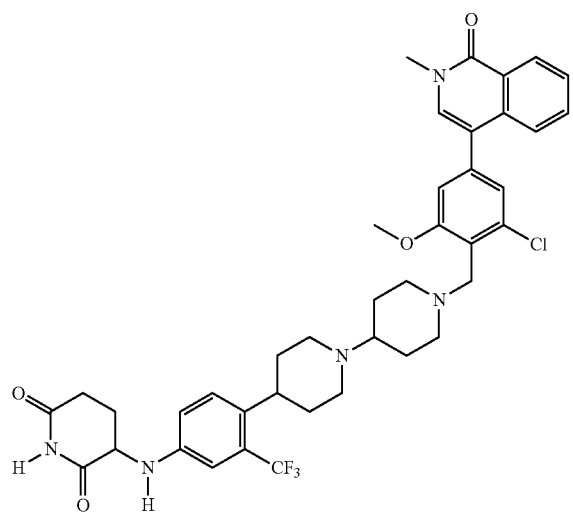
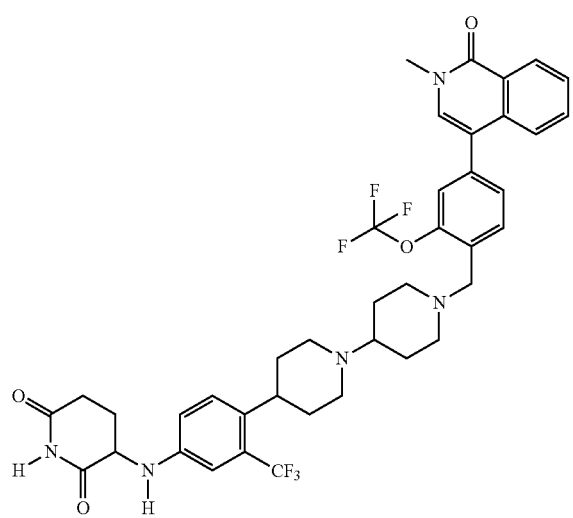
400
-continued
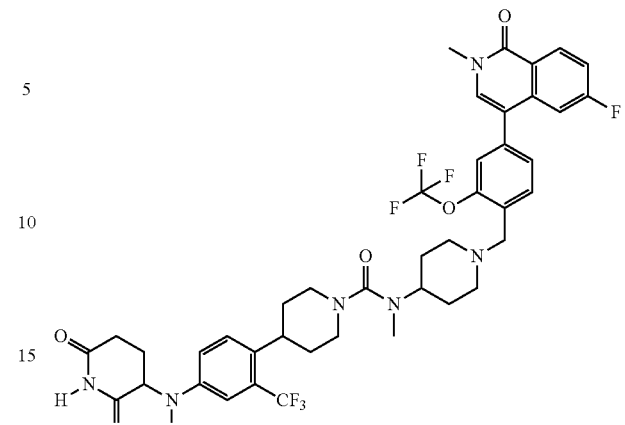
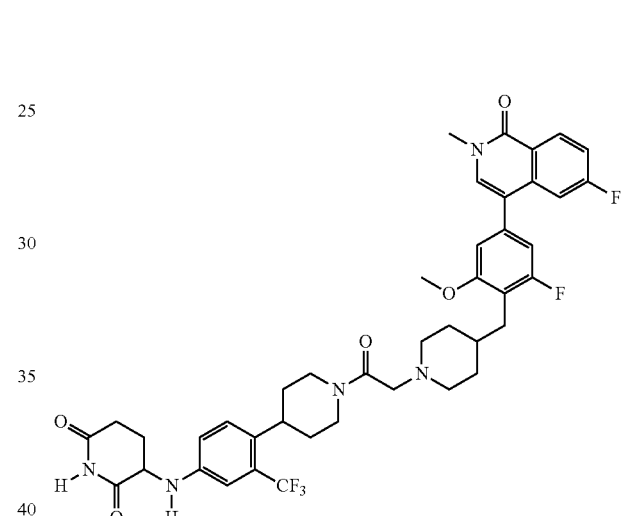
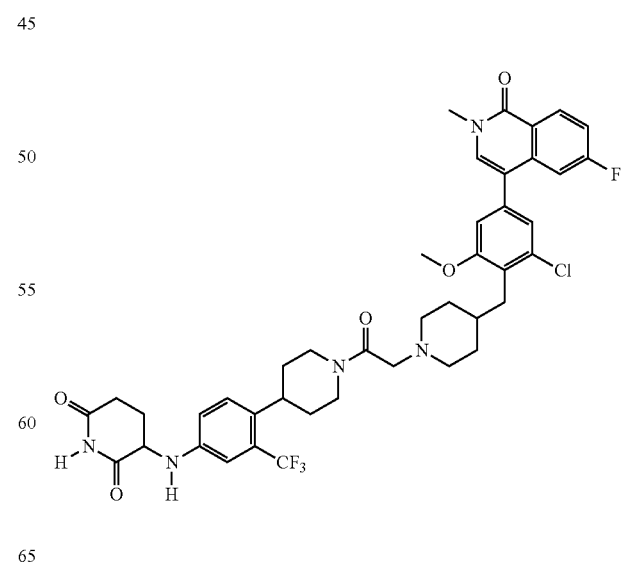

401
-continued
402
-continued
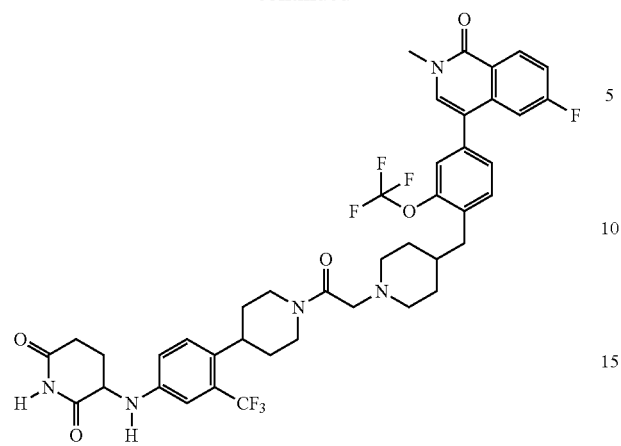
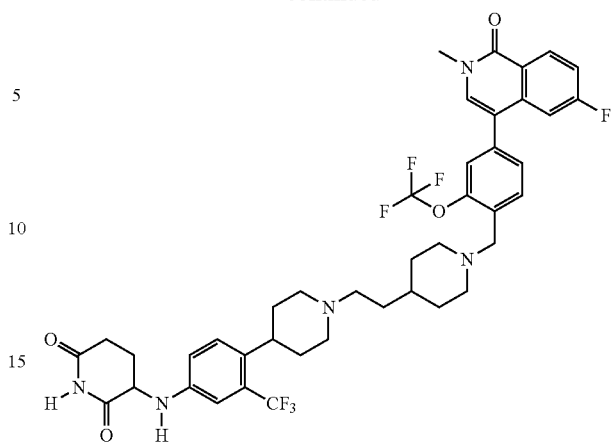

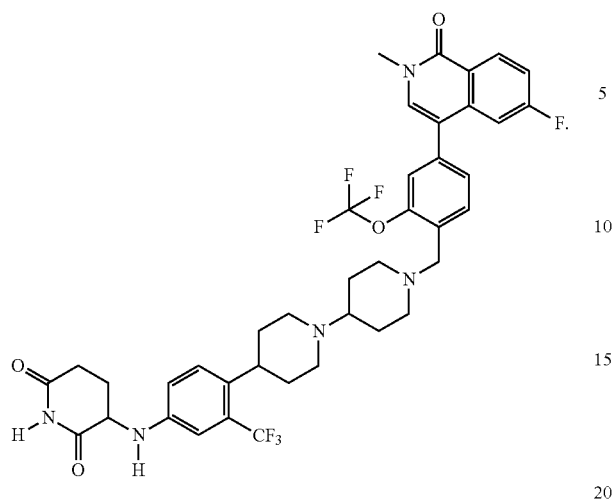
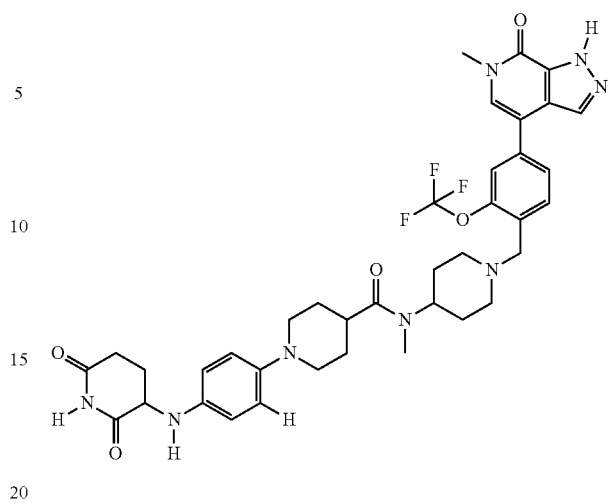
Nonlimiting examples of compounds of the present invention include:
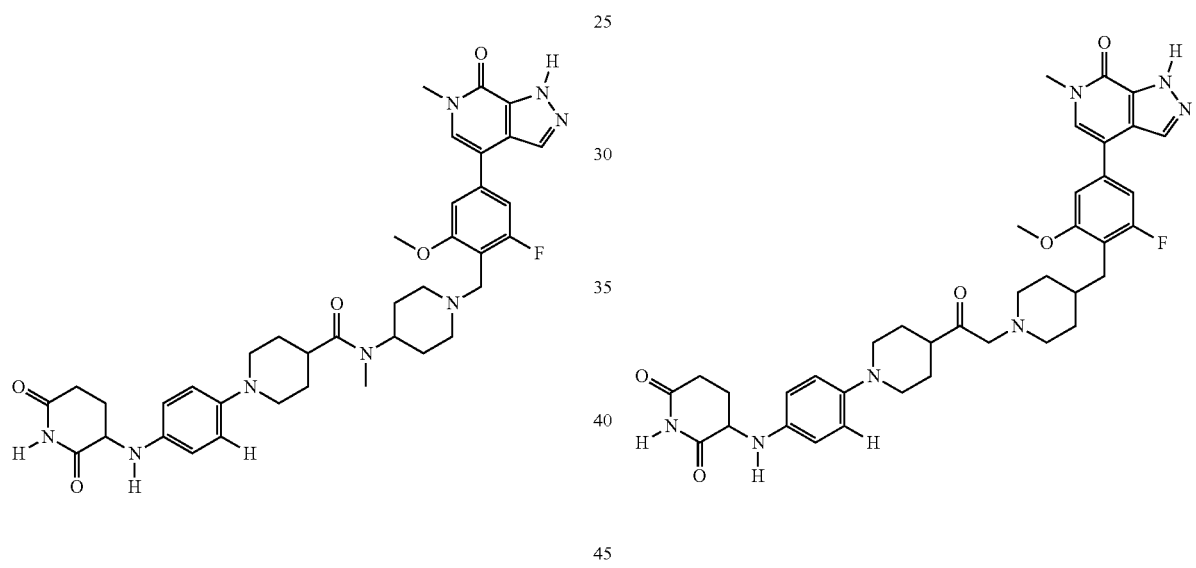
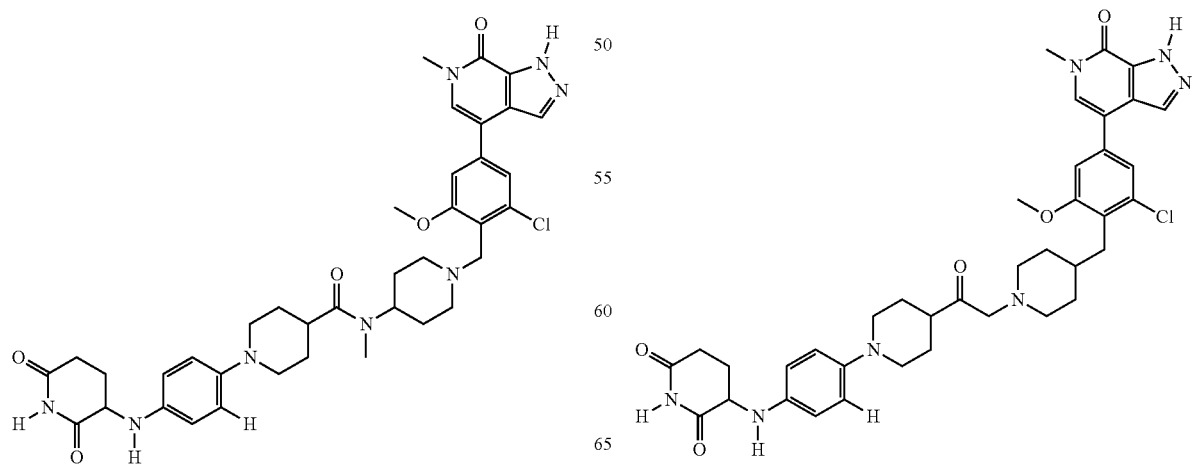

405
-continued
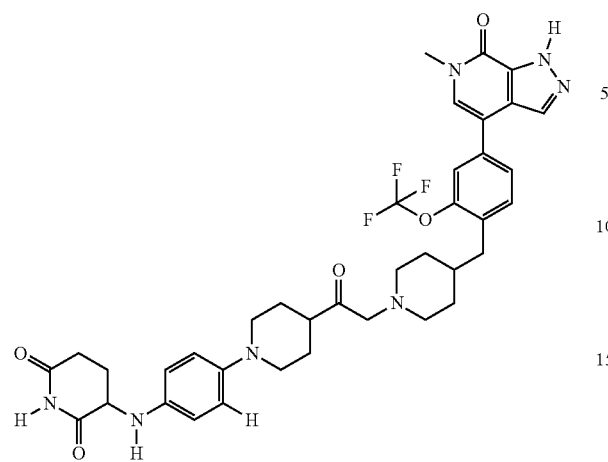
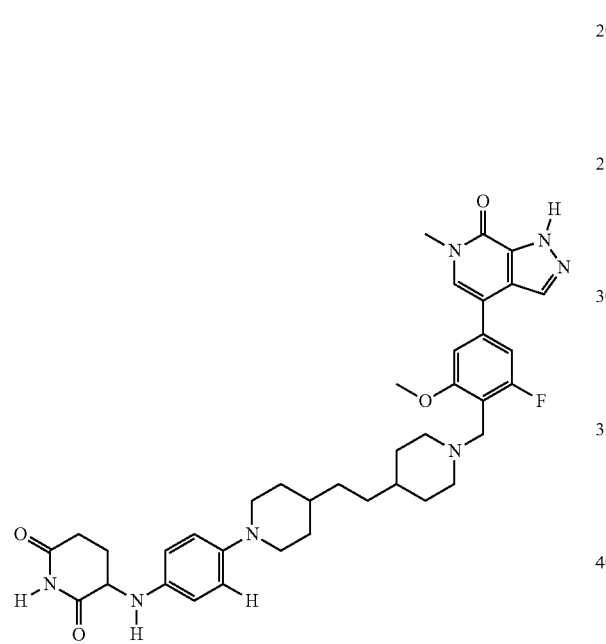
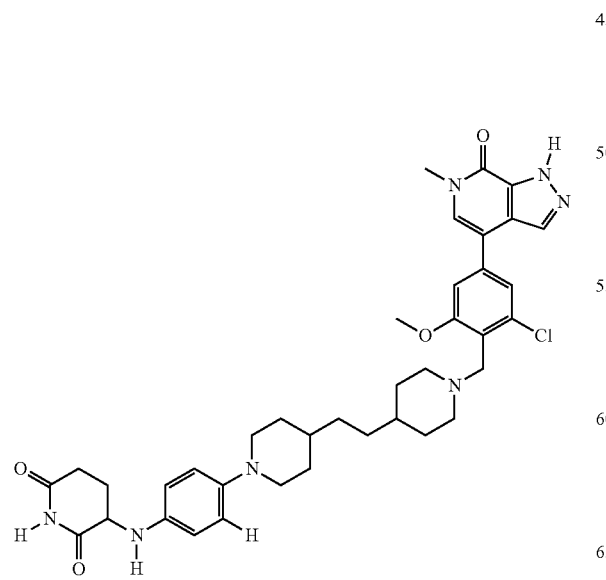
406
-continued
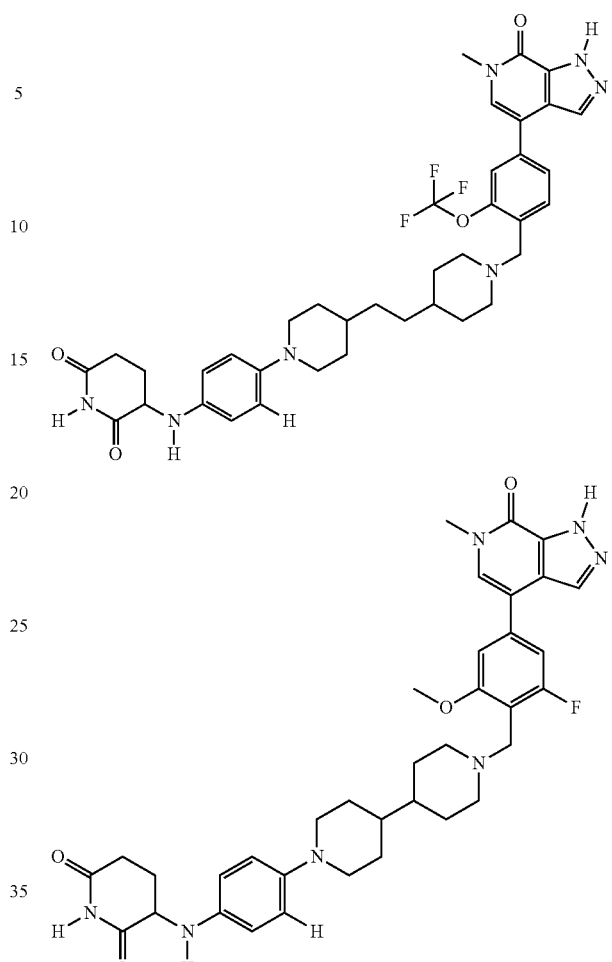
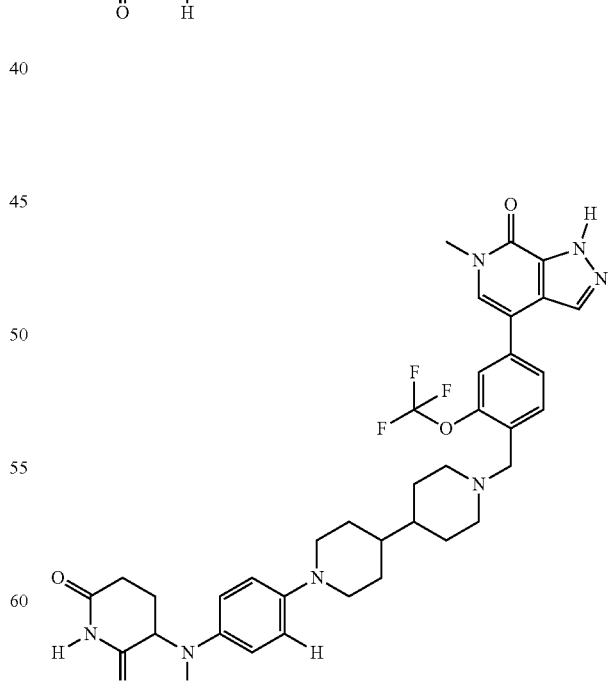

407
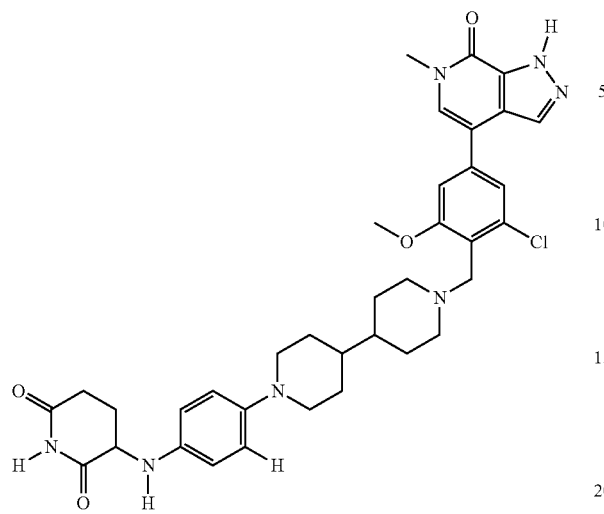
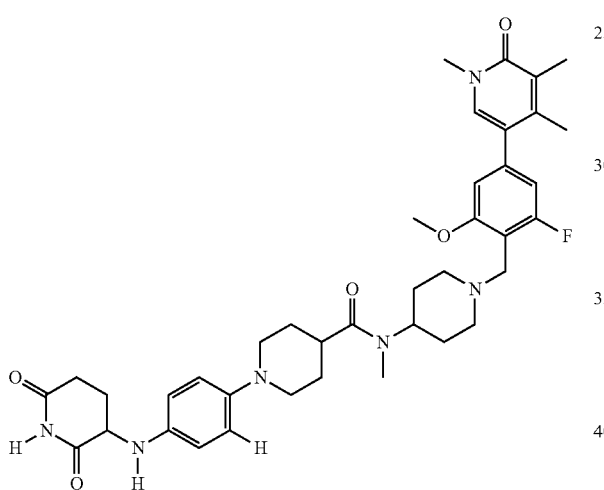
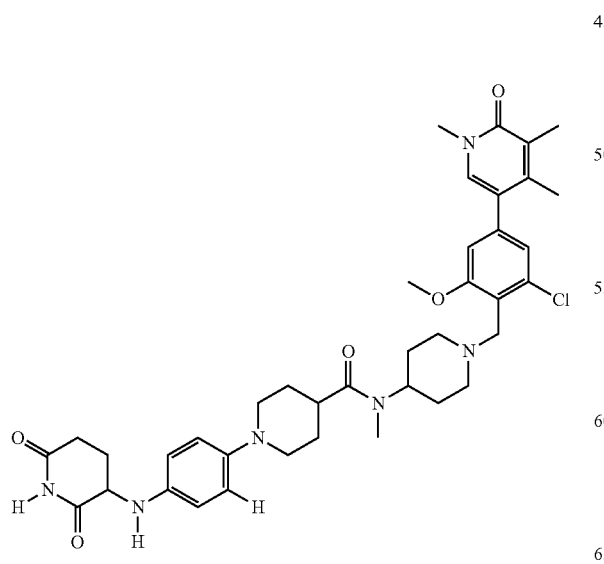
408
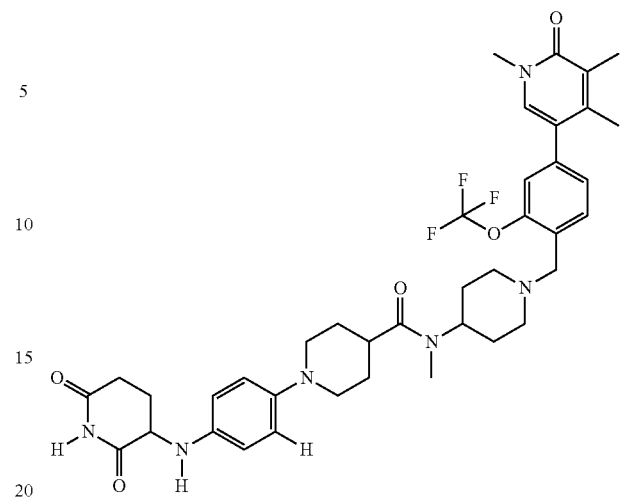
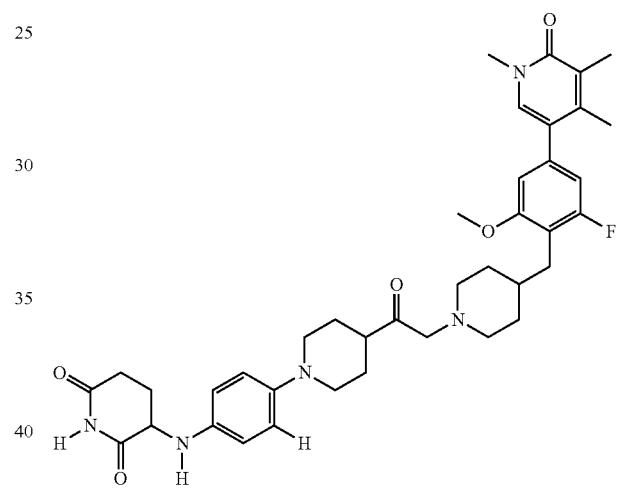
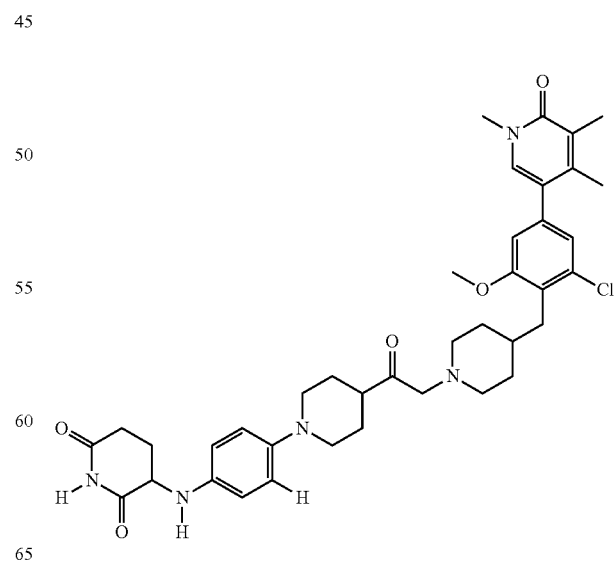

409
-continued
410
-continued
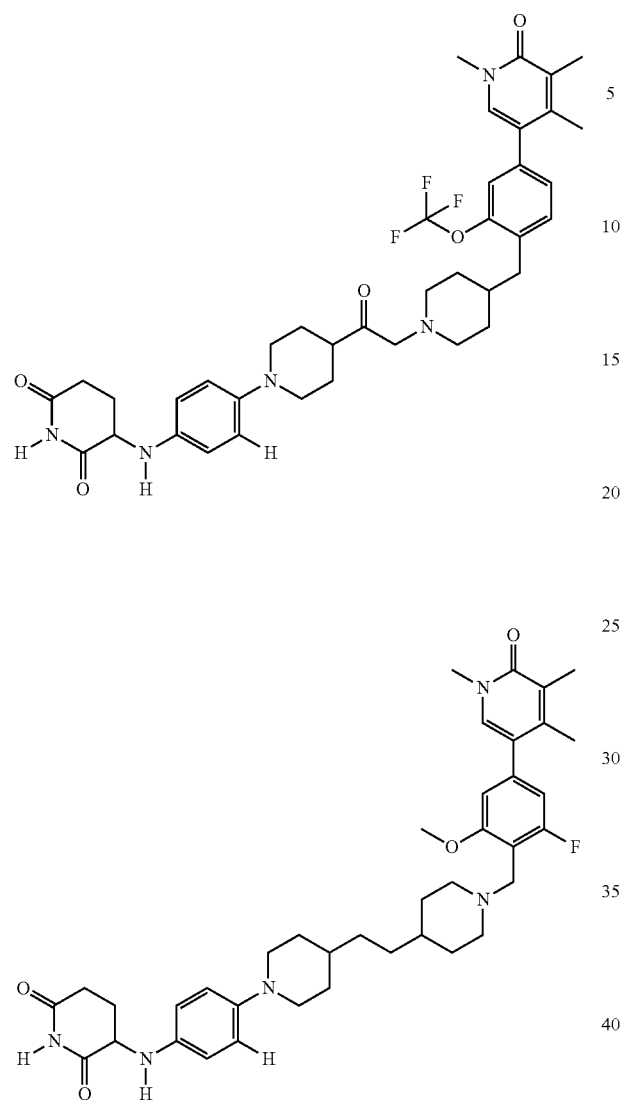
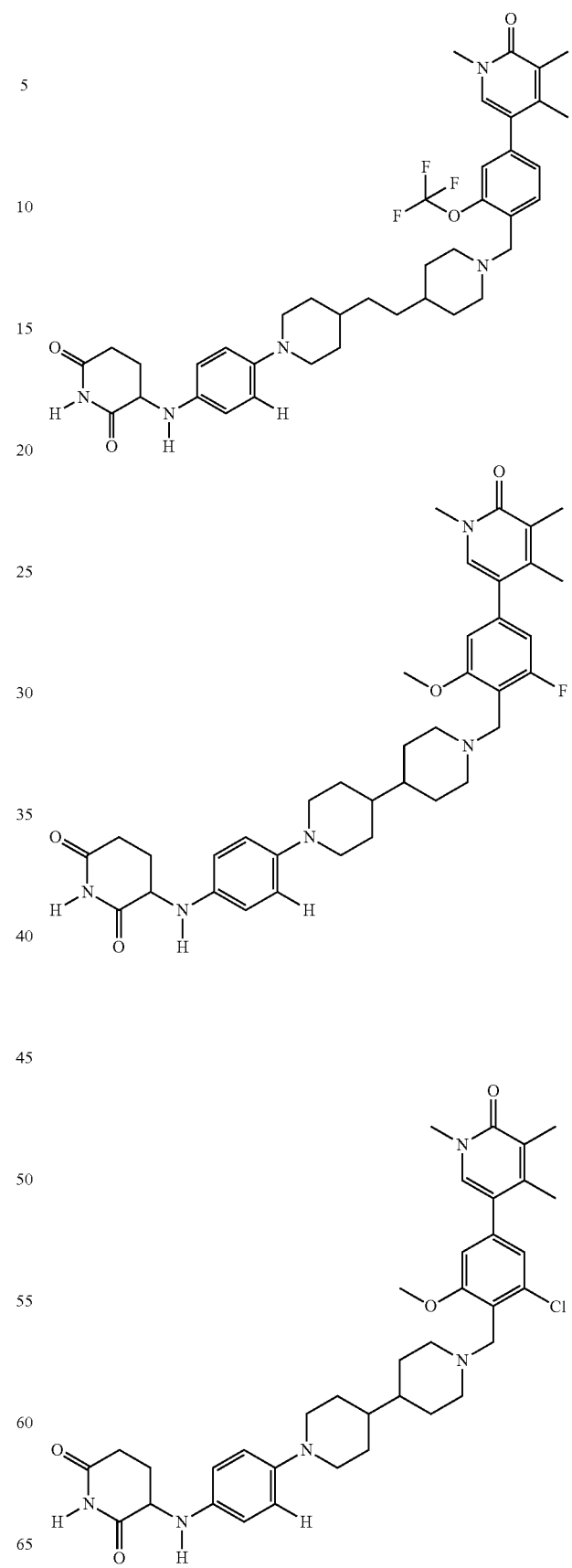

411
-continued
412
-continued
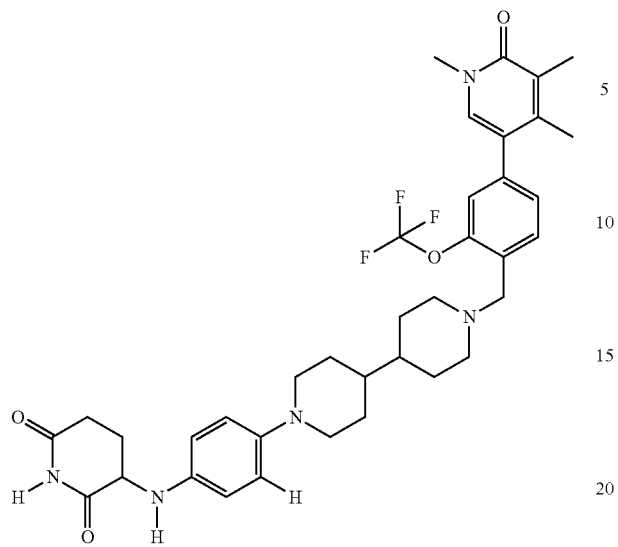
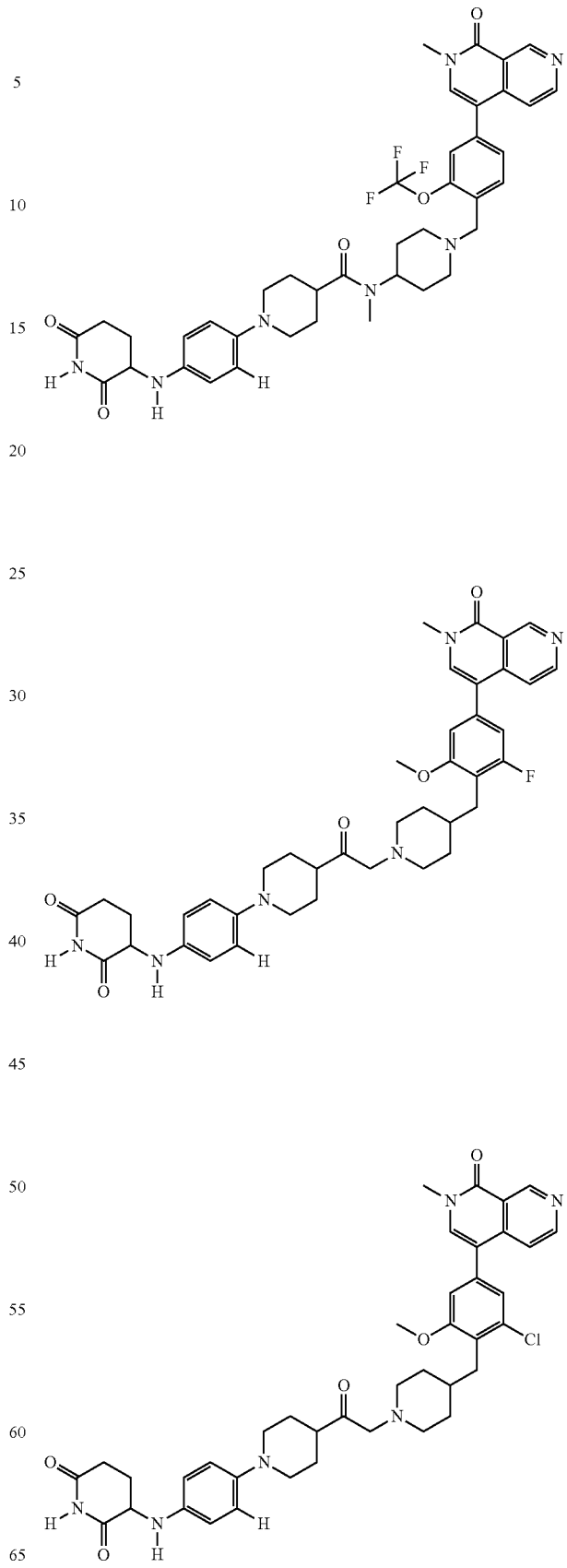

413
-continued
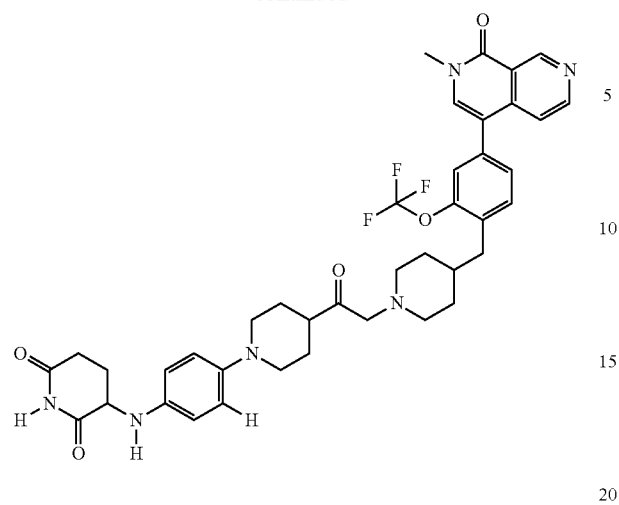
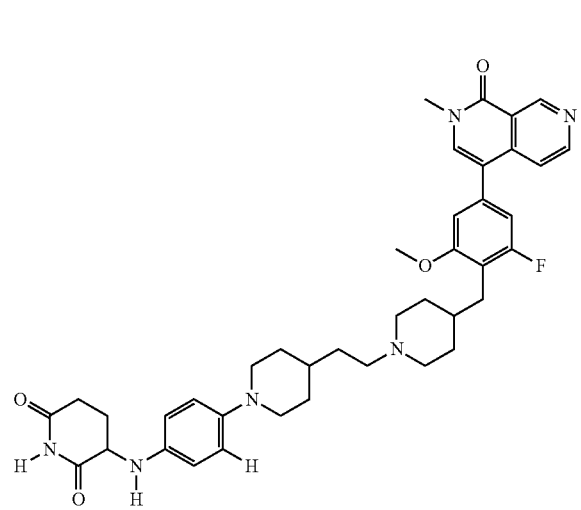
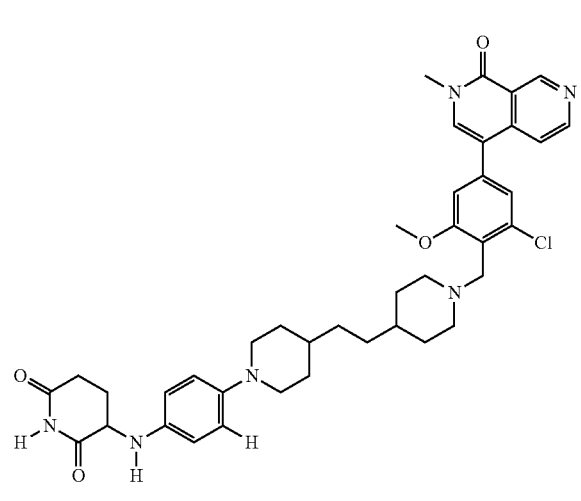
414
-continued
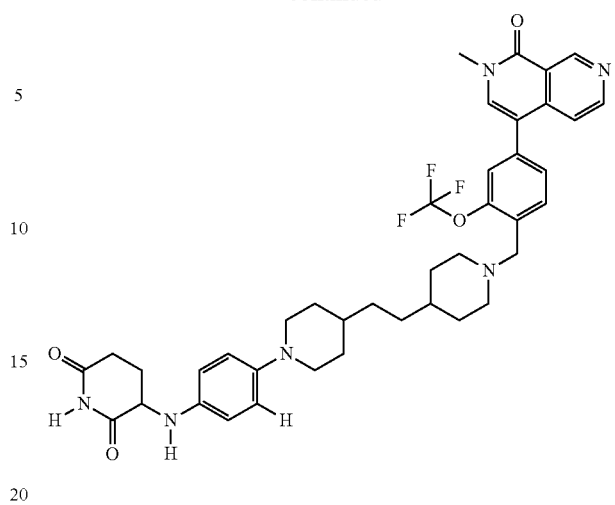
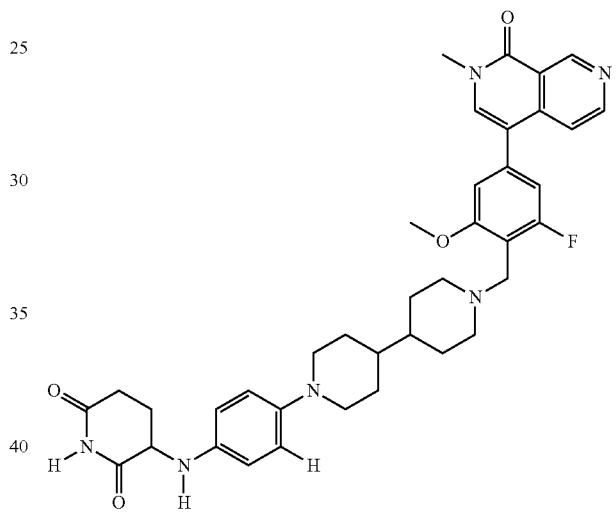
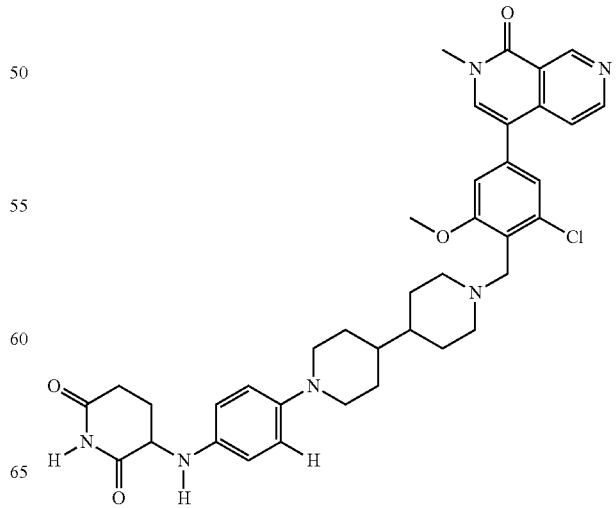

415
-continued
416
-continued
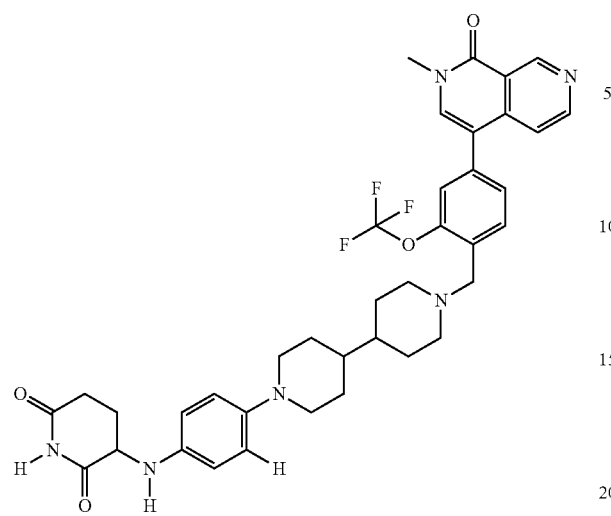
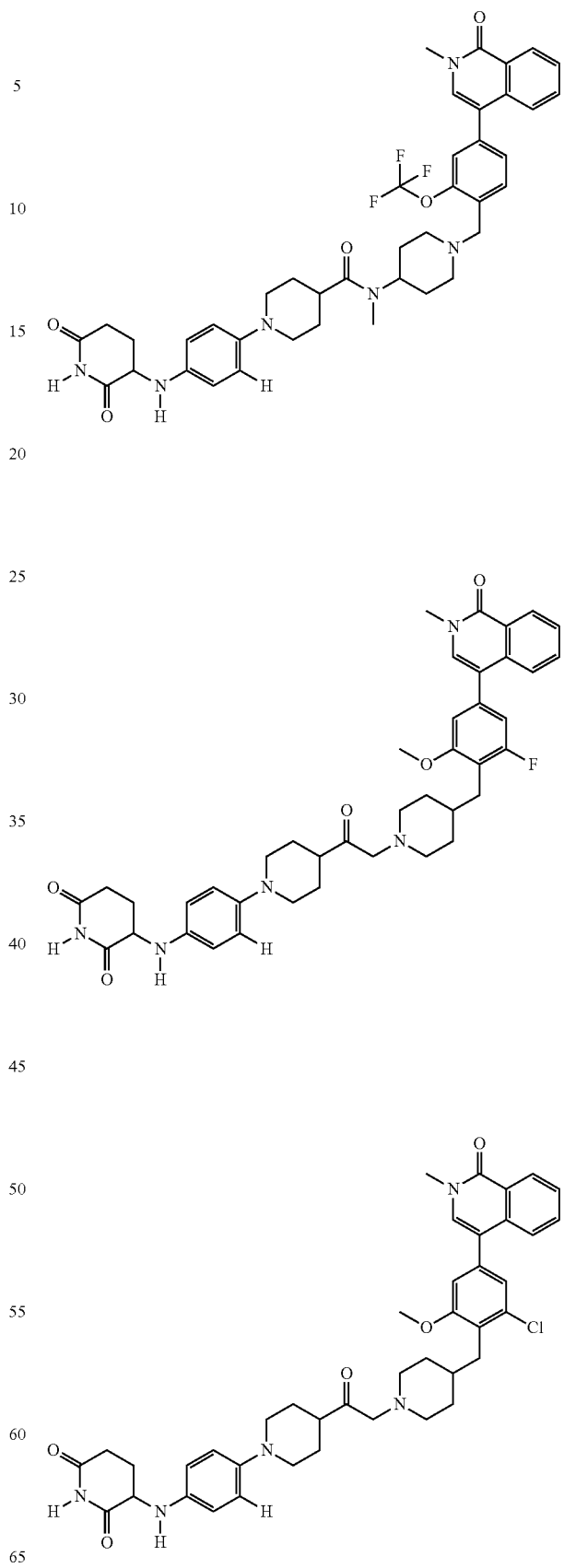

417
-continued
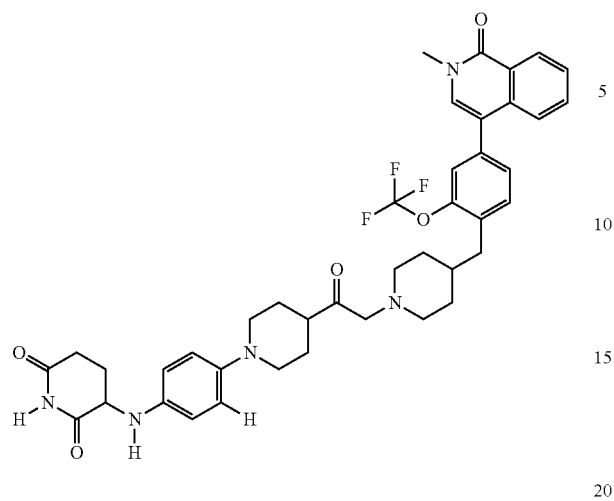
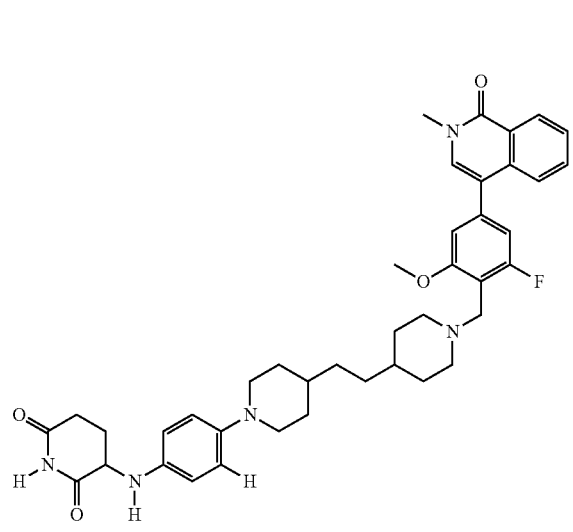
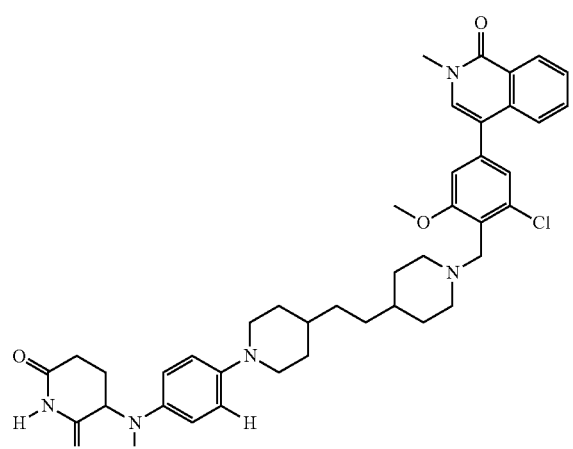
418
-continued
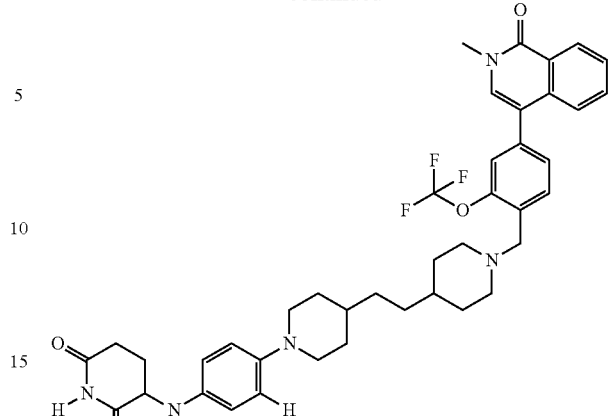
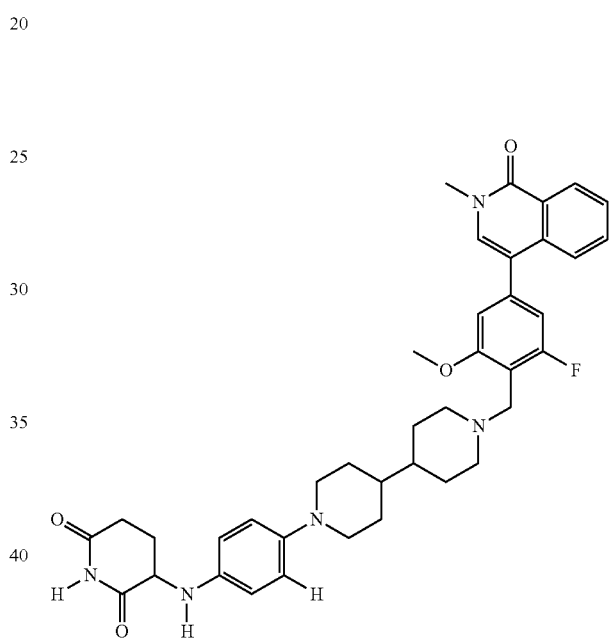
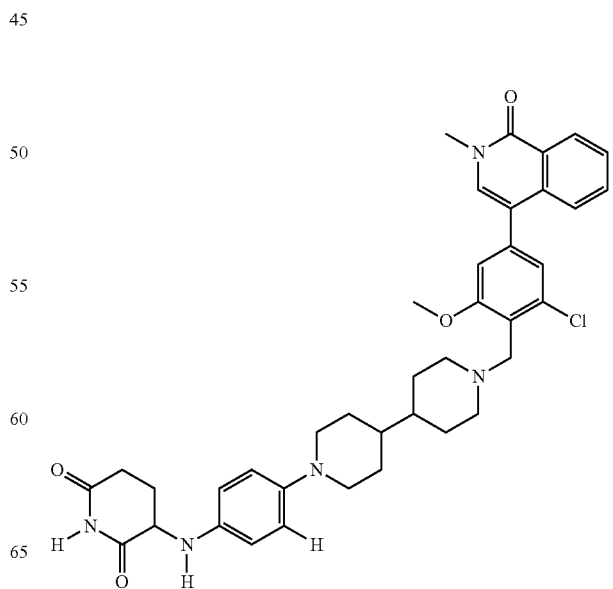

419
-continued
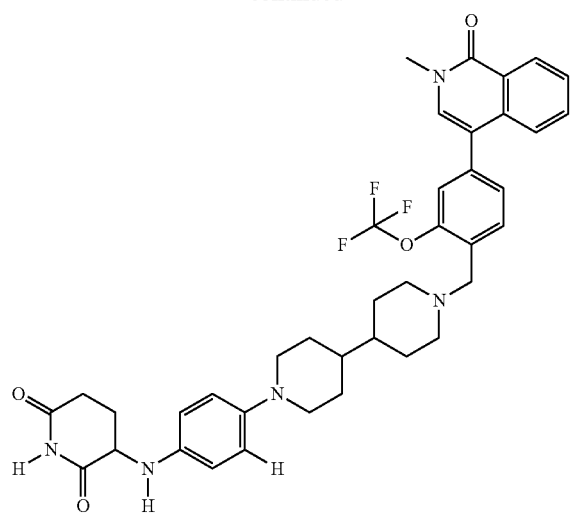
420
-continued
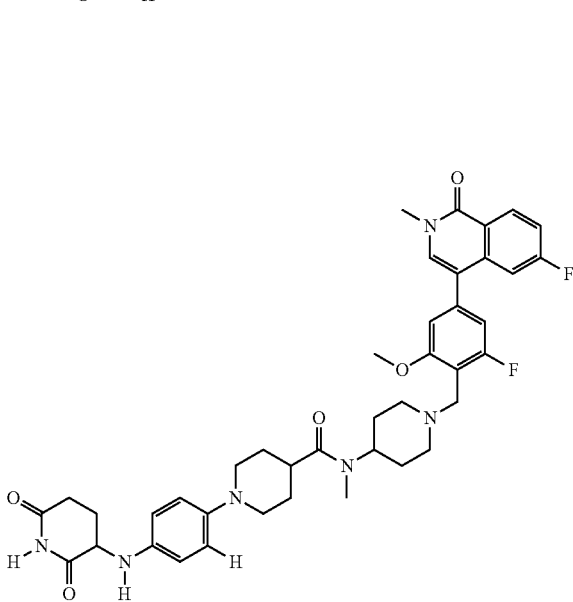
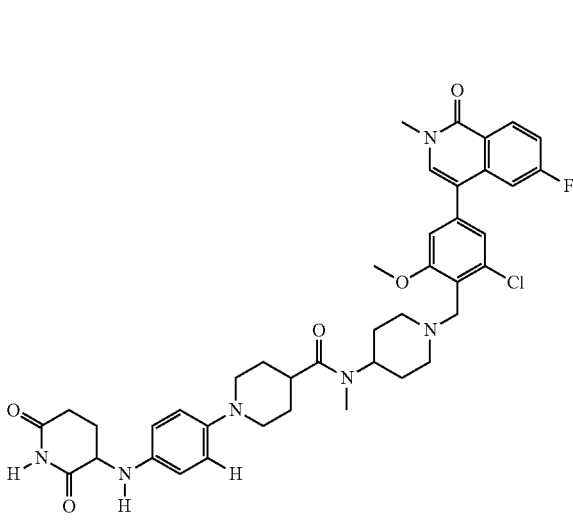

421
-continued
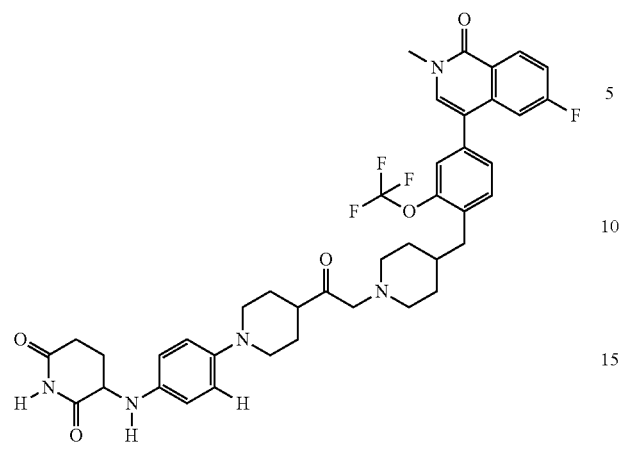
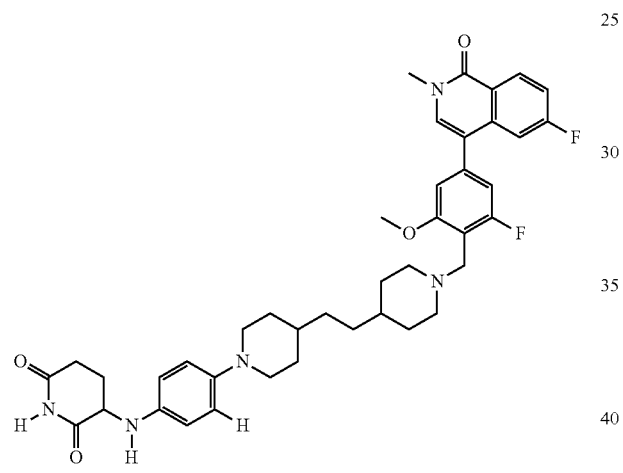
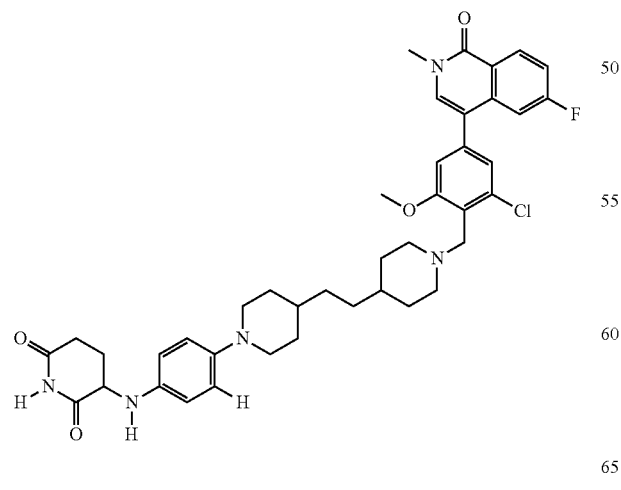
422
-continued
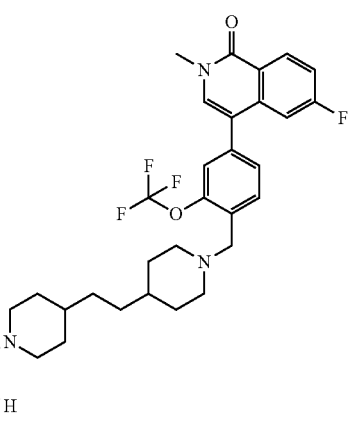
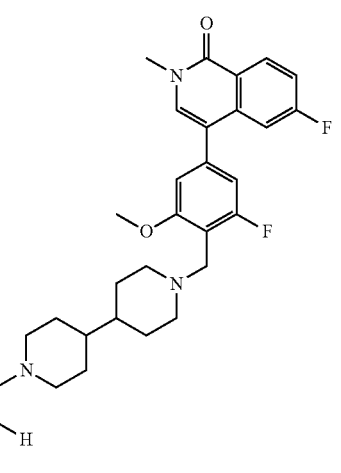
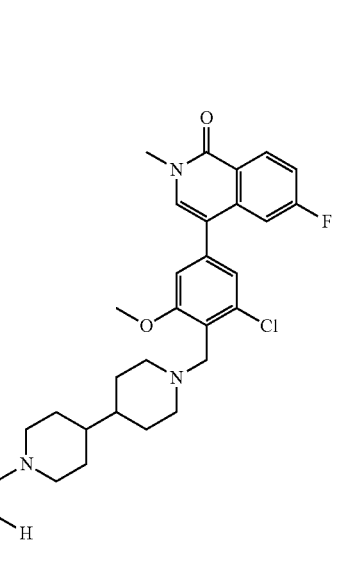

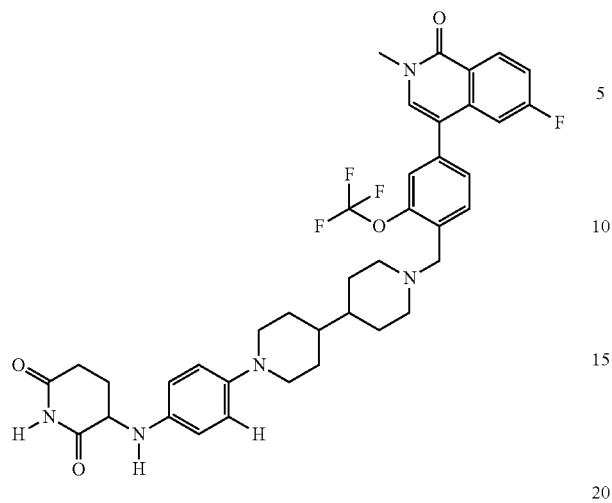
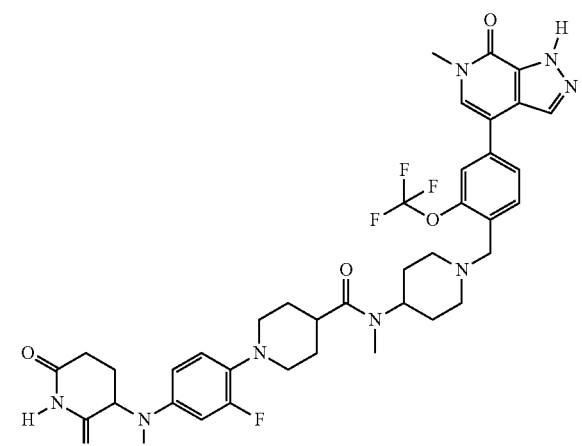
Nonlimiting examples of compounds of the present invention include:
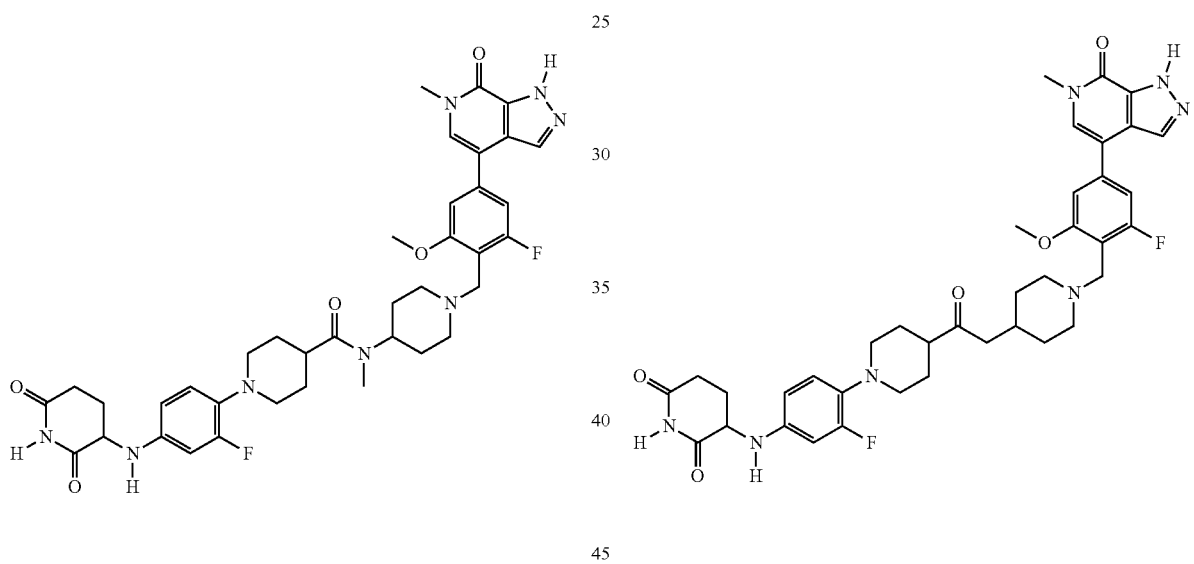
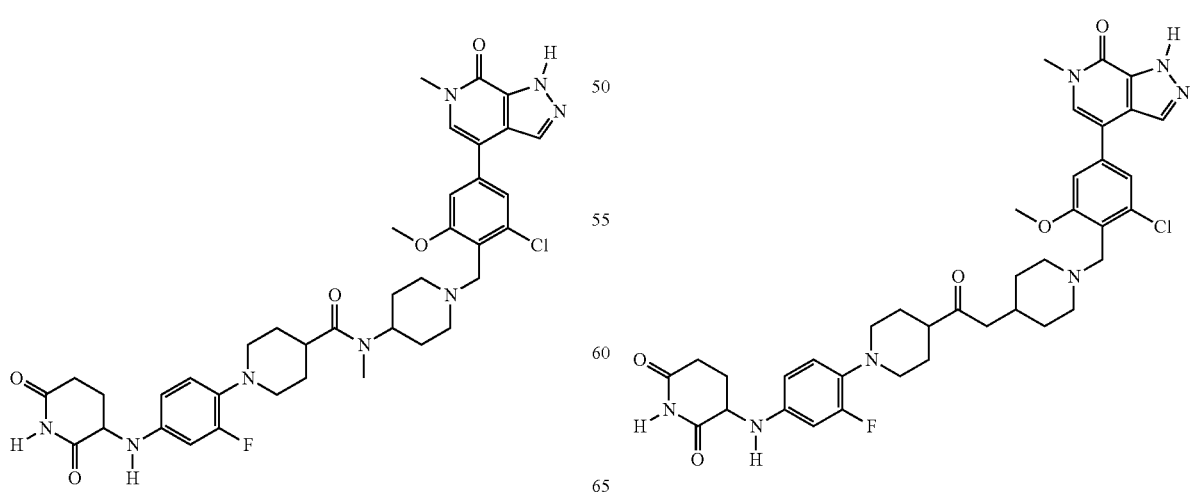

425
-continued
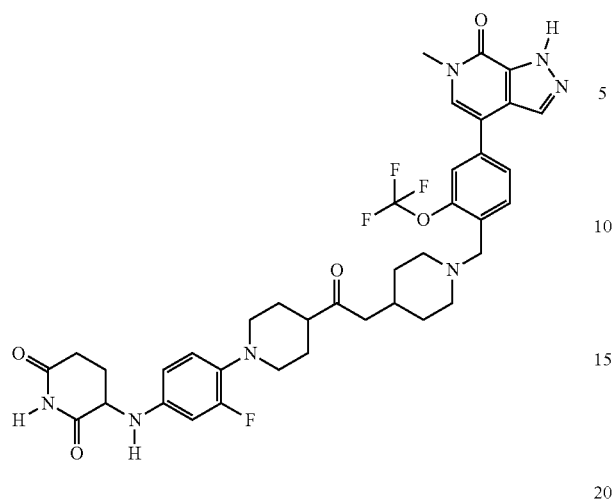
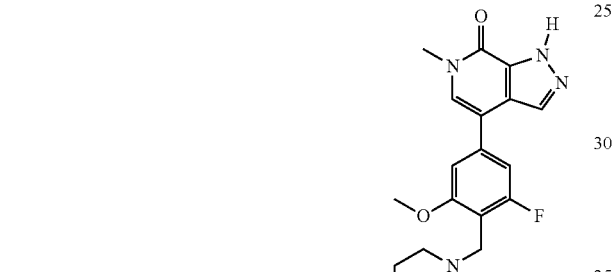
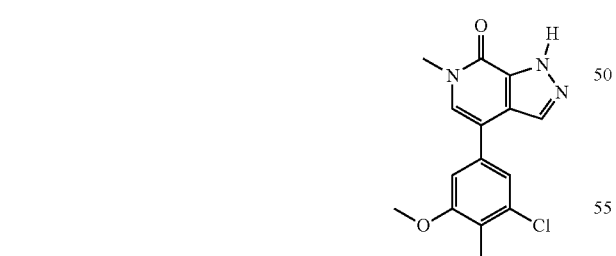
426
-continued
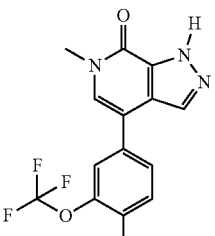
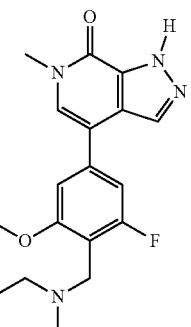
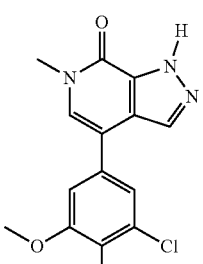

427
-continued
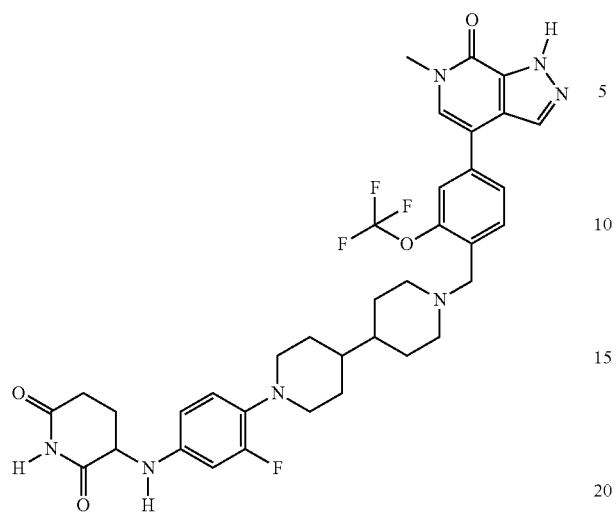
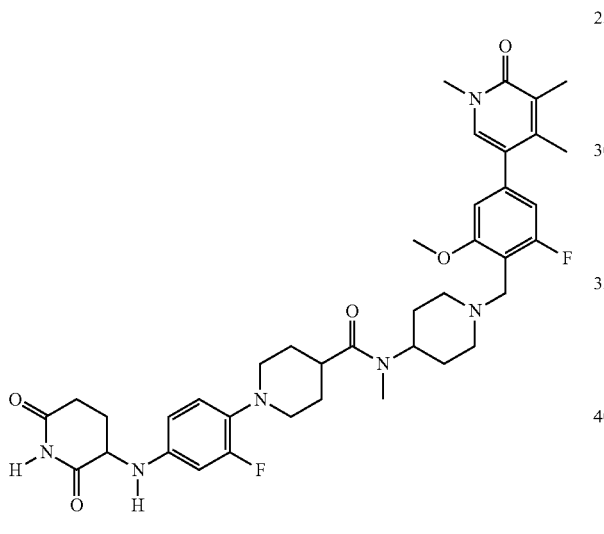
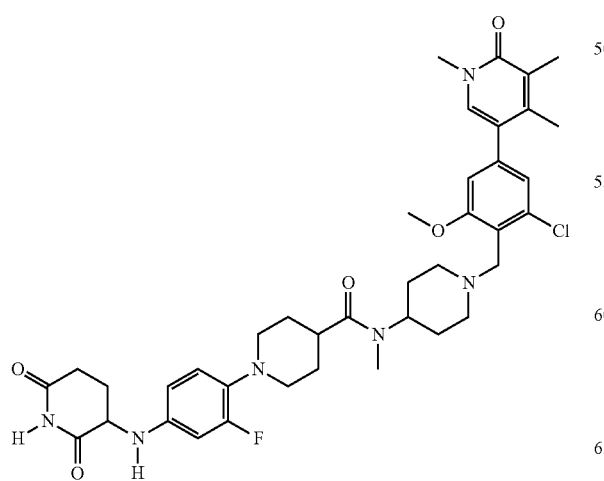
428
-continued
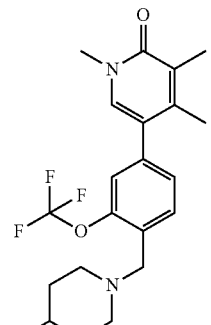
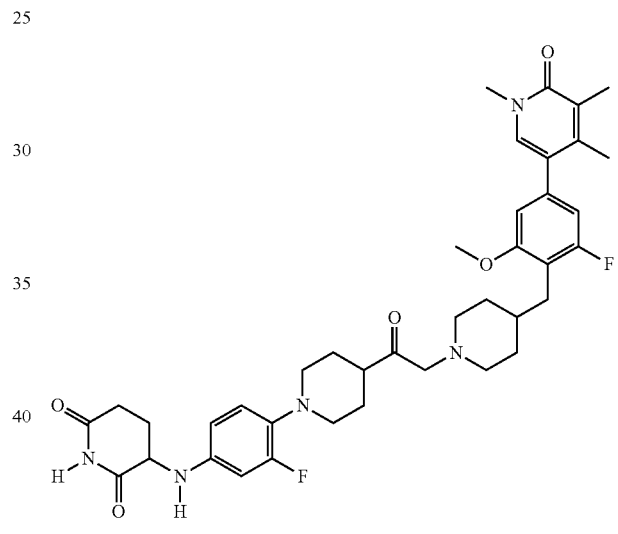
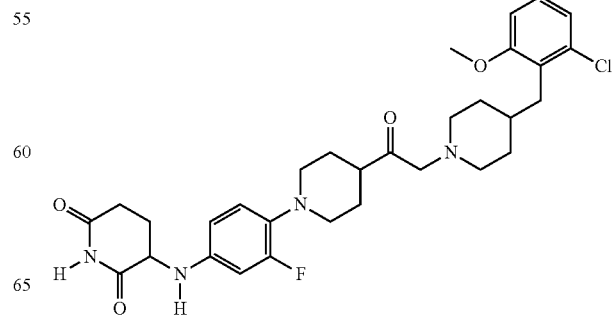

429
-continued
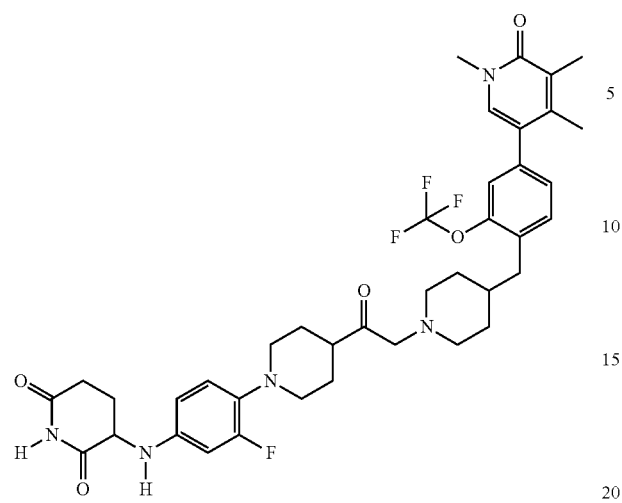
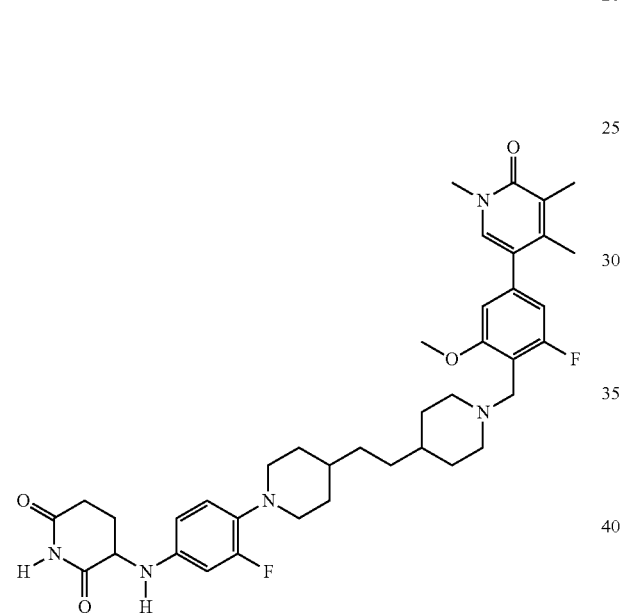
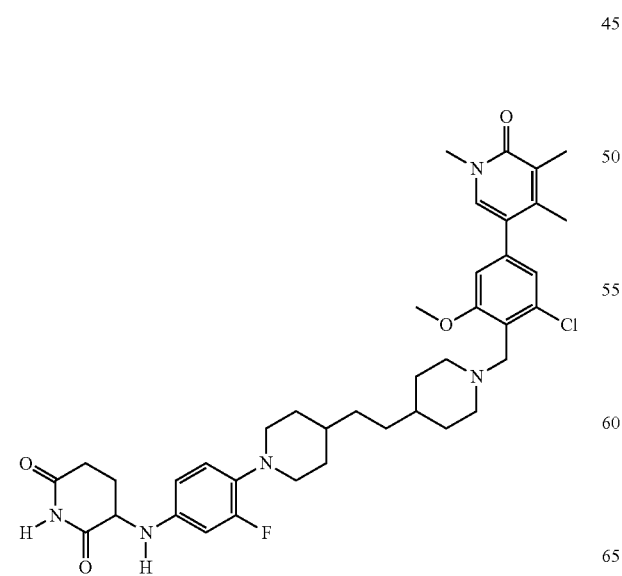
430
-continued
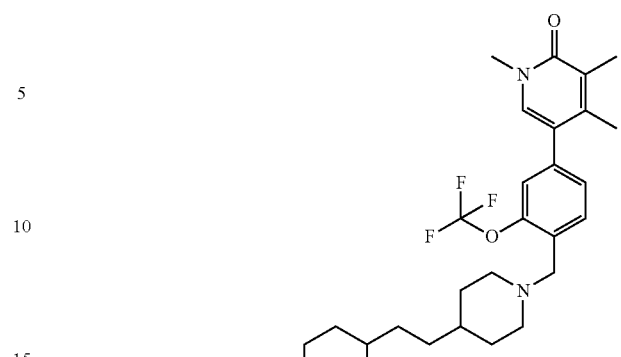
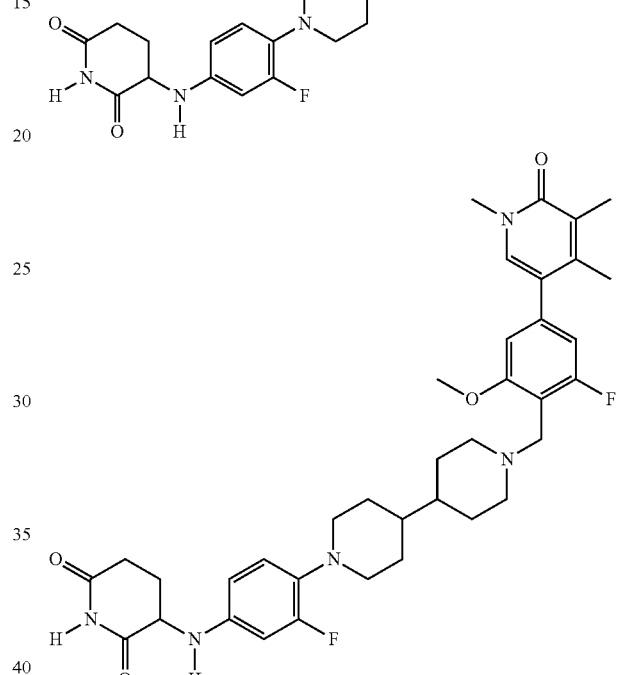
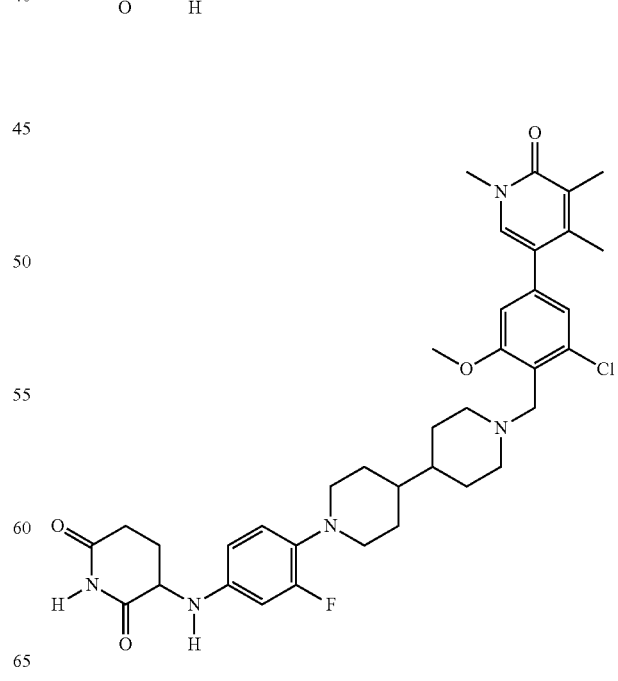

431
-continued
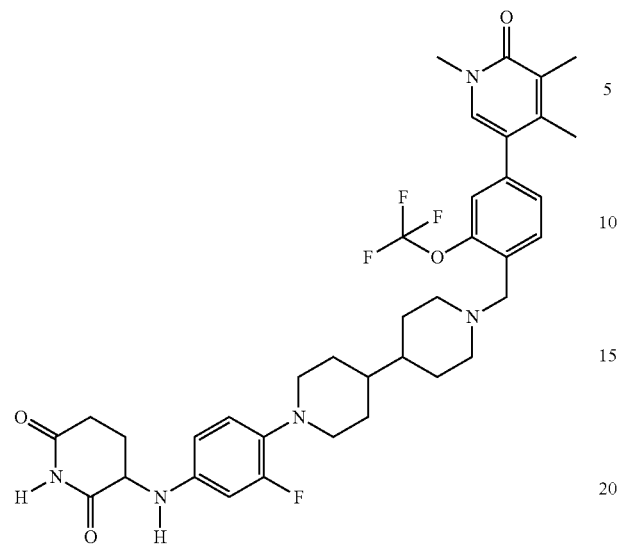
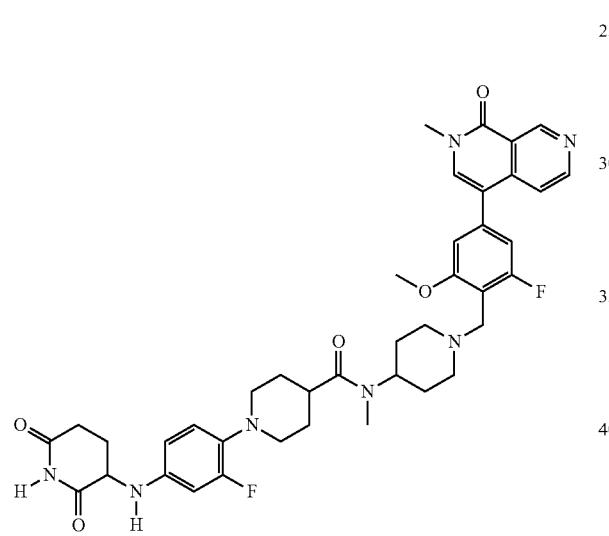
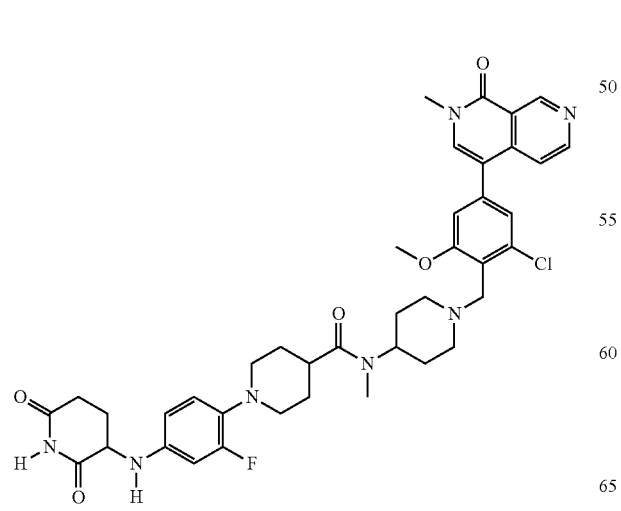
432
-continued
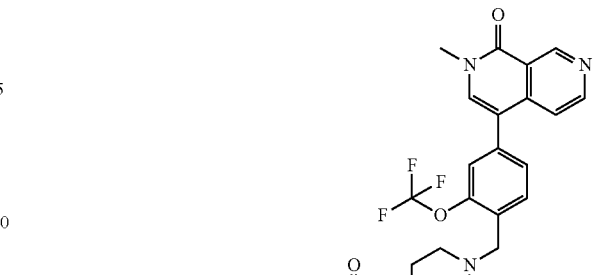
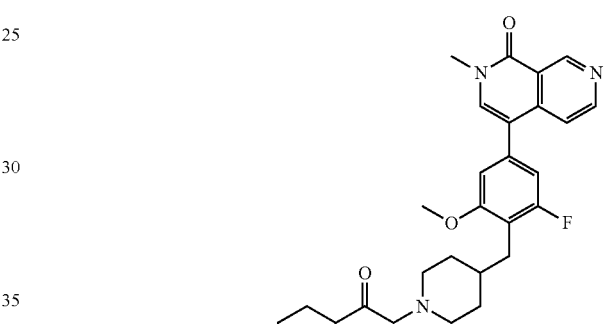

433
-continued
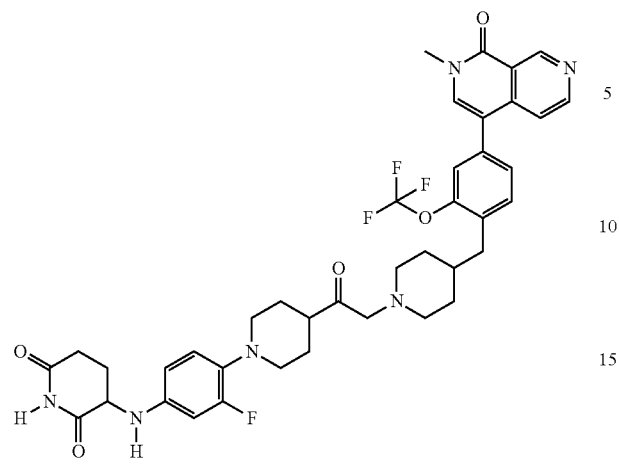
434
-continued
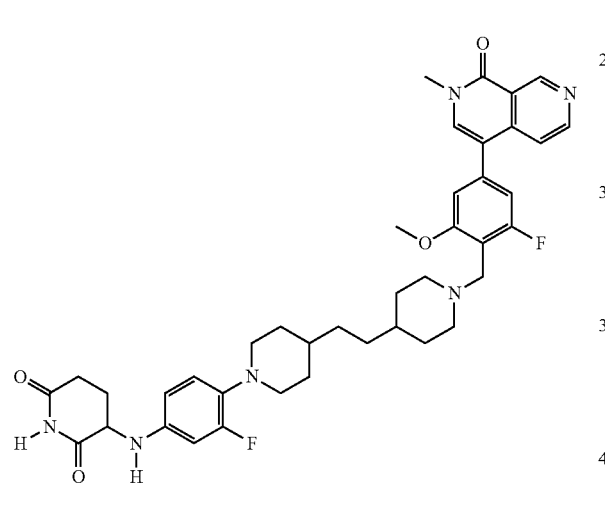
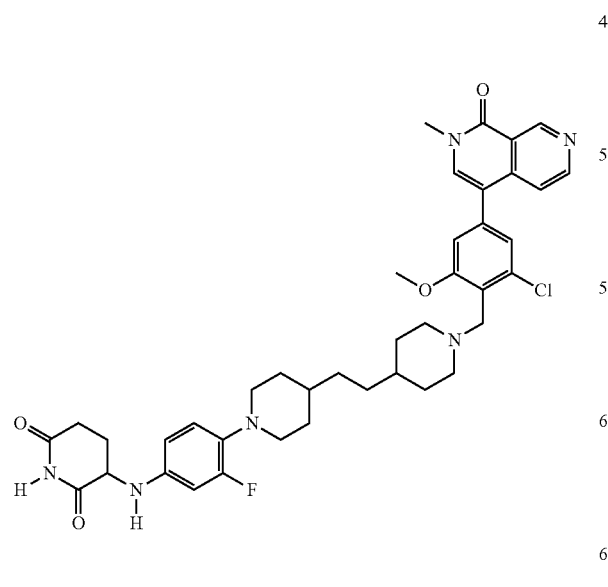

435
-continued

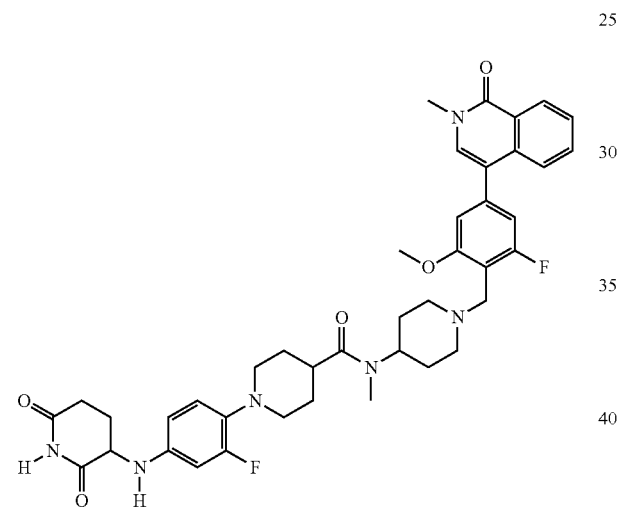
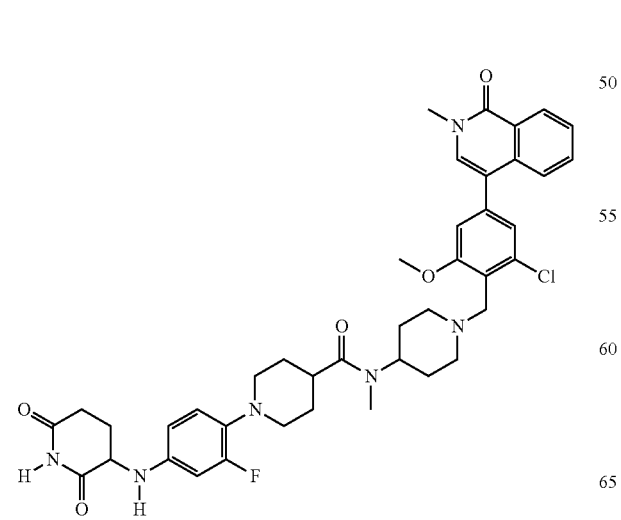
436
-continued
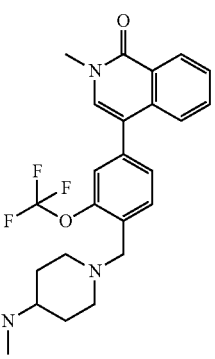
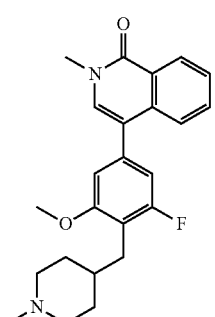
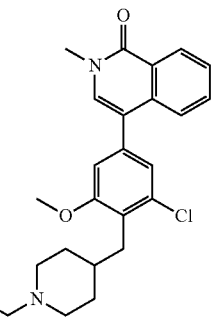

437
-continued
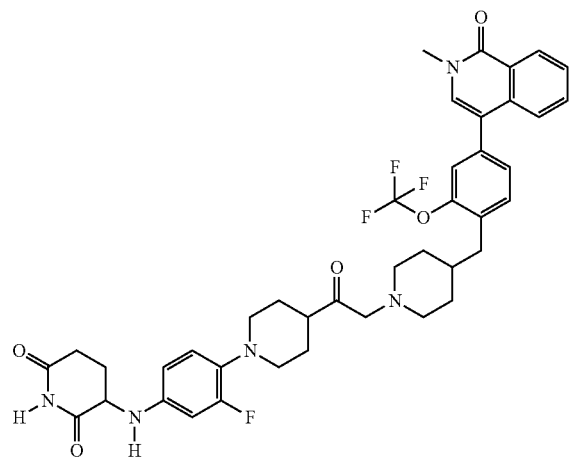
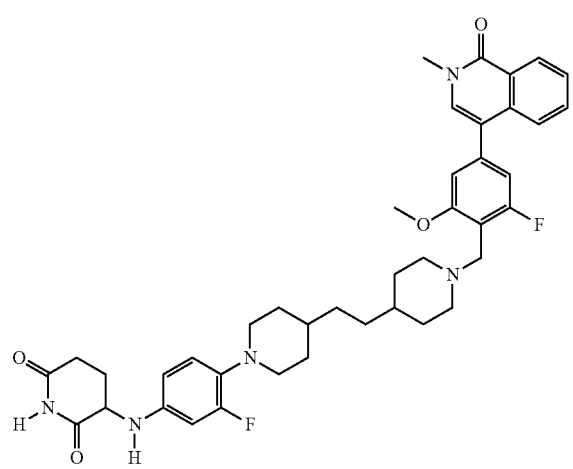
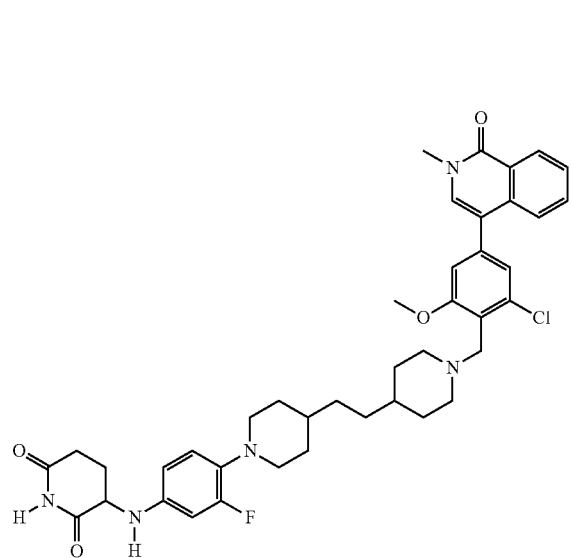
438
-continued
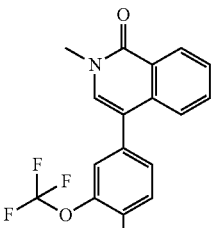
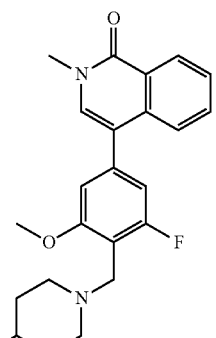
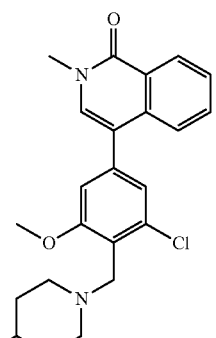

439
-continued
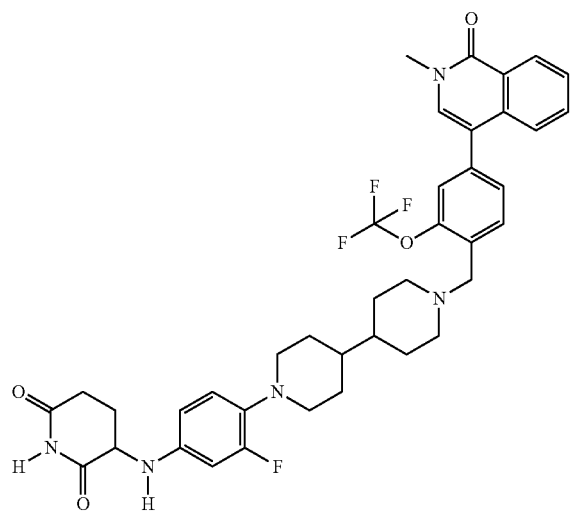
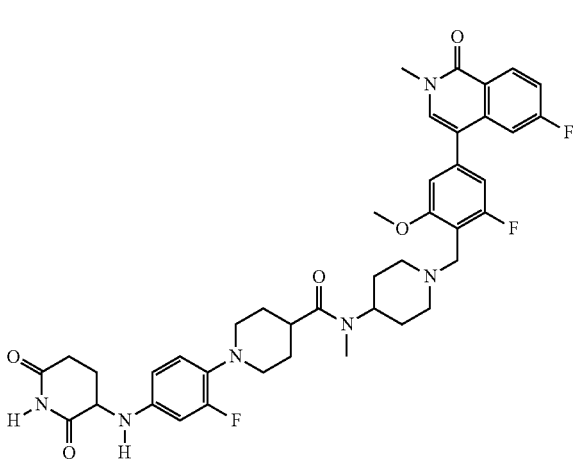
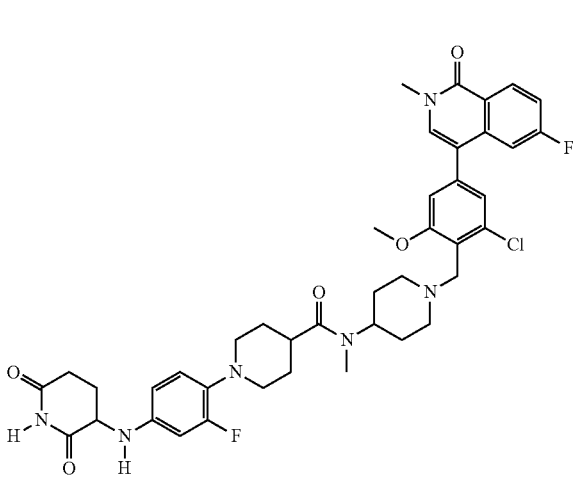
440
-continued
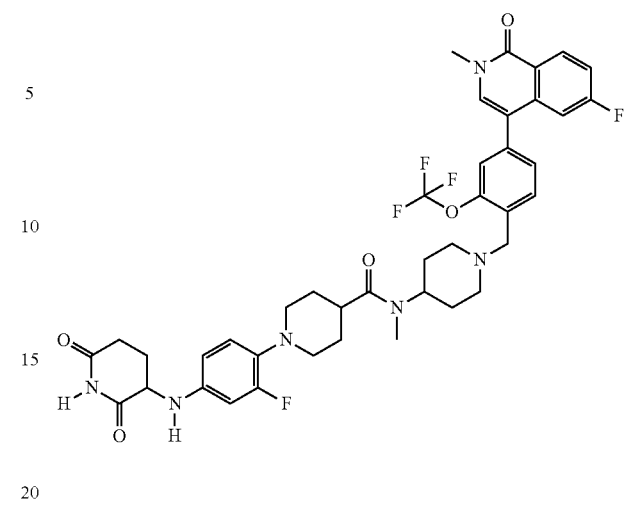
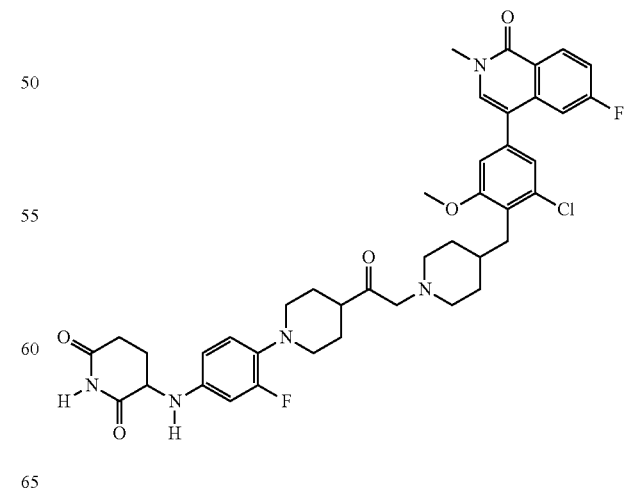

441
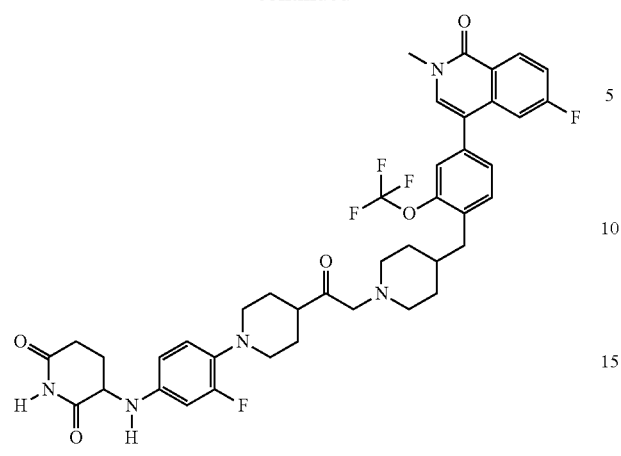
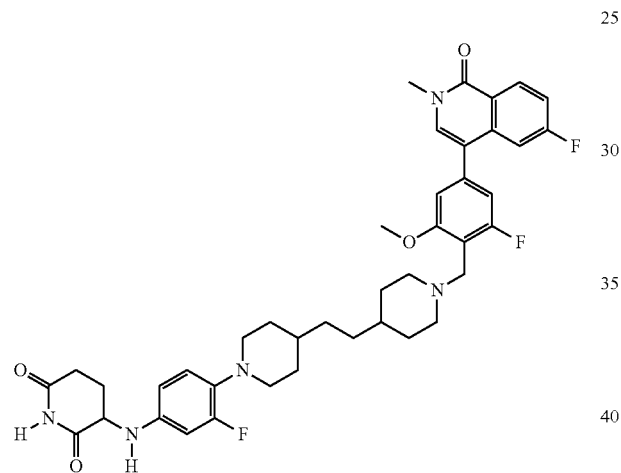
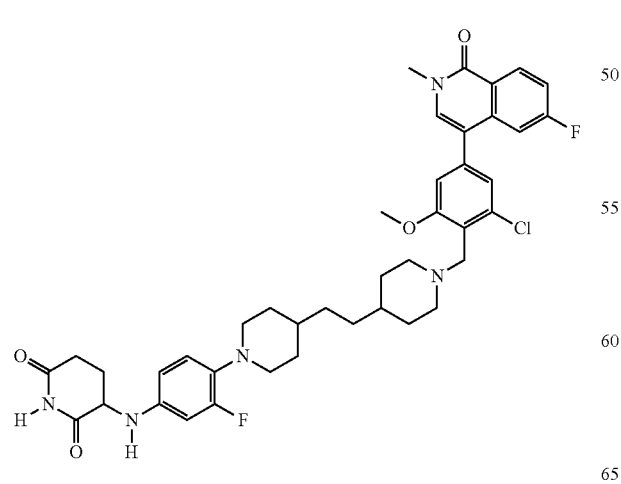
442
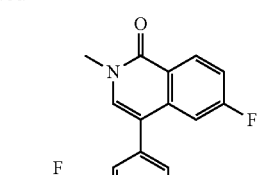
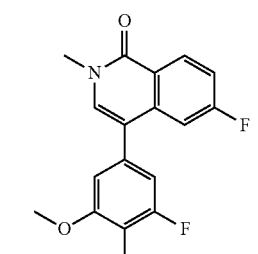
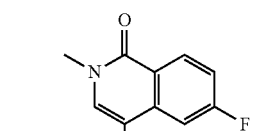

443
-continued
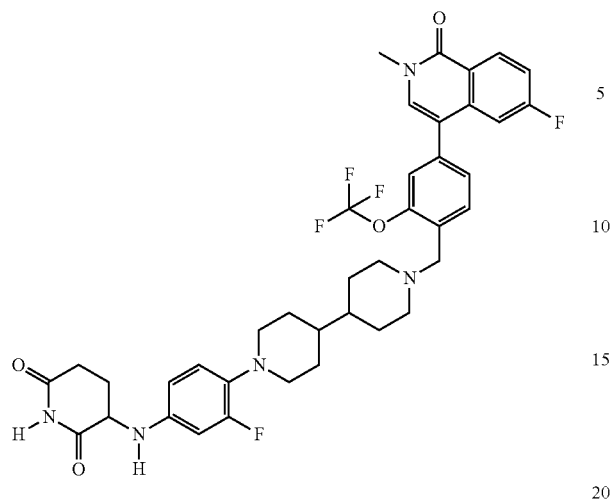
444
-continued
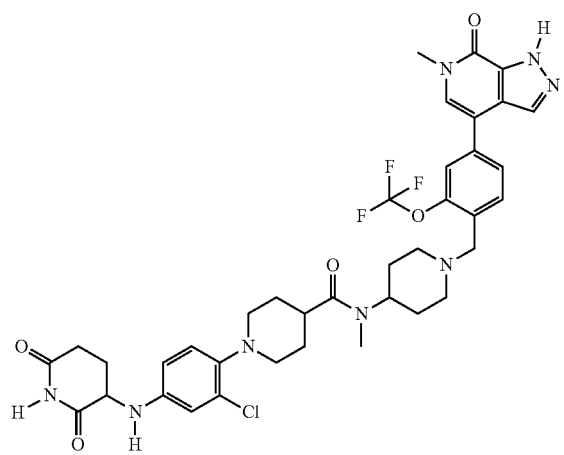
Nonlimiting examples of compounds of the present invention include:
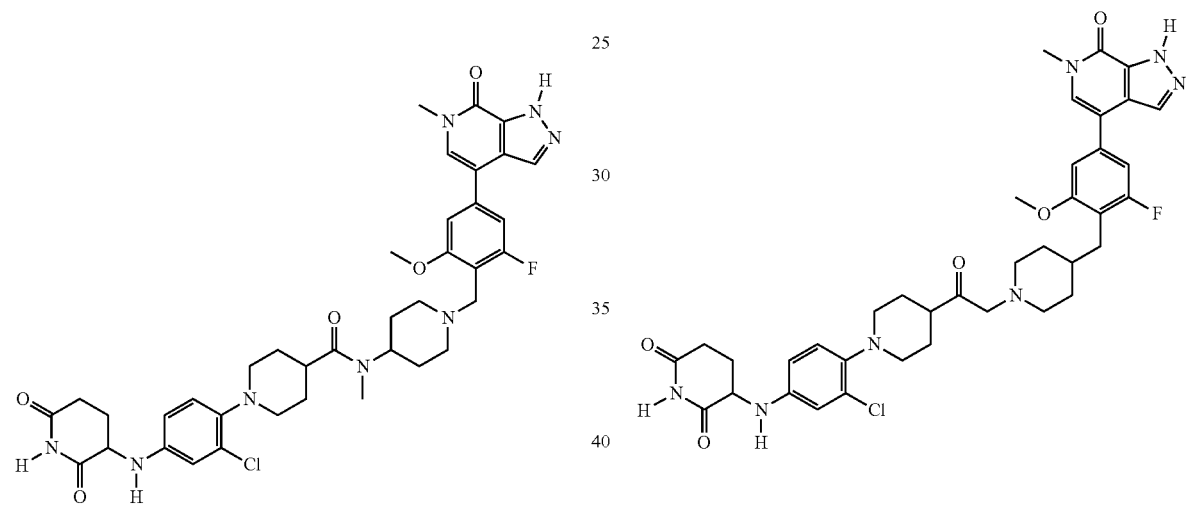
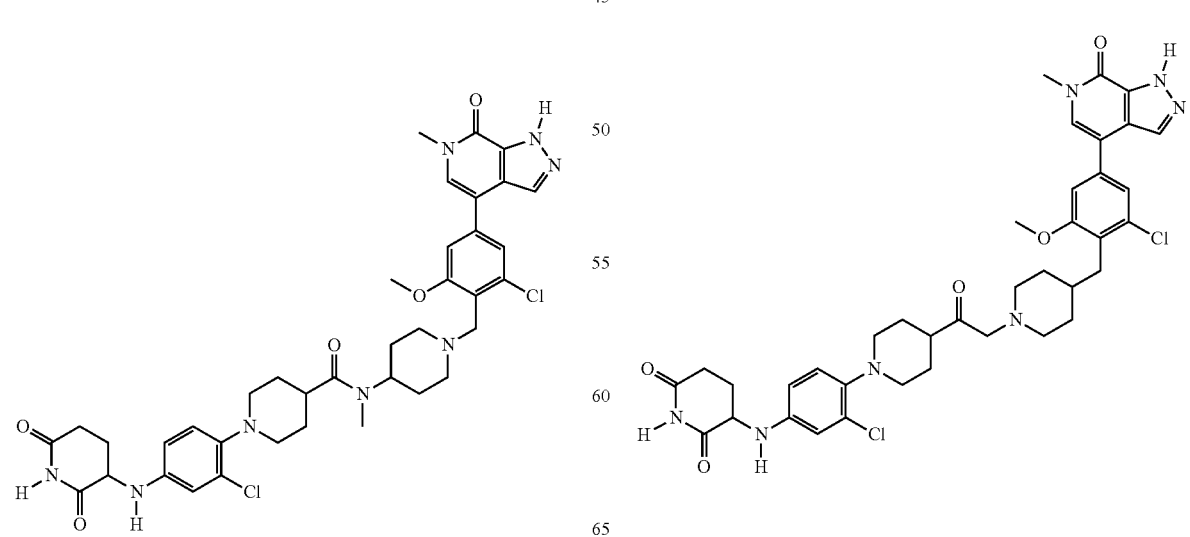

445
-continued
446
-continued
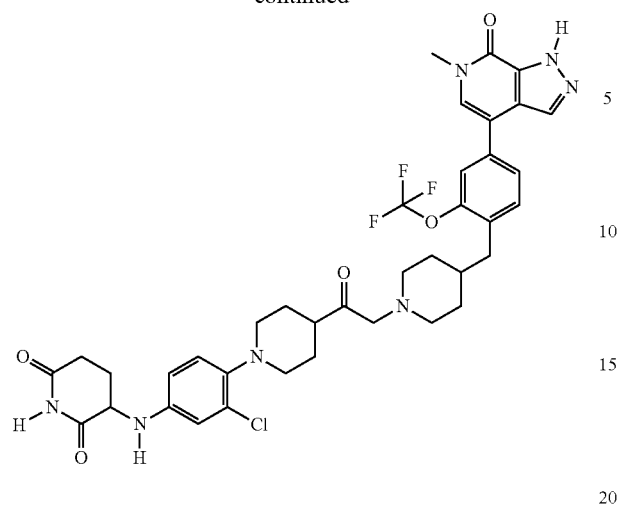
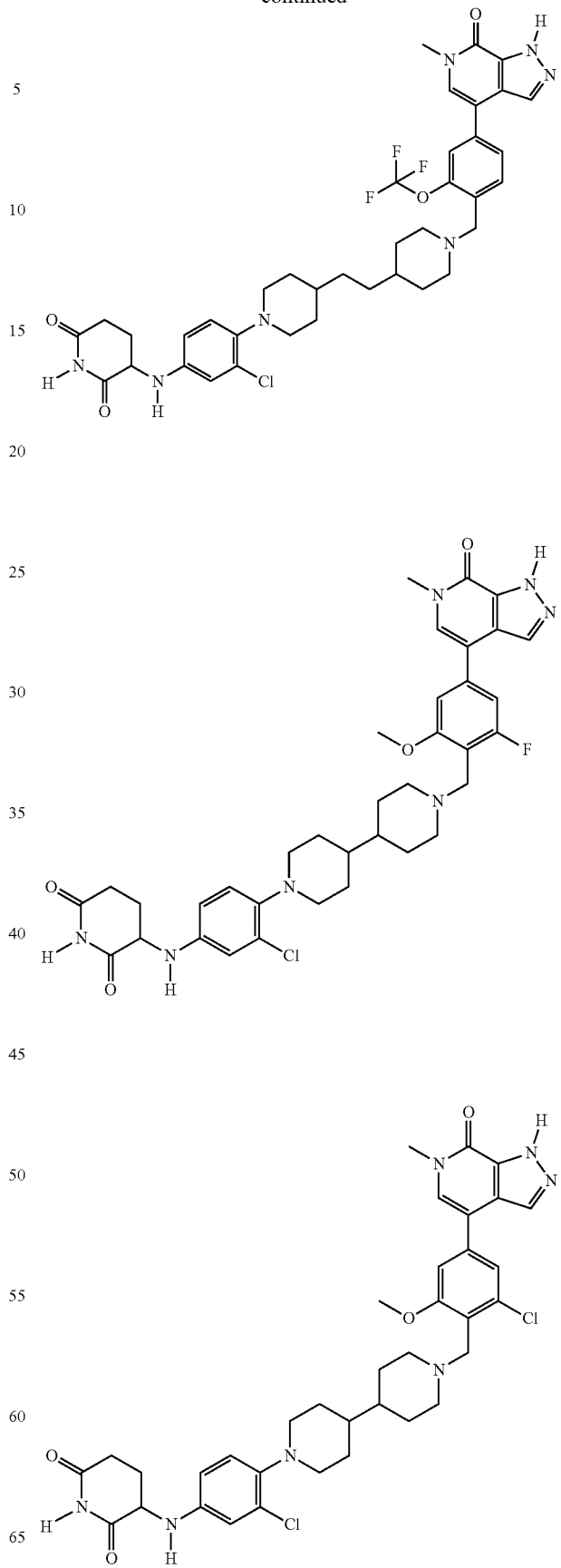

447
-continued
448
-continued
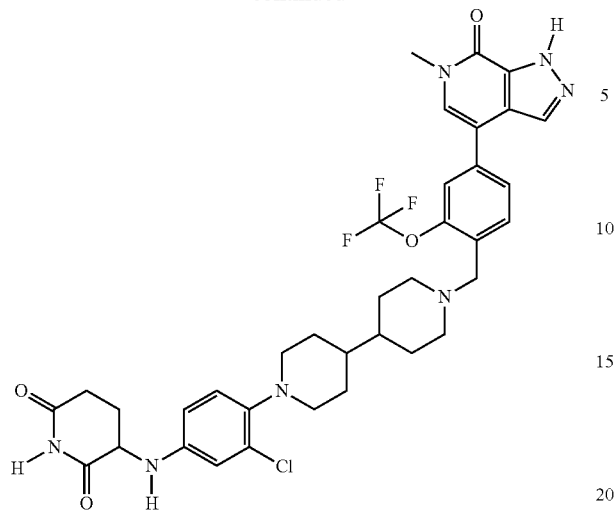
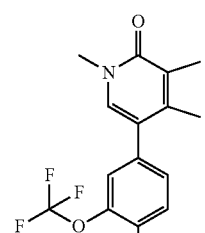
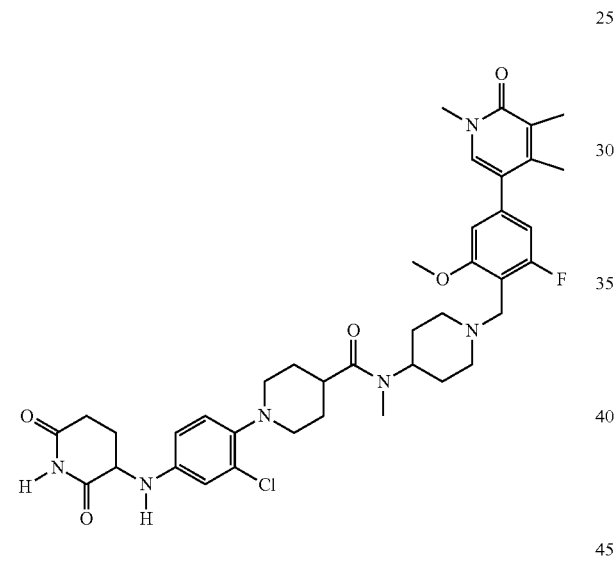
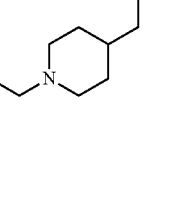
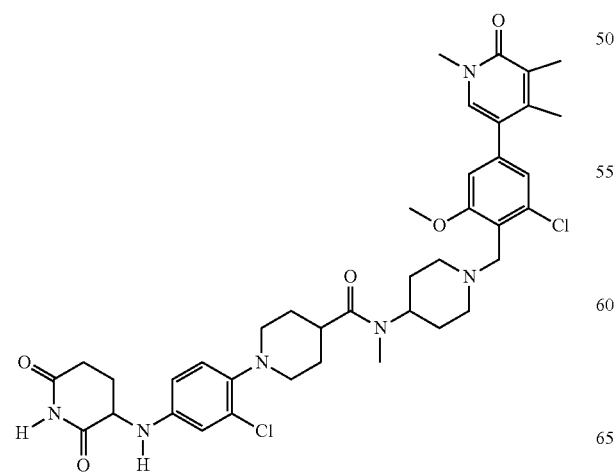
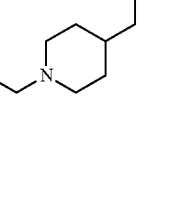

449
-continued
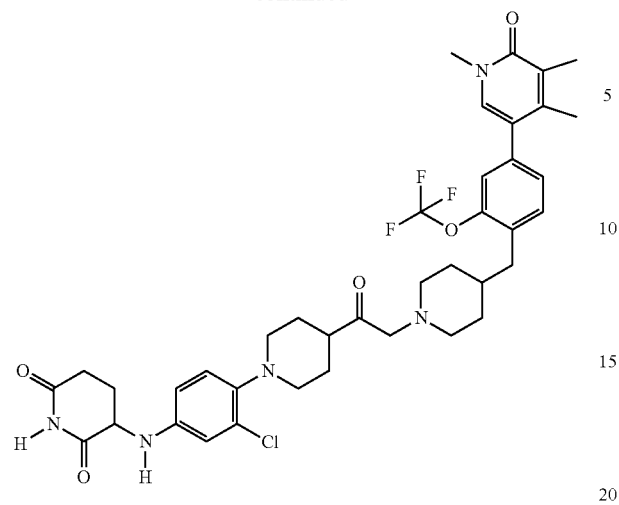
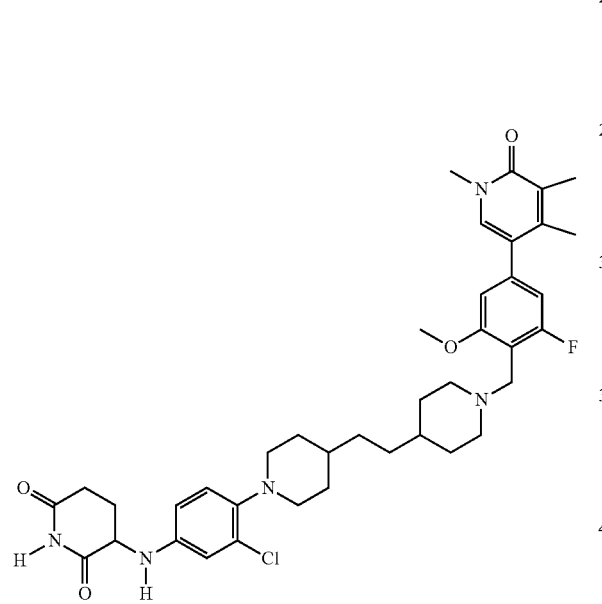
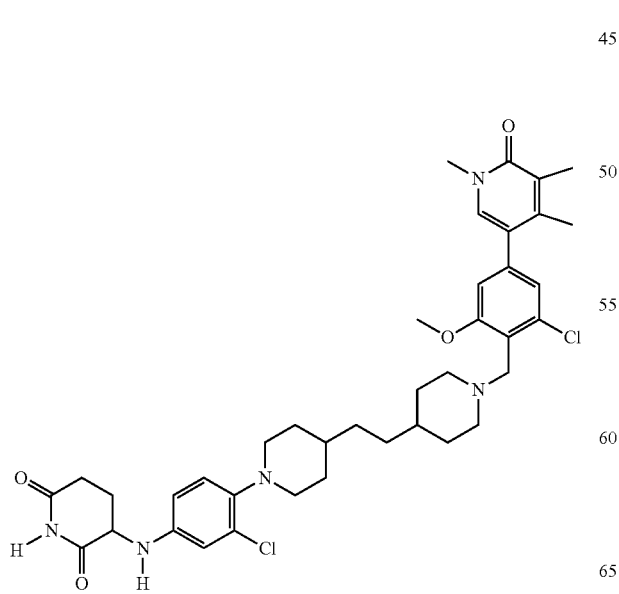
450
-continued
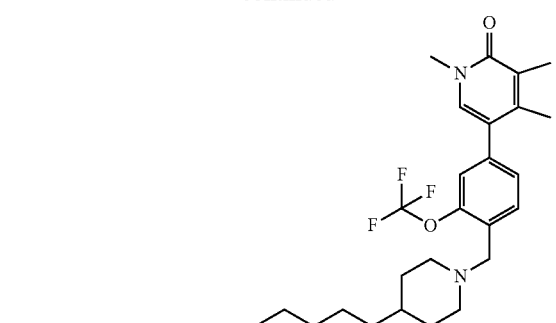
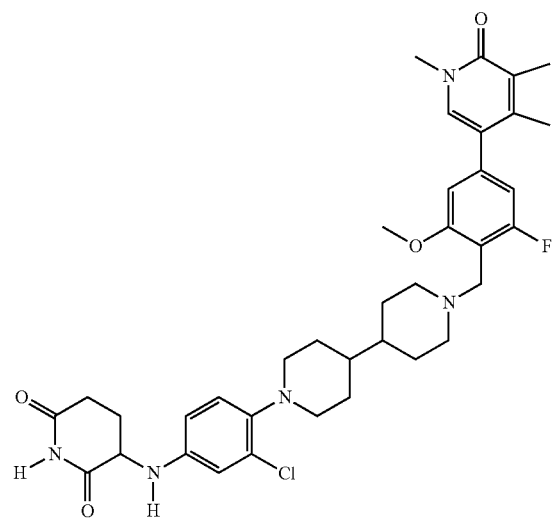
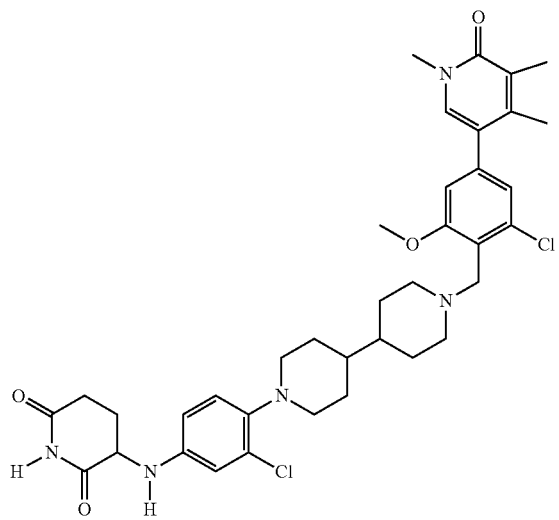

451
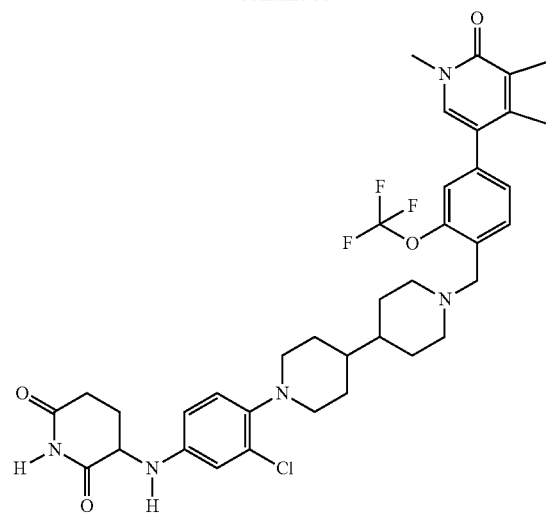
452
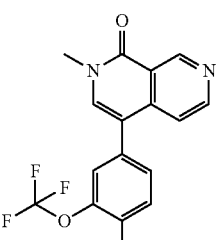
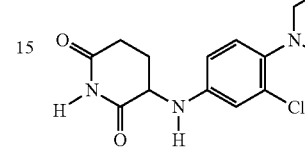
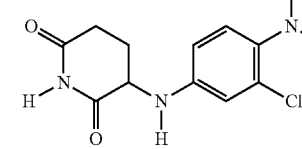
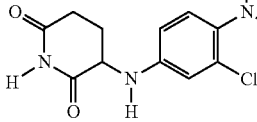
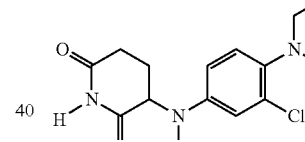
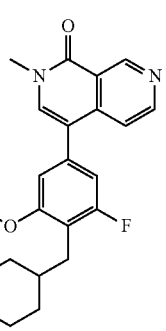
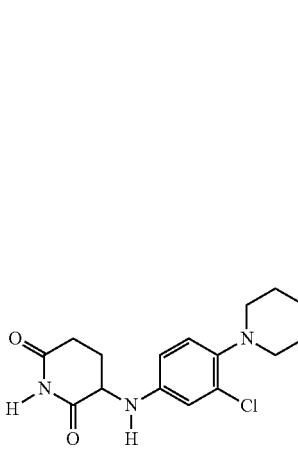
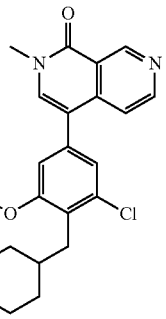

453
-continued
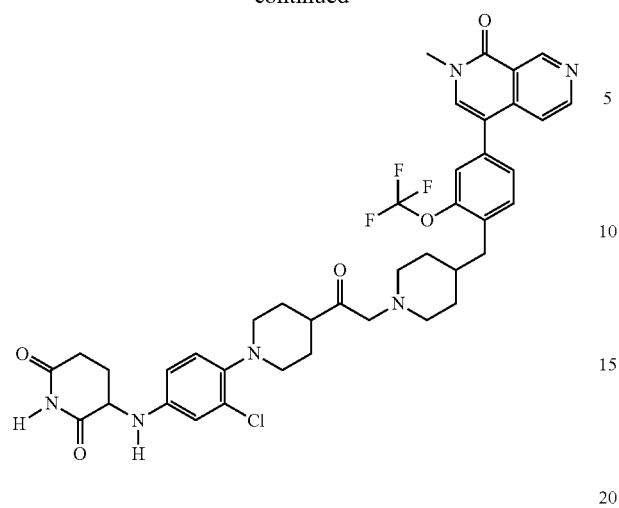
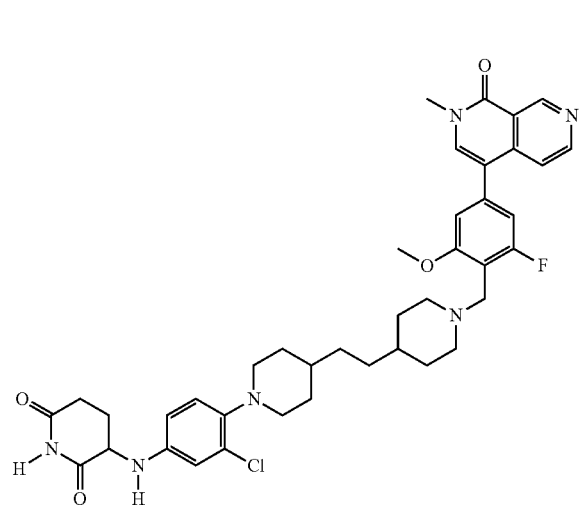
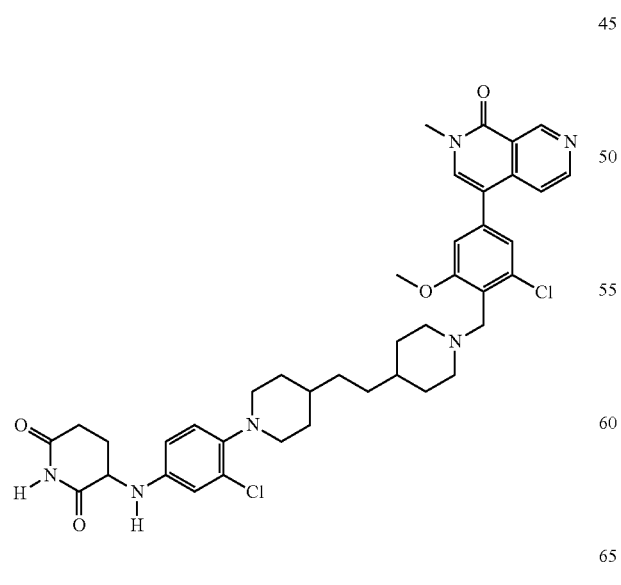
454
-continued
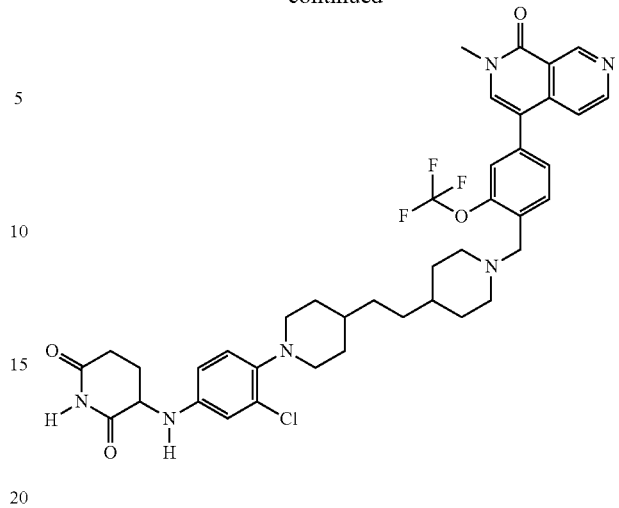
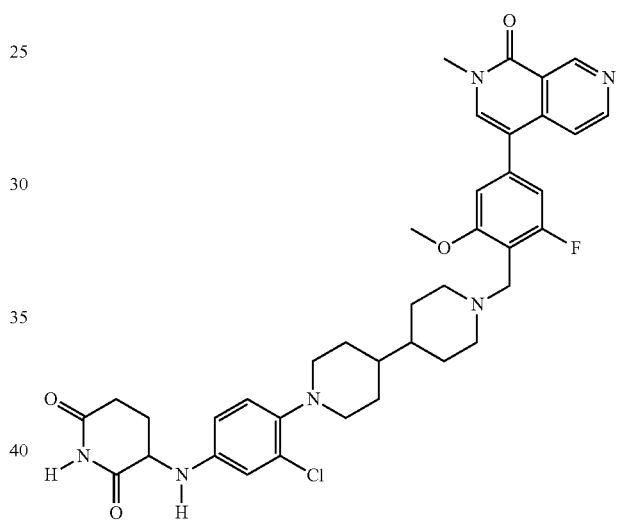
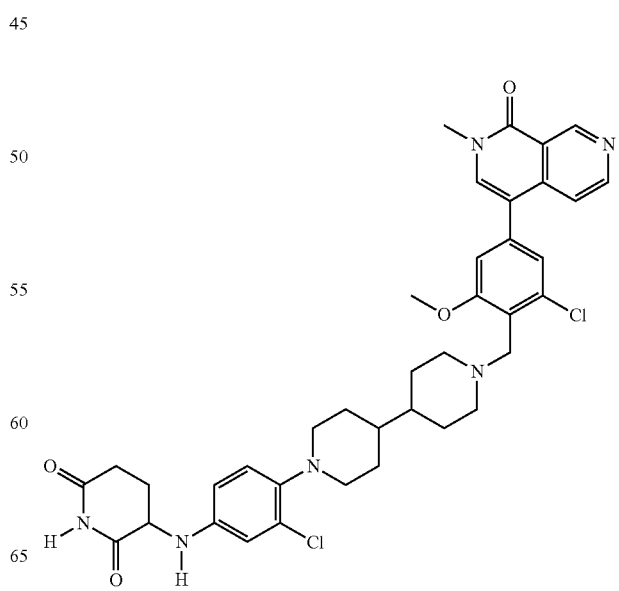

455
-continued
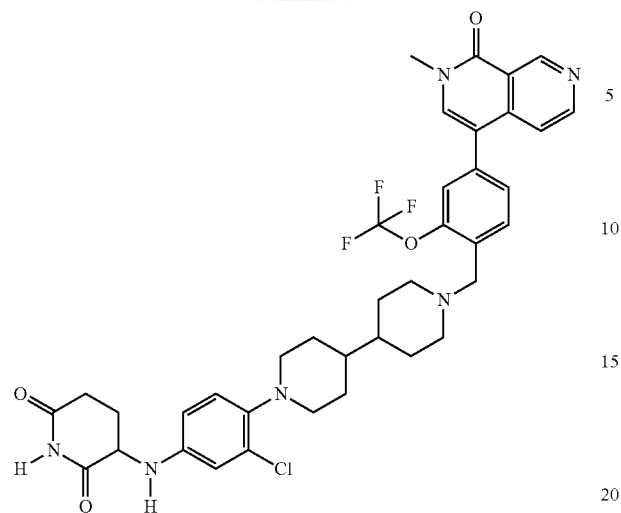
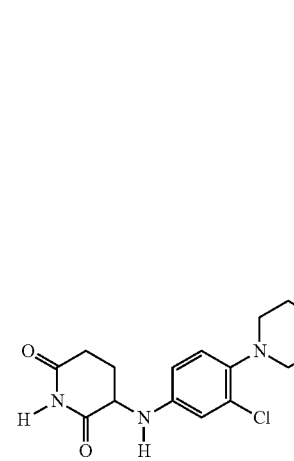
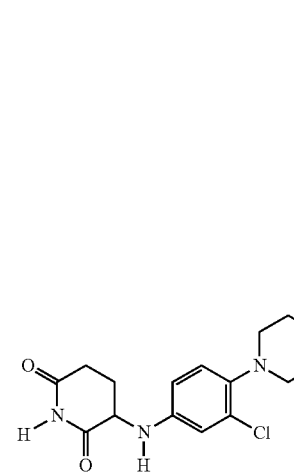
456
-continued
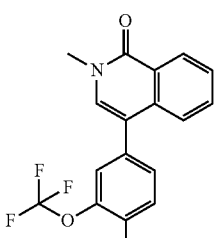
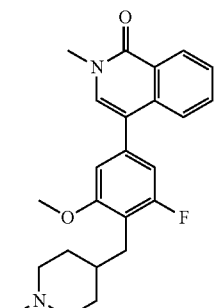
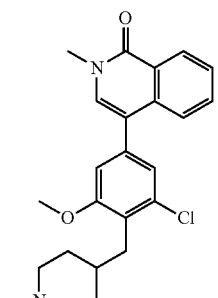

457
-continued
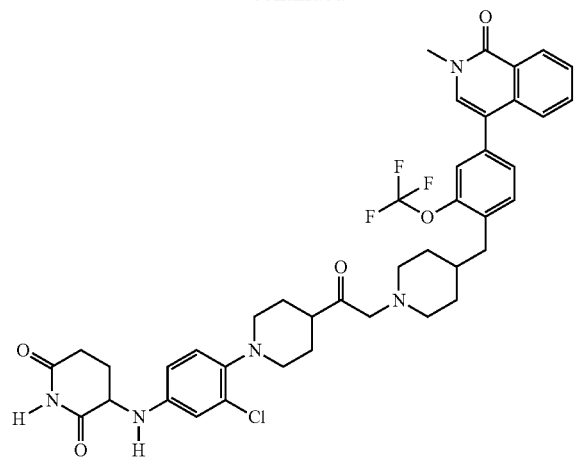
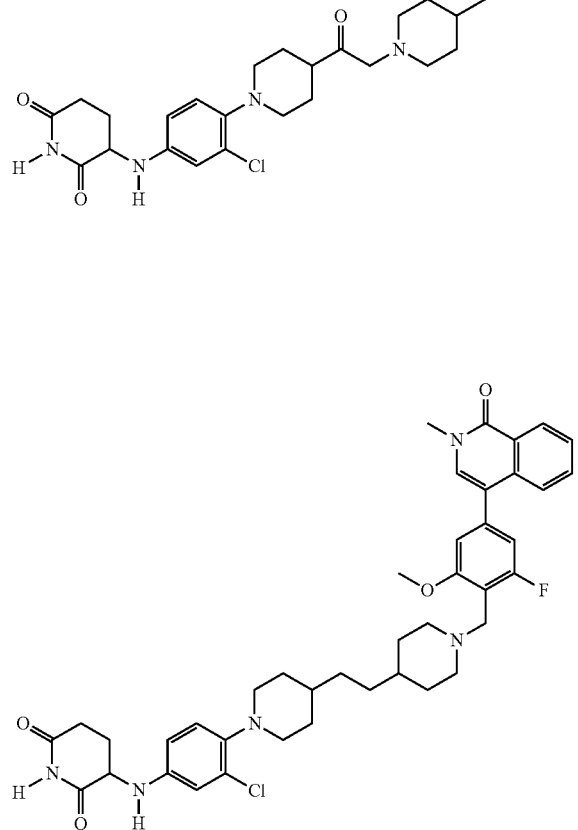
458
-continued
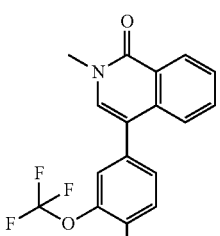
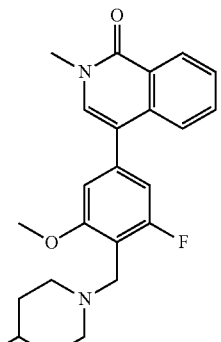

459
-continued
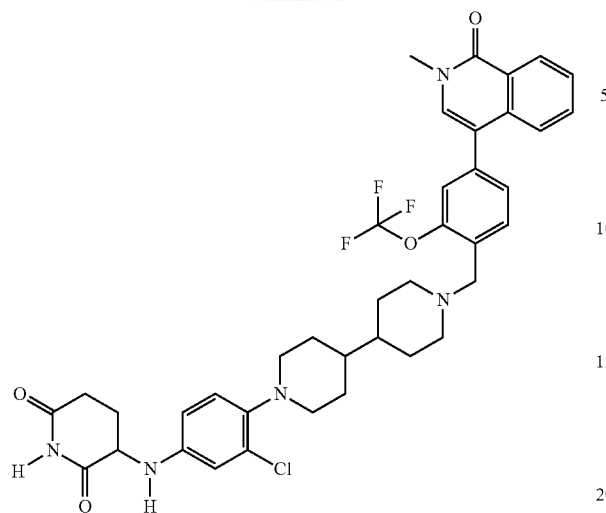
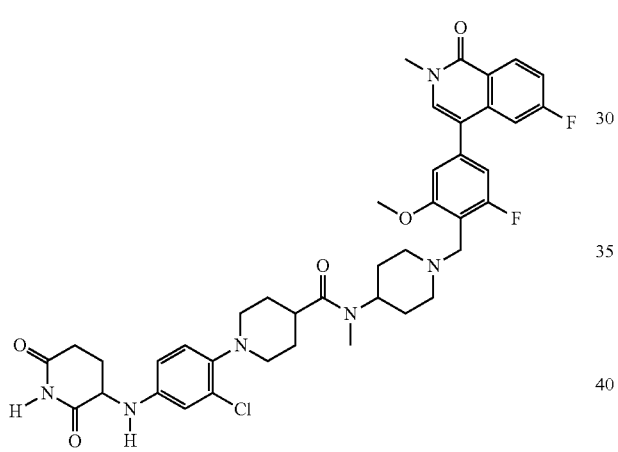
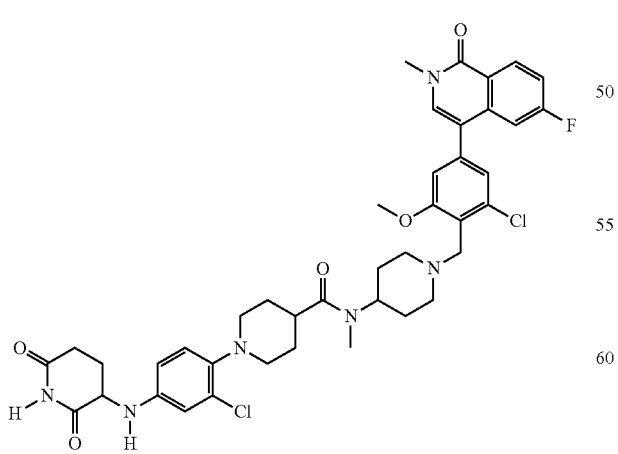
460
-continued
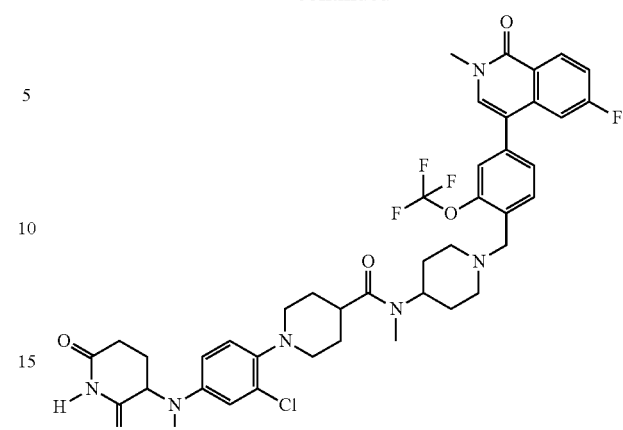
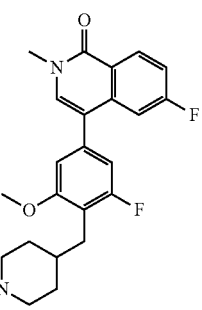
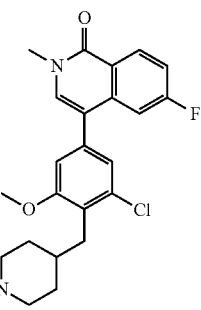

461
-continued
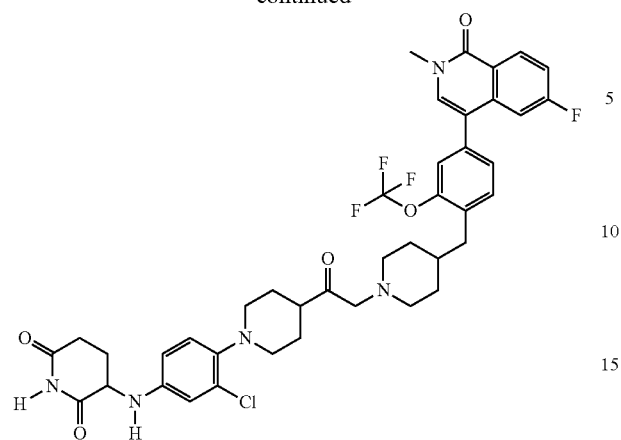
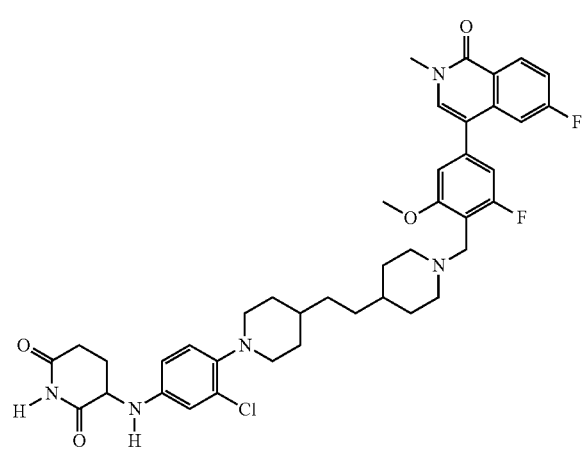
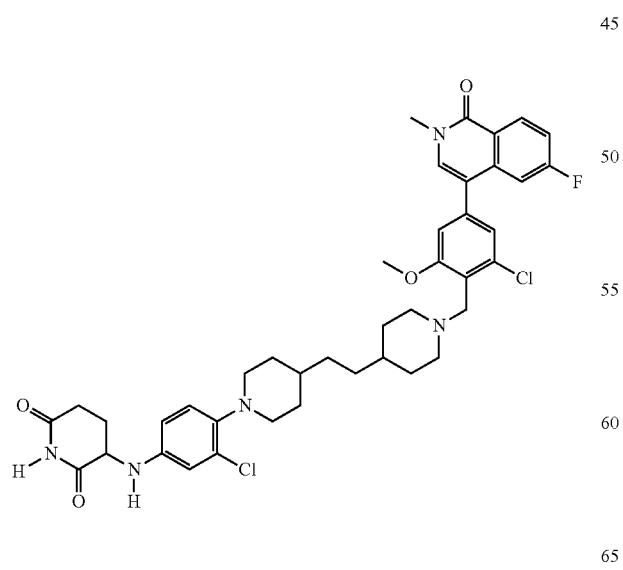
462
-continued
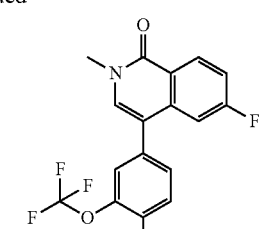
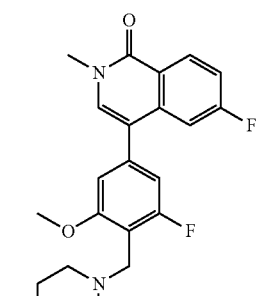
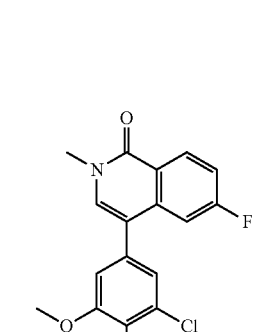

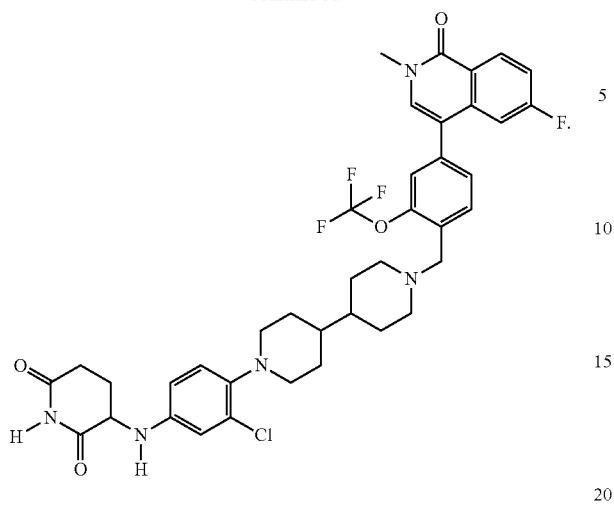
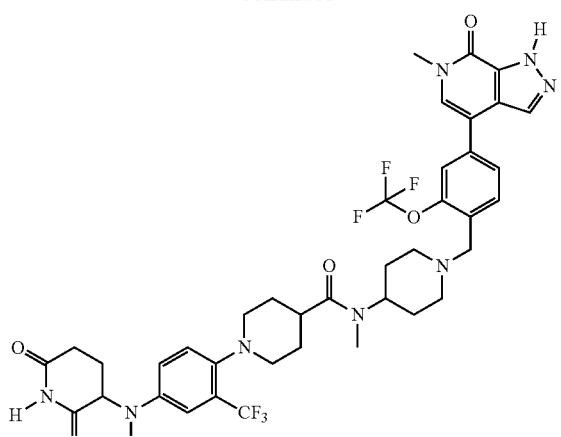
Nonlimiting examples of compounds of the present invention include:
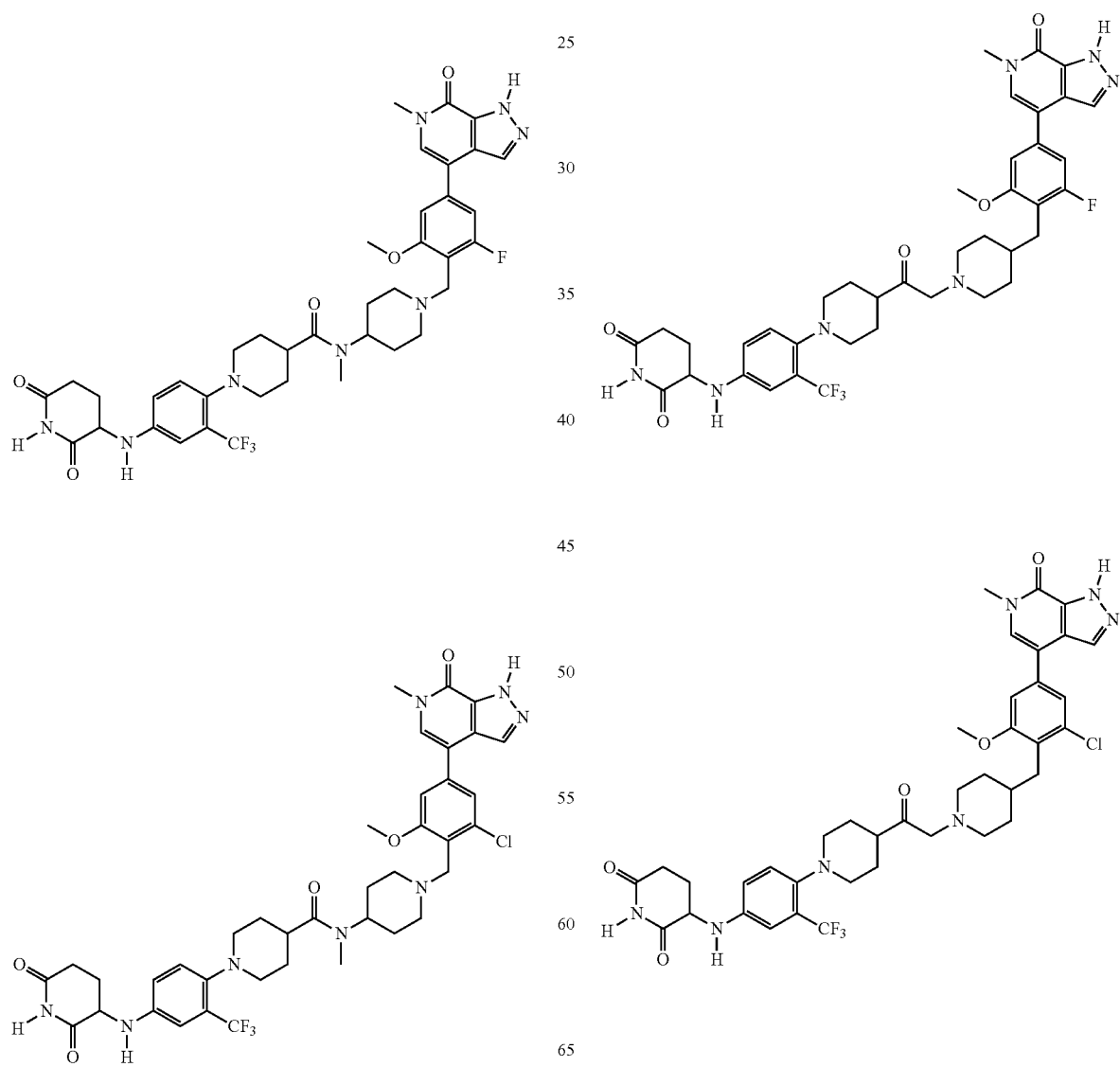

465
-continued
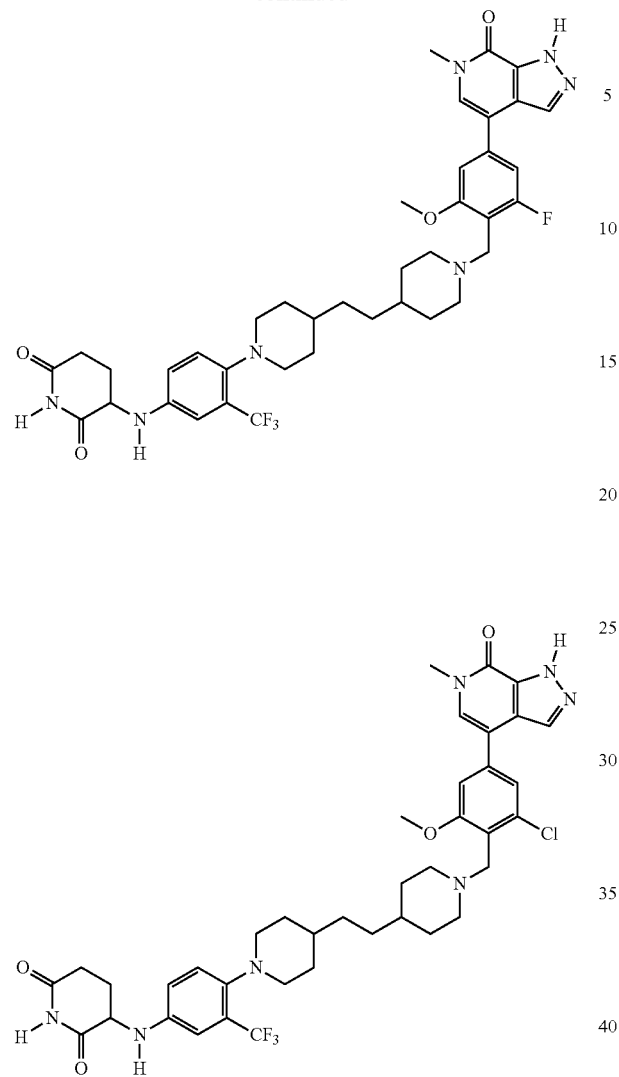
466
-continued
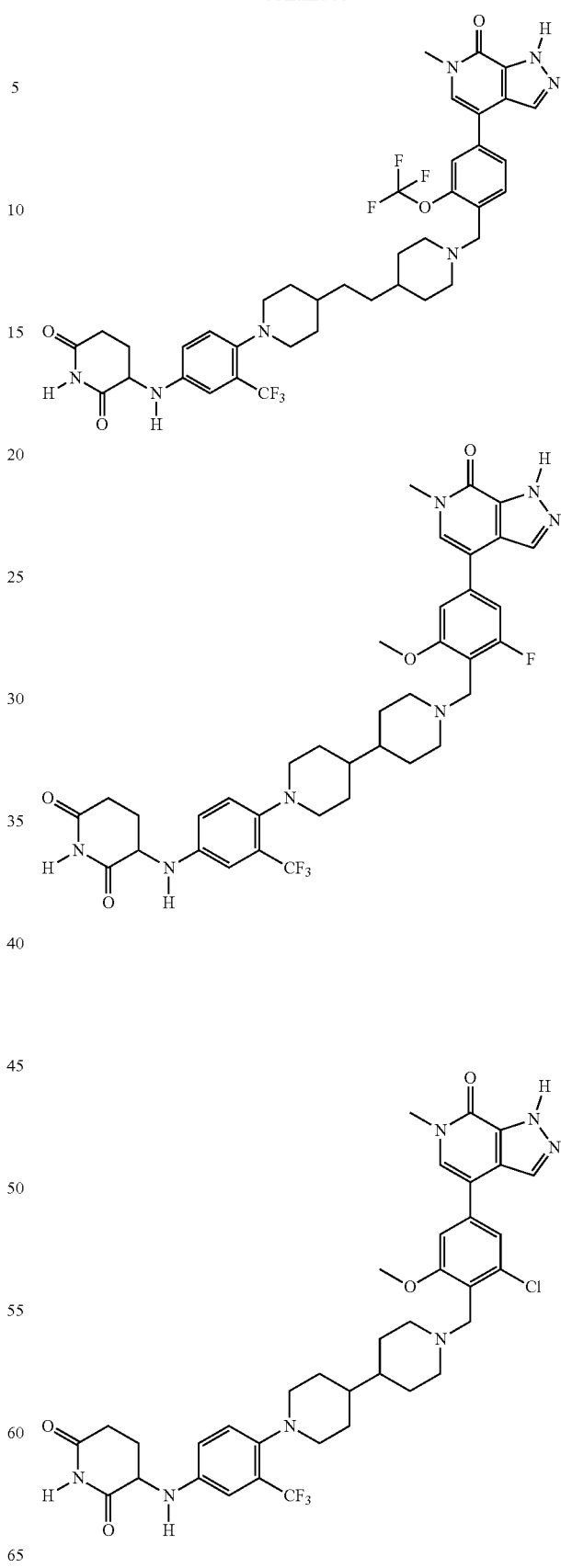

467
-continued
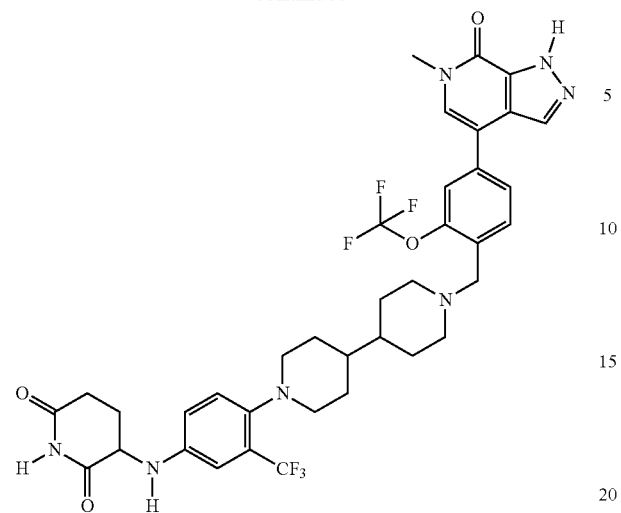
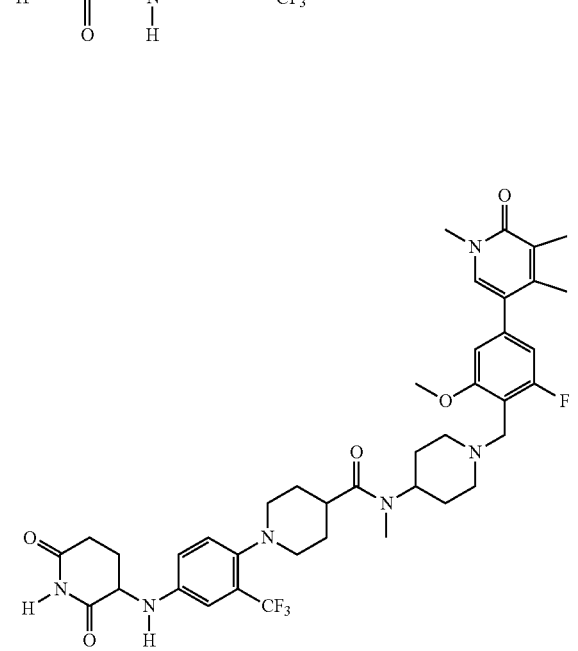
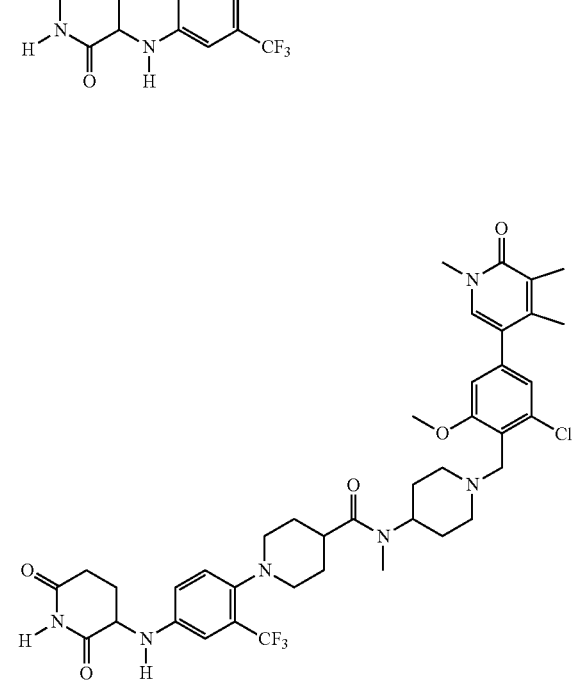
468
-continued
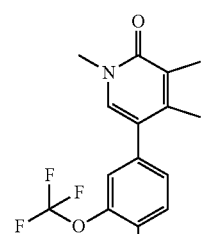
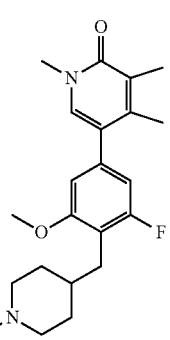
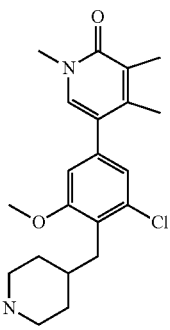

469
-continued
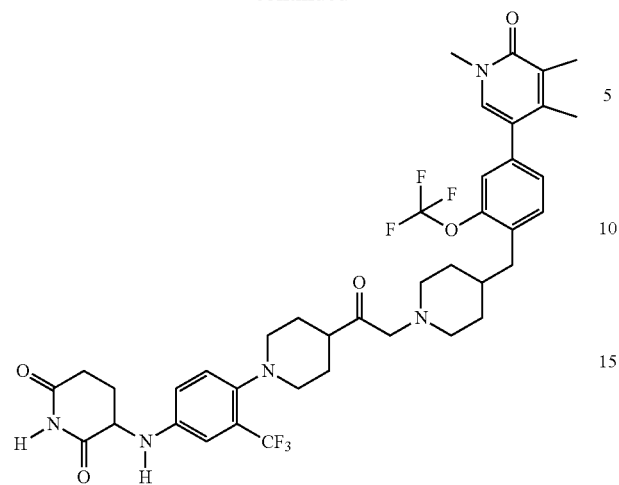
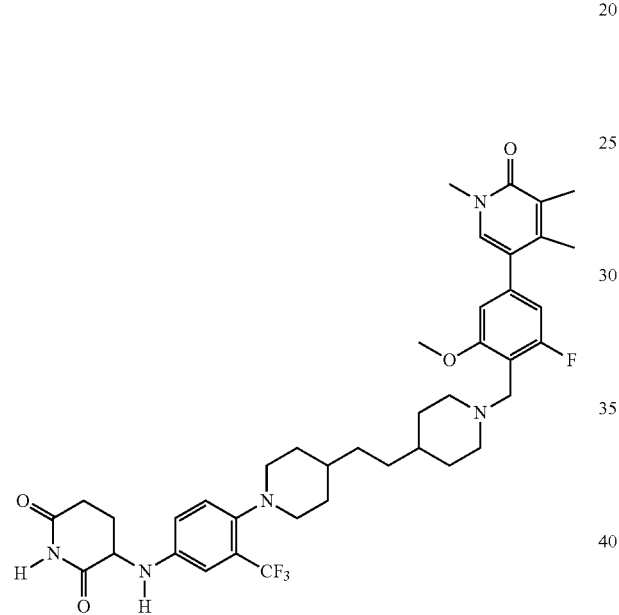
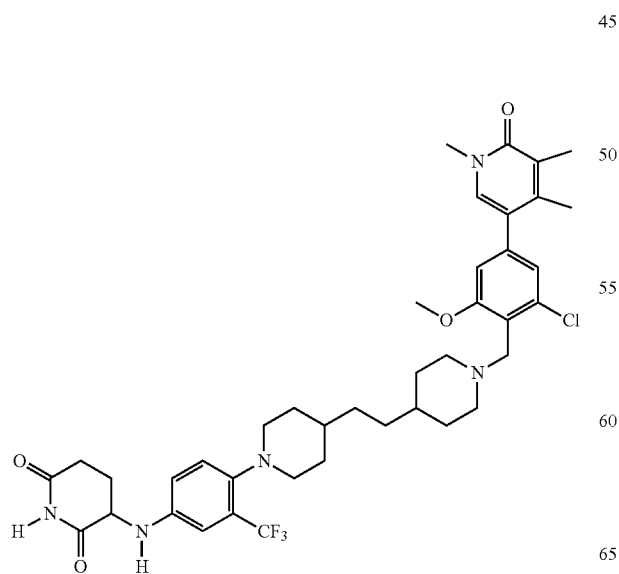
470
-continued
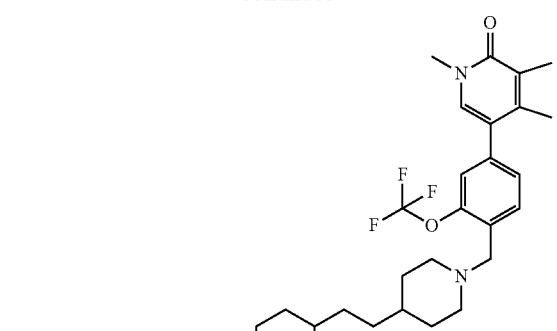
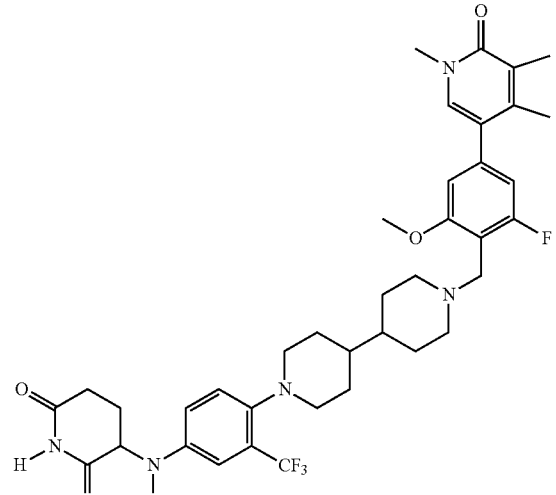
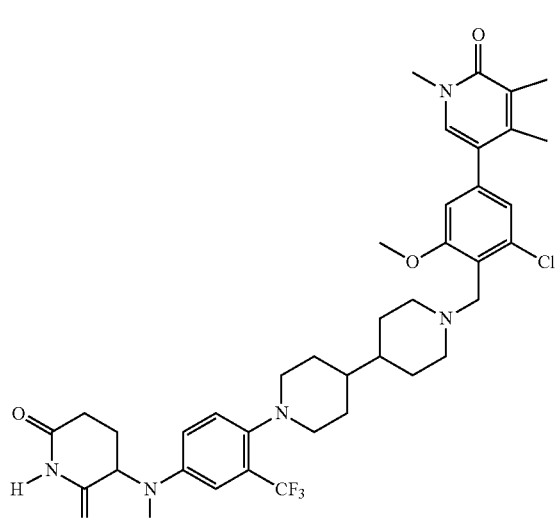

471
-continued
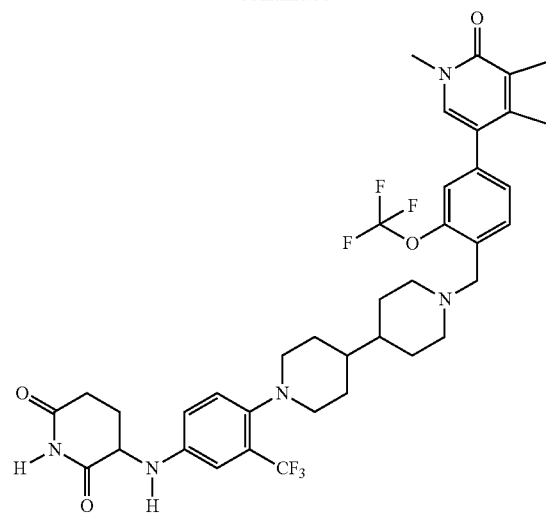
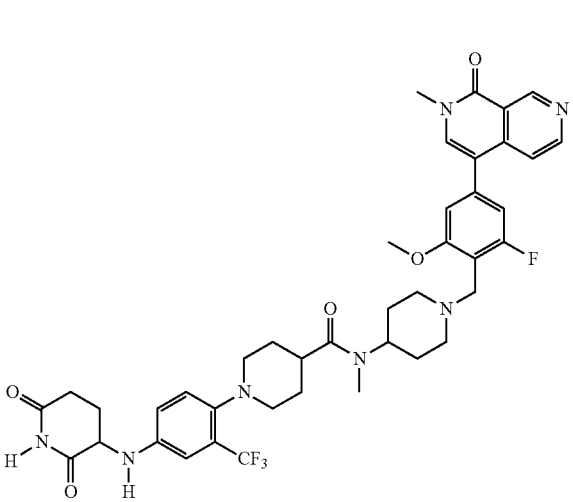
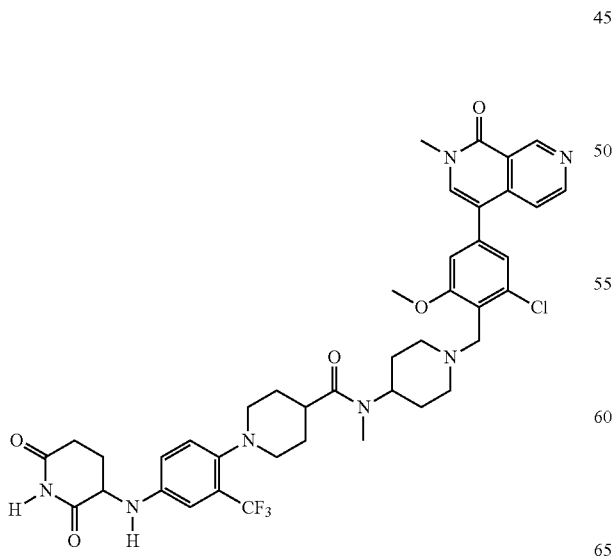
472
-continued
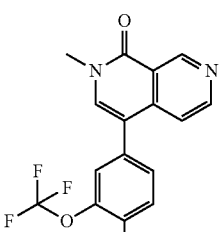
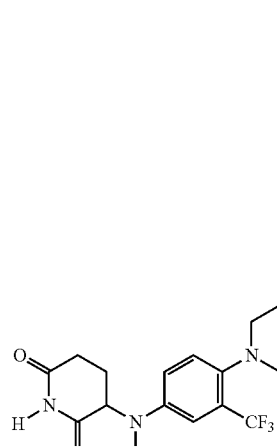
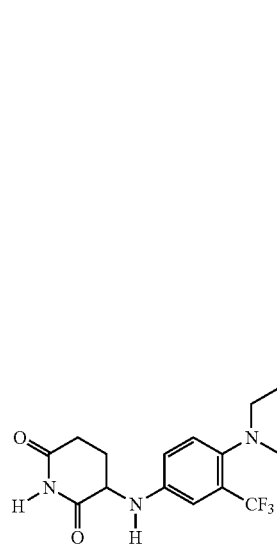

473
-continued
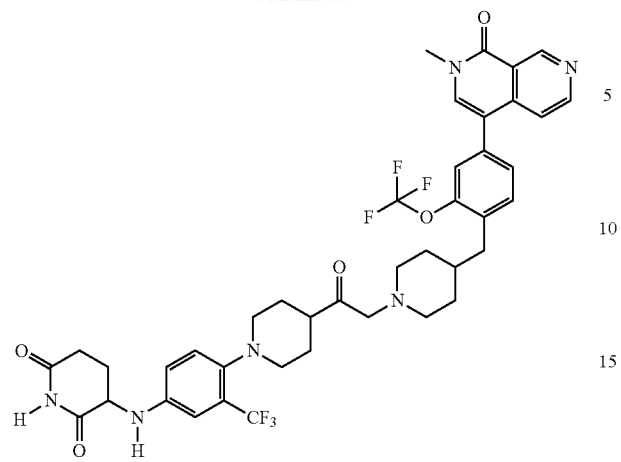
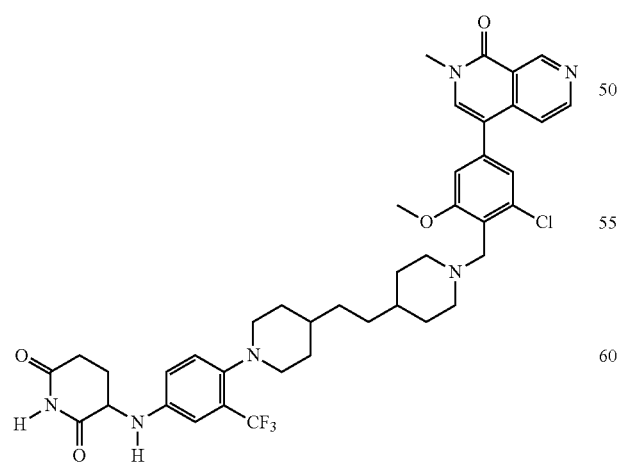
474
-continued
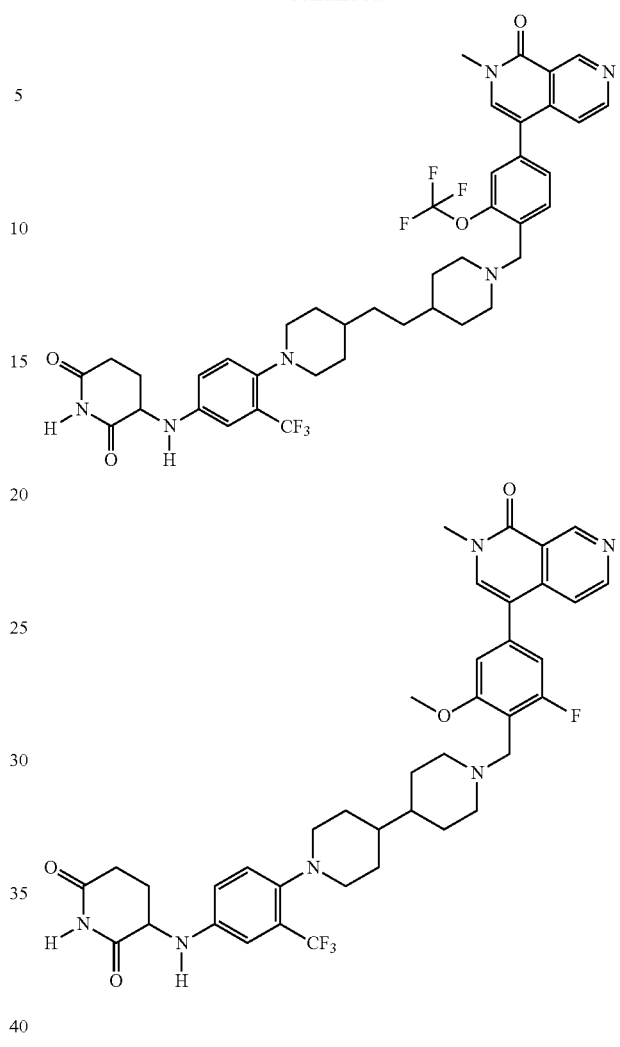
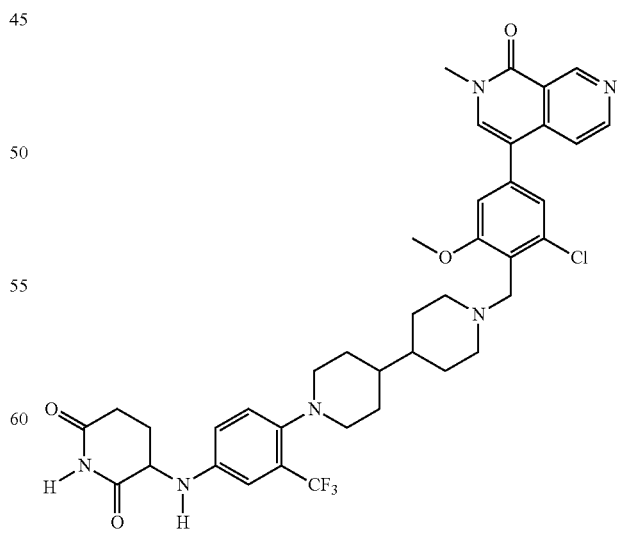

475
-continued
476
-continued
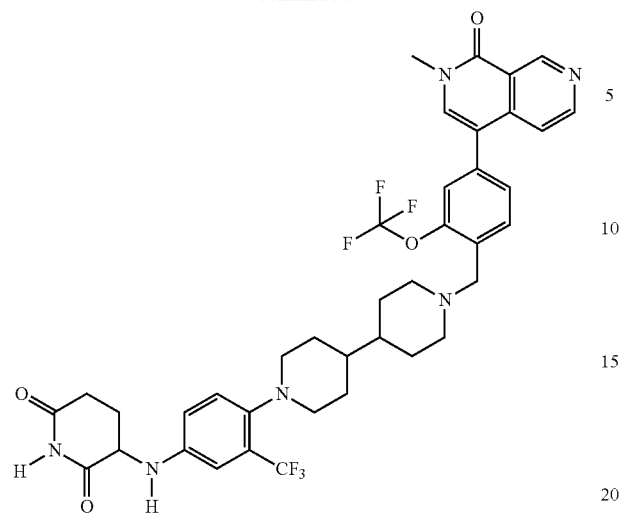
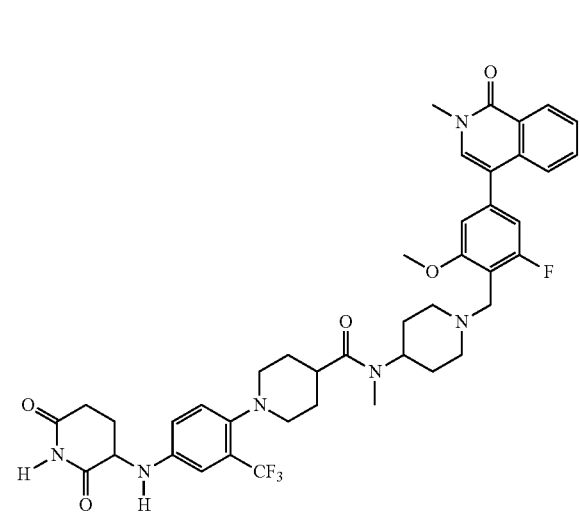
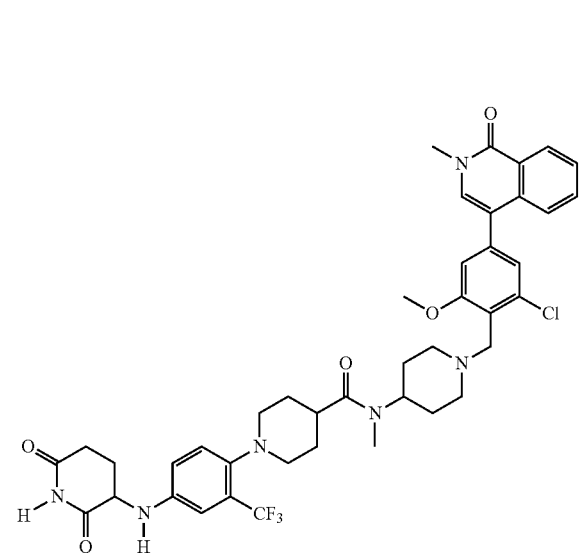
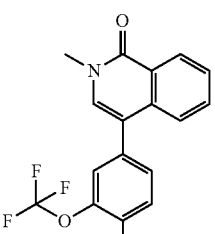
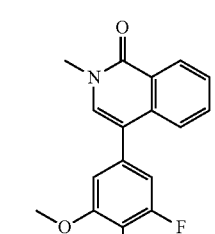
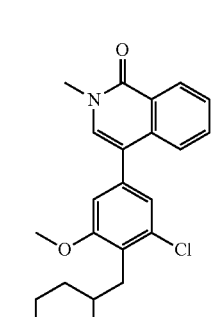

477
-continued
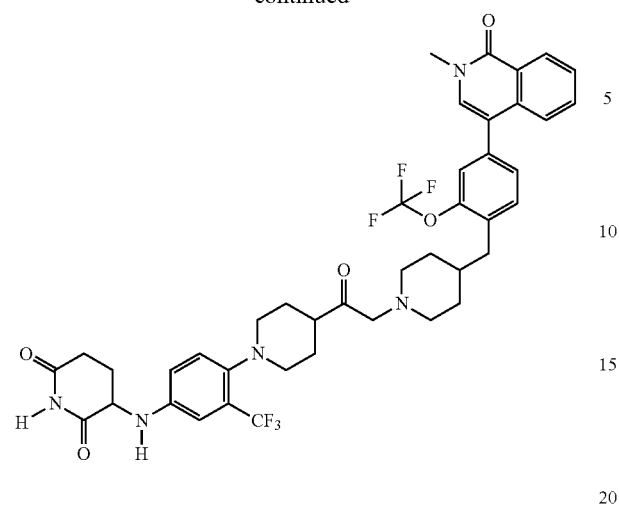
478
-continued
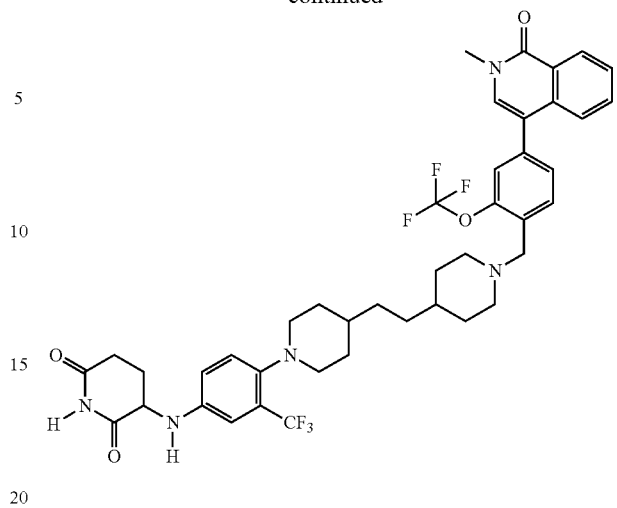
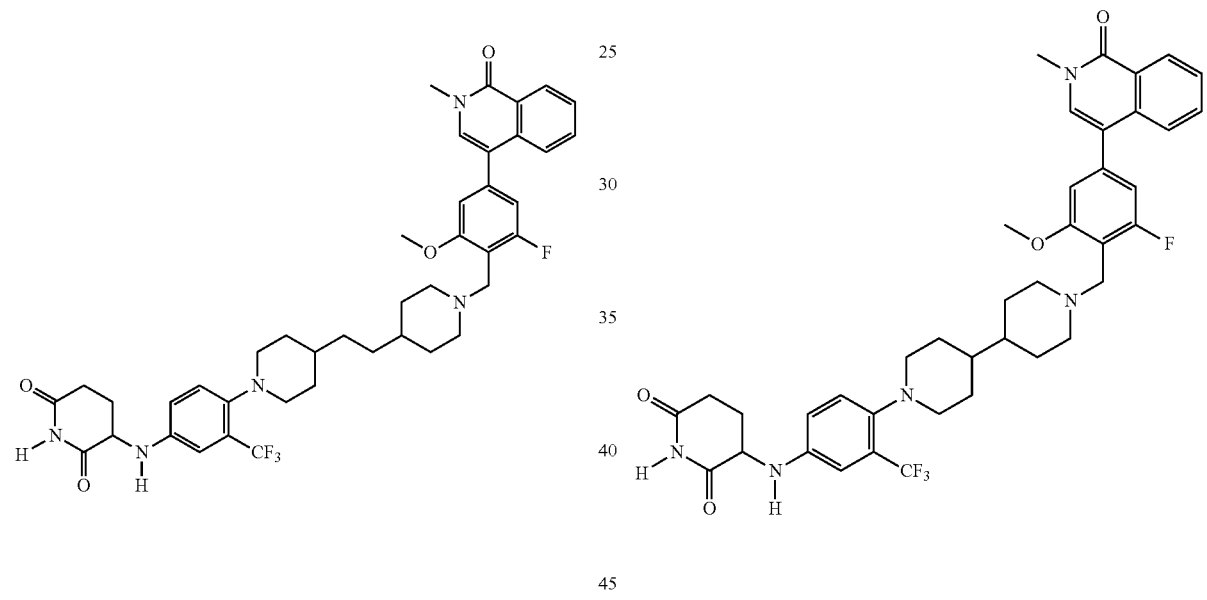
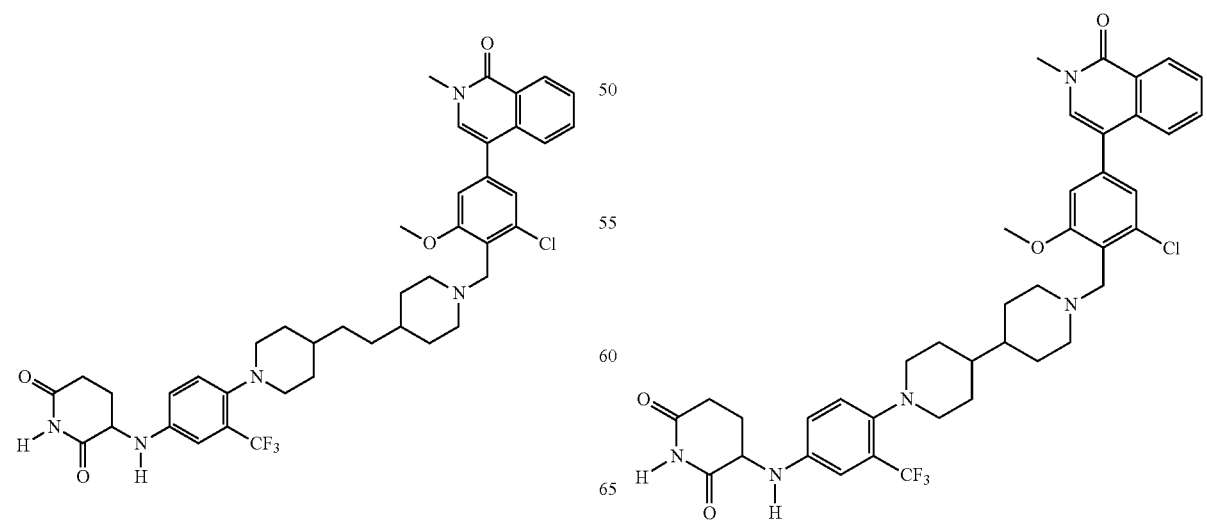

479
-continued
480
-continued
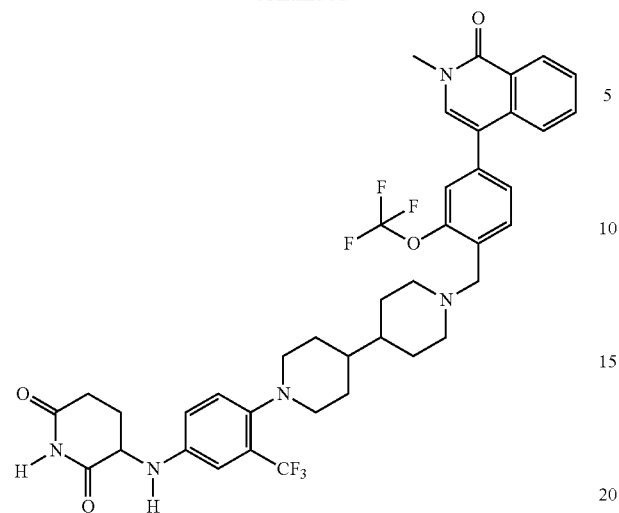
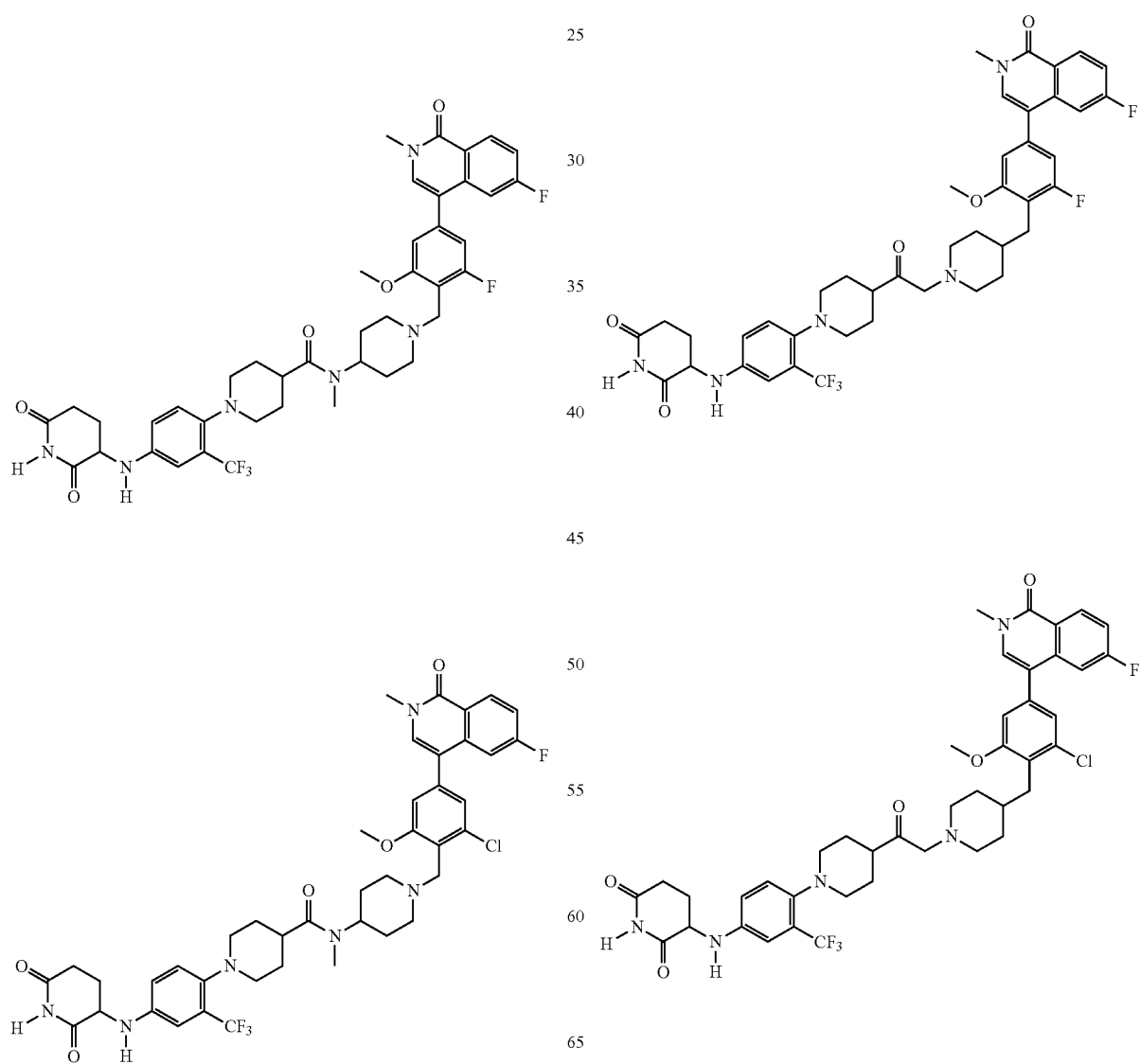

481
-continued
482
-continued
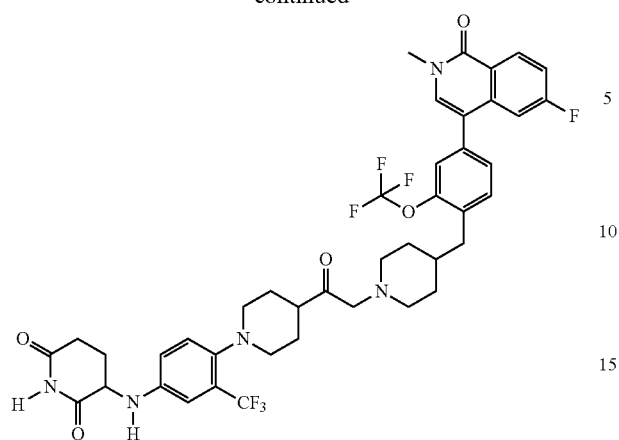
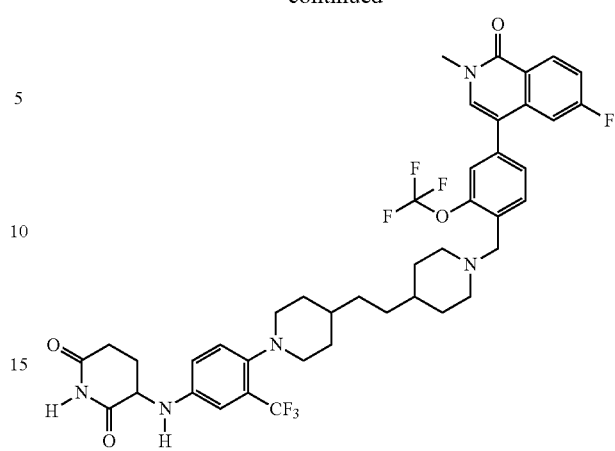

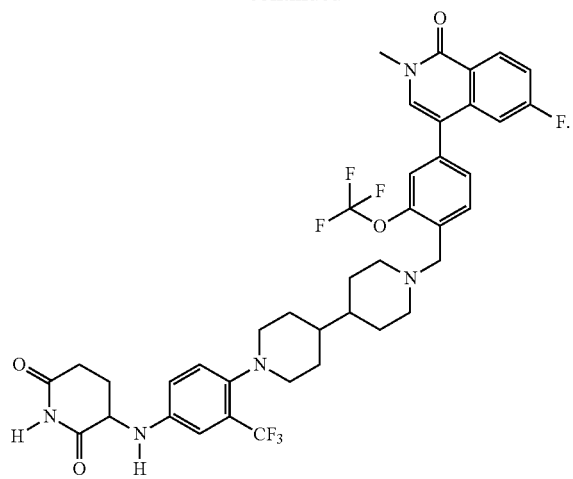
Nonlimiting examples of compounds of the present invention include:
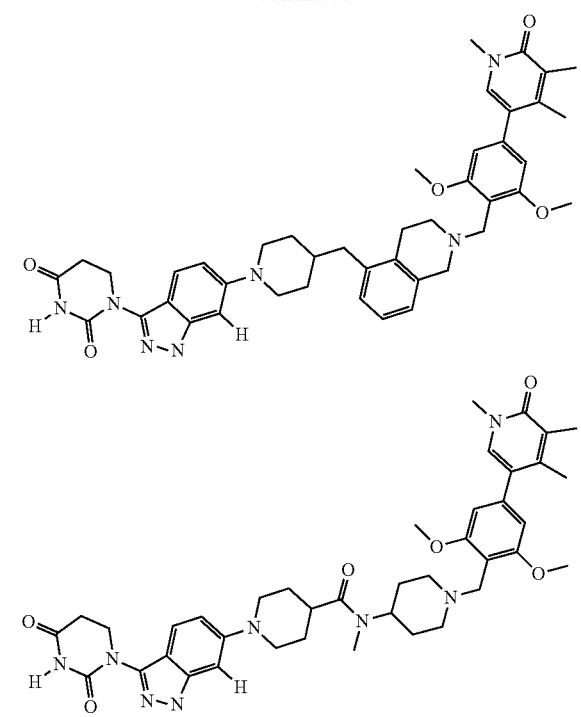
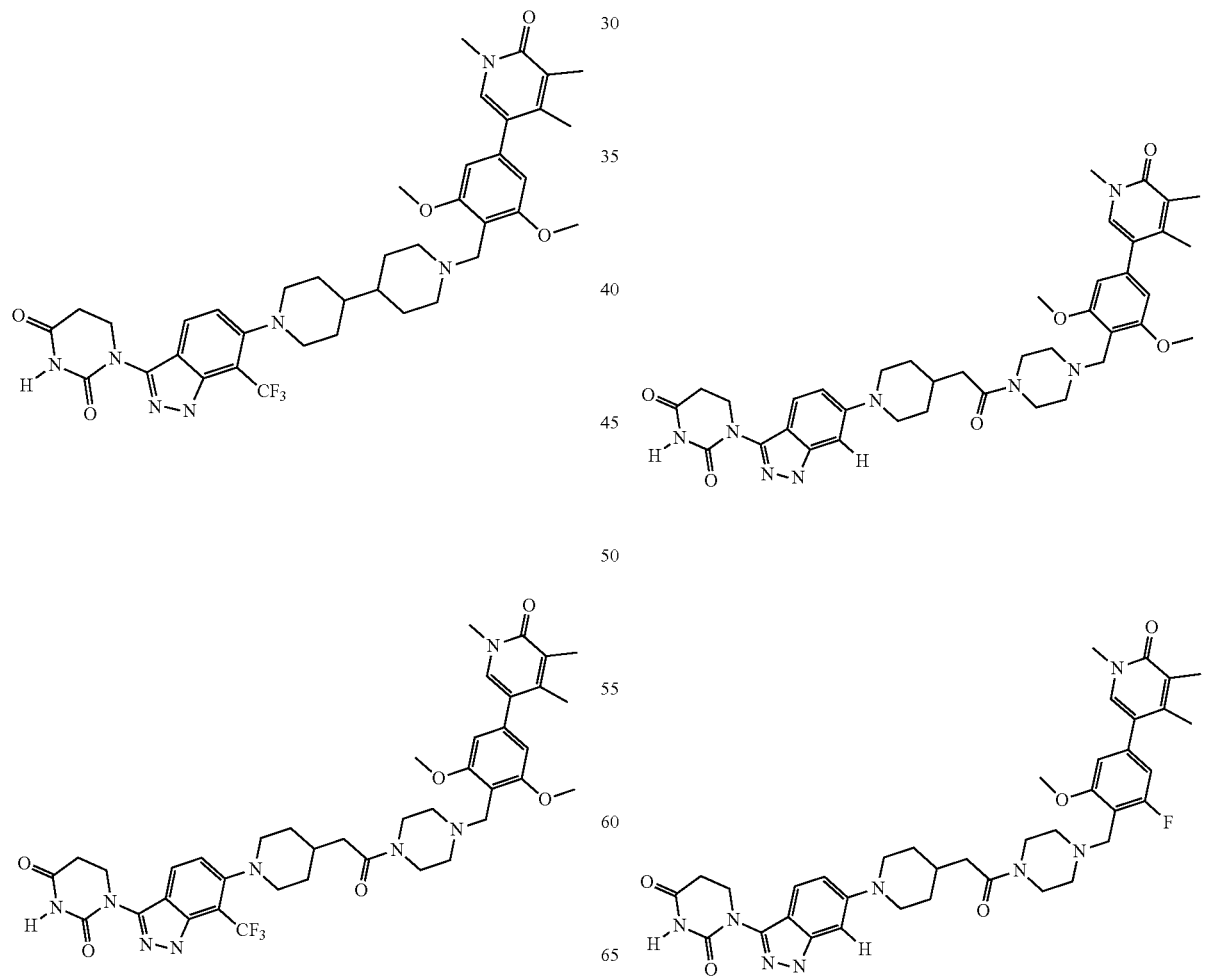

485
-continued
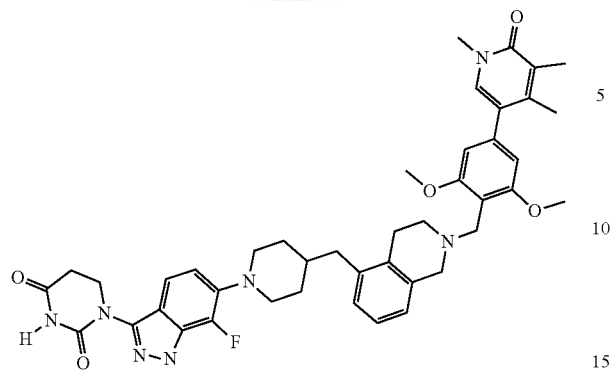
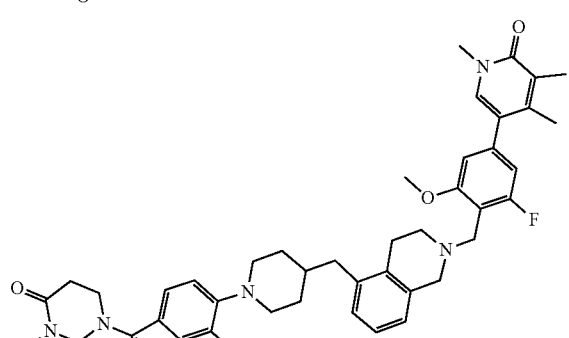
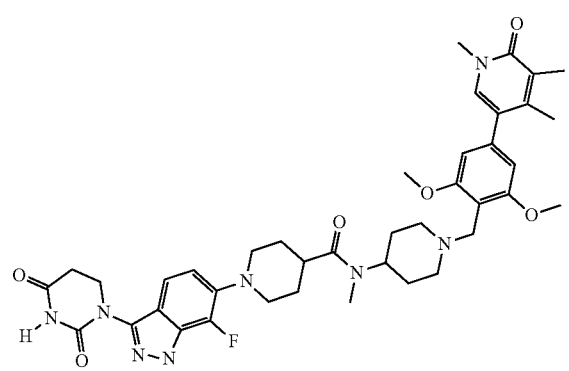
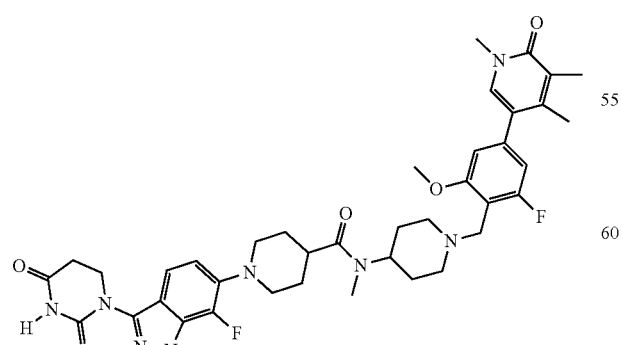
486
-continued
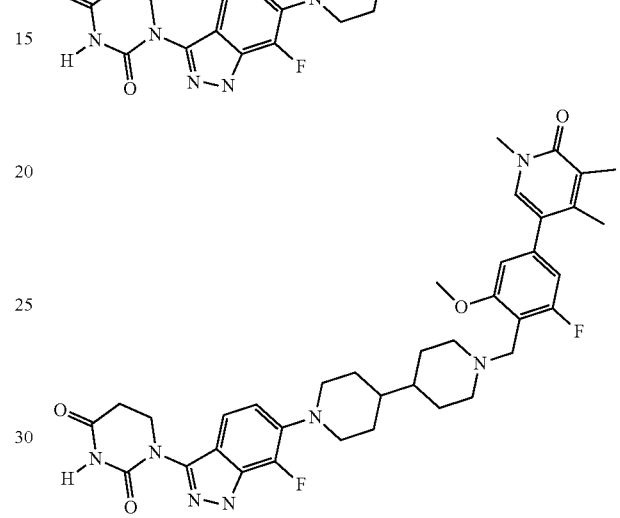
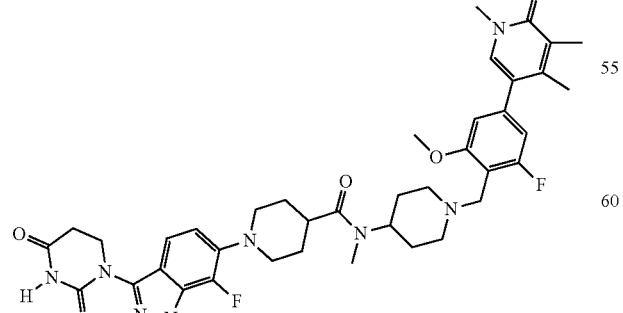

487
-continued
488
-continued
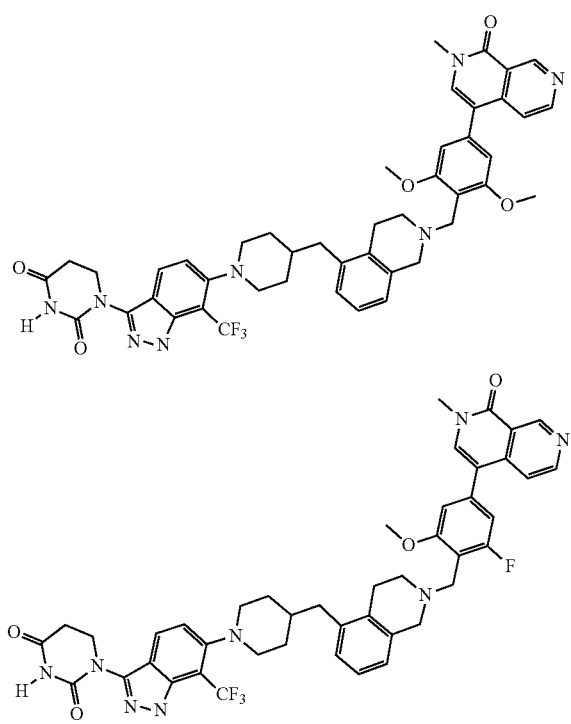
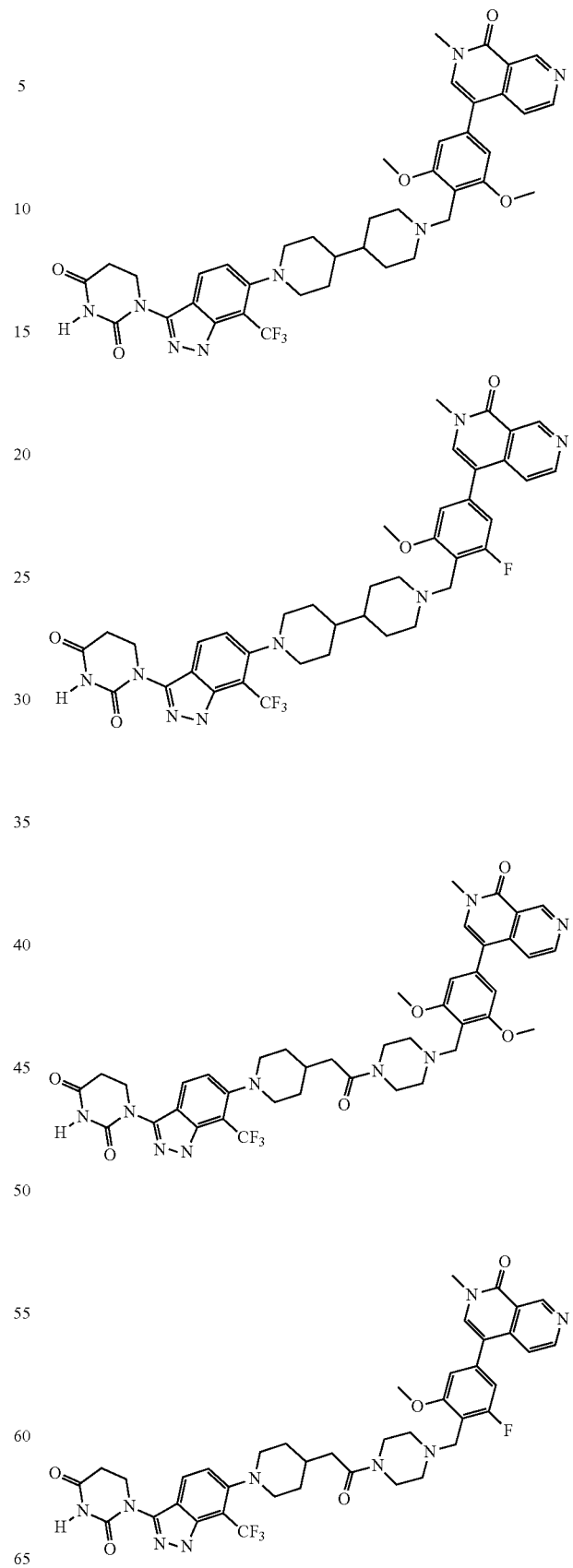

489
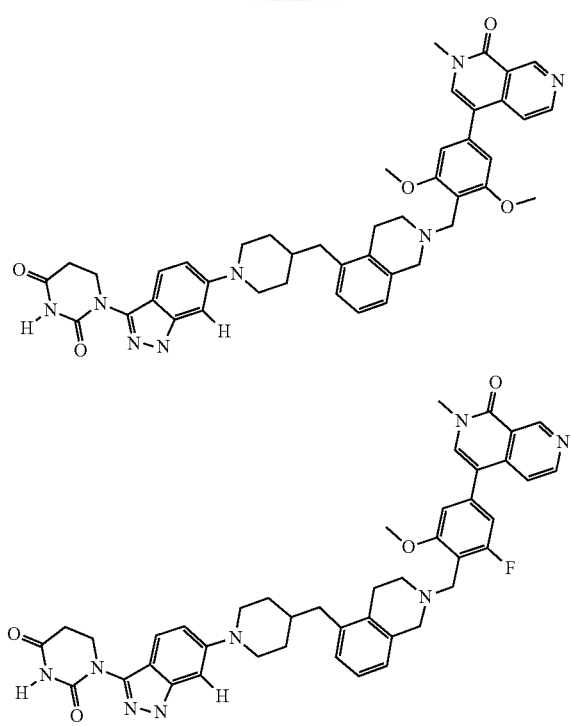
490
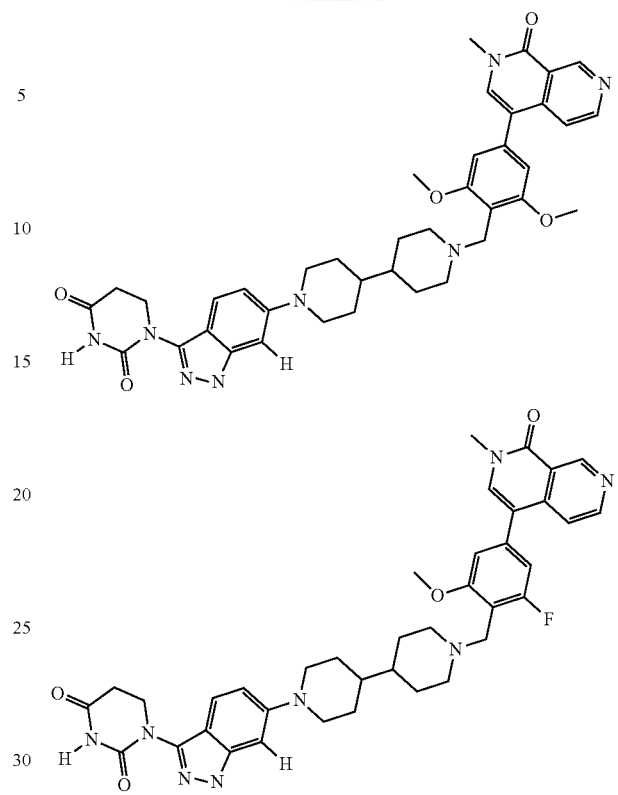
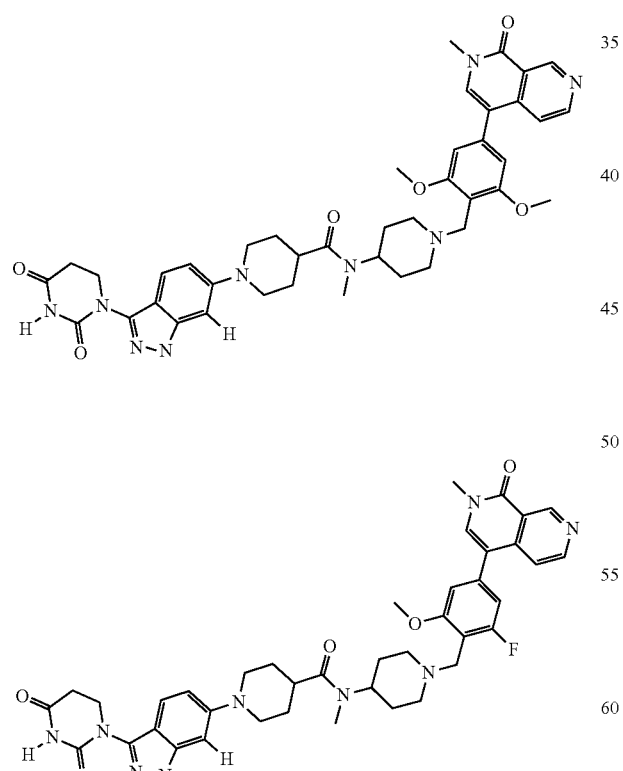
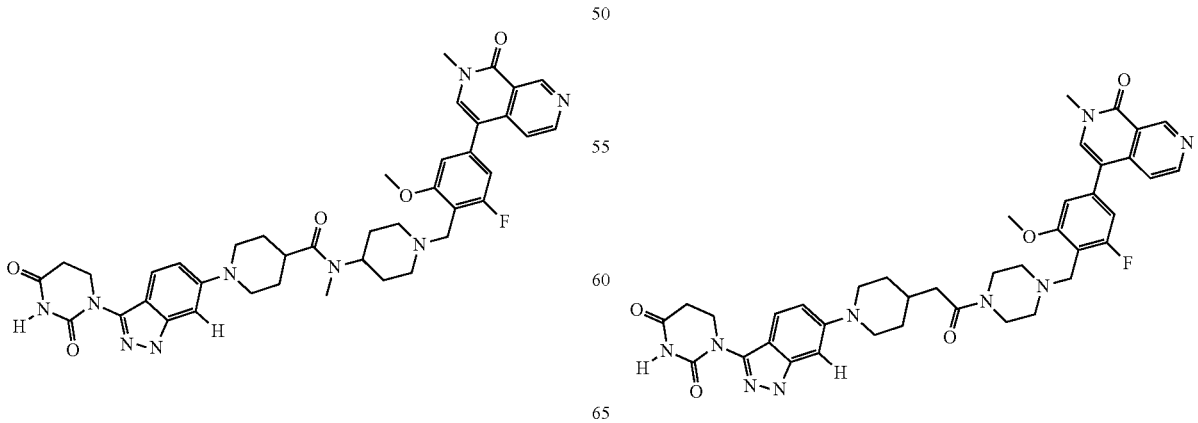

491
-continued
492
-continued
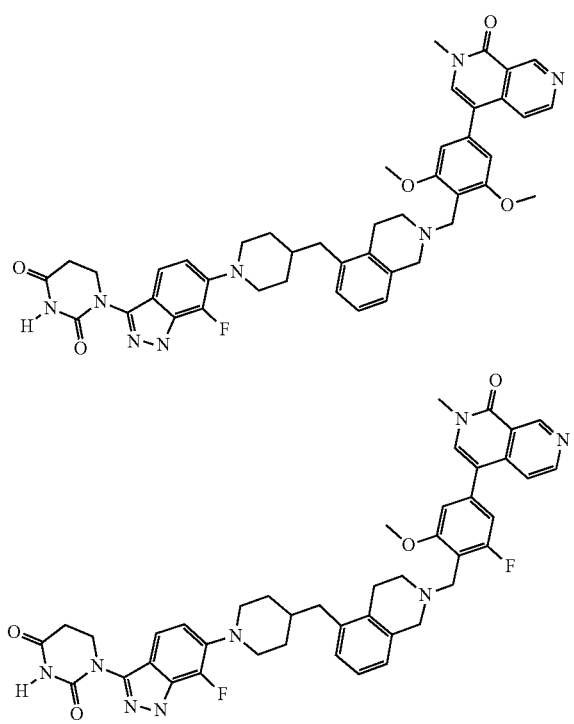
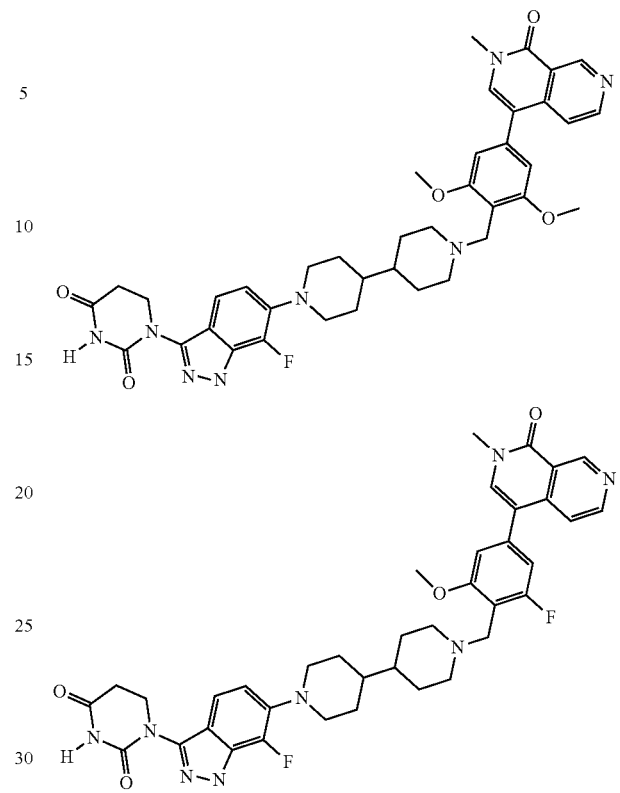
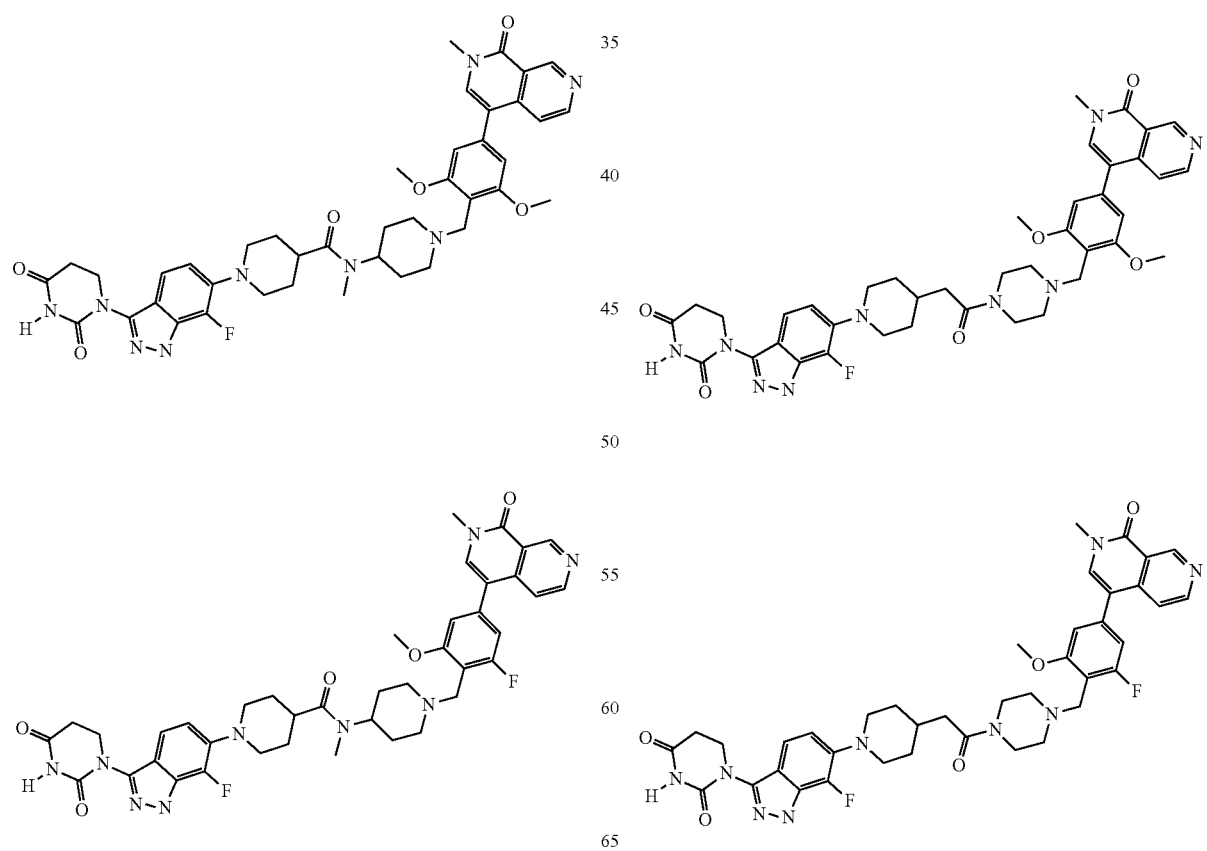

In certain embodiments, the compound of the present invention is:

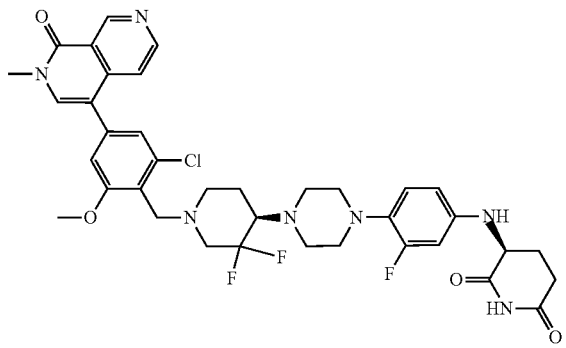

or a pharmaceutically acceptable salt thereof.

In certain embodiments, the compound of the present invention is:

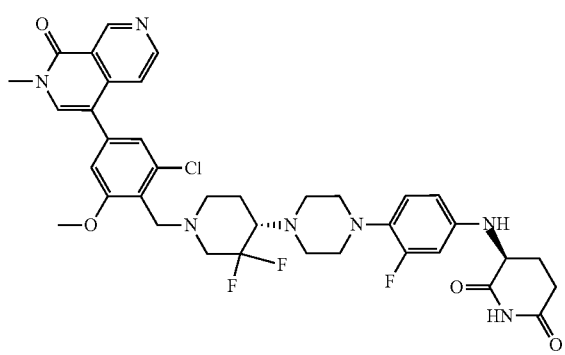

or a pharmaceutically acceptable salt thereof.

In certain embodiments, the compound of the present invention is:

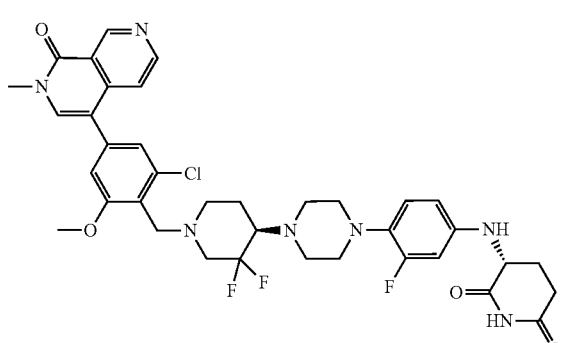

or a pharmaceutically acceptable salt thereof.

In certain embodiments, the compound of the present invention is:

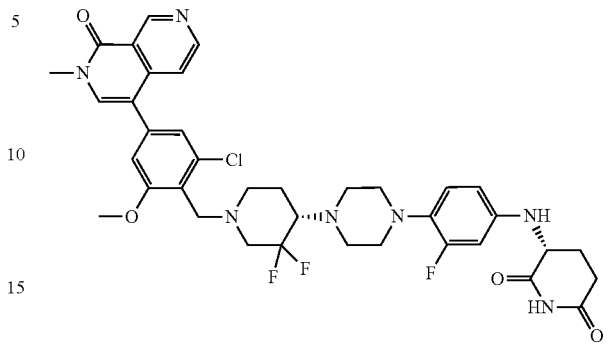

or a pharmaceutically acceptable salt thereof.

In certain embodiments, the compound of the present invention is:

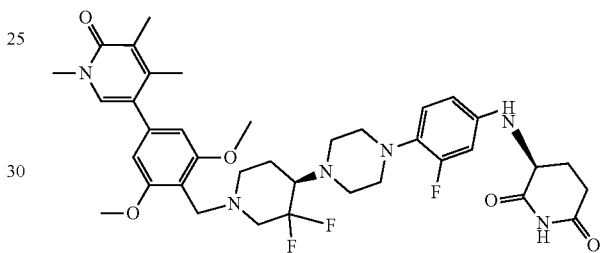

or a pharmaceutically acceptable salt thereof.

In certain embodiments, the compound of the present invention is:

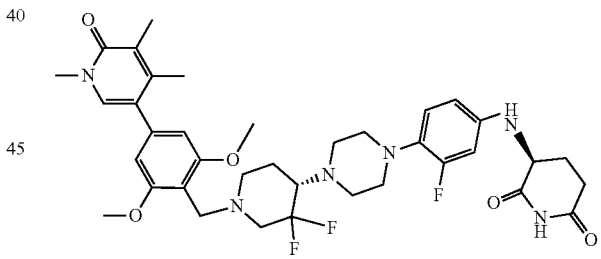

or a pharmaceutically acceptable salt thereof.

In certain embodiments, the compound of the present invention is:

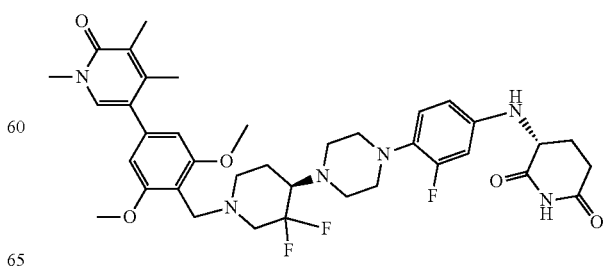

or a pharmaceutically acceptable salt thereof.

In certain embodiments, the compound of the present invention is:

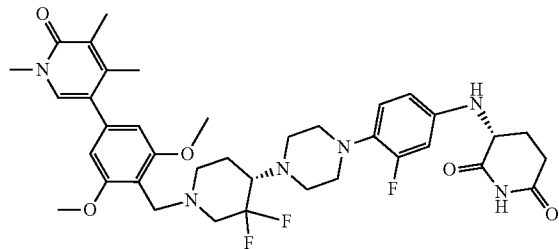

or a pharmaceutically acceptable salt thereof.

In certain embodiments, the compound of the present invention is:

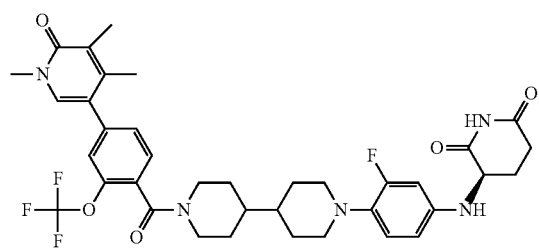

or a pharmaceutically acceptable salt thereof.

In certain embodiments, the compound of the present invention is:

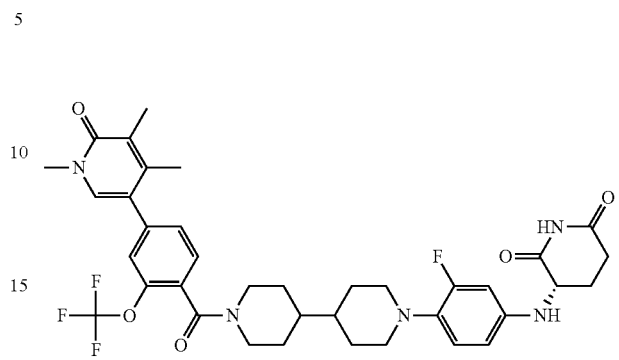

or a pharmaceutically acceptable salt thereof.

In certain embodiments, the compound of the present invention is:

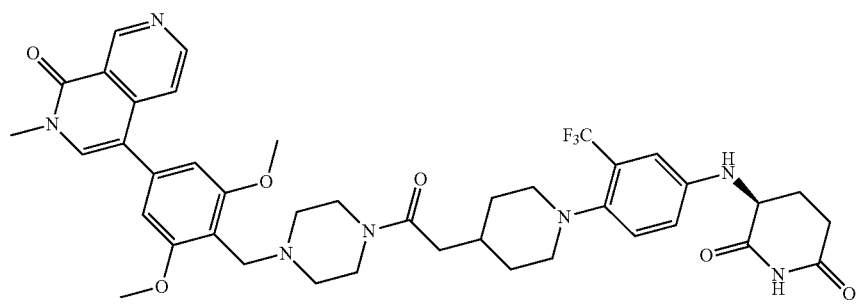 [SMILES: COc1cc(-c2cn(C)c(=O)c3cnccc23)cc(OC)c1CN1CCN(C(=O)CC2CCN(c3ccc(N[C@H]4CCC(=O)NC4=O)cc3C(F)(F)F)CC2)CC1]

or a pharmaceutically acceptable salt thereof.

In certain embodiments, the compound of the present invention is:

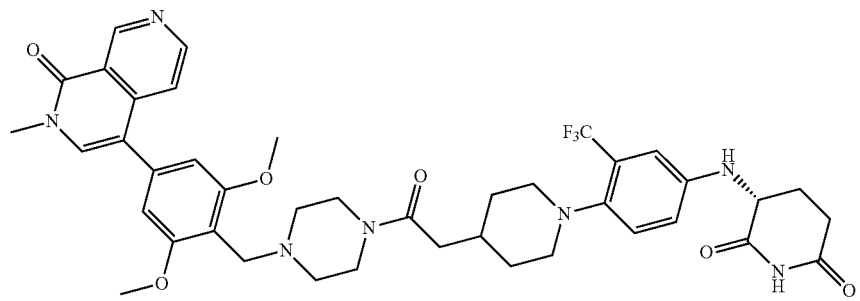 [SMILES: COc1cc(-c2cn(C)c(=O)c3cnccc23)cc(OC)c1CN1CCN(C(=O)CC2CCN(c3ccc(N[C@@H]4CCC(=O)NC4=O)cc3C(F)(F)F)CC2)CC1]

or a pharmaceutically acceptable salt thereof.

In certain embodiments, the compound of the present invention is:

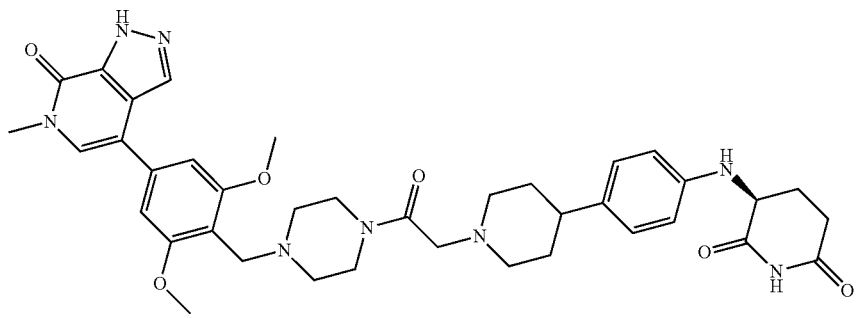 [SMILES: COc1cc(-c2cn(C)c(=O)c3[nH]ncc23)cc(OC)c1CN1CCN(C(=O)CN2CCC(c3ccc(N[C@H]4CCC(=O)NC4=O)cc3)CC2)CC1]

or a pharmaceutically acceptable salt thereof.

In certain embodiments, the compound of the present invention is:

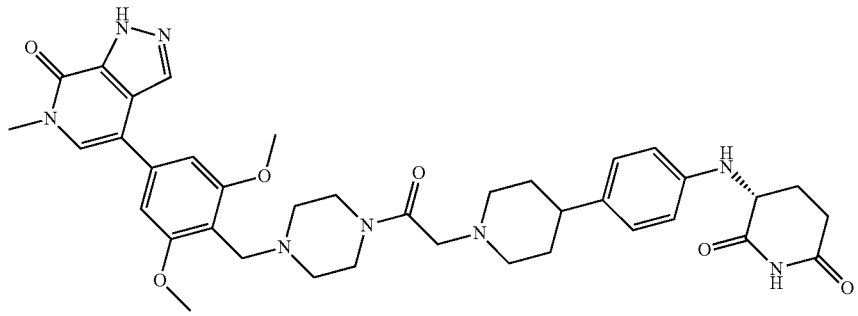

or a pharmaceutically acceptable salt thereof.

Non-Limiting BRD9 Degradation Embodiments

In certain embodiments, the compound of the presentation invention is characterized as having a BRD binding ($K_i$) of less than 200 nM. In certain embodiments, the compound of the presentation invention is characterized as having a BRD binding ($K_i$) of less than 100 nM.

In certain embodiments, the compound of the presentation invention is characterized as having a FP-E3 binding ($K_d$) of less than 2000 nM. In certain embodiments, the compound of the presentation invention is characterized as having a FP-E3 binding ($K_d$) of less than 1000 nM.

In certain embodiments, the compound of the presentation invention is characterized as having BRD9 degradation of less than 10 nM at 2 hours and/or a $K_{endo}$ of less than 10% after 17 hours.

In certain embodiments, the compound of the presentation invention is characterized as having BRD9 degradation kinetics $K_{pc}$ of less than 20 nM.

In certain embodiments, the compound of the presentation invention is characterized as having BRD7 degradation of greater than >999 nM and/or an $E_{max}$ of greater than 95% after 24 hours.

In certain embodiments, the compound of the presentation invention is characterized as having a BRD4 degradation of more than 1000 nM and less than 5000 nM and/or an $E_{max}$ of >60% and less than 90% after 24 hours.

In certain embodiments, the compound of the presentation invention is characterized as having IKZF1/SALL4/GSPT1 degradation of >999 nM.

In certain embodiments, the compound of the presentation invention is characterized as having HEPG2 viability of >999 nM. In certain embodiments, the compound of the presentation invention is characterized as having HEPG2 viability of >10,000 nM.

In certain embodiments, the compound of the presentation invention is characterized as having SW982 viability ($GI_{50}$) of >1000 nM. In certain embodiments, the compound of the presentation invention is characterized as having SW982 viability ($GI_{50}$) of >10,000 nM.

In certain embodiments, the compound of the presentation invention is characterized as having a hERG of >30. In certain embodiments, the compound of the presentation invention is characterized as having a hERG of >60.

VI. Methods of Treatment

A compound as described herein can be used in an effective amount to treat a patient, typically a human patient, in need thereof with a disorder mediated by BRD9.

Another aspect of the present invention provides a compound as described herein, or an enantiomer, diastereomer, or stereoisomer thereof, or pharmaceutically acceptable salt, hydrate, or solvate thereof, or a pharmaceutical composition, for use in the manufacture of a medicament for treating or preventing cancer or more generally abnormal cellular proliferation in a patient, for example a human, in need thereof, wherein the cancer or abnormally proliferating cell comprises an activated BRD9 or wherein there is a need of BRD9 inhibition for the treatment or prevention of cancer.

In certain embodiments, the method comprises administering an effective amount of the active compound or its salt as described herein, optionally including a pharmaceutically acceptable excipient, carrier, or adjuvant (i.e., a pharmaceutically acceptable composition), or optionally in combination or alternation with another bioactive agent or combination of agents, to a patient in need thereof.

In certain embodiments, the present invention provides a method of treating any of the disorders described herein, in a patient in need thereof.

In other embodiments, the patient is administered an additional therapeutic agent. In other embodiments, the compound as described herein, and the additional therapeutic agent are administered simultaneously or sequentially.

In certain embodiments, the application provides a method of preventing any of the disorders described herein, in a patient in need thereof.

In certain embodiments, the patient is a human.

In certain embodiments a compound of the present invention is used to treat a refractory disorder, for example a refractory cancer. In certain embodiments a compound of the present invention is used to treat a relapsed disorder, for example a relapsed cancer. In further embodiments a compound of the present invention is used to treat a refractory and reflapsed disorder, for example a refractory and relapsed cancer. In further embodiments a compound of the present invention is used to treat a multiply drug resistant disorder, for example a multiply drug resistant cancer.

In certain embodiments a compound of the present invention is used to treat a SMARCB1-perturbed cancer, for example a SMARCB1-perturbed solid tumor.

In certain embodiments the BRD9 mediated disorder is synovial sarcoma, malignant rhabdoid tumor, atypical teratoid or rhabdoid tumor, epitheliod sarcoma, renal medullary carcinoma, epitheliod malignant peripheral nerve sheath tumor, myoepithelial carcinoma, extraskeletal myxoid chondrosarcoma, chordoma, pancrease undifferentiated rhabdoid carcinoma, sinonasal basaloid carcinoma, or rhabdoid carcinoma of the gastrointestinal tract.

In certain embodiments the BRD9 mediated disorder is synovial sarcoma.

In certain embodiments the BRD9 mediated disorder is a malignant rhabdoid tumor.

In certain embodiments the BRD9 mediated disorder is a atypical teratoid or rhabdoid tumor.

In certain embodiments the BRD9 mediated disorder is epitheliod sarcoma.

In certain embodiments the BRD9 mediated disorder is a renal medullary carcinoma.

In certain embodiments the BRD9 mediated disorder is a epitheliod malignant peripheral nerve sheath tumor.

In certain embodiments the BRD9 mediated disorder is a myoepithelial carcinoma.

In certain embodiments the BRD9 mediated disorder is a extraskeletal myxoid chondrosarcoma.

In certain embodiments the BRD9 mediated disorder is chordoma.

In certain embodiments the BRD9 mediated disorder is pancrease undifferentiated rhabdoid carcinoma.

In certain embodiments the BRD9 mediated disorder is a sinonasal basaloid carcinoma.

In certain embodiments the BRD9 mediated disorder is rhabdoid carcinoma of the gastrointestinal tract.

As inhibitors of BRD9, the compounds and compositions of this application are particularly useful for treating or lessening the severity of a disease, condition, or disorder where a bromodomain protein is implicated in the disease, condition, or disorder.

In one aspect, the present invention provides a method for treating or lessening the severity of a disease, condition, or disorder where a bromodomain protein is implicated in the disease state.

Another aspect of the present invention provides a method of inhibiting or decreasing the amount of bromodomain protein in a patient in need thereof comprising administering an effective amount of a compound as described herein or an enantiomer, diastereomer, or stereoisomer thereof, or pharmaceutically acceptable salt, hydrate, or solvate thereof, and optionally a pharmaceutically acceptable carrier.

Another aspect of the prevent invention provides a method of treating a bromodomain protein mediated disorder, the method comprising administering to a patient in need thereof an effective amount of a compound as described herein, or an enantiomer, diastereomer, or stereoisomer thereof, or pharmaceutically acceptable salt, hydrate, or solvate thereof; and optionally a pharmaceutically acceptable carrier.

Another aspect of the present invention provides a method of treating or preventing a proliferative disease. The method comprises administering an effective amount of a pharmaceutical composition comprising a compound as described herein, or an enantiomer, diastereomer, or stereoisomer thereof, or pharmaceutically acceptable salt, hydrate, or solvate thereof and optionally a pharmaceutically acceptable carrier to a patient in need thereof.

In some embodiments, the disease is mediated by BRD9. In other embodiments, BRD9 plays a role in the initiation or development of the disease.

In certain embodiments, the BRD9 mediated disorder comprises a benign growth, metastasis, neoplasm, tumor, solid tumor, rhabdoid tumor, malignant rhabdoid tumor, carcinoma, leukemia, cancer, abnormal cellular proliferation, graft-versus-host rejection, an amyloid-based proteinopathy, a proteinopathy, fibrotic disorder, inflammation, arthritis, pulmonary disorders, and immune disorders.

In certain embodiments, the disorder treated by the present invention is a SS18-SSX fusion protein related disorder. In certain embodiments, the disorder treated by the present invention is a SS18 protein related disorder. In certain embodiments, the disorder treated by the present invention is a SSX protein related disorder.

In certain embodiments, the disease or disorder is cancer or a proliferation disease.

In certain embodiments, the BRD9 mediated disorder is an abnormal cell proliferation, including, but not limited to, a tumor or cancer, or a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder.

In certain embodiments, the hematological cancer is acute myelogenous leukemia (AML), acute lymphoblastic leukemia (ALL), lymphoblastic T-cell leukemia, chronic myelogenous leukemia (CML), chronic lymphocytic leukemia (CLL), hairy-cell leukemia, chronic neutrophilic leukemia (CNL), acute lymphoblastic T-cell leukemia, acute monocytic leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukemia (MLL), erythroleukemia, malignant lymphoma, Hodgkins lymphoma, non-Hodgkins lymphoma, lymphoblastic T-cell lymphoma, Burkitt's lymphoma, follicular lymphoma, B cell acute lymphoblastic leukemia, diffuse large B cell lymphoma, Myc and B-Cell Leukemia (BCL)2 and/or BCL6 rearrangements/overexpression [double- and triple-hit lymphoma], myelodysplastic/myeloproliferative neoplasm, mantle cell lymphoma including bortezomib resistant mantle cell lymphoma.

Solid tumors that can be treated with the compounds described herein include, but are not limited to lung cancers, including small cell lung cancer (SCLC) and non-small cell lung cancer (NSCLC), breast cancers including inflammatory breast cancer, ER-positive breast cancer including tamoxifen resistant ER-positive breast cancer, and triple negative breast cancer, colon cancers, midline carcinomas, liver cancers, renal cancers, prostate cancers including castrate resistant prostate cancer (CRPC), brain cancers including gliomas, glioblastomas, neuroblastoma, and medulloblastoma including MYC-amplified medulloblastoma, colorectal cancers, Wilm's tumor, Ewing's sarcoma, rhabdomyosarcomas, ependymomas, head and neck cancers, melanomas, squamous cell carcinomas, ovarian cancers, pancreatic cancers including pancreatic ductal adenocarcinomas (PDAC) and pancreatic neuroendocrine tumors (PanNET), osteosarcomas, giant cell tumors of bone, thyroid cancers, bladder cancers, urothelial cancers, vulval cancers, cervical cancers, endometrial cancers, mesotheliomas, esophageal cancers, salivary gland cancers, gastric cancers, nasopharangeal cancers, buccal cancers, cancers of the mouth, GIST (gastrointestinal stromal tumors), NUT-midline carcinomas, testicular cancers, squamous cell carcinomas, hepatocellular carcinomas (HCC), MYCN driven solid tumors, and NUT midline carcinomas (NMC).

In further embodiments, the disease or disorder is sarcoma of the bones, muscles, tendons, cartilage, nerves, fat, or blood vessels.

In further embodiments, the disease or disorder is soft tissue sarcoma, bone sarcoma, or osteosarcoma.

In further embodiments, the disease or disorder is angiosarcoma, fibrosarcoma, liposarcoma, leiomyosarcoma, Karposi's sarcoma, osteosarcoma, gastrointestinal stromal tumor, synovial sarcoma, Pleomorphic sarcoma, chondrosarcoma, Ewing's sarcoma, reticulum cell sarcoma, meningiosarcoma, botryoid sarcoma, rhabdomyosarcoma, or embryonal rhabdomyosarcoma.

In certain embodiments the disorder is a bone, muscle, tendon, cartilage, nerve, fat, or blood vessel sarcoma.

In further embodiments, the disease or disorder is multiple myeloma.

In further embodiments, the disease or disorder is synovial sarcoma. The connection between synovial sarcoma and BRD9 has been described in the literature. For example, the paper by Brien et al., titlted "Targeted degradation of BRD9 reverses oncogenic gene expression in synovial sarcoma" describes the high sensitivity of synovial sarcoma tumours to administration of BRD9 degraders. Similarly, the paper by Michel et al, titlted "A non-canonical SWI/SNF complex is a synthetic lethal target in cancers driven by BAF complex perturbation" describes the role of BAF in synovial sarcoma and BRD9's role in synovial sarcoma proliferation.

In certain embodiments, the BRD9 mediated disorder is an inflammatory disease, including but not limited to asthma, chronic peptic ulcers, tuberculosis, rheumatoid arthritis, periodontitis, ulcerative colitis, Crohn's disease, or hepatitis.

In other embodiments, the disease or disorder is inflammation, arthritis, rheumatoid arthritis, spondyiarthropathies, gouty arthritis, osteoarthritis, juvenile arthritis, and other arthritic conditions, neuroinflammation, allergy, pain, neuropathic pain, fever, pulmonary disorders, lung inflammation, adult respiratory distress chronic pulmonary inflammatory disease, and chronic obstructive pulmonary disease (COPD), liver disease and nephritis, gastrointestinal conditions, inflammatory bowel disease, Crohn's disease, gastritis, irritable bowel syndrome, ulcerative colitis, ulcerative diseases, gastric ulcers, autoimmune disease, graft vs. host reaction and allograft rejections, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, peripheral neuropathy, or B-Cell Lymphoma.

In other embodiments, the pharmaceutical composition comprising the compound as described herein and the additional therapeutic agent are administered simultaneously or sequentially.

In other embodiments, the disease or disorder is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, solid tumors, hematological cancers or solid cancers.

In some embodiments, said method is used to treat or prevent a condition selected from autoimmune diseases, inflammatory diseases, proliferative and hyperproliferative diseases, and immunologically-mediated diseases. In other embodiments, said condition is selected from a proliferative disorder.

In certain embodiments, the BRD9 mediated disorder is an immune disorder, including but not limited to, autoimmune disorders such as Addison disease, Celiac disease, dermatomyositis, Graves disease, thyroiditis, multiple sclerosis, pernicious anemia, reactive arthritis, lupus, or type I diabetes.

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers, such as oral, laryngeal, nasopharyngeal and esophageal, genitourinary cancers, such as prostate, bladder, renal, uterine, ovarian, testicular, lung cancer, such as small-cell and non-small cell, breast cancer, pancreatic cancer, melanoma and other skin cancers, stomach cancer, brain tumors, tumors related to Gorlin's syndrome, such as medulloblastoma or meningioma, and liver cancer.

Additional exemplary forms of cancer include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more compound as described herein, in the manufacture of a medicament for the treatment of cancer, including without limitation the various types of cancer disclosed herein.

In some embodiments, the compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compound as described herein is useful for treating hematopoietic disorders, in particular, acute-myelogenous leukemia (AML), chronic-myelogenous leukemia (CML), acute-promyelocytic leukemia, and acute lymphocytic leukemia (ALL).

In one embodiment, a compound or its corresponding pharmaceutically acceptable salt, or isotopic derivative, as described herein can be used in an effective amount to treat a host, for example a human, with a lymphoma or lymphocytic or myelocytic proliferation disorder or abnormality. For example, a compound as described herein can be administered to a host suffering from a Hodgkin's Lymphoma or a Non-Hodgkin's Lymphoma. For example, the host can be suffering from a Non-Hodgkin's Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); diffuse small-cleaved cell lymphoma (DSCCL); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; Langerhans cell histiocytosis; or Waldenstrom's Macroglobulinemia.

In another embodiment, a compound or its corresponding pharmaceutically acceptable salt, or isotopic derivative, as described herein can be used in an effective amount to treat a patient, for example a human, with a Hodgkin's lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin's Lymphoma; or Nodular Lymphocyte Predominant HL.

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

As inhibitors of BRD9 protein, the compounds and compositions of this application are also useful in biological samples. One aspect of the application is inhibiting protein activity in a biological sample, which method comprises contacting said biological sample with a compound or composition as described herein. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein activity in a biological sample is useful for a variety of purposes that are known to one of skill in the art. Examples of such purposes include, but are not limited to, blood transfusion, organ-transplantation, and biological specimen storage.

Another aspect of this application is the study of BRD9 protein in biological and pathological phenomena; the study of intracellular signal transduction pathways mediated by such proteins; and the comparative evaluation of new protein inhibitors. Examples of such uses include, but are not limited to, biological assays such as enzyme assays and cell-based assays.

The activity of the compounds and compositions of the present application as BRD9 inhibitors may be assayed in vitro, in vivo, or in a cell line. In vitro assays include assays that determine inhibition of either the enzyme activity or ATPase activity of the activated protein. Alternate in vitro assays quantitate the ability of the inhibitor to bind to the bromodomain protein and may be measured either by radio labelling the inhibitor prior to binding, isolating the inhibitor/bromodomain complex and determining the amount of radio label bound, or by running a competition experiment where new inhibitors are incubated with the bromodomain bound to known radioligands. Detailed conditions for assaying a compound utilized in this application as an inhibitor of various bromodomain proteins are set forth in the Examples below.

In accordance with the foregoing, the present application further provides a method for preventing or treating any of the diseases or disorders described above in a patient in need of such treatment, which method comprises administering to said patient a therapeutically effective amount of a compound as described herein, or an enantiomer, diastereomer, or stereoisomer thereof, or pharmaceutically acceptable salt, hydrate, or solvate thereof. For any of the above uses, the required dosage will vary depending on the mode of administration, the particular condition to be treated and the effect desired.

VII. Combination Therapy

The compounds of Formula I, Formula II, Formula III, Formula IV, Formula V, or Formula VI, or a pharmaceutically acceptable salt thereof can be used in an effective amount, either alone or in combination, to treat a patient such as a human with a disorder as described herein or a BRD9 mediated disorder.

The disclosed compounds described herein can be used in an effective amount alone or in combination with another compound of the present invention or another bioactive agent or second therapeutic agent to treat a patient such as a human with a disorder, including but not limited to those described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a patient in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In certain embodiments the checkpoint inhibitor is selected from nivolumab/OPDIVO®; pembrolizumab/KEYTRUDA®; and pidilizumab/CT-011, MPDL3280A/RG7446; MEDI4736; MSB0010718C; BMS 936559, a PDL2/Ig fusion protein such as AMP 224 or an inhibitor of B7-H3 (e.g., MGA271), B7-H4, BTLA, HVEM, TIM3, GAL9, LAG 3, VISTA, KIR, 2B4, CD160, CGEN-15049, CHK 1, CHK2, A2aR, B-7 family ligands, or a combination thereof.

In yet another embodiment, one of the active compounds described herein can be administered in an effective amount for the treatment of abnormal tissue of the female reproductive system such as breast, ovarian, endometrial, or uterine cancer, in combination or alternation with an effective amount of an estrogen inhibitor including, but not limited to, a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors.

Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138.

Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestratnt; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone.

Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including, but not limited to a selective androgen receptor modulator, a selective androgen receptor degrader, a complete androgen receptor degrader, or another form of partial or complete androgen antagonist. In one embodiment, the prostate or testicular cancer is androgen-resistant.

Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the bioactive agent is an HER-2 inhibitor. Examples of HER-2 inhibitors include trastuzumab, lapatinib, ado-trastuzumab emtansine, and pertuzumab.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl] amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl) phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one embodiment, the bioactive agent is a kinase inhibitor. In one embodiment, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include, but are not limited to, Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl] oxy}phosphonium)), BYL-719 ((2S)-N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl) amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl) thieno[3,2-d]pyrimidine), GDC-0980 ((S)-1-(4-((2-(2-aminopyrimidin-5-yl)-7-methyl-4-morpholinothieno[3,2-d] pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10, 13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422).

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R-N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)-N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)-N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-f{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, but are not limited to, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl] methyl dihydrogen phosphate), fostamatinib disodium salt (sodium (6-((5-fluoro-2-((3,4,5-trimethoxyphenyl)amino) pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In one embodiment, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl) acetamide), selumetinib (6-(4-bromo-2-chloroanilino)-7-fluoro-N-(2-hydroxyethoxy)-3-methylbenzimidazole-5- carboxamide), pimasertib/AS703026/MSC 1935369 ((S)-N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the bioactive agent is an AKT inhibitor, including, but not limited to, MK-2206, GSK690693, Perifosine, (KRX-0401), GDC-0068, Triciribine, AZD5363, Honokiol, PF-04691502, and Miltefosine, a FLT-3 inhibitor, including, but not limited to, P406, Dovitinib, Quizartinib (AC220), Amuvatinib (MP-470), Tandutinib (MLN518), ENMD-2076, and KW-2449, or a combination thereof.

In one embodiment, the bioactive agent is an mTOR inhibitor. Examples of mTOR inhibitors include, but are not limited to, rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)-N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, aFLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, of atumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR₁KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In certain embodiments the compound is administered in combination with ifosfamide.

In one embodiment, the bioactive agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilzomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™).

Examples of additional suitable chemotherapeutic agents include, but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In some embodiments, the compound of the present invention is administered in combination with a chemotherapeutic agent (e.g., a cytotoxic agent or other chemical compound useful in the treatment of cancer). Examples of chemotherapeutic agents include alkylating agents, antimetabolites, folic acid analogs, pyrimidine analogs, purine analogs and related inhibitors, vinca alkaloids, epipodopyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Inti. Ed Engl. 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epoth-ilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, NJ), ABRAXANE®, cremophor-free, albumin-engineered nanoparticle formulation of paclitaxel (American Pharmaceutical Partners, Schaumberg, IL), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-1 1); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the compound of the present invention. Suitable dosing regimens of combination chemotherapies are known in the ar. For example combination dosing regimes are described in Saltz et al., Proc. Am. Soc. Clin. Oncol. 18:233a (1999) and Douillard et al., Lancet 355(9209): 1041-1047 (2000).

Additional therapeutic agents that can be administered in combination with a Compound disclosed herein can include bevacizumab, sutinib, sorafenib, 2-methoxyestradiol or 2ME2, finasunate, vatalanib, vandetanib, aflibercept, voloximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one embodiment, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a SiP receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SVIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In some embodiments, the bioactive agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-1-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOURIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The combination therapy may include a therapeutic agent which is a non-drug treatment. For example, the compound could be administered in addition to radiation therapy, cryotherapy, hyperthermia, and/or surgical excision of tumor tissue.

In certain embodiments the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

In certain embodiments the second therapeutic agent is administered on a different dosage schedule than the compound of the present invention. For example the second therapeutic agent may have a treatment holiday of 1 day, 2 days, 3 days, 4 days, 5 days, 6 days, 7 days, 8 days, 9 days, 10 days, 11 days, 12 days, 13 days, or 14 days per treatment cycle. In another embodiment the first therapeutic agent has a treatment holiday. For example the first therapeutic agent may have a treatment holiday of 1 day, 2 days, 3 days, 4 days, 5 days, 6 days, 7 days, 8 days, 9 days, 10 days, 11 days, 12 days, 13 days, or 14 days per treatment cycle. In certain embodiments both the first and second therapeutic have a treatment holiday.

VIII. Pharmaceutical Compositions

The compound of Formula I, Formula II, Formula III, Formula IV, Formula V, or Formula VI, as described herein can be administered as the neat chemical, but are more typically administered as a pharmaceutical composition, that includes an effective amount for a patient, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt.

In an alternative embodiment patient can be treated with low dosage therapy. For example the pharmaceutical composition can be in a dosage form that contains from about 0.1 µg to about 2000 µg, from about 10 µg to about 1000 µg, from about 100 µg to about 800 µg, or from about 200 µg to about 600 µg of the active compound. Examples are dosage forms with at least 0.1, 1, 5, 10, 25, 50, 100, 200, 250, 300, 400, 500, 600, 700, or 750 mg of active compound, or its salt.

In some embodiments, compounds disclosed herein or used as described are administered once a day (QD), twice a day (BID), or three times a day (TID). In some embodiments, compounds disclosed herein or used as described are administered at least once a day for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a day, twice a day, three times a day, or four times a day.

In certain embodiments the compound of the present invention is administered orally once a day. In certain embodiments the compound of the present invention is administered orally twice a day. In certain embodiments the compound of the present invention is administered orally three times a day. In certain embodiments the compound of the present invention is administered orally four times a day.

In certain embodiments the compound of the present invention is administered intravenously once a day. In certain embodiments the compound of the present invention is administered intravenously twice a day. In certain embodiments the compound of the present invention is administered intravenously three times a day. In certain embodiments the compound of the present invention is administered intravenously four times a day.

In some embodiments, compounds disclosed herein or used as described are administered once a day (QD), twice a day (BID), or three times a day (TID). In some embodiments, compounds disclosed herein or used as described are administered at least once a day for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a day, twice a day, three times a day, or four times a day.

In certain embodiments the compound of the present invention is administered orally once a day. In certain embodiments the compound of the present invention is administered orally twice a day. In certain embodiments the compound of the present invention is administered orally three times a day. In certain embodiments the compound of the present invention is administered orally four times a day.

In certain embodiments the compound of the present invention is administered intravenously once a day. In certain embodiments the compound of the present invention is administered intravenously twice a day. In certain embodiments the compound of the present invention is administered intravenously three times a day. In certain embodiments the compound of the present invention is administered intravenously four times a day.

In some embodiments, compounds disclosed herein or used as described are administered once a week (QW), twice a week (BIW), or three times a week (TIW). In some embodiments, compounds disclosed herein or used as described are administered at least once a week for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a week, twice a week, three times a week, four times a week, five times a week, six times a week, or seven times a week.

In certain embodiments the compound of the present invention is administered orally once a week. In certain embodiments the compound of the present invention is administered orally twice a week. In certain embodiments the compound of the present invention is administered orally three times a week. In certain embodiments the compound of the present invention is administered orally four times a week.

In certain embodiments the compound of the present invention is administered intravenously once a week. In certain embodiments the compound of the present invention is administered intravenously twice a week. In certain embodiments the compound of the present invention is administered intravenously three times a week. In certain embodiments the compound of the present invention is administered intravenously four times a week.

In some embodiments the compound of the present invention is administered with a treatment holiday in between treatment cycles. For example the compound may have a treatment holiday of 1 day, 2 days, 3 days, 4 days, 5 days, 6 days, 7 days, 8 days, 9 days, 10 days, 11 days, 12 days, 13 days, or 14 days per treatment cycle.

The pharmaceutical composition may also include a molar ratio of the active compound and an additional active agent. For example the pharmaceutical composition may contain a molar ratio of about 0.5:1, about 1:1, about 2:1, about 3:1 or from about 1.5:1 to about 4:1 of an anti-inflammatory or immunosuppressing agent.

These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

A pharmaceutically or therapeutically effective amount of the composition will be delivered to the patient. The precise effective amount will vary from patient to patient, and will depend upon the species, age, the subject's size and health, the nature and extent of the condition being treated, recommendations of the treating physician, and the therapeutics or combination of therapeutics selected for administration. The effective amount for a given situation can be determined by routine experimentation. For purposes of the disclosure, a therapeutic amount may for example be in the range of about 0.01 mg/kg to about 250 mg/kg body weight, more typically about 0.1 mg/kg to about 10 mg/kg, in at least one dose. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

In certain embodiments the dose ranges from about 0.01-100 mg/kg of patient bodyweight, for example about 0.01 mg/kg, about 0.05 mg/kg, about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packed tablets, capsules, and powders in vials or ampoules. Also, the unit dosage form can be a capsule, tablet, cachet, or lozenge itself, or it can be the appropriate number of any of these in packaged form.

In certain embodiments the compound is administered as a pharmaceutically acceptable salt. Non-limiting examples of pharmaceutically acceptable salts include: acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

Thus, the composition of the disclosure can be administered as a pharmaceutical formulation including one suitable for oral (including buccal and sub-lingual), rectal, nasal, topical, transdermal, pulmonary, vaginal or parenteral (including intramuscular, intra-arterial, intrathecal, subcutaneous and intravenous), injections, inhalation or spray, intra-aortal, intracranial, subdermal, intraperitoneal, subcutaneous, or by other means of administration containing conventional pharmaceutically acceptable carriers. A typical manner of administration is oral, topical or intravenous, using a convenient daily dosage regimen which can be adjusted according to the degree of affliction.

Depending on the intended mode of administration, the pharmaceutical compositions can be in the form of solid, semi-solid or liquid dosage forms, such as, for example, tablets, suppositories, pills, capsules, powders, liquids, syrup, suspensions, creams, ointments, lotions, paste, gel, spray, aerosol, foam, or oil, injection or infusion solution, a transdermal patch, a subcutaneous patch, an inhalation formulation, in a medical device, suppository, buccal, or sublingual formulation, parenteral formulation, or an ophthalmic solution, or the like, preferably in unit dosage form suitable for single administration of a precise dosage.

Some dosage forms, such as tablets and capsules, are subdivided into suitably sized unit doses containing appropriate quantities of the active components, e.g., an effective amount to achieve the desired purpose. The compositions will include an effective amount of the selected drug in combination with a pharmaceutically acceptable carrier and, in addition, can include other pharmaceutical agents, adjuvants, diluents, buffers, and the like.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to adjuvants, binders, buffering agents, coloring agents, diluents, disintegrants, excipients, emulsifiers, flavorants, gels, glidents, lubricants, preservatives, stabilizers, surfactants, solubilizer, tableting agents, wetting agents or solidifying material.

Some carriers may be listed in more than one class, for example vegetable oil may be used as a lubricant in some formulations and a diluent in others.

Exemplary pharmaceutically acceptable carriers include sugars, starches, celluloses, powdered tragacanth, malt, gelatin; talc, petroleum jelly, lanoline, polyethylene glycols, alcohols, transdermal enhancers and vegetable oils. Optional active agents may be included in a pharmaceutical composition, which do not substantially interfere with the activity of the compound of the present invention.

Some excipients include, but are not limited, to liquids such as water, saline, glycerol, polyethylene glycol, hyaluronic acid, ethanol, and the like. The compound can be provided, for example, in the form of a solid, a liquid, spray dried material, a microparticle, nanoparticle, controlled release system, etc., as desired according to the goal of the therapy. Suitable excipients for non-liquid formulations are also known to those of skill in the art. A thorough discussion of pharmaceutically acceptable excipients and salts is available in *Remington's Pharmaceutical Sciences,* 18th Edition (Easton, Pennsylvania: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable, and which provides the formulation with the desired pH, i.e., a pH in the physiologically acceptable range. Examples of buffer solutions include saline, phosphate buffered saline, Tris buffered saline, Hank's buffered saline, and the like.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see *Remington's Pharmaceutical Sciences*, referenced above.

In yet another embodiment provided is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

In certain embodiments the excipient is selected from butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The pharmaceutical compositions/combinations can be formulated for oral administration. For oral administration, the composition will generally take the form of a tablet, capsule, a softgel capsule or can be an aqueous or nonaqueous solution, suspension or syrup. Tablets and capsules are typical oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

Parenteral formulations can be prepared in conventional forms, either as liquid solutions or suspensions, solid forms suitable for solubilization or suspension in liquid prior to injection, or as emulsions. Typically, sterile injectable suspensions are formulated according to techniques known in the art using suitable carriers, dispersing or wetting agents and suspending agents. The sterile injectable formulation can also be a sterile injectable solution or a suspension in a acceptably nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, typical methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Formulations for buccal administration include tablets, lozenges, gels and the like. Alternatively, buccal administration can be effected using a transmucosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like.

Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound may, for example generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve.

Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

Formulations suitable for rectal administration are typically presented as unit dose suppositories. These may be prepared by admixing the active compound with one or more conventional solid carriers, for example, cocoa butter, and then shaping the resulting mixture.

In certain embodiments, the pharmaceutical composition is suitable for topical application to the skin using a mode of administration and defined above.

In certain embodiments, the pharmaceutical composition is suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound.

In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Many methods and devices for drug delivery are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

IX. General Synthesis

The compounds described herein can be prepared by methods known by those skilled in the art. In one non-limiting example, the disclosed compounds can be made using the schemes below.

Compounds of the present invention with stereocenters may be drawn without stereochemistry for convenience. One skilled in the art will recognize that pure enantiomers and diastereomers can be prepared by methods known in the art. Examples of methods to obtain optically active materials include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the enantiomer is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step in the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e. chirality) in the product, which may be achieved by chiral catalysts or chiral auxiliaries;

vi) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;

vii) first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is place in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through;

xiv) simulated moving bed chromatography is used in one embodiment. A wide variety of chiral stationary phases are commercially available.

X. Synthesis of Building Blocks for Use in the Present Invention

Synthesis of 4-(3,5-dimethoxy-4-(piperazin-1-ylmethyl)phenyl)-6-methyl-1,6-dihydro-7H-pyrazolo[3,4-c]pyridin-7-one

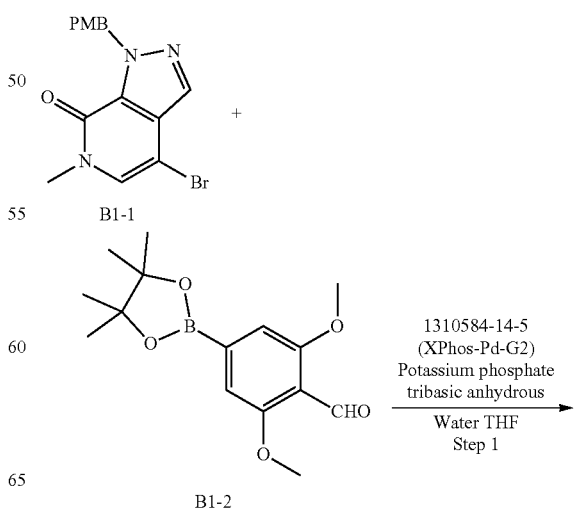

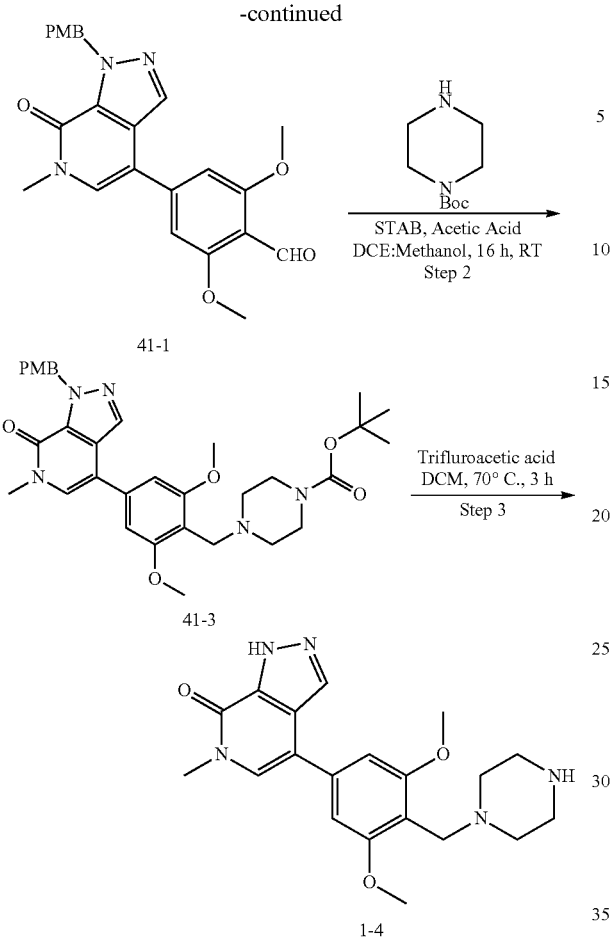

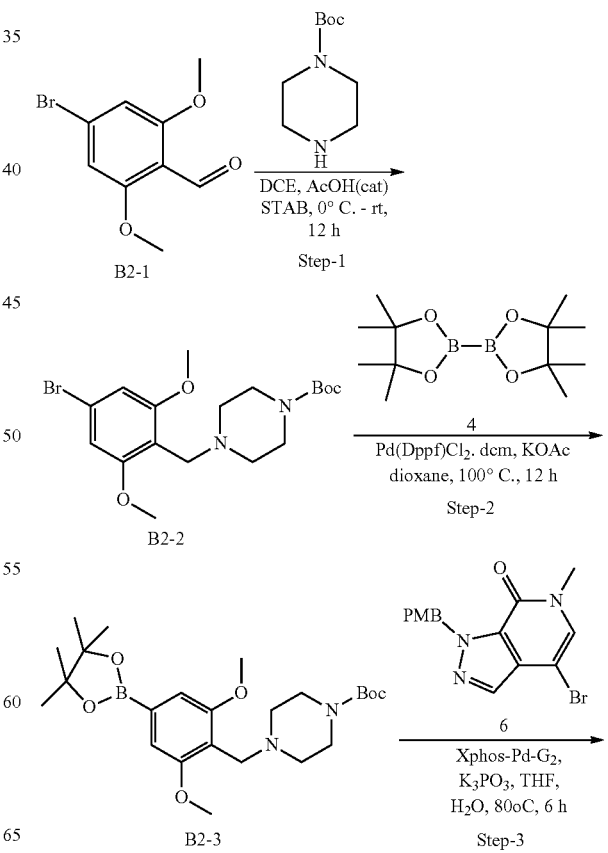

tion mixture was concentrated under vacuum. The residue was diluted with ethyl acetate (50 mL) and washed with water. The organic layer was dried over Na₂SO₄, filtered and concentrated under vacuum. The crude compound was purified by column chromatography (Davisil silica, 0-50% ethyl acetate in petroleum ether) to afford tert-butyl 4-(2,6-dimethoxy-4-(1-(4-methoxybenzyl)-6-methyl-7-oxo-6,7-dihydro-1H-pyrazolo[3,4-c]pyridin-4-yl)benzyl)piperazine-1-carboxylate (41-3) (500 mg) as a colourless solid. LC-MS (ES⁺): m/z 604.44 [M+H]⁺

Step 3: To a stirred solution of tert-butyl 4-[[2,6-dimethoxy-4-[1-[(4-methoxyphenyl)methyl]-6-methyl-7-oxo-pyrazolo[3,4-c]pyridin-4-yl]phenyl]methyl]piperazine-1-carboxylate (41-3) (0.88 g, 1.46 mmol) in DCM (10 mL) was added trifluoroacetic acid (2.25 ml, 29.15 mmol) and the reaction was stirred at 70° C. for 1 hour. The reaction progress was monitored by TLC and LCMS. After completion of the reaction, the reaction mixture was dried via rotoray evaporation and co-distilled with acetonitrile and toluene. The crude compound was triturated with diethyl ether to afford 4-[3,5-dimethoxy-4-(piperazin-1-ylmethyl)phenyl]-6-methyl-1H-pyrazolo[3,4-c]pyridin-7-one (1-4) (800 mg, 68.21% yield, 76% purity). LC-MS (ES⁺): m/z 384.35 [M+H]⁺

Synthesis of 4-(3,5-dimethoxy-4-(piperazin-1-ylmethyl)phenyl)-6-methyl-1,6-dihydro-7H-pyrazolo[3,4-c]pyridin-7-one (Alternative route)

Step 1: A stirred solution of anhydrous tribasic potassium phosphate (2.74 g, 12.92 mmol) in THF (150 mL) and water (5 mL) was purged with argon for 15 minutes. Then, 4-bromo-1-[(4-methoxyphenyl)methyl]-6-methyl-pyrazolo[3,4-c]pyridin-7-one (3.0 g, 8.62 mmol) and 2,6-dimethoxy-4-(4,4,5,5-tetramethyl-1,3,2-dioxaborolan-2-yl)benzaldehyde (3.78 g, 12.92 mmol) were added to the reaction mixture and purged with argon for 15 minutes. 1310584-14-5 (XPhos-Pd-G2) (338.60 mg) was added to the reaction mixture, purging with argon for 10 minutes, and allowed to stir for 16 hours at 70° C. The reaction progress was monitored by LCMS & TLC. After completion of the reaction, the residue was filtered through celite and purified by column chromatography (Reverse Phase, 0.1% Formic acid in acetonitrile) to afford 2,6-dimethoxy-4-[1-[(4-methoxyphenyl)methyl]-6-methyl-7-oxo-pyrazolo[3,4-c]pyridin-4-yl]benzaldehyde (41-1) (2.1 g, 4.24 mmol, 49.26% yield), LC-MS (ES⁺): m/z 434.25 [M+H]⁺

Step 2: To a stirred solution of 2,6-dimethoxy-4-[1-[(4-methoxyphenyl)methyl]-6-methyl-7-oxo-pyrazolo[3,4-c]pyridin-4-yl]benzaldehyde (41-1) (500 mg, 1.15 mmol) and tert-butyl piperazine-1-carboxylate (257.81 mg, 1.38 mmol) in DCE (3 ml) and MeOH (2 ml) at 0° C. was added acetic acid (32.99 uL, 576.76 mmol) and stirring was continued at room temperature for 4 hours. Sodium triacetoxyborohydride (488.96 mg, 2.31 mmol) was added to the reaction mixture at 0° C. and stirring was continued at room temperature for 16 hours. The progress of the reaction was monitored by TLC. After completion of reaction, the reac-

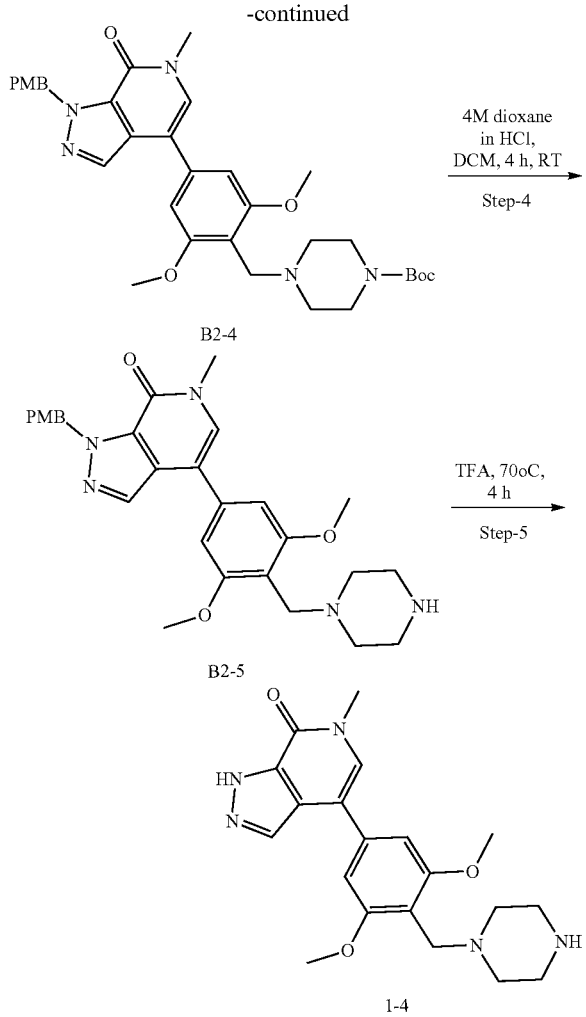

Step-1: To the stirred solution of 4-bromo-2,6-dimethoxybenzaldehyde B2-1 (15 g, 61.21 mmol) and tert-butyl piperazine-1-carboxylate (11.40 g, 61.21 mmol) in dry Dichloromethane (350 mL) was added acetic acid (3.68 g, 61.21 mmol, 3.50 mL) at 0° C. The reaction mixture was stirred at 0° C. for 3 h. Sodium; triacetoxyboranuide (25.95 g, 122.42 mmol) was added to the reaction mixture in one portion at 0° C. The reaction mixture was slowly warmed to RT over the period of 1 h and stirred at RT for another 9 h. After the completion of the reaction, the reaction mixture was quenched with water (500 mL) and extracted with DCM (2×500 mL). The combined organic layer was further washed with brine (1×250 mL) and dried over anhydrous $Na_2SO_4$, concentrated to get the crude product which was purified by column chromatography over the silica gel (100/200 mesh) and the product eluted at 30-40% EtOAc/Hexane to afford tert-butyl 4-[(4-bromo-2,6-dimethoxy-phenyl)methyl]piperazine-1-carboxylate (20.5 g, 48.38 mmol, 79.03% yield, 98.01% purity) as pale yellow pasty solid. $^1$HNMR (400 MHz, $CDCl_3$): δ 6.72 (s, 2H), 3.82 (s, 6H), 3.73 (s, 2H), 3.55 (s, 4H), 2.62 (s, 4H), 1.44 (s, 9H). LC-MS ($ES^+$): m/z 415[M+H]$^+$.

Step-2: To a stirred solution of tert-butyl 4-[(4-bromo-2,6-dimethoxy-phenyl)methyl]piperazine-1-carboxylate (15 g, 36.12 mmol) in 1,4 Dioxane (350 mL) was added 4,4,5,5-tetramethyl-2-(4,4,5,5-tetramethyl-1,3,2-dioxaborolan-2-yl)-1,3,2-dioxaborolane (13.76 g, 54.17 mmol) followed by the addition of Potassium Acetate (10.63 g, 108.35 mmol, 6.77 mL) at room temperature under argon atmosphere. The reaction mixture was degassed with argon repeatedly and cyclopentyl(diphenyl)phosphane; dichloromethane; dichloropalladium; iron (1.47 g, 1.81 mmol) was added in one portion under argon atmosphere. The reaction mixture was again degassed with argon repeatedly and then heated at 100° C. for 12 h. After the completion of the reaction, the reaction mixture was cooled to room temperature and filtered off through Celite, washed with ethyl acetate (300 mL). The filtrate was concentrated, and the resultant mass was dissolved with ethyl acetate (500 mL) and washed with water (2×100 mL), brine (1×100 mL) and dried over anhydrous $Na_2SO_4$, concentrated to get the crude product. The crude was further purified by column chromatography over silica gel (100/200 mesh) and the product eluted at 40-50% EtOAc/Hexane to afford tert-butyl 4-[[2,6-dimethoxy-4-(4,4,5,5-tetramethyl-1,3,2-dioxaborolan-2-yl)phenyl]methyl]piperazine-1-carboxylate (12 g, 25.69 mmol, 71.14% yield, 99% purity) as off-white pasty solid. $^1$HNMR (400 MHz, $CDCl_3$) δ 6.99 (s, 2H), 3.85 (s, 6H), 3.74 (s, 2H), 3.39 (t, J=5.0 Hz, 4H), 2.46 (t, J=5.0 Hz, 4H), 1.43 (s, 9H), 1.35 (s, 12H). LC MS: Boronic acid: RT: 1.26 min=381.41[M+H]$^+$ and Boronic ester:RT:1.75 min=463.48 [M+H]$^+$ Note: LCMS indicates 41% boronic acid mass and 58% boronic ester mass.

Step-3: To a stirred solution of 4-bromo-1-[(4-methoxyphenyl)methyl]-6-methyl-pyrazolo[3,4-c]pyridin-7-one (1.0 g, 2.87 mmol) in water (10 mL) THF (30 mL) was added tert-butyl 4-[[2,6-dimethoxy-4-(4,4,5,5-tetramethyl-1,3,2-dioxaborolan-2-yl)phenyl]methyl]piperazine-1-carboxylate 5 (1.33 g, 2.87 mmol) and $K_3PO_4$ (1.52 g, 7.18 mmol). The resulting solution was degassed with nitrogen for 15 minutes, then added XPhos-Pd-G2 (112.98 mg, 143.60 umol). After addition of catalyst reaction mixture heated at 80° C. for 6 h, while monitoring by LCMS and TLC. The reaction was filtered through Celite pad, washed with EtOAc (50 mL), filtrate were evaporated to obtain crude. The crude compound was purified by (silica gel mesh 100-200, 60-70% EtOAc in pet ether) to afford tert-butyl 4-[[2,6-dimethoxy-4-[1-[(4-methoxyphenyl)methyl]-6-methyl-7-oxo-pyrazolo[3,4-c]pyridin-4-yl]phenyl]methyl]piperazine-1-carboxylate 7 (0.75 g, 1.22 mmol, 42.58% yield, 98.44% purity) as an off white solid.
$^1$H NMR (400 MHz, $CDCl_3$) δ 8.35 (s, 1H), 7.70 (s, 1H), 7.31 (d, J=2 Hz, 2H), 6.86 (d, J=2 Hz, 2H), 6.61 (s, 2H), 5.50 (s, 2H), 4.15 (s, 2H), 3.83 (s, 6H), 3.78 (s, 3H), 3.68 (s, 3H), 3.58 (m, 4H), 2.98-2.96 (m, 4H) 1.44 (s, 9H); LC-MS ($ES^+$): m/z 604.44 [M+H]$^+$.

Step-4: To a stirred solution of tert-butyl 4-[[2,6-dimethoxy-4-[1-[(4-methoxyphenyl)methyl]-6-methyl-7-oxo-pyrazolo[3,4-c]pyridin-4-yl] phenyl]methyl] piperazine-1-carboxylate (0.75 g, 1.24 mmol) in $CH_2Cl_2$ (2 mL) was added 4M dioxane in HCl (0.4 ml, 12.4 mmol) at 0° C. and the reaction mixture was stirred at RT for 4 h, while monitoring by TLC. Reaction mixture was concentrated to obtain crude compound. The crude compound was triturated with diethyl ether (50×2) and n-pentane (20×2) to afford 4-[3,5-dimethoxy-4-(piperazin-1-ylmethyl)phenyl]-1-[(4-methoxyphenyl)methyl]-6-methyl-pyrazolo [3,4-c]pyridin-7-one HCl salt (0.65 g, 1.19 mmol, 95.50% yield, 98.57% purity) as a white solid. This was taken to next step without any purification.

Step-5: A stirred solution of 4-[3,5-dimethoxy-4-(piperazin-1-ylmethyl)phenyl]-1-[(4-methoxyphenyl)methyl]-6-methyl-pyrazolo[3,4-c]pyridin-7-one (1.63 g, 3.24 mmol) in TFA (2.49 mL, 32.37 mmol) was stirred at heated at 70° C. for 4 h, while monitoring by TLC. After completion reaction mixture was concentrated and crude compound was triturated with diethyl ether (100×2) to afford 4-[3,5-dimethoxy-4-(piperazin-1-ylmethyl)phenyl]-6-methyl-1H-pyrazolo[3,4-c]pyridin-7-one TFA salt (1.6 g, 3.14 mmol, 96.95% yield, 97.57% purity) as a white solid. ¹H NMR (400 MHz, DMSO-d6) δ 13.77 (s, 1H), 8.97 (bs, 2H) 8.22 (s, 1H), 7.63 (s, 1H), 6.98 (s, 2H) 4.25 (bs, 2H), 3.94 (s, 6H), 3.63 (s, 3H), 3.39-3.40 (bs, 8H); LC-MS (ES⁺): m/z 384.28 [M+H]⁺.

Synthesis of 2,6-dimethoxy-4-(6-methyl-7-oxo-6,7-dihydro-1H-pyrazolo[3,4-c]pyridin-4-yl)benzaldehyde

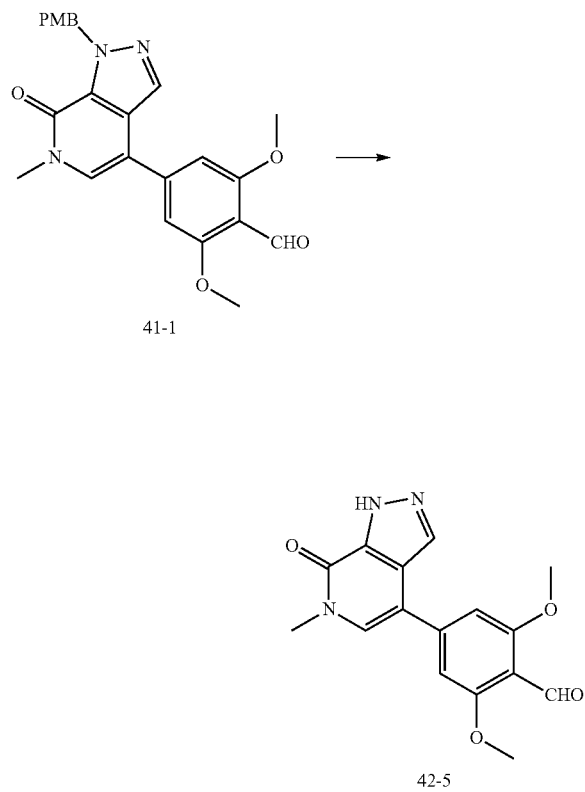

To a stirred solution of compound 2,6-dimethoxy-4-[1-[(4-methoxyphenyl)methyl]-6-methyl-7-oxo-pyrazolo[3,4-c]pyridin-4-yl]benzaldehyde (1.0 g, 2.31 mmol) was added TFA (2.63 g, 23.07 mmol, 1.78 mL) at 0° C. and the reaction mixture was stirred at RT for 16 h. The progress of the reaction was monitored by TLC and after completion, the reaction mixture was concentrated to provide crude compound. The crude compound was purified by reverse phase using 0.1% TFA and ACN, to provide 2,6-dimethoxy-4-(6-methyl-7-oxo-1H-pyrazolo[3,4-c]pyridin-4-yl)benzaldehyde (0.9 g, 1.90 mmol, 82.16% yield, 90% purity, 061) as a browan solid The desired compound was confirmed by LCMS), LC-MS (ES⁺): m/z 314.2 [M+H]⁺

Synthesis of 2-chloro-6-methoxy-4-(1-(4-methoxybenzyl)-6-methyl-7-oxo-6,7-dihydro-1H-pyrazolo[3,4-c]pyridin-4-yl)benzaldehyde

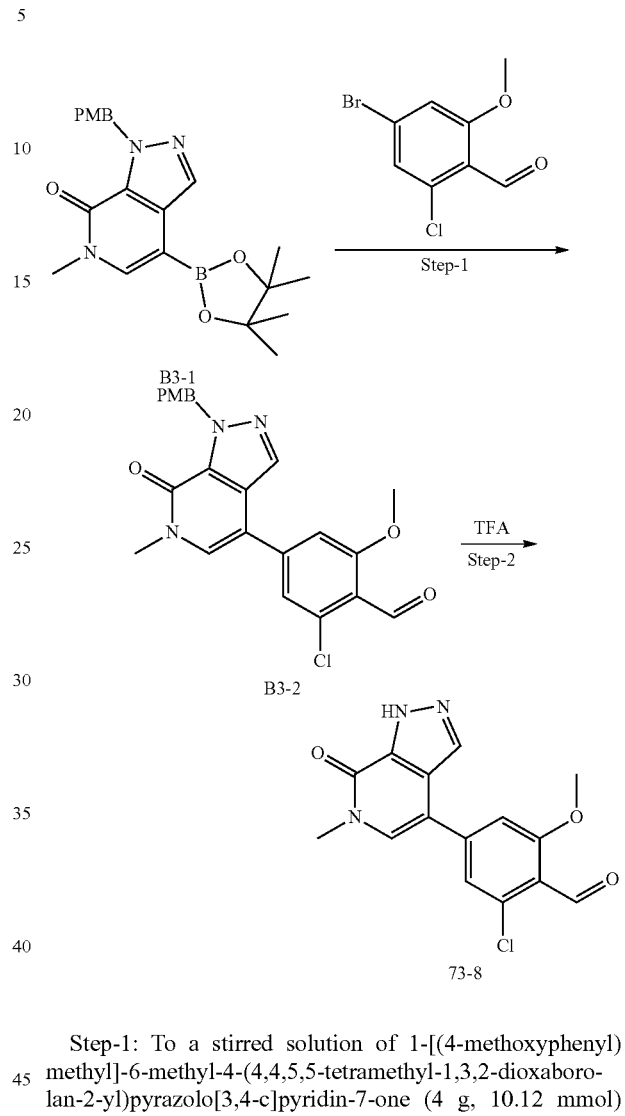

Step-1: To a stirred solution of 1-[(4-methoxyphenyl)methyl]-6-methyl-4-(4,4,5,5-tetramethyl-1,3,2-dioxaborolan-2-yl)pyrazolo[3,4-c]pyridin-7-one (4 g, 10.12 mmol) and 4-bromo-2-chloro-6-methoxy-benzaldehyde (2.27 g, 9.11 mmol) in THF (20.00 mL) was added potassium acetate (2.98 g, 30.36 mmol, 1.90 mL) in water (7 mL) solution. Then, argon gas was purged for 20 mins and followed by cyclopentyl(diphenyl)phosphane; dichloromethane; dichloropalladium; iron (413.22 mg, 506.00 umol) was added and degassed. Heated the mixture to 70° C. and maintained for 4 hr. The reaction was monitored by TLC. Then, the reaction mixture was diluted with water and extracted with ethyl acetate and washed the organic layer with brine solution, separated, dried over Na₂SO₄, concentrated. The crude product was purified by Biotage using 50% EA in PE afforded 2-chloro-6-methoxy-4-[1-[(4-methoxyphenyl)methyl]-6-methyl-7-oxo-pyrazolo[3,4-c]pyridin-4-yl]benzaldehyde (1.1 g, 2.51 mmol, 24.82% yield, pale yellow solid), LC-MS (ES⁺): m/z 438.30 [M+H]⁺

Step-2: To the compound 2-chloro-6-methoxy-4-[1-[(4-methoxyphenyl)methyl]-6-methyl-7-oxo-pyrazolo[3,4-c]pyridin-4-yl]benzaldehyde (0.25 g, 570.94 umol) was added Trifluoroacetic acid, 99% (2.96 g, 25.96 mmol, 2 mL). Reaction mixture was heated at 70° C. for 1 hr. Completion of the reaction monitored by TLC and LCMS. After completion of the reaction, excess TFA removed under Vacuo and the crude product washed with diethyl ether (2×5 mL) to afford 2-chloro-6-methoxy-4-(6-methyl-7-oxo-1H-pyrazolo[3,4-c]pyridin-4-yl)benzaldehyde (0.21 g, 470.97 umol, 82.49% yield, 96.83% purity, 061) as light brown solid.
LC-MS (ES$^+$): m/z 318.27 [M+H]$^+$ Synthesis of 2-chloro-6-methoxy-4-(1-(4-methoxybenzyl)-6-methyl-7-oxo-6,7-dihydro-1H-pyrazolo[3,4-c]pyridin-4-yl)benzaldehyde

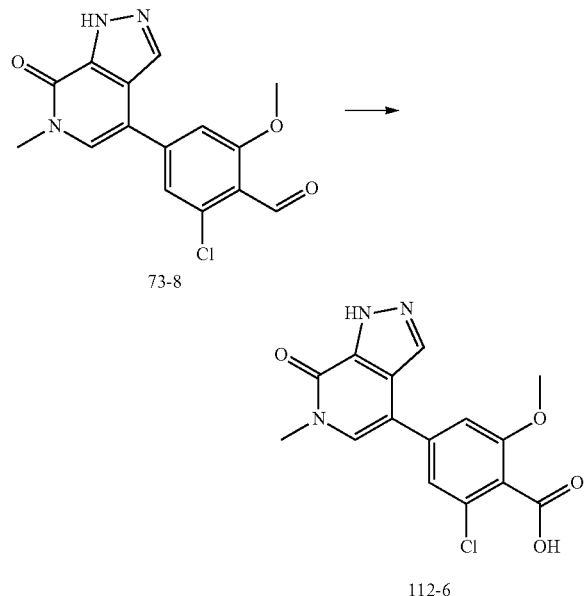

To a stirred solution of 2-chloro-6-methoxy-4-(6-methyl-7-oxo-1H-pyrazolo[3,4-c]pyridin-4-yl)benzaldehyde (0.3 g, 694.85 umol, 061) in 1,4-dioxane (5 mL), 2-methylbut-2-ene (389.85 mg, 5.56 mmol) was added. Then the mixture of sodium chlorite (314.22 mg, 3.47 mmol) and sodium dihydrogen phosphate (1.67 g, 13.90 mmol) was added slowly to the reaction mixture and allowed to stir at RT for 1 h. After completion the reaction mass was directly evaporated under reduced pressure. Crude was purified by using reverse phase. Desired product eluted 30% ACN in 1% FA in water.to afford 2-chloro-6-methoxy-4-(6-methyl-7-oxo-1H-pyrazolo[3,4-c]pyridin-4-yl)benzoic acid (100 mg, 282.39 umol, 40.64% yield, 94.24% purity), light brown solid. LC-MS (ES$^+$): m/z 334.32 [M+H]$^+$ Synthesis of 2-(trifluoromethoxy)-4-(1,4,5-trimethyl-6-oxo-1,6-dihydropyridin-3-yl)benzoic acid

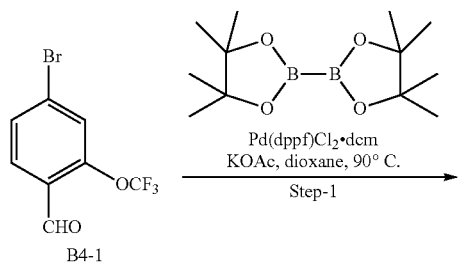

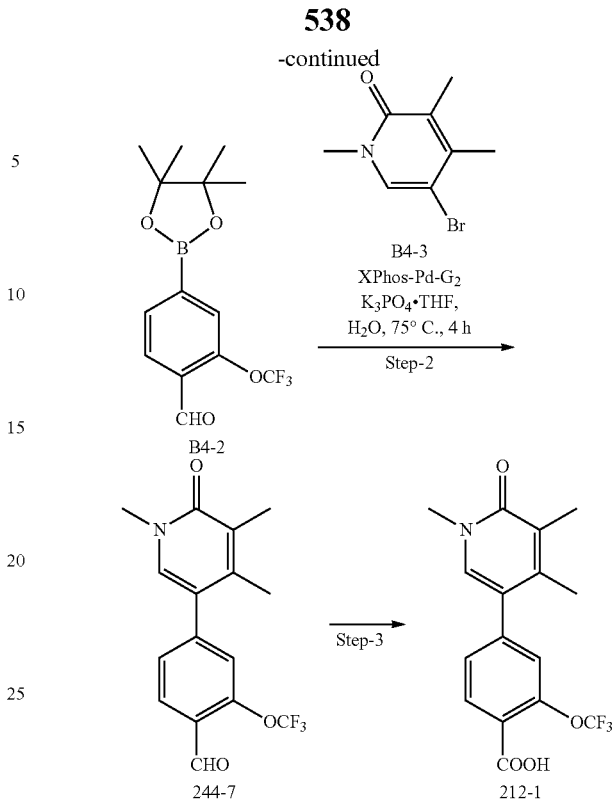

Step-1: To a solution of 4-bromo-2-(trifluoromethoxy) benzaldehyde (5 g, 18.59 mmol), in 1,4-dioxane (120 mL) was added Bis(pinacolato) diboron (7.08 g, 27.88 mmol) and potassium acetate (5.47 g, 55.76 mmol) and degassed with argon for 20 min. Finally, Pd(dppf)Cl$_2$·DCM complex (0.758 g, 0.929 mmol) was added and again degassed with argon for 10 min and stirred at 90° C. for 16 h while monitoring the reaction by TLC and LCMS. After completion, the reaction mass was filtered through Celite pad. The crude was quenched with water (200 ml) and extracted with EtOAc (2×200 ml). The combined organic layer was dried over anhydrous Na$_2$SO$_4$ and concentrated to afford crude compound 4-(4,4,5,5-tetramethyl-1,3,2-dioxaborolan-2-yl)-2-(trifluoromethoxy)benzaldehyde (5 g, 51.07% yield, 60% purity) as a brown solid. LC-MS (ES$^+$): m/z 233.94 [M–H]$^-$ (Boronic acid mass)

Step-2: To a stirred solution of 5-bromo-1,3,4-trimethyl-pyridin-2-one (3 g, 13.88 mmol) in THF (80 mL) was added 4-(4,4,5,5-tetramethyl-1,3,2-dioxaborolan-2-yl)-2-(trifluoromethoxy)benzaldehyde (4.39 g, 13.88 mmol) and K$_3$PO$_4$ (4.72 g, 34.71 mmol, 2.02 mL) which was dissolved in water (20 mL). The resulting solution was degassed with argon for 20 minutes, then added XPhos-Pd-G2 (0.544 g, 0.694 mmol) and again degassed with argon for 10 min and stirred at 75° C. for 4 h, while monitoring by LCMS and TLC. The reaction mixture was filtered through Celite pad, washed with EtOAc (100 mL), filtrate was evaporated to obtain crude. The crude compound was purified by (silica gel mesh 100-200, 60-70% EtOAc in pet ether) to afford 2-(trifluoromethoxy)-4-(1,4,5-trimethyl-6-oxo-3-pyridyl)benzaldehyde. 5 (3.5 g, 74.14% yield, 95.67% purity) as a light yellow solid. LC-MS (ES$^+$): m/z 326.30 [M+H]$^+$ Step-3: To the stirred solution of 2-(trifluoromethoxy)-4-(1,4,5-trimethyl-6-oxo-3-pyridyl)benzaldehyde (3.5 g, 10.76 mmol) in THF (130 mL) was added 2-methyl-2-butene (6.04 g, 86.08 mmol, 9.12 mL) at 25° C. followed by the addition of sodium chlorite (4.87 g, 53.80 mmol) and sodium dihydrogen phosphate (25.82 g, 215.20 mmol) dissolved in Water (70 mL) stirred at RT for 3 h. The completion of the reaction was confirmed by TLC. The reaction mixture was concentrated to half a quantity to obtain the crude product which was purified by trituration with methanol followed by washings by water to afford 2-(trifluoromethoxy)-4-(1,4,5-trimethyl-6-oxo-3-pyridyl)benzoic acid (2.3 g, 6.44 mmol, 59.87% yield, 95.58% purity) LC-MS (ES$^+$): m/z 342.12 [M+H]$^+$ Synthesis of 2-(trifluoromethoxy)-4-(1,4,5-trimethyl-6-oxo-1,6-dihydropyridin-3-yl)benzoic acid (Alternative Route)

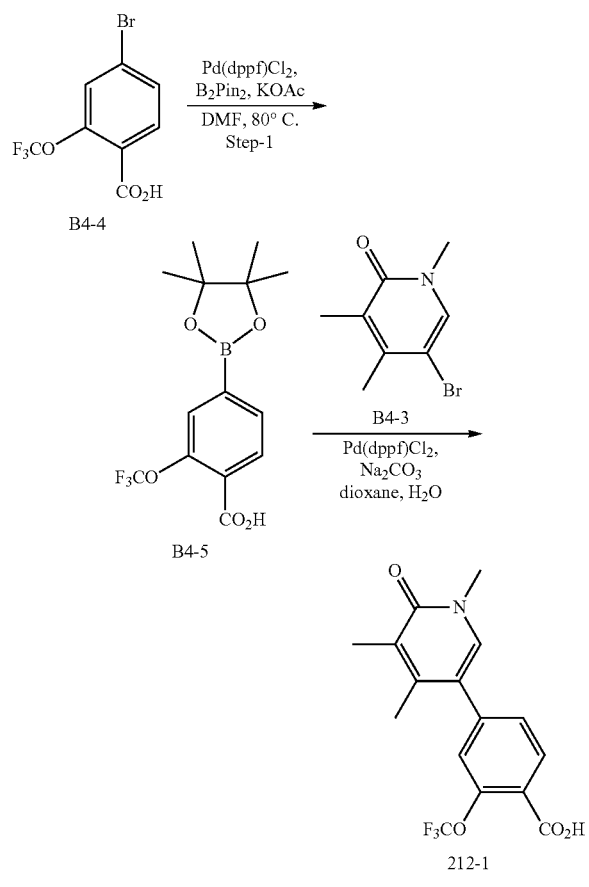

Step-1: To a mixture of B4-4 (10 g, 35.1 mmol, 1 eq) and B$_2$Pin$_2$ (13.4 g, 52.6 mmol, 1.5 eq) in N,N-dimethylformamide (150 mL) was added potassium acetate (17.2 g, 175 mmol, 5 eq), Pd(dppf)Cl$_2$ (2.57 g, 3.5 mmol, 0.1 eq) at 15° C. under nitrogen atmosphere. The mixture was stirred at 80° C. for 15 hours; After completion of the reaction monitored by HPLC, the reaction mixture was cooled to room temperature; The mixture was concentrated in vacuo to remove part of solvent; The residue was diluted in water (200 mL), extracted with ethyl acetate (100 mL×2). The combined organic layer was washed by brine (200 mL), dried over sodium sulfate, concentrated in vacuo to give a residue; The residue was triturated with petroleum ether (50 V), the suspension was filtered and the filtered cake was dried in vacuo to give the product (8.5 g, 73% yield) as a white solid.

$^1$H NMR (400 MHz, CDCl$_3$) δ 7.98 (d, J=7.8 Hz, 1H), 7.75 (d, J=7.6 Hz, 1H), 7.68 (s, 1H), 1.29 (s, 12H).

Step-2: To a mixture of B4-5 (5 g, 23.1 mmol, 1 eq) and compound-9 (8.45 g, 25.5 mmol, 1.1 eq) in dioxane (60 mL), water (20 mL) was added sodium carbonate (6.13 g, 57.9 mmol, 2.5 eq), Pd(dppf)Cl$_2$ (847 mg, 1.16 mmol, 0.05 eq) at 10° C. under nitrogen atmosphere. The mixture was stirred at 80° C. for 13 hours. The mixture was concentrated in vacuo to remove the dioxane; Then the aqueous phase was extracted with ethyl acetate (100 mL×2). The aqueous phase was acidified by HCl (2N) to pH 5, solid was precipitated out. The suspension was filtered, and the solid was dried in vacuo; The solid was triturated with ethyl acetate (10 mL) to give the product (5.5 g, 67% yield) as a white solid.

$^1$H NMR (400 MHz, MeOD-d$_4$) δ 8.03 (d, J=7.9 Hz, 1H), 7.50 (s, 1H), 7.41 (dd, J=8.0, 1.3 Hz, 1H), 7.35 (s, 1H), 3.60 (s, 3H), 2.17 (s, 3H), 2.13 (s, 3H).

Synthesis of 4-(2-methyl-1-oxo-1,2-dihydro-2,7-naphthyridin-4-yl)-2-(trifluoromethoxy)benzaldehyde

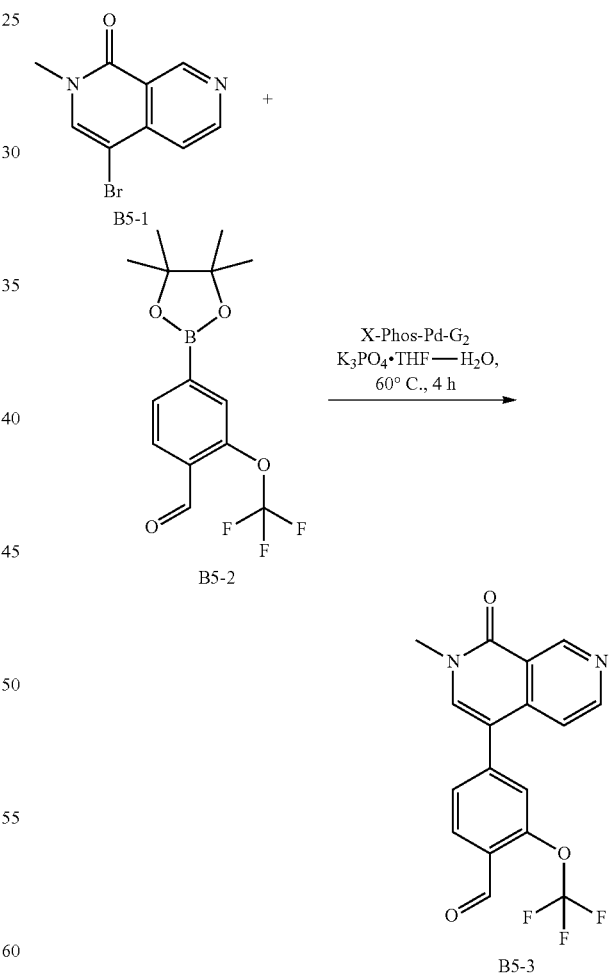

To a stirred solution of 4-(4,4,5,5-tetramethyl-1,3,2-dioxaborolan-2-yl)-2-(trifluoromethoxy)benzaldehyde (Compound-3) (3.98 g, 12.60 mmol) in dry THF (80 mL) was added 4-bromo-2-methyl-2,7-naphthyridin-1-one (3 g, 12.60 mmol) at room temperature under argon atmosphere followed by the addition of potassium phosphate (K₃PO₄) (6.69 g, 31.51 mmol) dissolved in water (20 mL) and resulting mixture was purged with argon gas for up to 30 minutes. After this 1310584-14-5 (Xphoss Pd G2) (0.495 g, 0.63 mmol) was added and resulting mixture was heated to reflux at 75° C. for up to 4 h. The completion of the reaction was monitored by TLC. After completion, the reaction mixture was allowed to room temperature and diluted with ice-cold water (100 mL) to resulting solid was filtered out and dried to high vacuum to get crude was triturated by n-pentane (100 mL) to get solid mixture was again refluxed in methanol (80 mL) and filtered to afford 4-(2-methyl-1-oxo-2,7-naphthyridin-4-yl)-2-(trifluoromethoxy)benzaldehyde (2.5 g, 6.54 mmol, 51.36% yield, 92% purity) as a brown solid. LC-MS (ES⁺): m/z 349.51 [M+H]⁺

Synthesis of 2-chloro-6-methoxy-4-(1,4,5-trimethyl-6-oxo-1,6-dihydropyridin-3-yl) benzaldehyde

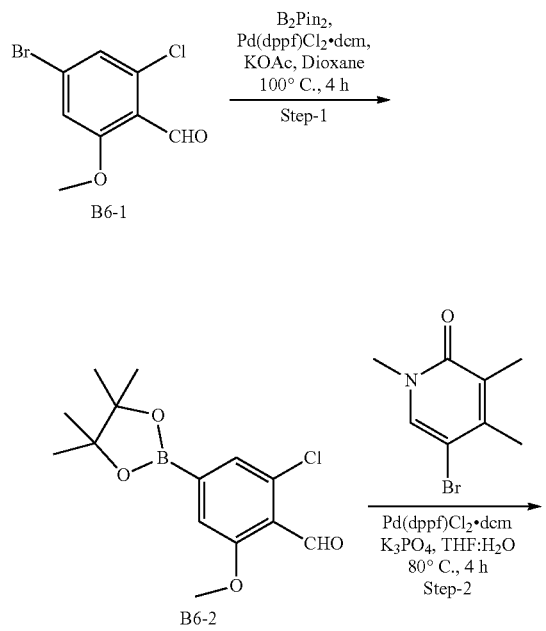

dioxaborolan-2-yl)-1,3,2-dioxaborolane (4.70 g, 18.52 mmol) followed by the addition of potassium acetate (3.79 g, 38.58 mmol) at room temperature under argon atmosphere. The reaction mixture was degassed with argon repeatedly and cyclopentyl (diphenyl)phosphane; dichloromethane; dichloropalladium; iron (0.63 g, 0.77 mmol) was added in one portion under argon atmosphere. The reaction mixture was again degassed with argon repeatedly and then heated to reflux at 90° C. for 4 h. After the completion of the reaction, the reaction mixture was cooled to room temperature and filtered off through Celite, washed with ethyl acetate (200 mL). The filtrate was concentrated to get the residual mass. The residual mass was dissolved in Ethyl acetate (200 mL) and washed with water (2×50 mL), brine (1×50 mL), dried over anhydrous Na₂SO₄, filtered and concentrated to get the crude product. The crude product was purified by column chromatography using silica gel (100/200 mesh) and the product eluted at 30-40% EtOAc/Hexane to get 2-chloro-6-methoxy-4-(4,4,5,5-tetramethyl-1,3,2-dioxaborolan-2-yl)benzaldehyde (4 g, 83.04% yield, 95% purity) as light yellow solid. LC-MS (ES⁺): m/z [M+H]⁺ 215.13 (corresponding Boronic acid mass was observed) Step-2: To the stirred a mixture of 5-bromo-1,3,4-trimethyl-pyridin-2-one (1 g, 4.63 mmol) and 2-chloro-6-methoxy-4-(4,4,5,5-tetramethyl-1,3,2-dioxaborolan-2-yl) benzaldehyde 2 (2.06 g, 6.94 mmol) in Dioxane (15 mL) and Water (5 mL) in a sealed tube was added tripotassium; phosphate (2.46 g, 11.57 mmol) at rt and resulting mixture was purged with argon for 10 minutes. cyclopentyl (diphenyl)phosphane; dichloromethane; dichloropalladium; iron (0.18 g, 0.23 mmol) was added to the reaction mixture and the reaction mixture was again degassed with argon for another 5 minutes and then heated at 80° C. for 4 h. After the completion of the reaction, the reaction mixture was cooled to room temperature and filtered-off through Celite, washed with ethyl acetate (100 mL). The organic layer was partitioned from the filtrate and concentrated to get the crude which was purified by column chromatography using silicagel (100/200 mesh) and the product eluted at 60% EtOAc/Pet ether to afford 2-chloro-6-methoxy-4-(1,4,5-trimethyl-6-oxo-3-pyridyl)benzaldehyde (0.920 g, 61.76% yield, 95% purity). LC-MS (ES⁺): m/z 306.31 [M+H]⁺

Synthesis of 2-chloro-6-methoxy-4-(1,4,5-trimethyl-6-oxo-1,6-dihydropyridin-3-yl)benzoic acid

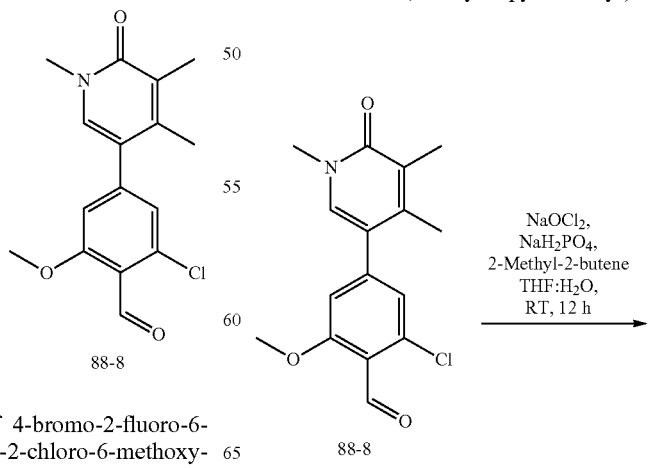

Step-1: To the stirred solution of 4-bromo-2-fluoro-6-methoxybenzaldehyde and 4-bromo-2-chloro-6-methoxybenzaldehyde (3.85 g, 15.43 mmol) in 1,4-dioxane (40 mL) was added 4,4,5,5-tetramethyl-2-(4,4,5,5-tetramethyl-1,3,2-

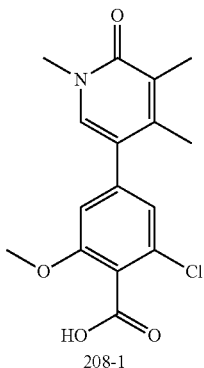

208-1

To the stirred solution of 2-chloro-6-methoxy-4-(1,4,5-trimethyl-6-oxo-1,6-dihydropyridin-3-yl)benzaldehyde (500 mg, 1.64 mmol) in THF (25 mL) was added dropwise 2-methyl-2-butene (917.50 mg, 13.08 mmol) at 0° C. followed by the addition of sodium chlorite (739.48 mg, 8.18 mmol) in one portion and sodium; dihydrogen phosphate (3.92 g, 32.71 mmol) dissolved in Water (20 mL) dropwise. The reaction mixture was slowly warmed to rt over the period of 30 mints and stirred at rt for another 6 h. The completion of the reaction was confirmed by TLC. The reaction mixture was concentrated as such to obtain the crude product which was purified by triturating with water/methanol and the solid precipitated out was filtered, dried well to afford 2-chloro-6-methoxy-4-(1,4,5-trimethyl-6-oxo-1,6-dihydropyridin-3-yl)benzoic acid (400 mg, 70.90% yield, 93.26% purity) as off-white solid. LC-MS (ES⁺): m/z 322.12 [M+H]⁺

Synthesis of 2-chloro-6-methoxy-4-(2-methyl-1-oxo-1,2-dihydro-2,7-naphthyridin-4-yl)benzaldehyde

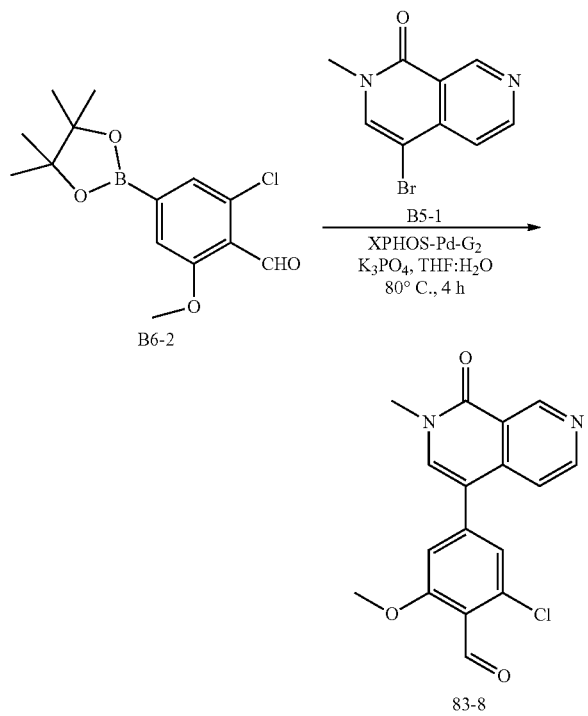

To a stirred solution of 4-bromo-2-methyl-2,7-naphthyridin-1-one (1 g, 4.18 mmol) in dry THF (40 mL) in a sealed tube was added 2-chloro-6-methoxy-4-(4,4,5,5-tetramethyl-1,3,2-dioxaborolan-2-yl)benzaldehyde (1.24 g, 4.18 mmol) at RT followed by the addition of tripotassium; phosphate (2.22 g, 10.46 mmol) dissolved in water (10 mL) under argon atm. The reaction mixture was degassed with argon repeatedly and Pd-Xphos-G2 catalyst (0.16 g, 0.20 mmol) was added to the reaction mixture in one portion. The reaction mixture was again degassed with argon and then heated at 80° C. for 4 h. After the completion of the reaction, the reaction mixture was cooled to room temperature and filtered-off through Celite, washed with ethyl acetate (100 mL). The organic layer was partitioned from the filtrate and concentrated to get the crude. The crude product was purified by reverse phase column chromatography using 0.1% FA in water and Acetonitrile as the eluent gradient to afford 2-chloro-6-methoxy-4-(2-methyl-1-oxo-2, 7-naphthyridin-4-yl)benzaldehyde (0.30 g, 21.46% yield, 85.97% purity) as off-white solid. LC-MS (ES⁺): m/z 329.17 [M+H]⁺

Synthesis of 2-chloro-4-(7-fluoro-2-methyl-1-oxo-1,2-dihydroisoquinolin-4-yl)-6-methoxybenzoic acid

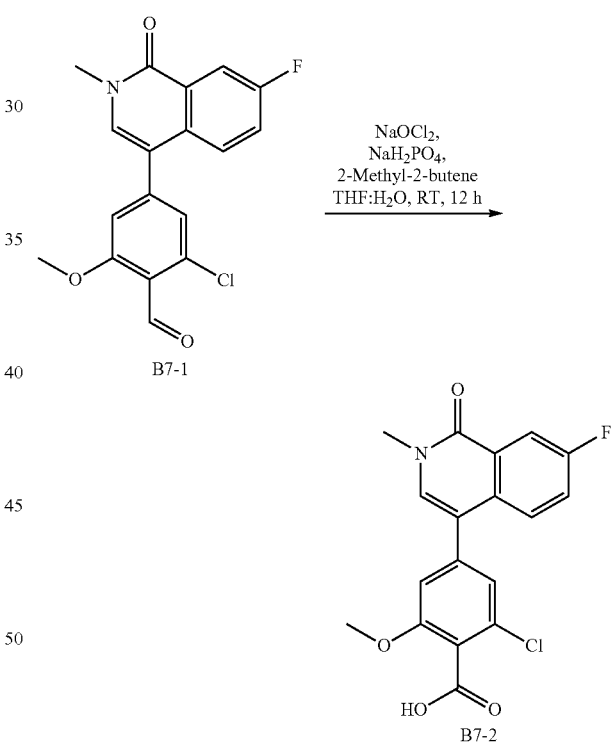

To the stirred solution of 2-chloro-4-(7-fluoro-2-methyl-1-oxo-4-isoquinolyl)-6-methoxy-benzaldehyde (0.17 g, 0.49 mmol) in THF (25 mL) was added 2-methyl-2-butene (0.27 g, 3.93 mmol) at 0° C. followed by the dropwise addition of sodium chlorite (0.22 g, 2.46 mmol) and sodium; dihydrogen phosphate (1.18 g, 9.83 mmol) dissolved in water (10 mL). The reaction mixture was slowly warmed to rt over the period of 30 mints and stirred at rt for 12 h. The completion of the reaction was confirmed by TLC. The reaction mixture was concentrated to half a quantity to obtain the crude product which was purified by trituration with methanol/water to afford 2-chloro-4-(7-fluoro-2- methyl-1-oxo-4-isoquinolyl)-6-methoxy-benzoic acid (0.12 g, 64.09% yield, 95% purity) as white solid. LC-MS (ES⁺): m/z 362.25 [M+H]⁺

Synthesis of 2-fluoro-6-methoxy-4-(1,4,5-trimethyl-6-oxo-1,6-dihydropyridin-3-yl)benzaldehyde

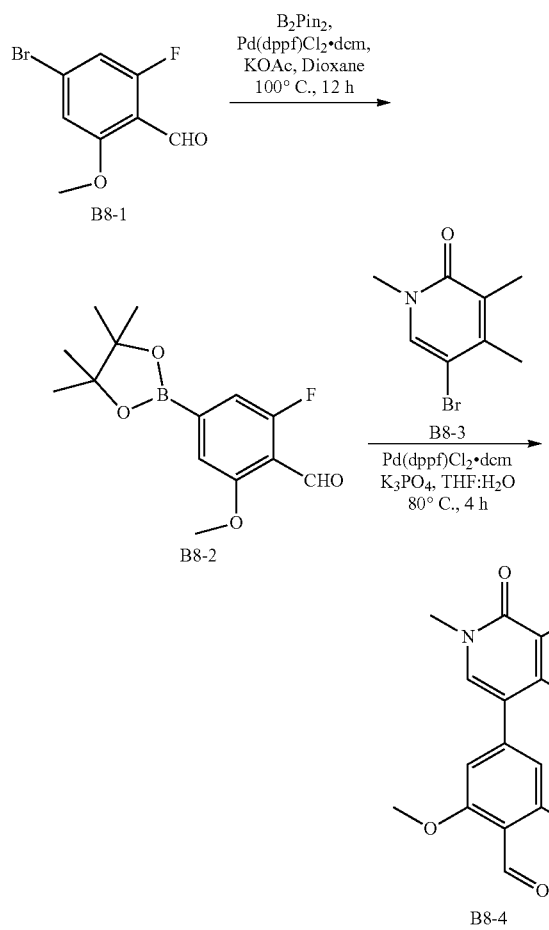

Step-1: To the stirred solution of 4-bromo-2-fluoro-6-methoxybenzaldehyde (7 g, 30.04 mmol) in 1,4-Dioxane (300 mL) was added 4,4,5,5-tetramethyl-2-(4,4,5,5-tetramethyl-1,3,2-dioxaborolan-2-yl)-1,3,2-dioxaborolane (11.44 g, 45.06 mmol) followed by the addition of Potassium Acetate (8.84 g, 5.63 mL) at room temperature under argon atmosphere. The reaction mixture was degassed with argon repeatedly and cyclopentyl (diphenyl)phosphane; dichloromethane; dichloropalladium; iron (1.23 g, 1.50 mmol) was added in one portion under argon atmosphere. The reaction mixture was again degassed with argon repeatedly and then heated to reflux at 90° C. for 12 h. After the completion of the reaction, the reaction mixture was cooled to room temperature and filtered off through Celite, washed with ethyl acetate (200 mL). The filtrate was concentrated to get the residual mass. The residual mass was dissolved in ethyl acetate (300 mL) and washed with water (2×100 mL), brine (1×50 mL), dried over anhydrous Na₂SO₄, filtered and concentrated to get the crude product. The crude product was triturated with pentane (500 mL), stirred well and filtered through Celite. The filtrate was concentrated to get the solid which was made slurry with hexane (25 mL), filtered-off, washed with hexane (10 mL), dried well to afford the product 2-fluoro-6-methoxy-4-(4,4,5,5-tetramethyl-1,3,2-dioxaborolan-2-yl)benzaldehyde (4.1 g, 46.29% yield, 95% purity) as pale brown solid. LC-MS (ES⁺): m/z 199.17 [M+H]⁺ (corresponding Boronic acid mass was observed)

Step-2: To a stirred solution of 5-bromo-1,3,4-trimethylpyridin-2(1H)-one (1 g, 4.63 mmol) in dry THF (50 mL) in a sealed tube was added 2-fluoro-6-methoxy-4-(4,4,5,5-tetramethyl-1,3,2-dioxaborolan-2-yl)benzaldehyde (1.30 g, 4.63 mmol) at RT followed by the addition of tripotassium; phosphate (2.46 g, 11.57 mmol) dissolved in water (15 mL) under argon atm. The reaction mixture was degassed with argon repeatedly and cyclopentyl (diphenyl)phosphane; dichloromethane; dichloropalladium; iron (0.18 g, 0.23 mmol) was added to the reaction mixture in one portion. The reaction mixture was again degassed with argon and then heated at 80° C. for 4 h. After the completion of the reaction, the reaction mixture was cooled to room temperature and filtered-off through Celite, washed with ethyl acetate (100 mL). The organic layer was partitioned from the filtrate and concentrated to get the crude. The crude product was purified by column chromatography using silicagel (100/200 mesh) and the product eluted at 4-5% MeOH/EtOAc to afford 2-fluoro-6-methoxy-4-(1, 4, 5-trimethyl-6-oxo-1,6-dihydropyridin-3-yl)benzaldehyde (0.45 g, 32.40% yield, 96.40% purity) as off-white solid. LC-MS (ES⁺): m/z 290.52 [M+H]⁺

Synthesis of 2-fluoro-6-methoxy-4-(2-methyl-1-oxo-1,2-dihydro-2,7-naphthyridin-4-yl)benzaldehyde

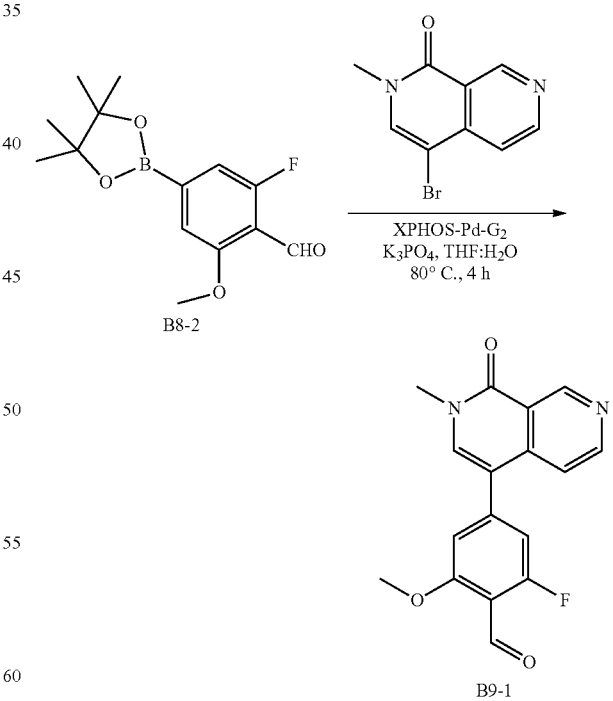

To the stirred solution of 4-bromo-2-methyl-2,7-naphthyridin-1-one (2 g, 8.37 mmol) in dry THF (50 mL) in a sealed tube was added 2-fluoro-6-methoxy-4-(4,4,5,5-tetramethyl-1,3,2-dioxaborolan-2-yl)benzaldehyde (2.34 g, 8.37 mmol) at RT followed by the addition of tripotassium; phosphate (4.44 g, 20.91 mmol) dissolved in water (15 mL) under argon atm. The reaction mixture was degassed with argon repeatedly and Pd-Xphos-G2 catalyst (0.32 g, 0.41 mmol) was added to the reaction mixture in one portion. The reaction mixture was again degassed with argon and then heated at 80° C. for 4 h. After the completion of the reaction, the reaction mixture was cooled to room temperature and filtered off through Celite, washed with ethyl acetate (100 mL). The organic layer was partitioned from the filtrate and concentrated to get the crude. The crude product was purified by reverse phase column chromatography using 0.1% FA in water and Acetonitrile as the eluent gradient to afford 2-fluoro-6-methoxy-4-(2-methyl-1-oxo-2, 7-naphthyridin-4-yl)benzaldehyde 7 (1.90 g, 72.15% yield, 99.21% purity) as off-white solid. LC-MS (ES+): m/z 313.14 [M+H]+

Synthesis of 2-fluoro-6-methoxy-4-(2-methyl-1-oxo-1,2-dihydro-2,7-naphthyridin-4-yl)benzoic acid

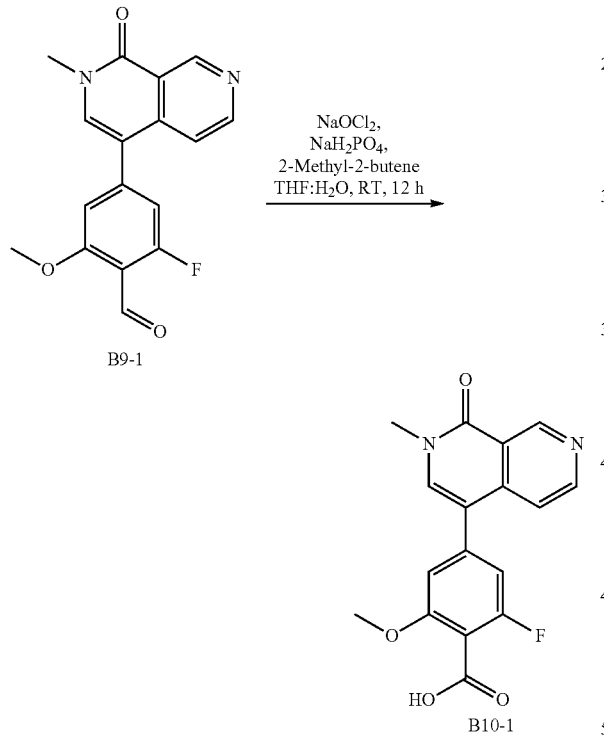

To the stirred solution of 2-fluoro-6-methoxy-4-(2-methyl-1-oxo-2,7-naphthyridin-4-yl)benzaldehyde 7 (0.40 g, 1.28 mmol) in THF (15 mL) was added 2-methyl-2-butene (0.71 g, 10.25 mmol) at 0° C. followed by the addition of sodium chlorite (0.57 g, 6.40 mmol) and sodium; dihydrogen phosphate (3.07 g, 25.62 mmol) dissolved in water (10 mL). The reaction mixture was slowly warmed to rt over the period of 30 mints and stirred at rt for 6 h. The completion of the reaction was confirmed by TLC. The reaction mixture was concentrated to half a quantity to obtain the crude product which was purified by trituration with methanol/water to afford 2-fluoro-6-methoxy-4-(2-methyl-1-oxo-2,7-naphthyridin-4-yl)benzoic acid (0.22 g, 50.46% yield, 96.44% purity) as off-white solid. LC-MS (ES+): m/z 329.22 [M+H]+

Synthesis of 2,6-dimethoxy-4-(1,4,5-trimethyl-6-oxo-1,6-dihydropyridin-3-yl)benzaldehyde

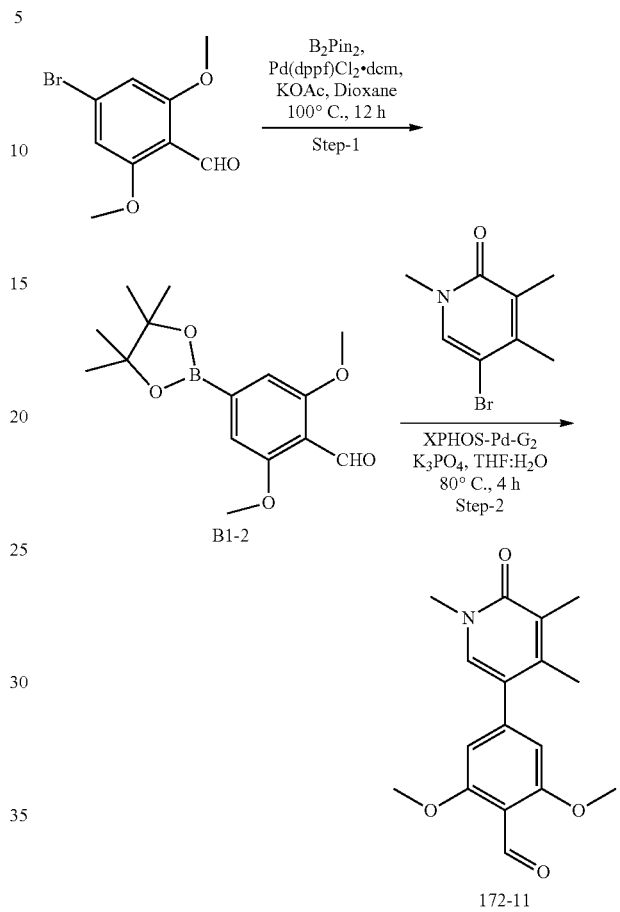

Step-1: To a stirred solution of 4-bromo-2,6-dimethoxybenzaldehyde (10 g, 40.80 mmol) in 1,4-Dioxane (300 mL) was added 4,4,5,5-tetramethyl-2-(4,4,5,5-tetramethyl-1,3,2-dioxaborolan-2-yl)-1,3,2-dioxaborolane (15.54 g, 61.21 mmol) followed by the addition of Potassium Acetate (12.01 g, 122.41 mmol) at room temperature under Argon atmosphere. The reaction mixture was degassed with argon repeatedly and cyclopentyl (diphenyl)phosphane; dichloromethane; dichloropalladium; iron (1.67 g, 2.04 mmol) was added in one portion under argon atmosphere. The reaction mixture was again degassed with argon repeatedly and then heated at reflux at 95° C. for 12 h. After the completion of the reaction, the reaction mixture was cooled to room temperature and filtered-off through Celite, washed with ethyl acetate (200 mL). The filtrate was concentrated to get the residual mass. The residual mass was dissolved in ethyl acetate (500 mL) and washed with water (2×100 mL), brine (1×50 mL), dried over anhydrous $Na_2SO_4$, filtered and concentrated to get the crude product. The crude product was purified by column chromatography over silica gel (100/200 mesh) and the product eluted at 30-40% EtOAc/Pet ether to afford 2,6-dimethoxy-4-(4,4,5,5-tetramethyl-1,3,2-dioxaborolan-2-yl)benzaldehyde 2 (7 g, 55.79% yield, 95% purity) as pale brown solid.

Step-2: To the stirred solution of 5-bromo-1,3,4-trimethyl-pyridin-2-one (2 g, 9.26 mmol) in dry THF (50 mL) in a sealed tube was added 2,6-dimethoxy-4-(4,4,5,5-tetramethyl-1,3,2-dioxaborolan-2-yl)benzaldehyde 2 (2.70 g, 9.26 mmol) at RT followed by the addition of tripotassium; phosphate (4.91 g, 23.14 mmol) dissolved in Water (15 mL) under argon atm. The reaction mixture was degassed with argon repeatedly and the XPhos-PdG$_2$ catalyst (0.36 g, 0.46 mmol) was added to the reaction mixture in one portion. The reaction mixture was again degassed with argon and then refluxed at 80° C. for 4 h. After the completion of the reaction, the reaction mixture was cooled to room temperature and filtered off through Celite, washed with ethyl acetate (100 mL). The organic layer was partitioned from the filtrate and concentrated. The resultant crude product was further purified by reverse phase column chromatography using 0.1% FA in water and Acetonitrile as the eluent gradient to afford 2, 6-dimethoxy-4-(1, 4, 5-trimethyl-6-oxo-3-pyridyl)benzaldehyde (1.45 g, 4.63 mmol, 96.22% purity) as off-white solid. LC-MS (ES$^+$): m/z 302.27 [M+H]$^+$ Synthesis of 2,6-dimethoxy-4-(1,4,5-trimethyl-6-oxo-1,6-dihydropyridin-3-yl)benzoic acid Synthesis of 2,6-dimethoxy-4-(2-methyl-1-oxo-1,2-dihydro-2,7-naphthyridin-4-yl)benzaldehyde

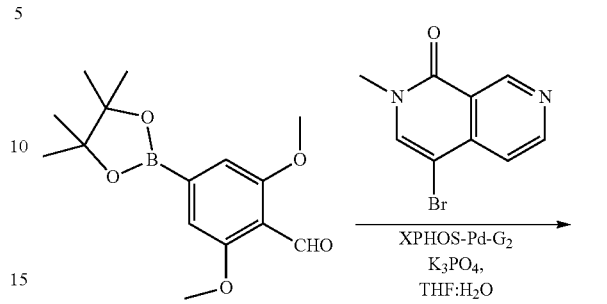

To the stirred solution of 2,6-dimethoxy-4-(1,4,5-trimethyl-6-oxo-1,6-dihydropyridin-3-yl)benzaldehyde (1 g, 3.32 mmol) in THF (50 mL) was added drop wise 2-methyl-2-butene (1.86 g, 26.55 mmol) at 0° C. followed by the addition of sodium chlorite (1.50 g, 16.59 mmol) and sodium; dihydrogen phosphate (7.96 g, 66.37 mmol) in water (20 mL). The reaction mixture was slowly warmed to rt over the period of 30 mints and stirred at room temperature for 12 h. After the completion of the reaction, the reaction mixture was concentrated to ¼$^{th}$ of the total volume and the colourless solid precipitated out was filtered, washed with water (10 mL), dried well to afford 2,6-dimethoxy-4-(1,4,5-trimethyl-6-oxo-1,6-dihydropyridin-3-yl)benzoic acid (0.65 g, 59.90% yield, 97.04% purity) as white solid. LC-MS (ES$^+$): m/z 318.32 [M+H]$^+$ To the stirred solution of 4-bromo-2-methyl-2,7-naphthyridin-1-one (2 g, 8.37 mmol) in dry THF (50 mL) in a sealed tube was added 2,6-dimethoxy-4-(4,4,5,5-tetramethyl-1,3,2-dioxaborolan-2-yl)benzaldehyde (2.44 g, 8.37 mmol) at RT followed by the addition of potassium phosphate (4.44 g, 20.91 mmol) dissolved in Water (20 mL) under argon atm. The reaction mixture was degassed with argon repeatedly and Pd-Xphos-G2 catalyst (0.32 g, 0.41 mmol) was added to the reaction mixture in one portion. The reaction mixture was again degassed with argon and then refluxed at 80° C. for 4 h. After the completion of the reaction, the reaction mixture was cooled to room temperature and filtered-off through Celite, washed with ethyl acetate (100 mL). The organic layer was partitioned from the filtrate and concentrated to get the crude. The crude product was purified by column chromatography using silicagel (100/200 mesh) and the product eluted at 4-5% MeOH in EtOAC to afford 2, 6-dimethoxy-4-(2-methyl-1-oxo-2, 7-naphthyridin-4-yl) benzaldehyde (1.8 g, 64.42% yield, 97.10% purity) as pale yellow solid. LC-MS (ES$^+$): m/z 325.29 [M+H]$^+$

Synthesis of 2,6-dimethoxy-4-(2-methyl-1-oxo-1,2-dihydro-2,7-naphthyridin-4-yl)benzoic acid

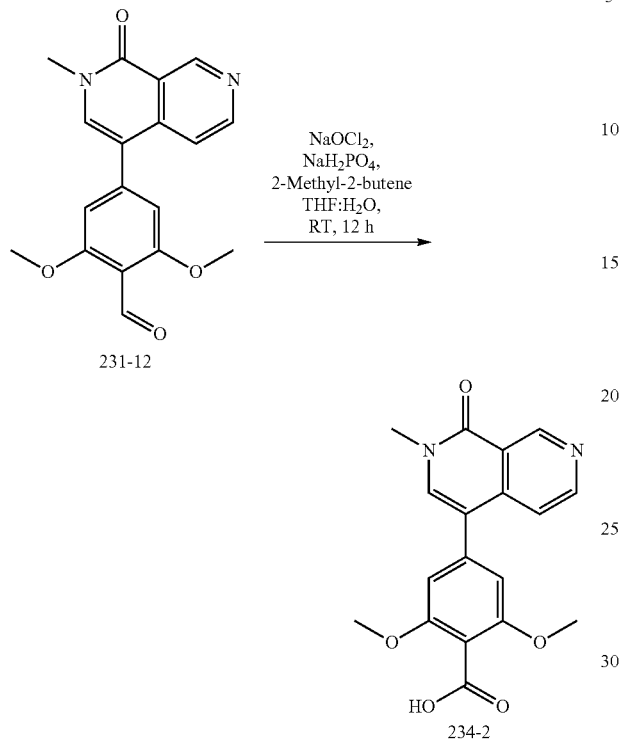

To the stirred solution of 2,6-dimethoxy-4-(2-methyl-1-oxo-2,7-naphthyridin-4-yl)benzaldehyde (0.35 g, 1.08 mmol) in THF (25 mL) was added dropwise 2-methyl-2-butene (0.60 g, 8.64 mmol) at 0° C. followed by the addition of sodium chlorite (0.48 g, 5.40 mmol) and sodium; dihydrogen phosphate (2.59 g, 21.60 mmol) in water (20 mL). The reaction mixture was slowly warmed to rt over the period of 30 mints and stirred at rt for another 12 h. After the completion of the reaction, the reaction mixture was concentrated to ¼ of the total volume and the colourless solid precipitated out was filtered, washed with water (10 mL) and dried well to afford 2,6-dimethoxy-4-(2-methyl-1-oxo-2,7-naphthyridin-4-yl)benzoic acid 8 (0.28 g, 62.95% yield, 82.64% purity) as off-white white solid.

LC-MS (ES$^+$): m/z 341.29 [M+H]$^+$

Synthesis of 2-ethoxy-5-methoxy-4-(1-(4-methoxybenzyl)-6-methyl-7-oxo-6,7-dihydro-1H-pyrazolo[3,4-c]pyridin-4-yl)benzaldehyde

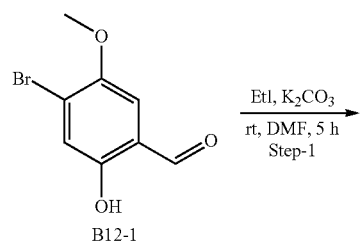

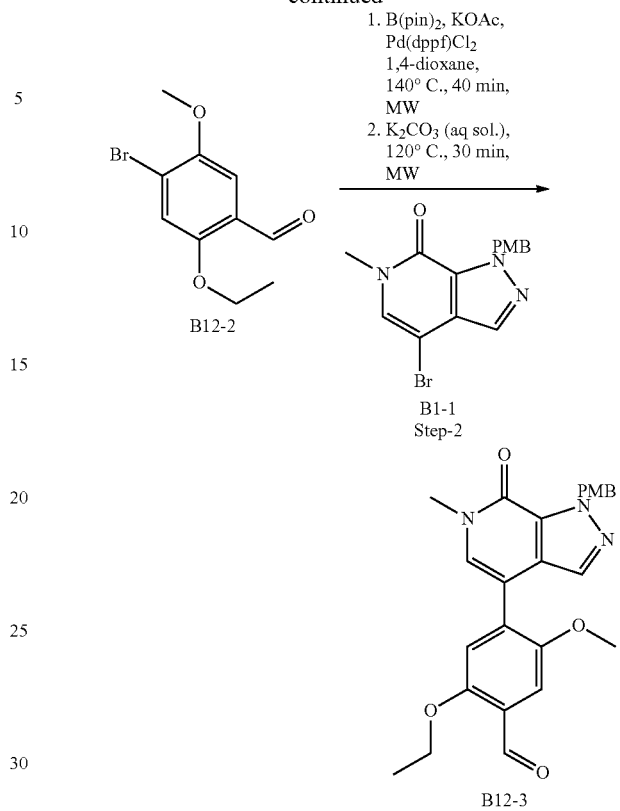

Step-1: To a solution of 4-bromo-2-hydroxy-5-methoxy-benzaldehyde (505 mg, 2.19 mmol) in DMF (4.89 mL) was added potassium carbonate-granular (906.24 mg, 6.56 mmol, 395.74 uL) before iodoethane (340.90 mg, 2.19 mmol, 175.72 uL) was added at room temperature and stirred for 5 hours under an argon atmosphere. Upon reaction completion the mixture was quenched by being poured into water (50 mL) before being extracted with ethyl acetate (50 mL×3). The organic layer was washed with LiCl (5% w/v aq. Solution. 50 mL) before being dried with brine (50 mL), Na$_2$SO$_4$, filtered and concentrated to a residue which was purified via flash column chromatography (hexanes: ethyl acetate 1:0 to 4:6) to afford 4-bromo-2-ethoxy-5-methoxybenzaldehyde as a white solid. Yield—504 mg, 89%; LC-MS (ES$^+$): m/z 260.0 [M+H]$^+$.

Step-2: Initially cyclopentyl(diphenyl)phosphane; dichloropalladium; iron (112.96 mg, 154.38 umol), 1-2 4-bromo-2-ethoxy-5-methoxy-benzaldehyde (400 mg, 1.54 mmol) Bis(pinacolato) diboron (470.44 mg, 1.85 mmol), Potassium Acetate (454.54 mg, 4.63 mmol, 289.52 uL) were charged into a MW vial (2-5 mL) and suspended under an argon atmosphere in 1,4-Dioxane (5.89 mL) and heated in a MW at 140° C. for 40 mins. The suspension then had 4-bromo-1-[(4-methoxyphenyl)methyl]-6-methyl-pyrazolo[3,4-c]pyridin-7-one (134.62 mg, 386.63 umol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), Na$_2$SO$_4$, filtered and concentrated to a residue which was purified via flash column chromatography (hexanes:ethyl acetate 1:0 to 0:1) to afford 2-ethoxy-5-methoxy-4-(1-(4-methoxybenzyl)-6-methyl-7-oxo-6,7-dihydro-1H- pyrazolo[3,4-c]pyridin-4-yl)benzaldehyde as a mixture of regioisomers. Yield—599 mg, 82%; LC-MS (ES+): m/z 448.5 [M+H]+.

Synthesis of 4-(2,5-dichloro-4-(piperazine-1-carbonyl)phenyl)-1-(4-methoxybenzyl)-6-methyl-1,6-dihydro-7H-pyrazolo[3,4-c]pyridin-7-one

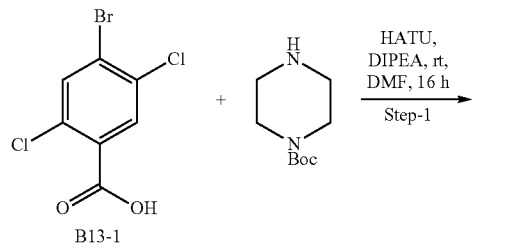

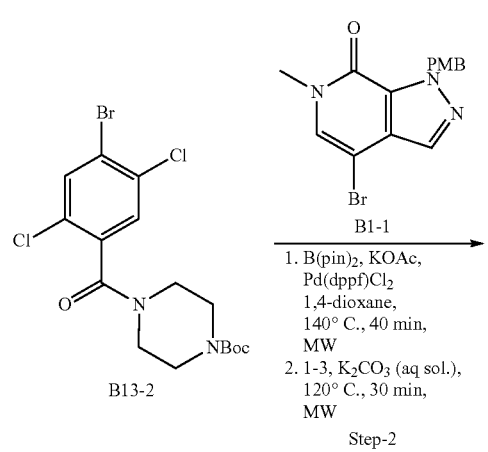

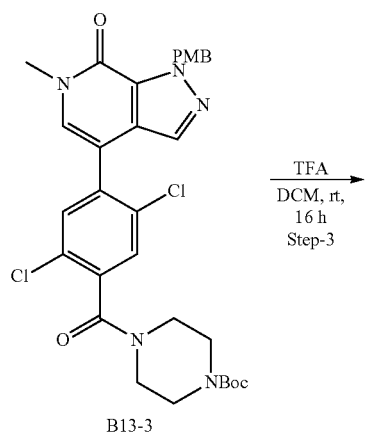

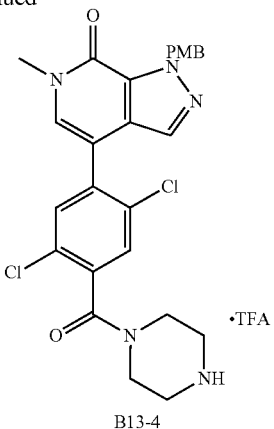

Step-1: Initially 4-bromo-2,5-dichloro-benzoic acid (609 mg, 2.26 mmol), tert-butyl piperazine-1-carboxylate (462.27 mg, 2.48 mmol, 45.96 uL), DIPEA (583.23 mg, 4.51 mmol, 786.02 uL) and HATU (943.71 mg, 2.48 mmol) were charged into a vial. The reactants were then dissolved in DMF (6.69 mL) and allowed to stir overnight at room temperature. Upon reaction completion the mixture was quenched with water before being extracted with EA (3×10 mL). The organic layer was washed with LiCl (5% w/v aq. Solution. 50 mL) before being dried with brine (50 mL), $Na_2SO_4$, filtered and concentrated to a residue which was purified via flash column chromatography (hexanes:ethyl acetate 1:0 to 0:1) to afford tert-butyl 4-(4-bromo-2,5-dichlorobenzoyl)piperazine-1-carboxylate as a white solid. Yield—535 mg, 54%; LC-MS (ES+): m/z 339.0 [M+H]+.

Step-2: Initially cyclopentyl(diphenyl)phosphane; dichloropalladium; iron (79.83 mg, 109.1 umol), tert-butyl 4-(4-bromo-2,5-dichloro-benzoyl)piperazine-1-carboxylate (478 mg, 1.09 mmol), bis(pinacolato) diboron (332.45 mg, 1.31 mmol), potassium acetate (321.21 mg, 3.27 mmol) were charged into a MW vial (2-5 mL) and suspended under an argon atmosphere in 1,4-Dioxane (5.89 mL) and heated in a MW at 140° C. for 40 mins. The suspension then had 4-bromo-1-[(4-methoxyphenyl)methyl]-6-methyl-pyrazolo[3,4-c]pyridin-7-one (417.86 mg, 1.20 mmol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), $Na_2SO_4$, filtered and concentrated to a residue which was purified via flash column chromatography (hexanes:ethyl acetate 1:0 to 0:1) to afford tert-butyl 4-[2,5-dichloro-4-[1-[(4-methoxyphenyl)methyl]-6-methyl-7-oxo-pyrazolo[3,4-c]pyridin-4-yl]benzoyl]piperazine-1-carboxylate as a mixture of regioisomers. Yield— 736 mg, 100%; LC-MS (ES+): m/z 626.5 [M+H]+.

Step-3: Initially tert-butyl 4-[2,5-dichloro-4-[1-[(4-methoxyphenyl)methyl]-6-methyl-7-oxo-pyrazolo[3,4-c]pyridin-4-yl]benzoyl]piperazine-1-carboxylate (736 mg, 1.17 mmol) was dissolved in DCM (5.69 mL) before TFA (267.89 mg, 2.35 mmol, 181.01 uL) was added dropwise and the mixture was allowed to stir overnight at room temperature. Upon reaction completion the mixture was concentrated to dryness and co-evaporated with DCM (10 mL×2) before being concentrated as a TFA salt and submitted to the following step without further purification. Yield—752 mg, 100%; LC-MS (ES+): m/z 526.4 [M+H]+.

Synthesis of 4-(2-chloro-5-methoxy-4-(piperazin-1-ylmethyl)phenyl)-1-(4-methoxybenzyl)-6-methyl-1,6-dihydro-7H-pyrazolo[3,4-c]pyridin-7-one

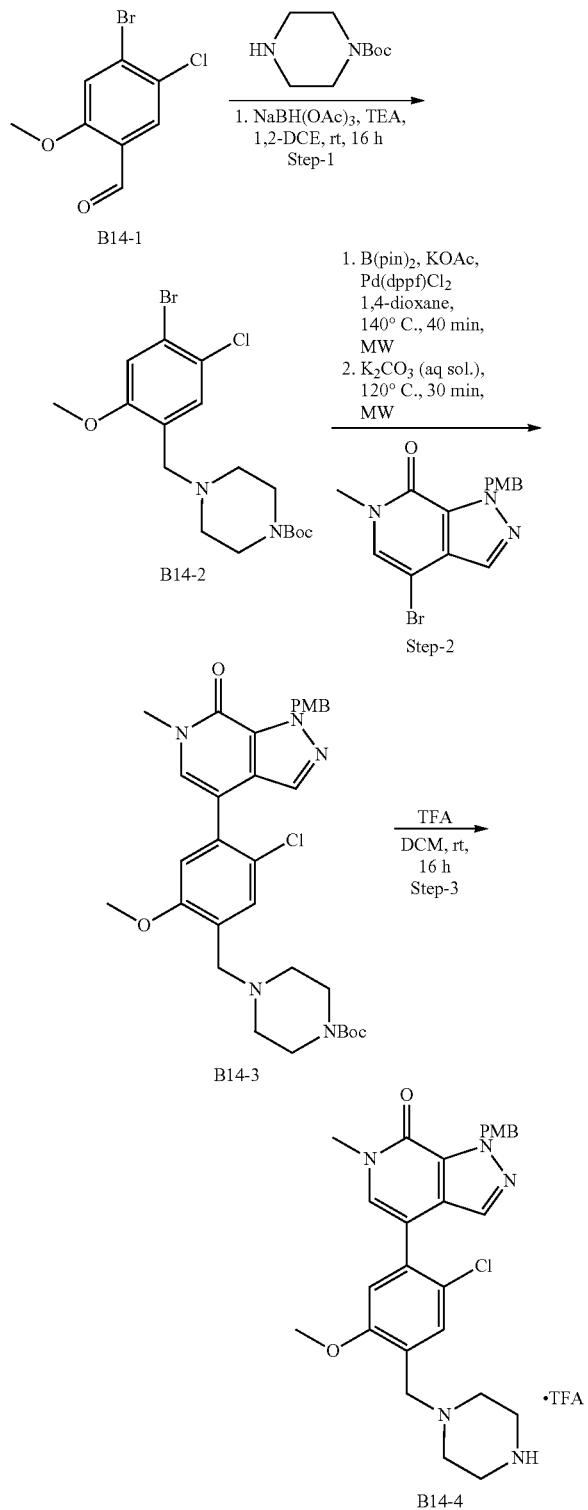

Step-1: Initially 4-bromo-5-chloro-2-methoxy-benzaldehyde (782 mg, 3.13 mmol) and 2tert-butyl piperazine-1-carboxylate (642.16 mg, 3.45 mmol) were charged into a reaction vial and dissolved in 1,2-DCE (10.45 mL) before Sodium triacetoxyborohydride, 95% (1.99 g, 9.40 mmol) was added in one portion. The reaction mixture was allowed to stir at room temperature and monitored by LCMS. Upon reaction completion the mixture was concentrated to dryness and purified via flash column chromatography (DCM:MeOH up to 10%) to give, tert-butyl 4-[(4-bromo-5-chloro-2-methoxy-phenyl)methyl]piperazine-1-carboxylate. Yield—1.01 g, 77%; LC-MS (ES$^+$): m/z 421.3 [M+H]$^+$.

Step-2: Initially cyclopentyl(diphenyl)phosphane; dichloropalladium; iron (127.78 mg, 174.63 umol), tert-butyl 4-[(4-bromo-5-chloro-2-methoxy-phenyl)methyl]piperazine-1-carboxylate (733 mg, 1.75 mmol) Bis(pinacolato)diboron (532.15 mg, 2.10 mmol), Potassium Acetate (514.16 mg, 5.24 mmol, 327.49 uL) were charged into a MW vial (2-5 mL) and suspended under an argon atmosphere in 1,4-Dioxane (2.58 mL) and heated in a MW at 140° C. for 40 mins. The suspension then had 4-bromo-1-[(4-methoxyphenyl)methyl]-6-methyl-pyrazolo[3,4-c]pyridin-7-one (134.62 mg, 386.63 umol) added under argon along with potassium carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), Na$_2$SO$_4$, filtered and concentrated to a residue which was purified via flash column chromatography (hexanes:ethyl acetate 1:0 to 0:1) to afford tert-butyl 4-[[5-chloro-2-methoxy-4-[1-[(4-methoxyphenyl)methyl]-6-methyl-7-oxo-pyrazolo[3,4-c]pyridin-4-yl]phenyl]methyl]piperazine-1-carboxylate as a mixture of regioisomers. Yield—751 mg, 71%; LC-MS (ES$^+$): m/z 608.5 [M+H]$^+$.

Step-3: Initially tert-butyl 4-[[5-chloro-2-methoxy-4-[1-[(4-methoxyphenyl)methyl]-6-methyl-7-oxo-pyrazolo[3,4-c]pyridin-4-yl]phenyl]methyl]piperazine-1-carboxylate (751 mg, 1.23 mmol) was dissolved in DCM (5.69 mL) before TFA (281.62 mg, 2.47 mmol, 190.28 uL) was added and the mixture was allowed to stir overnight. Upon reaction completion the mixture was concentrated to dryness and co-evaporated with DCM (10 mL×2) before being concentrated as a TFA salt and submitted to the following step without further purification. Yield—768 mg, 100%; LC-MS (ES$^+$): m/z 508.5 [M+H]$^+$.

Synthesis of 1-(4-methoxybenzyl)-6-methyl-4-(4-(piperazin-1-ylmethyl)-3-(trifluoromethoxy)phenyl)-1,6-dihydro-7H-pyrazolo[3,4-c]pyridin-7-one

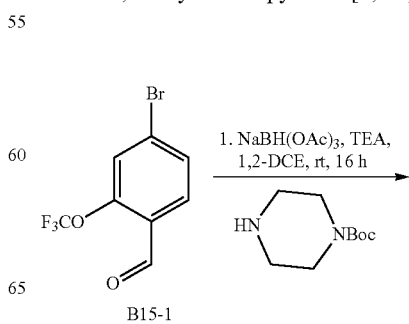

-continued

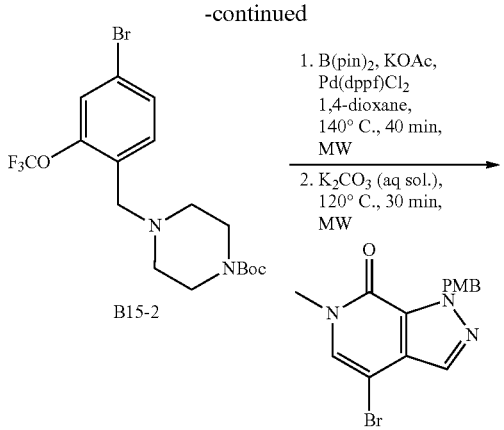

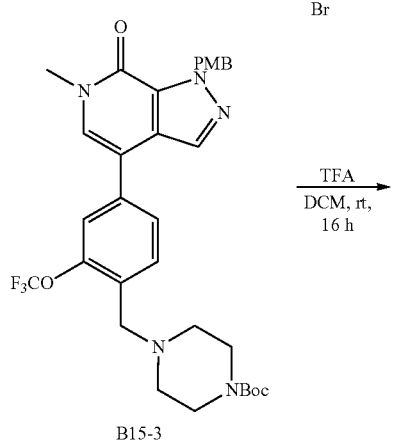

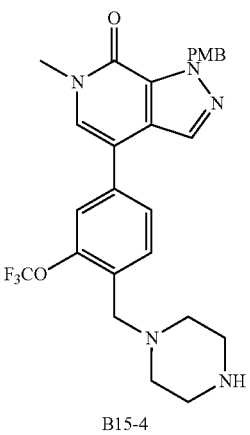

Step-1: Initially tert-butyl piperazine-1-carboxylate (761.58 mg, 4.09 mmol, 303.70 uL) and 4-bromo-2-(trifluoromethoxy)benzaldehyde (1000 mg, 3.72 mmol) were charged into a reaction vial and dissolved in 1,2-DCE (6.88 mL) before Sodium triacetoxyborohydride, 95% (1.18 g, 5.58 mmol) was added in one portion. The reaction mixture was allowed to stir at room temperature and monitored by LCMS. Upon reaction completion the mixture was concentrated to dryness and purified via flash column chromatography (Hexanes/EA up to 50%) to give tert-butyl 4-[[4-bromo-2-(trifluoromethoxy)phenyl]methyl]piperazine-1-carboxylate. Yield—1.60 g, 97%; LC-MS (ES$^+$): m/z 441.3 [M+H]$^+$.

Step-2: Initially cyclopentyl(diphenyl)phosphane; dichloropalladium; iron (131.93 mg, 180.30 umol), tert-butyl 4-[[4-bromo-2-(trifluoromethoxy)phenyl]methyl]piperazine-1-carboxylate (792 mg, 1.80 mmol), Bis(pinacolato)diboron (549.42 mg, 2.16 mmol), potassium acetate (530.85 mg, 5.41 mmol, 338.12 uL) were charged into a MW vial (2-5 mL) and suspended under an argon atmosphere in 1,4-dioxane (2.58 mL) and heated in a MW at 140° C. for 40 mins. The suspension then had 4-bromo-1-[(4-methoxyphenyl)methyl]-6-methyl-pyrazolo[3,4-c]pyridin-7-one (134.62 mg, 386.63 umol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), Na$_2$SO$_4$, filtered and concentrated to a residue which was purified via flash column chromatography (hexanes:ethyl acetate 1:0 to 0:1) to afford tert-butyl 4-[[4-[1-[(4-methoxyphenyl)methyl]-6-methyl-7-oxo-pyrazolo[3,4-c]pyridin-4-yl]-2-(trifluoromethoxy)phenyl]methyl]piperazine-1-carboxylate as a mixture of regioisomers. Yield—798 mg, 71%; LC-MS (ES$^+$): m/z 628.6 [M+H]$^+$.

Step-3: Initially tert-butyl 4-[[4-[1-[(4-methoxyphenyl)methyl]-6-methyl-7-oxo-pyrazolo[3,4-c]pyridin-4-yl]-2-(trifluoromethoxy)phenyl]methyl]piperazine-1-carboxylate (798 mg, 1.27 mmol) was dissolved in DCM (5.69 mL) before TFA (2.90 g, 25.43 mmol, 1.96 mL) was added and the mixture was allowed to stir overnight. Upon reaction completion the mixture was concentrated to dryness and co-evaporated with DCM (10 mL×2) before being concentrated as a TFA salt and submitted to the following step without further purification. Yield—815 mg, 100%; LC-MS (ES$^+$): m/z 528.6 [M+H]$^+$.

Synthesis of 2-(2,2-difluoroethoxy)-5-methoxy-4-(1-(4-methoxybenzyl)-6-methyl-7-oxo-6,7-dihydro-1H-pyrazolo[3,4-c]pyridin-4-yl)benzaldehyde

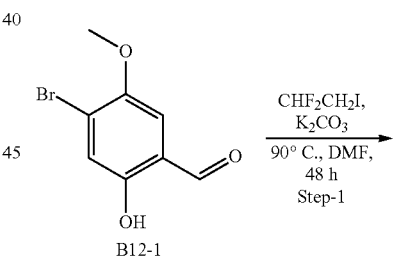

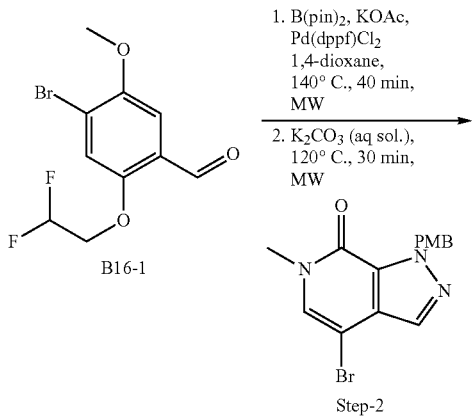

559
-continued

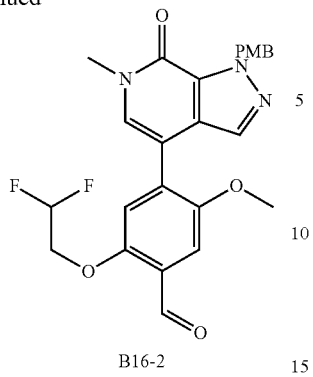

B16-2

Step-1: To a solution of 4-bromo-2-hydroxy-5-methoxy-benzaldehyde (622 mg, 2.69 mmol) in DMF (6.01 mL) was added Potassium carbonate-granular (1.12 g, 8.08 mmol, 487.43 uL) before 1,1-difluoro-2-iodo-ethane (516.75 mg, 2.69 mmol, 237.04 uL) was added at room temperature and stirred with heating to 90° C. for 48 hours under an argon atmosphere. Upon reaction completion the mixture was quenched by being poured into water (50 mL) before being extracted with ethyl acetate (50 mL×3). The organic layer was washed with LiCl (5% w/v aq. Solution 50 mL) before being dried with brine (50 mL), Na$_2$SO$_4$, filtered and concentrated to a residue which was purified via flash column chromatography (hexanes:ethyl acetate 1:0 to 4:6) to afford 4-bromo-2-(2,2-difluoroethoxy)-5-methoxy-benzaldehyde as a white solid. Yield—349 mg, 44%; LC-MS (ES$^+$): m/z 295.1 [M+H]$^+$.

Step-2: Initially cyclopentyl(diphenyl)phosphane; dichloropalladium; iron (69.43 mg, 94.89 umol), 4-bromo-2-(2,2-difluoroethoxy)-5-methoxy-benzaldehyde (280 mg, 948.90 umol) Bis(pinacolato) diboron (289.16 mg, 1.14 mmol), Potassium acetate (279.38 mg, 2.85 mmol, 177.95 uL) were charged into a MW vial (2-5 mL) and suspended under an argon atmosphere in 1,4-Dioxane (2.58 mL) and heated in a MW at 140° C. for 40 mins. The suspension then had 4-bromo-1-[(4-methoxyphenyl)methyl]-6-methyl-pyrazolo [3,4-c]pyridin-7-one (134.62 mg, 386.63 umol) added under argon along with potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), Na$_2$SO$_4$, filtered and concentrated to a residue which was purified via flash column chromatography (hexanes:ethyl acetate 1:0 to 0:1) to afford 2-(2,2-difluoroethoxy)-5-methoxy-4-(1-(4-methoxybenzyl)-6-methyl-7-oxo-6,7-dihydro-1H-pyrazolo[3,4-c]pyridin-4-yl)benzaldehyde as a mixture of Regio isomers. Yield—462 mg, 100%; LC-MS (ES$^+$): m/z 484.5 [M+H]$^+$.

560

Synthesis of 2-isopropoxy-5-methoxy-4-(1-(4-methoxybenzyl)-6-methyl-7-oxo-6,7-dihydro-1H-pyrazolo[3,4-c]pyridin-4-yl)benzaldehyde

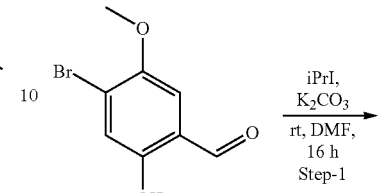

B12-1

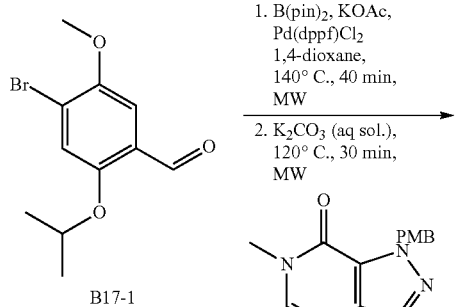

B17-1

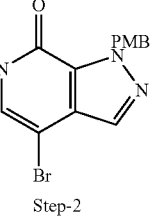

Step-2

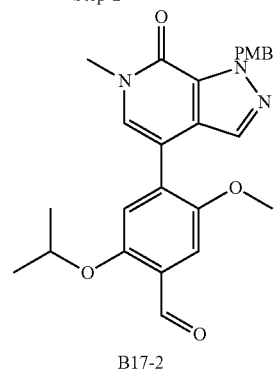

B17-2

Step-1: To a solution of 4-bromo-2-hydroxy-5-methoxy-benzaldehyde (556 mg, 2.41 mmol) in DMF (5.34 mL) was added Potassium carbonate-granular (997.77 mg, 7.22 mmol, 435.71 uL) before 2-iodopropane (409.08 mg, 2.41 mmol, 240.64 uL) was added at room temperature and stirred for 5 hours under an argon atmosphere. Upon reaction completion the mixture was quenched by being poured into water (50 mL) before being extracted with ethyl acetate (50 mL×3). The organic layer was washed with LiCl (5% w/v aq. Solution. 50 mL) before being dried with brine (50 mL), Na$_2$SO$_4$, filtered and concentrated to a residue which was purified via flash column chromatography (hexanes: ethyl acetate 1:0 to 4:6) to afford 4-bromo-2-isopropoxy-5-methoxy-benzaldehyde as a white solid. Yield 573 mg, 87%; LC-MS (ES$^+$): m/z 273.0 [M+H]$^+$.

Step-2: Initially cyclopentyl(diphenyl)phosphane; dichloropalladium; iron (127.52 mg, 174.28 umol), 4-bromo-2-isopropoxy-5-methoxy-benzaldehyde (476 mg, 1.74 mmol) Bis(pinacolato) diboron (531.08 mg, 2.09 mmol), Potassium Acetate (513.13 mg, 5.23 mmol, 326.83 uL) were charged into a MW vial (2-5 mL) and suspended under an argon atmosphere in 1,4-Dioxane (2.58 mL) and heated in a MW at 140° C. for 40 mins. The suspension then had 4-bromo-1-[(4-methoxyphenyl)methyl]-6-methyl-pyrazolo[3,4-c]pyridin-7-one (134.62 mg, 386.63 umol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), Na$_2$SO$_4$, filtered and concentrated to a residue which was purified via flash column chromatography (hexanes:ethyl acetate 1:0 to 0:1) to afford 2-isopropoxy-5-methoxy-4-(1-(4-methoxybenzyl)-6-methyl-7-oxo-6,7-dihydro-1H-pyrazolo[3,4-c]pyridin-4-yl)benzaldehyde as a mixture of regioisomers. Yield—715 mg, 89%; LC-MS (ES$^+$): m/z 462.9 [M+H]$^+$.

Synthesis of 4-(6-fluoro-2-methyl-1-oxo-1,2-dihydroisoquinolin-4-yl)-2,6-dimethoxybenzaldehyde

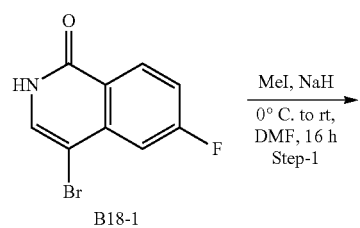

B18-1

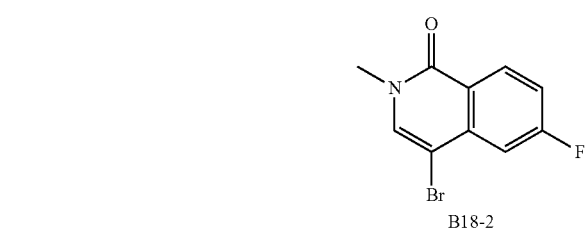

B18-2

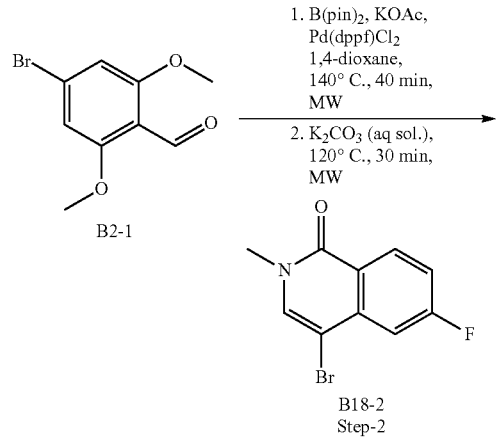

B2-1

B18-2
Step-2

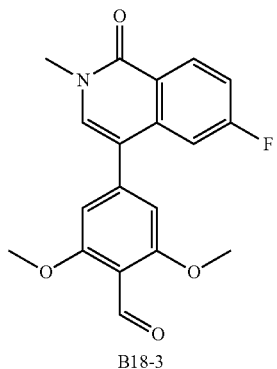

B18-3

Step-1: Initially 4-bromo-6-fluoro-2H-isoquinolin-1-one (1000 mg, 4.13 mmol) was dissolved in DMF (38.41 mL) and cooled to 0° C. before sodium hydride (198.29 mg, 8.26 mmol) was added in one portion and the mixture was stirred for 30 mins. Iodomethane (2.35 g, 16.53 mmol, 1.03 mL) was then added dropwise and the mixture was allowed to stir overnight at ambient temperature. The reaction was then quenched with ice water and the precipitated product was filtered off and washed with copious water followed by hexanes. The solid was dried to give 4-bromo-2,6-dimethoxy-benzaldehyde. Yield—759 mg, 72%; LC-MS (ES$^+$): m/z 256.0 [M+H]$^+$.

Step-2: Initially cyclopentyl(diphenyl)phosphane; dichloropalladium; iron (59.71 mg, 81.61 umol), 4-bromo-2,6-dimethoxy-benzaldehyde (200 mg, 816.09 umol) Bis(pinacolato) diboron (248.68 mg, 979.31 umol), Potassium Acetate (240.28 mg, 2.45 mmol, 153.04 uL) were charged into a MW vial (2-5 mL) and suspended under an argon atmosphere in 1,4-Dioxane (12.27 mL) and heated in a MW at 140° C. for 40 mins. The suspension then had 4-bromo-6-fluoro-2-methyl-isoquinolin-1-one (208.98 mg, 816.09 umol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), Na$_2$SO$_4$, filtered and concentrated to a residue which was purified via flash column chromatography (hexanes:ethyl acetate 1:0 to 0:1) to afford 4-(6-fluoro-2-methyl-1-oxo-1,2-dihydroisoquinolin-4-yl)-2,6-dimethoxybenzaldehyde. Yield—74 mg, 26%; LC-MS (ES$^+$): m/z 342.3 [M+H]$^+$.

Synthesis of 2,6-dimethoxy-4-(2-methyl-1-oxo-1,2-dihydroisoquinolin-4-yl)benzaldehyde

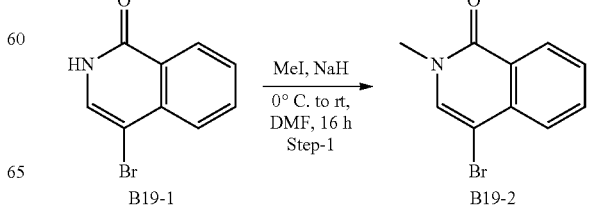

B19-1         B19-2

-continued

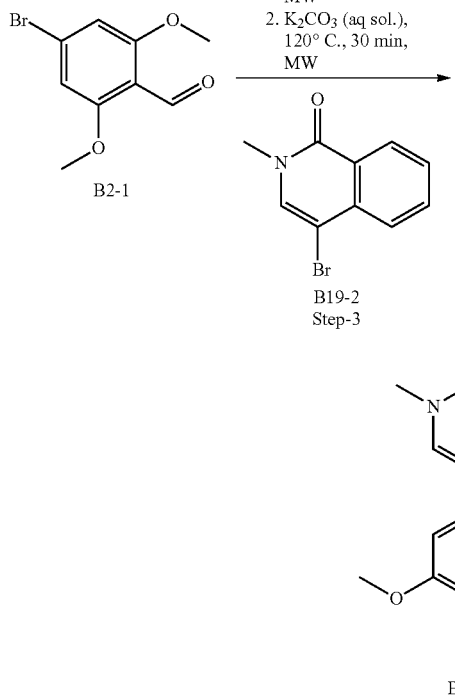

Step-1: Initially 4-bromo-2H-isoquinolin-1-one (1030 mg, 4.13 mmol) was dissolved in DMF (14.21 mL) and cooled to 0° C. before sodium hydride (221.1 mg, 9.21 mmol) was added in one portion and the mixture was stirred for 30 mins. Iodomethane (2.62 g, 18.42 mmol, 1.15 mL) was then added dropwise and the mixture was allowed to stir overnight at ambient temperature. The reaction was then quenched with ice water and the precipitated product was filtered off and washed with copious water followed by hexanes. The solid was dried to give 4-bromo-2,6-dimethoxy-benzaldehyde. Yield—784 mg, 72%; LC-MS (ES$^+$): m/z 238.0 [M+H]$^+$.

Step-2: Initially cyclopentyl(diphenyl)phosphane; dichloropalladium; iron (59.71 mg, 81.61 umol), 4-bromo-2,6-dimethoxy-benzaldehyde (200 mg, 816.09 umol) Bis(pinacolato) diboron (248.68 mg, 979.31 umol), Potassium Acetate (240.28 mg, 2.45 mmol, 153.04 uL) were charged into a MW vial (2-5 mL) and suspended under an argon atmosphere in 1,4-Dioxane (12.27 mL) and heated in a MW at 140° C. for 40 mins. The suspension then had 4-bromo-2-methyl-isoquinolin-1-one (194.30 mg, 816.09 umol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), Na$_2$SO$_4$, filtered and concentrated to a residue which was purified via flash column chromatography (hexanes:ethyl acetate 1:0 to 0:1) to afford 2,6-dimethoxy-4-(2-methyl-1-oxo-1,2-dihydroisoquinolin-4-yl)benzaldehyde. Yield—63 mg, 24%; LC-MS (ES$^+$): m/z 324.3 [M+H]$^+$.

Synthesis of 4-(7-chloro-2-methyl-1-oxo-1,2-dihydroisoquinolin-4-yl)-2,6-dimethoxybenzaldehyde

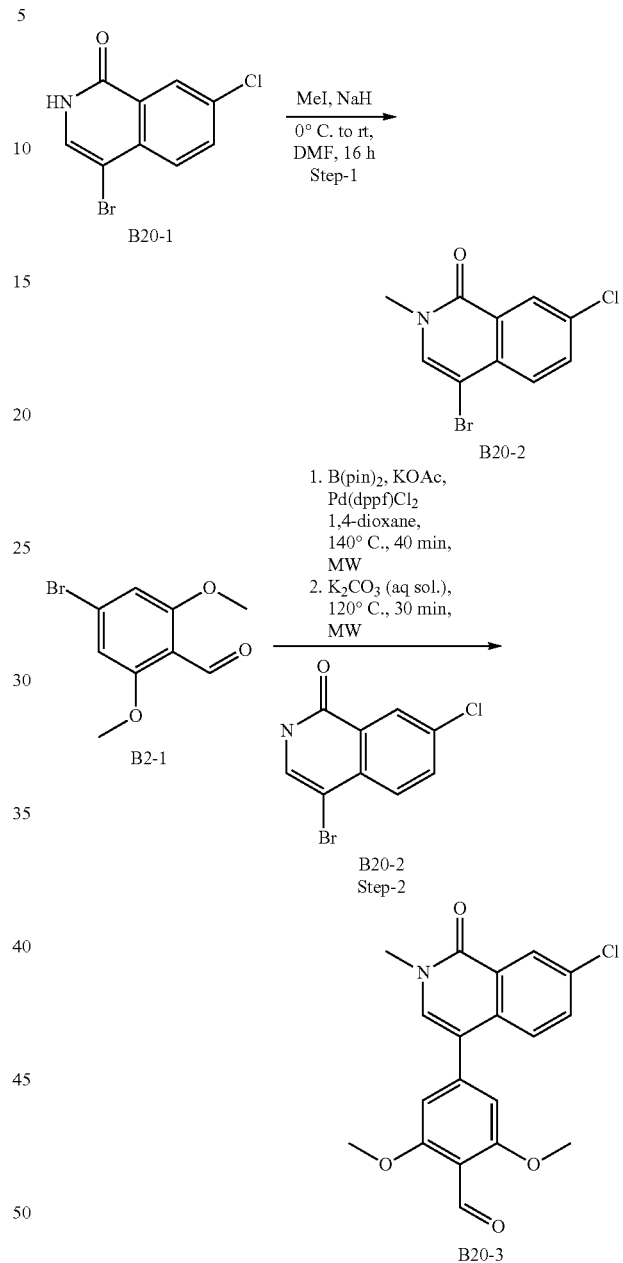

Step-1: Initially 4-bromo-7-chloro-2H-isoquinolin-1-one (916 mg, 3.54 mmol) was dissolved in DMF (38.41 mL) and cooled to 0° C. before sodium hydride (170.07 mg, 7.09 mmol) was added in one portion and the mixture was stirred for 30 mins. Iodomethane (2.01 g, 14.17 mmol, 882.39 uL) was then added dropwise and the mixture was allowed to stir overnight at ambient temperature. The reaction was then quenched with ice water and the precipitated product was filtered off and washed with copious water followed by hexanes. The solid was dried to give 4-bromo-2,6-dimethoxy-benzaldehyde. Yield—1.01 g, 100%; LC-MS (ES$^+$): m/z 274.0 [M+H]$^+$.

Step-2: Initially cyclopentyl(diphenyl)phosphane; dichloropalladium; iron (59.71 mg, 81.61 umol), 4-bromo-2,6- dimethoxy-benzaldehyde (200 mg, 816.09 umol) Bis(pinacolato) diboron (248.68 mg, 979.31 umol), Potassium Acetate (240.28 mg, 2.45 mmol, 153.04 uL) were charged into a MW vial (2-5 mL) and suspended under an argon atmosphere in 1,4-Dioxane (12.27 mL) and heated in a MW at 140° C. for 40 mins. The suspension then had 4-bromo-7-chloro-2-methyl-isoquinolin-1-one (222.41 mg, 816.09 umol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), $Na_2SO_4$, filtered and concentrated to a residue which was purified via flash column chromatography (hexanes:ethyl acetate 1:0 to 0:1) to afford 4-(7-chloro-2-methyl-1-oxo-1,2-dihydroisoquinolin-4-yl)-2,6-dimethoxybenzaldehyde. Yield—75 mg, 26%; LC-MS ($ES^+$): m/z 358.3 $[M+H]^+$.

Synthesis of 2,6-dimethoxy-4-(1,4,5-trimethyl-6-oxo-1,6-dihydropyridin-3-yl)benzaldehyde

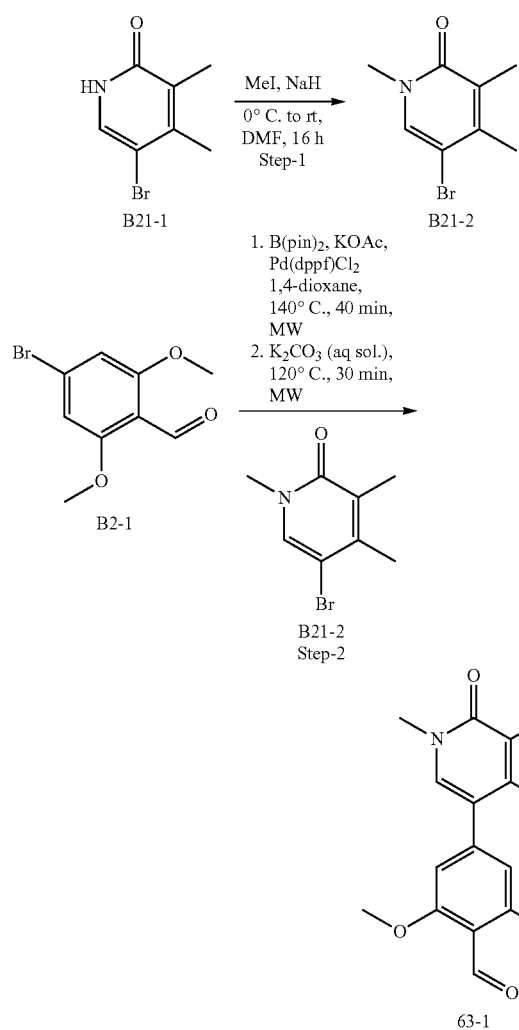

Step-1: Initially 5-bromo-3,4-dimethyl-1H-pyridin-2-one (2 g, 9.90 mmol) was dissolved in DMF (40.57 mL) and cooled to 0° C. before sodium hydride (475.09 mg, 19.80 mmol) was added in one portion and the mixture was stirred for 30 mins. Iodomethane (5.62 g, 39.59 mmol, 2.46 mL) was then added dropwise and the mixture was allowed to stir overnight at ambient temperature. The reaction was then quenched with ice water and the mixture was then extracted with ethyl acetate (3×50 mL), the combined organic layers were dried with brine (1×100 mL), $Na_2SO_4$, filtered and concentrated to a residue which was purified via flash column chromatography (hexanes:ethyl acetate 1:0 to 0:1) to afford 4-bromo-2,6-dimethoxy-benzaldehyde. Yield—1.35 g, 63%; LC-MS ($ES^+$): m/z 215.9 $[M+H]^+$.

Step-2: Initially cyclopentyl(diphenyl)phosphane; dichloropalladium; iron (59.71 mg, 81.61 umol), 4-bromo-2,6-dimethoxy-benzaldehyde (200 mg, 816.09 umol) Bis(pinacolato) diboron (248.68 mg, 979.31 umol), potassium acetate (240.28 mg, 2.45 mmol, 153.04 uL) were charged into a MW vial (2-5 mL) and suspended under an argon atmosphere in 1,4-Dioxane (12.27 mL) and heated in a MW at 140° C. for 40 mins. The suspension then had 5-bromo-1,3,4-trimethyl-pyridin-2-one (176.34 mg, 816.09 umol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), $Na_2SO_4$, filtered and concentrated to a residue which was purified via flash column chromatography (hexanes:ethyl acetate 1:0 to 0:1) to afford 2,6-dimethoxy-4-(1,4,5-trimethyl-6-oxo-1,6-dihydropyridin-3-yl)benzaldehyde. Yield—245 mg, 99%; LC-MS ($ES^+$): m/z 302.2 $[M+H]^+$.

Synthesis of 4-(1,5-dimethyl-6-oxo-1,6-dihydropyridin-3-yl)-2,6-dimethoxybenzaldehyde

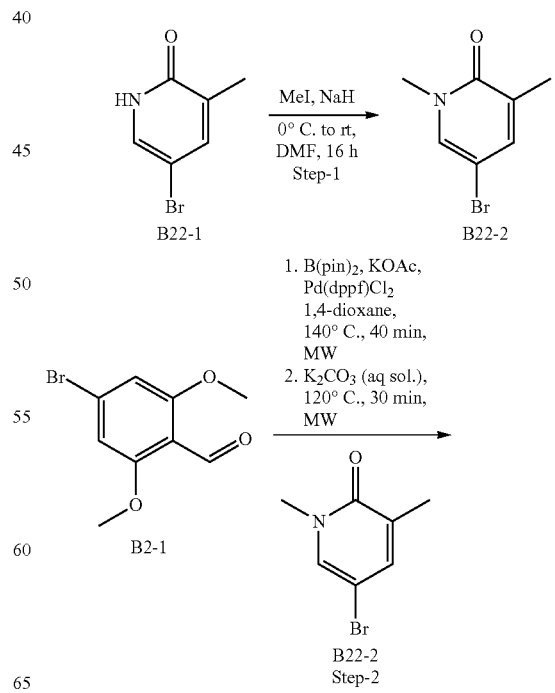

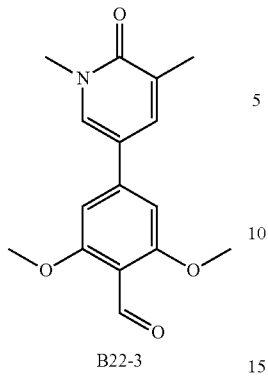

B22-3

Step-1: Initially 5-bromo-3-methyl-1H-pyridin-2-one (1.050 g, 5.58 mmol) was dissolved in DMF (17.22 mL) and cooled to 0° C. before sodium hydride (268.03 mg, 11.17 mmol) was added in one portion and the mixture was stirred for 30 mins. Iodomethane (3.17 g, 22.34 mmol, 1.39 mL) was then added dropwise and the mixture was allowed to stir overnight at ambient temperature. The reaction was then quenched with ice water and the mixture was then extracted with ethyl acetate (3×50 mL), the combined organic layers were dried with brine (1×100 mL), Na2SO4, filtered and concentrated to a residue which was purified via flash column chromatography (hexanes:ethyl acetate 1:0 to 0:1) to afford 4-bromo-2,6-dimethoxy-benzaldehyde. Yield—554 mg, 49%; LC-MS (ES+): m/z 201.9 [M+H]+.

Step-2: Initially cyclopentyl(diphenyl)phosphane; dichloropalladium; iron (91.36 mg, 124.86 umol), 4-bromo-2,6-dimethoxy-benzaldehyde (306 mg, 1.25 mmol) Bis(pinacolato) diboron (380.49 mg, 1.50 mmol), Potassium Acetate (367.63 mg, 3.75 mmol, 234.16 uL) were charged into a MW vial (2-5 mL) and suspended under an argon atmosphere in 1,4-Dioxane (12.27 mL) and heated in a MW at 140° C. for 40 mins. The suspension then had 5-bromo-1,3-dimethyl-pyridin-2-one (252.28 mg, 1.25 mmol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), Na₂SO₄, filtered and concentrated to a residue which was purified via flash column chromatography (hexanes:ethyl acetate 1:0 to 0:1) to afford 4-(1,5-dimethyl-6-oxo-1,6-dihydropyridin-3-yl)-2,6-dimethoxybenzaldehyde. Yield—62 mg, 17%; LC-MS (ES+): m/z 288.2 [M+H]+.

Synthesis of 2-chloro-6-methoxy-4-(2-methyl-1-oxo-1,2-dihydro-2,7-naphthyridin-4-yl)benzaldehyde

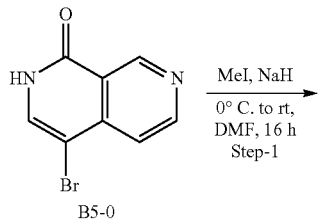

B5-0

MeI, NaH
0° C. to rt,
DMF, 16 h
Step-1

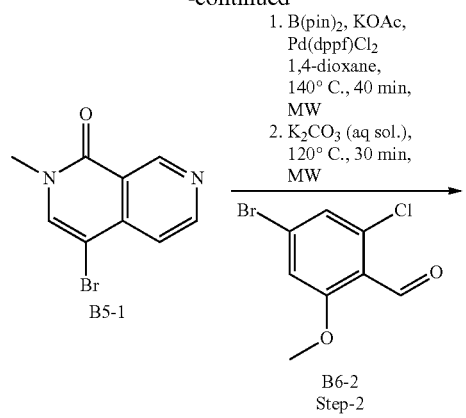

Step-1: Initially 4-bromo-2H-2,7-naphthyridin-1-one (1 g, 4.44 mmol) was dissolved in DMF (10.83 mL) and cooled to 0° C. before sodium hydride (213.27 mg, 8.89 mmol) was added in one portion and the mixture was stirred for 30 mins. Iodomethane (2.52 g, 17.77 mmol, 1.11 mL) was then added dropwise and the mixture was allowed to stir overnight at ambient temperature. The reaction was then quenched with ice water and the mixture was then extracted with ethyl acetate (3×50 mL), the combined organic layers were dried with brine (1×100 mL), Na2SO4, filtered and concentrated to a residue which was purified via flash column chromatography (hexanes:ethyl acetate 1:0 to 0:1) to afford 4-bromo-2-methyl-2,7-naphthyridin-1-one. Yield—811 mg, 76%; LC-MS (ES+): m/z 240.9 [M+H]+.

Step-2: Initially cyclopentyl(diphenyl)phosphane; dichloropalladium; iron (58.66 mg, 80.16 umol), 4-bromo-2-methyl-2,7-naphthyridin-1-one (191.65 mg, 801.64 umol) Bis(pinacolato) diboron (244.28 mg, 961.97 umol), Potassium Acetate (236.02 mg, 2.40 mmol, 150.33 uL) were charged into a MW vial (2-5 mL) and suspended under an argon atmosphere in 1,4-Dioxane (12.27 mL) and heated in a MW at 140° C. for 40 mins. The suspension then had 4-bromo-2-chloro-6-methoxy-benzaldehyde (200 mg, 801.64 umol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), Na₂SO₄, filtered and concentrated to a residue which was purified via flash column chromatography (hexanes:ethyl acetate 1:0 to 0:1) to afford 2-chloro-6-methoxy-4-(2-methyl-1-oxo-1,2-dihydro-2,7-naphthyridin-4-yl)benzaldehyde. Yield—121 mg, 54%; LC-MS (ES+): m/z 329.1 [M+H]+.

Synthesis of 2-chloro-6-methoxy-4-(2-methyl-1-oxo-1,2-dihydro-2,7-naphthyridin-4-yl)benzoic acid

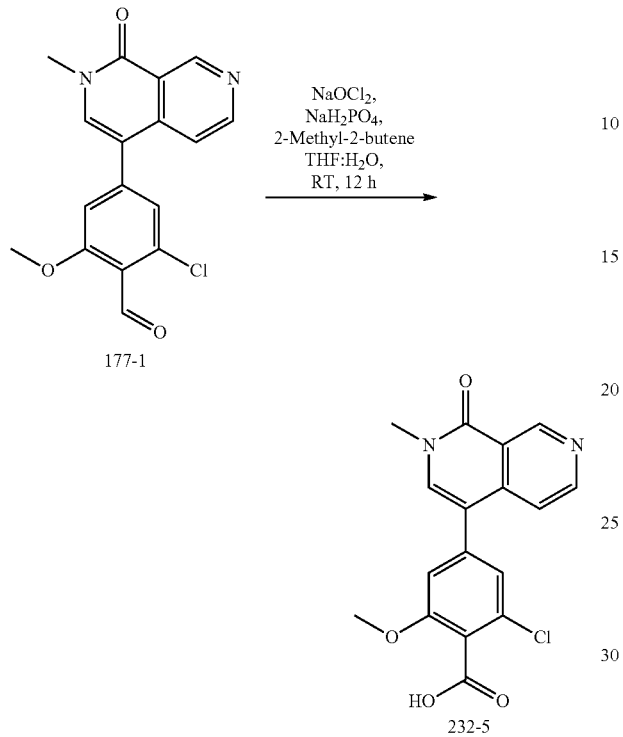

To the stirred solution of 2-chloro-6-methoxy-4-(2-methyl-1-oxo-1,2-dihydro-2,7-naphthyridin-4-yl)benzaldehyde (0.4 g, 1.22 mmol) in THF (25 mL) was added 2-methyl-2-butene (0.68 g, 9.73 mmol) at 0° C. followed by the addition of sodium chlorite (0.55 g, 6.08 mmol) and sodium; dihydrogen phosphate (2.92 g, 24.33 mmol) dissolved in water (20 mL). The reaction mixture was slowly warmed to rt over the period of 30 mints and stirred at rt for 12 h. The completion of the reaction was confirmed by TLC. The reaction mixture was concentrated to half a quantity to obtain the crude product which was purified by trituration with methanol followed by washings by water to afford 2-chloro-6-methoxy-4-(2-methyl-1-oxo-1,2-dihydro-2,7-naphthyridin-4-yl)benzoic acid (0.35 g, 71.16% yield, 85.28% purity) as white solid. LC-MS (ES+): m/z 345.18 [M+H]+

Synthesis of 4-(7-fluoro-2-methyl-1-oxo-1,2-dihydroisoquinolin-4-yl)-2-(trifluoromethoxy)benzaldehyde

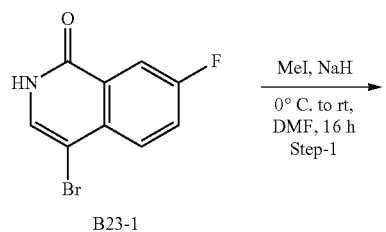

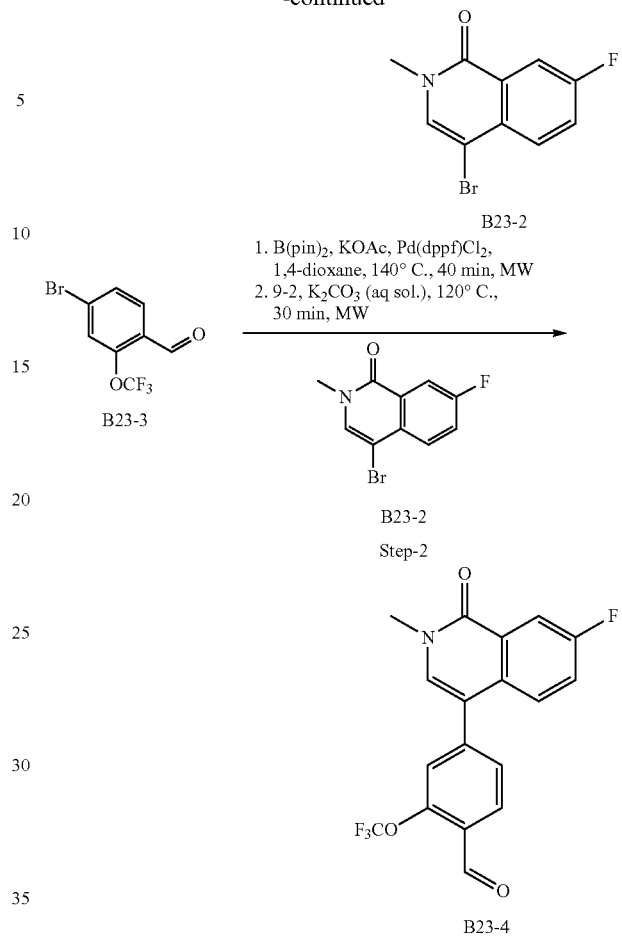

Step-1: Initially 4-bromo-7-fluoro-2H-isoquinolin-1-one (994 mg, 4.11 mmol) was dissolved in DMF (38.41 mL) and cooled to 0° C. before sodium hydride (197.10 mg, 8.21 mmol) was added in one portion and the mixture was stirred for 30 mins. Iodomethane (2.33 g, 16.43 mmol, 1.02 mL) was then added dropwise and the mixture was allowed to stir overnight at ambient temperature. The reaction was then quenched with ice water and the precipitated product was filtered off and washed with copious water followed by hexanes. The solid was dried to give had 4-bromo-7-fluoro-2-methyl-isoquinolin-1-one, Yield—902 mg, 86%; LC-MS (ES+): m/z 256.0 [M+H]+.

Step-2: Initially cyclopentyl(diphenyl)phosphane; dichloropalladium; iron (51.68 mg, 70.63 umol), 4-bromo-2-(trifluoromethoxy)benzaldehyde (190 mg, 706.28 umol) Bis(pinacolato) diboron (215.22 mg, 847.54 umol), Potassium Acetate (207.95 mg, 2.12 mmol, 132.45 uL) were charged into a MW vial (2-5 mL) and suspended under an argon atmosphere in 1,4-Dioxane (12.27 mL) and heated in a MW at 140° C. for 40 mins. The suspension then had 4-bromo-7-fluoro-2-methyl-isoquinolin-1-one (180.86 mg, 706.28 umol) added under argon along with Potassium Carbonate (2 M, 2 eq) and reheated at 120° C. for 30 mins before being checked by LCMS. Upon reaction completion the mixture was filtered through a Celite pad and washed with DCM/ethyl acetate. The filtrate was washed with water (10 mL) before being washed with brine (50 mL), Na2SO4, filtered and concentrated to a residue which was purified via flash column chromatography (hexanes:ethyl acetate 1:0 to 0:1) to afford 4-(7-fluoro-2-methyl-1-oxo-1,2-dihydroisoquinolin-4-yl)-2-(trifluoromethoxy)benzaldehyde. Yield—241 mg, 93%; LC-MS (ES+): m/z 366.2 [M+H]+.

Synthesis of 5-methoxy-1',4',5'-trimethyl-6'-oxo-1',6'-dihydro-[3,3'-bipyridine]-6-carbaldehy

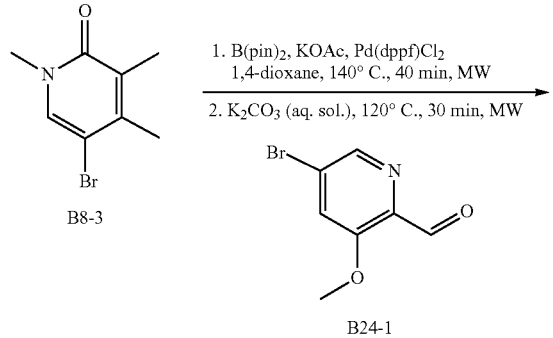

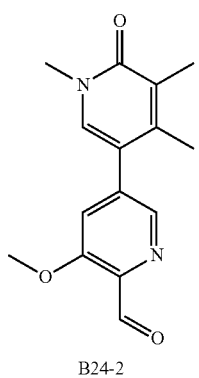

Initially cyclopentyl(diphenyl)phosphane; dichloropalladium; iron (135.45 mg, 185.12 umol), 5-bromo-1,3,4-trimethyl-pyridin-2-one (400 mg, 1.85 mmol) Bis(pinacolato)diboron (564.11 mg, 2.22 mmol), Potassium Acetate (545.05 mg, 5.55 mmol, 347.16 uL) were charged into a MW vial (2-5 mL) and suspended under an argon atmosphere in 1,4-Dioxane (11.89 mL) and heated in a MW at 140° C. for 40 mins. The suspension then had 5-bromo-3-methoxypicolinaldehyde (134.62 mg, 386.63 umol) added under argon along with Potassium Carbonate (2 M, 2 eq) and reheated at 120° C. for 30 mins before being checked by LCMS. Upon reaction completion the mixture was filtered through a Celite pad and washed with EA/DCM. The filtrate was then washed with H2O (10 mL), followed by brine (25 mL), then dried over Na2SO4 before being filtered and concentrated to a residue which was purified via flash column chromatography (Hexanes/EA up to 100%) to give the product as a solid 3-methoxy-5-(1,4,5-trimethyl-6-oxo-3-pyridyl)pyridine-2-carbaldehyde (202 mg, 741.83 umol, 40% yield). $^1$H NMR (400 MHz, Chloroform-d) δ 10.33 (s, 1H), 8.26 (d, J=1.7 Hz, 1H), 7.25 (d, J=1.7 Hz, 1H), 7.13 (s, 1H), 3.98 (s, 3H), 3.58 (s, 3H), 2.18 (s, 3H), 2.07 (s, 3H).

Synthesis of 4-(3,5-dimethoxy-4-(piperazin-1-ylmethyl)phenyl)-2-methyl-2,7-naphthyridin-1(2H)-one

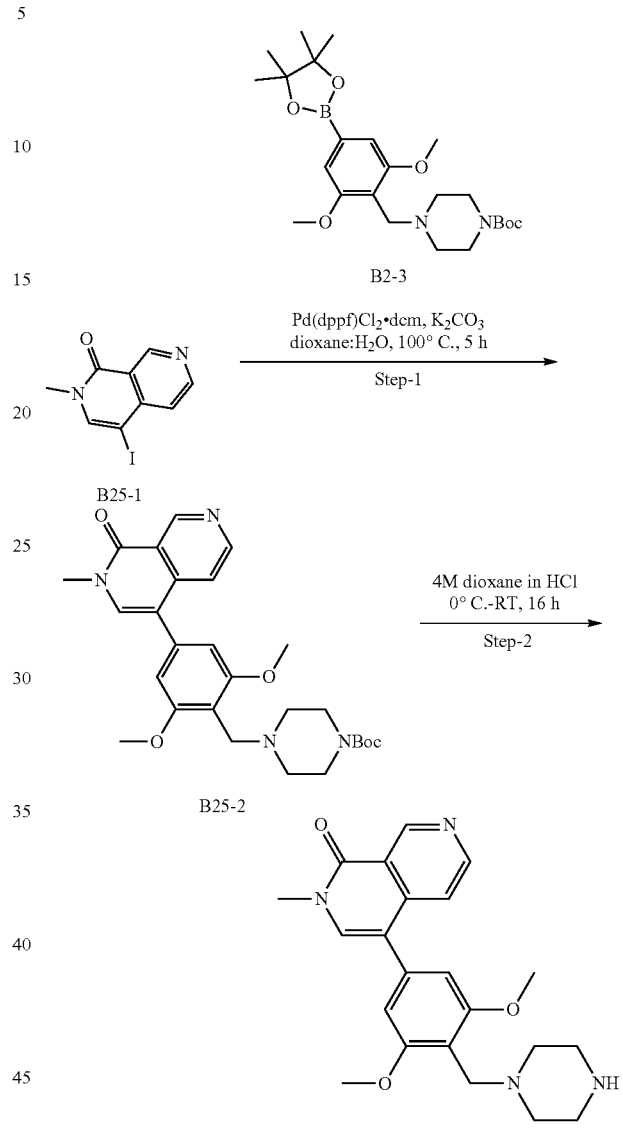

Step-1: To a stirred solution of 4-iodo-2-methyl-2,7-naphthyridin-1-one (2.0 g, 6.99 mmol) in DMF (15 mL) and water (2 mL), was added tert-butyl 2-[[2,6-dimethoxy-4-(4,4,5,5-tetramethyl-1,3,2-dioxaborolan-2-yl)phenyl]methyl-methyl-amino]acetate (3.53 g, 8.39 mmol) and sodium carbonate (1.85 g, 17.48 mmol). The resulting mixture was degassed with N2 (g) for 15 minutes, added Pd(dppf)Cl2·CH2Cl2 (570.94 mg, 6.99 mmol) and heated at 100° C. for 5 h, while monitoring by LCMS and TLC. The reaction mixture was diluted with ethyl acetate and filtered through Celite bed. The organic layer was washed with water, dried over Na2SO4 and concentrated under reduced pressure to afford tert-butyl 4-[[2,6-dimethoxy-4-(2-methyl-1-oxo-2,7-naphthyridin-4-yl)phenyl]methyl]piperazine-1-carboxylate (1 g, 1.86 mmol, 53.21% yield, 92.15% purity) brown gummy solid. This was taken to next step without further any purification. LC-MS (ES+): m/z 495.30 [M+H]+

Step-2: To a stirred solution of tert-butyl 4-[[2,6-dimethoxy-4-(2-methyl-1-oxo-2,7-naphthyridin-4-yl)phenyl]methyl]piperazine-1-carboxylate (1.0 g, 2.02 mmol) in dioxane was added 4M dioxane HCl (0.18 ml, 20.2 mmol) at 0° C. and the reaction mixture was stirred at RT for 16 h. After completion, the reaction mixture was concentrated and the crude compound was triturated with diethyl ether and dried to afford 4-[3,5-dimethoxy-4-(piperazin-1-ylmethyl)phenyl]-2-methyl-2,7-naphthyridin-1-one.HCl (0.8 g, 1.62 mmol, 80.02% yield, 87.15% purity) as an off white solid. 1H NMR (400 MHz, DMSO-d$_6$) δ 9.74 (bs, 2H), 9.54 (s, 1H), 8.77. (d, J=6 Hz, 1H), 8.12 (s, 1H), 7.90 (d, J=6 Hz, 1H), 6.88 (s, 2H), 4.49 (s, 2H), 3.90 (s, 6H), 3.62 (s, 3H), 3.59-3.58 (bs, 4H), 3.39 (bs, 4H); LC-MS (ES$^+$): m/z 395.35 [M+H]$^+$.

Synthesis of 5-(3,5-dimethoxy-4-(piperazin-1-ylmethyl)phenyl)-1,3,4-trimethylpyridin-2(1H)-one

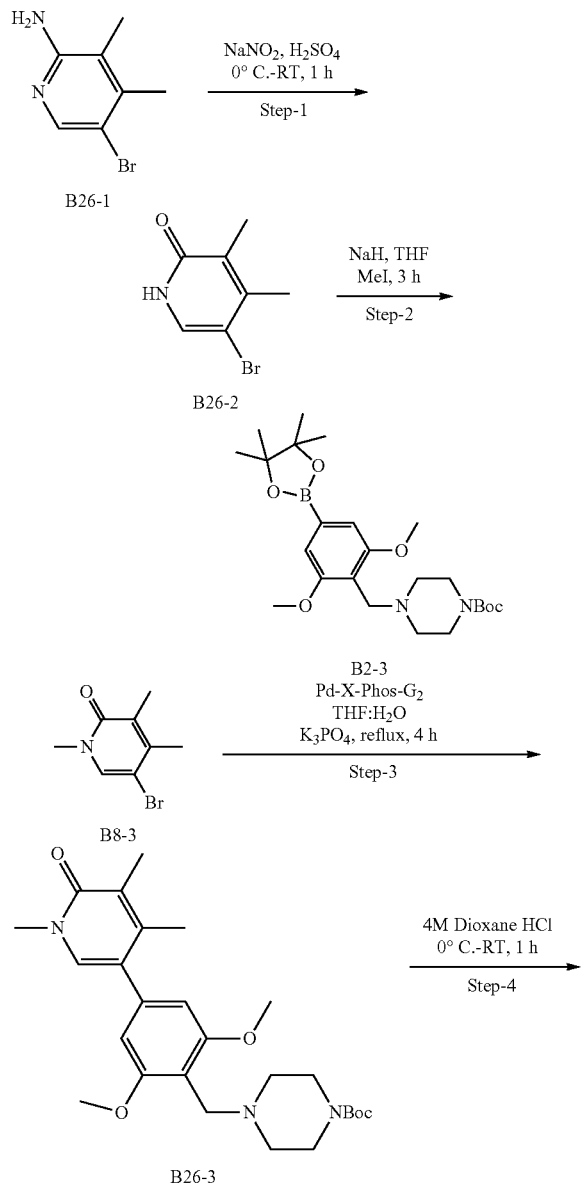

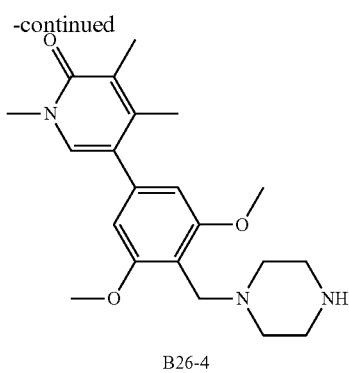

Step-1: To a mixture of 5-bromo-3,4-dimethylpyridin-2-amine (0.6 g, 2.98 mmol) in concentrated H$_2$SO$_4$ (20 mL) and water (60 mL) was added a solution of sodium nitrite (2.40 g, 34.81 mmol) in water (20 mL) at 0° C. The mixture was allowed to equilibrate to room temperature and stirred for 1 h. The precipitate was filtered and washed with water and dried to afford 5-bromo-3,4-dimethyl-1H-pyridin-2-one (5 g, 24.50 mmol, 98.52% yield, 99% purity) as an off-white solid. $^1$HNMR (400 MHz, CDCl$_3$): δ 13.14 (s, 1H), 7.47 (s, 1H), 2.32 (s, 3H), 2.18 (s, 3H).

Step-2: To a stirred solution 5-bromo-3,4-dimethyl-1H-pyridin-2-one (5 g, 24.75 mmol) in DMF (20 mL) was added sodium hydride (60% dispersion in mineral oil) (0.680 g, 29.70 mmol) at 0° C. and allowed to stir at same for 15 min, then added Iodomethane (4.62 mL, 74.24 mmol), slowly. After addition reaction mixture was allowed to warm at RT and stirred for 3 h. The reaction mass was diluted with ice cold water (150 ml), extracted with CH$_2$Cl$_2$ (200 ml×3). Organic layer was washed with ice cold water again (75 ml×2) and dried over Na$_2$SO$_4$, concentrated to afford 5-bromo-1,3,4-trimethyl-pyridin-2-one (5.1 g, 23.37 mmol, 94.42% yield, 99% purity) as an off-white solid $^1$HNMR (400 MHz, CDCl$_3$): δ 7.93 (s, 1H), 3.40 (s, 3H), 2.20 (s, 3H), 2.05 (s, 3H). LC-MS (ES$^+$): m/z 214 [M+H]$^+$ Step-3: To a stirred solution of 5-bromo-1,3,4-trimethyl-pyridin-2-one (1.5 g, 6.94 mmol) in THF (80 mL) and water (20 mL), was added tert-butyl 4-[[2,6-dimethoxy-4-(4,4,5,5-tetramethyl-1,3,2-dioxaborolan-2-yl)phenyl]methyl]piperazine-1-carboxylate (3.21 g, 6.94 mmol) and tripotassium phosphate (3.68 g, 17.36 mmol). The resulting mixture was degassed with N$_2$ (g) for 15 minutes, added Pd-Xphose-G2 (273.10 mg, 0.034 mmol) and heated at 100° C. for 4 h, while monitoring by LCMS and TLC. The reaction mixture filtered through Celite bed. Celite bed was washed with (2×100 ml) ethyl acetate. The reaction mixture concentrated under reduced pressure and crude was purified by column chromatography (silica gel (230-400 mesh) and product eluted with 4% EtOAc in MeOH) to afford tert-butyl 4-[[2,6-dimethoxy-4-(1,4,5-trimethyl-6-oxo-3-pyridyl)phenyl]methyl]piperazine-1-carboxylate) as an Brown colour gummy semi solid. $^1$HNMR (400 MHz, CDCl$_3$): δ 7.07 (s, 1H), 6.38 (s, 2H), 3.81 (s, 6H), 3.72 (s, 2H), 3.57 (s, 3H), 3.43 (t, J=5.0 Hz, 4H), 2.51 (t, J=4.8 Hz, 4H), 2.19 (s, 3H), 2.07 (s, 3H), 1.45 (s, 9H). LC-MS (ES$^+$): m/z 472 [M+H]$^+$.

Step-4: To a stirred solution of tert-butyl 4-[[2,6-dimethoxy-4-(1,4,5-trimethyl-6-oxo-3-pyridyl)phenyl]methyl]piperazine-1-carboxylate (1.35 g, 2.86 mmol) 9 in Dioxane was added 4M Dioxane HCl (2.09 g, 57.25 mmol) at 0° C. and the reaction mixture was stirred at RT for 1 h, while monitoring by TLC. The reaction mixture was concentrated and the crude compound was triturated with diethyl ether and dried to afford 5-[3,5-dimethoxy-4-(piperazin-1-ylmethyl)phenyl]-1,3,4-trimethyl-pyridin-2-one. HCl salt as a white solid. $^1$HNMR (400 MHz, CDCl$_3$): δ 11.25 (bs, 1H), 9.72 (d, J=47.9 Hz, 1H), 7.54 (s, 1H), 6.68 (s, 2H), 4.27 (s, 2H), 3.87 (s, 6H), 3.47 (s, 8H), 3.39 (s, 3H), 2.08 (d, J=8.8 Hz, 6H). LC-MS (ES$^+$): m/z 372 [M+H]$^+$.

Synthesis of 5-(3,5-dimethoxy-4-(piperidin-4-ylidenemethyl)phenyl)-1,3,4-trimethylpyridin-2(1H)-one hydrochloride

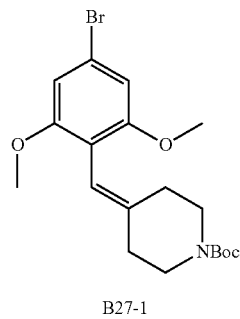

B27-1

Bis(pinacolato)diboron
Pd(dppf)Cl$_2$·dcm
KOAc, Dioxane,
100° C.
⎯⎯⎯⎯⎯⎯⎯⎯⎯→
Step-1

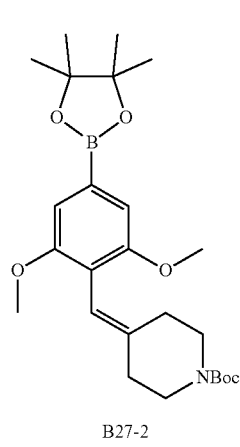

B27-2

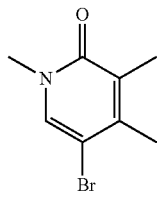

B8-3 pd(dppf)Cl$_2$·dcm, K$_3$PO$_4$,
1,4 Dioxane, H$_2$O, 80° C., 4 h
⎯⎯⎯⎯⎯⎯⎯⎯⎯→
Step-2

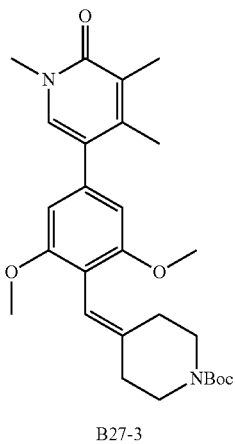

B27-3

4M Dioxane HCl,
RT, 2 h
⎯⎯⎯⎯⎯⎯⎯⎯⎯→
Step-3

-continued

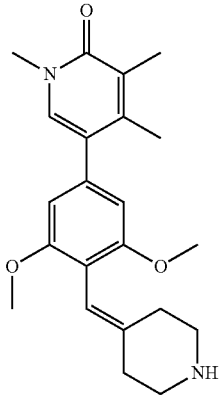

B27-4

Step-1: To a stirred solution tert-butyl 4-[(4-bromo-2,6-dimethoxy-phenyl)methylene]piperidine-1-carboxylate (0.7 g, 1.70 mmol) in 1,4 Dioxane (10 mL) was added Bis (pinacolato)diboron (0.647 g, 2.55 mmol) followed by the addition of Potassium Acetate (0.5 g, 5.09 mmol) at room temperature under argon atmosphere. The reaction mixture was degassed with argon repeatedly and cyclopentyl (diphenyl) phosphane; dichloromethane; dichloropalladium; iron (0.167 g, 0.204 mmol) was added in one portion under argon atmosphere. The reaction mixture was again degassed with argon repeatedly and then heated at 80° C. for 3 h, while monitoring by LCMS and TLC. After the completion of the reaction, the reaction mixture was cooled to room temperature and filtered through Celite bed, washed with ethyl acetate (20 mL). The filtrate was concentrated and the resultant crude mass was dissolved with Ethyl acetate (50 mL) and washed with water (2×20 mL) followed by brine (1×20 mL) and dried over anhydrous Na$_2$SO$_4$, concentrated to afford tert-butyl 4-[[2,6-dimethoxy-4-(4,4,5,5-tetramethyl-1,3,2-dioxaborolan-2-yl)phenyl]methylene]piperidine-1-carboxylate 2 (0.7 g, 1.52 mmol) as a semi solid. LC-MS (ES$^+$): m/z 360.2 [M+H]$^+$ (M-100 mass is dominated De-Boc mass)

Step-2: To the stirred solution of 5-bromo-1,3,4-trimethylpyridin-2(1H)-one (1 g, 4.63 mmol) in 1,4 Dioxane (20 mL) and water (2 mL) was added tert-butyl 4-(2,6-dimethoxy-4-(4,4,5,5-tetramethyl-1,3,2-dioxaborolan-2-yl)benzylidene)piperidine-1-carboxylate (3.19 g, 6.94 mmol) followed by the addition of tripotassium; phosphate (2.46 g, 11.57 mmol) at room temperature under argon atmosphere. The reaction mixture was degassed with argon repeatedly and cyclopentyl (diphenyl)phosphane; dichloromethane; dichloropalladium; iron (0.189 g, 0.231 mmol) was added in one portion under argon atmosphere. The reaction mixture was again degassed with argon repeatedly and then heated at reflux at 80° C. for 4 h. After the completion of the reaction, the reaction mixture was cooled to room temperature and filtered off through Celite, washed with ethyl acetate (200 mL). The filtrate was concentrated to get the residual mass. The residual mass was dissolved in Ethyl acetate (100 mL) and washed with water (1×50 mL), brine (1×25 mL), dried over anhydrous Na$_2$SO$_4$, filtered and concentrated to get the crude product. The crude was purified by reverse phase (0.1% FA in Water in ACN) to afford tert-butyl 4-(2,6-dimethoxy-4-(1,4,5-trimethyl-6-oxo-1,6-dihydropyridin-3-yl)benzylidene)piperidine-1-carboxylate (0.5 g, 0.896 mmol, 19.37% yield, 84% purity) as brown solid. LC-MS (ES$^+$): m/z 469.71 [M+H]$^+$.

Step-3: Stirred the solution of tert-butyl 4-[[2,6-dimethoxy-4-(1,4,5-trimethyl-6-oxo-3-pyridyl)phenyl]methylene]piperidine-1-carboxylate (0.5 g, 1.07 mmol) 4M HCl in Dioxane (3 mL) at RT for 2 h while monitoring by TLC and LCMS. After 2 h the reaction mixture was concentrated to dryness. The crude compound was triturated with Diethyl ether (2×20 ml) to afford 5-[3,5-dimethoxy-4-(4-piperidylidenemethyl)phenyl]-1,3,4-trimethyl-pyridin-2-one.HCl salt (0.450 g, 1.03 mmol, 96.17% yield, 92.34% purity) as an Off-white solid.

LC-MS (ES$^+$): m/z 369.68 [M+H]$^+$

Synthesis of 4-(3-fluoro-5-methoxy-4-(piperazin-1-ylmethyl)phenyl)-1-(4-methoxybenzyl)-6-methyl-1,6-dihydro-7H-pyrazolo[3,4-c]pyridin-7-one

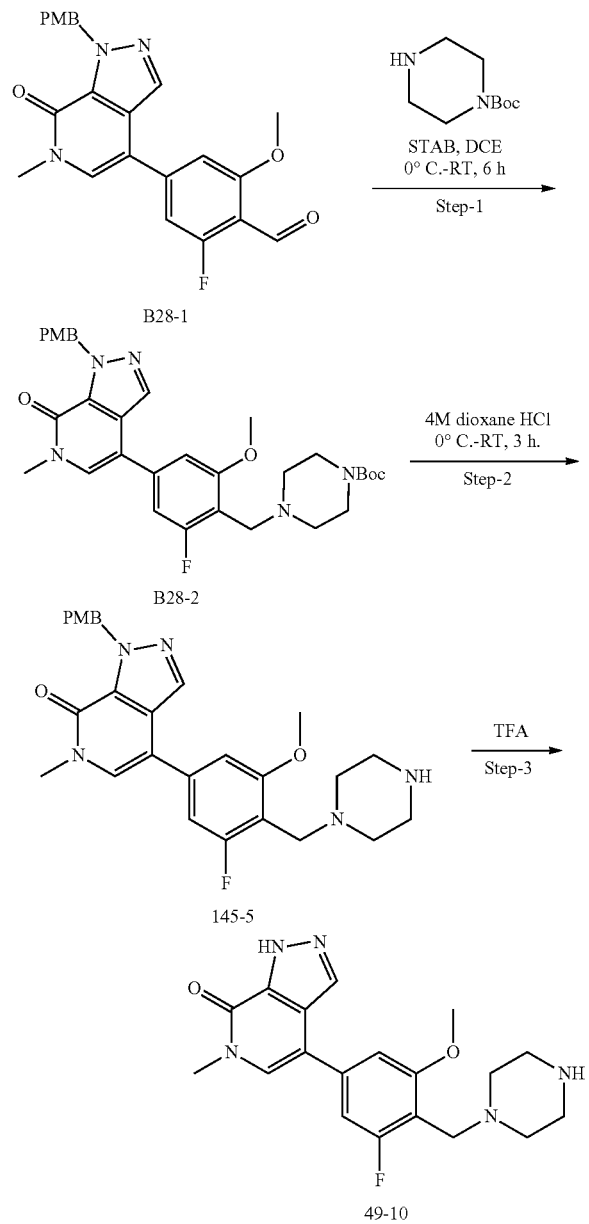

Step-1: To a stirred solution of 2-fluoro-6-methoxy-4-[1-[(4-methoxyphenyl)methyl]-6-methyl-7-oxo-pyrazolo[3,4-c]pyridin-4-yl]benzaldehyde (0.5 g, 1.19 mmol) in DCE (20 ml) were added Sodium acetate, anhydrous (0.292 g, 3.56 mmol) and acetic acid (0.071 g, 1.19 mmol). The resulting solution was stirred for 10 min, then added tert-butyl piperazine-1-carboxylate 2 (0.243 g, 1.31 mmol) and stir the reaction mixture at RT for 3 h then added sodium triacetoxyborahydride (1.26 g, 5.93 mmol). The stirring was continued at RT for 2 h, while monitoring the reaction by LCMS and TLC. After 2 h, the reaction mixture was quenched with water (30 ml) and extracted with CH$_2$Cl$_2$ (3×20 mL). The combined organic layer was dried over anhydrous Na$_2$SO$_4$, and concentrated to afford crude compound. The crude compound was triturated with Diethyl ether (2×20 ml) to afford tert-butyl 4-[[2-fluoro-6-methoxy-4-[1-[(4-methoxyphenyl)methyl]-6-methyl-7-oxo-pyrazolo[3,4-c]pyridin-4-yl]phenyl]methyl]piperazine-1-carboxylate 3 (0.6 g, 78.63% yield, 92% purity) as yellow solid. LC-MS (ES$^+$): m/z 592.17 [M+H]$^+$ Step-2: The solution of tert-butyl 4-[[2-fluoro-6-methoxy-4-[1-[(4-methoxyphenyl)methyl]-6-methyl-7-oxo-pyrazolo[3,4-c]pyridin-4-yl]phenyl]methyl]piperazine-1-carboxylate (0.6 g, 1.01 mmol) in 4 M HCl in Dioxane (5 mL) stir for 3 h at RT while monitoring by TLC and LCMS. After 3 h the reaction mixture was concentrated to dryness. The crude compound was triturated with Diethyl ether (2×20 ml) to afford 4-[3-fluoro-5-methoxy-4-(piperazin-1-ylmethyl)phenyl]-1-[(4-methoxyphenyl)methyl]-6-methyl-pyrazolo[3,4-c]pyridin-7-one.HCl (0.550 g, 82.17% yield, 80% purity) as brown solid. LC-MS (ES$^+$): m/z 492.17 [M+H]$^+$ Step-3: The mixture of 4-[3-fluoro-5-methoxy-4-(piperazin-1-ylmethyl)phenyl]-1-[(4-methoxyphenyl)methyl]-6-methyl-pyrazolo[3,4-c]pyridin-7-one (1.2 g, 2.44 mmol) in TFA (5.57 g, 48.82 mmol, 3.76 mL) was heated at 70° C. for 2 hr. The reaction was monitored by TLC and LCMS. After consumption of starting material, solvent was removed under reduced vacuum and co-distilled with dry DCM. The obtained crude compound was purified with reverse phase column chromatography to get 4-[3-fluoro-5-methoxy-4-(piperazin-1-ylmethyl)phenyl]-6-methyl-1H-pyrazolo[3,4-c]pyridin-7-one (1.1 g, 2.21 mmol, 90.58% yield, 97.58% purity, 061) as brown colored solid. LC-MS (ES$^+$): m/z 372.1 [M+H]$^+$ Synthesis of Synthesis of 3-((3-fluoro-4-(piperidin-4-yl)phenyl)amino)piperidine-2,6-dione

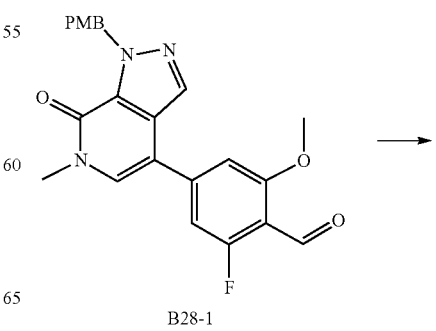

579

-continued 112-6

The solution of 2-fluoro-6-methoxy-4-[1-[(4-methoxy-phenyl)methyl]-6-methyl-7-oxo-pyrazolo[3,4-c]pyridin-4-yl]benzaldehyde (673.69 mg, 1.60 mmol) in TFA (14.80 g, 129.80 mmol, 10 mL) allowed to stir for 3 h at 70° C. After consumption of starting material, solvent was removed under reduced vacuum and co-distilled with dry DCM. The crude compound obtained was washed with diethyl-ether to get 2-fluoro-6-methoxy-4-(6-methyl-7-oxo-1H-pyrazolo[3,4-c]pyridin-4-yl)benzaldehyde (0.5 g, 1.11 mmol, 69.16% yield, 66.62% purity) as brown colored solid. LC-MS (ES+): m/z 302.27 [M+H]+

Synthesis of 3-((3-fluoro-4-(piperidin-4-yl)phenyl)amino)piperidine-2,6-dione

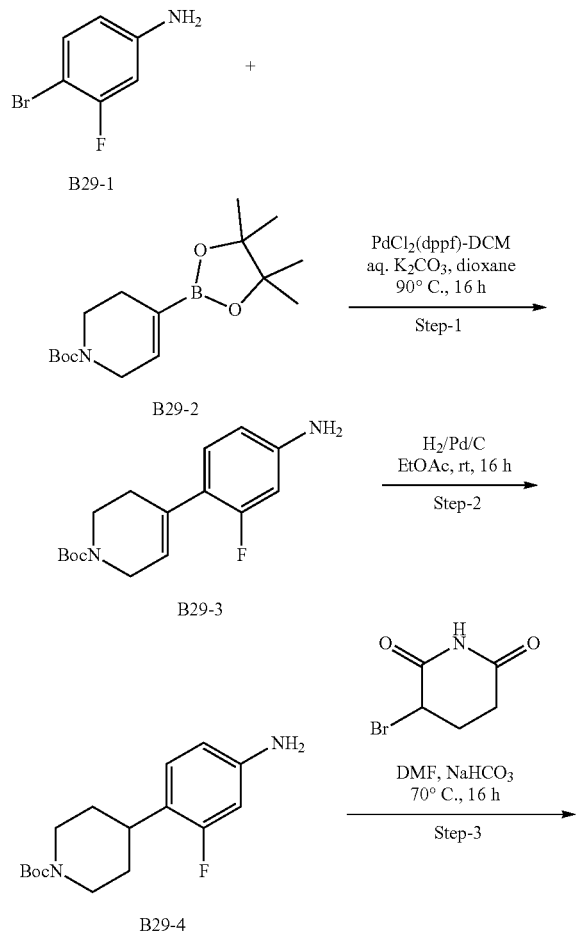

580

-continued

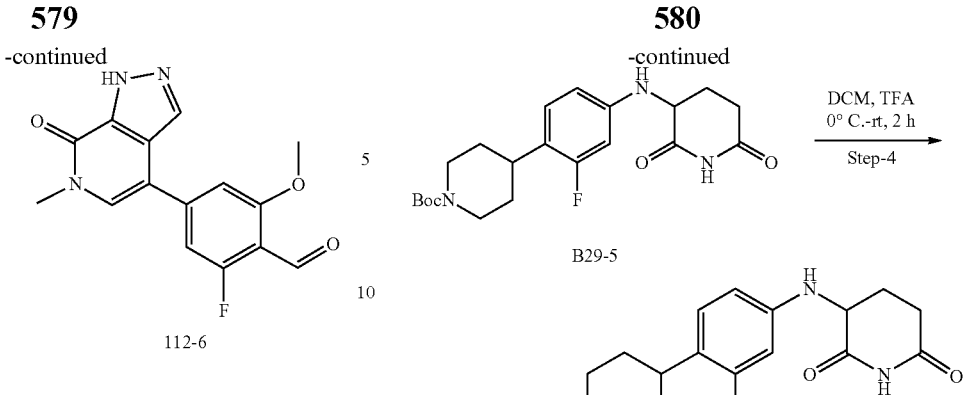

Step-1: To a stirred solution of 4-bromo-3-fluoroaniline (3.07 g, 16.17 mmol) and tert-butyl 4-(4,4,5,5-tetramethyl-1,3,2-dioxaborolan-2-yl)-3,6-dihydropyridine-1(2H)-carboxylate (5.0. g, 16.17 mmol) in 1,4-Dioxane (30 mL) at room temperature was added $K_2CO_3$ (3.71 g, 26.84 mmol) in Water (20 mL). The reaction mixture was degassed with Ar for 20 min followed by addition of $PdCl_2$(dppf)DCM (1.06 g, 1.29 mmol). The resulting reaction mixture was stirred at 90° C. for 16 h. After completion of reaction (monitored by TLC and LCMS), the reaction mixture was cooled to ambient temperature and diluted with water (400 mL) and extracted with EtOAc (2×250 mL). The combined organic layers were dried over anhydrous $Na_2SO_4$, filtered and evaporated in vacuo. The crude residue was purified by using flash column chromatography (Silica gel 230-400 mesh; gradient 0-100% EtOAc in pet ether) to afford the desired tert-butyl 4-(4-amino-2-fluorophenyl)-3,6-dihydropyridine-1(2H)-carboxylate (4.6 g, 15.58 mmol, 96.33% yield, 99% purity) LC-MS (ES+): m/z 293.32 [M+H]+

Step-2: To the tert-butyl 4-(4-amino-2-fluorophenyl)-3,6-dihydropyridine-1(2H)-carboxylate (4.6 g, 15.73 mmol) dissolved in EtOAc (48 mL) was added Pd/C (2.40 g, 22.51 mmol). The reaction flask was evacuated and back filled with hydrogen by using hydrogen bladder and the reaction was stirred under hydrogen atmosphere at rt for 16 h. The progress of reaction was monitored by LCMS. Reaction mixture was filtered through Celite bed and washed with ethyl acetate (2×30 mL). Filtrate was concentrated to yield the crude product which was purified by column chromatography using silica (230-400 mesh size) and 0-100% EtOAc/Pet.Ehter as eluent to afford tert-butyl 4-(4-amino-2-fluorophenyl)piperidine-1-carboxylate (4.5 g, 14.22 mmol, 90.36% yield, 93% purity) as yellow LC-MS (ES+): m/z 239.28 [M+H]+

Step-3: To the tert-butyl 4-(4-amino-2-fluorophenyl)piperidine-1-carboxylate (4.5 g, 15.29 mmol) dissolved in DMF (45 mL) was added $NaHCO_3$ (7.7 g, 91.72 mmol) and 3-bromopiperidine-2,6-dione (17.61 g, 91.72 mmol) at rt. The resulting reaction mixture was stirred at 70° C. for 16 h. After completion of reaction (monitored by TLC), the reaction mixture was cooled to rt, diluted with water and extracted with ethyl acetate (2×500 mL). The combined organic extracts were dried over $Na_2SO_4$, filtered and evaporated under in vacuo. The crude residue was purified by using flash column chromatography (Silica gel 230-400 mesh; gradient 0-100% EtOAc in pet ether) to afford the desired tert-butyl 4-(4-((2,6-dioxopiperidin-3-yl)amino)-2- fluorophenyl)piperidine-1-carboxylate (4.3 g, 9.54 mmol, 62.44% yield, 68% purity) LC-MS (ES⁻): m/z 404.23 [M−H]⁻

Step-4: To a stirred solution of tert-butyl 4-(4-((2,6-dioxopiperidin-3-yl)amino)-2-fluorophenyl)piperidine-1-carboxylate (4.3 g, 10.61 mmol) in DCM (40 mL) was added TFA (4.90 mL, 63.63 mmol) at 0° C. The resulting reaction mixture was stirred at rt for 2 h. After completion of reaction (monitored by TLC and LCMS), solvent was evaporated in vacuo. To the residue was added Et₂O (2×30 mL) to precipitate out the Compound 7 (4.1 g, 8.80 mmol, 82.97% yield, 90% purity, 061) as solid. The crude compound was filtered under vacuum, dried and directly used for the next step without further purification. LC-MS (ES⁺): m/z 306.21 [M+H]⁺

Synthesis of 3-((4-([4,4'-bipiperidin]-1-yl)-3-chlorophenyl)amino)piperidine-2,6-dione

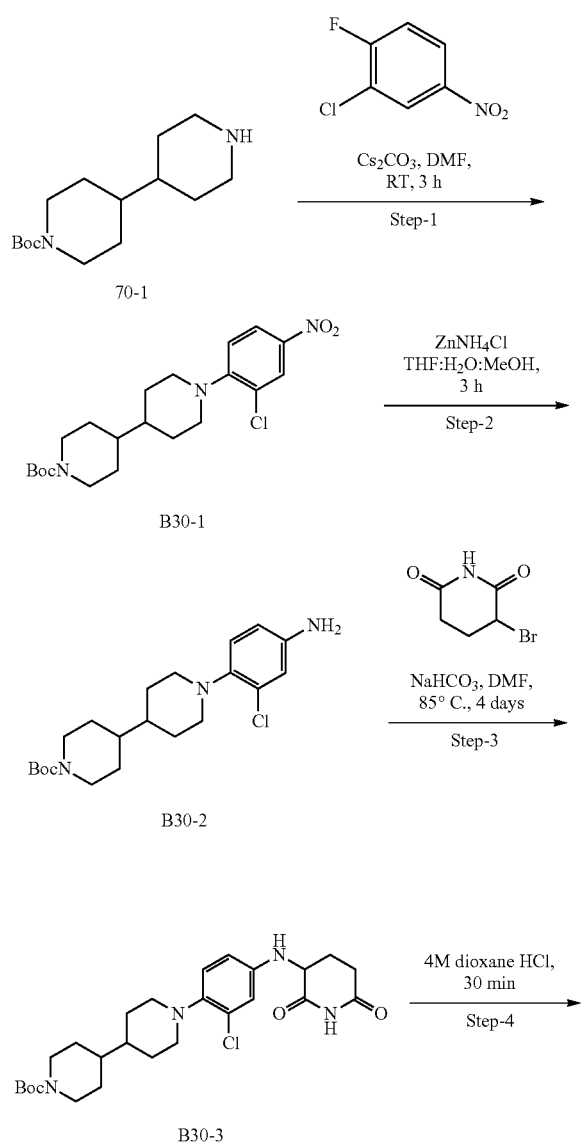

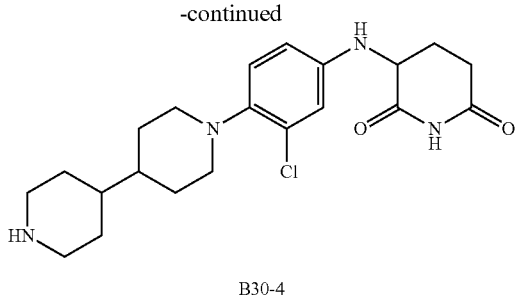

Step-1: To a stirred solution of compound tert-butyl 4-(4-piperidyl)piperidine-1-carboxylate (1 g, 3.73 mmol) in DMF (20 mL) was added Cesium carbonate (1.21 g, 3.73 mmol) and stirred for 15 min before adding 2-chloro-1-fluoro-4-nitro-benzene (0.654 g, 3.73 mmol). The reaction mixture was allowed to stir at RT for 3 h while monitoring by TLC. After completion the reaction mass was quenched with ice flakes and the precipitated solid was filtered to yield get tert-butyl 4-[1-(2-chloro-4-nitro-phenyl)-4-piperidyl]piperidine-1-carboxylate (1.4 g, 2.81 mmol, 75.34% yield, 85% purity) as yellow solid and used for the next step. ¹HNMR (400 MHz, CDCl₃): δ 1.10-1.40 (m, 4H), 1.46-1.53 (m, 11H), 1.72 (d, J=12.4 Hz, 2H), 1.83 (d, J=12.8 Hz, 2H), 2.6-2.8 (m, 4H), 3.63 (d, J=12 Hz, 2H), 4.14 (bs, 2H), 7.01 (d, J=9.2 Hz, 1H), 8.07 (dd, J₁=2.8 Hz, J₂=8.8 Hz, 1H), 8.24 (d, J=2.8 Hz, 1H), LC-MS (ES⁺): m/z 424.49 [M+H]⁺

Step-2: To the stirred solution of tert-butyl 4-[1-(2-chloro-4-nitro-phenyl)-4-piperidyl]piperidine-1-carboxylate (1 g, 2.36 mmol) in Methanol (5 mL), water (5 mL) and THF (10 mL) was added Zn dust (1.54 g, 23.59 mmol) at 0° C. followed by the addition of NH₄Cl (1.89 g, 35.38 mmol) portion wise at same temperature. After addition, the reaction was warmed to RT and stirred for 3 h, while monitoring by TLC. The reaction mixture was filtered through Celite and washed with methanol (50 mL). The filtrate was concentrated, the residual mass was dissolved with ice cold water (50 mL) and extracted with DCM (2×100 mL). The combined organic layer was washed with brine (1×50 mL), dried over anhydrous Na₂SO₄ and concentrated to afford tert-butyl 4-[1-(4-amino-2-chloro-phenyl)-4-piperidyl]piperidine-1-carboxylate (0.8 g, 1.83 mmol, 77.48% yield, 90% purity) as a yellow viscous liquid. ¹HNMR (400 MHz, CDCl₃): δ 1.1-1.2 (m, 3H), 1.2-1.35 (m, 2H), 1.48 (s, 9H), 1.48-1.50 (m, 1H), 1.73 (t, J=12.4 Hz, 4H), 2.531 (t, J=2 Hz, 2H), 2.65 (t, J=12.4 Hz, 2H), 3.26 (d, J=11.6 Hz, 2H), 3.51 (s, 2H), 4.05-4.2 (m, 2H), 6.54 (dd, J₁=2.4 Hz, J₂=8.8 Hz, 1H), 6.74 (d, J=2.8 Hz, 1H), 6.87 (d, J=8.4 Hz, 1H).

Step-3: To a stirred solution of tert-butyl 4-[1-(4-amino-2-chloro-phenyl)-4-piperidyl]piperidine-1-carboxylate (0.8 g, 2.03 mmol) in DMF (20 mL) was added 3-bromopiperidine-2,6-dione (0.77 g, 4.06 mmol), NaHCO₃ (1.02 g, 12.18 mmol) and stirred at 85° C. for 4 days, while monitoring by LCMS and TLC. After 24 h, the reaction was quenched with ice cold water (100 mL) and extracted with EtOAc (3×150 mL). The combined organic layer was dried over anhydrous Na₂SO₄ and concentrated to afford crude compound. Crude compound was purified by (silica gel mesh 100-200, 40% pet ether in ethyl acetate) column chromatography to afford benzyl afford tert-butyl 4-[1-[2-chloro-4-[(2,6-dioxo-3-piperidyl)amino]phenyl]-4-piperidyl]piperidine-1-carboxylate (0.35 g, 0.644 mmol, 31.74% yield, 93% purity) as light green solid. ¹HNMR (400 MHz, DMSO): δ 0.9-1.5 (m, 18H), 1.70 (t, J=12.8 Hz, 4H), 1.80-1.95 (m, 1H), 2.05-2.15

(m, 1H), 2.40-2.50 (m, 1H), 2.6-2.8 (m, 3H), 3.1 (d, J=11.24 Hz, 2H), 3.9-4.1 (m, 2H), 4.25-4.35 (m, 1H), 6.6 (dd, $J_1$=2.8 Hz, $J_2$=8.8 Hz, 1H), 6.75 (d, J=2.8 Hz, 1H), 6.94 (d, J=8.8 Hz, 1H), 10.87 (S, 1H). LC-MS (ES$^+$): m/z 505.13 [M+H]$^+$

Step-4: To a stirred solution of tert-butyl 4-[1-[2-chloro-4-[(2,6-dioxo-3-piperidyl)amino]phenyl]-4-piperidyl]piperidine-1-carboxylate (0.15 g, 0.297 mmol) in 1,4-Dioxane (3 mL) was added 4M HCl in dioxane (0.108 g, 2.97 mmol) at 0° C. and stirred for 30 minutes at RT. The reaction mixture was concentrated, residue triturated with diethyl ether (2×25 mL) and the solid precipitated out was dried to afford 3-[3-chloro-4-[4-(4-piperidyl)-1-piperidyl]anilino]piperidine-2,6-dione HCl salt (0.12 g, 0.252 mmol, 85.13% yield, 93% purity) as light green solid. $^1$H NMR (400 MHz, DMSO): δ 1.2-1.45 (m, 5H), 1.60 (s, 1H), 1.70-1.80 (m, 5H), 2.0-2.1 (m, 1H), 2.5-2.9 (m, 6H), 3.2-3.35 (m, 2H), 3.5-3.65 (m, 3H), 4.25-4.35 (m, 1H), 6.94 (d, J=8.8 Hz, 1H), 6.78 (s, 1H), 7.05 (bs, 1H), 8.35 (bs, 1H), 8.61 (bs, 1H), 10.87 (s, 1H). LC-MS (ES$^+$): m/z 405.32 [M+H]$^+$ Synthesis of 3-((4-(3,3-difluoro-1-((4,5,6,7-tetrahydrothieno[2,3-c]pyridin-3-yl)methyl)piperidin-4-yl)phenyl)amino)piperidine-2,6-dione

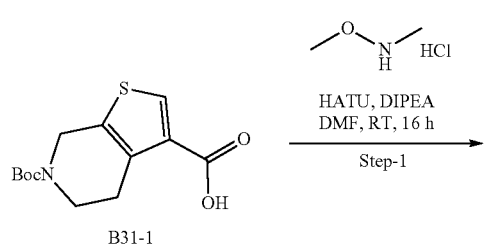

B31-1

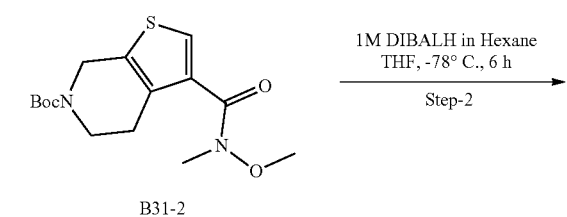

B31-2

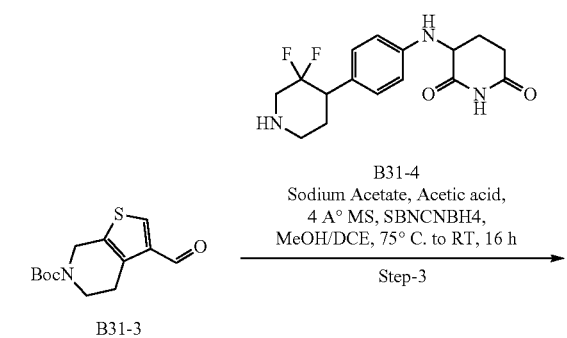

B31-4

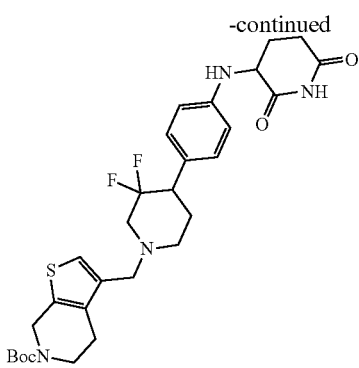

B31-5

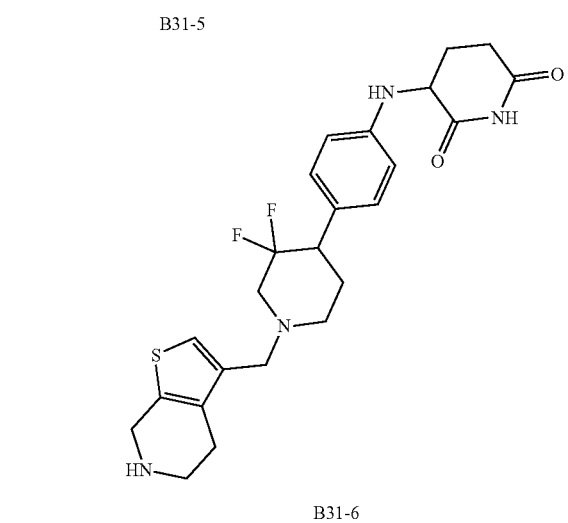

B31-6

Step-1: To a stirred solution of compound 6-(tert-butoxycarbonyl)-4,5,6,7-tetrahydrothieno[2,3-c]pyridine-3-carboxylic acid (500 mg, 1.76 mmol) and HATU (805.17 mg, 2.12 mmol) in DMF (7 mL) was added N-ethyldiisopropylamine (0.77 ml, 4.41 mmol) at RT and stirred for 5 min. N-methoxymethanamine (206.56 mg, 2.12 mmol) was added and continued stirring at RT for 16 h, while monitoring the progress of reaction by LCMS and TLC. The reaction mixture was diluted with ethyl acetate (50 mL) and washed with water (2×30 mL), saturated aqueous ammonium chloride (2×30 mL) and brine (50 mL). The organic layer was dried over sodium sulfate, filtered and concentrated under reduced pressure. The residue was purified by to column (Davisil silica, 0 to 50% ethyl acetate in pet ether) to obtain tert-butyl 3-[methoxy(methyl)carbamoyl]-5,7-dihydro-4H-thieno[2,3-c]pyridine-6-carboxylate (520 mg, 88.49% yield, 98.02% purity) yellow semisolid. LC-MS (ES$^+$): m/z 349.27 [M+Na]$^+$ Step-2: To a stirred solution of tert-butyl 3-[methoxy(methyl)carbamoyl]-5,7-dihydro-4H-thieno[2,3-c]pyridine-6-carboxylate (0.520 g, 1.59 mmol) in THF (10 mL) at −78° C. was added DIBAL-H (1M solution in hexane, 0.45 mL 2.23 mmol) drop wise under an atmosphere of argon. The progress of reaction was monitored by LCMS and TLC. After 5 h at −78° C. the crude LCMS showed 40% product formation. A solution DIBAL-H in THF (1M solution in hexane, 0.45 mL 2.23 mmol) was again added drop wise. After 30 min the reaction was quenched with saturated ammonium chloride (20 mL) at −78° C. and allowed the reaction mixture to warm to room temperature. The organic layer was washed with water (30 mL) and ethyl acetate (75 mL), which was forming a gel like suspension. The organic layer was filtered through a Celite pad. The filterate was washed with saturated aqueous sodium bicarbonate (25 mL) and brine (25 mL), dried over sodium sulfate, filtered and concentrated under reduced pressure. The residue was purified by column chromatography (Davisil silica, 0-20% ethyl acetate in pet ether) to obtain tert-butyl 3-formyl-5,7-dihydro-4H-thieno[2,3-c]pyridine-6-carboxylate (0.366 g, 84.76% yield, 98.63% purity) yellow semisolid.

Step-3: To a stirred solution of tert-butyl 3-formyl-5,7-dihydro-4H-thieno[2,3-c]pyridine-6-carboxylate (50 mg, 0.187 mmol) and compound 3-((4-(3,3-difluoropiperidin-4-yl)phenyl)amino)piperidine-2,6-dione (98.16 mg, 0.224 mmol) in a mixture of solvents ethylene dichloride (2 mL) and methanol (2 mL) was added sodium acetate anhydrous (30.68 mg, 0.374 mmol) and stirred at RT for 10 minutes. Acetic acid (10.70 µL, 0.187 mmol) and molecular sieves (50 mg) was added to the reaction mixture and stirred at 70° C. for 4 h. Reaction mixture was cooled to RT and added SiliaBond Cyanoborohydride (50 mg, 0.187 mmol) and stirred at RT for 16 h, while monitoring the progress of reaction by TLC and LCMS. After completion of reaction, reaction mixture was concentrated in vacuo and crude product was purified by column (Davisil silica, 0 to 40% ethyl acetate in Pet ether) to obtain tert-butyl 3-[[4-[4-[(2,6-dioxo-3-piperidyl)amino]phenyl]-3,3-difluoro-1-piperidyl]methyl]-5,7-dihydro-4H-thieno[2,3-c]pyridine-6-carboxylate (52 mg, 31.87% yield, 65.87% purity) as a green solid. LC-MS (ES$^+$): m/z 575.1 [M+H]$^+$ Step-4: To a stirred solution of tert-butyl 3-[[4-[4-[(2,6-dioxo-3-piperidyl)amino]phenyl]-3,3-difluoro-1-piperidyl]methyl]-5,7-dihydro-4H-thieno[2,3-c]pyridine-6-carboxylate (50 mg, 0.89 mmol) in DCM (3 mL) at 0° C. was added trifluoroacetic acid (82.44 uL, 1.07 mmol) drop wise and stirred the reaction mixture at RT for 3 h, while monitoring the progress of reaction by LCMS. After completion of reaction, reaction mixture was concentrated under reduced pressure and co-distilled with acetonitrile (5 mL×2), toluene (5 mL×2) and triturated with diethyl ether (5 ml) to obtain 3-[4-[3,3-difluoro-1-(4,5,6,7-tetrahydrothieno[2,3-c]pyridin-3-ylmethyl)-4-piperidyl]anilino]piperidin-2-one (60 mg, 92.17% yield, 94.46% purity) as a green solid. LC-MS (ES$^+$): m/z 474.46 [M+H]$^+$ Synthesis of 3-((3-fluoro-4-(4-(2-(piperidin-4-yl)ethyl)piperidin-1-yl)phenyl)amino)piperidine-2,6-dione

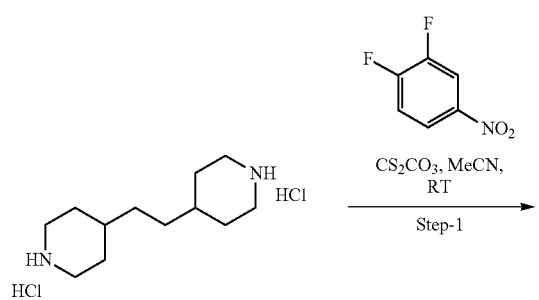

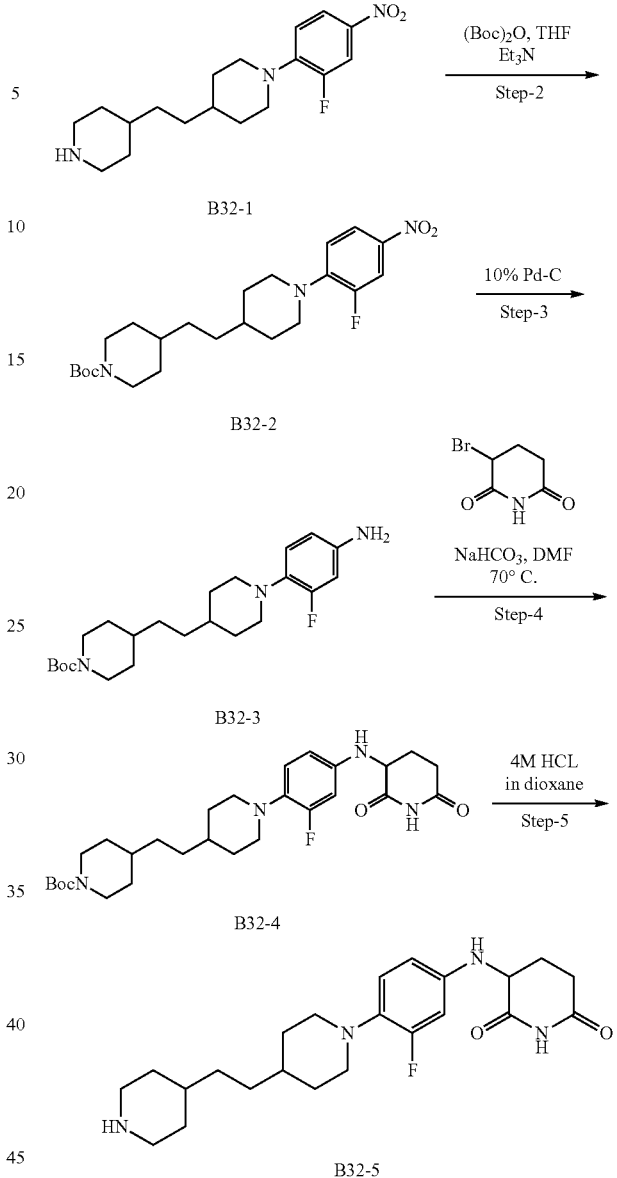

Step-1: To a stirred solution of compound 4-[2-(4-piperidyl)ethyl]piperidine 1 (0.5 g, 2.55 mmol) in acetonitrile (500 mL) was added Cesium carbonate (0.829 g, 2.55 mmol) and stirred for 15 min before adding 1,2-difluoro-4-nitrobenzene (0.243 g, 1.53 mmol) The reaction mixture was allowed to stir at RT for 16 h while monitoring by TLC. After completion reaction mixture was diluted with water (200 ml), extracted with ethyl acetate (2×200 ml). The combined organic layer was dried over anhydrous Na$_2$SO$_4$ and concentrated to afford crude compound. Crude compound was purified by normal phase column chromatography (silica gel mesh 100-200, with 50% pet ether in ethyl acetate as eluent) to afford 1-(2-fluoro-4-nitro-phenyl)-4-[2-(4-piperidyl)ethyl]piperidine (0.250 g, 0.739 mmol, 29.06% yield, 99.28% purity) as a yellow solid. $^1$HNMR (400 MHz, DMSO): δ 1.25-1.20 (m, 8H), 1.43 (bs, 2H), 1.79-1.73 (m, 4H), 2.73 (t, J=12.0 Hz, 2H), 2.90 (t, J=12.4 Hz, 2H), 3.16 (d, J=12.0 Hz, 2H), 3.68 (d, J=12.4 Hz, 2H), 7.17-7.12 (m, 1H), 7.98-7.96 (m, 1H), 8.38 (s, 1H). LC-MS (ES$^+$): m/z 336.80 [M+H]$^+$ Step-2: To a stirred solution of 1-(2-fluoro-4-nitro-phenyl)-4-[2-(4-piperidyl)ethyl]piperidine (0.25 g, 0.745 mmol) in THF (20 mL), were added triethylamine (0.226 g, 2.24 mmol) followed by the addition of tert-butoxycarbonyl tert-butyl carbonate (0.325 g, 1.49 mmol) and allowed to stir at RT for 2 hr while monitoring by TLC. After completion reaction mixture was diluted with water (50 ml), extracted with 10% MeOH: DCM (2×100 ml). The combined organic layer was dried over anhydrous $Na_2SO_4$ and concentrated to afford crude compound. Crude compound was purified was purified by normal phase column chromatography (silica gel mesh 100-200, with 40% pet ether in ethyl acetate as eluent) to afford tert-butyl 4-[2-[1-(2-fluoro-4-nitro-phenyl)-4-piperidyl]ethyl]piperidine-1-carboxylate (0.2 g, 444.06 umol, 59.58% yield, 96.70% purity) as a yellow solid. $^1$HNMR (400 MHz, DMSO): δ 1.29-1.11 (m, 2H), 1.40-1.38 (m, 8H), 1.45 (s, 9H), 1.70-1.63 (m, 2H), 1.90-1.79 (m, 2H), 2.67 (t, J=12.0 Hz, 2H), 2.85 (t, J=12 Hz, 2H), 3.70 (d, J=12.8 Hz, 2H), 4.07 (bs, 2H), 6.89 (t, J=8.8 Hz, 2H), 7.90-7.96 (m, 1H), 7.97-7.94 (m, 1H). LC-MS (ES$^+$): m/z 358.80 [M+Na]$^+$ Step-3: To a stirred solution of tert-butyl 4-[2-[1-(2-fluoro-4-nitro-phenyl)-4-piperidyl]ethyl]piperidine-1-carboxylate (0.2 g, 0.459 mmol) in EtOAc (10 mL) and methanol (10 mL) was added 10% wet Pd-C (146.61 mg, 1.38 mmol) and the reaction mixture was stirred under $H_2$ balloon pressure for 2 h, while monitoring by LCMS and TLC. The reaction mixture was filtered through Celite bed and the filtrate was concentrated. Crude compound was purified by (silica gel mesh 230-400, eluent 40% pet ether in ethyl acetate) column chromatography to afford to afford tert-butyl 4-[2-[1-(4-amino-2-fluoro-phenyl)-4-piperidyl]ethyl]piperidine-1-carboxylate (0.150 g, 0.322 mmol, 70.24% yield, 87.20% purity) as a yellow solid; LC-MS (ES$^+$): m/z 406.78 [M+H]$^+$ Step-4: To a stirred solution of tert-butyl 4-[2-[1-(4-amino-2-fluoro-phenyl)-4-piperidyl]ethyl]piperidine-1-carboxylate (0.6 g, 1.48 mmol) in DMF (50 mL) were added 3-bromopiperidine-2,6-dione (0.852 g, 4.44 mmol, $NaHCO_3$ (1.24 g, 14.79 mmol) and the reaction mixture was stirred at 80° C. for 46 h, while monitoring by TLC and LCMS. the reaction was quenched with ice cold water (100 mL) and extracted with EtOAc (3×150 mL). The combined organic layer was dried over anhydrous $Na_2SO_4$ and concentrated to afford crude compound. Crude compound was purified was purified by normal phase column chromatography (silica gel mesh 100-200, with 50-60% pet ether in ethyl acetate as eluent) to afford tert-butyl 4-[2-[1-[4-[(2,6-dioxo-3-piperidyl)amino]-2-fluoro-phenyl]-4-piperidyl]ethyl]piperidine-1-carboxylate ((0.2 g, 23.57% yield, 90.09% purity) as a brown solid. $^1$H NMR (400 MHz, DMSO-d$_6$): δ 0.98-0.92 (m, 2H), 1.34-1.24 (m, 7H), 1.38 (s, 11H), 1.69-1.61 (m, 4H), 1.86-1.82 (m, 1H), 2.10-2.05 (m, 1H), 2.74-2.51 (m, 5H), 3.09 (d, J=10 Hz, 2H), 4.23 (d, J=4.4 Hz, 2H), 4.31-4.21 (m, 1H), 5.76 (d, J=8 Hz, 1H), 6.41-6.38 (m, 1H), 6.51-6.46 (m, 1H), 6.81 (t, J=18.8 Hz, 1H), 10.97 (s, 1H), LC-MS (ES$^+$): m/z 517.83 [M+H]$^+$ Step-5: To a stirred solution of compound tert-butyl 4-[2-[1-[4-[(2,6-dioxo-3-piperidyl)amino]-2-fluoro-phenyl]-4-piperidyl]ethyl]piperidine-1-carboxylate (0.2 g, 387.11 mmol) in 1,4-dioxnae (10 ml) was added 4M HCL in dioxane (0.141 g, 3.87 mmol) at 0° C. and the reaction mixture was stirred at RT for 5 h, while monitoring by TLC. After completion, the reaction mixture was concentrated under reduced pressure and crude compound was triturated with ether to yield 3-[3-fluoro-4-[4-[2-(4-piperidyl) ethyl]-1-piperidyl] anilino] piperidine-2,6-dione. HCl salt (0.190 g, 97.50% yield, 89.99% purity) as an off white solid. $^1$H NMR (400 MHz, DMSO-d$_6$): δ 1.31-1.28 (m, 7H), 1.68-1.49 (m, 3H), 1.84-1.77 (m, 7H), 2.29-2.21 (m, 1H), 2.67-2.53 (m, 1H), 2.81-2.78 (m, 3H), 3.23-3.20 (m, 1H), 3.51-3.49 (m, 4H), 4.44-4.40 (m, 1H), 6.59-6.57 (m, 2H), 6.71-6.67 (m, 1H), 7.69 (bs, 1H), 8.71-8.69 (s, 1H), 8.93 (d, J=8.8 Hz, 1H), 10.84 (s, 1H LC-MS (ES$^+$): m/z 417.50 [M+H]$^+$ Synthesis of 3-((4-(4-((4,4-difluoro-1,2,3,4-tetrahydroisoquinolin-5-yl)methyl)piperidin-1-yl)-3-fluorophenyl)amino)piperidine-2,6-dione 234-1

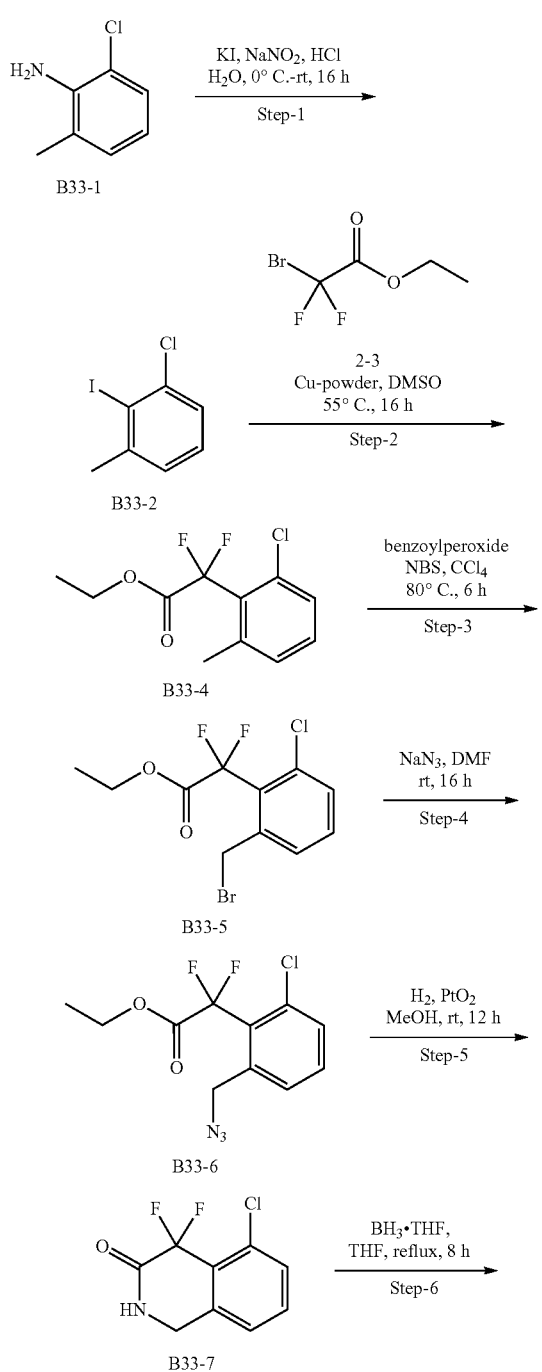

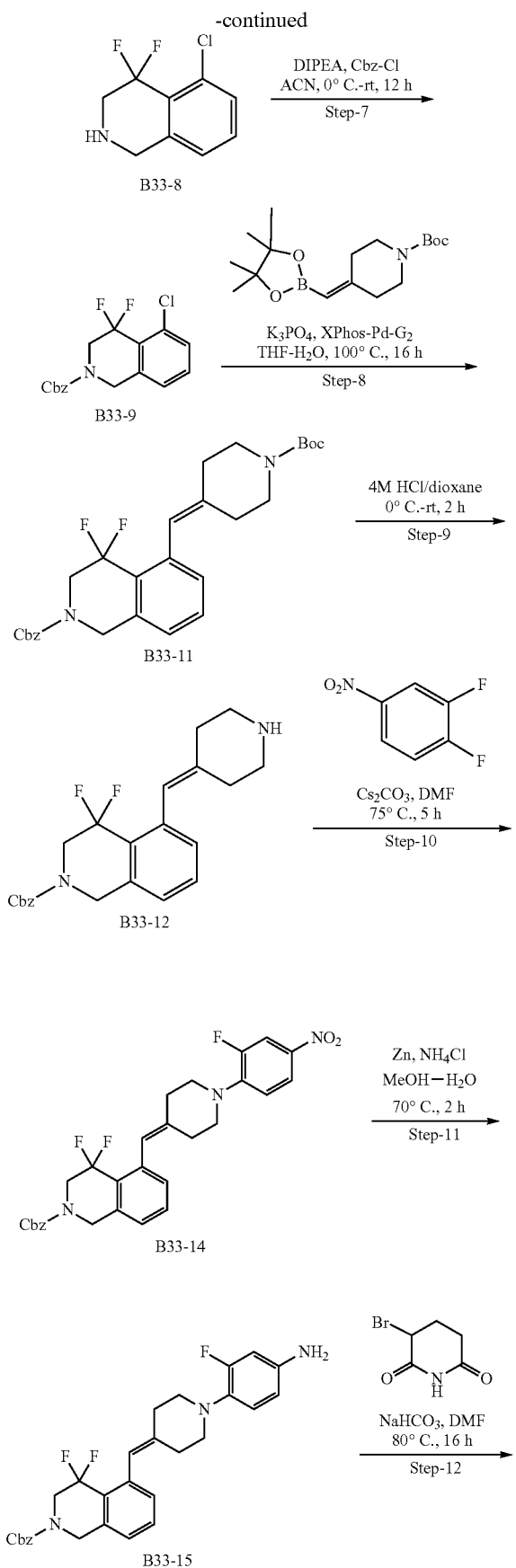

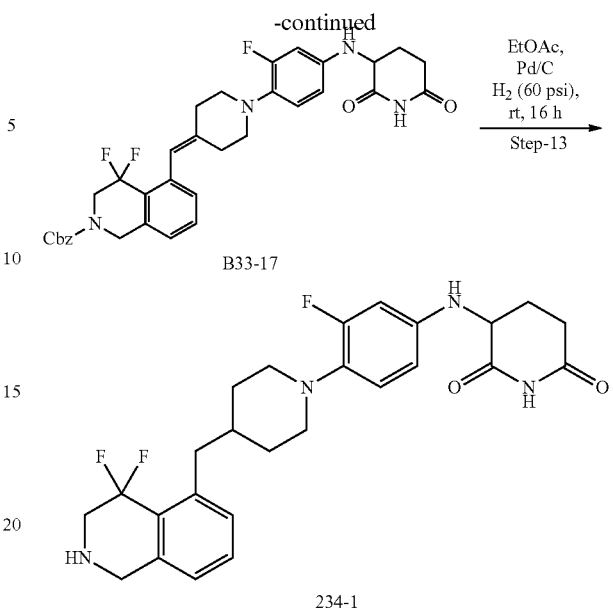

Step-1: An aqueous solution of sodium nitrite (19.88 g, 288.14 mmol, 9.16 mL) in water (400 mL) was added drop wise to a stirred suspension of B33-1 (51 g, 360.18 mmol, 44.35 mL) in concentrated hydrochloric acid (36-38%) (13.13 g, 360.18 mmol, 16.42 mL) and water (400 mL) at 0° C. The mixture was stirred for 15 minutes at the same temperature before drop-wise addition of an aqueous solution of potassium iodide (53.81 g, 324.16 mmol) in water (400 mL) at 0° C. The reaction mixture was stirred at ambient temperature for 16 h, while monitoring progress of the reaction by TLC. After completion of the reaction, Extraction was carried out using dichloromethane (3×100 mL); the combined extracts were washed sequentially with water (100 mL), 5% sodium thiosulfate (2×50 mL) and water (50 mL). It was dried over anhydrous $Na_2SO_4$, filtered and evaporated in vacuo to obtain crude residue. The residue was purified by flash column chromatography (Silica gel 230-400 mesh; 100% pet ether) to afford the desired compound 1-chloro-2-iodo-3-methyl-benzene B33-2 (51.10 g, 184.18 mmol, 51.14% yield, 91% purity) as a brown oil.

Step-2: Copper powder (8.39 g, 131.97 mmol) was added to a solution of compound 2-2 (11.9 g, 47.13 mmol) and compound B33-3 (9.57 g, 47.13 mmol, 6.06 mL) in DMSO (25 mL); and the resulting reaction mixture was stirred at 55° C. for 16 h. After completion of the reaction (monitored by TLC), it was cooled to room temperature and saturated solution of $NH_4Cl$ (40 mL) was added to it. Extraction was carried out using EtOAc (3×50 mL); the combined organic layers were washed with 1.0 N HCl solution (30 mL), water (50 mL×3), brine (50 mL), dried over anhydrous $Na_2SO_4$, filtered and concentrated in vacuo. The residue obtained was purified by flash column chromatography (Silica gel 230-400 mesh; gradient: 0-10% EtOAc in pet ether) to afford the desired compound ethyl 2-(2-chloro-6-methyl-phenyl)-2,2-difluoro-acetate B33-4 (8.25 g, 31.19 mmol, 66.17% yield, 94% purity) as a colourless oil.

Step-3: To a stirred solution of compound B33-4 (8.2 g, 32.98 mmol) and NBS (6.16 g, 34.63 mmol, 2.93 mL) in carbon tetrachloride (82 mL) was added benzoyl peroxide (0.798 g, 3.30 mmol) and the reaction mixture was stirred at 80° C. for 6 h, while monitoring progress of the reaction by TLC. After completion of the reaction (TLC and LCMS), it was cooled to room temperature and the residue observed was filtered off. The filtrate was concentrated in vacuo to afford crude compound ethyl 2-[2-(bromomethyl)-6-chloro-phenyl]-2,2-difluoro-acetate B33-5 (11.08 g, 13.87 mmol, 42.06% yield, 41% purity) as a pale yellow oil, which was carried forward for the next step without any purification.

Step-4: To a stirred solution of compound B33-5 (11.0 g, 33.58 mmol) in DMF (75 mL) was added sodium azide (4.37 g, 67.17 mmol, 2.36 mL) and the resulting reaction mixture was stirred at room temperature for 16 h. After completion of the reaction (TLC), it was diluted with EtOAc (200 mL) and the organic layer was washed with saturated $NaHCO_3$ solution (50 ml), water (3×75 mL), brine (75 mL), dried over anhydrous sodium sulphate, filtered and concentrated in vacuo. The crude residue was purified by flash column chromatography (Silica gel 230-400 mesh; gradient 0-6% EtOAc in pet ether) to afford desired compound ethyl 2-[2-(azidomethyl)-6-chloro-phenyl]-2,2-difluoro-acetate B33-6 (4.03 g, 11.39 mmol, 33.93% yield, 82% purity) as a colourless oil.

Step-5: $PtO_2$ (0.400 g, 1.76 mmol) was added to a stirred solution of compound B33-6 (4.0 g, 13.81 mmol) in methanol (40 mL) and the reaction mixture was stirred under hydrogen atmosphere (1 atmosphere pressure) for 12 h. After completion of the reaction (monitored by TLC and LCMS), the catalyst was filtered off through Celite bed and washed with DCM (20 mL) and methanol (20 mL). The filtrate was concentrated in vacuo and the crude residue was purified using flash column chromatography (Silica gel 230-400 mesh; gradient 0-20% EtOAc in DCM) to afford the desired compound 5-chloro-4,4-difluoro-1,2-dihydroisoquinolin-3-one B33-7 (2.20 g, 7.28 mmol, 52.71% yield, 72% purity) as an off-white solid. LC-MS ($ES^+$): m/z 218.20 $[M+H]^+$ Step-6: $BH_3$.THF complex solution (1.0 M in THF, 55.61 mL) was added to a stirred solution of compound B33-7 (2.20 g, 10.11 mmol) in THF (35 mL) at 0° C. and the resulting reaction mixture was refluxed for 4 h. The reaction mixture was allowed to cool to room temperature and was quenched with addition of hydrochloric acid (1.0 M, 40.44 mL) drop wise at 0° C. The resulting reaction mixture was again refluxed for 4 h. It was then allowed to cool to room temperature and concentrated in vacuo. Water (25 mL) was added to the residue and it was washed with $Et_2O$ (2×80 mL). The aqueous layer was then basified using 1N NaOH solution (pH: 10) and extracted with EtOAc (3×50 mL). The combined organic layers were dried over anhydrous $Na_2SO_4$, filtered and concentrated in vacuo to afford the desired compound 5-chloro-4,4-difluoro-2,3-dihydro-1H-isoquinoline B33-8 (1.94 g, 8.47 mmol, 83.79% yield, 89% purity) as an off-white solid. It was carried forward for the next step without any purification. LC-MS ($ES^+$): m/z 204.17 $[M+H]^+$ Step-7: To a solution of compound B33-8 (1.9 g, 9.33 mmol) in acetonitrile (25 mL) was added DIPEA (6.03 g, 46.66 mmol, 8.13 mL) and it was cooled to 0° C. To this was then added Cbz-Cl (3.18 g, 18.66 mmol, 2.65 mL) drop wise and the reaction mixture was allowed to warm to room temperature over 12 h. After completion of the reaction (monitored by TLC), ACN was removed in vacuo and the residue was diluted with EtOAc (60 mL). The organic layer was washed with water (20 mL), brine (20 mL), dried over anhydrous $Na_2SO_4$, filtered and concentrated in vacuo. The crude residue was purified using flash column chromatography (Silica gel 230-400 mesh; gradient 0-15% EtOAc in pet ether) to afford desired compound benzyl 5-chloro-4,4-difluoro-1,3-dihydroisoquinoline-2-carboxylate B33-9 (2.48 g, 6.38 mmol, 68.32% yield, 87% purity) as a pale yellow oil.

Step-8: To a stirred solution of compound B33-9 (2.4 g, 7.11 mmol) and tert-butyl 4-((4,4,5,5-tetramethyl-1,3,2-dioxaborolan-2-yl)methylene)piperidine-1-carboxylate (2.53 g, 7.82 mmol) in THF (16 mL) was added an aqueous solution of $K_3PO_4$ (3.32 g, 15.63 mmol, in 4 mL water) and argon gas was purged through it for 15 min. To this was then added XPhos-Pd-G2 (0.671 g, 0.852 mmol) and the resulting reaction mixture was again purged with argon for 15 min.

It was then stirred at 100° C. in a sealed tube for 16 h. After completion of the reaction (TLC and LCMS), it was cooled to room temperature and added water (30 mL) was added to it. Extraction was carried out using EtOAc (3×50 mL); the combined organic layers were washed with brine (20 mL), dried over anhydrous $Na_2SO_4$, filtered and evaporated in vacuo. The crude residue was purified using flash column chromatography (Silica 230-400 mesh; gradient 0-10% EtOAc in pet ether) to afford the desired product benzyl 5-[(1-tert-butoxycarbonyl-4-piperidylidene)methyl]-4,4-difluoro-1,3-dihydroisoquinoline-2-carboxylate B33-11 (1.7 g, 3.34 mmol, 47.03% yield, 98% purity) as a yellow oil; LC-MS ($ES^+$): m/z 521.46 $[M+Na]^+$ Step-9: To a stirred solution of compound B33-11 (1.7 g, 3.41 mmol) in 1,4-dioxane (10 mL) was added 4M HCl in 1,4-dioxane (4 M, 13.60 mL) at 0° C. The resulting reaction mixture was stirred at 0° C. for 15 minutes and then at room temperature for next 2 h. After completion of the reaction (monitored by TLC and LCMS), volatiles were evaporated in vacuo and $Et_2O$ (20 mL) was added to the residue. It was stirred for 15 min, filtered and dried to afford desired compound benzyl 4,4-difluoro-5-(4-piperidylidenemethyl)-1,3-dihydroisoquinoline-2-carboxylate B33-12 (HCl salt) (1.25 g, 2.82 mmol, 82.61% yield, 98% purity); LC-MS ($ES^+$): m/z 399.46 $[M+H]^+$, 421.42 $[M+Na]^+$ Step-10: To a stirred suspension of compound B33-12 (1.25 g, 2.87 mmol) and 1,2-difluoro-4-nitrobenzene (0.594 g, 3.74 mmol, 0.41 mL) in DMF (12 mL) was added cesium carbonate (2.81 g, 8.62 mmol) and the reaction mixture was stirred at 75° C. for 5 h. After completion of the reaction (monitored by TLC and LCMS), it was cooled to room temperature and saturated $NH_4Cl$ solution (30 mL) was added to it. Extraction was carried out using $Et_2O$ (3×25 mL); the combined organic layers were washed with water (2×40 mL), brine (1×10 mL), dried over $Na_2SO_4$, filtered and concentrated in vacuo. The crude residue was purified using flash column chromatography (Silica gel 230-400; gradient 0-15% EtOAc in pet ether) to afford desired compound benzyl 4,4-difluoro-5-[[1-(2-fluoro-4-nitro-phenyl)-4-piperidylidene]methyl]-1,3-dihydroisoquinoline-2-carboxylate B33-14 (1.3 g, 2.39 mmol, 83.30% yield, 99% purity) as a yellow solid. LC-MS ($ES^+$): m/z 538.23 $[M+H]^+$, 560.12 $[M+Na]^+$ Step-11: To a stirred solution of compound B33-14 (1.3 g, 2.42 mmol) in MeOH (14 mL) was added an aqueous solution of $NH_4Cl$ (1.29 g, 24.18 mmol, in 6 mL water) and Zn (1.58 g, 24.18 mmol). The reaction mixture was then stirred at 70° C. for 2 h. After completion of the reaction (monitored by TLC and LCMS), the hot suspension was filtered through Celite bed and washed with methanol (2×30 mL). The filtrate was evaporated in vacuo and water (25 mL) was added to the residue. Extraction was carried out using EtOAc (3×30 mL); the combined organic layers were washed with brine (10 mL), dried over $Na_2SO_4$, filtered and concentrated in vacuo. The crude residue was purified using flash column chromatography (silica gel 230-400; gradient 0-40% EtOAc in pet ether) to afford the desired compound benzyl 5-[[1-(4-amino-2-fluoro-phenyl)-4-piperidylidene]methyl]-4,4-difluoro-1,3-dihydroisoquinoline-2-carboxylate B33-15 (0.8 g, 1.53 mmol, 63.22% yield, 97% purity) as a brown oil. LC-MS (ES⁺): m/z 508.30 [M+H]⁺, 530.27 [M+Na]⁺

Step-12: To a stirred solution of compound B33-15 (0.79 g, 1.56 mmol) in DMF (8 mL) was added NaHCO₃ (0.784 g, 9.34 mmol) and compound 3-bromopiperidine-2,6-dione (1.34 g, 7.00 mmol). The reaction mixture was then stirred at 80° C. for 16 h. After completion of the reaction (monitored by TLC and LCMS), it was cooled to room temperature and water (20 mL) was added to it. The precipitated solid was filtered, washed with water (5 mL×2) and dried under vacuum. The crude solid was purified using flash column chromatography (Silica gel 230-400 mesh; gradient 0-50% EtOAc in pet ether) to afford the desired product benzyl 5-[[1-[4-[(2,6-dioxo-3-piperidyl)amino]-2-fluoro-phenyl]-4-piperidylidene]methyl]-4,4-difluoro-1,3-dihydroisoquinoline-2-carboxylate B33-17 (0.665 g, 1.01 mmol, 64.92% yield, 94% purity) as a dark blue solid. LC-MS (ES⁺): m/z 619.36 [M+H]⁺

Step-13: To a solution of compound B33-17 (0.650 g, 1.05 mmol) in EtOAc (10 mL) was added 10% Pd/C (0.650 g, 6.11 mmol) and the resulting reaction mixture was stirred under hydrogen atmosphere (50 psi) for 16 h in a steel bomb. After completion of the reaction (TLC and LCMS), the catalyst was filtered off through Celite and washed with EtOAc (10 mL×3). The filtrate was concentrated in vacuo to afford the desired product 3-[4-[4-[(4,4-difluoro-2,3-dihydro-1H-isoquinolin-5-yl)methyl]-1-piperidyl]-3-fluoro-anilino]piperidine-2,6-dione 234-1 (0.455 g, 0.888 mmol, 84.56% yield, 95% purity) as a light green solid, which was carried forward for the next step without any purification. LCMS (ES⁺): m/z; 487.30 [M+H]⁺

Synthesis of 3-((3,5-difluoro-4-(piperidin-4-yl)phenyl)amino)piperidine-2,6-dione

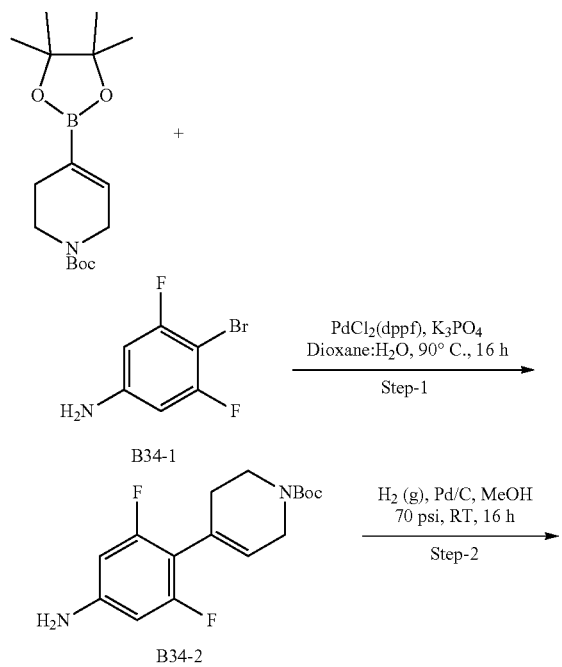

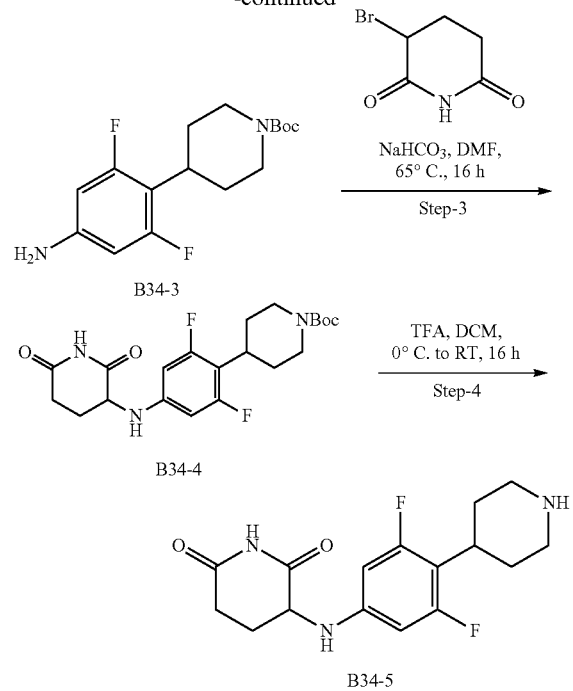

Step-1: Stirred solution of 4-bromo-3-(trifluoromethyl)aniline (1 g, 4.17 mmol) and tert-butyl 4-(4,4,5,5-tetramethyl-1,3,2-dioxaborolan-2-yl)-3,6-dihydro-2H-pyridine-1-carboxylate (1.93 g, 6.25 mmol) in Dioxane (40 mL) was degassed and purged with nitrogen gas for 10 minutes. Potassium phosphate (2.65 g, 12.50 mmol) dissolved in water (10 mL) was added to the reaction mixture. The reaction mixture degassed and purged with nitrogen gas for 10 minutes. PdCl₂(dppf) (0.3 g, 0.41 mmol) was added to the reaction mixture under nitrogen atmosphere. The reaction mixture stirred at 90° C. for 16 hr. The progress of the reaction was monitored by TLC and LCMS. After completion of reaction, solvent was removed by under reduced pressure. The crude was extracted with ethyl acetate (200 ml) and water (100 ml). The organic layer was washed with brine solution and dried over with sodium sulphate, filtered and concentrated under reduced pressure. The crude was purified with column chromatography (Davisil silica, 0-15% ethyl acetate in pet ether) to afford tert-butyl 4-[4-amino-2-(trifluoromethyl)phenyl]-3,6-dihydro-2H-pyridine-1-carboxylate (1.2 g, 75.12% yield, 93.42% purity) as a yellow solid. LCMS (ES⁺): m/z; 311.24 [M+H]⁺

Step-2: Stirred solution of tert-butyl 4-(4-amino-2,6-difluoro-phenyl)-3,6-dihydro-2H-pyridine-1-carboxylate (1.2 g, 3.87 mmol) in methanol (50 mL) was degassed under nitrogen gas. 10% Palladium on carbon (1.2 g, 3.87 mmol) was added to the reaction mixture and again the reaction mixture was degassed and reaction mixture was stirred under 70 psi pressure of Hydrogen gas at RT for 16 hr. The progress of the reaction was monitored by TLC and LCMS. After completion of reaction, reaction mixture filtered through celite bed and washed with excess amount of methanol and DCM. Filtrate was concentrated under reduced pressure to afford tert-butyl 4-(4-amino-2,6-difluoro-phenyl)piperidine-1-carboxylate (1.0 g, 69.55% yield, 84% purity) as a pale brown solid. LCMS (ES⁺): m/z; 213.19 [M-Boc]⁺ (In LCMS De-boc mass was observed)

Step-3: To a stirred solution of tert-butyl 4-(4-amino-2,6-difluoro-phenyl)piperidine-1-carboxylate (1 g, 3.20 mmol) in DMF (20 mL) was added Sodium bicarbonate (0.403 g, 4.80 mmol) followed by 3-bromopiperidine-2,6-dione (0.799 g, 4.16 mmol) and stirred the reaction mixture at 65° C. for 16 h. The progress of the reaction was monitored by the TLC and LCMS. After completion of reaction, reaction was quenched with ice cold water (100 ml) and compound was extracted with ethyl acetate (50 ml×2). The organic layer was dried over sodium sulphate, filtered and concentrated under reduced pressure. The crude was purified by column chromatography (Davisil silica, 0-40% Ethyl acetate in Pet ether) to afford tert-butyl 4-[4-[(2,6-dioxo-3-piperidyl)amino]-2,6-difluoro-phenyl]piperidine-1-carboxylate (0.27 g, 19.42% yield, 97.5% purity) as a pale green solid. LCMS (ES$^-$): m/z; 422.45 [M–H]$^-$ Step-4: To a stirred solution of tert-butyl 4-[4-[(2,6-dioxo-3-piperidyl)amino]-2,6-difluoro-phenyl]piperidine-1-carboxylate (0.27 g, 0.637 mmol) in DCM (5 mL) was added Trifluoroacetic acid (0.49 ml, 6.38 mmol) at 0° C. and the reaction mixture was stirred at RT for 16 h. The progress of the reaction was monitored by TLC and LCMS. After completion of reaction, the reaction mixture was concentrated under reduced pressure. The crude product was co-distilled with acetonitrile (25 ml) and toluene (25 ml) and triturated with diethyl ether (2×25 mL) to afford 3-[3,5-difluoro-4-(4-piperidyl)anilino]piperidine-2,6-dione (0.26 g, 69.53% yield, 94.02% purity) as a gummy liquid. LCMS (ES$^+$): m/z; 324.22 [M+H]$^+$ XI. Synthesis of Representative Compounds Synthesis of Compound 1

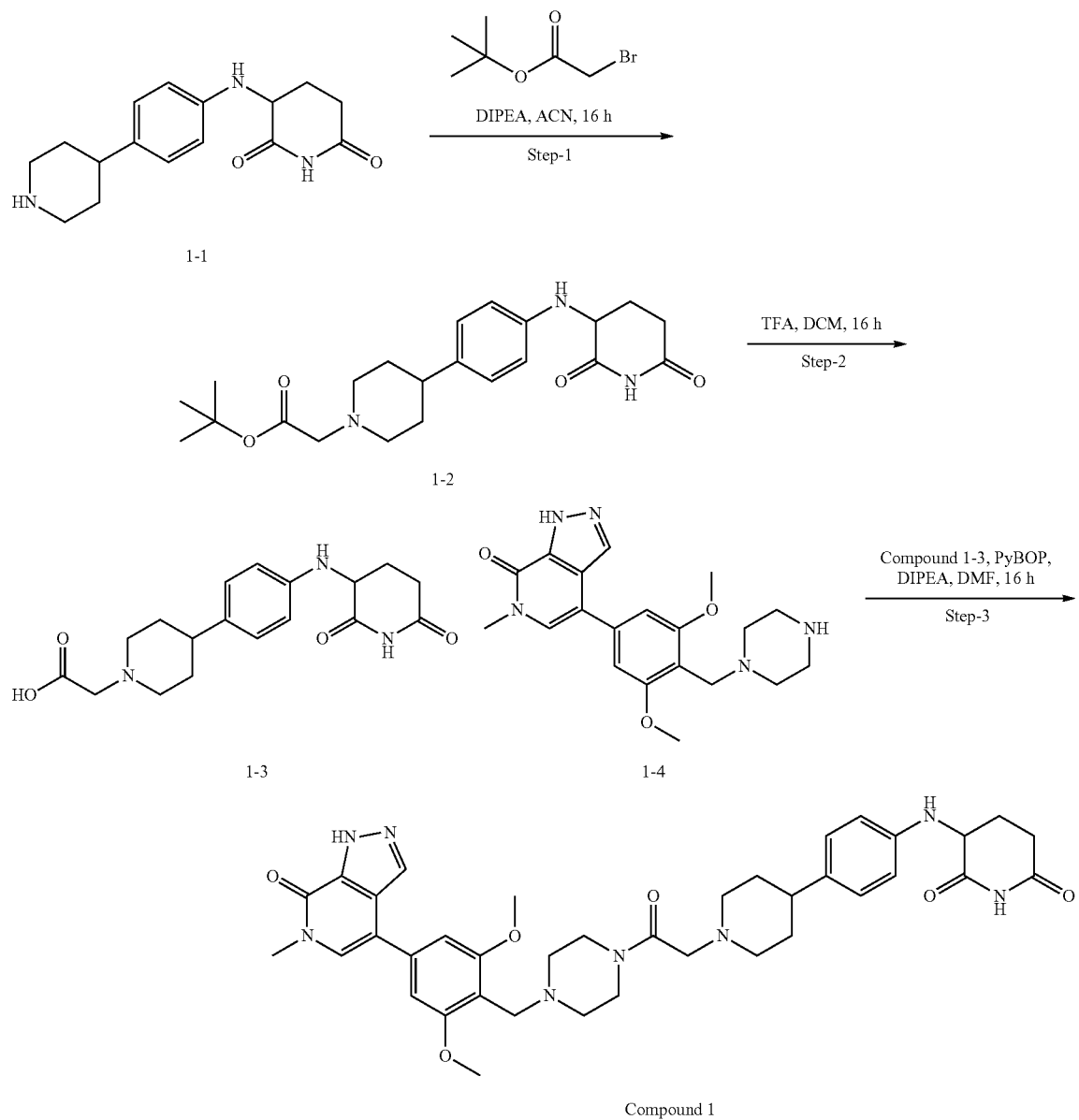

Compound 1

Step-1: To a stirred solution of 3-[4-(4-piperidyl)anilino]piperidine-2,6-dione 1-1 (2 g, 3.88 mmol) and N-ethyl-N-isopropyl-propan-2-amine (3.51 g, 4.73 mL, 27.16 mmol) in acetonitrile (40 mL) was added tert-butyl 2-bromoacetate (756.90 mg, 569.10 uL, 3.88 mmol) and the reaction mixture was heated at 70° C. in sealed tube for 16 h. The progress of the reaction was 2monitored by LCMS. After completion of reaction, the Reaction mixture was concentrated under reduced pressure and the residue was diluted with EtOAc (200 mL) and washed with saturated aq. NaHCO$_3$ solution (3×100 mL). The organic layer was dried over Na$_2$SO$_4$, filtered and concentrated under reduced pressure to get the crude compound which was triturated with diethyl ether and dried to afford tert-butyl 2-[4-[4-[(2,6-dioxo-3-piperidyl)amino]phenyl]-1-piperidyl]acetate (0.95 g, 2.27 mmol, 58.54% yield, 96% purity) as a light brown solid. $^1$H NMR (400 MHz, CDCl$_3$) δ 7.93 (bs, 1H), 7.09 (d, J=8.4 Hz, 2H), 6.63 (d, J=8.4 Hz, 2H), 4.65 (bs, 1H), 4.10-4.00 (m, 1H), 3.16 (s, 2H), 3.10-3.00 (m, 2H), 2.90-2.80 (m, 1H), 2.80-2.70 (m, 1H), 2.60-2.50 (m, 1H), 2.45-2.35 (m, 1H), 2.35-2.20 (m, 2H), 1.95-1.60 (m, 5H), 1.50 (s, 9H); LC-MS (ES$^+$): m/z 402.67 [M+H]$^+$.

Step-2: To a solution of tert-butyl 2-[4-[4-[(2,6-dioxo-3-piperidyl)amino]phenyl]-1-piperidyl]acetate 3 (0.95 g, 2.37 mmol) in DCM (10 mL) was added 2,2,2-trifluoroacetic acid (2.70 g, 1.82 mL, 23.66 mmol) dropwise at 0° C. and the reaction mixture was stirred for 16 h at room temperature. Progress of the reaction was monitored by LC-MS. After completion of reaction, the reaction mixture was concentrated under reduced pressure to get the crude product. The crude compound was triturated with diethyl ether and dried under vacuum to afford 2-[4-[4-[(2,6-dioxo-3-piperidyl)amino]phenyl]-1-piperidyl]acetic acid 1-3 (1.3 g, 3.39 mmol, 143.16% yield, 90% purity) as brown gummy solid as TFA salt. LC-MS (ES$^+$): m/z [M+H]$^+$ 346.37.

Step-3: To a stirred solution of 4-[3,5-dimethoxy-4-(piperazin-1-ylmethyl)phenyl]-6-methyl-1H-pyrazolo[3,4-c]pyridin-7-one 5 (0.5 g, 817.67 umol) and 2-[4-[4-[(2,6-dioxo-3-piperidyl)amino]phenyl]-1-piperidyl]acetic acid 1-3 (375.65 mg, 817.67 umol) in DMF (5 mL) was added N-ethyl-N-isopropyl-propan-2-amine (845.43 mg, 6.54 mmol, 1.14 mL) and the reaction mixture was stirred for 5 min at room temperature. PyBOP (510.61 mg, 981.21 umol) was added to the reaction mixture and stirring was continued for 16 h. The progress of the reaction was monitored by LCMS. After completion of reaction, DMF was evaporated using genevac to get the crude compound. The crude product was purified by prep HPLC to afford 3-[4-[1-[2-[4-[[2,6-dimethoxy-4-(6-methyl-7-oxo-1H-pyrazolo[3,4-c]pyridin-4-yl)phenyl]methyl]piperazin-1-yl]-2-oxo-ethyl]-4-piperidyl]anilino]piperidine-2,6-dione (0.253 g, 294.49 umol, 36.02% yield, 96.01% purity) as a pale green TFA salt. $^1$H NMR (400 MHz, DMSO-d6) δ 14.5 (bs, 1H), 10.78 (s, 1H), 9.78 (bs, 1H), 9.58 (bs, 1H), 8.23 (s, 1H), 7.66 (s, 1H), 7.10-6.90 (m, 4H), 6.64 (d, J=8.8 Hz, 2H), 4.50-4.20 (m, 6H), 3.97 (s, 6H), 3.90-3.80 (m, 2H), 3.64 (s, 3H), 3.40-3.00 (m, 9H), 2.80-2.70 (m, 1H), 2.70-2.60 (m, 1H), 2.20-2.10 (m, 1H), 2.00-1.80 (m, 5H); LC-MS (ES$^+$): m/z 711.49 [M+H]$^+$.

Synthesis of Compound 2 and Compound 3

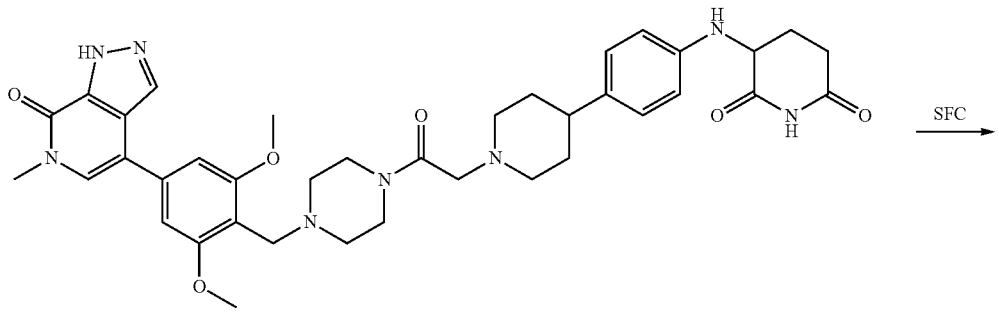

Compound 1

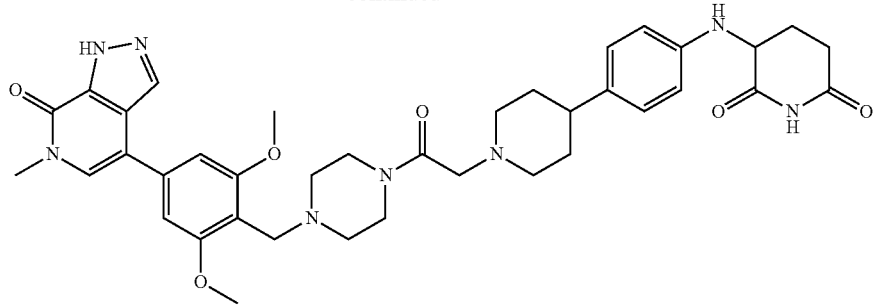

Compound 2

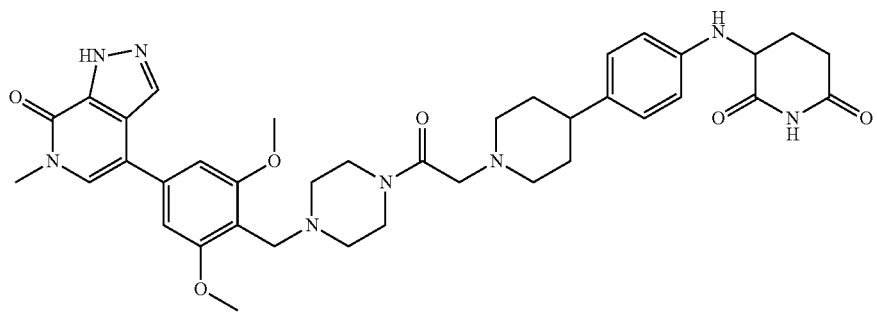

Compound 3

Procedure: Two enantiomers of Compound 1 were separated by chiral separation by SFC.
Preparative SFC Conditions Column/dimensions: Chiralpak AS-H (30*250) mm,
5u % C02:60% % Co solvent: 40% (0.2% 7M Methanolic Ammonia in Methanol:Acetonitrile (1:1))
Total Flow: 120.0 g/min
Back Pressure: 100 bar Temperature: 35° C. UV: 220 nm The basic conditions were used for SFC separation and fractions collected were neutralized with acidic (TFA) buffer. The fractions were evaporated and the residue was subjected for prep purification to remove the salts. 16.5 mg of Compound 2 (first eluted peak) and 12.1 mg of Compound 3 (second eluted peak).

Compound 2

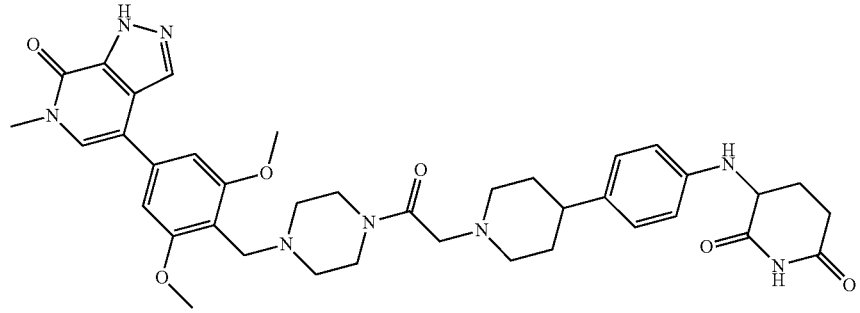

$^1$H NMR (400 MHz, DMSO-d6) δ 14.31 (s, 1H), 10.78 (s, 1H), 9.79 (ds, 2H), 8.22 (s, 1H), 7.66 (s, 1H), 7.22-6.95 (m, 4H), 6.65 (d, J=8.4 Hz, 1H), 5.77 (bs, 1H), 4.29 (m, 6H), 3.97 (s, 6H), 3.85 (m, 1H), 3.63 (m, 3H), 3.53-3.09 (m, 2H), 3.25 (m, 8H), 2.74 (m, 2H), 2.61 (m, 1H), 2.12 (m, 1H), 1.93 (m, 5H); LC-MS (ES$^+$): m/z 711.57 [M+H]$^+$

Compound 3
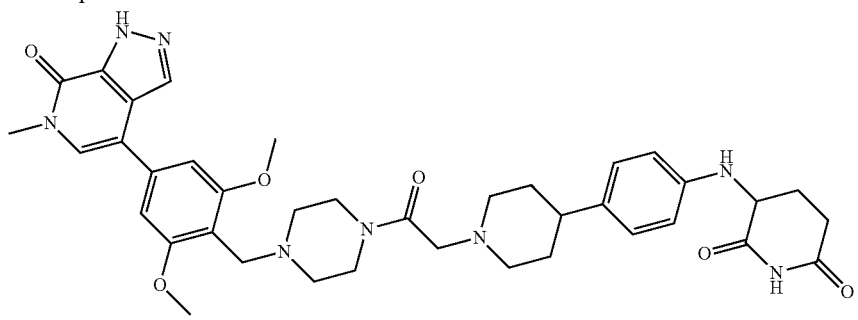
$^1$H NMR (400 MHz, DMSO-d6) δ 14.33 (s, 1H), 10.78 (s, 1H), 9.61 (ds, 2H), 8.21 (s, 1H), 7.66 (s, 1H), 7.21-6.95 (m, 4H), 6.64 (d, J=8.4 Hz, 1H), 5.76 (bs, 1H), 4.29 (m, 6H), 3.97 (s, 6H), 3.85 (m, 1H), 3.64 (m, 3H), 3.51-3.08 (m, 2H), 3.25 (m, 8H), 2.74 (m, 2H), 2.61 (m, 1H), 2.12 (m, 1H), 1.93 (m, 5H); LC-MS (ES$^+$): m/z 711.41 [M+H]$^+$
Compound 4 was prepared following the synthesis of Compound 1.
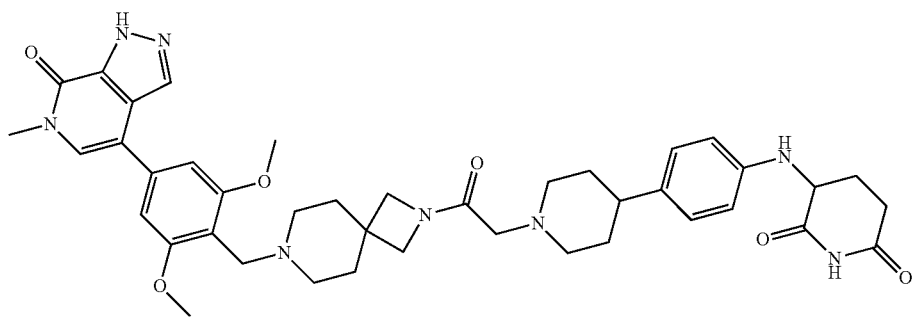 [SMILES: COc1cc(-c2cn(C)c(=O)c3[nH]ncc23)cc(OC)c1CN1CCC2(CC1)CN(C(=O)CN1CCC(c3ccc(NC4CCC(=O)NC4=O)cc3)CC1)C2]
$^1$H NMR (400 MHz, DMSO-d6) δ 14.31 (s, 1H), 10.82 (s, 1H), 9.68 (bs, 1H), 8.97 (bd, J=3.2 Hz, 1H), 8.23 (s, 1H), 7.65 (s, 1H), 6.98 (m, 4H), 6.65 (d, J=8.0 Hz, 2H), 5.69 (s, 1H), 4.44-4.22 (m, 3H), 3.99 (m, 12H), 3.63 (s, 3H), 3.58 (m, 1H), 3.36 (m, 3H), 3.09 (m, 4H), 2.74-2.61 (m, 3H), 2.11-2.08 (m, 3H), 1.92-1.86 (m, 7H); LC-MS (ES$^+$): m/z 751.56 [M+H]$^+$
Compound 5 was prepared following the synthesis of Compound 1.
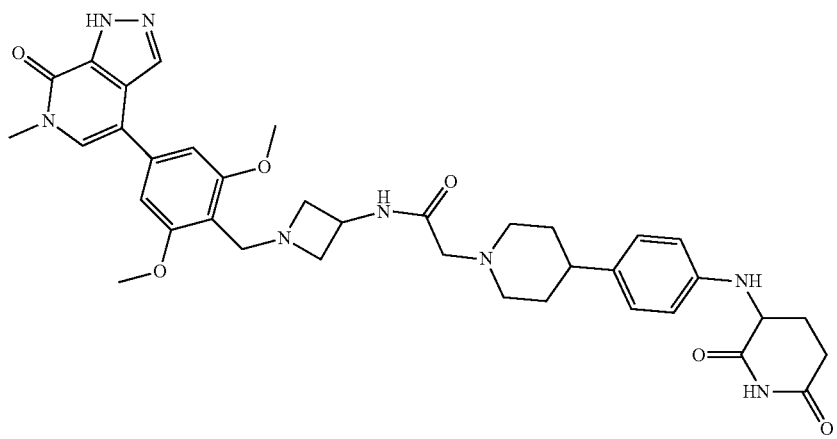 [SMILES: COc1cc(-c2cn(C)c(=O)c3[nH]ncc23)cc(OC)c1CN1CC(NC(=O)CN2CCC(c3ccc(NC4CCC(=O)NC4=O)cc3)CC2)C1]

$^1$H NMR (400 MHz, DMSO-d$_6$) δ 14.30 (s, 1H), 10.78 (s, 1H), 9.74 (bs, 1H), 9.37 (d, J=6.5 Hz, 1H), 8.23 (s, 1H), 7.65 (s, 1H), 7.08 (s, 4H), 6.64 (d, J=8.4 Hz, 2H), 4.49-4.08 (m, 8H), 3.96 (s, 7H), 3.63 (s, 3H), 3.53-3.49 (m, 2H), 3.33-3.16 (m, 3H), 2.74-2.57 (m, 3H), 2.08-2.07 (m, 1H), 1.92-1.85 (m, 5H). LC-MS (ES$^+$): m/z 697.46 [M+H]$^+$.

Compound 6 was prepared following the synthesis of Compound 1.

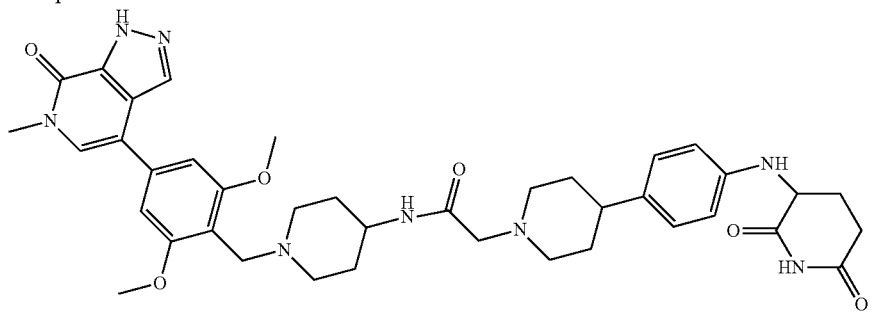

$^1$H NMR (400 MHz, DMSO-d$_6$) δ 14.27 (s, 1H), 10.78 (s, 1H), 9.66 (bs, 1H), 9.13 (bs, 1H), 8.70 (d, J=11.1 Hz, 1H), 8.23 (s, 1H), 7.65 (s, 1H), 7.08-6.90 (m, 4H), 6.65 (d, J=8.5 Hz, 1H), 4.30-4.20 (m, 3H), 3.96 (s, 6H), 3.95-3.85 (m, 3H), 3.63 (s, 3H), 3.60-3.00 (m, 8H), 2.80-2.60 (m, 3H), 2.10-1.65 (m, 10H); LCMS: LC-MS (ES$^+$): m/z 725.56 [M+H]$^+$

Compound 7 was prepared following the synthesis of Compound 1.

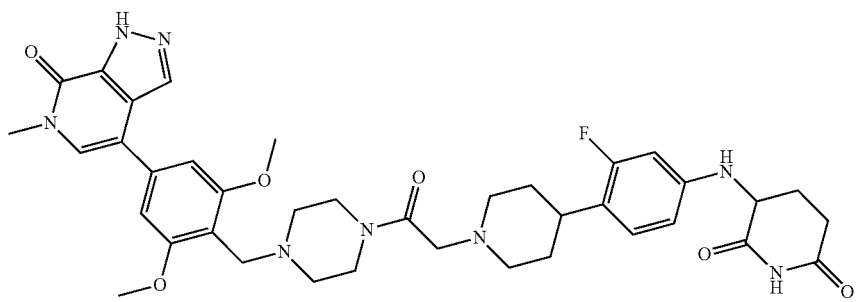 [SMILES: COc1cc(-c2cn(C)c(=O)c3[nH]ncc23)cc(OC)c1CN1CCN(C(=O)CN2CCC(c3ccc(NC4CCC(=O)NC4=O)cc3F)CC2)CC1]

$^1$H NMR (400 MHz, DMSO-d$_6$) δ 14.31 (s, 1H), 10.80 (s, 1H), 9.62 (bs, 2H), 8.23 (s, 1H), 7.66 (s, 1H), 7.00 (s, 2H), 6.97 (t, J=9.5 Hz, 1H), 6.51-6.46 (m, 2H), 6.10 (bs, 1H), 4.51-4.31 (m, 6H), 3.96 (s, 6H), 3.64 (s, 3H), 3.49-2.91 (m, 11H), 2.77-2.56 (m, 2H), 2.08-1.84 (m, 6H). LCMS: [M+H]$^+$ 729.51.

Compound 8 was prepared following the synthesis of Compound 1.

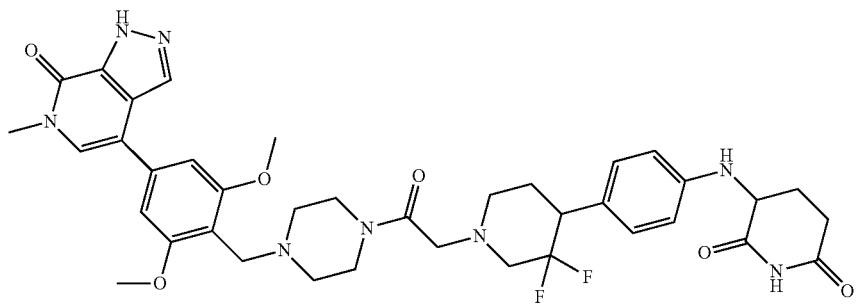 [SMILES: COc1cc(-c2cn(C)c(=O)c3[nH]ncc23)cc(OC)c1CN1CCN(C(=O)CN2CCC(c3ccc(NC4CCC(=O)NC4=O)cc3)C(F)(F)C2)CC1]

¹H NMR (400 MHz, DMSO-d₆) δ 14.38 (bs, 1H), 10.83 (s, 1H), 9.56 (bs, 1H), 8.23 (s, 1H), 7.64 (s, 1H), 7.02 (m, 4H), 7.16 (m, 2H), 6.64 (d, J=8.4 Hz, 1H), 4.45 (m, 1H), 4.37 (m, 3H), 4.10 (m, 2H), 3.97 (s, 6H), 3.62 (s, 3H), 3.46 (m, 6H), 3.16 (m, 6H), 2.74 (m, 1H), 2.61 (m, 1H), 2.12-2.07 (m, 2H), 1.89-1.83 (m, 2H). LC-MS (ES⁺): m/z 747.49 [M+H]⁺.

Compound 9 was prepared following the synthesis of Compound 1.

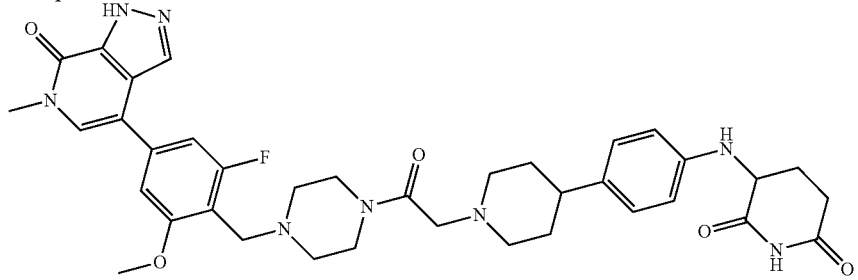 [SMILES: COc1cc(-c2cn(C)c(=O)c3[nH]ncc23)cc(F)c1CN1CCN(C(=O)CN2CCC(c3ccc(NC4CCC(=O)NC4=O)cc3)CC2)CC1]

¹H NMR (400 MHz, DMSO-d₆) δ 10.77 (s, 1H), 9.57 (s, 1H), 8.23 (s, 1H), 7.70 (s, 1H), 7.34-7.16 (m, 2H), 7.01 (dd, J=33.5, 8.3 Hz, 2H), 6.65 (dd, J=8.3, 4.7 Hz, 2H), 4.63-4.18 (m, 5H), 4.01 (s, 3H), 3.63 (s, 3H), 3.56-2.98 (m, 6H), 2.89-2.56 (m, 3H), 2.54 (s, 7H), 2.22-1.74 (m, 6H). LC-MS (ES⁺): m/z 699.1 [M+H]⁺.

Compound 10 was prepared following the synthesis of Compound 1.

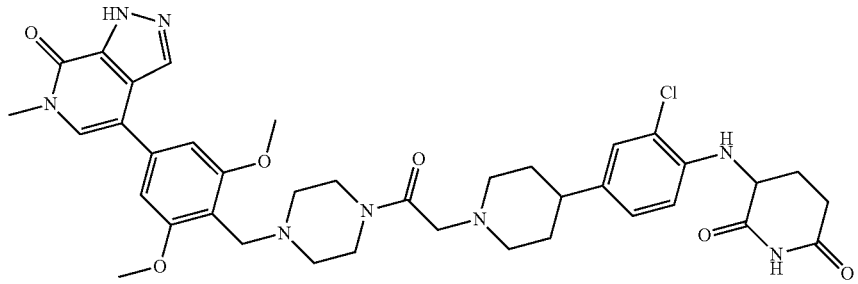 [SMILES: COc1cc(-c2cn(C)c(=O)c3[nH]ncc23)cc(OC)c1CN1CCN(C(=O)CN2CCC(c3ccc(NC4CCC(=O)NC4=O)c(Cl)c3)CC2)CC1]

¹H NMR (400 MHz, DMSO-d₆) δ 14.29 (s, 1H), 10.91 (s, 1H), 9.65 (ds, 2H), 8.23 (s, 1H), 7.66 (s, 1H), 7.28-6.95 (m, 4H), 6.64 (d, J=8.4 Hz, 1H), 4.51 (bd, 1H), 4.41-4.24 (s, 5H), 3.96 (s, 6H), 3.63 (m, 5H), 3.37 (bs, 2H), 3.19 (m, 3H), 2.77 (m, 3H), 2.61 (m, 1H), 2.37 (m, 2H), 2.07-1.79 (m, 6H), 1.56 (m, 2H); LC-MS (ES⁺): m/z 745.52 [M+H]⁺

Compound 11 was prepared following the synthesis of Compound 1.

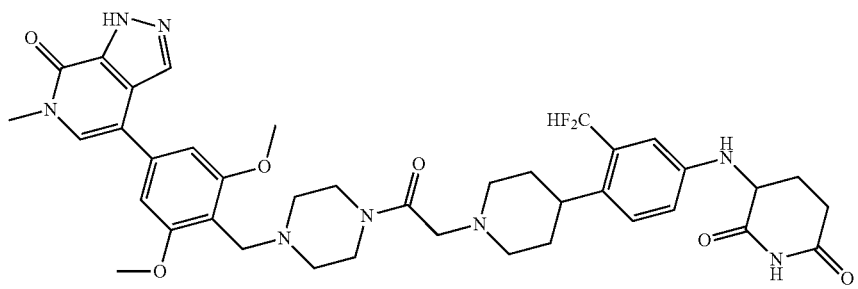

¹H NMR (400 MHz, DMSO-d₆) δ 14.26 (s, 1H), 10.80 (s, 1H), 9.71 (bs, 1H), 8.23 (s, 1H), 7.66 (s, 1H), 7.26-6.97 (m, 6H), 6.12 (bs, 1H), 4.51-4.31 (m, 5H), 3.97 (s, 6H), 3.64 (s, 3H), 3.52-3.02 (m, 13H), 2.79-2.62 (m, 2H), 2.09-1.86 (m, 6H). LC-MS (ES⁺): m/z 761.34 [M+H]⁺

Compound 12 was prepared following the synthesis of Compound 1.

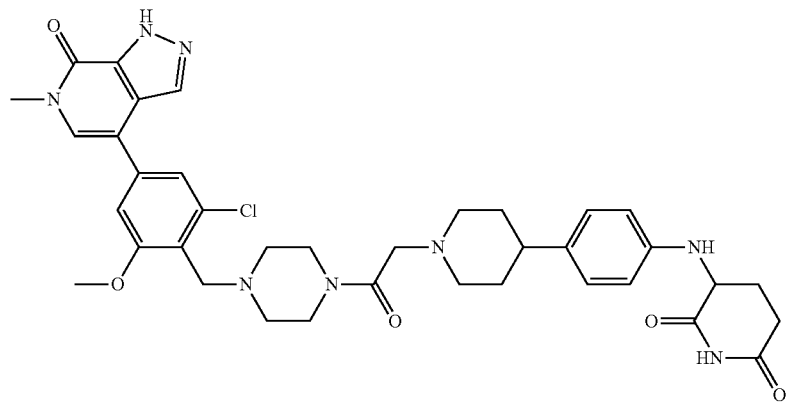 [SMILES: COc1cc(-c2cn(C)c(=O)c3[nH]ncc23)cc(Cl)c1CN1CCN(C(=O)CN2CCC(c3ccc(NC4CCC(=O)NC4=O)cc3)CC2)CC1]

LC-MS (ES⁺): m/z 715.7 [M+H]⁺

Compound 13 was prepared following the synthesis of Compound 1.

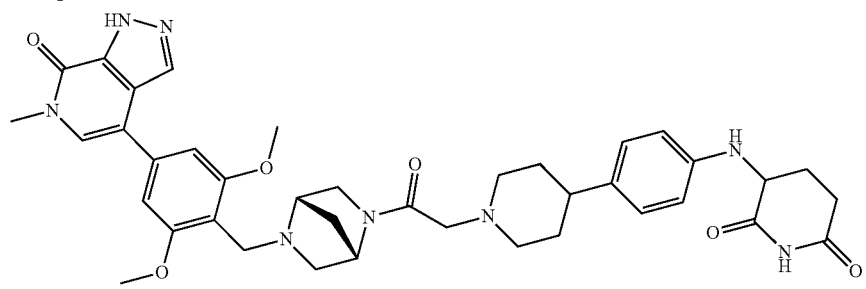

¹H NMR (400 MHz, DMSO-d₆) δ 14.31 (s, 1H), 10.82 (s, 1H), 9.71 (ds, 2H), 8.23 (s, 1H), 7.66 (s, 1H), 7.00 (m, 4H), 6.65 (d, J=8.4 Hz, 1H), 4.91-4.76 (m, 1H), 4.52-4.25 (m, 6H), 3.98 (s, 6H), 3.73 (m, 9H), 3.07 (m, 2H), 2.73-2.61 (m, 3H), 2.18-1.86 (m, 8H); LC-MS (ES⁺): m/z 723.50 [M+H]⁺

Compound 14 was prepared following the synthesis of Compound 1.

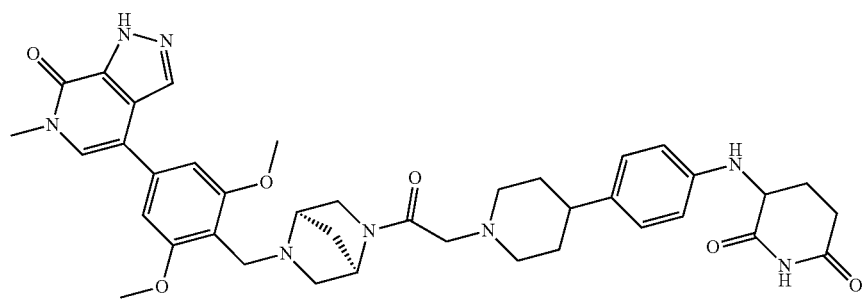 [SMILES: COc1cc(-c2cn(C)c(=O)c3[nH]ncc23)cc(OC)c1CN1C[C@H]2C[C@@H]1CN2C(=O)CN1CCC(c2ccc(NC3CCC(=O)NC3=O)cc2)CC1]

¹H NMR (400 MHz, DMSO-d₆) δ 14.29 (s, 1H), 10.82 (s, 1H), 9.71 (ds, 2H), 8.23 (s, 1H), 7.66 (s, 1H), 7.21-6.95 (m, 4H), 6.51 (d, J=8.4 Hz, 1H), 4.91-4.76 (m, 1H), 4.52-4.25 (m, 6H), 4.07 (s, 6H), 3.70 (m, 9H), 3.07 (m, 2H), 2.78-2.60 (m, 3H), 2.18-1.86 (m, 8H); LC-MS (ES⁺): m/z 723.36 [M+H]⁺

Compound 15 was prepared following the synthesis of Compound 1.

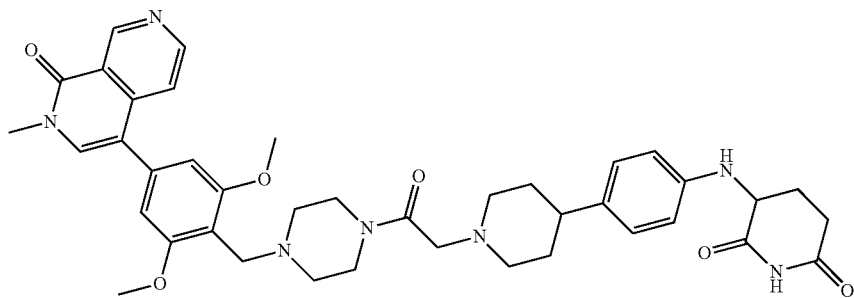 [SMILES: COc1cc(-c2cn(C)c(=O)c3cnccc23)cc(OC)c1CN1CCN(C(=O)CN2CCC(c3ccc(NC4CCC(=O)NC4=O)cc3)CC2)CC1]
$^1$H NMR (400 MHz, DMSO-d$_6$) δ 10.76 (s, 1H), 9.44 (s, 1H), 8.69 (d, J=5.6 Hz, 1H), 8.18 (s, 1H), 7.82 (s, 1H), 7.55 (d, J=5.3 Hz, 1H), 6.92 (d, J=8.5 Hz, 2H), 6.72 (s, 2H), 6.57 (d, J=8.6 Hz, 2H), 5.61 (d, J=7.4 Hz, 1H), 4.35-4.22 (m, 1H), 3.81 (s, 6H), 3.61 (s, 2H), 3.58 (s, 3H), 3.52 (bs, 4H), 3.12 (s, 2H), 2.86 (d, J=10.9 Hz, 1H), 2.58-2.51 (m, 2H), 2.49-2.30 (m, 5H), 2.09-2.02 (m, 3H), 1.89-1.71 (m, 1H), 1.69-1.66 (m, 2H), 1.53-1.49 (m, 2H). LC-MS (ES$^+$): m/z 722.2 [M+H]$^+$.
Compound 16 was prepared following the synthesis of Compound 1.
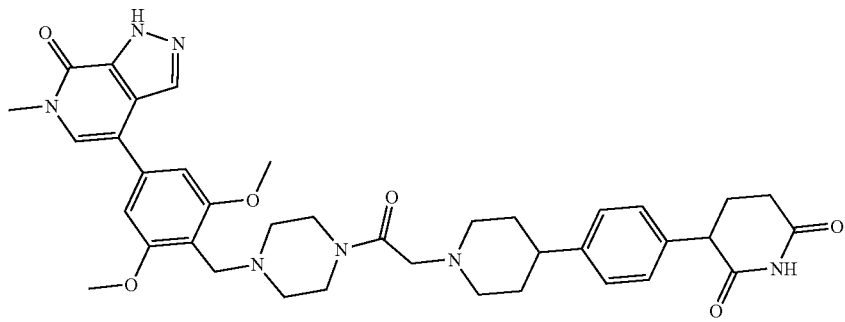 [SMILES: COc1cc(-c2cn(C)c(=O)c3[nH]ncc23)cc(OC)c1CN1CCN(C(=O)CN2CCC(c3ccc(C4CCC(=O)NC4=O)cc3)CC2)CC1]
$^1$H NMR (400 MHz, DMSO-d$_6$) δ 14.29 (s, 1H), 10.84 (s, 1H), 9.71 (s, 2H), 8.23 (s, 1H), 7.66 (s, 1H), 7.32-7.19 (m, 4H), 6.97 (s, 2H), 4.49-4.31 (m, 5H), 3.97 (s, 6H), 3.84-3.82 (m, 1H), 3.64 (s, 3H), 3.53-3.48 (m, 5H), 3.35-3.08 (m, 6H), 2.87-2.84 (m, 1H), 2.70-2.63 (m, 1H), 2.49-2.47 (m, 1H), 2.19-2.16 (m, 1H), 2.01-1.89 (m, 4H). LC-MS (ES$^+$): m/z 696.54 [M+H]$^+$
Compound 17 was prepared following the synthesis of Compound 1.
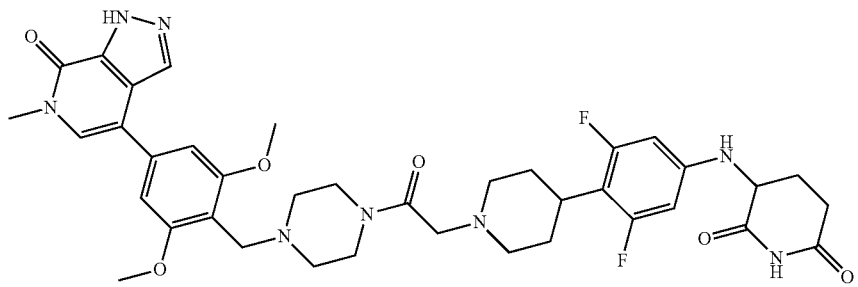 [SMILES: COc1cc(-c2cn(C)c(=O)c3[nH]ncc23)cc(OC)c1CN1CCN(C(=O)CN2CCC(c3c(F)cc(NC4CCC(=O)NC4=O)cc3F)CC2)CC1]

$^1$H NMR (400 MHz, DMSO-d$_6$) δ 14.31 (s, 1H), 10.82 (s, 1H), 9.73 (bs, 2H), 8.23 (s, 1H), 7.65 (s, 1H), 7.00 (s, 2H), 6.44 (m, 3H), 4.36-4.27 (m, 6H), 3.97 (s, 6H), 3.63 (s, 3H), 3.53-3.46 (m, 4H), 3.19-307 (m, 8H), 2.73 (m, 1H), 2.60 (m, 1H), 2.36-2.27 (m, 2H), 2.08-2.05 (m, 1H), 1.92-1.86 (m, 3H); LC-MS (ES$^+$): m/z 747.39 [M+H]$^+$

Compound 18 was prepared following the synthesis of Compound 1.

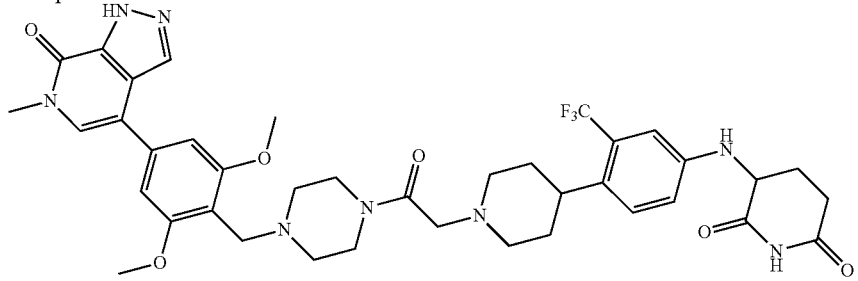

$^1$H NMR (400 MHz, DMSO-d$_6$) δ 14.31 (s, 1H), 10.82 (s, 1H), 9.63 (bs, 2H), 8.23 (s, 1H), 7.65 (s, 1H), 7.20-6.94 (m, 5H), 6.33 (bs, 1H), 4.44-4.31 (m, 6H), 3.98 (s, 6H), 3.81 (m, 2H), 3.634 (s, 3H), 3.17-3.95 (m, 10H), 2.79-2.70 (m, 1H), 2.62 (m, 1H), 2.10-2.08 (m, 3H), 1.96-1.92 (m, 1H), 1.85 (m, 2H); LC-MS (ES$^+$): m/z 779.40 [M+H]$^+$

Compound 19 was prepared following the synthesis of Compound 1.

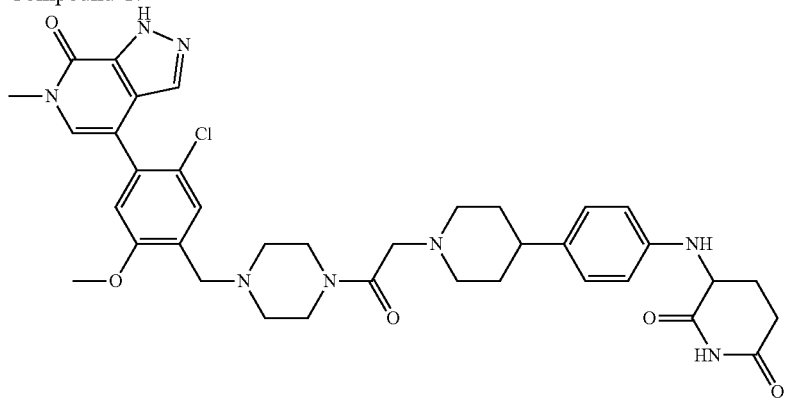

$^1$H NMR (400 MHz, DMSO-d$_6$) δ 10.77 (s, 1H), 9.59 (s, 1H), 7.72 (s, 2H), 7.37 (s, 1H), 7.25 (s, 1H), 7.01 (dd, J=33.6, 8.1 Hz, 3H), 6.65 (d, J=8.2 Hz, 2H), 4.60-4.15 (m, 8H), 3.89 (s, 4H), 3.74-3.43 (m, 6H), 3.44-2.98 (m, 4H), 2.92-2.54 (m, 2H), 2.20-1.77 (m, 8H). LC-MS (ES$^+$): m/z 715.6 [M+H]$^+$

Compound 20 was prepared following the synthesis of Compound 1.

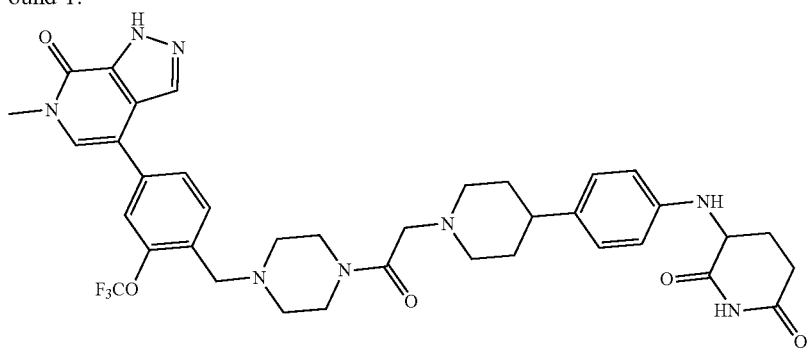

¹H NMR (400 MHz, DMSO-d₆) δ 10.77 (s, 1H), 9.59 (s, 1H), 8.11 (s, 1H), 7.81 (s, 2H), 7.67 (d, J=5.3 Hz, 2H), 7.01 (dd, J=34.3, 8.2 Hz, 2H), 6.65 (d, J=8.1 Hz, 2H), 4.55-4.03 (m, 4H), 3.62 (s, 8H), 3.41-2.81 (m, 7H), 2.82-2.51 (m, 3H), 2.09 (dt, J=13.7, 4.7 Hz, 1H), 2.04-1.69 (m, 7H). LC-MS (ES⁺): m/z 735.7 [M+H]⁺.

Compound 21 was prepared following the synthesis of Compound 1.

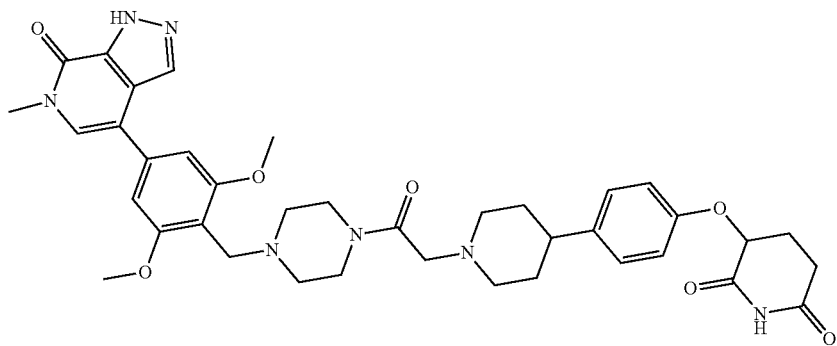 [SMILES: COc1cc(-c2cn(C)c(=O)c3[nH]ncc23)cc(OC)c1CN1CCN(C(=O)CN2CCC(c3ccc(OC4CCC(=O)NC4=O)cc3)CC2)CC1]

¹H NMR (400 MHz, DMSO-d₆) δ 14.29 (s, 1H), 10.93 (s, 1H), 9.85 (bs, 1H), 9.61 (bs, 1H), 8.23 (s, 1H), 7.66 (s, 1H), 7.26 (dd, J=8.8 Hz, 2H), 6.99 (d, J=8.0 Hz, 4H), 5.17 (m, 1H), 4.41 (m, 5H), 3.97 (s, 6H), 3.64 (s, 3H), 3.46-3.08 (m, 11H), 2.79-2.58 (m, 3H), 2.20-1.90 (m, 6H); LC-MS (ES⁺): m/z 712.58 [M+H]⁺.

Compound 22 was prepared following the synthesis of Compound 1.

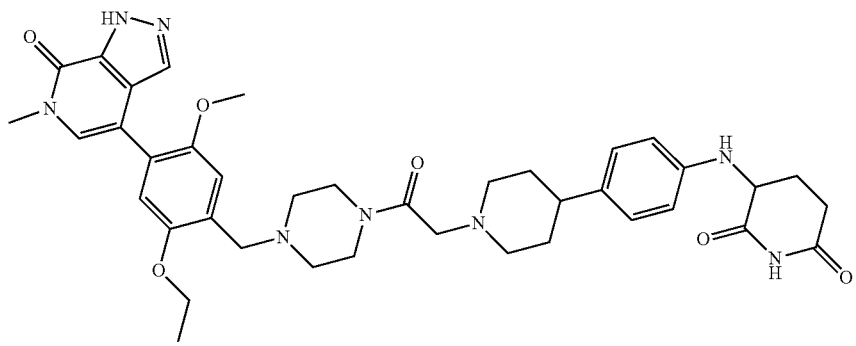 [SMILES: CCOc1cc(-c2cn(C)c(=O)c3[nH]ncc23)c(OC)cc1CN1CCN(C(=O)CN2CCC(c3ccc(NC4CCC(=O)NC4=O)cc3)CC2)CC1]

1H NMR (400 MHz, DMSO-d₆) δ 10.78 (s, 1H), 9.58 (s, 1H), 7.70 (s, 1H), 7.32 (d, J=10.7 Hz, 2H), 7.13 (s, 1H), 6.98 (d, J=8.3 Hz, 2H), 6.65 (d, J=8.3 Hz, 2H), 4.60-4.20 (m, 8H), 4.13 (q, J=6.9 Hz, 2H), 3.76 (s, 3H), 3.60 (s, 3H), 3.28 (s, 8H), 3.10 (s, 2H), 2.82-2.57 (m, 2H), 2.17-1.78 (m, 7H), 1.39 (t, J=6.9 Hz, 3H). LC-MS (ES⁺): m/z 725.8. [M+H]⁺.

Compound 23 was prepared following the synthesis of Compound 1.

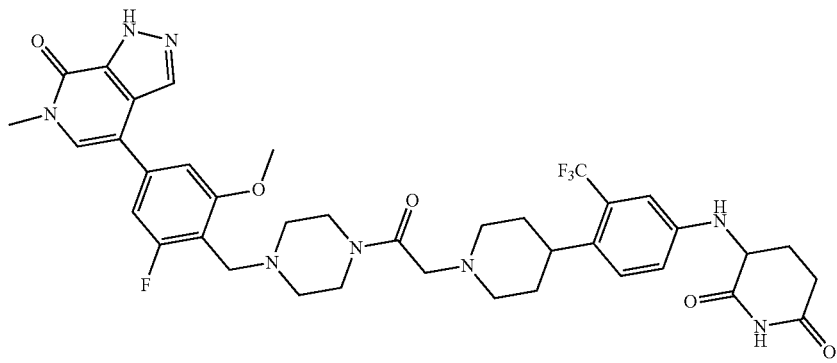 [SMILES: COc1cc(-c2cn(C)c(=O)c3[nH]ncc23)cc(F)c1CN1CCN(C(=O)CN2CCC(c3ccc(NC4CCC(=O)NC4=O)cc3C(F)(F)F)CC2)CC1]
¹H NMR (400 MHz, DMSO-d₆) δ 14.38 (bs, 1H), 10.83 (s, 1H), 9.62 (bs, 1H), 8.23 (s, 1H), 7.70 (s, 1H), 7.27 (m, 3H), 6.97 (m, 2H), 6.34 (bs, 1H), 4.50-4.31 (m, 3H), 4.19 (s, 4H), 3.62 (s, 3H), 3.54-3.15 (m, 13H), 2.94 (m, 1H), 2.79-2.70 (m, 1H), 2.67-2.55 (m, 1H), 2.15-2.05 (m, 3H), 1.95-1.81 (m, 3H). LC-MS (ES⁺): m/z 767.59 [M+H]⁺.
Compound 24 was prepared following the synthesis of Compound 1.
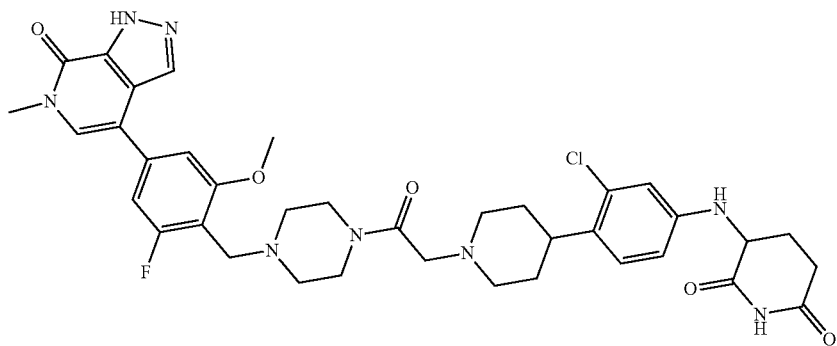 [SMILES: COc1cc(-c2cn(C)c(=O)c3[nH]ncc23)cc(F)c1CN1CCN(C(=O)CN2CCC(c3ccc(NC4CCC(=O)NC4=O)cc3Cl)CC2)CC1]
¹H NMR (400 MHz, DMSO-d₆) δ 14.32 (s, 1H), 10.80 (s, 1H), 9.61 (s, 1H), 8.23 (s, 1H), 7.70 (s, 1H), 7.25-6.97 (m, 3H), 6.74 (d, J=2.1 Hz, 1H), 6.68-6.65 (m, 1H), 6.12 (bs, 1H), 4.37-4.32 (m, 5H), 4.15 (s, 3H), 3.63 (s, 3H), 3.55-3.07 (m, 12H), 2.74-2.56 (m, 2H), 2.07-1.91 (m 6H). LC-MS (ES⁺): m/z 733.54 [M+H]⁺
Compound 25 was prepared following the synthesis of Compound 1.
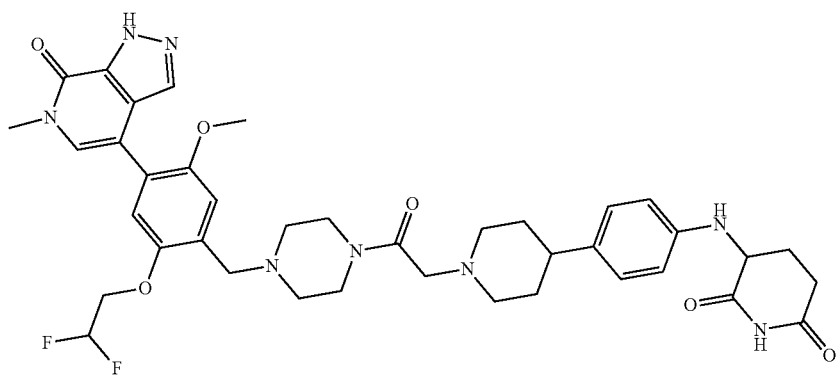 [SMILES: COc1cc(CN2CCN(C(=O)CN3CCC(c4ccc(NC5CCC(=O)NC5=O)cc4)CC3)CC2)c(OCC(F)F)cc1-c1cn(C)c(=O)c2[nH]ncc12]

¹H NMR (400 MHz, DMSO-d₆) δ 10.77 (s, 1H), 9.55 (s, 1H), 7.73 (s, 1H), 7.28 (d, J=49.1 Hz, 3H), 7.01 (dd, J=33.6, 8.2 Hz, 2H), 6.64 (d, J=8.2 Hz, 2H), 6.44 (t, J=54.9 Hz, 1H), 4.57-4.18 (m, 7H), 3.77 (s, 3H), 3.59 (s, 3H), 3.27 (s, 9H), 3.09 (s, 2H), 2.85-2.55 (m, 4H), 2.14-1.74 (m, 7H). LC-MS (ES⁺): m/z 761.8 [M+H]⁺.

Compound 26 was prepared following the synthesis of Compound 1.

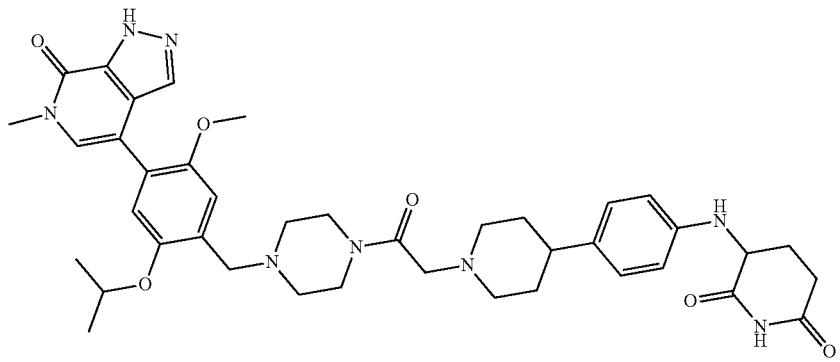 [SMILES: COc1cc(CN2CCN(C(=O)CN3CCC(c4ccc(NC5CCC(=O)NC5=O)cc4)CC3)CC2)c(OC(C)C)cc1-c1cn(C)c(=O)c2[nH]ncc12]

¹H NMR (400 MHz, DMSO-d₆) δ 10.78 (s, 1H), 9.62 (s, 1H), 7.67 (s, 1H), 7.32 (s, 2H), 7.14 (s, 1H), 7.01 (dd, J=32.8, 8.2 Hz, 2H), 6.65 (d, J=8.0 Hz, 2H), 4.69 (p, J=6.0 Hz, 1H), 4.50-4.15 (m, 6H), 3.75 (s, 4H), 3.55 (d, J=35.9 Hz, 8H), 3.43-2.92 (m, 4H), 2.82-2.53 (m, 4H), 2.15-1.72 (m, 7H), 1.31 (d, J=6.0 Hz, 6H). LC-MS (ES⁺): m/z 739.8 [M+H]⁺.

Compound 27 was prepared following the synthesis of Compound 1.

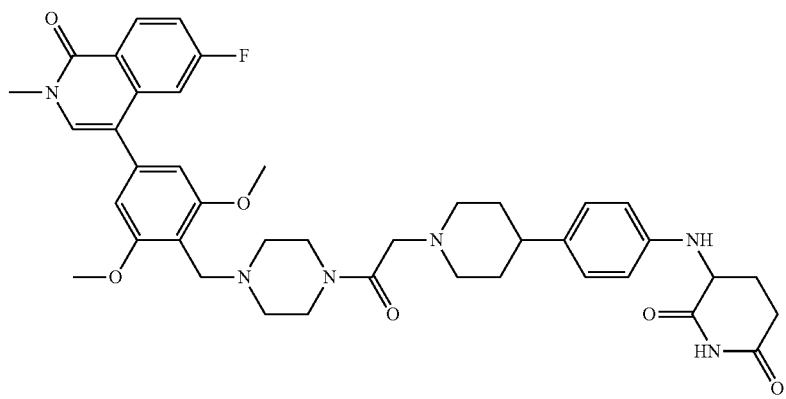 [SMILES: COc1cc(-c2cn(C)c(=O)c3ccc(F)cc23)cc(OC)c1CN1CCN(C(=O)CN2CCC(c3ccc(NC4CCC(=O)NC4=O)cc3)CC2)CC1]

¹H NMR (400 MHz, DMSO-d₆) δ 10.78 (s, 1H), 10.10 (s, 1H), 9.63 (s, 1H), 8.41 (dd, J=8.9, 6.0 Hz, 1H), 7.65 (s, 1H), 7.43 (td, J=8.6, 2.5 Hz, 1H), 7.30 (dd, J=10.6, 2.5 Hz, 1H), 7.02 (dd, J=33.6, 8.2 Hz, 2H), 6.87 (s, 2H), 6.65 (d, J=8.1 Hz, 2H), 4.32 (q, J=17.4, 11.3 Hz, 6H), 3.90 (s, 6H), 3.56 (d, J=25.4 Hz, 8H), 3.38-2.96 (m, 5H), 2.88-2.52 (m, 2H), 2.17-1.71 (m, 7H). LC-MS (ES⁺): m/z 739.8 [M+H]⁺.

Compound 28 was prepared following the synthesis of Compound 1.

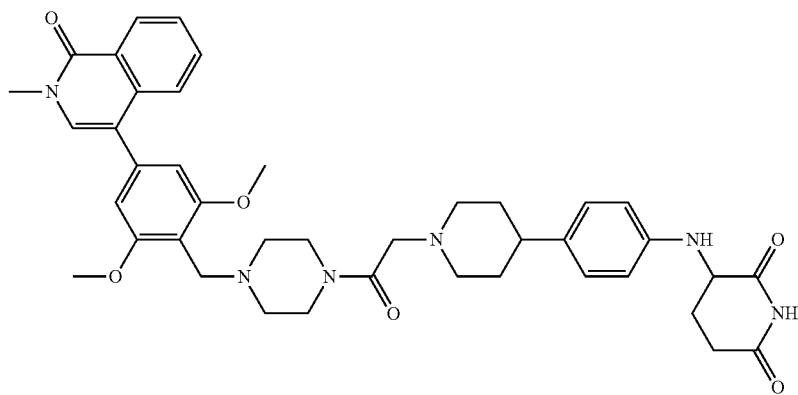 [SMILES: COc1cc(-c2cn(C)c(=O)c3ccccc23)cc(OC)c1CN1CCN(C(=O)CN2CCC(c3ccc(NC4CCC(=O)NC4=O)cc3)CC2)CC1]
$^1$H NMR (400 MHz, DMSO-d$_6$) δ 10.78 (s, 1H), 10.16 (s, 1H), 9.64 (s, 1H), 8.36 (d, J=8.0 Hz, 1H), 7.79-7.63 (m, 2H), 7.58 (d, J=4.4 Hz, 2H), 7.02 (dd, J=33.8, 8.1 Hz, 2H), 6.86 (s, 2H), 6.65 (d, J=8.1 Hz, 2H), 4.68-4.10 (m, 6H), 3.89 (s, 6H), 3.60 (s, 3H), 3.54 (d, J=12.1 Hz, 4H), 3.37-2.93 (m, 5H), 2.83-2.52 (m, 3H), 2.17-1.71 (m, 7H). LC-MS (ES$^+$): m/z: 721.8 [M+H]$^+$.
Compound 29 was prepared following the synthesis of Compound 1.
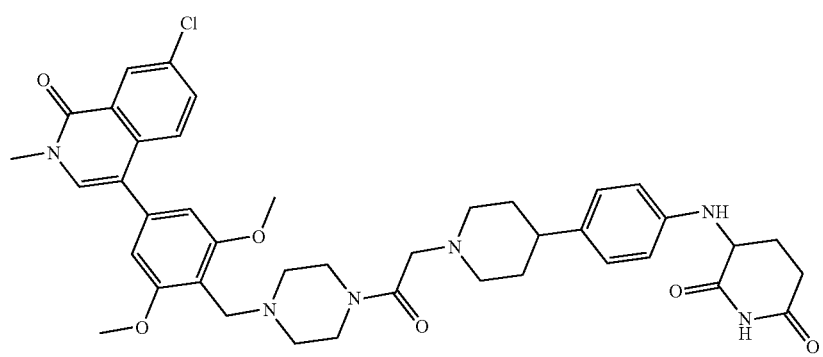 [SMILES: COc1cc(-c2cn(C)c(=O)c3cc(Cl)ccc23)cc(OC)c1CN1CCN(C(=O)CN2CCC(c3ccc(NC4CCC(=O)NC4=O)cc3)CC2)CC1]
$^1$H NMR (400 MHz, DMSO-d$_6$) δ 10.77 (s, 1H), 10.03 (s, 1H), 9.61 (s, 1H), 8.29 (d, J=2.4 Hz, 1H), 7.77 (dd, J=8.8, 2.4 Hz, 1H), 7.68 (d, J=8.8 Hz, 1H), 7.63 (s, 1H), 7.01 (dd, J=33.4, 8.2 Hz, 2H), 6.86 (s, 2H), 6.65 (d, J=8.0 Hz, 2H), 4.33 (q, J=21.3, 11.1 Hz, 8H), 3.89 (s, 5H), 3.61 (s, 3H), 3.54 (d, J=12.3 Hz, 5H), 3.38-2.91 (m, 4H), 2.82-2.52 (m, 2H), 2.19-1.66 (m, 7H). LC-MS (ES$^+$): m/z: 755.8 [M+H]$^+$.
Compound 30 was prepared following the synthesis of Compound 1.

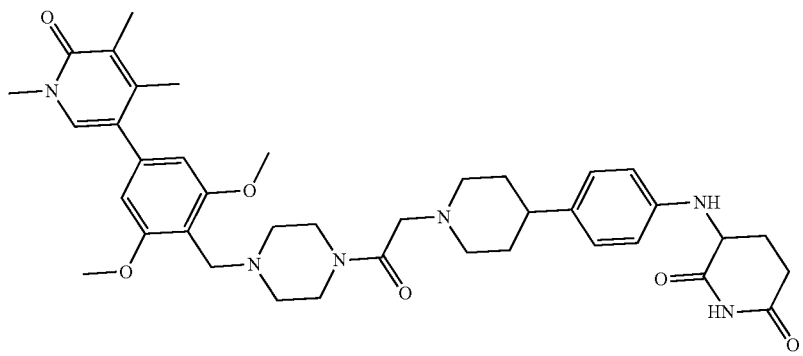 [SMILES: COc1cc(-c2cn(C)c(=O)c(C)c2C)cc(OC)c1CN1CCN(C(=O)CN2CCC(c3ccc(NC4CCC(=O)NC4=O)cc3)CC2)CC1]
¹H NMR (400 MHz, DMSO-d₆) δ 10.78 (s, 1H), 10.10 (s, 1H), 9.63 (s, 1H), 7.52 (s, 1H), 7.01 (dd, J=33.3, 8.2 Hz, 2H), 6.78-6.58 (m, 4H), 4.65-4.16 (m, 6H), 3.87 (s, 6H), 3.64-3.33 (m, 7H), 3.31-2.94 (m, 4H), 2.84-2.53 (m, 4H), 2.08 (d, J=7.7 Hz, 7H), 2.03-1.77 (m, 6H). LC-MS (ES⁺): m/z 699.7 [M+H]⁺.
Compound 31 was prepared following the synthesis of Compound 1.
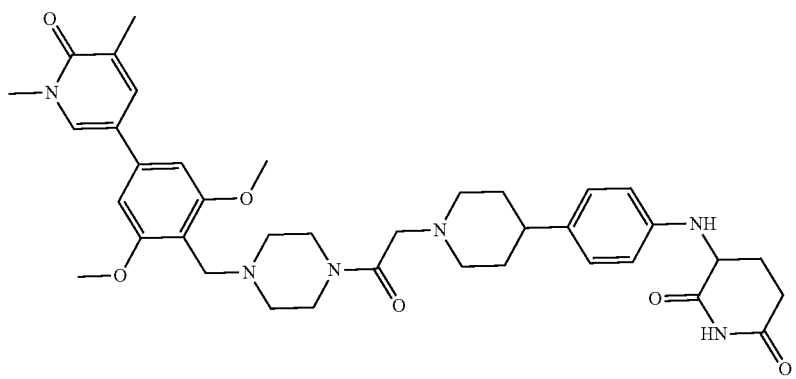 [SMILES: COc1cc(-c2cc(C)c(=O)n(C)c2)cc(OC)c1CN1CCN(C(=O)CN2CCC(c3ccc(NC4CCC(=O)NC4=O)cc3)CC2)CC1]
¹H NMR (400 MHz, DMSO-d₆) δ 10.77 (s, 1H), 9.97 (s, 1H), 9.60 (s, 1H), 8.16 (d, J=2.6 Hz, 1H), 7.97-7.75 (m, 1H), 7.17-6.88 (m, 4H), 6.65 (d, J=8.3 Hz, 2H), 4.59-4.17 (m, 7H), 3.94 (s, 6H), 3.82 (d, J=8.0 Hz, 0H), 3.55 (s, 3H), 3.49 (d, J=21.2 Hz, 5H), 3.32-2.94 (m, 3H), 2.81-2.51 (m, 4H), 2.11 (s, 4H), 2.04-1.77 (m, 5H). LC-MS (ES⁺): m/z 685.7 [M+H]⁺.
Compound 32 was prepared following the synthesis of Compound 1.
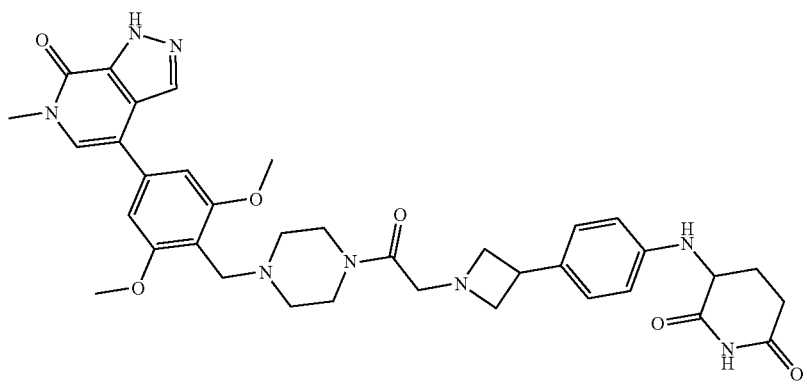 [SMILES: COc1cc(-c2cn(C)c(=O)c3[nH]ncc23)cc(OC)c1CN1CCN(C(=O)CN2CC(c3ccc(NC4CCC(=O)NC4=O)cc3)C2)CC1]

$^1$H NMR (400 MHz, DMSO-d$_6$) δ 14.34 (s, 1H), 10.78 (s, 1H), 10.05 (m, 2H), 8.23 (s, 1H), 7.66 (s, 1H), 7.22 (m, 4H), 6.71 (m, 2H), 5.80 (bs, 0.6H), 4.52-4.22 (m, 8H), 3.97 (m, 8H), 3.64 (s, 3H), 3.48 (m, 4H), 3.20-3.05 (m, 4H), 2.78-699 (m, 1H), 2.67 (m, 1H), 2.10-2.05 (m, 1H), 1.92-1.86 (m, 1H); LC-MS (ES$^+$): m/z 683.31 [M+H]$^+$.

Compound 33 was prepared following the synthesis of Compound 1.

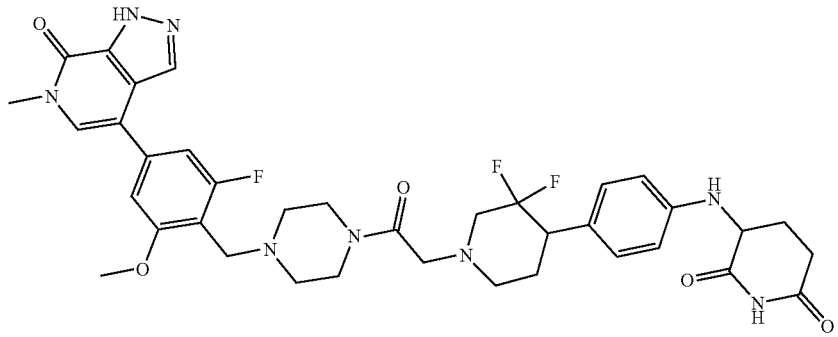 [SMILES: COc1cc(-c2cn(C)c(=O)c3[nH]ncc23)cc(F)c1CN1CCN(C(=O)CN2CCC(c3ccc(NC4CCC(=O)NC4=O)cc3)C(F)(F)C2)CC1]

$^1$H NMR (400 MHz, DMSO-d$_6$) δ 14.26 (s, 1H), 10.79 (s, 1H), 9.84 (s, 1H), 8.23 (s, 1H), 7.69 (s, 1H), 7.27-6.94 (m, 4H), 6.64 (d, J=8.3 Hz, 2H), 5.81 (s, 1H), 4.62-4.28 (m, 6H), 4.02 (s, 3H), 3.61 (s, 3H), 3.45-3.03 (m, 11H), 2.89-2.52 (m, 2H), 2.12-2.06 (m, 2H), 1.92-1.83 (m, 2H). LC-MS (ES$^+$): m/z 735.60 [M+H]$^+$.

Compound 34 was prepared following the synthesis of Compound 1.

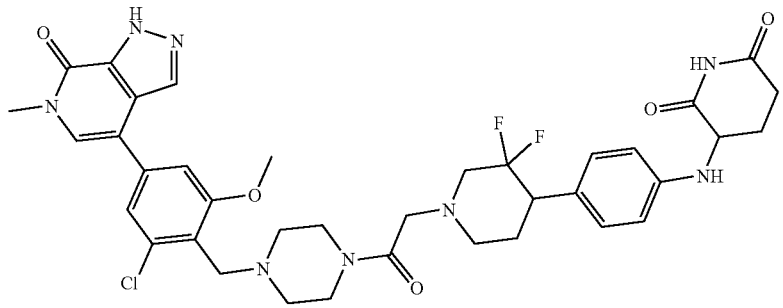 [SMILES: COc1cc(-c2cn(C)c(=O)c3[nH]ncc23)cc(Cl)c1CN1CCN(C(=O)CN2CCC(c3ccc(NC4CCC(=O)NC4=O)cc3)C(F)(F)C2)CC1]

$^1$H NMR (400 MHz, DMSO-d$_6$) δ 14.33 (s, 1H), 10.79 (s, 1H), 9.58 (s, 1H), 8.21 (s, 1H), 7.70 (s, 1H), 7.47 (s, 1H), 7.35 (s, 1H), 7.02 (d, J=8.4 Hz, 2H), 6.64 (d, J=8.6 Hz, 2H), 4.46-4.41 (m, 2H), 4.32-4.28 (m, 1H), 4.19-4.03 (m, 5H), 3.62 (s, 3H), 3.45-3.10 (m, 13H), 3.07-2.57 (m, 2H), 2.12-2.07 (m, 2H), 1.91-1.83 (m, 2H). LC-MS (ES$^+$): m/z 751.56 [M+H]$^+$.

Compound 35 was prepared following the synthesis of Compound 1.

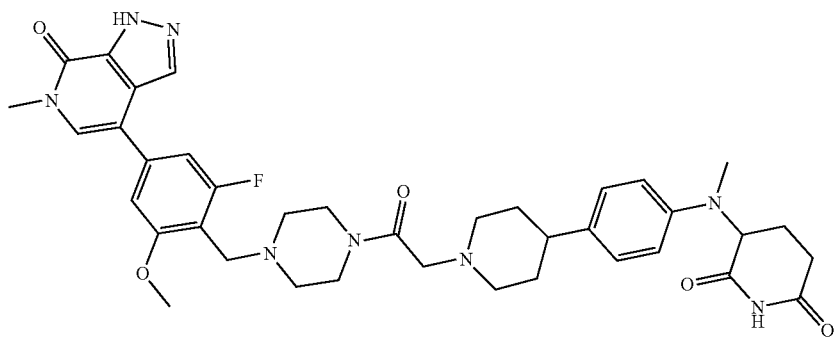 [SMILES: COc1cc(-c2cn(C)c(=O)c3[nH]ncc23)cc(F)c1CN1CCN(C(=O)CN2CCC(c3ccc(N(C)C4CCC(=O)NC4=O)cc3)CC2)CC1]
¹H NMR (400 MHz, DMSO-d₆) δ 14.34 (s, 1H), 10.79 (s, 1H), 9.55 (bs, 1H), 8.23 (s, 1H), 7.70 (s, 1H), 7.26 (m, 4H), 6.79 (d, J=8.8 Hz, 2H), 4.86-4.82 (m, 1H), 4.42 (m, 4H), 4.01 (s, 3H), 3.63 (s, 3H), 3.36-3.06 (m, 12H), 2.88-2.80 (m, 1H), 2.72 (m, 4H), 2.58 (m, 1H), 2.35 (m, 1H), 2.00-1.84 (m, 5H); LC-MS (ES⁺): m/z 713.63 [M+H]⁺.
Compound 36 was prepared following the synthesis of Compound 1.
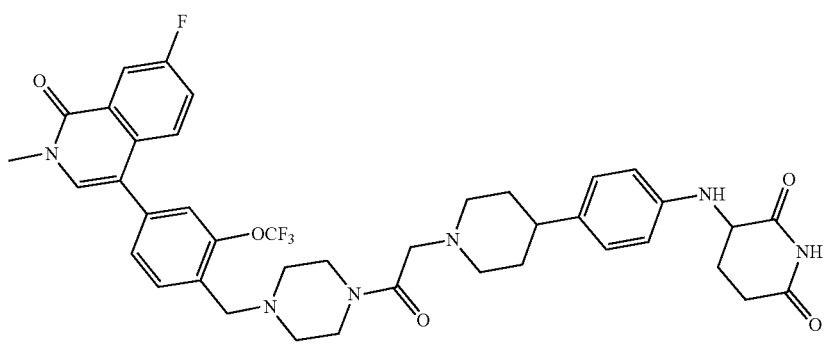 [SMILES: Cn1cc(-c2ccc(CN3CCN(C(=O)CN4CCC(c5ccc(NC6CCC(=O)NC6=O)cc5)CC4)CC3)c(OC(F)(F)F)c2)c2ccc(F)cc2c1=O]
¹H NMR (400 MHz, DMSO-d₆) δ 10.77 (s, 1H), 9.50 (s, 1H), 8.01 (dd, J=9.4, 2.9 Hz, 1H), 7.79 (d, J=7.9 Hz, 1H), 7.71-7.40 (m, 6H), 7.01 (dd, J=35.4, 8.2 Hz, 2H), 6.65 (d, J=8.0 Hz, 2H), 4.51-4.20 (m, 4H), 3.59 (s, 3H), 3.55 (d, J=15.9 Hz, 6H), 3.38-3.23 (m, 1H), 3.08 (d, J=10.6 Hz, 2H), 2.80-2.53 (m, 5H), 2.18-1.68 (m, 7H). LC-MS (ES⁺): m/z 763.8 [M+H]⁺.
Synthesis of Compound 37
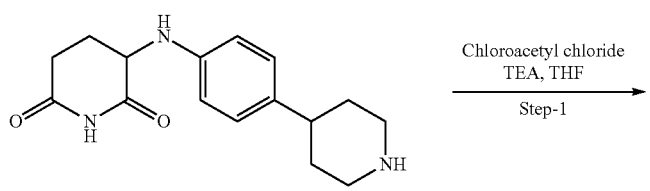
1-1
Chloroacetyl chloride
TEA, THF
———————→
Step-1

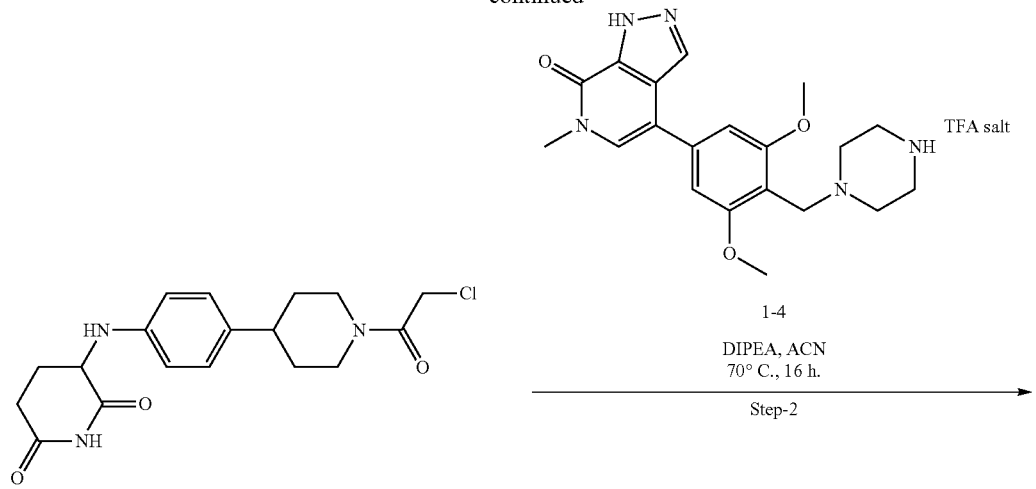

1-4

DIPEA, ACN
70° C., 16 h.

Step-2

37-2

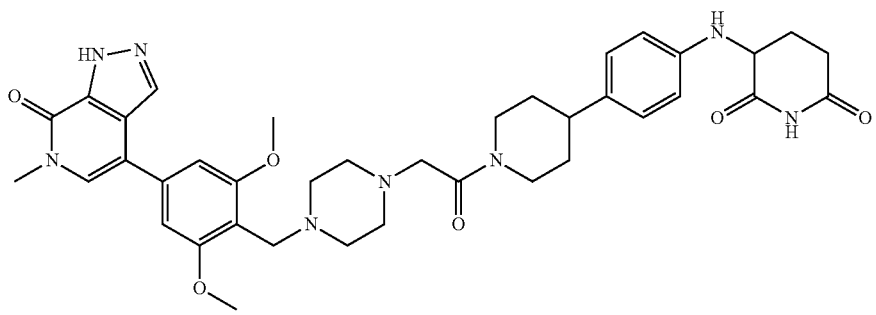

Compound 37

Step-1: To a stirred solution of 3-[4-(4-piperidyl)anilino]piperidine-2,6-dione 1-1 (0.400 g, 1.394 mmol) in THF (8 mL) was added triethylamine (0.141 g, 1.394 mmol) at 0° C., followed by chloroacetyl chloride (0.176 g, 1.394 mmol) was added and reaction mixture was stirred for 1 h at RT while monitoring by LCMS and TLC. After 1 h, the reaction was quenched with ice cold water (10 mL) and extracted with EtOAc (3×10 mL). The combined organic layer was dried over anhydrous $Na_2SO_4$, and concentrated to afford 3-[4-[1-(2-chloroacetyl)-4-piperidyl]anilino]piperidine-2,6-dione (0.160 g, 0.440 mmol, 50.68% yield, 89.44% purity). LC-MS (ES$^+$): m/z 364.23 (M+H)$^+$ Step-2: To a stirred solution of 4-(3,5-dimethoxy-4-(piperazin-1-ylmethyl)phenyl)-6-methyl-1,6-dihydro-7H-pyrazolo[3,4-c]pyridin-7-one. TFA salt (0.120 g, 0.196 mmol) in Acetonitrile (6 mL) were added DIPEA (0.20 g, 1.564 mmol) and 3-((4-(1-(2-chloroacetyl)piperidin-4-yl)phenyl)amino)piperidine-2,6-dione 37-2 (0.113 g, 0.131 mmol), and refluxed the reaction mixture at 70° C. for 16 h while monitoring by LCMS. After 16 h solvent was evaporated under reduce pressure and the crude compound was purified by prep-HPLC to afford 3-[4-[1-[2-[4-[[2,6-dimethoxy-4-(6-methyl-7-oxo-1H-pyrazolo[3,4-c]pyridin-4-yl)phenyl]methyl]piperazin-1-yl]acetyl]-4-piperidyl]anilino]piperidine-2,6-dione.TFA salt (0.017 g, 0.020 mmol, 10.31% yield, 98.19% purity) as an off-white solid. $^1$H NMR (400 MHz, DMSO-d$_6$) δ=14.3 (s, 1H), 12.0 (bs, 1H), 10.8 (s, 1H), 8.21 (s, 1H), 7.55 (s, 1H), 6.93 (d, J=8.4 Hz, 2H), 6.84 (s, 2H), 6.61 (d, J=8.4 Hz, 2H), 5.67 (d, J=7.6 Hz, 1H), 4.50-4.44 (m, 1H), 4.28 (m, 1H), 4.14-4.12 (m, 1H), 3.85 (s, 6H), 3.60 (s, 3H), 3.50 (s, 2H), 3.22-3.19 (m, 1H), 3.00-2.97 (m, 1H), 2.70-2.69 (m, 1H), 2.50-2.48 (m, 8H), 2.10-2.07 (m, 1H), 1.89 (s, 4H), 1.75-1.73 (m, 2H), 1.55-1.48 (m, 1H), 1.33-1.13 (m, 2H). LC-MS (ES$^+$): m/z 711.2 (M+H)$^+$ Compound 38 was prepared following the synthesis of Compound 37.

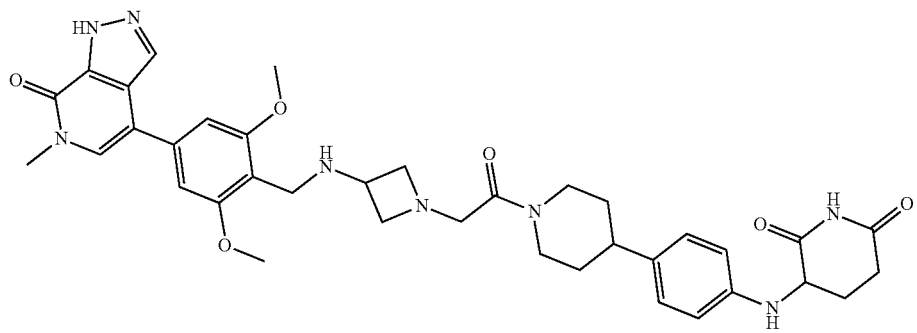 [SMILES: COc1cc(-c2cn(C)c(=O)c3[nH]ncc23)cc(OC)c1CNC1CN(CC(=O)N2CCC(c3ccc(NC4CCC(=O)NC4=O)cc3)CC2)C1]
$^1$H NMR (400 MHz, DMSO-d$_6$) δ 14.31 (s, 1H), 10.77 (s, 1H), 8.21 (s, 1H), 7.63 (s, 1H), 7.08 (m, 4H), 6.61 (d, J=8.4 Hz, 2H), 6.65 (bs, 1H), 5.69 (s, 1H), 4.44-4.00 (m, 10H), 3.95 (s, 6H), 3.63 (s, 3H), 3.17 (m, 1H), 2.75-2.60 (m, 5H), 1.52-1.36 (m, 2H), 1.24 (bm, 5H). LC-MS (ES$^+$): m/z 697.2 [M+H]$^+$
Compound 39 was prepared following the synthesis of Compound 37.
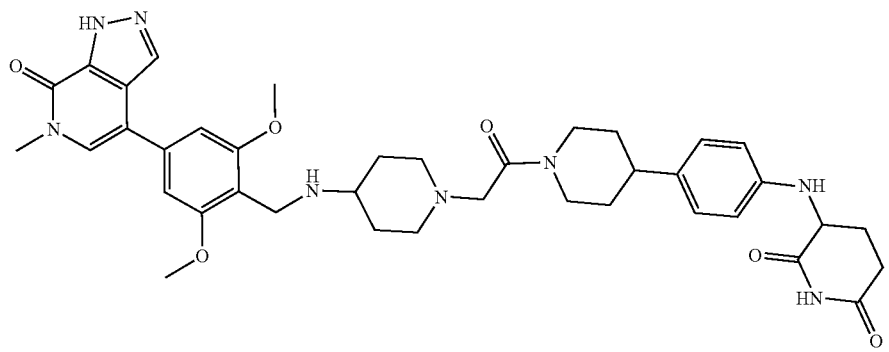 [SMILES: COc1cc(-c2cn(C)c(=O)c3[nH]ncc23)cc(OC)c1CNC1CCN(CC(=O)N2CCC(c3ccc(NC4CCC(=O)NC4=O)cc3)CC2)CC1]
$^1$H NMR (400 MHz, DMSO-d$_6$) δ 14.29 (s, 1H), 10.82 (s, 1H), 9.73 (bs, 1H), 8.77 (bs, 1H), 8.21 (s, 1H), 7.64 (s, 1H), 6.97 (m, 4H), 6.64 (d, J=8.4 Hz, 2H), 5.44 (bd, J=6.4 Hz, 1H), 4.44 (m, 6H), 3.97 (s, 6H), 3.86 (m, 1H), 3.64 (s, 3H), 3.29-3.08 (m, 10H), 2.84-2.73 (m, 2H), 2.54 (m, 1H), 2.10-1.97 (m, 6H); LC-MS (ES$^+$): m/z 725.56 [M+H]$^+$
Compound 40 was prepared following the synthesis of Compound 37.
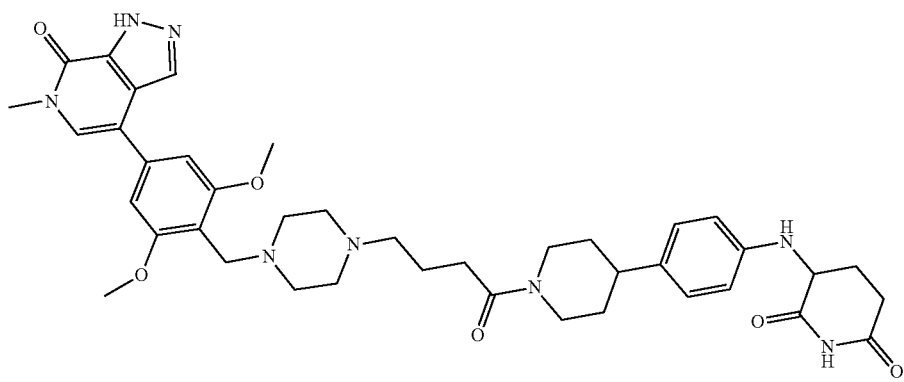 [SMILES: COc1cc(-c2cn(C)c(=O)c3[nH]ncc23)cc(OC)c1CN1CCN(CCCC(=O)N2CCC(c3ccc(NC4CCC(=O)NC4=O)cc3)CC2)CC1]

¹H NMR (400 MHz, DMSO-d₆) δ 14.29 (s, 1H), 10.77 (s, 1H), 9.74 (bs, 1H), 8.22 (s, 1H), 7.63 (s, 1H), 7.01-6.93 (m, 4H), 6.61 (d, J=8.6 Hz, 2H), 4.52 (d, J=12.0 Hz, 1H), 4.28-4.24 (m, 3H), 3.94 (s, 7H), 3.63 (s, 3H), 3.57-2.89 (m, 11H), 2.73-2.59 (m, 4H), 2.49-2.41 (m, 2H), 2.07-2.02 (m, 1H), 1.88-1.71 (m, 5H), 152-1.42 (m, 2H). LC-MS(ES⁺): m/z 739.55 [M+H]⁺.
Synthesis of Compound 41
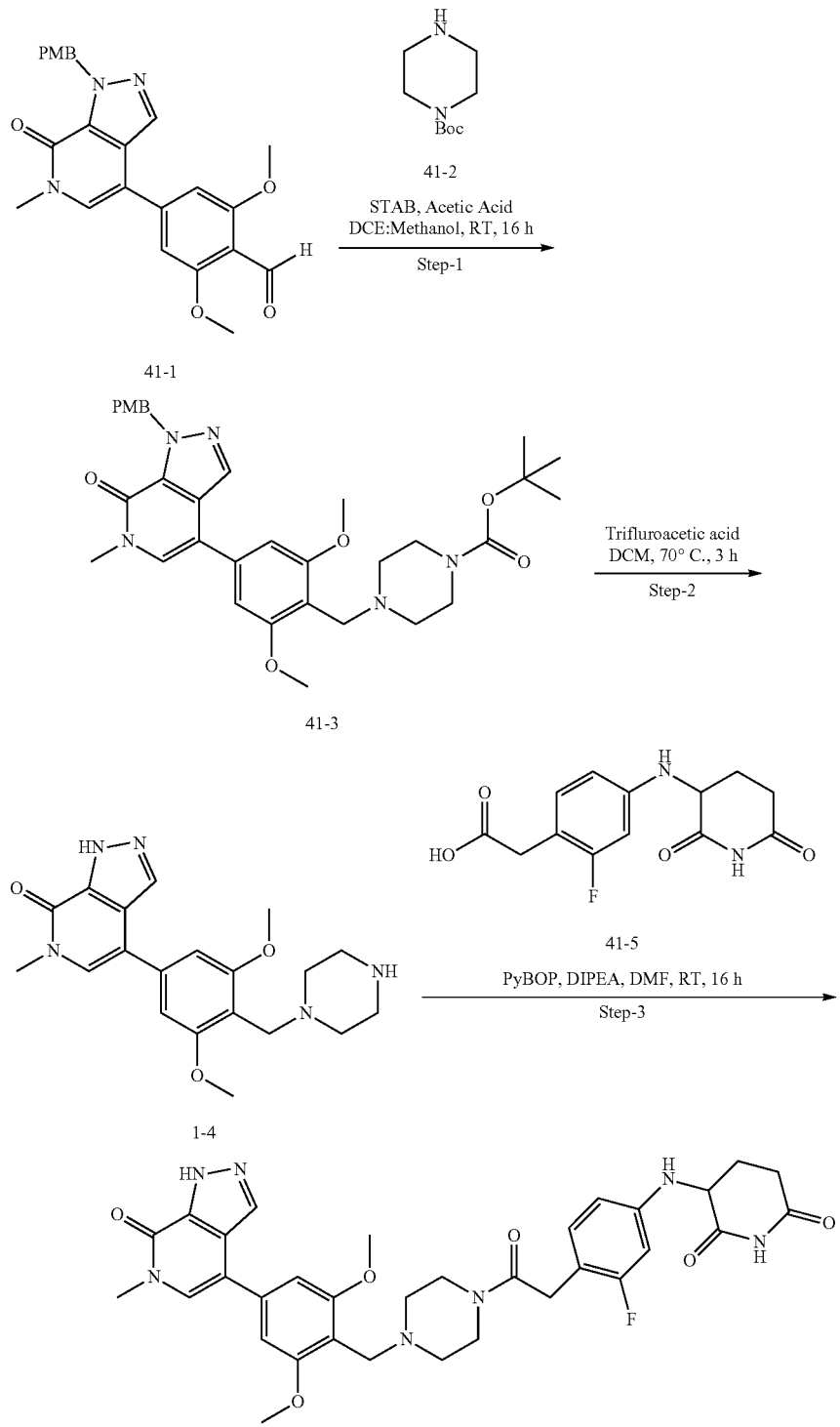
Compound 41

Step-1: To a stirred solution of 2,6-dimethoxy-4-[1-[(4-methoxyphenyl)methyl]-6-methyl-7-oxo-pyrazolo[3,4-c]pyridin-4-yl]benzaldehyde (500 mg, 1.15 mmol) and tert-butyl piperazine-1-carboxylate (257.81 mg, 1.38 mmol) in DCE (3 ml) and MeOH (2 ml) at 0° C. was added Acetic acid (32.99 uL, 576.76 mmol) and continued the stirring at room temperature for 4 h. Sodium triacetoxyborahydride (488.96 mg, 2.31 mmol) was added to reaction mixture at 0° C. and continued the stirring at RT for 16 hr. The progress of the reaction was monitor by TLC. After completion of reaction, the reaction mixture was concentrated under vacuum. The residue was diluted with ethyl acetate (50 mL) and washed with water. The organic layer was dried over $Na_2SO_4$, filtered and concentrated under vacuum. The crude compound was purified by column chromatography (Davisil silica, 0-50% ethyl acetate in pet ether) to afford the tert-butyl 4-(2,6-dimethoxy-4-(1-(4-methoxybenzyl)-6-methyl-7-oxo-6,7-dihydro-1H-pyrazolo[3,4-c]pyridin-4-yl)benzyl)piperazine-1-carboxylate (500 mg) as a colourless solid. Compound was matched with TLC of authentic compound on page number Step-2: To a stirred solution of tert-butyl 4-[[2,6-dimethoxy-4-[1-[(4-methoxyphenyl)methyl]-6-methyl-7-oxo-pyrazolo[3,4-c]pyridin-4-yl]phenyl]methyl]piperazine-1-carboxylate (0.88 g, 1.46 mmol) in DCM (10 mL) was added Trifluoroacetic acid (2.25 ml, 29.15 mmol) and stirred the reaction mixture at 70° C. for 1 hr. Reaction progress was monitored by TLC and LCMS. After completion of the reaction, reaction mixture was dried on rotavapor and co-distilled with acetonitrile and toluen. The crude compound was triturated with diethylether to afford 4-[3,5-dimethoxy-4-(piperazin-1-ylmethyl)phenyl]-6-methyl-1H-pyrazolo[3,4-c]pyridin-7-one (800 mg, 68.21% yield, 76% purity). LC-MS (ES$^+$): m/z 384.35 [M+H]$^+$ Step-3: To a stirred solution of 4-[3,5-dimethoxy-4-(piperazin-1-ylmethyl)phenyl]-6-methyl-1H-pyrazolo[3,4-c]pyridin-7-one (100 mg, 0.179 mmol) and 2-[4-[(2,6-dioxo-3-piperidyl)amino]-2-fluoro-phenyl]acetic acid (50.41 mg, 0.179 mmol) in DMF (2 mL) was added N-ethyl-N-isopropylpropan-2-amine (0.03 ml, 0.179 mmol) and stirred the reaction mixture for 5 min at room temperature. PyBOP (93.61 mg, 0.179 mmol) was added to the reaction mixture and stirred at RT for 16 h. Reaction progress was monitored by LCMS. After completion of the reaction, DMF was evaporated using genvac and the residue was purified by preparative HPLC to afford 3-[4-[2-[4-[[2,6-dimethoxy-4-(6-methyl-7-oxo-1H-pyrazolo[3,4-c]pyridin-4-yl)phenyl]methyl]piperazin-1-yl]-2-oxo-ethyl]-3-fluoro-anilino]piperidine-2,6-dione (53 mg, 38.49% yield, 99.24% purity) as a pale green solid. $^1$H NMR (400 MHz, DMSO-d$_6$) δ 14.22 (s, 1H), 10.80 (s, 1H), 9.41 (s, 1H), 8.23 (s, 1H), 7.65 (s, 1H), 7.08 (s, 2H), 6.91 (m, J=8.8 Hz, 1H), 6.48 (m, 2H), 6.08 (bs, 1H), 4.41-4.30 (m, 4H), 4.15 (bd, 1H), 3.97 (s, 6H), 3.63 (s, 3H), 3.46-3.05 (m, 4H), 3.17-3.048 (m, 4H), 2.75-2.60 (m, 1H), 2.60 (m, 1H), 2.11-2.07 (m, 1H), 1.90-1.86 (m, 1H); LC-MS (ES$^+$): m/z 646.42 [M+H]$^+$ Synthesis of Compound 42

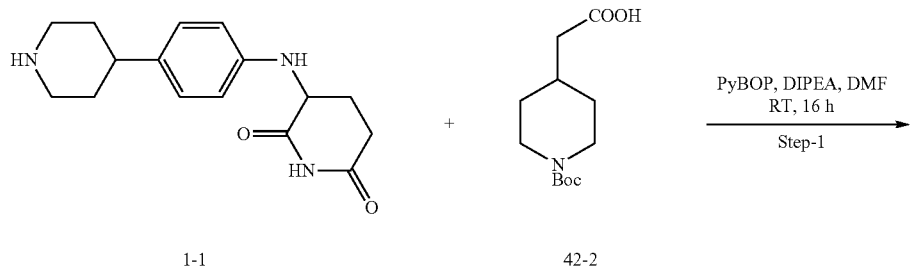

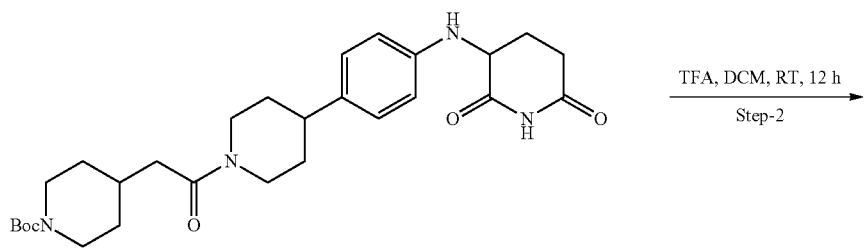

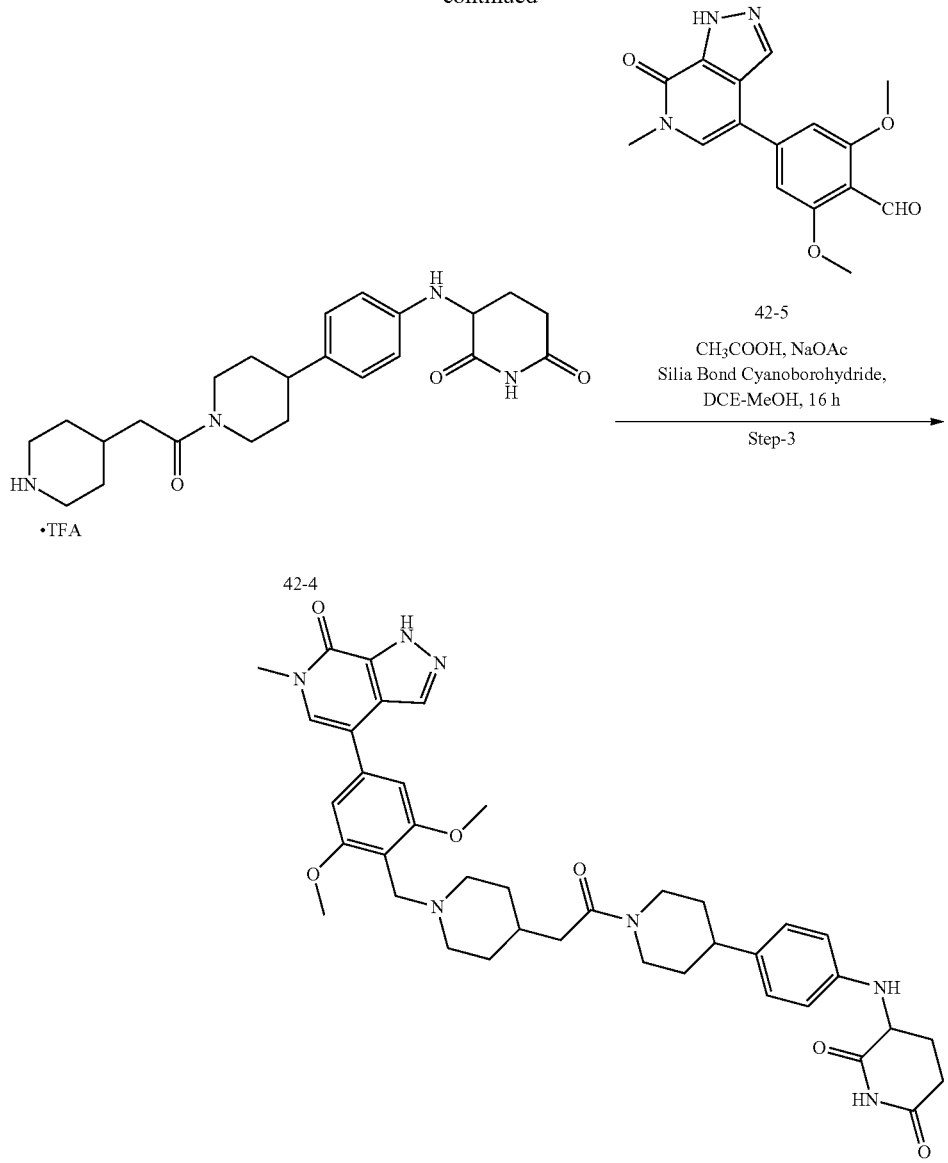

Compound 42

Step-1: To a stirred solution of 3-[4-(4-piperidyl)anilino]piperidine-2,6-dione (0.8 g, 1.55 mmol) in DMF (8 mL) was added N,N-Diisopropylethylamine (1.62 ml, 9.31 mmol) followed by 2-(1-tert-butoxycarbonyl-4-piperidyl)acetic acid (377.64 mg, 1.55 mmol) and stirred for 5 min. PyBOP was added (1.05 g, 2.02 mmol) to the reaction mixture and stirred at RT for 16 h. The progress of the reaction was monitored by LCMS. After completion of the reaction, the reaction mixture was diluted with water (50 ml) and extracted with ethyl acetate (30 mL×2). The organic layer was dried over sodium sulphate, filtered and concentrated under reduced pressure. The crude product was washed with diethyl ether (30 mL×2) to afford tert-butyl 4-[2-[4-[4-[(2,6-dioxo-3-piperidyl)amino]phenyl]-1-piperidyl]-2-oxo-ethyl]piperidine-1-carboxylate (0.92 g, 78.50% yield, 83% purity) as a TFA salt. LC-MS (ES$^+$): m/z 513.42 [M+H]$^+$ Step-2: To a stirred solution of tert-butyl 4-[2-[4-[4-[(2,6-dioxo-3-piperidyl)amino]phenyl]-1-piperidyl]-2-oxo-ethyl]piperidine-1-carboxylate (0.25 g, 0.487 mmol) in DCM (5 ml) was added Trifluoroacetic acid (0.37 ml, 4.88 mmol). The reaction mixture stirred at RT for 12 hr. The progress of the reaction checked by TLC and LCMS. After completion of reaction, the reaction mixture was concentrated under reduced pressure. The crude was co-distilled with acetonitrile (20 ml) and Toluene (20 ml) and triturated with diethyl ether (25 ml×2) to afford 3-[4-[1-[2-(4-piperidyl)acetyl]-4-piperidyl]anilino]piperidine-2,6-dione (0.18 g, 52.38% yield, 90.9% purity) as a TFA salt.

Step-3: To a stirred solution of 3-[4-[1-[2-(4-piperidyl)acetyl]-4-piperidyl]anilino]piperidine-2,6-dione 2 (0.5 g, 1.21 mmol) in ACN (10 ml) were added 4 Å molecular sieves (0.05 g), acetic acid (0.073 g, 1.21 mmol) and sodium acetate, anhydrous (0.1 g, 2.63 mmol). The resulting solution was stirred for 10 min, then 2,6-dimethoxy-4-(6-methyl-7-oxo-1H-pyrazolo[3,4-c]pyridin-4-yl)benzaldehyde 1 (0.380 g, 1.21 mmol) and heated the reaction mixture at 70° C. for 3 h then cooled it at RT and added Silia Bond Cyanoborohydride (0.352 g, 6.05 mmol). The stirring was continued at RT for 6 h, while monitoring the reaction by LCMS and TLC. After 6 h, the reaction mass was filtered, concentrated and purified by Prep-HPLC to 3-[4-[1-[2-[1-[[2,6-dimethoxy-4-(6-methyl-7-oxo-1H-pyrazolo[3,4-c]pyridin-4-yl)phenyl]methyl]-4-piperidyl]acetyl]-4-piperidyl]anilino]piperidine-2,6-dione.TFA Salt. (0.917 g, 9.07% yield, 98.73% purity) as a yellow solid. $^1$H NMR (400 MHz, DMSO-d$_6$) δ 14.17 (s, 1H), 10.77 (s, 1H), 8.78 (bs, 1H), 8.22 (bs, 1H), 7.65 (s, 1H), 7.21 (m, 4H), 6.63 (d, J=8.4 Hz, 2H), 5.57 (bs, 0.3H), 4.55 (m, 1H), 4.27-4.19 (m, 3H), 3.93 (m, 7H), 3.63 (s, 3H), 3.44 (m, 2H), 3.11-3.06 (m, 4H), 2.73-2.66 (m, 1H), 2.59 (m, 1H), 2.33-2.29 (m, 2H), 2.09-2.06 (m, 1H), 1.95-1.73 (m, 7H), 1.46-1.35 (m, 4H), LC-MS (ES$^+$): m/z 710.4 [M+H]$^+$.

Compound 43 was prepared following the synthesis of Compound 42.

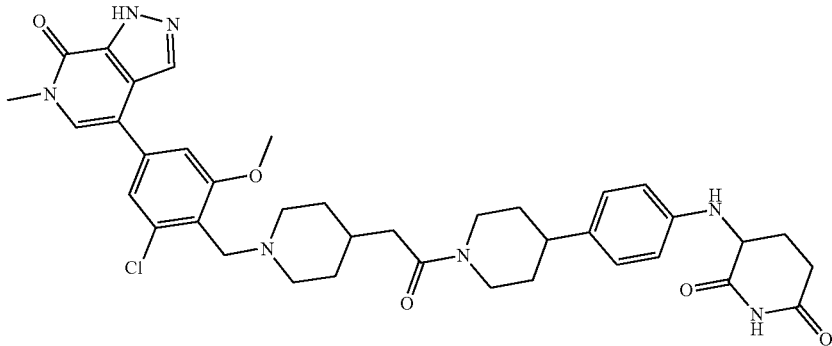 [SMILES: COc1cc(-c2cn(C)c(=O)c3[nH]ncc23)cc(Cl)c1CN1CCC(CC(=O)N2CCC(c3ccc(NC4CCC(=O)NC4=O)cc3)CC2)CC1]

$^1$H NMR (400 MHz, DMSO-d$_6$) δ 14.31 (s, 1H), 10.77 (s, 1H), 8.91 (s, 1H), 8.21 (s, 1H), 7.71 (s, 1H), 7.45 (d, J=1.4 Hz, 1H), 7.33 (d, J=1.2 Hz, 1H), 6.96-6.94 (m, 2H), 6.63-6.60 (m, 2H), 4.52-4.24 (m, 4H), 3.97 (s, 3H), 3.95-3.92 (m, 1H), 3.62 (s, 3H), 3.48-3.45 (m, 2H), 3.36-3.22 (m, 3H), 3.06-2.60 (m, 4H), 2.34-2.28 (m, 2H), 2.09-1.74 (m, 7H), 1.52-1.49 (m, 4H), LC-MS (ES$^+$): m/z 714.56 [M+H]$^+$.

Compound 44 was prepared following the synthesis of Compound 42.

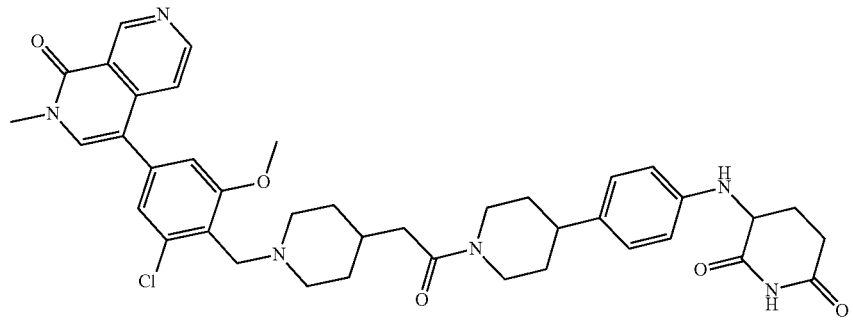 [SMILES: COc1cc(-c2cn(C)c(=O)c3cnccc23)cc(Cl)c1CN1CCC(CC(=O)N2CCC(c3ccc(NC4CCC(=O)NC4=O)cc3)CC2)CC1]

$^1$H NMR (400 MHz, DMSO-d$_6$) δ 10.78 (s, 1H), 9.49 (s, 1H), 8.94 (s, 1H), 8.77 (d, J=5.7 Hz, 1H), 7.97 (s, 1H), 7.55 (d, J=6.2 Hz, 1H), 7.33 (d, J=1.4 Hz, 1H), 7.27 (s, 1H), 6.96 (d, J=7.6 Hz, 2H), 6.62 (d, J=8.8 Hz, 2H), 4.55-4.52 (m, 1H), 4.42 (d, J=4.2 Hz, 2H), 4.28-4.24 (m, 1H), 3.96 (s, 3H), 3.61 (s, 3H), 3.49 (d, J=11.1 Hz, 2H), 3.29-3.20 (m, 3H), 3.09-3.06 (m, 1H), 2.73-2.50 (m, 3H), 2.33-2.29 (m, 2H), 2.08-2.07 (m, 1H), 1.93-1.72 (m, 7H), 1.50-1.45 (m, 4H). LC-MS (ES$^+$): m/z 725.56 [M+H]$^+$.

Compound 45 was prepared following the synthesis of Compound 42.

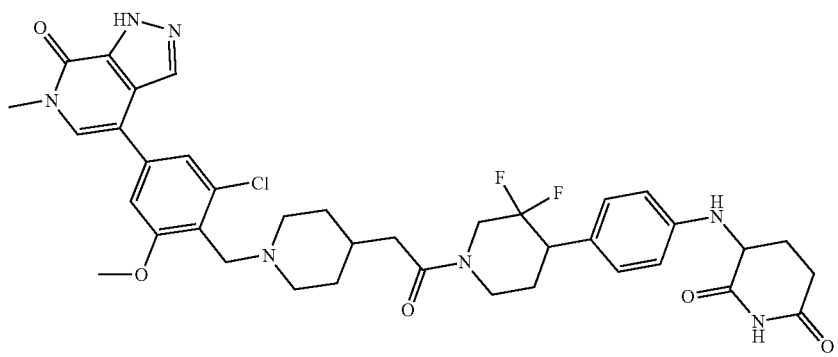 [SMILES: COc1cc(-c2cn(C)c(=O)c3[nH]ncc23)cc(Cl)c1CN1CCC(CC(=O)N2CCC(c3ccc(NC4CCC(=O)NC4=O)cc3)C(F)(F)C2)CC1]
$^1$H NMR (400 MHz, DMSO-d$_6$) δ 14.26 (s, 1H), 10.78 (s, 1H), 8.90 (bs, 1H), 8.21 (s, 1H), 7.71 (s, 1H), 7.45 (s, 1H), 7.33 (s, 1H), 7.21 (s, 1H), 7.00-6.95 (m, 2H), 6.64-6.62 (m, 2H), 5.83 (bs, 1H), 4.62-4.27 (m, 5H), 4.02 (s, 3H), 3.62 (s, 3H), 3.45-3.16 (m, 6H), 2.73-2.67 (m, 2H), 2.60-2.55 (m, 2H) 2.35-2.32 (m, 1H), 2.10-1.47 (m, 9H). LC-MS (ES$^+$): m/z 750.60 [M+H]$^+$.
Synthesis of Compound 46
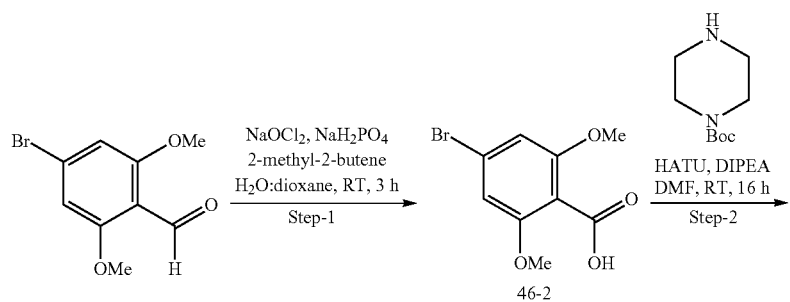
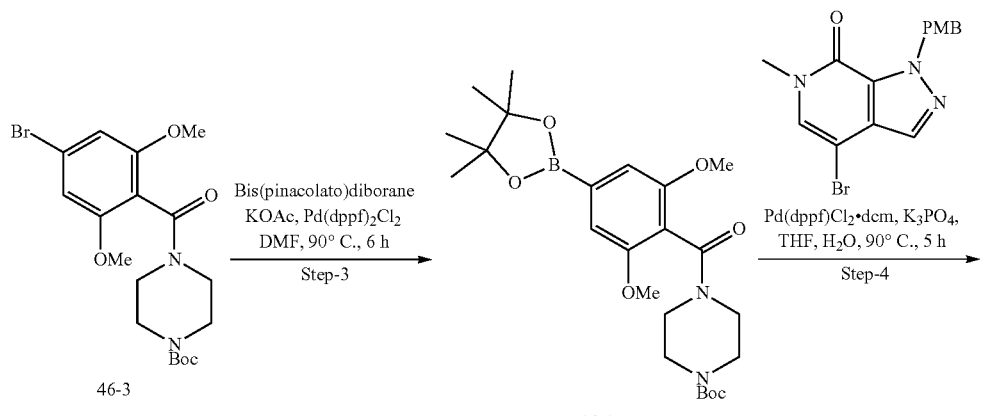

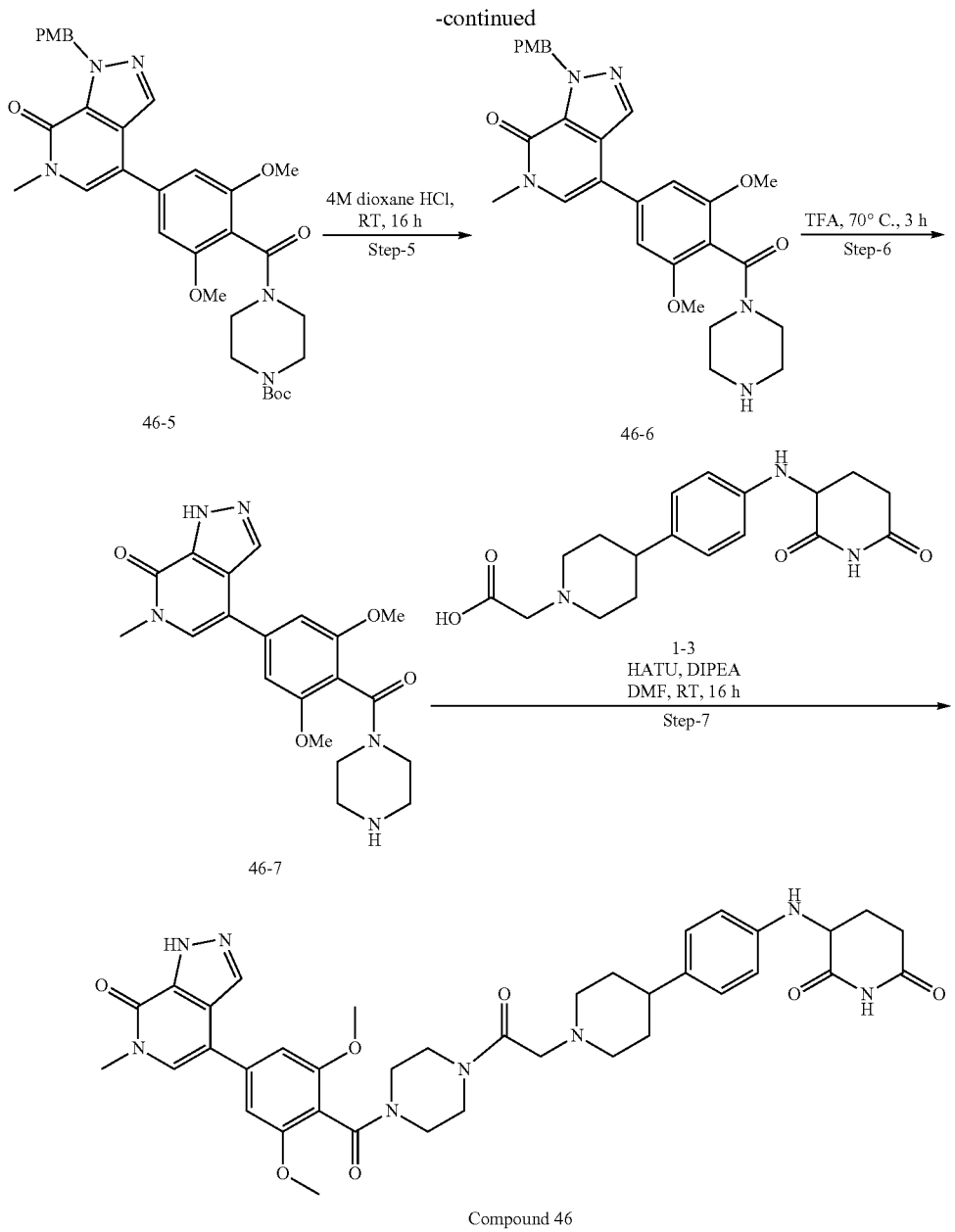

Step-1: To a stirred solution of 4-bromo-2,6-dimethoxy-benzaldehyde (5.0 g, 20.40 mmol) in 1,4-dioxane (20 mL), were added sequentially 2-methylbut-2-ene (11.45 g, 163.22 mmol), sodium chlorite (9.23 g, 102.01 mmol) and sodium dihydrogen phosphate (48.96 g, 408.05 mmol) in water (10 ml) over period of 5 min and allowed to stir at RT for 3 h, while monitoring the reaction by TLC. The reaction mass was evaporated under reduced pressure and purified by acid base workup to afford 4-bromo-2,6-dimethoxy-benzoic acid 46-2 (4.5 g, 16.75 mmol, 82.09% yield, 97.17% purity) as an off white solid. $^1$H NMR (400 MHz, DMSO-$d_6$) δ 12.89 (bs, 1H), 6.91 (s, 2H), 3.77 (s, 6H) LC-MS (ES$^+$): m/z 261.12 [M+H]$^+$.

Step-2: To a stirred solution of 4-bromo-2,6-dimethoxy-benzoic acid 46-2 (4.5 g, 17.24 mmol) in DMF (14 mL) was added DIPEA (6.68 g, 51.71 mmol) and HATU (13.11 g, 34.47 mmol) and stirred for 15 minutes. A solution of tert-butyl piperazine-1-carboxylate (3.85 g, 20.68 mmol) in DMF (1 mL) was added at RT and stirred for 16 h, while monitoring the reaction by TLC. The reaction mixture was quenched with ice cold water (100 ml) and precipitated solid was filtered and further purified by normal phase column chromatography [silica gel mesh 100-200, 10-20% pet ether in ethyl acetate] to afford tert-butyl 4-(4-bromo-2, 6-dimethoxy-benzoyl) piperazine-1-carboxylate 46-3 (5.0 g, 9.92 mmol, 57.58% yield, 85.21% purity) as a white solid. $^1$H NMR (400 MHz, DMSO-$d_6$): δ 6.72 (s, 2H), 3.79 (s, 6H) 3.78-3.75 (m, 2H) 3.50-3.40 (m, 2H) 3.37-3.34 (m, 2H) 3.21-3.18 (m, 2H) 1.46 (s, 9H) LC-MS (ES$^+$): m/z 431.22 [M+H]$^+$.

Step-3: To a stirred solution of tert-butyl 4-(4-bromo-2, 6-dimethoxy-benzoyl)piperazine-1-carboxylate 3 (5.0 g, 11.65 mmol) in DMF (20 mL) was added Bis(pinacolate) diborane (2.96 g, 11.65 mmol) and potassium acetate (3.43 g, 34.94 mmol). The resulting solution was degassed with N₂ for 15 minutes and Pd(dppf)Cl₂.DCM (0.951 g, 1.16 mmol) was added. The reaction mixture was heated at 90° C. for 6 h, while monitoring the reaction by TLC. The reaction mixture was filtered through Celite bed and washed with ethyl acetate (300 ml×2) and filtrate was concentrated. The reaction mixture was diluted with water (400 mL) and extracted with ethyl acetate (4×250 mL). The combined organic extracts was dried over anhydrous Na₂SO₄, evaporated under reduced pressure to afford tert-butyl 4-[2,6-dimethoxy-4-(4,4,5,5-tetramethyl-1,3,2-dioxaborolan-2-yl) benzoyl]piperazine-1-carboxylate 46-4 (5.0 g, 5.46 mmol, 46.86% yield, 52% purity) as black gummy semisolid. This was taken for the next step without further purification. LC-MS:Boronic acid: RT:1.51 min=395.28 [M+H]⁺ and Boronate ester:RT: 2.15 min=477.39 [M+H]⁺

Note: Crude LCMS indicates 16% boronic acid mass and 22% boronate ester mass.

Step-4: To a stirred solution of 4-bromo-1-(4-methoxybenzyl)-6-methyl-1,6-dihydro-7H-pyrazolo[3,4-c]pyridin-7-one (2.0 g, 5.74 mmol) in THF (30 mL) and water (5 mL), was added tert-butyl tert-butyl 4-[2,6-dimethoxy-4-(4,4,5,5-tetramethyl-1,3,2-dioxaborolan-2-yl)benzoyl]piperazine-1-carboxylate 46-4 (4.10 g, 8.62 mmol) and K₃PO₄ (3.66 g, 17.23 mmol). The resulting reaction mixture was degassed by purging N₂ (g) for 15 minutes and added Pd(dppf) Cl₂.CH₂Cl₂ (0.526 g, 0.68 mmol). The reaction mixture was stirred at 90° C. for 5 h while monitoring the reaction by TLC and LCMS. The reaction mixture was filtered through Celite bed and washed with ethyl acetate (150 ml×2) and filtrate was concentrated and worked up using water (100 ml×1) and ethyl acetate (150 ml×2). The organic layer was dried over Na₂SO₄, concentrated and purified by reverse phase C18 column using 0.1% FA in H₂O:ACN to afford tert-butyl 4-(2,6-dimethoxy-4-(1-(4-methoxybenzyl)-6-methyl-7-oxo-6,7-dihydro-1H-pyrazolo[3,4-c]pyridin-4-yl) benzoyl)piperazine-1-carboxylate 46-5 (1.8 g, 2.23 mmol, 38.89% yield, 82.37% purity) as an off white solid. ¹H NMR (400 MHz, DMSO-d₆): δ 7.87 (s, 1H), 7.45 (d, J=8.8 Hz, 2H) 6.97 (s, 1H), 6.68 (s, 1H), 6.86 (d, J=8.8 Hz, 2H) 6.66 (s, 2H) 5.93 (s, 2H) 3.87 (s, 6H) 3.83-3.80 (m, 1H) 3.76 (s, 3H) 3.68 (s, 3H) 3.53-3.51 (m, 2H) 3.42-3.39 (m, 2H) 3.30-3.27 (m, 2H), 1.47 (s, 9H) LC-MS (ES⁺): m/z 618.63 [M+H]⁺.

Step-5: To a stirred solution of tert-butyl 4-(2,6-dimethoxy-4-(1-(4-methoxybenzyl)-6-methyl-7-oxo-6,7-dihydro-1H-pyrazolo[3,4-c]pyridin-4yl)benzoyl) piperazine-1-carboxylate 5 (1.0 g, 1.62 mmol) in 1,4-dioxane (10 ml) was added 4M dioxane HCl (0.1 ml, 1.62 mmol) at 0° C. and the reaction mixture was stirred at RT for 16 h. After completion of the reaction, the reaction mixture was concentrated to obtain crude compound 4-[3,5-dimethoxy-4-(piperazine-1-carbonyl)phenyl]-1-[(4-methoxyphenyl) methyl]-6-methyl-pyrazolo[3,4-c] pyridin-7-one 46-6 HCl salt (1.0 g, 1.57 mmol, 97.13% yield, 87.12% purity) as a brown solid. ¹H NMR (400 MHz, DMSO-d6) δ 9.31 (s, 2H) 8.17 (s, 1H) 7.64 (s, 1H) 7.29-7.20 (m, 2H) 6.98-6.87 (m, 4H) 5.87 (s, 2H) 3.88-3.85 (m 8H), 3.71 (s, 3H), 3.64 (s, 3H), 3.40-3.35 (m, 4H), 3.12 (bs, 2H), 2.98 (bs, 2H). LC-MS (ES⁺): m/z 518.38 [M+H]⁺

Step 6: 4-[3,5-dimethoxy-4-(piperazine-1-carbonyl)phenyl]-1-[(4methoxyphenyl)methyl]-6-methyl-pyrazolo[3,4-c]pyridin-7-one 6 (1.0 g, 1.80 mmol, 021) was dissolved in TFA (1.39 ml, 18.05 mmol) at 0° C. and then heated at 70° C. for 3 h, while monitoring the reaction by TLC. After completion, the reaction mixture was concentrated to obtain crude compound, which was washed with diethyl ether (20 ml×2) and dried, to yield 4-[3,5-dimethoxy-4-(piperazine-1-carbonyl)phenyl]-6-methyl-1H-pyrazolo[3,4-c]pyridin-7-one 7 TFA salt (1.0 g, 1.69 mmol, 93.68% yield, 86.48% purity) as an off white solid. ¹H NMR (400 MHz, DMSO-d₆) δ 8.24 (s, 1H) 7.60 (s, 1H) 6.92 (s, 2H) 3.86-3.87 (m, 8H) 3.62 (s, 3H) 3.40-3.42 (bs, 2H) 3.15-3.17 (bs, 2H) 3.029-3.053 bs, 2H) LC-MS (ES⁺): m/z 398.41 [M+H]⁺

Step-7: To a stirred solution of 2-[4-[4-[(2,6-dioxo-3-piperidyl)amino]phenyl]-1-piperidyl]acetic acid 8 (0.5 g, 1.09 mmol) in DMF (3 mL) was added DIPEA (0.703 g, 5.44 mmol), HATU (0.827 g, 2.18 mmol) and stirred for 15 minutes before adding a solution of 4-[3,5-dimethoxy-4-(piperazine-1-carbonyl)phenyl]-6-methyl-1H-pyrazolo[3,4-c]pyridin-7-one 7 (0.432 g, 0.845 mmol) in DMF (2.0 mL). The reaction mixture was stirred at RT for 16 h, while monitoring by TLC and LCMS. The reaction mixture was quenched with ice cold water (100 ml) and the precipitated solid was filtered and concentrated under reduced pressure. Purified by prep-HPLC to afford 3-[4-[1-[2-[4-[2,6-dimethoxy-4-(6-methyl-7-oxo-1H-pyrazolo[3,4-c]pyridin-4-yl) benzoyl]piperazin-1-yl]-2-oxo-ethyl]-4-piperidyl]anilino] piperidine-2,6-dione TFA salt (236 mg, 274.14 umol, 25.19% yield, 97.44% purity) as an off white solid. ¹H NMR (400 MHz, DMSO-d₆) δ 14.28 (s, 1H), 10.78 (s, 1H), 9.48 (s, 1H), 8.25 (s, 1H), 7.62 (d, J=4.2 Hz, 1H), 7.09-6.95 (m, 4H), 6.64 (d, J=8.5 Hz, 2H), 4.24-4.20 (m, 3H), 3.87 (s, 6H), 3.73-3.48 (m, 11H), 3.28-3.15 (m, 4H), 2.74-2.65 (m, 3H), 2.19-2.15 (m, 1H), 1.98-1.90 (m, 5H). LC-MS (ES⁺): m/z 725.56 [M+H]⁺

Compound 47 was prepared following the synthesis of Compound 46.

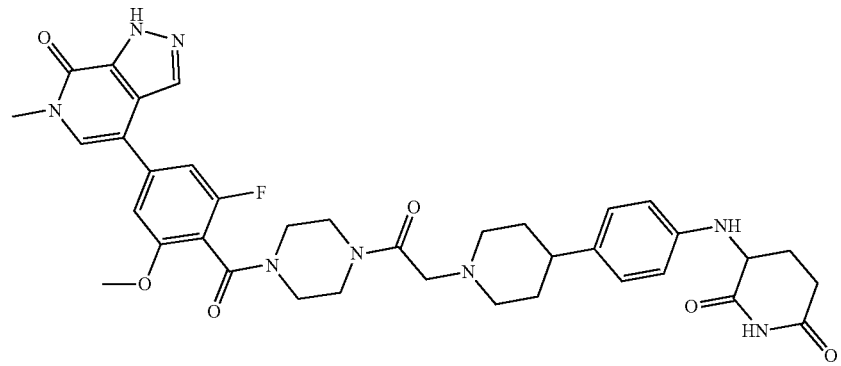 [SMILES: COc1cc(-c2cn(C)c(=O)c3[nH]ncc23)cc(F)c1C(=O)N1CCN(C(=O)CN2CCC(c3ccc(NC4CCC(=O)NC4=O)cc3)CC2)CC1]

¹H NMR (400 MHz, DMSO-d₆) δ 14.29 (s, 1H), 10.78 (s, 1H), 9.49 (s, 1H), 8.26 (s, 1H), 7.67 (d, J=4.6 Hz, 1H), 7.22-6.96 (m, 4H), 6.65 (d, J=8.5 Hz, 2H), 4.49-4.26 (m, 3H), 3.94 (d, J=3.4 Hz, 3H), 3.52-3.28 (m, 14H), 3.09 (bs, 2H), 2.74-2.60 (m, 2H), 2.08-1.85 (m, 6H). LC-MS (ES⁺): m/z 713.47 [M+H]⁺.
Compound 48 was prepared following the synthesis of Compound 46.
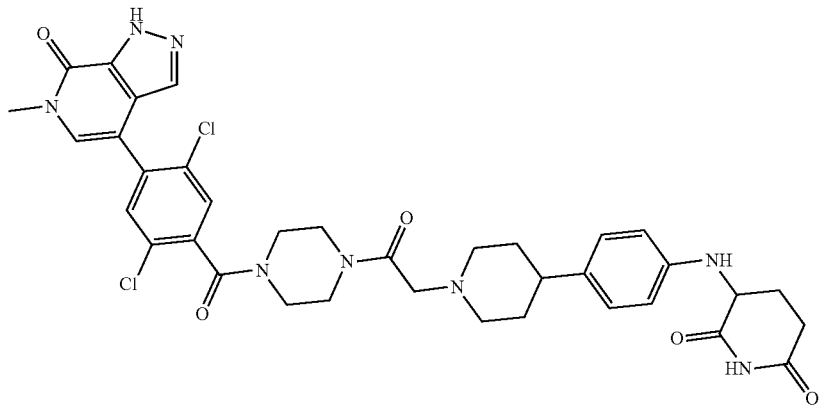 [SMILES: Cn1cc(-c2cc(Cl)c(C(=O)N3CCN(C(=O)CN4CCC(c5ccc(NC6CCC(=O)NC6=O)cc5)CC4)CC3)cc2Cl)c2cn[nH]c2c1=O]
¹H NMR (400 MHz, DMSO-d₆) δ 10.77 (s, 1H), 9.50 (s, 1H), 7.83 (s, 1H), 7.69 (d, J=11.6 Hz, 2H), 7.40 (s, 1H), 6.97 (d, J=8.1 Hz, 2H), 6.65 (d, J=8.2 Hz, 2H), 4.52-4.20 (m, 3H), 4.00 (s, 1H), 3.56 (d, J=21.5 Hz, 7H), 3.32 (d, J=23.0 Hz, 1H), 3.23-3.03 (m, 3H), 2.84 (s, 1H), 2.94-2.54 (m, 4H), 2.37 (d, J=37.0 Hz, 2H), 2.20-1.60 (m, 8H). LC-MS (ES⁺): m/z 733.6 [M+H]⁺.
Synthesis of Compound 49
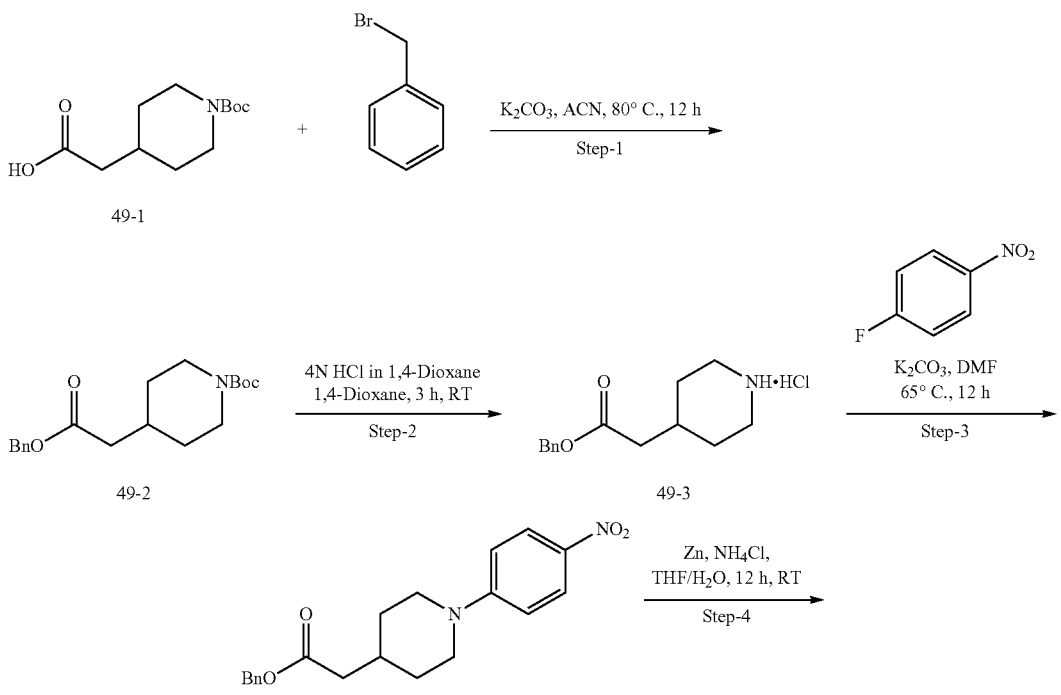

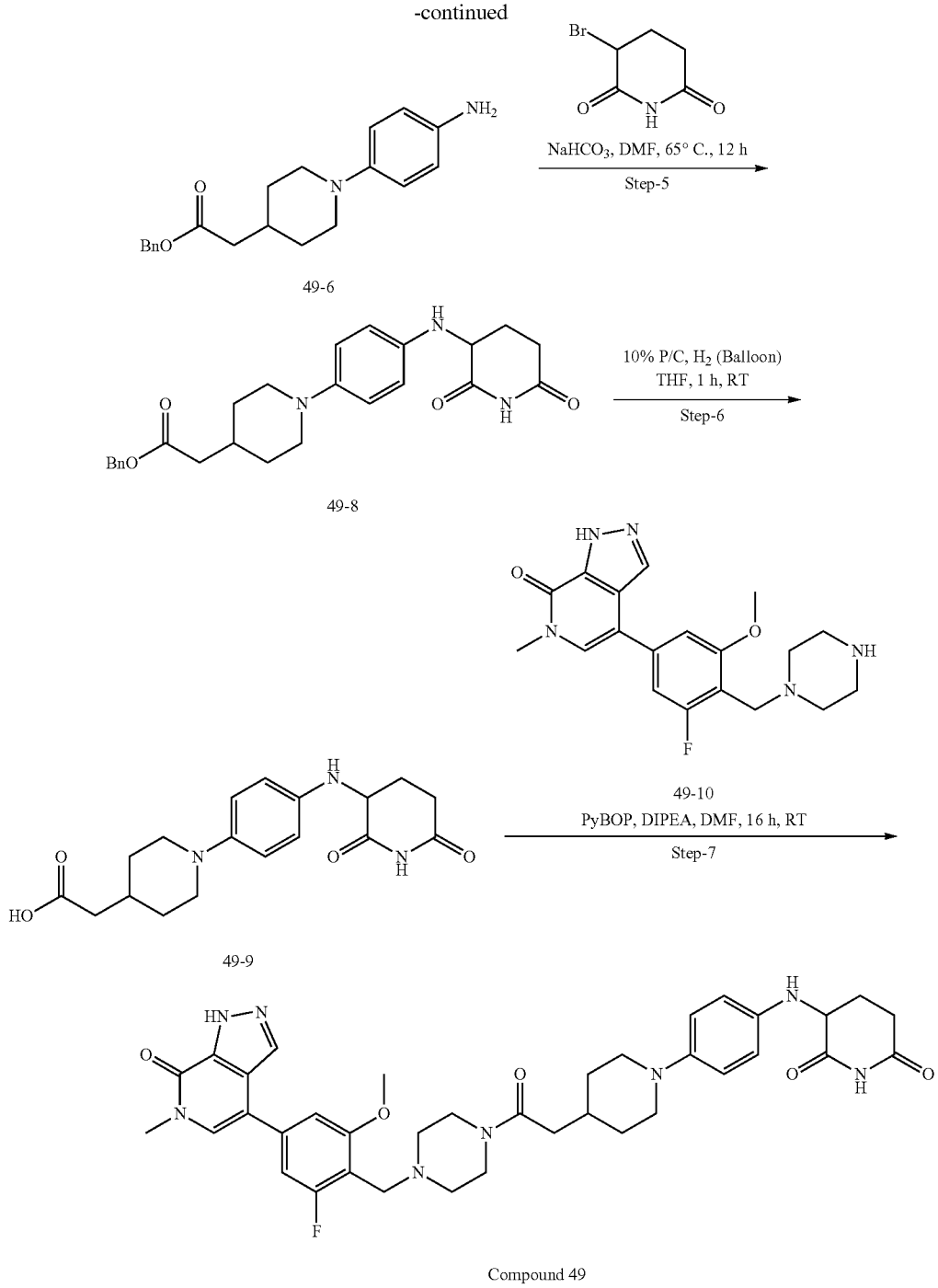

Compound 49

Step-1: To a stirred solution of 2-(1-tert-butoxycarbonyl-4-piperidyl)acetic acid (2.12 g, 8.72 mmol) in ACN (30 mL) was added Potassium carbonate-granular (1.81 g, 13.08 mmol) and stirred at RT for 15 minutes. Bromomethylbenzene (1.24 mL, 10.47 mmol) was added to the reaction mixture and continued the stirring at 80° C. for 12 h. After completion of reaction, the volatiles were evaporated under vacuum and the crude compound was purified by column chromatography (Davisil silica, 0-8% Methanol in DCM) to obtain tert-butyl 4-(2-benzyloxy-2-oxo-ethyl)piperidine-1-carboxylate (2.5 g, 77.36% yield, 90% purity). Compound was confirmed by HNMR. $^1$H NMR (400 MHz, CDCl$_3$) δ 7.40-7.26 (m, 5H), 5.11 (s, 2H), 4.06 (bs, 2H); 2.70 (t, J=12 Hz, 2H), 2.29 (d, J=6.8 Hz, 2H), 1.96-1.92 (m, 1H), 1.69-1.65 (bd, J=13.6 Hz, 2H), 1.46 (s, 9H), 1.21-1.11 (m, 2H).

Step-2: To a stirred solution of tert-butyl 4-(3-benzyloxy-2-oxo-propyl)piperidine-1-carboxylate (2.5 g, 7.20 mmol) in 1,4-Dioxane (20 mL) was added 4M HCl in Dioxane (7.20 mmol, 20 mL) and stirred the reaction mixture at RT for 3 h. After completion of reaction volatiles were evaporated under reduced pressure and co-distilled with toluene (15 ml×2) and triturated with diethyl ether (15 mL) to obtain 1-benzyloxy-3-(4-piperidyl)propan-2-one (2 g, 97.94% yield, 0% purity) as a HCl salt. Compound was confirmed by HNMR. ¹H NMR (400 MHz, DMSO-d₆): δ 8.94 (bs, 1H), 8.67 (bs, 1H), 7.40-7.31 (m, 5H), 5.10 (s, 2H), 3.22 (bd, J=12.4 Hz, 2H), 2.89 (q, J=12.0 Hz, 22.8 Hz, 2H), 2.37 (d, J=7.2 Hz, 2H), 2.03-1.95 (m, 1H), 1.79 (bd, 2H), 1.44-1.33 (m, 2H).

Step-3: To a stirred solution of 1-fluoro-4-nitro-benzene (645.08 mg, 4.57 mmol) in DMF (10 mL) was added Potassium carbonate (1.90 g, 13.72 mmol) and stirred at RT for 15 minutes. Benzyl 2-(4-piperidyl)acetate HCl salt (1.4 g, 4.57 mmol) was added to reaction mixture and continued for stirring at 65° C. for 12 h. After completion of reaction, the volatiles were evaporated under reduced pressure and crude compound was purified by column chromatography (Davisil silica, 0-8% Methanol in DCM) to afford benzyl 2-[1-(4-nitrophenyl)-4-piperidyl]acetate (800 mg, 48.82% yield, 98.88% purity). LC-MS (ES⁺): m/z 355.36 [M+H]⁺

Step-4 To a stirred solution of benzyl 2-[1-(4-nitrophenyl)-4-piperidyl]acetate (1.4 g, 3.95 mmol) in THF (42 mL):Water (14 mL) was added Zinc (2.07 g, 31.60 mmol) portion wise and continued stirring at room temp for 12 hr. Progress of reaction was monitored by TLC. After completion of reaction, the reaction mixture was filtered through the Celite bed and concentrated the filtrate under reduced pressure. Residue was purified by column chromatography (Davisil silica, 70% EtOAc in Pet ether) to obtain benzyl 2-[1-(4-aminophenyl)-4-piperidyl]acetate (1 g, 76.86% yield, 98.5% purity). LC-MS (ES⁻): m/z 323.27 [M−H]⁻.

Step-5: To a stirred solution of benzyl 2-[1-(4-aminophenyl)-4-piperidyl]acetate (1.2 g, 3.70 mmol) in DMF (12 mL) was added Sodium bicarbonate (621.47 mg, 7.40 mmol) and stirred at RT for 15 minutes. 3-bromopiperidine-2,6-dione (852.29 mg, 4.44 mmol) was added to the reaction mixture and continued stirring at 65° C. for 12 h. Reaction progress was monitored by TLC/LCMS. After completion of reaction, the volatiles were evaporated under vacuum and the crude compound was purified by column chromatography (Davisil silica, 0-8% Methanol in DCM) to obtain benzyl 2-[1-[4-[(2,6-dioxo-3-piperidyl)amino]phenyl]-4-piperidyl]acetate (800 mg, 49.16% yield, 99% purity). LC-MS (ES⁺): m/z 436.60 [M+H]⁺

Step-6: Stirred solution of benzyl 2-[1-[4-[(2,6-dioxo-3-piperidyl)amino]phenyl]-4-piperidyl]acetate (150 mg, 0.344 mmol) in THF (4 mL) was degassed for 10 minutes under nitrogen followed by addition of 10% Palladium on carbon (73.31 mg, 0.688 mmol.).). The reaction mixture was stirred at RT under hydrogen gas (under balloon pressure) for 16 hr. The progress of reaction was monitored by TLC. After completion of the reaction, reaction mixture was filtered through Celite bed. Filtrate was concentrated under reduced pressure to afford 2-(1-(4-((2,6-dioxopiperidin-3-yl)amino)phenyl)piperidin-4-yl)acetic acid (100 mg, 71.45% yield) Compound was used in next step without further purification.

Step-7: To a stirred solution of 4-[3-fluoro-5-methoxy-4-(piperazin-1-ylmethyl)phenyl]-6-methyl-1H-pyrazolo[3,4-c]pyridin-7-one (105.4 mg, 0.217 mmol) and 2-[1-[4-[(2,6-dioxo-3-piperidyl)amino]phenyl]-4-piperidyl]acetic acid (75 mg, 0.217 mmol) in DMF (3 mL) was added N,N-Diisopropylethylamine (0.23 ml, 1.30 mmol) and stirred the reaction mixture for 5 min at room temperature. PyBOP (146.90 mg, 282.29 umol) was added to the reaction mixture and stirring was continued for 16 h. Progress of the reaction was monitored by LCMS. After completion of the reaction, DMF was evaporated using genevac and the residue was purified by preparative HPLC to afford 3-[4-[4-[2-[4-[[2-fluoro-6-methoxy-4-(6-methyl-7-oxo-1H-pyrazolo[3,4-c]pyridin-4-yl)phenyl]methyl]piperazin-1-yl]-2-oxo-ethyl]-1-piperidyl]anilino]piperidine-2,6-dione (38 mg, 21.21% yield, 98.53% purity) as a pale yellow solid TFA salt. ¹H NMR (400 MHz, DMSO-d₆): δ 14.37 (s, 1H), 10.82 (s, 1H), 9.99 (s, 1H), 8.23 (bs, 1H), 7.70 (s, 1H), 7.39 (bs, 2H), 7.26 (m, 2H), 6.76 (d, J=8.8 Hz, 2H), 6.37 (s, 1H), 4.39 (m, 3H), 4.02 (s, 3H), 3.63 (s, 3H), 3.40 (m, 4H), 3.17 (m, 8H), 2.74 (m, 1H), 2.61 (m, 1H), 2.40 (bs, 2H), 2.10-2.07 (m, 2H), 1.99-1.90 (m, 3H), 1.61 (m, 2H); LC-MS (ES⁺): m/z 699.34 [M+H]⁺

Compound 50 was prepared following the synthesis of Compound 49.

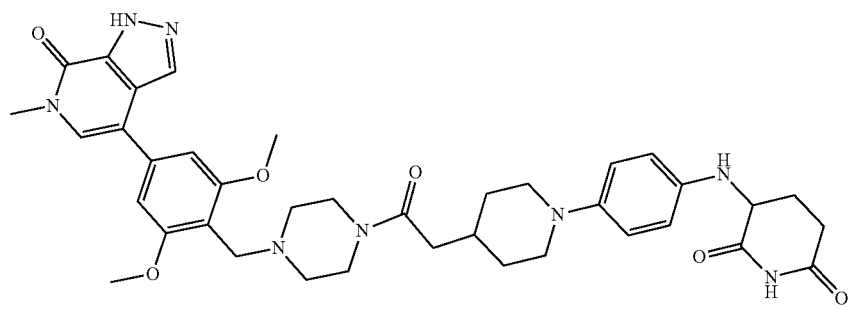 [SMILES: COc1cc(-c2cn(C)c(=O)c3[nH]ncc23)cc(OC)c1CN1CCN(C(=O)CC2CCN(c3ccc(NC4CCC(=O)NC4=O)cc3)CC2)CC1]

¹H NMR (400 MHz, DMSO-d₆) δ 14.38 (bs, 1H), 10.83 (s, 2H), 9.59 (bs, 1H), 8.23 (s, 1H), 7.65 (s, 1H), 7.46 (bd, J=7.6 Hz, 2H), 6.98 (s, 2H), 6.78 (d, J=8.8 Hz, 2H), 6.34 (bs, 1H), 4.44-4.29 (m, 4H), 3.96 (s, 7H), 3.63-3.41 (m, 10H), 3.19-3.02 (m, 3H), 2.75-2.67 (m, 1H), 2.61-2.55 (m, 1H), 2.40-2.32 (bm, 2H), 2.11-2.19 (m, 5H), 1.62 (bs, 2H). LC-MS (ES⁺): m/z 711.39 [M+H]⁺.

Compound 51 was prepared following the synthesis of Compound 49.

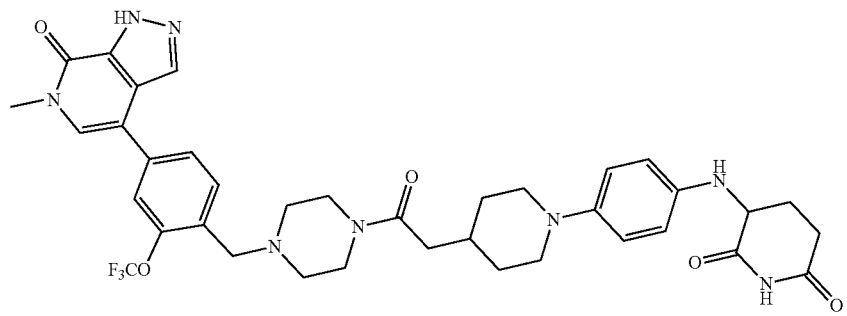 [SMILES: Cn1cc(-c2ccc(CN3CCN(C(=O)CC4CCN(c5ccc(NC6CCC(=O)NC6=O)cc5)CC4)CC3)c(OC(F)(F)F)c2)c2cn[nH]c2c1=O]
¹H NMR (400 MHz, DMSO-d₆) δ 14.39 (s, 1H), 10.83 (s, 1H), 8.11 (s, 1H), 7.81 (s, 2H), 7.67 (s, 2H), 7.39 (s, 2H), 6.76 (d, J=8.9 Hz, 2H), 6.37 (bs, 1H), 4.39-3.90 (m, 7H), 3.62 (s, 3H), 3.47-2.57 (m, 10H), 2.39 (bs, 2H), 2.10-1.90 (m, 5H), 1.61-1.50 (m, 2H). LC-MS (ES⁺): m/z 735.48 [M+H]⁺
Synthesis of Compound 52
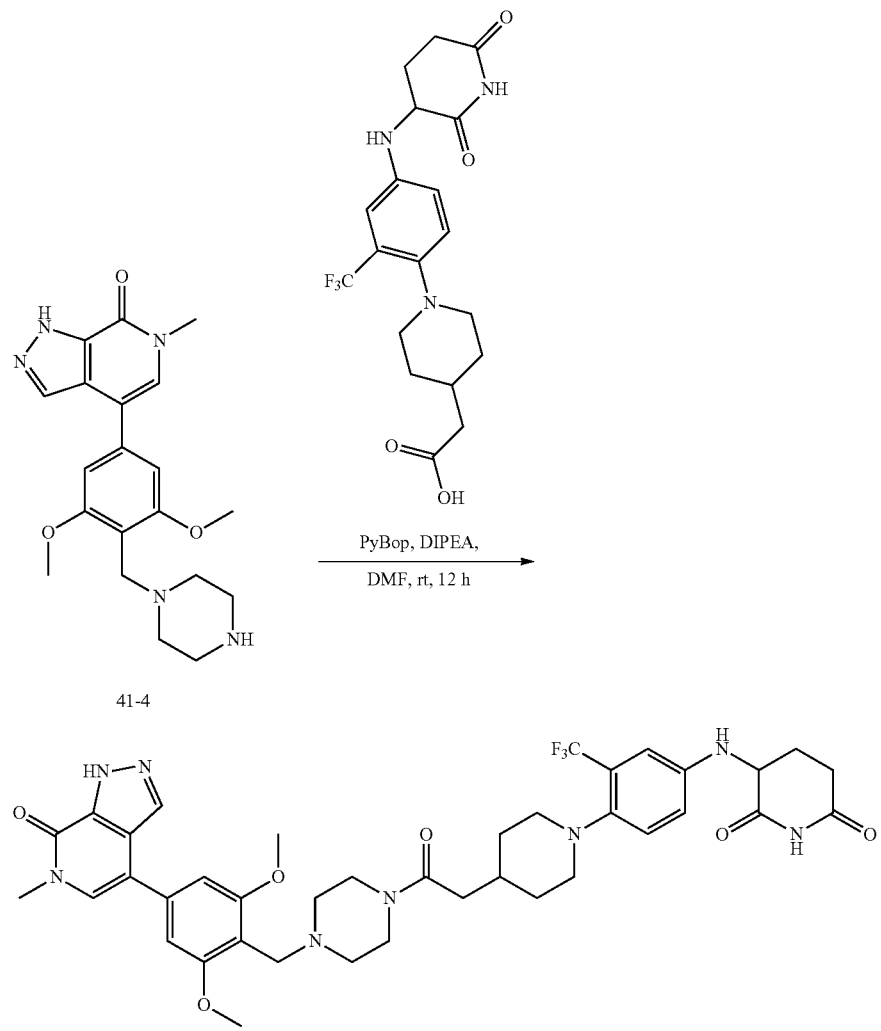
Coompound 52

To a stirred solution of 4-[3,5-dimethoxy-4-(piperazin-1-ylmethyl)phenyl]-6-methyl-1H-pyrazolo[3,4-c]pyridin-7-one (0.101 g, 0.26 mmol) in DMF was added DIPEA (0.187 g, 1.45 mmol) at 0° C. and reaction stirred for 15 min. After 15 min 2-[1-[4-[(2,6-dioxo-3-piperidyl)amino]-2-(trifluoromethyl)phenyl]-4-piperidyl]acetic acid (0.100 g, 0.24 mmol) followed by PyBOP (163 mg, 0.52 mmol) were added at same temperature. The reaction mixture was slowly warmed to rt and stirred for 12 h, while monitoring the by TLC and LCMS. The reaction mixture was concentrated under Genvaccum to obtain the crude product. The crude product was purified by Prep HPLC to afford the product 3-[4-[4-[2-[4-[[2,6-dimethoxy-4-(6-methyl-7-oxo-1H-pyrazolo[3,4-c]pyridin-4-yl)phenyl]methyl]piperazin-1-yl]-2-oxo-ethyl]-1-piperidyl]-3-(trifluoromethyl)anilino]piperidine-2,6-dione TFA salt (0.100 g, 0.11 mmol, 42.77% yield, 99.59% purity) as pale brown solid. $^1$H NMR (400 MHz, DMSO-$d_6$) δ 14.34 (s, 1H), 10.78 (s, 1H), 9.40 (s, 1H), 8.23 (s, 1H), 7.65 (s, 1H), 7.30 (d, J=8.6 Hz, 2H), 6.98 (s, 2H), 6.88-6.85 (m, 2H), 6.11 (s, 1H), 4.41-4.29 (m, J=7.0 Hz, 5H), 3.97 (s, 6H), 3.63 (s, 3H), 3.40-3.38 (m, 3H), 3.16 (d, J=8.1 Hz, 1H), 3.03 (d, J=9.0 Hz, 2H), 2.77-2.58 (m, 6H), 2.35 (t, J=5.0 Hz, 2H), 2.08-2.05 (m, 1H), 1.92-1.72 (m, 4H), 1.40-1.29 (m, 2H). LC-MS (ES$^+$): m/z 779.50 [M+H]$^+$.

Compound 53 was prepared following the synthesis of Compound 52.

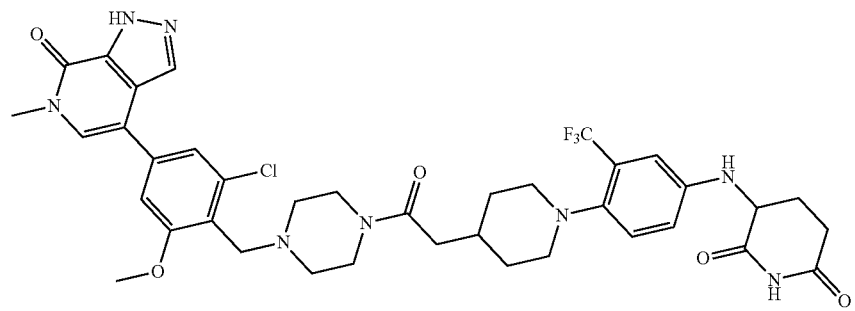 [SMILES: COc1cc(-c2cn(C)c(=O)c3[nH]ncc23)cc(Cl)c1CN1CCN(C(=O)CC2CCN(c3ccc(NC4CCC(=O)NC4=O)cc3C(F)(F)F)CC2)CC1]

$^1$H NMR (400 MHz, DMSO-$d_6$) δ 14.40 (s, 1H), 10.79 (s, 1H), 9.52 (s, 1H), 7.72 (s, 1H), 7.47 (d, J=1.2 Hz, 1H), 7.35 (s, 1H), 7.30 (d, J=8.6 Hz, 1H), 6.91-6.87 (m, 2H), 6.14 (bs, 1H), 4.51-4.02 (m, 5H), 3.89 (s, 3H), 3.61 (s, 3H), 3.44-3.15 (m, 6H), 2.80-2.56 (m, 6H), 2.36-2.32 (m, 2H), 2.08-2.05 (m, 1H), 1.92-1.71 (m, 4H), 1.31-1.28 (m, 2H). LC-MS (ES$^+$): m/z 783.57 [M+H]$^+$

Compound 54 was prepared following the synthesis of Compound 52.

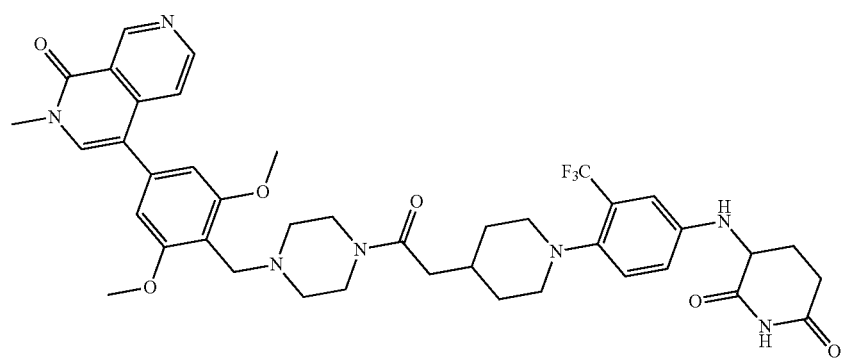 [SMILES: COc1cc(-c2cn(C)c(=O)c3cnccc23)cc(OC)c1CN1CCN(C(=O)CC2CCN(c3ccc(NC4CCC(=O)NC4=O)cc3C(F)(F)F)CC2)CC1]

¹H NMR (400 MHz, DMSO-d₆) δ 10.79 (s, 1H), 9.49 (s, 1H), 8.75 (d, J=5.8 Hz, 1H), 7.93 (s, 1H), 7.62 (d, J=5.7 Hz, 1H), 7.30 (d, J=8.6 Hz, 1H), 6.90-6.86 (m, 4H), 4.43-4.32 (m, 4H), 4.14-4.09 (m, 1H), 3.91 (s, 6H), 3.62 (s, 3H), 3.40 (bs, 2H), 3.18-3.03 (m, 5H), 2.79-2.66 (m, 6H), 2.35-2.33 (m, 2H), 2.12-1.27 (m, 7H). m/z 790.25 [M+H]⁺.

Two enantiomers of Compound 54 were separated by chiral separation by SFC.

During SFC separation fractions were collected in TFA buffer to avoid Glutarimide ring opening; as SFC Separation method involved use of basic additive. The obtained fraction of were submitted again for prepHPLC purification to remove the salt.

Preparative SFC Conditions Column/dimensions:
Chiralpak-AD-H (30*250) mm,
5u % CO2:50% % Co solvent: 50%(0.2% 7M Methanolic ammonia in ACN:MEOH)
Total Flow: 120.0 g/min
Back Pressure: 100 bar Temperature: 30 0C UV: 220 nm
Solubility: MEOH
Prep-HPLC Conditions Column/dimensions:
Mobile Phase (A): 0.05% TFA in H2O Mobile Phase (B): 100% ACETONITRILE
Flow Rate:18 ml/min
Column: X-SELECT C18 5 μm (19*250)
Gradient Time % B: 0/10, 5/10, 10/45, 13/45

Compound 55

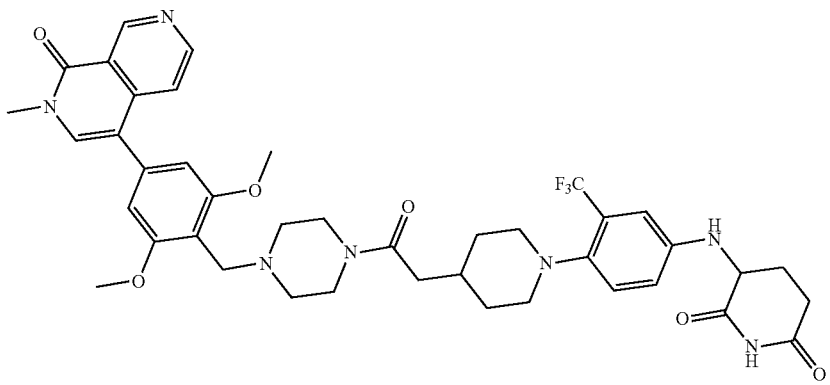 [SMILES: COc1cc(-c2cn(C)c(=O)c3cnccc23)cc(OC)c1CN1CCN(C(=O)CC2CCN(c3ccc(NC4CCC(=O)NC4=O)cc3C(F)(F)F)CC2)CC1]

¹H NMR (400 MHz, DMSO-d₆) δ 10.78 (s, 1H), 9.48 (s, 1H), 8.75 (d, J=5.7 Hz, 1H), 7.91 (s, 1H), 7.59 (d, J=5.7 Hz, 1H), 7.30 (d, J=8.7 Hz, 1H), 6.89-6.86 (m, 4H), 6.14 (bs, 1H), 4.33-4.30 (m, 5H), 3.91 (s, 6H), 3.61 (s, 3H), 3.40 (bs, 3H), 3.33-3.03 (m, 3H), 2.78-2.61 (m, 6H), 2.34-2.33 (m, 2H), 2.08-2.05 (m, 1H), 1.92-1.70 (m, 4H), 1.31-1.28 (m, 2H). LC-MS (ES⁺): m/z 790.49 [M+H]⁺, [α]²⁵_D: +19.44.

Compound 56

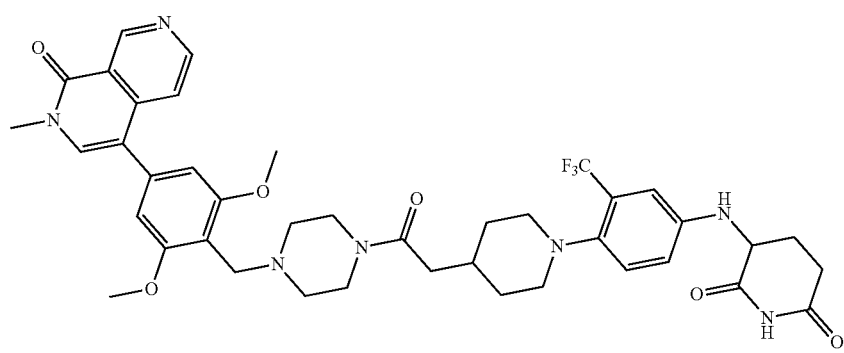 [SMILES: COc1cc(-c2cn(C)c(=O)c3cnccc23)cc(OC)c1CN1CCN(C(=O)CC2CCN(c3ccc(NC4CCC(=O)NC4=O)cc3C(F)(F)F)CC2)CC1]

1H NMR (400 MHz, DMSO-d$_6$) δ 10.78 (s, 1H), 9.48 (s, 1H), 8.75 (d, J=5.7 Hz, 1H), 7.91 (s, 1H), 7.59 (d, J=5.6 Hz, 1H), 7.30 (d, J=8.6 Hz, 1H), 6.91-6.86 (m, 4H), 6.14 (bs, 1H), 4.33-4.30 (m, 5H), 3.91 (s, 6H), 3.61 (s, 3H), 3.40 (bs, 3H), 3.33-3.03 (m, 3H), 2.78-2.61 (m, 6H), 2.34-2.33 (m, 2H), 2.08-2.05 (m, 1H), 1.92-1.70 (m, 4H), 1.31-1.28 (m, 2H). LC-MS (ES$^+$): m/z 790.52 [M+H]$^+$, [α]$^{25}_D$: −32.26.

Compound 57 was prepared following the synthesis of Compound 52.

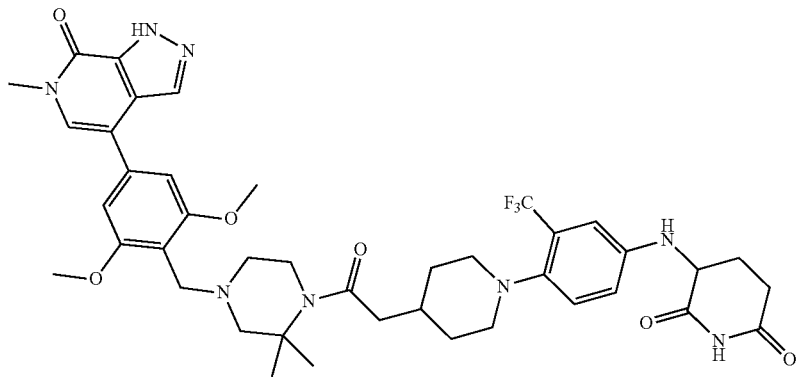 [SMILES: COc1cc(-c2cn(C)c(=O)c3[nH]ncc23)cc(OC)c1CN1CCN(C(=O)CC2CCN(c3ccc(NC4CCC(=O)NC4=O)cc3C(F)(F)F)CC2)C(C)(C)C1]

$^1$H NMR (400 MHz, DMSO-d$_6$) δ 14.31 (s, 1H), 10.78 (s, 1H), 9.20 (s, 1H), 8.24 (s, 1H), 7.66 (s, 1H), 7.28 (d, J=9.6 Hz, 1H), 7.09 (m, 1H), 6.84 (s, 1H), 6.88 (d, J=5.2 Hz, 2H), 4.38-4.32 (m, 3H), 3.97 (s, 6H), 3.63 (m, 3H), 3.30-3.07 (m, 5H), 2.78-2.69 (m, 7H), 2.32-2.30 (m, 2H), 2.07 (m, 1H), 1.90 (m, 2H), 1.70-1.68 (m, 2H), 1.54 (m, 3H), 1.53 (m, 3H), 1.23 (m, 2H). LC-MS (ES$^+$): m/z 807.55 [M+H]$^+$.

Compound 58 was prepared following the synthesis of Compound 52.

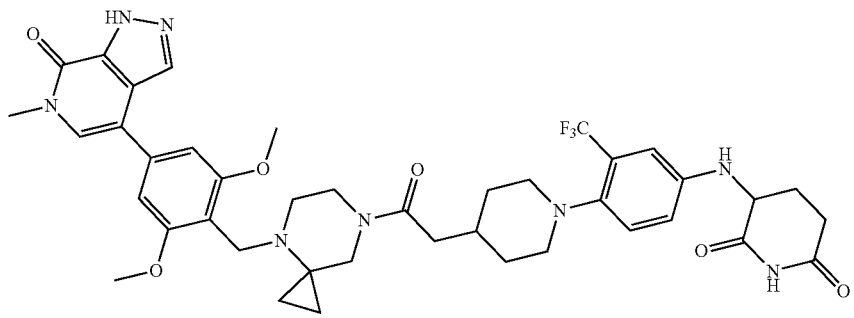 [SMILES: COc1cc(-c2cn(C)c(=O)c3[nH]ncc23)cc(OC)c1CN1CCN(C(=O)CC2CCN(c3ccc(NC4CCC(=O)NC4=O)cc3C(F)(F)F)CC2)CC12CC2]

$^1$H NMR (400 MHz, CDCl$_3$): δ 14.30 (bs, 1H); 10.79 (s, 1H); 8.84 (bs, 1H); 8.22 (s, 1H); 7.65 (s, 1H); 7.32 (d, J=8.4 Hz, 1H); 6.87-6.98 (m, 3H); 6.15 (bs, 1H); 4.86-5.00 (m, 1H); 4.15-4.70 (m, 4H); 3.90-4.10 (m, 1H); 3.97 and 3.98 (s, total 6H); 3.64 (s, 3H); 3.60-3.80 (m, 1H); 3.10-3.24 (m, 2H); 2.60-2.90 (m, 6H); 2.3-2.40 (m, 2H); 2.04-2.14 (m, 1H); 1.68-1.98 (m, 4H); 0.7-1.40 (m, 6H). LC-MS (ES$^+$): m/z 805.74 [M+H]$^+$ Compound 59 was prepared following the synthesis of Compound 52.

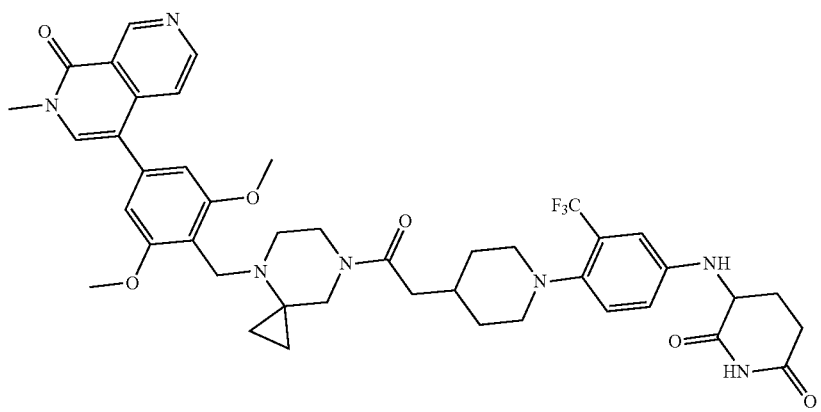 [SMILES: COc1cc(-c2cn(C)c(=O)c3cnccc23)cc(OC)c1CN1CCN(C(=O)CC2CCN(c3ccc(NC4CCC(=O)NC4=O)cc3C(F)(F)F)CC2)CC12CC2]
¹H NMR (400 MHz, DMSO) δ 10.78 (s, 1H), 9.44 (s, 1H), 8.71 (d, J=5.3 Hz, 1H), 7.85 (s, 1H), 7.56 (d, J=5.6 Hz, 1H), 7.31 (d, J=8.6 Hz, 1H), 6.90-6.87 (m, 2H), 6.70 (d, J=2.4 Hz, 2H), 6.15 (d, J=7.8 Hz, 1H), 4.37-4.24 (m, 1H), 3.90 (s, 2H), 3.80 (d, J=2.0 Hz, 6H), 3.59 (bs, 2H), 3.43 (s, 3H), 3.32 (s, 2H), 2.77-2.56 (m, 8H), 2.33-2.22 (m, 2H), 2.07-2.06 (m, 1H), 1.91-1.67 (m, 4H), 1.29-1.24 (m, 2H), 0.61-0.48 (m, 4H). LC-MS (ES⁺): m/z 816.50 [M+H]⁺
Compound 60 was prepared following the synthesis of Compound 52.
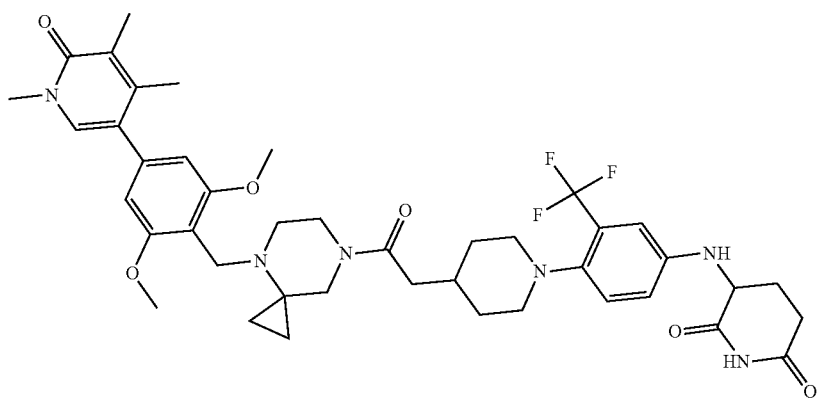 [SMILES: COc1cc(-c2cn(C)c(=O)c(C)c2C)cc(OC)c1CN1CCN(C(=O)CC2CCN(c3ccc(NC4CCC(=O)NC4=O)cc3C(F)(F)F)CC2)CC12CC2]
¹H NMR (400 MHz, DMSO-d₆): δ 0.44-0.70 (m, 4H); 1.20-1.38 (m, 2H); 1.64-1.74 (m, 2H); 1.76-1.94 (m, 2H); 2.05 (s, 3H); 2.07 (s, 3H); 2.07-2.08 (m, 1H); 2.19-2.36 (m, 2H); 2.52-2.75 (m, 8H); 3.41 (s, 2H); 3.45 (s, 3H); 3.58-3.66 (m, 2H); 3.76 (s, 3H); 3.77 (s, 3H); 3.88 (s, 2H); 3.34-3.42 (m, 1H); 6.15 (d, J=8.0 Hz, 1H); 6.50 (s, 1H); 6.51 (s, 1H); 6.84-6.91 (m, 2H); 7.31 (d, J=8.4 Hz, 1H); 7.49 (s, 1H); 10.78 (s, 1H), LC-MS (ES⁺): m/z 793.52 [M+H]⁺.
Compound 61 was prepared following the synthesis of Compound 52.

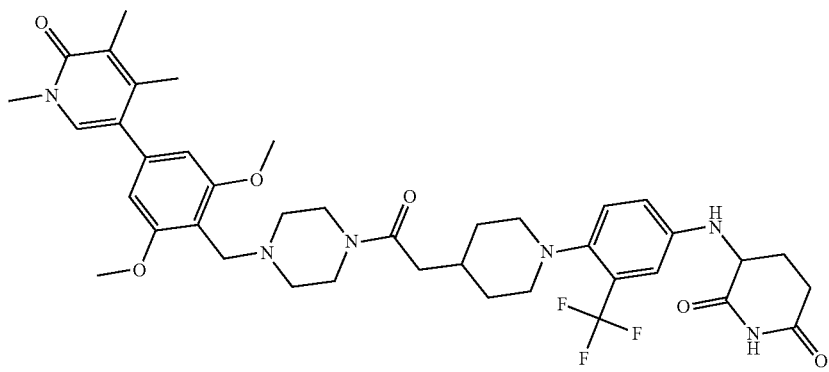 [SMILES: COc1cc(-c2cn(C)c(=O)c(C)c2C)cc(OC)c1CN1CCN(C(=O)CC2CCN(c3ccc(NC4CCC(=O)NC4=O)cc3C(F)(F)F)CC2)CC1]
¹H NMR (400 MHz, DMSO-d₆) δ 10.78 (s, 1H), 9.36 (s, 1H), 7.52 (s, 1H), 7.30 (d, J=8.7 Hz, 1H), 6.90-6.86 (m, 2H), 6.69 (s, 2H), 6.09 (s, 1H), 4.41-4.35 (m, 2H), 4.28 (d, J=2.2 Hz, 2H), 4.12 (d, J=14.7 Hz, 1H), 3.88 (s, 6H), 3.47 (s, 3H), 3.41-3.35 (m, 3H), 3.08 (t, J=29.9 Hz, 1H), 3.02 (d, J=8.9 Hz, 2H), 2.79-2.59 (m, 6H), 2.34 (t, J=6.1 Hz, 2H), 2.07 (d, J=6.4 Hz, 7H), 1.94-1.90 (m, 1H), 1.81-1.27 (m, 4H). LC-MS (ES⁺): m/z 767.24 [M+H]⁺
Compound 62 was prepared following the synthesis of Compound 52.
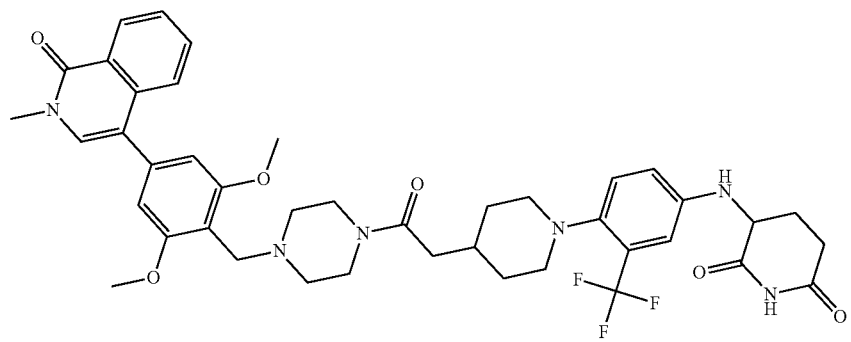 [SMILES: COc1cc(-c2cn(C)c(=O)c3ccccc23)cc(OC)c1CN1CCN(C(=O)CC2CCN(c3ccc(NC4CCC(=O)NC4=O)cc3C(F)(F)F)CC2)CC1]
¹H NMR (400 MHz, DMSO-d₆) δ 10.78 (s, 1H), 9.45 (bs, 1H), 8.36 (d, J=8.0 Hz, 1H), 7.74 (t, J=7.2 Hz, 1H), 7.66 (d, J=8.0 Hz, 1H), 7.60 (t, J=6.0 Hz, 2H), 7.31 (d, J=8.0 Hz, 1H), 6.90 (m, 4H), 6.16 (bs, 1H), 4.45-4.32 (m, 4H), 4.15 (bd, 1H), 3.90 (s, 6H), 3.59 (s, 3H), 3.17-3.03 (m, 6H), 2.77-2.59 (m, 6H), 2.36-2.33 (m, 2H), 2.09-2.05 (m, 1H), 1.94-1.70 (m, 4H), 1.31-1.22 (m, 2H). LC-MS (ES⁺): m/z 789.59 [M+H]⁺.
Synthesis of Compound 63
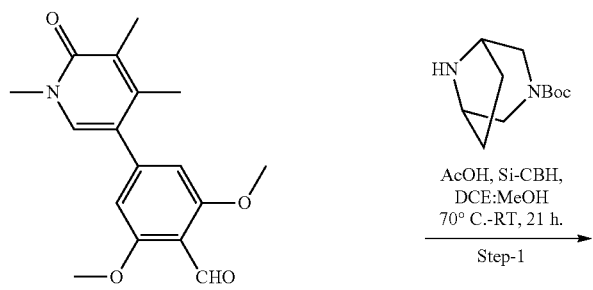
63-1
AcOH, Si-CBH,
DCE:MeOH
70° C.-RT, 21 h.
───────────→
Step-1

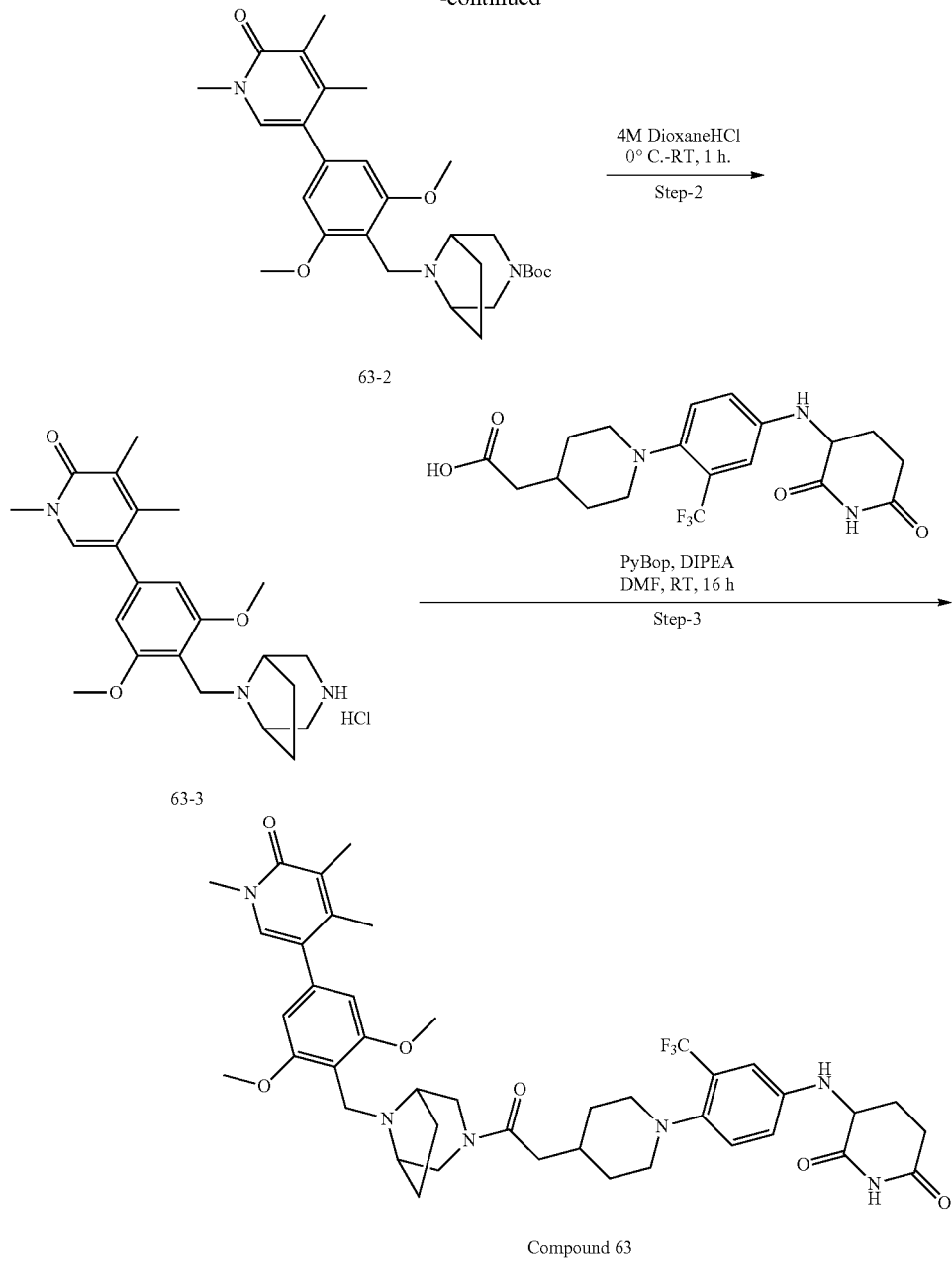

Compound 63

Step-1: To a stirred solution of tert-butyl 3,8-diazabicyclo[3.2.1]octane-3-carboxylate (0.352 g, 1.66 mmol) in DCE:MeOH (10:10 ml) were added 4 Å molecular sieves (0.5 g) and acetic acid (0.1 g, 1.66 mmol). The resulting solution was stirred for 10 min, then 2,6-dimethoxy-4-(1,4,5-trimethyl-6-oxo-3-pyridyl)benzaldehyde (63-1, 0.500 g, 1.66 mmol) and heated the reaction mixture at 70° C. for 3 h then cooled it at RT and added Silia Bond Cyanoborohydride (0.481 g, 8.30 mmol). The stirring was continued at RT for 16 h, while monitoring the reaction by LCMS and TLC. After 16 h, the reaction mass was filtered, concentrated and purified by reverse phase column chromatography (using C-18 column with 0.1% FA in Water:MeCN) to afford tert-butyl 8-[[2,6-dimethoxy-4-(1,4,5-trimethyl-6-oxo-3-pyridyl)phenyl]methyl]-3, 8-diazabicyclo[3.2.1]octane-3-carboxylate 3 (0.6 g, 1.03 mmol, 62.35% yield, 85.8% purity) as a pale yellow semi-solid. LC-MS (ES+): m/z 398.36. [M+H]+

Step-2: The solution of tert-butyl 8-[[2,6-dimethoxy-4-(1, 4,5-trimethyl-6-oxo-3-pyridyl)phenyl]methyl]-3,8-diazabicyclo[3.2.1]octane-3-carboxylate 63-2 (0.450 g, 904.30 mmol) in 4M HCl in Dioxane (3 mL) stir for 1 h at RT while monitoring by TLC and LCMS. After 1 h the reaction mixture was concentrated to dryness. The crude compound was triturated with Diethyl ether (2×20 ml) to afford 5-[4-(3,8-diazabicyclo[3.2.1]octan-8-ylmethyl)-3,5-dimethoxy-phenyl]-1,3,4-trimethyl-pyridin-2-one.HCl salt 63-3 (0.400 g, 0.832 mmol, 91.95% yield, 90.21% purity) as Brown solid. LC-MS (ES+): m/z 398.34 [M+H]+.

Step-3: To a stirred solution of 5-[4-(3,8-diazabicyclo[3.2.1]octan-8-ylmethyl)-3,5-dimethoxy-phenyl]-1,3,4- trimethyl-pyridin-2-one.HCl salt (0.1 g, 0.230 mmol) in dry DMF (3 mL) was added DIPEA (0.089 g, 0.230 mmol) at 0° C. followed by PyBOP (0.144 g, 0.276 mmol), and 2-[1-[4-[(2,6-dioxo-3-piperidyl)amino]-2-(trifluoromethyl)phenyl]-4-piperidyl]acetic acid (0.095 g, 0.230 mmol) were added and the reaction mixture was stirred at RT for 16 h while the reaction monitoring by LCMS. After 16 h most of the DMF was evaporated using genvac and the crude compound was purified by prep-HPLC to afford 3-[4-[4-[2-[8-[[2,6-dimethoxy-4-(1,4,5-trimethyl-6-oxo-3-pyridyl)phenyl]methyl]-3,8-diazabicyclo[3.2.1]octan-3-yl]-2-oxo-ethyl]-1-piperidyl]-3-(trifluoromethyl)anilino]piperidine-2,6-dione, TFA salt Compound 63 (0.071 g, 0.078 mmol, 33.97% yield, 99.6% purity) as a brown solid. $^1$H NMR (400 MHz, DMSO-$d_6$) δ 10.78 (s, 1H), 9.34 (s, 1H), 7.53 (s, 1H), 7.30 (d, J=8.6 Hz, 1H), 6.90-6.87 (m, 1H), 6.71 (s, 2H), 4.39-4.35 (m, 1H), 4.30-4.27 (m, 1H), 4.13 (bs, 2H), 4.05 (bs, 2H), 3.98-3.95 (m, 1H), 3.90 (s, 6H), 3.61-3.56 (m, 1H), 3.48 (s, 3H), 3.14-3.10 (m, 1H), 2.78-2.64 (m, 6H), 2.33-2.27 (m, 4H), 2.08 (d, J=8.9 Hz, 7H), 1.94-1.69 (m, 6H), 1.31-1.29 (m, 2H). LC-MS (ES$^+$): m/z 793.44 [M+H]$^+$.

Compound 64 was prepared following the synthesis of Compound 63

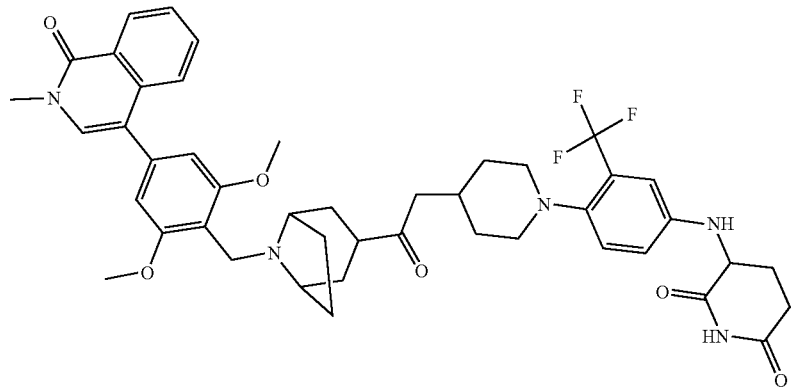 [SMILES: COc1cc(-c2cn(C)c(=O)c3ccccc23)cc(OC)c1CN1C2CCC1CC(C(=O)CC1CCN(c3ccc(NC4CCC(=O)NC4=O)cc3C(F)(F)F)CC1)C2]

$^1$H NMR (400 MHz, DMSO-$d_6$) δ 10.79 (s, 1H), 9.37 (s, 1H), 8.37 (dd, J=8.1, 1.4 Hz, 1H), 7.75 (ddd, J=8.4, 6.9, 1.5 Hz, 1H), 7.67 (d, J=7.9 Hz, 1H), 7.60 (s, 1H), 7.64-7.55 (m, 1H), 7.31 (d, J=8.5 Hz, 1H), 6.94-6.84 (m, 4H), 4.42-4.27 (m, 2H), 4.20 (t, J=4.5 Hz, 2H), 4.10 (s, 2H), 3.99 (d, J=12.8 Hz, 1H), 3.93 (s, 6H), 3.63 (d, J=13.0 Hz, 1H), 3.61 (s, 3H), 2.90 (s, 1H), 2.77 (dd, J=13.2, 7.1 Hz, 3H), 2.74 (s, 1H), 2.73-2.67 (m, 1H), 2.63 (d, J=14.9 Hz, 1H), 2.59-2.52 (m, 1H), 2.37-2.26 (m, 2H), 2.07 (t, J=6.7 Hz, 1H), 1.99-1.86 (m, 1H), 1.72 (d, J=12.1 Hz, 4H), 1.35-1.21 (m, 4H); LC-MS (ES$^+$): m/z 815 [M+H]$^+$ Compound 65 was prepared following the synthesis of Compound 63

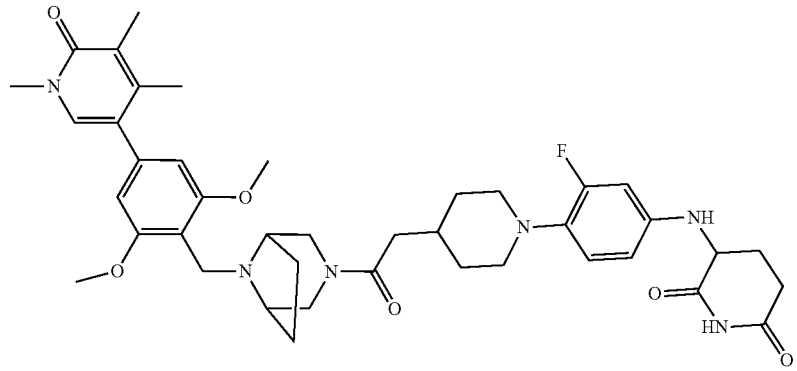 [SMILES: COc1cc(-c2cn(C)c(=O)c(C)c2C)cc(OC)c1CN1C2CCC1CN(C(=O)CC1CCN(c3ccc(NC4CCC(=O)NC4=O)cc3F)CC1)C2]

¹H NMR (400 MHz, DMSO-d₆) δ 10.80 (s, 1H), 9.39 (s, 1H), 7.53 (s, 1H), 7.30 (bs, 1H), 6.70 (s, 2H), 6.59-6.48 (m, 2H), 4.30-3.95 (m, 7H), 3.89 (s, 8H), 3.62-3.59 (m, 1H), 3.48 (s, 3H), 3.15-3.11 (m, 3H), 2.73-2.55 (m, 2H), 2.49-2.40 (m, 1H), 2.33-2.30 (m, 3H), 2.08 (d, J=8.6 Hz, 7H), 1.94-1.71 (m, 6H), 1.49 (bs, 2H). LC-MS (ES⁺): m/z 743.58 [M+H]⁺

Compound 66 was prepared following the synthesis of Compound 63

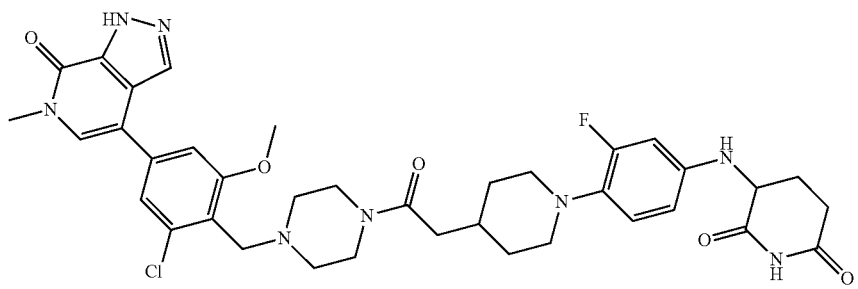 [SMILES: COc1cc(-c2cn(C)c(=O)c3[nH]ncc23)cc(Cl)c1CN1CCN(C(=O)CC2CCN(c3ccc(NC4CCC(=O)NC4=O)cc3F)CC2)CC1]

¹H NMR (400 MHz, DMSO-d₆) δ 14.29 (s, 1H), 10.80 (s, 1H), 9.59 (s, 1H), 8.21 (s, 1H), 7.72 (s, 1H), 7.47 (s, 1H), 7.35 (s, 1H), 6.58-6.47 (m, 2H), 4.46 (bs, 3H), 4.32-4.12 (m, 4H), 4.03 (s, 3H), 3.62 (s, 3H), 3.39-3.01 (m, 8H), 2.78-2.67 (m, 1H), 2.60-2.56 (m, 1H), 2.37-2.33 (m, 3H), 2.08-2.06 (m, 1H), 1.91-185 (m, 4H), 1.51-147 (m, 2H). LC-MS (ES⁺): m/z 733.54 [M+H]⁺

Compound 67 was prepared following the synthesis of Compound 63

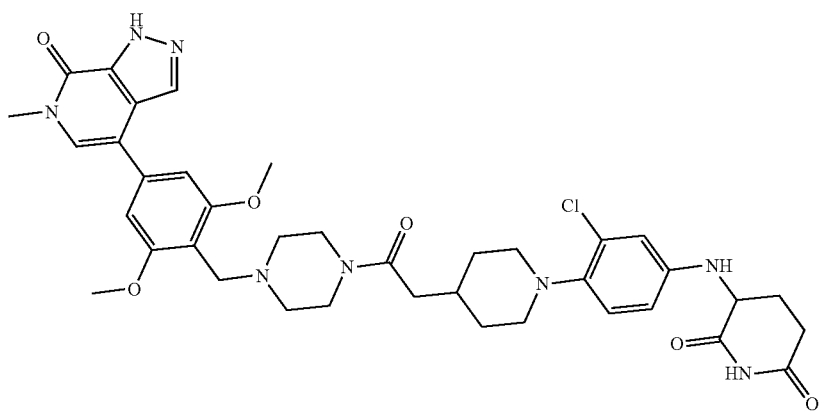 [SMILES: COc1cc(-c2cn(C)c(=O)c3[nH]ncc23)cc(OC)c1CN1CCN(C(=O)CC2CCN(c3ccc(NC4CCC(=O)NC4=O)cc3Cl)CC2)CC1]

¹H NMR (400 MHz, DMSO-d₆): δ 1.34-1.42 (m, 2H); 1.70-1.90 (m, 4H); 2.05-2.10 (m, 1H); 2.30-2.40 (m, 2H); 2.55-2.60 (m, 1H); 2.66-2.74 (m, 1H); 2.98-3.30 (m, 10H); 3.63 (s, 3H); 3.97 (s, 6H); 4.08-4.14 (m, 1H); 4.26-4.32 (m, 3H); 4.40-4.45 (m, 1H); 6.59 (dd, J1=2.4 Hz, J2=8.8 Hz, 1H); 6.74 (d, J=2.0 Hz, 1H); 6.94-7.09 (m, 1H); 6.98 (s, 2H); 7.65 (s, 1H); 8.23 (s, 1H); 9.42 (bs, 1H); 10.77 (s, 1H); 14.60 (bs, 1H). LC-MS (ES⁺): m/z; 745.56 [M+H]⁺

Synthesis of Compound 68
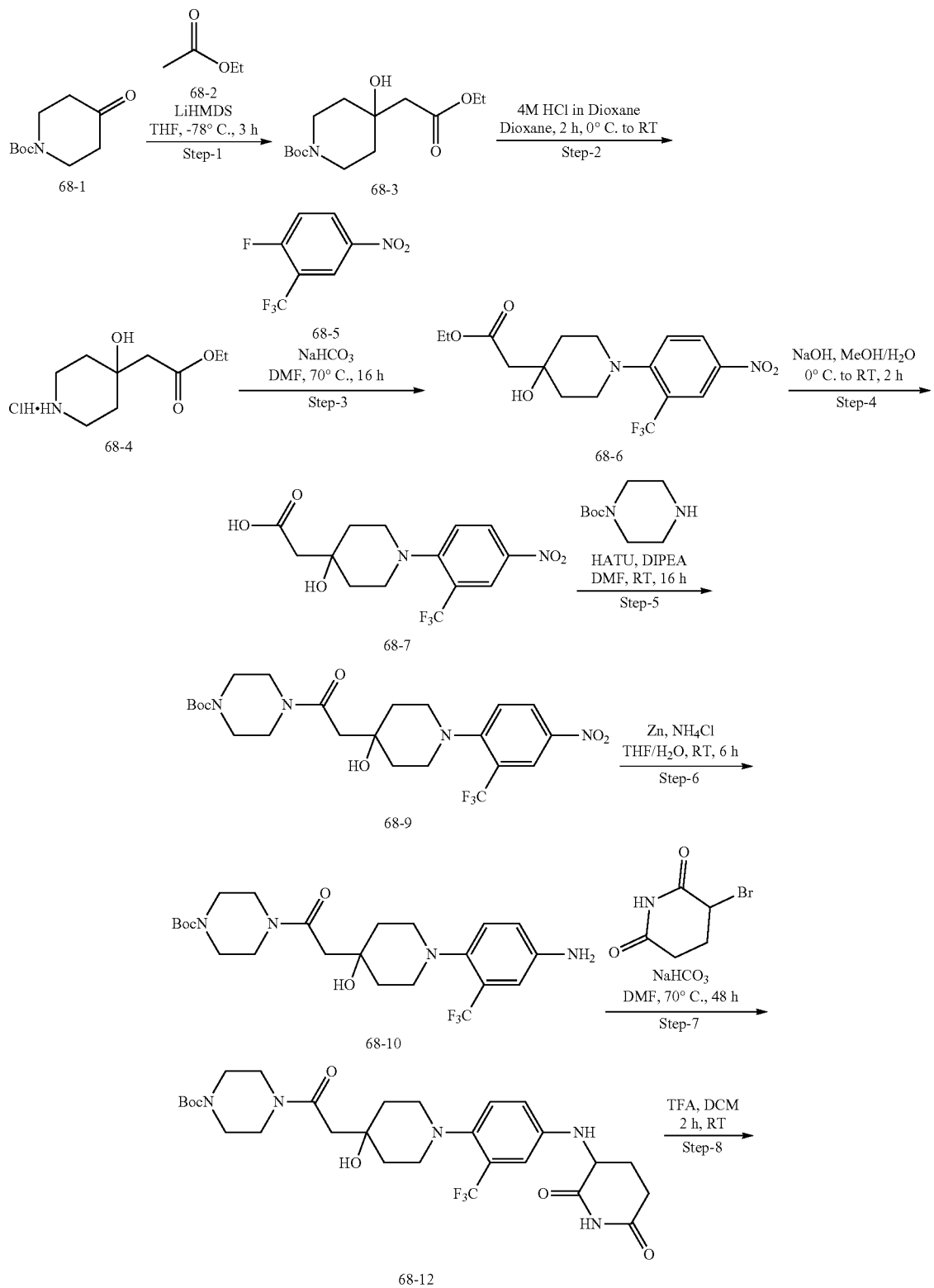

-continued

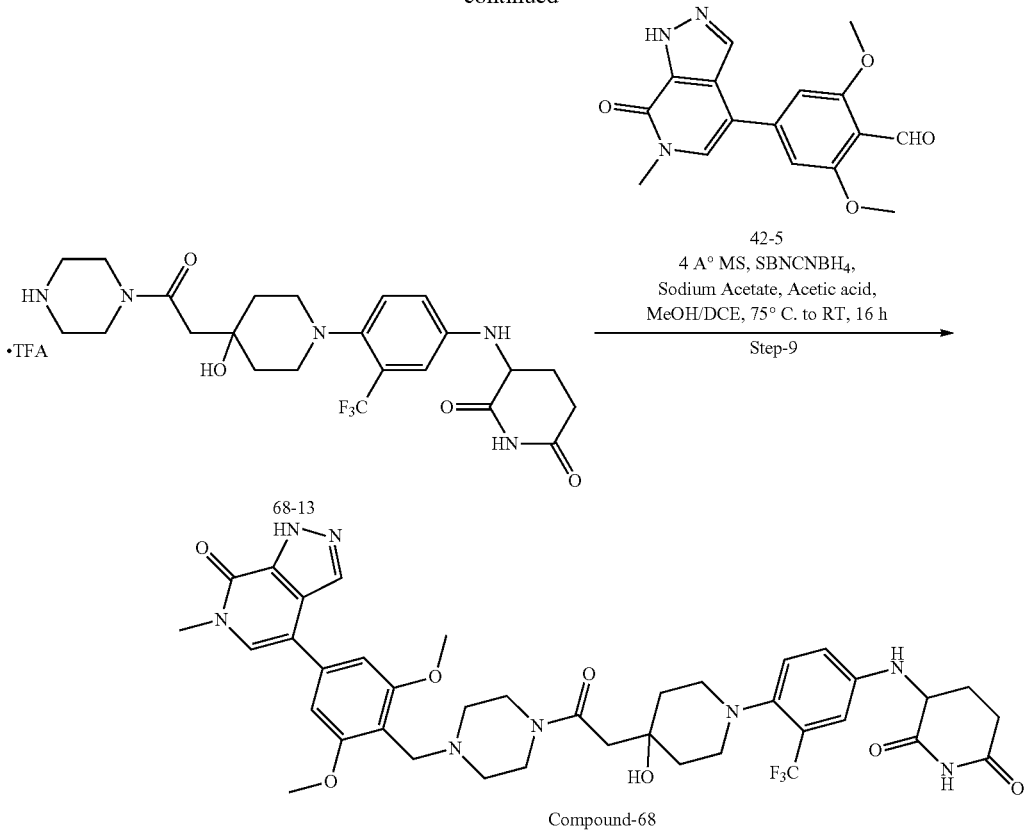

Step-1: To a stirred solution of Lithium bis(trimethylsilyl) amide (60 mL, 60.23 mmol) in THF (10 mL) under inert atmosphere was added ethyl acetate (2.65 g, 30.11 mmol, 2.94 mL) drop wise at −78° C. The reaction mixture was stirred for 30 minutes. Tert-butyl 4-oxopiperidine-1-carboxylate (6 g, 30.11 mmol) in THF (20 mL) was added to the reaction mixture. The reaction mixture was stirred at −78° C. for 2 hr. The reaction progress was monitored by TLC. After completion of reaction, the reaction mixture was diluted with water (20 mL) and extracted with $CH_2Cl_2$ (2×20 mL). The combined organic layer was dried over $Na_2SO_4$ and concentrated under reduced pressure to obtain tert-butyl 4-(2-ethoxy-2-oxo-ethyl)-4-hydroxy-piperidine-1-carboxylate (4.5 g, 46.8% yield). Compound TLC was matched with authentic compound from previous batch on page NBK0308-149. $^1$H NMR (400 MHz, $CDCl_3$) δ 4.21 (q, J=7.2 Hz, 14.8 Hz, 2H), 3.82 (bs, 2H), 3.58 (s, 1H), 3.20 (bt, 2H), 2.46 (s, 2H), 1.71 (m, 2H), 1.52 (m, 2H), 1.45 (s, 9H), 1.29 (t, J=7.2 Hz, 3H).

Step-2: To a stirred solution of tert-butyl 4-(2-ethoxy-2-oxo-ethyl)-4-hydroxy-piperidine-1-carboxylate (4.5 g, 15.66 mmol) in 1,4-Dioxane (20 mL) was added 4M HCl in Dioxane (15.66 mmol, 25 mL) and stirred the reaction mixture at RT for 3 h. After completion of reaction, volatiles were evaporated under reduced pressure and co-distilled with toluene (30 ml×2) and triturated with diethyl ether (30 mL) to obtain 3-[4-[4-(1,2,3,4-tetrahydroisoquinolin-5-ylmethyl)-1-piperidyl]anilino]piperidine-2,6-dione (140 mg, 71.94% yield, 90% purity) as a HCl salt. $^1$H NMR (400 MHz, DMSO-$d_6$) δ 5.07 (s, 1H), 4.8 (q, J=6.8 Hz, 14.0 Hz, 2H), 3.05 (m, 4H), 2.51 (s, 1H), 1.89 (m, 4H), 1.21 (t, J=6.8 Hz, 3H).

Step-3: To solution of ethyl 2-(4-hydroxy-4-piperidyl) acetate (2.67 g, 11.96 mmol) in DMF (30 mL) at room temperature was added sodium bicarbonate (1.00 g, 11.96 mmol) and the reaction mixture was stirred at 70° C. for 16 h. Reaction progress was monitored by TLC. After completion of the reaction, reaction mixture was poured in the ice cold water to obtain the solid. The solid was filtered and dried, which was taken to the next step next step without further purification. $^1$H NMR (400 MHz, DMSO-$d_6$) δ 8.38 (m, 2H), 7.53 (d, J=9.6 Hz, 1H), 4.75 (s, 1H), 4.09 (q, J=6.8 Hz, 14.0 Hz, 2H), 3.32-3.19 (m, 2H), 3.14 (m, 2H), 2.49 (s, 1H), 1.83-1.71 (m, 4H), 1.21 (t, J=6.8 Hz, 3H). LC-MS (ES$^+$): m/z 363.30 [M+H]$^+$ Step-4: To solution of ethyl 2-[4-hydroxy-1-[4-nitro-2-(trifluoromethyl)phenyl]-4-piperidyl]acetate (2 g, 5.31 mmol) in methanol (10 mL) and Water (4 mL) at room temperature was added sodium hydroxide pellets (0.21 g, 5.31 mmol) and the mixture was heated 75° C. for 1 h. After completion of the reaction, solvent was evaporated under vacuum and the residue was diluted with water (2 mL) and acidified with 2N HCl to obtain the solid. The solid was filtered and dried to afford 2-[4-hydroxy-1-[4-nitro-2-(trifluoromethyl)phenyl]-4-piperidyl]acetic acid (1.2 g, 62.89% yield, 97% purity). $^1$H NMR (400 MHz, DMSO-$d_6$) δ 8.36 (m, 2H), 7.52 (d, J=9.6 Hz, 1H), 3.27-3.21 (m, 2H), 3.14-3.11 (m, 2H), 2.25 (s, 2H), 1.67 (s, 4H); LC-MS (ES$^+$): m/z 349.27 [M+H]$^+$ Step-5: To a stirred solution of tert-butyl piperazine-1-carboxylate (1.2 g, 6.44 mmol) and 2-[4-hydroxy-1-[4-nitro-2-(trifluoromethyl)phenyl]-4-piperidyl]acetic acid (2.24 g, 6.44 mmol) in DMF (15 mL) was added N,N-Diisopropylethylamine (4.49 mL, 25.77 mmol) and stirred the reaction mixture for 5 min at room temperature. HATU (2.45 g, 6.44 mmol) was added to the reaction mixture and stirring was continued for 16 h. Reaction progress was monitored by TLC. After completion of the reaction, the reaction mixture was diluted with water (50 mL), extracted with EtOAc (2×100 mL) and washed with brine. The combined organic layer was dried over anhydrous sodium sulphate, filtered and concentrated under reduced pressure. The crude compound was purified first by column chromatography (Davisil silica gel, 10-60% EtOAC in Pet ether) to afford tert-butyl 4-[2-[4-hydroxy-1-[4-nitro-2-(trifluoromethyl)phenyl]-4-piperidyl]acetyl]piperazine-1-carboxylate (1.3 g, 38.28% yield, 98% purity). $^1$H NMR (400 MHz, DMSO-d$_6$) δ 8.38 (m, 2H), 7.53 (d, J=9.6 Hz, 1H), 4.95 (s, 1H), 3.54-3.44 (m, 4H), 3.33-3.21 (m, 4H), 3.15-3.12 9 m, 2H), 2.56 (s, 2H), 1.80-1.72 (m, 4H), 1.41 (s, 9H); LC-MS (ES$^+$): m/z 517.24 [M+H]$^+$ Step-6: To a stirred solution of tert-butyl 4-[2-[4-hydroxy-1-[4-nitro-2-(trifluoromethyl)phenyl]-4-piperidyl]acetyl]piperazine-1-carboxylate (1.2 g, 2.32 mmol) in methanol (20 mL) was added 10% wet Pd/C (247.24 mg, 2.32 mmol) and stirred the reaction mixture under H$_2$ atmosphere (Balloon pressure) at RT for 16 hrs. Reaction progress was monitored by TLC/LCMS. After completion of reaction, the reaction mixture was filtered through Celite bed and the filtrate was concentrated under vacuum. The residue was dissolved in ethyl acetate (50 mL) and washed with water (20 mL). The organic layer was dried over sodium sulphate, filtered and concentrated under vacuum. The crude was taken to the next step without further purification. $^1$H NMR (400 MHz, DMSO-d$_6$) δ7.24 (d, J=8.8 Hz, 1H), 6.80-6.75 (m, 2H), 5.80 (s, 2H), 4.84 (s, 1H), 3.54-3.46 (m, 4H), 3.35-3.22 (m, 2H), 3.30-3.28 (m, 2H), 2.92 (m, 2H), 2.58-2.51 (m, 4H), 1.63 (m, 4H), 1.41 (s, 9H); LCMS: 487.86 [M+H]$^+$ Step-7: To a stirred solution of tert-butyl 4-[2-[1-[4-amino-2-(trifluoromethyl)phenyl]-4-hydroxy-4-piperidyl]acetyl]piperazine-1-carboxylate (1 g, 2.06 mmol) in DMF (10 mL) was added Sodium bicarbonate (777.00 mg, 9.25 mmol) 70° C. for 64 h. The progress of the reaction was monitor by LCMS and TLC, after completion the reaction mixture was quenched with ice water and filtered the solid. The crude solid was purified by column chromatography (Davisil silica, 10-60% ethyl acetate in pet ether) to afford tert-butyl 4-[2-[1-[4-[(2,6-dioxo-3-piperidyl)amino]-2-(trifluoromethyl)phenyl]-4-hydroxy-4-piperidyl]acetyl]piperazine-1-carboxylate (550 mg, 40.30% yield, 90% purity). $^1$H NMR (400 MHz, DMSO-d$_6$) 10.78 (s, 1H) 7.39 (d, J=8.8 Hz, 1H), 6.91-6.87 (m, 2H), 6.16 (d, J=8.0 Hz, 1H), 4.84 (s, 1H), 4.38-4.35 (m, 1H), 3.54 (s, 2H), 3.52 (s, 2H), 3.38 (m, 2H), 2.96-2.92 (m, 2H), 2.74-2.70 (m, 1H), 2.60-2.55 (m, 3H), 2.53 (s, 2H), 2.09-2.06 (m, 1H), 1.92-1.89 (m, 1H), 1.67-1.61 (m, 4H), 1.41 (s, 9H).

Step-8: To a stirred solution of tert-butyl 4-[2-[1-[4-[(2,6-dioxo-3-piperidyl)amino]-2-(trifluoromethyl)phenyl]-4-hydroxy-4-piperidyl]acetyl]piperazine-1-carboxylate (150 mg, 250.99 umol) in DCM (5 mL) was added Trifluoroacetic acid (193.37 uL, 2.51 mmol) and stirred the reaction mixture at RT for 3 h. After completion of reaction volatiles were evaporated under reduced pressure and co-distilled with toluene (15 ml×2) and triturated with diethyl ether (15 mL×2) to obtain 3-[4-[4-hydroxy-4-(2-oxo-2-piperazin-1-yl-ethyl)-1-piperidyl]-3-(trifluoromethyl)anilino]piperidine-2,6-dione (150 mg, 97.73% yield, 99.30 purity) as a TFA salt. LC-MS (ES$^+$): m/z 498.30 [M+H]$^+$ Step-9: To a stirred solution of 2,6-dimethoxy-4-(6-methyl-7-oxo-1H-pyrazolo[3,4-c]pyridin-4-yl)benzaldehyde (75 mg, 0.175 mmol) and 3-[4-[4-hydroxy-4-(2-oxo-2-piperazin-1-yl-ethyl)-1-piperidyl]-3-(trifluoromethyl)anilino]piperidine-2,6-dione (140.08 mg, 0.229 mmol) in Methanol/DCE (4 ml: 4 ml) was added molecular sieves 4 Å (0.1 g), acetic acid (10.54 mg, 0.175 mmol) and sodium acetate (43.19 mg0.526 mmol). The reaction mixture was stirred at 75° C. for 4 h. Reaction mixture was cooled to 0° C. and SiliaBond Cyanoborohydride (200 mg, 0.175 mmol) was added to the reaction mixture at 0° C. and continued the stirring at RT for 16 h. Progress of reaction was monitored by LCMS. After completion of the reaction, reaction mixture was filtered through Celite bed and filtrate was concentrated under vacuum. Crude compound was purified by RP-Prep HPLC to afford 3-[4-[4-[2-[4-[[2,6-dimethoxy-4-(6-methyl-7-oxo-1H-pyrazolo[3,4-c]pyridin-4-yl)phenyl]methyl]piperazin-1-yl]-2-oxo-ethyl]-4-hydroxy-1-piperidyl]-3-(trifluoromethyl)anilino]piperidine-2,6-dione (24 mg, 16.03% yield, 98.59% purity) as a formate salt and as an off white solid. $^1$H NMR (400 MHz, DMSO-d$_6$) δ 14.22 (s, 1H), 10.78 (s, 1H), 8.39 (s, 1H), 8.22 (s, 1H), 7.56 (s, 1H), 7.31 (d, J=8.8 Hz, 1H), 6.90 (m, 4H), 6.15 (d, J=8.8 Hz, 1H), 4.96 (s, 1H) 4.36 (m, 1H), 3.86 (s, 6H), 3.61 (s, 3H), 3.56 (s, 1H), 3.51 (m, 6H), 2.93 (m, 2H), 2.78-2.69 (m, 1H), 2.60 (m, 3H), 2.43 (bs, 2H), 2.36 (bs, 2H), 2.10-2.07 (m, 1H), 1.95-1.84 (m, 1H), 1.67 (m, 4H). LC-MS (ES$^+$): m/z 795.54 [M+H]$^+$ Synthesis of Compound 69

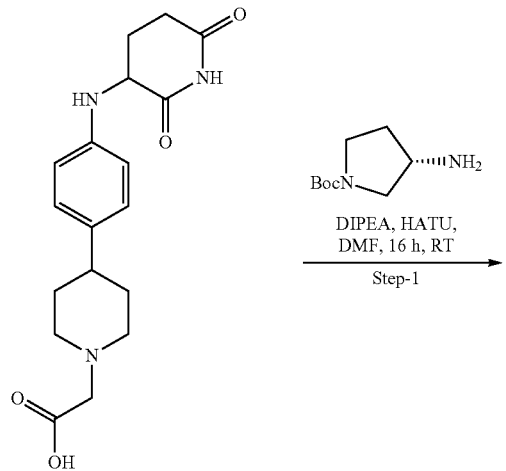

1-3

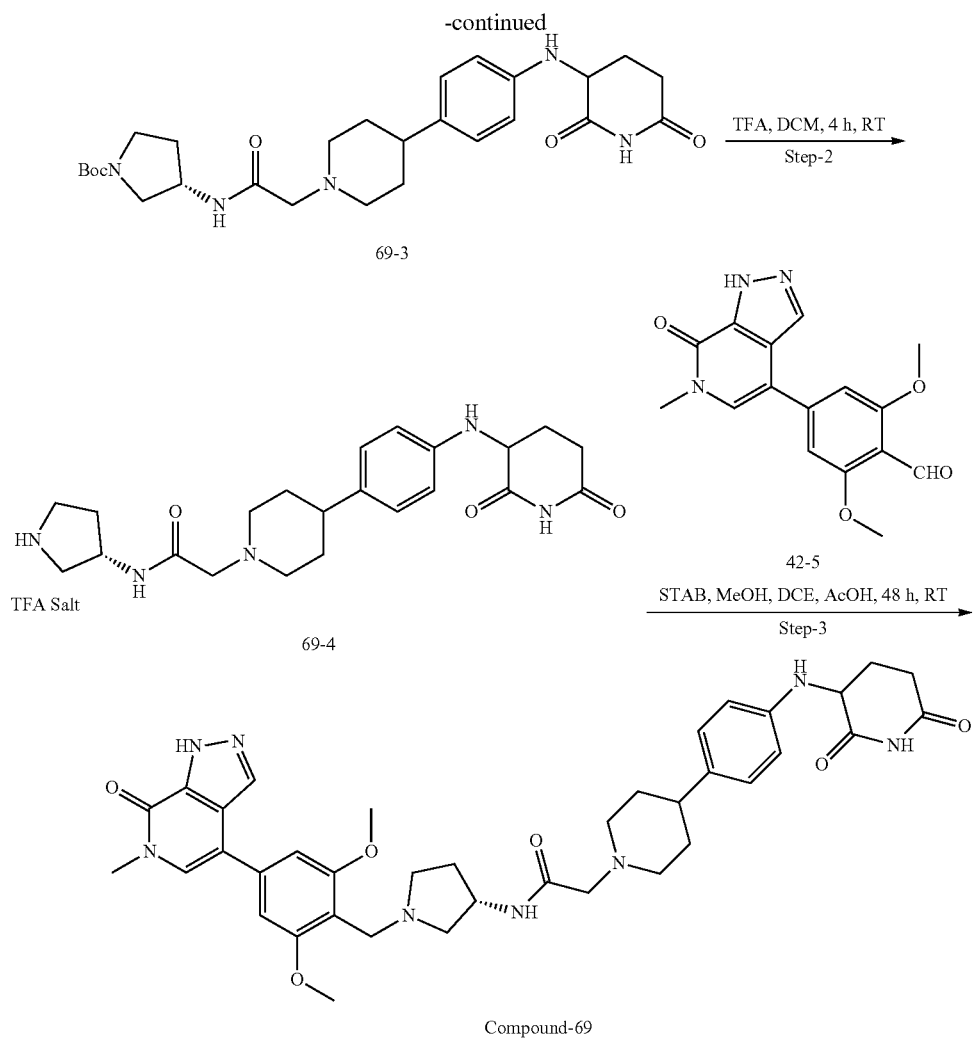

Compound-69

Step-1: To a solution of 2-[4-[4-[(2,6-dioxo-3-piperidyl)amino]phenyl]-1-piperidyl]acetic acid (0.2 g, 0.348 mmol) in DMF (2 mL) was added N-ethyl-N-isopropyl-propan-2-amine (0.48 mL, 2.79 mmol) and tert-butyl 3-aminopyrrolidine-1-carboxylate (71.46 mg, 0.383 mmol) at RT. HATU (265.23 mg, 0.697 mmol) was added to the reaction mixture and stirred for 16 h at RT. Progress of the reaction was monitored by LCMS. After completion of the reaction, reaction mixture was diluted with EtOAc (200 mL) and washed with ice cold water (3×100 mL) followed by saturated brine solution. Organic layer was dried over $Na_2SO_4$, filtered and concentrated to obtain tert-butyl 3-[[2-[4-[4-[(2,6-dioxo-3-piperidyl)amino]phenyl]-1-piperidyl]acetyl]amino]pyrrolidine-1-carboxylate (0.125 g, 65.59% yield, 94% purity) crude product which was used in the next step without further purification. LC-MS (ES$^+$): m/z 514.53 [M+H]$^+$ Step-2: To a solution of tert-butyl 3-[[2-[4-[4-[(2,6-dioxo-3-piperidyl)amino]phenyl]-1-piperidyl]acetyl]amino]pyrrolidine-1-carboxylate (0.125 g, 0.243 mmol) in DCM (2 mL) was added 2,2,2-trifluoroacetic acid (0.18 ml, 2.43 mmol) at 0° C. and stirred for 4 h at RT. Progress of the reaction was monitored by LCMS. After completion of the reaction, reaction mixture was concentrated under reduced pressure to get the crude product. The crude product was triturated with diethyl ether to afford 2-[4-[4-[(2,6-dioxo-3-piperidyl)amino]phenyl]-1-piperidyl]-N-[pyrrolidin-3-yl]acetamide (0.110 g, 83.1% yield, 97.8% purity) as brown color solid TFA salt.

Step-3: To a solution of 2,6-dimethoxy-4-(6-methyl-7-oxo-1H-pyrazolo[3,4-c]pyridin-4-yl)benzaldehyde (100.0 mg, 0.184 mmol) and 2-[4-[4-[(2,6-dioxo-3-piperidyl)amino]phenyl]-1-piperidyl]-N-[pyrrolidin-3-yl]acetamide (118.51 mg, 0.184 mmol) in Methanol (1 mL) and DCE (1 mL) was added acetic acid (0.2 mL) at 0° C. and stirred the reaction mixture for 16 h at RT. Then sodium triacetoxyborohydride (78.30 mg, 0.369 mmol) was added to the reaction mixture at 0° C. and stirred for 48 h at RT. Progress of the reaction was monitored by LCMS. After completion of reaction, reaction mixture was evaporated under reduced pressure to get the crude compound.

Resulting crude product was purified by preparative HPLC to afford N-[1-[[2,6-dimethoxy-4-(6-methyl-7-oxo-1H-pyrazolo[3,4-c]pyridin-4-yl)phenyl]methyl]pyrrolidin-3-yl]-2-[4-[4-[(2,6-dioxo-3-piperidyl)amino]phenyl]-1-piperidyl]acetamide (32 mg, 20.78% yield, 98.93% purity) as a TFA salt brown color solid. $^1$H NMR (400 MHz, DMSO-$d_6$) δ 14.31 (s, 1H), 10.82 (s, 1H), 9.81 (m, 2H), 9.10 (dd, J=6.0 Hz, 5.6 Hz, 1H), 8.23 (s, 1H), 7.65 (s, 1H), 6.98 (m, 4H), 6.65 (d, J=8.4 Hz, 2H), 5.76 (s, 0.5H), 4.55-4.26 (m, 4H), 3.96 (m, 8H), 3.63 (s, 3H), 3.53 (m, 4H), 3.17 (bm, 4H), 2.74-2.67 (m, 1H), 2.63-2.56 (m, 2H), 2.30-1.85 (m, 8H); LC-MS (ES+): m/z 711.53 [M+H]+

Synthesis of Compound 70

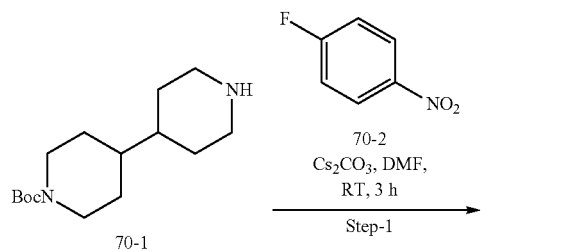

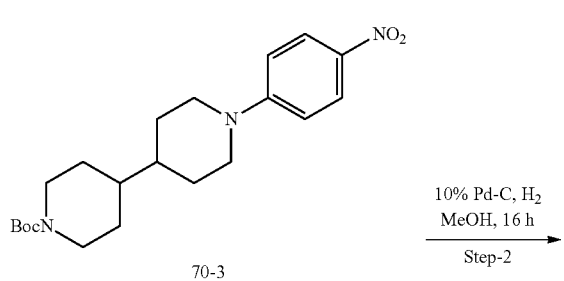

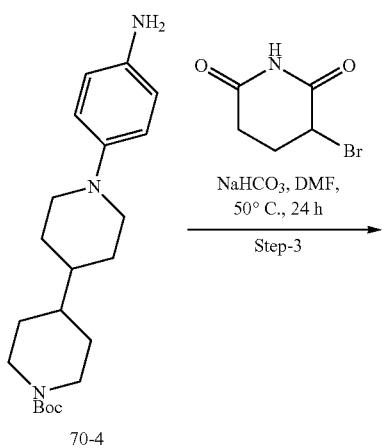

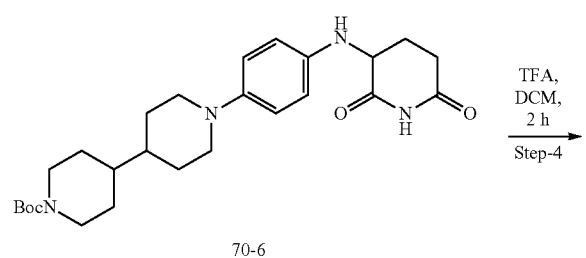

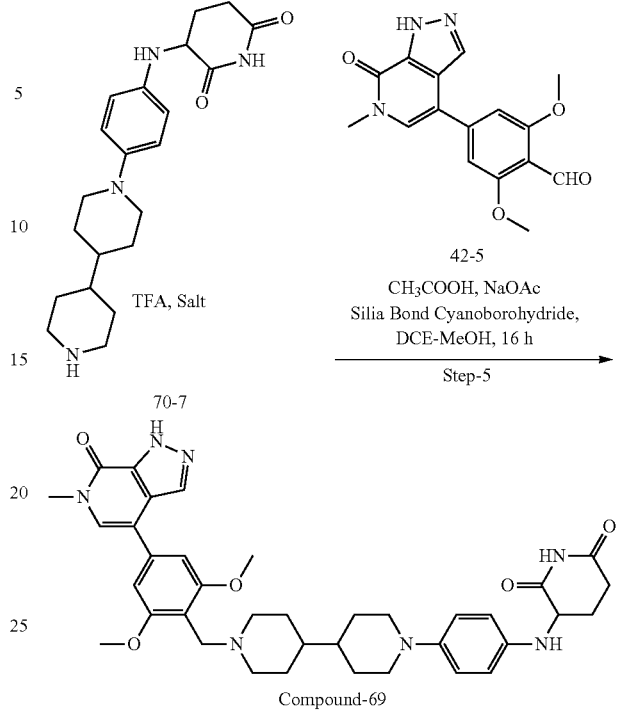

Step-1: To a stirred solution of compound tert-butyl 4-(4-piperidyl) piperidine-1-carboxylate 70-1 (0.5 g, 1.86 mmol) in DMF (10 mL) was added cesium carbonate (0.6 g, 1.86 mmol) and stirred for 15 min before adding 1-fluoro-4-nitro-benzene 70-2 (0.263 g, 1.86 mmol). The reaction mixture was allowed to stir at RT for 3 h while monitoring by TLC. After completion the reaction mass was quenched with ice flakes and the precipitated solid was filtered to tert-butyl 4-[1-(4-nitrophenyl)-4-piperidyl]piperidine-1-carboxylate 70-3 (0.55 g, 71.97% yield, 95% purity) as a yellow semi-solid and used as such for the next step. LC-MS (ES+): m/z [M+H]+ 390.23.

Step-2: To a stirred solution of tert-butyl 4-[1-(4-nitrophenyl)-4-piperidyl]piperidine-1-carboxylate 70-3 (0.55 g, 1.41 mmol) in Methanol (10 mL) and was added 10% wet Pd-C (0.525 g, 4.94 mmol) and the reaction mixture was stirred under $H_2$ balloon pressure for 16 h, while monitoring by LCMS and TLC. The reaction mixture was filtered through Celite bed and the filtrate was concentrated to afford tert-butyl 4-[1-(4-aminophenyl)-4-piperidyl]piperidine-1-carboxylate 70-4 (0.5 g, 91.60% yield, 93% purity) as an yellow solid. This was taken to the next step without any purification. LC-MS (ES+): m/z [M+H]+ 360.13

Step-3: To a stirred solution of tert-butyl 4-[1-(4-aminophenyl)-4-piperidyl]piperidine-1-carboxylate 70-4 (0.5 g, 1.39 mmol) in DMF (15 mL) were added 3-bromopiperidine-2,6-dione 70-5 (0.385 g, 2.01 mmol), NaHCO3 (0.280 g, 3.34 mmol) and stirred at 50° C. for 24 h, while monitoring the reaction by LCMS and TLC. After 24 h, the reaction was quenched with ice cold water (100 mL). The obtained solid was filtered and co-distilled with toluene to afford tert-butyl 4-[1-[4-[(2,6-dioxo-3-piperidyl)amino]phenyl]-4-piperidyl]piperidine-1-carboxylate 70-6 (0.4 g, 37.64% yield, 74% purity) as a purple solid. LC-MS (ES+): m/z 471.42 [M+H]+

Step-4: To a stirred solution of tert-butyl 4-[1-[4-[(2,6-dioxo-3-piperidyl)amino]phenyl]-4-piperidyl]piperidine-1-carboxylate 70-6 (0.4 g, 0.849 mmol) in $CH_2Cl_2$ (2 mL) was added Trifluoroacetic acid (0.969 mg, 8.50 mmol) at 0° C.

and the reaction mixture was stirred at RT for 2 h, while monitoring by TLC. After consuming the starting material, the reaction mixture was concentrated under reduced pressure, residue triturated with diethyl ether (2×50 mL) and the solid precipitated out was dried to afford 3-[4-[4-(4-piperidyl)-1-piperidyl]anilino]piperidine-2,6-dione. TFA salt 70-7 (0.27 g, 51.79% yield, 79% purity) as green solid. LC-MS (ES$^+$): m/z 371.40 [M+H]$^+$ Step-5: To a stirred solution of 3-[4-[4-(4-piperidyl)-1-piperidyl]anilino]piperidine-2,6-dione 70-7 (0.236 g, 0.638 mmol) in ethylene dichloride (5 mL):Methanol (5 mL) was added Acetic acid (0.019 g, 0.319 mmol) and Sodium acetate, anhydrous (0.052 g, 0.638 mmol). The resulting solution was stirred for 10 min, added 2,6-dimethoxy-4-(6-methyl-7-oxo-1H-pyrazolo[3,4-c]pyridin-4-yl)benzaldehyde 70-8 (0.1 g, 0.319 mmol) and allowed to reflux for 3 h. After 3 h, the reaction mass was cooled to RT and SiliaBond Cyanoborohydride (0.166 g, 3.87 mmol) was added and allowed to stir at RT for 16 h, while monitoring by LCMS. After completion, the reaction mixture was evaporated under reduced pressure and purified by prep HPLC to obtain 3-[4-[4-[1-[[2,6-dimethoxy-4-(6-methyl-7-oxo-1H-pyrazolo[3,4-c]pyridin-4-yl)phenyl]methyl]-4-piperidyl]-1-piperidyl]anilino]piperidine-2,6-dione.TFA salt Compound 70 (0.029 g, 11.66% yield, 97.99% purity)) as alight green solid. $^1$H NMR (400 MHz, DMSO-d$_6$) δ 14.17 (s, 1H), 10.77 (s, 1H), 8.92 (bs, 1H), 8.22 (bs, 1H), 7.65 (s, 1H), 7.37 (bs, 2H), 6.98 (s, 2H), 6.75 (s, 2H), 6.37 (bs, 1H), 4.36-4.21 (m, 3H), 3.96 (s, 6H), 3.63 (s, 3H), 3.49-3.35 (m, 6H), 3.03-3.01 (m, 2H), 2.74-2.60 (m, 2H), 2.10-2.04 (m, 1H), 1.91-1.86 (m, 5H), 1.50-1.44 (m, 6H). LC-MS (ES$^+$): m/z 668.46 [M+H]$^+$ Compound 71 was prepared following the synthesis of Compound 70

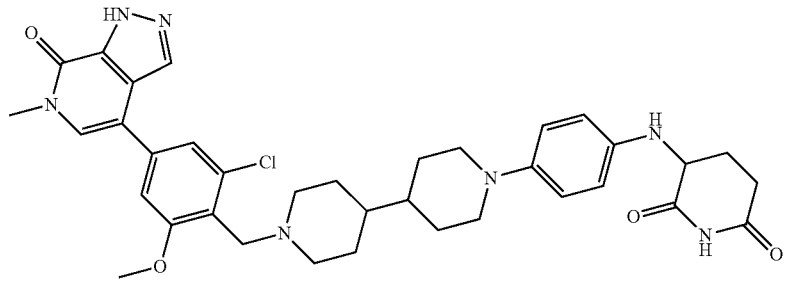 [SMILES: COc1cc(-c2cn(C)c(=O)c3[nH]ncc23)cc(Cl)c1CN1CCC(C2CCN(c3ccc(NC4CCC(=O)NC4=O)cc3)CC2)CC1]

$^1$H NMR (400 MHz, DMSO-d$_6$) δ 14.36 (s, 1H), 10.83 (s, 1H), 9.13 (bs, 1H), 8.22 (s, 1H), 7.72 (s, 1H), 7.41 (d, J=1.2 Hz, 1H), 7.35 (bs, 3H), 6.79-6.75 (m, 2H), 6.39 (bs, 1H), 4.40-4.38 (m, 3H), 4.02 (s, 3H), 3.62 (s, 3H), 3.53-3.51 (m, 6H), 3.31-3.16 (m, 2H), 2.77-2.67 (m, 1H), 2.61-2.58 (m, 1H), 2.08-2.06 (m, 1H), 1.93-1.87 (m, 5H), 1.56-1.49 (m, 6H). LC-MS (ES$^+$): m/z 672.48 [M+H]$^+$

Compound 72 was prepared following the synthesis of Compound 70

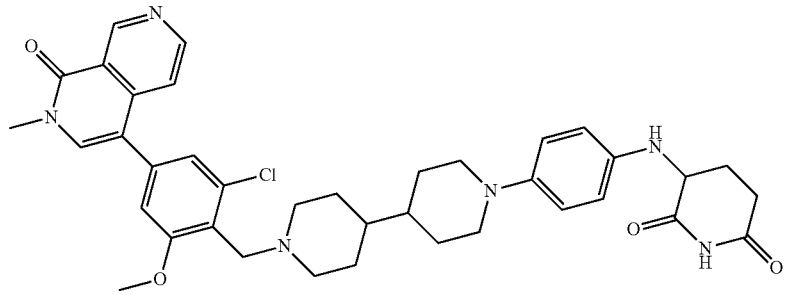 [SMILES: COc1cc(-c2cn(C)c(=O)c3cnccc23)cc(Cl)c1CN1CCC(C2CCN(c3ccc(NC4CCC(=O)NC4=O)cc3)CC2)CC1]

$^1$H NMR (400 MHz, DMSO-d$_6$) δ 10.83 (s, 1H), 9.47 (s, 1H), 9.17 (s, 1H), 8.77 (d, J=5.7 Hz, 1H), 7.94 (s, 1H), 7.54 (d, J=5.6 Hz, 1H), 7.36-7.27 (m, 5H), 6.77 (d, J=8.8 Hz, 1H), 6.32 (bs, 1H), 4.52-4.38 (m, 3H), 3.94 (s, 3H), 3.62 (s, 3H), 3.55-3.46 (m, 6H), 3.20-3.17 (m, 2H), 2.79-2.57 (m, 2H), 2.08-1.90 (m, 6H), 1.57-1.49 (m, 6H). LC-MS (ES$^+$): m/z 683.56 [M+H]$^+$

Synthesis of 73

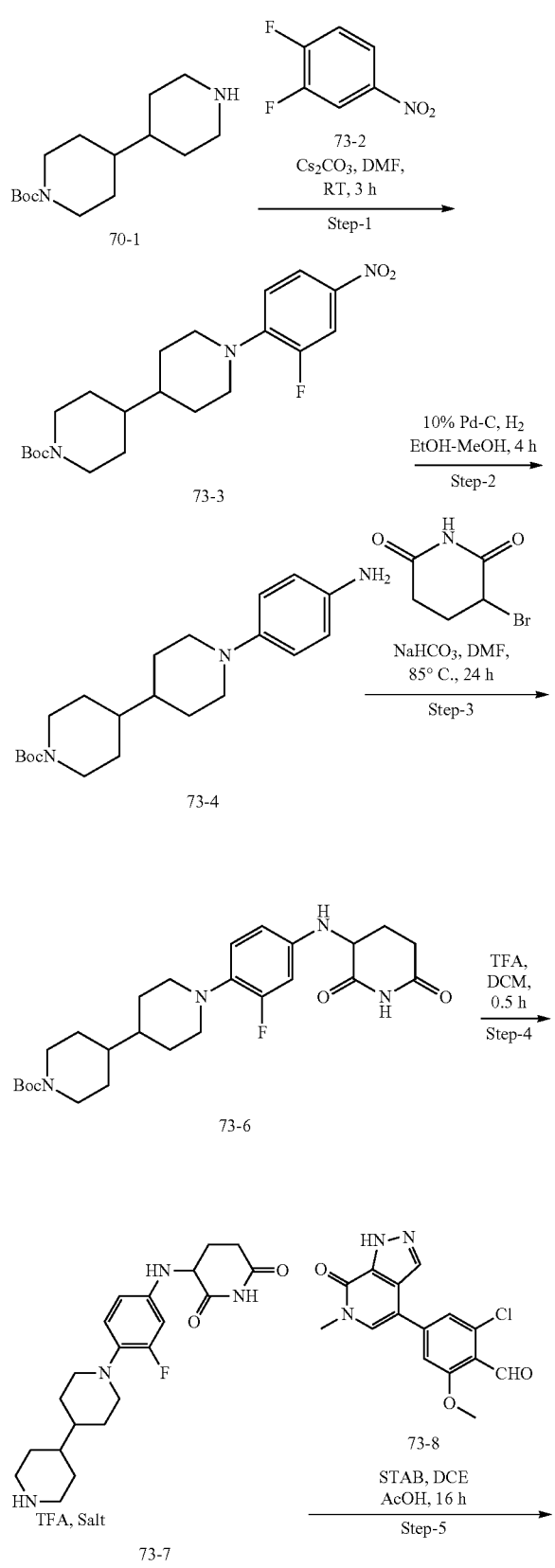

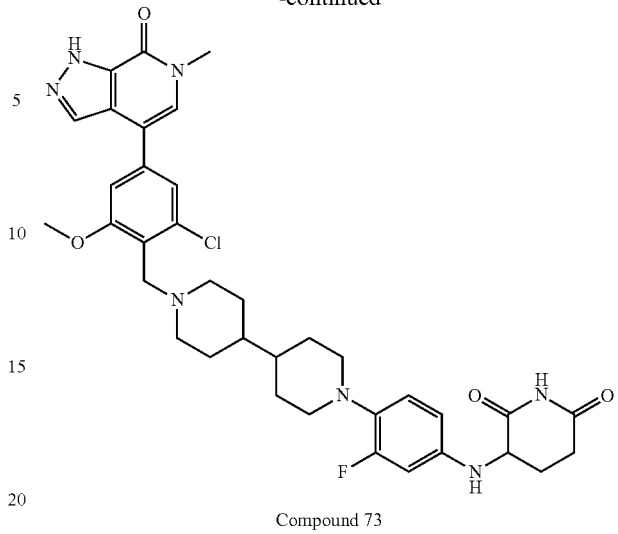

Compound 73

Step-1: To a stirred solution of compound tert-butyl 4-(4-piperidyl) piperidine-1-carboxylate 70-1 (1 g, 3.73 mmol) in DMF (20 mL) was added cesium carbonate (1.21 g, 3.73 mmol) and stirred for 15 min before adding 1,2-difluoro-4-nitro-benzene 73-2 (0.592 g, 3.73 mmol). The reaction mixture was allowed to stir at RT for 3 h while monitoring by TLC. After completion the reaction mass was quenched with ice flakes and the precipitated solid was filtered to yield tert-butyl 4-[1-(2-fluoro-4-nitro-phenyl)-4-piperidyl] piperidine-1-carboxylate 73-3 (1.4 g, 2.78 mmol, 74.69% yield, 81% purity) as yellow solid. $^1$HNMR (400 MHz, CDCl$_3$): δ 1.1-1.25 (m, 2H), 1.25-1.35 (in, 2H), 1.35-1.50 (m, 11H), 1.70 (d, J=12.4 Hz, 2H), 1.82 (d, J=12.8 Hz, 2H), 2.65 (t, J=11.2 Hz, 2H), 2.82 (t, J=12.4 Hz, 2H), 3.74 (d, J=12.4 Hz, 2H), 4.14 (bs, 2H), 6.89 (t, J=8.8 Hz, 1H), 7.89 (dd, J$_1$=2.8 Hz, J$_2$=13.2 Hz, 1H), 7.96 (dd, J$_1$=2.8 Hz, J$_2$=9.0 Hz, 1H). LC-MS (ES$^+$): m/z 408.22 [M+H]$^+$ Step-2: To a stirred solution of benzyl of tert-butyl 4-[1-(2-fluoro-4-nitro-phenyl)-4-piperidyl]piperidine-1-carboxylate 73-3 (1.4 g, 3.44 mmol) in Methanol (15 mL) and Ethanol (15 mL) was added 10% wet Pd-C (1.46 g, 13.74 mmol) and the reaction mixture was stirred under H$_2$ balloon pressure for 4 h, while monitoring by LCMS and TLC. The reaction mixture was filtered through Celite bed and the filtrate was concentrated to afford tert-butyl 4-[1-(4-amino-2-fluoro-phenyl)-4-piperidyl] piperidine-1-carboxylate 73-4 (1.2 g, 3.05 mmol, 88.82% yield, 96% purity) as pale pink solid. This was taken to the next step without any purification. LC-MS (ES$^+$): m/z 378.60 [M+H]$^+$ Step-3: To a stirred solution of tert-butyl 4-[1-(4-amino-2-fluoro-phenyl)-4-piperidyl]piperidine-1-carboxylate 73-4 (0.6 g, 1.59 mmol) in DMF (20 mL) was added 3-bromopiperidine-2,6-dione (0.61 g, 3.18 mmol), NaHCO$_3$ (0.801 g, 9.54 mmol) and stirred at 85° C. for 24 h, while monitoring by LCMS and TLC. After 24 h, the reaction was quenched with ice cold water (100 mL) and extracted with EtOAc (3×150 mL). The combined organic layer was dried over anhydrous Na$_2$SO$_4$, and concentrated to afford crude compound. Crude compound was purified by (silica gel mesh 100-200, eluent 50% pet ether in ethyl acetate) column chromatography to afford benzyl afford tert-butyl4-[1-[4-[(2,6-dioxo-3-piperidyl)amino]-2-fluoro-phenyl]-4-piperidyl]piperidine-1-carboxylate 6 (0.25 g, 486.09 mmol, 30.58% yield, 95% purity) as pale brown solid. $^1$HNMR (400 MHz, DMSO-d$_6$): δ 0.95-1.2 (m, 2H), 1.39 (s, 9H), 1.2-1.45 (m, 4H), 1.69 (t, J=12 Hz, 4H), 1.8-1.9 (m, 1H), 2.05-2.15 (m, 1H), 2.45-2.51 (m, 1H), 2.51-2.53 (m, 5H), 3.14 (d, J=11.6 Hz, 2H), 3.97 (d, J=12 Hz, 2H), 4.2-4.3 (m, 1H), 6.42 (dd, J$_2$=2.4 Hz, J$_2$=8.4 Hz 1H), 6.49 (dd, J$_1$=2.8 Hz, J$_2$=14.8 Hz 1H), 6.83 (t, J=9.2 Hz, 1H), 7.94 (s, 1H), 10.87 (s, 1H). LC-MS (ES$^+$): m/z 489.73 [M+H]$^+$ Step-4: To a stirred solution of tert-butyl 4-[1-[4-[(2,6-dioxo-3-piperidyl)amino]-2-fluoro-phenyl]-4-piperidyl]piperidine-1-carboxylate 73-6 (0.25 g, 0.51 mmol) in CH$_2$Cl$_2$ (2 mL) was added Trifluoroacetic acid (1.2 ml, 15.35 mmol) at 0° C. and stirred for 30 minutes at RT. The reaction mixture was concentrated, residue triturated with diethyl ether (2×50 mL) and the solid precipitated out was dried to afford 3-[3-fluoro-4-[4-(4-piperidyl)-1-piperidyl]anilino]piperidine-2,6-dione. TFA 73-7 (0.1 g, 199.00 mmol, 38.89% yield, 90% purity) as pale green solid. $^1$HNMR (400 MHz, DMSO-d$_6$): δ 1.20-1.5 (m, 6H), 1.70-1.95 (m, 5H), 2.00-2.15 (m, 1H), 2.55-2.65 (m, 1H), 2.89-2.68 (m, 5H), 3.30 (d, J=11.6 Hz, 4H), 4.25-4.35 (m, 1H), 6.48 (d, J=8.4 Hz, 1H), 6.57 (d, J=14.8 Hz, 1H), 7.04 (bs, 1H), 8.20-8.35 (m, 1H), 8.55 (d, J=8.8 Hz, 1H), 8.14 (s, 1H), 10.87 (s, 1H). LC-MS (ES$^+$): m/z 389.38 [M+H]$^+$ Step-5: To a stirred solution of 3-[3-fluoro-4-[4-(4-piperidyl)-1-piperidyl]anilino]piperidine-2,6-dione 7 (0.1 g, 0.257 mmol) in DCE (5 mL) and methanol (5 mL) was added 4 Å Molecular sieves (0.1 g, 0.257 mmol), Acetic acid (0.023 g, 0.386 mmol) and sodium acetate, anhydrous (0.042 g, 0.514 mmol). The resulting solution was stirred for 10 min, added 2-chloro-6-methoxy-4-(6-methyl-7-oxo-1H-pyrazolo [3,4-c]pyridin-4-yl) benzaldehyde (0.081 g, 0.257 mmol) and allowed to reflux for 3 h. After 3 h, the RM was cooled to RT and Silia bond cyanoborohydride (0.1 g, 0.257 mmol) was added and allowed to stir at RT for 17 h, while monitoring by LCMS. After completion, the reaction mixture was evaporated under reduced pressure and purified by prep HPLC to obtain 3-[4-[4-[1-[[2-chloro-6-methoxy-4-(6-methyl-7-oxo-1H-pyrazolo[3,4-c]pyridin-4-yl)phenyl]methyl]-4-piperidyl]-1-piperidyl]-3-fluoro-anilino]piperidine-2,6-dione. TFA (0.056 g, 67.75 mol, 26.32% yield, 96.26% purity) as an off white solid. $^1$HNMR (400 MHz, DMSO-d$_6$): δ 14.32 (s, 1H), 10.80 (s, 1H), 9.07 (bs, 1H), 8.22 (s, 1H), 7.71 (s, 1H), 7.46 (d, J=1.4 Hz, 1H), 7.34 (s, 1H), 6.57-6.54 (m, 2H), 4.44-4.39 (m, 3H), 4.02 (s, 3H), 3.62 (s, 3H), 3.52-3.49 (m, 2H), 3.27-3.15 (m, 6H), 2.75-2.66 (m, 2H), 2.57 (d, J=10.2 Hz, 1H), 2.09-2.07 (m, 1H), 1.89-1.74 (m, 5H), 1.53-1.46 (m, 6H). LC-MS (ES$^+$): m/z 690.53 [M+H]$^+$.

Compound 74 was prepared following the synthesis of Compound 73

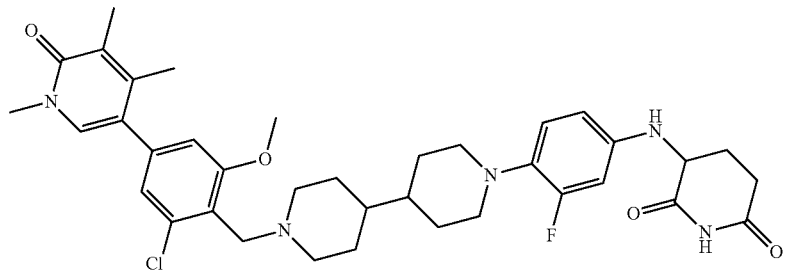 [SMILES: COc1cc(-c2cn(C)c(=O)c(C)c2C)cc(Cl)c1CN1CCC(C2CCN(c3ccc(NC4CCC(=O)NC4=O)cc3F)CC2)CC1]

$^1$H NMR (400 MHz, DMSO-d$_6$) δ 10.80 (s, 1H), 8.95 (s, 1H), 7.57 (s, 1H), 7.28 (t, J=9.2 Hz, 1H), (7.15 (s, 1H), 7.08 (s, 1H), 6.65-6.55 (m, 2H), 4.47-4.28 (m, 3H), 3.93 (s, 3H), 3.47 (s, 3H), 3.28-3.15 (m, 8H), 2.77-2.58 (m, 2H), 2.07 (d, J=5.3 Hz, 7H), 1.89-1.73 (m, 5H), 1.53-1.24 (m, 6H). LC-MS (ES$^+$): m/z 678.53 [M+H]$^+$

Compound 75 was prepared following the synthesis of Compound 73

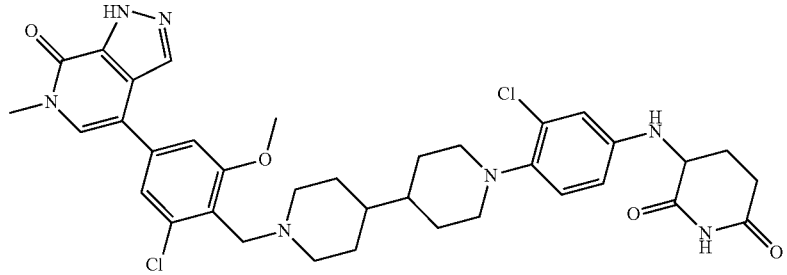 [SMILES: COc1cc(-c2cn(C)c(=O)c3[nH]ncc23)cc(Cl)c1CN1CCC(C2CCN(c3ccc(NC4CCC(=O)NC4=O)cc3Cl)CC2)CC1]

¹H NMR (400 MHz, DMSO-d₆) δ 14.26 (s, 1H), 10.77 (s, 1H), 8.93 (s, 1H), 8.22 (s, 1H), 7.71 (s, 1H), 7.46 (d, J=1.0 Hz, 1H), 7.34 (s, 1H), 7.02 (t, J=28.0 Hz, 1H), 6.75 (d, J=2.4 Hz, 1H), 6.60 (q, J=3.6 Hz, 1H), 4.39 (d, J=4.0 Hz, 2H), 4.31-4.29 (m, 1H), 4.02 (s, 3H), 3.62 (s, 3H), 3.50-2.98 (m, 8H), 2.75-2.62 (m, 1H), 2.10-2.06 (m, 2H), 1.93-1.80 (m, 5H), 1.54-1.50 (m, 5H), 1.34 (bs, 1H). LC-MS (ES⁻): m/z 704.42 [M−H]⁻

Compound 76 was prepared following the synthesis of Compound 73

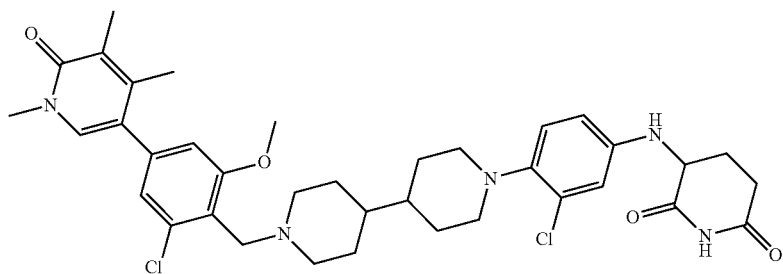 [SMILES: COc1cc(-c2cn(C)c(=O)c(C)c2C)cc(Cl)c1CN1CCC(C2CCN(c3ccc(NC4CCC(=O)NC4=O)cc3Cl)CC2)CC1]

¹H NMR (400 MHz, DMSO-d₆) δ 10.77 (s, 1H), 8.87 (s, 1H), 7.57 (s, 1H), 7.15 (s, 1H), 7.08 (s, 1H), 6.94 (d, J=9.4 Hz, 1H), 6.60 (d, J=2 Hz, 1H) 6.59 (dd, J=2 Hz, 8.4 Hz, 1H), 4.46-4.36 (m, 2H), 4.30-4.26 (m, 1H), 3.93 (s, 3H), 3.47 (s, 5H), 3.27-3.15 (m, 6H), 2.78-2.63 (m, 2H), 2.07 (d, J=5.2 Hz, 7H), 1.93-1.91 (m, 3H), 1.80 (d, J=11.6 Hz, 2H), 1.48-1.26 (m, 6H). LC-MS (ES⁺): m/z 694.45 [M+H]⁺

Compound 77 was prepared following the synthesis of Compound 73

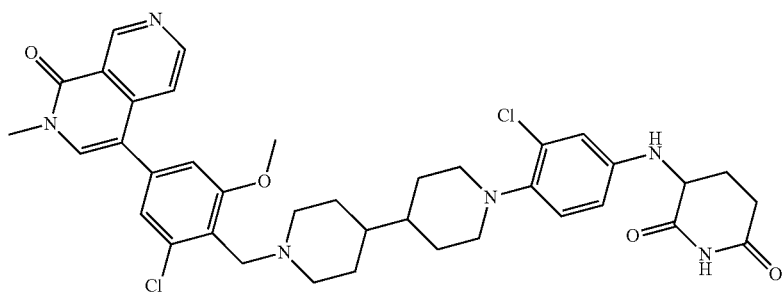 [SMILES: COc1cc(-c2cn(C)c(=O)c3cnccc23)cc(Cl)c1CN1CCC(C2CCN(c3ccc(NC4CCC(=O)NC4=O)cc3Cl)CC2)CC1]

¹H NMR (400 MHz, DMSO-d₆) δ 10.76 (s, 1H), 9.44 (s, 1H), 8.73 (d, J=5.6 Hz, 1H), 7.92 (s, 1H), 7.53 (d, J=5.6 Hz, 1H), 7.14 (d, J=1.3 Hz, 1H), 7.08 (s, 1H), 6.92 (d, J=8.8 Hz, 1H), 6.74 (d, J=2.5 Hz, 1H), 6.60-6.57 (m, 1H), 5.82 (d, J=7.8 Hz, 1H), 4.28-4.24 (m, 1H), 3.86 (s, 3H), 3.59 (s, 5H), 3.08 (d, J=10.6 Hz, 2H), 2.89 (d, J=10.8 Hz, 2H), 2.74-2.61 (m, 2H), 2.48-2.45 (m, 2H), 2.11-2.06 (m, 3H), 1.74-1.64 (m, 4H), 1.31-1.12 (m, 7H), LC-MS (ES⁺): m/z 717.19 [M+H]⁺

Compound 78 was prepared following the synthesis of Compound 73

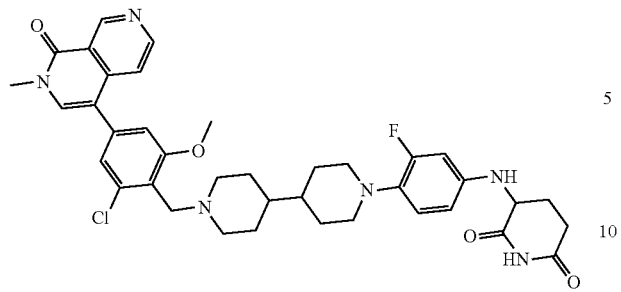

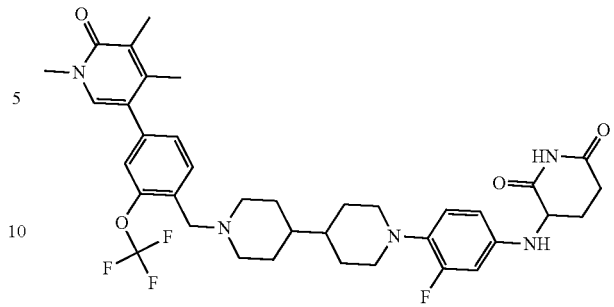

¹H NMR (400 MHz, DMSO-d₆) δ 10.80 (s, 1H), 9.48 (s, 1H), 9.16 (s, 1H), 8.78 (s, 1H), 7.95 (s, 1H), 7.55 (d, J=5.4 Hz, 1H), 7.33 (s, 1H), 7.27 (s, 1H), 6.56 (d, J=14.7 Hz, 1H), 6.48 (d, J=7.1 Hz, 1H), 4.51-4.30 (m, 3H), 3.96 (s, 3H), 3.61 (s, 3H), 3.24-3.19 (m, 6H), 2.77-2.55 (m, 4H), 2.08-2.05 (m, 1H), 1.91-1.74 (m, 5H), 1.55-1.22 (m, 6H). LC-MS (ES⁺): m/z 701.16 [M+H]⁺

Compound 79 was prepared following the synthesis of Compound 73

¹H NMR (400 MHz, DMSO-d₆) δ 10.82 (s, 1H), 9.92 (s, 1H), 7.79 (d, J=8.0 Hz, 1H), 7.57 (s, 1H), 7.47 (dd, J=8.0, 1.7 Hz, 1H), 7.41 (p, J=1.8 Hz, 1H), 7.20 (s, 1H), 6.62 (dd, J=15.0, 2.5 Hz, 1H), 6.58-6.36 (m, 1H), 4.55-4.29 (m, 3H), 3.45 (d, J=17.2 Hz, 7H), 3.07 (s, 4H), 2.85-2.52 (m, 2H), 2.05 (d, J=5.1 Hz, 7H), 1.99-1.76 (m, 4H), 1.67-1.14 (m, 7H). LC-MS (ES⁺): m/z 698.6

Compound 81 was prepared following the synthesis of Compound 73

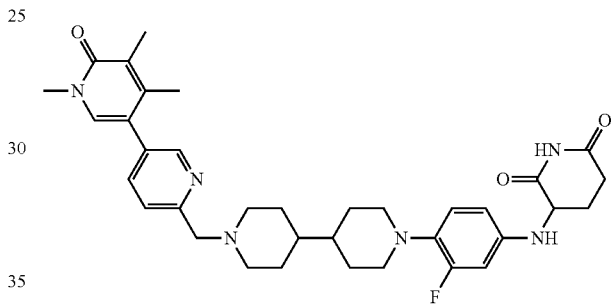

¹H NMR (400 MHz, DMSO-d₆) δ 10.81 (s, 1H), 10.02 (s, 1H), 9.48 (s, 1H), 8.76 (d, J=5.7 Hz, 1H), 8.03-7.85 (m, 2H), 7.75-7.55 (m, 2H), 7.49 (d, J=5.8 Hz, 1H), 7.16 (s, 1H), 6.71-6.38 (m, 2H), 4.46 (s, 2H), 4.34 (dd, J=11.7, 4.8 Hz, 1H), 3.61 (s, 3H), 3.48 (d, J=11.3 Hz, 2H), 3.39 (d, J=10.3 Hz, 2H), 3.08 (s, 3H), 2.84-2.52 (m, 2H), 2.20-2.02 (m, 1H), 2.02-1.70 (m, 5H), 1.70-1.16 (m, 7H). LC-MS (ES⁺): m/z 721.6 [M+H]⁺

Compound 80 was prepared following the synthesis of Compound 73

¹H NMR (400 MHz, DMSO-d₆) δ 10.82 (s, 1H), 9.98 (s, 1H), 8.62 (dd, J=2.3, 0.8 Hz, 1H), 7.90 (dd, J=8.0, 2.3 Hz, 1H), 7.60 (t, J=4.1 Hz, 2H), 7.20 (s, 1H), 6.62 (dd, J=14.9, 2.5 Hz, 1H), 6.53 (dd, J=8.9, 2.5 Hz, 1H), 4.50 (s, 2H), 4.36 (dd, J=11.6, 4.8 Hz, 1H), 3.47 (s, 6H), 3.06 (s, 4H), 2.87-2.54 (m, 2H), 2.05 (d, J=11.3 Hz, 7H), 1.88 (ddd, J=20.0, 13.6, 8.5 Hz, 5H), 1.54 (s, 5H), 1.41 (s, 2H). LC-MS (ES⁺): m/z: 615.5 [M+H]⁺.

Compound 82 was prepared following the synthesis of Compound 73.

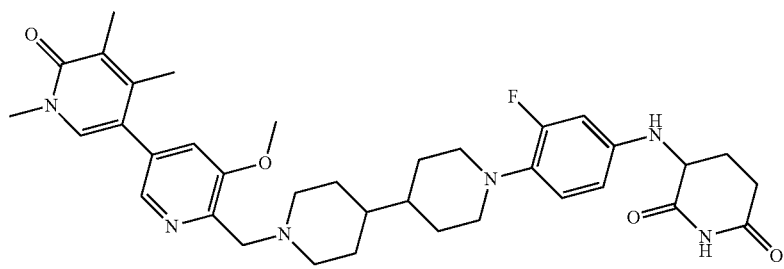 [SMILES: COc1cc(-c2cn(C)c(=O)c(C)c2C)cnc1CN1CCC(C2CCN(c3ccc(NC4CCC(=O)NC4=O)cc3F)CC2)CC1]

¹H NMR (400 MHz, DMSO-d₆) δ 10.83 (s, 1H), 9.85 (s, 1H), 8.18 (d, J=1.7 Hz, 1H), 7.74-7.51 (m, 2H), 7.24 (s, 1H), 6.64 (dd, J=15.0, 2.5 Hz, 1H), 6.55 (dd, J=9.1, 2.4 Hz, 1H), 4.47 (s, 2H), 4.37 (dd, J=11.8, 4.9 Hz, 1H), 3.92 (s, 3H), 3.57 (d, J=11.3 Hz, 2H), 3.50-3.29 (m, 5H), 3.14 (d, J=18.3 Hz, 3H), 2.88-2.54 (m, 2H), 2.07 (s, 7H), 1.89 (ddd, J=16.8, 12.7, 6.3 Hz, 5H), 1.58 (s, 4H), 1.42 (s, 3H). LC-MS (ES⁺): 645.6 [M+H]⁺.

Synthesis of Compound 83
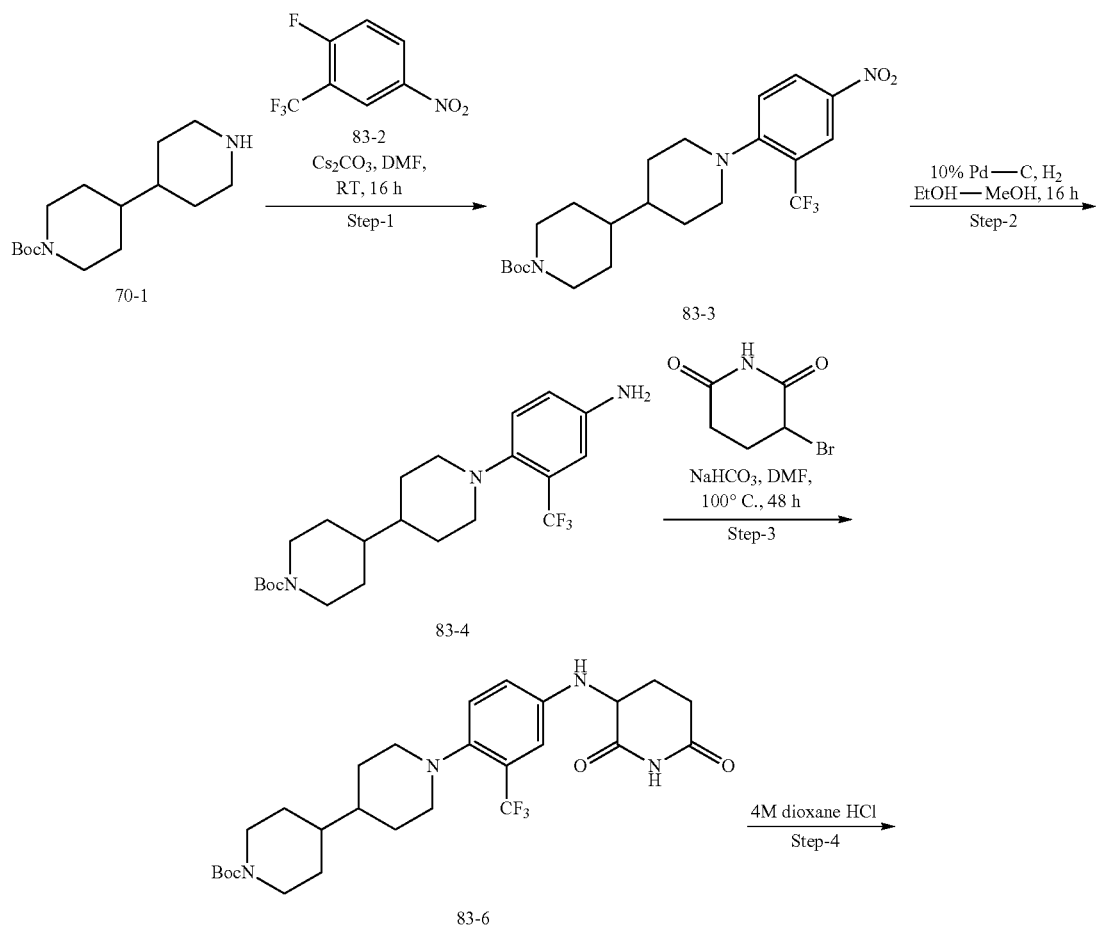
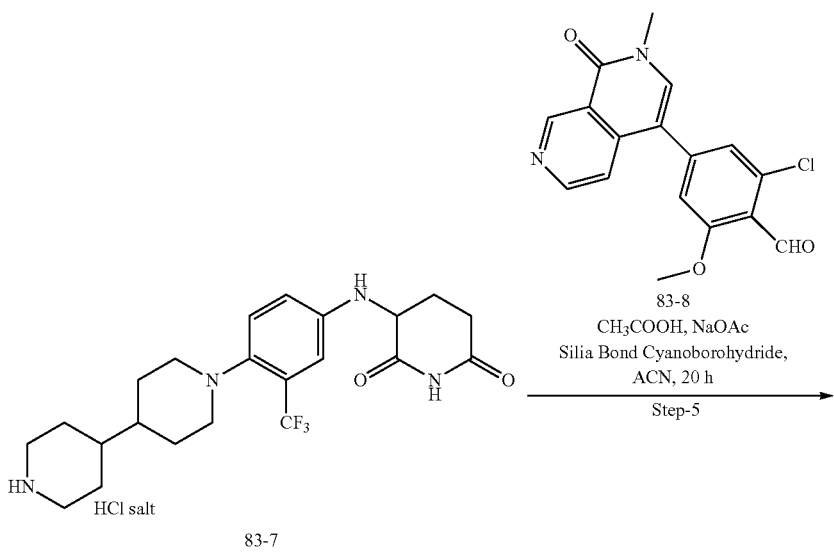

-continued

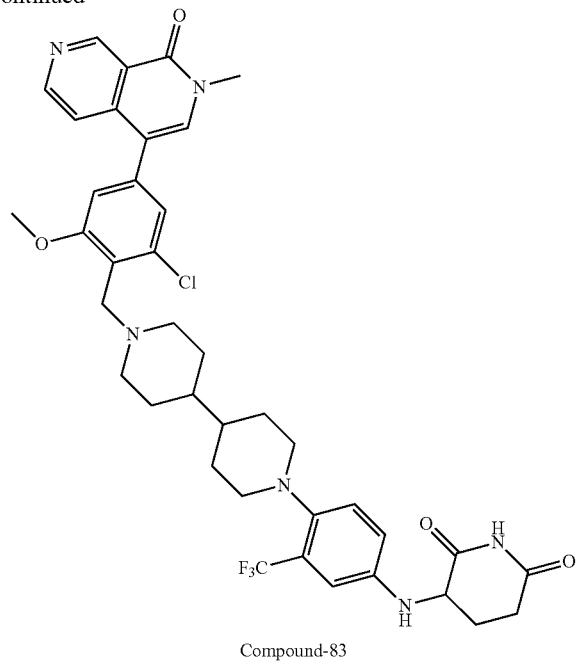

Compound-83

Step-1: To a stirred solution of compound tert-butyl 4-(4-piperidyl) piperidine-1-carboxylate 70-1 (2 g, 7.45 mmol) in DMF (15 mL) was added cesium carbonate (2.43 g, 7.45 mmol) and stirred for 15 min before adding 1-fluoro-4-nitro-2-(trifluoromethyl) benzene 83-2 (0.247 g, 7.45 mmol) The reaction mixture was allowed to stir at RT for 16 h while monitoring by TLC. After completion the reaction mass was quenched with ice flakes and the precipitated solid was filtered to tert-butyl 4-[1-[4-nitro-2-(trifluoromethyl)phenyl]-4-piperidyl] piperidine-1-carboxylate 83-3 (2.8 g, 4.28 mmol, 82% yield, 98% purity) as a yellow semi-solid. $^1$H NMR (400 MHz, CDCl$_3$) δ 8.49 (d, J=2.4 Hz, 1H), 8.29 (dd, J$_1$=2.8 Hz, J$_2$=9.2 Hz, 1H), 7.21 (d, J=9.2 Hz, 1H), 4.14 (bs, 2H), 3.43 (d, J=12.4 Hz, 2H), 2.82 (t, J=11.6 Hz, 2H), 2.66 (t, J=11.6 Hz, 2H), 1.81 (d, J=12.4 Hz, 2H), 1.72 (d, J=12 Hz, 2H), 1.44-1.46 (m, 11H), 1.28 (m, 4H) LC-MS (ES$^+$): m/z 458.31 [M+H]$^+$ Step-2: To a stirred solution of tert-butyl 4-[1-[4-nitro-2-(trifluoromethyl)phenyl]-4-piperidyl]piperidine-1-carboxylate 83-3 (2.5 g, 5.46 mmol) in Methanol (10 mL) and Ethanol (10 mL) was added 10% wet Pd-C (2.33 g, 21.86 mmol) and the reaction mixture was stirred under H$_2$ balloon pressure for 16 h, while monitoring by LCMS and TLC. The reaction mixture was filtered through Celite bed and the filtrate was concentrated to afford tert-butyl 4-[1-[4-amino-2-(trifluoromethyl)phenyl]-4-piperidyl]piperidine-1-carboxylate 83-4 (2 g, 4.67 mmol, 85.61% yield, 99% purity) as an yellow solid. This was taken to the next step without any purification. $^1$H NMR (400 MHz, DMSO-d$_6$) δ 7.18 (d, J=8.8 Hz, 1H), 6.79 (d, J=2.8 Hz, 1H), 6.75 (dd, J$_1$=2.4 Hz, J$_2$=8.4 Hz, 1H), 5.29 (bs, 2H), 3.96 (d, J=11.6 Hz, 2H), 2.79 (d, J=11.2 Hz, 2H), 2.67-2.56 (m, 2H), 1.68-1.65 (m, 4H), 1.39 (s, 9H), 1.29 (d, 4H), 1.29-1.19 (m, 4H), LC-MS (ES$^+$): m/z 428.37 [M+H]$^+$ Step-3: To a stirred solution of tert-butyl 1'-(4-amino-2-(trifluoromethyl)phenyl)-[4,4'-bipiperidine]-1-carboxylate 83-4 (2 g, 4.68 mmol) in DMF (40 mL) were added 3-bromopiperidine-2,6-dione (2.69 g, 14.04 mmol), NaHCO$_3$ (5.38 g, 28.07 mmol) and stirred at 100° C. for 48 h, while monitoring the reaction by LCMS and TLC. After 48 h, the reaction was quenched with ice cold water (100 mL) and extracted with EtOAc (3×150 mL). The combined organic layer was dried over anhydrous Na$_2$SO$_4$ and concentrated to afford crude compound. Crude compound was purified by (silica gel mesh 100-200, and product eluted with 50% ethyl acetate in pet ether-neat ethyl acetate) column chromatography to afford tert-butyl 1'-(4-((2,6-dioxopiperidin-3-yl)amino)-2-(trifluoromethyl)phenyl)-[4,4'-bipiperidine]-1-carboxylate 83-6 (0.65 g, 1.17 mmol, 25.02% yield, 84.14% purity) as a purple solid. H NMR (400 MHz, DMSO-d$_6$) δ 10.78 (s, 1H), 7.26 (d, J=8.6 Hz, 1H), 6.88 (q, J=6.3 Hz, 1H), 6.15 (d, J=7.9 Hz, 1H), 4.44-4.37 (m, 1H), 3.95-4.1 (m, 3H), 3.31-254 (m, 11H), 2.07-1.99 (m, 1H), 1.90-1.6 (m, 7H), 1.26-1.14 (m, 7H), 1.08-1.00 (m, 3H). LC-MS (ES$^+$): m/z 539.98 [M+H]$^+$ Step-4: To a tert-butyl 4-[1-[4-[(2,6-dioxo-3-piperidyl)amino]-2-(trifluoromethyl)phenyl]-4-piperidyl]piperidine-1-carboxylate 83-6 (0.65 g, 1.21 mmol) was added 4M HCl in dioxane (10 ml, 24.14 mmol) at 0° C. and the reaction mixture was stirred at RT for 2 h, while monitoring by TLC. After consuming the starting material, the reaction mixture was concentrated under reduced pressure, residue triturated with diethyl ether (2×50 mL) and the solid precipitated out was dried to afford 3-[4-[4-(4-piperidyl)-1-piperidyl]-3-(trifluoromethyl)anilino]piperidine-2,6-dione.HCl salt 7 (0.7 g) as a brown solid. This was taken to next step without any purification. LC-MS (ES$^+$): m/z 439.33 [M+H]$^+$ Step-5: To a stirred solution of 3-[4-[4-(4-piperidyl)-1-piperidyl]-3-(trifluoromethyl)anilino]piperidine-2,6-dione 83-7 (0.073 g, 0.167 mmol) in ethylene dichloride (5 mL): Methanol (5 mL) was added 4 Å molecular sieves (0.1 g), Acetic acid (0.011 g, 0.167 mmol) and Sodium acetate, anhydrous (0.027 g, 0.334 mmol). The resulting solution was stirred for 10 min, added 2-chloro-6-methoxy-4-(2-methyl-1-oxo-2,7-naphthyridin-4-yl)benzaldehyde 83-8 (0.063 g, 0.193 mmol) and allowed to reflux for 3 h. After 3 h, the reaction mass was cooled to RT and SiliaBond Cyanoborohydride (0.048 g, 0.835 mmol) was added and allowed to stir at RT for 16 h, while monitoring by LCMS. After completion, the reaction mixture was evaporated under reduced pressure and purified by prep HPLC to obtain 3-[4-[4-[1-[[2-chloro-6-methoxy-4-(2-methyl-1-oxo-2,7-naphthyridin-4-yl)phenyl]methyl]-4-piperidyl]-1-piperidyl]-3-(trifluoromethyl) anilino] piperidine-2,6-dione.TFA salt (21 mg, 0.023 mmol, 13.97% yield, 96.33% purity) as a white solid. $^1$H NMR (400 MHz, DMSO-$d_6$) δ 10.79 (s, 1H), 9.48 (s, 1H), 9.09 (bs, 1H), 8.77 (d, J=5.3 Hz, 1H), 7.97 (s, 1H), 7.56 (d, J=5.7 Hz, 1H), 7.33-7.22 (m, 3H), 6.91-6.86 (m, 2H), 4.42-4.34 (m, 3H), 3.96 (s, 3H), 3.62 (s, 3H), 3.52 (d, J=11.9 Hz, 2H), 3.30-3.15 (m, 2H), 2.89-2.60 (m, 6H), 2.08-2.05 (m, 1H), 1.92-1.89 (m, 3H), 1.70-1.23 (m, 8H). LC-MS (ES$^+$): m/z 751.59 [M+H]$^+$.

Compound 84 was prepared following the synthesis of Compound 83.

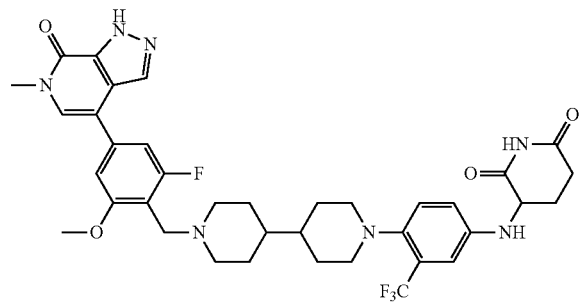 [SMILES: COc1cc(-c2cn(C)c(=O)c3[nH]ncc23)cc(F)c1CN1CCC(C2CCN(c3ccc(NC4CCC(=O)NC4=O)cc3C(F)(F)F)CC2)CC1]

$^1$H NMR (400 MHz, DMSO-$d_6$) δ 14.31 (s, 1H), 11.90 (s, 1H), 10.78 (s, 1H), 9.10 (s, 1H), 8.20 (s, 1H), 7.70 (s, 1H), 7.25-7.20 (m, 2H), 6.90-6.85 (m, 2H), 6.16 (d, J=7.6 Hz, 1H), 4.62-4.27 (m, 5H), 4.39-4.33 (m, 2H), 3.99 (s, 3H), 3.62-3.44 (m, 3H), 3.02-2.99 (m, 2H), 2.82-2.60 (m, 4H), 2.09-2.04 (m, 1H) 1.93-1.87 (m, 5H), 1.75-1.69 (m, 2H), 1.47-1.42 (bs, 2H), 1.26-1.15 (m, 2H). LC-MS (ES$^+$): m/z 724.64 [M+H]$^+$.

Compound 85 was prepared following the synthesis of Compound 83.

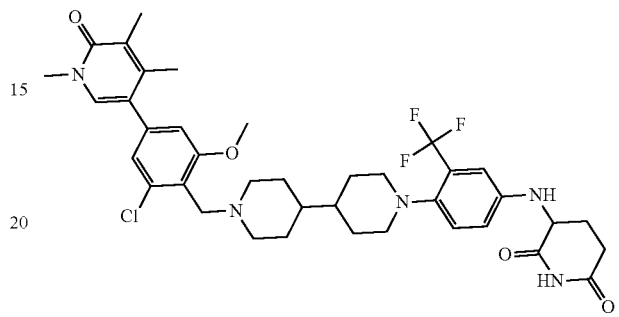

$^1$H NMR (400 MHz, DMSO-$d_6$) δ 10.78 (s, 1H), 7.57 (s, 1H), 7.27 (d, J=8.6 Hz, 1H), 6.95 (d, J=1.6 Hz, 1H), 6.90-6.84 (m, 3H), 6.14 (d, J=8.0 Hz, 1H), 4.38-4.33 (m, 1H), 3.82 (s, 3H), 3.54 (s, 2H), 3.45 (s, 3H), 2.86-2.82 (m, 4H), 2.73-2.57 (m, 4H), 2.05 (s, 9H), 1.93-1.89 (m, 1H), 1.70-1.62 (m, 4H), 1.24-1.07 (m, 6H). LC-MS (ES$^+$): m/z 728.57 [M+H]$^+$

Compound 86 was prepared following the synthesis of Compound 83.

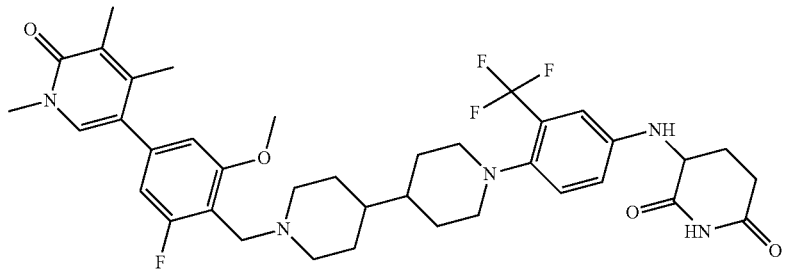 [SMILES: COc1cc(-c2cn(C)c(=O)c(C)c2C)cc(F)c1CN1CCC(C2CCN(c3ccc(NC4CCC(=O)NC4=O)cc3C(F)(F)F)CC2)CC1]

$^1$H NMR (400 MHz, DMSO-$d_6$) δ 10.77 (s, 1H), 8.21 (s, 1H), 7.56 (s, 1H), 7.26 (d, J=8.7 Hz, 1H), 6.90-6.84 (m, 2H), 6.75-6.713 (m, 2H), 6.14 (d, J=7.9 Hz, 1H), 4.36-4.34 (m, 1H), 3.82 (s, 3H), 3.49 (s, 2H), 3.45 (s, 3H), 2.86-2.54 (m, 8H), 2.07 (s, 7H), 1.96-1.85 (m, 3H), 1.65 (t, J=14.6 Hz, 4H), 1.22-1.01 (m, 6H). LC-MS (ES$^+$): m/z 712.74 [M+H]$^+$.

Compound 87 was prepared following the synthesis of Compound 83.

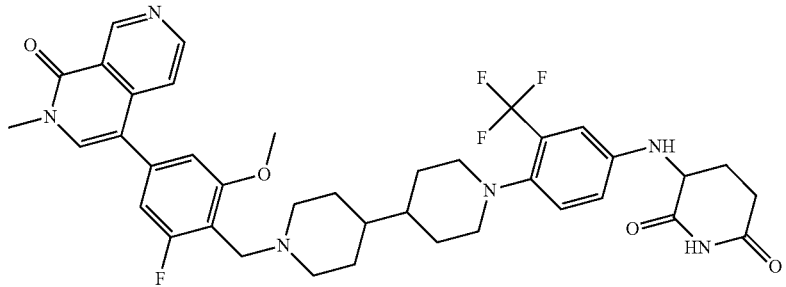 [SMILES: COc1cc(-c2cn(C)c(=O)c3cnccc23)cc(F)c1CN1CCC(C2CCN(c3ccc(NC4CCC(=O)NC4=O)cc3C(F)(F)F)CC2)CC1]

$^1$H NMR (400 MHz, DMSO-d$_6$) δ 10.78 (s, 1H), 9.48 (s, 1H), 9.25 (s, 1H), 8.76 (d, J=6 Hz, 1H), 7.97 (s, 1H), 7.60 (d, J=5.6 Hz, 1H), 7.26 (d, J=8.8 Hz, 1H), 7.13-7.11 (m, 2H), 6.91-6.86 (m, 2H), 6.19 (bs, 1H), 4.42-4.38 (m, 3H), 3.95 (s, 3H), 3.61 (s, 3H), 3.50-3.47 (m, 2H), 3.09-3.06 (m, 2H), 2.89-2.61 (m, 6H), 2.11-2.07 (m, 1H), 1.92-1.69 (m, 5H), 1.45-1.40 (m, 3H), 1.32-1.11 (m, 3H). LC-MS (ES$^+$): m/z 735.29. [M+H]$^+$
Synthesis of Compound 88
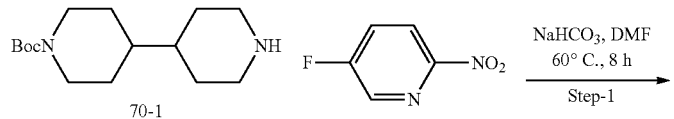
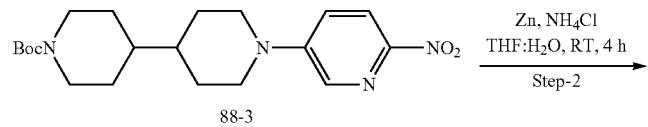
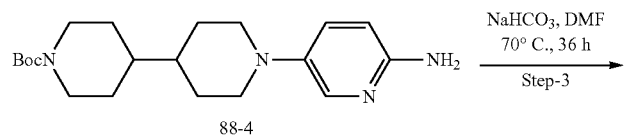
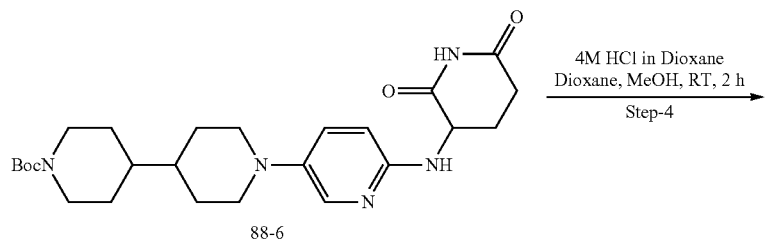
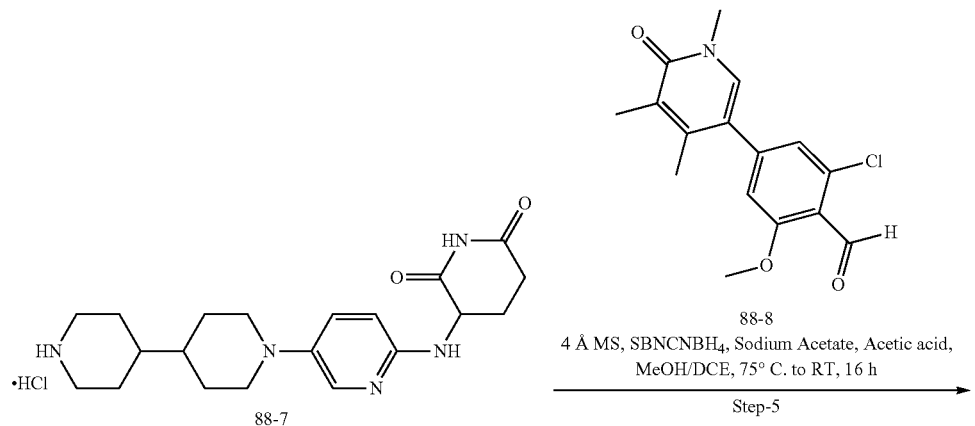

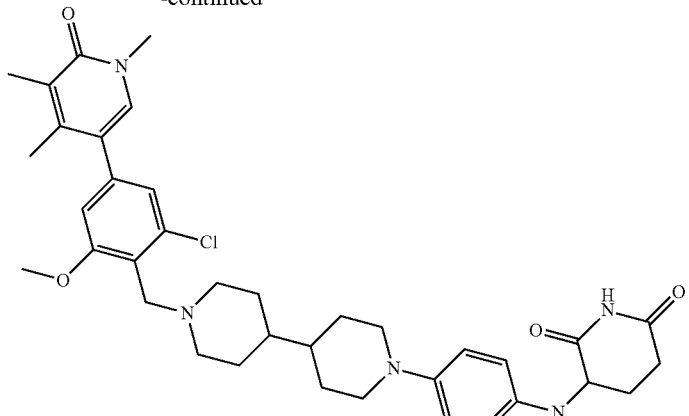

Compound 88

Step-1: To a solution of tert-butyl 4-(4-piperidyl)piperidine-1-carboxylate (0.7 g, 2.61 mmol) and 5-fluoro-2-nitropyridine (0.37 g, 2.61 mmol) in DMF (7 mL) was added sodium bicarbonate (0.44 g, 5.22 mmol) and reaction mixture was stirred at 60° C. for 8 hr. Progress of reaction was monitored by TLC. After completion of the reaction, reaction mixture was diluted with cold water and extracted with ethyl acetate (3×150 mL). Combined organic layer was dried over anhydrous Na$_2$SO$_4$, filtered and concentrated under vacuo. Crude product was purified by column chromatography (silica gel mesh 100-200, 20-40% ethyl acetate in pet ether) to afforded tert-butyl 4-[1-(6-nitro-3-pyridyl)-4-piperidyl]piperidine-1-carboxylate (0.63 g, 1.61 mmol, 61.79% yield, 99.88% purity) as a yellow solid. LC-MS (ES$^+$): m/z 413.25 [M+Na]$^+$ Step-2: To a solution of tert-butyl 4-[1-(6-nitro-3-pyridyl)-4-piperidyl]piperidine-1-carboxylate (0.63 g, 1.61 mmol) in Water (2 mL) and THF (8 mL) was added zinc (844.01 mg, 12.91 mmol) and ammonium chloride (690.43 mg, 12.91 mmol). The reaction mixture was stirred at 25° C. for 4 hr. Progress of reaction was monitored by TLC. After completion of the reaction, reaction mixture was filtered through Celite bed and filtrate was concentrated under vacuo. The crude product was diluted with water (100 mL) and extracted with DCM (3×50 mL). Combined organic layer dried with anhy. Na$_2$SO$_4$, filtered and concentrated under vacuo to afforded tert-butyl 4-[1-(6-amino-3-pyridyl)-4-piperidyl]piperidine-1-carboxylate (0.53 g, 90.85% yield, 99.7% purity) an orange solid. LC-MS (ES$^+$): m/z 361.38 [M+H]$^+$ Step-3: To a stirred solution of tert-butyl 4-[1-(6-amino-3-pyridyl)-4-piperidyl]piperidine-1-carboxylate (0.52 g, 1.44 mmol) in DMF (7 mL) was added sodium bicarbonate (1.21 g, 14.42 mmol) and 3-bromopiperidine-2,6-dione (1.38 g, 7.21 mmol). The reaction mixture was stirred at 70° C. for 48 hr. Progress of the reaction was monitored by TLC and LCMS. After completion of the reaction, reaction mixture was diluted with the cold water (100 mL) and extracted with ethyl acetate (2×100 mL). Combined organic layer was dried with anhydrous Na$_2$SO$_4$, filtered and concentrated under vacuo. Crude product was purified by column chromatography (silica gel mesh 100-200, 20-40% ethyl acetate in pet ether) to afforded tert-butyl 4-[1-[6-[(2,6-dioxo-3-piperidyl)amino]-3-pyridyl]-4-piperidyl]piperidine-1-carboxylate (0.25 g, 31.75% yield, 86.39%) as a pale green solid. LC-MS (ES$^+$): m/z 472.32 [M+H]$^+$ Step-4: To a suspension of tert-butyl 4-[1-[6-[(2,6-dioxo-3-piperidyl)amino]-3-pyridyl]-4-piperidyl]piperidine-1-carboxylate (0.23 g, 0.954 mmol) in dioxane (4 mL) was added 4 M HCl in Dioxane (1 mL) solution and methanol (0.5 mL) (Methanol added for solubility) and the reaction mixture was stirred at 25° C. for 2 hr. Progress of the reaction was monitored by LCMS. After completion of the reaction, solvents were removed under vacuo and the product was triturated with diethyl ether (5 ml×2) to afforded 3-[[5-[4-(4-piperidyl)-1-piperidyl]-2-pyridyl]amino]piperidine-2,6-dione (0.20 g, 99.48% yield, 98.96% purity) as a HCl salt and an off white solid. LC-MS (ES$^+$): m/z 372.32 [M+H]$^+$ Step-5: To a stirred solution of 2-chloro-6-methoxy-4-(1,4,5-trimethyl-6-oxo-3-pyridyl)benzaldehyde (55 mg, 0.180 mmol) and 3-[[5-[4-(4-piperidyl)-1-piperidyl]-2-pyridyl]amino]piperidine-2,6-dione (73.38 mg, 0.180 mmol) in DCE (4 mL) and methanol (4 mL) was added sodium acetate, anhydrous (44.27 mg, 0.540 mmol), molecular sieves (300 mg, 0.180 mmol) and acetic acid (16.20 mg, 0.270 mmol). Reaction mixture was stirred at 70° C. for 5 hr. Reaction mixture was cooled to room temperature and added Si-CBH (60 mg)). Reaction mixture was stirred at 25° C. for 16 hr. Progress of the reaction was monitored by LCMS. After completion of the reaction, reaction mixture filtered, and residue was washed with methanol. Organic layer was concentrated under vacuo and the crude product was purified by RP-Prep-HPLC to afforded 3-[[5-[4-[1-[[2-chloro-6-methoxy-4-(6-methyl-7-oxo-1H-pyrazolo[3,4-c]pyridin-4-yl)phenyl]methyl]-4-piperidyl]-1-piperidyl]-2-pyridyl]amino]piperidine-2,6-dione (33.4 mg, 30.34% yield, 99.39% purity) as a TFA salt and as a pale yellow solid. $^1$H NMR (400 MHz, DMSO-d$_6$) δ 11.05 (s, 1H), 8.99 (bs, 1H), 7.86 (bs, 1H), 7.56 (s, 2H), 7.22 (m, 3H), 4.67 (bm, 1H), 4.37 (bs, 2H), 3.92 (s, 3H), 3.52 (s, 3H), 3.19 (m, 6H), 2.73-2.59 (m, 4H), 2.11 (m, 8H), 1.89-1.75 (m, 4H), 1.52-1.24 (m, 6H). LC-MS (ES$^+$): m/z 661.59 [M+H]$^+$.

Compound 89 was prepared following the synthesis of Compound 88.

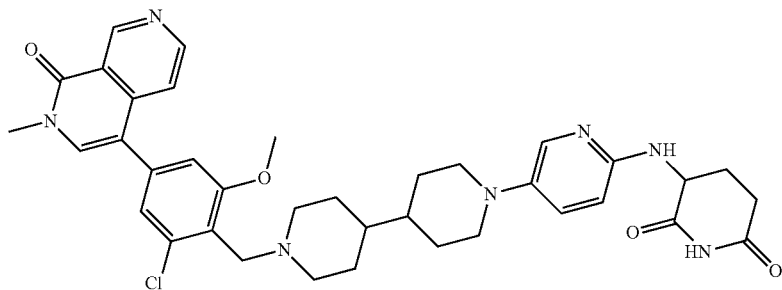 [SMILES: COc1cc(-c2cn(C)c(=O)c3cnccc23)cc(Cl)c1CN1CCC(C2CCN(c3ccc(NC4CCC(=O)NC4=O)nc3)CC2)CC1]
¹H NMR (400 MHz, DMSO-d₆) δ 11.05 (s, 1H), 9.48 (s, 1H), 9.04 (bs, 1H), 8.77 (d, J=5.6 Hz, 1H), 7.95 (bs, 2H), 7.54 (bd, 1H), 7.33 (d, J=1.2 Hz, 1H), 7.27 (s, 1H), 7.02 (bs, 1H), 4.68 (bs, 1H), 4.42 (bd, J=2.0 Hz, 2H), 3.95 (s, 3H), 3.61 (s, 3H), 3.54-3.51 (m, 4H), 3.32-3.16 (m, 2H), 2.77-2.61 (m, 4H), 2.11 (m, 2H), 1.92-1.77 (bd, J=12.8 Hz, 2H), 1.80 (bs, J=11.6 Hz, 2H), 1.54-1.32 (m, 6H); LC-MS (ES⁺): m/z 684.58 [M+H]⁺
Compound 90 was prepared following the synthesis of Compound 88.
¹H NMR (400 MHz, DMSO-d₆) δ δ 11.00 (s, 1H), 10.67 (s, 1H), 8.25 (s, 1H), 8.13-7.89 (m, 2H), 7.58 (s, 2H), 7.46 (dd, J=8.0, 1.7 Hz, 1H), 7.39 (p, J=1.8 Hz, 1H), 7.02 (d, J=9.6 Hz, 1H), 4.81 (d, J=6.6 Hz, 0H), 4.38 (d, J=4.1 Hz, 2H), 3.55 (d, J=11.2 Hz, 2H), 3.46 (s, 3H), 3.40 (d, J=11.4 Hz, 2H), 3.02 (d, J=11.4 Hz, 2H), 2.91-2.53 (m, 4H), 2.19-1.97 (m, 8H), 1.89 (d, J=13.1 Hz, 2H), 1.79 (d, J=12.5 Hz, 2H), 1.70-1.51 (m, 2H), 1.42 (s, 2H), 1.26 (d, J=22.9 Hz, 2H). LC-MS (ES⁺): m/z 681.6 [M+H]⁺.
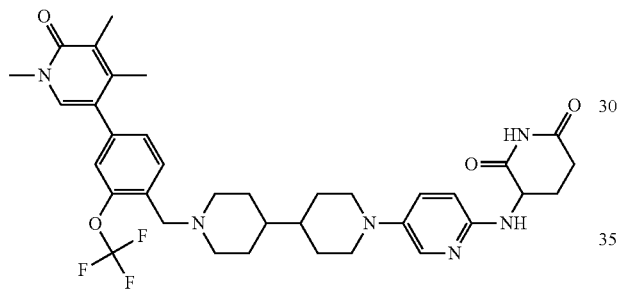
Synthesis of Compound 91
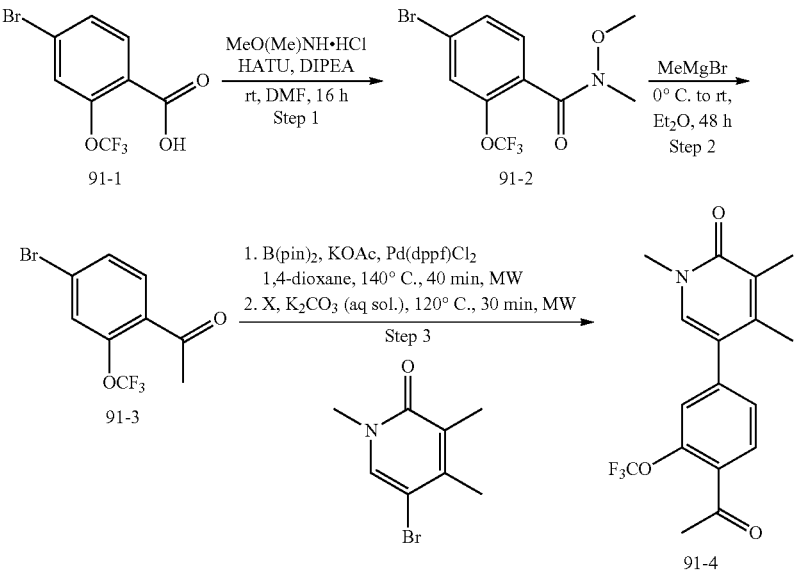

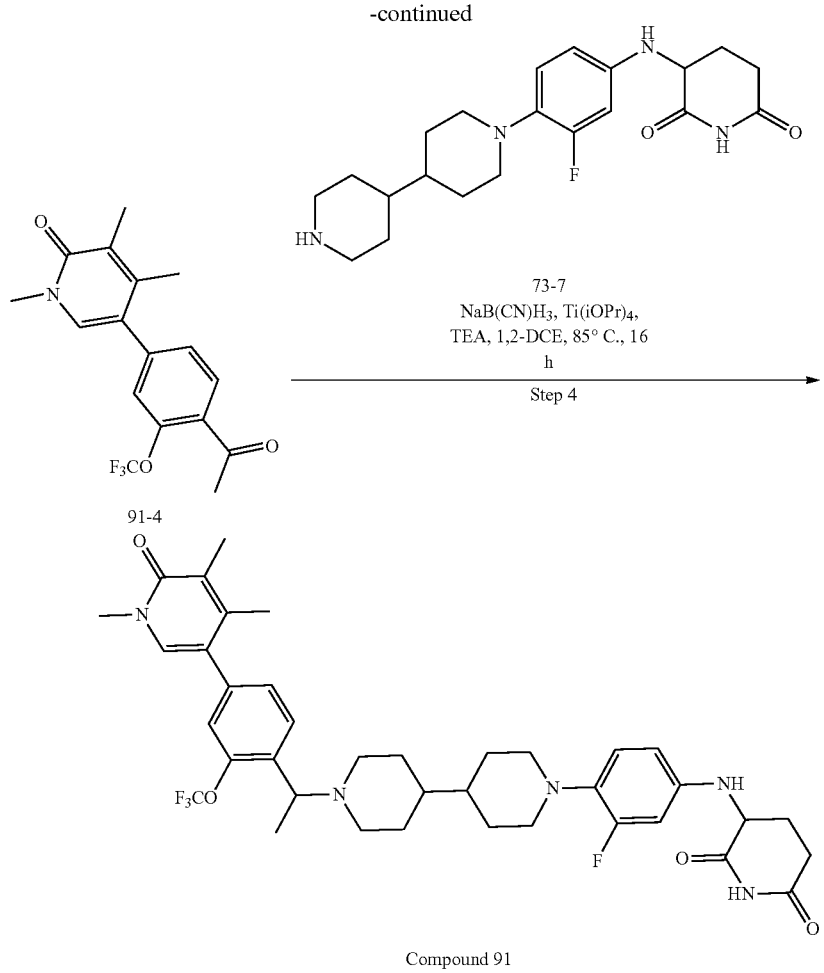

Compound 91

Step 1: Initially 4-bromo-2-(trifluoromethoxy)benzoic acid (5 g, 17.54 mmol) and N-methoxymethanamine (1.71 g, 17.54 mmol, 021) were suspended in DMF (49.31 mL) before DIPEA (6.80 g, 52.63 mmol, 9.17 mL) and HATU (6.67 g, 17.54 mmol) were added sequentially at room temperature and the mixture was stirred for 48 h. Upon reaction completion the mixture was diluted with $H_2O$ (25 mL) and extracted with EA (50 mL×3), before being washed with LiCl (5% aq. Solution, 2×50 mL), brine (1×25 mL) and being dried over $Na_2SO_4$, filtered and concentrated to a residue which was purified via flash column chromatography (Hexanes/EA up to 50%) to give 4-bromo-N-methoxy-N-methyl-2-(trifluoromethoxy)benzamide as a solid. Yield 5.14 g, 89%; LC-MS (ES+): m/z 328.1[M+H]+.

Step 2: Initially 4-bromo-N-methoxy-N-methyl-2-(trifluoromethoxy)benzamide (2.65 g, 8.07 mmol) was dissolved in Ether (7.14 mL) and cooled to 0° C. under an argon atmosphere. Methylmagnesium bromide (3 M in $Et_2O$, 4.03 mL) was then added dropwise and the mixture was allowed to warm to room temperature and stirred for 48 h. Upon reaction completion sat. ammonium chloride (10 mL) was added and mixture was extracted with EA, before being dried with brine and $Na_2SO_4$, filtered and concentrated to a residue which was purified via flash column chromatography (Hexanes/EA up to 50%) to give 1-[4-bromo-2-(trifluoromethoxy)phenyl]ethanone as a solid. Yield—1.988 g, 87%; LC-MS (ES+): m/z 284.0 [M+H]+.

Step 3: Initially cyclopentyl(diphenyl)phosphane; dichloropalladium; iron (51.70 mg, 70.66 umol), 1-[4-bromo-2-(trifluoromethoxy)phenyl]ethenone (200 mg, 706.61 umol) Bis(pinacolato) diboron (215.32 mg, 847.93 umol), Potassium Acetate (208.04 mg, 2.12 mmol, 132.51 uL) were charged into a MW vial (2-5 mL) and suspended under an argon atmosphere in 1,4-Dioxane (8.39 mL) and heated in a MW at 140° C. for 40 mins. The suspension then had 4-bromo-1-[(4-methoxyphenyl)methyl]-6-methyl-pyrazolo[3,4-c]pyridin-7-one (134.62 mg, 386.63 umol) added under argon along with Potassium Carbonate (2 M, 2 eq) and reheated at 120° C. for 30 mins before being checked by LCMS. Upon reaction completion the mixture was filtered through a Celite pad and washed with EA/DCM. The filtrate was then concentrated to a residue which was purified via flash column chromatography (Hexanes/EA up to 100%) to give 5-[4-acetyl-3-(trifluoromethoxy)phenyl]-1,3,4-trimethyl-pyridin-2-one (181 mg, 533.44 umol, 75.49% yield). LC-MS (ES+): m/z 340.3 [M+H]+.

Step 4: Initially 5-[4-acetyl-3-(trifluoromethoxy)phenyl]-1,3,4-trimethyl-pyridin-2-one (45 mg, 132.62 umol) Titanium(IV) isopropoxide, 97+% (113.08 mg, 397.87 umol, 118.41 uL) and 3-[3-fluoro-4-[4-(4-piperidyl)-1-piperidyl]anilino]piperidine-2,6-dione (91.79 mg, 198.93 umol, 022) were charged into a reaction vial and dissolved in 1,2-DCE (2.99 mL) before TEA (46.97 mg, 464.18 umol, 64.70 uL) was added in one portion and the mixture was allowed to stir overnight at 85° C. Upon reaction completion, the mixture was concentrated to a residue and purified via reverse phase flash column chromatography to (Water/MeCN 1:0 to 1:1, 0.1% TFA) and lyophilized to afford the product Compound 91 as a TFA salt Yield—42 mg, 36%; $^1$H NMR (400 MHz, DMSO-$d_6$) δ 10.80 (s, 1H), 9.78 (s, 1H), 7.89 (d, J=8.2 Hz, 1H), 7.58 (s, 1H), 7.52 (dd, J=8.1, 1.8 Hz, 1H), 7.42 (t, J=1.8 Hz, 1H), 7.13 (s, OH), 6.70-6.56 (m, 1H), 6.51 (d, J=8.9 Hz, 1H), 4.74 (s, 1H), 4.33 (dd, J=11.8, 4.8 Hz, 1H), 3.79 (d, J=11.5 Hz, 1H), 3.47 (s, 3H), 3.36 (s, 2H), 3.21 (d, J=11.4 Hz, 1H), 3.12-2.87 (m, 2H), 2.82-2.52 (m, 3H), 2.06 (s, 6H), 2.01-1.08 (m, 17H). LC-MS (ES$^+$): m/z 712.7[M+H]$^+$.

Compound 92 was prepared following the synthesis of Compound 91.

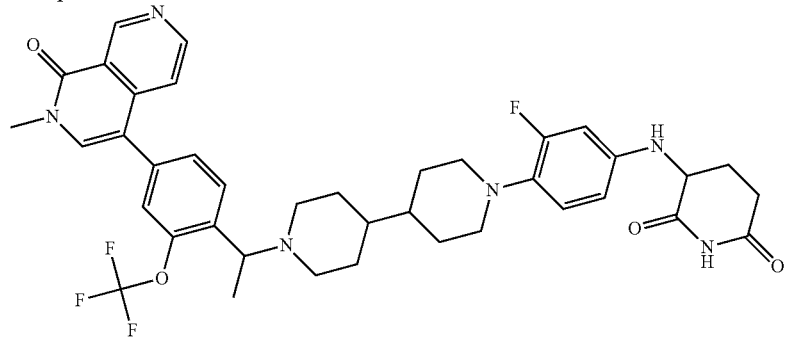

$^1$H NMR (400 MHz, DMSO-$d_6$) δ 10.80 (s, 1H), 9.72 (s, 1H), 9.48 (s, 1H), 8.77 (d, J=5.7 Hz, 1H), 8.03-7.92 (m, 2H), 7.71 (dd, J=8.2, 1.8 Hz, 1H), 7.61 (t, J=1.8 Hz, 1H), 7.50 (d, J=5.8 Hz, 1H), 7.09 (d, J=18.7 Hz, 1H), 6.58 (d, J=14.9 Hz, 1H), 6.49 (d, J=8.7 Hz, 1H), 4.80 (s, 1H), 4.31 (dd, J=11.3, 4.7 Hz, 1H), 3.81 (d, J=11.8 Hz, 1H), 3.61 (s, 3H), 3.30 (t, J=13.5 Hz, 4H), 3.03 (s, 1H), 2.90-2.54 (m, 2H), 2.12-2.02 (m, 1H), 2.02-0.98 (m, 16H). LC-MS (ES$^+$): m/z 735.7[M+H]$^+$.

Compound 93 was prepared following the synthesis of Compound 91.

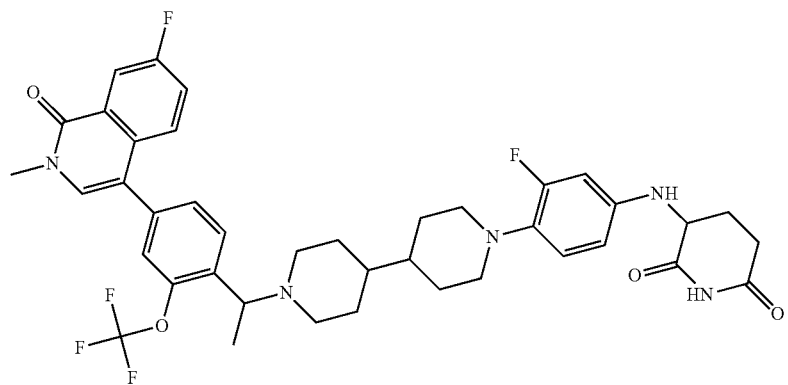 [SMILES: CC(c1ccc(-c2cn(C)c(=O)c3cc(F)ccc23)cc1OC(F)(F)F)N1CCC(C2CCN(c3ccc(NC4CCC(=O)NC4=O)cc3F)CC2)CC1]

$^1$H NMR (400 MHz, DMSO-$d_6$) δ 10.80 (s, 1H), 9.70 (s, 1H), 8.14-7.87 (m, 2H), 7.82-7.49 (m, 5H), 7.06 (s, 1H), 6.53 (dd, J=35.1, 11.9 Hz, 2H), 4.79 (d, J=7.5 Hz, 1H), 4.31 (dd, J=11.7, 4.8 Hz, 1H), 3.81 (d, J=11.6 Hz, 1H), 3.59 (s, 3H), 3.29 (d, J=12.2 Hz, 3H), 3.04 (d, J=11.2 Hz, 1H), 2.96-2.52 (m, 5H), 2.16-1.61 (m, 9H), 1.61-1.16 (m, 6H). LC-MS (ES$^+$): m/z 752.7 [M+H]$^+$.

Synthesis of Compound 94
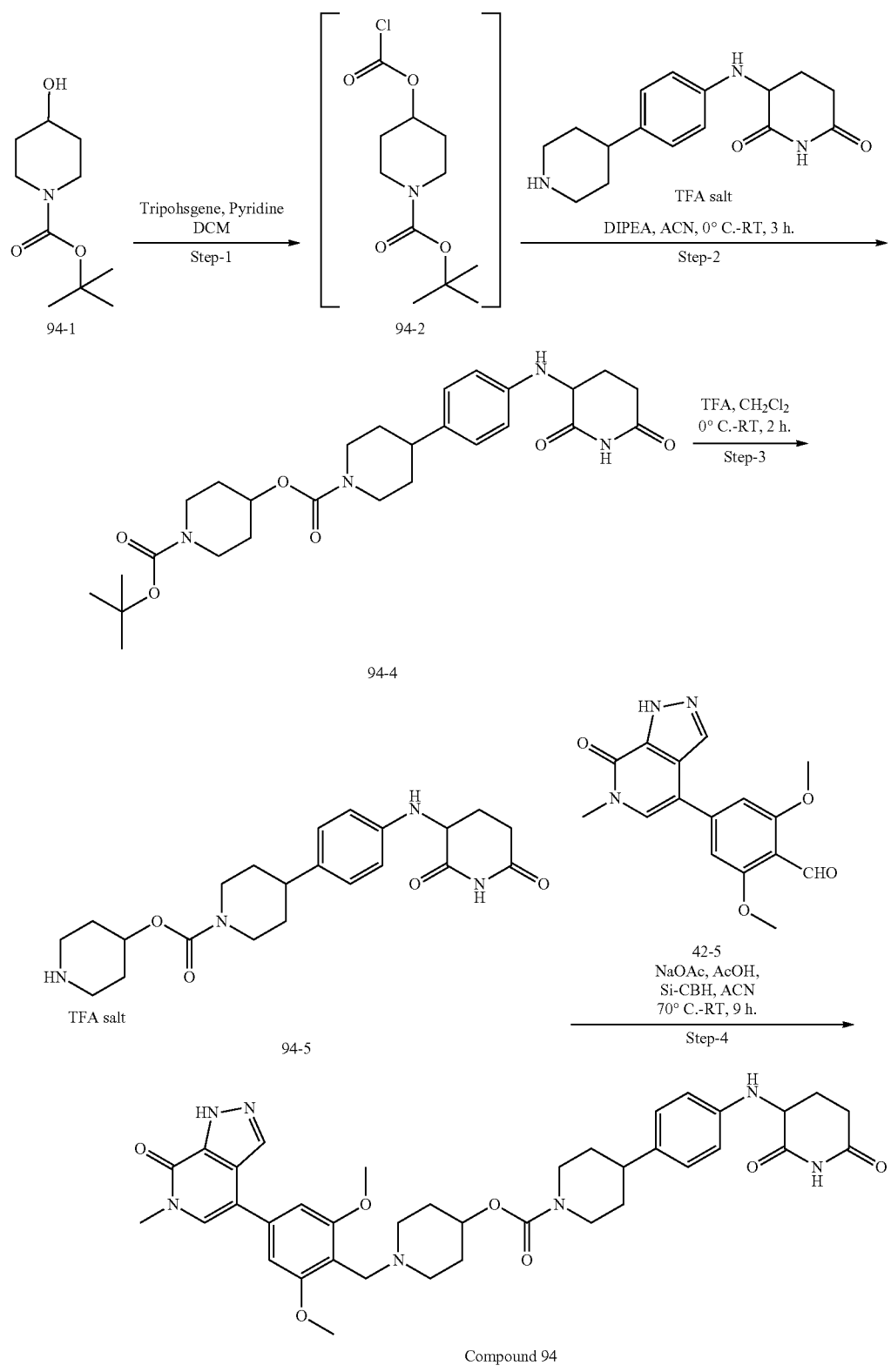

Step-1: To a solution of tert-butyl 4-hydroxypiperidine-1-carboxylate 94-1 (1 g, 4.97 mmol in $CH_2Cl_2$ (30 mL) were added Pyridine (0.629 g, 7.95 mmol) at 0° C. followed by solution of Triphosgene (634.00 mg, 2.14 mmol) in $CH_2Cl_2$ (10 mL) slowly over the period of 10 min. RM was allowed to stir at RT for 1 h while monitoring by TLC. The reaction mixture was evaporated to afford tert-butyl 4-chlorocarbonyloxypiperidine-1-carboxylate 94-2 (1.2 g, 77.84% yield, 85% purity based on TLC) as a yellow semi-solid. This was taken for the next step without further purification.

Step-2: A solution of 3-[4-(4-piperidyl)anilino]piperidine-2,6-dione (0.400 g, 1.39 mmol) in dry ACN (40 mL) was cooled to 0° C. and added DIPEA (0.540 g, 4.18 mmol). After 10 min, a solution of tert-butyl 4-chlorocarbonyloxypiperidine-1-carboxylate 94-2 (0.367 g, 1.39 mmol) in dry ACN (10 ml) was added at 0° C. and after addition RM allowed to stir at RT for 3 h while monitoring by TLC and LCMS. The reaction mass was quenched with $H_2O$ (50 ml) and extracted with $CH_2Cl_2$ (2×70 ml). The organic layer was washed with brine (25 ml), dried over $Na_2SO_4$ and evaporated under reduced pressure, crude residue triturated with ether (20 ml) to afford (1-tert-butoxycarbonyl-4-piperidyl) 4-[4-[(2,6-dioxo-3-piperidyl)amino] phenyl]piperidine-1-carboxylate 94-4 (500 mg, 59.33% yield, 85% purity) as a yellow solid. LC-MS (ES$^+$): m/z 514.40 [M+H]$^+$ 514.4

Step-3: A solution of (1-tert-butoxycarbonyl-4-piperidyl) 4-[4-[(2,6-dioxo-3-piperidyl)amino]phenyl]piperidine-1-carboxylate 94-4 (0.5 g, 0.972 mmol in dry $CH_2Cl_2$ (2 mL) was added TFA (1.1. g, 8.53 mmol) at 0° C. The reaction mixture was slowly warmed to RT and allowed to stir for 2 h while monitoring the reaction by TLC. Most of the solvent was removed under reduced pressure and crude compound was purified by reverse phase column chromatography (C18/30 g column using 0.1% formic acid in MeCN:$H_2O$) to afford 4-piperidyl 4-[4-[(2,6-dioxo-3-piperidyl)amino]phenyl]piperidine-1-carboxylate, TFA salt 94-5 (150 mg, 27.75% yield, 95% purity) as blue solid. LC-MS (ES$^+$): m/z 415.46 [M+H]$^+$ Step-4: To a stirred solution of 4-piperidyl 4-[4-[(2,6-dioxo-3-piperidyl)amino]phenyl]piperidine-1-carboxylate 94-5 (0.1 g, 0.241 mmol) in ACN (20 ml) were added 4 Å molecular sieves (0.05 g), acetic acid (0.022 g, 0.362 mmol) and sodium acetate, anhydrous (0.040 g, 0.482 mmol). The resulting solution was stirred for 10 min, then added 2,6-dimethoxy-4-(6-methyl-7-oxo-1H-pyrazolo[3,4-c]pyridin-4-yl)benzaldehyde (0.076 g, 0.241 mmol) and heated the reaction mixture at 70° C. for 3 h then cooled it at RT and added Silia Bond Cyanoborohydride (0.070 g, 1.21 mmol). The stirring was continued at RT for 6 h, while monitoring the reaction by LCMS and TLC. After 6 h, the reaction mass was filtered through Celite bed and filtrate concentrated and crude residue was purified by Prep-HPLC to afford [1-[[2,6-dimethoxy-4-(6-methyl-7-oxo-1H-pyrazolo[3,4-c]pyridin-4-yl)phenyl]methyl]-4-piperidyl] 4-[4-[(2,6-dioxo-3-piperidyl) amino]phenyl]piperidine-1-carboxylate. TFA salt Compound 94 (0.010 g, 5.00% yield, 99.56% purity) as an off white solid. $^1$H NMR (400 MHz, DMSO-d$_6$) δ 14.14 (s, 1H), 10.77 (s, 1H), 9.03 (d, J=43.3 Hz, 1H), 8.23 (d, J=3.9 Hz, 1H), 7.63 (d, J=12.8 Hz, 1H), 6.98-6.91 (m, 4H), 6.61-6.59 (m, 2H), 5.88 (bs, 1H), 4.97 (bs, 1H), 4.81-4.79 (m, 1H), 4.30-4.24 (m, 3H), 4.19-3.99 (m, 2H), 3.96 (d, J=3.0 Hz, 6H), 3.62 (d, J=8.3 Hz, 2H), 3.43-3.34 (m, 2H), 3.23-3.20 (m, 2H), 2.99-2.55 (m, 4H), 2.07-1.98 (m, 4H), 1.86-1.84 (m, 2H), 1.72-1.69 (m, 2H), 1.49-1.41 (m, 2H). LC-MS (ES$^+$): m/z 712.40 [M+H]$^+$.

Synthesis of Compound 95

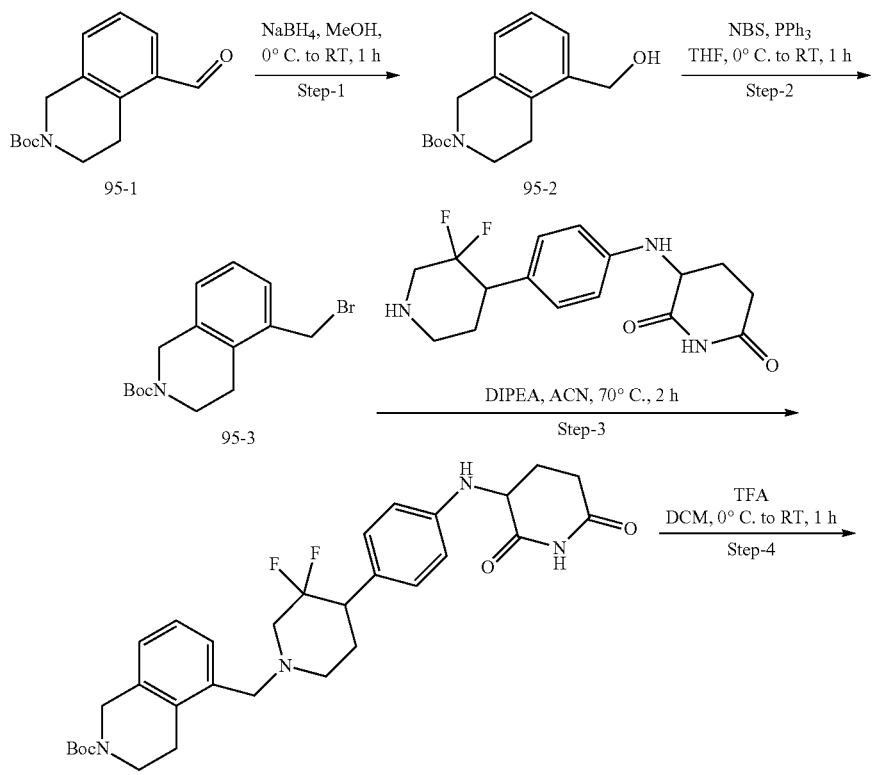

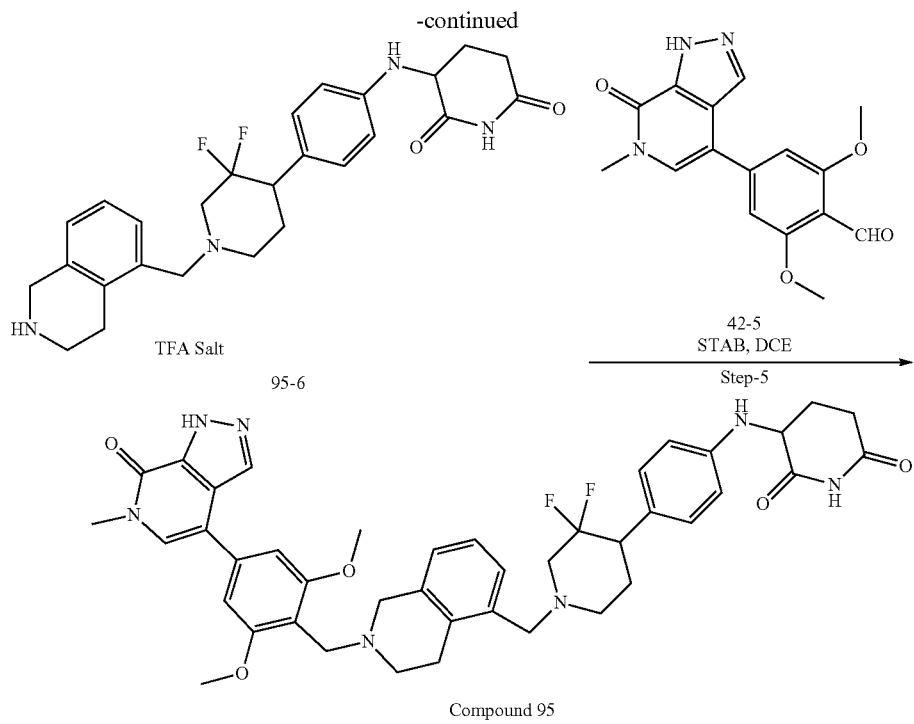

Step-1: To a stirred solution of tert-butyl 5-formyl-3,4-dihydroisoquinoline-2(1H)-carboxylate 95-1 (1 g, 3.83 mmol) in methanol (20 mL) was added sodium borohydride (144.77 mg, 3.83 mmol) and continued stirring at RT for 2 h. After completion of the reaction by TLC, the volatiles were evaporated under vacuum, the residue was dissolved in ethyl acetate (50 mL) and washed with water (20 mL×3). The organic layer was dried over sodium sulphate, filtered and concentrated under vacuum to obtain tert-butyl 5-(hydroxymethyl)-3,4-dihydroisoquinoline-2(1H)-carboxylate 95-2 (1 g, 92%) as an off white solid. Compound 2 was taken for the next step without further purification. $^1$H NMR (400 MHz, CDCl$_3$) δ 7.24-7.18 (m, 2H), 7.08 (d, J=8.4 Hz, 1H), 4.70 (d, J=3.6 Hz, 2H), 4.59 (s, 2H), 3.68 (t, J=5.6 Hz, 2H), 2.88 (t, J=6.0 Hz, 2H), 1.48 (s, 9H). LC-MS (ES$^+$): m/z 286.23 [M+Na]$^+$ Step-2: To a stirred solution of tert-butyl 5-(hydroxymethyl)-3,4-dihydroisoquinoline-2(1H)-carboxylate 95-2 (1 g, 3.80 mmol) in THF (20 mL) at 0° C. was added triphenylphosphine (2.99 g, 11.39 mmol) followed by drop wise addition of N-Bromosuccinimide (2.70 g, 15.19 mmol, 1.29 mL) in THF (20 mL). After completion of the reaction by TLC, the reaction mixture was quenched with saturated aqueous sodium bicarbonate solution (50 mL) and extracted with ethylacetate (30 mL×3). The combined organic layer was dried over anhydrous sodium sulfate and concentrated under reduced pressure. The crude compound was purified by flash column chromatography (silica gel mesh 100-200, 10-20% pet ether in ethyl acetate) to afford pure tert-butyl 5-(bromomethyl)-3,4-dihydro-1H-isoquinoline-2-carboxylate 95-3 (800 mg, 96%) as a yellow colour solid. $^1$H NMR (400 MHz, CDCl$_3$) δ 7.22-7.15 (m, 2H), 7.09 (d, J=7.6 Hz, 1H), 4.58 (s, 2H), 4.49 (s, 2H), 3.72 (t, J=5.6 Hz, 2H), 2.92 (t, J=5.6 Hz, 2H), 1.49 (s, 9H). LC-MS (ES$^+$): m/z 286.23 [M+H-Boc]$^+$ Step-3: To a stirred solution of 3-((4-(3,3-difluoropiperidin-4-yl)phenyl)amino)piperidine-2,6-dione (175 mg, 0.541 mmol) in ACN (10 ml) was added DIPEA (104.93 mg, 0.841 mmol, 0.14 mL) and stirred at RT for 15 minutes. tert-butyl 5-(bromomethyl)-3,4-dihydroisoquinoline-2(1H)-carboxylate (211.88 mg, 0.649 mmol) was added to reaction mixture and continued stirring at 80° C. for 3 h, while monitoring the reaction by LCMS. The volatiles were evaporated under vacuum and the crude compound was purified by column chromatography (Davisil silica, 0-8% methanol in DCM) to obtain tert-butyl 5-[[4-[4-[(2,6-dioxo-3-piperidyl)amino]phenyl]-3,3-difluoro-1-piperidyl]methyl]-3,4-dihydro-1H-isoquinoline-2-carboxylate 95-5 (170 mg, 54.13%) as a grey colour solid. $^1$H NMR (400 MHz, CDCl$_3$) δ 10.80 (s, 1H), 7.16 (m, 2H), 7.10 (m, 1H), 7.01 (d, J=8.4 Hz, 2H), 6.63 (d, J=8.4 Hz, 2H), 5.80 (d, J=7.2 Hz, 1H), 4.50 (s, 2H), 4.32-4.26 (m, 1H), 3.59 (m, 4H), 3.05 (m, 5H), 2.78 (m, 1H), 2.59 (m, 1H), 2.45 (m, 1H), 2.19 (t, 1H), 2.11 (m, 1H), 1.98 (m, 2H), 1.72 (m, 1H), 1.43 (s, 9H). LC-MS (ES$^+$): m/z 269.51 [M+H]$^+$ Step-4: To a stirred solution of tert-butyl 5-((4-(4-((2,6-dioxopiperidin-3-yl)amino)phenyl)-3,3-difluoropiperidin-1-yl)methyl)-3,4-dihydroisoquinoline-2(1H)-carboxylate 95-5 (150 mg, 0.263 mmol) in DCM (5 mL) was added Trifluoroacetic acid (300.77 mg, 2.64 mmol) and stirred at RT and stirred for 3 h. After completion of the reaction by LCMS, the volatiles were evaporated under vacuum and the residue was co-distilled with toluene (10 mL×2) and triturated with diethyl ether to afford 3-[4-[3,3-difluoro-1-(1,2,3,4-tetrahydroisoquinolin-5-ylmethyl)-4-piperidyl]anilino]piperidine-2,6-dione 95-6 (170 mg, 78.37%) as an off white solid. LC-MS (ES$^+$): m/z 469.46 [M+H]$^+$ Step-5: To a stirred solution of 3-((4-(3,3-difluoro-1-((1,2,3,4-tetrahydroisoquinolin-5-yl)methyl)piperidin-4-yl)phenyl)amino)piperidine-2,6-dione 95-6 (100 mg, 0.234 mmol) and 2,6-dimethoxy-4-(6-methyl-7-oxo-6,7-dihydro-1H-pyrazolo[3,4-c]pyridin-4-yl)benzaldehyde 95-7 (163.63 mg, 0.281 mmol) in the DCE:MeOH (3 mL, 1:1) was added Sodium acetate, anhydrous (38.39 mg, 0.468 mmol) and acetic acid (14.05 mg, 0.234 mmol, 13.38 uL) and the reaction mixture was stirred at 75° C. for 4 h. After 4 h, the reaction mixture was cooled to 0° C. and Siliabond cyanoborohydride (200 mg, 234.01 umol) was added and continued stirring at RT for 12 hr. After completion of the reaction by LCMS, the volatiles were evaporated under vacuum. The crude compound was purified by PrepHPLC to obtain 3-[4-[1-[[2-[[2,6-dimethoxy-4-(6-methyl-7-oxo-1H-pyrazolo[3,4-c]pyridin-4-yl)phenyl]methyl]-3,4-dihydro-1H-isoquinolin-5-yl]methyl]-3,3-difluoro-4-piperidyl]anilino] piperidine-2,6-dione Compound 95 (52 mg, 23.89%) as an off white solid. $^1$H NMR (400 MHz, DMSO-d$_6$): δ 14.30 (s, 1H), 10.78 (s, 1H), 9.63 (s, 1H), 8.25 (s, 1H), 7.66 (s, 1H), 7.30 (m, 2H), 7.21 (m, 6H), 6.62 (d, J=8.8 Hz, 2H), 4.46 (bs, 2H), 4.38 (bd, J=4.2 Hz, 2H), 4.28 (m, 1H), 3.96 (s, 6H), 3.63 (bs, 5H), 3.49 (s, 1H), 3.11-2.93 (m, 6H), 2.72 (m, 1H), 2.58 (t, 1H), 2.28 (bs, 1H), 2.04 (m, 2H), 1.88 (m, 2H). LC-MS (ES$^+$): m/z 766.3 [M+H]$^+$ Compound 96 was prepared following the synthesis of Compound 95.

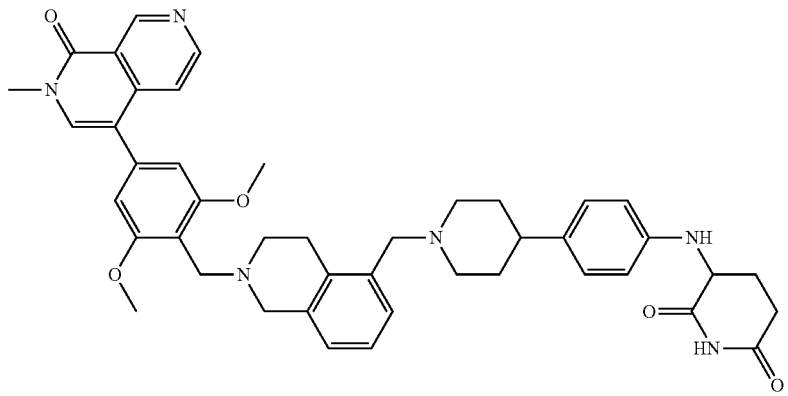 [SMILES: COc1cc(-c2cn(C)c(=O)c3cnccc23)cc(OC)c1CN1CCc2c(CN3CCC(c4ccc(NC5CCC(=O)NC5=O)cc4)CC3)cccc2C1]

$^1$H NMR (400 MHz, DMSO-d$_6$) δ 10.76 (s, 1H), 9.96 (s, 1H), 9.50 (d, J=16.1 Hz, 2H), 8.75 (d, J=5.7 Hz, 1H), 7.91 (s, 1H), 7.58 (dd, J=10.0, 6.6 Hz, 2H), 7.48-7.30 (m, 2H), 7.02-6.78 (m, 4H), 6.63 (d, J=8.2 Hz, 2H), 4.70-4.09 (m, 8H), 3.89 (s, 6H), 3.74 (s, 1H), 3.62 (s, 3H), 3.58-3.46 (m, 1H), 3.45-3.07 (m, 4H), 2.82-2.53 (m, 2H), 2.16-2.01 (m, 1H), 1.87 (d, J=13.6 Hz, 6H); LC-MS (ES$^+$): m/z 741.8 [M+H]$^+$.

Compound 97 was prepared following the synthesis of Compound 95.

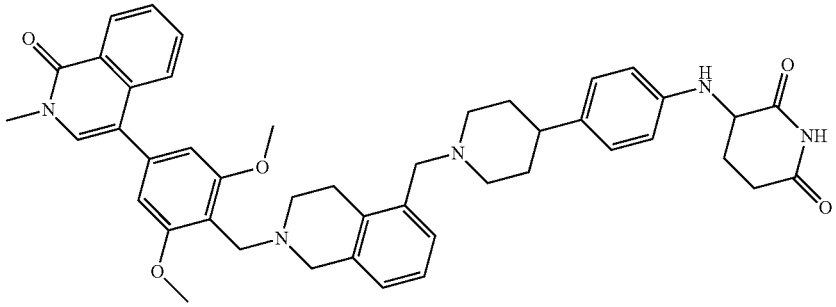 [SMILES: COc1cc(-c2cn(C)c(=O)c3ccccc23)cc(OC)c1CN1CCc2c(CN3CCC(c4ccc(NC5CCC(=O)NC5=O)cc4)CC3)cccc2C1]

$^1$H NMR (400 MHz, DMSO-d$_6$) δ 10.77 (s, 1H), 10.08 (s, 1H), 9.69 (s, 1H), 8.36 (d, J=8.0 Hz, 1H), 7.69 (dq, J=18.3, 8.9, 8.4 Hz, 3H), 7.61-7.53 (m, 3H), 7.53-7.29 (m, 3H), 6.94 (d, J=8.1 Hz, 2H), 6.87 (s, 2H), 6.62 (dd, J=11.3, 7.7 Hz, 2H), 4.65-4.30 (m, 6H), 4.27 (dd, J=11.4, 4.8 Hz, 1H), 3.88 (s, 6H), 3.79-3.68 (m, 1H), 3.60 (s, 3H), 3.50 (s, 2H), 3.39 (d, J=11.1 Hz, 0H), 3.25 (dd, J=22.5, 13.8 Hz, 1H), 2.63 (ddt, J=46.4, 17.6, 4.9 Hz, 3H), 2.08 (dt, J=13.7, 4.7 Hz, 1H), 2.01-1.70 (m, 6H). LC-MS (ES$^+$): m/z 740.8 [M+H]$^+$.

Compound 98 was prepared following the synthesis of Compound 95.

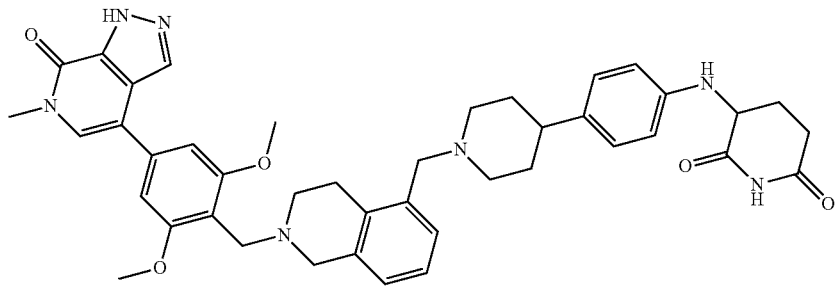 [SMILES: COc1cc(-c2cn(C)c(=O)c3[nH]ncc23)cc(OC)c1CN1CCc2c(CN3CCC(c4ccc(NC5CCC(=O)NC5=O)cc4)CC3)cccc2C1]
¹H NMR (400 MHz, DMSO-d₆) δ 10.76 (s, 1H), 9.84 (s, 1H), 9.43 (s, 1H), 8.24 (s, 1H), 7.66 (s, 1H), 7.56 (d, J=7.6 Hz, 1H), 7.46-7.29 (m, 2H), 7.00 (s, 2H), 6.94 (d, J=8.1 Hz, 2H), 6.63 (d, J=8.1 Hz, 2H), 4.61-4.15 (m, 8H), 3.95 (s, 6H), 3.73 (s, 1H), 3.64 (s, 3H), 3.50 (d, J=11.2 Hz, 2H), 3.39 (d, J=11.7 Hz, 1H), 3.23 (d, J=27.3 Hz, 4H), 2.83-2.53 (m, 2H), 2.18-2.02 (m, 1H), 1.99-1.65 (m, 5H). LC-MS (ES⁺): m/z 730.8 [M+H]⁺.
Compound 99 was prepared following the synthesis of Compound 95.
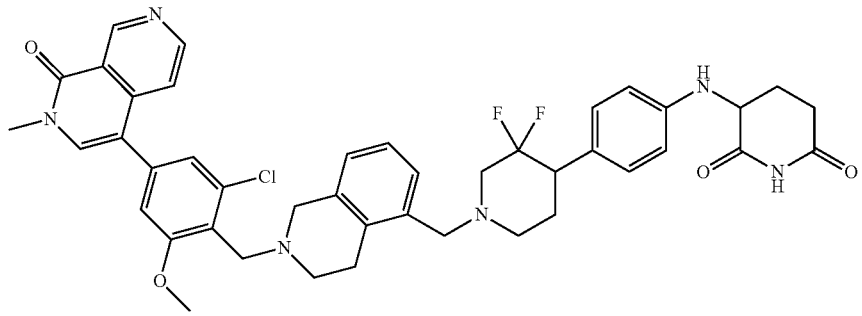 [SMILES: COc1cc(-c2cn(C)c(=O)c3cnccc23)cc(Cl)c1CN1CCc2c(cccc2CN2CCC(c3ccc(NC4CCC(=O)NC4=O)cc3)C(F)(F)C2)C1]
¹H NMR (400 MHz, DMSO-d₆) δ 10.78 (s, 1H), 9.85 (s, 1H), 9.48 (s, 1H), 8.77 (d, J=5.7 Hz, 1H), 7.97 (s, 1H), 7.57 (d, J=5.7 Hz, 1H), 7.34-7.21 (m, 5H), 6.99 (d, J=8.2 Hz, 2H), 6.62 (d, J=8.6 Hz, 2H), 4.62 (s, 2H), 4.55 (s, 2H), 4.29 (q, J=5.4 Hz, 1H), 4.01-3.98 (m, 2H), 3.95 (s, 3H), 3.62 (s, 6H), 3.24-3.10 (m, 6H), 2.78-2.72 (m, 1H), 2.65-2.57 (m, 1H), 2.12-1.93 (m, 4H). LC-MS (ES⁺): m/z 781.51 [M+H]⁺
Compound 100 was prepared following the synthesis of Compound 95.
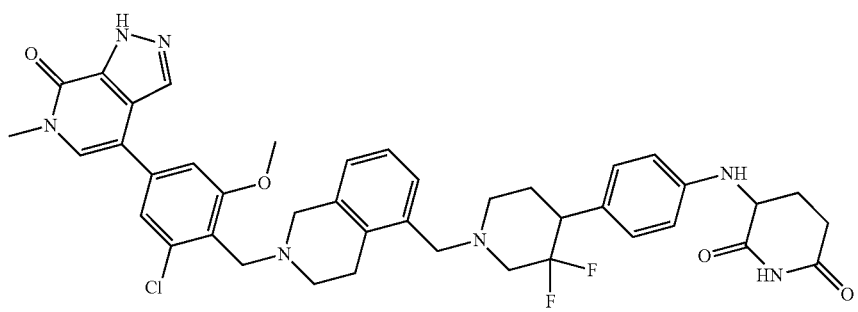 [SMILES: COc1cc(-c2cn(C)c(=O)c3[nH]ncc23)cc(Cl)c1CN1CCc2c(cccc2CN2CCC(c3ccc(NC4CCC(=O)NC4=O)cc3)C(F)(F)C2)C1]

$^1$H NMR (400 MHz, DMSO-d$_6$) δ 14.31 (s, 1H), 10.78 (s, 1H), 9.82 (s, 1H), 8.23 (s, 1H), 7.73 (s, 1H), 7.47 (d, J=1.1 Hz, 1H), 7.35-7.28 (m, 3H), 7.23-7.21 (m, 1H), 6.98 (d, J=7.7 Hz, 2H), 6.62 (d, J=8.6 Hz, 2H), 5.55 (bs, 1H), 4.55 (s, 4H), 4.35-4.26 (m, 1H), 4.02 (s, 3H), 3.83-3.78 (m, 1H), 3.63 (s, 6H), 3.33-2.70 (m, 6H), 2.69-2.54 (m, 2H), 2.39-1.75 (m, 5H). LC-MS (ES$^+$): m/z 770.59 [M+H]$^+$.

Compound 101 was prepared following the synthesis of Compound 95.

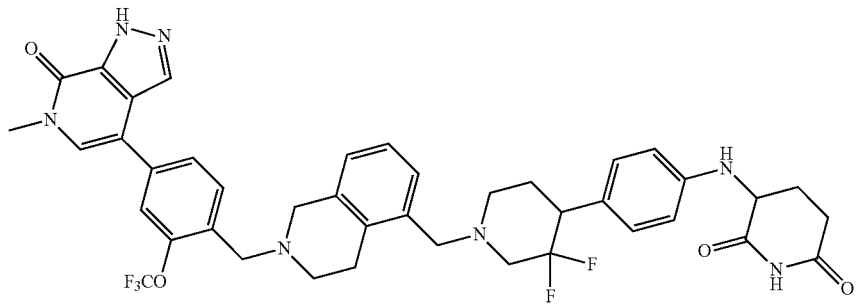 [SMILES: Cn1cc(-c2ccc(CN3CCc4c(cccc4CN4CCC(c5ccc(NC6CCC(=O)NC6=O)cc5)C(F)(F)C4)C3)c(OC(F)(F)F)c2)c2cn[nH]c2c1=O]

$^1$H NMR (400 MHz, DMSO-d$_6$) δ 10.78 (s, 1H), 8.14 (s, 1H), 7.99-7.84 (m, 2H), 7.72 (d, J=11.1 Hz, 2H), 7.27 (ddt, J=31.1, 16.0, 7.6 Hz, 7H), 7.12 (d, J=7.7 Hz, 2H), 6.99 (d, J=8.2 Hz, 2H), 6.63 (d, J=8.3 Hz, 2H), 4.60 (s, 2H), 4.49 (s, 3H), 4.29 (t, J=4.9 Hz, 2H), 3.64 (s, 3H), 3.41 (d, J=6.9 Hz, 2H), 3.23 (s, 1H), 2.94 (t, J=6.4 Hz, 3H), 2.85-2.53 (m, 2H), 2.14-1.62 (m, 3H). LC-MS (ES$^+$): m/z 790.7 [M+H]$^+$.

Compound 102 was prepared following the synthesis of Compound 95.

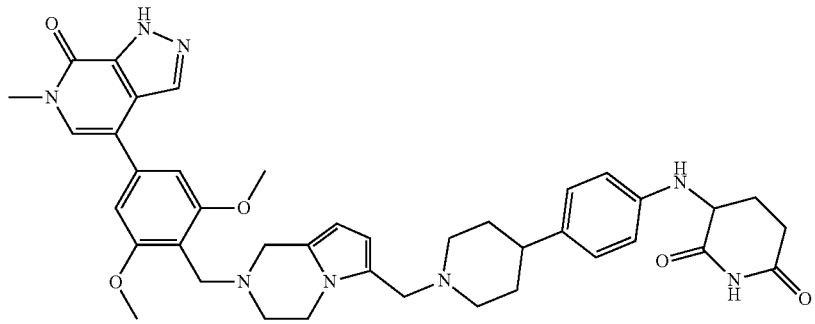 [SMILES: COc1cc(-c2cn(C)c(=O)c3[nH]ncc23)cc(OC)c1CN1CCn2c(CN3CCC(c4ccc(NC5CCC(=O)NC5=O)cc4)CC3)ccc2C1]

$^1$H NMR (400 MHz, DMSO-d$_6$) δ 14.27 (s, 1H), 10.78 (s, 1H), 10.03 (bs, 1H), 9.35 (bs, 1H), 8.24 (s, 1H), 7.66 (s, 1H), 7.22 (m, 4H), 6.64 (d, J=8.4 Hz, 2H), 6.41 (d, J=2.8 Hz, 1H), 6.15 (s, 1H), 5.67 (s, 0.33H), 4.43-414 (m, 10H), 3.97 (s, 6H), 3.64 (s, 3H), 3.44 (m, 4H), 3.04 (s, 2H), 2.73-2.67 (m, 1H), 2.60 (m, 1H), 2.10-2.06 (m, 1H), 1.97-1.75 (m, 5H); LC-MS (ES$^-$): m/z 717.58 [M–H]$^-$.

Compound 103 was prepared following the synthesis of Compound 95.

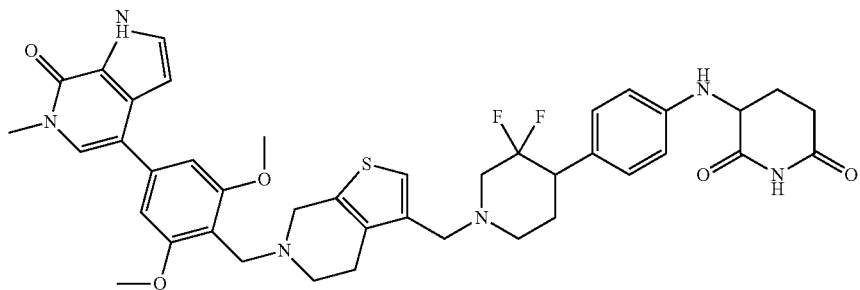 [SMILES: COc1cc(-c2cn(C)c(=O)c3[nH]ccc23)cc(OC)c1CN1CCc2c(CN3CCC(c4ccc(NC5CCC(=O)NC5=O)cc4)C(F)(F)C3)csc2C1]
$^1$H NMR (400 MHz, DMSO-d$_6$): δ 14.28 (s, 1H), 10.78 (s, 1H), 9.77 (s, 1H), 8.25 (s, 1H), 7.66 (s, 1H), 7.46 (bs, 1H), 7.09 (m, 5H), 6.63 (d, J=8.4 Hz, 2H), 4.55 (m, 1H), 4.42 (m, 4H), 4.31 (m, 1H), 3.96 (s, 6H), 3.70 (m, 5H), 3.51 (m, 2H), 3.01 (m, 6H), 2.73 (m, 1H), 2.60 (m, 1H), 2.11 (m, 2H), 1.89 (m, 2H). LC-MS (ES$^+$): m/z 772.1 [M+H]$^+$
Synthesis of Compound 104
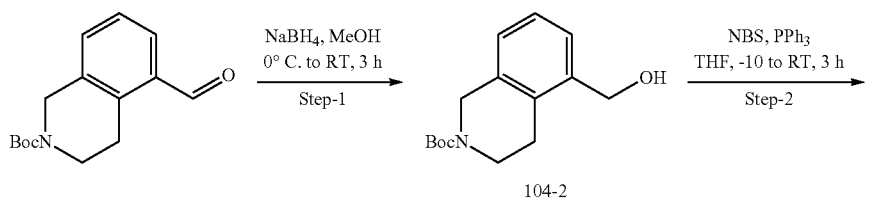
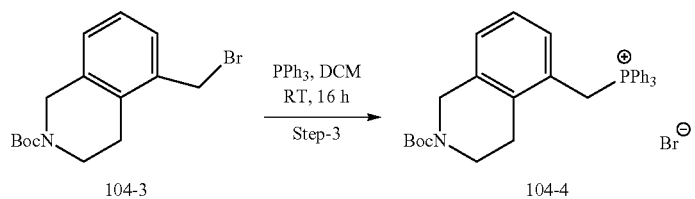
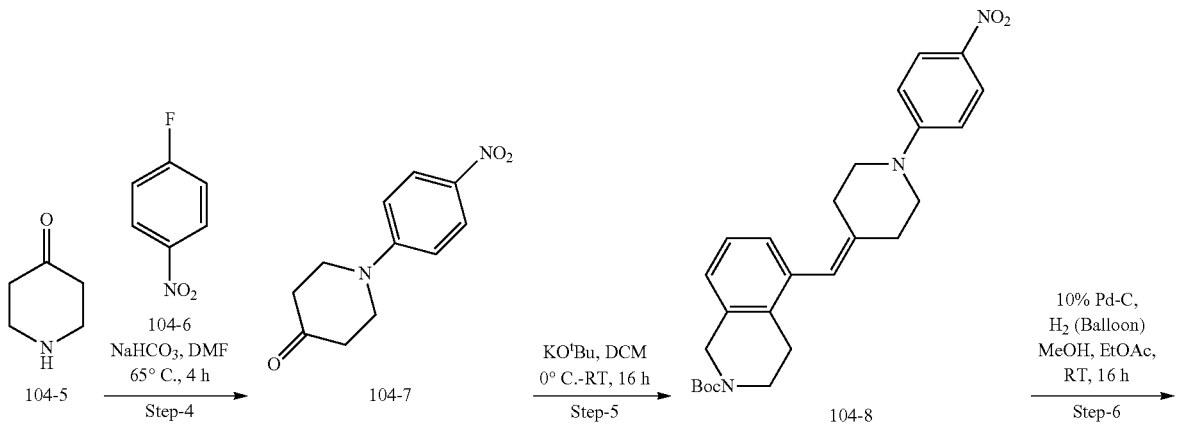

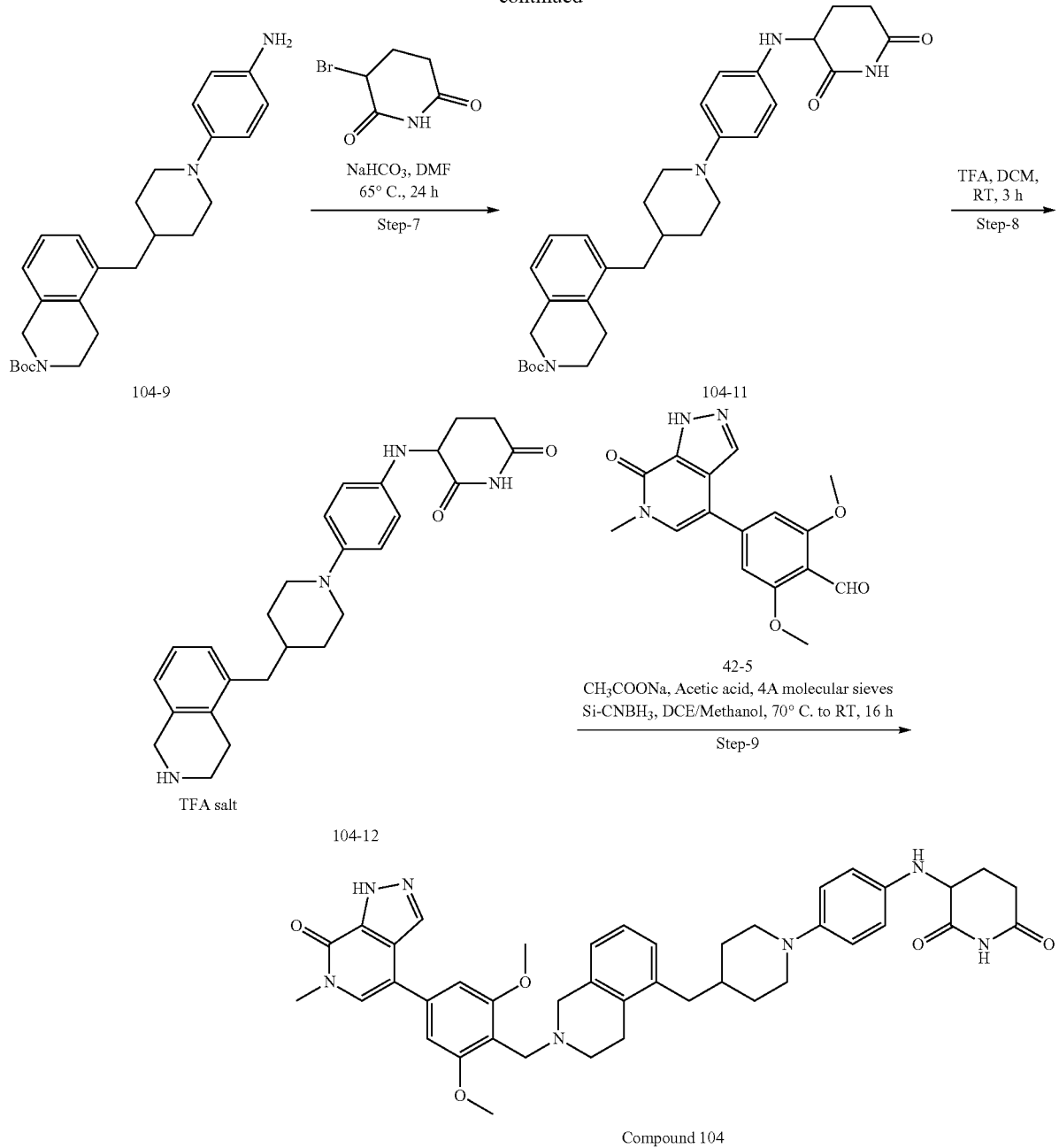

Step-1: To a stirred solution of tert-butyl 5-formyl-3,4-dihydro-1H-isoquinoline-2-carboxylate (4 g, 15.31 mmol) in methanol (60 mL) at 0° C. was added sodium borohydride (868.66 mg, 22.96 mmol) and the mixture was stirred to room temperature for 3 h while monitoring the reaction by TLC. After completion of the reaction by TLC, the solvent was removed and residue was triturated with water (30 mL) and dried to obtain tert-butyl 5-(hydroxymethyl)-3,4-dihydroisoquinoline-2(1H)-carboxylate 104-2 as a colorless solid. Compound 104-2 was used in next step without further purification.

Step-2: To a stirred solution of tert-butyl 5-(hydroxymethyl)-3,4-dihydro-1H-isoquinoline-2-carboxylate 104-2 (3.7 g, 14.05 mmol) in THF (60 mL) at −10° C. was added triphenylphosphine (11.06 g, 42.15 mmol) and stirred for 10 min. NBS (10.00 g, 56.20 mmol) in THF (30 mL) was added drop wise to the reaction mixture and continued the stirring for 3 h at room temperature, while monitoring the reaction by TLC. After completion of the reaction, the reaction mixture was quenched with aqueous sodium bicarbonate solution (100 mL) and extracted with ethyl acetate (100 ml×2). Collected organic layer was washed with water (100 mL). The organic layer was dried over anhydrous sodium sulphate, filtered and concentrated under vacuum. The crude product was purified by column (silica gel mesh 100-200, 10% ethyl acetate in pet ether) to obtain tert-butyl 5-(bromomethyl)-3,4-dihydro-1H-isoquinoline-2-carboxylate 104-3 (2.5 g, 54.54% yield) as a colourless solid.

Step-3: To a stirred solution of tert-butyl 5-(bromomethyl)-3,4-dihydro-1H-isoquinoline-2-carboxylate 104-3

(2.4 g, 7.36 mmol) in DCM (100 mL) at 0° C. was added triphenylphosphine (2.12 g, 8.09 mmol) and continued the stirring for 16 h at room temperature. After completion of the reaction, the solvent was evaporated under vacuum. The residue was triturated with diethyl ether (50 mL) to obtain the solid. The solid was filtered and used for next step without further purification.

Step-4 To a stirred solution of piperidin-4-one 104-5 (2.40 g, 17.72 mmol, 021) in DMF (25 mL) was added sodium bicarbonate (3.13 g, 37.21 mmol) followed by addition of 1-fluoro-4-nitro-benzene 104-6 (2.5 g, 17.72 mmol) and the reaction mixture was stirred at 80° C. for 12 h, while monitoring the progress of the reaction by TLC. After completion of the reaction, the reaction mixture quenched with cold water (100 mL) and stirred over 30 minutes to obtain the yellow colour solid. Filtered the solid and washed with water and dried to afford the desired product 1-(4-nitrophenyl)piperidin-4-one 104-7 (2 g, 41.15% yield, 80.29% purity) as a yellow colour solid. LC-MS (ES$^+$): m/z 221.18 (M+H)$^+$ Step-5: To a stirred solution of 1-(4-nitrophenyl)piperidin-4-one 104-7 (0.7 g, 3.18 mmol) & ((2-(tert-butoxycarbonyl)-1,2,3,4-tetrahydroisoquinolin-5-yl)methyl)triphenylphosphonium bromide 104-4 (1.87 g, 3.18 mmol) in DCM (10 mL) at 0° C. was added potassium tert-butoxide (0.713 g, 6.36 mmol) and continued the stirring at room temperature for 16 h, while monitoring the progress of the reaction by LCMS. After completion of the reaction, solvent was evaporated under vacuum and the residue was diluted with ethyl acetate (50 mL) and washed with water (50 mL). The organic layer was dried over Na$_2$SO$_4$, filtered and concentrated under reduced pressure to obtain the crude. The crude product was purified by column (Davisil silica, 0-30% ethyl acetate in pet ether) to afford tert-butyl 5-[[1-(4-nitrophenyl)-4-piperidylidene]methyl]-3,4-dihydro-1H-isoquinoline-2-carboxylate (0.6 g, 41.74% yield, 99.4% purity). LC-MS (ES$^+$): m/z 472.35 (M+Na)$^+$ Step-6: To a suspension of tert-butyl 5-[[1-(4-nitrophenyl)-4-piperidylidene]methyl]-3,4-dihydro-1H-isoquinoline-2-carboxylate 104-8 (650 mg, 1.45 mmol) in methanol (10 mL) and ethyl acetate (10 mL) was degassed for 5 minutes under nitrogen atmosphere. 10% Palladium on carbon (153.87 mg, 1.45 mmol) was added to the reaction mixture and stirred under H$_2$ atmosphere (Balloon) for 16 h. The progress of the reaction was monitored by LCMS. After completion of the reaction, the reaction mixture was filtered through the Celite bed and washed with MeOH. The filtrate was evaporated under reduced pressure and crude product was purified by column (Davisil silica, 0-40% ethyl acetate in pet ether) to afford tert-butyl 5-[[1-(4-aminophenyl)-4-piperidyl]methyl]-3,4-dihydro-1H-isoquinoline-2-carboxylate 104-9 (500 mg, 78.75% yield, 96% purity). LC-MS (ES$^+$): m/z 422.51 (M+H)$^+$ Step-7: To a stirred solution of tert-butyl 5-[[1-(4-aminophenyl)-4-piperidyl]methyl]-3,4-dihydro-1H-isoquinoline-2-carboxylate 104-9 (400 mg, 0.948 mmol) in DMF (6 mL) was added NaHCO$_3$ (239.12 mg, 2.85 mmol) and continued the stirring at 60° C. for 24 hr. After completion of the reaction, the reaction mixture was diluted with ethyl acetate (25 mL) and filtered through Celite bed and washed with ethyl acetate (10 mL). The filtrate was washed with brine (40 mL). The organic layer was dried over Na$_2$SO$_4$ and concentrated to obtain the crude. The crude was purified by column (davisil silica, 40% ethyl acetate in pet ether) to afford the tert-butyl 5-[[1-[4-[(2,6-dioxo-3-piperidyl)amino]phenyl]-4-piperidyl]methyl]-3,4-dihydro-1H-isoquinoline-2-carboxylate (350 mg, 68.56% yield, 99% purity). LC-MS (ES$^+$): m/z 533.64 (M+H)$^+$ Step-8: To a stirred solution of tert-butyl 5-[[1-[4-[(2,6-dioxo-3-piperidyl)amino]phenyl]-4-piperidyl]methyl]-3,4-dihydro-1H-isoquinoline-2-carboxylate 104-11 (130 mg, 0.244 mmol) in DCM (5 mL) at 0° C. was added trifluoroacetic acid (0.19 mL, 2.44 mmol) and stirred the reaction mixture at RT for 3 h. After completion of reaction, volatiles were evaporated under reduced pressure and co-distilled with toluene (15 ml×2) and triturated with diethyl ether (15 mL) to obtain 3-[4-[4-(1,2,3,4-tetrahydroisoquinolin-5-ylmethyl)-1-piperidyl]anilino]piperidine-2,6-dione 104-12 (140 mg, 85.10% yield, 98% purity). LC-MS (ES$^+$): m/z 433.25 (M+H)$^+$ Step-9: To a stirred solution of 2,6-dimethoxy-4-(6-methyl-7-oxo-1H-pyrazolo[3,4-c]pyridin-4-yl)benzaldehyde (60 mg, 0.191 mmol), 3-[4-[4-(1,2,3,4-tetrahydroisoquinolin-5-ylmethyl)-1-piperidyl]anilino]piperidine-2,6-dione (126.51 mg, 0.191 mmol), sodium acetate, anhydrous (47.13 mg, 0.574 mmol) stirred at 75° C. for 4 h. SiliaBond Cyanoborohydride (CBH)(150 mg) was added to reaction mixture and continued stirring at RT for 12 hr. After completion of reaction, the volatiles were evaporated under vacuum and the crude compound was purified by Prep HPLC to obtain 3-[4-[4-[[2-[[2,6-dimethoxy-4-(6-methyl-7-oxo-1H-pyrazolo[3,4-c]pyridin-4-yl)phenyl]methyl]-3,4-dihydro-1H-isoquinolin-5-yl]methyl]-1-piperidyl]anilino]piperidine-2,6-dione.TFA (85 mg, 50.74% yield, 96.47% purity) as a Greenish yellow solid. $^1$H NMR (400 MHz, DMSO-d$_6$) δ 14.31 (s, 1H), 10.82 (s, 2H), 9.64 (s, 1H), 8.24 (s, 1H), 7.66 (s, 1H), 7.34 (m, 8H), 6.77 (d, J=8.8 Hz, 2H), 6.37 (s, 1H), 4.45 (m, 5H), 3.96 (s, 6H), 3.88 (s, 8H), 3.17 (m, 3H), 2.78 (m, 1H), 2.59 (m, 3H), 2.09 (m, 1H), 1.94 (m, 4H), 1.67 (m, 2H). LC-MS (ES$^+$): m/z 730.69 (M+H)$^+$ Synthesis of Compound 105

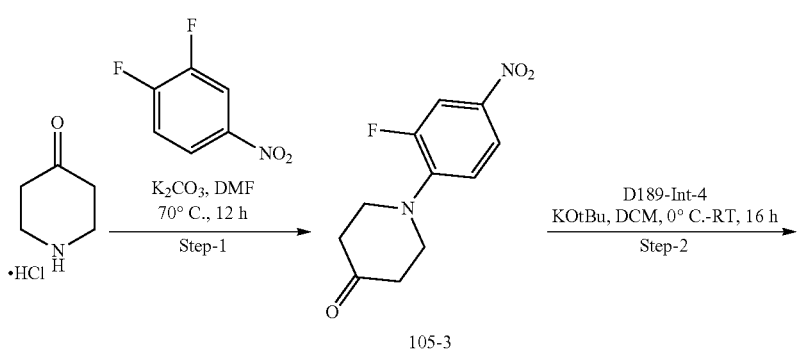

105-3

-continued
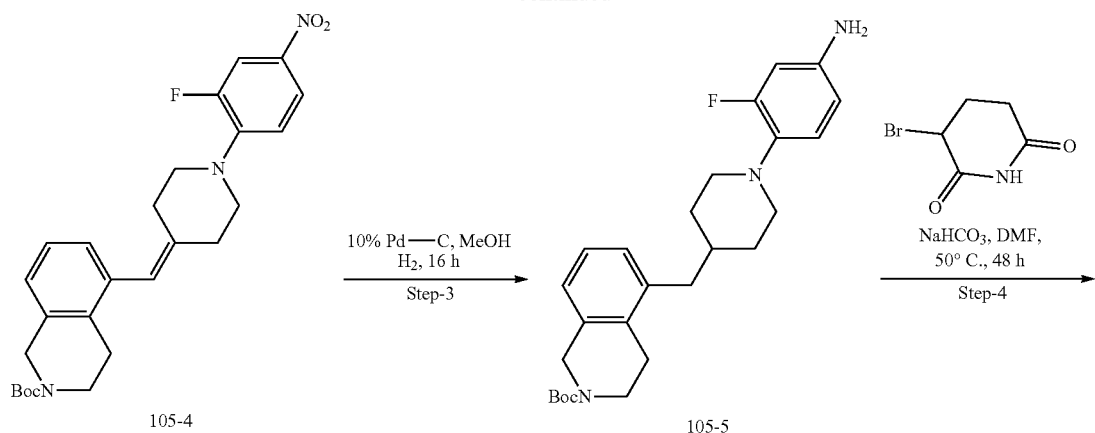
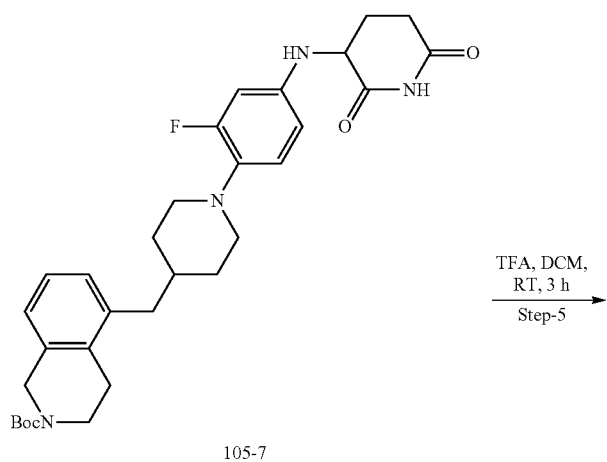
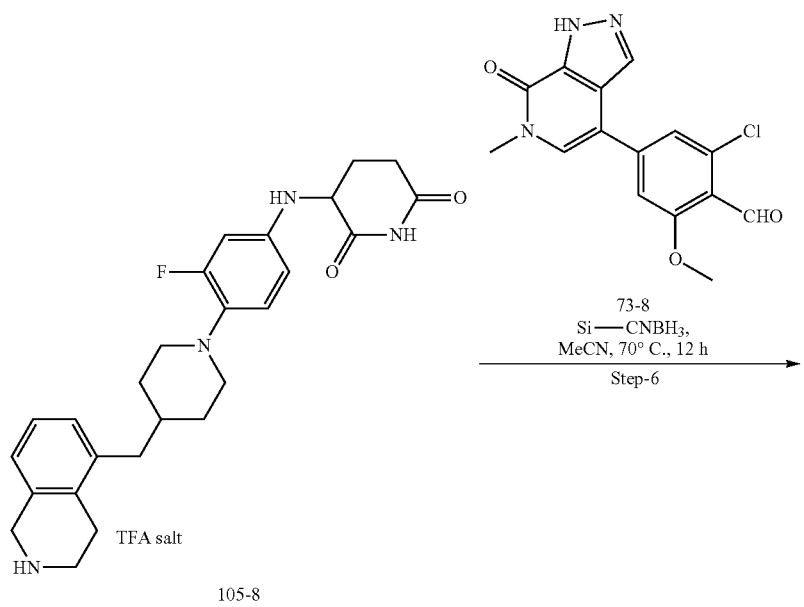

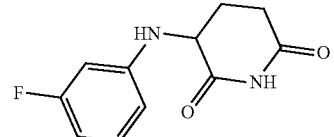
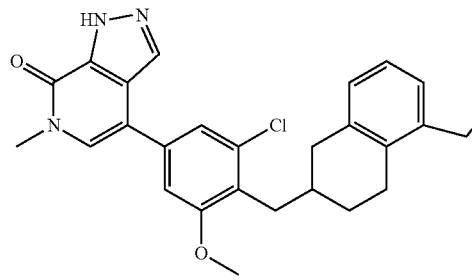

Compound 105

Step-1: To a stirred solution of piperidin-4-one (HCl salt) (1.87 g, 13.79 mmol) in DMF (15 mL) was added Potassium carbonate (6.52 g, 47.14 mmol) and stirred for 10 minutes. To this solution was added 1,2-difluoro-4-nitro-benzene (2.5 g, 15.71 mmol) and reaction mixture stirred at 80° C. for 12 hr. The progress of the reaction monitored by TLC and LCMS. After completion of the reaction, reaction mixture was quenched with ice cold water and extracted with ethylacetate (100×2). Collected organic layer was washed with brine solution (100 mL×2). The organic layer was dried over sodium sulphate, filtered and concentrated in vacuo. The crude material was purified by column chromatography (Devisil silica, 5-15% EtOAc in pet ether) to afford 1-(2-fluoro-4-nitro-phenyl)piperidin-4-one 105-3 (2 g, 44.31% yield). $^1$H NMR (400 MHz, CDCl$_3$) δ 8.03-8.00 (m, 1H), 7.98 (dd, J=2.8 Hz, 1H), 7.00 (t, J=8.8 Hz, 1H), 3.67 (t, J=6.4 Hz, 4H), 2.67 (t, J=6.0 Hz, 4H). LC-MS (ES$^+$): m/z 239.1 [M+H]$^+$ Step-2: To a stirred solution of 1-(2-fluoro-4-nitro-phenyl)piperidin-4-one 105-3 (0.5 g, 2.10 mmol) in DCM (10 mL) was added (2-(tert-butoxycarbonyl)-1,2,3,4-tetrahydroisoquinolin-5-yl)methyl)triphenylphosphonium bromide (1.24 g, 2.10 mmol) followed by Potassium tert-butoxide (0.47 g, 4.20 mmol) at 0° C. and stirred the reaction mixture at RT for 16 h. The progress of the reaction monitored by TLC and LCMS. After completion of the reaction, solvent was removed under vacuo. Water was added to the residue and crude product was extracted with ethyl acetate. The organic layer was dried over sodium sulphate, filtered and concentrated under vacuo. The crude was purified with column chromatography (Devisil silica, 5-30% EtOAc in pet ether) to afford tert-butyl 5-[[1-(2-fluoro-4-nitro-phenyl)-4-piperidylidene]methyl]-3,4-dihydro-1H-isoquinoline-2-carboxylate 105-4 (0.53 g, 52.07% yield) as Yellow colour solid. $^1$H NMR (400 MHz, CDCl$_3$) δ 7.99-9.96 (m, 1H), 7.93 (dd, J=2.8 Hz, 12.8 Hz, 1H), 7.17 (d, J=8.0 Hz, 1H), 7.04 (t, J=7.6 Hz, 2H), 6.93 (t, J=8.8 Hz, 1H), 6.32 (s, 1H), 4.59 (s, 2H), 3.66 (m, 2H), 3.44 (t, J=5.6 Hz, 2H), 3.29 (t, J=5.6 Hz, 2H), 2.75 (t, J=5.6 Hz, 2H), 2.57 (t, J=5.2 Hz, 2H), 2.48 (t, J=5.2 Hz, 2H), 1.49 (s, 9H); LC-MS (ES$^+$): m/z 490.28 [M+H]$^+$ Step-3: Stirred mixture of tert-butyl 5-[[1-(2-fluoro-4-nitro-phenyl)-4-piperidylidene]methyl]-3,4-dihydro-1H-isoquinoline-2-carboxylate 105-4 (0.53 g, 1.13 mmol) in Methanol (5 mL) and ethyl acetate (5 ml) was degassed for 10 minutes followed by addition of Palladium on carbon (10%) (0.53 g, 1.13 mmol. The reaction mixture was again degassed and filled stirred under hydrogen (under balloon pressure) for 16 hr at RT. The progress of the reaction was monitored by TLC and LCMS. After completion of the reaction, reaction mixture was filtered through Celite bed and washed with methanol and ethylacetate. The filterte was removed under vacuo to afford tert-butyl 5-[[1-(4-amino-2-fluoro-phenyl)-4-piperidyl]methyl]-3,4-dihydro-1H-isoquinoline-2-carboxylate 105-5 (0.29 g, 49.10% yield) as colourless gummy solid. $^1$H NMR (400 MHz, CDCl$_3$) δ 7.14 (t, J=7.2 Hz, 1H), 7.02 (m, 2H), 6.80 (t, J=9.2 Hz, 1H), 6.43-6.36 (m, 2H), 4.57 (s, 2H), 3.65 (bs, 2H), 3.51 (bs, 2H), 3.26 (bd, J=12.0 Hz, 2H), 2.82 (bt, J=5.6 Hz, 2H), 2.59-2.49 (m, 4H), 1.72 (d, J=10.0 Hz, 2H), 1.49 (s, 9H); LC-MS (ES$^+$): m/z 440.28 [M+H]$^+$ Step-4: To a stirred solution of tert-butyl 5-[[1-(4-amino-2-fluoro-phenyl)-4-piperidyl]methyl]-3,4-dihydro-1H-isoquinoline-2-carboxylate 105-5 (0.3 g, 0.63 mmol) in DMF (4.5 mL) was added sodium bicarbonate (0.23 g, 2.73 mmol). The reaction mixture was stirred at RT for 10 minutes. 3-bromopiperidine-2,6-dione 7 (0.262 g, 1.36 mmol) was added to reaction mixture and stirred at 65° C. for 24 hr in sealed tube. Again 1 equivalent of 3-bromopiperidine-2,6-dione 6 (0.128 g, 0.63 mmol) was added to reaction mixture and stirred at 65° C. for 24 hr in sealed tube. The progress of the reaction was monitored by TLC and LCMS. After completion of reaction, the reaction mixture was quenched with ice water and extracted with ethylacetate. The organic layer was dried over sodium sulphate, filtered and concentrated under reduced pressure to get crude product. The crude was purified by column chromatography to afford tert-butyl 5-[[1-[4-[(2,6-dioxo-3-piperidyl)amino]-2-fluoro-phenyl]-4-piperidyl]methyl]-3,4-dihydro-1H-isoquinoline-2-carboxylate 105-7 (0.28 g, 73.02% yield) as an off white solid. $^1$H NMR (400 MHz, CDCl$_3$) δ 7.88 (bs, 1H), 7.14 (t, J=7.2 Hz, 1H), 7.02 (m, 2H), 6.88 (t, J=10.0 Hz, 1H), 6.44-6.38 (m, 2H), 4.57 (s, 2H), 4.01 (m, 1H), 3.65 (bs, 2H), 3.27 (bd, J=11.2 Hz, 2H), 2.96 (s, 1H), 2.85 (s, 1H), 2.88-2.78 (m, 3H), 2.69-2.50 (m, 5H), 1.73 (d, 2H), 1.49 (s, 9H); LC-MS (ES$^+$): m/z 551.82 [M+H]$^+$ Step-5: To a stirred solution of tert-butyl 5-[[1-[4-[(2,6-dioxo-3-piperidyl)amino]-2-fluoro-phenyl]-4-piperidyl]methyl]-3,4-dihydro-1H-isoquinoline-2-carboxylate 105-7 (0.14 g, 254.24 umol) was added Trifluoroacetic acid (144.95 mg, 1.27 mmol, 97.94 µL) at RT. The reaction mixture was stirred at RT for 3 hr. The reaction progress was monitored by LCMS. After completion of reaction, the solvent was removed by under vacuo. The crude was co-distilled with Toluene and acetonitrile and dried to afford 3-[3-fluoro-4-[4-(1,2,3,4-tetrahydroisoquinolin-5-ylmethyl)-1-piperidyl]anilino]piperidine-2,6-dione 105-8 (0.115 g, 63.98% yield) as a TFA Salt and as a green solid. LC-MS (ES$^+$): m/z 451.41 [M+H]$^+$ Step-6: To a stirred solution of 2-chloro-6-methoxy-4-(6-methyl-7-oxo-1H-pyrazolo[3,4-c]pyridin-4-yl)benzaldehyde 9 (60 mg, 0.138 mmol) and 3-[3-fluoro-4-[4-(1,2,3,4-tetrahydroisoquinolin-5-ylmethyl)-1-piperidyl]anilino]piperidine-2,6-dione 105-8 (113 mg, 0.166 mmol) in Methanol (3 mL) and DCE (3 mL) was added Acetic acid (8.35 mg, 0.138 mmol) and Sodium acetate, anhydrous (34.20 mg, 0.417 mmol) and the reaction mixture was stirred at 75° C. for 4 h. SiliaBond Cyanoborohydride (CBH) (200 mg) was added to the reaction mixture at 0° C. and continued stirring at RT for 12 hr. The progress of the reaction was monitored by TLC and LCMS. After completion of reaction, the volatiles were evaporated under vacuo and the crude compound was purified by Prep-HPLC to obtain 3-[4-[4-[[2-[[2-chloro-6-methoxy-4-(6-methyl-7-oxo-1H-pyrazolo[3,4-c]pyridin-4-yl)phenyl]methyl]-3,4-dihydro-1H-isoquinolin-5-yl]methyl]-1-piperidyl]-3-fluoro-anilino]piperidine-2,6-dione (66.8 mg, 54.91% yield) as a TFA salt and as an Off white solid. $^1$H NMR (400 MHz, DMSO-d$_6$) δ 14.26 (s, 1H), 10.79 (s, 1H), 9.79 (s, 1H), 8.23 (s, 1H), 7.73 (s, 1H), 7.47 (d, J=1.2 Hz, 1H), 7.35 (s, 1H), 7.19-7.09 (m, 3H), 6.97 (bs, 1H), 6.56 (d, J=14.8 Hz, 1H), 6.45 (d, J=7.6 Hz, 1H), 4.55 (d, J=10.4 Hz, 4H), 4.29 (m, 1H), 4.01 (s, 3H), 3.78 (m, 2H), 3.63 (s, 5H), 3.22-3.09 (m, 4H), 2.72-2.67 (m, 3H), 2.59 (m, 3H), 2.08 (m, 1H), 1.88 (m, 1H), 1.69 (m, 5H); LC-MS (ES$^+$): m/z 752.61 [M+H]$^+$ Compound 106 was prepared following the synthesis of Compound 105.

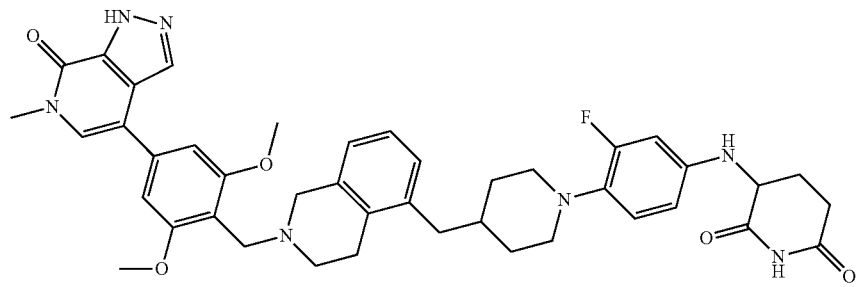 [SMILES: COc1cc(-c2cn(C)c(=O)c3[nH]ncc23)cc(OC)c1CN1CCc2c(CC3CCN(c4ccc(NC5CCC(=O)NC5=O)cc4F)CC3)cccc2C1]

$^1$H NMR (400 MHz, DMSO-d$_6$) δ 14.34 (s, 1H), 10.79 (s, 1H), 9.58 (bs, 1H), 8.24 (s, 1H), 7.66 (s, 1H), 7.26-6.96 (m, 6H), 6.56 (d, J=14.8 Hz, 1H), 6.46 (d, J=8.8 Hz, 1H), 4.44 (d, J=4.4 Hz, 2H), 4.39 (d, J=4.0 Hz, 2H), 4.30 (m, 1H), 3.95 (s, 6H), 3.63 (s, 3H), 3.36-3.04 (m, 8H), 2.75-2.67 (m, 1H), 2.59 (m, 3H), 2.09 (m, 1H), 1.91-1.89 (m, 1H), 1.75-1.50 (m, 5H); LC-MS (ES$^+$): m/z 748.62 [M+H]$^+$

Compound 107 was prepared following the synthesis of Compound 105.

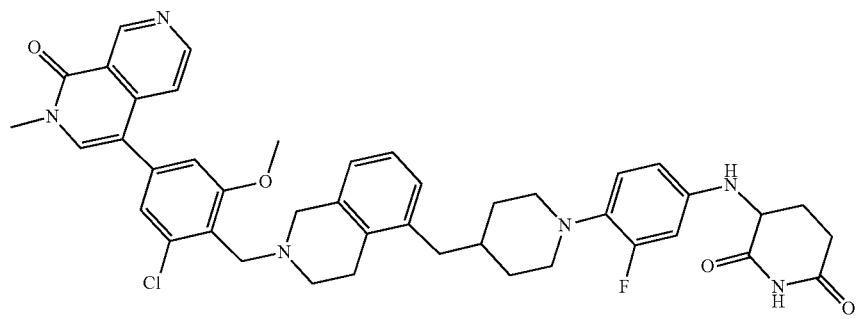 [SMILES: COc1cc(-c2cn(C)c(=O)c3cnccc23)cc(Cl)c1CN1CCc2c(CC3CCN(c4ccc(NC5CCC(=O)NC5=O)cc4F)CC3)cccc2C1]

¹H NMR (400 MHz, DMSO-d₆) δ 10.76 (s, 1H), 9.44 (s, 1H), 8.74 (d, J=5.6 Hz, 1H), 8.25 (s, 1H), 7.55 (d, J=5.6 Hz, 1H), 7.17 (s, 1H), 7.13 (s, 1H), 7.06 (t, J=7.2 Hz, 1H), 6.92 (d, J=7.2 Hz, 1H), 6.89 (d, J=7.6 Hz, 1H), 6.81 (t, J=9.2 Hz, 1H), 6.50 (dd, J=2.4 Hz, 14.8 Hz, 1H), 6.40 (dd, J=8.8 Hz, 1H), 5.77 (d, J=7.6 Hz, 1H), 4.26 (m, 1H), 3.89 (s, 3H), 3.78 (s, 2H), 3.67 (s, 2H), 3.59 (s, 3H), 3.09 (d, J=10.8 Hz, 2H), 2.79-2.67 (m, 5H), 2.80 (m, 1H), 2.47 (m, 4H), 2.07 (m, 1H), 1.88-1.75 (m, 1H), 1.63-1.52 (m, 3H), 1.38 (m, 2H). LC-MS (ES⁺): m/z 763.40 [M+H]⁺

Compound 108 was prepared following the synthesis of Compound 105.

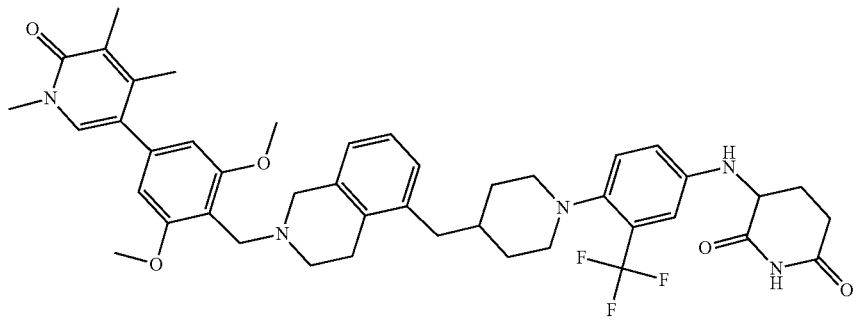 [SMILES: COc1cc(-c2cn(C)c(=O)c(C)c2C)cc(OC)c1CN1CCc2c(CC3CCN(c4ccc(NC5CCC(=O)NC5=O)cc4C(F)(F)F)CC3)cccc2C1]

¹H NMR (400 MHz, DMSO-d₆) δ 10.77 (s, 1H), 9.59 (s, 1H), 7.54 (s, 1H), 7.35-7.13 (m, 3H), 7.08 (d, J=7.4 Hz, 1H), 6.93-6.82 (m, 2H), 6.69 (s, 2H), 4.53-4.27 (m, 5H), 3.87 (s, 6H), 3.74-3.61 (m, 1H), 3.48 (s, 4H), 3.20-2.93 (m, 2H), 2.86-2.66 (m, 3H), 2.57 (d, J=15.6 Hz, 4H), 2.08 (d, J=9.3 Hz, 8H), 1.89 (qd, J=12.3, 4.8 Hz, 1H), 1.61 (dd, J=20.0, 12.3 Hz, 3H), 1.44-1.19 (m, 2H). LC-MS (ES⁺): m/z 786.8 [M+H]⁺.

Compound 109 was prepared following the synthesis of Compound 105.

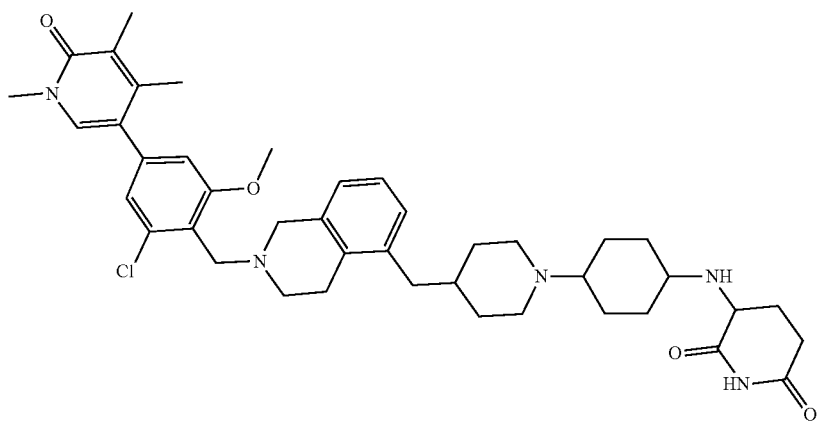 [SMILES: COc1cc(-c2cn(C)c(=O)c(C)c2C)cc(Cl)c1CN1CCc2c(CC3CCN(C4CCC(NC5CCC(=O)NC5=O)CC4)CC3)cccc2C1]

¹H NMR (400 MHz, DMSO-d₆) δ 10.78 (s, 1H), 9.44 (s, 1H), 7.58 (s, 1H), 7.26-6.96 (m, 6H), 6.55 (bd, J=14.8 Hz, 1H), 6.45 (bd, J=7.6 Hz, 1H), 4.53 (m, 3H), 4.28 (bd, J=6.8 Hz, 1H), 3.92 (s, 3H), 3.47 (m, 7H), 3.47-3.06 (m, 4H), 2.76-2.67 (m, 1H), 2.59 (m, 3H), 2.08 (d, 6H), 2.08 (m, 1H), 1.90-1.85 (m, 1H), 1.72-1.64 (m, 3H), 1.49 (bs, 2H). LC-MS (ES⁺): m/z 740.54 [M+H]⁺

Synthesis of Compound 110

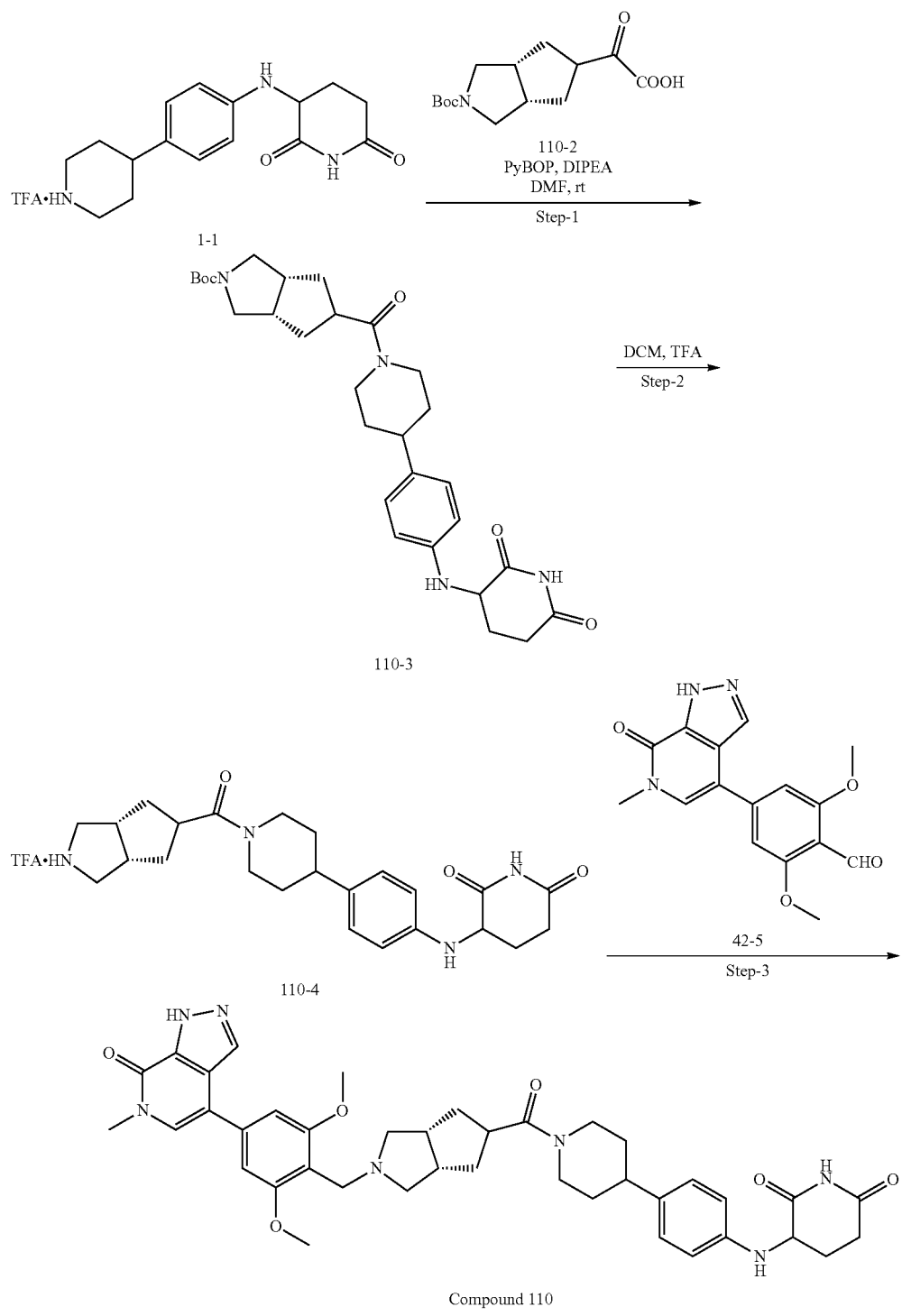

Step-1: To a stirred solution of 110-2 (190.70 mg, 0.747 mmol) and 1-1 (0.3 g, 0.747 mmol) in DMF (5 mL) was added DIPEA (0.8 mL) and followed by PyBOP (0.7785 g, 1.50 mmol) under inert atmosphere. Then the reaction mixture was allowed to stir for 16 h while monitoring by TLC and LCMS analysis. After completion of the reaction, it was quenched with H2O (20 mL) and extracted with EtOAc (2×20 mL). The combined organic layer was dried over Na2SO4 and evaporated under reduced pressure. Crude was washed with diethyl ether to afford compound 110-3 (0.050 g, 89.5% purity) as a light green solid. LC-MS (ES+): m/z 525.39 [M+H]+

Step-2: To a stirred solution of 110-3 (50 mg, 0.095 mmol) in DCM (1 mL) was added TFA (0.5 mL) under inert atmosphere. Then, the reaction mixture was stirred for 2 h while monitoring by TLC. After completion of reaction, solvent was evaporated under reduced pressure and the resulting solid was co-distilled with toluene followed by diethyl ether washings to afford compound 110-4 TFA salt (0.043 g, 66.19% yield, 79% purity, 061) as a brown solid which was used for next step as such. LC-MS (ES$^+$): m/z 425.49 [M+H]$^+$ Step-3: To a stirred solution of 110-4 (43 mg, 0.007 mmol, 061) in DCE (5 mL) and Methanol (5 mL) was added Sodium acetate, anhydrous (13.10 mg, 0.159 mmol), Acetic acid (0.01 mL) and stirred for 5 minutes. Then, molecular sieves (50 mg) followed by compound-5 (37.5 mg, 0.119.76 mmol) was added and allowed to heat at 70° C. for 4 h and then cooled to rt and added Si-CBH (86 mg) and stirring was continued for 16 h while monitoring by LCMS. After completion the reaction mixture was filtered through Celite pad and washed with DCM and filtrate was concentrated under reduced pressure. The crude was purified by Prep-HPLC to afford 3-[4-[1-[(3aR,6aS)-2-[[2,6-dimethoxy-4-(6-methyl-7-oxo-1H-pyrazolo[3,4-c]pyridin-4-yl)phenyl]methyl]-3,3a,4,5,6,6a-hexahydro-1H-cyclopenta[c]pyrrole-5-carbonyl]-4-piperidyl]anilino]piperidine-2,6-dione (10.6 mg, 15.72% yield, 99% purity, 061) as a brown solid. $^1$H NMR (400 MHz, DMSO-d$_6$) δ=14.3 (s, 1H), 10.76 (s, 1H), 9.83 (s, 2H), 9.47 (s, 1H), 8.22 (s, 1H), 7.62 (d, J=4.4 Hz, 1H), 6.96-6.92 (m, 4H), 6.61-6.59 (m, 2H), 4.61-4.49 (m, 1H), 4.32-4.28 (m, 2H), 4.25-4.24 (m, 1H), 3.96 (m, 6H), 3.62-3.61 (m, 3H), 3.37-3.25 (m, 2H), 3.16-3.13 (m, 2H), 3.09-2.96 (m, 2H), 2.79-2.77 (m, 2H), 2.67-2.60 (m, 3H), 2.07-2.00 (m, 4H), 1.90-1.61 (m, 4H), 1.54-1.02 (m, 2H). LC-MS (ES$^+$): m/z 722.58 [M+H]$^+$.

Synthesis of Compound 111

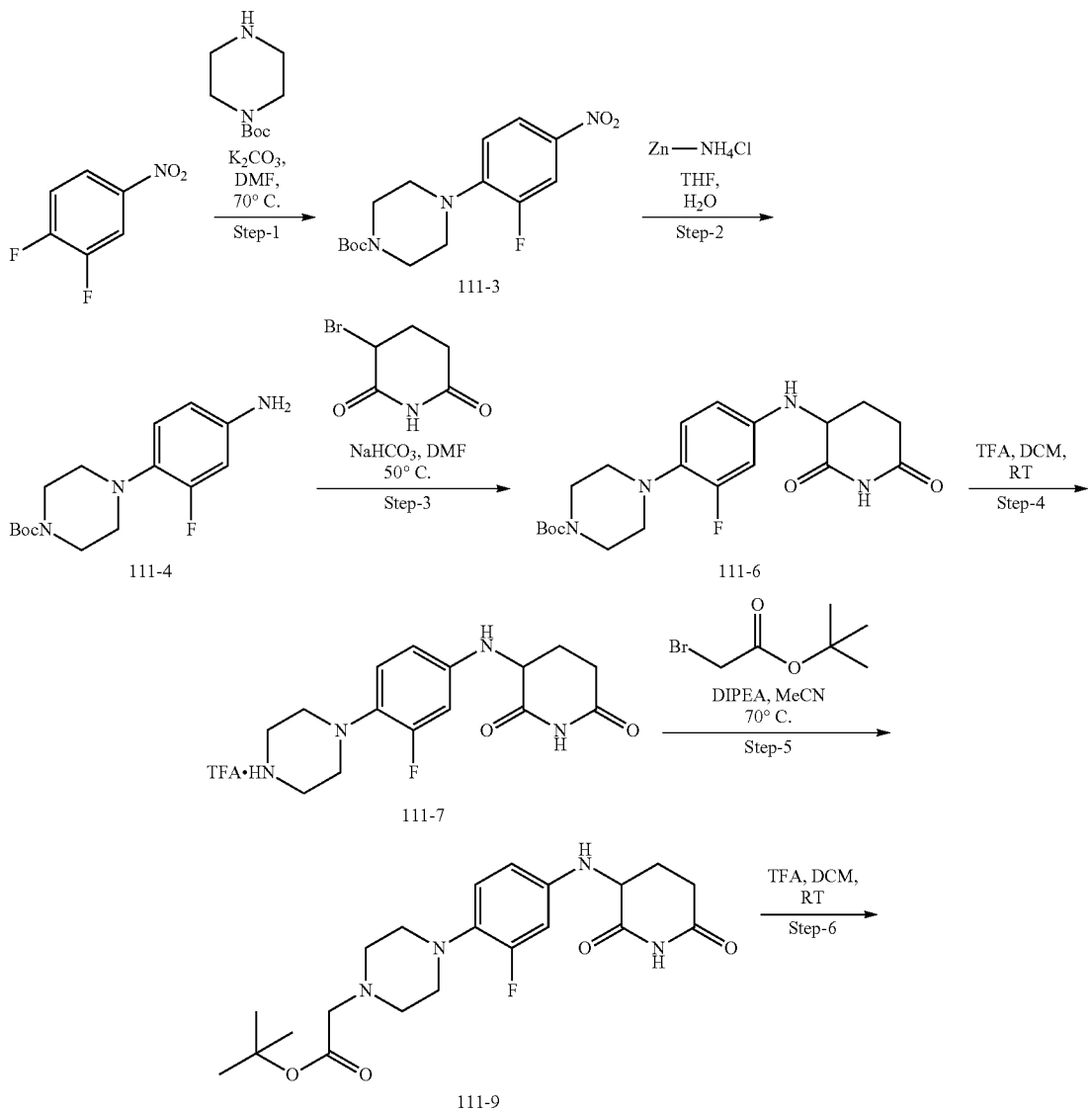

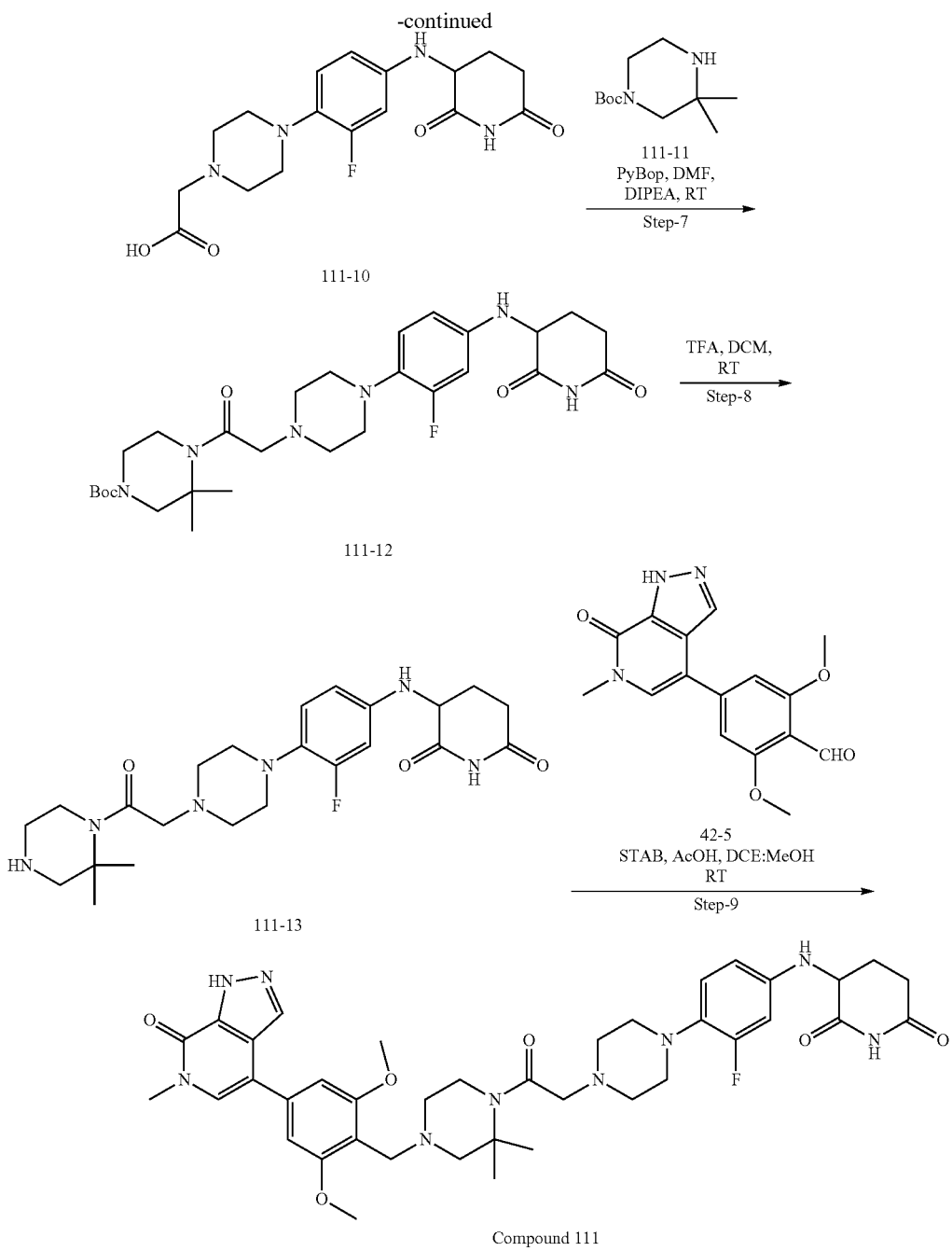

Step-1: To a stirred solution of compound tert-butyl piperazine-1-carboxylate (4.27 g, 26.85 mmol) in DMF (50 mL) was added cesium carbonate (25.95 g, 40.27 mmol) and stirred for 15 min before adding 1,2-difluoro-4-nitro-benzene (5 g, 26.85 mmol). The reaction mixture stirred at RT for 16 h while monitoring by TLC. After completion, the reaction mass was quenched with ice flakes and the precipitated solid was filtered, dried under vacuum to afford tert-butyl 4-(2-fluoro-4-nitro-phenyl) piperazine-1-carboxylate 111-3 (8.2 g, 92.01% yield, 98% purity) as a yellow solid. LC-MS (ES+): m/z 326.14 [M+H]+

Step-2: To a stirred solution of tert-butyl 4-(2-fluoro-4-nitro-phenyl)piperazine-1-carboxylate 111-3 (5 g, 15.37 mmol) in methanol (120 mL) was added 10% wet Pd-C (1.847 g, 15.37 mmol) and the reaction mixture was stirred under $H_2$ balloon pressure for 5 h, while monitoring by LCMS and TLC. The reaction mixture was filtered through Celite bed and the filtrate was concentrated to afford tert-butyl 4-(4-amino-2-fluoro-phenyl) piperazine-1-carboxylate 111-4 (3.9 g, 80% purity) as a yellow solid. LC-MS (ES+): m/z 296.17 [M+H]+

Step-3: To a stirred solution of tert-butyl 4-(4-amino-2-fluoro-phenyl)piperazine-1-carboxylate 111-4 (4.5 g, 15.24 mmol) in DMF (30 mL) were added 3-bromopiperidine-2, 6-dione 111-5 (8.78 g, 45.71 mmol), NaHCO$_3$ (12.80 g, 152.36 mmol) and stirred at 85° C. for 48 h, while monitoring the reaction by LCMS and TLC. After 48 h, the reaction was quenched with ice cold water (250 mL) and extracted with EtOAc (3×250 mL). The combined organic layer was dried over anhydrous Na$_2$SO$_4$ and concentrated. The crude compound was purified by (silica gel mesh 100-200, and product eluted with 50% ethyl acetate in pet ether-neat ethyl acetate) column chromatography to afford tert-butyl 4-[4-[(2,6-dioxo-3-piperidyl)amino]-2-fluoro-phenyl]piperazine-1-carboxylate 111-6 (3.5 g, 56.52% yield) as a purple solid. LC-MS (ES$^+$): m/z 407.20 [M+H]$^+$ Step-4: To a stirred solution of compound-6 (2 g, 4.92 mmol) in DCM (10 mL) was added TFA (1.5 mL) and stirred the reaction mixture at 28° C. for 2 hr while monitoring by TLC and LCMS analysis. After completion of reaction, the reaction mass was concentrated under reduced pressure. The resulting solid was co-distilled with toluene and solid was washed with diethyl ether, dried to afford as a light solid (1.3 g, 55% yield). LC-MS (ES$^+$): m/z 307.54 [M+H]$^+$ Step-5: To a stirred solution of compound-7 (1.3 g, 4.24 mmol) in ACN (15 mL) was added DIPEA (5.17 mL) and followed by Compound-8 (0.823 g, 4.24 mmol) under inert atmosphere. Then the reaction mixture was allowed to stir at 70° C. for 16 h while monitoring by TLC and LCMS analysis. After completion of the reaction, it was concentrated under reduced pressure and quenched with H$_2$O (20 mL) and extracted with EtOAc (2×20 mL). The combined organic layer was dried over Na$_2$SO$_4$ and evaporated under reduced pressure. Crude was purified by Column chromatography (davisil) using 0-50% EA in PE to afford compound 111-9 (0.61, 97% purity) as off-white solid. LC-MS (ES$^+$): m/z 421.60 [M+H]$^+$ Step-6: To a stirred solution of 111-9 (0.6 g, 1.43 mmol) in DCM (5 mL) was added TFA (0.5 mL) under inert atmosphere. Then, the reaction mixture was stirred at 40° C. for 3 h while monitoring by TLC. After completion of reaction, solvent was evaporated under reduced pressure and the resulting solid was co-distilled with toluene followed by diethyl ether washings to afford compound 111-10 (0.45 g, 52.74% yield, 80% purity, 061) as a light green solid which was used for next step as such. LC-MS (ES$^+$): m/z 365.35 [M+H]$^+$ Step-7: To a stirred solution of 111-10 (0.45 g, 1.24 mmol) and compound-11 in DMF (10 mL) was added DIPEA (1.5 mL) under inert atmosphere. Then, pyBOP (0.64 g 1.24 mmol) was added the reaction mixture was stirred at RT for 16 h while monitoring by TLC. After completion of reaction, reaction mixture was quenched with ice water and extracted with ethyl acetate (2×20 mL). The organic layer was washed with brine solution, combined organic layer was dried over Na2SO4, concentrated, the crude was purified by column chromatography using (100-200 silica gel mesh) afforded 111-12 (0.6 g, 77.99% yield, 90% purity) as light yellow solid. LC-MS (ES$^+$): m/z 559.55 [M−H]$^+$ Step-8: To a stirred solution of 111-12 (0.4 g, 0.713 mmol) in DCM (5 mL) was added TFA (0.27 mL) and stirred the reaction mixture at 28° C. for 3 hr while monitoring by TLC and LCMS. After completion, reaction mixture was concentrated to dryness and co-distilled with toluene (2×20 mL) finally washed with diethyl ether afforded 111-13 (0.25 g, 54.28% yield, 89% purity, 061) as light green solid. LC-MS (ES$^+$): m/z 461.53 [M−H]$^+$ Step-9: To a stirred solution of 111-13 (0.15 g, 0.269 mmol) in DCE (5 mL) and Methanol (5 mL) was added Sodium acetate, anhydrous (44 mg, 0.539 mmol), Acetic acid (0.01 mL) and stirred for 5 minutes. Then, 2,6-dimethoxy-4-(6-methyl-7-oxo-6,7-dihydro-1H-pyrazolo[3,4-c]pyridin-4-yl)benzaldehyde (84 mg, 0.269 mmol) was added and allowed to heat at 70° C. for 4 h and then cooled to rt and added SBCBH (0.15 mg) and stirring was continued for 16 hr. After completion of reaction by LCMS, the reaction mixture was filtered through Celite pad and washed with DCM and filtrated was concentrated under reduced pressure. The crude was purified by Prep-HPLC to afford 3-[4-[4-[2-[4-[[2,6-dimethoxy-4-(6-methyl-7-oxo-1H-pyrazolo[3,4-c]pyridin-4-yl)phenyl]methyl]-2,2-dimethyl-piperazin-1-yl]-2-oxo-ethyl]piperazin-1-yl]-3-fluoro-anilino]piperidine-2,6-dione (20 mg, 8.48% yield, 99.63% purity, 061). $^1$H NMR (400 MHz, DMSO-d$_6$) δ=14.3 (s, 1H), 10.76 (s, 1H), 9.78 (s, 2H), 8.24 (s, 1H), 7.65 (s, 1H), 7.21-7.00 (m, 1H), 6.89-6.85 (m, 1H), 6.55 (d, J=2 Hz, 1H), 6.50 (d, J=8.4 Hz, 1H), 4.29-4.25 (m, 5H), 3.97 (s, 6H), 3.63 (s, 3H), 3.57-3.24 (m, 6H), 3.29-3.08 (m, 8H), 2.69-2.66 (m, 1H), 2.59-2.54 (m, 1H), 2.08-2.07 (m, 1H), 1.88-1.84 (m, 1H), 1.61-1.49 (m, 6H). LC-MS (ES$^+$): m/z 758.58 [M+H]$^+$ Synthesis of Compound 112

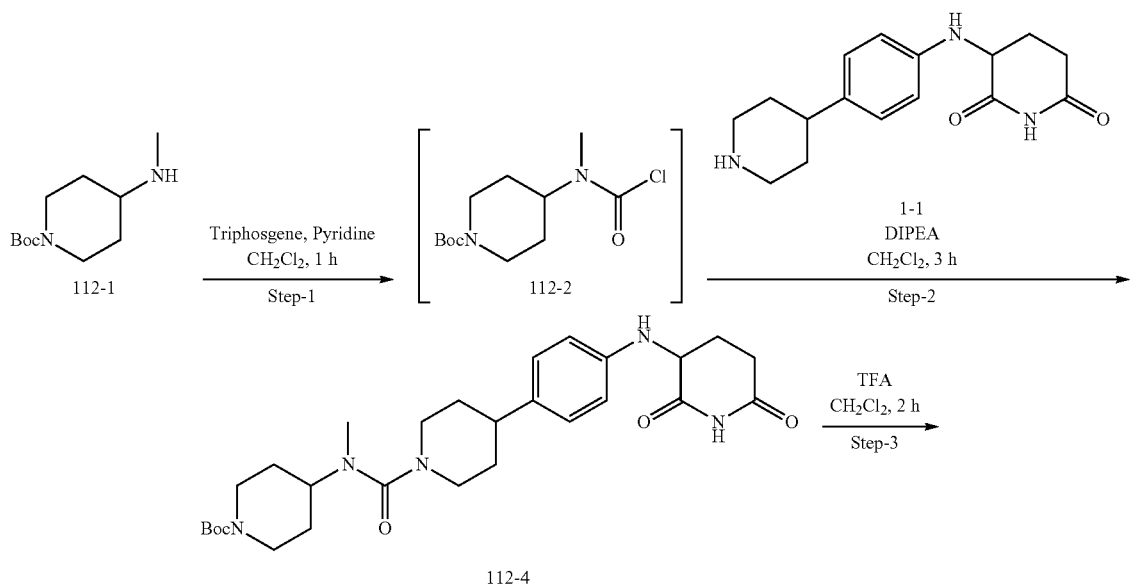

-continued

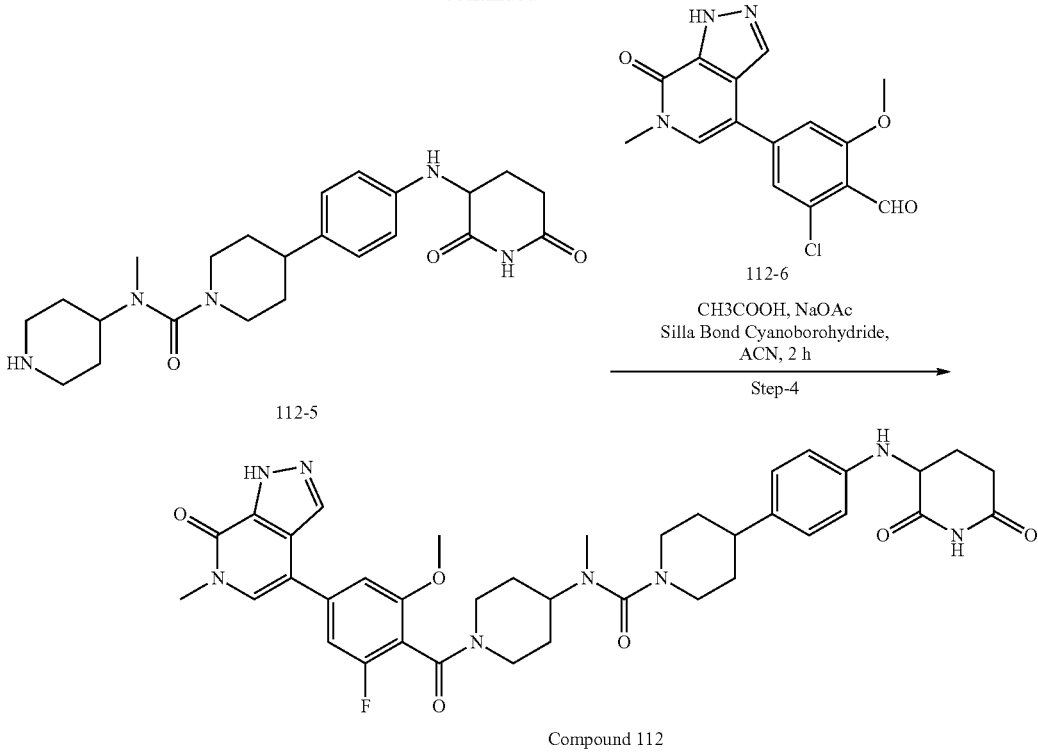

Compound 112

Step-1: To a solution of tert-butyl 4-(methylamino)piperidine-1-carboxylate 112-1 (1 g, 4.67 mmol) in CH$_2$Cl$_2$ (20 mL) was added drop wise Pyridine (0.553 g, 7.00 mmol) at 0° C. and stirred for 10 min. A solution of Triphosgene (0.692 g, 2.33 mmol) in CH$_2$Cl$_2$ (20 mL) was added slowly at same temperature and stirred for 1 h while monitoring the reaction by TLC. The reaction mixture was evaporated to obtain tert-butyl 4-[chlorocarbonyl(methyl)amino]piperidine-1-carboxylate 112-2 (1 g, 2.71 mmol, 58.08% yield, 75% purity) as a yellow semi-solid. This was taken for the next step without further purification.

Step-2: A solution of 3-[4-(4-piperidyl)anilino]piperidine-2,6-dione 1-1 (0.5 g, 1.74 mmol) in DCM (20 mL) was cooled to 0° C. and added DIPEA (0.674 g, 5.22 mmol). After 10 min, a solution of tert-butyl 4-[chlorocarbonyl(methyl)amino]piperidine-1-carboxylate 112-2 (0.481 g, 1.74 mmol) in dry CH$_2$Cl$_2$ was added at 0° C. and stirred at RT for 3 h while monitoring the reaction by TLC and LCMS. The reaction mass was quenched with H$_2$O (10 ml) and extracted with CH$_2$Cl$_2$ (2×50 ml). The organic layer was washed with brine (25 ml), dried over Na$_2$SO$_4$ and evaporated under reduced pressure to obtain tert-butyl 4-[[4-[4-[(2,6-dioxo-3-piperidyl)amino]phenyl]piperidine-1-carbonyl]-methyl-amino]piperidine-1-carboxylate 112-4 (0.6 g, 0.796 mmol, 65.5% yield, 98.46% purity) as a yellow solid. $^1$H NMR (400 MHz, DMSO-d$_6$) δ 10.87 (s, 1H), 6.95 (d, J=8.4 Hz, 2H), 6.60 (d, J=8.4 Hz, 2H), 5.65 (d, J=7.6 Hz, 1H), 4.27-4.23 (m, 1H), 4.03-4.00 (m, 2H), 3.59-3.57 (m, 3H), 3.39 (dd, 2H), 2.76-2.73 (m, 6H), 2.67 (s, 3H), 2.13-2.10 (m, 1H), 2.09-1.88 (m, 1H), 1.71-1.68 (d, 2H), 1.58-1.52 (m, 6H), 1.40 (s, 9H). LC-MS (ES$^+$): m/z 528.39 [M+H]$^+$ Step-3: A solution of tert-butyl 4-[[4-[4-[(2,6-dioxo-3-piperidyl)amino]phenyl]piperidine-1-carbonyl]-methyl-amino]piperidine-1-carboxylate 112-4 (0.45 g, 0.852 mmol) in dry CH$_2$Cl$_2$ (2 mL) was added TFA (0.972. g, 8.53 mmol) at 0° C. The reaction mixture was slowly warmed to RT and allowed to stir for 2 h while monitoring the reaction by TLC and LCMS. Most of the solvent was removed under reduced pressure and co-distilled with dry CH$_2$Cl$_2$. The crude compound was purified by reverse phase column chromatography (MeCN in 0.1% formic acid) to afford 4-[4-[(2,6-dioxo-3-piperidyl)amino]phenyl]-N-methyl-N-(4-piperidyl)piperidine-1-carboxamide.TFA salt 112-5 (0.15 g, 0.268 mmol, 31.52% yield, 97.06% purity) as brown solid. LC-MS (ES$^+$): m/z 428.39 [M+H]$^+$ Step-4: To a stirred solution of 4-[4-[(2,6-dioxo-3-piperidyl)amino]phenyl]-N-methyl-N-(4-piperidyl)piperidine-1-carboxamide 112-5 (0.1 g, 0.233 mmol) were added 4 Å molecular sieves (0.05 g), AcOH (0.014 g, 0.233 mmol) and sodium acetate, anhydrous (0.057 g, 0.701 mmol). The resulting solution was stirred for 10 min, then added 2-fluoro-6-methoxy-4-(6-methyl-7-oxo-1H-pyrazolo[3,4-c]pyridin-4-yl)benzaldehyde 6 (0.070 g, 0.233 mmol) and heated the reaction mixture at 70° C. for 4 h then cooled it at RT and added Silia Bond Cyanoborohydride (67.78 mg, 1.17 mmol). The stirring was continued at RT for 16 h, while monitoring the reaction by LCMS and TLC. After 16 h, the reaction mass was filtered, concentrated and purified by Prep-HPLC to afford 4-[4[(2,6-dioxo-3-piperidyl)amino]phenyl]-N-[1-[[2-fluoro-6-methoxy-4-(6-methyl-7-oxo-1H-pyrazolo[3,4-c]pyridin-4-yl)phenyl]methyl]-4-piperidyl]-N-methyl-piperidine-1-carboxamide Compound 112 (35.8 mg, 0.42 mmol, 18.11% yield, 97.84% purity) as an off white solid as a TFA salt. $^1$H NMR (400 MHz, DMSO-d$_6$) δ 14.34 (s, 1H), 10.77 (s, 1H), 9.16 (s, 1H), 8.24 (s, 1H), 7.70 (s, 1H), 7.26-7.22 (m, 2H), 6.95 (d, J=8.5 Hz, 2H), 6.61 (d, J=8.5 Hz, 2H), 4.28-4.25 (m, 3H), 4.02 (s, 3H), 3.79 (t, J=11.5 Hz, 1H), 3.62-3.59 (m, 5H), 3.26-3.23 (m, 5H), 2.82-2.73 (m, 6H), 2.63-2.61 (m, 1H), 2.11-2.00 (m, 3H), 1.88-1.80 (m, 3H), 1.70 (d, J=11.2 Hz, 2H), 1.51 (q, J=11.1 Hz, 2H). LC-MS (ES$^+$): m/z 713.51 [M+H]$^+$ Compound 113 was prepared following the synthesis of Compound 112.

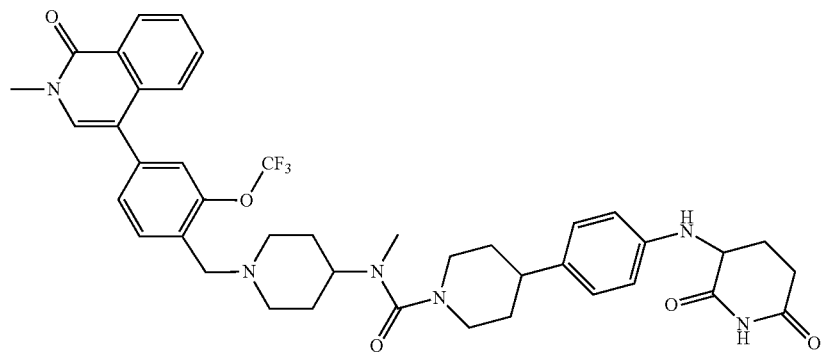 [SMILES: CN(C(=O)N1CCC(c2ccc(NC3CCC(=O)NC3=O)cc2)CC1)C1CCN(Cc2ccc(-c3cn(C)c(=O)c4ccccc34)cc2OC(F)(F)F)CC1]

¹H NMR (400 MHz, DMSO-d₆) δ 10.76 (s, 1H), 9.59 (s, 1H), 8.36 (d, J=8.0 Hz, 1H), 7.87 (d, J=8.0 Hz, 1H), 7.81-7.68 (m, 1H), 7.68-7.45 (m, 5H), 6.96 (d, J=8.2 Hz, 2H), 6.62 (d, J=8.2 Hz, 2H), 4.46 (s, 2H), 4.26 (dd, J=11.3, 4.8 Hz, 1H), 3.83 (d, J=12.7 Hz, 1H), 3.59 (s, 5H), 3.49 (d, J=11.2 Hz, 2H), 3.28 (s, 2H), 2.74 (d, J=25.1 Hz, 6H), 2.57 (dd, J=17.8, 4.5 Hz, 2H), 2.28-1.95 (m, 3H), 1.86 (dd, J=12.3, 4.3 Hz, 3H), 1.71 (d, J=12.4 Hz, 2H), 1.60-1.40 (m, 2H). LC-MS (ES⁺): m/z 759.7 [M+H]⁺.

Compound 114 was prepared following the synthesis of Compound 112.

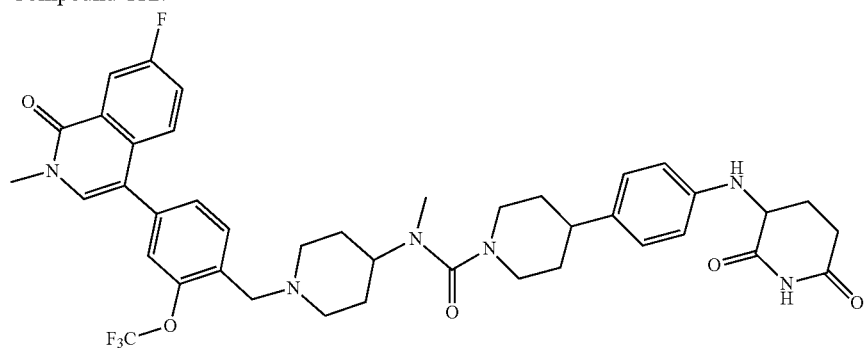

¹H NMR (400 MHz, DMSO-d₆) δ 10.76 (s, 1H), 9.55 (s, 1H), 8.01 (dd, J=9.4, 2.8 Hz, 1H), 7.88 (d, J=8.0 Hz, 1H), 7.77-7.51 (m, 5H), 6.96 (d, J=8.2 Hz, 2H), 6.62 (d, J=8.3 Hz, 2H), 4.46 (s, 2H), 4.26 (dd, J=11.3, 4.8 Hz, 1H), 3.79 (d, J=13.0 Hz, 1H), 3.60 (s, 5H), 3.48 (d, J=11.4 Hz, 2H), 3.27 (s, 2H), 2.74 (d, J=24.6 Hz, 6H), 2.57 (dd, J=17.6, 4.3 Hz, 2H), 2.19-1.95 (m, 3H), 1.86 (dd, J=12.7, 3.8 Hz, 3H), 1.71 (d, J=12.5 Hz, 2H), 1.51 (q, J=12.4, 12.0 Hz, 2H). LC-MS (ES⁺): m/z 777.8. [M+H]⁺.

Compound 115 was prepared following the synthesis of Compound 112.

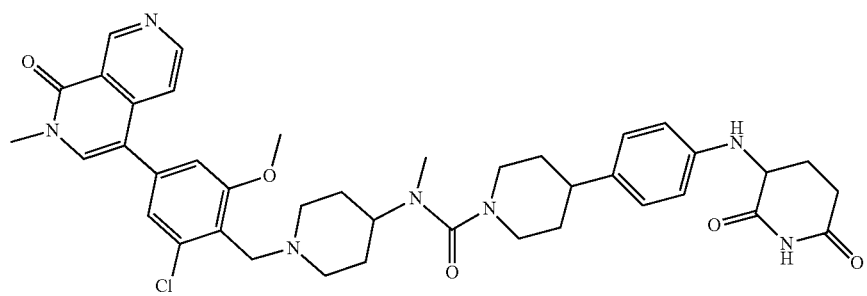 [SMILES: COc1cc(-c2cn(C)c(=O)c3cnccc23)cc(Cl)c1CN1CCC(N(C)C(=O)N2CCC(c3ccc(NC4CCC(=O)NC4=O)cc3)CC2)CC1]

¹H NMR (400 MHz, DMSO-d₆) δ 10.77 (s, 1H), 9.49 (s, 1H), 9.07 (s, 1H), 8.77 (d, J=5.8 Hz, 1H), 7.98 (s, 1H), 7.57 (d, J=5.8 Hz, 1H), 7.33 (d, J=1.5 Hz, 1H), 7.27 (d, J=1.6 Hz, 1H), 6.96 (d, J=8.5 Hz, 2H), 6.62 (d, J=8.4 Hz, 2H), 4.43 (d, J=4.1 Hz, 2H), 4.27 (dd, J=11.3, 4.8 Hz, 1H), 3.96 (s, 3H), 3.82 (d, J=12.1 Hz, 1H), 3.69-3.48 (m, 8H), 3.36 (p, J=11.5 Hz, 2H), 2.86-2.55 (m, 8H), 2.09 (dd, J=13.1, 4.1 Hz, 2H), 1.99-1.77 (m, 3H), 1.71 (d, J=12.4 Hz, 2H), 1.52 (q, J=12.1 Hz, 2H). LC-MS (ES⁺): m/z 740.8 [M+H]⁺.

Compound 116 was prepared following the synthesis of Compound 112.

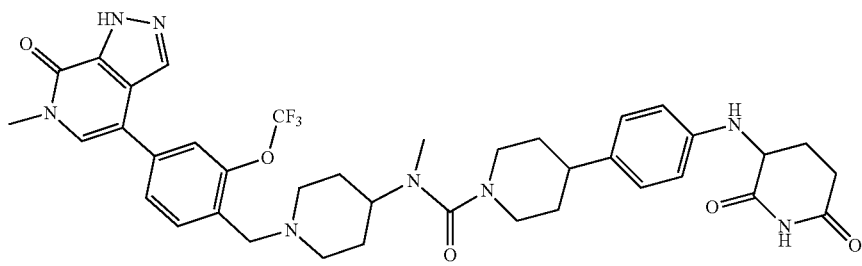 [SMILES: CN(C(=O)N1CCC(c2ccc(NC3CCC(=O)NC3=O)cc2)CC1)C1CCN(Cc2ccc(-c3cn(C)c(=O)c4[nH]ncc34)cc2OC(F)(F)F)CC1]

¹H NMR (400 MHz, DMSO-d₆) δ 10.76 (s, 1H), 9.53 (s, 1H), 8.12 (s, 1H), 7.85 (d, J=1.9 Hz, 2H), 7.70 (d, J=11.1 Hz, 2H), 6.95 (d, J=8.3 Hz, 2H), 6.62 (d, J=8.3 Hz, 2H), 4.43 (s, 2H), 4.26 (dd, J=11.3, 4.8 Hz, 1H), 3.90-3.72 (m, 1H), 3.62 (s, 6H), 3.46 (d, J=11.5 Hz, 2H), 3.26 (s, 2H), 2.89-2.64 (m, 7H), 2.64-2.53 (m, 1H), 2.20-1.92 (m, 3H), 1.87 (tt, J=13.1, 5.3 Hz, 3H), 1.70 (d, J=12.4 Hz, 2H), 1.51 (td, J=13.8, 10.2 Hz, 2H). LC-MS (ES⁺): m/z 749.8 [M+H]⁺.

Compound 117 was prepared following the synthesis of Compound 112.

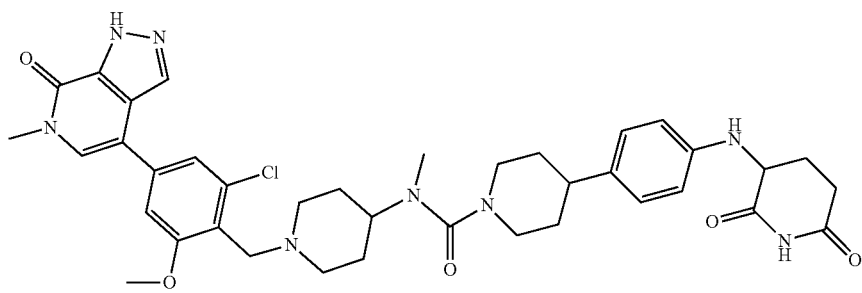 [SMILES: COc1cc(-c2cn(C)c(=O)c3[nH]ncc23)cc(Cl)c1CN1CCC(N(C)C(=O)N2CCC(c3ccc(NC4CCC(=O)NC4=O)cc3)CC2)CC1]

¹H NMR (400 MHz, DMSO-d₆) δ 14.31 (s, 1H), 10.78 (s, 1H), 8.91 (s, 1H), 8.21 (s, 1H), 7.71 (s, 1H), 7.46 (s, 1H), 7.35 (s, 1H), 6.95 (d, J=7.6 Hz, 2H), 7.09 (s, 1H), 6.61 (d, J=7.6 Hz, 2H), 4.40-4.39 (m, 2H), 4.28-4.24 (m, 1H), 3.97 (s, 6H), 3.49-3.33 (m, 9H), 2.77-2.70 (m, 6H), 2.69-2.60 (m, 1H), 2.11-2.06 (m, 2H), 1.88-1.87 (m, 3H), 1.72-1.69 (m, 2H), 1.55-1.50 (m, 2H), 1.54 (m, 3H), 1.27-1.22 (m, 2H). LC-MS (ES⁺): m/z 729.59 [M+H]⁺.

Compound 118 was prepared following the synthesis of Compound 112.

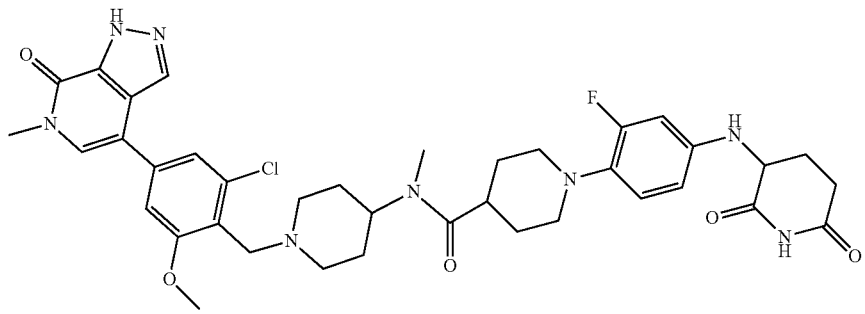 [SMILES: COc1cc(-c2cn(C)c(=O)c3[nH]ncc23)cc(Cl)c1CN1CCC(N(C)C(=O)C2CCN(c3ccc(NC4CCC(=O)NC4=O)cc3F)CC2)CC1]
¹H NMR (400 MHz, DMSO-d₆) δ 14.36 (s, 1H), 10.80 (s, 1H), 9.03 (s, 1H), 8.22 (s, 1H), 7.72 (s, 1H), 7.47 (d, J=7.2 Hz, 1H), 7.36 (d, J=6.0 Hz, 1H), 7.24 (bs, 1H), 6.55 (d, J=14.7 Hz, 1H), 6.46 (d, J=8.2 Hz, 1H), 4.58-4.51 (m, 1H), 4.40 (bs, 2H), 4.29 (d, J=7.6 Hz, 1H), 4.04 (d, J=3.6 Hz, 3H), 3.62 (s, 3H), 3.40-2.55 (m, 14H), 2.18-2.00 (m, 3H), 1.88-1.66 (m, 7H). LCMS (ES⁺): m/z; 747.31[M+H]⁺.
Compound 119 was prepared following the synthesis of Compound 112.
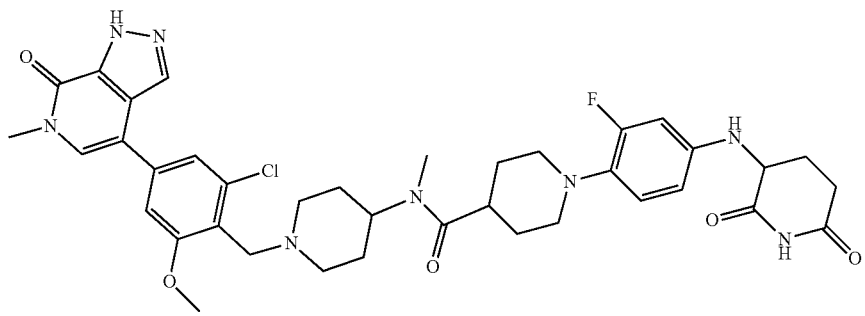 [SMILES: COc1cc(-c2cn(C)c(=O)c3[nH]ncc23)cc(Cl)c1CN1CCC(N(C)C(=O)C2CCN(c3ccc(NC4CCC(=O)NC4=O)cc3F)CC2)CC1]
¹H NMR (400 MHz, DMSO-d₆) δ 10.77 (s, 1H), 9.34 (bs, 1H), 8.36 (d, J=8.0 Hz, 1H), 7.77 (t, J=7.2 Hz, 1H), 7.66-7.58 (m, 3H), 7.11 (d, J=7.2 Hz, 2H), 6.97 (d, J=8.4 Hz, 2H), 6.62 (d, J=8.8 Hz, 2H), 5.68 (bs, 1H), 4.50-4.24 (m, 3H), 3.95 (s, 3H), 3.81 (m, 1H), 3.63-3.49 (m, 5H), 3.52 (m, 2H), 3.17 (m, 2H), 2.83-2.69 (m, 6H), 2.60 (m, 2H), 2.11-2.01 (m, 3H), 1.88-1.82 (m, 3H), 1.72-1.69 (m, 2H), 1.56-1.50 (m, 2H). LCMS (ES⁺): m/z; 723.57 [M+H]⁺.
Compound 120 was prepared following the synthesis of Compound 112.
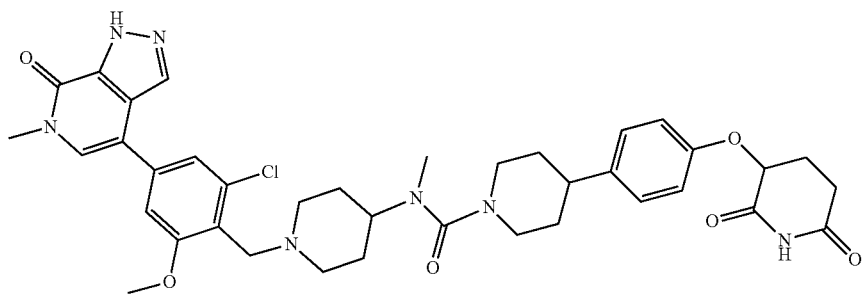 [SMILES: COc1cc(-c2cn(C)c(=O)c3[nH]ncc23)cc(Cl)c1CN1CCC(N(C)C(=O)N2CCC(c3ccc(OC4CCC(=O)NC4=O)cc3)CC2)CC1]

¹H NMR (400 MHz, DMSO-d₆): δ 14.28 (bs, 1H), 10.91 (s, 1H), 8.92 (bs, 1H), 8.21 (s, 1H), 7.71 (s, 1H), 7.46 (d, J=1.2 Hz, 1H), 7.35 (s, 1H), 7.17 (d, J=8.8 Hz, 2H), 6.95 (d, J=8.8 Hz, 2H), 5.17 (q, J=5.2 Hz, 10.8 Hz, 1H), 4.40 (d, J=4.0 Hz, 2H), 4.03 (s, 3H), 3.82 (t, J=11.2 Hz, 1H), 3.62 (m, 4H), 3.42 (m, 4H), 2.85 (m, 8H), 2.18 (m, 4H), 1.83 (dd, J=10.4 Hz, 4H), 1.56 (m, 2H). LCMS (ES⁺): m/z; 730.6 [M+H]⁺

Compound 121 was prepared following the synthesis of Compound 112.

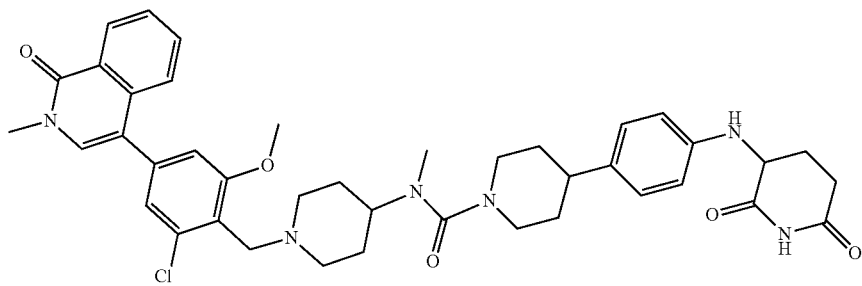 [SMILES: COc1cc(-c2cn(C)c(=O)c3ccccc23)cc(Cl)c1CN1CCC(N(C)C(=O)N2CCC(c3ccc(NC4CCC(=O)NC4=O)cc3)CC2)CC1]

¹H NMR (400 MHz, DMSO-d6) δ 10.76 (s, 1H), 8.93 (s, 1H), 8.44-8.27 (m, 1H), 7.86-7.67 (m, 1H), 7.67-7.53 (m, 2H), 7.28 (dd, J=20.6, 1.5 Hz, 2H), 7.07-6.83 (m, 2H), 6.62 (d, J=8.2 Hz, 2H), 4.43 (d, J=4.6 Hz, 2H), 4.26 (dd, J=11.3, 4.8 Hz, 1H), 3.96 (s, 3H), 3.82 (d, J=8.2 Hz, 1H), 3.70-3.48 (m, 6H), 3.38 (q, J=11.9 Hz, 2H), 2.93-2.65 (m, 6H), 2.60 (s, 1H), 2.54 (s, 4H), 2.08 (tt, J=11.9, 5.8 Hz, 2H), 1.85 (td, J=12.4, 4.4 Hz, 3H), 1.75-1.65 (m, 2H), 1.52 (dd, J=12.2, 3.7 Hz, 2H). LCMS (ES⁺): m/z; 739.1[M+H]⁺.

Compound 122 was prepared following the synthesis of Compound 112.

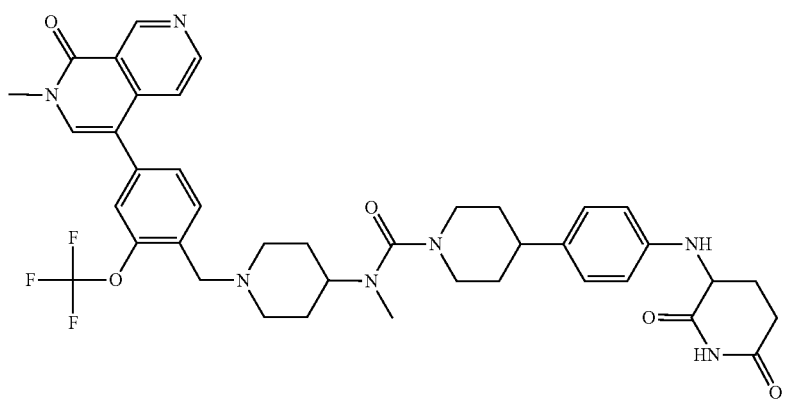 [SMILES: CN(C(=O)N1CCC(c2ccc(NC3CCC(=O)NC3=O)cc2)CC1)C1CCN(Cc2ccc(-c3cn(C)c(=O)c4cnccc34)cc2OC(F)(F)F)CC1]

¹H NMR (400 MHz, DMSO-d₆) δ 10.76 (s, 1H), 9.56 (s, 1H), 9.48 (s, 1H), 8.76 (d, J=5.7 Hz, 1H), 7.94 (s, 1H), 7.89 (d, J=8.0 Hz, 1H), 7.68 (dd, J=8.0, 1.7 Hz, 1H), 7.61 (t, J=1.8 Hz, 1H), 7.46 (d, J=5.7 Hz, 1H), 6.99-6.86 (m, 2H), 6.61 (d, J=8.5 Hz, 2H), 4.46 (s, 2H), 4.26 (dd, J=11.3, 4.8 Hz, 1H), 3.80 (d, J=11.0 Hz, 1H), 3.61 (s, 5H), 3.48 (d, J=11.5 Hz, 2H), 3.27 (s, 2H), 2.88-2.54 (m, 7H), 2.12-1.95 (m, 3H), 1.88 (td, J=12.5, 4.5 Hz, 3H), 1.71 (d, J=12.5 Hz, 2H), 1.52 (q, J=13.0, 11.4 Hz, 2H), 1.24 (s, 1H). LCMS (ES⁺): m/z; 760.7 [M+H]⁺.

Compound 123 was prepared following the synthesis of Compound 112.

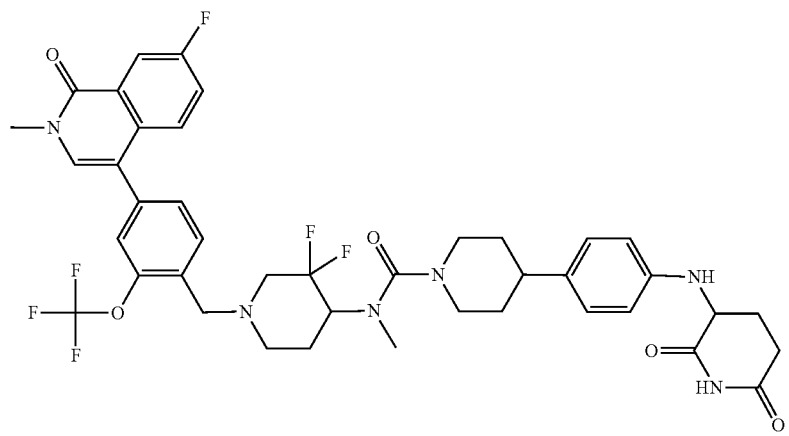 [SMILES: CN(C(=O)N1CCC(c2ccc(NC3CCC(=O)NC3=O)cc2)CC1)C1CCN(Cc2ccc(-c3cn(C)c(=O)c4cc(F)ccc34)cc2OC(F)(F)F)CC1(F)F]
$^1$H NMR (400 MHz, DMSO-d$_6$): δ 1.38-1.48 (m, 1H); 1.56-1.90 (m, 5H); 2.05-2.18 (m, 2H); 2.52-2.62 (m, 2H); 2.68-2.78 (m, 2H); 2.84-2.90 (m, 1H); 2.87 (s, 3H); 2.96-3.04 (m, 1H); 3.10-3.20 (m, 1H); 3.60-3.90 (m, 9H); 4.20-4.40 (m, 2H); 6.62 (d, J=8.4 Hz, 2H); 6.96 (d, J=8.4 Hz, 2H); 7.43 (s, 1H); 7.50-7.67 (m, 4H); 7.72 (d, J=8.0 Hz, 1H); 8.00 (dd, J$_1$=2.8 Hz, J$_2$=9.2 Hz, 1H); 10.78 (s, 1H). LCMS (ES$^+$): m/z; 813.26 [M+H]$^+$
Compound 124 was prepared following the synthesis of Compound 112.
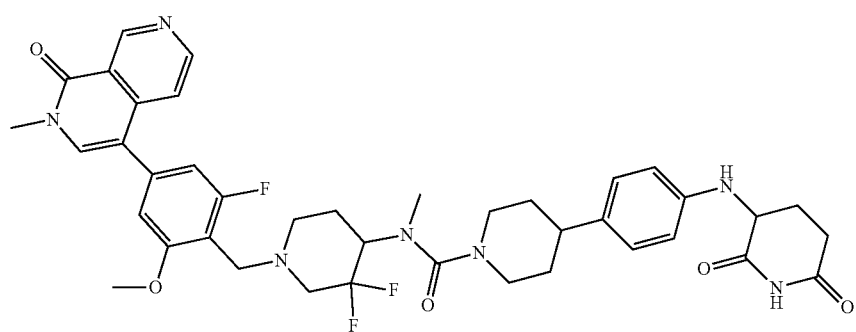 [SMILES: COc1cc(-c2cn(C)c(=O)c3cnccc23)cc(F)c1CN1CCC(N(C)C(=O)N2CCC(c3ccc(NC4CCC(=O)NC4=O)cc3)CC2)C(F)(F)C1]
$^1$H NMR (400 MHz, DMSO-d$_6$) δ 1.38-1.48 (m, 1H); 1.56-1.90 (m, 5H); 2.05-2.20 (m, 2H); 2.52-2.80 (m, 3H); 2.82-2.92 (m, 1H); 2.85 (s, 3H); 3.10-3.20 (m, 1H); 3.35-3.75 (m, 4H); 3.61 (s, 3H); 3.89 (s, 3H); 3.90-4.70 (m, 6H); 6.61 (d, J=8.4 Hz, 2H); 6.95 (d, J=8.4 Hz, 2H); 7.01-7.04 (m, 2H); 7.63 (d, J=6.0 Hz, 1H); 7.98 (s, 1H); 8.75 (d, J=6.0 Hz, 1H); 9.48 (s, 1H); 10.77 (s, 1H). LCMS (ES$^+$): m/z; 760.51 (M+H)$^+$
Compound 125 was prepared following the synthesis of Compound 112.

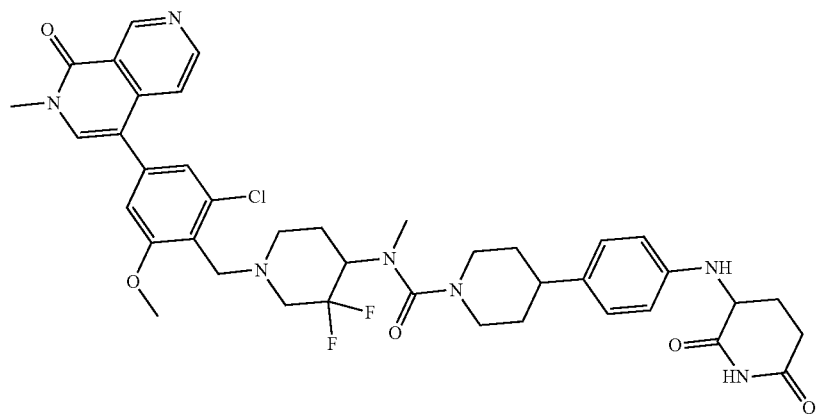 [SMILES: COc1cc(-c2cn(C)c(=O)c3cnccc23)cc(Cl)c1CN1CCC(N(C)C(=O)N2CCC(c3ccc(NC4CCC(=O)NC4=O)cc3)CC2)C(F)(F)C1]

¹H NMR (400 MHz, DMSO-d₆) δ 1.38-1.48 (m, 1H); 1.58-1.78 (m, 4H); 1.80-2.15 (m, 3H); 2.30-2.42 (m, 1H); 2.50-2.62 (m, 3H); 2.66-2.76 (m, 3H); 2.76 (s, 3H); 2.95-3.10 (m, 2H); 3.52-3.70 (m, 2H); 3.59 (s, 3H); 3.76 (s, 2H); 3.88 (s, 3H); 4.12-4.30 (m, 2H); 5.67 (d, J=7.6 Hz, 1H); 6.61 (d, J=8.8 Hz, 2H); 6.95 (d, J=8.4 Hz, 2H); 7.12 (d, J=1.2 Hz, 1H); 7.18 (d, J=1.2 Hz, 1H); 7.54 (d, J=5.6 Hz, 1H); 7.94 (s, 1H); 8.74 (d, J=5.6 Hz, 1H); 9.44 (s, 1H); 10.76 (s, 1H). LCMS (ES⁺): m/z 776.51[M+H]⁺

Synthesis of Compound 126

To a stirred solution of compound 112-5 (87.53 mg, 0.18 mmol) in DMF (10 mL) was added N-ethyl-N-isopropyl-propan-2-amine (178.29 uL, 1.02 mmol) and followed by HATU (155.68 mg, 0.41 mmol). After 10 mins, 2-chloro-6-methoxy-4-(6-methyl-7-oxo-6,7-dihydro-1H-pyrazolo[3,4-c]pyridin-4-yl)benzoic acid (0.08 g, 0.2 mmol) in DMF was added to the above reaction mixture and it was stirred at RT for 16 h while monitoring by TLC and LCMS. After completion of reaction, the reaction mixture was poured onto ice cold water mixture and resulting solid was filtered. The crude mixture was purified by Prep HPLC to afford N-[1-[2-chloro-6-methoxy-4-(2-methyl-1-oxo-2,7-naphthy-

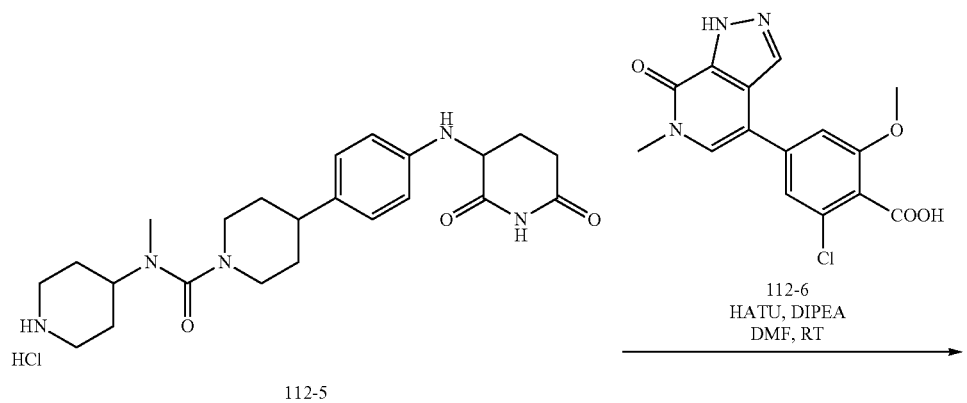

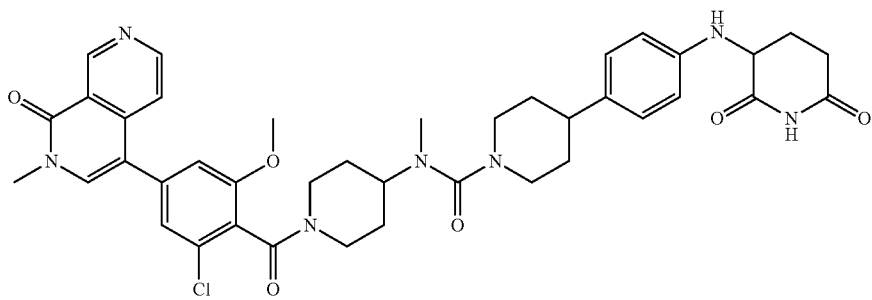

Compound 126 ridin-4-yl)benzoyl]-4-piperidyl]-4-[4-[(2,6-dioxo-3-piperidyl)amino]phenyl]-N-methyl-piperidine-1-carboxamide (20.6 mg, 11.09% yield, 95.69% purity, 061) as a brown solid. $^1$H NMR (400 MHz, DMSO-d$_6$) δ 10.82 (s, 1H), 9.46 (bs, 1H), 8.74 (d, J=5.6 Hz, 1H), 7.99 (s, 1H), 7.61 (d, J=3.2 Hz, 1H), 7.23-7.17 (m, 2H), 6.96 (d, J=8 Hz, 2H), 6.61 (d, J=8.4 Hz, 2H), 4.62-4.61 (m, 1H), 4.28-4.24 (s, 1H), 3.88 (s, 3H), 3.77 (m, 2H), 3.60-3.56 (m, 5H), 3.45-3.16 (m, 2H), 2.73-2.67 (m, 7H), 2.66-2.51 (m, 1H), 2.10-2.08 (m, 1H), 1.75-1.71 (m, 1H), 1.68-1.50 (m, 8H). LCMS (ES$^+$): m/z 754.59[M+H]$^+$.

Compound 127 was prepared following the synthesis of Compound 126.

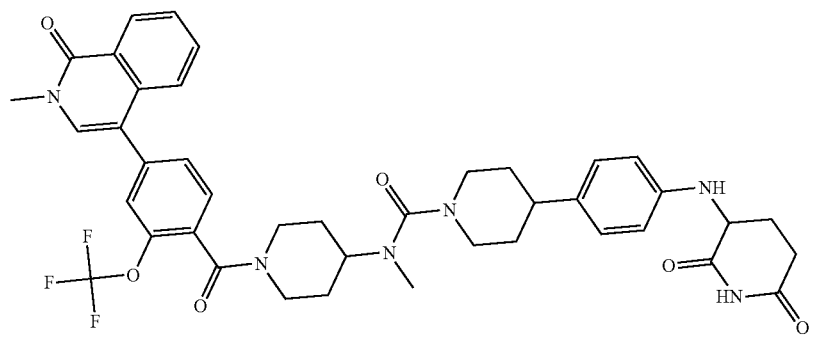 [SMILES: CN(C(=O)N1CCC(c2ccc(NC3CCC(=O)NC3=O)cc2)CC1)C1CCN(C(=O)c2ccc(-c3cn(C)c(=O)c4ccccc34)cc2OC(F)(F)F)CC1]

$^1$H NMR (400 MHz, DMSO-d$_6$) δ 10.77 (s, 1H), 8.35 (dd, J=8.0, 1.4 Hz, 1H), 7.82-7.62 (m, 2H), 7.56 (dt, J=17.4, 6.4 Hz, 5H), 6.97 (d, J=8.2 Hz, 2H), 6.63 (d, J=8.3 Hz, 2H), 4.65 (d, J=12.7 Hz, 1H), 4.27 (dd, J=11.4, 4.8 Hz, 1H), 3.83 (s, 1H), 3.58 (s, 5H), 3.48 (d, J=13.2 Hz, 1H), 3.17 (d, J=14.1 Hz, 1H), 2.93-2.63 (m, 8H), 2.57 (dt, J=24.1, 5.1 Hz, 1H), 2.49 (d, J=2.1 Hz, 3H), 2.08 (dq, J=8.8, 5.4, 4.9 Hz, 1H), 1.97-1.40 (m, 7H). LCMS (ES$^+$): m/z 773.8 [M+H]$^+$.

Compound 128 was prepared following the synthesis of Compound 126.

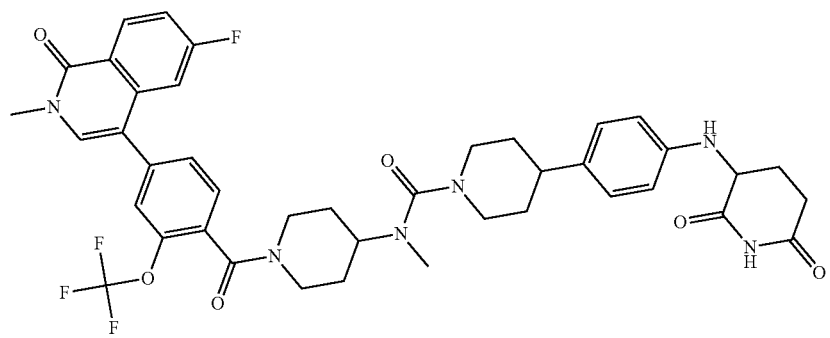 [SMILES: CN(C(=O)N1CCC(c2ccc(NC3CCC(=O)NC3=O)cc2)CC1)C1CCN(C(=O)c2ccc(-c3cn(C)c(=O)c4ccc(F)cc34)cc2OC(F)(F)F)CC1]

$^1$H NMR (400 MHz, DMSO-d$_6$) δ 10.77 (s, 1H), 8.41 (dd, J=8.9, 6.0 Hz, 1H), 7.72 (s, 1H), 7.64-7.50 (m, 3H), 7.43 (td, J=8.6, 2.5 Hz, 1H), 7.23 (dd, J=10.5, 2.5 Hz, 1H), 6.97 (d, J=8.2 Hz, 2H), 6.63 (d, J=8.3 Hz, 2H), 4.65 (d, J=12.7 Hz, 1H), 4.27 (dd, J=11.4, 4.8 Hz, 1H), 3.82 (s, 1H), 3.57 (s, 6H), 3.54-3.45 (m, 1H), 3.16 (d, J=13.5 Hz, 1H), 2.97-2.53 (m, 10H), 2.16-2.04 (m, 1H), 1.97-1.36 (m, 8H). LCMS (ES$^+$): m/z 791.9 [M+H]$^+$.

Compound 129 was prepared following the synthesis of Compound 126.

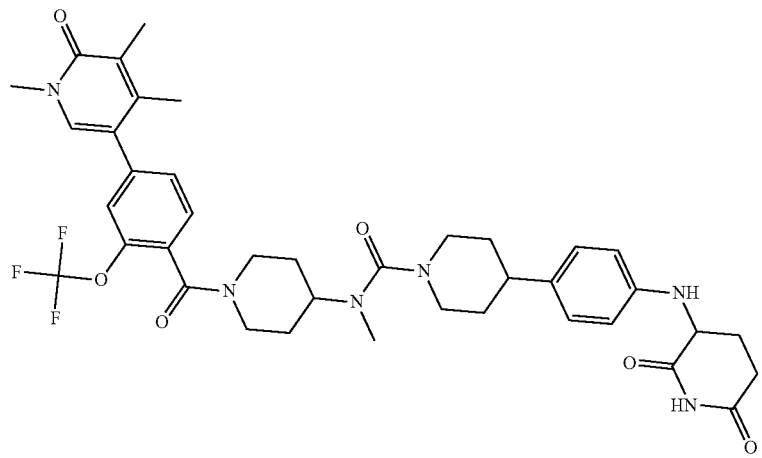 [SMILES: Cc1c(-c2ccc(C(=O)N3CCC(N(C)C(=O)N4CCC(c5ccc(NC6CCC(=O)NC6=O)cc5)CC4)CC3)c(OC(F)(F)F)c2)cn(C)c(=O)c1C]

$^1$H NMR (400 MHz, DMSO-d$_6$) δ 10.77 (s, 1H), 7.69-7.28 (m, 4H), 6.97 (d, J=8.3 Hz, 2H), 6.63 (d, J=8.2 Hz, 2H), 4.63 (d, J=12.7 Hz, 1H), 4.27 (dd, J=11.3, 4.8 Hz, 1H), 3.80 (s, 1H), 3.60 (d, J=12.6 Hz, 2H), 3.46 (s, 3H), 3.40 (d, J=13.3 Hz, 1H), 3.13 (d, J=11.1 Hz, 1H), 2.90-2.53 (m, 9H), 2.05 (d, J=5.7 Hz, 7H), 1.94-1.40 (m, 10H). LCMS (ES$^+$): m/z 751.7 [M+H]$^+$.

Compound 130 was prepared following the synthesis of Compound 126.

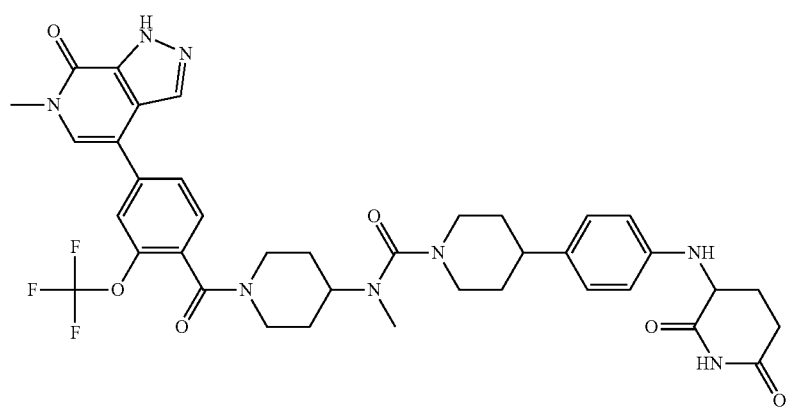 [SMILES: CN(C(=O)N1CCC(c2ccc(NC3CCC(=O)NC3=O)cc2)CC1)C1CCN(C(=O)c2ccc(-c3cn(C)c(=O)c4[nH]ncc34)cc2OC(F)(F)F)CC1]

$^1$H NMR (400 MHz, DMSO-d$_6$) δ 10.77 (s, 1H), 8.14 (s, 1H), 7.78 (dd, J=8.0, 1.6 Hz, 1H), 7.67 (d, J=4.8 Hz, 3H), 6.97 (d, J=8.4 Hz, 2H), 6.64 (s, 2H), 4.64 (d, J=12.7 Hz, 1H), 4.27 (dd, J=11.4, 4.8 Hz, 1H), 3.80 (d, J=9.4 Hz, 1H), 3.61 (s, 5H), 3.45 (d, J=13.2 Hz, 1H), 3.15 (d, J=12.9 Hz, 1H), 2.96-2.51 (m, 10H), 2.16-2.02 (m, 1H), 1.95-1.35 (m, 10H). LCMS (ES$^+$): m/z 763.8 [M+H]$^+$.

Compound 131 was prepared following the synthesis of Compound 126.

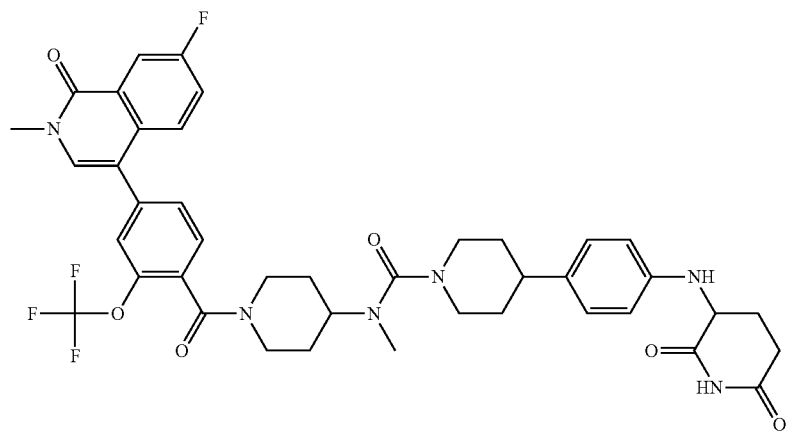 [SMILES: CN(C(=O)N1CCC(c2ccc(NC3CCC(=O)NC3=O)cc2)CC1)C1CCN(C(=O)c2ccc(-c3cn(C)c(=O)c4cc(F)ccc34)cc2OC(F)(F)F)CC1]
$^1$H NMR (400 MHz, DMSO-d$_6$) δ 10.77 (s, 1H), 8.00 (dd, J=9.3, 2.5 Hz, 1H), 7.67-7.61 (m, 3H), 7.60-7.55 (m, 2H), 7.53 (s, 1H), 6.97 (d, J=8.5 Hz, 2H), 6.65-6.60 (m, 2H), 4.65 (d, J=13.0 Hz, 1H), 4.27 (dd, J=11.4, 4.8 Hz, 1H), 3.83 (s, OH), 3.62 (s, 1H), 3.59 (s, 4H), 3.47 (d, J=12.9 Hz, 1H), 3.26-3.09 (m, 1H), 2.90-2.65 (m, 7H), 2.62-2.53 (m, 1H), 2.14-2.05 (m, 1H), 1.93-1.80 (m, 1H), 1.79-1.45 (m, 8H), 1.28-1.20 (m, 1H). LCMS (ES$^+$): m/z 791.284 [M+H]$^+$
Compound 132 was prepared following the synthesis of Compound 126.
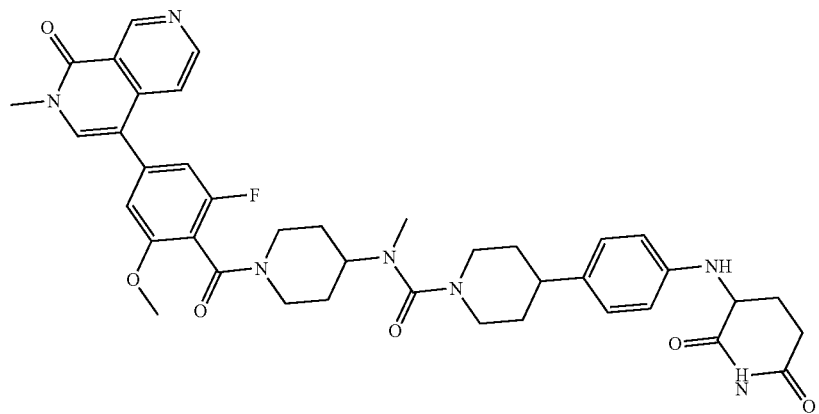 [SMILES: COc1cc(-c2cn(C)c(=O)c3cnccc23)cc(F)c1C(=O)N1CCC(N(C)C(=O)N2CCC(c3ccc(NC4CCC(=O)NC4=O)cc3)CC2)CC1]
$^1$H NMR (400 MHz, DMSO-d$_6$) δ 10.76 (s, 1H), 9.47 (s, 1H), 8.74 (d, J=5.6 Hz, 1H), 8.00 (s, 1H), 7.64 (d, J=5.6 Hz 1H), 7.04 (d, J=6.4 Hz, 2H), 6.96 (d, J=8.4 Hz 2H), 6.61 (d, J=8.4 Hz, 2H), 4.63 (m, 2H), 4.28-4.24 (m, 1H), 3.90 (s, 3H), 3.86 (m, 1H), 3.60 (m, 6H), 3.15 (m, 1H), 2.82-2.71 (m, 4H), 2.58-2.55 (m, 1H), 2.11-2.07 (m, 1H), 1.87-1.84 (m, 1H), 1.71-1.51 (m, 4H), 1.51-1.22 (m, 6H). LCMS (ES$^+$): m/z 738.64 [M+H]$^+$.
Compound 133 was prepared following the synthesis of Compound 126.

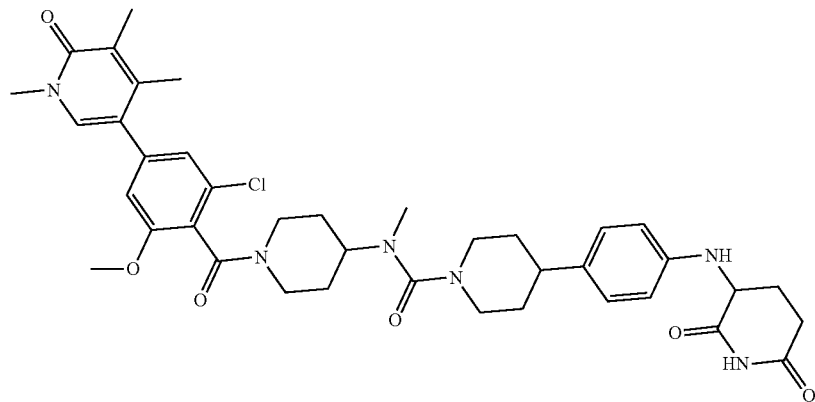 [SMILES: COc1cc(-c2cn(C)c(=O)c(C)c2C)cc(Cl)c1C(=O)N1CCC(N(C)C(=O)N2CCC(c3ccc(NC4CCC(=O)NC4=O)cc3)CC2)CC1]
¹H NMR (400 MHz, DMSO-d₆) δ 10.77 (s, 1H), 7.60 (s, 1H), 7.00 (dd, J=24.7, 8.8 Hz, 4H), 6.62 (d, J=8.2 Hz, 2H), 4.62 (d, J=12.9 Hz, 1H), 4.27 (dd, J=11.4, 4.8 Hz, 1H), 3.81 (t, J=15.5 Hz, 5H), 3.60 (d, J=12.6 Hz, 2H), 3.45 (s, 3H), 3.33 (s, 1H), 3.11 (d, J=5.1 Hz, 1H), 2.86-2.59 (m, 9H), 2.06 (d, J=6.0 Hz, 6H), 1.99-1.79 (m, 1H), 1.79-1.38 (m, 8H), 1.33-1.16 (m, 1H). LCMS (ES⁺): m/z 731.1 [M+H]⁺.
Compound 134 was prepared following the synthesis of Compound 126.
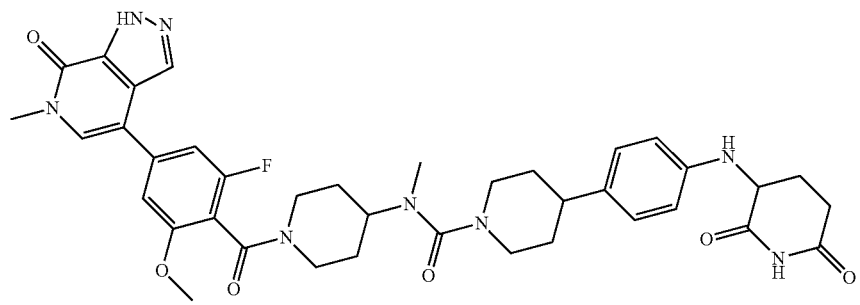 [SMILES: COc1cc(-c2cn(C)c(=O)c3[nH]ncc23)cc(F)c1C(=O)N1CCC(N(C)C(=O)N2CCC(c3ccc(NC4CCC(=O)NC4=O)cc3)CC2)CC1]
¹H NMR (400 MHz, DMSO-d₆) δ 14.30 (s, 1H), 10.77 (s, 1H), 8.27 (s, 1H), 7.67 (s, 1H), 7.17-6.94 (m, 4H), 6.62 (d, J=8.5 Hz, 1H), 4.63 (d, J=12.6 Hz, 1H), 4.29-4.25 (m, 1H), 3.94 (d, J=15.5 Hz, 3H), 3.78-3.56 (m, 8H), 3.44-3.11 (m, 1H), 2.88-2.67 (m, 7H), 2.60-2.55 (m, 1H), 2.07-2.06 (m, 1H), LCMS (ES⁺): m/z 727.67 [M+H]⁺.
Compound 135 was prepared following the synthesis of Compound 126.
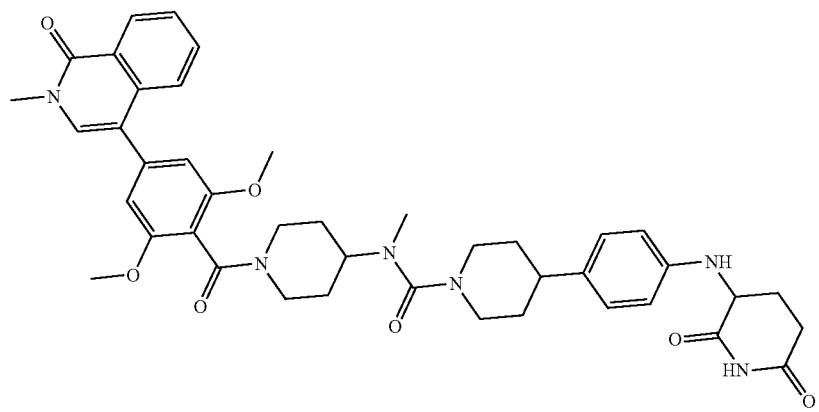 [SMILES: COc1cc(-c2cn(C)c(=O)c3ccccc23)cc(OC)c1C(=O)N1CCC(N(C)C(=O)N2CCC(c3ccc(NC4CCC(=O)NC4=O)cc3)CC2)CC1]

¹H NMR (400 MHz, DMSO-d₆) δ 10.76 (s, 1H), 8.34 (d, J=8.0 Hz, 1H), 7.81-7.63 (m, 1H), 7.63-7.50 (m, 1H), 7.03-6.90 (m, 2H), 6.77 (d, J=6.9 Hz, 1H), 6.62 (dd, J=7.2, 5.1 Hz, 2H), 4.63 (d, J=12.6 Hz, 1H), 4.26 (dd, J=11.4, 4.8 Hz, 1H), 3.79 (d, J=17.9 Hz, 7H), 3.55 (d, J=27.7 Hz, 13H), 2.95-2.54 (m, 9H), 2.09 (dt, J=8.8, 4.8 Hz, 1H), 1.86 (qd, J=12.1, 4.6 Hz, 1H), 1.69 (d, J=9.4 Hz, 3H), 1.62-1.39 (m, 3H). LCMS (ES⁺): m/z 749.1 [M+H]⁺.

Compound 136 was prepared following the synthesis of Compound 126.

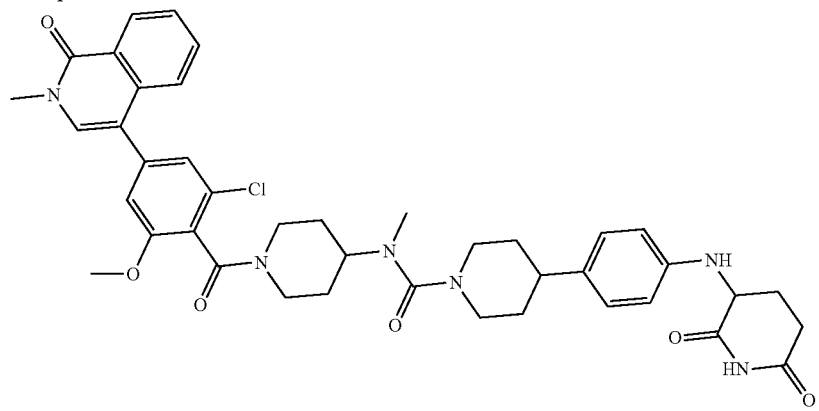

¹H NMR (400 MHz, DMSO-d₆) δ 10.76 (s, 1H), 8.34 (d, J=8.0 Hz, 1H), 7.83-7.69 (m, 1H), 7.67-7.54 (m, 3H), 7.26-7.10 (m, 2H), 6.96 (d, J=8.2 Hz, 2H), 6.61 (d, J=8.2 Hz, 2H), 4.64 (d, J=13.2 Hz, 1H), 4.26 (dd, J=11.3, 4.8 Hz, 1H), 3.98-3.74 (m, 4H), 3.58 (s, 5H), 3.39 (d, J=12.4 Hz, 1H), 3.14 (t, J=11.8 Hz, 1H), 2.98-2.55 (m, 11H), 2.19-2.02 (m, 1H), 2.02-1.79 (m, 1H), 1.79-1.39 (m, 7H). LCMS (ES⁺): m/z 753.1 [M+H]⁺.

Compound 137 was prepared following the synthesis of Compound 126.

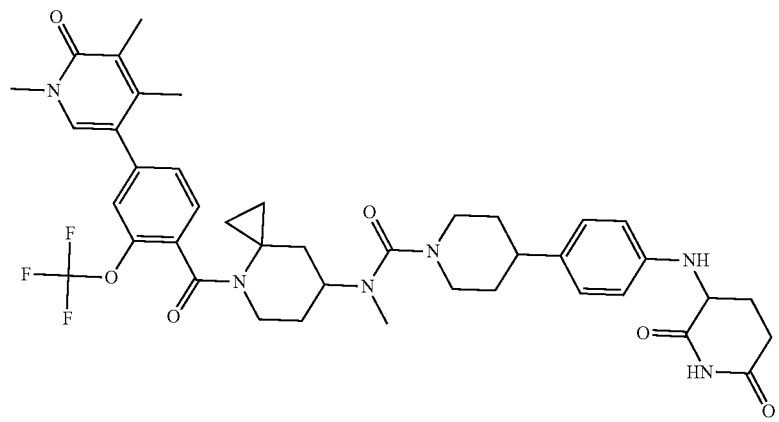 [SMILES: Cc1c(-c2ccc(C(=O)N3CCC(N(C)C(=O)N4CCC(c5ccc(NC6CCC(=O)NC6=O)cc5)CC4)CC34CC4)c(OC(F)(F)F)c2)cn(C)c(=O)c1C]

¹H NMR (400 MHz, DMSO-d₆) δ 10.77 (s, 1H), 8.00-7.14 (m, 3H), 6.96 (d, J=8.2 Hz, 2H), 6.63 (d, J=8.5 Hz, 2H), 4.27 (dd, J=11.3, 4.8 Hz, 1H), 3.98 (s, 1H), 3.58 (d, J=12.4 Hz, 2H), 3.46 (d, J=5.5 Hz, 3H), 3.42-3.08 (m, 1H), 2.98-2.52 (m, 9H), 2.45-2.17 (m, 1H), 2.18-1.98 (m, 7H), 1.98-1.71 (m, 2H), 1.71-1.40 (m, 5H), 1.42-0.91 (m, 3H), 0.52 (d, J=45.0 Hz, 4H). LCMS (ES⁺): m/z 777.7 [M+H]⁺.

Compound 138 was prepared following the synthesis of Compound 126.

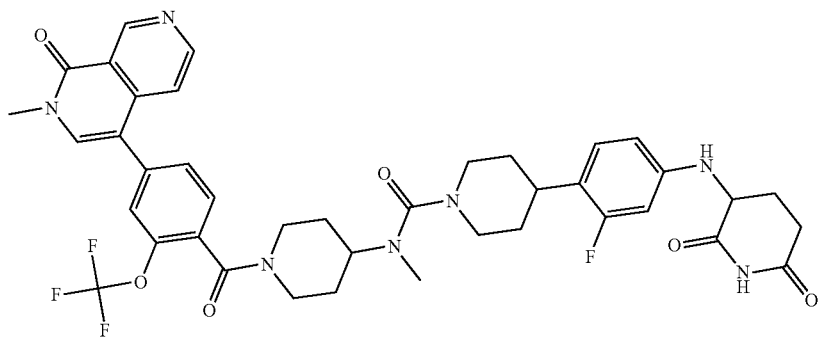 [SMILES: CN(C(=O)N1CCC(c2ccc(NC3CCC(=O)NC3=O)cc2F)CC1)C1CCN(C(=O)c2ccc(-c3cn(C)c(=O)c4cnccc34)cc2OC(F)(F)F)CC1]
¹H NMR (400 MHz, DMSO-d₆) δ 10.78 (s, 1H), 9.49 (s, 1H), 8.75 (d, J=5.8 Hz, 1H), 8.02 (s, 1H), 7.85-7.38 (m, 5H), 6.99 (t, J=8.8 Hz, 1H), 6.62-6.29 (m, 2H), 4.65 (d, J=12.8 Hz, 1H), 4.30 (dd, J=11.5, 4.8 Hz, 1H), 3.80 (d, J=15.8 Hz, 1H), 3.61 (s, 5H), 3.47 (d, J=13.1 Hz, 1H), 3.17 (d, J=13.4 Hz, 1H), 2.96-2.53 (m, 10H), 2.17-2.01 (m, 1H), 1.96-1.14 (m, 8H). LCMS (ES⁺): m/z 792.8 [M+H]⁺.
Compound 139 was prepared following the synthesis of Compound 126.
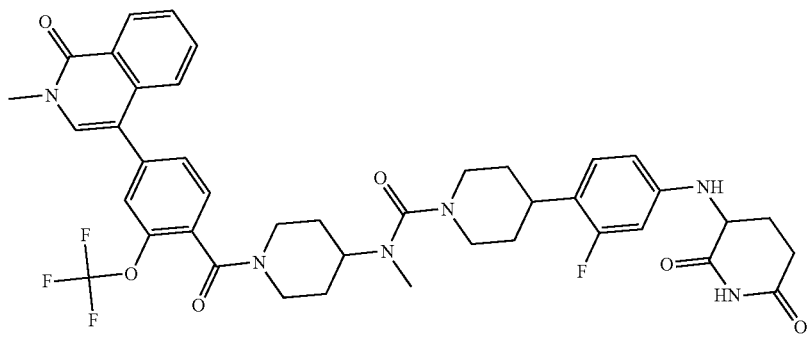 [SMILES: CN(C(=O)N1CCC(c2ccc(NC3CCC(=O)NC3=O)cc2F)CC1)C1CCN(C(=O)c2ccc(-c3cn(C)c(=O)c4ccccc34)cc2OC(F)(F)F)CC1]
¹H NMR (400 MHz, DMSO-d₆) δ 10.78 (s, 1H), 8.35 (dd, J=8.1, 1.4 Hz, 1H), 7.82-7.68 (m, 1H), 7.65 (s, 1H), 7.56 (dt, J=17.0, 6.6 Hz, 4H), 6.99 (t, J=8.8 Hz, 1H), 6.52-6.37 (m, 2H), 4.65 (d, J=12.7 Hz, 1H), 4.31 (dd, J=11.5, 4.8 Hz, 1H), 3.82 (s, 1H), 3.58 (s, 8H), 3.48 (d, J=13.1 Hz, 1H), 3.17 (d, J=13.8 Hz, 1H), 2.91-2.65 (m, 6H), 2.57 (dt, J=17.6, 4.4 Hz, 1H), 2.17-1.99 (m, 1H), 1.87 (dt, J=12.2, 6.0 Hz, 2H), 1.83-1.49 (m, 8H). LCMS (ES⁺): m/z 791.8 [M+H]⁺.
Compound 140 was prepared following the synthesis of Compound 126.

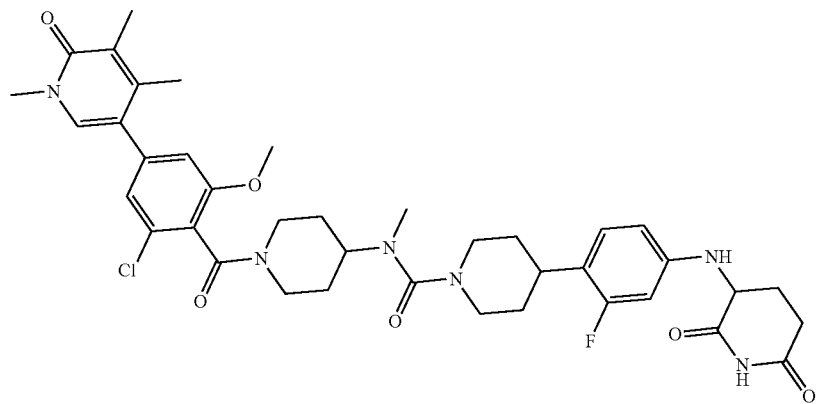 [SMILES: COc1cc(-c2cn(C)c(=O)c(C)c2C)cc(Cl)c1C(=O)N1CCC(N(C)C(=O)N2CCC(c3ccc(NC4CCC(=O)NC4=O)cc3F)CC2)CC1]

$^1$H NMR (400 MHz, DMSO-d$_6$) δ 10.71 (s, 1H), 7.53 (s, 1H), 6.93 (dt, J=11.4, 8.1 Hz, 3H), 6.51-6.33 (m, 2H), 4.55 (d, J=12.6 Hz, 1H), 4.24 (dd, J=11.5, 4.8 Hz, 1H), 3.77 (d, J=15.6 Hz, 4H), 3.54 (d, J=12.7 Hz, 2H), 3.39 (s, 3H), 3.26 (s, 1H), 3.04 (dd, J=13.7, 9.0 Hz, 1H), 2.85-2.56 (m, 8H), 2.56-2.47 (m, 1H), 1.99 (d, J=6.0 Hz, 8H), 1.80 (dt, J=12.3, 6.1 Hz, 1H), 1.59 (dd, J=32.3, 19.9 Hz, 8H). LCMS (ES$^+$): m/z 749.8 [M+H]$^+$.

Compound 141 was prepared following the synthesis of Compound 126.

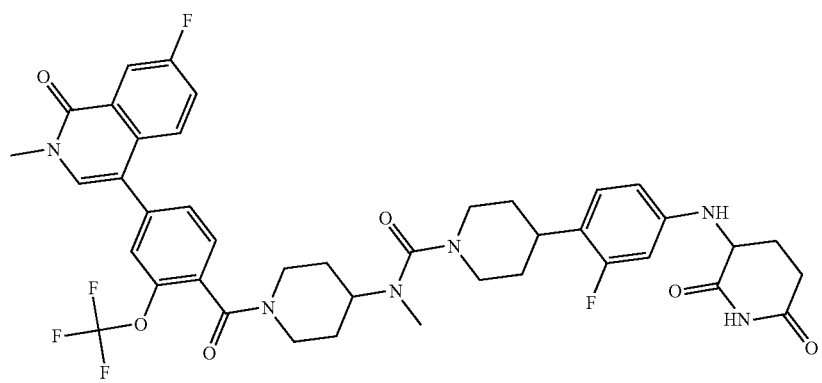 [SMILES: CN(C(=O)N1CCC(c2ccc(NC3CCC(=O)NC3=O)cc2F)CC1)C1CCN(C(=O)c2ccc(-c3cn(C)c(=O)c4cc(F)ccc34)cc2OC(F)(F)F)CC1]

$^1$H NMR (400 MHz, DMSO-d$_6$) δ 10.78 (s, 1H), 8.00 (dd, J=9.3, 2.5 Hz, 1H), 7.81-7.43 (m, 7H), 6.99 (t, J=8.8 Hz, 1H), 6.53-6.35 (m, 2H), 4.65 (d, J=12.6 Hz, 1H), 4.30 (dd, J=11.5, 4.8 Hz, 1H), 3.82 (s, 1H), 3.58 (s, 5H), 3.47 (d, J=13.1 Hz, 1H), 3.17 (d, J=13.3 Hz, 1H), 2.93-2.62 (m, 7H), 2.57 (dt, J=17.4, 4.2 Hz, 1H), 2.16-2.02 (m, 1H), 1.93-1.39 (m, 10H), 1.74-1.51 (m, 9H). LCMS (ES$^+$): m/z 809.7 [M+H]$^+$

Compound 142 was prepared following the synthesis of Compound 126.

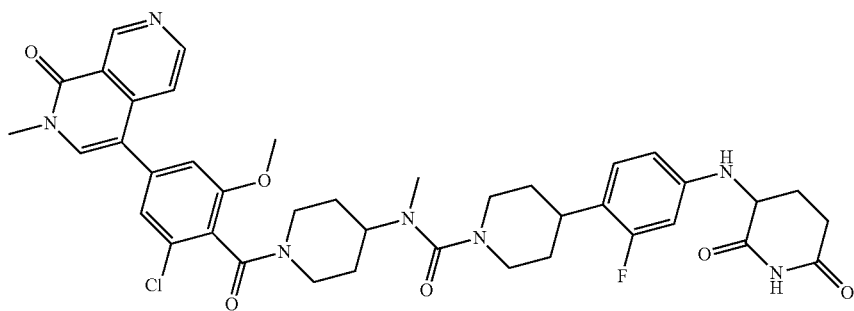 [SMILES: COc1cc(-c2cn(C)c(=O)c3cnccc23)cc(Cl)c1C(=O)N1CCC(N(C)C(=O)N2CCC(c3ccc(NC4CCC(=O)NC4=O)cc3F)CC2)CC1]

¹H NMR (400 MHz, DMSO-d₆) δ 10.78 (s, 1H), 9.50 (s, 1H), 8.75 (d, J=5.9 Hz, 1H), 8.06 (d, J=1.7 Hz, 1H), 7.69 (dd, J=5.9, 2.0 Hz, 1H), 7.29-7.15 (m, 2H), 6.99 (t, J=8.8 Hz, 1H), 6.53-6.38 (m, 2H), 4.64 (d, J=12.7 Hz, 1H), 4.30 (dd, J=11.6, 4.8 Hz, 1H), 3.87 (d, J=15.5 Hz, 4H), 3.61 (s, 4H), 3.40 (s, 1H), 3.14 (t, J=11.7 Hz, 1H), 2.92-2.62 (m, 9H), 2.61-2.53 (m, 1H), 2.18-1.98 (m, 1H), 1.86 (qd, J=12.3, 4.6 Hz, 1H), 1.80-1.45 (m, 9H). LCMS (ES⁺): m/z 772.7 [M+H]⁺.

Compound 143 was prepared following the synthesis of Compound 126.

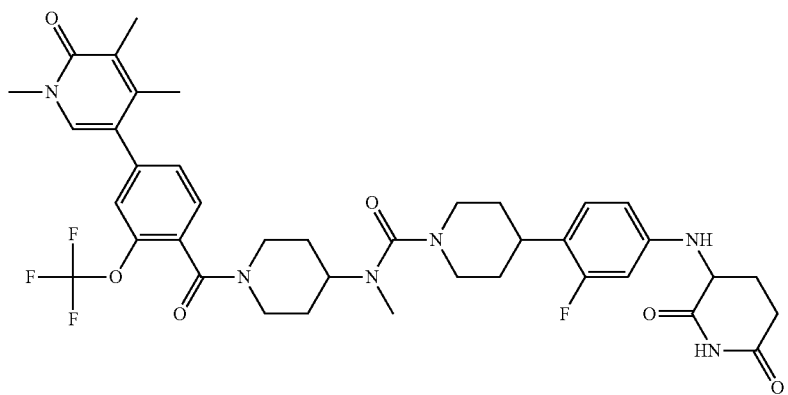 [SMILES: Cc1c(-c2ccc(C(=O)N3CCC(N(C)C(=O)N4CCC(c5ccc(NC6CCC(=O)NC6=O)cc5F)CC4)CC3)c(OC(F)(F)F)c2)cn(C)c(=O)c1C]

¹H NMR (400 MHz, DMSO-d₆) δ 10.78 (s, 1H), 7.60 (s, 1H), 7.51-7.46 (m, 1H), 7.44-7.35 (m, 2H), 6.99 (t, J=8.8 Hz, 1H), 6.49-6.40 (m, 2H), 6.01 (s, 1H), 4.63 (d, J=12.6 Hz, 1H), 4.30 (dd, J=11.5, 4.8 Hz, 1H), 3.80 (s, 1H), 3.61 (d, J=12.7 Hz, 2H), 3.53 (s, 1H), 3.46 (s, 3H), 3.40 (d, J=13.2 Hz, 1H), 3.13 (s, 1H), 2.88-2.73 (m, 3H), 2.70 (ddd, J=14.3, 9.3, 4.4 Hz, 4H), 2.57 (dt, J=17.4, 4.2 Hz, 1H), 2.05 (d, J=5.6 Hz, 7H), 1.87 (tt, J=12.2, 6.2 Hz, 1H), 1.74 (s, 1H), 1.70-1.45 (m, 7H). LCMS (ES⁺): m/z 769.7 [M+H]⁺.

Compound 144 was prepared following the synthesis of Compound 91

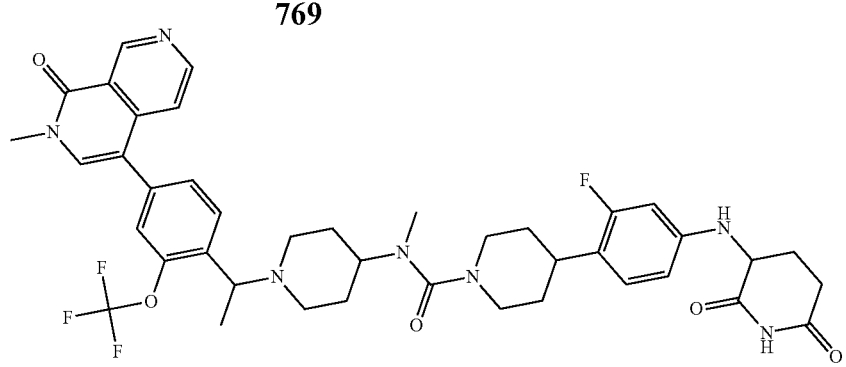
¹H NMR (400 MHz, DMSO-d₆) δ 10.78 (s, 1H), 9.48 (s, 2H), 8.77 (d, J=5.8 Hz, 1H), 7.97 (d, J=10.1 Hz, 2H), 7.71 (dd, J=8.1, 1.7 Hz, 1H), 7.62 (t, J=1.7 Hz, 1H), 7.50 (d, J=5.8 Hz, 1H), 6.96 (t, J=8.8 Hz, 1H), 6.55-6.39 (m, 2H), 4.81 (s, 1H), 4.30 (dd, J=11.6, 4.8 Hz, 1H), 3.80 (d, J=12.0 Hz, 2H), 3.61 (s, 5H), 3.26 (s, 2H), 2.98 (s, 1H), 2.88-2.53 (m, 10H), 2.20-1.76 (m, 4H), 1.76-1.37 (m, 7H). LCMS (ES⁺): m/z 792.7 [M+H]⁺.
Synthesis of Compound 145
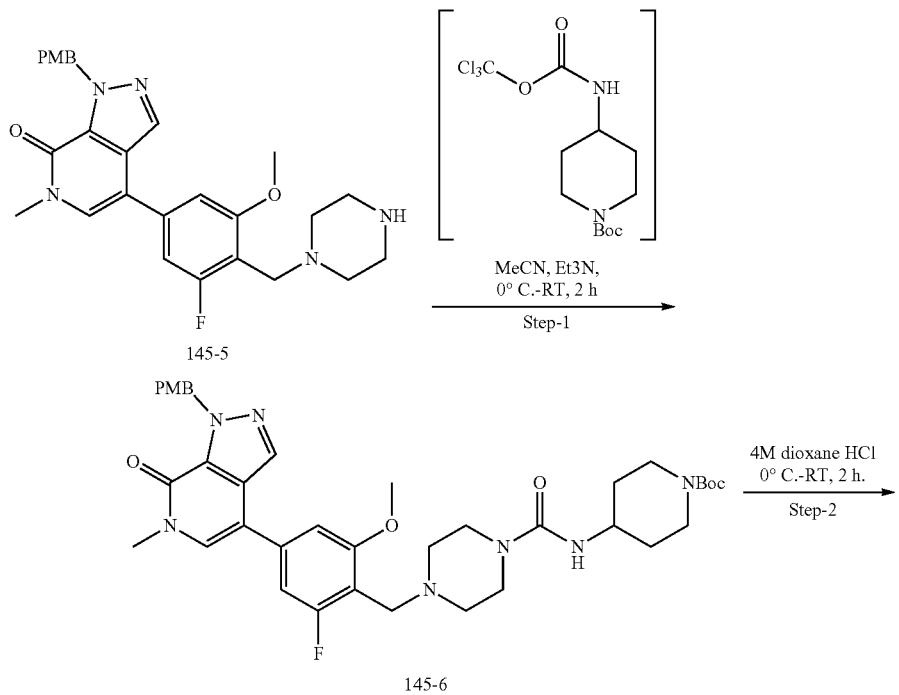
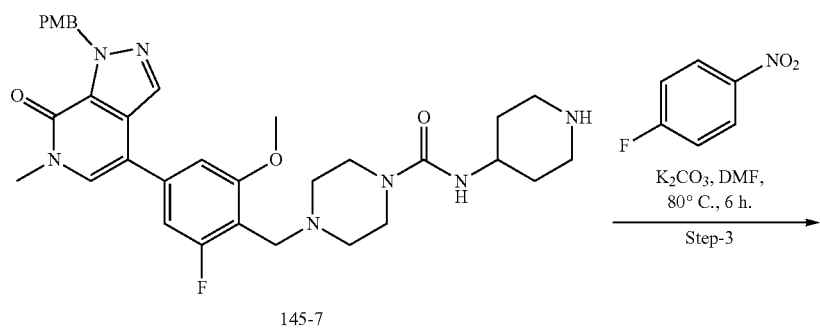

-continued
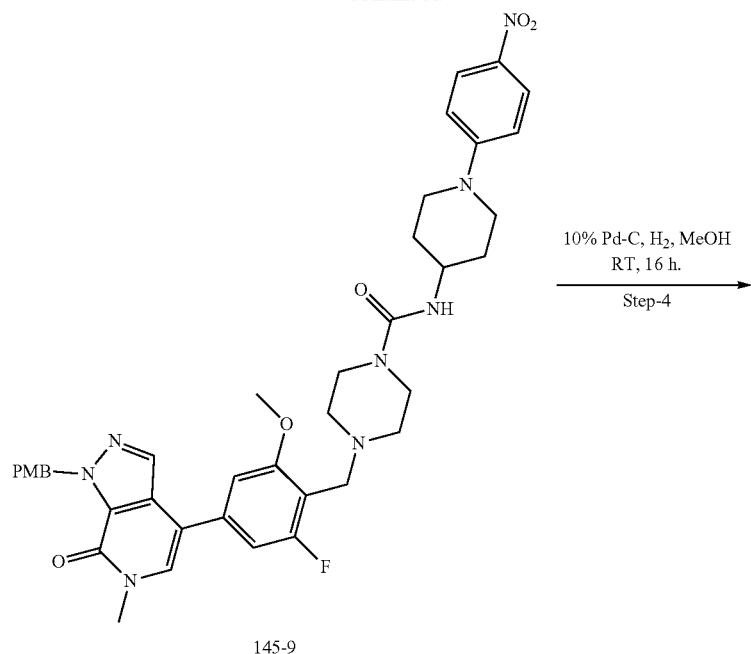
145-9
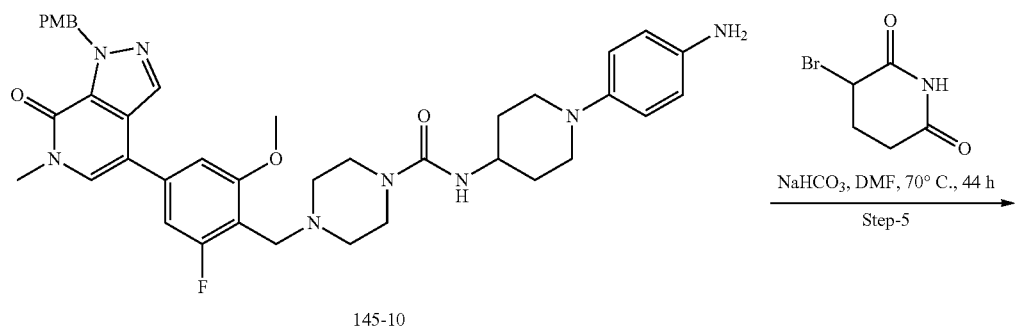
145-10
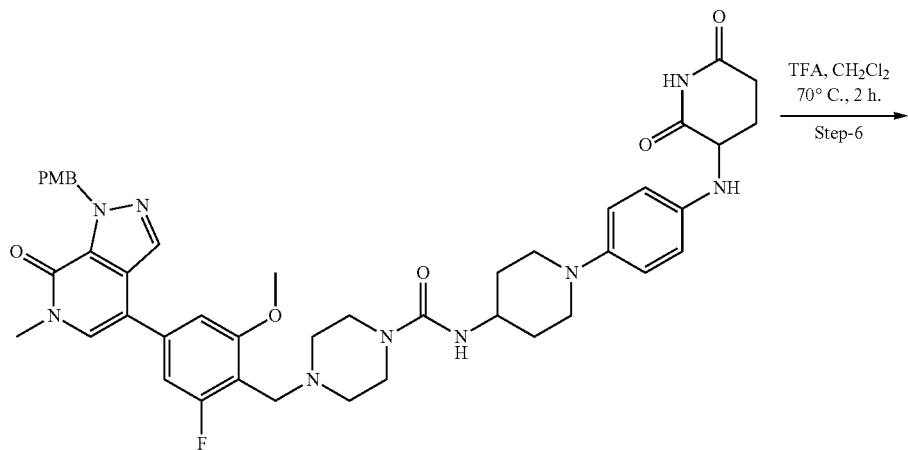
145-12

-continued

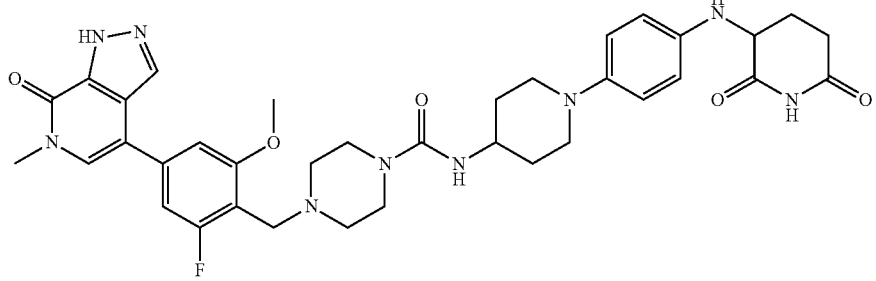

Compound 145

Step-1: To a stirred solution of a 4-[3-fluoro-5-methoxy-4-(4-piperidylmethyl)phenyl]-1-[(4-methoxyphenyl)methyl]-6-methyl-pyrazolo[3,4-c]pyridin-7-one.HCl (0.5 g, 1.02 mmol) in ACN (30 mL) was added TEA (0.309 g, 3.06 mmol) at 0° C. and the reaction mixture was stirred for 5 min. To the reaction mixture, tert-butyl 4-(chlorocarbonylamino)piperidine-1-carboxylate 5 (0.267 g, 1.02 mmol) was added and the reaction mixture was stirred at RT for 2 h while monitoring by TLC and LCMS. After 2 h, the reaction mixture was quenched with water (30 ml) and extracted with $CH_2Cl_2$ (3×20 mL). The combined organic layer was dried over anhydrous $Na_2SO_4$ and concentrated to afford crude compound. The crude compound was purified by revers phase (0.1% FA (in water) in ACN) to afford tert-butyl 4-[[4-[[2-fluoro-6-methoxy-4-[1-[(4-methoxyphenyl)methyl]-6-methyl-7-oxo-pyrazolo[3,4-c]pyridin-4-yl]phenyl]methyl]piperidine-1-carbonyl]amino]piperidine-1-carboxylate 145-6 (0.340 g, 37.45% yield, 80.48% purity) as brown solid. LCMS (ES$^+$): m/z 718.87 [M+H]$^+$.

Step-2: The solution of tert-butyl 4-[[4-[[2-fluoro-6-methoxy-4-[1-[(4-methoxyphenyl)methyl]-6-methyl-7-oxo-pyrazolo[3,4-c]pyridin-4-yl]phenyl]methyl]piperidine-1-carbonyl]amino]piperidine-1-carboxylate 145-6 (0.340 g, 0.474 mmol) in 4M HCl in Dioxane (5 mL) was stirred for 2 h at RT while monitoring by TLC and LCMS. After completion, reaction mixture was concentrated to dryness. The resulting solid was triturated with Diethyl ether (2×20 ml) to afford 4-[[2-fluoro-6-methoxy-4-[1-[(4-methoxyphenyl)methyl]-6-methyl-7-oxo-pyrazolo[3,4-c]pyridin-4-yl]phenyl]methyl]-N-(4-piperidyl)piperidine-1-carboxamide.HCl 145-7 (0.250 g, 72.54% yield, 89.89% purity) as white solid. LCMS (ES$^+$): m/z 618.55 [M+H]$^+$ Step 5: To a stirred solution of 4-[[2-fluoro-6-methoxy-4-[1-[(4-methoxyphenyl)methyl]-6-methyl-7-oxo-pyrazolo[3,4-c]pyridin-4-yl]phenyl]methyl]-N-(4-piperidyl)piperazine-1-carboxamide 145-7 (0.400 g, 0.648 mmol) in DMF (2 mL) were added Potassium carbonate (0.269 g, 1.95 mmol) and followed by 1-fluoro-4-nitro-benzene (0.091 g, 0.648 mol) and stirred at 80° C. for 6 h, while monitoring by LCMS and TLC. After completion, the reaction mixture was quenched with ice cold water and resulting solid was filtered, dried over vacuum to afford 4-[[2-fluoro-6-methoxy-4-[1-[(4-methoxyphenyl)methyl]-6-methyl-7-oxo-pyrazolo[3,4-c]pyridin-4-yl]phenyl]methyl]-N-[1-(4-nitrophenyl)-4-piperidyl]piperazine-1-carboxamide 145-9 (0.450 g, 79.82% yield, 85% purity) as yellow solid. LCMS (ES$^+$): m/z 739.66 [M+H]$^+$.

Step 6: To a stirred solution of 4-[[2-fluoro-6-methoxy-4-[1-[(4-methoxyphenyl)methyl]-6-methyl-7-oxo-pyrazolo[3,4-c]pyridin-4-yl]phenyl]methyl]-N-[1-(4-nitrophenyl)-4-piperidyl]piperazine-1-carboxamide 145-9 (0.45 mg, 0.609 mmol) in MeOH (5 mL) was degassed for 10 minutes followed by addition of 10% Pd/C (0.4 g). The reaction mixture was again degassed and stirred under hydrogen (balloon) pressure for 16 h at RT while monitoring by TLC and LCMS. After completion of the reaction, reaction mixture was filtered through Celite pad and washed with methanol (20 ml). The filtrate was removed under vacuum to afford N-[1-(4-aminophenyl)-4-piperidyl]-4-[[2-fluoro-6-methoxy-4-[1-[(4-methoxyphenyl)methyl]-6-methyl-7-oxo-pyrazolo[3,4-c]pyridin-4-yl]phenyl]methyl]piperazine-1-carboxamide 145-10 (0.2 g, 43.52% yield, 93.93% purity) as a yellow solid. LCMS (ES$^+$): m/z 709.31 [M+H]$^+$ Step-7: To a stirred solution of N-[1-(4-aminophenyl)-4-piperidyl]-4-[[2-fluoro-6-methoxy-4-[1-[(4-methoxyphenyl)methyl]-6-methyl-7-oxo-pyrazolo[3,4-c]pyridin-4-yl]phenyl]methyl]piperazine-1-carboxamide 145-10 (0.2 g, 0.282 mmol) in DMF (3 mL) was added NaHCO$_3$ (0.071 g, 0.846 mmol) and followed by 3-bromopiperidine-2,6-dione 11 (0.270 g, 1.41 mmol) and stirred at 70° C. for 44 h, while monitoring by LCMS and TLC. After 44 h, the reaction mixture was poured on to ice cold water (20 mL) and extracted with EtOAc (3×50 mL). The combined organic layer was dried over anhydrous Na$_2$SO$_4$, and concentrated to afford N-[1-[4-[(2,6-dioxo-3-piperidyl)amino]phenyl]-4-piperidyl]-4-[[2-fluoro-6-methoxy-4-[1-[(4-methoxyphenyl)methyl]-6-methyl-7-oxo-pyrazolo[3,4-c]pyridin-4-yl]phenyl]methyl]piperazine-1-carboxamide 145-12 (0.2 g, 74.10% yield, 85.72% purity) as grey solid. LCMS (ES$^+$): m/z 820.06 [M+H]$^+$.

Step-8: The solution of N-[1-[4-[(2,6-dioxo-3-piperidyl)amino]phenyl]-4-piperidyl]-4-[[2-fluoro-6-methoxy-4-[1-[(4-methoxyphenyl)methyl]-6-methyl-7-oxo-pyrazolo[3,4-c]pyridin-4-yl]phenyl]methyl]piperazine-1-carboxamide 145-12 (0.15 g, 0.183 mmol) in TFA (2 mL) was heated at 70° C. for 2 hr while monitoring by TLC and LCMS. After 2 h the reaction mixture was concentrated to dryness. The crude compound was purified by Prep-HPLC to afford N-[1-[4-[(2,6-dioxo-3-piperidyl)amino]phenyl]-4-piperidyl]-4-[[2-fluoro-6-methoxy-4-(6-methyl-7-oxo-1H-pyrazolo[3,4-c]pyridin-4-yl)phenyl]methyl]piperazine-1-carboxamide.TFA Compound-145 (0.019 g, 12.41% yield, 97.22% purity) as an off-White solid. $^1$H NMR (400 MHz, DMSO-d$_6$) δ 14.34 (s, 1H), 10.82 (m, 2H), 9.88 (s, 1H), 8.23 (s, 1H), 7.70 (s, 1H), 7.41-6.97 (m, 4H), 6.87-6.35 (m, 2H), 4.40-4.35 (m, 3H), 4.10-3.79 (s, 8H), 3.62 (s, 3H), 3.18-3.09 (m, 8H), 2.74-2.67 (m, 1H), 2.61-2.60 (m, 1H), 2.10-1.88 (m, 6H). LCMS (ES$^+$): m/z 700.61 [M+H]$^+$.

Synthesis of Compound 146
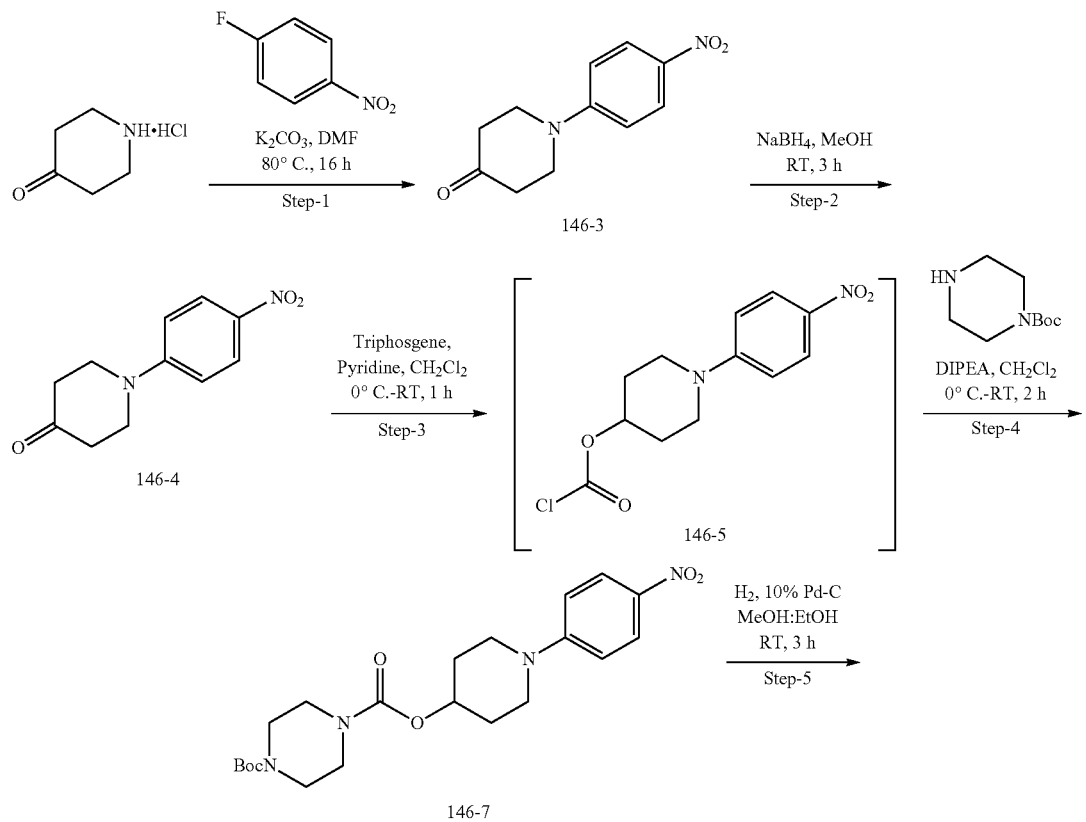
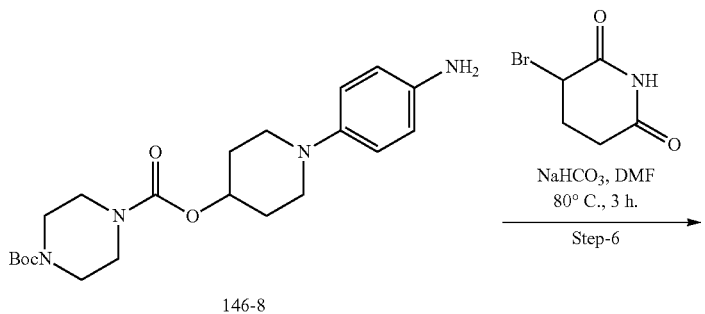
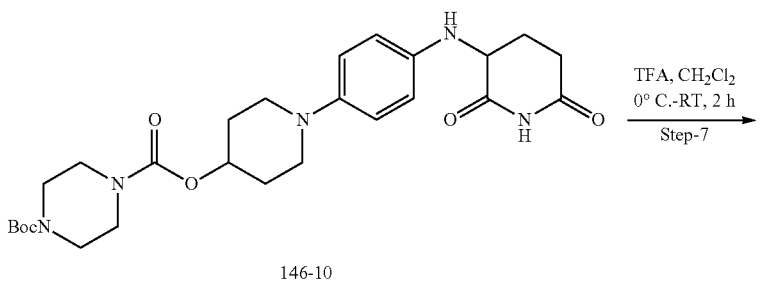

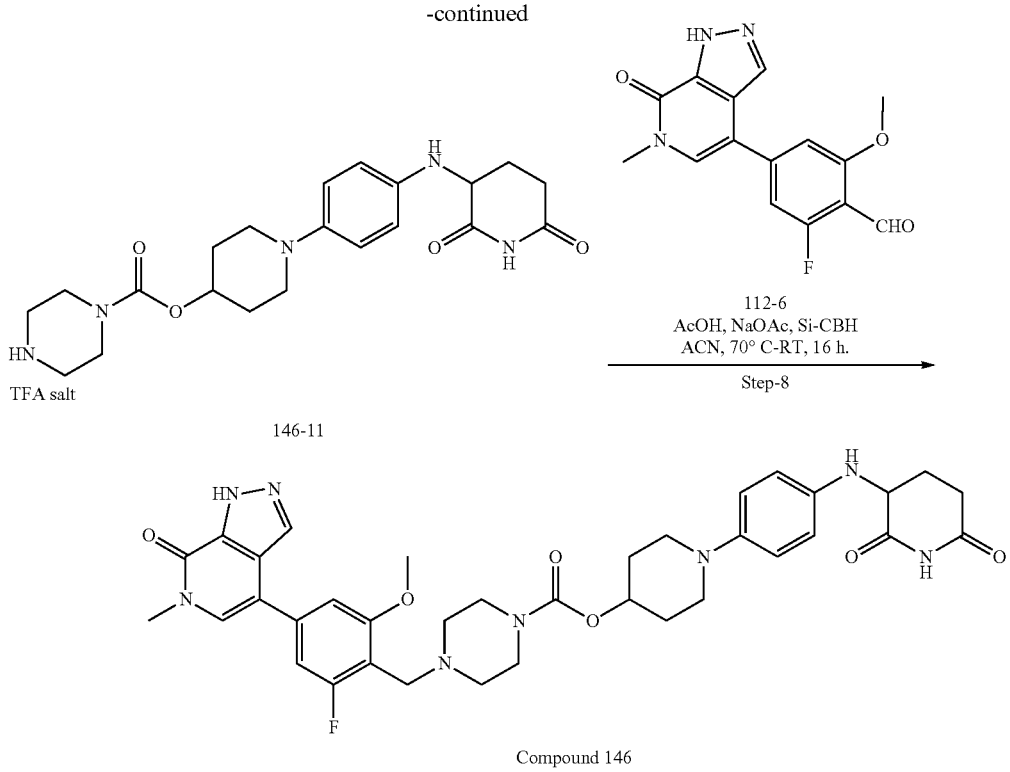

Compound 146

Step-1: To a stirred solution of piperidin-4-one (1.5 g, 15.13 mmol) in DMF (10 mL) were added Potassium carbonate (4.18 g, 30.26 mmol) and 1-fluoro-4-nitro-benzene (2.14 g, 15.13 mmol) and stirred at 80° C. for 16 h, while monitoring by LCMS and TLC. After 16 h, the reaction was quenched with ice cold water and solid precipitate was filtered, dried over vacuum to afford 1-(4-nitrophenyl)piperidin-4-one 146-3 (0.85 g, 22.96% yield, 90% purity) as yellow solid.

Step-2: To the stirred solution of 1-(4-nitrophenyl)piperidin-4-one 146-3 (1.5 g, 6.81 mmol) in Methanol (20 mL) was added Sodium Borohydride (0.644 g, 17.03 mmol) and allowed to stirred at RT for 3 h while monitoring by TLC and LCMS. After 3 h the reaction mass was quenched with saturated solution of NH$_4$Cl (15 ml), and extracted with CH$_2$Cl$_2$ (3×50 mL). The combined organic layer was dried over anhydrous Na$_2$SO$_4$, and concentrated to afford 1-(4-nitrophenyl)piperidin-4-ol 146-4 (1.5 g, 77.88% yield, 78.59% purity) as yellow solid. LCMS (ES$^+$): m/z 223.28 [M+H]$^+$.

Step 3: To a stirred solution of 1-(4-nitrophenyl)piperidin-4-ol 146-4 (1.5 g, 6.75 mmol) in CH$_2$Cl$_2$ (6 mL) was added Pyridine (0.800 g, 10.12 mmol) at 0° C. under N2 atm. After 10 min, the solution of Triphosgene (1.00 g, 3.37 mmol) in CH$_2$Cl$_2$ (4 mL) was added to the reaction mixture and stir stirred at RT for 1 h. while monitoring by TLC. After 1 h the reaction mass was concentrated to dryness to afford [1-(4-nitrophenyl)-4-piperidyl] carbonochloridate 146-(1.5 g, 3.95 mmol, 58.55% yield, 75% purity) as a pale yellow gummy crude compound.

Step-4: To a solution of a tert-butyl piperazine-1-carboxylate 146-6 (1.47 g, 7.90 mmol) in dry CH$_2$Cl$_2$ (15 ml) was added DIPEA (0.680 g, 5.27 mmol) 0° C. under N$_2$ atm. After 10 min, the solution of [1-(4-nitrophenyl)-4-piperidyl] carbonochloridate 146-5 (1.5 g, 5.27 mmol) in CH$_2$Cl$_2$ (5 mL) was added to the reaction mixture at 0° C. and stir at RT for 1 h while monitoring by TLC. After 1 hr reaction mixture was quenched with cold water (20 mL) and extracted with CH$_2$Cl$_2$ (3×50 mL). The combined organic layer was dried over anhydrous Na$_2$SO$_4$, and concentrated to afford 1-(tert-butyl) 4-(1-(4-nitrophenyl)piperidin-4-yl) piperazine-1,4-dicarboxylate 146-7 (1.7 g, 3.01 mmol, 57.08% yield, 76.87% purity) as a yellow solid. LCMS (ES$^+$): m/z 435.21 [M+H]$^+$.

Step 5: Stirred the mixture of 1-(tert-butyl) 4-(1-(4-nitrophenyl)piperidin-4-yl) piperazine-1,4-dicarboxylate (1.7 g, 3.91 mmol) in MeOH:Ethanol (5 mL:5 mL) was degassed for 10 minutes followed by addition of 10% Pd/C (2 g). The reaction mixture was again degassed and stirred under hydrogen (balloon) pressure for 3 h at RT, while monitoring by TLC and LCMS. After completion of the reaction, reaction mixture was filtered through Celite pad and washed with methanol (20 ml). The filtrate was removed under vacuum to afford 1-(1-(4-aminophenyl)piperidin-4-yl) 4-(tert-butyl) piperazine-1,4-dicarboxylate 146-8 (1.5 g, 3.34 mmol, 85.30% yield, 90% purity) as a yellow solid. $^1$H-NMR (DMSO-d$_6$, 400 MHz) δ 6.73 (d, J=6.8 MHz, 2H), 6.53 (d, J=7.2 MHz, 2H), 4.98 (bs, 2H), 3.32 (m, 6H), 3.13-3.10 (m, 4H), 2.86-2.84 (m, 2H), 1.91-1.85 (m, 2H), 1.65-1.60 (m, 2H)

Step 6: To a stirred solution of 1-(1-(4-aminophenyl) piperidin-4-yl) 4-(tert-butyl) piperazine-1,4-dicarboxylate 146-8 (0.5 g, 1.24 mmol) in DMF (3 mL) was added 3-bromopiperidine-2,6-dione 9 (0.712 g, 3.71 mmol), NaHCO$_3$ (0.519 g, 6.18 mmol) and stirred at 80° C. for 3 h, while monitoring by LCMS and TLC. After 3 h, the reaction was quenched with ice cold water (20 mL) and extracted with EtOAc (3×50 mL). The combined organic layer was dried over anhydrous Na$_2$SO$_4$, and concentrated to afford 1-(tert-butyl) 4-(1-(4-((2,6-dioxopiperidin-3-yl)amino)phenyl)piperidin-4-yl) piperazine-1,4-dicarboxylate 146-10

(0.450 g, 0.702 mmol, 56.80% yield, 80.45% purity) as an Off-white solid. LCMS (ES+): m/z 516.81 [M+H]+.

Step-7: To a stirred solution of 1-(tert-butyl) 4-(1-(4-((2,6-dioxopiperidin-3-yl)amino)phenyl)piperidin-4-yl) piperazine-1,4-dicarboxylate 146-10 (0.5 g, 0.969 mmol) in CH$_2$Cl$_2$ (2 mL) was added Trifluoroacetic acid (1.11 g, 9.70 mmol) at 0° C. and stir for 2 h at RT while monitoring by TLC and LCMS. After 2 h the reaction mixture was concentrated to dryness. The crude compound was purified by reverse phase column chromatography to afford [1-[4-[(2,6-dioxo-3-piperidyl)amino]phenyl]-4-piperidyl] piperazine-1-carboxylate.TFA salt 146-11 (0.15 g, 26.29% yield, 90% purity) as green solid. $^1$H-NMR (DMSO-d$_6$, 400 MHz) δ 10.8 (s, 1H), 8.90 (m, 3H), 7.33 (1H), 6.75 (m, 2H), 4.95-4.85 (m, 1H), 4.45-4.35 (m, 3H), 4.10-3.90 (m, 1H), 3.50-3.34 (m, 8H), 3.16-3.13 (m, 5H), 2.74-2.60 (m, 2H), 2.58-2.50 (m, 2H).

Step-8: To a stirred solution of [1-[4-[(2,6-dioxo-3-piperidyl)amino]phenyl]-4-piperidyl]piperazine-1-carboxylate 146-11 (0.100 g, 0.240 mmol) in ACN (10 ml) were added 4 Å molecular sieves (0.05 g), acetic acid (0.014 g, 0.240 mmol) and sodium acetate, anhydrous (0.059 g, 0.722 mmol). The resulting solution was stirred for 10 min, then added 2-fluoro-6-methoxy-4-(6-methyl-7-oxo-1H-pyrazolo [3,4-c]pyridin-4-yl)benzaldehyde 112-6 (0.072 g, 0.240 mmol) and heated the reaction mixture at 70° C. for 3 h then cooled it at RT and added Silia Bond Cyanoborohydride (0.069 g, 1.20 mmol). The stirring was continued at RT for 12 h, while monitoring the reaction by LCMS and TLC. After 12 h, the reaction mass was filtered, concentrated and purified by Prep-HPLC to afford [1-[4-[(2,6-dioxo-3-piperidyl)amino]phenyl]-4-piperidyl] 4-[[2-fluoro-6-methoxy-4-(6-methyl-7-oxo-1H-pyrazolo[3,4-c]pyridin-4-yl)phenyl]methyl]piperazine-1-carboxylate.TFA salt Compound 146 (0.036 g, 18.10% yield, 97.51% purity) $^1$H-NMR (DMSO-d$_6$, 400 MHz) δ 14.38 (s, 1H), 10.78 (s, 1H), 9.87 (s, 1H), 8.23 (s, 1H), 7.71 (s, 1H), 7.35-7.22 (m, 4H), 6.776 (d, J=9.2 Hz, 2H), 4.94-4.85 (m, 1H), 4.30 (s, 3H), 4.01 (s, 3H), 3.62 (s, 3H), 3.52-3.16 (m, 12H), 2.75-2.70 (m, 1H), 2.61-2.60 (m, 1H), 2.18-2.06 (m, 6H). LCMS (ES+): m/z 701.54 [M+H]+.

Synthesis of Compound 147

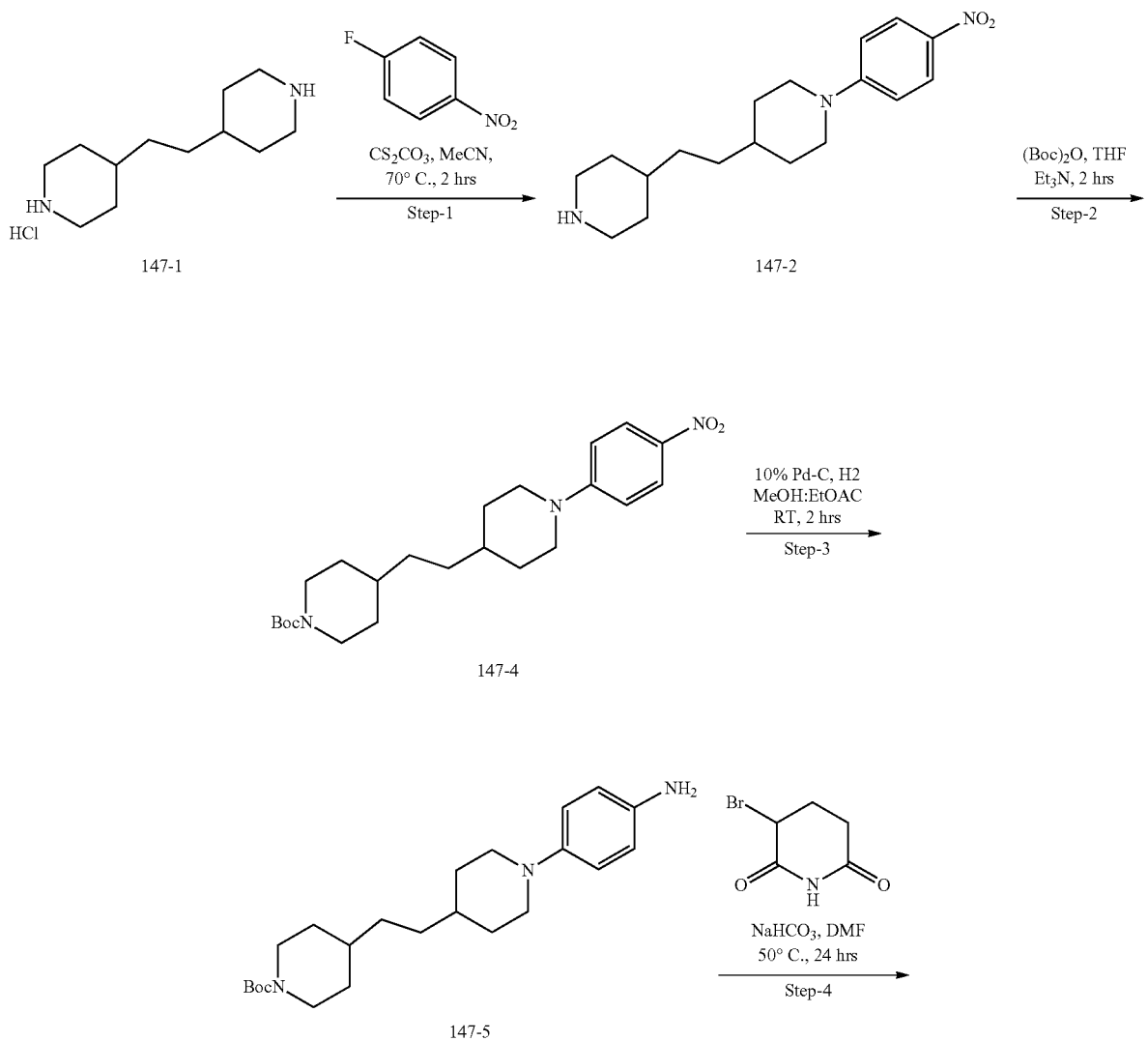

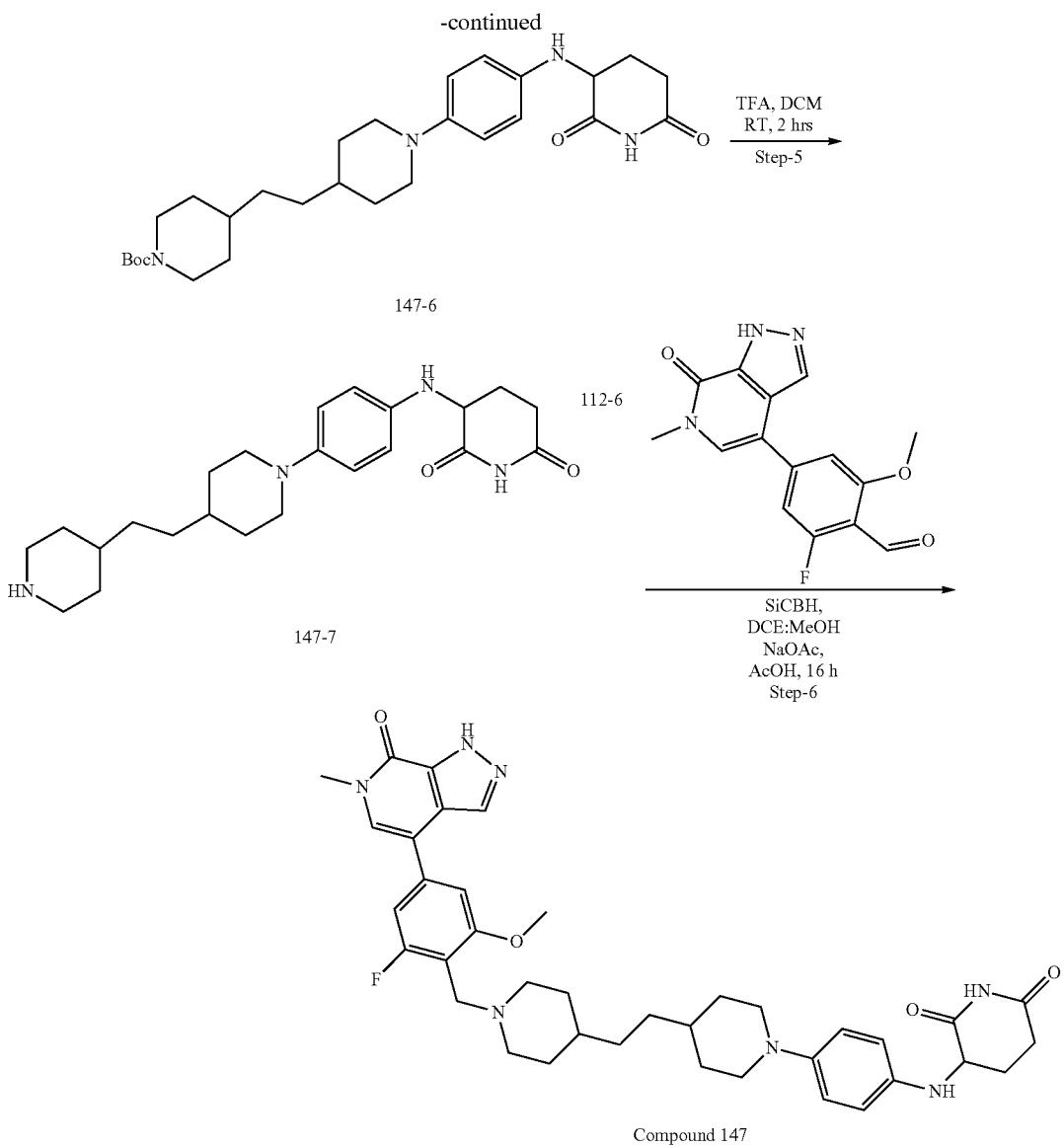

Compound 147

Step-1: To a stirred solution of compound 4-[2-(4-piperidyl)ethyl]piperidine 147-1 (0.5 g, 2.55 mmol) in Acetonitrile (500 mL) was added Cesium carbonate (0.829 g, 2.55 mmol) and stirred for 15 min before adding 1-fluoro-4-nitrobenzene (0.179 g, 1.27 mmol). The reaction mixture was allowed to reflux at 70° C. for 2 h while monitoring by TLC. After completion reaction mixture was diluted with water (200 ml), extracted with ethyl acetate (2×200 ml). The combined organic layer was dried over anhydrous $Na_2SO_4$, and concentrated to afford crude compound. Crude compound was purified by normal phase column chromatography (silica gel mesh 100-200, with 50% pet ether in ethyl acetate as eluent) to afford 1-(4-nitrophenyl)-4-[2-(4-piperidyl)ethyl]piperidine 147-3 (0.32 g, 0.957 mmol, 37.61% yield, 95% purity) as a yellow solid.

Step-2: 1-(4-nitrophenyl)-4-[2-(4-piperidyl)ethyl]piperidine 147-3 (0.32 g, 1.01 mmol) in THF (10 mL), were added triethylamine (0.306 g, 3.02 mmol) followed by the addition of tert-butoxycarbonyl tert-butyl carbonate (0.330 g, 1.51 mmol) and allowed to stir at RT for 2 hr while monitoring by TLC. After completion reaction mixture was diluted with water (50 ml), extracted with 10% MeOH:DCM (2×100 ml). The combined organic layer was dried over anhydrous $Na_2SO_4$, and concentrated to afford crude compound. Crude compound was purified was purified by normal phase column chromatography (silica gel mesh 100-200, with 40% pet ether in ethyl acetate as eluent) to tert-butyl 4-[2-[1-(4-nitrophenyl)-4-piperidyl]ethyl]piperidine-1-carboxylate 147-4 (0.240 g, 0.563 mmol, 55.88% yield, 98% purity) as a yellow solid. LCMS (ES$^+$): m/z 358.80 [M+Na]$^+$ Step-3: To a stirred solution of tert-butyl 4-[2-[1-(4-nitrophenyl)-4-piperidyl]ethyl]piperidine-1-carboxylate 147-4 (0.24 g, 0.574 mmol) in EtOAc (10 mL) and methanol (10 mL) was added 10% wet Pd-C (0.244 g, 2.30 mmol) and the reaction mixture was stirred under $H_2$ balloon pressure for 2 h, while monitoring by LCMS and TLC. The reaction mixture was filtered through Celite bed and the filtrate was concentrated. Crude compound was purified by (silica gel mesh 100-200, eluent 40% pet ether in ethyl acetate) column chromatography to tert-butyl 4-[2-[1-(4-aminophenyl)-4-piperidyl]ethyl]piperidine-1-carboxylate 147-5 (0.23 g, 0.540 mmol, 93.96% yield, 91% purity) as a colourless solid. LCMS (ES⁺): m/z 388.49 [M+H]⁺.

Step-4: To a stirred solution of tert-butyl 4-(2-(1-(4-aminophenyl)piperidin-4-yl)ethyl)piperidine-1-carboxylate 147-5 (0.230 g, 0.593 mmol) in DMF (25 mL) were added 3-bromopiperidine-2,6-dione (0.341 g, 1.78 mmol), NaHCO₃ (0.299 g, 3.56 mmol) and the reaction mixture was stirred at 50° C. for 24 h, while monitoring by TLC and LCMS. the reaction was quenched with ice cold water (100 mL) and extracted with EtOAc (3×150 mL). The combined organic layer was dried over anhydrous Na₂SO₄ and concentrated to afford crude compound. Crude compound was purified was purified by normal phase column chromatography (silica gel mesh 100-200, with 50-60% pet ether in ethyl acetate as eluent) to afford tert-butyl 4-(2-(1-(4-((2,6-dioxopiperidin-3-yl)amino)phenyl)piperidin-4-yl)ethyl)piperidine-1-carboxylate 147-6 (0.25 g, 0.451 mmol, 76.03% yield, 90% purity) as a brown solid.

Step-5: To a stirred solution of compound tert-butyl tert-butyl 4-[2-[1-[4-[(2,6-dioxo-3-piperidyl)amino]phenyl]-4-piperidyl]ethyl]piperidine-1-carboxylate 147-6 (0.23 g, 0.461 mmol) in CH₂Cl₂ (2 ml) was added Trifluoroacetic acid (1.05 g, 9.22 mmol) at 0° C. and the reaction mixture was stirred at RT for 2 h, while monitoring by TLC. After completion, the reaction mixture was concentrated under reduced pressure and crude compound was triturated with ether to yield 3-[4-[4-[2-(4-piperidyl)ethyl]-1-piperidyl]anilino]piperidine-2,6-dione. TFA salt 147-7 (0.2 g, 0.347 mmol, 50.93% yield, 89% purity) as an off white solid. LCMS (ES⁺): m/z 399.30 [M+H]⁺.

Step-6: To a stirred solution of 3-[4-[4-[2-(4-piperidyl)ethyl]-1-piperidyl]anilino]piperidine-2,6-dione 147-7 (0.132 g, 0.331 mmol) in Methanol (5 mL) DCE (5 mL) were added 4 Å Molecular sieves (0.1 g), AcOH (0.019 g, 0.331 mmol) and Sodium acetate, anhydrous (0.054 g, 0.663 mmol). The resulting solution was stirred for 10 min and added 2-fluoro-6-methoxy-4-(6-methyl-7-oxo-1H-pyrazolo[3,4-c]pyridin-4-yl)benzaldehyde 147-8 (0.1 g, 0.331 mmol) was added and heated the reaction mixture at 70° C. for 3 h. The reaction mixture was cooled to RT, added Siliabond Cyanoborohydride (0.1 g, 1.659 mmol) and stirred for 16 h, while monitoring by LCMS. The reaction mass was filtered through Celite bed and filtrate was concentrated under vacuum and purified by Prep HPLC to afford to afford 3-[4-[4-[2-[1-[[2-fluoro-6-methoxy-4-(6-methyl-7-oxo-1H-pyrazolo[3,4-c]pyridin-4-yl)phenyl]methyl]-4-piperidyl]ethyl]-1-piperidyl]anilino]piperidine-2,6-dione. TFA salt Compound 147 (0.04 g, 14.48% yield, 95.86% purity) as light green solid. ¹H NMR (400 MHz, DMSO-d₆) δ 14.32 (s, 1H), 10.82 (s, 2H), 9.28 (s, 1H), 8.23 (s, 1H), 7.70 (s, 1H), 7.37-7.22 (m, 4H), 6.76 (d, J=8.8 Hz, 2H), 6.38 (bs, 1H), 4.38 (bs, 1H), 4.28 (bs, 2H), 4.01 (s, 3H), 3.62 (s, 3H), 3.51-3.45 (m, 6H), 3.04-3.02 (m, 2H), 2.74-2.60 (m, 2H), 2.08-2.06 (m, 1H), 1.93-1.85 (m, 5H) 1.52-1.25 (m, 10H). LCMS (ES⁺): m/z 684.57 [M+H]⁺.

Compound 148 was prepared following the synthesis of Compound 147

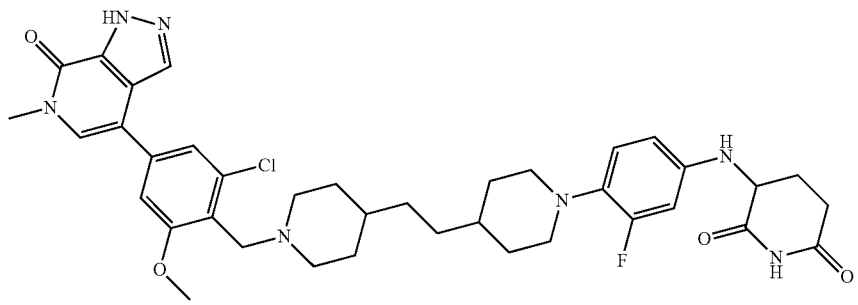 [SMILES: COc1cc(-c2cn(C)c(=O)c3[nH]ncc23)cc(Cl)c1CN1CCC(CCC2CCN(c3ccc(NC4CCC(=O)NC4=O)cc3F)CC2)CC1]

¹H NMR (400 MHz, DMSO-d₆) δ 14.45 (bs, 1H), 10.80 (s, 1H), 8.92 (bs, 1H), 8.21 (s, 1H), 7.71 (s, 1H), 7.45 (s, 1H), 7.34 (s, 1H), 6.58-6.45 (m, 2H), 4.49-4.37 (m, 3H), 3.98 (s, 3H), 3.63 (s, 3H), 3.46-3.12 (m, 8H), 2.76-2.56 (m, 2H), 2.11-2.09 (m, 1H), 1.98-1.86 (m, 5H), 1.57-1.28 (m, 10H). LCMS (ES⁺): m/z 718.53 [M+H]⁺.

Compound 149 was prepared following the synthesis of Compound 147

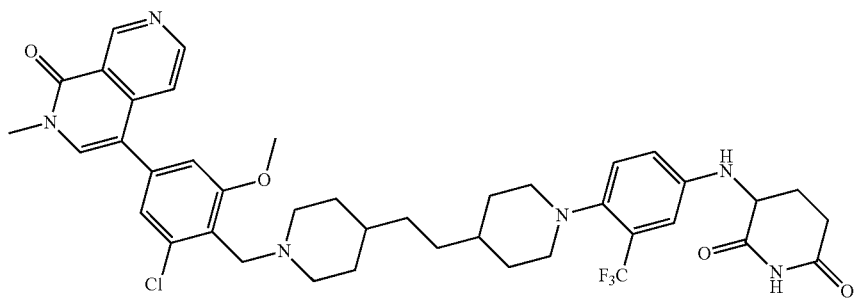 [SMILES: COc1cc(-c2cn(C)c(=O)c3cnccc23)cc(Cl)c1CN1CCC(CCC2CCN(c3ccc(NC4CCC(=O)NC4=O)cc3C(F)(F)F)CC2)CC1]

¹H NMR (400 MHz, DMSO-d₆) δ 10.77 (s, 1H), 9.47 (s, 1H), 8.98 (s, 1H), 8.76 (d, J=5.7 Hz, 1H), 7.95 (s, 1H), 7.54 (d, J=5.7 Hz, 1H), 7.32 (d, J=1.5 Hz, 1H), 7.29-7.19 (m, 2H), 7.03-6.82 (m, 2H), 4.53-4.28 (m, 3H), 3.95 (s, 3H), 3.61 (s, 3H), 3.48 (d, J=11.8 Hz, 2H), 3.18 (q, J=11.4, 10.9 Hz, 2H), 2.86-2.53 (m, 6H), 2.07 (dt, J=8.8, 4.3 Hz, 1H), 1.97-1.82 (m, 3H), 1.68 (d, J=11.4 Hz, 2H), 1.58-1.35 (m, 2H), 1.25 (s, 8H). LCMS (ES⁺): m/z 779.7 [M+H]⁺.

Compound 150 was prepared following the synthesis of Compound 147

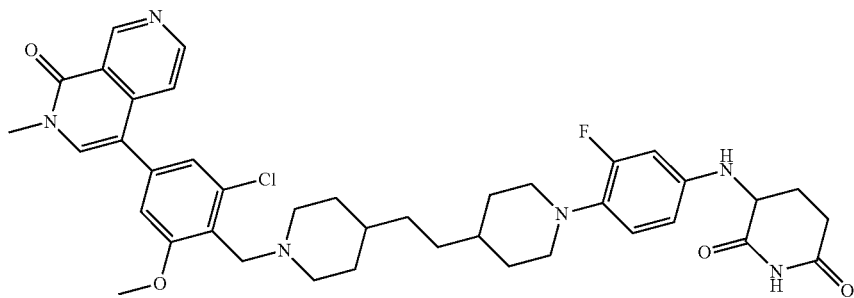 [SMILES: COc1cc(-c2cn(C)c(=O)c3cnccc23)cc(Cl)c1CN1CCC(CCC2CCN(c3ccc(NC4CCC(=O)NC4=O)cc3F)CC2)CC1]
$^1$HNMR (400 MHz, DMSO-d$_6$): δ 10.77 (s, 1H), 9.44 (s, 1H), 8.73 (d, J=5.6 Hz, 1H), 7.92 (s, 1H), 7.53 (d, J=5.6 Hz, 1H), 7.13 (d, J=1.0 Hz, 1H), 7.07 (s, 1H), 6.81 (t, J=9.3 Hz, 1H), 6.51-6.47 (m, 1H), 6.40 (d, J=8.7 Hz, 1H), 5.77 (d, J=7.6 Hz, 1H), 4.26-4.24 (m, 1H), 3.85 (s, 3H), 3.59 (s, 5H), 3.09 (d, J=10.3 Hz, 2H), 2.83 (d, J=11.0 Hz, 2H), 2.71-2.66 (m, 1H), 2.58-2.49 (m, 2H), 2.07 (t, J=11.1 Hz, 3H), 1.84-1.82 (m, 1H), 1.67-1.59 (m, 4H), 1.15-1.05 (m, 11H).
LCMS (ES$^+$): m/z 729.5 [M+H]$^+$.
Synthesis of Compound 151
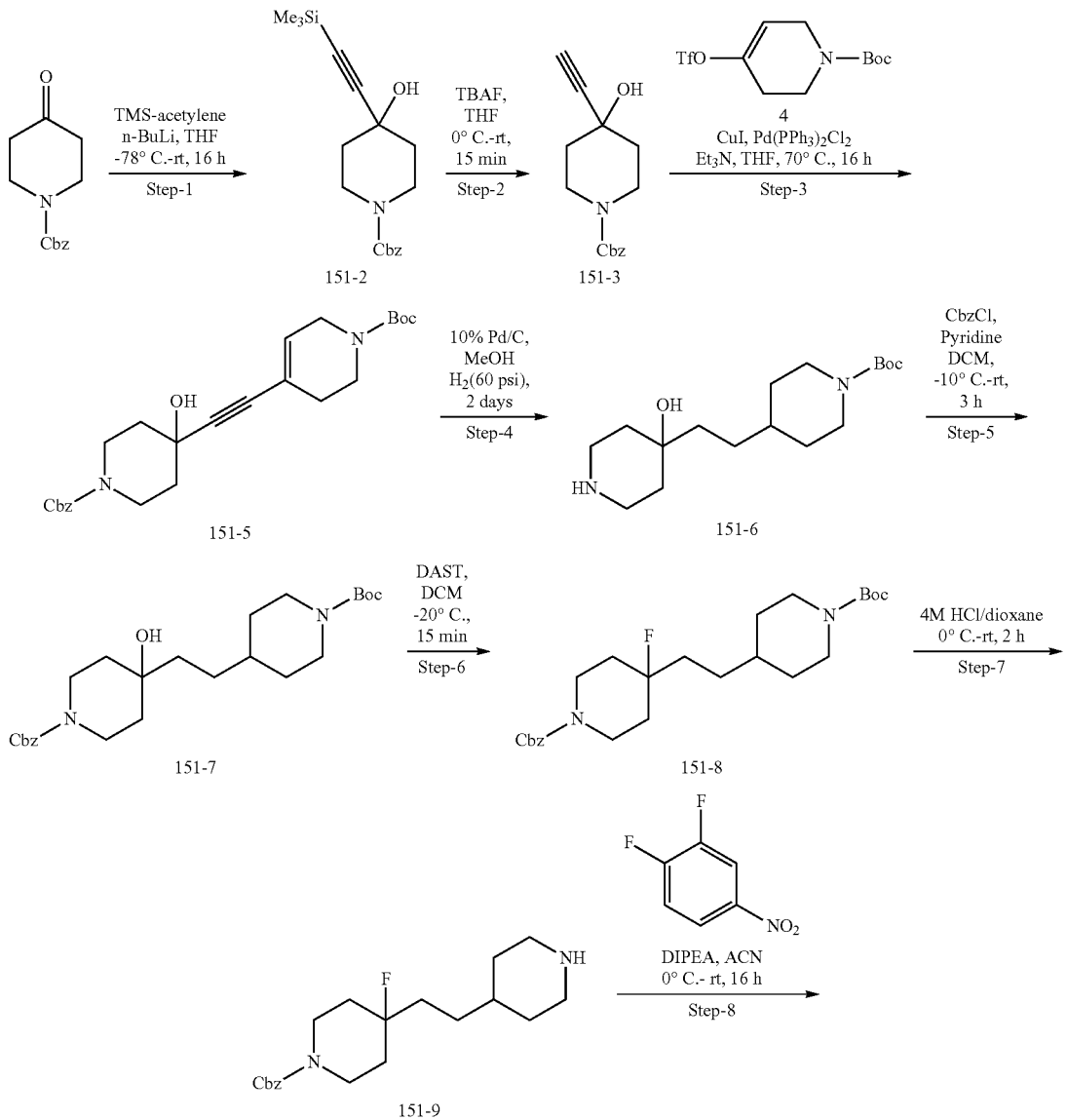

-continued
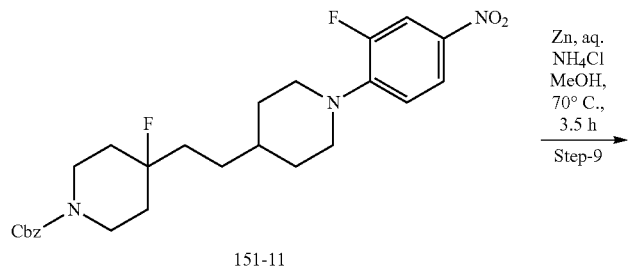
151-11
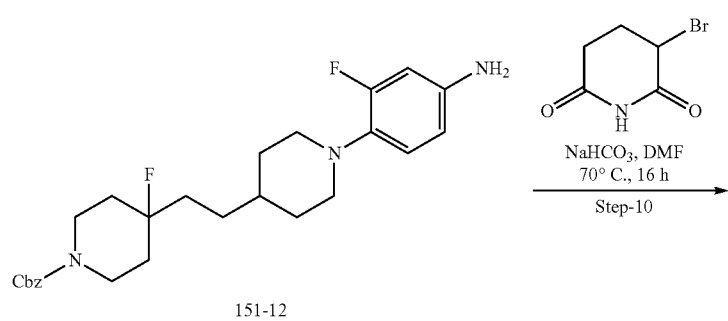
151-12
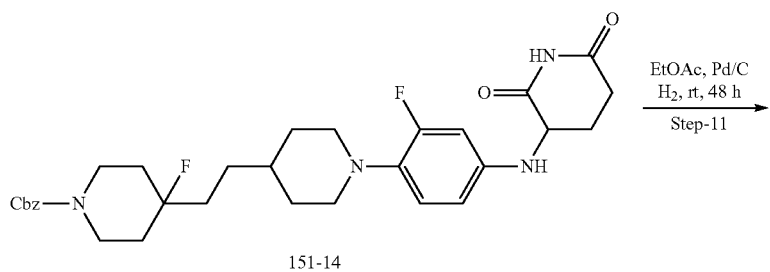
151-14
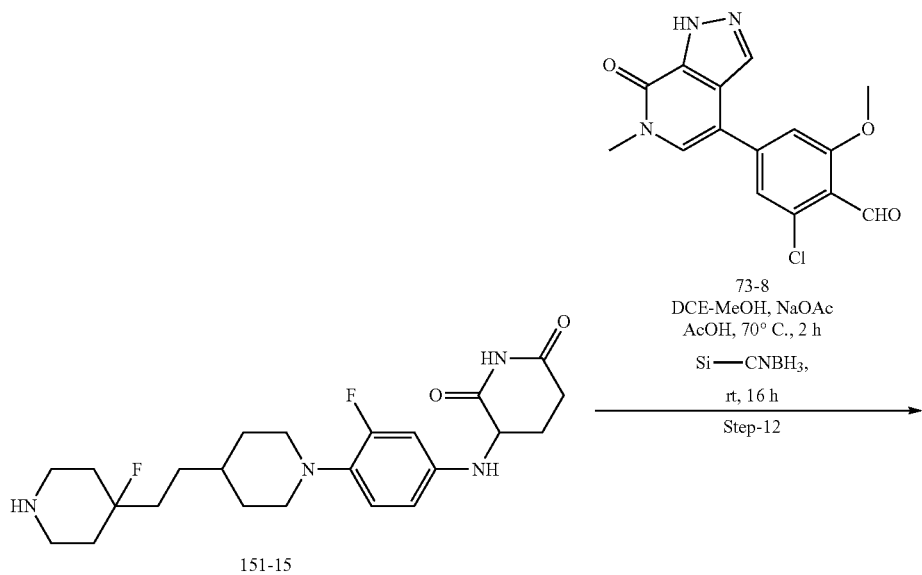
151-15

-continued

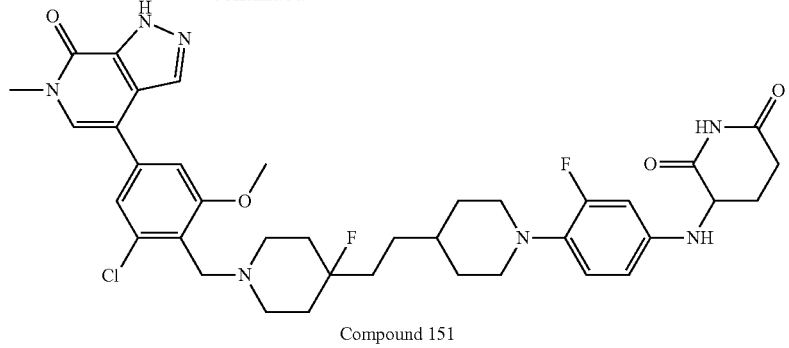

Compound 151

Step-1: To stirred solution of TMS-acetylene (12.63 g, 128.6 mmol) in THF (250 mL) was added n-butyl lithium (2.5 M in hexane) (51.4 mL, 128.6 mmol) at −78° C. and stirred for 30 min at −78° C. To this was then added a solution of benzyl 4-oxopiperidine-1-carboxylate (25 g, 107.2 mmol) in THF (50 mL) drop wise at −78° C. and stirred for 1 h at the same temperature. The reaction mixture was then allowed to warm to room temperature over 16 h, while monitoring progress of the reaction by TLC. After completion the reaction, it was quenched with addition of saturated ammonium chloride solution (50 mL) and extraction was carried out using EtOAc (2×100 mL). The combined organic layers were dried over anhydrous sodium sulphate, filtered and evaporated under reduce pressure.

Step-2: To stirred a solution of benzyl 4-hydroxy-4-(2-trimethylsilylethynyl)piperidine-1-carboxylate 151-2 (50.0 g, 150.8 mmol) in THF (400 mL) was added TBAF (1M in THF) (150.8 mL, 150.8 mmol) at 0° C. and the reaction mixture was allowed to warm to room temperature over 15 min, while monitoring progress of the reaction by TLC. After completion, saturated ammonium chloride solution (100 mL) was added to it and extraction was carried out using ethyl acetate (2×100 mL). The combined organic layers were then dried over anhydrous sodium sulphate, filtered and concentrated under reduced pressure.

Step-3: Argon gas was purged through a solution of benzyl 4-ethynyl-4-hydroxy-piperidine-1-carboxylate 151-3 (15.0 g, 57.8 mmol) and tert-butyl 4-(trifluoromethylsulfonyloxy)-3,6-dihydro-2H-pyridine-1-carboxylate 151-4 (19.17 g, 57.8 mmol) in THF (150 mL) for 10 minutes before addition of Pd(PPh$_3$)$_2$Cl$_2$ (2.03 g, 2.89 mmol), triethyl amine (105.3 g, 1040 mmol) and CuI (1.10 g, 5.78 mmol). The reaction mixture was then stirred at 70° C. for 16 h; while monitoring progress of the reaction by LCMS and TLC. After completion, it was cooled to ambient temperature and water (100 mL) was added to it. Extraction was carried out using ethyl acetate (2×50 mL); the combined organic extracts were washed with brine (100 mL), dried over anhydrous sodium sulphate, filtered and evaporated under reduced pressure. The residue was purified by silica gel column chromatography (using 230-400 mesh silica gel, 0-100% gradient elution of ethyl acetate in pet-ether) to afford desired compound tert-butyl 4-[2-(1-benzyloxycarbonyl-4-hydroxy-4-piperidyl)ethynyl]-3,6-dihydro-2H-pyridine-1-carboxylate 151-5 (38 g, 86.3 mmol, 89% yield, 99% purity) as an off white solid. LCMS (ES$^+$): m/z 463.3 [M+Na]$^+$.

Step-4: To stirred solution of tert-butyl 4-[2-(1-benzyloxycarbonyl-4-hydroxy-4-piperidyl)ethynyl]-3,6-dihydro-2H-pyridine-1-carboxylate 151-5 (10 g, 22.7 mmol) in MeOH (100 mL) was added 10% Pd/C (5 g) and the reaction mixture was stirred for 48 h under H$_2$ atmosphere (60 psi pressure), while monitoring progress of the reaction by LCMS. After completion of the reaction, the catalyst was filtered off through Celite and washed with MeOH (50 mL×2). The combined organic layers were evaporated under reduced pressure to afford crude compound tert-butyl 4-[2-(4-hydroxy-4-piperidyl)ethyl]piperidine-1-carboxylate 151-6 (7.0 g, 22.4 mmol, quantitative yield, 82% purity) as a yellow thick oil.

Step-5: To a stirred solution of tert-butyl 4-[2-(4-hydroxy-4-piperidyl)ethyl]piperidine-1-carboxylate 151-6 (6.5 g, 20.81 mmol) and pyridine (3.29 g, 41.62 mmol) in DCM (65 mL) was added benzyl chloroformate (50% in toluene) (5.32 g, 31.21 mmol) drop wise at −10° C. and the reaction mixture was allowed to warm to room temperature over 3 h. After complete consumption of starting material (as indicated by LCMS), volatiles were removed under reduced pressure and the residue was dissolved in THF (25 mL). To this was then added an aqueous solution of 1N NaOH (60 mL) and the reaction mixture was stirred at room temperature for 1 h. Extraction was then carried out using ethyl acetate (2×50 mL), the combined organic layers were washed with brine solution (50 mL), dried over anhydrous sodium sulphate, filtered and concentrated under reduced pressure. The residue was purified by silica gel column chromatography (230-400 mesh silica gel, using 0-100% gradient elution of ethyl acetate in pet-ether) to afford benzyl 4-[2-(1-tert-butoxycarbonyl-4-piperidyl)ethyl]-4-hydroxy-piperidine-1-carboxylate (3.8 g, 8.40 mmol, 40.9% yield, 98% purity) as a thick oil.

Step-6 To a stirred solution of benzyl 4-[2-(1-tert-butoxycarbonyl-4-piperidyl)ethyl]-4-hydroxy-piperidine-1-carboxylate 151-7 (4.7 g, 10.52 mmol) in DCM (50 mL) was added DAST (2.54 g, 15.79 mmol) at −20° C. and the reaction mixture was stirred for 15 min at the same temperature, while monitoring the progress of reaction by TLC. After completion of the reaction, it was quenched with addition of saturated sodium bicarbonate solution (40 mL) and extraction was carried out using DCM (2×50 mL). The combined organic extracts were washed with brine (50 mL), dried over anhydrous sodium sulphate, filtered and evaporated under reduce pressure. The resulting crude was purified by silica gel column chromatography (230-400 mesh silica gel, using 0-100% gradient elution of ethyl acetate in pet-ether) to afford desired compound benzyl 4-[2-(1-tert-butoxycarbonyl-4-piperidyl)ethyl]-4-fluoro-piperidine-1-carboxylate 151-8 (3.7 g, 7.17 mmol, 78% yield, 86% purity) as a light yellow liquid.

Step-7 To a stirring solution of benzyl 4-[2-(1-tert-butoxycarbonyl-4-piperidyl)ethyl]-4-fluoro-piperidine-1-carboxylate 151-8 (3.7 g, 8.25 mmol) in 1,4-dioxane (15 mL) was added a 4M solution of HCl in 1,4-dioxane (18.5 mL) at 0° C. and the reaction mixture was allowed to warm to room temperature over 2 h, while monitoring progress of the reaction by TLC. After completion of the reaction, volatiles were evaporated under reduced pressure and diethyl ether (20 mL) was added to the residue. It was stirred for 15 min and the solid obtained was filtered, washed with diethyl ether (5 mL×2) and dried to afford desired compound benzyl 4-fluoro-4-[2-(4-piperidyl) ethyl] piperidine-1-carboxylate 151-9 (3.2 g of HCl salt, 8.06 mmol, quantitative yield, 97% purity) as a white solid. LCMS (ES+): m/z 349.44 [M+H]+.

Step-8: To a stirred solution of benzyl 4-fluoro-4-[2-(4-piperidyl)ethyl]piperidine-1-carboxylate 151-9 (3.7 g, 9.61 mmol) in acetonitrile (30 mL) was added DIPEA (8.27 mL, 48.0 mmol) and stirred for 15 min before addition of 1,2-difluoro-4-nitro-benzene 151-10 (1.68 g, 26.85 mmol). The reaction mixture stirred at room temperature for 16 h, while monitoring progress of the reaction by TLC. After completion, saturated sodium bicarbonate solution (50 mL) was added to it and extraction was carried out using ethyl acetate (3×50 mL). The combined organic extracts were washed with brine (100 mL), dried over anhydrous sodium sulphate, filtered and evaporated under reduce pressure. The resulting crude was purified by silica gel column chromatography (230-400 mesh, using 0-100% gradient elution of ethyl acetate in pet-ether) to afford desired compound benzyl 4-fluoro-4-[2-[1-(2-fluoro-4-nitro-phenyl)-4-piperidyl]ethyl]piperidine-1-carboxylate 151-11 (3.4 g, 6.76 mmol, 73% yield, 97% purity) as a yellow solid. LCMS (ES+): m/z 488.45 [M+H]+.

Step-9: To a stirred solution of 4-fluoro-4-[2-[1-(2-fluoro-4-nitro-phenyl)-4-piperidyl]ethyl]piperidine-1-carboxylate 151-11 (3.4 g, 6.97 mmol) in MeOH (22 mL) was added zinc dust (5.93 g, 90.65 mmol) and an aqueous solution of ammonium chloride (5.60 g, 104.55 mmol, in 10 mL water) at room temperature. The reaction mixture was stirred at 70° C. for 3.5 h, while monitoring progress of the reaction by LCMS and TLC. After completion, it was cooled to room temperature and zinc dust was filtered off through Celite bed. It was washed with MeOH (10 mL×2) and the filtrate was evaporated under reduced pressure. Water (30 mL) was added to the residue and extraction was carried out using EtOAc (30 mL×2). The combined organic layers were dried over anhydrous sodium sulphate, filtered and concentrated under reduced pressure. The resulting crude was purified by silica gel column chromatography (230-400 mesh silica gel, using 0-100% gradient elution of ethyl acetate in pet-ether) to afford desired compound benzyl 4-[2-[1-(4-amino-2-fluoro-phenyl)-4-piperidyl]ethyl]-4-fluoro-piperidine-1-carboxylate 151-12 (2.8 g, 5.94 mmol, 85.12% yield, 97% purity) as a light brown solid.

Step-10: To a stirred solution of benzyl 4-[2-[1-(4-amino-2-fluoro-phenyl)-4-piperidyl]ethyl]-4-fluoro-piperidine-1-carboxylate 151-12 (2.8 g, 6.12 mmol) in DMF (28 mL) was added sodium bicarbonate (3.08 g, 36.72 mmol) and 3-bromopiperidine-2,6-dione (7.05 g, 36.72 mmol). The reaction mixture was stirred at 70° C. for 16 h in a sealed tube, while monitoring progress of the reaction by TLC. After completion of the reaction, it was cooled to room temperature and saturated sodium bicarbonate solution (25 mL) was added to it. Extraction was carried out using ethyl acetate (3×70 mL); the combined organic layers were washed with water (50 mL×2), brine (50 mL), dried over anhydrous Na$_2$SO$_4$, filtered and concentrated under reduced pressure. The crude compound was purified by silica gel column chromatography (230-400 mesh silica gel, using 0-100% gradient elution of ethyl acetate in pet-ether) to afford desired compound benzyl 4-[2-[1-[4-[(2,6-dioxo-3-piperidyl)amino]-2-fluoro-phenyl]-4-piperidyl]ethyl]-4-fluoro-piperidine-1-carboxylate 151-14 (2.46 g, 4.15 mmol, 67.86% yield, 96% purity) as a purple solid. LCMS (ES+): m/z 435.34 [M+H]+.

Step-11: To stirred solution of benzyl 4-[2-[1-[4-[(2,6-dioxo-3-piperidyl)amino]-2-fluoro-phenyl]-4-piperidyl]ethyl]-4-fluoro-piperidine-1-carboxylate (0.58 g, 1.02 mmol) in EtOAc (4 mL) and THF (2 mL) was added 10% Pd/C (108 mg); and the reaction mixture was stirred under hydrogen atmosphere (bladder) for 48 h. After completion of the reaction (as indicated by LCMS), the catalyst was filtered off through Celite and washed with EtOAc (10 mL×2). The filtrate was concentrated under reduced pressure and the residue was dried to yield crude product 3-[3-fluoro-4-[4-[2-(4-fluoro-4-piperidyl)ethyl]-1-piperidyl]anilino]piperidine-2,6-dione (435 mg, 0.821 mmol, 80.48% yield, 82% purity) as a thick brown oil. LCMS (ES+): m/z 435.34 [M+H]+.

Step-12: To a stirred solution of 3-[3-fluoro-4-[4-[2-(4-fluoro-4-piperidyl)ethyl]-1-piperidyl]anilino]piperidine-2,6-dione (0.479 g, 1.1 mmol) in MeOH (12 mL) and DCE (12 mL) was added NaOAc (0.272 g, 3.31 mmol), MS (0.35 g) and AcOH (0.132 g, 2.2 mmol). To this was then added 2-chloro-6-methoxy-4-(6-methyl-7-oxo-1H-pyrazolo[3,4-c]pyridin-4-yl)benzaldehyde (0.35 g, 1.1 mmol) and the reaction mass was stirred at 80° C. for 3 h. It was then cooled to 0° C. and then Si-CNBH$_3$ (0.347 g, 5.5 mmol) was added to it. The reaction mixture was stirred at room temperature for 16 h. It was then filtered through a pad of Celite and washed with DCE-MeOH (1:1; 3×5 mL). The filtrate was concentrated under reduced pressure. The crude obtained was purified by preparative HPLC to afford desired compound 3-[4-[4-[2-[1-[[2-chloro-6-methoxy-4-(6-methyl-7-oxo-1H-pyrazolo[3,4-c]pyridin-4-yl)phenyl] methyl]-4-fluoro-4-piperidyl]ethyl]-1-piperidyl]-3-fluoro-anilino]piperidine-2,6-dione (TFA salt) (63 mg, 0.073 mmol, 6.60% yield, 98.34% purity)$^1$H NMR (400 MHz, DMSO-d$_6$) δ 1.28-1.48 (m, 5H); 1.60-2.10 (m, 10H); 2.55-2.80 (m, 2H); 3.10-3.45 (m, 8H); 3.62 (s, 3H); 4.03 (s, 3H); 4.25-4.32 (m, 1H); 4.45-4.60 (m, 2H); 6.40-6.60 (m, 2H); 6.80-7.10 (m, 1H); 7.35 (s, 1H); 7.47 (s, 1H); 7.72 (s, 1H); 8.21 (s, 1H); 9.12 & 9.32 (two bs, 1H); 10.80 (s, 1H); 14.35 (bs, 1H). LCMS (ES+): m/z 736.53 (M+H)+, Compound 152 was prepared following the synthesis of Compound 151

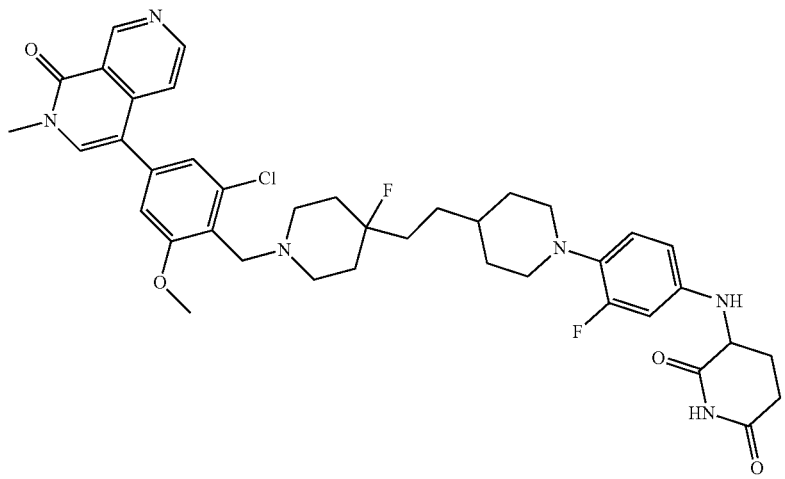 [SMILES: COc1cc(-c2cn(C)c(=O)c3cnccc23)cc(Cl)c1CN1CCC(F)(CCC2CCN(c3ccc(NC4CCC(=O)NC4=O)cc3F)CC2)CC1]
¹H NMR (400 MHz, DMSO-d₆) δ 0.80-1.40 (m, 6H); 1.50-1.90 (m, 10H); 2.04-2.10 (m, 1H); 2.30-2.42 (m, 2H); 2.52-2.60 (m, 1H); 2.62-2.78 (m, 3H); 3.05-3.12 (m, 2H); 3.59 (s, 3H); 3.64 (s, 2H); 3.86 (s, 3H); 4.20-4.30 (m, 1H); 5.76 (d, J=7.6 Hz, 1H); 6.40 (dd, J₁=2.0 Hz, J₂=8.8 Hz, 1H); 6.49 (dd, J₁=2.0 Hz, J₂=15.2 Hz, 1H); 6.81 (t, J=9.2 Hz, 1H); 7.09 (s, 1H); 7.14 (s, 1H); 7.52 (d, J=5.6 Hz, 1H); 7.92 (s, 1H); 8.73 (d, J=5.6 Hz, 1H); 9.44 (s, 1H); 10.78 (s, 1H). LCMS (ES⁺): m/z 747.35 [M+H]⁺.
Compound 153 was prepared following the synthesis of Compound 147
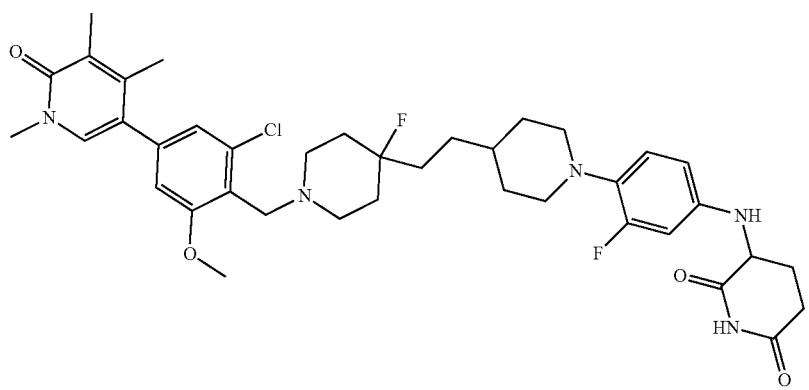 [SMILES: COc1cc(-c2cn(C)c(=O)c(C)c2C)cc(Cl)c1CN1CCC(F)(CCC2CCN(c3ccc(NC4CCC(=O)NC4=O)cc3F)CC2)CC1]
¹H NMR (400 MHz, DMSO-d₆) δ 10.77 (s, 1H), 7.56 (s, 1H), 6.96 (d, J=1.4 Hz, 1H), 6.89 (d, J=1.2 Hz, 1H), 6.81 (t, J=9.4 Hz, 1H), 6.51-6.47 (m, 1H), 6.41-6.39 (m, 1H), 5.77 (d, J=7.7 Hz, 1H), 4.38-4.24 (m, 1H), 3.82 (s, 3H), 3.59 (s, 2H), 3.45 (s, 3H), 3.09 (d, J=10.5 Hz, 2H), 2.72-2.57 (m, 6H), 2.37-2.32 (m, 2H), 2.08 (s, 7H), 1.90-1.89 (m, 1H), 1.84-1.54 (m, 8H), 1.31-1.16 (m, 5H). LCMS (ES⁺): m/z 724.20 [M+H]⁺.

Synthesis of Compound 154
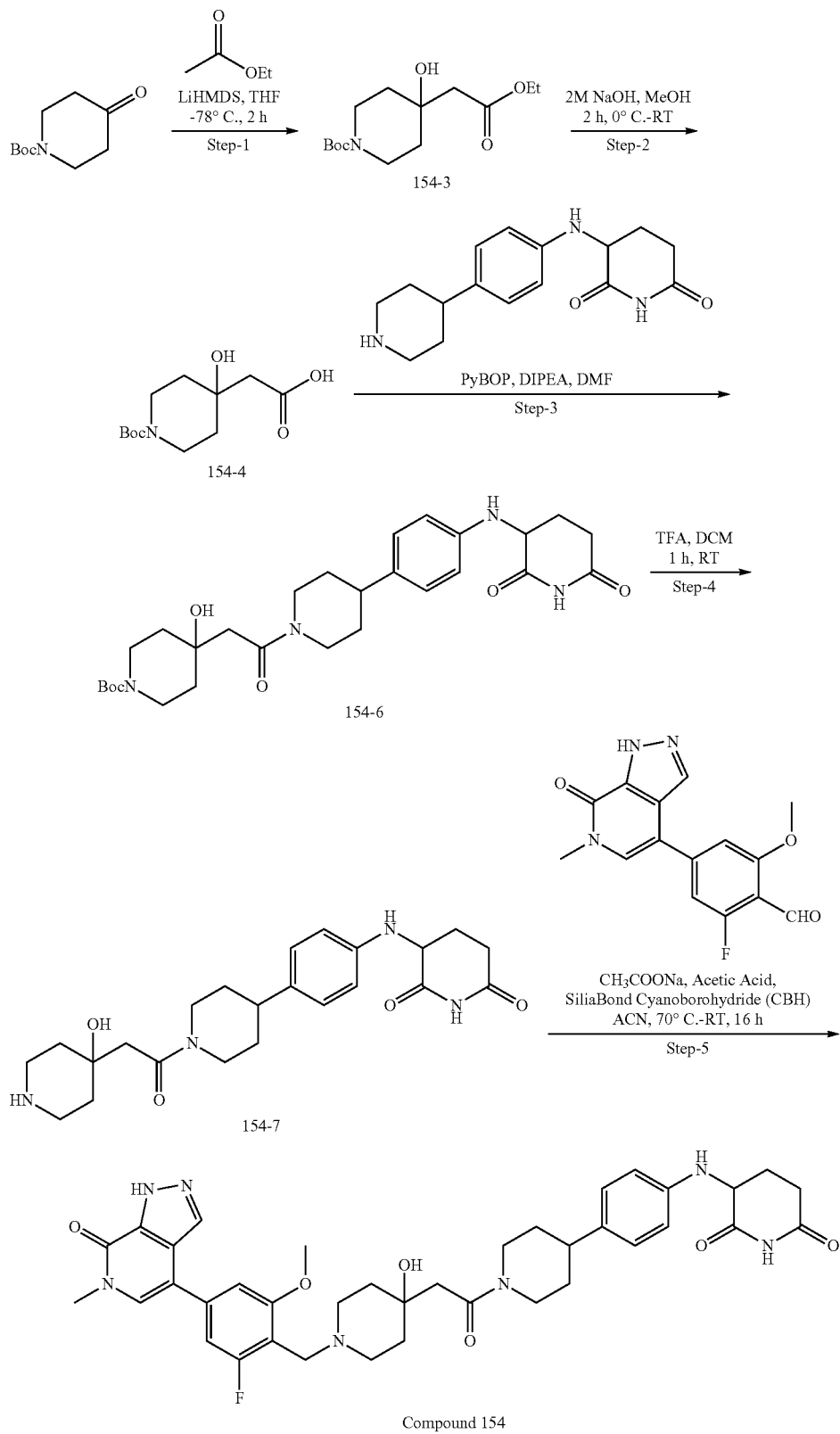
Compound 154

Step-1: To a stirred solution of Lithium bis(trimethylsilyl) amide (1.68 g, 10.04 mmol, 11 mL) in THF (5 mL) under inert atmosphere was added ethyl acetate (1.33 g, 15.06 mmol, 1.47 mL) drop wise at −78° C. The reaction mixture was stirred for 30 minutes. Then tert-butyl 4-oxopiperidine-1-carboxylate (2 g, 10.04 mmol) in THF (5 mL) was added to the reaction mixture. The reaction mixture was stirred at −78° C. for 1 h. The progress of reaction was monitored by TLC; On completion of reaction, the reaction mixture was diluted with water (20 mL) and extracted with $CH_2Cl_2$ (2×20 mL). The combined organic extract was dried over $Na_2SO_4$ and concentrated under reduced pressure to obtain tert-butyl 4-(2-ethoxy-2-oxo-ethyl)-4-hydroxy-piperidine-1-carboxylate (2 g, 6.96 mmol, 69.34% yield) as colourless oil.

Step-2: To a stirred solution of tert-butyl 4-(2-ethoxy-2-oxo-ethyl)-4-hydroxy-piperidine-1-carboxylate (1 g, 3.48 mmol) in $MeOH:H_2O$ (4:1.20 mL) at 0° C. was added Sodium hydroxide (139.19 mg, 3.48 mmol, 65.35 uL). The reaction mixture was warmed to RT and stirred for 1 h. The progress of reaction was monitored by TLC; after completion of reaction, the solvents were removed under reduced pressure. The residue was diluted with water (50 mL) and extracted with diethyl ether (2×50 mL). The aqueous layer was acidified with Con. HCl (pH ~3-4) and extracted with DCM (50 mL×3). The combined organic layer was dried over $Na_2SO_4$, and concentrated under reduced pressure to obtain the 2-(1-tert-butoxycarbonyl-4-hydroxy-4-piperidyl) acetic acid (800 mg, 2.78 mmol, 79.79% yield, 90% purity) as colourless oil.

Step-3: To a stirred solution of 2-(1-tert-butoxycarbonyl-4-hydroxy-4-piperidyl)acetic acid (250 mg, 964.14 umol) was added Diisopropylethylamine (747.65 mg, 5.78 mmol, 1.01 mL) and reaction mixture was stirred at RT for 10 min. HATU (476.57 mg, 1.25 mmol) was added to reaction mixture and stirring was continued at RT for 16 h. After completion of reaction, the reaction mixture was poured into the ice water and extracted with ethyl acetate, organic layer was dried over sodium sulphate and concentred under vacuum. The crude was purified by column chromatography using 2% MeOH/DCM to afford tert-butyl 4-[2-[4-[4-[(2,6-dioxo-3-piperidyl)amino]phenyl]-1-piperidyl]-2-oxo-ethyl]-4-hydroxy-piperidine-1-carboxylate (380 mg, 718.83 umol, 74.56% yield). LCMS ($ES^+$): m/z 529.52 $[M+H]^+$.

Step-4: To a stirred solution of tert-butyl 4-[2-[4-[4-[(2,6-dioxo-3-piperidyl)amino]phenyl]-1-piperidyl]-2-oxo-ethyl]-4-hydroxy-piperidine-1-carboxylate (150 mg, 283.75 umol) in DCM (5 mL) was added Trifluoroacetic acid (323.53 mg, 2.84 mmol, 218.60 uL) and reaction mixture was stirred at RT for 1 h. After completion of reaction, the volatiles were evaporated under vacuum, the crude was co-distilled with toluene and triturated with diethyl ether to obtain 3-[4-[1-[2-(4-hydroxy-4-piperidyl)acetyl]-4-piperidyl]anilino]piperidine-2,6-dione (140 mg, 174.85 umol, 61.62% yield, 82% purity) LCMS ($ES^+$): m/z 529.52 $[M+H]^+$.

Step-5: To a stirred solution of 2-fluoro-6-methoxy-4-(6-methyl-7-oxo-1H-pyrazolo[3,4-c]pyridin-4-yl)benzaldehyde (59.56 mg, 197.68 umol) was added Sodium acetate, anhydrous (48.65 mg, 593.05 umol, 31.80 uL) and Acetic acid (11.87 mg, 197.68 umol, 11.31 uL) and reaction mixture was stirred at 75° C. for 4 h. SiliaBond Cyanoborohydride (CBH) (200 mg, 197.68 umol) was added to reaction mixture and continued stirring at room temperature for 16 h. After completion of reaction, the volatiles were evaporated under vacuum and the crude compound was purified by PrepHPLC to obtain 3-[4-[1-[2-[1-[[2-fluoro-6-methoxy-4-(6-methyl-7-oxo-1H-pyrazolo[3,4-c]pyridin-4-yl)phenyl]methyl]-4-hydroxy-4-piperidyl]acetyl]-4-piperidyl]anilino]piperidine-2,6-dione (20.4 mg, 24.12 umol, 12.20% yield, 97.89% purity) LCMS ($ES^+$): m/z 714.56 $[M+H]^+$. $^1H$ NMR (400 MHz, DMSO-$d_6$) δ 1.40-1.60 (m, 3H), 1.70-2.00 (m, 7H), 2.05-2.15 (m, 1H), 2.55-2.65 (m, 4H), 2.65-2.80 (m, 2H), 3.00-3.40 (m, 5H), 3.62 (s, 3H), 4.05 (s, 3H), 4.20-4.35 (m, 3H), 4.40-4.60 (m, 2H), 6.55-6.65 (m, 2H), 6.90-7.00 (m, 2H), 7.20-7.30 (m, 2H), 7.71 (s, 1H), 8.25 (s, 1H), 9.31 (s, 1H), 10.85 (s, 1H), 14.25 (bs, 1H).

Synthesis of Compound 155

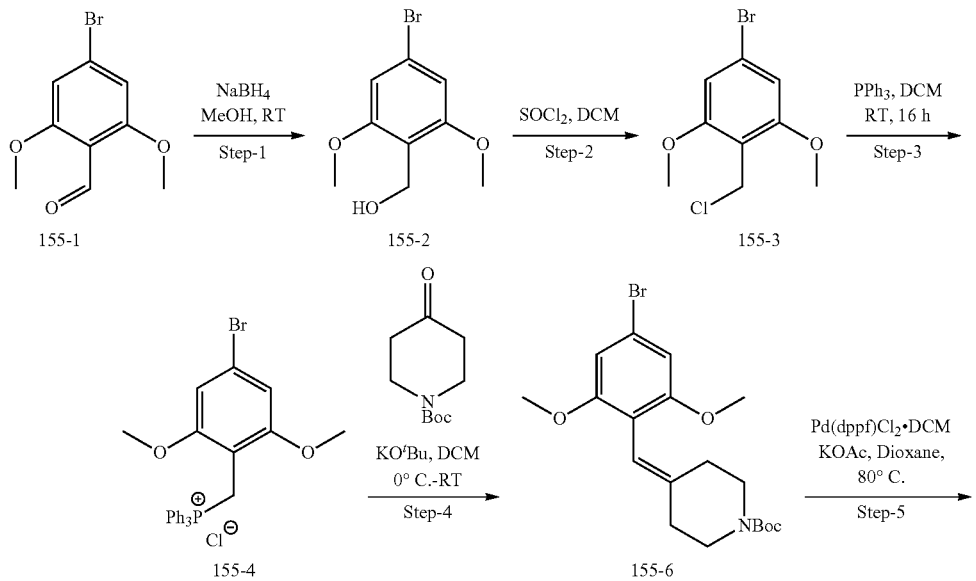

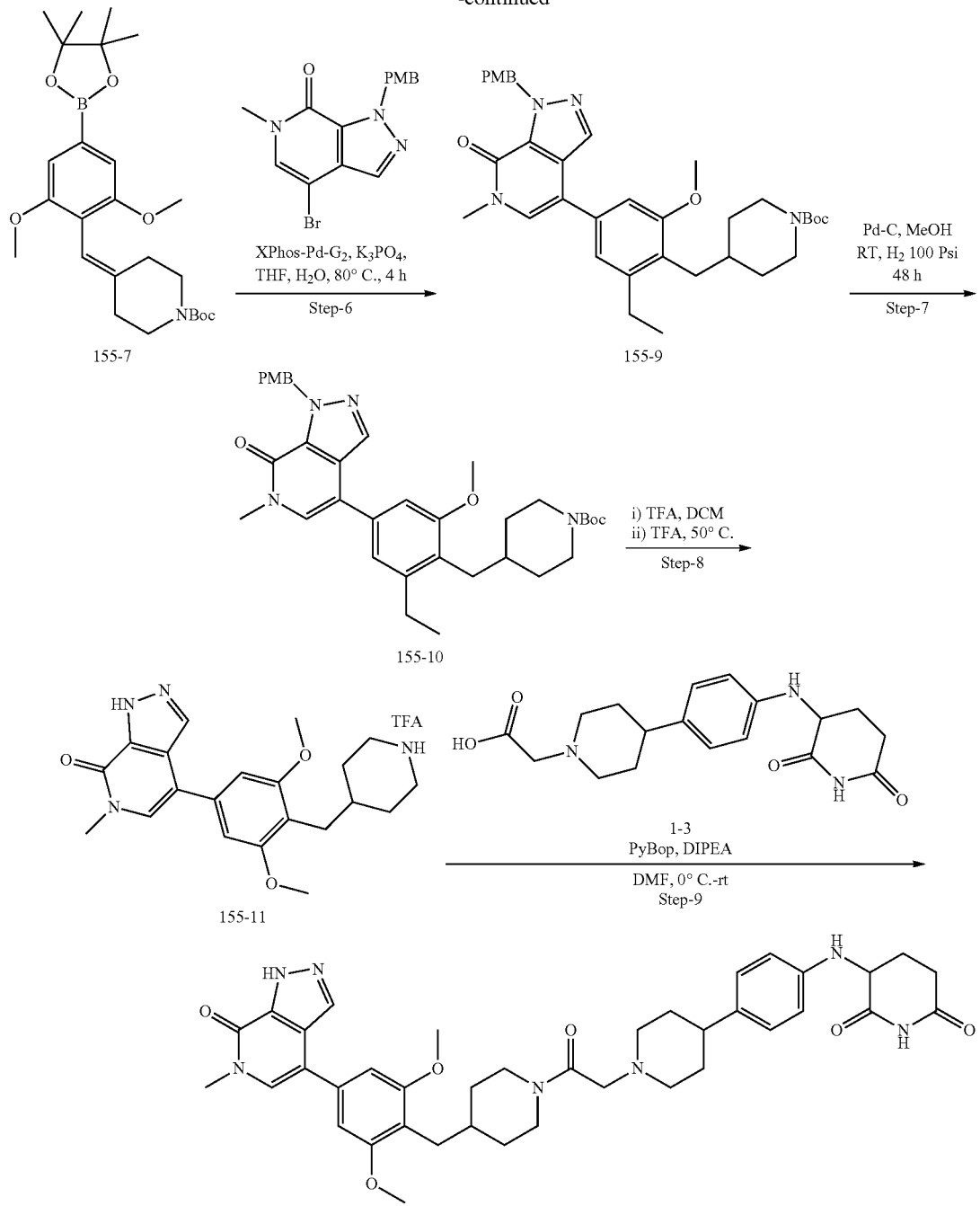

Compound 155

Step-1: To a stirred solution of 4-bromo-2,6-dimethoxybenzaldehyde (5 g, 20.49 mmol) in Methanol (70 mL) was added portion wise sodium Borohydride (1.16 g, 38.03 mmol) at 0° C. and reaction mixture was allowed to stirred at room temperature for 1 h, while monitoring the reaction by TLC. After completion, reaction mixture was diluted with H$_2$O (100 mL) and extracted with EtOAc (2×100 mL). The combined organic layer was dried with Na$_2$SO$_4$ and solvent was evaporated under reduced pressure. The crude compound was purified by column chromatography (100-200 mesh silica gel, 20% EtOAc in Pet ether) to afford (4-bromo-2,6-dimethoxyphenyl)methanol (4.95 g, 88.37% yield, 90% purity) as an white solid Step-2: To a stirred solution of (4-bromo-2,6-dimethoxyphenyl)methanol (4.95 g, 20.03 mmol) in DCM (50 mL) was added slowly thionyl chloride (4.76 g, 40.06 mmol) at 0° C. and then reaction mixture was allowed to stir at room temperature for 3 h, while monitoring by TLC. After completion, solvent was removed under reduced pressure and crude was co-distilled with toluene to afford 5-bromo-2-(chloromethyl)-1,3-dimethoxybenzene (4.9 g, 92.1% yield, 95% purity) as a white solid Step-3: To a stirred solution of 5-bromo-2-(chloromethyl)-1,3-dimethoxy-benzene (4.9 g, 18.45 mmol) in DCM (50 mL) was added triphenylphosphine (5.8 g, 22.14 mmol) at room temperature and stirring was continued for 16 h at same temperature, while monitoring the reaction by TLC. After completion, precipitated solid was filtered and triturated with 20% EtOAc in pet ether to afford to afford (4-bromo-2,6-dimethoxybenzyl)triphenylphosphonium chloride (8.0 g, 82.3% yield, 90% purity) as a white solid.

Step-4: To a stirred solution of (4-bromo-2,6-dimethoxyphenyl)methyl-triphenyl-phosphoniumchloride (3.0 g, 7.6 mmol) in IPA (30 mL) were added Potassium carbonate-granular (1.18 g, 8.55 mmol) followed by tert-butyl 4-oxopiperidine-1-carboxylate (1.7 g, 8.55 mmol) and then reaction mixture was allowed to stirred at 70° C. for 16 h, while monitoring the reaction by TLC. After completion, reaction mixture was diluted with $H_2O$ (100 mL) and extracted with EtOAc (2×100 mL). The combined organic layer was dried over $Na_2SO_4$ and solvent was evaporated under reduced pressure. The crude compound was purified by column chromatography (100-200 mesh silica gel, with 10% EtOAc in pet ether as eluent) to afford tert-butyl 4-[(4-bromo-2,6-dimethoxy-phenyl)methylene]piperidine-1-carboxylate (1.0 g, 42.6% yield, 90% purity) as a gummy solid Step-5: To a degassed (with argon gas) solution of tert-butyl 4-[(4-bromo-2,6-dimethoxy-phenyl)methylene]piperidine-1-carboxylate (1.0 g, 2.43 mmol), bis(pinacolato)diboron (0.9235 g, 3.64 mmol) and Potassium Acetate (0.714 g, 7.27 mmol) in 1,4-dioxane (20 mL) was added Pd(dppf)Cl$_2$.DCM complex (0.2368 g, 0.29 mmol) and stirred at 80° C. for 4 h while monitoring the reaction by TLC and LCMS. After 4 h, the reaction mass was quenched with water (100 ml) and extracted with EtOAc (2×100 ml). The combined organic layer was dried over anhydrous $Na_2SO_4$ and concentrated to afford crude compound tert-butyl 4-[[2,6-dimethoxy-4-(4,4,5,5-tetramethyl-1,3,2-dioxaborolan-2-yl)phenyl]methylene]piperidine-1-carboxylate (1.1 g, 52.6% yield, 59% purity) as a brown gummy solid. LCMS (ES$^+$): m/z 459.27 [M+H]$^+$. (Boronate ester) LCMS (ES$^+$): m/z 360.31 [M+H]$^+$.

Step-6: A mixture of tert-butyl tert-butyl 4-[[2,6-dimethoxy-4-(4,4,5,5-tetramethyl-1,3,2-dioxaborolan-2-yl)phenyl]methylene]piperidine-1-carboxylate (1.1 g, 2.39 mmol), 4-bromo-1-[(4-methoxyphenyl)methyl]-6-methyl-pyrazolo[3,4-c]pyridin-7-one (0.832 g, 2.39 mmol), and Potassium phosphate tribasic anhydrous (1.01 g, 4.78 mmol) in THF (18 mL) water (2 mL) was degassed for 30 min using argon before adding X-phos-Pd-G2 (0.094 g, 0.1197 mmol). The RM was stirred at 80° C. for 4 h, while monitoring the reaction by TLC and LCMS. The reaction mass was filtered over a Celite bed and the bed was thoroughly washed with EtOAc. The combined filtrate was washed with brine, dried over anhydrous $Na_2SO_4$, and concentrated. The crude compound was purified by column chromatography (Devisil Silica, 80% EtOAc in pet ether) to afford tert-butyl 4-[[2,6-dimethoxy-4-[1-[(4-methoxyphenyl)methyl]-6-methyl-7-oxo-pyrazolo[3,4-c]pyridin-4-yl]phenyl]methylene]piperidine-1-carboxylate (0.5 g, 82% purity) as an light yellow solid. LCMS (ES$^+$): m/z 601.21 [M+H]$^+$.

Step-7: To a stirred solution of tert-butyl 4-[[2,6-dimethoxy-4-[1-[(4-methoxyphenyl)methyl]-6-methyl-7-oxo-pyrazolo[3,4-c]pyridin-4-yl]phenyl]methylene] piperidine-1-carboxylate (0.2 g, 0.33 mmol) in Methanol (5 mL) in steal bomb was added 10% wet Pd-C (0.2 g) at room temperature and filled $H_2$ gas (100 PSI), reaction mixture was allowed to stir for 20 h, while monitoring the reaction by TLC and LCMS. After completion, the reaction mass was filtered over a Celite bed and the bed was thoroughly washed with EtOAc (10 mL) and MeOH (10 mL). The combined filtrate was evaporated and crude was triturated with diethyl ether to afford tert-butyl 4-[[2,6-dimethoxy-4-[1-[(4-methoxyphenyl)methyl]-6-methyl-7-oxo-pyrazolo[3,4-c]pyridin-4-yl]phenyl]methyl]piperidine-1-carboxylate (0.170 g, 92.38% purity) as a white solid. LCMS (ES$^+$): m/z 603.09 [M+H]$^+$.

Step-8: To a stirred solution of tert-butyl 4-[[2,6-dimethoxy-4-[1-[(4-methoxyphenyl)methyl]-6-methyl-7-oxo-pyrazolo[3,4-c]pyridin-4-yl]phenyl]methyl]piperidine-1-carboxylate (0.17 g, 0.28 mmol) in DCM (0.5 mL) was added Trifluoroacetic acid (1.27 g, 11.2 mmol) at room temperature for 2 h, while monitoring the reaction by TLC and LCMS. After completion, solvent was evaporated and again fresh Trifluoroacetic acid (2.96 g, 25.96 mmol, 2 mL) was added to the crude and reaction mixture was allowed to stir at 50° C. for 3 h, while monitoring the reaction by LCMS. After completion solvent was evaporated and crude was co-distilled with toluene to afford 4-[3,5-dimethoxy-4-(4-piperidylmethyl)phenyl]-6-methyl-1H-pyrazolo[3,4-c]pyridin-7-one TFA salt (0.150 g, 68.01% purity, 062) as a brown solid. LCMS (ES$^+$): m/z 383.41 [M+H]$^+$.

Step-9: To a stirred solution of 4-[3,5-dimethoxy-4-[[1-(2,2,2-trifluoroacetyl)-4-piperidyl]methyl]phenyl]-6-methyl-1H-pyrazolo[3,4-c]pyridin-7-one (0.075 g, 0.106 mmol) in DMF (3 mL) were added DIPEA (0.1522 g, 1.18 mmol) followed by 2-[4-[4-[(2,6-dioxo-3-piperidyl)amino]phenyl]-1-piperidyl]acetic acid (0.0608 g, 0.106 mmol) and PyBOP (0.153 g, 0.294 mmol) at 0° C. and then reaction mixture was allowed to stirred at room temperature for 16 h, while monitoring the reaction by LCMS. After completion, solvent was evaporated through GENVAC and crude sample was purified by preparative HPLC to afford 3-[4-[1-[2-[4-[[2,6-dimethoxy-4-(6-methyl-7-oxo-1H-pyrazolo[3,4-c]pyridin-4-yl)phenyl]methyl]-1-piperidyl]-2-oxo-ethyl]-4-piperidyl]anilino]piperidine-2,6-dione (0.0243 g, 26.42% yield, 95.09% purity) as an light brown solid. $^1$H NMR (400 MHz, DMSO-d$_6$) δ 14.23 (s, 1H), 10.78 (s, 1H), 9.38 (s, 1H), 8.21 (s, 1H), 7.24 (s, 1H), 6.99 (d, J=8.6 Hz, 2H), 6.86 (s, 2H), 6.65 (d, J=8.6 Hz, 2H), 5.58 (bs, 1H), 4.34-4.26 (m, 4H), 3.87 (s, 6H), 3.61 (s, 3H), 3.11-2.98 (m, 6H), 2.74-2.56 (m, 6H), 2.09-2.07 (m, 1H), 1.93-1.82 (m, 6H), 1.63 (d, J=11.2 Hz, 2H), 1.31-1.19 (m, 2H). LCMS (ES$^+$): m/z 710.36 [M+H]$^+$.

Synthesis of Compound 156

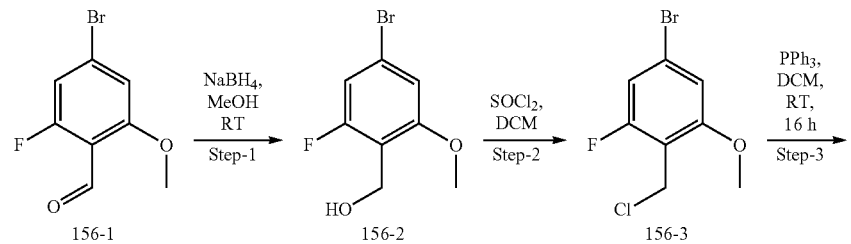

-continued
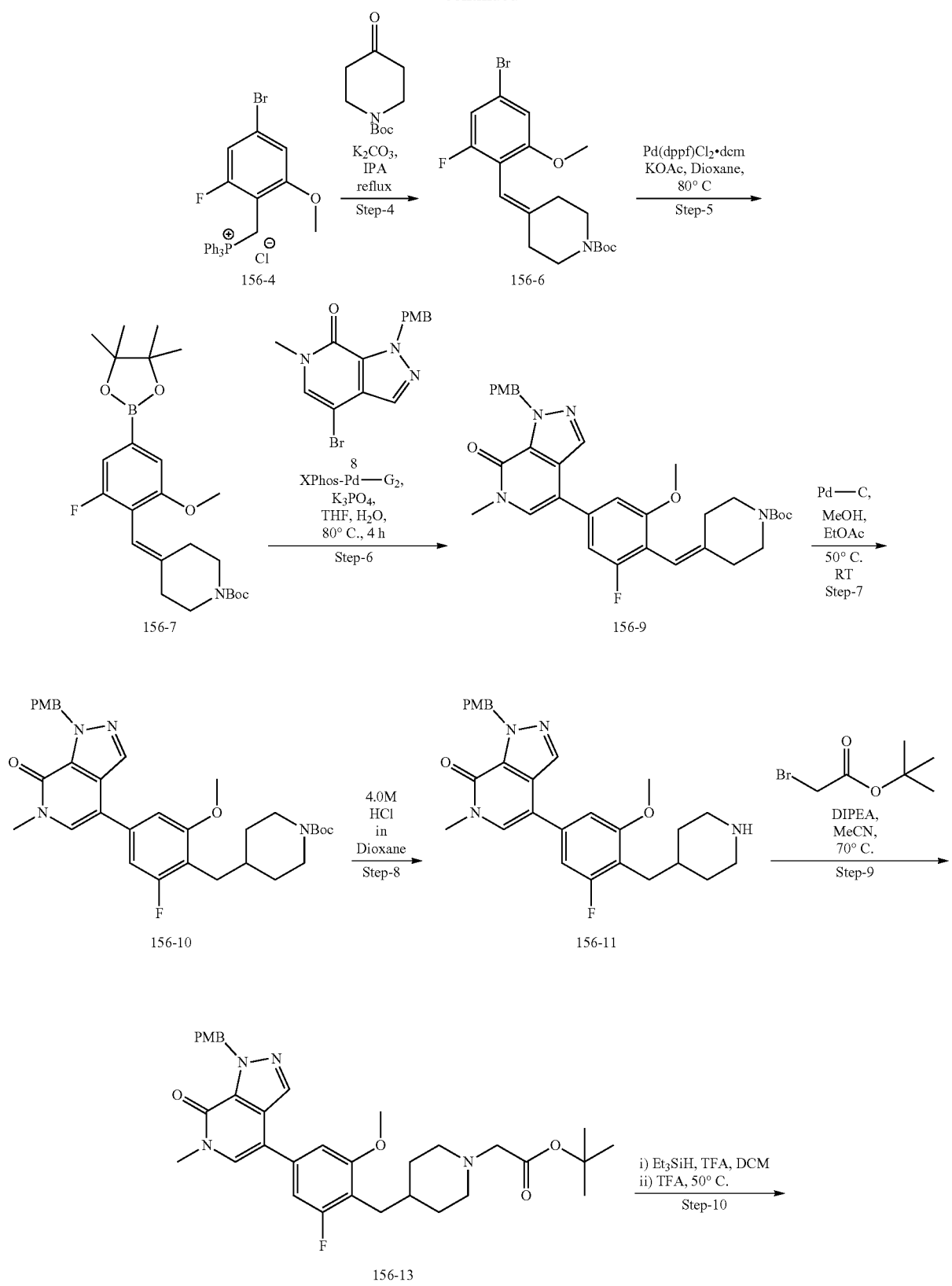

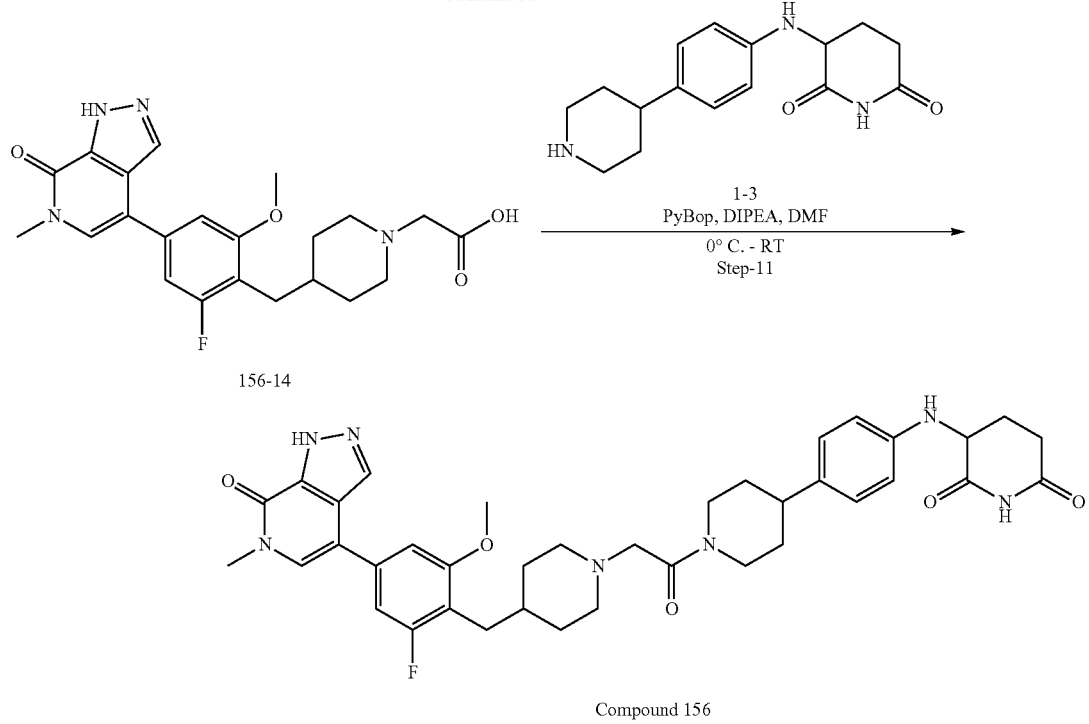

Compound 156

Step-1: To a stirred solution of 4-bromo-2-fluoro-6-methoxy-benzaldehyde (5 g, 42.92 mmol) in Methanol (60 mL) was added portion wise Sodium Borohydride (2.46 g, 32.51 mmol) at 0° C. and reaction mixture was allowed to stir at room temperature for 1 h, while monitoring the reaction by TLC. After completion, reaction mixture was diluted with H₂O (100 mL) and extracted with EtOAc (2×150 mL). The combined organic layer was dried with Na₂SO₄ and solvent was evaporated under reduced pressure. The crude compound was purified by column chromatography (100-200 mesh silica gel, 20% EtOAc in Pet ether) to afford (4-bromo-2-fluoro-6-methoxy-phenyl) methanol (9.5 g, 95% purity) as a white solid Step-2: To a stirred solution of (4-bromo-2-fluoro-6-methoxy-phenyl)methanol (9.5 g, 40.42 mmol) in DCM (30 mL) was added slowly thionyl chloride (15.69 g, 131.88 mmol) at 0° C. and then reaction mixture was allowed to stir at room temperature for 3 h, while monitoring the reaction by TLC. After completion, solvent was removed under reduced pressure and crude was co-distilled with toluene to afford 5-bromo-2-(chloromethyl)-1-fluoro-3-methoxy-benzene (9.0 g, 95% purity) as a white solid.

Step-3: To a stirred solution of 5-bromo-2-(chloromethyl)-1-fluoro-3-methoxy-benzene (9.0 g, 35.5 mmol) in DCM (50 mL) was added triphenylphosphine (13.97 g, 53.25 mmol) at room temperature and stirring was continued for 16 h at the same temperature, while monitoring the reaction by TLC. After completion, precipitated solid was filtered and triturated with 20% EtOAc in pet ether to afford ((4-bromo-2-fluoro-6-methoxy-phenyl)methyl-triphenyl-phosphonium (15 g, 81.9% yield, 95% purity) as white solid Step-4: To a stirred solution of (4-bromo-2-fluoro-6-methoxy-phenyl)methyl-triphenyl-phosphonium (11 g, 22.32 mmol) in IPA (30 mL) were added Potassium carbonate (4.42 g, 31.98 mmol) followed by tert-butyl 4-oxopiperidine-1-carboxylate (6.37 g, 31.98 mmol) and then reaction mixture was allowed to stir at 70° C. for 16 h, while monitoring by TLC. After completion, reaction mixture was diluted with H₂O (100 mL) and extracted with EtOAc (2×150 mL). The combined organic layer was dried over Na₂SO₄ and evaporated under reduced pressure. The crude compound was purified by column chromatography (100-200 mesh silica gel, with 10% EtOAc in pet ether as eluent) to afford tert-butyl 4-[(4-bromo-2-fluoro-6-methoxy-phenyl) methylene] piperidine-1-carboxylate (4 g, 43.64% yield, 90% purity) as an white solid. LCMS (ES⁺): m/z 400 [M+H]⁺.

Step-5: To a degassed (with argon gas) solution of tert-butyl 4-[(4-bromo-2-fluoro-6-methoxy-phenyl)methylene] piperidine-1-carboxylate (4 g, 9.99 mmol), Bis(pinacolato) diboron (3.82 g, 15.03 mmol) and Potassium Acetate (2.95 g, 30.06 mmol) in 1,4-dioxane (20 mL) was added Pd(dppf) Cl₂.DCM complex (0.98 g, 1.20 mmol) and stirred at 80° C. for 4 h while monitoring the reaction by TLC and LCMS. After 4 h, the reaction mass was quenched with water (200 ml) and extracted with EtOAc (2×200 ml). The combined organic layer was dried over anhydrous Na₂SO₄ and concentrated to afford crude compound tert-butyl 4-[[2-fluoro-6-methoxy-4-(4,4,5,5-tetramethyl-1,3,2-dioxaborolan-2-yl) phenyl]methylene]piperidine-1-carboxylate (6 g, 47% purity) as an brown gummy solid Step-6: A mixture of tert-butyl 4-[[2-fluoro-6-methoxy-4-(4,4,5,5-tetramethyl-1,3,2-dioxaborolan-2-yl)phenyl]methylene]piperidine-1-carboxylate (1.2 g, 2.68 mmol), 4-bromo-1-[(4-methoxyphenyl)methyl]-6-methyl-pyrazolo[3,4-c]pyridin-7-one (0.93 g, 2.41 mmol) and Potassium phosphate tribasic anhydrous (1.14 g, 5.36 mmol) in THF (18 mL) water (2 mL) was degassed for 30 min using argon before adding X-phos-Pd-G2 (0.0526 g, 0.067 mmol). The RM was stirred at 80° C. for 4 h, while monitoring the reaction by TLC and LCMS. The reaction mass was filtered over a Celite bed and the bed was thoroughly washed with EtOAc. The combined filtrate was washed with brine, dried over anhydrous $Na_2SO_4$, and concentrated. The crude compound was purified by column chromatography (Devisil Silica, 80% EtOAc in pet ether) to afford tert-butyl 4-(2-fluoro-6-methoxy-4-(1-(4-methoxybenzyl)-6-methyl-7-oxo-6,7-dihydro-1H-pyrazolo[3,4-c]pyridin-4-yl)benzylidene)piperidine-1-carboxylate (0.6 g, 38% yield, 64% purity) as an Off-white solid LCMS (ES$^+$): m/z 589.32 [M+H]$^+$.

Step-7: To a stirred solution of tert-butyl 4-[[2-fluoro-6-methoxy-4-[1-[(4-methoxyphenyl)methyl]-6-methyl-7-oxo-pyrazolo[3,4-c]pyridin-4-yl]phenyl]methylene]piperidine-1-carboxylate (0.6 g, 1.02 mmol) in Methanol (5 mL) and EtOAc (5 mL) was added 10% Pd/C (0.6 g) and kept hydrogen gas using hydrogen balloon bladder and reaction mixture was allowed to stirred at 50° C. for 16 h, while monitoring the reaction by TLC and LCMS. After completion, reaction mass was filtered over a Celite bed and the bed was thoroughly washed with EtOAc and MeOH. Combined filtrate was evaporated and crude was purified by column chromatography (Devisil silica gel, 50% EtOAc in pet ether) to afford tert-butyl 4-[[2-fluoro-6-methoxy-4-[1-[(4-methoxyphenyl)methyl]-6-methyl-7-oxo-pyrazolo[3,4-c]pyridin-4-yl]phenyl]methyl] piperidine-1-carboxylate (0.3 g, 92.7% purity) as a white solid. LCMS (ES$^+$): m/z 591.29 [M+H]$^+$.

Step-8: 4.0 M HCl in 1,4-dioxane (2 mL) was added to the tert-butyl 4-[[2-fluoro-6-methoxy-4-[1-[(4-methoxyphenyl)methyl]-6-methyl-7-oxo-pyrazolo[3,4-c]pyridin-4-yl]phenyl]methyl]piperidine-1-carboxylate (0.3 g, 0.507 mmol) at 0° C. and then reaction mixture was allowed to stirred at rt for 3 h, while monitoring the reaction by TLC and LCMS. After completion, solvent was evaporated and crude was co-distilled with toluene to afford 4-[3-fluoro-5-methoxy-4-(4-piperidylmethyl)phenyl]-1-[(4-methoxyphenyl)methyl]-6-methyl-pyrazolo[3,4-c]pyridin-7-one; hydrochloride (0.25 g, 86.92% yield, 99.5% purity, 021) as a brown solid. LCMS (ES$^+$): m/z 491.77 [M+H]$^+$.

Step-9: To a stirred solution of 4-[3-fluoro-5-methoxy-4-(4-piperidylmethyl)phenyl]-1-[(4-methoxyphenyl)methyl]-6-methyl-pyrazolo[3,4-c]pyridin-7-one; hydrochloride (0.2 g, 0.355 mmol, 021) in CH3CN (5 mL) were added DIPEA (0.3165 g, 2.45 mmol) followed by tert-butyl 2-bromoacetate (79.80 mg, 0.409 mmol) and then reaction mixture was allowed reflux for 4 h, while monitoring the reaction by TLC. After completion, the reaction mass was quenched with water (50 ml) and extracted with EtOAc (2×50 ml). The combined organic layer was dried over anhydrous Na2SO4 and concentrated. The crude was purified by column chromatography (devisil silica, 70% EtOAc in pet ether) to afford tert-butyl 2-[4-[[2-fluoro-6-methoxy-4-[1-[(4-methoxyphenyl)methyl]-6-methyl-7-oxo-pyrazolo[3,4-c]pyridin-4-yl]phenyl]methyl]-1-piperidyl]acetate (0.2 g, 48.4% purity) as a gummy solid. LCMS (ES$^+$): m/z 605.95 [M+H]$^+$.

Step-10: To a suspension of tert-butyl 2-[4-[[2-fluoro-6-methoxy-4-[1-[(4-methoxyphenyl)methyl]-6-methyl-7-oxo-pyrazolo[3,4-c]pyridin-4-yl]phenyl]methyl]-1-piperidyl]acetate (0.1 g, 0.165 mmol) were added triethylsilane (57.69 mg, 0.496 mmol) followed by TFA (0.377 g, 3.31 mmol) and reaction mixture was allowed stirred at room temperature for 3 h, while monitoring by TLC. As TLC indicates t-Butyl cleavage TFA was removed under vacuum and again fresh TFA (0.377 g, 3.31 mmol) was added and reaction mixture was allowed stir at 50° C. for 4 h, while monitoring the reaction by LCMS. After completion, TFA was removed and crude was co-distilled with toluene to afford 2-[4-[[2-fluoro-6-methoxy-4-(6-methyl-7-oxo-1H-pyrazolo[3,4-c]pyridin-4-yl)phenyl]methyl]-1-piperidyl] acetic acid. TFA salt (0.05 g, 35.46% yield, 77% purity) as a brown solid. LCMS (ES$^+$): m/z 429.33 [M+H]$^+$.

Step-11: To a stirred solution of 2-[4-[[2-fluoro-6-methoxy-4-(6-methyl-7-oxo-1H-pyrazolo[3,4-c]pyridin-4-yl)phenyl]methyl]-1-piperidyl]acetic acid TFA salt (0.05 g, 0.076 mmol, 062) in DMF (3 mL) were added DIPEA (0.090 g, 0.696 mmol), 3-[4-(4-piperidyl)anilino]piperidine-2,6-dione TFA salt (0.046.80 g, 0.116 mmol, 061) followed by PyBOP (91.17 g, 0.1752 mol) at 0° C. and reaction mixture was allowed to stir at room temperature for 16 h, while monitoring the reaction by LCMS. After completion, solvent was removed using GENVAC and crude was purified by prep-HPLC to afford 3-[4-[1-[2-[4-[[2-fluoro-6-methoxy-4-(6-methyl-7-oxo-1H-pyrazolo[3,4-c]pyridin-4-yl)phenyl]methyl]-1-piperidyl]acetyl]-4-piperidyl]anilino] piperidine-2,6-dione TFA salt (0.0395 g, 98.09% purity) as a brown solid. $^1$H NMR (400 MHz, DMSO-d$_6$) δ 14.04 (s, 1H), 10.77 (s, 1H), 9.30 (s, 1H), 8.20 (s, 1H), 7.59 (s, 1H), 7.09-7.07 (m, 2H), 6.96-6.93 (m, 2H), 6.64-6.60 (m, 2H), 4.46-4.16 (m, 4H), 4.01 (s, 3H), 3.71-3.66 (m, 1H), 3.61 (s, 3H), 3.48 (d, J=10.5 Hz, 2H), 3.39-2.89 (m, 4H), 2.73-2.59 (m, 5H), 2.07-2.06 (m, 1H), 1.88-1.39 (m, 10H). LCMS (ES$^-$): m/z 696.51 [M–H]$^-$.

Synthesis of Compound 157

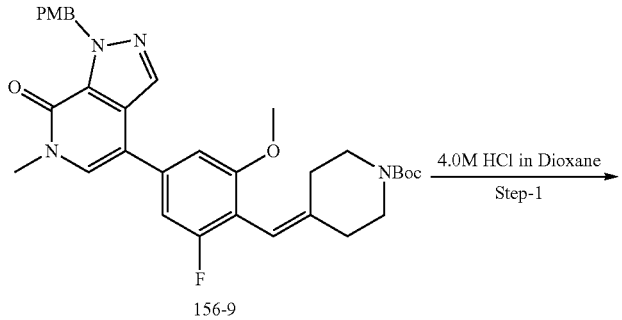

156-9

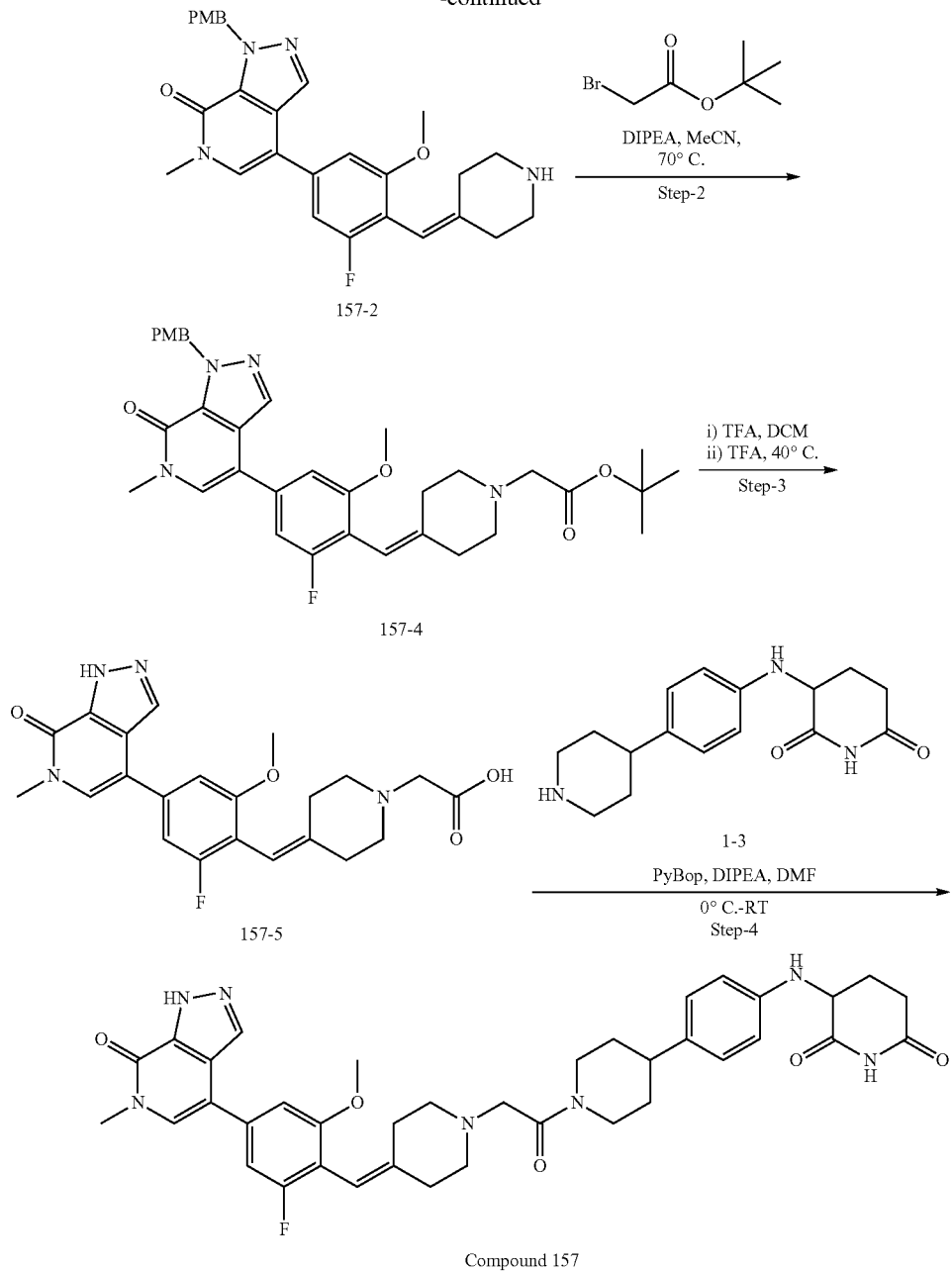

Compound 157

Step 1: 4.0 M HCl in 1,4-dioxane (2 mL) was added to the tert-butyl 4-[[2-fluoro-6-methoxy-4-[1-[(4-methoxyphenyl)methyl]-6-methyl-7-oxo-pyrazolo[3,4-c]pyridin-4-yl]phenyl]methylene]piperidine-1-carboxylate (0.350 g, 0.594 mmol) at 0° C. and reaction mixture was allowed to stir at rt for 3 h, while monitoring the reaction by TLC. After completion, solvent was evaporated and crude was co-distilled with toluene to afford 4-[3-fluoro-5-methoxy-4-(4-piperidylidenemethyl)phenyl]-1-[(4-methoxyphenyl)methyl]-6-methyl-pyrazolo[3,4-c]pyridin-7-one; hydrochloride (0.35 g, 99% purity) as an light brown solid. LCMS (ES+): m/z 489.69 [M+H]+.

Step-2: To a stirred solution of 4-[3-fluoro-5-methoxy-4-(4-piperidylidenemethyl)phenyl]-1-[(4-methoxyphenyl)methyl]-6-methyl-pyrazolo[3,4-c]pyridin-7-one; hydrochloride (0.350 g, 0.623 mmol) in $CH_3CN$ (5 mL) were added DIPEA (0.5560 g, 4.30 mmol) followed by tert-butyl 2-bromoacetate (0.154 g, 0.788 mmol) and reaction mixture was allowed to reflux for 4 h, while monitoring the reaction by TLC. After completion, the reaction mass was quenched with water (50 ml) and extracted with EtOAc (2×75 ml). The combined organic layer was dried over anhydrous $Na_2SO_4$ and concentrated. The crude was purified by column chromatography (Devisil silica, 70% EtOAc in pet ether) to afford tert-butyl 2-[4-[[2-fluoro-6-methoxy-4-[1-[(4-methoxyphenyl)methyl]-6-methyl-7-oxo-pyrazolo[3,4-c]pyridin-4-yl]phenyl]methylene]-1-piperidyl]acetate (0.3 g, 90% purity) as a white solid.

Step-3: To a stirred solution of tert-butyl 2-[4-[[2-fluoro-6-methoxy-4-[1-[(4-methoxyphenyl)methyl]-6-methyl-7- oxo-pyrazolo[3,4-c]pyridin-4-yl]phenyl]methylene]-1-piperidyl]acetate (0.2 g, 0.332 mmol) in DCM (0.5 mL) was added TFA (0.756 g, 6.63 mmol) and stirring was continued for 3 h, while monitoring the reaction by TLC and LCMS. After completion, TFA was removed under vacuum and again TFA (0.7559 g, 6.63 mmol) was added and reaction mixture was allowed to stir at 40° C. for 3 h, while monitoring the reaction by TLC and LCMS. After completion, TFA was removed under vacuum and crude was co-distilled with toluene to afford 2-[4-[[2-fluoro-6-methoxy-4-(6-methyl-7-oxo-1H-pyrazolo[3,4-c]pyridin-4-yl)phenyl]methyl]-1-piperidyl]acetic acid TFA salt (0.05 g, 35.46% yield, 77% purity) as a brown solid LCMS (ES+): m/z 427.28 [M+H]+.

Step-4: To a stirred solution of 2-[4-[[2-fluoro-6-methoxy-4-(6-methyl-7-oxo-1H-pyrazolo[3,4-c]pyridin-4-yl)phenyl]methylene]-1-piperidyl]acetic acid (0.120 g, 0.183 mmol, 062) in DMF (3 mL) were added DIPEA (0.2171 g, 1.68 mmol), 3-[4-(4-piperidyl)anilino]piperidine-2,6-dione (0.1122 g, 0.279 mmol, 061) followed by PyBOP (0.2185 g, 0.419 mmol) at 0° C. and reaction mixture was allowed to stir at room temperature for 16 h, while monitoring by LCMS. After solvent was evaporated using GENVAC and crude was purified by preparative HPLC to afford 3-[4-[1-[2-[4-[[2-fluoro-6-methoxy-4-(6-methyl-7-oxo-1H-pyrazolo[3,4-c]pyridin-4-yl)phenyl]methylene]-1-piperidyl]acetyl]-4-piperidyl]anilino] piperidine-2,6-dione TFA salt (0.0317 g, 98.17% purity, 061) as brown solid. $^1$H NMR (400 MHz, DMSO-$d_6$) δ 14.24 (s, 1H), 10.78 (s, 1H), 9.79 (s, 1H), 8.23 (s, 1H), 7.63 (s, 1H), 7.10-6.94 (m, 4H), 6.64-6.61 (m, 2H), 6.15 (s, 1H), 4.53-4.26 (m, 4H), 3.93 (s, 3H), 3.73-3.69 (m, 2H), 3.61 (s, 3H), 3.43-3.01 (m, 5H), 2.78-2.54 (m, 5H), 2.50-2.33 (m, 2H), 2.09-2.07 (m, 1H), 1.88-1.79 (m, 3H), 1.58-1.45 (m, 2H). LCMS (ES+): m/z 696.58 [M+H]+.

Synthesis of Compound 158

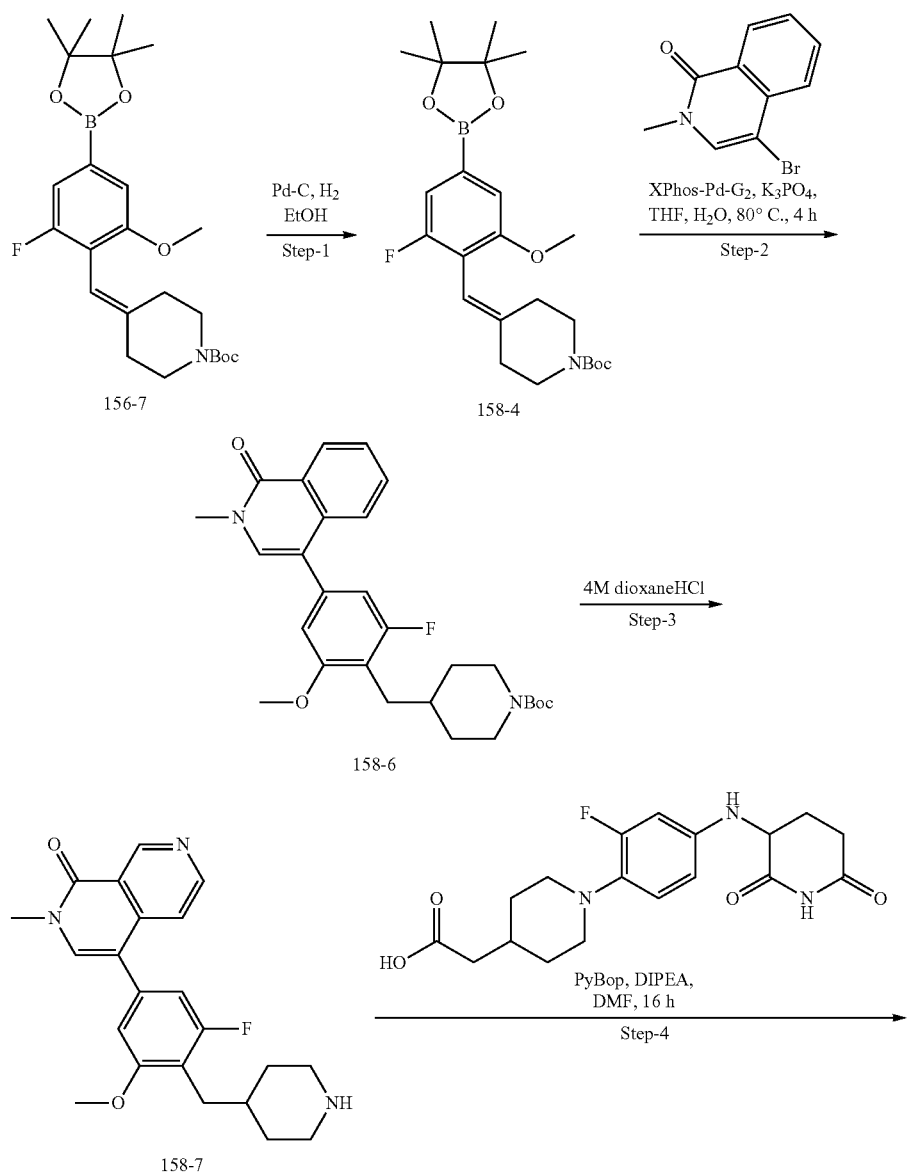

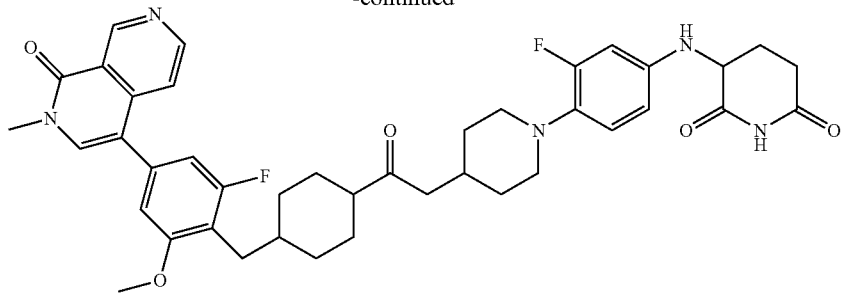

Compound 158

Step-1: Stirred mixture of tert-butyl 4-[[2-fluoro-6-methoxy-4-(4,4,5,5-tetramethyl-1,3,2-dioxaborolan-2-yl)phenyl]methylene]piperidine-1-carboxylate (1 g, 2.24 mmol) in Ethanol (3 mL) was degassed for 10 minutes followed by addition of wet 10% Palladium on carbon ((1 g). The reaction mixture was stirred under hydrogen balloon pressure for 16 h at RT. The progress of the reaction was monitored by TLC and LCMS. After completion of the reaction, reaction mixture was filtered through Celite bed and washed with Ethanol. The filtrate was removed under vacuum to afford tert-butyl 4-[[2-fluoro-6-methoxy-4-(4,4,5,5-tetramethyl-1,3,2-dioxaborolan-2-yl)phenyl]methyl]piperidine-1-carboxylate 158-4 (0.6 g, 56.74% yield, 57% purity) as a brown semi-solid. LCMS indicates Boronate ester mass @ RT: 2.97 min LCMS (ES+): m/z 450 [M+H]+. (M+Na mass dominated) and boronic acid mass @ RT: 1.66 min LCMS (ES+): m/z 268 [M+H]+. (M-100 mass dominated).

Step-2: To a stirred solution of 4-bromo-2-methyl-2,7-naphthyridin-1-one 158-5 (0.5 g, 2.09 mmol) in THF (5 mL) and water (1 mL), was added tert-butyl 4-[[2-fluoro-6-methoxy-4-(4,4,5,5-tetramethyl-1,3,2-dioxaborolan-2-yl)phenyl]methyl]piperidine-1-carboxylate 158-4 (0.1 g, 2.09 mmol) and tripotassium phosphate (1.1 g, 5.23 mmol). The resulting mixture was degassed with $N_2$ for 15 minutes, added Pd-Xphos-G2 (0.082 g, 0.105 mmol) and heated at 100° C. for 4 h, while monitoring by LCMS and TLC. The reaction mixture filtered through Celite bed. Celite bed was washed with (2×50 ml) ethyl acetate. The reaction mixture concentrated under reduced pressure to afford tert-butyl 4-[[2-fluoro-6-methoxy-4-(2-methyl-1-oxo-2,7-naphthyridin-4-yl)phenyl]methyl]piperidine-1-carboxylate (0.100 mg, 0.058 mmol, 27.76% yield, 27.76% purity) as a brown solid. LCMS (ES+): m/z 482.52 [M+H]+.

Step-3: The solution of tert-butyl 4-[[2-fluoro-6-methoxy-4-(2-methyl-1-oxo-2,7-naphthyridin-4-yl)phenyl]methyl]piperidine-1-carboxylate (500 mg, 1.04 mmol) in 4M Dioxane HCl (1.5 ml) stir for 1 h at RT while monitoring by TLC and LCMS. After 1 h the reaction mixture was concentrated to dryness. The crude compound was purified by reverse phase (Using C18 column with 0.1% formic acid in MeCN:$H_2O$ buffer) column chromatography to afford 4-[3-fluoro-5-methoxy-4-(4-piperidylmethyl)phenyl]-2-methyl-2,7-naphthyridin-1-one HCl (0.4 g, 0.948 mmol, 91.26% yield, 99% purity) as a yellow solid. LCMS (ES+): m/z 382.28 [M+H]+.

Step-4: To a stirred solution of 4-[3-fluoro-5-methoxy-4-(4-piperidylmethyl)phenyl]-2-methyl-2,7-naphthyridin-1-one hydrochloride 158-7 (0.1 g, 0.262 mmol) in dry DMF (2 mL) were added DIPEA (0.102 g, 0.787 mmol) and 2-(1-(4-((2,6-dioxopiperidin-3-yl)amino)-2-fluorophenyl)piperidin-4-yl)acetic acid 158-8 (0.096 g, 0.262 mmol) at 0° C. under $N_2$. The reaction mixture was allowed to warm at RT and added PyBop (0.164 g, 0.315 mmol) after addition of PyBop reaction mixture was stirred at RT for 16 h, while monitoring by TLC and LCMS. The reaction mixture was concentrated under reduced pressure to obtain the crude product. The crude was purified by Prep HPLC to afford 3-[3-fluoro-4-[4-[2-[4-[[2-fluoro-6-methoxy-4-(2-methyl-1-oxo-2,7-naphthyridin-4-yl)phenyl]methyl]-1-piperidyl]-2-oxo-ethyl]-1-piperidyl]anilino]piperidine-2,6-dione.TFA salt Compound 158 (0.114 g, 0.134 mmol, 51.10% yield, 98.81% purity) as a yellow solid. $^1$H NMR (400 MHz, DMSO-$d_6$) δ 10.82 (s, 1H), 9.47 (s, 1H), 8.73 (d, J=5.8 Hz, 1H), 7.95 (s, 1H), 7.60 (d, J=5.8 Hz, 1H), 6.96-6.91 (m, 3H), 6.64-6.53 (m, J=15.8 Hz, 2H), 4.37 (bs, 2H), 3.87 (s, 5H), 3.60 (s, 3H), 3.37 (s, 4H), 2.96 (t, J=12.1 Hz, 1H), 2.76-2.59 (m, 4H), 2.33 (d, J=1.7 Hz, 2H), 2.08-2.04 (m, 1H), 1.95-1.80 (m, 5H), 1.67-1.58 (m, 4H), 1.18-1.05 (m, 2H). LCMS (ES+): m/z 727.31 [M+H]+.

Compound 159 was prepared following the synthesis of Compound 158

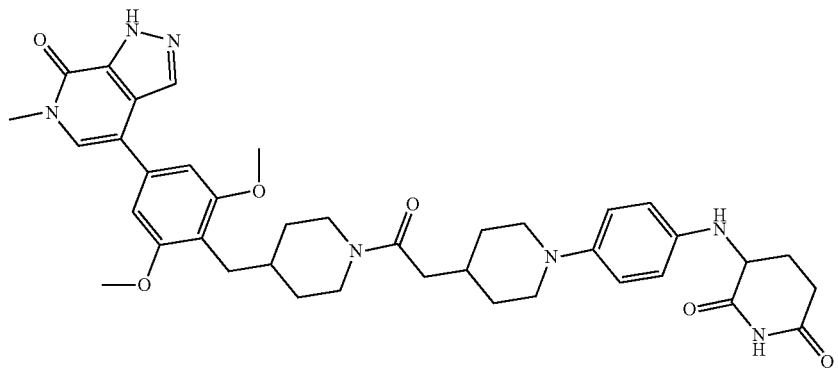 [SMILES: COc1cc(-c2cn(C)c(=O)c3[nH]ncc23)cc(OC)c1CC1CCN(C(=O)CC2CCN(c3ccc(NC4CCC(=O)NC4=O)cc3)CC2)CC1]

815
¹H NMR (400 MHz, DMSO-d₆) δ 14.31 (s, 1H), 10.82 (s, 1H), 10.78 (s, 1H), 8.20 (s, 1H), 7.53 (s, 1H), 7.40 (d, J=8.4 Hz, 2H), 6.84 (s, 1H), 6.76 (d, J=8.8 Hz, 2H), 6.35 (bs, 1H), 4.41-4.33 (m, 2H), 3.86 (s, 6H), 3.61 (m, 7H), 2.97-2.74 (m, 1H), 2.73-2.70 (m, 1H), 2.67-2.56 (m, 3H), 2.49 (m, 2H), 2.10-2.01 (m, 2H), 1.93-1.87 (m, 3H), 1.85-1.70 (m, 1H), 1.62-1.50 (m, 4H), 1.19-1.03 (m, 3H). LCMS (ES⁺): m/z 710.65 [M+H]⁺.
Compound 160 was prepared following the synthesis of Compound 158
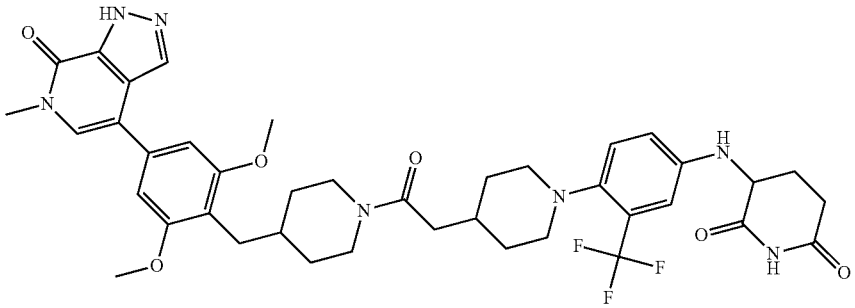 [SMILES: COc1cc(-c2cn(C)c(=O)c3[nH]ncc23)cc(OC)c1CC1CCN(C(=O)CC2CCN(c3ccc(NC4CCC(=O)NC4=O)cc3C(F)(F)F)CC2)CC1]
¹H NMR (400 MHz, DMSO-d₆) 14.26 (s, 1H), 10.78 (s, 1H), 8.20 (s, 1H), 7.53 (s, 1H), 7.30 (d, J=8.6 Hz, 1H), 6.91-6.84 (m, 4H), 6.15 (bs, 1H), 4.39-4.326 (m, 2H), 3.84 (s, 7H), 3.61 (s, 3H), 2.92-254 (m, 10H), 2.33-2.26 (m, 2H), 2.07-2.04 (m, 1H), 1.91-1.68 (m, 5H), 1.61-1.50 (m, 2H), 1.29-0.98 (m, 4H). LCMS (ES⁺): m/z 779.07 [M+H]⁺.
Synthesis of Compound 161
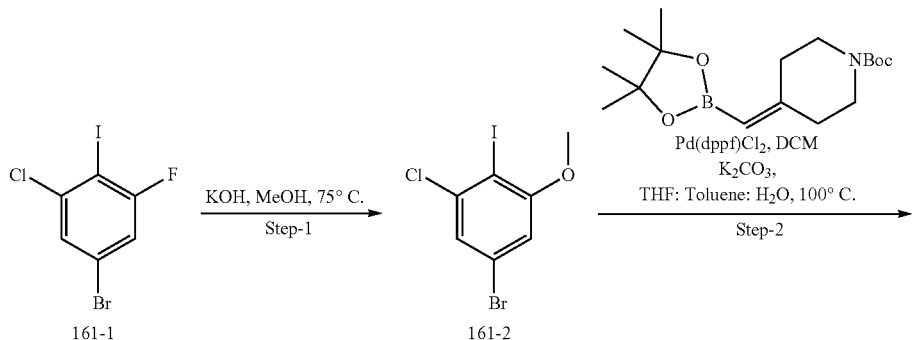
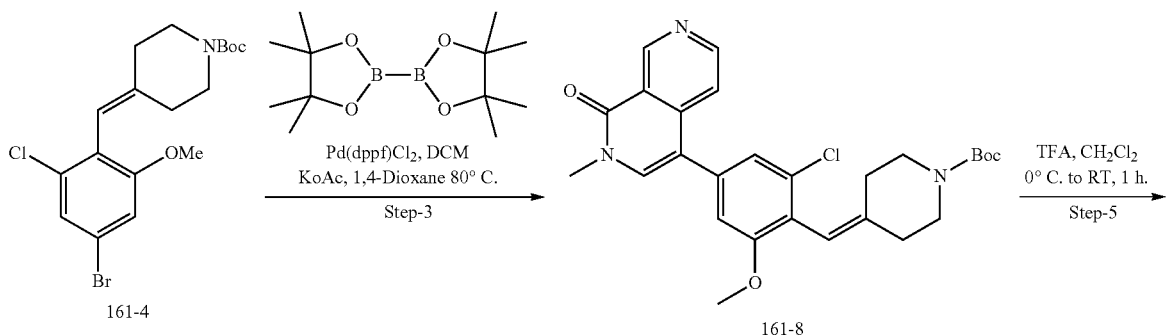

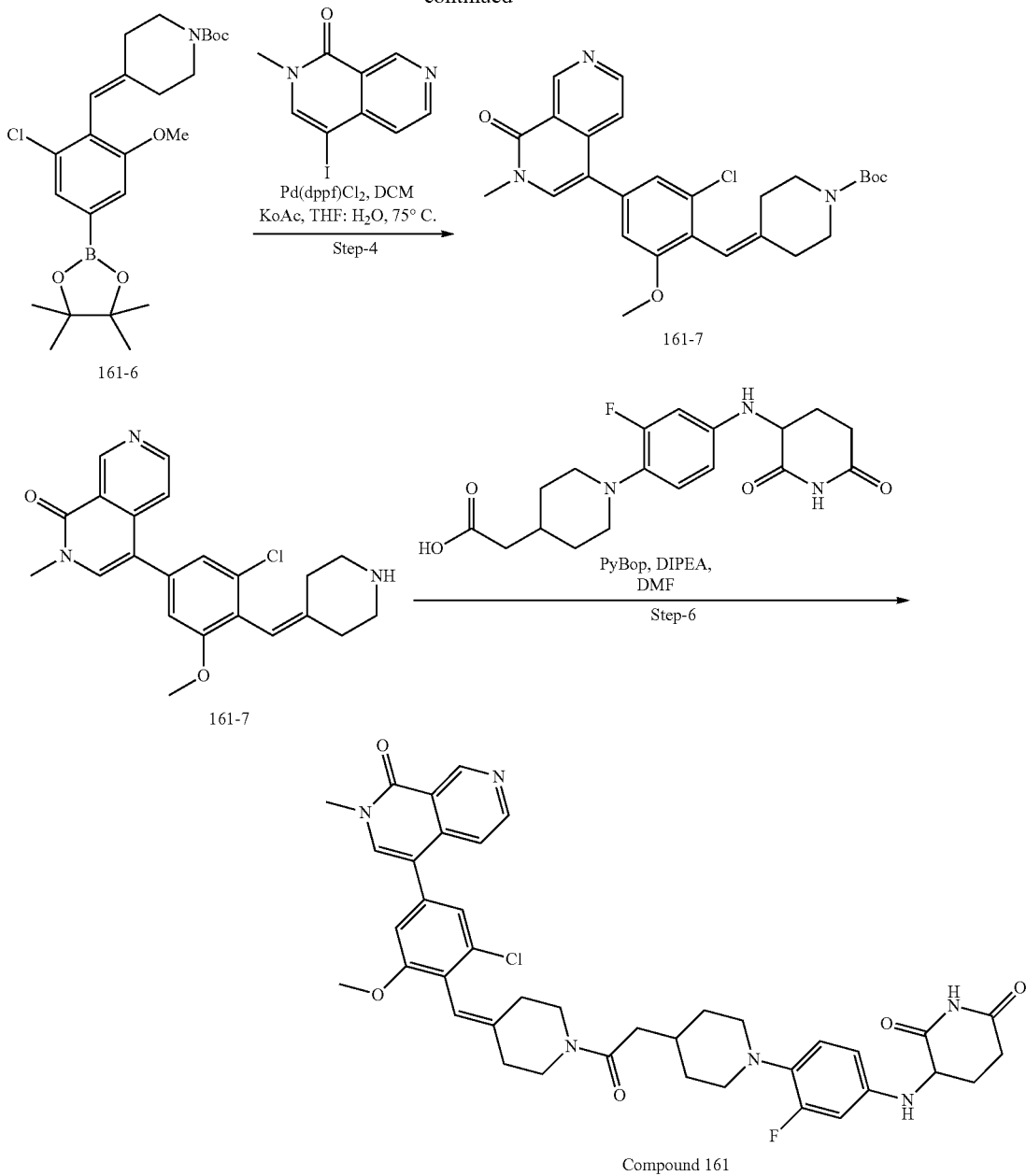

Compound 161

Step-1: To a stirred solution of KOH (1.25 g, 22.37 mmol) in methanol (50 mL) was added 5-bromo-1-chloro-3-fluoro-2-iodo-benzene 161-1 (5 g, 14.91 mmol) in methanol (15 ml) drop wise using an addition funnel and refluxed for 36 h, while monitoring the reaction by TLC. The reaction mass was concentrated to dryness and the residue was quenched with water (100 ml) and extracted with ethyl acetate (2×100 ml). The organic layer was washed with brine (50 ml), dried over anhydrous $Na_2SO_4$ and concentrated under reduced pressure. The crude compound was triturated with n-pentane (2×50 mL) to obtain 5-bromo-1-chloro-2-iodo-3-methoxy-benzene (3.1 g, 53.87% yield, 95% purity) as a colourless solid. $^1$H NMR (400 MHz, $CDCl_3$) δ 7.26 (d, J=2 Hz, 1H), 6.81 (d, J=2 Hz, 1H), 3.89 (s, 3H).

Step-2: In a clean 250 mL RM Flask equipped with an argon balloon and a septum was added 5-bromo-1-chloro-2-iodo-3-methoxy-benzene 161-2 (5 g, 14.39 mmol), tert-butyl4-[(4,4,5,5-tetramethyl-1,3,2-dioxaborolan-2-yl)methylene]piperidine-1-arboxylate (4.65 g, 14.39 mmol) and dissolved in Toluene:Dioxane (1:1) (20 mL each). An aqueous solution of $K_2CO_3$ (5.97 g, 43.18 mmol) in water (10 ml) was added and the RM was degassed using argon for 30 min before adding $Pd(dppf)Cl_2.DCM$ (587.72 mg, 0.720 mmol). The RM was then stirred at 90° C. for 4 h while monitoring the reaction by TLC. The reaction mixture was filtered through Celite bed, and the bed was washed thoroughly with EtOAc. The combined filtrate was washed with brine (50 ml), dried over anhydrous $Na_2SO_4$, and concentrated. The crude compound was purified by (silica gel mesh 100-200, and product eluted with 10% ethyl acetate in pet ether-neat ethyl acetate) column flash chromatography to afford tert-butyl 4-[(4-bromo-2-chloro-6-methoxy-phenyl)methylene]

piperidine-1-carboxylate 161-4 (2.2 g, 33.01% yield, 90% purity) as gummy liquid. $^1$H NMR (400 MHz, CDCl$_3$) δ 7.18 (d, J=1.6 Hz, 1H), 6.91 (d, J=2 Hz, 1H), 5.91 (s, 1H), 3.79 (s, 3H), 3.52 (t, J=5.6 Hz, 2H), 3.38 (t, J=5.6 Hz, 2H), 2.36 (t, J=5.6 Hz, 2H), 1.98 (t, J=5.6 Hz, 2H), 1.47 (s, 9H) LCMS (ES$^+$): m/z 416.74 [M+H]$^+$. (−100 fragment dominated).

Step-3: To a degassed (with argon gas) solution of tert-butyl 4-[(4-bromo-2-chloro-6-methoxy-phenyl)methylene]piperidine-1-carboxylate 161-4 (1 g, 2.40 mmol), 4,4,5,5-tetramethyl-2-(4,4,5,5-tetramethyl-1,3,2-dioxaborolan-2-yl)-1,3,2-dioxaborolane (0.731 g, 2.88 mmol) and Potassium Acetate (0.518 g, 5.28 mmol) in 1,4-Dioxane (5 mL) was added Pd(dppf)Cl$_2$.DCM (0.050 g, 0.060 mmol) and stirred at 80° C. for 3 h while monitoring the reaction by TLC and LCMS. After 3 h, the reaction mass was quenched with water (5 ml) and extracted with EtOAc (2×10 ml). The combined organic layer was dried over anhydrous Na$_2$SO$_4$ and concentrated to afford crude tert-butyl 4-[[2-chloro-6-methoxy-4-(4,4,5,5-tetramethyl-1,3,2-dioxaborolan-2-yl)phenyl]methylene]piperidine-1-carboxylate 161-6 (0.8 g, 50.32% yield, 70% purity) as brown colored semi-solid. LCMS (ES$^+$): m/z 463.81 [M+H]$^+$.

Step-4: A mixture of tert-butyl 4-[[2-chloro-6-methoxy-4-(4,4,5,5-tetramethyl-1,3,2-dioxaborolan-2-yl)phenyl]methylene]piperidine-1-carboxylate 161-6 (0.8 g, 1.72 mmol), 4-iodo-2-methyl-2,7-naphthyridin-1-one (0.494 g, 1.72 mmol) and Potassium Acetate (0.423 g, 4.31 mmol) in Toluene (10 mL):THF (10 mL):Water (2 mL) was degassed for 30 min using argon before adding Pd(dppf)Cl$_2$.DCM (0.070 g, 0.086 mmol). The RM was stirred at 90° C. for 16 h, while monitoring the reaction by TLC and LCMS. The reaction mass was filtered over a Celite bed and the bed was thoroughly washed with EtOAc. The combined filtrate was washed with brine, dried over anhydrous Na$_2$SO$_4$, and concentrated. The crude compound was purified by reverse phase column chromatography (0.1% formic acid in water in ACN) to afford tert-butyl 4-[[2-chloro-6-methoxy-4-(2-methyl-1-oxo-2,7-naphthyridin-4-yl)phenyl] methylene] piperidine-1-carboxylate 161-8 (0.30 g, 27.35% yield, 90.00% purity) as brown colour solid. $^1$H NMR (400 MHz, CDCl$_3$) δ 9.70 (s, 1H), 8.74 (d, J=5.6 Hz, 1H), 7.43 (d, J=5.6 Hz, 1H), 7.29 (s, 1H), 7.06 (d, J=1.2 Hz 1H), 6.78 (d, J=1.2 Hz 1H), 6.06 (s, 1H), 3.78 (s, 3H), 3.65 (s, 3H), 3.56 (t, J=5.6 Hz, 2H), 3.44 (t, J=5.6 Hz, 2H), 2.42 (t, J=5.6 Hz, 2H), 2.08 (t, J=5.6 Hz, 2H), 1.47 (m, 9H)) LCMS (ES$^+$): m/z 496.24 [M+H]$^+$.

Step-5: To a stirred solution of tert-butyl 4-[[2-chloro-6-methoxy-4-(2-methyl-1-oxo-2,7-naphthyridin-4-yl)phenyl]methylene]piperidine-1-carboxylate 161-8 (0.300 g, 0.604 mmol) in CH$_2$Cl$_2$ (2 mL) was added TFA (0.23 ml, 3.02 mmol) at 0° C. and stirred the reaction at RT for 1 h. The solvent was evaporated under reduced pressure and co-distilled with dry CH$_2$Cl$_2$ (3×20 ml) to afford crude compound. The crude compound was triturated with diethyl-ether to afford 4-[3-chloro-5-methoxy-4-(4-piperidylidenemethyl)phenyl]-2-methyl-2,7-naphthyridin-1-one.TFA salt 9 (0.2 g, 59.66% yield, 92% purity) as brown solid. LCMS (ES$^+$): m/z 396.32 [M+H]$^+$.

Step 6: To a stirred solution of 4-[3-chloro-5-methoxy-4-(4-piperidylidenemethyl)phenyl]-2-methyl-2,7-naphthyridin-1-one 161-9 (0.350 g, 0.884 mmol) in dry DMF (3 mL) was added DIPEA (0.343 g, 2.65 mmol) at 0° C. and the reaction mixture was stirred for 5 min. To the reaction mixture was added, 2-[1-[4-[(2,6-dioxo-3-piperidyl)amino]-2-fluoro-phenyl]-4-piperidyl]acetic acid (0.321 g, 0.884 mmol) and the reaction mixture was stirred for another 15 min. PyBOP (0.552 g, 1.06 mmol) was added and stirring continued at room temperature for 16 h. After 16 h, most of the DMF was evaporated using genvac and the crude compound was purified by prep-HPLC to afford 3-[4-[4-[2-[4-[[2-chloro-6-methoxy-4-(2-methyl-1-oxo-2,7-naphthyridin-4-yl)phenyl]methylene]-1-piperidyl]-2-oxo-ethyl]-1-piperidyl]-3-fluoro-anilino]piperidine-2,6-dione TFA salt Compound 161 (0.528 g, 69.35% yield, 99.34% purity) as a pale yellow solid. $^1$H NMR (400 MHz, DMSO-d$_6$) δ 10.81 (s, 1H), 9.47 (s, 1H), 8.74 (d, J=5.7 Hz, 1H), 7.99 (d, J=1.2 Hz, 1H), 7.64-7.60 (m, 1H), 7.31 (bs, 1H), 7.58 (t, J=6.3 Hz, 1H), 7.19-7.10 (m, 2H), 6.61-6.56 (m, 2H), 6.09-6.06 (m, 1H), 4.49-4.39 (m, 1H), 3.83 (s, 3H), 3.61-3.53 (m, 5H), 3.50-343 (m, 6H), 2.76-2.65 (m, 1H), 2.60-2.55 (m, 1H), 2.42-2.33 (m, 4H), 2.07-1.89 (m, 7H), 1.62-1.51 (m, 2H). LCMS (ES$^+$): m/z 741.23 [M+H]$^+$.

Compound 162 was prepared following the synthesis of Compound 161

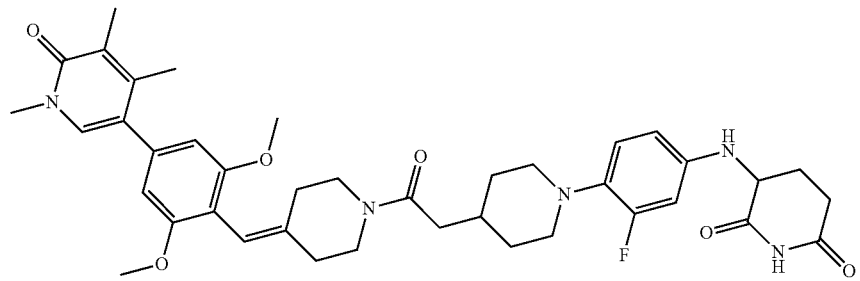 [SMILES: COc1cc(-c2cn(C)c(=O)c(C)c2C)cc(OC)c1C=C1CCN(C(=O)CC2CCN(c3ccc(NC4CCC(=O)NC4=O)cc3F)CC2)CC1]

$^1$H NMR (400 MHz, DMSO-d$_6$) δ 10.83 (s, 1H), 7.53 (s, 1H), 6.66-6.63 (m, 2H), 6.54 (d, J=2.0 Hz, 2H), 5.96 (d, J=5.5 Hz, 2H), 4.38 (d, J=7.0 Hz, 1H), 3.76 (d, J=2.3 Hz, 6H), 3.56-3.45 (m, 11H), 2.73-2.67 (m, 1H), 2.60-2.56 (m, 1H), 2.36-2.27 (m, 3H), 2.07-1.92 (m, 14H), 1.60 (bs, 2H). LCMS (ES$^+$): m/z 714.43 [M+H]$^+$.

Compound 163 was prepared following the synthesis of Compound 158

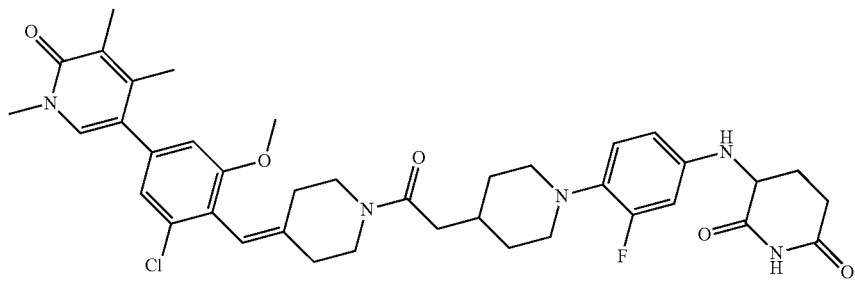 [SMILES: COc1cc(-c2cn(C)c(=O)c(C)c2C)cc(Cl)c1C=C1CCN(C(=O)CC2CCN(c3ccc(NC4CCC(=O)NC4=O)cc3F)CC2)CC1]
$^1$H NMR (400 MHz, DMSO-d$_6$) δ 10.84 (s, 1H), 7.58 (s, 1H), 7.34 (bs, 1H), 6.98 (d, J=2.5 Hz, 1H), 7.91 (s, 1H), 6.68-6.56 (m, 2H), 6.04 (d, J=5.2 Hz, 1H), 4.40-4.37 (m, 1H), 3.80 (d, J=2.5 Hz, 3H), 3.58-3.45 (m, 11H), 2.73-2.56 (m, 2H), 2.41-2.32 (m, 3H), 2.07-1.93 (m, 14H), 1.63 (bs, 2H). LCMS (ES$^+$): m/z 718.09 [M+H]$^+$.
Synthesis of 164
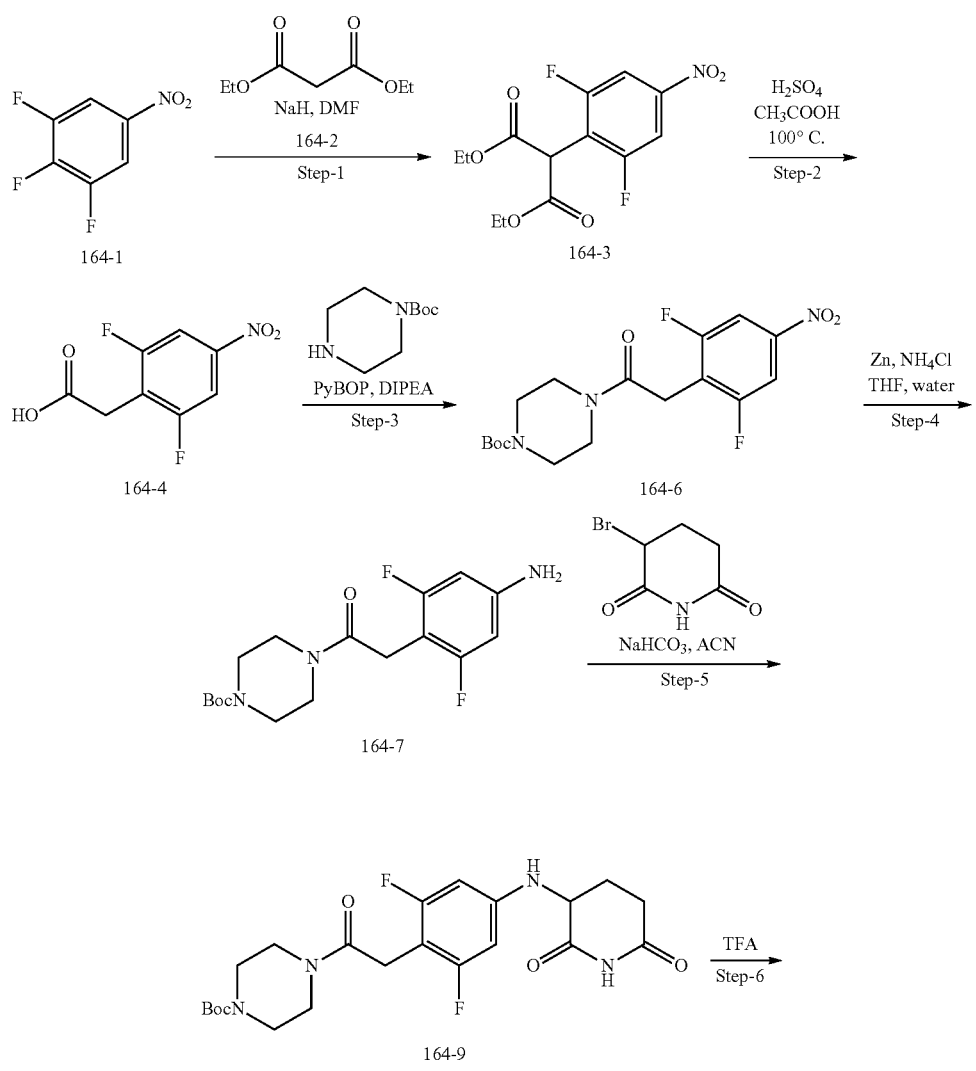

-continued

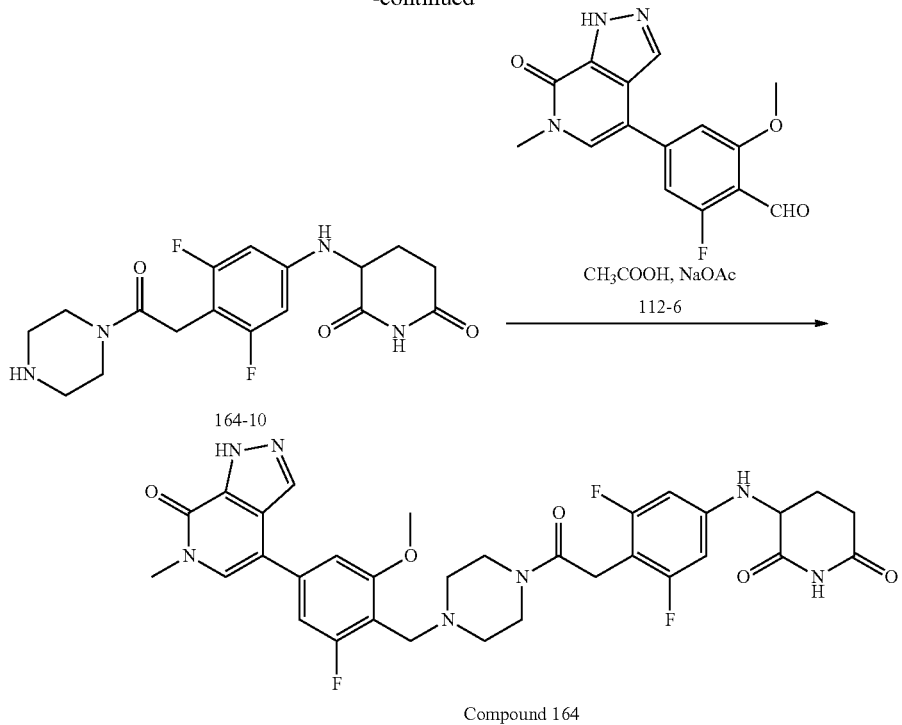

Compound 164

Step-1: To a stirred solution of Sodium hydride (60% dispersion in mineral oil) (1.95 g, 84.71 mmol) in DMF (60 mL) was added diethyl propanedioate (8.14 g, 50.82 mmol, 7.68 mL) at 0° C. and the reaction mixture was stirred for 1.5 h. A solution of 1,2,3-trifluoro-5-nitro-benzene (3 g, 16.94 mmol) in DMF (10 mL) added was added to the reaction mixture at 0° C. and the reaction mixture was stirred at RT for 16 h. The progress of the reaction was monitored by TLC and LCMS. On completion, the reaction mixture was quenched with ice and extracted by the ethyl acetate (3×100 mL). The organic layer was washed with brine solution (100 mL) and dried over sodium sulphate. The organic layer was concentrated in vacuo. The crude product was purified by Davisil silica column chromatography using 10% ethyl acetate in pet ether to afford desired product diethyl 2-(2,6-difluoro-4-nitrophenyl)malonate (3.5 g, 9.93 mmol, 58.61% yield). LCMS (ES+): m/z 318.41 [M+H]+.

Step-2: To a stirred solution diethyl 2-(2,6-difluoro-4-nitro-phenyl)propanedioate (1.7 g, 5.36 mmol) in Acetic acid (17 mL) was added Sulfuric acid (6.37 mL) followed by Water (4.25 mL) and the reaction mixture was stirred at 100° C. for 12 h. The progress of the reaction monitored by TLC and LCMS. After completion of the reaction, the reaction mixture concentrated in vacuo. The residue was dissolved in ethyl acetate (150 mL) and washed with water (20 mL). The organic layer was dried over sodium sulphate and concentrated in vacuo. The crude residue was dissolved in diethyl ether and crystallised out with pet ether. The solid obtained was filtered and washed with n-pentane (2×10 mL) to afford 2-(2,6-difluoro-4-nitrophenyl)acetic acid (0.8 g, 3.62 mmol, 67.60% yield).

Step-3: To a stirred solution of 2-(2,6-difluoro-4-nitrophenyl)acetic acid (0.8 g, 3.68 mmol) and tert-butyl piperazine-1-carboxylate (823.49 mg, 4.42 mmol) in DMF (8 mL) was added N,N-Diisopropylethylamine (2.86 g, 22.11 mmol, 3.85 mL) and the reaction mixture was stirred for 5 min. PyBOP (2.49 g, 4.79 mmol) was added to the reaction mixture and stirring was continued at RT for 16 h. The progress of the reaction was monitored by TLC and LCMS. On completion, the reaction mixture was extracted with Ethyl acetate (2×75 mL) and washed with water (50 mL) The organic layer was washed with brine solution (50 mL) and dried over with sodium sulphate and concentrated in vacuo. The crude residue was purified using column Chromatography (Davisil silica) using 5% MeOH in DCM as eluent to afford tert-butyl 4-[2-(2,6-difluoro-4-nitro-phenyl)acetyl]piperazine-1-carboxylate (0.8 g, 1.76 mmol, 47.89% yield, 85% purity), LCMS (ES−): m/z 384.29 [M−H]−

Step-4: To a stirred solution of tert-butyl 4-[2-(2,6-difluoro-4-nitro-phenyl)acetyl]piperazine-1-carboxylate (0.8 g, 2.08 mmol) in THF (12 mL) was added Zinc Powder (1.09 g, 16.61 mmol) followed by solution of ammonium chloride (888.37 mg, 16.61 mmol) in Water (6 mL). The reaction mixture was stirred at RT for 4 h. The progress of the reaction was monitored by TLC. After completion of the reaction, the reaction mixture was filtered through the Celite bed and washed with Ethyl acetate (100 mL), The organic layer was washed with brine solution (50 mL), dried over sodium sulphate and concentrated in vacuo to afford tert-butyl 4-[2-(4-amino-2,6-difluoro-phenyl)acetyl]piperazine-1-carboxylate (0.7 g, 866.68 umol, 41.75% yield, 44% purity). The crude product was taken for the next step as such, LCMS (ES+): m/z 356.37 [M+H]+.

Step-5: To a stirred solution of tert-butyl 4-[2-(4-amino-2,6-difluoro-phenyl)acetyl]piperazine-1-carboxylate (0.8 g, 2.25 mmol) in DMF (5 mL) was added sodium bicarbonate (283.67 mg, 3.38 mmol) and 3-bromopiperidine-2,6-dione (518.69 mg, 2.70 mmol). The reaction mixture was stirred at 70° C. for 16 h. The progress of the reaction was monitored by TLC and LCMS. After completion, the reaction mixture was poured into water (50 mL) and extracted with ethyl acetate (2×75 mL). The organic layer washed with brine solution (50 mL), dried over sodium sulphate and concentrated in vacuo. The crude residue was purified by column chromatography (Davisil silica, 0-60% Ethylacetate in Pet ether) to afford tert-butyl 4-[2-[4-[(2,6-dioxo-3-piperidyl)amino]-2,6-difluoro-phenyl]acetyl]piperazine-1-carboxylate (0.070 g, 91.31 umol, 4.06% yield).

LCMS (ES+): m/z 467.09 [M+H]+.

Step-6: To a stirred solution of tert-butyl 4-[2-[4-[(2,6-dioxo-3-piperidyl)amino]-2,6-difluoro-phenyl]acetyl]piperazine-1-carboxylate (0.07 g, 150.06 umol) in DCM (3 nL) was added trifluoroacetic acid (171.10 mg, 1.50 mmol). The reaction mixture was stirred at RT for 16 h. The progress of the reaction was monitored by LCMS After completion of the reaction, the reaction mixture was concentrated in vacuo. The crude residue was co-distilled with toluene and acetonitrile and dried to afford 3-[3,5-difluoro-4-(2-oxo-2-piperazin-1-yl-ethyl)anilino]piperidine-2,6-dione (0.08 g, 91.52 umol, 60.99% yield) as a TFA Salt. LCMS (ES+): m/z 367.20 [M+H]+

Step-7: To a stirred solution of 2-fluoro-6-methoxy-4-(6-methyl-7-oxo-1H-pyrazolo[3,4-c]pyridin-4-yl)benzaldehyde (0.05 g, 120.40 umol) and 3-[3,5-difluoro-4-(2-oxo-2-piperazin-1-yl-ethyl)anilino]piperidine-2,6-dione (71.56 mg, 120.40 umol) in acetonitrile was added acetic acid (7.23 mg, 120.40 umol, 6.89 uL) and sodium acetate (29.63 mg, 361.19 umol, 19.37 uL) and the reaction mixture was stirred at 75° C. for 4 h. SiliaBond Cyanoborohydride (200 mg, 120.40 umol) was added to the reaction mixture at 0° C. and stirring was continued for at RT for 2 hr. The progress of the reaction monitored by TLC and LCMS. After completion, the volatiles were evaporated in vacuo and the crude compound was purified by Prep-HPLC to obtain 3-[3,5-difluoro-4-[2-[4-[[2-fluoro-6-methoxy-4-(6-methyl-7-oxo-1H-pyrazolo[3,4-c]pyridin-4-yl)phenyl]methyl]piperazin-1-yl]-2-oxo-ethyl]anilino]piperidine-2,6-dione (24 mg, 31.21 umol, 25.92% yield, 99.57% purity) as TFA salt LCMS (ES−): m/z 650.35 [M−H]−. 1H NMR (400 MHz, DMSO-d6) δ 1.85-1.95 (m, 1H), 2.05-2.15 (m, 1H), 2.55-2.65 (m, 1H), 2.70-2.80 (m, 1H), 3.00-3.40 (m, 8H), 3.63 (s, 3H), 4.02 (s, 3H), 4.20-4.60 (m, 5H), 6.35 (d, J=10.8 Hz, 2H), 7.20-7.30 (m, 2H), 7.72 (s, 1H), 8.24 (s, 1H), 9.87 (bs, 1H), 10.85 (s, 1H), 14.25 (bs, 1H).

Synthesis of Compound 165

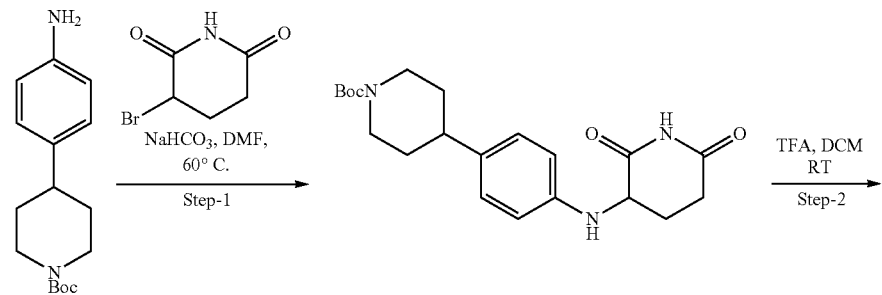

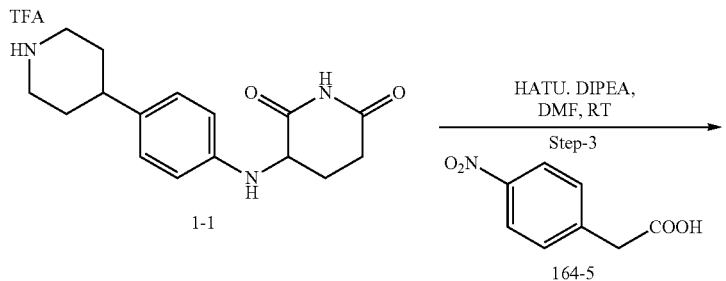

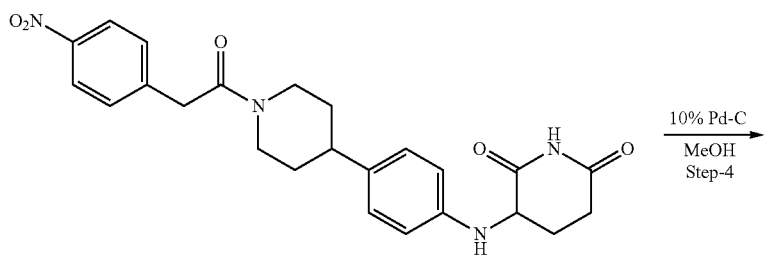

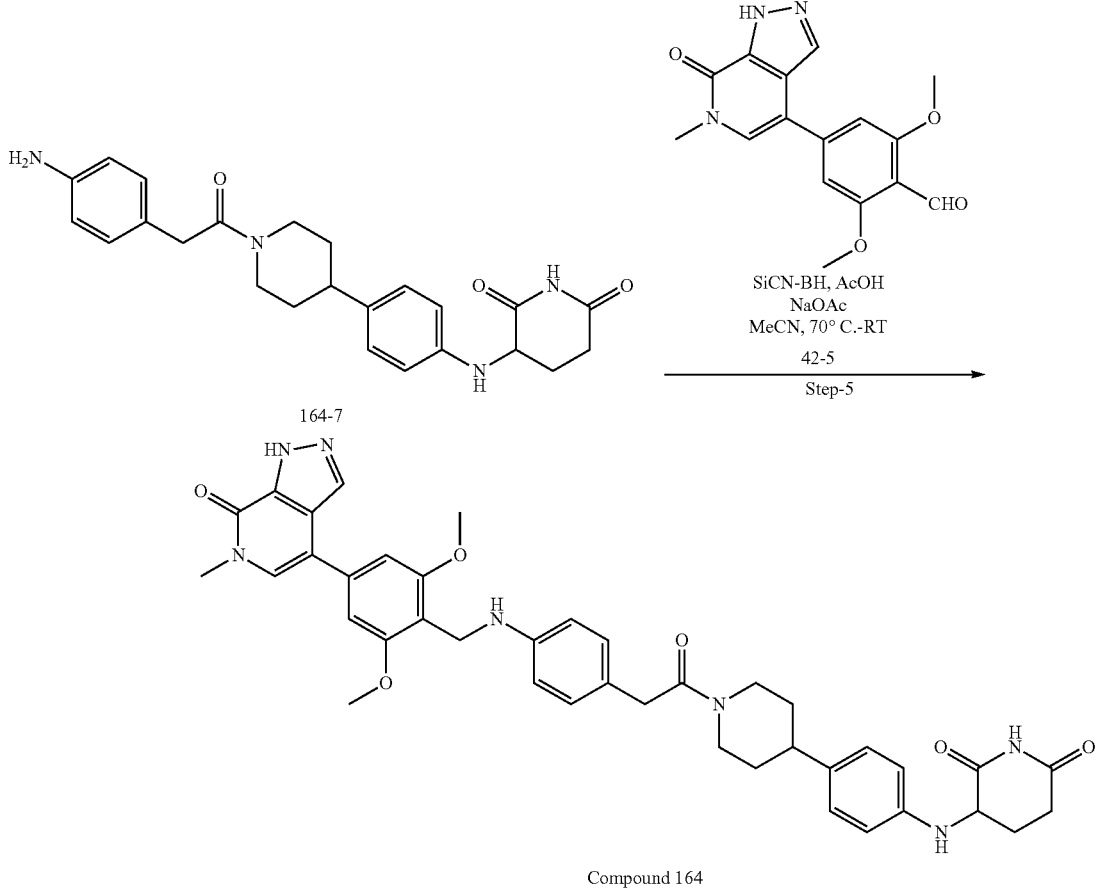

Compound 164

Step-1: To a stirred solution of tert-butyl 4-(4-aminophenyl)piperidine-1-carboxylate (10 g, 36.18 mmol) in DMF (50 mL) was added Sodium bicarbonate (18.24 g, 217.10 mmol) and followed by 4-bromopiperidine-2,6-dione (7.64 g, 39.80 mmol). The reaction mixture was allowed to heat at 60° C. for 16 h, while monitoring the reaction by TLC. After completion, the reaction mixture was diluted with water (100 mL) and extracted with ethyl acetate (2×250 mL). The combined organic layer was dried over anhydrous $Na_2SO_4$ and solvent was removed under reduced pressure. The crude product was purified by column chromatography (silica gel, 230-400 mesh, 30% EtOAc in pet ether) to afford tert-butyl4-[4-[(2,6-dioxo-3-piperidyl)amino]phenyl]piperidine-1-carboxylate (9 g, 59.06% yield, 92% purity) as an grey color solid. LCMS (ES$^+$): m/z 388.34 [M+H]$^+$.

Step-2: To a stirred solution of tert-butyl 4-[4-[(2,6-dioxo-3-piperidyl)amino]phenyl]piperidine-1-carboxylate (5 g, 12.90 mmol) in DCM (15 mL) was added TFA (14.71 g, 129.04 mmol) and reaction mixture was allowed to stir at RT for 2 hr, while monitoring reaction by TLC. After completion, solvent was evaporated under reduced pressure. The resulting crude was purified by reverse phase column chromatography using (C18/100 g column using 0.1 formic acid in MeCN:H2O) to afford 3-[4-(4-piperidyl)anilino]piperidine-2,6-dione (3 g, 47.50% yield, 82% purity, 061) as an grey color solid. LCMS (ES$^+$): m/z 288.33 [M+H]$^+$.

Step-3: To a stirred solution of 4-((4-(piperidin-4-yl)phenyl)amino)piperidine-2,6-dione (0.6 g, 2.09 mmol) in DMF (5 mL) was added DIPEA (1.62 g, 12.53 mmol) and stirred at RT for 5 min. before adding compound 164-5 (0.454 g, 2.51 mmol) and HATU (1.59 g, 4.18 mmol) After addition reaction mixture was allowed stir at RT for 4 h, while monitoring reaction by TLC and LCMS. After completion, solvent was evaporated under reduced pressure. The resulting crude was purified by column chromatography (Silica gel 230-300 mesh and product eluted with 50% EtOAc in pet ether) to afford 4-((4-(1-(2-(4-nitrophenyl)acetyl)piperidin-4-yl)phenyl)amino)piperidine-2,6-dione (0.350 g, 33.49% yield, 90% purity) as an white solid. LCMS (ES$^+$): m/z 451.61 [M+H]$^+$.

Step-4: To a stirred solution of 4-((4-(1-(2-(4-nitrophenyl)acetyl)piperidin-4-yl)phenyl)amino)piperidine-2,6-dione (0.350 g, 0.077 mmol) in Ethanol (10 mL) and Methanol (5 mL) mixture was added wet 10% Palladium, on carbon, (0.300 g, 2.82 mmol) and allowed to stir at RT under hydrogen gas (balloon pressure) for 3 h, while monitoring the reaction by TLC. After completion, reaction mixture was filtered over Celite bed and bed was thoroughly washed with methanol. The combined filtrate was concentrated under reduced pressure to afford 4-[4-[1-[2-(4-aminophenyl)acetyl]-4-piperidyl]anilino]piperidine-2,6-dione (0.150 g, 371.90% yield, 81% purity) as an black sticky compound; LCMS (ES$^+$): m/z 421.19 [M+H]$^+$.

Step-5: To a stirred solution of 3-[4-[1-[2-(4-aminophenyl)acetyl]-4-piperidyl]anilino]piperidine-2,6-dione (0.150 g, 0.356 mmol) in acetonitrile (10 mL) were added sodium acetate, anhydrous (0.081 g, 0.995 mmol) and followed by acetic acid (0.019 g, 0.331 mmol), molecular sieves (0.050 g). The resulting solution was stirred for 10 min, then added 2,6-dimethoxy-4-(6-methyl-7-oxo-1H-pyrazolo[3,4-c]pyridin-4-yl)benzaldehyde (42-5, 0.103 g, 0.331 mmol) and reaction mixture was allowed stirred at 70° C. for 3 hr, then RM was allowed to cool at RT and was added Si-CBH (0.096 g, 1.66 mmol) and stirring was continued for 16 h, while monitoring the reaction by LCMS and TLC. After completion, RM was filtered over Celite bed and bed was washed with acetonitrile and solvent was concentrated. The crude residue was purified by Prep-HPLC to afford 3-[4-[1-[2-[4-[[2,6-dimethoxy-4-(6-methyl-7-oxo-1H-pyrazolo[3,4-c]pyridin-4-yl)phenyl]methylamino]phenyl]acetyl]-4-piperidyl]anilino] piperidine-2,6-dione.TFA salt (0.046 g, 16.58% yield, 99.51% purity) as an off white solid. $^1$H NMR (400 MHz, DMSO-$d_6$) δ 14.44 (bs, 1H), 10.77 (s, 1H), 8.20 (s, 1H), 7.58 (s, 1H), 7.11-7.09 (m, 2H), 6.92-6.89 (m, 6H), 6.60 (d, J=8.5 Hz, 2H), 4.51 (d, J=12.5 Hz, 1H), 4.29-4.24 (m, 3H), 4.07-4.03 (m, 1H), 4.01 (s, 6H), 3.81-3.61 (m, 5H), 3.01 (t, J=12.3 Hz, 1H), 2.73-2.67 (m, 1H), 2.59-2.52 (m, 3H), 2.11-2.06 (m, 1H), 1.87-1.83 (m, 1H), 1.68 (t, J=12.8 Hz, 2H), 1.35-1.32 (m, 2H). LCMS (ES$^+$): m/z 718.13 [M+H]$^+$ Synthesis of Compound 166

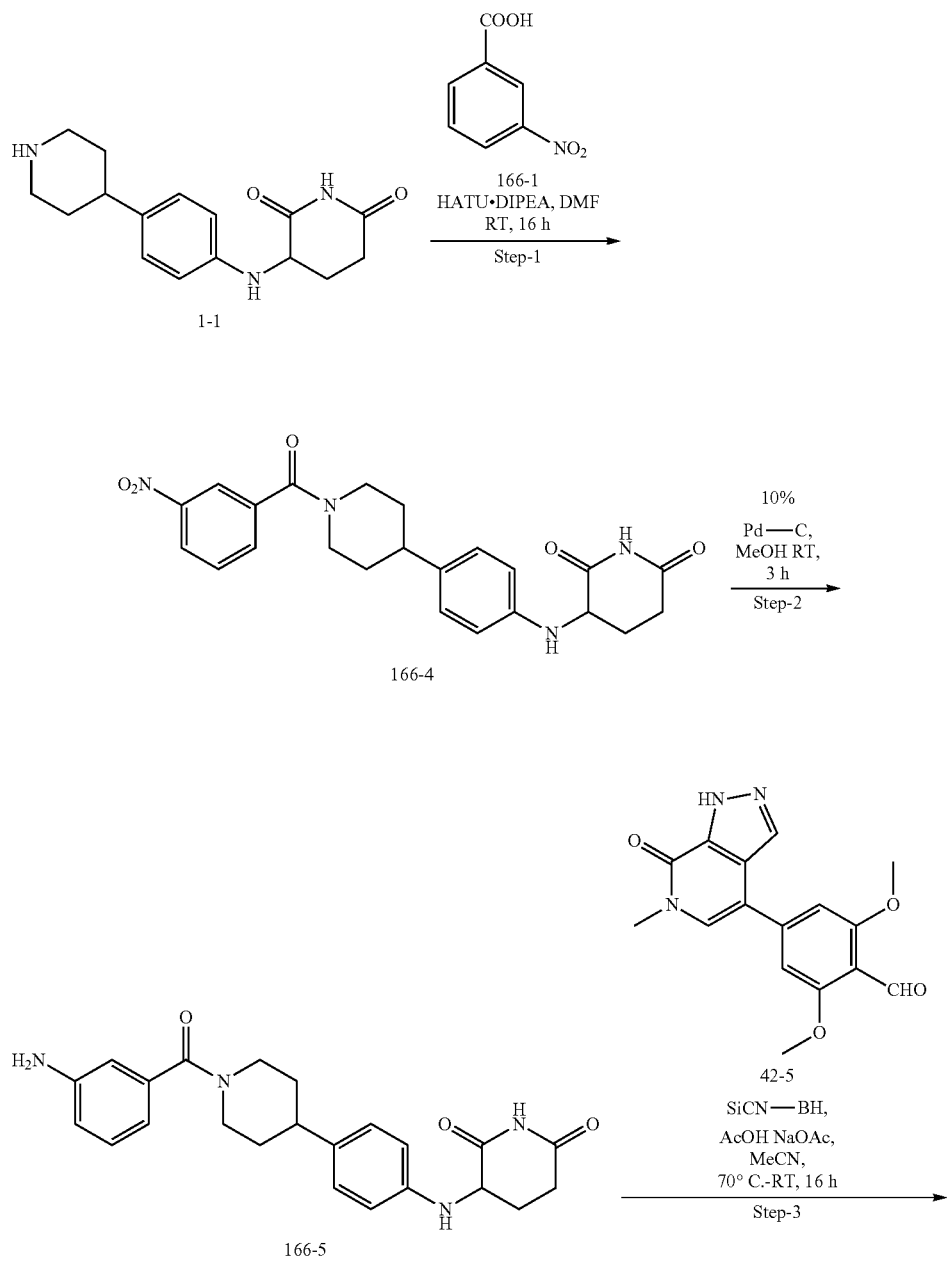

-continued

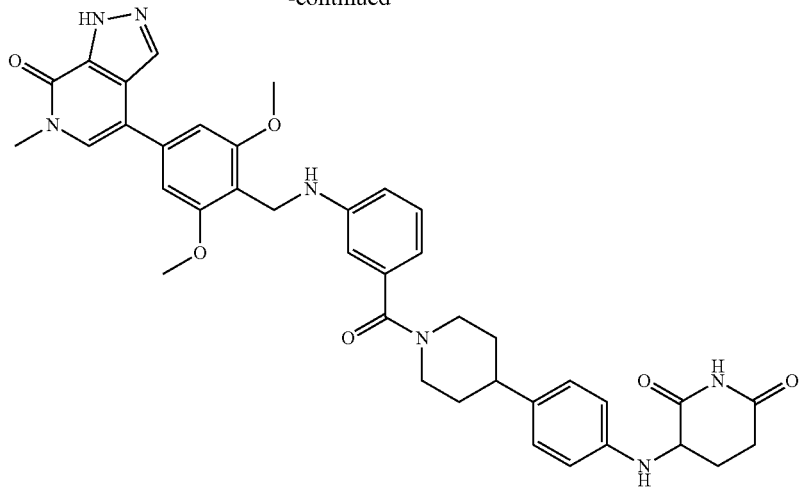

Compound 166

Step-1: To a solution of 3-[4-(4-piperidyl)anilino]piperidine-2,6-dione 1-1 (1 g, 3.48 mmol) in DMF (20 mL) cooled to 0° C., was added DIPEA (1.35 g, 10.44 mmol), HATU (2.00 g, 5.22 mmol) and stirred for 10 min. 3-nitrobenzoic acid 166-1 (639.73 mg, 3.83 mmol) was added to the reaction mixture and stirred at RT for 16 h while monitoring by LCMS and TLC. After completion of reaction, ice cold water was added to the reaction mixture. The solid was filtered out and triturated with diethyl ether. Diethyl ether was decanted and resulting residue was dried under vacuum to afford 3-[4-[1-(3-nitrobenzoyl)-4-piperidyl]anilino]piperidine-2,6-dione 166-4 (0.4 g, 23.17% yield, 88% purity) as pale yellow solid LCMS (ES+): m/z 437.70 [M+H]+.

Step-3: To a stirred solution of 3-[4-[1-(3-nitrobenzoyl)-4-piperidyl]anilino]piperidine-2,6-dione 166-4 (0.4 g, 0.916 mmol) in Methanol (10 mL) and Ethanol (10 mL), wet 10% Palladium on carbon, (0.48 g, 4.582 mmol) was added. Reaction flask was evacuated and back filled with hydrogen by using hydrogen bladder and the reaction was stirred under hydrogen atmosphere at room temperature for 3 h while monitoring by TLC. The reaction mixture was filtered over Celite bed, concentrated under vacuum, co-distilled with toluene and dried to afford 3-[4-[1-(3-aminobenzoyl)-4-piperidyl]anilino]piperidine-2,6-dione 166-5 (0.35 g, 93.95% yield, 85% purity) as white solid LCMS: [M+H]+ 407.36.

Step-4: To a stirred solution of 3-[4-[1-(3-aminobenzoyl)-4-piperidyl]anilino]piperidine-2,6-dione (0.1 g, 0.246 mmol) in acetonitrile (10 mL) was added molecular sieves (50 mg), Acetic acid (0.014 g, 0.246 mmol) and Sodium acetate, anhydrous (0.060 g, 0.738 mmol). The resulting solution was stirred for 10 min, then added 2,6-dimethoxy-4-(6-methyl-7-oxo-1H-pyrazolo[3,4-c]pyridin-4-yl)benzaldehyde 166-6 (0.077 g, 0.246 mmol) and stirred at 80° C. for 5 h. The reaction mixture was cooled to RT, added Silia Bond Cyanoborohydride (0.071 g, 1.23 mmol) and allowed to stir at RT for 16 h, while monitoring by TLC and LCMS. The reaction mass was filtered through Celite bed, concentrated under reduced pressure and purified by prep-HPLC to afford 3-[4-[1-[3-[[2,6-dimethoxy-4-(6-methyl-7-oxo-1H-pyrazolo[3,4-c]pyridin-4-yl)phenyl]methylamino]benzoyl]-4-piperidyl]anilino]piperidine-2,6-dione Compound 166 (13.4 mg, 16.14 umol, 6.56% yield, 98.51% purity) as an off white solid. $^1$H NMR (400 MHz, DMSO-$d_6$), δ 10.77 (s, 1H), 8.19 (s, 1H), 7.55 (s, 1H), 7.06 (m, J=19.3 Hz, 1H), 6.88 (s, 1H), 6.76 (t, J=10.4 Hz, 1H), 6.59 (q, J=9.6 Hz, 1H), 4.58 (s, 1H), 4.25 (m, J=7.1 Hz, 1H), 3.90 (s, 1H), 3.60 (s, 1H), 3.12 (d, J=40.4 Hz, 1H), 2.69 (m, J=7.1 Hz, 1H), 2.09 (m, J=3.4 Hz, 1H), 1.78 (m, J=10.7 Hz, 1H), 1.49 (s, 1H). LCMS (ES−): m/z 702.46 [M−H]−.

Synthesis of Compound 167

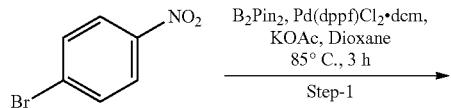

-continued
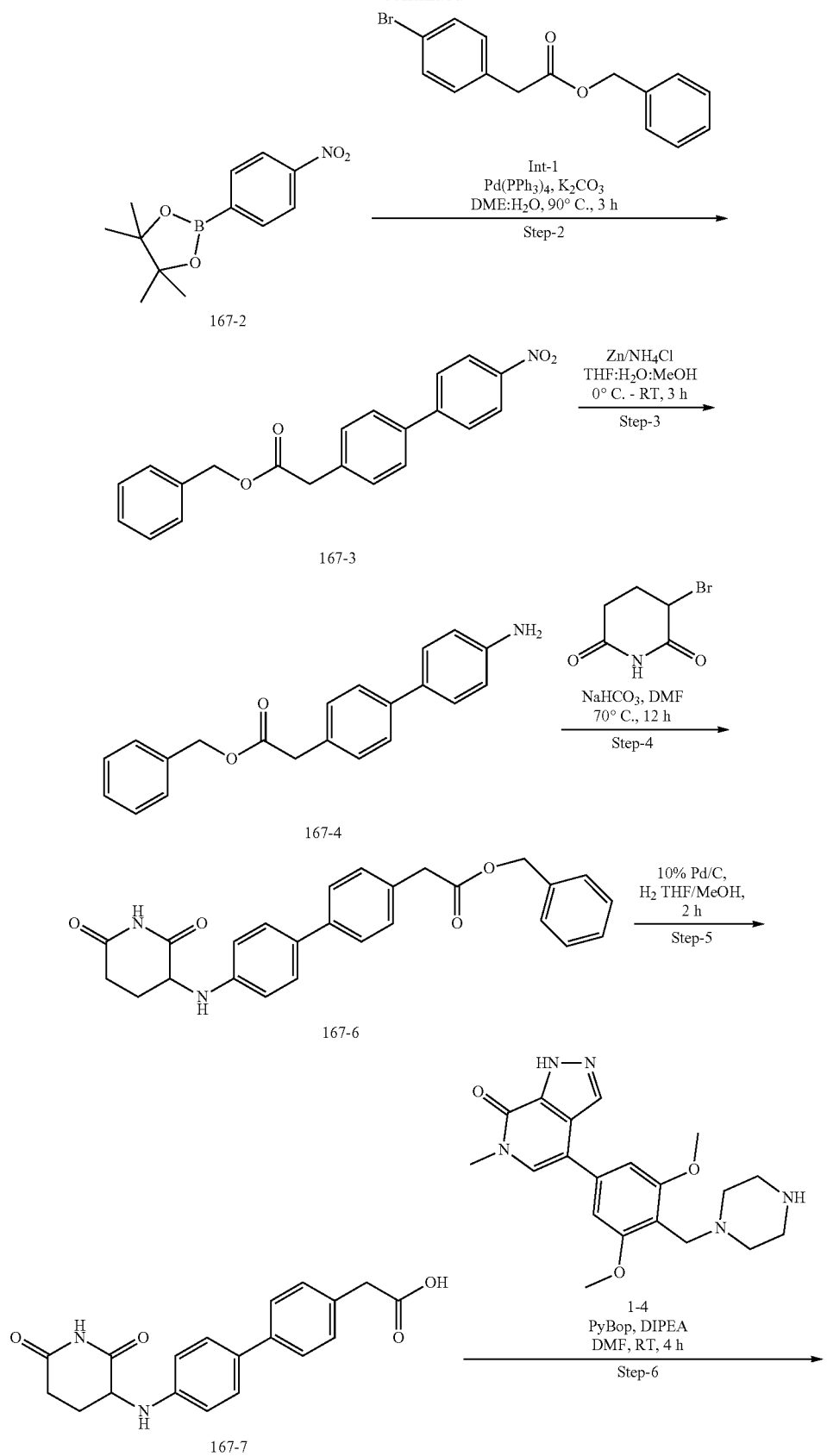

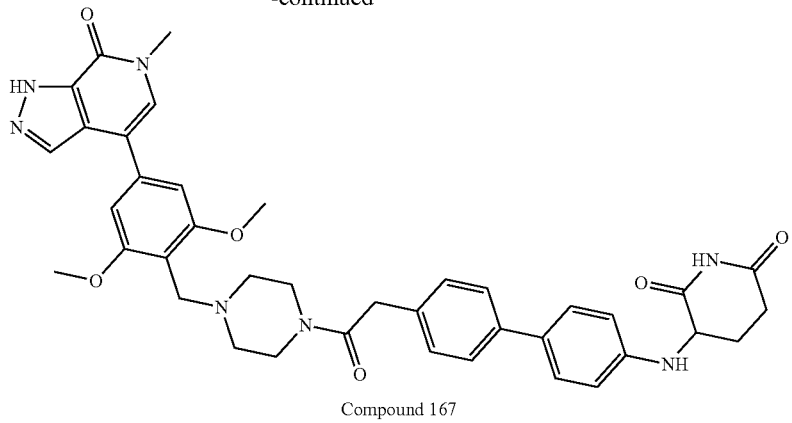

Compound 167

Step-1: To a stirred solution of 1-bromo-4-nitrobenzene (3 g, 14.85 mmol) in 1, 4 Dioxane (150 mL) was added Bis(pinacolato)diboron (5.66 g, 22.28 mmol) followed by the addition of potassium acetate (4.37 g, 44.55 mmol) at room temperature under argon atmosphere. The reaction mixture was degassed with argon repeatedly and Pd(dppf)Cl$_2$.dcm (0.36 g, 0.44 mmol) was added in one portion under argon atmosphere. The reaction mixture was again degassed with argon repeatedly and then heated at reflux at 85° C. for 3 h. After the completion of the reaction, the reaction mixture was cooled to room temperature and filtered off through Celite, washed with ethyl acetate (200 mL). The filtrate was concentrated to get the residual mass. The residual mass was dissolved in Ethyl acetate (250 mL) and washed with water (1×100 mL), brine (1×50 mL) and dried over anhydrous Na$_2$SO$_4$, filtered, concentrated to get the crude product. The crude was triturated with hexane (100 mL), decanted the organic layer and concentrated the organic layer to afford 4,4,5,5-tetramethyl-2-(4-nitrophenyl)-1,3,2-dioxaborolane 167-2 (2.5 g, 63.28% yield, 93.63% purity) as yellow solid. LCMS (ES$^-$): m/z [M–H]$^-$ 166.12 (Boronic acid mass).

Step-2: To a stirred solution of 4,4,5,5-tetramethyl-2-(4-nitrophenyl)-1,3,2-dioxaborolane 167-2 (0.5 g, 2.01 mmol) in 1,2-Dimethoxyethane (25 mL) was added benzyl 2-(4-bromophenyl)acetate (0.612 g, 2.01 mmol) at RT under argon atm followed by the addition of Potassium carbonate (0.83 g, 6.02 mmol) dissolved in Water (5 mL). The reaction mixture was degassed with argon repeatedly and Pd(PPh$_3$)$_4$ (0.11 g, 0.1 mmol) was added in one portion under argon atmosphere. The reaction mixture was again degassed with argon and then refluxed at 90° C. for 3 h. After the completion of the reaction, the reaction mixture was cooled to room temperature and filtered off through Celite, washed with ethyl acetate (50 mL). The filtrate was concentrated to get the residual mass. The residual mass was dissolved in Ethyl acetate (100 mL) and washed with water (1×50 mL), brine (1×25 mL), dried over anhydrous Na$_2$SO$_4$, filtered and concentrated to get the crude compound. The crude was purified by column chromatography over silicagel (230/400 mesh) and the product eluted at 6-8% EtOAc/Hexane to afford benzyl 2-[4-(4-nitrophenyl) phenyl] acetate 167-3 (0.15 g, 20.44% yield, 95% purity) as white solid.

Step-3: To the stirred solution of benzyl 2-(4'-nitro-[1,1'-biphenyl]-4-yl)acetate 167-3 (0.1 g, 0.28 mmol) in dry THF (12 mL) was added Zinc (0.18 g, 2.8 mmol) at 0° C. followed by the dropwise addition of ammonium chloride (0.30 g, 5.6 mmol) in water (4 mL) at 0° C. The reaction mixture was stirred at RT for 30 minutes. Methanol (6 mL) was added to the reaction mixture and the reaction was continued at RT for 2 h, while monitoring by TLC. After the completion of the reaction, the reaction mixture was filtered-off through Celite and washed with THF (50 mL). The filtrate was concentrated and the residual mass was dissolved in Ethyl acetate (100 mL) and washed with water (2×50 mL), brine (1×25 mL), dried over anhydrous Na$_2$SO$_4$, filtered and concentrated to afford benzyl 2-(4'-amino-[1,1'-biphenyl]-4-yl)acetate 167-4 (0.09 g, 86.42% yield, 87.73% purity) as orange solid. LCMS (ES$^+$): m/z 318.28 [M+H]$^+$ Step-4: To the stirred solution of benzyl 2-[4-(4-aminophenyl)phenyl]acetate 167-4 (0.130 g, 0.4 mmol) in dry DMF (3 mL) was added Sodium bicarbonate (0.201 g, 2.4 mmol) at RT followed by the addition of 3-bromopiperidine-2,6-dione (0.314 g, 1.6 mmol) in a sealed tube. The reaction mixture was heated at 70° C. for 12 h. After the completion of the reaction, the reaction mixture was concentrated to get the crude compound. The crude was purified by column chromatography over silica gel (100/200 mesh) and the product eluted at 40-50% EtOAc/Hexane to afford benzyl 2-[4-[4-[(2,6-dioxo-3-piperidyl)amino]phenyl]phenyl]acetate 6 (0.120 g, 66.01% yield, 96.55% purity) as pale green solid. LCMS (ES$^+$): m/z 429.30 [M+H]$^+$ Step-5: To the stirred solution of benzyl 2-[4-[4-[(2,6-dioxo-3piperidyl)amino]phenyl]phenyl]acetate 167-5 (0.120 g, 0.28 mmol) in THF (10 mL) and Methanol (5 mL) was added 10% Palladium on carbon wet (0.029 g, 0.28 mmol) at RT. The reaction mixture was degassed and stirred at RT under H$_2$ balloon pressure for 2 h while monitored by TLC. After the completion of the reaction, the reaction mixture was filtered-off though Celite and washed with methanol (50 mL). The filtrate was concentrated, the residual mass thus obtained was triturated with pentane (10 mL) and the solid precipitated out. The supernatant organic layer was decanted, the solidified product was dried well to afford the 2-[4-[4-[(2,6-dioxo-3-piperidyl)amino]phenyl]phenyl]acetic acid 167-7 (0.09 g, 91.15% yield, 95.97% purity) as off-white solid. LCMS (ES$^+$): m/z 339.28 [M+H]$^+$ Step-6: To the stirred solution of 4-[3,5-dimethoxy-4-(piperazin-1-ylmethyl)phenyl]-6-methyl-1H-pyrazolo[3,4-c]pyridin-7-one 0.10 g, 0.2 mmol) in DMF (3 mL) was added DIPEA (0.13 g, 1.0 mmol) at RT under N$_2$ atm. The reaction mixture was stirred at RT for 30 minutes. The pH of the reaction mixture was basic. The reaction mixture was cooled to 0° C. and 2-[4-[4-[(2,6-dioxo-3-piperidyl)amino]phenyl]

phenyl]acetic acid 167-7 (0.068 g, 0.20 mmol) was added to the reaction mixture followed by the addition of PyBop (0.13 g, 0.26 mmol). The reaction mixture was slowly warmed to rt over the period of 30 min and stirred at rt for 12 h while monitoring the reaction by TLC and LC-MS. After the completion of the reaction, the reaction mixture was concentrated under Genevaccum to get the crude compound. The crude was purified by Prep HPLC to afford 3-[4-[4-[2-[4-[[2,6-dimethoxy-4-(6-methyl-7-oxo-1H-pyrazolo[3,4-c]pyridin-4-yl)phenyl]methyl]piperazin-1-yl]-2-oxo-ethyl]phenyl]anilino]piperidine-2,6-dione TFA Compound 167 (0.08 g, 47.88% yield, 98.40% purity) as pale green solid. $^1$H NMR (400 MHz, DMSO) δ 14.25 (s, 1H), 10.81 (s, 1H), 9.41 (s, 1H), 8.23 (s, 1H), 7.64 (s, 1H), 7.50 (d, J=8.3 Hz, 2H), 7.40 (d, J=8.7 Hz, 2H), 7.23 (d, J=8.3 Hz, 2H), 6.97 (s, 2H), 6.74 (d, J=8.7 Hz, 2H), 4.44-4.36 (m, 2H), 4.28 (bs, 2H), 4.16 (d, J=14.1 Hz, 1H), 3.95 (s, 6H), 3.83-3.72 (m, 2H), 3.63 (s, 3H), 3.49-3.33 (m, 3H), 3.07-3.05 (m, 3H), 2.80-2.73 (m, 1H), 2.67-2.57 (m, 1H), 2.15-2.07 (m, 1H), 1.93-1.89 (m, 1H). LCMS (ES$^+$): m/z 704.56 [M+H]$^+$ Synthesis of Compound 168

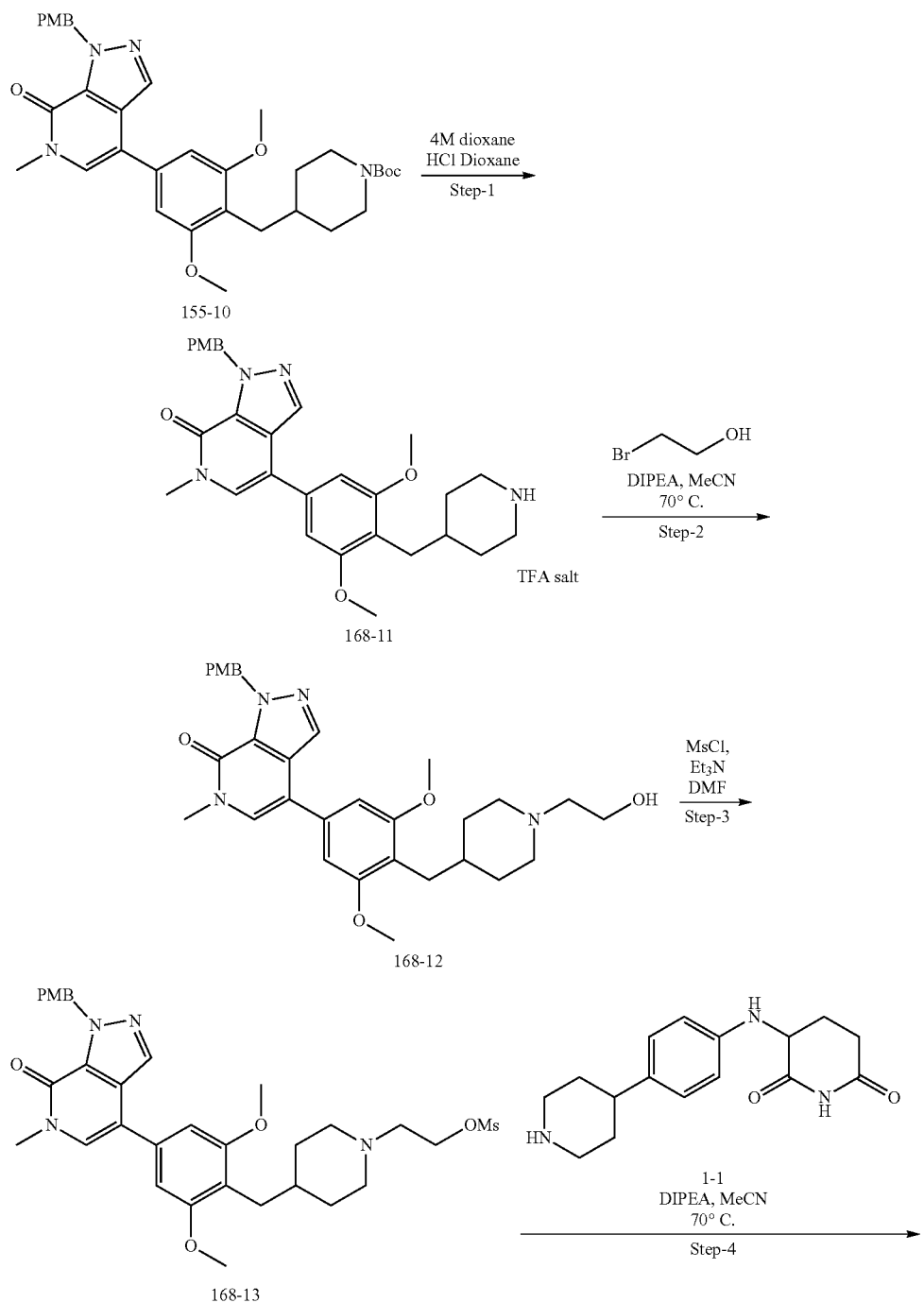

-continued

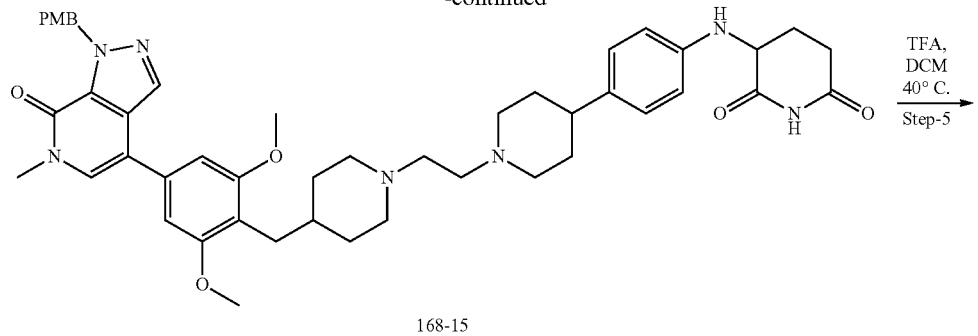

168-15

TFA, DCM 40° C. Step-5

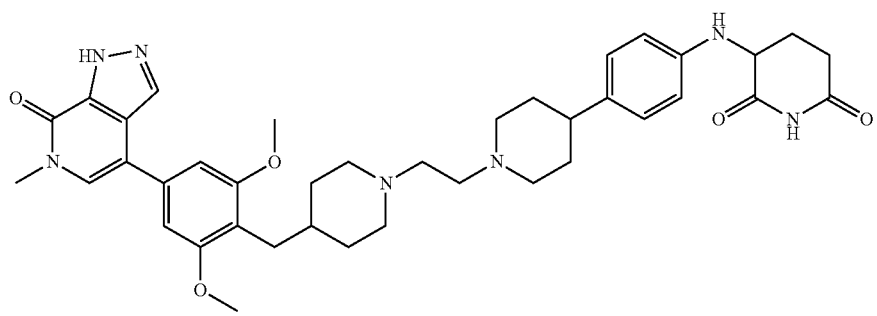

Compound 168

Step-1: 4.0 M HCl in 1,4-dioxane (2 mL) was added to 155-10 (0.4 g, 0.663 mmol) at 0° C. and then reaction mixture was allowed to stir at rt for 3 h, while monitoring the reaction by TLC and LCMS. After completion, solvent was evaporated under reduced pressure and crude was co-distilled with toluene to afford 4-[3,5-dimethoxy-4-(4-piperidylmethyl)phenyl]-1-[(4-methoxyphenyl)methyl]-6-methyl-pyrazolo[3,4-c]pyridin-7-one (0.35 g, 89.61% yield, 91.6% purity) as a brown solid. LCMS (ES$^+$): m/z 503.95 [M+H]$^+$.

Step-2: To a stirred solution of 155-11 (0.35 g, 0.694 mmol, 021) in CH$_3$CN (10 mL) were added DIPEA (0.87 mL 4.85 mmol) followed by 155-12 (104 mg, 0.833 mmol) and then reaction mixture was allowed to stir at 70° C. for 3 h, while monitoring the reaction by TLC. After completion, the reaction mass was quenched with water (50 ml) and extracted with 10% MeOH in DCM (2×50 ml). The combined organic layer was dried over anhydrous Na2SO4 and concentrated. The crude was purified by column chromatography (devisil silica, 5% MeOH in DCM) to afford 4-[4-[[1-(2-hydroxyethyl)-4-piperidyl]methyl]-3, 5-dimethoxy-phenyl]-1-[(4-methoxyphenyl)methyl]-6-methyl-pyrazolo[3,4-c]pyridin-7-one (0.25 g, 68.32% yield) as a white solid. LCMS (ES$^+$): m/z 547.96 [M+H]$^+$.

Step-3: To a suspension of 155-13 (0.3 g, 0.548 mmol) were added TEA (0.15 mL, 1.097 mmol) followed by methane sulfonyl chloride (0.063 g 0.548 mmol) and reaction mixture was allowed to stir at room temperature for 4 h, while monitoring by TLC. After completion of reaction by TLC and LCMS, Solvent was evaporated and crude was co-distilled with toluene and washed with diethyl ether afford 2-[4-[[2,6-dimethoxy-4-[1-[(4-methoxyphenyl) methyl]-6-methyl-7-oxo-pyrazolo[3,4-c]pyridin-4-yl]phenyl]methyl]-1-piperidyl]ethyl methane sulfonate (0.2 g, 54% purity). LCMS (ES$^+$): m/z 625.15 [M+H]$^+$.

Step-4: To a stirred solution of 155-15 (0.13 g, 0.319 mmol) in ACN (5 mL) were added DIPEA (0.29 g, 2.25 mmol), and followed by 1-1 (0.2 g, 0.32 mmol) was added at RT and reaction mixture was allowed to stir for 16 h in seal tube while monitoring the reaction by LCMS. After completion, solvent was removed under reduced pressure and the resulting crude was diluted with water and extracted with 10% MeOH in DCM. The organic layer was washed with brine solution. The crude was purified by Biotage using 5% MeOH in DCM to afford 155-16 (0.15 g, 89% purity) as a brown solid. LCMS: [M−H] 816.2.

Step-5: To a stirred solution of 3-[4-[1-[2-[4-[[2,6-dimethoxy-4-[1-[(4-methoxyphenyl)methyl]-6-methyl-7-oxo-pyrazolo[3,4-c]pyridin-4-yl]phenyl]methyl]-1-piperidyl] ethyl]-4-piperidyl]anilino]piperidine-2,6-dione (0.120 g, 0.147 mmol) in DCM (1 mL) was added TFA (1 mL) and heated the reaction mixture at 50° C. for 6 hr, while monitoring the reaction by TLC and LCMS. After completion, solvent was removed under reduced pressure and crude was purified by prep-HPLC to afford 3-[4-[1-[2-[4-[[2,6-dimethoxy-4-(6-methyl-7-oxo-1H-pyrazolo[3,4-c]pyridin-4-yl)phenyl]methyl]-1-piperidyl]ethyl]-4-piperidyl]anilino] piperidine-2,6-dione (50.3 mg, 93.35% purity) as a light green solid. $^1$H NMR (400 MHz, DMSO-d$_6$) δ=14.2 (s, 1H), 10.78 (s, 1H), 9.47-9.25 (m, 2H), 8.19 (s, 1H), 7.21-6.95 (m, 2H), 6.87 (s, 2H), 6.64 (d, J=8 Hz, 2H), 4.30-4.26 (m, 1H), 3.87 (s, 6H), 3.61 (m, 3H), 3.51 (m, 8H), 3.06 (m, 4H), 2.78-2.73 (m, 1H), 2.62-2.60 (m, 4H), 2.11-2.07 (m, 1H), 1.92-1.80 (m, 8H), 1.49-1.46 (m, 2H) LCMS: [M+H]$^+$ 696.66.

Synthesis of Compound 169
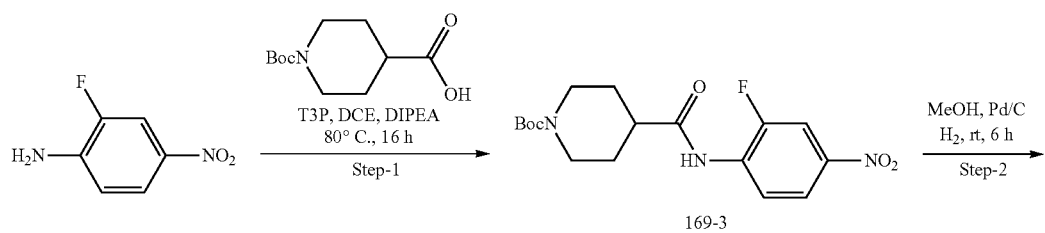
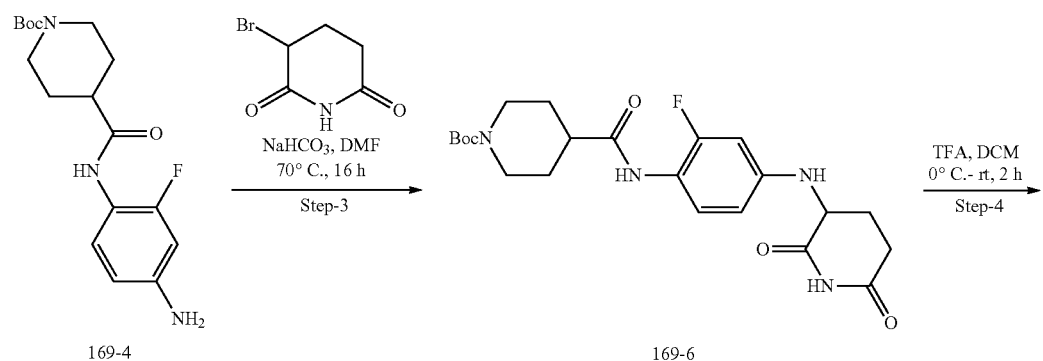
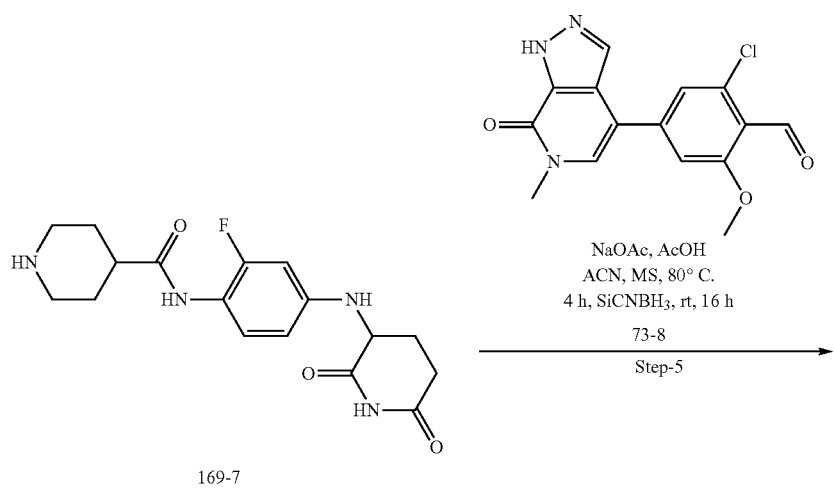

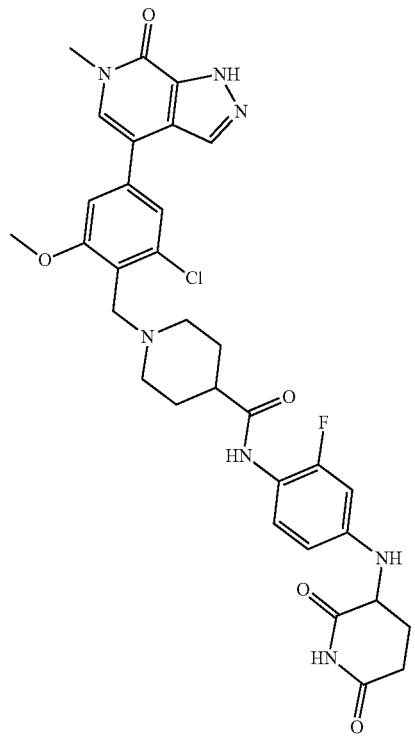

Compound 169

Step-1: To a stirred solution of 1-tert-butoxycarbonylpiperidine-4-carboxylic acid (2.0 g, 8.7 mmol) in DCE (20 mL) was added T3P (50% in EtOAc) (16.6 mL, 26.1 mmol) and DIPEA (5.6 g, 43.5 mmol, 7.44 mL) at room temperature. The reaction mixture was stirred for 15 min before addition of 2-fluoro-4-nitro-aniline (1.6 g, 10.4 mmol). The reaction mixture was then stirred at 80° C. for 16 h. It was then cooled to room temperature and volatiles were removed under reduced pressure. Saturated NaHCO₃ solution (30 mL) was added to the residue and extraction was carried out using EtOAc (30 mL×3). The combined organic layers were dried over sodium sulphate, filtered and concentrated under reduced pressure. The residue was purified by silica gel column chromatography (230-400 mesh size, gradient elution of 0-100% EtOAc in pet-ether) to afford desired compound tert-butyl 4-[(2-fluoro-4-nitro-phenyl)carbamoyl]piperidine-1-carboxylate (2.8 g, 7.62 mmol, 88% yield) as an off-white solid.

Step-2: To a stirred solution of tert-butyl 4-[(2-fluoro-4-nitro-phenyl)carbamoyl]piperidine-1-carboxylate (2.5 g, 6.8 mol) in MeOH (70 mL) was added Pd/C (0.5 g) and the reaction mixture was stirred at room temperature for 6 h in an atmosphere of hydrogen (hydrogen balloon). After completion of the reaction (as indicated by TLC), the catalyst was filtered off through Celite and washed with MeOH. The filtrate was concentrated under reduced pressure and the residue was purified by silica gel column chromatography (230-400 mesh size, gradient elution of 0-100% EtOAc-pet-ether) to afford tert-butyl 4-[(4-amino-2-fluoro-phenyl)carbamoyl]piperidine-1-carboxylate (1.9 g, 5.6 mmol, 82.3% yield) as an off-white solid product. LCMS (ES⁻): m/z 336.45 [M−H]⁻.

Step-3: 169-4 (0.5 g, 1.5 mmol) in (7 mL) was added sodium bicarbonate (0.74 g, 9.0 mmol) and compound 3-bromopiperidine-2,6-dione (0.86 g, 4.5 mmol). The reaction mixture was stirred at 70° C. for 16 h. After completion of the reaction (as indicated by TLC), it was cooled to room temperature and water (20 mL) was added to it. Extraction was carried out using EtOAc (20 mL×3); the combined organic layers were washed with water (30 mL×3), brine (30 mL), dried over anhydrous sodium sulphate, filtered and concentrated under reduced pressure. The residue was purified by silica gel column chromatography (230-400 mesh, gradient elution of 0-100% EtOAc-pet ether) to afford desired compound tert-butyl-4-[[4-[(2,6-dioxo-3-piperidyl)amino]-2-fluoro-phenyl]carbamoyl]piperidine-1-carboxylate (0.4 g, 0.9 mmol, 60% yield) as a white solid. LCMS (ES⁺): m/z 471.39 [M+Na]⁺.

Step-4: To a stirred solution of tert-butyl 4-[[4-[(2,6-dioxo-3-piperidyl)amino]-2-fluoro-phenyl]carbamoyl]piperidine-1-carboxylate (0.170 g, 0.4 mmol) in DCM (2 mL) was added TFA (0.45 g, 4.0 mmol) at 0° C. and the reaction mixture was allowed to warm to room temperature over 2 h. After completion of the reaction (as indicated by TLC), volatiles were removed under reduced pressure and Et₂O (5 mL) was added to the residue. The solid observed was filtered and dried to afford desired compound N-[4-[(2,6-dioxo-3-piperidyl)amino]-2-fluoro-phenyl]piperidine-4-carboxamide (TFA salt, 0.11 g, 0.23 mmol, 60% yield) as a white solid. LCMS (ES⁺): m/z 349.32 [M+H]⁺.

Step-5: To a stirred solution of N-[4-[(2,6-dioxo-3-piperidyl)amino]-2-fluoro-phenyl]piperidine-4-carboxamide (40 mg, 0.086 mmol) in ACN (1.0 mL) was added sodium acetate (28 mg, 0.34 mmol), molecular sieves (50 mg) and AcOH (6.9 mg, 0.115 mmol). The resulting mixture was stirred for 10 minutes and then 2-chloro-6-methoxy-4-(6-methyl-7-oxo-1H-pyrazolo[3,4-c]pyridin-4-yl)benzaldehyde (50 mg, 0.115 mmol) was added to it. The reaction mixture was then stirred at 80° C. for 4 h before it was cooled to 0° C. To this was then added Si-CNBH₃ (50 mg) and the reaction mixture was stirred at room temperature for 16 h. The progress of the reaction was monitored by LCMS. It was then filtered through Celite and washed with THF (5 mL×2). The filtrate was then concentrated under reduced pressure and the residue was purified by prep-HPLC to afford desired compound 1-[[2-chloro-6-methoxy-4-(6-methyl-7-oxo-1H-pyrazolo[3,4-c]pyridin-4-yl)phenyl]methyl]-N-[4-[(2,6-dioxo-3-piperidyl)amino]-2-fluoro-phenyl]piperidine-4-carboxamide (13.2 mg, 0.017 mmol, 15% yield, 97.46% purity) as an off white solid. LCMS (ES⁺): m/z 650.0 [M+H]⁺; ¹H NMR (400 MHz, DMSO-d₆) δ 1.80-2.20 (m, 6H); 2.58-2.80 (m, 3H); 3.20-3.30 (m, 2H); 3.50-3.60 (m, 2H); 3.63 (s, 3H); 4.02 (s, 3H); 4.30-4.38 (m, 1H); 4.40-4.50 (m, 2H); 6.12 (bs, 1H); 6.45 (d, J=8.8 Hz, 1H); 6.53 (d, J=13.6 Hz, 1H); 7.21-7.26 (m, 1H); 7.34 (s, 1H); 7.45 (s, 1H); 7.72 (s, 1H); 8.22 (s, 1H); 8.98 (bs, 1H); 9.41 (s, 1H); 10.80 (s, 1H); 14.40 (bs, 1H).

Synthesis of Compound 170

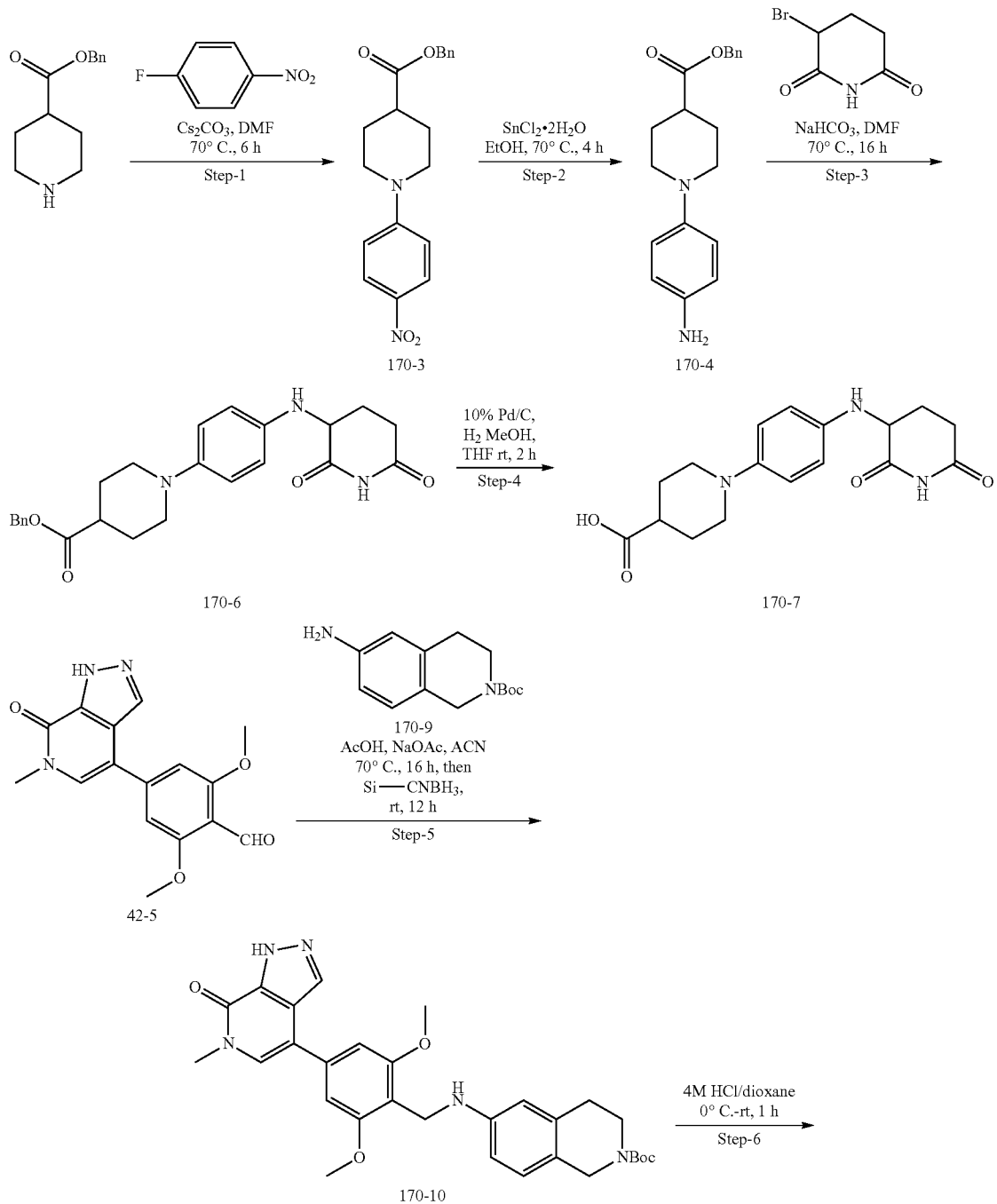

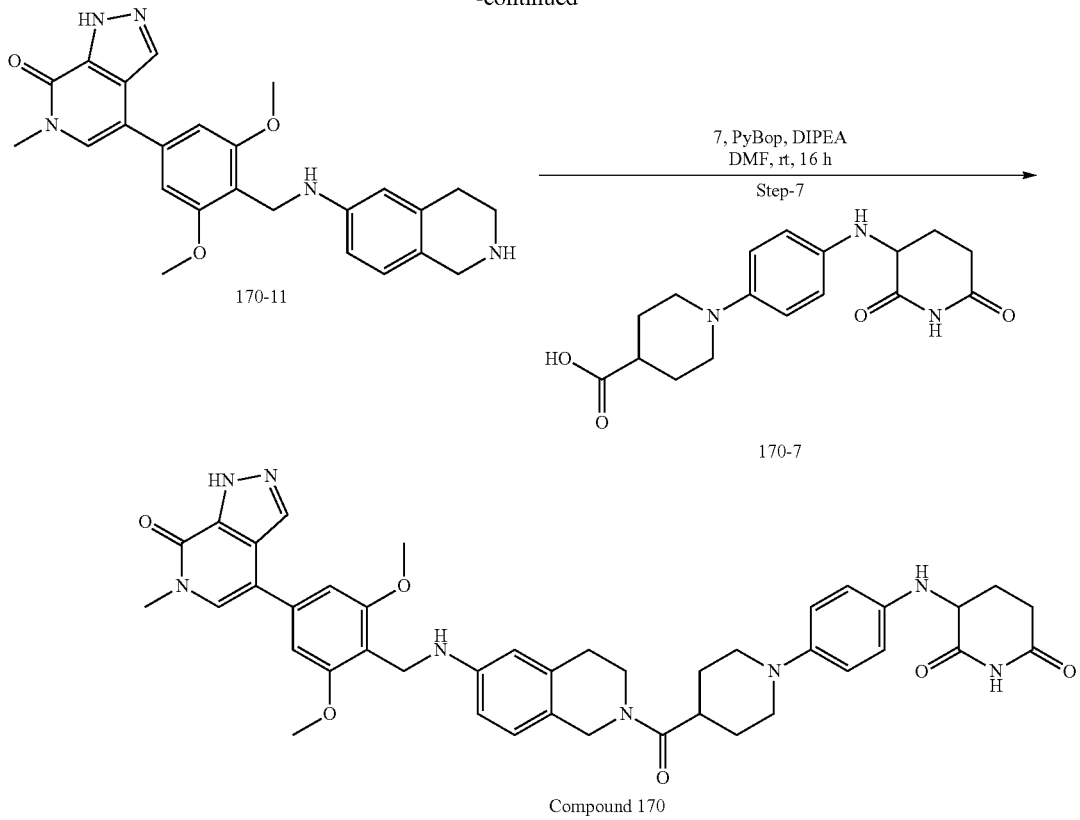

Compound 170

Step-1: To stirred solution of benzyl piperidine-4-carboxylate (HCl salt) (1.4 g, 5.474 mmol) in DMF (15 ml) was added 1-fluoro-4-nitro-benzene (1.16 g, 8.221 mmol) and $Cs_2CO_3$ (5.35 g, 16.420 mmol) at room temperature. The reaction mixture was stirred for 6 h at 70° C. After completion of the reaction (as indicated by TLC); the reaction mixture was cooled to ambient temperature and water (30 mL) was added to it. Extraction was carried out using EtOAc (2×50 mL); the combined organic layers were washed with water (50 mL×2), brine (50 mL), dried over anhydrous sodium sulphate, filtered and evaporated under reduce pressure. The resulting crude was purified by silica gel column chromatography (0-100% gradient elution of ethyl acetate in pet ether) to afford benzyl 1-(4-nitrophenyl)piperidine-4-carboxylate (1.6 g, 4.7 mmol, 86.02% yield).

Step-2: To a stirred solution of benzyl 1-(4-nitrophenyl) piperidine-4-carboxylate (1.5 g, 4.406 mmol) in EtOH (15 mL) was added stannous chloride dihydrate (2.09 g, 11.022 mmol) at room temperature and the reaction mass was stirred at 70° C. for 4 h. After completion of the reaction, it was cooled to ambient temperature and EtOH was removed under reduced pressure. Saturated sodium bicarbonate solution (30 mL) was added to the residue and extraction was carried out using EtOAc (3×30 mL). The combined organic extracts were dried over anhydrous sodium sulphate, filtered and evaporated under reduce pressure. The resulting crude was purified by silica gel column chromatography (Davisil, 0-100% gradient elution of ethyl acetate in pet ether) to afford benzyl 1-(4-aminophenyl)piperidine-4-carboxylate (0.9 g, 2.89 mmol, 66.176% yield, 70% purity) LCMS $(ES^+)$: m/z 311.26 $[M+H]^+$ Step-3: To a stirred solution of benzyl 1-(4-aminophenyl) piperidine-4-carboxylate (900 mg, 2.90 mmol) in DMF (10 mL) was added anhydrous $NaHCO_3$ (1.46 g, 17.378 mmol) and 3-bromopiperidine-2,6-dione (3.34 g, 17.394 mmol). The reaction mixture was then stirred at 70° C. for 16 h. After completion of the reaction, it was cooled to room temperature and ice-cold water (30 mL) was added to it. The solid obtained was filtered, washed with water and dried. It was purified by silica gel column chromatography (using 230-400 mesh silica gel, gradient elution of 0-100% EtOAc in pet-ether) to afford benzyl 1-[4-[(2,6-dioxo-3-piperidyl)amino]phenyl]piperidine-4-carboxylate (0.35 g, 0.830 mmol, 28.68% yield, 92% purity) as an off-white color solid. LCMS $(ES^+)$: m/z $[M+H]^+$ 422.51

Step-4: To a stirred solution of benzyl 1-[4-[(2,6-dioxo-3-piperidyl)amino] phenyl]piperidine-4-carboxylate (0.35 g, 830.39 mmol) in MeOH (3 mL) and THF (3 mL) was added 10% palladium carbon (120 mg) and the reaction mixture was stirred under hydrogen atmosphere at room temperature for 2 h. After completion of the reaction (as indicated by TLC), the catalyst was filtered off through Celite and washed with THF (5 mL×2). The filtrate was concentrated under reduced pressure to afford desired compound 1-[4-[(2,6-dioxo-3-piperidyl)amino]phenyl]piperidine-4-carboxylic acid (0.25 g, 0.754 mmol, 91% yield, 65.7% purity) as a thick brown oil. LCMS $(ES^+)$: m/z $[M+H]^+$ 332.28.

Step-5: To a stirred solution of tert-butyl 6-amino-3,4-dihydroisoquinoline-2(1H)-carboxylate (0.190 g, 0.765 mmol) in ACN (9 mL) was added NaOAc (0.188 g, 2.291 mmol), 4 Å MS (0.2 g) and AcOH (0.212 g, 3.530 mmol). To this was then added 2,6-dimethoxy-4-(6-methyl-7-oxo-6,7-dihydro-1H-pyrazole[3,4-c]pyridin-4-yl)benzaldehyde (0.240 g, 0.766 mmol) and the reaction mass was stirred at 70° C. for 16 h. It was then cooled to 0° C. and then Si-CNBH₃ (0.240 g, 3.819 mmol) was added to it. The reaction mixture was stirred at room temperature for 12 h. It was then filtered through a pad of Celite and washed with 10% MeOH in DCM (3×20 mL). The filtrate was concentrated under reduced pressure and saturated NaHCO₃ solution (30 mL) was added to the residue. Extraction was carried out using EtOAc (30 mL×3); the combined organic layers were washed with water (30 mL), brine (30 mL), dried over anhydrous sodium sulphate, filtered and concentrated under reduced pressure. The residue obtained was purified by column chromatography (230-400 mesh silica gel, gradient elution of 0-100% EtOAc in pet-ether) to afford tert-butyl 6-[[2-hydroxy-6-methoxy-4-(6-methyl-7-oxo-1H-pyrazolo[3,4-c]pyridin-4-yl)phenyl]methylamino]-3,4-dihydro-1H-isoquinoline-2-carboxylate (0.35 g, 0.659 mmol, 83.95% yield) as a white solid, LCMS (ES⁻): m/z 544.43 [M−H]⁻

Step-6: To a solution of tert-butyl 6-[[2-hydroxy-6-methoxy-4-(6-methyl-7-oxo-1H-pyrazolo[3,4-c]pyridin-4-yl)phenyl]methylamino]-3,4-dihydro-1H-isoquinoline-2-carboxylate (0.35 g, 0.641 mmol) in 1,4-dioxane (2 mL) was added 4M HCl in dioxane (0.8 mL, 3.21 mmol) at 0° C. The reaction mass was stirred at room temperature for 3 h. After completion of the reaction, volatiles were removed under reduced pressure and the residue was washed with diethyl ether (3 mL×2) to afford desired compound 4-[3-hydroxy-5-methoxy-4-[(1,2,3,4-tetrahydroisoquinolin-6-ylamino)methyl]phenyl]-6-methyl-1H-pyrazolo[3,4-c]pyridin-7-one (0.15 g of HCl salt, 337.64 mmol, 48% yield, 78.99% purity) as a white solid product. LCMS (ES⁺): m/z 446.31 [M+H]⁺

Step-7: To a solution of 4-[3,5-dimethoxy-4-[(1,2,3,4-tetrahydroisoquinolin-6-ylamino)methyl]phenyl]-6-methyl-1H-pyrazolo[3,4-c]pyridin-7-one (80.0 mg, 0.166 mmol) in DMF (3 mL) was added DIPEA (107 mg, 0.827 mmol) and 1-[4-[(2,6-dioxo-3-piperidyl)amino]phenyl]piperidine-4-carboxylic acid (95 mg, 0.286 mmol). It was stirred for 15 min before addition of PyBOP (0.172 g, 0.330 mmol) and the reaction mixture was stirred at room temperature for 16 h. After completion of the reaction, it was cooled to 0° C. and saturated NaHCO₃ solution (10 mL) was added to it. The solid thus obtained was filtered, washed with water (1 mL×2) and dried. It was then purified by preparative HPLC to afford 3-((4-(4-96-((2,6-dimethoxy-4-(6-methyl-7-oxo-6,7-dihydro-1-pyrazolo(3,4)pyridine-4 yl)benzyl)amino)1,2,3,4-tetrahydroisoquinoline-2-carbonyl)piperinin-1-yl)phenyl)amino) piperidine-2,6-dione (40.7 mg, 0.0497 mmol, 30.4% yield) as a light brown solid. LCMS (ES⁺): m/z 759.65 [M+H]⁺, ¹H NMR (400 MHz, DMSO-d₆) δ 14.20 (bs, 1H); 10.78 (bs, 1H); 8.19 (bs, 1H); 7.55 (s, 1H); 6.92-6.80 (m, 3H); 6.78-6.70 (m, 2H); 6.64-6.48 (m, 4H); 5.40-5.34 (m, 1H); 5.30-5.20 (m, 1H); 4.55-4.42 (m, 2H); 4.22-4.12 (m, 3H); 3.91 (s, 6H); 3.72-3.58 (m, 2H); 3.61 (s, 3H); 3.46-3.36 (m, 2H); 2.70-2.50 (m, 7H); 2.14-2.06 (m, 1H); 1.90-1.78 (m, 1H); 1.74-1.60 (m, 4H).

Synthesis of Compound 171

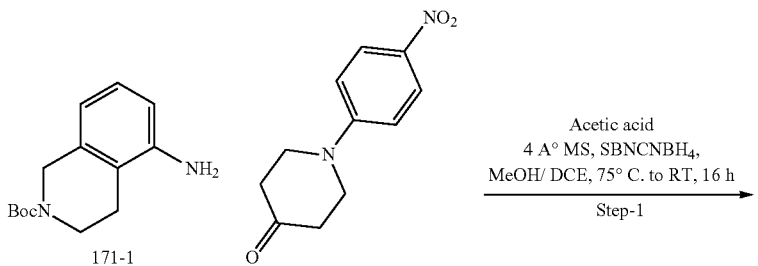

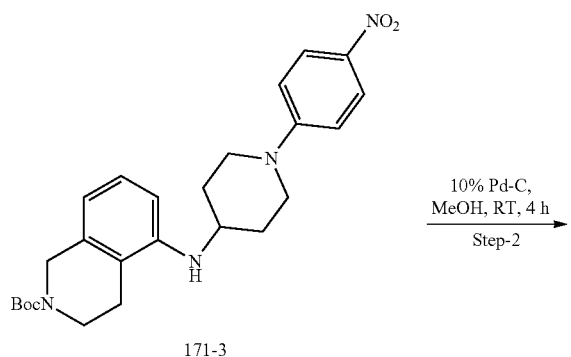

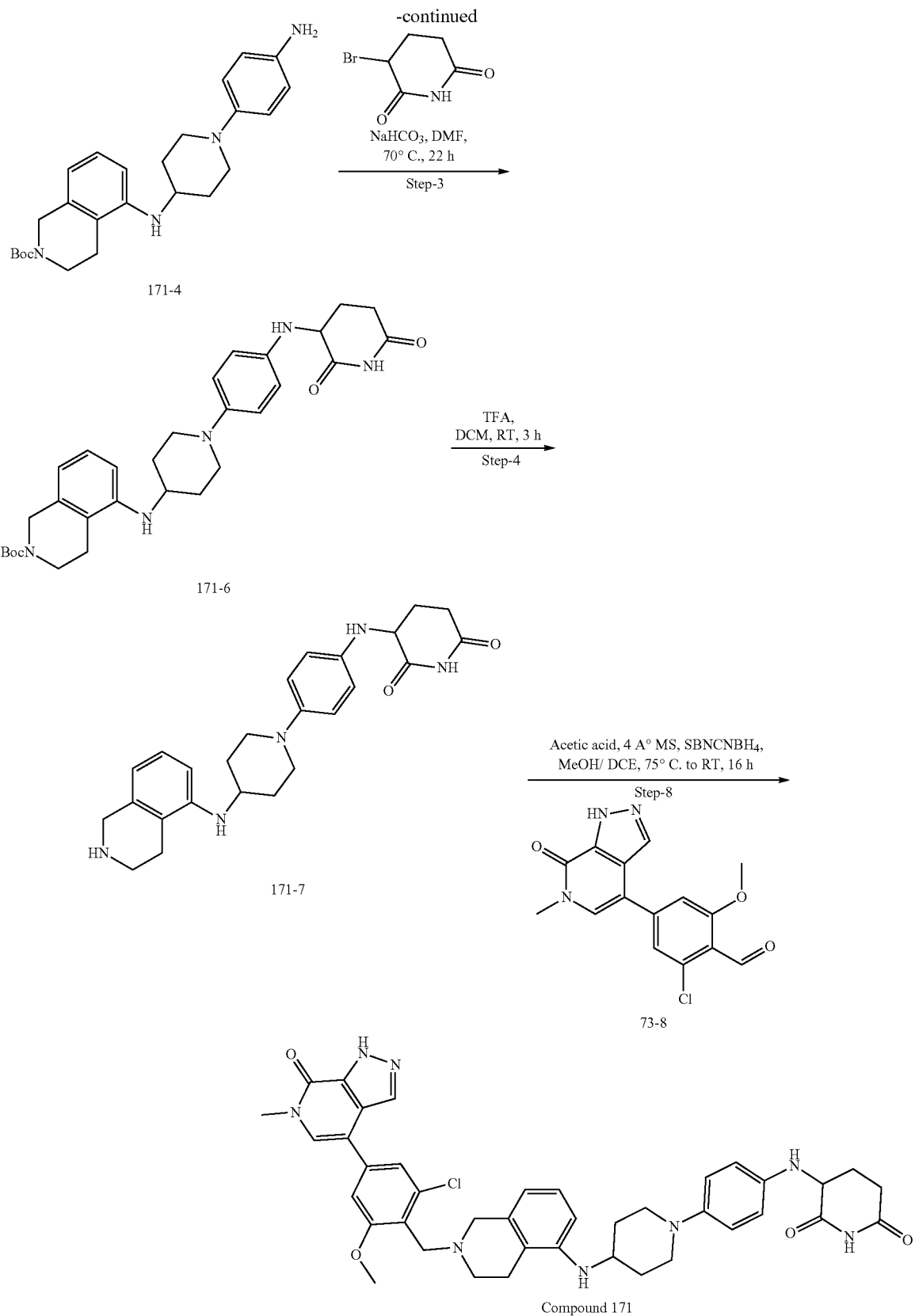
Step-1: To a stirred solution of tert-butyl 5-amino-3,4-dihydro-1H-isoquinoline-2-carboxylate (0.5 g, 2.01 mmol) and 1-(4-nitrophenyl)piperidin-4-one (443.43 mg, 2.01 mmol) in DCE (5 mL) and methanol (5 mL) was added acetic acid (0.17 mL, 3.02 mmol) and 4 Å molecular sieves (450 mg). The reaction mixture was heated to 70° C. for 5 h. Reaction mixture was cooled down to 25° C. and was added Si-CBH (0.45 g). The reaction mixture was stirred at 25° C. for 16 h. Progress of the reaction was monitored by LCMS. After completion of reaction, reaction mixture was filtered and the solid was washed thoroughly with methanol (2×50 mL) and ethyl acetate (2×50 mL). The combined organic solvent was concentrated under vacuo. The crude product was purified by column chromatography (silica gel mesh 100-200, 10-20% ethyl acetate in pet ether) to yield tert-butyl 5-[[1-(4-nitrophenyl)-4-piperidyl]amino]-3,4-dihydro-1H-isoquinoline-2-carboxylate (0.58 g, 51.10% yield, 80.28% purity) as a pale yellow solid. LCMS (ES$^+$): m/z 475.36 [M+Na]$^+$ Step-2: Stirred solution of tert-butyl 5-[[1-(4-nitrophenyl)-4-piperidyl]amino]-3,4-dihydro-1H-isoquinoline-2-carboxylate (0.5 g, 1.10 mmol) in methanol (20 mL) was degassed for 10 minutes under nitrogen followed by addition of palladium on carbon (10%) (0.5 g, 4.70 mmol). The reaction mixture was stirred at RT under hydrogen gas (under balloon pressure) for 4 h hr. Progress of reaction was monitored by TLC. After completion of the reaction, reaction mixture filtered through Celite bed and washed with methanol (2×25 mL). Combined organic layer was concentrated under vacuo to afforded tert-butyl 5-[[1-(4-aminophenyl)-4-piperidyl]amino]-3,4-dihydro-1H-isoquinoline-2-carboxylate (0.437 g, 91.21% yield, 97.44% purity) as a brown solid. The amine product was used for further reaction without any further purification. LCMS (ES$^+$): m/z 423.33 [M+H]$^+$ Step-3: To a stirred solution of tert-butyl 5-[[1-(4-aminophenyl)-4-piperidyl]amino]-3,4-dihydro-1H-isoquinoline-2-carboxylate (0.3 g, 0.71 mmol) and 3-bromopiperidine-2,6-dione (136.32 mg, 1.06 mmol) in DMF (6 mL) was added sodium bicarbonate (179 mg, 2.13 mmol) in a seal tube. The reaction mixture was stirred at 70° C. for 22 hr. Reaction progress was monitored by TLC. After completion of the reaction, reaction mixture was diluted with cold water and extracted with ethyl acetate (3×50 mL). Combined organic layer was dried over sodium sulfate, filtered and concentrated under vacuo. The crude residue was purified by column chromatography to afford tert-butyl 5-[[1-[4-[(2,6-dioxo-3-piperidyl)amino]phenyl]-4-piperidyl]amino]-3,4-dihydro-1H-isoquinoline-2-carboxylate (0.379 g, 97.76% yield, 97.73% purity) as a dark brown solid. LCMS (ES$^+$): m/z 534.48 [M+H]$^+$ Step-4: To a stirred solution of tert-butyl 5-[[1-[4-[(2,6-dioxo-3-piperidyl)amino]phenyl]-4-piperidyl]amino]-3,4-dihydro-1H-isoquinoline-2-carboxylate (0.150 g, 0.281 mmol) in DCM (2 mL) was added TFA (0.22 mL, 2.81 mmol). The reaction mixture was stirred at RT for 3 hr. Reaction progress was monitored by LCMS. After completion of the reaction, reaction mixture was dried under reduced pressure and co-distilled with toluene (10 ml). Crude compound was triturated diethyl ether (10 ml×2) to get 3-[4-[4-(1,2,3,4-tetrahydroisoquinolin-5-ylamino)-1-piperidyl]anilino]piperidine-2,6-dione (0.12 g, 211.00 umol, 75.07% yield, 96.28% purity) as a dark grey solid. LCMS (ES$^+$): m/z 434.40 [M+H]$^+$ Step-5: To a stirred solution of 2-chloro-6-methoxy-4-(6-methyl-7-oxo-1H-pyrazolo[3,4-c]pyridin-4-yl)benzaldehyde (60 mg, 138.97 umol) and 3-[4-[4-(1,2,3,4-tetrahydroisoquinolin-5-ylamino)-1-piperidyl]anilino]piperidine-2,6-dione (76.10 mg, 138.97 umol) in methanol (2 mL) and 1,2 dichloroethane (2 mL) was added acetic acid (11.92 uL, 208.45 umol), sodium acetate, anhydrous (34.20 mg, 416.91 umol, 22.35 uL) and 4 Å molecular sieves (2 g, 138.97 umol) and reaction mixture was allowed to stirred at 70° C. for 5 hr. Reaction mixture was cooled to 25° C. and added Si-CBH (60 mg). Further, the reaction mixture was stirred at 25° C. for 16 h. Progress of the reaction was monitored by LCMS. After completion of reaction, reaction mixture was filtered and the solid was washed thoroughly with methanol (2×5 mL) and ethyl acetate (2×5 mL). The combined organic solvent was concentrated in vacuo. The crude product was purified by RP-prep HPLC to obtain product 3-[4-[4-[[2-[[2-chloro-6-methoxy-4-(6-methyl-7-oxo-1H-pyrazolo[3,4-c]pyridin-4-yl)phenyl]methyl]-3,4-dihydro-1H-isoquinolin-5-yl]amino]-1-piperidyl]anilino]piperidine-2,6-dione (43.8 mg, 35.68% yield, 96.14 purity) as a light grey solid. $^1$H NMR (400 MHz, DMSO-d$_6$) δ 14.28 (s, 1H), 11.12 (bs, 0.7H), 10.83 (s, 1H), 9.81 (bs, 1H), 8.23 (bs, 1H), 7.73 (s, 1H), 7.46 (m, 4H), 7.17 (m, 1H), 6.79 (d, J=8.4 Hz, 2H), 6.71 (d, J=8.0 Hz, 1H), 6.54 (d, J=7.6 Hz, 1H), 6.35 (bs, 1H), 4.95 (bs, 1H), 4.54 (bs, 2H), 4.40 (m, 3H), 4.00 (s, 3H), 3.77 (m, 10H), 2.17 (bm, 2H), 2.75 (m, 1H), 2.67 (m, 1H), 2.17 (bm, 2H), 2.11-2.07 (m, 1H), 1.97-1.88 (m, 3H). LCMS (ES$^+$): m/z 735.48 [M+H]$^+$ Synthesis of Compound 172

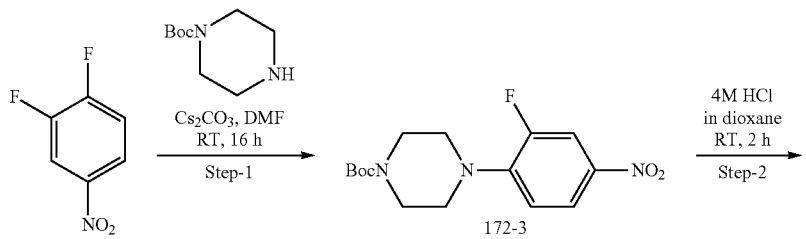

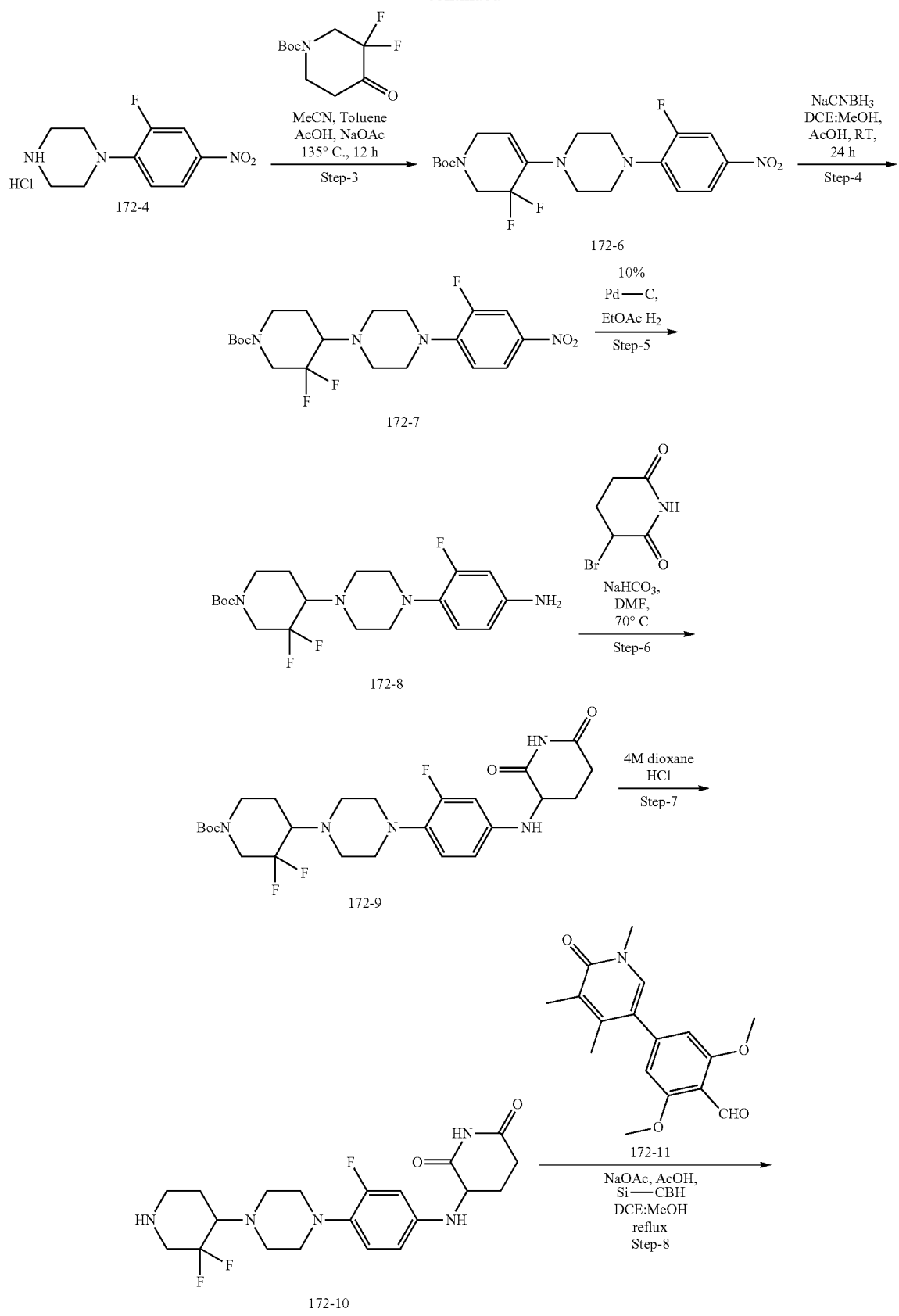

-continued

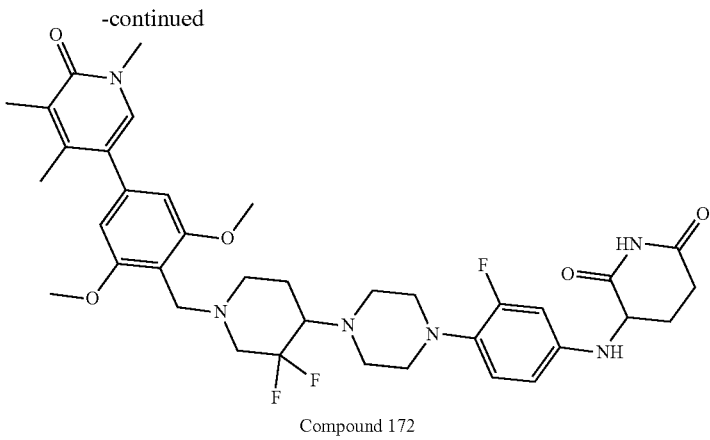

Compound 172

Step-1: To a stirred solution of compound tert-butyl piperazine-1-carboxylate (85.40 g, 536.82 mmol) in DMF (500 mL) was added cesium carbonate (262.4 g, 805.4 mmol) and stirred for 15 min before adding 1,2-difluoro-4-nitro-benzene (100 g, 536.82 mmol). The reaction mixture stirred at RT for 16 h while monitoring by TLC. After completion, the reaction mass was quenched with ice flakes and the precipitated solid was filtered, dried under vacuum to afford tert-butyl 4-(2-fluoro-4-nitro-phenyl) piperazine-1-carboxylate 172-3 (152 g, 88.85% yield, 97.94% purity) as a yellow solid.

Step-2: To a stirred solution of tert-butyl 4-(2-fluoro-4-nitrophenyl)piperazine-1-carboxylate 172-3 (50.0 g, 153.69 mmol) in 20 ml dioxane was added 4M dioxane HCl (30 ml) and reaction mixture stirred for 2 h at RT while monitoring by TLC. The solvent was evaporated to dryness under reduced pressure and crude solid was triturated with diethyl ether (75 ml) and n-pentane (100 ml) to afford HCl salt of 1-(2-fluoro-4-nitrophenyl) piperazine 172-4 (36.0 g, 136.2 mmol, 88.62% yield, 99% purity). LCMS (ES$^+$): m/z 226.10 [M+H]$^+$ Step-3: To stirred solution of 1-(2-fluoro-4-nitrophenyl)piperazine 172-4 (8.0 g, 35.52 mmol) in toluene (200 ml) and ACN (100 ml) was added NaOAc (7.28 g, 88.80 mmol), followed by AcOH (8 ml) and molecular sieves 4 Å (10 g) and stirred for 15 min. After 15 min tert-butyl 3,3-difluoro-4-oxo-piperidine-1-carboxylate (11.49 g, 48.84 mmol, co-distilled with toluene before use) was added and the reaction mixture was allowed to reflux for 12 h, while monitoring by LCMS and TLC. After completion, reaction mixture was cooled to room temperature and filtered through Celite bed. The filtrate was concentrated under vacuum to dryness to afford crude residue 3,3-difluoro-4-(4-(2-fluoro-4-nitrophenyl)piperazin-1-yl)-3,6-dihydropyridine-1(2H)-carboxylate 172-6 (12.2 g, 98.89% purity) which was used for next step without any purification. LCMS (ES$^+$): m/z 443.75 [M+H]$^+$ Step-4: The compound 172-6 (8 g, 18.08 mmol) was dissolved in a mixture of methanol (20 mL), DCE (20 mL) and AcOH (2 ml), allowed to stir for 15 min, before adding sodium cyanoborohydride (5.68 g, 90.41 mmol). After addition, the reaction mixture was stirred for 24 h at room temperature, while monitoring by LCMS and TLC. The reaction mixture was filtered through Celite bed and filtrate was concentrated under vacuum. Crude compound purified by (silica gel mesh 100-200, and product eluted with 30% ethyl acetate in pet ether-neat ethyl acetate) column chromatography to afford tert-butyl-3,3-difluoro-4-[4-(2-fluoro-4-nitro-phenyl)piperazin-1-yl]piperidine-1-carboxylate 172-7 (7.2 g, 15.39 mmol, 85.11% yield, 98% purity). LCMS (ES$^+$): m/z 445.35 [M+H]$^+$ Step-5: To the stirred solution of tert-butyl 3, 3-difluoro-4-(4-(2-fluoro-4-nitrophenyl)piperazin-1-yl)piperidine-1-carboxylate 172-7 (5 g, 11.25 mmol) in ethyl acetate (100 mL) was added 10% Palladium on carbon wet (3.59 g, 33.75 mmol) at RT. The reaction mixture was stirred at RT under H$_2$ balloon pressure for 12 h was monitored by TLC. After the completion of the reaction, the reaction mixture was filtered-off through Celite and washed with ethyl acetate (200 mL). The filtrate was concentrated to obtain the crude product which was triturated with pentane, decanted the organic layer and the solidified product was filtered, dried well to afford tert-butyl 4-[4-(4-amino-2-fluoro-phenyl)piperazin-1-yl]-3,3-difluoro-piperidine-1-carboxylate 172-8 (3 g, 61.48% yield, 95.56% purity) as pale pink solid. LCMS (ES$^+$): m/z 415.56 [M+H]$^+$ Step-6: To a stirred solution of tert-butyl 4-[4-(4-amino-2-fluoro-phenyl)piperazin-1-yl]-3,3-difluoro-piperidine-1-carboxylate 172-8 (5 g, 12.06 mmol) in DMF (20 mL) taken in a seal tube was added 3-bromopiperidine-2,6-dione (6.95 g, 36.19 mmol) at rt followed by the addition of sodium bicarbonate (6.08 g, 72.38 mmol) and the reaction mixture was allowed to stir at 90° C. for 12 h. After the completion of the reaction, the reaction mixture was cooled to room temperature, diluted with ethyl acetate (200 mL) and filtered off through Celite. The filtrate washed with water (2×100 mL), brine (1×25 mL), dried over anhydrous Na$_2$SO$_4$, filtered and concentrated to get the crude product. The crude product was purified by column chromatography using silica gel (100/200 mesh) and the product eluted at 2-3% MeOH/DCM to afford (tert-butyl 4-(4-(4-((2,6-dioxopiperidin-3-yl)amino)-2-fluorophenyl)piperazin-1-yl)-3,3-difluoropiperidine-1-carboxylate 172-9 (4.2 g, 56.31% yield, 91.08% purity) as a purple solid. LCMS (ES$^+$): m/z 526.48 [M+H]$^+$ Step-7: To the stirred solution of tert-butyl 4-[4-[4-[(2,6-dioxo-3-piperidyl)amino]-2-fluoro-phenyl]piperazin-1-yl]-3,3-difluoro-piperidine-1-carboxylate 172-9 (7 g, 13.32 mmol) in 1,4-dioxane (30 mL) was added 4M HCl in dioxane (30.35 mL, 665.95 mmol, 30.35 mL) at 0° C. The reaction mixture was stirred at 0° C. for 30 minutes, slowly warmed to RT and stirred at RT for 6 h. After the completion of the reaction, the reaction mixture was concentrated and the residual mass was triturated with diethyl ether (3×100 mL) and the solid precipitated out was dried well to afford 3-[4-[4-(3,3-difluoro-4-piperidyl)piperazin-1-yl]-3-fluoroanilino]piperidine-2,6-dione 172-10 as HCl salt (5.54 g, 90.05% yield, 91.71% purity) as pale blue solid. LCMS (ES$^+$): m/z 426.22 [M+H]$^+$ Step 8: To a stirred solution of 3-[4-[4-(3,3-difluoro-4-piperidyl)piperazin-1-yl]-3-fluoro-anilino]piperidine-2,6-dione HCl 172-10 (5.65 g, 12.23 mmol) in DCE:MeOH (60:60 ml) were added 4 Å molecular sieves (3 g), acetic acid (0.797 g, 13.27 mmol) and sodium acetate (3.27 g, 39.82 mmol). The resulting solution was stirred for 10 min, then added 2,6-dimethoxy-4-(1,4,5-trimethyl-6-oxo-3-pyridyl)benzaldehyde 172-11 (4 g, 13.27 mmol) and heated the reaction mixture at 70° C. for 5 h then cooled it at RT and added Silia Bond Cyanoborohydride (3.85 g, 66.37 mmol). The stirring was continued at RT for 16 h, while monitoring the reaction by LCMS and TLC. After 16 h, the reaction mass was filtered through Celite, concentrated and purified by (Devisil silica gel, and product eluted with 1% to 5% MeOH in CH$_2$C2) column flash chromatography to afford compound was dissolved in dry DCM (10 ml) and TFA (5 ml) was added at 0° C., stirred it for 30 min. After 30 min, reaction crude was concentrated to dryness and obtained crude was washed with diethyl ether (3×20 ml) to afford 3-[4-[4-[1-[[2,6-dimethoxy-4-(1,4,5-trimethyl-6-oxo-3-pyridyl)phenyl]methyl]-3,3-difluoro-4-piperidyl]piperazin-1-yl]-3-fluoro-anilino]piperidine-2,6-dione TFA Compound 172 (3.21 g, 3.83 mmol, 28.85% yield, 98.40% purity) as a light green solid. $^1$H NMR (400 MHz, DMSO-d$_6$) δ 10.78 (s, 1H), 9.97 (s, 1H), 7.52 (s, 1H), 6.84 (t, J=9.3 Hz, 1H), 6.66 (s, 2H), 6.51 (d, J=15.0 Hz, 1H), 6.42 (d, J=8.5 Hz, 1H), 4.28-4.24 (m, 3H), 3.86 (s, 7H), 3.47 (s, 6H), 2.90 (bs, 9H), 2.76-2.68 (m, 1H), 2.53-2.54 (m, 1H), 2.08 (d, J=10.7 Hz, 9H), 1.91-1.87 (m, 1H). LCMS (ES$^+$): m/z 711.20 [M+H]$^+$ Synthesis of Compound 177

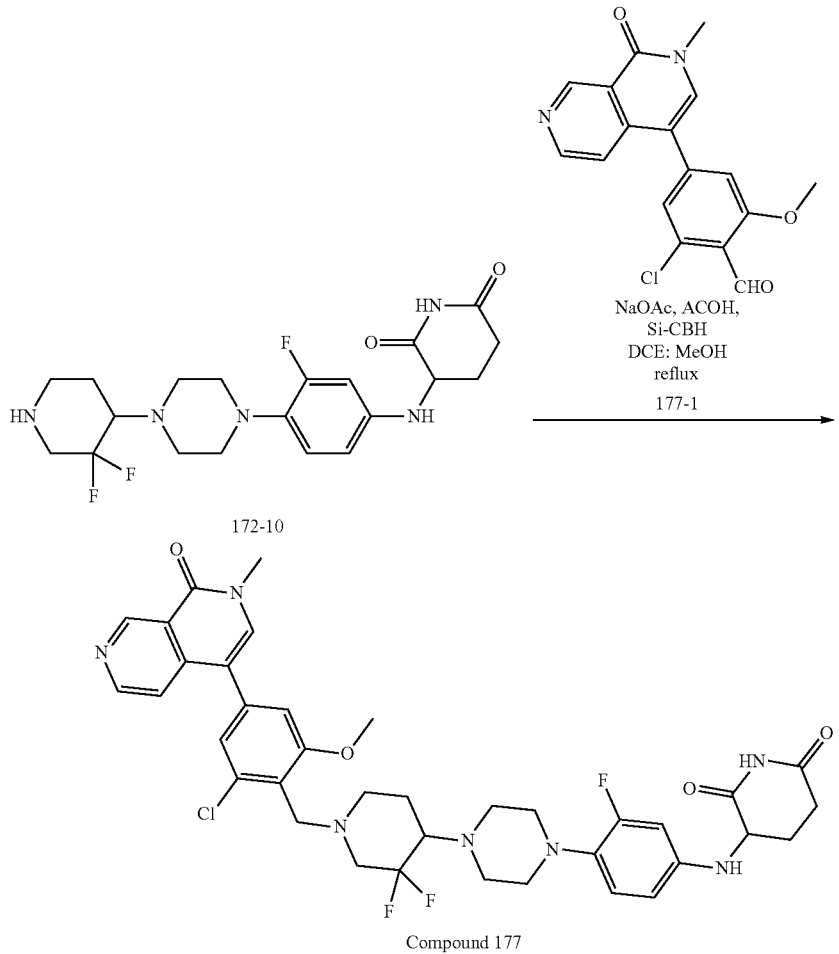

To a stirred solution of 3-[4-[4-(3,3-difluoro-4-piperidyl) piperazin-1-yl]-3-fluoro-anilino]piperidine-2,6-dione HCl salt 172-10 (4.22 g, 9.13 mmol) in DCE:MeOH (60:60 ml) were added 4 Å molecular sieves (4 g), acetic acid (0.822 g, 13.69 mmol) and sodium acetate (1.50 g, 18.25 mmol). The resulting solution was stirred for 10 min, then added 2-chloro-6-methoxy-4-(2-methyl-1-oxo-2,7-naphthyridin-4-yl)benzaldehyde 177-1 (3 g, 9.13 mmol) and heated the reaction mixture at 70° C. for 5 h then cooled it at RT and added Silica Bond Cyanoborohydride (2.64 g, 45.63 mmol). The stirring was continued at RT for 16 h, while monitoring the reaction by LCMS and TLC. After 16 h, the reaction mass was filtered through Celite, concentrated and crude compound was purified prep HPLC to afford 3-[4-[4-[1-[[2-chloro-6-methoxy-4-(2-methyl-1-oxo-2,7-naphthyridin-4-yl)phenyl]methyl]-3,3-difluoro-4-piperidyl]piperazin-1-yl]-3-fluoro-anilino]piperidine-2,6-dione TFA salt (1.50 g, 8.85% yield, 97.72% purity) Compound 177 as light yellow solid. $^1$H NMR (400 MHz, DMSO-d$_6$) δ 10.79 (s, 1H), 9.48

(s, 1H), 8.75 (d, J=5.7 Hz, 1H), 7.99 (s, 1H), 7.60 (d, J=5.8 Hz, 1H), 7.22 (s, 1H), 7.16 (s, 1H), 6.89 (t, J=9.1 Hz, 1H), 6.54 (d, J=14.9 Hz, 1H), 6.45 (d, J=8.7 Hz, 1H), 4.30-4.24 (m, 1H), 3.94 (s, 2H), 3.90 (s, 3H), 3.61 (s, 4H), 3.27-3.08 (m, 10H), 2.72-2.67 (m, 1H), 2.59-2.58 (m, 3H), 2.08-2.05 (m, 2H), 1.89-1.83 (m, 2H), LCMS (ES$^+$): m/z 738.33 [M+H]$^+$.

Prep HPLC Condition:
Column/dimensions: XSELECT C18 (19*150*5 um))
Mobile phase A 0.1% TFA IN WATER Mobile phase B: Acetonitrile (org) Gradient (Time/% B): 0/5, 3/5, 10/20, 14.35/20, 16.36/95, 19/95, 19.1/5, 22/5 Flow rate: 18 ml/min Compound 182 was prepared following the synthesis of Compound 177.

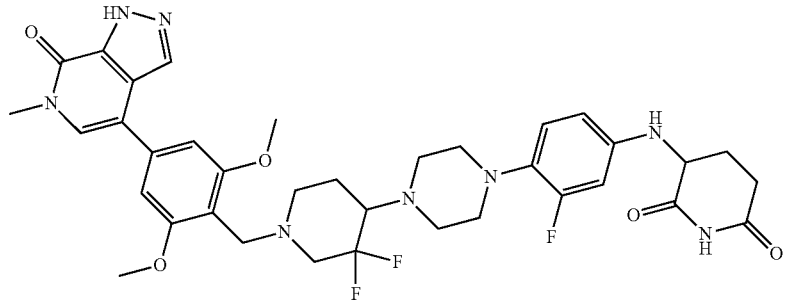 [SMILES: COc1cc(-c2cn(C)c(=O)c3[nH]ncc23)cc(OC)c1CN1CCC(N2CCN(c3ccc(NC4CCC(=O)NC4=O)cc3F)CC2)C(F)(F)C1]

$^1$H NMR (400 MHz, DMSO-d$_6$) δ 14.34 (s, 1H), 10.78 (s, 1H), 8.24 (s, 1H), 7.64 (s, 1H), 6.97 (s, 2H), 6.85 (t, J=9.2 Hz, 1H) 6.53-6.49 (m, 1H), 6.42 (d, J=8.5 Hz, 1H), 4.28-4.24 (m, 3H), 3.95 (s, 6H), 3.63 (s, 3H), 3.31-2.90 (m, 13H), 2.73-2.67 (m, 1H), 2.59-2.53 (m, 1H), 2.08-2.05 (m, 3H), 1.90-1.81 (m, 1H). LCMS (ES$^+$): m/z 723.1 [M+H]$^+$

Compound 183 was prepared following the synthesis of Compound 177.

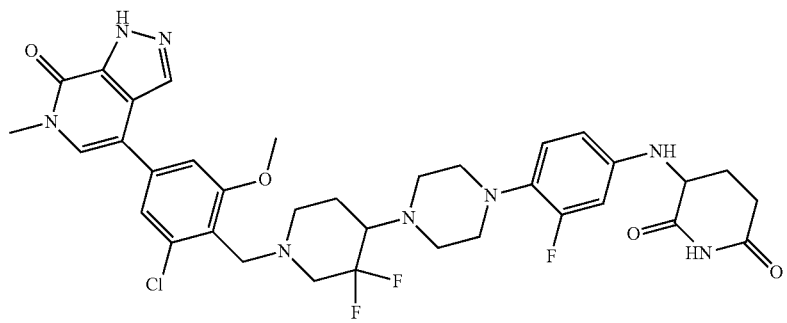 [SMILES: COc1cc(-c2cn(C)c(=O)c3[nH]ncc23)cc(Cl)c1CN1CCC(N2CCN(c3ccc(NC4CCC(=O)NC4=O)cc3F)CC2)C(F)(F)C1]

$^1$H NMR (400 MHz, DMSO-d$_6$) δ 10.79 (s, 1H), 8.22 (s, 1H), 7.66 (s, 1H), 7.35 (s, 1H), 7.25 (s, 1H), 7.22 (s, 1H), 6.88 (t, J=9.2 Hz, 1H), 6.55-6.50 (m, 1H), 6.45 (d, J=8.6 Hz, 1H), 4.28-4.26 (m, 1H), 3.96 (s, 7H), 3.61 (s, 3H), 3.26-3.07 (m, 11H), 2.77-2.67 (m, 1H), 2.59-2.56 (m, 1H), 2.08-2.05 (m, 2H), 1.90-1.83 (m, 2H). LCMS (ES$^+$): m/z 727.07 [M+H]$^+$

Compound 184 was prepared following the synthesis of Compound 177.

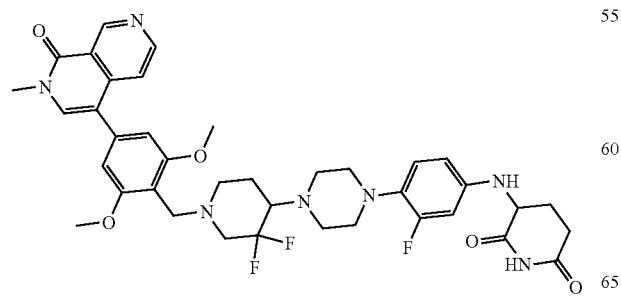

¹H NMR (400 MHz, DMSO-d₆) δ 10.78 (s, 1H), 9.49 (s, 1H), 8.76 (d, J=5.8 Hz, 1H), 7.92 (s, 1H), 7.65 (d, J=5.7 Hz, 1H), 6.89-6.83 (m, 3H), 6.54-6.42 (m, 2H), 4.30-4.26 (m, 3H), 3.89 (s, 7H), 3.78-3.62 (m, 1H), 3.67 (s, 3H), 3.55-3.37 (m, 3H), 2.94 (bs, 8H), 2.77-2.72 (m, 1H), 2.57 (t, J=8.8 Hz, 1H), 2.18-2.05 (m, 3H), 1.94-1.87 (m, 1H). LCMS (ES⁺): m/z 734.12 [M+H]⁺

Compound 185 was prepared following the synthesis of Compound 177.

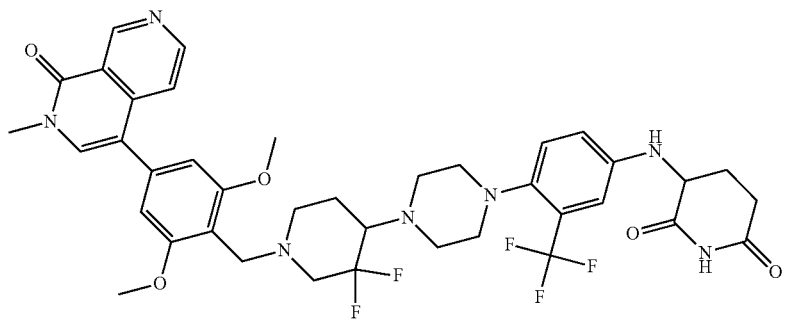 [SMILES: COc1cc(-c2cn(C)c(=O)c3cnccc23)cc(OC)c1CN1CCC(N2CCN(c3ccc(NC4CCC(=O)NC4=O)cc3C(F)(F)F)CC2)C(F)(F)C1]

¹H NMR (400 MHz, DMSO-d₆) δ 10.78 (s, 1H), 9.45 (s, 1H), 8.73 (d, J=5.6 Hz, 1H), 7.90 (s, 1H), 7.59 (d, J=5.6 Hz, 1H), 7.32 (d, J=8.6 Hz, 1H), 6.91-6.84 (m, J=5.6 Hz, 2H), 6.75 (s, 2H), 6.17 (d, J=7.9 Hz, 1H), 4.38-4.34 (m, 1H), 3.82 (s, 6H), 3.67 (s, 2H), 3.60 (s, 3H), 2.98-2.95 (m, 2H), 2.78-2.54 (m, 11H), 2.34-2.33 (m, 1H), 2.17 (t, J=9.9 Hz, 1H), 2.09-2.05 (m, 1H), 1.91-1.70 (m, 3H) LCMS (ES⁺): m/z 784.02 [M+H]⁺

Compound 186 was prepared following the synthesis of Compound 177.

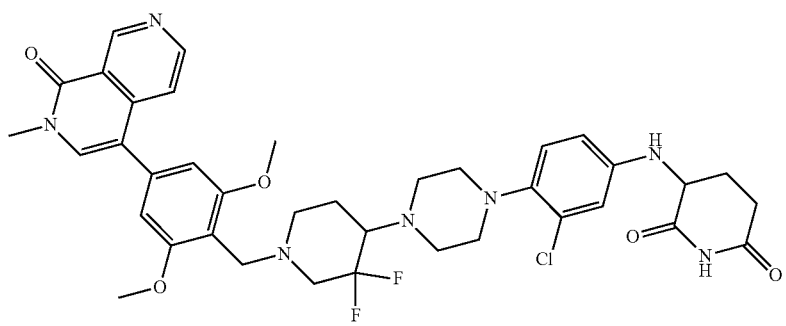 [SMILES: COc1cc(-c2cn(C)c(=O)c3cnccc23)cc(OC)c1CN1CCC(N2CCN(c3ccc(NC4CCC(=O)NC4=O)cc3Cl)CC2)C(F)(F)C1]

¹H NMR (400 MHz, DMSO-d₆) δ 10.78 (s, 1H), 9.48 (s, 1H), 8.75 (d, J=5.8 Hz, 1H), 7.98 (s, 1H), 7.59 (d, J=5.7 Hz, 1H), 7.22 (s, 1H), 7.16 (s, 1H), 6.98 (d, J=8.7 Hz, 1H), 6.77 (d, J=2.5 Hz, 1H), 6.62-6.61 (m, 1H), 5.91 (bs, 1H), 4.31-4.29 (m, 1H), 3.90 (s, 3H), 3.61 (s, 3H), 3.54-2.51 (m, 17H), 2.33-2.03 (m, 2H), 1.92-1.83 (m, 2H) LCMS (ES⁺): m/z 754.12 [M+H]⁺

Compound 187 was prepared following the synthesis of Compound 177.

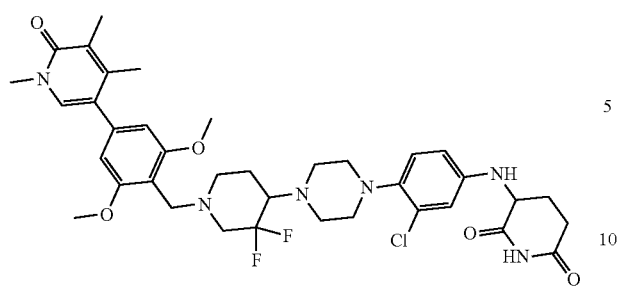

¹H NMR (400 MHz, DMSO-d₆) δ 10.77 (s, 1H), 10.04 (s, 1H), 7.52 (s, 1H), 6.96 (d, J=8.7 Hz, 1H), 6.75 (d, J=2.4 Hz, 1H), 6.67 (s, 2H), 6.62-6.57 (m, 1H), 4.31-4.20 (m, 3H), 3.86 (s, 7H), 3.47 (s, 3H), 3.35 (bs, 3H), 2.87-2.67 (m, 11H), 2.08 (d, J=11.2 Hz, 9H), 1.81-1.85 (m, 1H). LCMS (ES⁺): m/z 727.56 [M+H]⁺

Compound 188 was prepared following the synthesis of Compound 177.

¹H NMR (400 MHz, DMSO-d₆) δ 10.77 (s, 1H), 10.04 (s, 1H), 7.52 (s, 1H), 6.96 (d, J=8.7 Hz, 1H), 6.75 (d, J=2.4 Hz, 1H), 6.67 (s, 2H), 6.62-6.57 (m, 1H), 4.31-4.20 (m, 3H), 3.86 (s, 7H), 3.47 (s, 3H), 3.35 (bs, 3H), 2.87-2.67 (m, 11H), 2.08 (d, J=11.2 Hz, 9H), 1.81-1.85 (m, 1H). LCMS (ES⁺): m/z 750.05 [M+H]⁺

Compound 189 was prepared following the synthesis of Compound 177.

¹H NMR (400 MHz, DMSO-d₆) δ 10.78 (s, 1H), 9.48 (s, 1H), 8.76 (d, J=5.8 Hz, 1H), 7.96 (s, 1H), 7.62 (d, J=5.7 Hz, 1H), 7.09-7.01 (m, 3H), 6.87 (t, J=9.0 Hz 1H), 6.55-6.51 (m, 1H), 6.45-6.42 (m, 1H), 4.28-4.25 (m, 1H), 3.91 (s, 5H), 3.61 (s, 3H), 3.39-2.55 (m, 15H), 2.08-2.05 (m, 2H), 1.91-1.82 (m, 2H). LCMS (ES⁺): m/z 722.12 [M+H]⁺

Compound 190 was prepared following the synthesis of Compound 177.

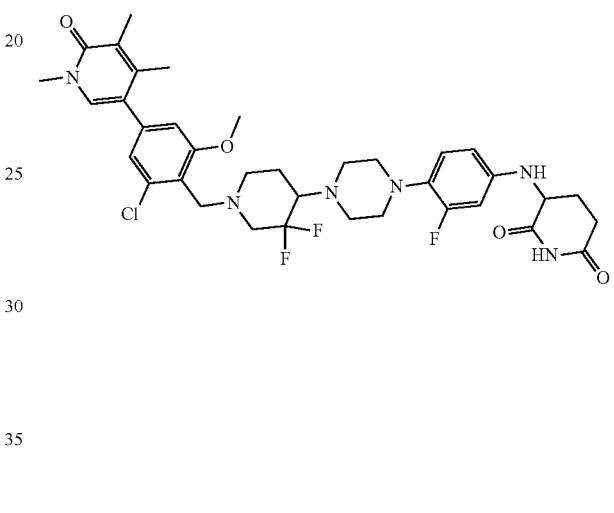

¹H NMR (400 MHz, DMSO-d₆) δ 10.78 (s, 1H), 7.57 (s, 1H), 7.03-6.94 (m, 2H), 6.88 (t, J=9.0 Hz, 1H), 6.54-6.51 (m, 1H), 6.44-6.43 (m, 1H), 4.29-4.25 (m, 1H), 4.12-3.90 (m, 4H), 3.86 (s, 3H), 3.46 (s, 3H), 3.28-2.58 (m, 13H), 2.06 (d, J=3.2 Hz, 8H), 1.88-1.84 (m, 2H). LCMS (ES⁺): m/z 715.31 [M+H]⁺.

Compound 191 was prepared following the synthesis of Compound 177.

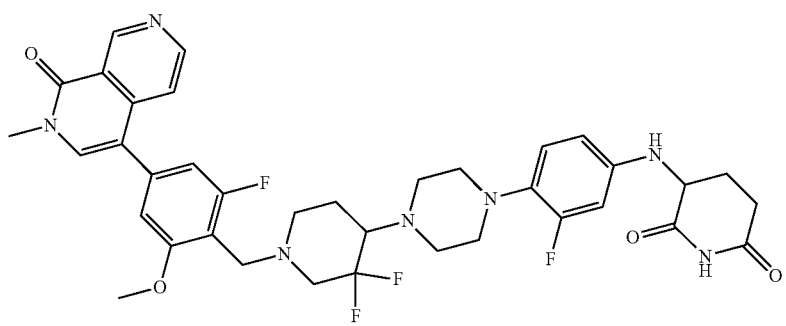 [SMILES: COc1cc(-c2cn(C)c(=O)c3cnccc23)cc(F)c1CN1CCC(N2CCN(c3ccc(NC4CCC(=O)NC4=O)cc3F)CC2)C(F)(F)C1]

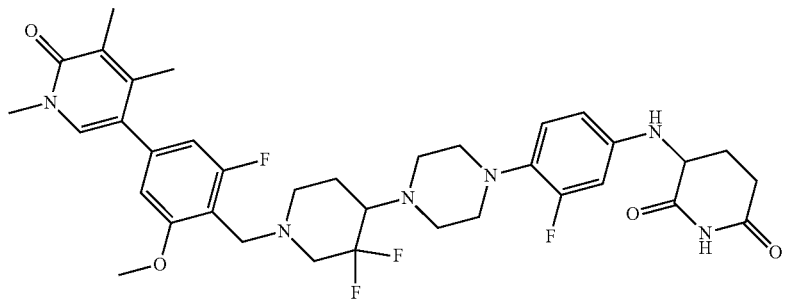 [SMILES: COc1cc(-c2cn(C)c(=O)c(C)c2C)cc(F)c1CN1CCC(N2CCN(c3ccc(NC4CCC(=O)NC4=O)cc3F)CC2)C(F)(F)C1]

¹H NMR (400 MHz, DMSO-d₆) δ 10.78 (s, 1H), 7.56 (s, 1H), 6.90-6.83 (m, 3H), 6.55-6.51 (m, 1H), 6.45-6.43 (m, 1H), 4.29-4.25 (m, 1H), 3.87 (s, 2H), 3.46 (s, 3H), 3.28-2.59 (m, 16H), 2.07 (d, J=7.8 Hz, 8H), 1.90-1.82 (m, 2H) LCMS (ES⁺): m/z 699.17 [M+H]⁺

Compound 192 was prepared following the synthesis of Compound 177.

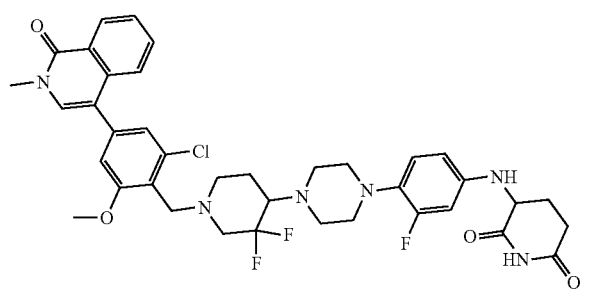 [SMILES: COc1cc(-c2cn(C)c(=O)c3ccccc23)cc(Cl)c1CN1CCC(N2CCN(c3ccc(NC4CCC(=O)NC4=O)cc3F)CC2)C(F)(F)C1]

¹H NMR (400 MHz, DMSO-d₆) δ 10.79 (s, 1H), 8.35 (d, J=7.4 Hz, 1H), 7.75-7.72 (m, 1H), 7.61-7.56 (m, 3H), 7.19-7.14 (m, 2H), 6.88 (t, J=9.2 Hz, 1H), 6.56-6.52 (m, 1H), 6.46-6.42 (m, 1H), 5.93 (s, 1H), 4.28-4.24 (m, 1H), 3.89 (s, 5H), 3.58 (s, 3H), 3.51-2.60 (m, 15H), 2.08-2.04 (m, 2H), 1.91-1.84 (m, 2H). LCMS (ES⁺): m/z 737.32 [M+H]⁺

10.79 (s, 1H), 8.35 (d, J=7.4 Hz, 1H), 7.75-7.72 (m, 1H), 7.61-7.56 (m, 3H), 7.19-7.14 (m, 2H), 6.88 (t, J=9.2 Hz, 1H), 6.56-6.52 (m, 1H), 6.46-6.42 (m, 1H), 5.93 (s, 1H), 4.28-4.24 (m, 1H), 3.89 (s, 5H), 3.58 (s, 3H), 3.51-2.60 (m, 15H), 2.08-2.04 (m, 2H), 1.91-1.84 (m, 2H). LCMS: [M+H]⁺ 737.32

Compound 193 was prepared following the synthesis of Compound 177.

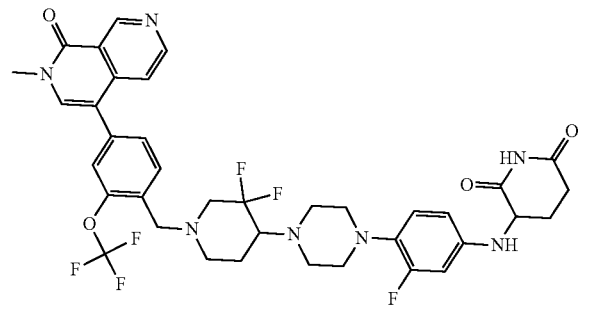 [SMILES: Cn1cc(-c2ccc(CN3CCC(N4CCN(c5ccc(NC6CCC(=O)NC6=O)cc5F)CC4)C(F)(F)C3)c(OC(F)(F)F)c2)c2ccncc2c1=O]

¹H NMR (400 MHz, DMSO-d₆) δ 10.79 (s, 1H), 9.53 (s, 1H), 8.76 (d, J=6.0 Hz, 1H), 8.06 (s, 1H), 7.72 (d, J=8.0 Hz, 1H), 7.63-7.52 (m, 2H), 7.50 (p, J=1.6 Hz, 1H), 6.92 (t, J=9.3 Hz, 1H), 6.56 (dd, J=15.0, 2.5 Hz, 1H), 6.46 (dd, J=8.7, 2.5 Hz, 1H), 4.29 (dd, J=11.5, 4.8 Hz, 1H), 3.83 (s, 3H), 3.62 (s, 3H), 3.34 (d, J=50.7 Hz, 5H), 3.17 (s, 4H), 3.04 (d, J=11.4 Hz, 1H), 2.84-2.52 (m, 4H), 2.38 (t, J=11.7 Hz, 1H), 2.26 (s, 1H), 2.16-2.00 (m, 1H), 1.88 (td, J=14.7, 12.1, 7.2 Hz, 2H). LCMS (ES⁺): m/z 758.32[M+H]⁺.

Compound 194 was prepared following the synthesis of Compound 177.

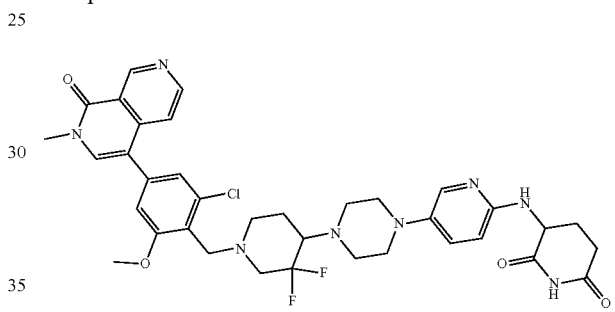

¹H NMR (400 MHz, DMSO-d₆): δ 11.07 (s, 1H), 9.48 (s, 1H), 8.75 (d, J=5.8 Hz, 1H), 8.29 (s, 1H), 7.98 (s, 1H), 7.59 (d, J=5.7 Hz, 1H), 7.35 (s, 1H), 7.22 (s, 1H), 7.16 (s, 1H), 7.08 (d, J=10.1 Hz, 1H), 4.65-4.62 (m, 1H), 3.89 (s, 5H), 3.61 (s, 3H), 3.50-3.01 (m, 12H), 2.77-2.62 (m, 3H), 2.13-2.07 (m, 2H), 1.93-1.87 (m, 2H). LCMS (ES⁺): m/z 721.24 [M+H]⁺

Compound 195 was prepared following the synthesis of Compound 177.

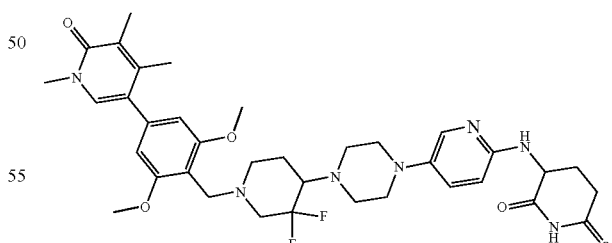

¹H NMR (400 MHz, DMSO-d₆) δ 11.06 (s, 1H), 8.29 (s, 1H), 7.91 (d, J=8.3 Hz, 1H), 7.52 (s, 1H), 7.33 (s, 1H), 7.07 (d, J=9.4 Hz, 1H), 6.67 (s, 2H), 4.68-4.64 (m, 1H), 4.21 (bs, 2H), 3.86 (s, 8H), 3.47 (s, 4H), 3.30 (bs, 3H), 3.05 (bs, 4H), 2.88 (bs, 4H), 2.70-2.67 (m, 2H), 2.14-2.07 (m, 10H). LCMS (ES⁺): m/z 694.36 [M+H]⁺

Compound 196 was prepared following the synthesis of Compound 177.

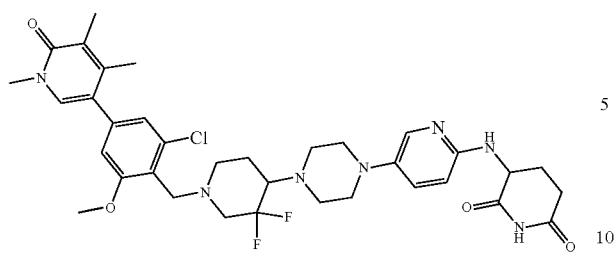

$^1$H NMR (400 MHz, DMSO-d$_6$) δ 11.07 (s, 1H), 8.30 (bs, 1H), 7.93 (d, J=8.2 Hz, 1H), 7.57 (s, 1H), 7.34 (s, 1H), 7.08-6.97 (m, 3H), 4.67-4.65 (m, 1H), 3.86 (s, 5H), 3.47 (s, 3H), 3.28-2.98 (m, 12H), 2.72-2.67 (m, 2H), 2.13-2.10 (m, 2H), 2.06 (d, J=2.8 Hz, 6H), 1.94-1.87 (m, 2H). LCMS (ES$^+$): m/z 698.22 [M+H]$^+$.

Synthesis of Four Stereoisomers of Compound 172

Synthesis of 172-7-Peak-1 and 172-7-Peak-2

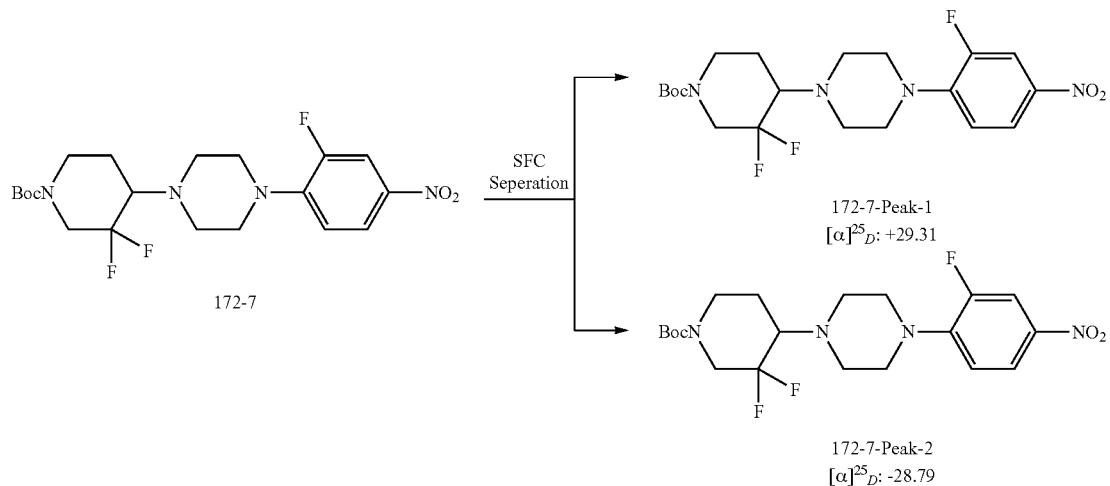 [SMILES: CC(C)(C)OC(=O)N1CCC(N2CCN(c3ccc([N+](=O)[O-])cc3F)CC2)C(F)(F)C1 ; CC(C)(C)OC(=O)N1CCC(N2CCN(c3ccc([N+](=O)[O-])cc3F)CC2)C(F)(F)C1 ; CC(C)(C)OC(=O)N1CCC(N2CCN(c3ccc([N+](=O)[O-])cc3F)CC2)C(F)(F)C1]

20 g Compound-7 was separated by SFC to afford 8.5 g of 172-7-Peak-1 (First eluted peak during SFC) and 8.5 g of 172-7-Peak-2 (Second eluted peak during SFC separation)
Preparative SFC Conditions:
Column/dimensions: Chiralpak-IC (30×250) mm, 5
% CO$_2$: 70%
% Co solvent: 30% (MeOH)
Total Flow: 100.0 g/min
Back Pressure: 100 bar
Temperature: 30° C.
UV: 220 nm
Instrument details: Make/Model: SFC-200
Synthesis of Compound 173 and Compound 174:

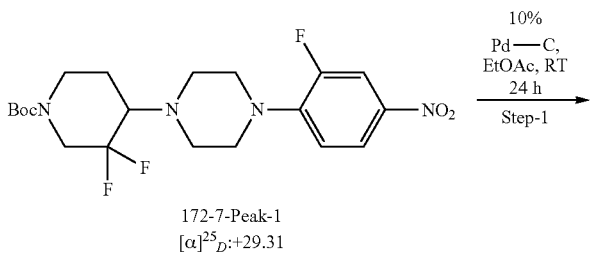

-continued
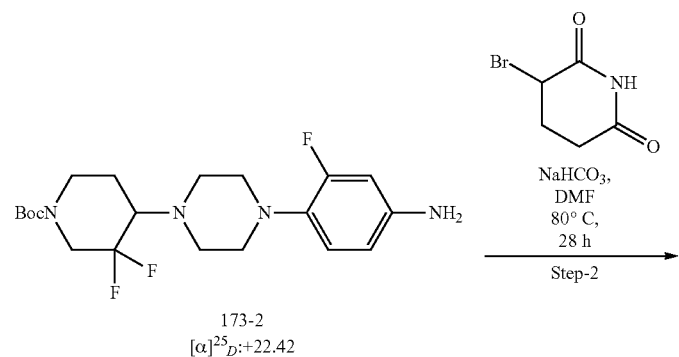
173-2
$[\alpha]^{25}_D$:+22.42
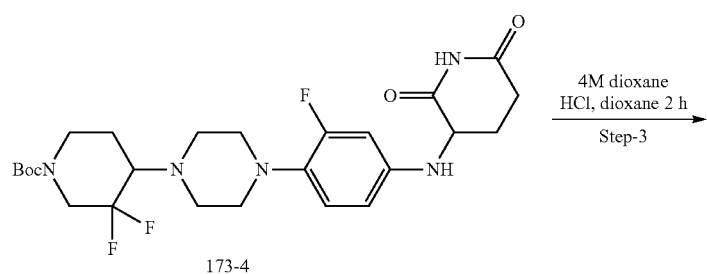
173-4
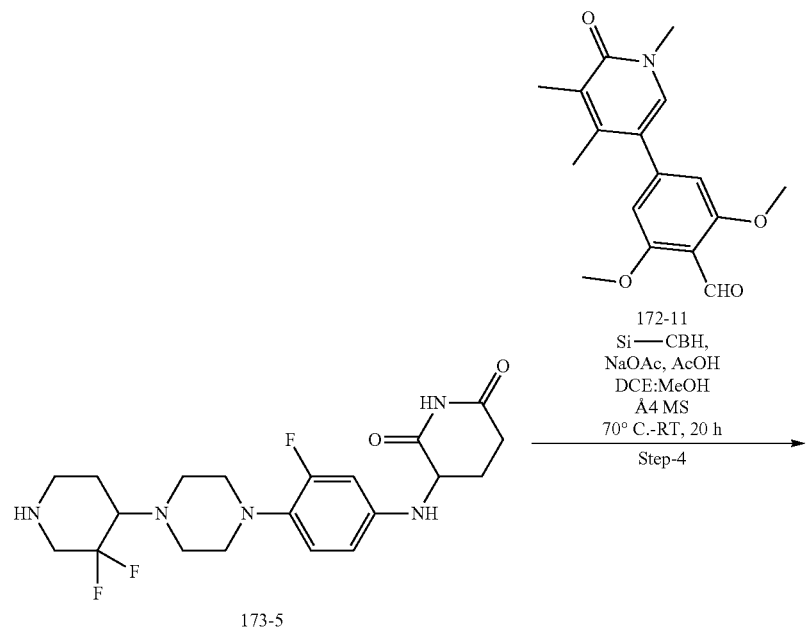
173-5

-continued

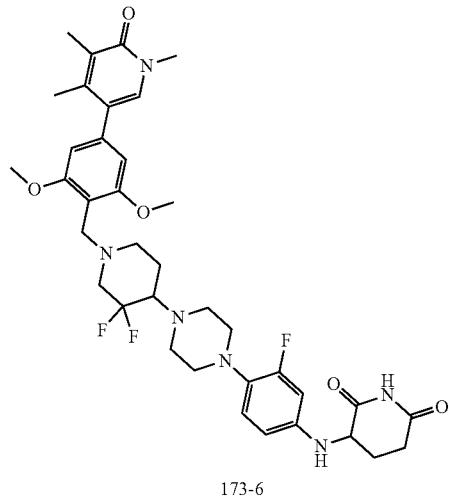

173-6 ii) SFC
iii) PrepHPLC
Step-6

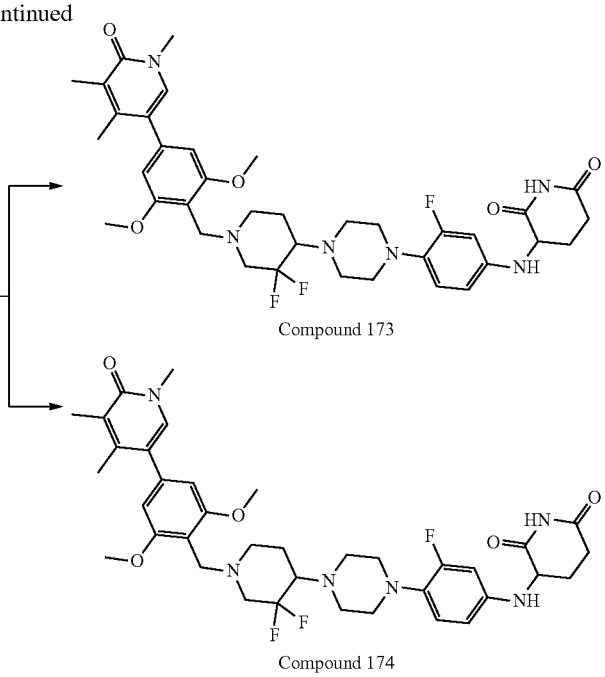

Compound 173

Compound 174

Step-1: A solution of tert-butyl 3,3-difluoro-4-[4-(2-fluoro-4-nitro-phenyl)piperazin-1-yl]piperidine-1-carboxylate 172-7-Peak-1 (4.5 g, 10.12 mmol) in Ethyl Acetate (40 mL) was degassed using nitrogen for 10 minutes and added wet 10% Palladium on carbon (2.15 g). The reaction mixture was again degassed using hydrogen and allowed to stir under hydrogen (under balloon pressure) for 24 h at RT. The progress of the reaction was monitored by TLC and LCMS. After completion of the reaction, reaction mixture was filtered through Celite bed and washed with ethyl acetate (200 ml). The filtrate was removed under vacuum to afford crude compound which was purified by (using 100-200 mesh silica gel and product compound eluted in 45% EtOAc in Pet-Ether) column chromatography, to afford tert-butyl 4-(4-(4-amino-2-fluorophenyl)piperazin-1-yl)-3,3-difluoropiperidine-1-carboxylate 173-2 (3.5 g, 8.44 mmol, 83.40% yield, 97% purity) as a yellow solid. LCMS (ES+): m/z 415.43 [M+H]+

Step-2: To a stirred solution of tert-butyl 4-(4-(4-amino-2-fluorophenyl)piperazin-1-yl)-3,3-difluoropiperidine-1-carboxylate 173-2 (5 g, 12.06 mmol) in DMF (30 mL) was added 3-bromopiperidine-2,6-dione 3 (6.95 g, 36.19 mmol), NaHCO$_3$ (10.13 g, 120.6 mmol) and stirred at 85° C. for 28 h, while monitoring by LCMS and TLC. After 16 h, the reaction was quenched with ice cold water (100 mL) and extracted with EtOAc (3×150 mL). The combined organic layer was dried over anhydrous Na$_2$SO$_4$ and concentrated to afford crude compound. Crude compound was purified by (silica gel mesh 100-200, 40% ethyl acetate in pet ether) column chromatography to afford tert-butyl tert-butyl 4-[4-[4-[(2,6-dioxo-3-piperidyl)amino]-2-fluoro-phenyl]piperazin-1-yl]-3,3-difluoro-piperidine-1-carboxylate (4.5 g, 8.47 mmol, 70.19% yield, 98.89% purity) as a purple solid. LCMS (ES+): m/z 526.72 [M+H]+.

Step-3: The solution of tert-butyl 4-[4-[4-[(2,6-dioxo-3-piperidyl)amino]-2-fluoro-phenyl]piperazin-1-yl]-3,3-difluoro-piperidine-1-carboxylate 173-4 (2.0 g, 3.81 mmol) in dioxane (5 ml) was added 4M HCl in Dioxane (10 mL) stir for 2 h at RT while monitoring by TLC and LCMS. After 2 h the reaction mixture was concentrated to dryness. The crude compound was triturated with Diethyl ether (2×40 ml) to afford 3-[4-[4-[3,3-difluoro-4-piperidyl]piperazin-1-yl]-3-fluoro-anilino]piperidine-2,6-dione 173-5 (1.6 g, 3.36 mmol, 88.29% yield, 97% purity) as a blue solid. LCMS (ES+): m/z 426.26 [M+H]+

Step-4: To a stirred solution of 3-((4-(4-(3,3-difluoropiperidin-4-yl)piperazin-1-yl)-3-fluorophenyl)amino)piperidine-2,6-dione HCl 173-5 (1.6 g, 3.76 mmol) in DCE:MeOH (20:20 ml) were added 4 Å molecular sieves (1.6 g), acetic acid (2 ml) and sodium acetate, anhydrous (0.616 g, 7.52 mmol). The resulting solution was stirred for 10 min, then added 2,6-dimethoxy-4-(1,4,5-trimethyl-6-oxo-3-pyridyl)benzaldehyde (1.13 g, 3.76 mmol) and heated the reaction mixture at 80° C. for 5 h then cooled it at RT and added Silica Bond Cyanoborohydride (1.12 g, 19.50 mmol). The stirring was continued at RT for 16 h, while monitoring the reaction by LCMS and TLC. After 16 h, the reaction mass was filtered through Celite, concentrated and purified (using Devisil silica and product eluted with 5% MeOH in CH$_2$C2) to afford 3-[4-[4-[-1-[[2,6-dimethoxy-4-(1,4,5-trimethyl-6-oxo-3-pyridyl)phenyl]methyl]-3,3-difluoro-4piperidyl]piperazin-1-yl]-3-fluoro-anilino]piperidine-2,6-dione (0.9 g, 1.20 mmol, 31.99% yield, 95% purity) as an off white solid as free base. LCMS (ES+): m/z 711.50 [M+H]+. To a stirred solution of 3-[4-[4-[1-[[2,6-dimethoxy-4-(1,4,5-trimethyl-6-oxo-3-pyridyl)phenyl]methyl]-3,3-difluoro-4-piperidyl]piperazin-1-yl]-3-fluoro-anilino]piperidine-2,6-dione (1 g, 1.41 mmol) free base in dry DCM (6 mL) was added TFA (0.160 g) at 0° C. and allowed to stirred at RT for 1 h. After 1 h the reaction mass was concentrated to dryness and triturated with diethyl ether (3×20 ml) to afford 3-[4-[4-[1-[[2,6-dimethoxy-4-(1,4,5-trimethyl-6-oxo-3-pyridyl)phenyl]methyl]-3,3-difluoro-4-piperidyl]piperazin-1-yl]-3-fluoro-anilino]piperidine-2,6-dione TFA salt 173-6 (1.0 g, 1.15 mmol, 81.87% yield, 95% purity) as a light green solid. LCMS (ES+): m/z [M+H]+ 711.50 SFC separation Procedure: 3.2 g of 173-6 was separated by SFC to obtain single stereoisomer. During SFC separation, fraction of Compound 173 and Compound 174 were collected in TFA buffer to avoid Glutarimide ring opening. As SFC separation method involved use of basic additive, the obtained fraction of Compound 173 and Compound 174 were submitted for prep HPLC purification to remove the salt.

| Preparative SFC Conditions Column/dimensions: | |
| --- | --- |
| Column/dimensions: | Chiralpak-AS-H (30 × 250) mm, 5μ |
| % CO2: | 60% |
| % Co solvent: | 40% (0.2% 7M Methanolic Ammonia in Acetonitile:Methanol)(1:1) |
| Total Flow: | 110.0 g/min |
| Back Pressure: | 100 bar |
| Temperature: | 30° C. |
| UV: | 220 nm |
| Solubility: | Methanol |

Prep-HPLC Method:
Column/dimensions: XTERRA C18 (19*150, 5 um) Mobile phase A: 0.050% TFA IN WATER MobilephaseB: 100% AcetonitrileGradient (Time/% B)0/5, 5/5, 12/30, 16/30, 16.1/100, 18/100, 18.1/5, 21/5 Flow rate:17 ml/min Solubility: WATE+ACN
(Note: the first eluted peak during SFC separation was assigned as Compound 173 and second eluted peak was assigned as Compound 174).

| Structure | Spectral data |
| --- | --- |
| 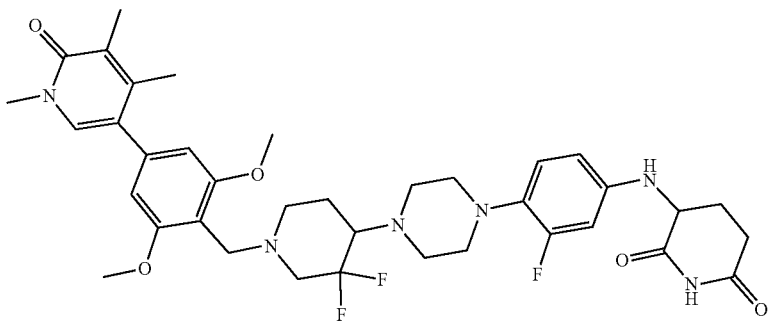<br>Compound 173 | $^1$H NMR (400 MHz, DMSO-d$_6$) δ 10.78 (s, 1H), 10.04 (s, 1H), 7.52 (s, 1H), 6.86 (t, J = 9.1 Hz, 1H), 6.67 (s, 2H), 6.53 – 6.45 (m, 1H), 6.43 (d, J = 8.6 Hz, 1H), 4.28 – 4.20 (m, 2H), 3.86 (s, 7H), 3.47 (s, 3H), 3.34 (bs, 4H), 2.92 (bs, 9H), 2.77 – 2.58 (m, 2H), 2.08 (d, J = 11.1 Hz, 9H), 1.90 – 1.83 (m, 1H). LCMS (ES$^+$): m/z 711.69. [M + H]$^+$, [a]$^{25}_D$: +34.14 |
| Compound 174 | $^1$H NMR (400 MHz, DMSO-d$_6$) δ 10.78 (s, 1H), 10.04 (s, IH), 7.52 (s, 1H), 6.85 (t, J = 9.1 Hz, 1H), 6.67 (s, 2H), 6.53 – 6.50 (m, 1H), 6.43 (d, J = 8.6 Hz, 1H), 4.54 – 4.24 (m, 3H), 3.86 (s, 7H), 3.47 (s, 3H), 3.34 (bs, 3H), 2.91 (bs, 9H), 2.77 – 2.58 (m, 2H), 2.08 (d, J = 11.1 Hz, 9H), 1.87 – 1.83 (m, 1H). LCMS (ES$^+$): m/z 711.24 [M + H]$^+$, [α]$^{25}_D$: −15.12 |

Synthesis of Compound 175 and Compound 176 was Prepared Following the Synthesis of Compound 173 and Compound 174, Staring with 172-7-Peak-2

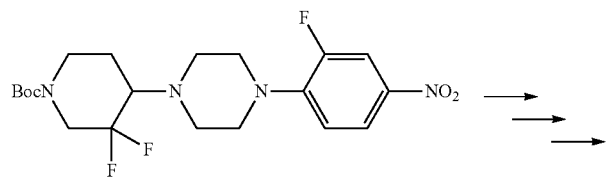

172-7-Peak-2
[α]$^{25}_D$: -28.79

-continued

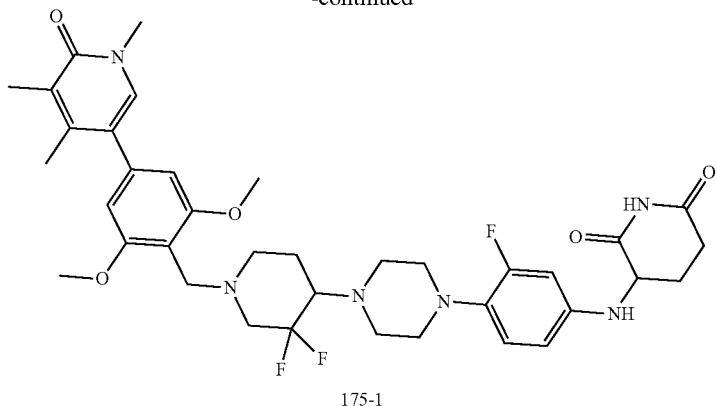
175-1

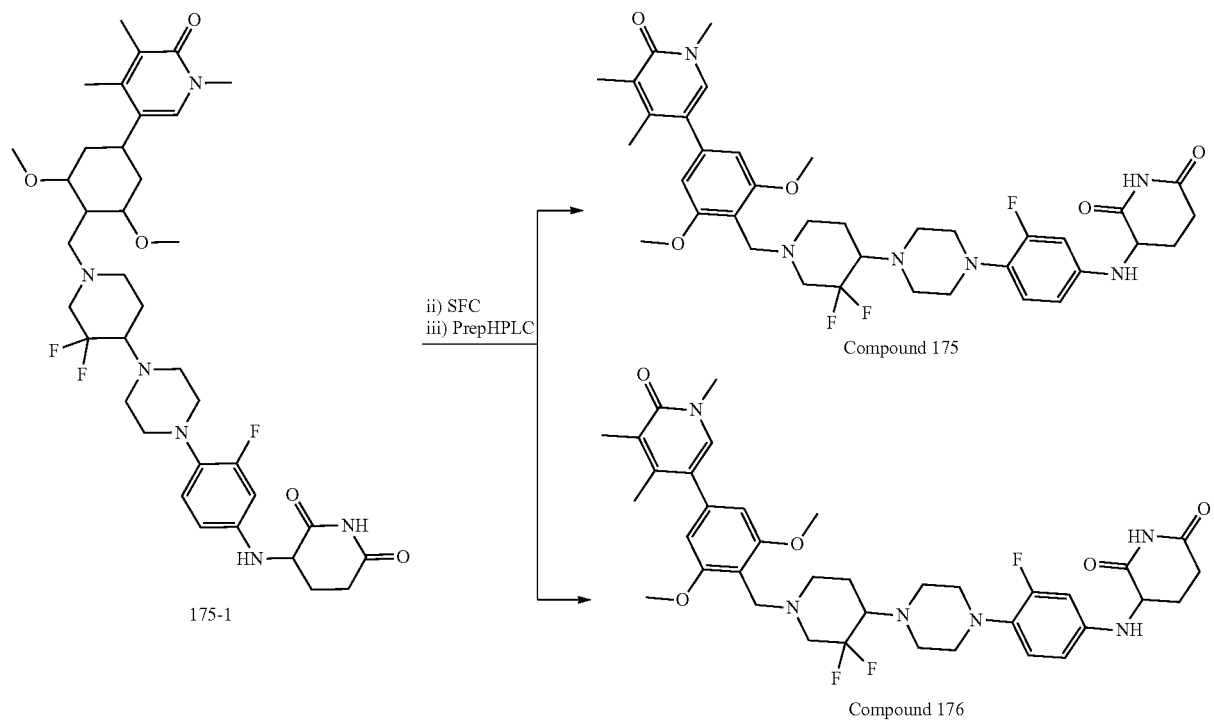

SFC separation procedure: 3.6 g of 175-1 (diastereomer mixture) was separated by SFC to obtain single stereoisomer. During SFC separation, fractions of Compound 175 and of Compound 176 were collected in TFA buffer to avoid Glutarimide ring opening. As SFC separation method involved use of basic additive, the obtain fractions of Compound 175 and of Compound 176 were submitted for prepHPLC purification to remove the salt.
Preparative SFC Conditions:
Column/dimensions: Chiralpak AS-H (30×250) mm, 5μ
% $CO_2$: 60%
% Co solvent: 40% (0.2% 7M Methanolic ammonia in ACN:MeOH)
Total Flow: 110.0 g/min
Back Pressure: 100 bar
Temperature: 30° C.
UV: 220 nm
Instrument details: Make/Model: SFC-150-I
Prep-HPLC Conditions:
Mobile Phase (A): 0.1% TFA in H2O Mobile Phase (B): 100% Acetonitrile
Flow Rate: 18 ml/min
Column: SUNFIRE C18, 5 μm (19×150 mm)
(Note: the first eluted peak during SFC separation was assigned as Compound 175 and second eluted peak was assigned as Compound 176)

| Structure | Spectral data |
|---|---|
| 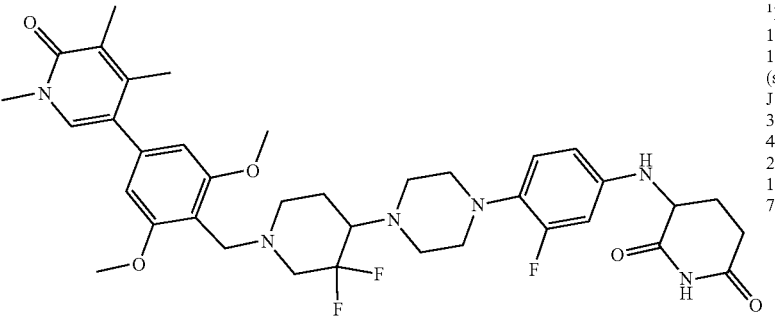<br>Compound 175 | ¹H NMR (400 MHz, DMSO-d₆) δ 10.78 (s, 1H), 10.01 (s, 1H), 7.52 (s, 1H), 6.85 (t, J = 9.3 Hz, 1H), 6.67 (s, 2H), 6.53 – 6.50 (m, 1H), 6.43 (d, J = 8.5 Hz, 1H), 4.28 – 4.19 (m, 2H), 3.86 (s, 8H), 3.47 (s, 3H), 3.35 (bs, 4H), 2.92 (bs, 8H), 2.77 – 2.55 (m, 2H), 2.08 (d, J = 11.1 Hz, 9H), 1.90 – 1.83 (m, 1H). LCMS (ES⁺): m/z 711.41 [M + H]⁺, [α]²⁵_D: = +19.44 |
| 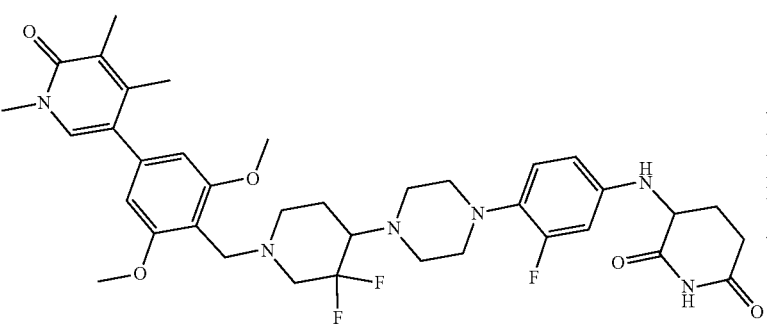<br>Compound 176 | ¹H NMR (400 MHz, DMSO-d₆) δ 10.78 (s, 1H), 10.03 (s, 1H), 7.52 (s, 1H), 6.85 (t, J = 9.2 Hz, 1H), 6.67 (s, 2H), 6.54 – 6.50 (m, 1H), 6.43 (d, J = 8.5 Hz, 1H), 4.35 – 4.24 (m, 2H), 3.86 (s, 6H), 3.68 (bs, 2H), 3.47 (s, 3H), 3.35 (s, 4H), 2.93 (bs, 8H), 2.78 – 2.55 (m, 2H), 2.08 (d, J = 11.1 Hz, 9H), 1.90 – 1.81 (m, 1H). LCMS (ES⁺): m/z 711.58 [M + H]⁺, [α]²⁵_D: = −32.26 |
Synthesis of Compound 179 and Compound 180
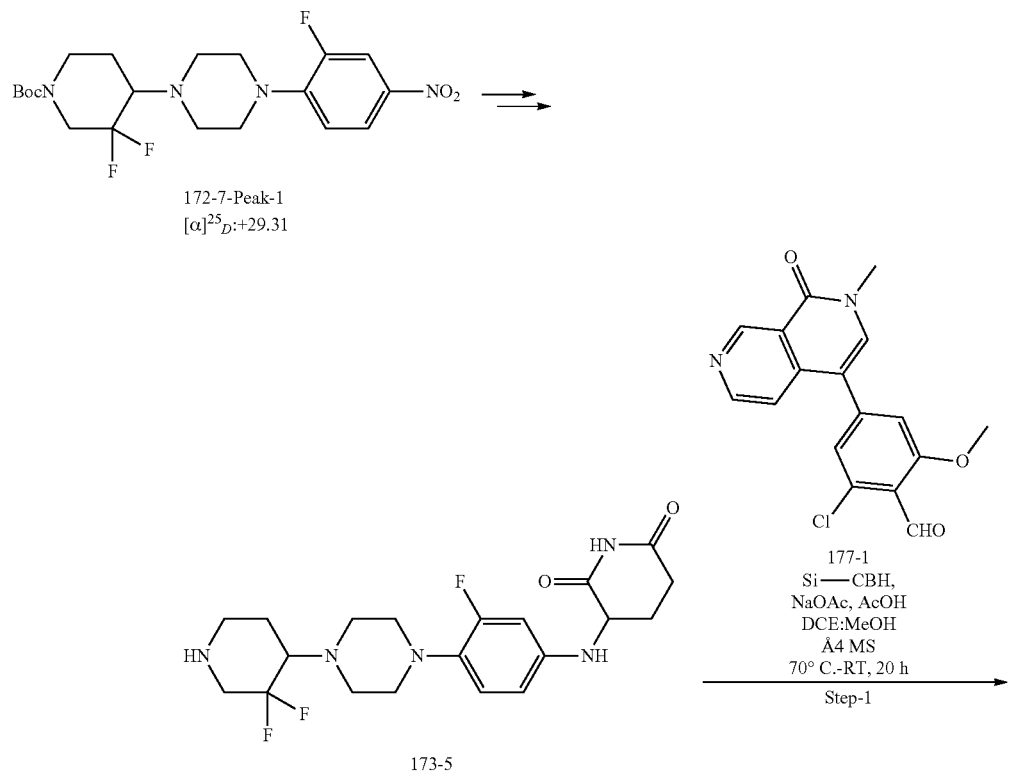

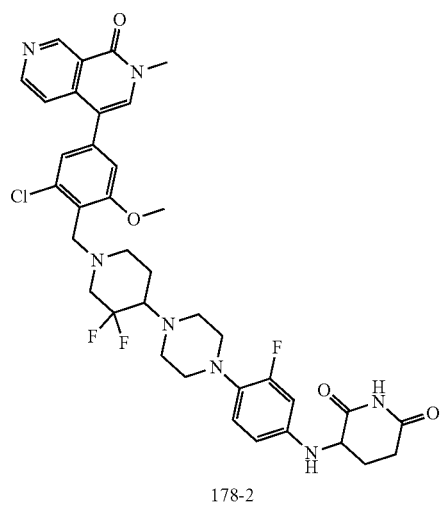

178-2 i) SFC
ii) PrepHPLC

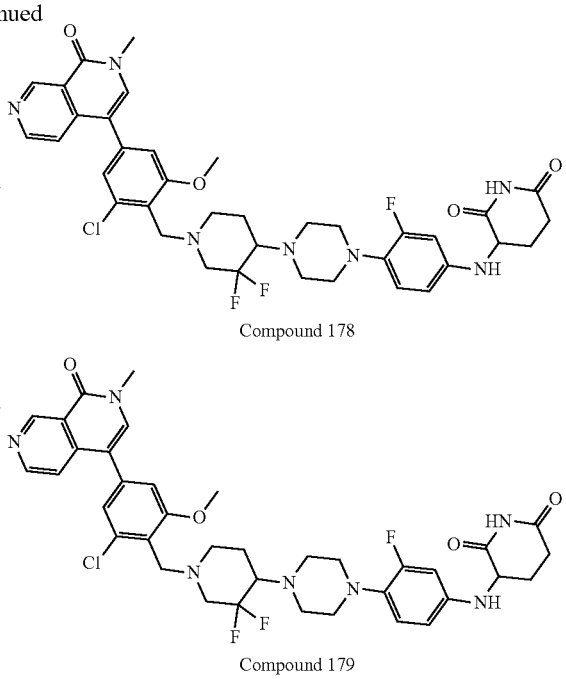

Compound 178

Compound 179

Step-1: To a stirred solution of 3-[4-[4-(3,3-difluoro-4-piperidyl)piperazin-1-yl]-3-fluoro-anilino]piperidine-2,6-dione.HCl 173-5 (1.41 g, 3.04 mmol) in DCE:MeOH (30:30 ml) were added 4 Å molecular sieves (1 g), Acetic Acid (0.273 g, 4.56 mmol) and Sodium acetate (0.499 g, 6.08 mmol). The resulting solution was stirred for 10 min, then added 2-chloro-6-methoxy-4-(2-methyl-1-oxo-2,7-naphthyridin-4-yl)benzaldehyde (1 g, 3.04 mmol) and heated the reaction mixture at 70° C. for 5 h then cooled it at RT and added Silia Bond Cyanoborohydride (0.881 g, 15.21 mmol). The stirring was continued at RT for 16 h, while monitoring the reaction by LCMS and TLC. After 16 h, the reaction mass was filtered through Celite, concentrated and purified by (using Devisil silica and product eluted with 5% MeOH in $CH_2Cl_2$) to afford 3-[4-[4-[1-[[2-chloro-6-methoxy-4-(2-methyl-1-oxo-2,7-naphthyridin-4-yl)phenyl]methyl]-3,3-difluoro-4-piperidyl]piperazin-1-yl]-3-fluoro-anilino]piperidine-2,6-dione free base (0.9 g, 0.978 mmol, 32.18% yield, 80.29% purity) as green solid. To a stirred solution of 3-[4-[4-[1-[[2-chloro-6-methoxy-4-(2-methyl-1-oxo-2,7-naphthyridin-4-yl)phenyl]methyl]-3,3-difluoro-4-piperidyl]piperazin-1-yl]-3-fluoro-anilino]piperidine-2,6-dione free base (3 g, 4.06 mmol) in dry $CH_2Cl_2$ (10 mL) was added TFA (2 mL) at 0° C. and allowed to stirred at RT for 1 h. After 1 h the reaction mass was concentrated to dryness and triturated with diethyl ether (2×100 ml) to afford 3-[4-[4-[1-[[2-chloro-6-methoxy-4-(2-methyl-1-oxo-2,7-naphthyridin-4-yl)phenyl]methyl]-3,3-difluoro-4-piperidyl]piperazin-1-yl]-3-fluoro-anilino]piperidine-2,6-dione. TFA 178-2 (3.4 g, 3.34 mmol, 82.13% yield, 83.66% purity). as a light green solid. LCMS (ES$^+$): m/z 738.45 [M+H]$^+$ SFC separation of 178-2

3.4 g of 178-2 was separated by SFC to obtain single stereoisomer. During SFC separation fraction of Compound 178 and Compound 179 were collected in TFA buffer to avoid Glutarimide ring opening. As SFC separation method involved use of basic additive, the obtain fractions of Compound 178 and of Compound 179 were submitted again for prepHPLC purification to remove the salt.

| Preparative SFC Conditions Column/dimensions: | |
|---|---|
| Column/dimensions: | Chiiralpak-AS-H (30 × 250) mm, 5μ |
| % CO2: | 55% |
| % Co solvent: | 45% (0.2% 7M Methanolic Ammonia in ACN:MEOH)(70:30) |
| Total Flow: | 100.0 g/min |
| Back Pressure: | 100 bar |
| Temperature: | 30° C. |
| UV: | 254 nm |
| Solubility: | MeOH + ACN |

Prep-HPLC Method:

Column/dimensions XSELECT-C18 (50*19*5μ)

Mobile phase A:0.05% TFAWATER (AQ)

Mobile phase B: ACN(ORG)

(Note: the first eluted peak during SFC separation was assigned as Compound 178 and second eluted peak was assigned as Compound 179).

| Structure | Spectral data |
|---|---|
| 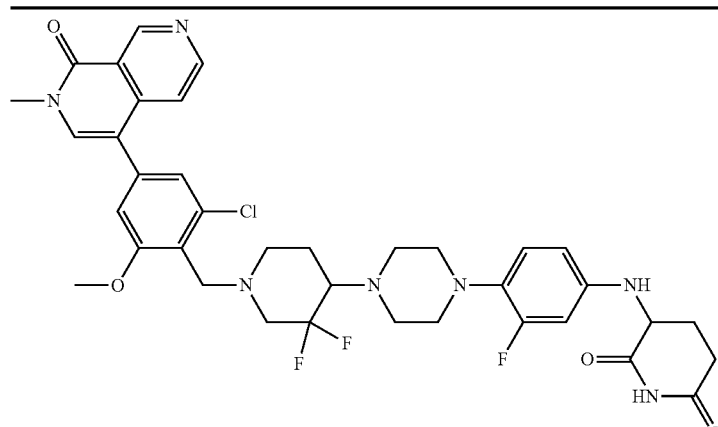<br>Compound 178 | ¹H NMR (400 MHz, DMSO-d₆) δ 10.79 (s, 1H), 9.48 (s, 1H), 8.75 (d, J = 5.8 Hz, 1H), 7.99 (s, 1H), 7.61 (d, J = 5.8 Hz, 1H), 7.22 (s, 1H), 7.16 (s, 1H), 6.89 (t, J = 9.1 Hz, 1H), 6.53 – 6.52 (m, 1H), 6.46 – 6.44 (m, 1H), 4.28 – 4.26 (m, 1H), 3.90 (s, 6H), 3.61 (s, 3H), 3.28 – 3.17 (m, 10H), 2.76 – 2.67 (m, 2H), 2.59 – 2.55 (m, 2H), 2.08 – 2.05 (m, 2H), 1.90 – 1.84 (m, 2H). LCMS (ES⁺): m/z 738.33 [M + H]⁺; [α]²⁵_D = +27.22 |
| 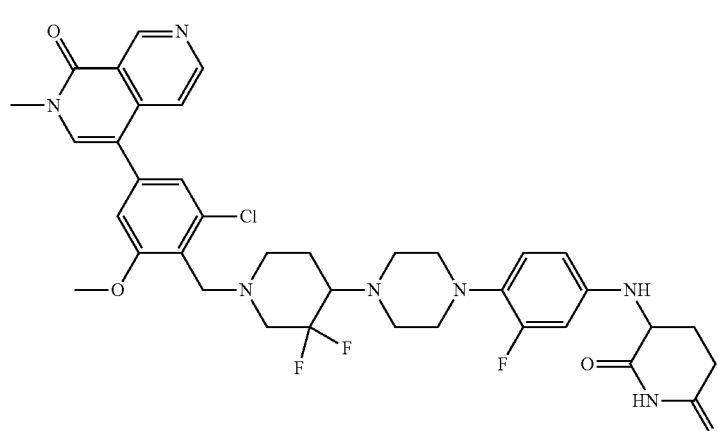<br>Compound 179 | ¹H NMR (400 MHz, DMSO-d₆) δ 10.79 (s, 1H), 9.48 (s, 1H), 8.75 (d, J = 5.7 Hz, 1H), 7.98 (s, 1H), 7.59 (d, J = 5.7 Hz, 1H), 7.22 (s, 1H), 7.16 (s, 1H), 6.88 (t, J = 9.1 Hz, 1H), 6.53 – 6.50 (m, 1H), 6.46 – 6.44 (m, 1H), 4.28 – 4.24 (m, 1H), 3.90 (s, 5H), 3.61 (s, 3H), 3.42 – 3.26 (m, 11H), 2.77 – 2.67 (m, 1H), 2.59 – 2.54 (m, 3H), 2.08 – 2.04 (m, 2H), 1.90 – 1.88 (m, 2H). LCMS (ES⁺): m/z 738.45 [M + H]⁺; [α]²⁵_D = −13.80 |

Synthesis of Compound 180 and Compound 181 was Prepared Following the Synthesis of Compound 178 and Compound 179, Staring with 172-7-Peak-2

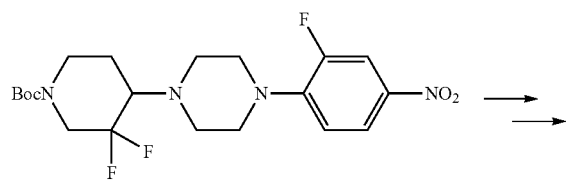

172-7-Peak-2
[α]²⁵_D : −28.79

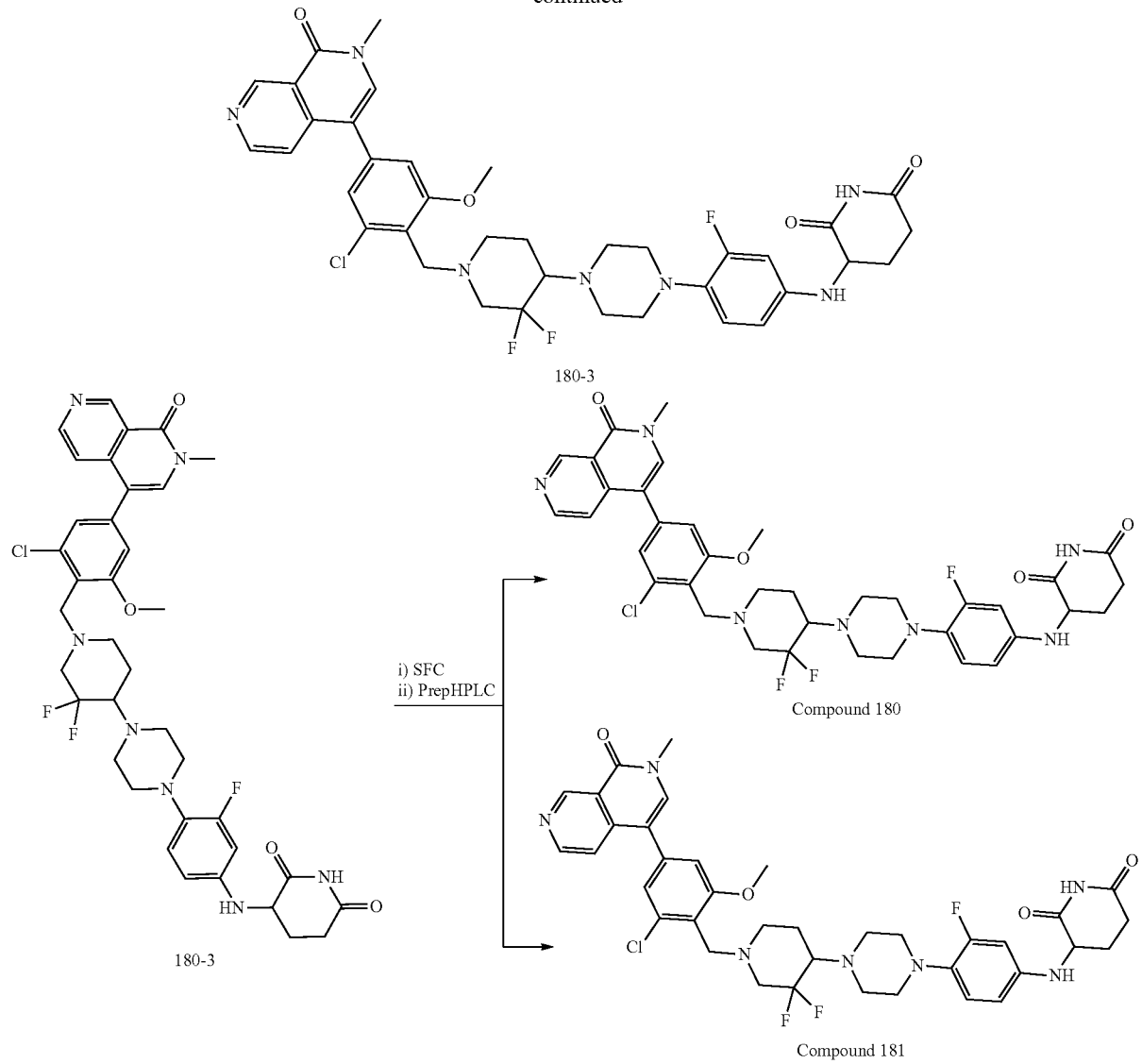

Compound 180

Compound 181

SFC Separation of 180-3

2.9 g of 180-3 was separated by SFC to obtain single stereoisomer. During SFC separation fraction of Compound 180 and of Compound 181 were collected in TFA buffer to avoid Glutarimide ring opening. As SFC separation method involved use of basic additive, the obtain fractions of Compound 180 and of Compound 181 were submitted again for prepHPLC purification to remove the salt. The obtain fraction of Compound 180 and of Compound 181 were submitted again for prepHPLC purification to remove the salt.

| Preparative SFC Conditions Column/dimensions: | |
|---|---|
| Column/dimensions: | Chiiralpak-AS-H (30 × 250) mm, 5µ |
| % CO2: | 55% |
| % Co solvent: | 45% (0.2% 7M Methanolic Ammonia in ACN:MEOH)(70:30) |
| Total Flow: | 100.0 g/min |

| Preparative SFC Conditions Column/dimensions: | |
|---|---|
| Back Pressure: | 100 bar |
| Temperature: | 30° C. |
| UV: | 254 nm |

Prep-HPLC Method:

Mobile Phase (A):0.05% TFA IN WATER

Mobile Phase (B):100% ACETONITRILE

Flow Rate: 17 ml/min

Column: X-SELECT C18 5 µm (19×250 mm)

Gradient Time % B: 0/10, 2/10, 2.5/10, 15.6/39, 15.7/95, 18.5/95, 18.6/95, 21/10

(The first eluted peak during SFC separation was assigned as Compound 180 and second eluted peak was assigned as Compound 181)

| Structure | Spectral data |
|---|---|
| 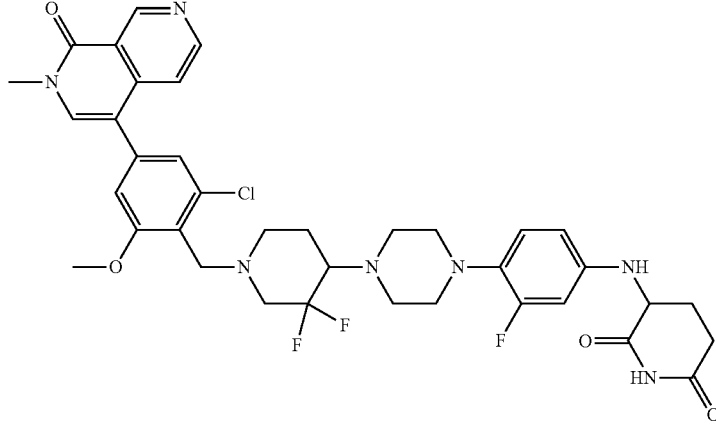
Compound 180 | $^1$H NMR (400 MHz, DMSO-$d_6$) δ 10.79 (s, 1H), 9.49 (s, 1H), 8.76 (d, J = 5.8 Hz, 1H), 8.00 (s, 1H), 7.62 (d, J = 5.8 Hz, 1H), 7.22 (s, 1H), 7.16 (s, 1H), 6.88 (t, J = 9.1 Hz, 1H), 6.56 – 6.52 (m, 1H), 6.46 – 6.44 (m, 1H), 4.30 – 4.26 (m, 1H), 3.90 (s, 5H), 3.61 (s, 3H), 3.30 – 3.09 (m, 10H), 2.77 – 2.54 (m, 4H), 2.18 – 2.04 (m, 2H), 1.90 – 1.87 (m, 2H). LCMS (ES$^+$): m/z 738.41 [M + H]$^+$; [a]$^{25}_D$: = +16.60 |
| 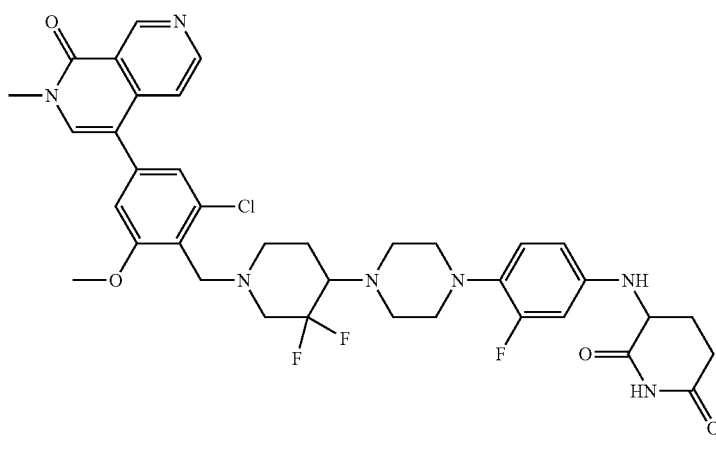
Compound 181 | $^1$H NMR (400 MHz, DMSO-$d_6$) δ 10.79 (s, 1H), 9.50 (s, 1H), 8.76 (d, J = 5.8 Hz, 1H), 8.01 (s, 1H), 7.63 (d, J = 5.8 Hz, 1H), 7.23 (s, 1H), 7.17 (s, 1H), 6.90 (t, J = 9.1 Hz, 1H), 6.57 – 6.52 (m, 1H), 6.46 – 6.44 (m, 1H), 4.30 – 4.26 (m, 1H), 3.90 (s, 5H), 3.61 (s, 3H), 3.30 – 3.10 (m, 10H), 2.77 – 2.54 (m, 4H) 2.19 (bs, 1H), 2.10 – 2.04 (m, 1H), 1.90 – 1.87 (m, 2H) LCMS (ES$^+$): m/z 738.45 [M + H]$^+$; [a]$^{25}_D$: = − 29.35 |
Synthesis of Compound 197
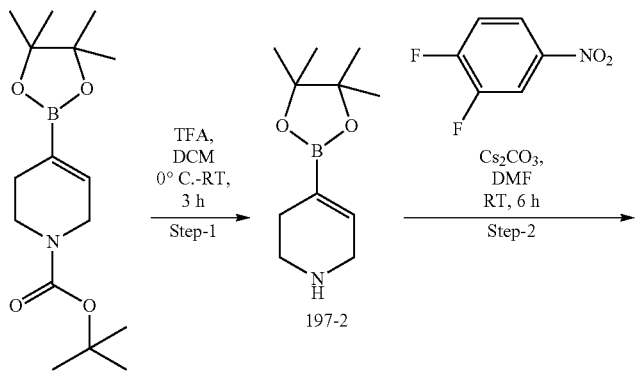

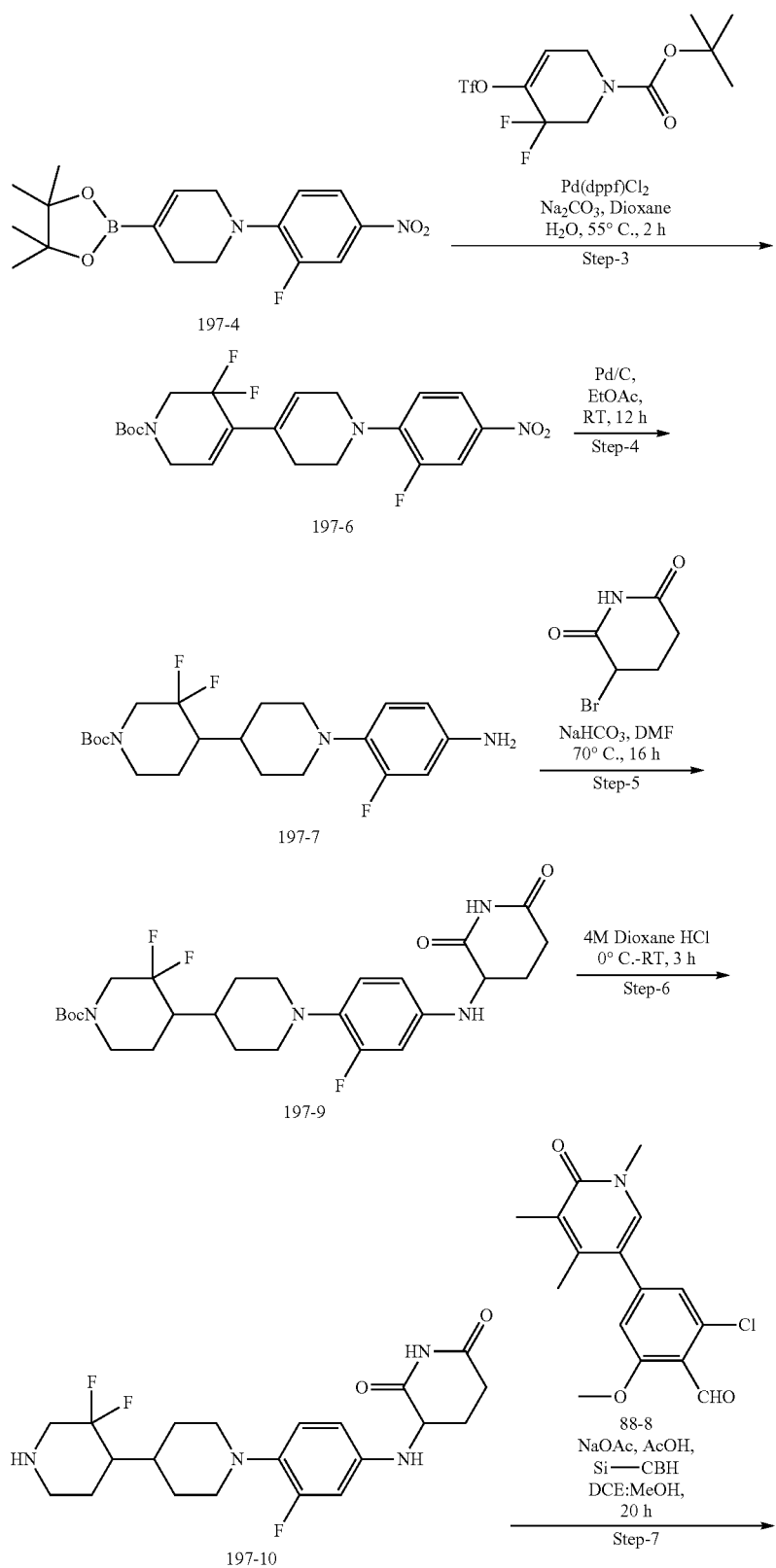

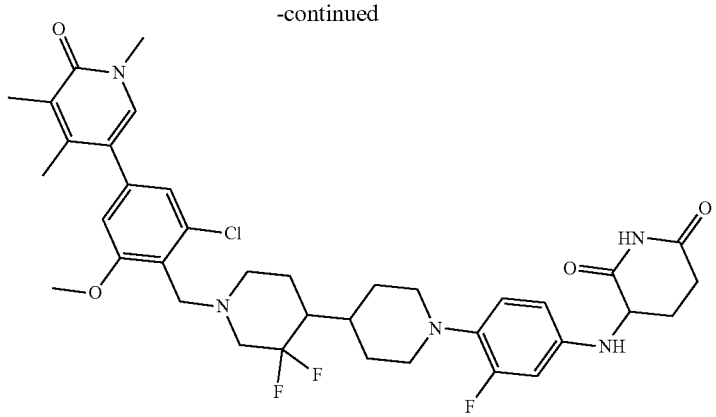

Compound 197

Step-1: To a stirred solution of tert-butyl 4-(4,4,5,5-tetramethyl-1,3,2-dioxaborolan-2-yl)-3,6-dihydro-2H-pyridine-1-carboxylate (5 g, 16.17 mmol) in DCM (10 mL) was added TFA (20 mL) at 0° C. and then reaction mixture was allowed to stir at RT for 2 hr while monitored by TLC. After completion of reaction, the reaction mixture was evaporated to dryness under reduced pressure and crude mixture was co-distilled with toluene (50 mL) to afford 4-(4,4,5,5-tetramethyl-1,3,2-dioxaborolan-2-yl)-1,2,3,6-tetrahydropyridine (5 g) as a colourless liquid.

Step-2: To a stirred solution of 197-2 (2 g, 6.19 mmol) in DMF (15 mL) were added $CsCO_3$ (6.05 g, 18.57 mmol) under nitrogen atmosphere. Then, 1,2-difluoro-4-nitrobenzene (1.18 g, 7.43 mmol, 820.61 uL) was added through syringe and it was stirred for 6 hr at rt. After completion of the reaction by TLC, reaction mixture was quenched with ice cold water and the resulting precipitate was filtered and dried completely to afford 1-(2-fluoro-4-nitro-phenyl)-4-(4,4,5,5-tetramethyl-1,3,2-dioxaborolan-2-yl)-3,6-dihydro-2H-pyridine (2 g, 5.17 mmol, 83.52% yield, 90% purity) as a yellow color solid.

Step-3: To a stirred solution of tert-butyl 3,3-difluoro-4-(((trifluoromethyl)sulfonyl)oxy)-3,6-dihydropyridine-1(2H)-carboxylate (1 g, 2.72 mmol) and 197-4 (947.96 mg, 2.72 mmol) in 1, 4-dioxane (15 mL) was purged argon for 20 mins. Then, sodium carbonate (721.43 mg, 6.81 mmol) in water (5 mL) was added to the above mixture and again continue purging for another 10 mins. Finally, $Pd(dppf)Cl_2$ (0.1 g, 136.13 umol) was added and degassed. Heated the mixture to 55° C. and maintained for 2 hr. The reaction was monitored by TLC and after completion of reaction by TLC, it was cooled to RT and diluted with ethyl acetate (50 mL) and washed the organic layer with water and brine solution. Concentrated under reduced pressure. The crude product was purified by Biotage using 0-20% afforded tert-butyl 3,3-difluoro-4-[1-(2-fluoro-4-nitro-phenyl)-3,6-dihydro-2H-pyridin-4-yl]-2,6-dihydropyridine-1-carboxylate (0.74 g, 52.57% yield, 85% purity) as yellow solid. LCMS ($ES^+$): m/z 440.30 $[M+H]^+$ Step-4: Compound 197-6 (0.7 g, 1.59 mmol) was taken in Ethyl acetate (20 mL) and Palladium, 10% on carbon was added (678.10 mg). The reaction mixture was stirred for 12 h with hydrogen gas (balloon pressure) while monitored by TLC. After completion of reaction, was filtered through Celite pad and washed with ethyl acetate. The organic layer was washed with brine solution, concentrated under reduced pressure. The crude product was purified by Biotage using 0-40% EA in PE afforded tert-butyl 4-[1-(4-amino-2-fluoro-phenyl)-4-piperidyl]-3,3-difluoro-piperidine-1-carboxylate (0.5 g, 60.73% yield, 80% purity) as off-white solid. LCMS ($ES^+$): m/z 414.76 $[M+H]^+$.

Step-5: 197-7 (0.5 g, 1.21 mmol) was taken in DMF (7 mL) and Sodium bicarbonate (609.5 mg, 7.26 mmol) was added followed by 197-8 (696.57 mg, 3.63 mmol) was added all at once in seal tube. Heated the reaction mixture at 80° C. and maintained for 16 hr while monitoring by TLC and LCMS. After completion of reaction, the reaction mixture was quenched with ice-water mixture and passed through Celite pad and washed with water and ethylacetate (25 mL). The organic layer was separated out and washed with brine solution and dried over $Na_2SO_4$, concentrated under reduced pressure. The crude product was purified by biotage using 0-50% EA in PE afforded tert-butyl 4-[1-[4-[(2,6-dioxo-3-piperidyl)amino]-2-fluoro-phenyl]-4-piperidyl]-3,3-difluoro-piperidine-1-carboxylate (0.41 g, 52.35% yield, 81% purity) as pale green solid. LCMS ($ES^+$): m/z 525.92 $[M+H]^+$.

Step-6: To a stirred solution of 197-9 (0.4 g, 0.76 mmol) in 1,4-dioxane (3 mL) at 0° C. was added 4M dioxane HCl (4 M, 1.91 mL) through syringe under nitrogen atmosphere. Then, the reaction mixture was stirred for 3 h at rt. The reaction was monitored by TLC and after completion, it was concentrated to dryness under reduced pressure. The resulting solid was washed with diethyl ether afforded 3-[4-[4-(3,3-difluoro-4-piperidyl)-1-piperidyl]-3-fluoro-anilino]piperidine-2,6-dione (0.35 g, 759.35 umol, 99.58% yield, 021) as pale green solid. LCMS ($ES^+$): m/z 425.41 $[M+H]^+$ Step-7: 197-10 (0.125 g, 0.245 mmol) was taken in DCE (5 mL) and Methanol (5 mL) mixture and was added sodium acetate, anhydrous (0.06 g, 0.738 mmol) followed by acetic acid (0.045 g, 0.738 mmol) and molecular sieves (0.1 g) stirred for 10 mins. Then, compound 2-chloro-6-methoxy-4-(1,4,5-trimethyl-6-oxo-1,6-dihydropyridin-3-yl)benzaldehyde (0.075 g, 245.29 mmol) was added to the above mixture and heated the mixture to 75° C. for 5 hrs. Then, cooled to RT and added Siliabond cyanoborohydride (0.125 g). It was stirred at RT for 16 h while monitoring by TLC and LCMS analysis. After completion of reaction, it was filtered through Celite pad and washed with methanol then concentrated to dryness under reduced pressure. The crude mixture was purified by prep purification to afford 3-[4-[4-[1-[[2-chloro-6-methoxy-4-(1,4,5-trimethyl-6-oxo-3-pyridyl)phenyl]methyl]-3,3-difluoro-4-piperidyl]-1-piperidyl]-3-fluoro-anilino]piperidine-2,6-dione TFA salt (92.9 mg, 44.26% yield, 96.8 purity) as an off-white solid. ¹H NMR (400 MHz, DMSO-d₆) δ 10.80 (s, 1H), 7.57 (s, 1H), 7.04-7.99 (m, 3H), 6.58-6.50 (m, 2H), 4.31 (bs, 1H), 3.97 (s, 3H), 3.82-3.50 (m, 4H), 3.46 (s, 3H), 3.30-3.09 (m, 6H), 2.77-2.58 (m, 2H), 2.06 (d, J=4.0 Hz, 7H), 1.89-1.75 (m, 9H). LCMS (ES⁺): m/z 714.08 [M+H]⁺.

Compound 198 was prepared following the synthesis of Compound 197

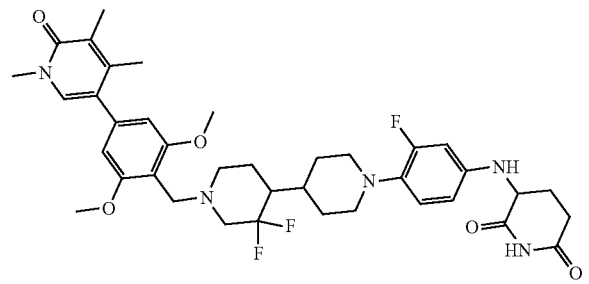 [SMILES: COc1cc(-c2cn(C)c(=O)c(C)c2C)cc(OC)c1CN1CCC(C2CCN(c3ccc(NC4CCC(=O)NC4=O)cc3F)CC2)C(F)(F)C1]

¹H NMR (400 MHz, DMSO-d₆) δ 10.80 (s, 1H), 10.00 (s, 1H), 7.52 (s, 1H), 6.68 (s, 2H), 7.09 (bs, 1H), 6.56 (d, J=14.6 Hz, 1H), 6.47 (d, J=8.7 Hz, 1H), 4.31-4.29 (m, 3H), 3.87 (s, 6H), 3.47-3.01 (m, 11H), 2.77-2.54 (m, 2H), 2.08 (d, J=12.0 Hz, 9H), 1.88-1.53 (m, 7H). LCMS (ES⁺): m/z 710.13 [M+H]⁺

Compound 199 was prepared following the synthesis of Compound 197.

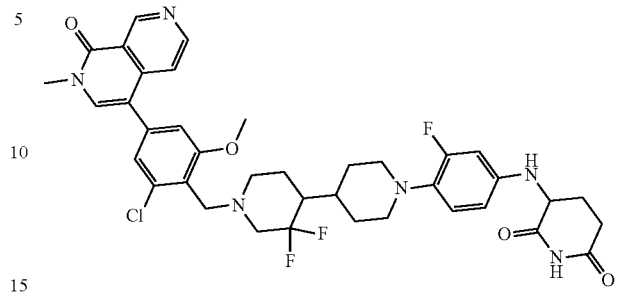

¹H NMR (400 MHz, DMSO-d₆) δ 10.76 (s, 1H), 9.44 (s, 1H), 8.74 (d, J=5.6 Hz, 1H), 8.34 (s, 1H), 7.94 (s, 1H), 7.54 (d, J=5.6 Hz, 1H), 7.14 (d, J=23.9 Hz, 2H), 6.82 (t, J=9.3 Hz, 1H), 6.49 (d, J=14.8 Hz, 1H), 6.41 (d, J=8.5 Hz, 1H), 5.78 (d, J=7.6 Hz, 1H), 4.30-4.20 (m, 1H), 3.87 (s, 3H), 3.70 (s, 2H), 3.59 (s, 3H), 3.17-2.54 (m, 6H), 2.42-2.33 (m, 4H), 2.22-2.16 (m, 1H), 2.08-2.04 (m, 1H), 1.84-1.38 (m, 8H). LCMS (ES⁺): m/z 737.07 [M+H]⁺

Compound 200 was prepared following the synthesis of Compound 197.

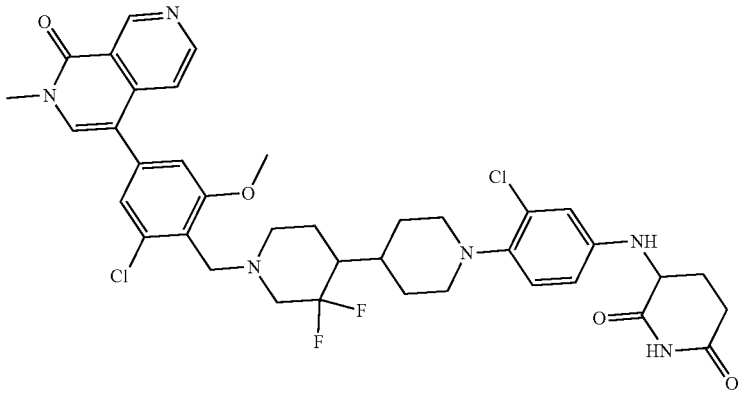 [SMILES: COc1cc(-c2cn(C)c(=O)c3cnccc23)cc(Cl)c1CN1CCC(C2CCN(c3ccc(NC4CCC(=O)NC4=O)cc3Cl)CC2)C(F)(F)C1]

¹H NMR (400 MHz, DMSO-d₆) δ 10.77 (s, 1H), 9.45 (s, 1H), 8.74 (d, J=5.4 Hz, 1H), 8.51 (s, 1H), 7.94 (s, 1H), 7.54 (d, J=5.6 Hz, 1H), 7.17 (d, J=1.2 Hz, 1H), 7.11 (s, 1H), 6.93 (d, J=8.8 Hz, 1H), 6.74 (d, J=2.5 Hz, 1H), 6.59 (q, J=3.8 Hz, 1H), 5.83 (d, J=7.8 Hz, 1H), 4.35-4.22 (m, 1H), 3.87 (s, 3H), 3.71 (s, 2H), 3.59 (s, 3H), 3.10-2.92 (m, 4H), 2.73-2.56 (m, 4H), 2.44-2.33 (m, 1H), 2.20 (t, J=11.2 Hz, 1H), 2.07-2.05 (m, 1H), 1.86-1.67 (m, 7H), 1.42-1.40 (m, 2H). LCMS (ES⁺): m/z 753.12 [M+H]⁺

Synthesis of Compound 201

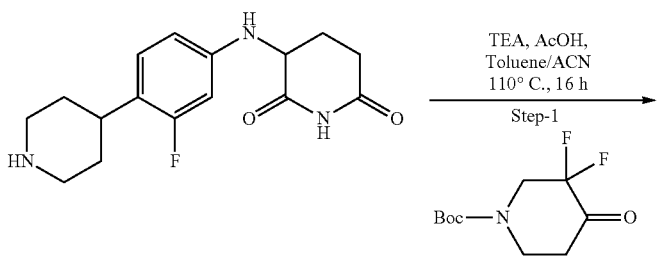

-continued
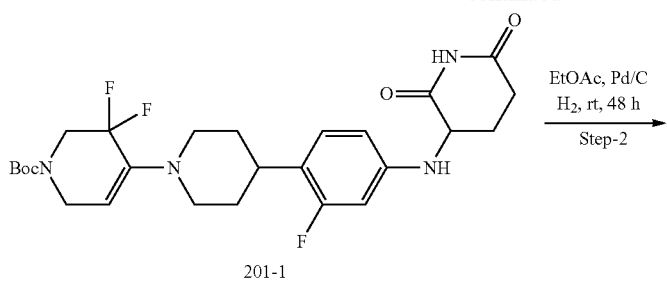
201-1
EtOAc, Pd/C
H₂, rt, 48 h
Step-2
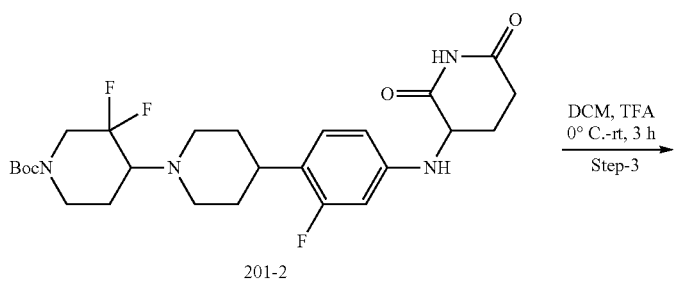
201-2
DCM, TFA
0° C.-rt, 3 h
Step-3
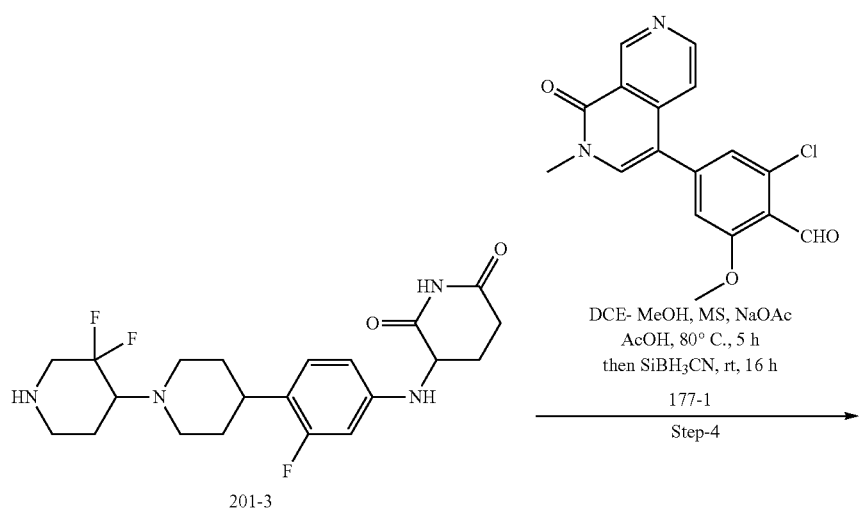
201-3
DCE- MeOH, MS, NaOAc
AcOH, 80° C., 5 h
then SiBH₃CN, rt, 16 h
177-1
Step-4
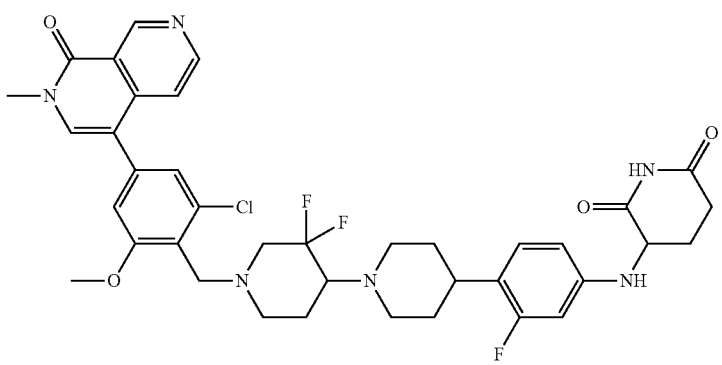
Compound 201

Step-1: To the 3-((3-fluoro-4-(piperidin-4-yl)phenyl)amino)piperidine-2,6-dione (1.0 g, 2.38 mmol, 061) suspended in ACN (24 mL) and Toluene (24 mL) was added TEA (0.361 g, 3.568 mmol, 0.5 mL) under argon at rt. The resulting reaction mixture was stirred for 5 minutes to confirm pH of the reaction becomes basic (8 to 9). Further to the reaction mixture was added tert-butyl 3,3-difluoro-4-oxopiperidine-1-carboxylate (1.12 g, 4.761 mmol) and AcOH (0.429 g, 7.144 mmol, 0.4 mL). The resulting reaction mixture was stirred for 5-10 minutes to confirm pH of the reaction becomes acidic (4 to 5). Next, to the reaction mixture was added Molecular Sieves (1.0 g) and the reaction mixture was refluxed at 110° C. for 16 h.

After completion of reaction (monitored by TLC and LCMS), the reaction mixture was allowed to cool to the rt and solvent was evaporated in vacuum. To the residue was added saturated solution of NaHCO$_3$ (aq.) to adjust the pH to 8-9. The product was extracted in EtOAc (3×30 mL). The combined organic layers were washed with brine (15 mL), dried over Na$_2$SO$_4$ and concentrated in vacuum to afford the Compound 201-1 (1.8 g, 2.07 mmol, 86.67% yield, 60% purity) as greenish blue oil. The crude product was directly used for the next step without further purification. LCMS (ES$^+$): m/z 523.32 [M+H]$^+$ Step-2: A steel-bomb pressure reactor with Compound 201-1 (2.0 g, 3.8273 mmol) dissolved in EtOAc (30 mL) was charged with Pd/C (0.407 g, 3.8273 mmol) and the resulting reaction mixture was stirred under hydrogen atmosphere (100 psi) for 48 hr. After completion of reaction (TLC and LCMS), the reaction mixture was filtered through Celite bed, washed with EtOAc (2×35 mL) and filtrate concentrated in vacuum. The crude residue was purified by using flash column chromatography (Silica gel 230-400 mesh; gradient 0-100% EtOAc in pet ether) to afford the desired Compound 201-2 (0.750 g, 1.39 mmol, 36.24% yield, 97% purity) as solid. LCMS (ES$^+$): m/z 525.57 [M+H]$^+$ Step-3: To the Compound 201-2 (1.03 g, 1.963 mmol) in DCM (6 mL) was added TFA (12.20 g, 106.95 mmol, 8.24 mL) at 0° C. The resulting reaction mixture was stirred at 0° C. for 15 minutes and then for rt for 2 hr. After completion of reaction (monitored by TLC and LCMS), the solvent was evaporated in vacuo. To the residue was added Et$_2$O (2×30 mL) to precipitate out the Compound 201-3 (1.10 g, 1.86 mmol, 94.67% yield, 91% purity, 061) as off-white solid. The crude compound was filtered under vacuum, dried and directly used for next step without further purification. LCMS (ES$^+$): m/z 425.48 [M+H]$^+$ Step-4: To a stirred solution of Compound 201-3 (0.460 g, 0.8542 mmol, 061) in DCE (4 mL) and MeOH (4 mL) was added NaOAc (0.210 g, 2.56 mmol), AcOH (0.128 g, 2.131 mmol, 0.122 mL) and Molecular Sieves (0.460 g) at rt under argon atmosphere. The reaction mixture was stirred at rt for 15 minutes followed by addition of 2-chloro-6-methoxy-4-(2-methyl-1-oxo-1,2-dihydro-2,7-naphthyridin-4-yl)benzaldehyde (0.308 g, 0.9368 mmol). The resulting reaction mixture was heated at 80° C. for 4 hr followed by cooled to 0° C. and added SiCNBH$_3$ (0.800 g, 4.266 mmol). The resulting reaction mixture was stirred at rt for next 12 hr. After completion of reaction (monitored by LCMS), the reaction mixture was filtered through Celite bed, washed with EtOAc (2×10 mL) and THF (2×10 mL). The filtrate was evaporated in vacuo to afford the crude residue. The crude residue was purified by using reverse phase chromatography to afford the desired Compound 201 as TFA salt (yellow solid).To the solid was added saturated NaHCO$_3$ solution (till pH of the solution becomes basic) and the product was extracted in DCM (3×20 mL). The combined organic layers were dried over Na$_2$SO$_4$ and concentrated in vacuo to afford the desired product Compound 201 (138 mg, 186.57 umol, 99.67% purity) as light green solid.

$^1$H NMR (400 MHz, DMSO-d$_6$): δ 10.78 (s, 1H); 9.45 (s, 1H); 8.74 (d, J=5.6 Hz, 1H); 7.94 (s, 1H); 7.54 (d, J=5.6 Hz, 1H); 7.17 (d, J=1.2 Hz, 1H); 7.11 (s, 1H); 6.98 (t, J=8.8 Hz, 1H); 6.48-6.40 (m, 2H); 5.98 (d, J=7.6 Hz, 1H); 4.34-4.26 (m, 1H); 3.87 (s, 3H); 3.72 (s, 2H); 3.59 (s, 3H); 3.16-2.90 (m, 4H); 2.90-2.50 (m, 6H); 2.48-2.24 (m, 2H); 2.12-2.02 (m, 1H); 1.90-1.70 (m, 3H); 1.66-1.50 (m, 4H) LCMS (ES$^+$): m/z 737.16 [M+H]$^+$.

Compound 202 was prepared following the synthesis of Compound 201.

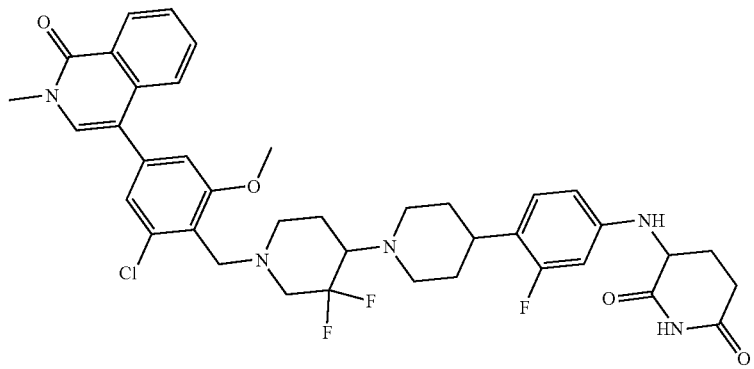 [SMILES: COc1cc(-c2cn(C)c(=O)c3ccccc23)cc(Cl)c1CN1CCC(N2CCC(c3ccc(NC4CCC(=O)NC4=O)cc3F)CC2)C(F)(F)C1]

$^1$H NMR (400 MHz, DMSO-d$_6$): δ 1.80-2.10 (m, 7H); 2.22-2.48 (m, 2H); 2.54-2.80 (m, 2H); 2.90-3.40 (m, 6H); 3.58 (s, 3H); 3.81 (s, 3H); 3.88 (s, 3H); 3.90-4.10 (m, 2H); 4.28-4.36 (m, 1H); 6.00-6.20 (m, 1H); 6.42-6.52 (m, 2H); 6.90-6.99 (m, 1H); 7.13 (s, 1H); 7.17 (s, 1H); 7.55-7.65 (m, 3H); 7.71-7.78 (m, 1H); 8.35 (d, J=7.6 Hz, 1H); 9.88 (bs, 1H); 10.80 (s, 1H). LCMS (ES$^+$): m/z 734.47 [M−H]$^−$

Synthesis of Compound 203

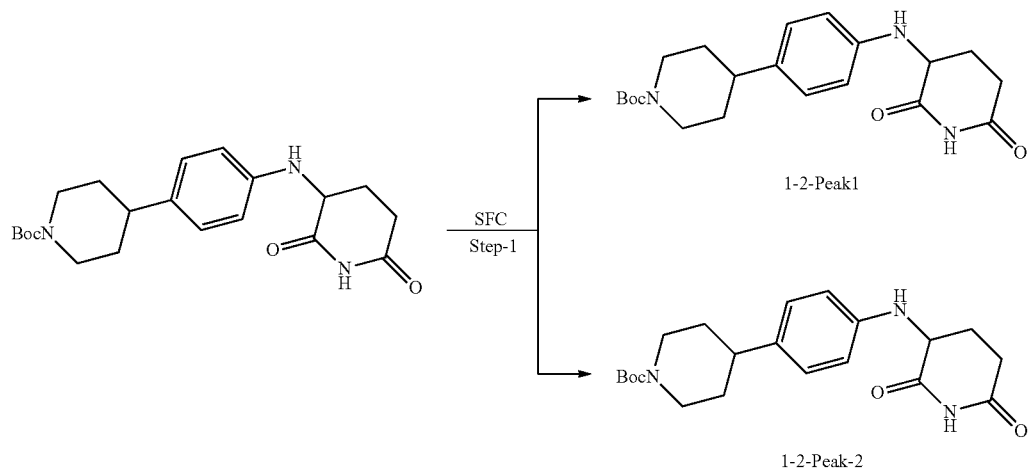

Tert-butyl 4-(4-((2,6-dioxopiperidin-3-yl)amino)phenyl)piperidine-1-carboxylate was separated by SFC to afford 1-2-Peak-1 (First eluted peak during SFC) and 1-2-Peak-2 (Second eluted peak during SFC separation)

SFC Method: Preparative SFC Conditions Column/dimensions Chiralpak AD-H (30×250 mm), 5p % $CO_2$: 60% % Co solvent: 40% (IPA) Total Flow: 100.0 g/min Back Pressure: 100 bar Temperature: 35 0C UV: 240 nm

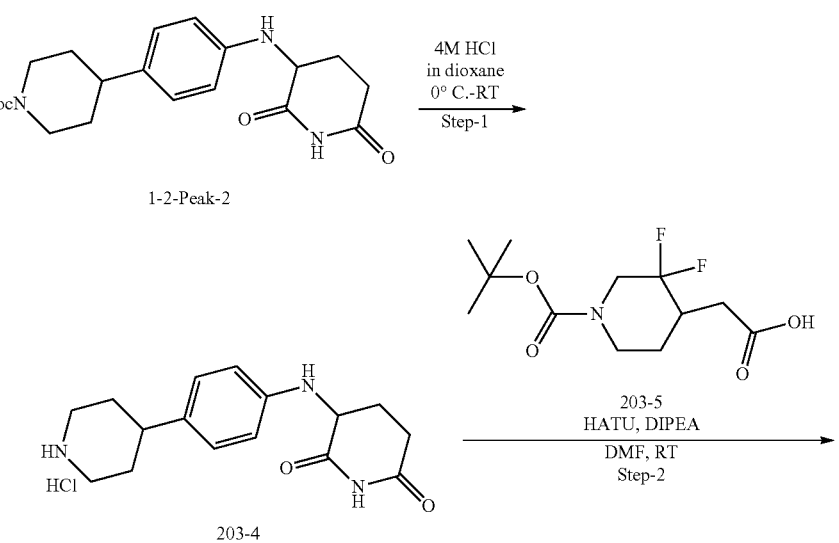

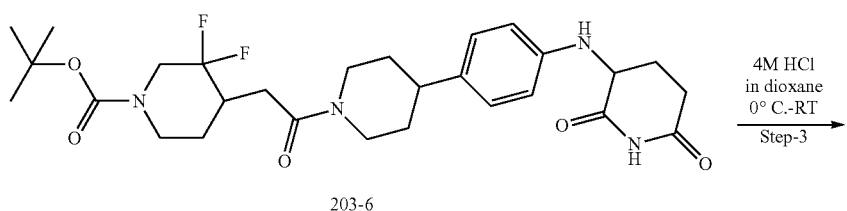

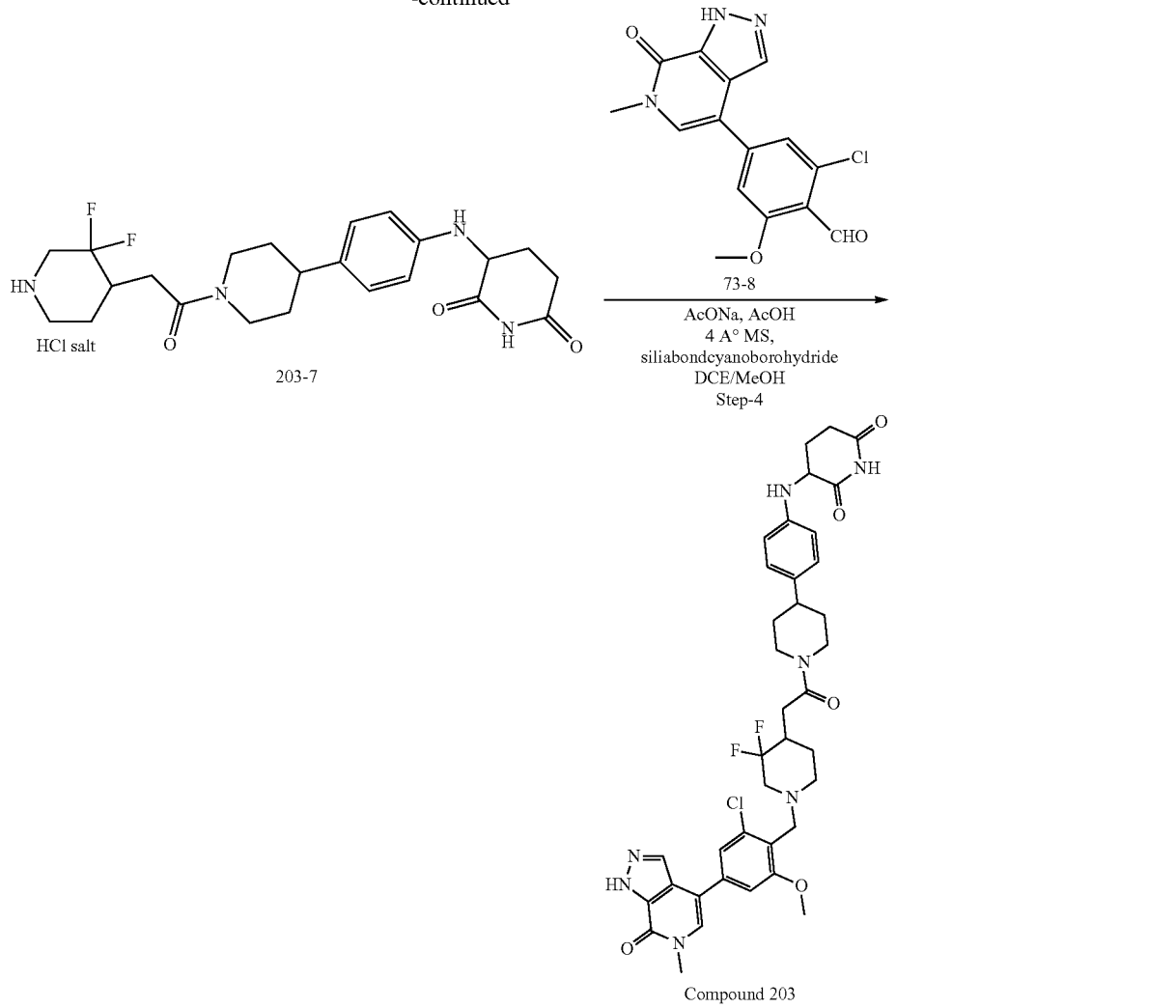

Compound 203

Step-1: 4.0 M HCl in 1,4-dioxane (3 mL) was added to the 1-2-Peak-2 tert-butyl 4-[4-[[2,6-dioxo-3-piperidyl]amino]phenyl]piperidine-1-carboxylate (0.22 g, 0.567 mmol) at 0° C. and then reaction mixture was allowed stirred at room temperature for 4 h, while monitoring the reaction by LCMS. After completion, solvent was evaporated under reduced pressure and crude was co-distilled with toluene to afford 3-[4-(4-piperidyl)anilino]piperidine-2,6-dione (0.25 g, 99.77% purity) as a brown color solid. LCMS (ES$^+$): m/z 288.41 [M+H]$^+$ Step-2: To a stirred solution of 3-[4-(4-piperidyl)anilino]piperidine-2,6-dione (0.250 g, 0.772 mmol) in DMF (5 mL) were added DIPEA (0.6754 g, 5.23 mmol), 2-(1-tert-butoxycarbonyl-3,3-difluoro-4-piperidyl)acetic acid (0.218 g, 0.783 mmol) followed by HATU (0.6623 g, 1.74 mmol) at 0° C. and then reaction mixture was allowed to stirred at room temperature for 6 h, while monitoring the reaction by LCMS. After completion, solvent was evaporated under GENVAC and crude was purified by column chromatography (Devisil silica with 80% EtOAc:pet ether) to afford tert-butyl 4-[2-[4-[4-[[2,6-dioxo-3-piperidyl]amino]phenyl]-1-piperidyl]-2-oxo-ethyl]-3,3-difluoro-piperidine-1-carboxylate (0.3 g, 55.3% purity) as a brown sticky solid, LCMS (ES$^+$): m/z 549.24 [M+H]$^+$ Step-3: 4.0 M HCl in 1,4-dioxane (4 mL) was added to the tert-butyl 4-[2-[4-[4-[[2,6-dioxo-3-piperidyl]amino]phenyl]-1-piperidyl]-2-oxo-ethyl]-3,3-difluoro-piperidine-1-carboxylate (0.3 g, 0.546 mmol) at 0° C. and then reaction mixture was allowed to stirred at room temperature 4 h, while monitoring the reaction by LCMS. After completion, solvent was evaporated under vacuum and crude was co-distilled with toluene to afford 3-[4-[1-[2-(3,3-difluoro-4-piperidyl)acetyl]-4-piperidyl]anilino]piperidine-2,6-dione (0.3 g, 78.94% purity) as a brown gummy solid LCMS (ES$^+$): m/z 449.32 [M+H]$^+$ Step-4: To a stirred solution of 3-[4-[1-[2-(3,3-difluoro-4-piperidyl)acetyl]-4-piperidyl]anilino]piperidine-2,6-dione hydrochloride (0.108 g, 242.35 mmol) in DCE (5 mL): MeOH (5 mL) were added sodium acetate, anhydrous (0.0542 g, 0.66 mmol), 4 A° molecular sieves (0.100 g) followed by 2-chloro-6-methoxy-4-(6-methyl-7-oxo-1H-pyrazolo[3,4-c]pyridin-4-yl)benzaldehyde (0.070 g, 0.220 mmol) and acetic acid (0.0132 g, 0.220 mmol) and the resulting solution was stirred for 10 min. Reaction mixture was allowed to stirred at 70° C. for 3 h and then RM was allowed to come to RT and was added Si-CBH (0.07 g) and stirring was continued for 16 h, while monitoring the reaction by LCMS. After completion, the reaction mass was diluted with MeOH and filtered over Celite bed and bed was thoroughly washed with methanol, Concentrated and crude was purified by prep-HPLC to afford 3-[4-[1-[2-[1-[[2-chloro-6-methoxy-4-(6-methyl-7-oxo-1H-pyrazolo[3,4-c]pyridin-4-yl)phenyl]methyl]-3,3-difluoro-4-piperidyl]acetyl]-4-piperidyl]anilino]piperidine-2,6-dione TFA salt (0.0335 g, 16.93% yield, 96.24% purity) as a light brown solid. $^1$H NMR (400 MHz, DMSO-$d_6$) δ 14.44 (bs, 1H), 10.77 (s, 1H), 8.22 (s, 1H), 7.69 (s, 1H), 7.40 (s, 1H), 7.29 (s, 1H), 6.95 (d, J=8.5 Hz, 2H), 6.61 (d, J=8.4 Hz, 2H), 4.53 (bs, 1H), 4.29-4.25 (m, 3H), 3.97 (s, 6H), 3.62 (s, 3H), 3.22-3.03 (m, 3H), 2.76-2.58 (m, 6H), 2.49-2.33 (m, 1H), 2.11-2.05 (m, 2H), 1.86-1.73 (m, 1H), 1.53-1.48 (m, 2H), 1.35-1.24 (m, 3H), LCMS (ES$^+$): m/z [M+H]$^+$ 750.56.

Compound 204 was prepared following the synthesis of Compound 203, but start with 1-2-Peak-1

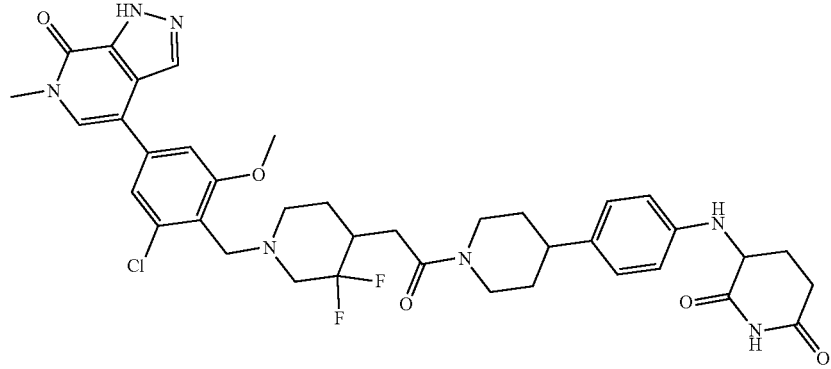 [SMILES: COc1cc(-c2cn(C)c(=O)c3[nH]ncc23)cc(Cl)c1CN1CCC(CC(=O)N2CCC(c3ccc(NC4CCC(=O)NC4=O)cc3)CC2)C(F)(F)C1]

$^1$H NMR (400 MHz, DMSO-$d_6$) δ 14.31 (s, 1H), 10.80 (s, 1H), 8.21 (s, 1H), 7.68 (s, 1H), 7.40 (s, 1H), 7.21 (s, 1H), 7.09 (s, 1H), 6.95 (d, J=8.4 Hz, 2H), 6.61 (d, J=8.0 Hz, 2H), 4.52-4.51 (m, 1H), 4.28-4.22 (m, 3H), 3.97 (s, 6H), 3.61 (m, 4H), 3.16-3.10 (m, 3H), 2.76-2.70 (m, 6H), 2.32 (m, 1H), 2.11-2.06 (m, 2H), 1.87-1.86 (m, 1H), 1.75-1.73 (m, 2H), 1.52-1.49 (m, 2H). LCMS (ES$^+$): m/z [M+H]$^+$ 750.60.

Synthesis of Compound 205

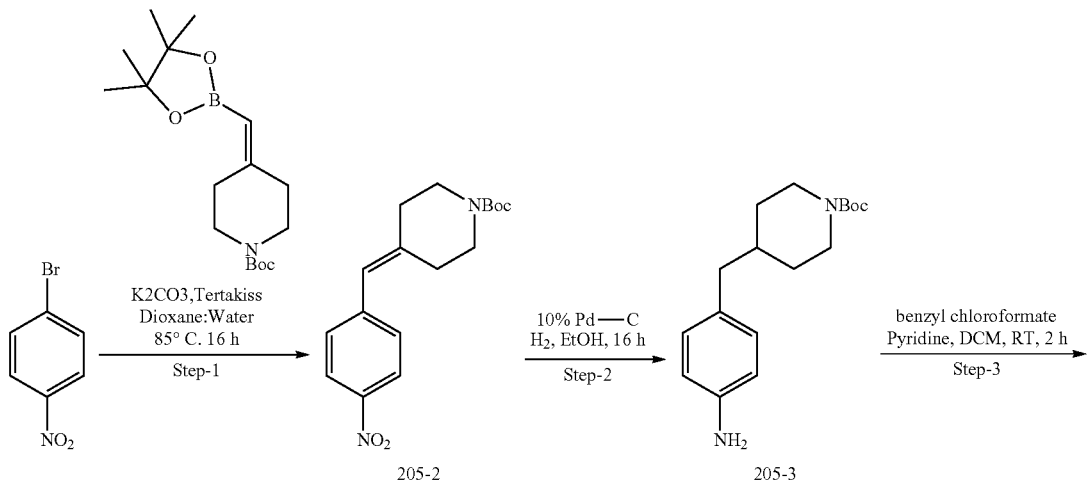

-continued
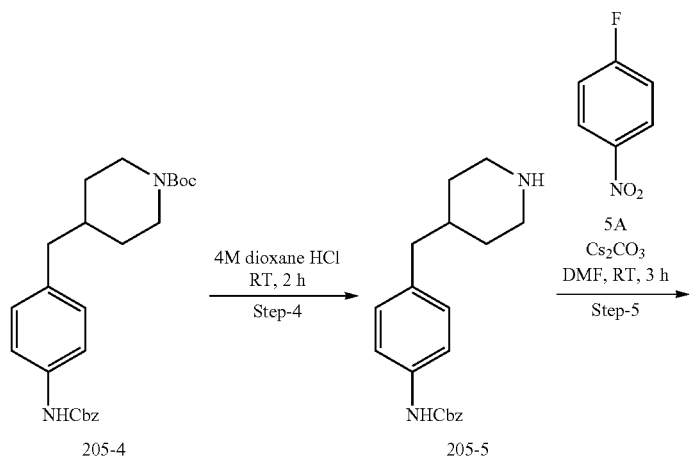
205-4 → 205-5
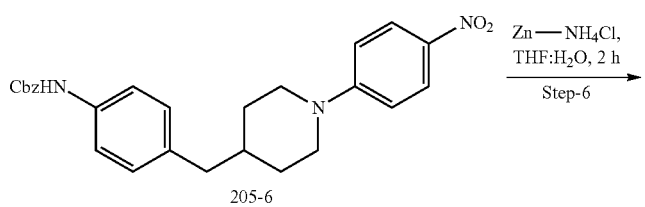
205-6
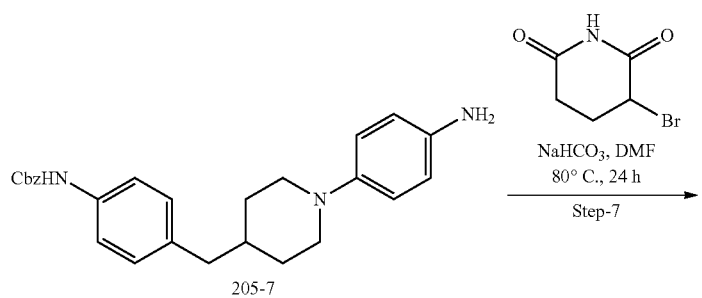
205-7
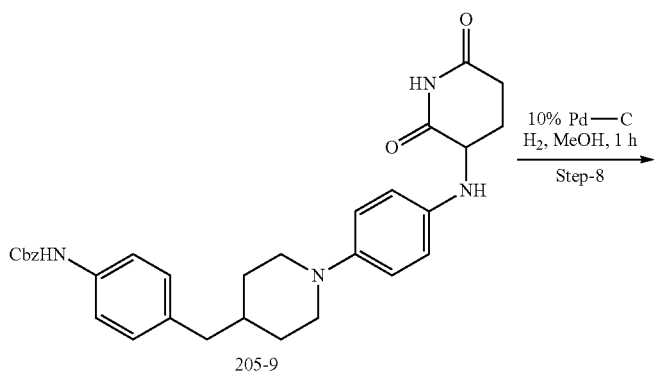
205-9

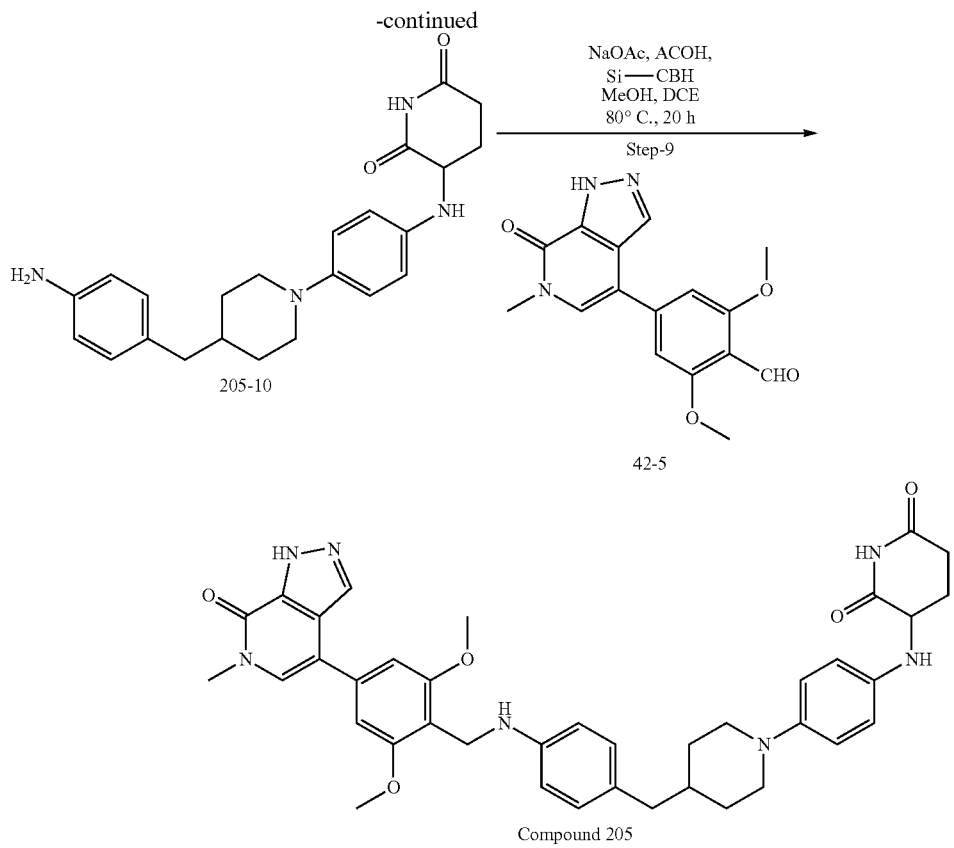

Step-1: To a stirred solution of 1-bromo-4-nitro-benzene (3 g, 14.85 mmol, 1.54 mL) in 1,4 Dioxane (25 mL) and water (25 ml) was added tert-butyl 4-[(4,4,5,5-tetramethyl-1,3,2-dioxaborolan-2-yl)methylene]piperidine-1-carboxylate (6.24 g, 19.31 mmol) followed by the addition of Potassium carbonate, (5.13 g, 37.13 mmol, 2.24 mL) at room temperature under argon atmosphere. The reaction mixture was degassed with argon repeatedly and Pd(PPh$_3$)$_4$ (0.7 g, 0.594 mmol) was added in one portion under argon atmosphere. The reaction mixture was heated at 85° C. for 16 h, while monitoring by LCMS and TLC. After the completion of the reaction, the reaction mixture was cooled to room temperature and filtered through Celite bed, washed with ethyl acetate (300 mL). The filtrate was concentrated and the resultant crude mass was dissolved with Ethyl acetate (500 mL) and washed with water (2×100 mL) followed by brine (1×100 mL) and dried over anhydrous Na$_2$SO$_4$. Organic layer was concentrated and crude was purified by column chromatography (Silica gel 100/200 mesh and the product eluted at 40-50% EtoAc:Pet ether) to afford tert-butyl 4-[(4-nitrophenyl)methylene]piperidine-1-carboxylate (4 g, 81.22% yield, 96% purity) $^1$HNMR (400 MHz, CDCl$_3$): δ 8.19-8.17 (m, 2H), 7.33 (d, J=8.4 Hz, 2H), 6.40 (s, 1H), 3.54 (t, J=5.6 Hz, 2H), 3.43 (t, J=5.6 Hz, 2H), 2.46 (t, J=6 Hz, 2H), 2.38 (t, J=6 Hz, 2H), 1.48 (s, 9H) LCMS (ES$^+$): m/z 319.17 [M+H]$^+$ Step-2: To a stirred solution of tert-butyl 4-[(4-nitrophenyl) methylene] piperidine-1-carboxylate (4 g, 12.56 mmol) in methanol (10 mL) and ethanol (10 mL) was added 10% wet Pd-C (6 g) and the reaction mixture was stirred under H$_2$ balloon pressure for 16 h, while monitored by TLC. The reaction mixture was filtered through Celite bed and the filtrate was concentrated to afford tert-butyl 4-[(4-aminophenyl) methyl] piperidine-1-carboxylate (3.5 g, 74% yield, 80% purity). This was taken to the next step without any purification $^1$HNMR (400 MHz, DMSO-d$_6$): δ 6.789 (d, J=8 Hz, 2H), 6.48-6.45 (m, 2H), 4.80 (s, 2H), 3.90-3.88 (m, 2H), 2.67-2.62 (m, 2H), 2.30 (d, J=6.8 Hz, 2H), 1.59-1.52 (m, 5H), 1.48 (s, 9H) LCMS (ES$^+$): m/z 291.44 [M+H]$^+$ Step-3: To a stirred solution of tert-butyl 4-[(4-aminophenyl)methyl]piperidine-1-carboxylate (3.5 g, 12.05 mmol) in DCM (40 mL) and Pyridine (0.7 g, 9.64 mmol) under nitrogen atmosphere at −10° C. was added drop wise benzyl chloroformate (0.7 g, 8.44 mmol) in dichloromethane (10 ml) over the period of 10 min. After addition reaction mixture was allowed to warm at ambient temperature and stirred for 2 h, while monitoring by LCMS and TLC. Reaction mixture quenched with Ice cold water (1×200 ml) and extracted with Ethyl acetate (2×250 ml). The organic phase separated, washed with brine (50 ml) dried over Na$_2$SO$_4$ and evaporated under reduced pressure to afford tert-butyl 4-(4 (benzyloxy)carbonyl)amino) benzyl)piperidine-1-carboxylate. LCMS (ES$^+$): m/z 447.32 [M+Na]$^+$ Step-4: To a stirred solution of tert-butyl 4-[[4-(benzyloxycarbonylamino) phenyl] methyl]piperidine-1-carboxylate (5 g, 11.78 mmol) in DCM (10 mL) was added 4M Dioxane HCl (10 ml) at 0° C. and the reaction mixture was stirred at RT for 2 h, while monitoring by LCMS and TLC. After completion, the reaction mixture was concentrated and the crude compound was triturated with diethyl ether and dried to afford benzyl N-[4-(4-piperidylmethyl) phenyl] carbonate (4 g, 90.35% yield, 96%) as a white solid. LCMS (ES$^+$): m/z 325.18 [M+H]$^+$ Step-5: To a stirred solution of compound benzyl N-[4-(4-piperidylmethyl)phenyl]carbamate (2 g, 6.16 mmol) in DMF (10 mL) was added cesium carbonate (4.02 g, 12.33 mmol) and stirred for 15 min before adding 1-fluoro-4-nitrobenzene (1.04 g, 7.40 mmol) The reaction mixture was allowed to stir at RT for 16 h while monitoring by TLC. After completion the reaction mass was quenched with ice flakes and the precipitated solid was filtered to afford benzyl N-[4-[[1-(4-nitrophenyl)-4-piperidyl]methyl]phenyl]carbamate (2.5 g, 72.82% yield, 80% purity) LCMS (ES$^+$): m/z 446.30 [M+H]$^+$ Step-6: To the solution of benzyl N-[4-[[1-(4-nitrophenyl)-4-piperidyl] methyl]phenyl]carbamate (2.5 g, 5.61 mmol) in THF:Water (40 mL) was added Zinc Powder (3.67 g, 56.12 mmol) and NH$_4$Cl (4.50 g, 84.17 mmol). Reaction mixture was stirred at room temperature for 2 h. TLC and LCMS showed the completion of the reaction. Reaction mixture was filtered through Celite bed and bed washed with ethyl acetate and THF mixture (1:1) (100 ml). Filtrate was concentrated to yield the crude product benzyl N-[4-[[1-(4-aminophenyl)-4-piperidyl] methyl]phenyl] carbamate (2.2 g, 4.24 mmol, 75.48% yield, 80% purity) LCMS (ES$^+$): m/z 416.23 [M+H]$^+$ Step-7: To a stirred solution of 3-bromopiperidine-2,6-dione (2 g, 10.59 mmol) and benzyl N-[4-[[1-(4-aminophenyl)-4-piperidyl]methyl]phenyl]carbamate (2.8 g, 14.457 mmol) in DMF (10 mL) was added Sodium bicarbonate (2.42 g, 28.915 mmol) and stirred at 80° C. for 24 h. The reaction mixture was cooled to ambient temperature and the reaction mixture was diluted with water (100 mL) and extracted with ethyl acetate (3×100 mL). The combined organic extracts were washed brine solution, dried over anhydrous sodium sulphate, filtered and concentrated under reduced pressure. The resulting crude was purified by column chromatography (100-200 mesh silica gel desired product eluted with 50-80% gradient ethyl acetate in pet ether) to afford benzyl N-[4-[[1-[4-[(2,6-dioxo-3-piperidyl)amino]phenyl]-4-piperidyl]methyl]phenyl]carbamate (1.47 g, 46.92% yield, 89% purity) $^1$HNMR (400 MHz, DMSO-d$_6$): δ 10.78 (S, 1H), 9.65 (s, 1H), 7.54-7.31 (m, 7H), 7.08 (d, J=3.6 Hz, 2H), 6.72 (d, J=8.8 Hz, 2H), 6.58 (d, J=8.8 Hz, 2H), 5.34 (d, J=7.2 Hz, 1H) (5.14 (s, 2H), 4.19-4.15 (m, 1H), 2.73-2.69 (m, 1H), 2.55-2.50 (m, 1H), 2.48-2.42 (m, 4H), 2.11-2.06 (m, 1H), 1.83-1.80 (m, 1H), 1.63-152 (m, 3H), 1.31-1.22 (m, 4H). LCMS (ES$^+$): m/z 527.26 [M+H]$^+$ Step-8: To a stirred solution of benzyl N-[4-[[1-[4-[(2,6-dioxo-3-piperidyl)amino]phenyl]-4-piperidyl]methyl]phenyl]carbamate (0.5 g, 0.950 mmol) in methanol (10 mL) was added 10% wet Palladium on carbon (0.5 g) at room temperature. After addition reaction was stirred under H2 atmosphere for 1 h, while monitoring by TLC. Volatiles were evaporated under reduced pressure. The resulting residue was co-evaporated with toluene (5 mL) then triturated with ether. Ether layer was decanted and resulting residue was dried under vacuum to yield 3-[4-[4-[(4-aminophenyl)methyl]-1-piperidyl]anilino]piperidine-2,6-dione (0.22 g, 53.13% yield, 90% purity). $^1$HNMR (400 MHz, DMSO-d$_6$): δ 10.8 (s, 1H), 6.81 (d, J=8.4 Hz, 2H), 6.72 (d, J=8.8 Hz, 2H), 6.58 (d, J=9.2 Hz, 2H), 6.48 (d, J=8.4 Hz, 2H), 5.33 (d, J=7.2 Hz, 1H), 4.80 (s, 2H), 4.30-4.19 (m, 1H), 2.59-2.53 (m, 2H), 2.45-2.42 (m, 1H), 2.42-2.34 (m, 4H), 2.11-2.06 (m, 1H), 1.83-1.80 (m, 1H), 1.63-161 (m, 2H), 1.49-1.44 (m, 1H), 1.28-1.23 (m, 3H). LCMS (ES$^+$): m/z 393.33 [M+H]$^+$ Step-9: To a stirred solution of 3-[4-[4-[(4-aminophenyl)methyl]-1-piperidyl]anilino]piperidine-2,6-dione HCl salt (0.1 g, 0.233 Mmol) and 2,6-dimethoxy-4-(6-methyl-7-oxo-1H-pyrazolo[3,4-c]pyridin-4-yl)benzaldehyde.TFA (0.1 g, 0.233 mmol, 061) in methanol (5 mL) and DCE (5 mL), were added sodium acetate (0.06 g, 0.702 mmol) and 0.5 ml of acetic acid. After addition, reaction mixture allowed to stir at 80° C. for 5 h. Then cooled at room temperature and added Si-CBH (0.115 g, 1.86 mmol) and allowed to stir at RT for 15 h, while monitoring by LCMS. After completion of the reaction, the reaction mass was filtered through Celite bed and concentrated under vacuum. The crude residue was purified by prep-HPLC to afford 3-[4-[4-[[4-[[2,6-dimethoxy-4-(6-methyl-7-oxo-1H-pyrazolo[3,4-c]pyridin-4-yl)phenyl]methylamino]phenyl]methyl]-1-piperidyl]anilino] piperidine-2,6-dione TFA salt (71 mg, 35.51% yield, 94.09% purity). $^1$H NMR (400 MHz, DMSO-d$_6$) δ 14.43 (bs, 1H), 10.82 (s, 1H), 10.69 (s, 1H), 8.19 (s, 1H), 7.56 (s, 2H), 7.36 (d, J=7.3 Hz, 2H), 6.97 (d, J=5.4 Hz, 2H), 6.88 (s, 2H), 6.75 (d, J=8.7 Hz, 4H), 6.35 (s, 1H), 4.38 (d, J=7.5 Hz, 1H), 4.20 (s, 2H), 3.90 (s, 6), 3.61 (s, 3H), 2.79-2.67 (m, 1H), 3.48-3.39 (m, 4H), 2.61-2.56 m, 1H), 2.53-2.49 (m, 2H), 2.09-2.05 (m, 1H), 1.92-1.82 (m, 4H), 1.69-1.49 (m, 2H), LCMS (ES$^+$): m/z 690.45 [M+H]$^+$ Synthesis of Compound 206

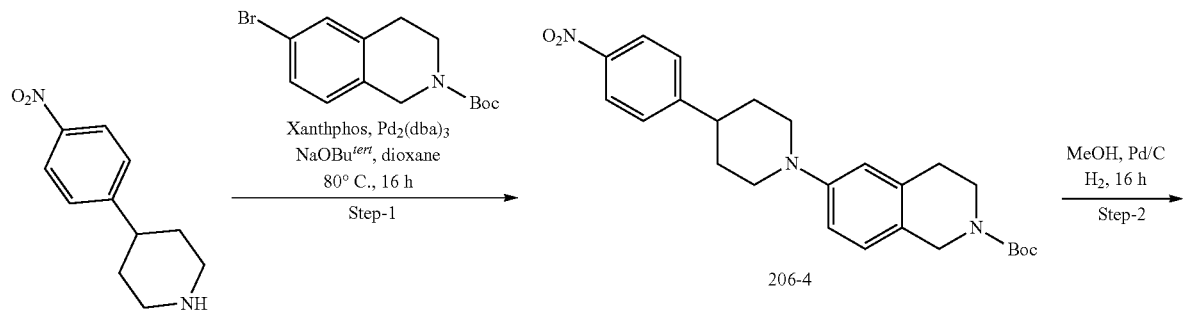

206-4

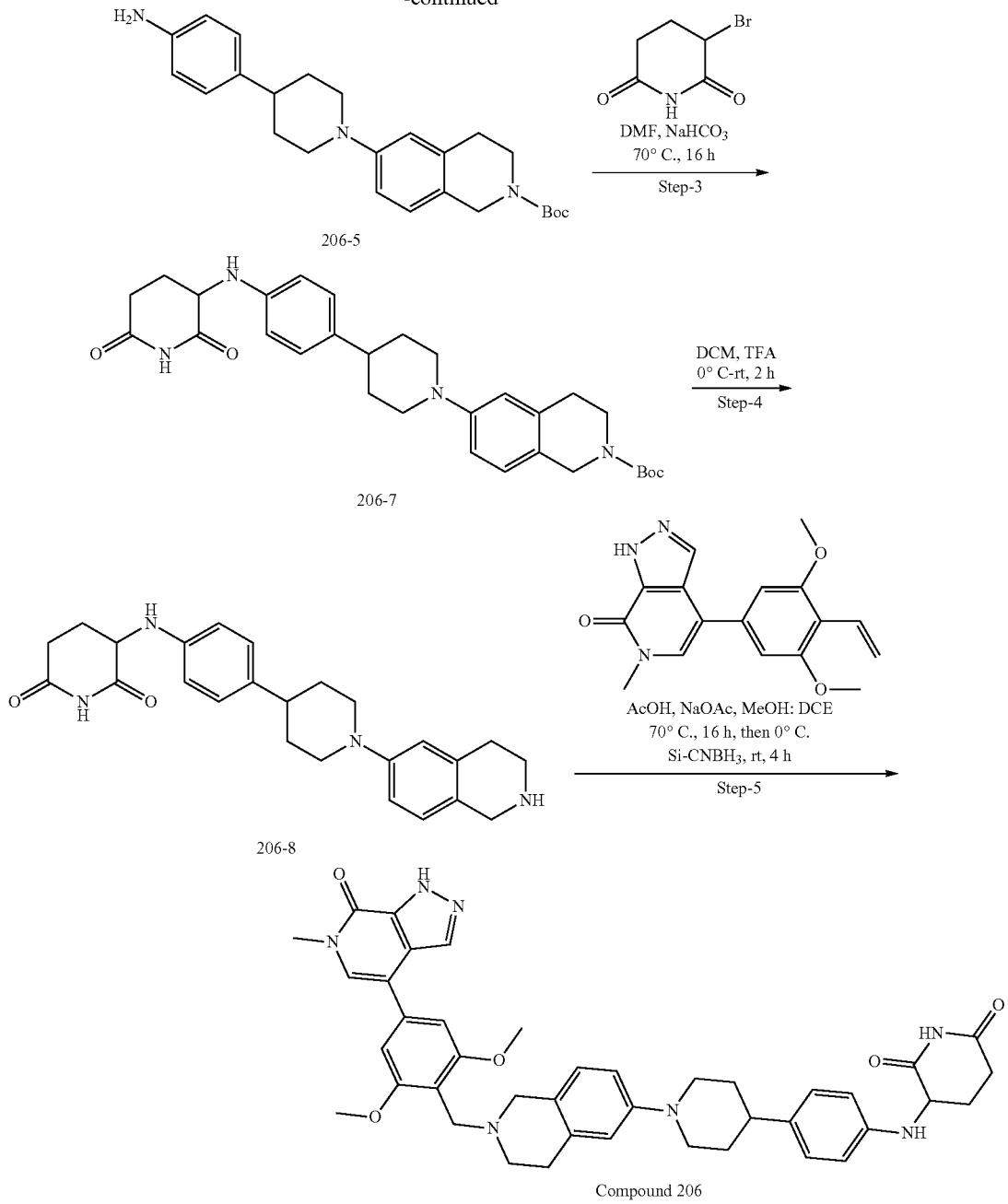

Step-1: Argon gas was purged through a solution of 4-(4-nitrophenyl)piperidine (1.7 g, 7.0 mmol), sodium tert-butoxide (1.58 g, 16.48 mmol) and tert-butyl 6-bromo-3,4-dihydroisoquinoline-2(1H)-carboxylate (2.31 g, 7.41 mmol) in 1,4 dioxane (15 mL) for 10 minutes before addition of tris(dibenzylideneacetone)dipalladium(0) (0.905 g, 0.98 mmol) and xanthphos (0.238 g, 0.412 mmol). The reaction mixture was then stirred at 80° C. for 16 h; while monitoring progress of the reaction by LCMS and TLC. After completion, it was cooled to ambient temperature and water (50 mL) was added to it. Extraction was carried out using ethyl acetate (2×50 mL); the combined organic extracts were washed with brine (50 mL), dried over anhydrous sodium sulphate, filtered and evaporated under reduced pressure. The residue was purified by silica gel column chromatography (using 230-400 mesh silica gel, 0-100% gradient elution of ethyl acetate in pet-ether) to afford desired compound tert-butyl 6-[4-(4-nitrophenyl)-1-piperidyl]-3,4-dihydro-1H-isoquinoline-2-carboxylate 206-4 (0.57 g, 1.3 mmol, 17.50% yield, 94% purity) as an off white solid. LCMS (ES$^+$): m/z 438.1 [M+H]$^+$ Step-2: To stirred solution of tert-butyl 6-[4-(4-nitrophenyl)-1-piperidyl]-3,4-dihydro-1H-isoquinoline-2-carboxylate 206-4 (0.570 g, 1.30 mmol) in methanol (10 mL) was added 10% Pd/C (130 mg); and the reaction mixture was stirred under hydrogen atmosphere (bladder) for 16 h. After completion of the reaction (as indicated by LCMS), the catalyst was filtered off through Celite and washed with methanol (20 mL×2). The filtrate was concentrated under reduced pressure and the residue was purified by silica gel column chromatography (using 230-400 mesh silica gel, 0-100% gradient elution of ethyl acetate in pet-ether) to afford desired compound tert-butyl 6-[4-(4-aminophenyl)-1-piperidyl]-3,4-dihydro-1H-isoquinoline-2-carboxylate 206-5 (0.420 g, 1.031 mmol, 79% yield, 81% purity) as a thick brown oil. LCMS (ES$^+$): m/z 408.1 [M+H]$^+$ Step-4: To a stirred solution of tert-butyl 6-[4-(4-aminophenyl)-1-piperidyl]-3,4-dihydro-1H-isoquinoline-2-carboxylate 206-5 (0.420 g, 1.03 mmol) in DMF (10 mL) was added sodium bicarbonate (0.520 g, 6.18 mmol) and 3-bromopiperidine-2,6-dione (0.520 g, 6.18 mmol). The reaction mixture was stirred at 70° C. for 16 h in a sealed tube, while monitoring progress of the reaction by TLC. After completion of the reaction, it was cooled to room temperature and saturated sodium bicarbonate solution (20 mL) was added to it. Extraction was carried out using ethyl acetate (3×25 mL); the combined organic layers were washed with water (20 mL×2), brine (20 mL), dried over anhydrous Na$_2$SO$_4$, filtered and concentrated under reduced pressure. The crude compound was purified by silica gel column chromatography (230-400 mesh silica gel, using 0-100% gradient elution of ethyl acetate in pet-ether) to afford desired compound tert-butyl 6-[4-[4-[(2,6-dioxo-3-piperidyl)amino]phenyl]-1-piperidyl]-3,4-dihydro-1H-isoquinoline-2-carboxylate 206-7 (0.300 g, 0.58 mmol, 45% yield, 79.5% purity) as a purple solid. LCMS (ES$^+$): m/z 519.1 [M+H]$^+$ Step-5: To a stirred solution of tert-butyl 6-[4-[4-[(2,6-dioxo-3-piperidyl)amino]phenyl]-1-piperidyl]-3,4-dihydro-1H-isoquinoline-2-carboxylate 206-7 (0.3 g, 0.578 mmol) in DCM (5 mL) was added TFA (66 mg, 0.578 mmol) at 0° C. and the reaction mixture was allowed to warm to room temperature over 2 h, while monitoring progress of the reaction by TLC. After completion of the reaction, volatiles were evaporated under reduced pressure and diethyl ether (5 mL) was added to the residue. It was stirred for 15 min and the solid obtained was filtered, washed with diethyl ether (5 mL×2) and dried to afford desired compound 3-[4-[1-(1,2,3,4-tetrahydroisoquinolin-6-yl)-4-piperidyl]anilino]piperidine-2,6-dione 206-8 (TFA salt) (0.280 g, 0.526 mmol, 90% yield, 85.4% purity) as an off-white solid. LCMS (ES$^+$): m/z 419.1 [M+H]$^+$ Step-6: To a stirred solution of 3-[4-[1-(1,2,3,4-tetrahydroisoquinolin-6-yl)-4-piperidyl]anilino]piperidine-2,6-dione 206-8 (58.76 mg, 210 mmol) in DCE (5 mL) and methanol (5 mL) was added NaOAc (23.04 mg, 280.81 mmol), MS (100 mg) and AcOH (8.43 mg, 140.41 mmol). To this was then added 3,6-dimethoxy-4-(6-methyl-7-oxo-1H-pyrazolo[3,4-c]pyridin-4-yl)benzaldehyde (0.09 g, 165 mmol) and the reaction mixture was stirred at 70° C. for 16 h. It was then cooled to 0° C. and Si—CNBH$_3$ (49.11 mg, 702.03 mmol) was added to it. The reaction mixture was stirred at room temperature for 4 h. It was then filtered through a pad of Celite and washed with DCE-MeOH (1:1; 3×5 mL). The filtrate was concentrated under reduced pressure. The crude obtained was purified by preparative HPLC to afford desired compound 3-[4-[1-[2-[[2,6-dimethoxy-4-(6-methyl-7-oxo-1H-pyrazolo[3,4-c]pyridin-4-yl)phenyl]methyl]-3,4-dihydro-1H-isoquinolin-6-yl]-4-piperidyl]anilino]piperidine-2,6-dione (TFA salt) Compound 204 (40 mg, 0.05 mmol, 42% yield, 96.05% purity) as a light yellow solid. $^1$H NMR (400 MHz, DMSO-d$_6$) δ 1.60-1.72 (m, 2H); 1.78-1.92 (m, 3H); 2.06-2.12 (m, 1H); 2.55-2.65 (m, 2H); 2.68-2.82 (m, 3H); 3.04-3.10 (m, 2H); 3.62 (s, 3H); 3.58-3.70 (m, 2H); 3.78-3.86 (m, 2H); 3.95 (s, 6H); 4.22-4.40 (m, 5H); 6.62 (d, J=8.4 Hz, 2H); 6.84 (s, 1H); 6.91-7.20 (m, 7H), 7.66 (s, 1H), 8.25 (s, 1H); 9.50 (bs, 1H), 10.80 (s, 1H); 14.30 (bs, 1H). LCMS (ES$^+$): m/z 716.51 [M+H]$^+$ Synthesis of Compound 207

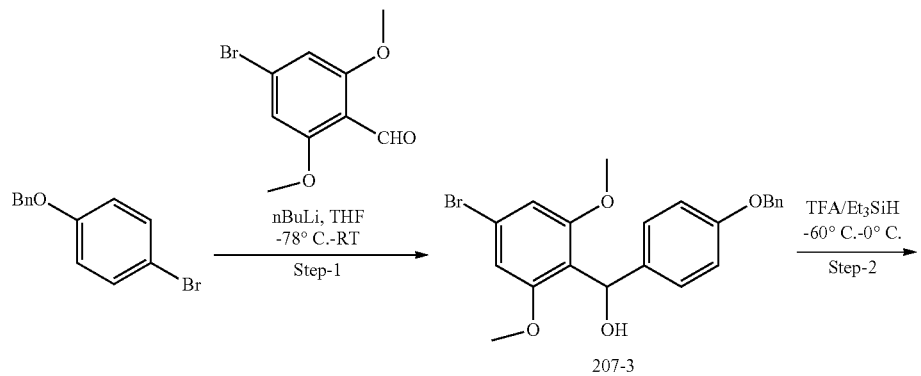

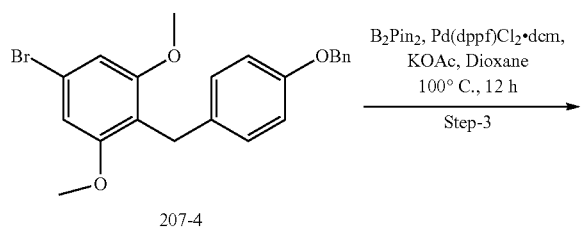

-continued
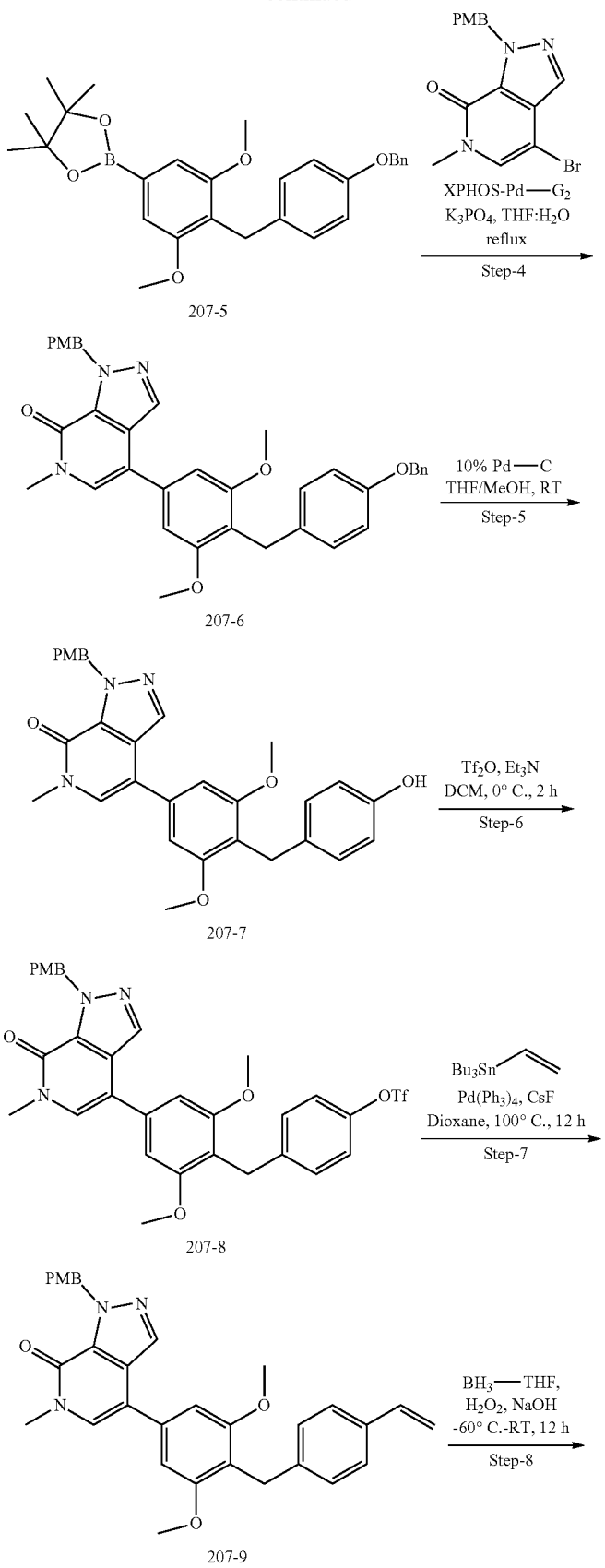

-continued
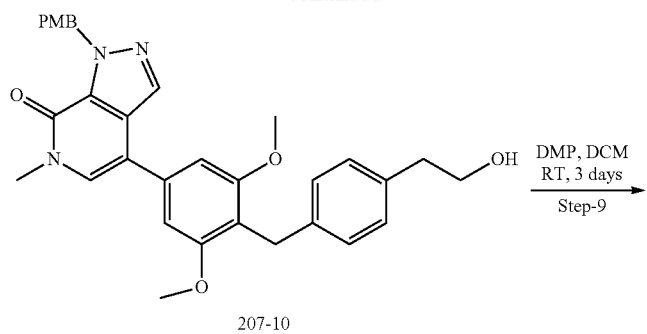
207-10
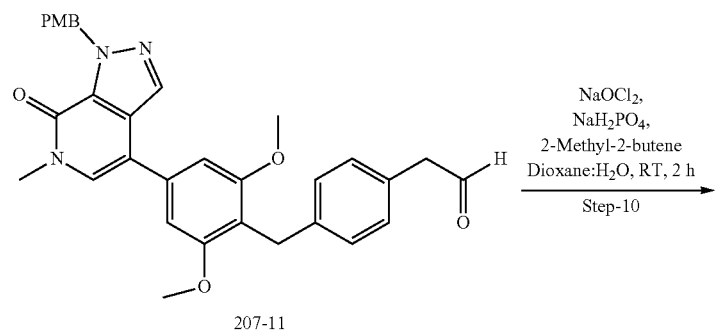
207-11
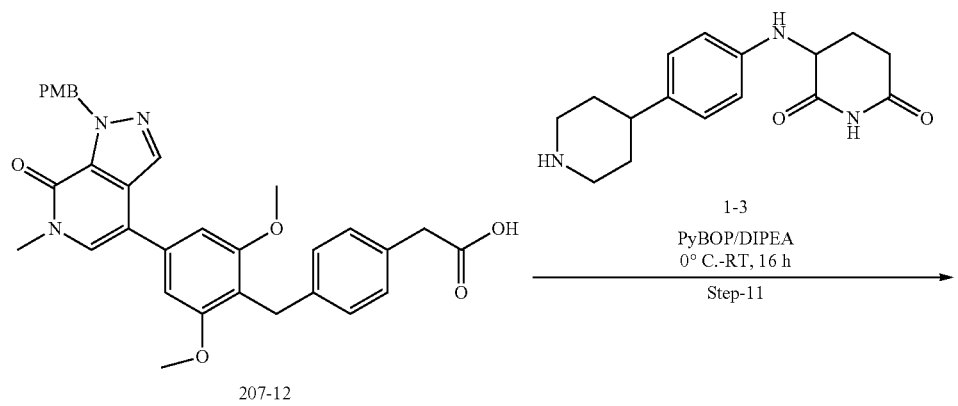
207-12

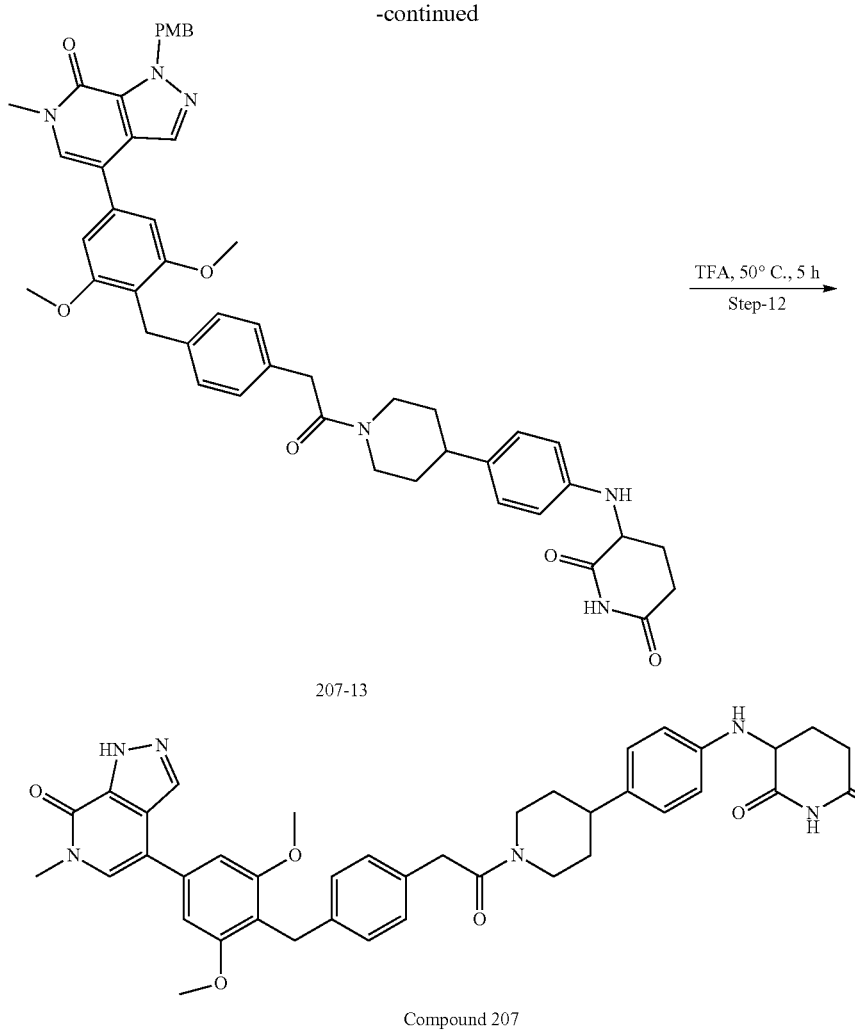

Compound 207

Step-1: To the stirred solution of 1-benzyloxy-4-bromobenzene (5 g, 19.00 mmol) in dry THF (40 mL) was added drop wise n-Butyl lithium (2.5 M solution in THF) (8.36 mL) at −78° C. The reaction mixture was stirred at −78° C. for 30 minutes. The reaction mixture was slowly warmed to −30° C. for the period of 1 h. The reaction mixture was again cooled to −78° C. and added drop wise 4-bromo-2,6-dimethoxybenzaldehyde (4.66 g, 19.00 mmol) in dry THF (20 mL). The reaction mixture was slowly warmed to 0° C. for the period of 3 h while monitoring the reaction by TLC. After the completion of the reaction, the reaction mixture was quenched with ice cold saturated ammonium chloride solution (100 mL) and extracted with ethyl acetate (2×100 mL). The combined organic layer was washed by water (1×50 mL) and brine (1×50 mL), dried over anhydrous Na$_2$SO$_4$, filtered and concentrated to afford the crude product. The crude was purified by column chromatography over silica gel (100/200 mesh) and the product eluted at 30% EtOAc/Hexane to afford (4-benzyloxyphenyl)-(4-bromo-2,6-dimethoxy-phenyl)methanol 207-3 (4 g, 46.58% yield, 95% purity) as pale brown solid.

Step-2: To the stirred solution of (4-benzyloxyphenyl)-(4-bromo-2,6-dimethoxy-phenyl)methanol 207-3 (1.60 g, 3.73 mmol) in dry DCM (80 mL) was added triethyl silane (2.17 g, 18.63 mmol, 2.98 mL) at −60° C. under N$_2$ atm. TFA (2.12 g, 18.63 mmol, 1.44 mL) in dry DCM (10 mL) was added drop wise to the reaction mixture at −60° C. The reaction was slowly warmed to 0° C. for 3 h while monitoring by TLC. After the completion the reaction mixture was diluted with excess of DCM (200 mL) and quenched with ice cold saturated sodium carbonate (100 mL), extracted with DCM (2×100 mL). The combined organic layer was washed by water (1×100 mL) followed by brine (1×50 mL), dried over anhydrous Na$_2$SO$_4$, filtered and concentrated to afford the crude product. The crude product was further triturated with pentane (2×50 mL) and the solid precipitated out was filtered to afford 2-[(4-benzyloxyphenyl) methyl]-5-bromo-1, 3-dimethoxy-benzene 207-4 (1.20 g, 77.90% yield) as white solid. LCMS (ES$^+$): m/z [M+H]$^+$ 413.08

Step-3: To the stirred solution of 2-[(4-benzyloxyphenyl) methyl]-5-bromo-1,3-dimethoxy-benzene 207-4 (1.2 g, 2.90 mmol) in 1,4 Dioxane (40 mL) was added 4,4,5,5-tetramethyl-2-(4,4,5,5-tetramethyl-1,3,2-dioxaborolan-2-yl)-1,3,2-dioxaborolane (1.1 g, 4.3 mmol) followed by the addition of potassium acetate (0.85 g, 8.71 mmol) at room temperature under argon atmosphere. The reaction mixture was degassed with argon repeatedly and Pd(dppf)Cl$_2$.dcm (0.12 g, 0.14 mmol) was added in one portion under argon atmosphere. The reaction mixture was again degassed with argon repeatedly and then heated at reflux at 100° C. for 12 h. After the completion the reaction mixture was cooled to room temperature and filtered off through Celite, washed with ethyl acetate (200 mL). The filtrate was concentrated, and the residual mass was dissolved in Ethyl acetate (100 mL) and washed with water (1×50 mL), brine (1×25 mL), dried over anhydrous $Na_2SO_4$, filtered and concentrated to yield the crude product. The crude was purified by column chromatography over silica gel (100/200 mesh) and the product eluted at 5% EtOAc/Pet ether to afford 2-[4-[(4-benzyloxyphenyl)methyl]-3,5-dimethoxy-phenyl]-4,4,5,5-tetramethyl-1,3,2-dioxaborolane 207-5 (1.3 g, 77.81% yield, 80% purity) as pale brown pasty solid. LCMS (ES$^+$): m/z [M+H]$^+$ 461.1

Step-4: To a stirred solution of 4-bromo-1-[(4-methoxyphenyl)methyl]-6-methyl-pyrazolo[3,4-c]pyridin-7-one (1.35 g, 3.88 mmol) in dry THF (100 mL) was added 2-(4-(4-(benzyloxy)benzyl)-3,5-dimethoxyphenyl)-4,4,5,5-tetramethyl-1,3,2-dioxaborolane 207-5 (1.78 g, 3.88 mmol) at RT followed by the addition of potassium phosphate tribasic anhydrous (1.65 g, 7.75 mmol) dissolved in Water (20 mL). The reaction mixture was degassed with argon repeatedly and the Xphos-Pd-G2 catalyst, (1310584-14-5) (0.15 g, 0.19 mmol) was added in one portion under argon atmosphere. The reaction mixture was again degassed with argon and then refluxed at 80° C. for 12 h. After the completion of the reaction, the reaction mixture was cooled to room temperature and filtered off through Celite, washed with ethyl acetate (50 mL). The organic layer was partitioned from the filtrate and concentrated. The resultant crude product was purified by column chromatography over silica gel (230/400 mesh) and the product eluted at 50-60% EtOAc/Pet ether to afford 4-(4-(4-(benzyloxy)benzyl)-3,5-dimethoxyphenyl)-1-(4-methoxybenzyl)-6-methyl-1,6-dihydro-7H-pyrazolo[3,4-c]pyridin-7-one 207-6 (1.25 g, 50.90% yield, 95% purity) as pale yellow solid. LCMS (ES$^+$): m/z [M+H]$^+$ 602.21

Step-5: To the stirred solution of 4-[4-[(4-benzyloxyphenyl)methyl]-3,5-dimethoxy-phenyl]-1-[(4-methoxyphenyl)methyl]-6-methyl-pyrazolo[3,4-c]pyridin-7-one 207-6 (1.60 g, 2.66 mmol) in dry THF (80 mL) and methanol (20 mL) was added wet 10% Palladium on carbon (0.28 g, 2.66 mmol) at RT. The reaction mixture was stirred at RT under $H_2$ atm for 12 h. After the completion of the reaction, the reaction mixture was filtered-off through Celite and washed with methanol (100 mL). The filtrate was concentrated and the residual mass was triturated with pentane (2×50 mL), decanted the organic layer and the solid precipitated out was dried well to afford the product 4-[4-[(4-hydroxyphenyl)methyl]-3,5-dimethoxy-phenyl]-1-[(4-methoxyphenyl)methyl]-6-methyl-pyrazolo[3,4-c]pyridin-7-one 207-7 (1.20 g, 83.80% yield, 95% purity) as off-white solid. LCMS (ES$^+$): m/z [M+H]$^+$ 512.1

Step-6: To the stirred solution of 4-(4-(4-hydroxybenzyl)-3,5-dimethoxyphenyl)-1-(4-methoxybenzyl)-6-methyl-1,6-dihydro-7H-pyrazolo[3,4-c]pyridin-7-one 207-7 (1.2 g, 2.35 mmol) in DCM (100 mL) was added drop wise triethylamine (0.71 g, 7.04 mmol) at 0° C. followed by the drop wise addition of trifluoromethanesulfonic anhydride (0.69 g, 2.46 mmol) under $N_2$ atm. The reaction mixture was stirred at 0° C. for another 2 h. The completion of the reaction was confirmed by TLC. The reaction mixture was quenched with ice cold saturated solution of $NaHCO_3$ (100 mL) and extracted with DCM (2×100 mL). The combined organic layer was washed with brine (1×50 mL), dried over anhydrous $Na_2SO_4$, filtered and concentrated to yield the crude product. The crude product was purified by column chromatography over silica gel (100/200 mesh) and the product eluted at 50% EtOAc/Pet ether to afford 4-(2,6-dimethoxy-4-(1-(4-methoxybenzyl)-6-methyl-7-oxo-6,7-dihydro-1H-pyrazolo[3,4-c]pyridin-4-yl)benzyl)phenyl trifluoromethanesulfonate 207-8 (1.30 g, 83.19% yield, 96.62% purity) as white solid. LCMS (ES$^+$): m/z [M+H]$^+$ 644.59

Step-7: To a stirred solution of 4-(2,6-dimethoxy-4-(1-(4-methoxybenzyl)-6-methyl-7-oxo-6,7-dihydro-1H-pyrazolo[3,4-c]pyridin-4-yl)benzyl)phenyl trifluoromethanesulfonate 207-8 (0.65 g, 1.01 mmol) in dry 1,4-Dioxane (30 mL) in a sealed tube was added tributyl(vinyl)stannane (0.96 g, 3.03 mmol) followed by the addition of Lithium chloride, anhydrous, (0.42 g, 10.10 mmol) at RT. The reaction mixture was degassed with argon repeatedly and Pd(Ph$_3$)$_4$ (0.058 g, 0.05 mmol) was added under argon atmosphere. The reaction mixture was again degassed with argon and then heated at 110° C. for 12 h, while monitoring by TLC. After completion the reaction mixture was cooled to room temperature and filtered off through Celite, washed with ethyl acetate (100 mL). The organic layer was concentrated and the resultant crude product was purified by column chromatography over silica gel (100/200 mesh) and the product eluted at 70-80% EtOAc/Hexane to afford 4-(3,5-dimethoxy-4-(4-vinylbenzyl)phenyl)-1-(4-methoxybenzyl)-6-methyl-1,6-dihydro-7H-pyrazolo[3,4-c]pyridin-7-one 207-9 (0.35 g, 64.20% yield, 96.63% purity) as white solid. LCMS (ES$^+$): m/z [M+H]$^+$ 522.47

Step-8: To the stirred solution of 4-(3,5-dimethoxy-4-(4-vinylbenzyl)phenyl)-1-(4-methoxybenzyl)-6-methyl-1,6-dihydro-7H-pyrazolo[3,4-c]pyridin-7-one 207-9 (0.25 g, 0.47 mmol) in THF (20 mL) was added dropwise Borane-tetrahydrofuran complex, 1M in THF (0.20 g, 2.40 mmol) at −60° C. under $N_2$ atm. The reaction mixture was slowly warmed to RT and stirred at rt for 16 h while monitoring the reaction by TLC. After the consumption of the starting material, the reaction mixture was cooled to 0° C. Hydrogen peroxide 35% (0.16 g, 4.79 mmol) and sodium hydroxide (0.19 g, 4.79 mmol) dissolved in water (1 mL) was added in sequence to the reaction mixture at this temperature. The reaction mixture was stirred at 0° C. for 30 minutes, warmed to RT and stirred another 2 h. The completion of the reaction was confirmed by TLC. The reaction mixture was quenched with ice cold water (50 mL) and extracted with EtOAc (2×50 mL). The combined organic layer was washed with brine (1×25 mL), dried over anhydrous $Na_2SO_4$, filtered and concentrated to yield the crude product. The crude product was purified by column chromatography over silica gel (230/400 mesh) and the product eluted at 60-70% EtOAc/Hexane to afford 4-(4-(4-(2-hydroxyethyl)benzyl)-3,5-dimethoxyphenyl)-1-(4-methoxybenzyl)-6-methyl-1,6-dihydro-7H-pyrazolo[3,4-c]pyridin-7-one 207-10 (0.16 g, 61.86% yield, 98.59% purity) as white solid. LCMS (ES$^+$): m/z [M+H]$^+$ 540.21

Step-9: To the stirred solution of 4-[4-[[4-(2-hydroxyethyl)phenyl]methyl]-3,5-dimethoxy-phenyl]-1-[(4-methoxyphenyl)methyl]-6-methyl-pyrazolo[3,4-c]pyridin-7-one 207-10 (0.12 g, 0.22 mmol) in DCM (25 mL) was added Dess Martin-DMP (0.94 g, 2.22 mmol) in one portion at 0° C. under $N_2$ atm. The reaction mixture was stirred at rt for 3 days while monitoring the reaction by TLC and LC-MS. After the completion of the reaction, the reaction mixture was quenched with ice cold saturated solution of sodium bicarbonate (50 mL) and extracted with DCM (2×25 mL). The combined organic layer was washed with brine (1×25 mL), dried over anhydrous $Na_2SO_4$, filtered and concentrated to yield the crude product. The crude product was purified by column chromatography over silica gel (230/400 mesh) and the product eluted at 60-70% EtOAc/Hexane to afford 2-[4-[[2,6-dimethoxy-4-[1-[(4-methoxyphenyl)methyl]-6-methyl-7-oxo-pyrazolo[3,4-c]pyridin-4-yl]phenyl] methyl]phenyl] acetaldehyde 207-11 (0.065 g, 48.93% yield, 90% purity) as white solid. LCMS (ES⁺): m/z [M+H]⁺ 538.21

Step-10: To the stirred solution of 2-(4-(2,6-dimethoxy-4-(1-(4-methoxybenzyl)-6-methyl-7-oxo-6,7-dihydro-1H-pyrazolo[3,4-c]pyridin-4-yl)benzyl)phenyl)acetaldehyde 207-11 (0.06 g, 0.12 mmol) in dry dioxane (5 mL) was added dropwise 2-methyl-2-butene (0.067 g, 0.96 mmol) at 0° C. followed by the addition of sodium chlorite (0.054 g, 0.60 mmol) and sodium dihydrogen phosphate (0.29 g, 2.42 mmol) in water (5 mL) The reaction mixture was slowly warmed to rt over the period of 30 mints and stirred at rt for another 2 h while monitoring the reaction by TLC. After the completion the reaction mixture was concentrated as such to afford 2-(4-(2,6-dimethoxy-4-(1-(4-methoxybenzyl)-6-methyl-7-oxo-6,7-dihydro-1H-pyrazolo[3,4-c]pyridin-4-yl)benzyl)phenyl)acetic acid 207-12 (0.25 g, 74% purity)) and proceeded as such for the next step without further purification. LCMS (ES⁺): m/z [M+H]⁺ 554.18

Step-11: To the stirred solution of 3-((4-(piperidin-4-yl)phenyl)amino)piperidine-2,6-dione 1-3 (0.035 g, 0.10 mmol) in dry DMF (6 mL) was added DIPEA (0.056 g, 0.43 mmol) dropwise at 0° C. under $N_2$ atm. The reaction mixture was warmed to RT over the period of 15 min. The pH of the reaction was basic. 2-(4-(2,6-dimethoxy-4-(1-(4-methoxybenzyl)-6-methyl-7-oxo-6,7-dihydro-1H-pyrazolo[3,4-c]pyridin-4-yl)benzyl)phenyl)acetic acid 207-12 (0.04 g, 0.25 g crude, 0.072 mmol) was added to the reaction mixture at rt followed by the addition of PyBop (0.048 g, 0.093 mmol) and reaction was allowed to stir at RT for 16 h, while monitoring by TLC and LCMS. After the completion the reaction mixture was concentrated to yield the crude product and purified by reverse phase column chromatography (C18/30 g) using 0.1% Formic acid in water and acetonitrile as the mobile phase to afford 3-((4-(1-(2-(4-(2,6-dimethoxy-4-(1-(4-methoxybenzyl)-6-methyl-7-oxo-6,7-dihydro-1H-pyrazolo[3,4-c]pyridin-4-yl)benzyl)phenyl) acetyl)piperidin-4-yl)phenyl)amino)piperidine-2,6-dione 207-13 (0.043 g, 57.23% yield, 79.14% purity) as pale yellow solid. LCMS (ES⁺): m/z [M+H]⁺ 823.43

Step-12: To a suspension of 3-[4-[1-[2-[4-[[2,6-dimethoxy-4-[1-[(4-methoxyphenyl)methyl]-6-methyl-7-oxo-pyrazolo[3,4-c]pyridin-4-yl]phenyl]methyl]phenyl]acetyl]-4-piperidyl]anilino]piperidine-2,6-dione 207-13 (0.043 g, 0.052 mmol) was added TFA (0.59 g, 5.23 mmol) and reaction mixture heated at 50° C. under $N_2$ atm for 5 h while monitoring the reaction by TLC and LC-MS. After completion, the reaction mixture was concentrated to yield the crude which was purified by Prep HPLC by to afford 3-[4-[1-[2-[4-[[2,6-dimethoxy-4-(6-methyl-7-oxo-1H-pyrazolo[3,4-c]pyridin-4-yl)phenyl]methyl]phenyl]acetyl]-4-piperidyl]anilino]piperidine-2,6-dione TFA Compound 207 (0.0102 g, 23.85% yield, 99.78% purity) as off-white solid. ¹H NMR (400 MHz, DMSO-d₆) δ 14.17 (s, 1H), 10.76 (s, 1H), 8.21 (s, 1H), 7.54 (s, 1H), 7.21 (s, 1H), 7.14-7.06 (m, 4H), 6.89 (d, J=8.4 Hz, 2H), 6.86 (s, 2H), 6.60 (d, J=8.4 Hz, 2H), 5.56 (s, 1H), 4.50 (d, J=12.1 Hz, 1H), 4.28-4.24 (m, 1H), 4.02 (d, J=12.7 Hz, 1H), 3.88-3.84 (m, 8H), 3.63 (s, 5H), 3.03-3.01 (m, 1H), 2.97-2.54 (m, 4H), 2.11-2.06 (m, 1H), 1.85-1.83 (m, 1H), 1.70-1.65 (m, 2H), 1.35-1.31 (m, 2H). LCMS (ES⁺): m/z [M+H]⁺ 703.30

Synthesis of Compound 208

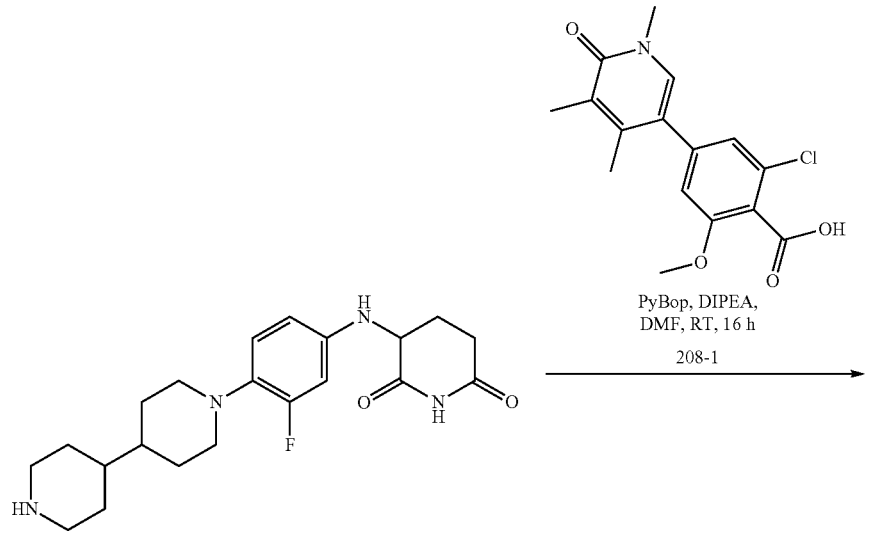

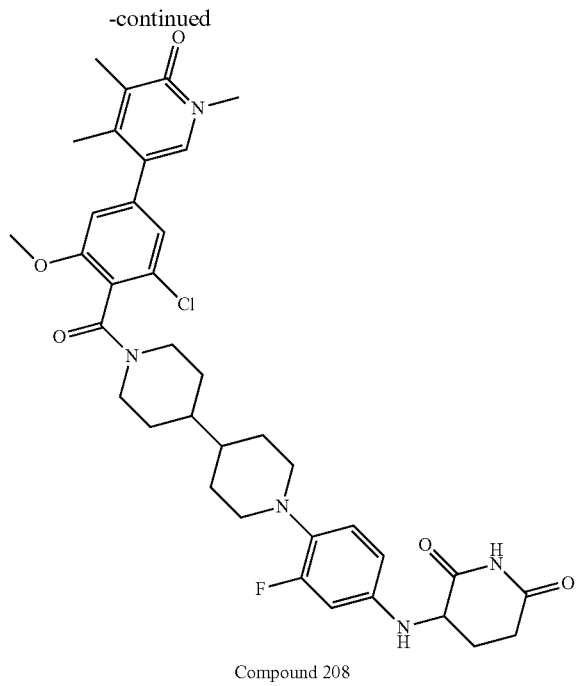

Compound 208

To a stirred solution of 3-[3-fluoro-4-[4-(4-piperidyl)-1-piperidyl]anilino]piperidine-2,6-dione HCl 73-7 (0.096 g, 0.248 mmol) in DMF (5 mL) was added DIPEA and stirred for 15 min. Before adding 2-chloro-6-methoxy-4-(1,4,5-trimethyl-6-oxo-3-pyridyl)benzoic acid (0.080 g, 0.248 mmol) and PyBOP (0.194 g, 0.372 mmol). Reaction mixture was allowed to stir at for 16 h while monitoring by LCMS. After completion of the reaction, DMF was evaporated under reduced pressure and the residue was purified by preparative HPLC to afford 3-[4-[4-[1-[2-chloro-6-methoxy-4-(1,4,5-trimethyl-6-oxo-3-pyridyl)benzoyl]-4-piperidyl]-1-piperidyl]-3-fluoro-anilino]piperidine-2,6-dione.TFA salt Compound 208 (0.028 g, 13.65% yield, 97.74% purity). $^1$H NMR (400 MHz, DMSO-d$_6$) δ 10.82 (s, 1H), 7.59 (s, 1H), 7.20 (bs, 1H), 7.03-7.01 (m, 1H), 6.98 (s, 1H), 6.62 (d, J=14.0 Hz, 1H), 6.53 (d, J=5.2 Hz, 1H), 4.58 (d, J=10.4 Hz, 1H), 4.35 (d, J=7.2 Hz, 1H) 3.82-3.81 (m, 4H), 3.78 (m, 3H), 3.46 (s, 3H), 3.30-3.03 (m, 1H), 3.03-3.00 (m, 1H), 2.76-2.73 (m, 2H), 2.60-2.59 (m, 1H), 2.06 (d, J=4.9 Hz, 7H), 1.90-1.83 (m, 4H), 1.68-1.42 (m, 5H), 1.15-1.12 (m, 2H). LCMS (ES$^+$): m/z [M+H]$^+$ 692.59

Compound 209 was prepared following the synthesis of Compound 208.

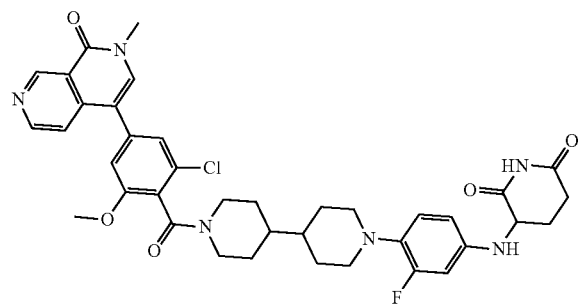 [SMILES: COc1cc(-c2cn(C)c(=O)c3cnccc23)cc(Cl)c1C(=O)N1CCC(C2CCN(c3ccc(NC4CCC(=O)NC4=O)cc3F)CC2)CC1]

$^1$H NMR (400 MHz, DMSO-d$_6$) δ 10.81 (s, 1H), 9.47 (s, 1H), 8.75 (d, J=5.7 Hz, 1H), 7.98 (s, 1H), 7.60 (d, J=5.8 Hz, 1H), 7.22-7.17 (m, 3H), 6.60 (d, J=14.1 Hz, 1H), 6.51 (d, J=8.2 Hz, 1H), 4.60 (d, J=11.5 Hz, 1H), 4.34 (d, J=7.1 Hz, 1H), 3.85 (d, J=6.3 Hz, 3H), 3.60 (s, 3H), 3.40-3.38 (m, 5H), 3.07-2.65 (m, 3H), 2.58-2.56 (m, 1H), 2.07-2.00 (m, 1H), 1.90-1.84 (m, 4H), 1.70-1.67 (m, 1H), 1.51-1.15 (m, 6H) LCMS (ES$^+$): m/z [M+H]$^+$ 715.52

Compound 210 was prepared following the synthesis of Compound 208.

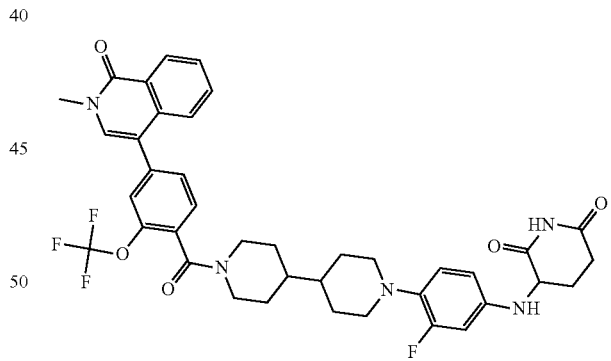

$^1$H NMR (400 MHz, DMSO-d$_6$) δ 10.81 (s, 1H), 8.35 (dd, J=8.1, 1.4 Hz, 1H), 7.81-7.69 (m, 1H), 7.71-7.48 (m, 7H), 6.76-6.41 (m, 2H), 4.62 (d, J=12.7 Hz, 1H), 4.35 (d, J=10.9 Hz, 1H), 3.58 (s, 3H), 3.46 (t, J=8.6 Hz, 2H), 3.07 (s, 2H), 2.85-2.53 (m, 4H), 2.18-2.01 (m, 1H), 1.96-1.76 (m, 6H), 1.71 (s, 1H), 1.42 (d, J=40.7 Hz, 4H), 1.16 (d, J=12.1 Hz, 2H). LCMS (ES$^+$): m/z [M+H]$^+$ 734.9.

Compound 211 was prepared following the synthesis of Compound 208.

927
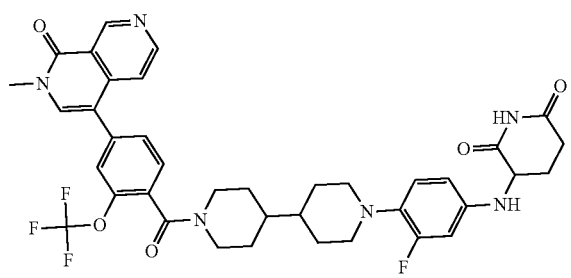 [SMILES: Cn1cc(-c2ccc(C(=O)N3CCC(C4CCN(c5ccc(NC6CCC(=O)NC6=O)cc5F)CC4)CC3)c(OC(F)(F)F)c2)c2ccncc2c1=O]
928
¹H NMR (400 MHz, DMSO-d₆) δ 10.82 (s, 1H), 9.50 (s, 1H), 8.76 (s, 1H), 8.14-7.98 (m, 1H), 7.75-7.45 (m, 5H), 7.29 (s, 1H), 6.65 (dd, J=15.1, 2.5 Hz, 1H), 6.56 (d, J=8.8 Hz, 1H), 4.62 (d, J=12.6 Hz, 1H), 4.38 (dd, J=11.8, 4.8 Hz, 1H), 3.61 (s, 3H), 3.46 (d, J=12.1 Hz, 3H), 3.25 (s, 2H), 3.07 (q, J=9.3, 6.5 Hz, 1H), 2.86-2.54 (m, 3H), 2.08 (td, J=7.0, 5.7, 3.8 Hz, 1H), 1.89 (tt, J=12.6, 5.7 Hz, 4H), 1.62 (d, J=13.7 Hz, 2H), 1.46 (s, 2H), 1.19 (d, J=34.2 Hz, 3H). LCMS (ES⁺): m/z [M+H]⁺ 735.7.
Synthesis of Compound 212, Compound 213, and Compound 214
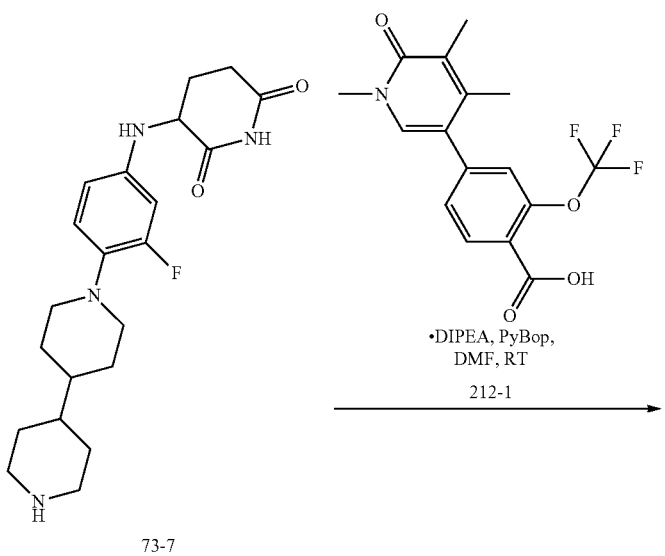
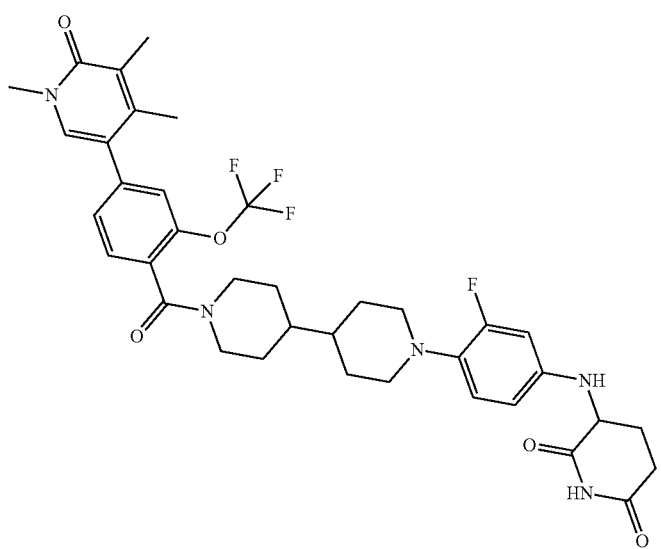
Compound 212

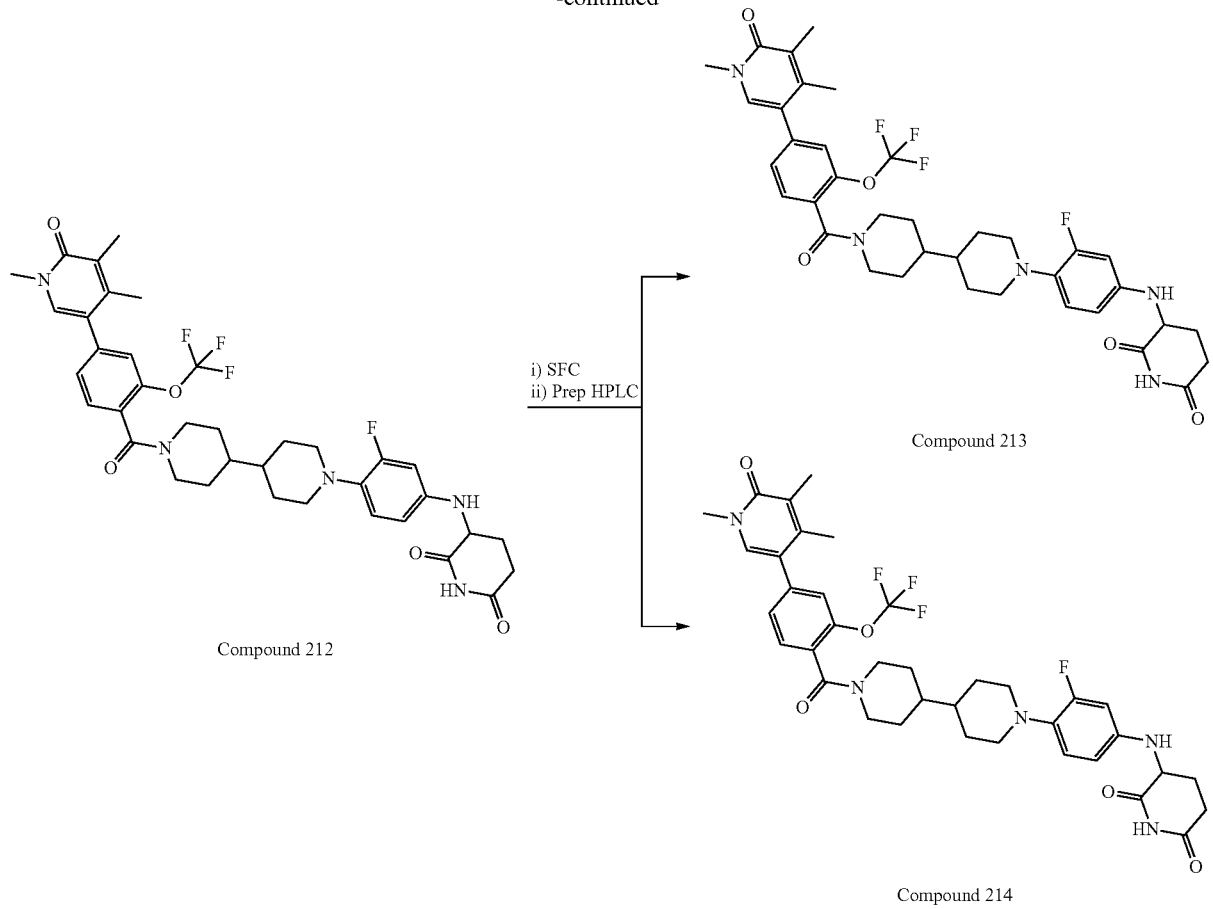

Compound 212

Compound 213

Compound 214

To a stirred mixture of 3-[3-fluoro-4-[4-(4-piperidyl)-1-piperidyl]anilino]piperidine-2,6-dione. 73-7 (0.921 g, 2.17 mmol) in DMF (10 mL) was added DIPEA (1.51 mL) followed by the addition of 2-(trifluoromethoxy)-4-(1,4,5-trimethyl-6-oxo-3-pyridyl)benzoic acid (0.740 g, 2.17 mmol) and stirred for 5 min at room temperature. PyBOP (1.69 g, 3.25 mmol) was added to the above reaction mixture and stirred for 16 h while monitoring by TLC and LCMS. After completion, reaction mixture was poured on to ice flakes to obtain solid. The solid was filtered to obtain crude. The crude was purified by (silica gel davisil, eluent 6% methanol in $CH_2C2$) column chromatography to afford 3-[3-fluoro-4-[4-[1-[2-(trifluoromethoxy)-4-(1,4,5-trimethyl-6-oxo-3-pyridyl)benzoyl]-4-piperidyl]-1-piperidyl]anilino]piperidine-2,6-dione Compound 212 free base (0.9 g, 55.40% yield, 95% purity) as yellow solid. To a stirred solution of 3-[3-fluoro-4-[4-[1-[2-(trifluoromethoxy)-4-(1,4,5-trimethyl-6-oxo-3-pyridyl)benzoyl]-4-piperidyl]-1-piperidyl]anilino]piperidine-2,6-dione Compound 212 free base (0.9 g, 1.26 mmol) in dry DCM (5 mL) was added TFA (0.7 mL) at 0° C. and allowed to stirred at RT for 1 h. After 1 h the reaction mass was concentrated to dryness and triturated with diethyl ether (2×30 ml) to afford 3-[3-fluoro-4-[4-[1-[2-(trifluoromethoxy)-4-(1,4,5-trimethyl-6-oxo-3-pyridyl)benzoyl]-4-piperidyl]-1-piperidyl]anilino]piperidine-2,6-dione (1 g, 90.49% yield, 94.49% purity) Compound 212 TFA salt as a light green solid. $^1$H NMR (400 MHz, DMSO-$d_6$) δ 10.75 (s, 1H), 7.53 (s, 1H), 7.48-7.38 (m, 2H), 7.37-7.27 (m, 2H), 7.19 (s, 1H), 6.57 (d, J=14.8 Hz, 1H), 6.48 (d, J=8.9 Hz, 1H), 4.53 (d, J=12.6 Hz, 1H), 4.30 (dd, J=11.8, 4.9 Hz, 1H), 3.39 (s, 3H), 3.33 (d, J=14.2 Hz, 2H), 2.98 (s, 1H), 2.73-2.60 (m, 2H), 2.51 (dt, J=17.5, 4.2 Hz, 1H), 1.98 (d, J=6.9 Hz, 7H), 1.90-1.75 (m, 4H), 1.62 (s, 1H), 1.53 (s, 3H), 1.36 (s, 3H), 1.17 (s, 1H), 1.10-1.03 (m, 2H). LCMS (ES$^+$): m/z [M+H]$^+$ 712.7.

SFC Separation for Compound 212—TFA Salt:

Procedure: 2.4 g of Compound 212 TFA salt was separated by SFC to obtain single enantiomers. During SFC separation fraction of Compound 213 and Compound 214 were collected in TFA buffer to avoid Glutarimide ring opening as SFC separation method involved use of basic additive. Hence the obtain fraction of Compound 213 and Compound 214 were submitted again for prep HPLC purification to remove the salt.

| Preparative SFC Conditions Column/dimensions: | |
|---|---|
| Column/dimensions: | Chiralpak-AS-H (30 × 250) mm, 5µ |
| % CO2: | 50% |
| % Co solvent: | 50% (0.2% 7M Methanolic Ammonia in MEOH) |
| Total Flow: | 120.0 g/min |
| Back Pressure: | 100 bar |
| Temperature: | 30° C. |
| UV: | 220 nm |
| Solubility: | MEOH |

Prep-HPLC Method:
Mobile Phase (A): 0.1% TFA in H2O Mobile Phase (B): 10000 Acetonitrile Flow Rate: 18 ml/min Column: SUN-FIRE-C18, 5 µm (19×150 mm) Gradient Time % B: 0/10, 1/10, 10/30, 12.5/30, 13.5/80, 16/80, 16.1/100, 18/100, 18.1/10, 20/10.

| Structure | Spectral data |
|---|---|
| 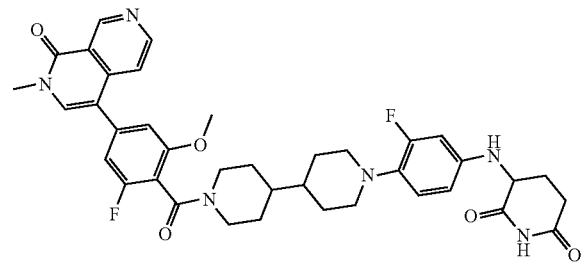 [SMILES: COc1cc(-c2cn(C)c(=O)c3cnccc23)cc(F)c1C(=O)N1CCC(C2CCN(c3ccc(NC4CCC(=O)NC4=O)cc3F)CC2)CC1]
Compound 213 | δ 10.81 (s, 1H), 7.59 (s, 1H), 7.52 – 7.47 (m, 1H), 7.41 – 6.96 (m, 3H), 6.62 – 6.58 (m, 1H), 6.52 – 6.50 (m, 1H) 4.60 – 4.58 (m, 1H), 4.33 – 4.30 (m, 1H), 3.46 (s, 8H), 3.16 – 3.02 (m, 1H), 2.77 – 2.67 (m, 2H), 2.59 – 2.58 (m, 1H), 2.09 – 2.04 (m, 7H), 2.02 – 1.89 (m, 7H), 1.93 – 1.64 (m, 4H). LCMS (ES+): m/z [M + H]+ 712.43 |
| 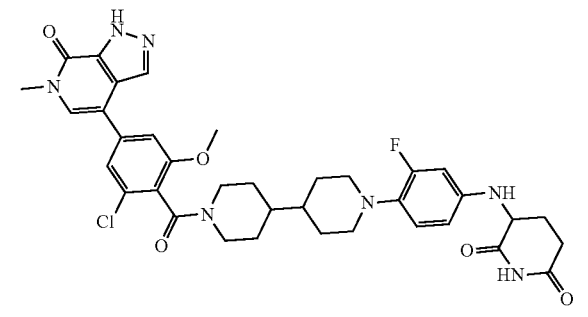 [SMILES: COc1cc(-c2cn(C)c(=O)c3[nH]ncc23)cc(Cl)c1C(=O)N1CCC(C2CCN(c3ccc(NC4CCC(=O)NC4=O)cc3F)CC2)CC1]
Compound 214 | δ 10.81 (s, 1H), 7.59 (s, 1H), 7.52 – 7.47 (m, 1H), 7.41 – 7.37 (m, 2H), 7.21 – 6.75 (m, 1H), 6.62 – 6.52 (m, 2H), 4.60 – 4.58 (m, 1H), 4.33 – 4.30 (m, 1H), 3.63 (s, 8H), 3.16 – 3.02 (m, 1H), 2.77 – 2.67 (m, 3H), 2.09 – 2.04 (m, 7H), 2.04 – 1.89 (m, 7H), 1.89 – 1.45 (m, 4H). LCMS (ES+): m/z [M + H]+ 712.25 |

Compound 215 was prepared following the synthesis of Compound 212.

[Structure of Compound 215]

¹H NMR (400 MHz, DMSO-d₆) δ 10.82 (s, 1H), 9.47 (s, 1H), 8.75 (d, J=5.7 Hz, 1H), 7.99 (s, 1H), 7.63 (d, J=5.7 Hz, 1H), 7.39-7.03 (m, 3H), 6.63-6.52 (m, 2H), 4.60 (d, J=12.6 Hz, 1H), 4.35 (d, J=8.3 Hz, 1H), 3.87 (d, J=7.9 Hz, 3H), 3.61 (s, 8H), 3.17-3.02 (m, 1H), 2.77-2.54 (m, 3H), 2.07-2.06 (m, 1H), 1.88-1.70 (m, 4H), 1.55-1.11 (m, 7H), LCMS (ES+): m/z [M+H]+ 699.56

Compound 216 was prepared following the synthesis of Compound 212.

[Structure of Compound 216]

¹H NMR (400 MHz, DMSO) δ 14.45 (bs, 1H), 10.81 (s, 1H), 8.23 (s, 1H), 7.66 (s, 1H), 7.33-7.31 (m, 1H), 7.25 (s, 2H), 6.59 (d, J=13.2 Hz, 1H), 6.51 (bs, 1H), 4.59 (d, J=10.8 Hz, 1H), 4.41-4.37 (m, 1H), 3.91 (d, J=6.2 Hz, 3H), 3.61 (s, 3H), 3.53 (bs, 1H), 3.42 (bs, 3H), 3.04 (t, J=14.7 Hz, 1H), 3.80-3.60 (m, 3H) 12.3 Hz, 1H), 2.11-2.07 (m, 1H), 1.95-1.67 (m, 4H), 1.75-1.48 (m, 5H), 1.39-1.17 (m, 2H). LCMS (ES+): m/z 704.42 [M+H]+.

Compound 217 was prepared following the synthesis of Compound 212.

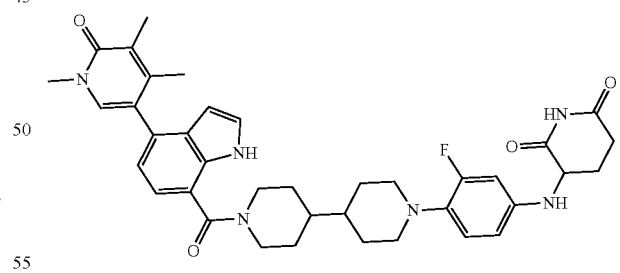

¹H NMR (400 MHz, DMSO-d₆) δ 11.19 (t, J=2.3 Hz, 1H), 10.83 (s, 1H), 7.52 (s, 1H), 7.35 (t, J=2.9 Hz, 2H), 7.11 (d, J=7.3 Hz, 1H), 6.89 (d, J=7.3 Hz, 1H), 6.63 (d, J=15.0 Hz, 1H), 6.54 (d, J=8.9 Hz, 1H), 6.21 (dd, J=3.2, 1.9 Hz, 1H), 4.37 (dd, J=11.1, 4.8 Hz, 1H), 3.46 (s, 5H), 3.24-2.82 (m, 3H), 2.80-2.53 (m, 2H), 2.07 (s, 4H), 1.94-1.80 (m, 6H), 1.75 (s, 2H), 1.59 (s, 2H), 1.42 (s, 4H), 1.23 (s, 4H). LCMS (ES+): m/z 667.5 [M+H]+.

Synthesis of Compound 218
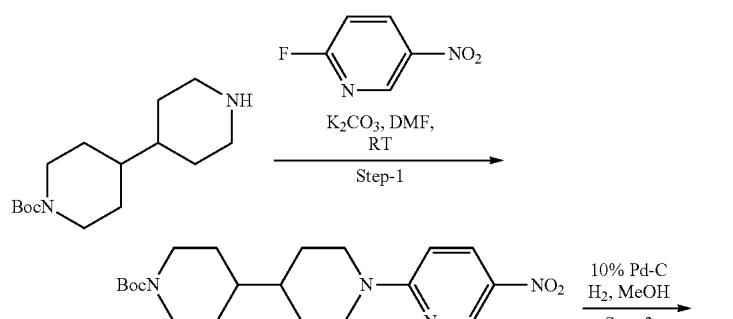
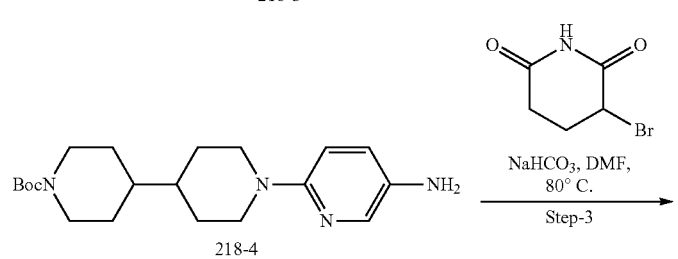
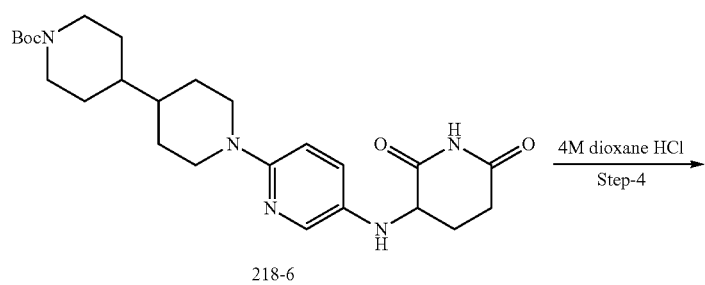
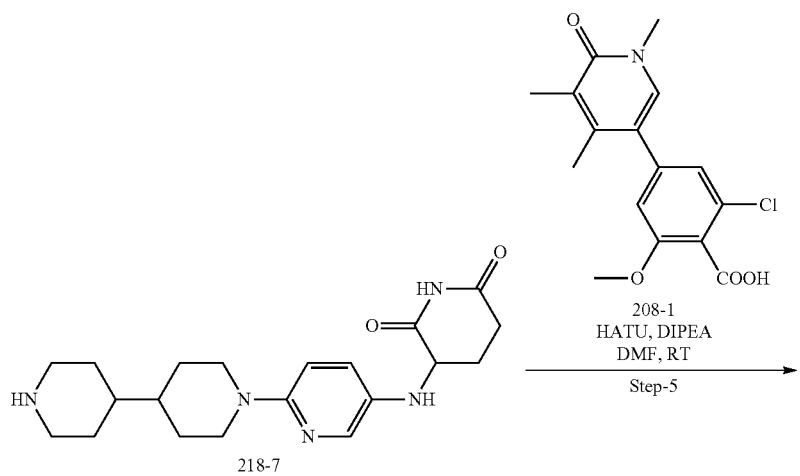

-continued

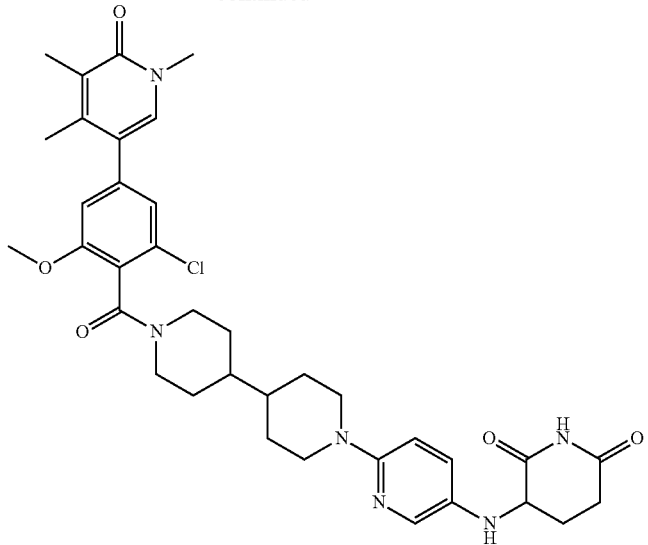

Compound 218

Step-1: To a stirred solution of compound tert-butyl [4,4'-bipiperidine]-1-carboxylate (1 g, 3.73 mmol) in DMF (10 mL) was added potassium carbonate, anhydrous, 99% (1.03 g, 7.45 mmol) and stirred for 15 min, before adding 2-fluoro-5-nitropyridine (529.40 mg, 3.73 mmol) and reaction mixture stirred at RT for 3 h, while monitoring by TLC. After completion of reaction and diluted with water (150 ml) and extracted with ethyl acetate (75 ml×3). Organic layer was dried over $Na_2SO_4$ and concentrated to afford crude compound. Crude compound was purified by normal phase column chromatography (silica gel mesh 100-200, with 90% ethyl acetate in pet ether as eluent) to afford isolated tert-butyl 1'-(5-nitropyridin-2-yl)-[4,4'-bipiperidine]-1-carboxylate (1 g, 68.05% yield, 99% purity) as a white solid. $^1$H NMR (400 MHz, DMSO-$d_6$) δ 9.02 (d, J=2.4 Hz, 1H), 8.17 (dd, $J_1$=9.6 Hz, $J_2$=2.8 Hz, 1H), 6.56 (d, J=9.2 Hz, 1H), 4.57 (d, J=12.8 Hz, 2H), 4.12 (bs, 2H), 2.98-2.91 (m, 2H), 2.64 (t, J=12 Hz, 2H), 1.85 (d, J=12.8 Hz, 2H), 1.68 (d, J=12.4 Hz, 2H), 1.44 (s, 10H), 1.31-1.20 (m, 5H), LCMS (ES$^+$): m/z 335.27 [M+H−56]$^+$ Step-2: To a stirred solution of tert-butyl 1'-(5-nitropyridin-2-yl)-[4,4'-bipiperidine]-1-carboxylate (1 g, 2.56 mmol) in Methanol (20 mL) was added wet 10% Palladium on carbon (1.09 g, 10.24 mmol) and the reaction mixture was stirred under $H_2$ balloon pressure for 4 h, while monitoring by LCMS and TLC. The reaction mixture was filtered through Celite bed and the filtrate was concentrated under reduced pressure to afford tert-butyl 1'-(5-aminopyridin-2-yl)-[4,4'-bipiperidine]-1-carboxylate (0.65 g, 66.89% yield, 95% purity) as a black solid. $^1$H NMR (400 MHz, DMSO-$d_6$) δ 7.79 (d, J=2.8 Hz, 1H), 6.96 (dd, $J_1$=8.8 Hz, $J_2$=2.8 Hz, 1H), 6.59 (d, J=8.8 Hz, 1H), 4.08 (bs, 2H), 3.27 (bs, 2H), 2.62 (t, J=10.4 Hz, 4H), 1.79-1.64 (m, 5H), 1.47 (s, 9H), 1.35-1.25 (m, 7H), LCMS (ES$^+$): m/z 361.40 [M+H]$^+$ Step-3: To a stirred solution of tert-butyl 1'-(5-aminopyridin-2-yl)-[4,4'-bipiperidine]-1-carboxylate (0.65 g, 1.80 mmol) in DMF (20 mL) taken in sealed tube, were added $NaHCO_3$ (908.83 mg, 10.82 mmol) followed by 3-bromopiperidine-2,6-dione (1.04 g, 5.41 mmol) and allowed and stirred at 80° C. for 48 h, while monitoring by LCMS and TLC. After 48 h, the reaction was quenched with ice cold water (100 mL) and extracted with EtOAc (3×150 mL). The combined organic layer was dried over anhydrous $Na_2SO_4$ and concentrated to afford crude compound. Crude compound was purified by normal phase column chromatography (silica gel mesh 100-200, and product eluted with 50% ethyl acetate in pet ether-neat ethyl acetate) to afford tert-butyl tert-butyl 1'-(5-((2,6-dioxopiperidin-3-yl)amino)pyridin-2-yl)-[4,4'-bipiperidine]-1-carboxylate (0.5 g, 954.22 umol, 52.9% yield, 90% purity) as a purple solid. $^1$H NMR (400 MHz, DMSO-$d_6$) δ 10.78 (s, 1H), 7.68 (d, J=2.8 Hz, 1H), 7.02 (dd, $J_1$=8.8 Hz, $J_2$=2.8 Hz, 1H), 6.67 (d, J=8.8 Hz, 1H), 5.35 (d, J=7.6 Hz, 1H), 4.20-4.17 (m, 1H), 4.16-3.95 (m, 4H), 2.71-2.54 (m, 4H), 2.12-2.07 (m, 1H), 1.89-1.74 (m, 1H), 1.71-1.64 (m, 4H), 1.37 (s, 9H), 1.95-0.98 (m, 7H), LCMS (ES$^+$): m/z 472.39 [M+H]$^+$ Step-4: To a stirred solution of compound tert-butyl 1'-(5-((2,6-dioxopiperidin-3-yl)amino)pyridin-2-yl)-[4,4'-bipiperidine]-1-carboxylate (0.5 g, 1.06 mmol) in 1,4 dioxane (5 mL), was added 4M dioxane HCl (10 mL) at 0° C. and the reaction mixture was stirred at RT for 2 h, while monitoring by TLC and LCMS. After completion, the reaction mixture was concentrated to obtain crude compound. The crude compound was washed with diethyl ether and dried under vacuum to afford 3-((6-([4,4'-bipiperidin]-1-yl) pyridin-3-yl)amino)piperidine-2,6-dione HCl salt (0.49 g, 87.23% yield, 77% purity) as a brown solid the desired compound was confirmed by LCMS. LCMS (ES$^+$): m/z 371.48 [M+H]$^+$ Step-5: To a stirred solution of 3-[[6-[4-(4-piperidyl)-1-piperidyl]-3-pyridyl]amino]piperidine-2,6-dione hydrochloride (115 mg, 0.31 mmol), in DMF (5 mL) was added N-ethyl-N-isopropyl-propan-2-amine (240 mg, 1.86 mmol), and stirred for 10 min, before adding 2-chloro-6-methoxy-4-(1,4,5-trimethyl-6-oxo-3-pyridyl)benzoic acid (0.1 g, 0.31 mmol) and HATU (176 mg, 0.46 mmol), After addition, reaction mixture stirred for 16 h, while monitoring by LCMS. After completion DMF was removed under vacuum and crude compound was purified by prep-HPLC to afford 3-[[6-[4-[1-[2-chloro-6-methoxy-4-(1,4,5-trimethyl-6-oxo-3-pyridyl)benzoyl]-4-piperidyl]-1-piperidyl]-3-pyridyl] amino]piperidine-2,6-dione TFA salt (25 mg, 10% yield, 98.72% purity) as a light brown solid. ¹H NMR (400 MHz, DMSO-d₆) δ 10.83 (s, 1H), 7.63 (d, J=9.6 Hz, 1H), 7.55 (s, 1H), 7.31-7.29 (m, 2H), 7.03 (d, J=6.8 Hz, 1H) 6.96 (s, 1H), 4.57 (d, J=7.7 Hz, 1H), 4.32 (s, 1H), 4.00 (s, 2H), 3.81 (d, J=7.7 Hz, 3H), 3.45 (s, 4H), 3.11-2.88 (m, 3H), 2.74-2.62 (m, 3H), 2.06 (d, J=3.7 Hz, 7H), 1.93-1.64 (m, 5H), 1.49-1.22 (m, 7H). LCMS (ES⁺): m/z 675.41 [M+H]⁺

Compound 219 was prepared following the synthesis of Compound 218.

¹H NMR (400 MHz, DMSO-d₆) δ 13.07 (s, 1H), 10.85 (s, 1H), 9.46 (s, 1H), 8.75 (d, J=5.6 Hz, 1H), 7.95 (s, 1H), 7.57 (d, J=5.6 Hz, 2H), 7.32 (s, 2H), 7.21-7.15 (m, 2H), 6.20 (s, 1H), 4.58 (bs, 1H), 4.32-4.28 (m, 2H), 3.96 (d, J=9.6 Hz, 2H), 3.85 (d, J=7.3 Hz, 3H), 3.60 (s, 1H), 3.49-3.35 (m, 1H), 3.05-3.02 (m, 3H), 2.76-2.61 (m, 3H), 2.15-2.11 (m, 1H), 1.95-1.66 (5H), 1.51-1.48 (bs, 2H), 1.23-1.15 (m, 4H). LCMS (ES⁺): m/z 798.18 [M+H]⁺

Compound 220 was prepared following the synthesis of Compound 218.

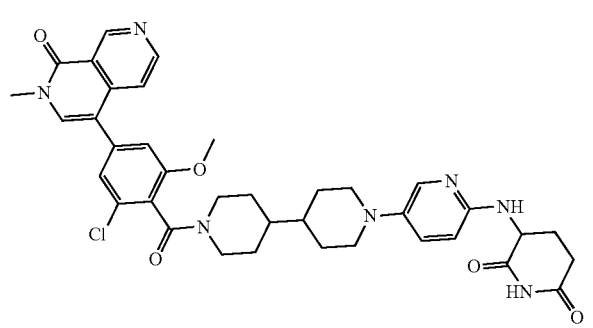 [SMILES: COc1cc(-c2cn(C)c(=O)c3cnccc23)cc(Cl)c1C(=O)N1CCC(C2CCN(c3ccc(NC4CCC(=O)NC4=O)nc3)CC2)CC1]

¹H NMR (400 MHz, DMSO-d₆) δ 14.25 (bs, 1H), 10.86 (s, 1H), 8.23 (s, 1H), 7.65 (s, 1H), 7.60 (s, 1H), 7.33-7.22 (m, 4H), 6.20 (bs, 1H), 4.57 (bs, 1H), 4.35-4.31 (m, 1H), 3.99 (bs, 2H), 3.91 (d, J=7.4 Hz, 3H), 3.61 (s, 3H), 3.47-3.36 (m, 1H), 3.17-2.89 (m, 3H), 2.75-2.63 (m, 3H), 2.12-2.07 (m, 1H), 1.93-1.80 (m, 4H), 1.67-164 (1H), 1.41-1.11 (m, 6H), LCMS (ES⁺): m/z M+H]⁺ 687.38

Compound 221 was prepared following the synthesis of Compound 218.

¹H NMR (400 MHz, DMSO-d₆) δ 12.73 (bs, 1H), 10.74 (s, 1H), 9.45 (s, 1H), 8.75 (d, J=5.6 Hz, 1H), 7.95 (s, 1H), 7.63 (s, 1H), 7.56 (d, J=5.6 Hz, 1H), 7.24 (m, 3H), 6.57 (d, J=8.8 Hz, 1H), 6.43 (bs, 1H), 4.66 (m, 2H), 3.86 (d, 3H), 3.59 (s, 3H), 3.39 (m, 3H), 3.05 (t, J=12.8 Hz, 1H), 2.78-2.67 (m, 2H), 2.55 (m, 2H), 2.49 (m, 1H), 2.10 (m, 1H), 2.07 (m, 1H), 1.83-1.76 (m, 4H), 1.43-1.12 (m, 6H). LCMS (ES⁺): m/z 698.45 [M+H]⁺

Compound 222 was prepared following the synthesis of Compound 218.

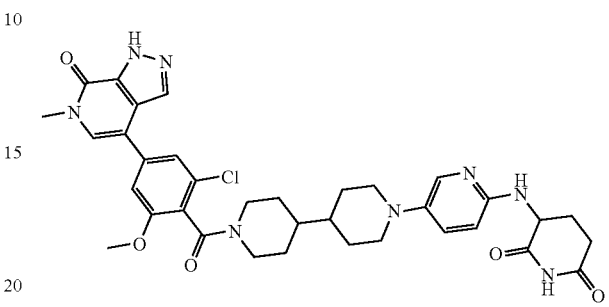

¹H NMR (400 MHz, DMSO-d₆) δ 10.78 (s, 1H), 8.44 (bs, 1H), 8.23 (s, 1H), 7.66 (m, 2H), 7.33 (d, J=6.8 Hz, 1H), 7.24-7.19 (m, 2H), 6.54 (d, J=8.8 Hz, 1H), 6.39 (d, J=7.6 Hz, 1H), 6.15 (d, J=8.0 Hz, 1H), 4.64-4.56 (m, 2H), 3.92 (d, 3H), 3.61 (s, 3H), 3.38 (m, 3H), 3.01 (t, 1H), 2.75-2.68 (m, 2H), 2.54 (m, 1H), 2.49 (m, 2H), 2.10-2.07 (m, 1H), 2.03-1.92 (m, 1H), 1.82-1.65 (m, 4H), 1.39-1.11 (m, 6H). LCMS (ES⁺): m/z 687.45 [M+H]⁺.

Compound 223 was prepared following the synthesis of Compound 218.

¹H NMR (400 MHz, DMSO-d₆) δ 10.79 (s, 1H), 7.61 (d, J=8.6 Hz, 1H), 7.54 (d, J=7.8 Hz, 1H), 7.43 (td, J=11.1, 10.2, 5.4 Hz, 3H), 6.93 (t, J=9.4 Hz, 1H), 6.55 (dd, J=15.0, 2.5 Hz, 1H), 6.45 (dd, J=8.8, 2.5 Hz, 1H), 4.87-4.58 (m, 1H), 4.29 (dd, J=11.6, 4.8 Hz, 1H), 3.46 (s, 5H), 3.27 (t, J=12.8 Hz, 1H), 3.05 (s, 9H), 2.83-2.53 (m, 2H), 2.05 (d, J=3.2 Hz, 8H), 1.93-1.66 (m, 2H). LCMS (ES⁺): m/z 749.6 [M+H]⁺.

Compound 224 was prepared following the synthesis of Compound 218.

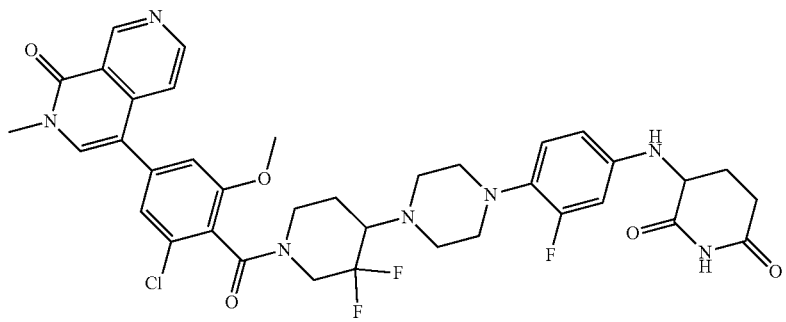 [SMILES: COc1cc(-c2cn(C)c(=O)c3cnccc23)cc(Cl)c1C(=O)N1CCC(N2CCN(c3ccc(NC4CCC(=O)NC4=O)cc3F)CC2)C(F)(F)C1]

¹H NMR (400 MHz, DMSO-d₆) δ 10.77 (s, 1H), 9.46 (s, 1H), 8.75 (d, J=5.6 Hz, 1H), 8.00-7.98 (m, 1H), 7.64-7.60 (m, 1H), 7.24-7.18 (m, 2H), 6.88-6.84 (m, 1H), 6.52 (d, J=15.6 Hz, 1H), 6.43 (d, J=8.4 Hz, 1H), 4.75-4.70 (m, 1H), 4.30-4.26 (m, 1H), 3.97 (s, 3H), 3.60 (s, 3H), 3.50-3.47 (m, 2H), 3.30-3.20 (m, 2H), 3.16-2.93 (m, 6H), 2.75-2.60 (m, 2H), 2.10-2.06 (m, 2H), 1.90-1.75 (m, 4H). LCMS (ES⁺): m/z 752.45 [M+H]⁺.

Compound 225 was prepared following the synthesis of Compound 218.

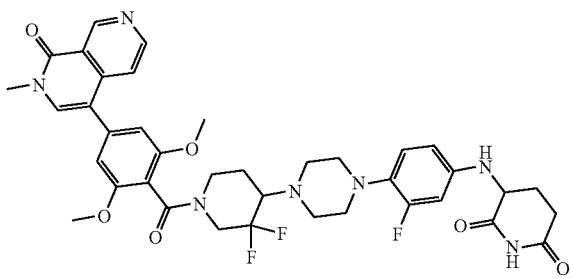 [SMILES: COc1cc(-c2cn(C)c(=O)c3cnccc23)cc(OC)c1C(=O)N1CCC(N2CCN(c3ccc(NC4CCC(=O)NC4=O)cc3F)CC2)C(F)(F)C1]

¹H NMR (400 MHz, DMSO-d₆) δ 10.78 (s, 1H), 9.49 (s, 1H), 8.74 (d, J=5.6 Hz, 1H), 7.98 (d, J=7.5 Hz, 1H), 7.69 (t, J=6 Hz, 1H), 6.91 (t, J=8.4 Hz, 1H), 6.82-6.79 (m, 2H), 6.55 (d, J=2 Hz, 1H), 6.51-6.44 (m, 1H), 4.77-4.73 (m, 1H), 4.28-4.25 (m, 1H), 3.82-3.78 (m, 6H), 3.62 (s, 3H), 3.58-3.49 (m, 2H), 3.25-2.92 (m, 10H), 2.73-2.67 (m, 1H), 2.59-2.55 (m, 1H), 2.10-2.06 (m, 1H), 1.91-1.83 (m, 3H). LCMS (ES⁺): m/z 748.48 [M+H]⁺

Compound 226 was prepared following the synthesis of Compound 218.

¹H NMR (400 MHz, DMSO-d₆) δ 10.78 (s, 1H), 9.48 (s, 1H), 8.75 (d, J=5.7 Hz, 1H), 8.01 (d, J=8.1 Hz, 1H), 7.68-7.65 (m, 1H), 7.09-7.03 (m, 3H), 6.90 (t, J=8.4 Hz, 1H), 6.53 (d, J=15.1 Hz, 1H), 6.44 (d, J=8.7 Hz, 1H), 4.82-4.76 (m, 1H), 4.28-4.24 (m, 1H), 3.87 (s, 3H), 3.61 (s, 3H), 3.36-3.17 (m, 2H), 2.97 (bs, 10H), 2.77-2.55 (m, 2H), 2.10-2.04 (m, 2H), 1.88-1.74 (m, 2H). LCMS (ES⁺): m/z 736.46 [M+H]⁺

Compound 227 was prepared following the synthesis of Compound 218.

¹H NMR (400 MHz, DMSO-d₆) δ 10.80 (s, 1H), 9.51 (s, 1H), 8.77 (d, J=5.9 Hz, 1H), 8.06 (d, J=7.9 Hz, 1H), 7.79-7.49 (m, 4H), 7.28-6.84 (m, 1H), 6.65-6.40 (m, 2H), 4.90-4.58 (m, 1H), 4.29 (dd, J=11.5, 4.8 Hz, 1H), 3.62 (s, 4H), 3.31 (t, J=13.4 Hz, 1H), 3.09 (d, J=19.5 Hz, 10H), 2.83-2.53 (m, 2H), 2.21-1.95 (m, 2H), 1.86 (qd, J=12.3, 4.8 Hz, 2H), 1.44-1.06 (m, 1H). LCMS (ES⁺): m/z 772.5[M+H]⁺.

Compound 228 was prepared following the synthesis of Compound 218.

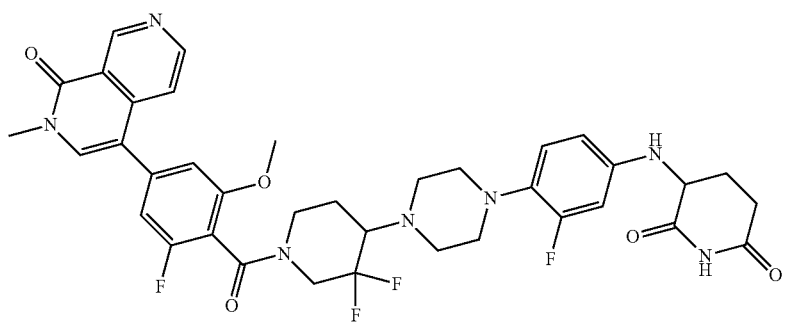 [SMILES: COc1cc(-c2cn(C)c(=O)c3cnccc23)cc(F)c1C(=O)N1CCC(N2CCN(c3ccc(NC4CCC(=O)NC4=O)cc3F)CC2)C(F)(F)C1]

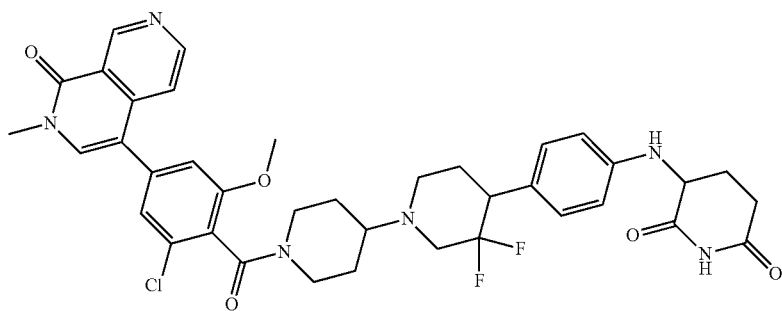 [SMILES: COc1cc(-c2cn(C)c(=O)c3cnccc23)cc(Cl)c1C(=O)N1CCC(N2CCC(c3ccc(NC4CCC(=O)NC4=O)cc3)C(F)(F)C2)CC1]
¹H NMR (400 MHz, DMSO-d₆) δ 10.79 (s, 1H), 9.46 (s, 1H), 8.75 (t, J=5.2 Hz, 1H), 7.96 (s, 1H), 7.57 (t, J=5.6 Hz, 1H), 7.23-6.95 (m, 4H), 6.66 (d, J=8.1 Hz, 2H), 5.86 (s, 1H), 4.66 (s, 1H), 4.31-4.28 (m, 1H), 3.87 (d, J=14.7 Hz, 3H), 3.60 (s, 3H), 3.49-3.30 (m, 6H), 3.10-2.86 (m, 2H), 2.77-2.58 (m, 3H), 2.18-1.56 (m, 8H), LCMS (ES⁺): m/z 733.57 [M+H]⁺
Compound 229 was prepared following the synthesis of Compound 218.
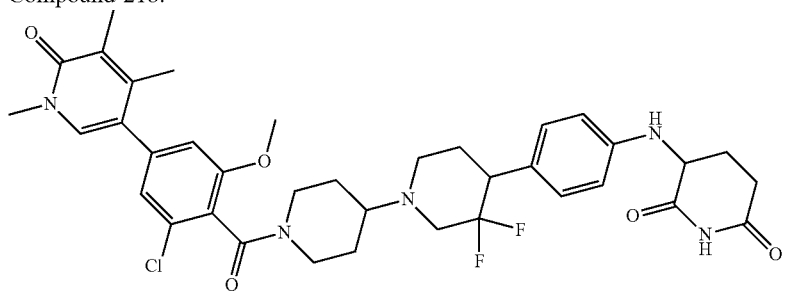
¹H NMR (400 MHz, DMSO-d₆) δ 10.79 (s, 1H), 7.59 (s, 1H), 7.04-6.96 (m, 4H), 6.66 (d, J=8.0 Hz, 2H), 5.89 (s, 1H), 4.67 (d, J=13.2 Hz, 1H), 4.31-4.01 (m, 1H), 3.86-3.81 (m, 4H), 3.51-3.46 (m, 6H), 3.09-3.06 (m, 4H), 2.84-2.55 (m, 3H), 2.07 (d, J=6.3 Hz, 11H), 1.91-1.86 (m, 1H), 1.57 (bs, 2H). LCMS (ES⁺): m/z [M+H]⁺ 710.06
Synthesis of Compound 230
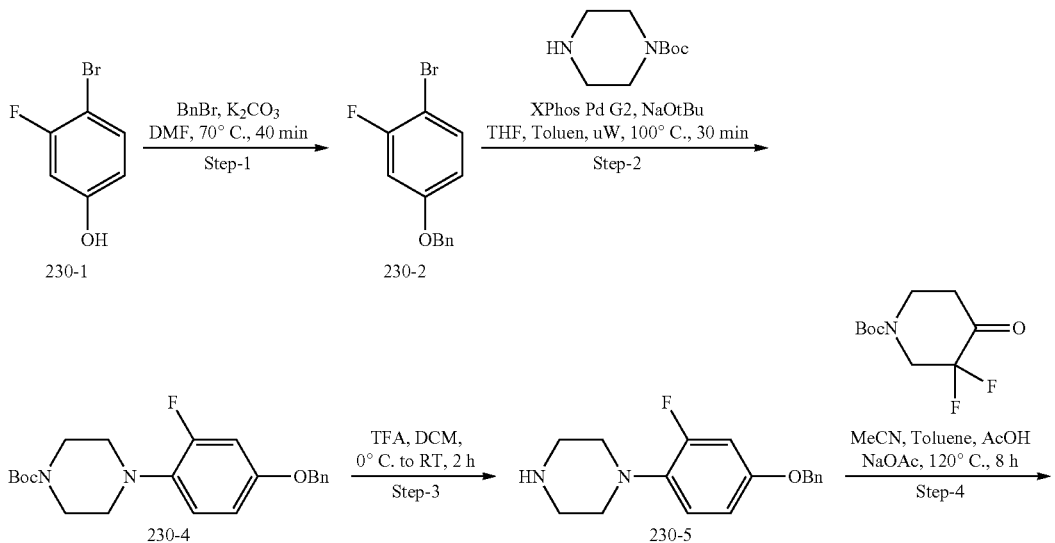

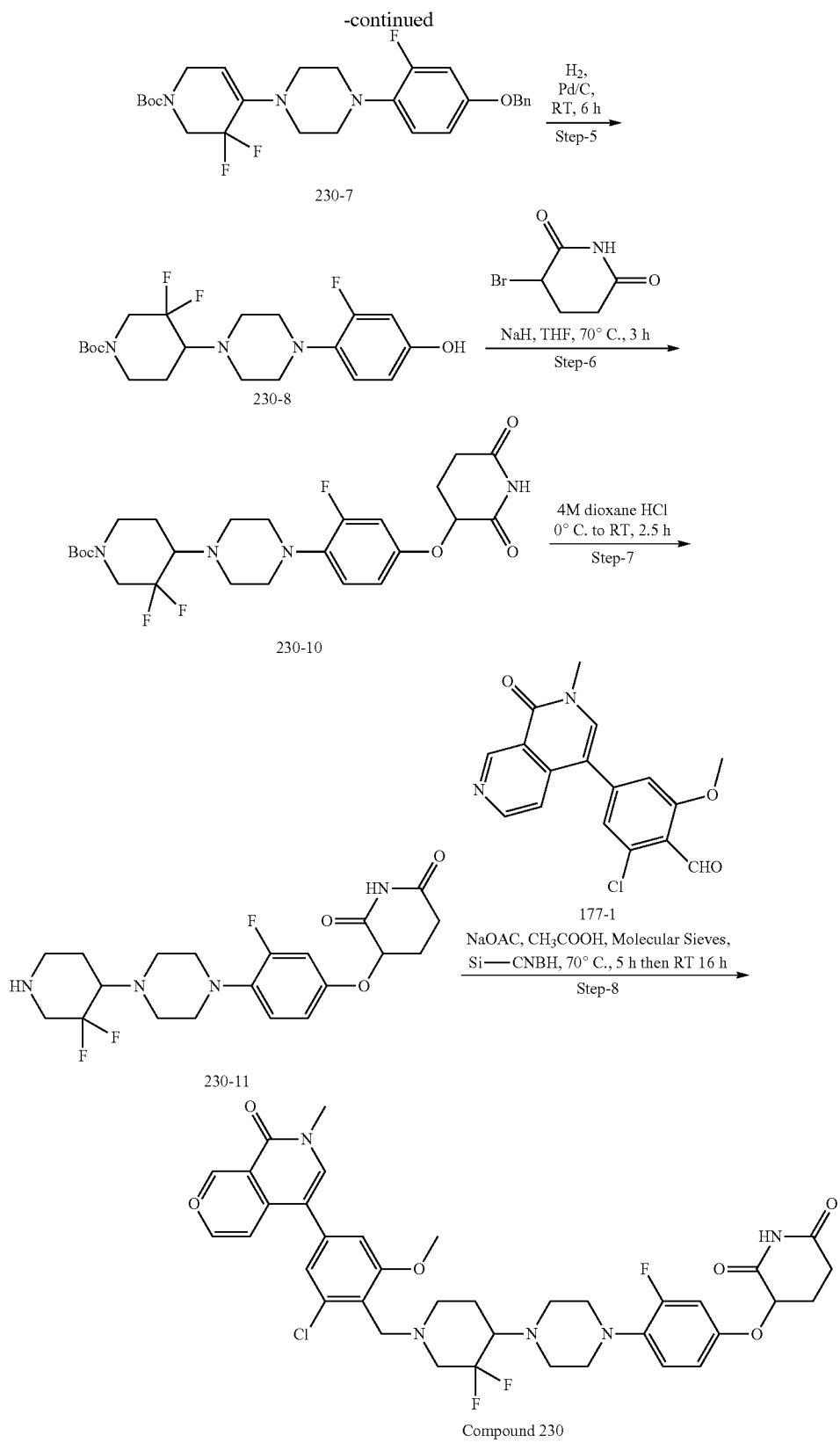
Step-1: To a stirred solution of 4-bromo-3-fluorophenol 230-1 (10 g, 52.36 mmol) in DMF (80 mL) was added potassium carbonate (14.47 g, 104.71 mmol) and benzyl bromide (9.85 g, 57.59 mmol) at room temperature, and the reaction mixture was stirred at room temperature for 20 minutes and then at 70° C. for 40 minutes. Reaction progress was monitored by TLC/LCMS. After completion of reaction, the reaction mixture was cooled to room temperature and water (200 mL) was added to the reaction mixture. The crude compound was extracted with ethyl acetate (200 mL×2). The combine organic layer was washed with water (200 mL) and then with brine (200 mL). The organic layer was dried over anhydrous sodium sulfate, filtered and concentrated in vacuo to furnish product 4-(benzyloxy)-1-bromo-2-fluorobenzene, 230-2 (14.5 g, 88.20% yield, 89.53% purity) as a brown coloured liquid.

Step-2: In a microwave vial, the stirred solution of sodium tert-butoxide (0.855 g, 8.89 mmol) in mixture of solvent THE (10 mL) and toluene (10 mL) was purged with argon for 5 minutes. To this solution was added 4-(benzyloxy)-1-bromo-2-fluorobenzene (1 g, 3.56 mmol) and tert-butyl piperazine-1-carboxylate (0.861 g, 4.62 mmol) and purged with argon for 10 minutes. XPhos Pd G2 (0.280 g, 0.355 mmol) was added to the reaction mixture and irradiated under microwave condition at 100° C. for 30 minutes. The progress of reaction was monitored by LCMS and TLC. After completion of reaction, reaction mixture was concentrated in vacuo and crude compound was purified by column chromatography (Davisil silica, 0-8% ethyl acetate and pet ether as an eluent) to furnish tert-butyl 4-(4-benzyloxy-2-fluoro-phenyl)piperazine-1-carboxylate (0.5 g, 1.18 mmol, 33.28% yield, 91.51% purity) as a yellow solid. Reaction was performed in 3 batches of 1 g to obtain 1.5 g of pure tert-butyl 4-(4-benzyloxy-2-fluoro-phenyl)piperazine-1-carboxylate. LCMS (ES$^+$): m/z 387.28 [M+H]$^+$ Step-3: To a stirred solution of tert-butyl 4-(4-benzyloxy-2-fluoro-phenyl)piperazine-1-carboxylate (2.8 g, 7.25 mmol) in a DCM (30 mL) was added TFA (9.91 g, 86.94 mmol, 6.70 mL) at 0° C. and stirred reaction mixture at RT for 2 hr. The progress of reaction was monitored by LCMS. After completion of reaction, reaction mixture was concentrated in vacuo and co-distilled with acetonitrile (5 mL×2), toluene (5 mL×2) to furnish 1-(4-benzyloxy-2-fluoro-phenyl)piperazine TFA (2.4 g, 78.00% yield, 94.27% purity) as a brown solid. LCMS (ES$^+$): m/z 287.43 [M+H]$^+$ Step-4: To a stirred solution of 1-(4-benzyloxy-2-fluoro-phenyl)piperazine TFA (2.5 g, 6.24 mmol) in mixture of solvents toluene (25 mL) and acetonitrile (13 mL) in a two neck 100 mL round bottom flask attached with Dean stark apparatus was added sodium acetate, anhydrous (2.05 g, 24.98 mmol) and stirred at RT for 10 minutes. Tert-butyl 3,3-difluoro-4-oxo-piperidine-1-carboxylate (1.76 g, 7.49 mmol), acetic acid (1.87 mL, 31.22 mmol) and molecular sieves (0.5 g) were added to the reaction mixture and stirred at 120° C. for 8 hr. The progress of reaction was monitored by TLC and LCMS. After completion of reaction, the reaction was filtered through Celite bed, washed with ethyl acetate (25 mL×2) and acetonitrile (25 mL×2). The organic layer was concentrated in vacuo and crude material was purified by column chromatography (Davisil silica, 0 to 30% ethyl acetate and pet ether as eluent) to yielded the tert-butyl tert-butyl 4-[4-(4-benzyloxy-2-fluoro-phenyl)piperazin-1-yl]-3,3-difluoro-2,6-dihydropyridine-1-carboxylate (2.5 g, 58.84% yield, 74.30% purity) as a yellow solid. The major product formed found to have mass of enamine product in LCMS (ES$^+$): m/z 526.26 [M+Na]$^+$ Step-5: The stirred solution of tert-butyl 4-[4-(4-benzyloxy-2-fluoro-phenyl)piperazin-1-yl]-3,3-difluoro-2,6-dihydropyridine-1-carboxylate (2.5 g, 4.96 mmol) in ethanol (20 mL) and THE (20 mL) was purged with nitrogen for 10 minutes. Palladium on carbon, 10 wt % (3 g, 4.96 mmol) was added to the reaction mixture and stirred reaction mixture under hydrogen atmosphere (under balloon pressure) at RT for 6 hr. The progress of reaction was monitored by TLC and LCMS. After completion of reaction, reaction mixture was filtered through Celite bed and washed with THE (25 mL×2), ethyl acetate (25 mL×2). Collected organic layer was concentrated to furnish crude tert-butyl 3,3-difluoro-4-[4-(2-fluoro-4-hydroxy-phenyl)piperazin-1-yl]piperidine-1-carboxylate (1.77 g, 71.19% yield, 82.96% purity) as a brown solid. Compound was used in next step without further purification. LCMS (ES$^+$): m/z 416.78 [M+H]$^+$ Step-6: To a stirred solution of tert-butyl 3,3-difluoro-4-[4-(2-fluoro-4-hydroxy-phenyl)piperazin-1-yl]piperidine-1-carboxylate (1.77 g, 4.26 mmol) in THE (80 mL) was added sodium hydride (60% dispersion in mineral oil) (0.098 g, 4.26 mmol) and stirred at 70° C. for 30 minutes. Solution of 3-bromopiperidine-2,6-dione (0.818 g, 4.26 mmol) in THE (5 mL) was added to the reaction mixture at 70° C. and continued stirring at 70° C. for 3 hr. The progress of reaction was monitor by LCMS and TLC. After completion of reaction, the reaction mixture was quenched with ice cold water (100 mL) and extracted with ethyl acetate (3×70 mL). Combined organic layer was dried over sodium sulphate, filtered and concentrated in vacuo. The crude material was purified by column chromatography (Davisili silica, 0 to 60% of EtOAc in pet ether) to afford tert-butyl 4-[4-[4-[(2,6-dioxo-3-piperidyl)oxy]-2-fluoro-phenyl]piperazin-1-yl]-3,3-difluoro-piperidine-1-carboxylate (0.890 g, 38.64% yield, 97.39% purity) aa an off white solid. LCMS (ES$^+$): m/z 527.94 [M+H]$^+$ Step-7: To a stirred solution of tert-butyl 4-[4-[4-[(2,6-dioxo-3-piperidyl)oxy]-2-fluoro-phenyl]piperazin-1-yl]-3,3-difluoro-piperidine-1-carboxylate (0.890 g, 1.69 mmol) in DCM (20 mL) was added 4M dioxane HCl (1.23 g, 33.81 mmol, 1.54 mL) at 0° C. and stirred the reaction mixture at RT for 2.5 hr. The progress of reaction was monitored by LCMS. After completion of reaction, reaction mixture was concentrated in vacuo and triturated with diethyl ether (25 mL×2) to afford 1-(4-benzyloxy-2-fluoro-phenyl)piperazine HCl (0.860 g, 94.74% yield, 98.15% purity) as a brown solid. LCMS (ES$^+$): m/z 427.31 [M+H]$^+$ Step-8: To a stirred solution of 3-[4-[4-(3,3-difluoro-4-piperidyl)piperazin-1-yl]-3-fluoro-phenoxy]piperidine-2,6-dione (0.2 g, 0.432 mmol) and 2-chloro-6-methoxy-4-(2-methyl-1-oxo-2,7-naphthyridin-4-yl)benzaldehyde (0.15 g, 0.456 mmol) in a mixture of solvent methanol (20 mL) and dichloroethane (20 mL) was added sodium acetate (0.071 g, 0.864 mmol) and stirred for 10 minutes at RT. Acetic acid (0.026 g, 0.432 mmol, 25 µL) and molecular sieves (0.2 g) was added to the reaction mixture and stirred at 70° C. for 5 hr. Reaction mixture was cool down to RT and SiliaBond Cyanoborohydride (0.25 g) was added to the reaction mixture at RT and stirred reaction mixture at RT for 16 hr. The progress of reaction was monitored by LCMS. After completion of reaction, reaction mixture was filtered through Celite bed and Celite bed was washed with mixture of ethylene dichloride and methanol (25 mL×2). Filtrate was concentrated in vacuo and crude compound was purified by preparative HPLC to afford 3-[4-[4-[1-[[2-chloro-6-methoxy-4-(2-methyl-1-oxo-2,7-naphthyridin-4-yl)phenyl]methyl]-3,3-difluoro-4-piperidyl]piperazin-1-yl]-3-fluoro-phenoxy]piperidine-2,6-dione (113.21 mg, 29.19% yield, 95.06% purity) as a brown solid. $^1$H NMR (400 MHz, DMSO-d$_6$) δ 10.93 (s, 1H), 9.48 (s, 1H), 8.76 (d, J=6.0 Hz, 1H), 7.99 (s, 1H), 7.61 (d, J=6.0 Hz, 1H), 7.22 (s, 1H), 7.16 (s, 1H), 7.02-6.92 (m, 2H), 6.81 (bd, J=8.8 Hz, 1H), 5.16 (m, 1H), 3.89 (m, 5H), 3.621 (s, 3H), 3.55-3.08 (m, 12H), 2.73-2.54 (m, 3H), 2.21-2.09 (m, 3H), 1.89 (m, 1H). LCMS (ES$^+$): m/z 739.19 [M+H]$^+$. Preparative HPLC Method:
Column: X select C18 5 µm (19×250 mm)
Mobile Phase (A): 0.05% TFA IN WATER, Mobile Phase (B): ACETONITRILE,
Gradient Time % B: 0/10, 2.5/15, 26/33.1, 26.10/100, 28.10/100, 28.20/10, 30.20/10
Flow Rate: 17 ml/min Synthesis of Compound 231
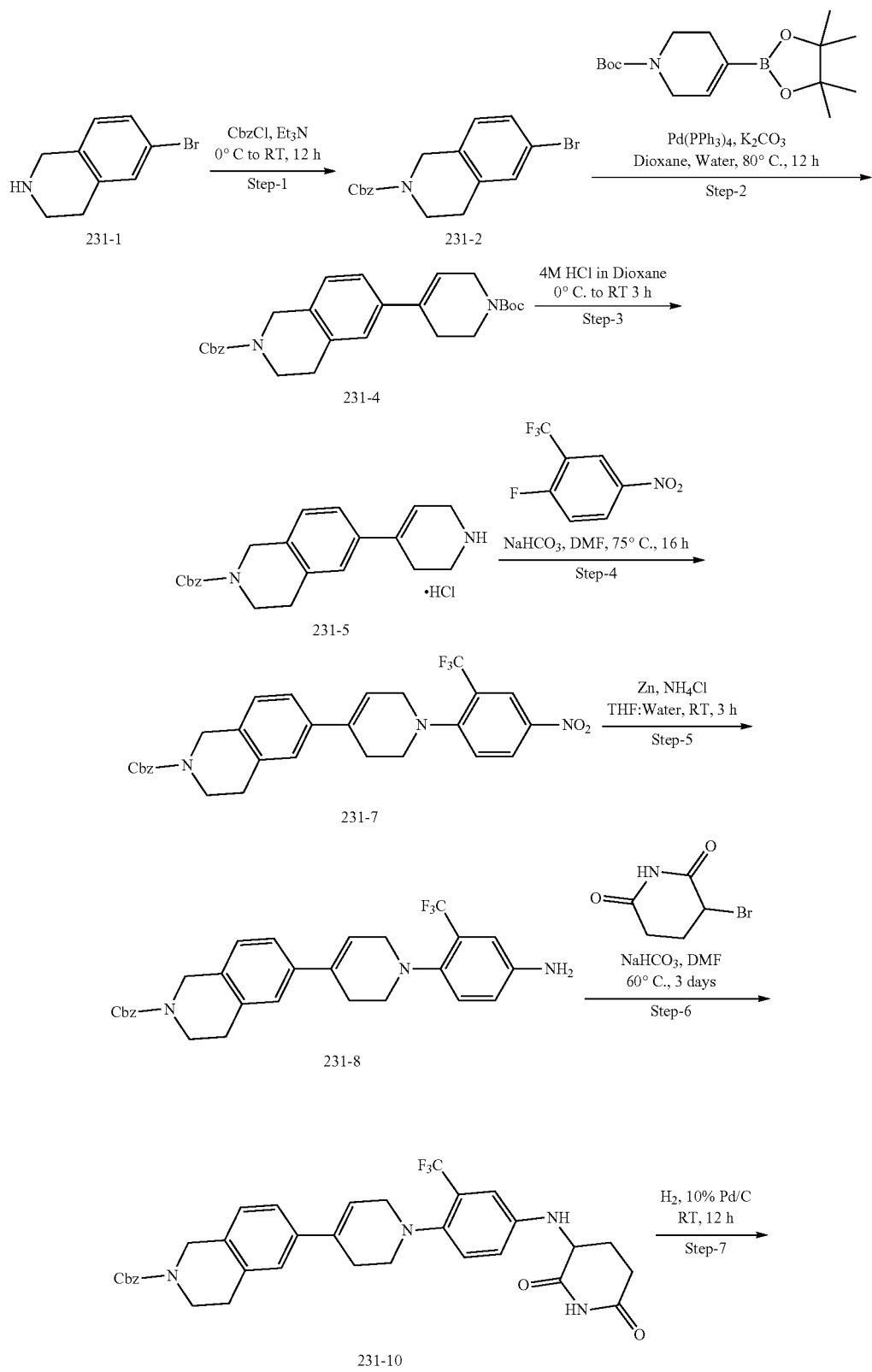

-continued

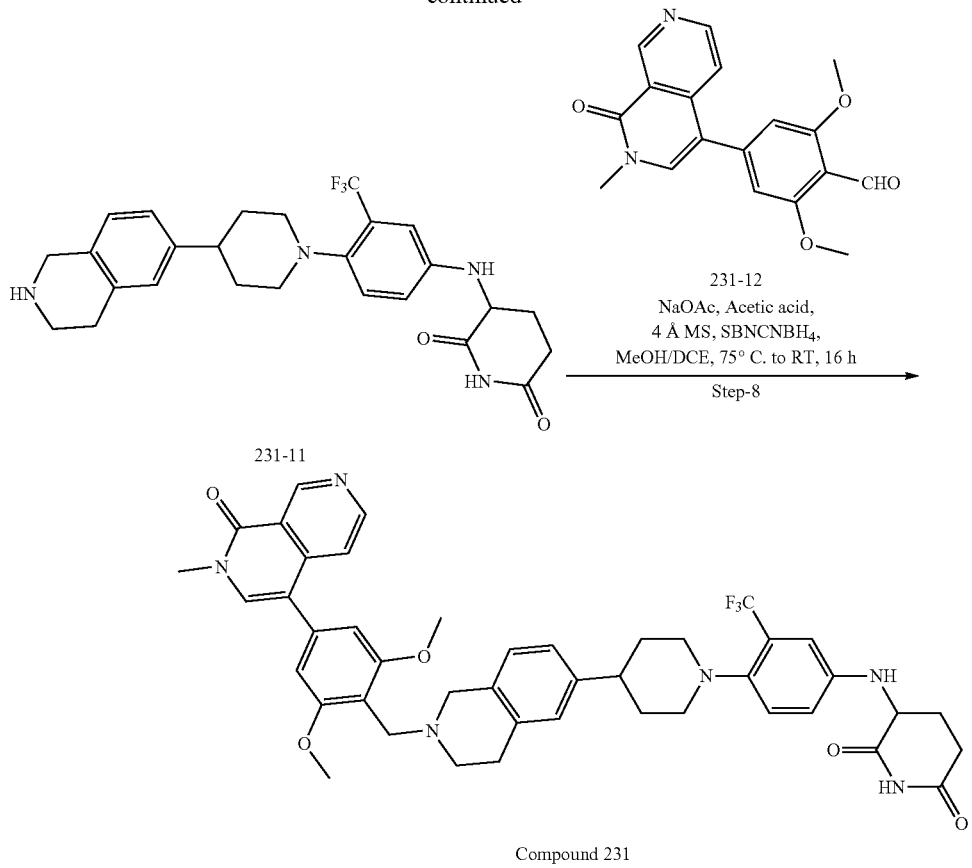

231-12

NaOAc, Acetic acid,
4 Å MS, SBNCNBH₄,
MeOH/DCE, 75° C. to RT, 16 h

Step-8

Compound 231

Step-1: To a stirred solution of 6-bromo-1,2,3,4-tetrahydroisoquinoline (1.5 g, 7.07 mmol) and triethylamine (2.15 g, 21.22 mmol, 2.96 mL) in DCM (20 mL) was added benzyl carbonochloridate (1.81 g, 10.61 mmol) drop wise at 0° C. and stirred for 12 h at room temperature. The progress of the reaction was monitored by LCMS/TLC. After completion of the reaction, the reaction was quenched by adding ice cold saturated aqueous sodium bicarbonate solution (50 ml) and extracted with ethyl acetate (30 mL×2). Combined organic layer was dried over sodium sulfate, filtered and concentrated under reduced pressure. The crude product was purified by column chromatography (Davisil silica, 20% ethyl acetate in pet ether) to afford the benzyl 6-bromo-3,4-dihydro-1H-isoquinoline-2-carboxylate (2 g, 79.55% yield, 97.4% purity) as colourless solid. LCMS (ES⁺): m/z 347.18 [M+H]⁺

Step-2: To a stirred solution of benzyl 6-bromo-3,4-dihydro-1H-isoquinoline-2-carboxylate (1.5 g, 4.33 mmol) and tert-butyl 5-(4,4,5,5-tetramethyl-1,3,2-dioxaborolan-2-yl)-3,4-dihydro-2H-pyridine-1-carboxylate (2.01 g, 6.50 mmol) in a mixture of water (15 mL) and 1,4-Dioxane (60 mL) was purged with argon for 5 min. Potassium carbonate (1.80 g, 13.00 mmol) and Tetrakis(triphenylphosphine)palladium(0) (500.65 mg, 0.433 mmol) were added to the reaction mixture and again purged with argon for 10 min. The reaction mixture was stirred for 12 h at 80° C. The progress of the reaction was monitored by LCMS & TLC. After completion of reaction, reaction mixture was diluted with water (50 mL) and compound was extracted with ethyl acetate (30 ml×2). Combined organic layer was dried over anhydrous sodium sulfate, filtered and concentrated under reduced pressure. The residue was purified by column chromatography (Davisil silica, 30% ethyl acetate in pet ether) to afford the benzyl 6-(1-tert-butoxycarbonyl-3,4-dihydro-2H-pyridin-5-yl)-3,4-dihydro-1H-isoquinoline-2-carboxylate (1.5 g, 75.56% yield, 97.9% purity) as a colourless solid. LCMS (ES⁺): m/z 471.42 [M+Na]⁺

Step-3: To a stirred solution of benzyl 6-(1-tert-butoxycarbonyl-3,6-dihydro-2H-pyridin-4-yl)-3,4-dihydro-1H-isoquinoline-2-carboxylate (1.5 g, 3.34 mmol) in 1,4-Dioxane (15 mL) was added 4M HCl in Dioxane (0.91 mL, 20.06 mmol) at 0° C. and stirred for 3 h at room temperature. The progress of the reaction was monitored by TLC and LCMS. After completion of the reaction volatiles were removed under reduced pressure. The residue was co-evaporated with toluene (20 mL×2 times) and triturated with diethyl ether (20 mL×2) to afford the benzyl 6-(1,2,3,6-tetrahydropyridin-4-yl)-3,4-dihydro-1H-isoquinoline-2-carboxylate.HCl (1.25 g, 89.35% yield, 92% purity) as a white solid. LCMS (ES⁺): m/z 349.30 [M+H]⁺

Step-4: To a stirred solution of benzyl 6-(1,2,3,6-tetrahydropyridin-4-yl)-3,4-dihydro-1H-isoquinoline-2-carboxylate HCl (1.3 g, 3.38 mmol) and 1-fluoro-4-nitro-2-(trifluoromethyl)benzene (706.23 mg, 3.38 mmol) in DMF (20 mL) in a sealed tube was added sodium bicarbonate (851.20 mg, 10.13 mmol) and stirred for 16 h at 75° C. The progress of the reaction was monitored by LCMS and TLC. After completion of reaction mixture was cooled to RT and ice-cold water was added. Crude compound was extracted with ethyl acetate and purified by column chromatography (silica gel mesh 100-200, 30% ethyl acetate in pet ether as eluent) to afford the benzyl 6-[1-[4-nitro-2-(trifluoromethyl)

phenyl]-3,6-dihydro-2H-pyridin-4-yl]-3,4-dihydro-1H-iso-quinoline-2-carboxylate (1.0 g, 53.65% yield, 97.4% purity) as a yellow solid. LCMS (ES$^+$): m/z 538.30 [M+H]$^+$ Step-5: To a stirred solution of benzyl 6-[1-[4-nitro-2-(trifluoromethyl)phenyl]-3,6-dihydro-2H-pyridin-4-yl]-3,4-dihydro-1H-isoquinoline-2-carboxylate (1.0 g, 1.86 mmol) and Zinc (973.19 mg, 14.88 mmol) in a mixture of water (3 mL) and THF (12 mL) was added ammonium Chloride (796.11 mg, 14.88 mmol) and stirred for 3 h at 25° C. The progress of the reaction was monitored by TLC & LCMS. After completion of the reaction, the reaction mixture was filtered through Celite and purified by column chromatography (Davisil silica, using 20% ethyl acetate in pet ether as an eluent) to afford the benzyl 6-[1-[4-amino-2-(trifluoromethyl)phenyl]-3,6-dihydro-2H-pyridin-4-yl]-3,4-dihydro-1H-isoquinoline-2-carboxylate (0.8 g, 83.62% yield, 98.7% purity) as a light yellow solid. LCMS (ES$^+$): m/z 508.25 [M+H]$^+$ Step-6: To a stirred solution of benzyl 6-[1-[4-amino-2-(trifluoromethyl)phenyl]-3,6-dihydro-2H-pyridin-4-yl]-3,4-dihydro-1H-isoquinoline-2-carboxylate (0.8 g, 1.58 mmol) and sodium bicarbonate (397.24 mg, 4.73 mmol) in DMF (20 mL) was added 3-bromopiperidine-2,6-dione (453.97 mg, 2.36 mmol) and stirred for 3 days at 60° C. in sealed tube. The progress of the reaction was monitored by LCMS. The reaction mixture was poured into ice cold water (80 mL) in a separating funnel and extracted with ethyl acetate (25 mL×2). Combined organic layer was dried over sodium sulfate, filtered and concentrated under reduced pressure. Crude product was purified by column chromatography (Davisil silica, 30% ethyl acetate in pet ether as an eluent) to afford the benzyl 6-[1-[4-[(2,6-dioxo-3-piperidyl)amino]-2-(trifluoromethyl)phenyl]-3,6-dihydro-2H-pyridin-4-yl]-3,4-dihydro-1H-isoquinoline-2-carboxylate (0.3 g, 25.01% yield, 81.3% purity) as solid. LCMS (ES$^+$): m/z 619.64 [M+H]$^+$ Step-7: The stirred solution of benzyl 6-[1-[4-[(2,6-dioxo-3-piperidyl)amino]-2-(trifluoromethyl)phenyl]-3,6-dihydro-2H-pyridin-4-yl]-3,4-dihydro-1H-isoquinoline-2-carboxylate (0.3 g, 0.484 mmol) in a mixture of ethyl acetate (3 mL) and THF (3 mL) was degassed for 10 minutes under nitrogen followed by addition of 10% Palladium on carbon (206.43 mg, 1.94 mmol). The reaction mixture was stirred at RT under hydrogen gas (under balloon pressure) for 12 h at 25° C. The progress of the reaction was monitored by LCMS and TLC. After completion of the reaction, reaction mixture was filtered through Celite and washed with methanol (10 ml) and ethyl acetate (20 ml). Filtrate was concentrated under reduced pressure to afford 3-[4-[4-(1,2,3,4-tetrahydroisoquinolin-6-yl)-1-piperidyl]-3-(trifluoromethyl)anilino]piperidine-2,6-dione (0.180 g, 66.99% yield, 87.8% purity) as light brown semi solid. LCMS (ES$^+$): m/z 487.32 [M+H]$^+$ Step 8: To a stirred solution of 3-[4-[4-(1,2,3,4-tetrahydroisoquinolin-6-yl)-1-piperidyl]-3-(trifluoromethyl)anilino]piperidine-2,6-dione (75.01 mg, 0.154 mmol) and 2,6-dimethoxy-4-(2-methyl-1-oxo-2,7-naphthyridin-4-yl)benzaldehyde (0.050 g, 0.154 mmol) in a mixture of 1,2-Dichloroethane (3 mL) and methanol (3 mL) was added sodium acetate, anhydrous (37.94 mg, 0.462 mmol), acetic acid (27.77 mg, 0.462 mmol) and molecular sieve (70 mg) and stirred for 5 hr at 75° C. The reaction mixture was cooled to 0° C. and Si-CBH (89.36 mg, 1.54 mmol) was added to reaction mixture and stirred for 12 hr at 25° C. The progress of the reaction was monitored by LCMS. The reaction mixture was filtered through Celite bed and filtrate was concentrated under reduced pressure. The residue was purified by preparative HPLC to afford the 3-[4-[4-[2-[[2,6-dimethoxy-4-(2-methyl-1-oxo-2,7-naphthyridin-4-yl)phenyl]methyl]-3,4-dihydro-1H-isoquinolin-6-yl]-1-piperidyl]-3-(trifluoromethyl)anilino]piperidine-2,6-dione.TFA (18.7 mg, 12.71% yield, 95.26% purity) as a brown semi solid. $^1$H NMR (400 MHz, DMSO-d$_6$) δ 10.79 (s, 1H), 9.55 (bd, 2H), 8.76 (bs, 1H), 7.92 (s, 1H), 7.62 (d, J=6.0 Hz, 1H), 7.35 (d, J=8.8 Hz, 1H), 7.22 (m, 3H), 6.96 (m, 4H), 6.20 (bs, 1H), 4.41 (m, 5H), 3.89 (s, 6H), 3.62 (m, 4H), 3.17-3.14 (s, 2H), 2.92-2.80 (m, 4H), 3.74 (m, 1H), 2.62 (m, 2H), 2.07 (m, 2H), 1.92 (m, 1H), 1.79 (m, 4H). LCMS (ES$^+$): m/z 795.67 [M+H]$^+$ Synthesis of Compound 232

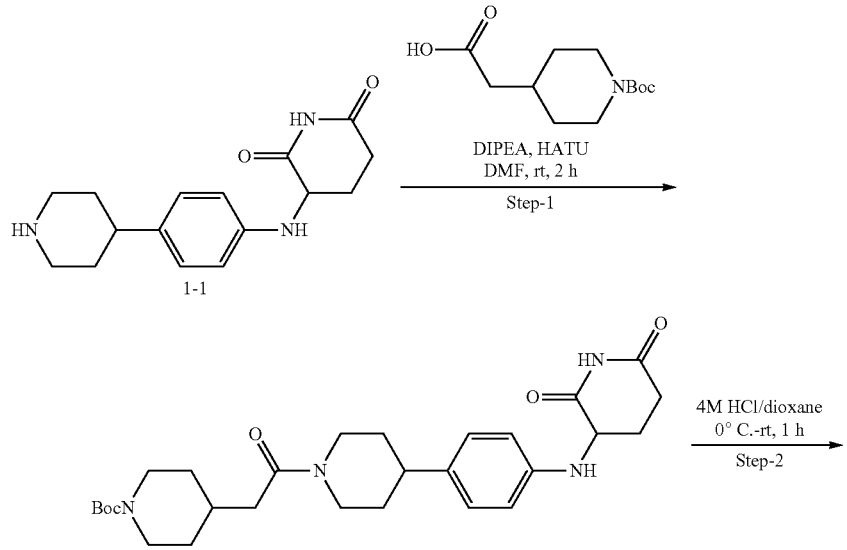

232-3

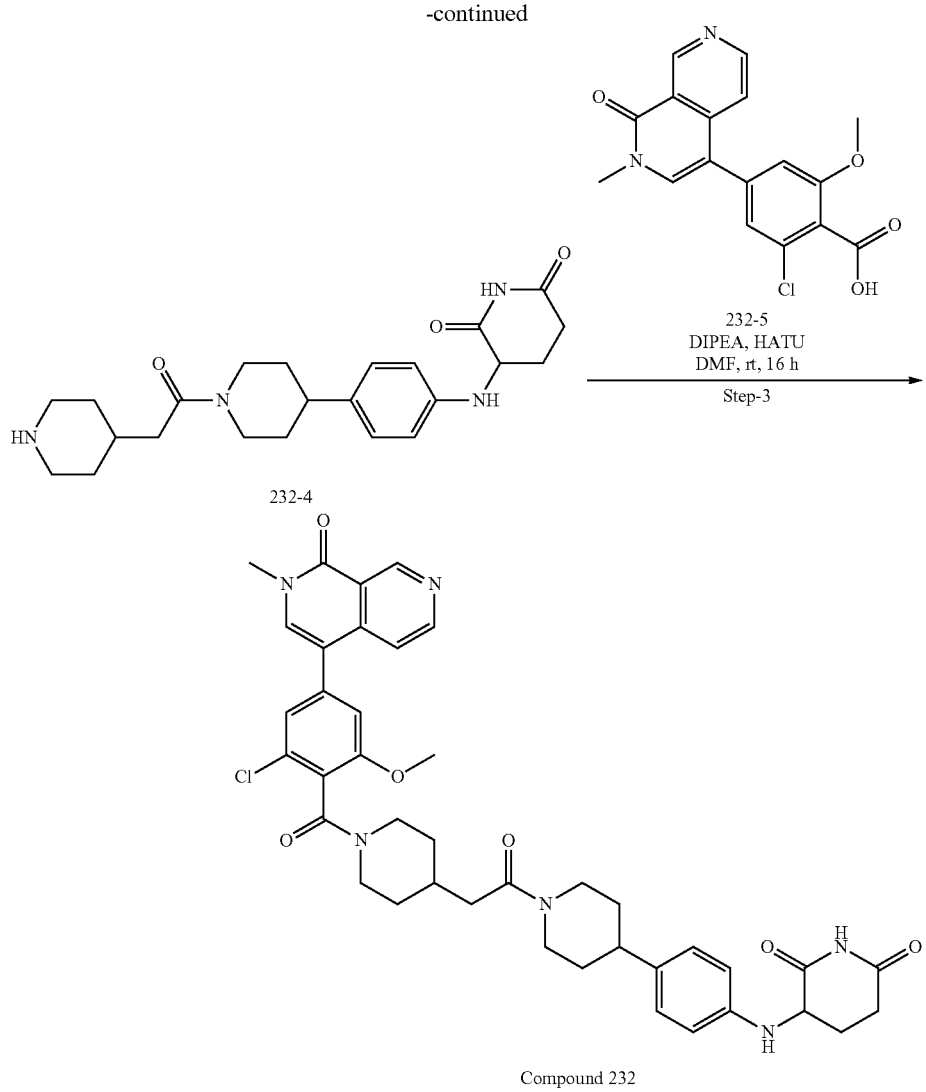

Compound 232

Step-1: To a stirred solution of 3-[4-(4-piperidyl)anilino]piperidine-2,6-dione (hydrochloride salt) (0.1 g, 0.3088 mmol) in DMF (1.0 mL) was added N-ethyl-N-isopropylpropan-2-amine (199.56 mg, 1.54 mmol, 268.95 uL) at 0° C. and then 2-(1-tert-butoxycarbonyl-4-piperidyl)acetic acid (75.13 mg, 0.3088 mmol) was added to the reaction mixture at the same temperature. Then N,N,N',N'-tetramethyl-1-(3-oxido-2,3-dihydrotriazolo[4,5-b]pyridin-3-ium-1-yl)methanediamine; hexafluorophosphate (177.07 mg, 0.463 mmol) was added to it at 0° C. and the reaction mixture was stirred at room temperature for 2 h. Saturated NaHCO$_3$ solution (10 mL) was added to it and extraction was carried out using EtOAc (2×20 mL). The combined organic layers were washed with brine (30 mL), dried over anhydrous sodium sulphate, filtered and concentrated under reduced pressure. The residue was purified by silica gel column chromatography (230-400 mesh size, gradient elution of 0-100% EtOAc/pet-ether) to afford desired product tert-butyl 4-[2-[4-[4-[(2,6-dioxo-3-piperidyl)amino]phenyl]-1-piperidyl]-2-oxo-ethyl]piperidine-1-carboxylate (0.093 g, 0.1814 mmol, 58.86% yield). LCMS (ES$^-$): m/z 511.2 [M−H]$^-$ Step-2: To stirred of tert-butyl 4-[2-[4-[4-[(2,6-dioxo-3-piperidyl)amino]phenyl]-1-piperidyl]-2-oxo-ethyl]piperidine-1-carboxylate (0.0938 g, 0.1814 mmol) in 1,4-dioxane (5 mL) was added 4M solution of HCl in dioxane (6.46 mL) at 0° C. and the reaction mixture was stirred for 1 h. After completion of the reaction, volatiles were removed under reduced pressure and Et2O (3 mL) was added to the residue. It was stirred for 15 min and the solid observed was collected by filtration and dried to afford desired compound 3-[4-[1-[2-(4-piperidyl)acetyl]-4-piperidyl]anilino]piperidine-2,6-dione (hydrochloride salt) (0.090 g, 0.200 mmol, quantitative yield, 97% purity) as a light brown solid. LCMS (ES$^+$): m/z 413.1 [M+H]$^+$ Step-3: To a stirred solution 3-[4-[1-[2-(4-piperidyl)acetyl]-4-piperidyl]anilino]piperidine-2,6-dione (80.43 mg, 0.179 mmol, 021) in DMF (1.2 mL) at room temperature was added DIPEA (115.76 mg, 0.8975 mmol, 156.00 uL) at 0° C. After stirring for 5 min at 0° C., 2-chloro-6-methoxy-4-(2-methyl-1-oxo-2,7-naphthyridin-4-yl)benzoic acid (0.070 g, 0.179 mmol) and HATU (102.17 mg, 0.268 mmol) were added to it and the reaction mixture was stirred at room temperature for 16 h. The reaction mass was directly evaporated under reduce pressure and the resulting residue was purified by reverse phase purification using acetonitrile and water (formic acid as buffer). The obtained residue (108 mg)

was further purified by preparative HPLC to afford title compound 3-[4-[1-[2-[1-[2-chloro-6-methoxy-4-(2-methyl-1-oxo-2,7-naphthyridin-4-yl)benzoyl]-4-piperidyl]acetyl]-4-piperidyl]anilino] piperidine-2,6-dione (28 mg, 0.0379 mmol, 94.42% purity) as a green solid. $^1$H NMR (400 MHz, DMSO-d$_6$) δ 1.10-1.50 (m, 6H); 1.60-1.90 (m, 4H); 1.95-2.15 (m, 2H); 2.25-2.40 (m, 2H); 2.55-2.90 (m, 4H); 3.00-3.10 (m, 2H); 3.38-3.42 (m, 1H); 3.60 (s, 3H); 3.84 & 3.86 (two s, 3H); 3.95-4.05 (m, 1H); 4.22-4.30 (m, 1H); 4.48-4.60 (m, 2H); 5.67 (d, J=8.4 Hz, 1H); 6.61 (d, J=6.4 Hz, 2H); 6.95 (d, J=6.0 Hz, 2H); 7.16 (s, 1H); 7.20 (dd, J$_1$=1.2 Hz, J$_2$=6.0 Hz, 1H); 7.56 (d, J=5.6 Hz, 1H); 7.95 (s, 1H); 8.74 (d, J=5.6 Hz, 1H); 9.45 (s, 1H); 10.78 (s, 1H). LCMS (ES$^+$): m/z 739.59 (M+H)$^+$.

Compound 233 was prepared following the synthesis of Compound 232.

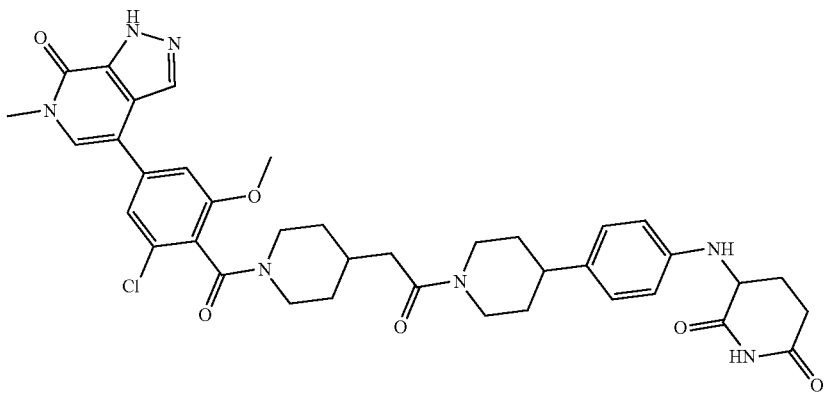 [SMILES: COc1cc(-c2cn(C)c(=O)c3[nH]ncc23)cc(Cl)c1C(=O)N1CCC(CC(=O)N2CCC(c3ccc(NC4CCC(=O)NC4=O)cc3)CC2)CC1]

$^1$H NMR (400 MHz, DMSO-d$_6$): δ 1.08-1.22 (m, 2H); 1.28-1.60 (m, 2H); 1.62-1.90 (m, 6H); 1.95-2.12 (m, 2H); 2.25-2.35 (m, 2H); 2.50-2.60 (m, 2H); 2.66-2.74 (m, 2H); 2.98-3.10 (m, 2H); 3.22-3.32 (m, 1H); 3.61 (s, 3H); 3.80-4.10 (m, 4H); 4.22-4.30 (m, 1H); 4.45-4.60 (m, 2H); 6.58-6.64 (m, 2H); 6.90-6.98 (m, 2H); 7.21 (s, 1H); 7.32 (d, J=6.0 Hz, 1H); 7.66 (s, 1H); 8.23 (s, 1H); 10.80 (s, 1H); 14.30 (bs, 1H). LCMS (ES$^+$): m/z 728.59 [M+H]$^+$

Synthesis of Compound 234

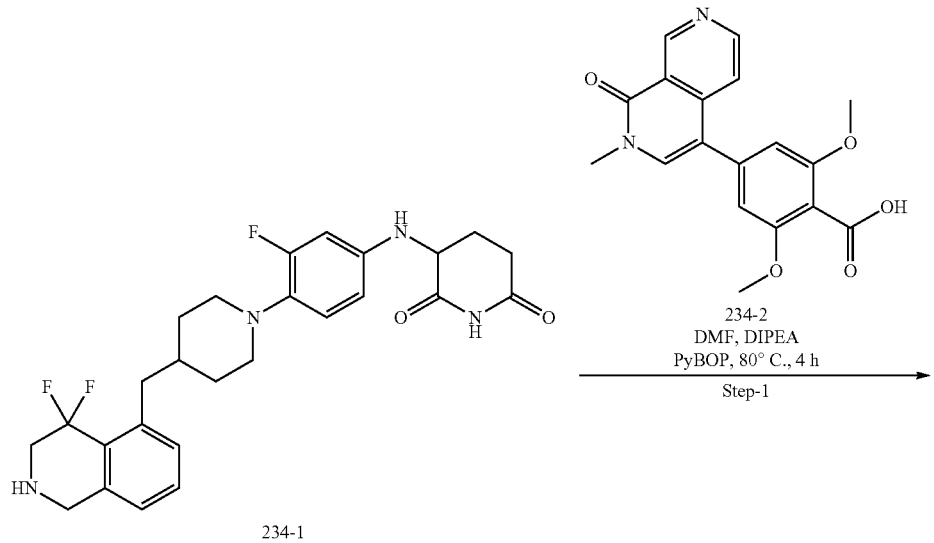

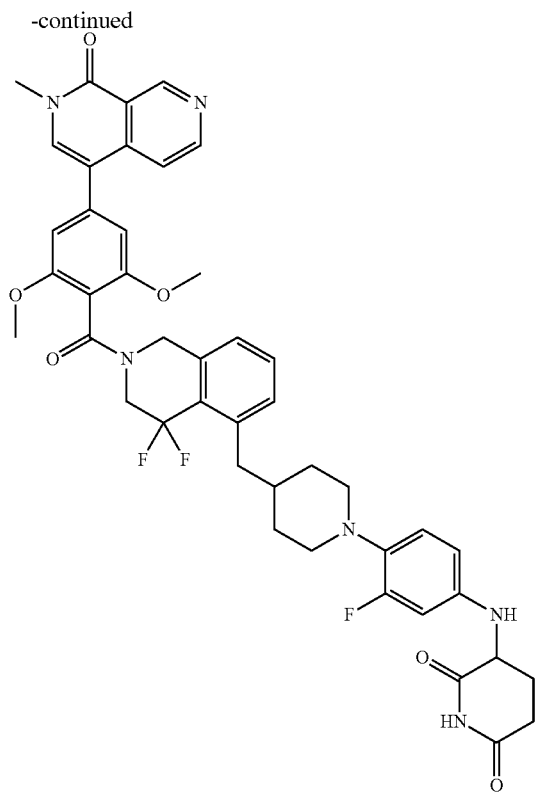

Compound 234

To a stirred solution of compound 236-1 (0.3 g, 0.62 mmol) and compound 2,6-dimethoxy-4-(2-methyl-1-oxo-1, 2-dihydro-2,7-naphthyridin-4-yl)benzoic acid (0.211 g, 0.62 mmol) in DMF (3 mL) was added DIPEA (0.4 g, 3.1 mmol); and the reaction mixture was stirred for 15 minutes. To this was then added PyBOP (0.745 g, 1.24 mmol) and the reaction mixture was stirred at 80° C. for 4 h. After completion of the reaction (as indicated by LCMS), it was cooled to room temperature and saturated $NaHCO_3$ solution (15 mL) was added to it. The solid obtained was filtered, washed with water (3 mL×2) and dried. It was then purified by preparative HPLC to afford desired compound Compound 234 (TFA salt) (0.160 g, 172.68 mol, 24.13% yield, 99.60% purity) as a white solid.

Preparative HPLC conditions:
Column/dimensions: SUNFIRE-C18 (150*19*5μ)
Mobile phase A: 0.1% TFA in water
Mobile phase B: Acetonitrile (ORG)
Gradient (Time/% B): 0/10, 3/10, 10/25, 18/25, 18.1/100, 24/100, 24.1/10, 26/10
Flow rate: 16 ml/min
LCMS (ES$^+$): m/z 809.48 [M+H]$^+$
$^1$H NMR (400 MHz, DMSO-$d_6$): δ 10.80 (s, 1H); 9.48 (d, J=4.8 Hz, 1H); 8.75 (t, J=5.2 Hz, 1H); 7.97 (d, J=22.0 Hz, 1H); 7.68 (t, J=6.8 Hz, 1H); 7.46 (dt, $J_1$=7.6 Hz, $J_2$=33.6 Hz, 7.6 Hz, 1H); 7.35-7.05 (m, 3H); 6.84 (s, 1H); 6.78 (s, 1H); 6.68-6.45 (m, 2H); 4.94 (s, 1H); 4.53 (s, 1H); 4.48-4.28 (m, 2H); 4.00-3.88 (m, 1H); 3.79 (s, 3H); 3.50-3.20 (m, 10H); 2.90-2.50 (m, 4H); 2.12-2.00 (m, 1H); 1.95-1.40 (m, 6H).

Compound 235 was prepared following the synthesis of Compound 234.

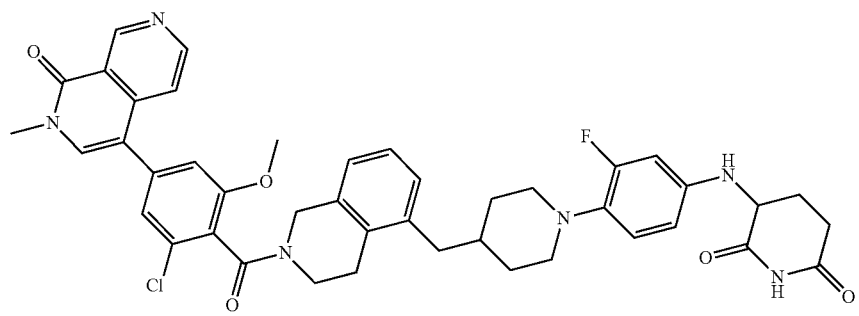 [SMILES: COc1cc(-c2cn(C)c(=O)c3cnccc23)cc(Cl)c1C(=O)N1CCc2c(CC3CCN(c4ccc(NC5CCC(=O)NC5=O)cc4F)CC3)cccc2C1]

¹H NMR (400 MHz, DMSO-d₆) δ 10.79 (s, 1H), 9.49 (s, 1H), 8.77 (m, 1H), 8.01 (s, 1H), 7.66 (m, 1H), 7.25-6.92 (m, 6H), 6.65-6.53 (m, 2H), 4.85-4.77 (m, 1H), 4.40 (m, 2H), 3.96 (m, 1H), 3.83 (s, 3H), 3.71 (s, 1H) 3.62 (s, 3H), 3.50-3.39 (m, 5H), 2.92-2.81 (m, 2H), 2.73-2.55 (m, 3H), 2.07-2.05 (m, 1H), 1.90-1.59 (m, 6H); LCMS (ES⁺): m/z 777.47 [M+H]⁺

Compound 236 was prepared following the synthesis of Compound 234.

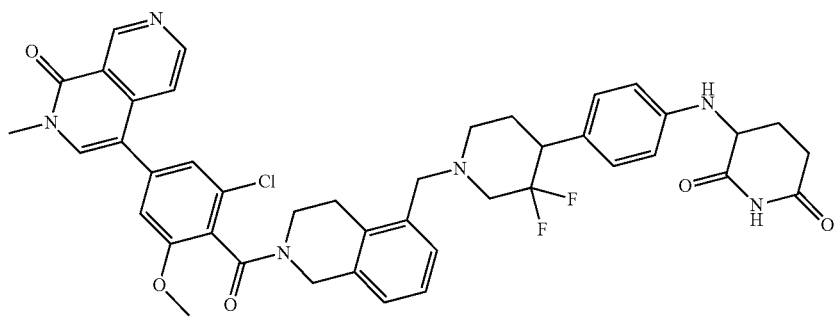 [SMILES: COc1cc(-c2cn(C)c(=O)c3cnccc23)cc(Cl)c1C(=O)N1CCc2c(CN3CCC(c4ccc(NC5CCC(=O)NC5=O)cc4)C(F)(F)C3)cccc2C1]

¹H NMR (400 MHz, DMSO-d₆): δ 1.70-2.15 (m, 4H); 2.50-2.60 (m, 1H); 2.66-2.78 (m, 1H); 2.90-3.30 (m, 8H); 3.62 (s, 3H); 3.86 (s, 3H); 3.87 (s, 3H); 4.34-4.42 (m, 1H); 4.42-4.48 (m, 1H); 4.84-4.94 (m, 1H); 6.60-6.65 (m, 2H); 6.96-7.30 (m, 7H); 7.62-7.65 (m, 1H); 8.00 (d, J=4.0 Hz, 1H); 8.72-8.80 (s, 1H); 9.48 (d, J=1.6 Hz, 1H); 10.78 (s, 1H). LCMS (ES⁺): m/z 795.20 [M+H]⁺

Compound 237 was prepared following the synthesis of Compound 234.

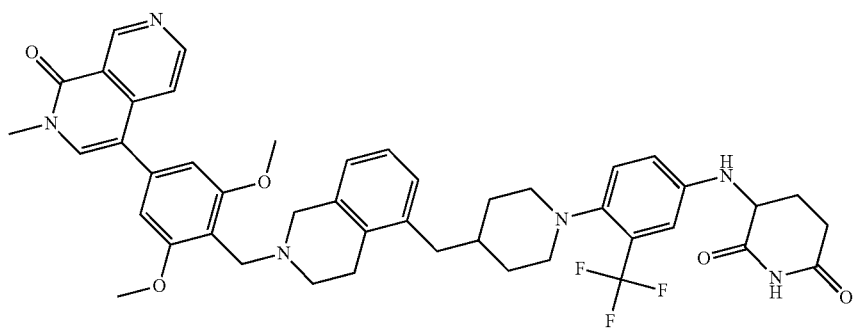 [SMILES: COc1cc(-c2cn(C)c(=O)c3cnccc23)cc(OC)c1CN1CCc2c(CC3CCN(c4ccc(NC5CCC(=O)NC5=O)cc4C(F)(F)F)CC3)cccc2C1]

¹H NMR (400 MHz, DMSO-d₆) δ 10.77 (s, 1H), 9.64 (bs, 1H), 9.48 (s, 1H), 8.76 (d, J=5.6 Hz, 1H), 7.94 (s, 1H), 7.63 (d, J=5.6 Hz, 1H), 7.26 (m, 3H), 7.11 (d, J=6.8 Hz, 1H), 6.91 (m, 4H), 6.15 (bs, 1H), 4.45-4.34 (m, 5H), 3.90 (s, 6H), 3.73-3.70 (m, 1H), 3.63 (s, 3H), 3.47 (m, 1H), 3.12 (m, 2H), 2.81-2.63 (m, 3H), 2.61-2.54 (m, 5H), 2.07-2.04 (m, 1H), 1.91 (m, 1H), 1.66-1.58 (m, 3H), 1.37 (m, 2H). LCMS (ES⁺): m/z 809.48 [M+H]⁺.

Compound 238 was prepared following the synthesis of Compound 234.

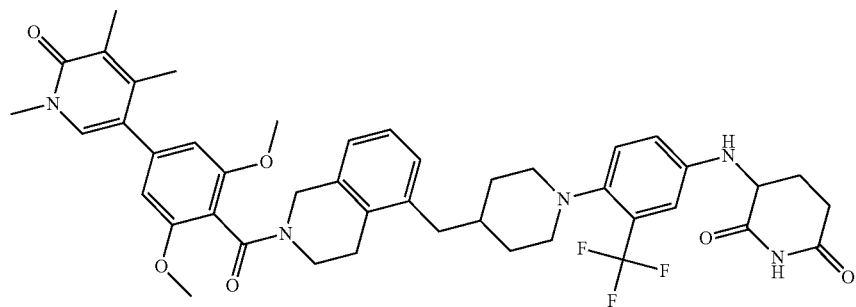 [SMILES: COc1cc(-c2cn(C)c(=O)c(C)c2C)cc(OC)c1C(=O)N1CCc2c(CC3CCN(c4ccc(NC5CCC(=O)NC5=O)cc4C(F)(F)F)CC3)cccc2C1]
$^1$H NMR (400 MHz, DMSO-d$_6$) δ 10.78 (s, 1H), 7.58 (d, J=6.4 Hz, 1H), 7.23 (m, 4H), 6.91-6.79 (m, 2H), 6.64 (d, J=24.0 Hz, 2H), 6.15 (d, J=8.0 Hz, 1H), 4.77 (s, 1H), 4.36-4.31 (m, 2H), 3.85 (t, 1H), 3.76 (s, 4H), 3.59 (s, 2H), 3.47 (m, 3H), 3.43 (m, 1H), 2.84-2.53 (m, 10H), 2.10-2.06 (m, 7H), 1.90-1.87 (m, 1H), 1.59 (m, 3H), 1.35 (m, 2H). LCMS (ES$^+$): m/z 800.24 [M+H]$^+$.
Synthesis of Compound 239
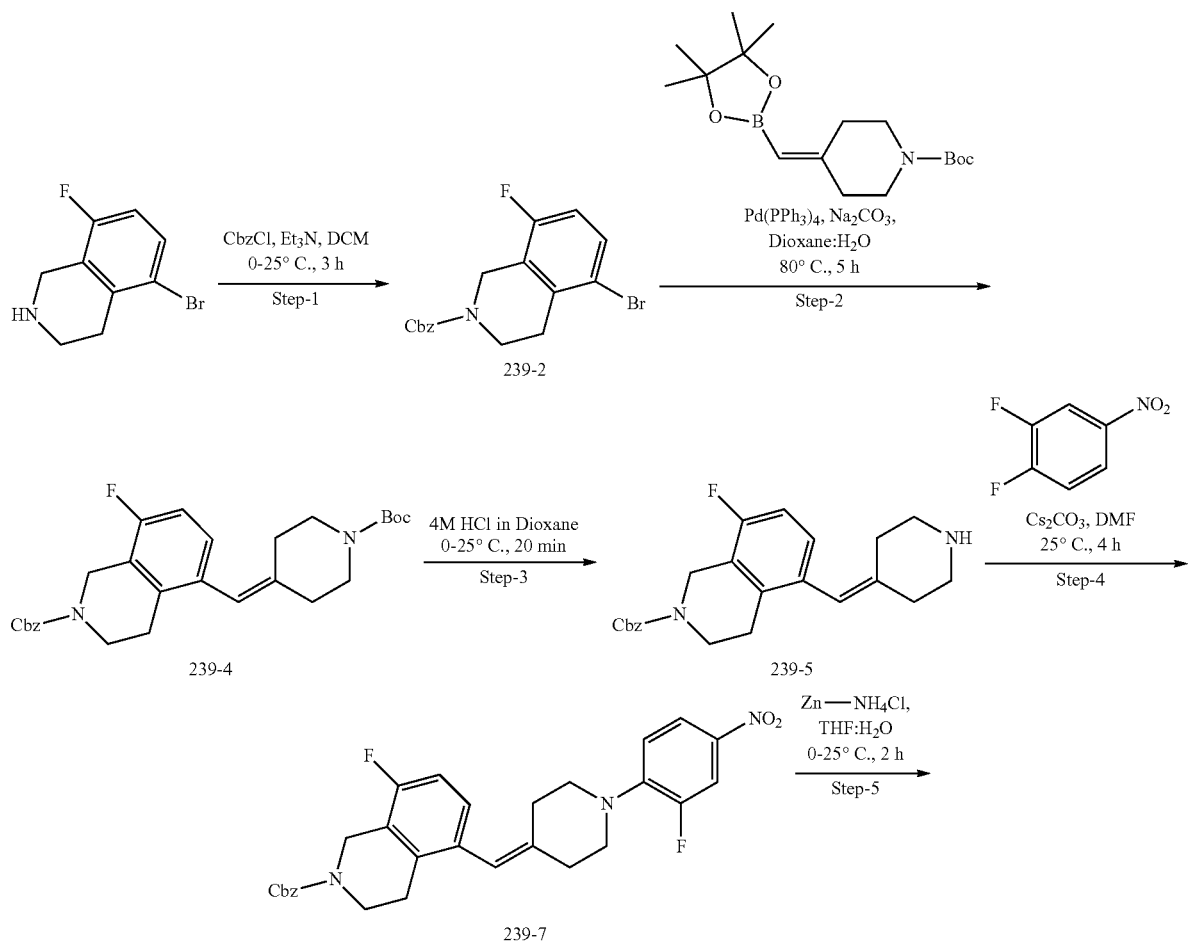

-continued

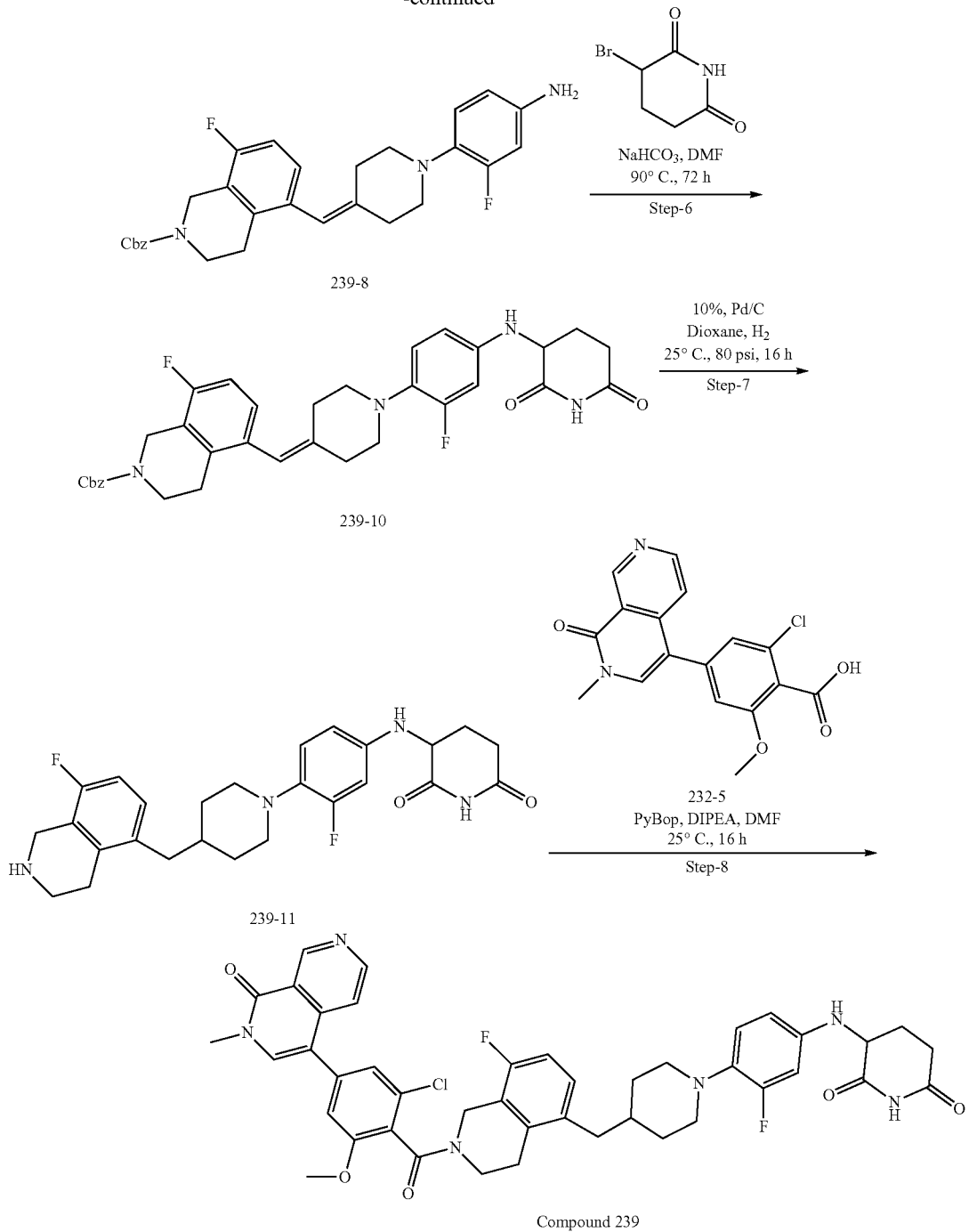

Step-1: To a stirred solution of 5-bromo-8-fluoro-1,2,3,4-tetrahydroisoquinoline (3 g, 13.04 mmol) in DCM (10 mL) were added pyridine (0.721 g, 9.13 mmol) and Benzyl chloroformate (1.78 g, 10.43 mmol) at 0° C. sequentially and allowed to stir at RT for 3 h while monitoring by TLC. After the completion of the reaction, the reaction mixture was poured over cold sodium bicarbonate solution (50 mL) and the organic layer was separated. The aqueous layer was extracted with DCM (100 mL×2). The combined organic layer was washed with brine, dried over sodium sulphate and concentrated on rota evaporator to afford a crude product. The resulting crude was purified by column chromatography (silica gel mesh 100-200) eluted with 0-7% gradient elution of pet ether: ethyl acetate to give benzyl 5-bromo-8-fluoro-3,4-dihydro-1H-isoquinoline-2-carboxylate 2 (2.8 g, 56.01% yield, 94.96% purity) as colourless liquid. LCMS (ES+): m/z 364.15 [M+H]+

Step-2: To a stirred solution of benzyl 5-bromo-8-fluoro-3,4-dihydroisoquinoline-2(1H)-carboxylate 2 (2.8 g, 7.69 mmol) in 1,4 dioxane (50 mL) and water (10 mL) was added tert-butyl 4-((4,4,5,5-tetramethyl-1,3,2-dioxaborolan-2-yl)methylene)piperidine-1-carboxylate (2.48 g, 7.69 mmol) followed by the addition of potassium carbonate, (2.66 g, 19.22 mmol) at room temperature under argon atmosphere.

The reaction mixture was degassed with argon repeatedly and Pd(PPh$_3$)$_4$ (355.35 mg, 0.307 mmol) was added in one portion under argon atmosphere. The reaction mixture was heated at 80° C. for 5 h, while monitoring by LCMS and TLC. After the completion the reaction mixture was cooled to room temperature, filtered through Celite bed and washed with ethyl acetate (100 mL). The filtrate was concentrated, and the resultant crude mass was dissolved with ethyl acetate (100 mL) and washed with water (2×50 mL) followed by brine (1×50 mL) and dried over anhydrous Na$_2$SO$_4$, concentrated to afford crude product. The crude was purified by column chromatography (silica gel 100-200 mesh and the product eluted at 8-10% EtOAc: Pet ether) to give benzyl 5-((1-(tert-butoxycarbonyl)piperidin-4-ylidene) methyl)-8-fluoro-3,4-dihydroisoquinoline-2(1H)-carboxylate 239-4 (2 g, 48.72% yield, 90% purity) as brown gummy solid. LCMS (ES$^+$): m/z [M+Na] 503 (M-100 fragment dominated).

Step-3: To a stirred solution of benzyl 5-[(1-tert-butoxycarbonyl-4-piperidylidene)methyl]-8-fluoro-3,4-dihydro-1H-isoquinoline-2-carboxylate 239-4 (2 g, 4.16 mmol) in 1,4-Dioxane (1 mL) at 0° C. 4M HCl in Dioxane (1.52 g, 41.62 mmol) was added and allowed to stir at RT for 20 min, while monitoring reaction by TLC. After completion of reaction, volatiles were evaporated under reduced pressure. The solid was co-evaporated with toluene (10 mL) then triturated with diethyl ether (20 mL×2). Diethyl ether was decanted and resulting solid was dried under vacuum to afford benzyl 8-fluoro-5-(4-piperidylidenemethyl)-3, 4-dihydro-1H-isoquinoline-2-carboxylate.HCl salt 239-5 (1.7 g, 88.18% yield, 96.62% purity) as an off white solid. LCMS (ES$^+$): m/z [M+H]$^+$ 381.62

Step-4: To a stirred solution of compound benzyl 8-fluoro-5-(4-piperidylidenemethyl)-3,4-dihydro-1H-isoquinoline-2-carboxylate (1.8 g, 4.73 mmol) in DMF (20 mL) was added cesium carbonate (3.08 g, 9.46 mmol) and allowed to stir for 15 min before adding 1,2-difluoro-4-nitro-benzene (0.752 g, 4.73 mmol). The reaction mixture was allowed to stir at RT for 4 h while monitoring by TLC. After completion of reaction, ice cold water was added to the reaction mixture and extracted with ethyl acetate. The combined organic extracts were dried over anhydrous sodium sulphate, filtered and evaporated under reduced pressure. Crude was purified by column chromatography (silica gel 100-200 mesh, 0-7% EtOAc: pet ether gradient solvent) to yield benzyl 8-fluoro-5-[[1-(2-fluoro-4-nitro-phenyl)-4-piperidylidene]methyl]-3,4-dihydro-1H-isoquinoline-2-carboxylate 239-7 (1.3 g, 49.71% yield, 94% purity) as yellow gummy liquid. LCMS (ES$^+$): m/z [M+H]$^+$ 381.62

Step-5: To a stirred solution of benzyl 8-fluoro-5-[[1-(2-fluoro-4-nitro-phenyl)-4-piperidylidene]methyl]-3,4-dihydro-1H-isoquinoline-2-carboxylate 239-7 (1.3 g, 2.50 mmol) in Methanol (5 mL), THF (5 mL) and water (10 mL), Zinc Powder (1.64 g, 25.02 mmol) was added. Reaction mixture was cooled at 0° C. and ammonium chloride (2.01 g, 37.53 mmol) was added portion wise and stirred at RT for 2 h, while monitoring by TLC and LCMS. After the completion, reaction mixture was filtered over Celite bed and filtrate was concentrated and crude compound was purified by column chromatography using (silica gel 100-200 mesh, 0-20% EtOAc: petether gradient solvent) to yield benzyl 5-[[1-(4-amino-2-fluoro-phenyl)-4-piperidylidene]methyl]-8-fluoro-3,4-dihydro-1H-isoquinoline-2-carboxylate (1 g, 1.94 mmol, 77.55% yield, 95% purity) as yellow solid. LCMS (ES$^+$): m/z [M+H]$^+$ 490.52.

Step-6: To a stirred solution of benzyl 5-[[1-(4-amino-2-fluoro-phenyl)-4-piperidylidene]methyl]-8-fluoro-3,4-dihydro-1H-isoquinoline-2-carboxylate 239-8 (1 g, 2.04 mmol)) in DMF (30 mL) were added 3-bromopiperidine-2,6-dione (Note: It was added in three lots 4eq each after each 24 h) (4.71 g, 24.51 mmol), NaHCO$_3$ (2.06 g, 24.51 mmol) and stirred at 90° C. for 72 h, while monitoring the reaction by LCMS and TLC. After 72 h, the reaction was quenched with ice cold water (100 mL) and extracted with EtOAc (3×150 mL). The combined organic layer was dried over anhydrous Na$_2$SO$_4$, and concentrated to afford crude compound and was purified by (silica gel mesh 100-200, and product eluted with 0-50% gradient elution of ethyl acetate in pet ether) column chromatography to yield benzyl 5-[[1-[4-[(2,6-dioxo-3-piperidyl)amino]-2-fluoro-phenyl]-4-piperidylidene]methyl]-8-fluoro-3,4-dihydro-1H-isoquinoline-2-carboxylate 239-10 (0.85 g, 63.04% yield, 91% purity) as blue solid. LCMS (ES$^+$): m/z 601.62 [M+H]$^+$.

Step-7: To a stirred solution of benzyl 5-[[1-[4-[(2,6-dioxo-3-piperidyl)amino]-2-fluoro-phenyl]-4-piperidylidene]methyl]-8-fluoro-3,4-dihydro-1H-isoquinoline-2-carboxylate 239-10 (0.1 g, 0.166 mmol) in Dioxane (15 mL) wet Palladium, 10% on carbon, (88.59 mg, 0.832 mmol) was added. Reaction mixture was stirred under hydrogen atmosphere at room temperature for 16 h in a steel bomb with 80 psi pressure while monitoring by TLC and LCMS. After the completion of reaction, reaction mixture was filtered through Celite bed and washed with ethyl acetate and THF mixture (1:1) (20 mL). Filtrate was concentrated to yield the crude product which was triturated with diethyl ether (5 mL×2). Diethyl ether was decanted and dried to yield 3-((3-fluoro-4-(4-((8-fluoro-1,2,3,4-tetrahydroisoquinolin-5-yl)methyl)piperidin-1-yl)phenyl)amino) piperidine-2,6-dione 239-11 (0.07 g, 0.109 mmol, 62.51% yield, 88.9% purity) as an off white solid. LCMS (ES$^+$): m/z 469.36 [M+H]$^+$ Step-8: To a stirred solution of 3-[3-fluoro-4-[4-[(8-fluoro-1,2,3,4-tetrahydroisoquinolin-5-yl)methyl]-1-piperidyl]anilino]piperidine-2,6-dione 239-11 (0.08 g, 0.170 mmol) in dry DMF (3 mL) was added N-ethyl-N-isopropyl-propan-2-amine (66.20 mg, 0.512 mmol) under N$_2$ and allowed to warm at RT. 2-chloro-6-methoxy-4-(2-methyl-1-oxo-2,7-naphthyridin-4-yl)benzoic acid (58.86 mg, 0.170 mmol) and PyBOP (106.62 mg, 0.204 mmol) were added and the reaction mixture was stirred at RT for 16 h, while monitoring by TLC and LCMS. After the completion the reaction mixture was concentrated under reduced pressure to obtain the crude residue and it was purified by Prep HPLC to afford 3-[4-[4-[[2-[2-chloro-6-methoxy-4-(2-methyl-1-oxo-2,7-naphthyridin-4-yl)benzoyl]-8-fluoro-3,4-dihydro-1H-isoquinolin-5-yl]methyl]-1-piperidyl]-3-fluoro-anilino] piperidine-2,6-dione.TFA salt Compound 239 (43 mg, 0.0460 mmol, 26.95% yield, 97.31% purity) as a brown solid. $^1$H NMR (400 MHz, DMSO-d$_6$) δ 10.80 (s, 1H), 9.47 (s, 1H), 8.76 (t, J=5.8 Hz, 1H), 8.01 (d, J=12.6 Hz, 1H), 7.60 (q, J$_1$=8.8 Hz, J$_2$=5.4 Hz, 1H), 7.26-6.96 (m, 6H), 6.58-6.49 (m, 2H), 4.84 (q, J=19.5 Hz, 2H), 4.40-4.32 (m, 2H), 4.03-3.98 (m, 2H), 3.86 (s, 3H), 3.61 (s, 3H), 3.54-3.42 (m, 8H), 3.17-2.67 (m, 5H), 2.07-2.05 (m, 1H), 1.97-1.85 (m, 2H) LCMS (ES$^+$): m/z 795.54 [M+H]$^+$ Compound 240 was prepared following the synthesis of Compound 239.

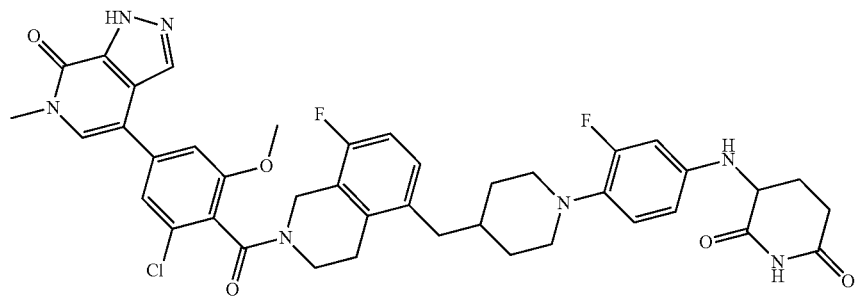 [SMILES: COc1cc(-c2cn(C)c(=O)c3[nH]ncc23)cc(Cl)c1C(=O)N1CCc2c(CC3CCN(c4ccc(NC5CCC(=O)NC5=O)cc4F)CC3)ccc(F)c2C1]
$^1$H NMR (400 MHz, DMSO-d$_6$) δ 14.31 (s, 1H), 10.79 (s, 1H), 8.25 (d, J=7.8 Hz, 1H), 7.38-6.95 (m, 5H), 6.67-6.40 (m, 2H), 7.04 (m, J=8.1 Hz, 1H), 6.51 (d, J=38.6 Hz, 1H), 4.82 (q, J=20.7 Hz, 1H), 4.38 (s, 1H), 4.28 (bs, 1H), 3.99-3.77 (m, 10H), 3.49-3.16 (m, 4H), 2.90-2.57 (m, 4H), 2.09-2.04 (m, 1H), 1.88-1.47 (m, 6H). LCMS (ES$^+$): m/z 784.58 [M+H]$^+$
Synthesis of Compound 241
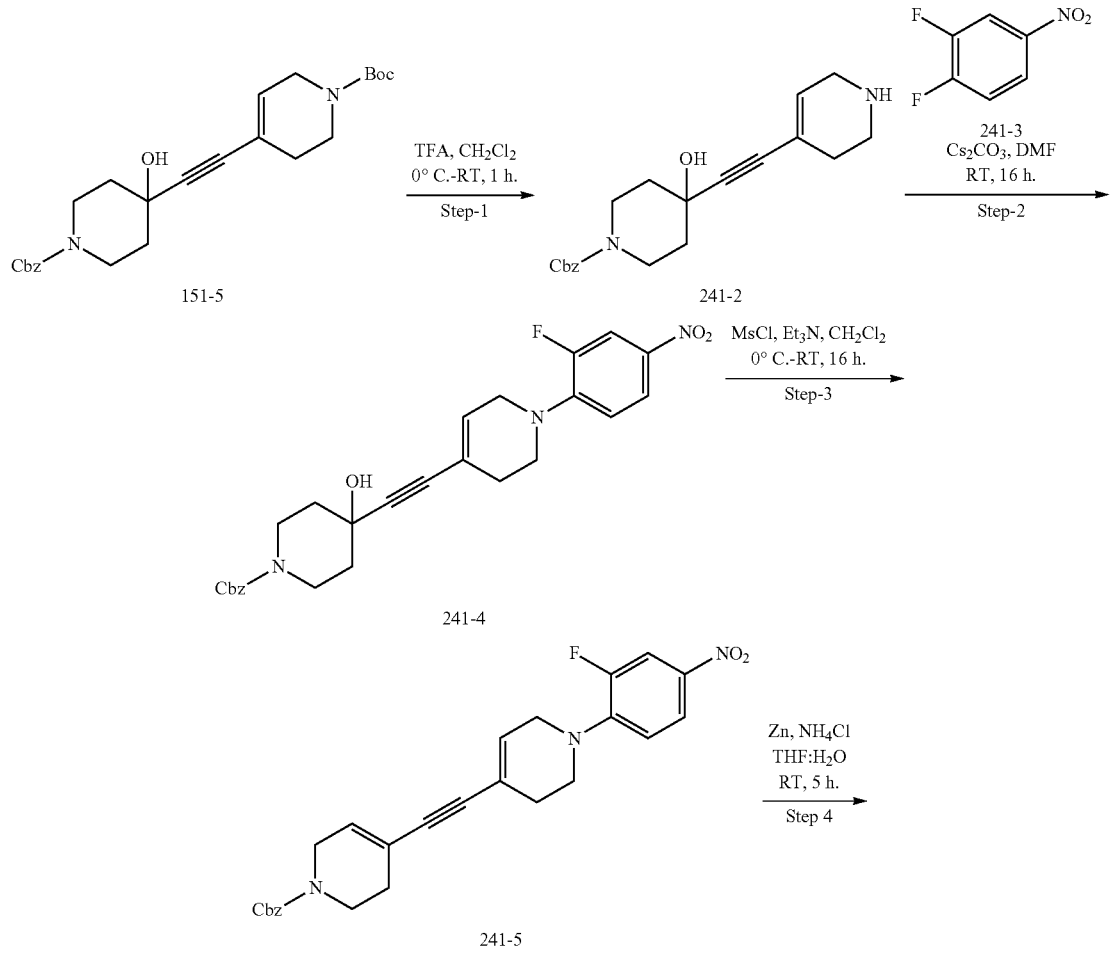

-continued
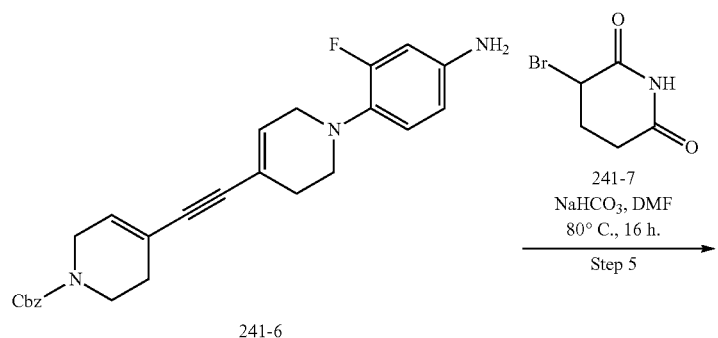
241-6
241-7
NaHCO₃, DMF
80° C., 16 h.
Step 5
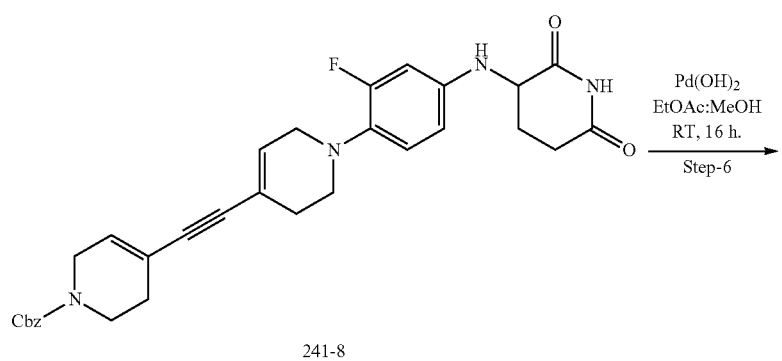
241-8
Pd(OH)₂
EtOAc:MeOH
RT, 16 h.
Step-6
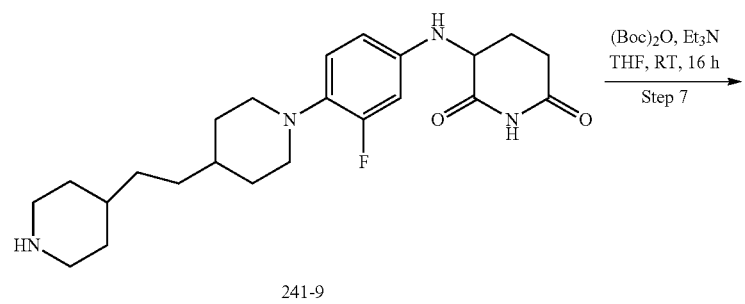
241-9
(Boc)₂O, Et₃N
THF, RT, 16 h
Step 7
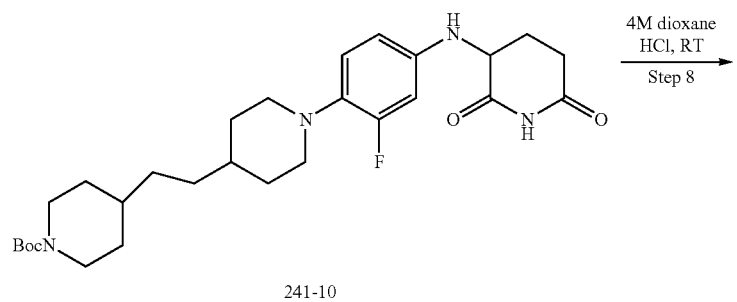
241-10
4M dioxane
HCl, RT
Step 8

-continued

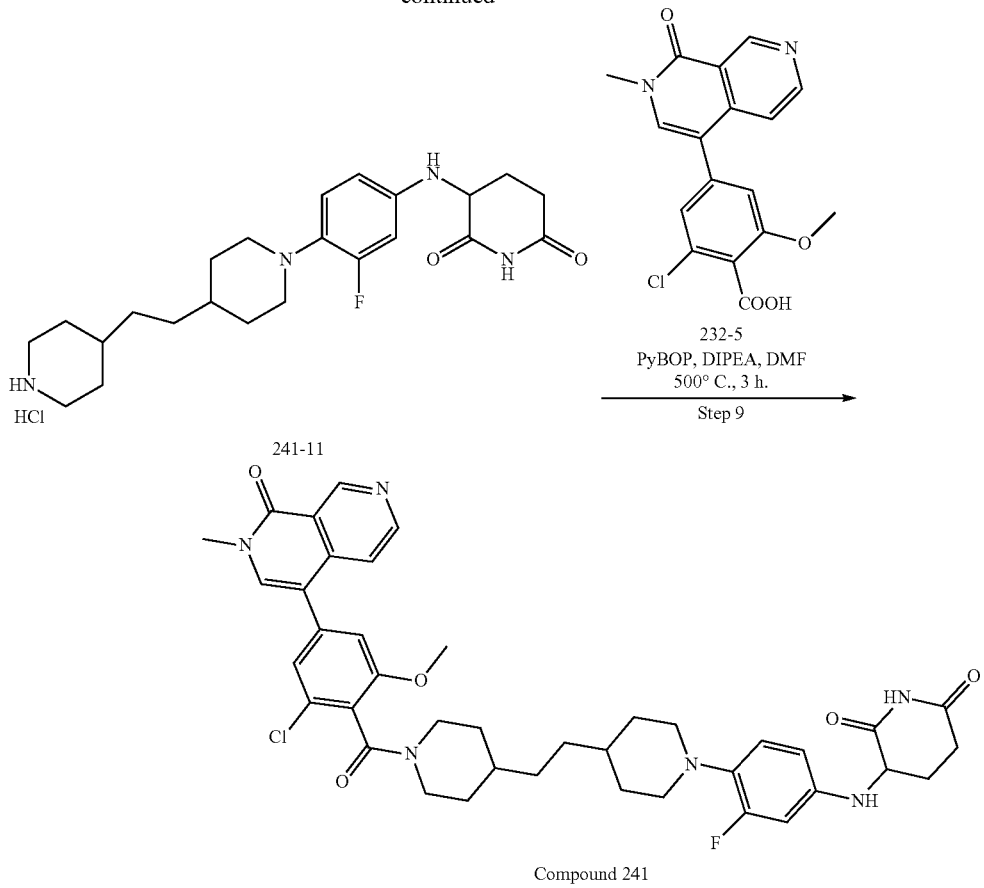

232-5
PyBOP, DIPEA, DMF
500° C., 3 h.
Step 9

Compound 241

Step-1: To a stirred solution of tert-butyl 4-[2-(1-benzyloxycarbonyl-4-hydroxy-4-piperidyl)ethynyl]-3,6-dihydro-2H-pyridine-1-carboxylate 151-5 (5 g, 11.35 mmol) in $CH_2Cl2$ (30 mL) was added Trifluoroacetic acid (25.88 g, 227.00 mmol) at 0° C. and stir for 1 h at RT while monitoring by TLC and LCMS. After 1 h the reaction mixture was concentrated to dryness. The crude compound was triturated with Diethyl ether (2×40 ml) to afford benzyl 4-hydroxy-4-[2-(1,2,3,6-tetrahydropyridin-4-yl)ethynyl]piperidine-1-carboxylate.TFA salt 241-2 (5 g, 8.80 mol, 77.55% yield, 80% purity) as a brown solid. LCMS (ES$^+$): m/z [M+H]$^+$ 341.32.

Step-2: To a stirred solution of benzyl 4-hydroxy-4-[2-(1,2,3,6-tetrahydropyridin-4-yl)ethynyl]piperidine-1-carboxylate 241-2 (8 g, 23.50 mmol) in DMF (40 mL) were added 1,2-difluoro-4-nitro-benzene (3.36 g, 21.15 mmol), cesium carbonate (30.63 g, 94.00 mmol) and stirred at RT for 16 h, while monitoring by LCMS and TLC. After 16 h, the reaction was quenched with ice cold water (100 mL) and extracted with EtOAc (3×50 mL). The combined organic layer was dried over anhydrous $Na_2SO_4$ and concentrated to afford crude compound. Crude compound was purified by (silica gel mesh 100-200, 40% ethyl acetate in pet ether) column chromatography to afford benzyl 4-[2-[1-(2-fluoro-4-nitro-phenyl)-3,6-dihydro-2H-pyridin-4-yl]ethynyl]-4-hydroxy-piperidine-1-carboxylate 241-4 (4 g, 7.26 mmol, 30.88% yield, 87% purity) as a pale yellow semisolid. LCMS (ES$^+$): m/z [M+H]$^+$ 480.24.

Step-3: To a stirred solution of benzyl 4-[2-[1-(2-fluoro-4-nitro-phenyl)-3,6-dihydro-2H-pyridin-4-yl]ethynyl]-4-hydroxy-piperidine-1-carboxylate 241-4 (4 g, 8.34 mmol) in $CH_2Cl_2$ (40 mL) were added $Et_3N$ (2.53 g, 25.03 mmol), methylsulfonyl chloride (0.955 g, 8.34 mmol) at 0° C. and stirred at RT for 16 h while monitoring by TLC and LCMS. After 16 h the reaction mixture was quenched with saturated $NaHCO_3$ solution (30 ml) and extracted with EtOAc (3×50 mL). The combined organic layer was dried over anhydrous $Na_2SO_4$, and concentrated to afford crude which was purified by (silica gel mesh 100-200, 20% ethyl acetate in pet ether) column chromatography to afford benzyl 4-[2-[1-(2-fluoro-4-nitro-phenyl)-3,6-dihydro-2H-pyridin-4-yl]ethynyl]-3,6-dihydro-2H-pyridine-1-carboxylate 241-5 (2.5 g, 3.95 mmol, 47.41% yield, 73% purity) as a yellow solid. LCMS (ES$^+$): m/z [M+H]$^+$ 462.19.

Step-4: To the stirred solution of benzyl 4-[2-[1-(2-fluoro-4-nitro-phenyl)-3,6-dihydro-2H-pyridin-4-yl]ethynyl]-3,6-dihydro-2H-pyridine-1-carboxylate 241-5 (2.5 g, 5.42 mmol) in THF (20 mL) and Water (10 mL) was added Zinc dust in one portion (2.83 g, 43.34 mmol) at RT followed by the addition of Ammonium chloride (2.32 g, 43.34 mmol) portion wise at RT. The reaction mixture was stirred at RT for 5 h while monitoring by TLC. After 5 h the reaction mixture was filtered off though Celite bed and washed with methanol (20 mL). The filtrate was concentrated and the residual mass was dissolved with ice cold water (50 mL) and extracted with EtOAc (2×100 mL). The combined organic layer was dried over anhydrous $Na_2SO_4$, and concentrated to afford crude compound, which was purified by (silica gel mesh 100-200, 20% ethyl acetate in pet ether) column chromatography to afford benzyl 4-[2-[1-(4-amino-2-fluorophenyl)-3,6-dihydro-2H-pyridin-4-yl]ethynyl]-3,6-dihydro-2H-pyridine-1-carboxylate 241-6 (1.2 g, 2.36 mmol, 43.64% yield, 85% purity) as a yellow semisolid. LCMS (ES+): m/z 432.24 [M+H]+.

Step-5: To a stirred solution of benzyl 4-[2-[1-(4-amino-2-fluoro-phenyl)-3,6-dihydro-2H-pyridin-4-yl]ethynyl]-3,6-dihydro-2H-pyridine-1-carboxylate 241-6 (1.1 g, 2.55 mmol) in DMF (8 mL) was added 3-bromopiperidine-2,6-dione 7 (1.47 g, 7.65 mmol), NaHCO$_3$ (0.856 g, 10.2 mmol) and stirred at 80° C. for 16 h, while monitoring by LCMS and TLC. After 16 h, the reaction was quenched with ice cold water (20 mL) and extracted with EtOAc (3×50 mL). The combined organic layer was dried over anhydrous Na$_2$SO$_4$ and concentrated to afford crude compound. Crude compound was purified by (silica gel mesh 100-200, 20% ethyl acetate in pet ether) column chromatography to afford benzyl 4-[2-[1-[4-[(2,6-dioxo-3-piperidyl)amino]-2-fluoro-phenyl]-3,6-dihydro-2H-pyridin-4-yl]ethynyl]-3,6-dihydro-2H-pyridine-1-carboxylate 241-8 (1.1 g, 1.68 mmol, 66.01% yield, 83% purity) as a brown semi solid. LCMS (ES+): m/z 543.66 [M+H]+.

Step-6: Stirred mixture of benzyl 4-[2-[1-[4-[(2,6-dioxo-3-piperidyl)amino]-2-fluoro-phenyl]-3,6-dihydro-2H-pyridin-4-yl]ethynyl]-3,6-dihydro-2H-pyridine-1-carboxylate 241-8 (0.5 g, 0.921 mmol) in methanol (7 mL) and ethyl acetate (7 mL) was degassed for 10 minutes followed by addition of Palladium hydroxide on carbon, 20 wt. % 50% water (0.129 g, 0.921 mmol) and HCl (0.034 g, 0.921 mmol). The reaction mixture was again degassed and stirred under hydrogen pressure (@90 Psi) in steel bomb for 16 h at RT. The progress of the reaction was monitored by TLC and LCMS. After completion of the reaction, reaction mixture was filtered through Celite bed and washed with methanol (20 ml). The filtrate was removed under vacuum to afford 3-[3-fluoro-4-[4-[2-(4-piperidyl)ethyl]-1-piperidyl]anilino]piperidine-2,6-dione 241-9 (0.3 g, 0.518 mmol, 56.28% yield, 72% purity) as a grey solid. LCMS (ES+): m/z 417.82 [M+H]+.

Step-7: To a stirred solution of 3-[3-fluoro-4-[4-[2-(4-piperidyl)ethyl]-1-piperidyl]anilino]piperidine-2,6-dione 241-9 (0.7 g, 1.68 mmol) in THF (10 mL) were added DIPEA (0.260 g, 2.02 mmol) and DMAP (0.002 g, 0.017 mmol) and Di-tert-butyl dicarbonate (0.55 g, 2.52 mmol) at 0° C. allowed to stirred for 16 h at RT while monitoring by LCMS and TLC. After 16 h the reaction mass was diluted with water (20 ml) and extracted with ethyl acetate (3×30 ml) and the combined organic layer was dried over anhydrous Na$_2$SO$_4$, and concentrated to afford crude compound was purified by (silica gel mesh 230-400, 30% ethyl acetate in pet ether) column chromatography to afford tert-butyl 4-[2-[1-[4-[(2,6-dioxo-3-piperidyl)amino]-2-fluoro-phe-nyl]-4-piperidyl]ethyl]piperidine-1-carboxylate 241-10 (0.200 g, 0.340 mmol, 20.27% yield, 88% purity) as a grey solid. LCMS (ES+): m/z 517.32 [M+H]+.

Step-8: To a stirred solution of tert-butyl 4-[2-[1-[4-[(2,6-dioxo-3-piperidyl)amino]-2-fluoro-phenyl]-4-piperidyl]ethyl]piperidine-1-carboxylate 241-10 (0.700 g, 1.35 mmol) in 1,4 Dioxane (2 ml) was added 4M HCl in 1,4 Dioxane (3 mL) at 0° C. and stirred at RT while monitoring by TLC and LCMS. After 2 h the reaction mixture was concentrated to dryness. The crude compound was triturated with Diethyl ether (2×20 ml) to afford 3-[3-fluoro-4-[4-[2-(4-piperidyl)ethyl]-1-piperidyl]anilino]piperidine-2,6-dione.HCl salt 241-11 (0.200 g, 0.393 mmol, 29.00% yield, 89% purity) grey solid. LCMS (ES+): m/z 417.44 [M+H]+

Step-9: To a stirred solution of 3-[3-fluoro-4-[4-[2-(4-piperidyl)ethyl]-1-piperidyl]anilino]piperidine-2,6-dione.HCl 241-11 (0.100 mg, 0.240 mmol) in dry DMF (3 mL) was added DIPEA (0.109 g, 0.840 mmol) at 0° C. and the reaction mixture was stirred for 5 min. To the reaction mixture, and 2-chloro-6-methoxy-4-(2-methyl-1-oxo-2,7-naphthyridin-4-yl)benzoic acid (0.083 g, 0.240 mmol) was added and the reaction mixture was stirred for another 5 min. PyBOP (0.125 g, 0.240 mmol) was added and the reaction mixture was stirred at 50° C. for 3 h while the reaction monitoring by LCMS. After 3 h most of the DMF was evaporated using genvac and the crude compound was purified by prep-HPLC to afford 3-[4-[4-[2-[1-[2-chloro-6-methoxy-4-(2-methyl-1-oxo-2,7-naphthyridin-4-yl)benzoyl]-4-piperidyl]ethyl]-1-piperidyl]-3-fluoro-anilino]piperidine-2,6-dione TFA salt Compound 241 (0.0658 g, 0.082 mol, 92.9% purity) as a pale pink solid. $^1$H NMR (400 MHz, DMSO-d$_6$) δ 10.77 (s, 1H), 9.45 (s, 1H), 8.74 (d, J=5.6 Hz, 1H), 7.95 (s, 1H), 7.56 (d, J=5.4 Hz, 1H), 7.18 (t, J=9.6 Hz, 2H), 6.82 (t, J=9.3 Hz, 1H), 6.48 (d, J=14.9 Hz, 1H), 6.40 (d, J=8.6 Hz, 1H), 5.76 (d, J=7.4 Hz, 1H), 4.53 (t, J=10.5 Hz, 1H), 4.20 (s, 1H), 3.85 (d, J=6.0 Hz, 3H), 3.60 (s, 3H), 3.10-2.98 (m, 3H), 2.75-2.67 (m, 2H), 2.55-2.54 (m, 3H), 2.10-2.04 (m, 1H), 1.80-1.64 (m, 5H), 1.49-0.90 (m, 11H). LCMS (ES+): m/z 743.48 [M+H]+

Compound 242 was prepared following the synthesis of Compound 241.

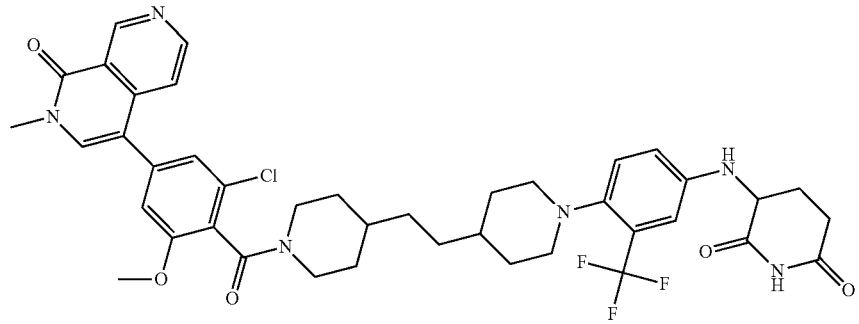 [SMILES: COc1cc(-c2cn(C)c(=O)c3cnccc23)cc(Cl)c1C(=O)N1CCC(CCC2CCN(c3ccc(NC4CCC(=O)NC4=O)cc3C(F)(F)F)CC2)CC1]

$^1$H NMR (400 MHz, DMSO-d$_6$) δ 10.78 (s, 1H), 9.45 (s, 1H), 8.74 (d, J=5.6 Hz, 1H), 7.95 (s, 1H), 7.56 (d, J=5.6 Hz, 1H), 7.27 (d, J=8.7 Hz, 1H), 7.18-7.14 (m, 1H), 6.91-6.86 (m, 2H), 6.15 (d, J=7.9 Hz, 1H), 4.53 (t, J=11.5 Hz, 1H), 4.37-4.35 (m, 1H), 3.85 (d, J=5.4 Hz, 3H), 3.60 (s, 3H), 3.02-2.56 (m, 7H), 2.08-2.05 (m, 1H), 1.91-1.50 (m, 6H), 1.27 (bs, 1H), 1.24-1.06 (m, 10H). LCMS (ES+): m/z 793.39 [M+H]+

Compound 243 was prepared following the synthesis of Compound 234.

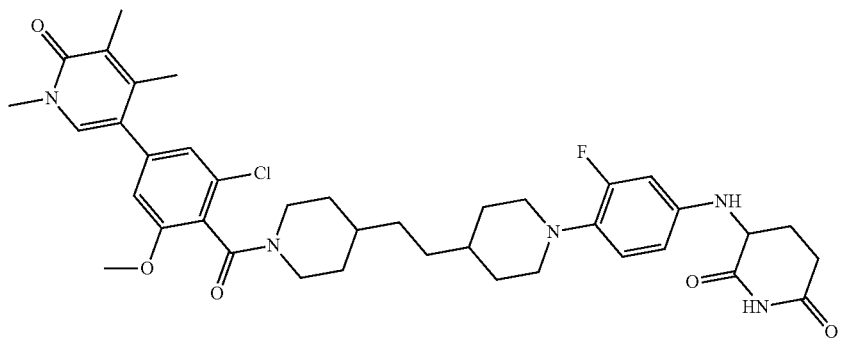 [SMILES: COc1cc(-c2cn(C)c(=O)c(C)c2C)cc(Cl)c1C(=O)N1CCC(CCC2CCN(c3ccc(NC4CCC(=O)NC4=O)cc3F)CC2)CC1]
$^1$H NMR (400 MHz, DMSO-d$_6$) δ 10.80 (s, 1H), 7.59 (s, 1H), 7.02-6.96 (m, 3H), 6.55-6.49 (m, 2H), 4.51 (t, J=11.5 Hz, 1H), 4.31 (bs, 1H), 3.81 (d, J=5.6 Hz, 3H), 3.45 (s, 8H), 2.98-2.67 (m, 4H), 2.06 (d, J=4.2 Hz, 7H), 1.90-1.01 (m, 15H). LCMS (ES$^+$): m/z 720.50 [M+H]$^+$
Synthesis of Compound 244
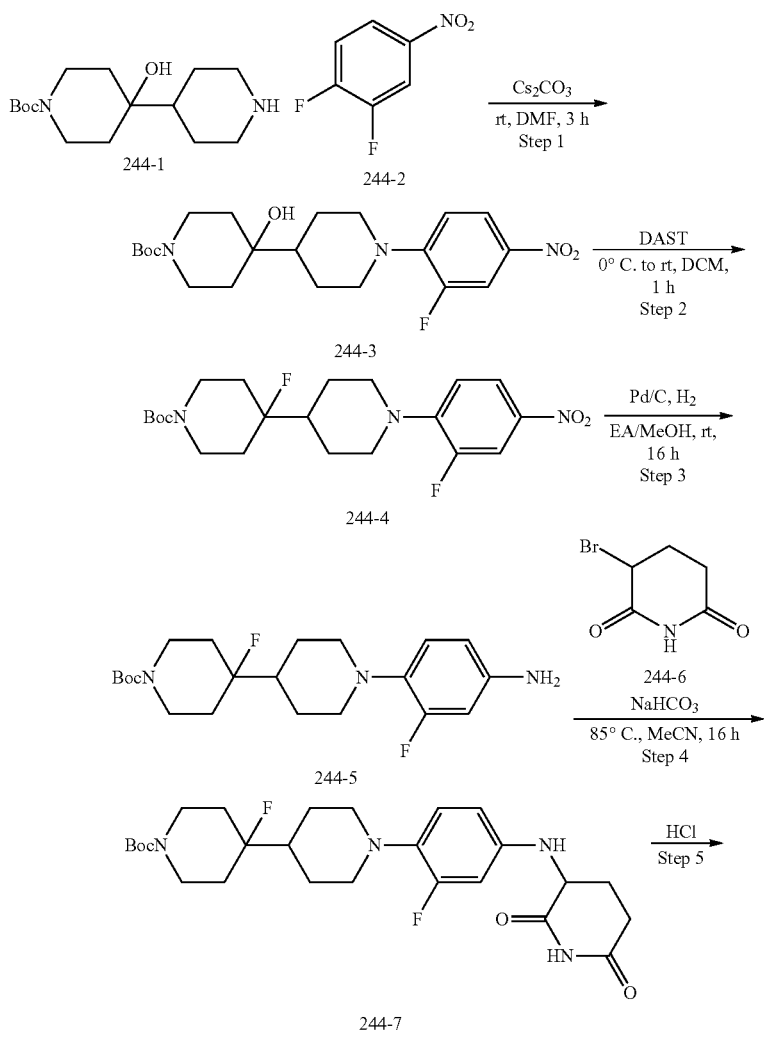

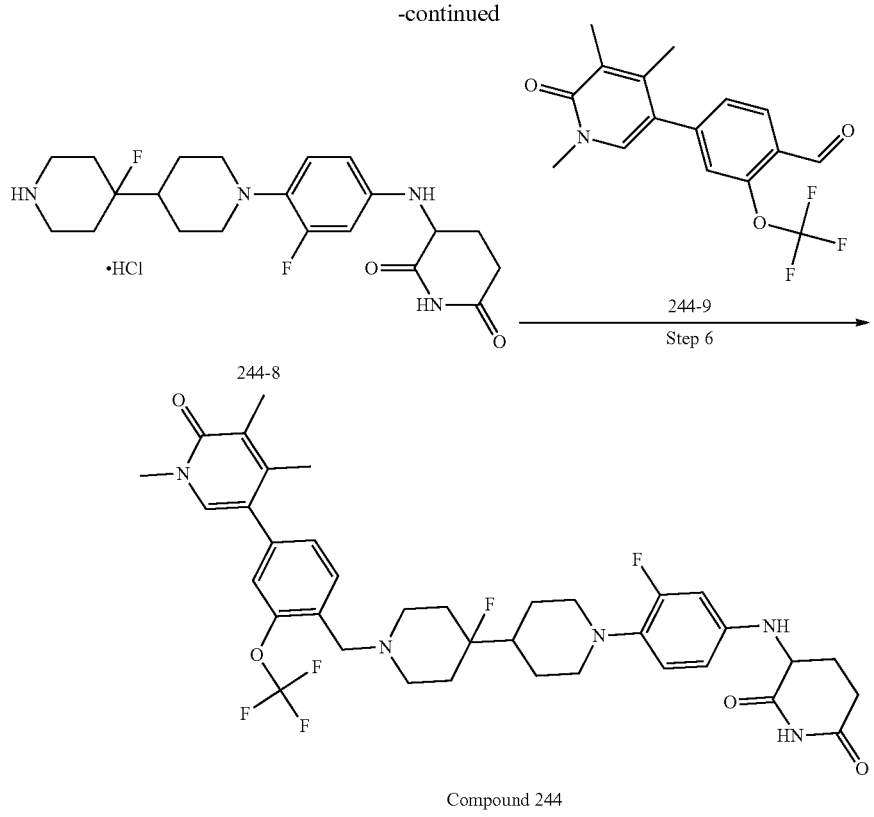

Compound 244

Step 1: Initially 1,2-difluoro-4-nitro-benzene (2.24 g, 14.07 mmol, 1.55 mL) was dissolved in DMF (68.77 mL) before cesium carbonate (4.58 g, 14.07 mmol) was added followed by tert-butyl 4-hydroxy-4-(4-piperidyl)piperidine-1-carboxylate (4 g, 14.07 mmol) at room temperature and the mixture was stirred for 3 h. Upon reaction completion $H_2O$ (100 mL) was added to the mixture to which a yellow precipitate formed. The flask was cooled with ice water for 20 minutes before the precipitate was filtered off and washed with copious water followed by hexanes. The yellow powder was dried and submitted to the following step without further purification. Yield-5.03 g, 84%; LCMS (ES$^+$): m/z 424.3 [M+H]$^+$ Step 2: Initially tert-butyl 4-[1-(2-fluoro-4-nitro-phenyl)-4-piperidyl]-4-hydroxy-piperidine-1-carboxylate (684 mg, 1.62 mmol) was dissolved in DCM (7.82 mL) and cooled to 0° C. before DAST (312.42 mg, 1.94 mmol, 256.09 µL) was added dropwise and stirring was continued for 15 minutes before the mixture was warmed to room temperature. After stirring for 1 hour the mixture was quenched with sodium bicarbonate sat. solution before being extracted with EA (20 mL×2). The combined organic layers were dried over sodium sulfate before being filtered and concentrated to a residue which was purified via flash column chromatography (Hexanes/EA up to 80%) to give the product as a solid. Yield—221 mg, 32%; LCMS (ES$^+$): m/z 426.4 [M+H]$^+$.

Step 3: Initially tert-butyl 4-fluoro-4-[1-(2-fluoro-4-nitro-phenyl)-4-piperidyl]piperidine-1-carboxylate (204 mg, 479.47 µmol) was dissolved in EA (1.82 mL) and methanol (1.82 mL) before the addition of Palladium, 10% on carbon, Type 487, dry (51.03 mg, 479.47 µmol). The atmosphere was purged with a $H_2$ balloon and the mixture was allowed to stir at room temperature for 16 hours. Upon reaction completion the mixture was filtered through a Celite pad and washed with EA/MeOH. The filtrate was concentrated to an off-white solid as the product which was used in the following step without further purification. Yield—154 mg, 81%; LCMS (ES$^+$): m/z 396.4. [M+H]$^+$ Step 4: Initially 3-bromopiperidine-2,6-dione (100.01 mg, 520.88 µmol) and tert-butyl 4-[1-(4-amino-2-fluoro-phenyl)-4-piperidyl]-4-fluoro-piperidine-1-carboxylate (103 mg, 260.44 µmol) were dissolved in MeCN (5.18 mL) before sodium hydrogen carbonate (65.64 mg, 781.32 µmol, 30.39 µL) was added in one portion and the mixture was heated to 85° C. with stirring for 16 hours. Upon reaction completion the mixture was concentrated to a residue and purified via flash column chromatography (DCM/MeOH up to 15%) to give the product as an off white solid. Yield—104 mg, 78%; LCMS (ES$^+$): m/z 507.4 [M+H]$^+$.

Step 5: Initially tert-butyl 4-[1-[4-[(2,6-dioxo-3-piperidyl)amino]-2-fluoro-phenyl]-4-piperidyl]-4-fluoro-piperidine-1-carboxylate (104 mg, 205.30 µmol) was suspended in HCl (4 M, 1.03 mL) at room temperature and stirred for 2 hours with monitoring via LCMS. Upon reaction completion the mixture was concentrated to a crude solid which was resuspended in Toluene, concentrated to dryness, then resuspended in hexanes and finally concentrated to a HCl salt which was used in the subsequent step without further purification. Yield—90 mg, 100%; LCMS (ES$^+$): m/z 407.3 [M+H]$^+$.

Step 6: To a mixture of 2-(trifluoromethoxy)-4-(1,4,5-trimethyl-6-oxo-1,6-dihydropyridin-3-yl)benzaldehyde (31.58 mg, 97.08 µmol) and 244-6 (43 mg, 97.08 µmol) dissolved in 1,2-DCE (0.1 M) was added triethylamine (19.65 mg, 194.16 µmol, 27.06 µL) followed by sodium triacetoxyborohydride (30.86 mg, 145.62 µmol) at room temperature before being stirred for 2-16 h at room temperature or 85° C. Following reaction completion the mixture was concentrated to a residue and purified via reverse phase flash column chromatography to (Water/MeCN 1:0 to 1:1, 0.1% TFA) and lyophilized to afford Compound 244 as a TFA salt (27 mg, 31.8% yield). 1H NMR (400 MHz, DMSO-$d_6$) δ 10.80 (s, 1H), 9.94 (s, 1H), 7.80 (d, J=8.0 Hz, 1H), 7.58 (s, 1H), 7.48 (dd, J=7.9, 1.7 Hz, 1H), 7.42 (q, J=1.8 Hz, 1H), 6.98 (d, J=10.8 Hz, 1H), 6.55 (dd, J=14.8, 2.5 Hz, 1H), 6.47 (dd, J=8.7, 2.5 Hz, 1H), 4.51 (s, 2H), 4.30 (dd, J=11.6, 4.8 Hz, 1H), 3.47 (s, 3H), 3.40 (d, J=11.2 Hz, 2H), 3.28 (d, J=13.9 Hz, 6H), 2.97-2.52 (m, 4H), 2.05 (d, J=6.3 Hz, 10H), 2.00-1.41 (m, 5H). LCMS (ES$^+$): m/z 716.6 [M+H]$^+$.

Compound 245 was prepared following the synthesis of Compound 244.

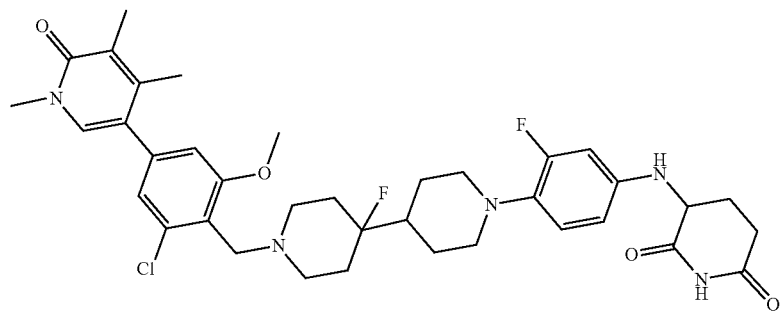 [SMILES: COc1cc(-c2cn(C)c(=O)c(C)c2C)cc(Cl)c1CN1CCC(F)(C2CCN(c3ccc(NC4CCC(=O)NC4=O)cc3F)CC2)CC1]

$^1$H NMR (400 MHz, DMSO-$d_6$) δ 10.79 (s, 1H), 9.38 (d, J=74.0 Hz, 1H), 7.58 (s, 1H), 7.16 (d, J=1.5 Hz, 1H), 7.09 (d, J=1.6 Hz, 1H), 6.98 (s, 1H), 6.55 (d, J=14.9 Hz, 1H), 6.49-6.32 (m, 1H), 4.47 (s, 2H), 4.29 (dd, J=11.6, 4.7 Hz, 1H), 3.93 (s, 3H), 3.47 (s, 5H), 3.31 (d, J=17.0 Hz, 5H), 2.95-2.52 (m, 3H), 2.07 (d, J=5.8 Hz, 10H), 1.92-1.19 (m, 7H). LCMS (ES$^+$): m/z 696.5 [M+H]$^+$.

Compound 246 was prepared following the synthesis of Compound 151.

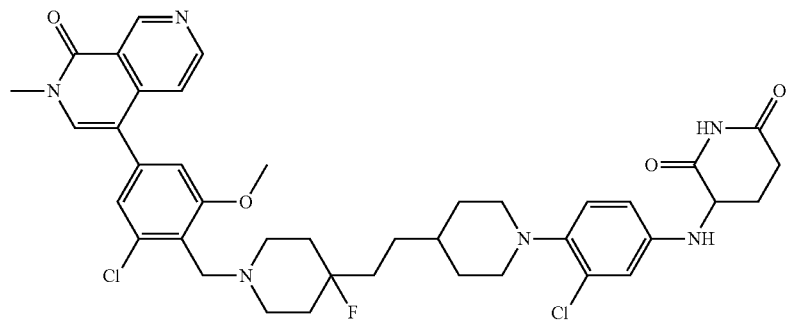 [SMILES: COc1cc(-c2cn(C)c(=O)c3cnccc23)cc(Cl)c1CN1CCC(F)(CCC2CCN(c3ccc(NC4CCC(=O)NC4=O)cc3Cl)CC2)CC1]

$^1$H NMR (400 MHz, DMSO-$d_6$) δ 10.76 (s, 1H), 9.44 (s, 1H), 8.73 (d, J=5.2 Hz, 1H), 7.92 (s, 1H), 7.52 (d, J=5.6 Hz, 1H), 7.11 (d, J=24 Hz, 2H), 6.92 (d, J=8.8 Hz, 1H), 6.74 (s, 1H), 6.58 (d, J=8.8 Hz, 1H), 5.82 (d, J=7.6 Hz, 1H), 4.30-4.20 (m, 1H), 3.86 (s, 3H), 3.61 (d, J=18.4 Hz, 5H), 3.04 (d, J=10 Hz, 2H), 2.69-2.58 (m, 4H), 2.37-2.32 (m, 4H), 2.08-2.04 (m, 1H), 1.87-1.62 (m, 10H), 1.42-1.26 (m, 4H). LCMS (ES$^+$): m/z 763.13 [M+H]$^+$.

Compound 247 was prepared following the synthesis of Compound 244.

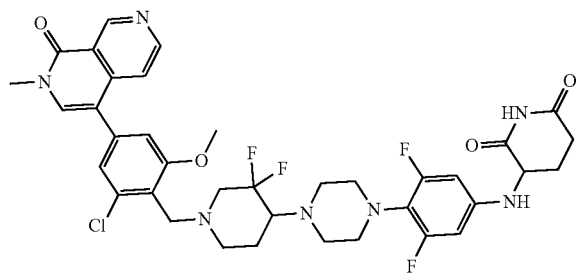 [SMILES: COc1cc(-c2cn(C)c(=O)c3cnccc23)cc(Cl)c1CN1CCC(N2CCN(c3c(F)cc(NC4CCC(=O)NC4=O)cc3F)CC2)C(F)(F)C1]
¹H NMR (400 MHz, DMSO-d₆) δ 1.70-1.90 (m, 3H); 2.00-2.10 (m, 1H); 2.24-2.34 (m, 1H); 2.38-2.44 (m, 1H); 2.55-2.60 (m, 1H); 2.66-3.04 (m, 12H); 3.59 (s, 3H); 3.69 (s, 2H); 3.87 (s, 3H); 4.26-4.36 (m, 1H); 6.25 (d, J=7.6 Hz, 1H); 6.32 (d, J=12 Hz, 1H); 7.11 (s, 1H); 7.17 (s, 1H); 7.54 (d, J=5.6 Hz, 1H); 7.94 (s, 1H); 8.74 (d, J=5.6 Hz, 1H); 9.45 (s, 1H); 10.80 (s, 1H). LCMS (ES⁺): m/z 756.12 [M+H]⁺.
Compound 248 was prepared following the synthesis of Compound 244.
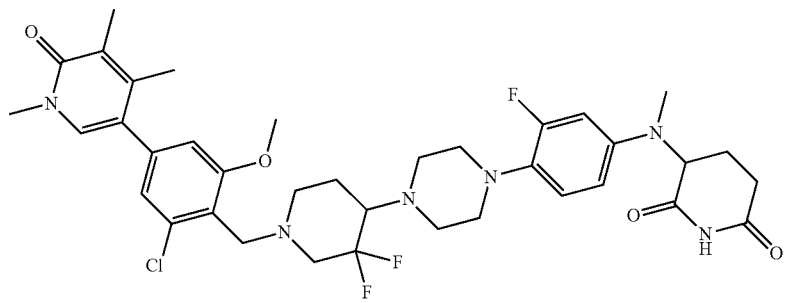 [SMILES: COc1cc(-c2cn(C)c(=O)c(C)c2C)cc(Cl)c1CN1CCC(N2CCN(c3ccc(N(C)C4CCC(=O)NC4=O)cc3F)CC2)C(F)(F)C1]
¹H NMR (400 MHz, DMSO-d₆) δ 10.79 (s, 1H), 7.57 (s, 1H), 7.03-6.90 (m, 3H), 6.70 (d, J=15.6 Hz, 1H), 6.55 (d, J=8.8 Hz, 1H), 4.83-4.78 (m, 1H), 3.86 (s, 5H), 3.45 (s, 3H), 3.27-3.05 (m, 11H), 2.86-2.77 (m, 1H), 2.69 (s, 3H), 2.56 (s, 3H), 2.32-2.28 (m, 1H), 2.08-2.05 (m, 7H), 1.86-1.83 (m, 2H). LCMS (ES⁺): m/z 729.38 [M+H]⁺.
Compound 249 and Compound 250 was prepared following the synthesis of Compound 105 followed by SFC separation.
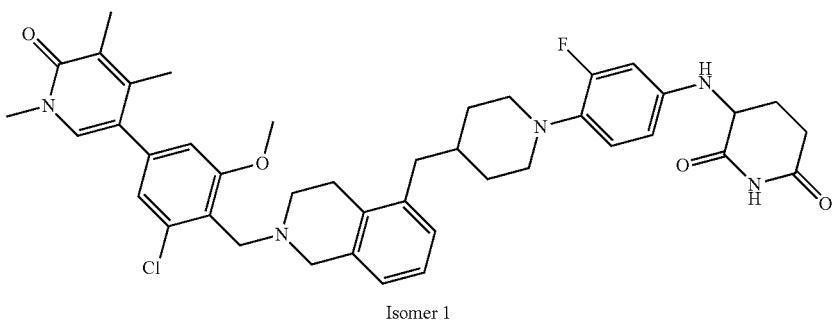
Isomer 1
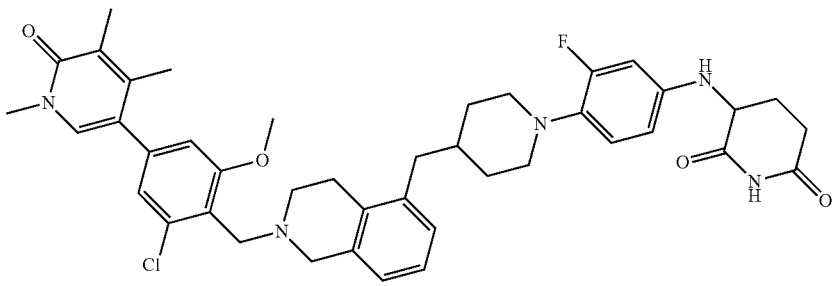
Isomer 2

Preparative SFC Conditions Column/dimensions:
Column/dimensions: Chiralpak-ASH (30*250) mm
5u % $CO_2$: 60% % Co solvent: 40% (0.2% 7M Methanolic ammonia in ACN:MeOH)
Total Flow: 100.0 g/min
Back Pressure: 100 bar Temperature: 30° C. UV: 220 nm
Solubility: Methanol Compound 249 isomer 1: $^1$H NMR (400 MHz, DMSO-$d_6$): δ 10.78 (s, 1H), 9.71 (s, 1H), 7.57 (s, 1H), 7.26-7.20 (m, 1H), 7.18-7.12 (m, 2H), 7.08-6.95 (m, 2H), 6.82 (bs, 1H), 6.53 (d, J=14.4 Hz, 1H), 6.41 (d, J=8 Hz, 1H), 4.53-4.47 (m, 4H), 4.26 (m, 1H), 3.91 (s, 3H), 3.72 (s, 2H), 3.47 (s, 3H), 3.16-3.08 (m, 6H), 2.71-2.58 (m, 4H), 2.08 (s, 3H), 2.06 (s, 3H), 1.86-1.60 (m, 4H), 1.50-1.41 (m, 2H). LCMS (ES$^+$): m/z 740.05 [M+H]$^+$.

Compound 250 isomer 2: $^1$H NMR (400 MHz, DMSO-$d_6$): δ 10.78 (s, 1H), 9.85 (s, 1H), 7.57 (s, 1H), 7.25-7.22 (m, 1H), 7.18-7.12 (m, 2H), 7.10-7.08 (m, 2H), 6.96 (bs, 1H), 6.52 (d, J=14.4 Hz, 1H), 6.43 (d, J=8 Hz, 1H), 4.53-4.51 (m, 4H), 4.27 (m, 1H), 3.91 (s, 3H), 3.60 (s, 2H), 3.47 (s, 3H), 3.29-3.06 (m, 6H), 2.76-2.58 (m, 4H), 2.08 (s, 3H), 2.06 (s, 3H), 1.90-1.81 (m, 4H), 1.70-1.67 (m, 1H). LCMS (ES$^+$): m/z 740.35 [M+H]$^+$.

Synthesis of Compound 251

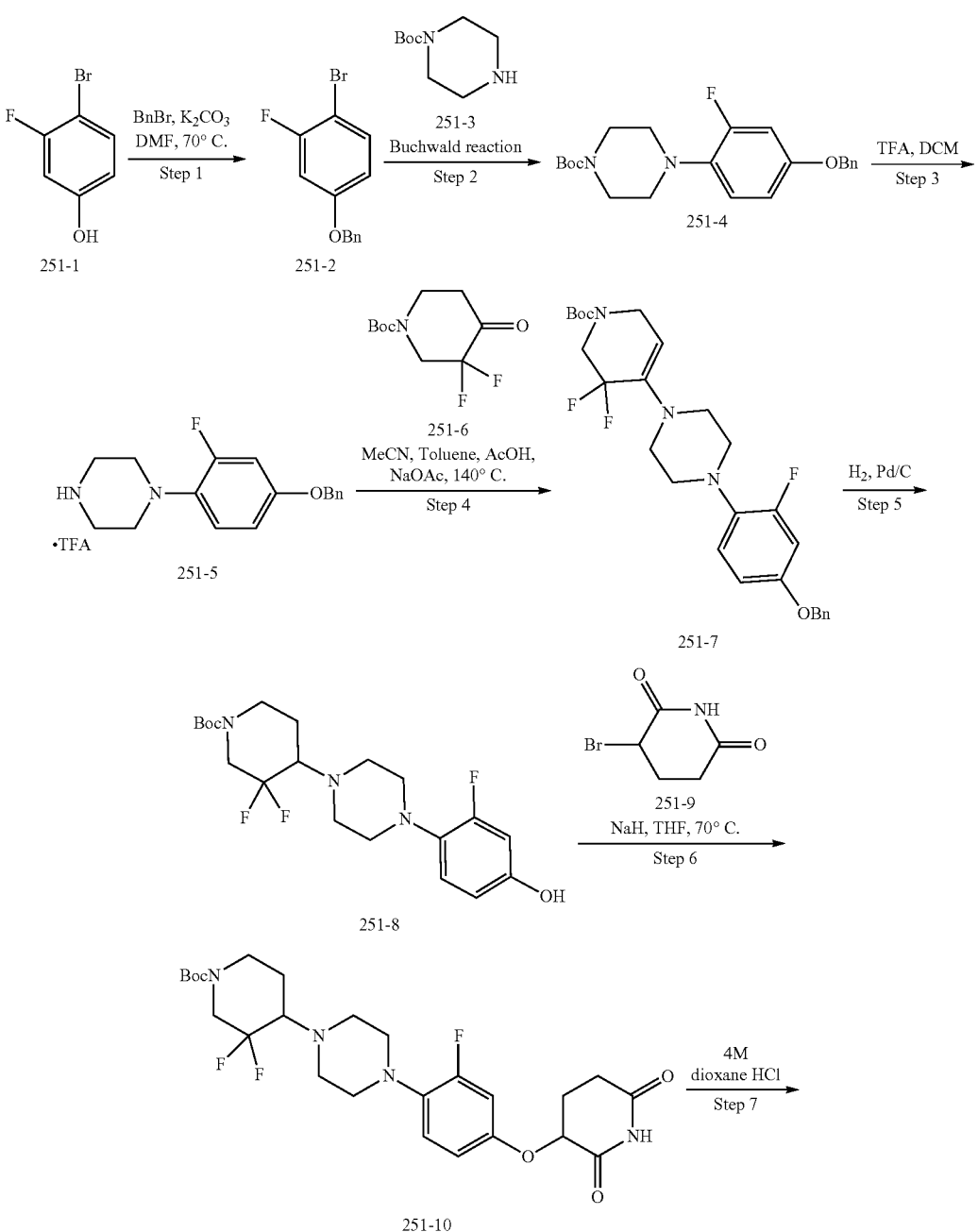

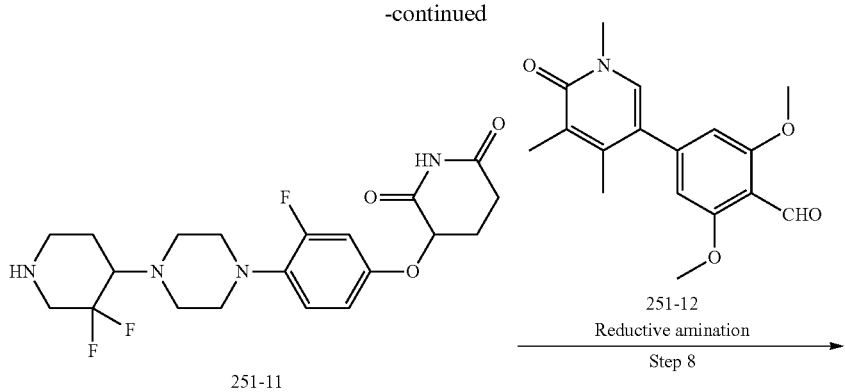

251-11

251-12

Reductive amination
Step 8

Compound 251

Step-1: To a stirred solution of compound 4-bromo-3-fluorophenol (10 g, 52.36 mmol) in DMF (80 mL) was added potassium carbonate-granular (14.47 g, 104.71 mmol, 6.32 mL) and benzyl bromide (9.85 g, 57.59 mmol) at room temperature, and the resultant mixture was stirred at room temperature for 20 minutes and then at 70° C. for 40 minutes. The reaction mixture was cooled to room temperature, then water was added to the reaction mixture, and the resultant solution was extracted with ethyl acetate. An organic layer was washed with water and then with saturated brine. An organic layer was dried over anhydrous sodium sulfate and concentrated in vacuo to furnish brown colored liquid product 4-benzyloxy-1-bromo-2-fluoro-benzene (14.5 g, 88% yield).

Step-2: In a microwave vial, the stirred solution of sodium tert-butoxide (0.855 g, 8.89 mmol) in mixture of solvent THF (10 mL) and toluene (10 mL) was purged with argon for 5 minutes. To this solution was added compound 4-(benzyloxy)-1-bromo-2-fluorobenzene (1 g, 3.56 mmol) and compound 3 (0.861 g, 4.62 mmol) and purged with argon for 10 minutes. To this reaction mixture added XPhos Pd G2 (0.280 g, 0.355 mmol) and irradiated with microwave at 100° C. for 30 minutes. The progress of reaction was monitored by LCMS and TLC. After completion of reaction, reaction mixture was concentrated in vacuo and crude compound was purified by column chromatography (Davisil silica, 0 to 8% ethyl acetate and pet ether as an eluent) to furnish the yellow colored pure solid product tert-butyl 4-(4-benzyloxy-2-fluoro-phenyl)piperazine-1-carboxylate (0.5 g, 1.18 mmol, 33% yield). Repeated five more same reactions in microwave for 1 g scale of 4-benzyloxy-1-bromo-2-fluoro-benzene to furnish 2.5 g of pure product.

Step-3: To a stirred solution of compound 4-benzyloxy-1-bromo-2-fluoro-benzene (2.8 g, 7.25 mmol) in a DCM (30 mL) was added TFA (9.91 g, 86.94 mmol, 6.70 mL) at 0° C. and stirred reaction mixture at RT for 2 hr. The progress of reaction was monitored by LCMS. After completion of reaction, reaction mixture was concentrated in vacuo and co-distilled with acetonitrile (5 mL×2), toluene (5 mL×2) to furnish the brown colored solid product 1-(4-benzyloxy-2-fluoro-phenyl)piperazine (2.4 g, 5.65 mmol, 78% yield)

Step-4: In a two neck 100 mL round bottom flask attached with Dean stark apparatus, to a stirred solution of compound 1-(4-benzyloxy-2-fluoro-phenyl)piperazine (2.5 g, 6.24 mmol) in mixture of solvent toluene (25 mL) and acetonitrile (13 mL) was added Sodium acetate, anhydrous (2.05 g, 24.98 mmol, 1.34 mL) and stirred at RT for 10 minutes. To this solution was added compound tert-butyl 3,3-difluoro-4-oxopiperidine-1-carboxylate (1.76 g, 7.49 mmol), Acetic acid (1.87 g, 31.22 mmol, 1.8 mL) and Molecular Sieves (500 mg) then heated at 120° C. for 8 hr. The progress of reaction was monitored by TLC and LCMS. After completion of reaction, the reaction was filtered through celite bed, washed with ethyl acetate (25 mL×2) and acetonitrile (25 mL×2). The organic layer then concentrated in vacuo and crude material was purified by column chromatography (Davisil silica, 0 to 30% ethyl acetate and pet ether as eluent) to yield the yellow colored solid product tert-butyl 4-[4-(4-benzyloxy-2-fluoro-phenyl)piperazin-1-yl]-3,3-difluoro-piperidine-1-carboxylate (2.5 g, 59% yield).

Step-5: The stirred solution of compound tert-butyl 4-[4-(4-benzyloxy-2-fluoro-phenyl)piperazin-1-yl]-3,3-difluoro-piperidine-1-carboxylate (2.5 g, 4.96 mmol) in Ethanol (8 mL) and THF (4 mL) was purged with nitrogen for 10 minutes. To this solution was added Palladium on carbon, 10 wt % loading (3 g, 4.96 mmol) and stirred reaction mixture under hydrogen atmosphere (Rubber bladder filled with hydrogen gas) at RT for 6 hr. The progress of reaction was monitored by TLC and LCMS. After completion of reaction, reaction mixture was filtered through celite bed and washed with THF (25 mL×2), ethyl acetate (25 mL×2) and organic layer was concentrated to furnish the brown colored crude product tert-butyl 3,3-difluoro-4-[4-(2-fluoro-4-hydroxy-phenyl)piperazin-1-yl]piperidine-1-carboxylate (1.77 g, 71% yield).

Step-6: To a stirred solution of compound tert-butyl 3,3-difluoro-4-[4-(2-fluoro-4-hydroxy-phenyl)piperazin-1-yl]piperidine-1-carboxylate in THF (80 mL) was added Sodium hydride (in oil dispersion) 60% dispersion in mineral oil (0.098 g, 4.26 mmol) and stirred at 70° C. for 30 minutes. To this solution was added drop wise compound 3-bromopiperidine-2,6-dione (0.818 g, 4.26 mmol) dissolved in THF (5 mL) at 70° C. and continued stirring at 70° C. for 3 hr. The progress of reaction was monitor by LCMS and TLC. After completion of reaction, the reaction mixture was quenched in ice water (100 mL) and extracted with ethyl acetate (3×70 mL) and combined organic layer was dried over sodium sulfate. The organic layer was concentrated in vacuo and the crude material purified by column chromatography (Davisili silica, 0 to 60% of EtOAc: pet ether) to furnish the off white solid product tert-butyl 4-[4-[4-[(2,6-dioxo-3-piperidyl)oxy]-2-fluoro-phenyl]piperazin-1-yl]-3,3-difluoro-piperidine-1-carboxylate (0.890 g, 39% yield).

Step-7: To a stirred solution of compound tert-butyl 4-[4-[4-[(2,6-dioxo-3-piperidyl)oxy]-2-fluoro-phenyl]piperazin-1-yl]-3,3-difluoro-piperidine-1-carboxylate (0.890 g, 1.69 mmol) in a DCM (20 mL) was added 4M dioxane HCl (1.23 g, 33.81 mmol, 1.54 mL) at 0° C. and stirred reaction mixture at RT for 2.5 hr. The progress of reaction was monitored by LCMS. After completion of reaction, reaction mixture was concentrated in vacuo and triturated with diethyl ether to furnish the brown colored solid product 3-(4-(4-(3,3-difluoropiperidin-4-yl)piperazin-1-yl)-3-fluorophenoxy)piperidine-2,6-dione (0.860 g, 95% yield).

Step-8: To a stirred solution of compound 3-(4-(4-(3,3-difluoropiperidin-4-yl)piperazin-1-yl)-3-fluorophenoxy)piperidine-2,6-dione (0.430 g, 0.929 mmol) and compound A (307.92 mg, 1.02 mmol) in a mixture of solvent Methanol (15 mL) and ethylene dichloride (15 mL) was added Sodium acetate, anhydrous (152.41 mg, 1.86 mmol) and stirred for 10 minutes at RT. To this solution was added Acetic acid (55.78 mg, 0.929 mmol, 53.13 uL) and Molecular Sieves (0.430 g) and stirred at 70° C. for 5 hr. Further, added Si-CBN (0.430 g) to the reaction mixture at RT and stirred reaction mixture at RT for 16 hr. The progress of reaction was monitored by LCMS. After completion of reaction, reaction mixture was filtered through celite bed and celite bed was washed with mixture of ethylene dichloride and methanol (25 mL×2). Filtrate was concentrated in vacuo and crude compound was purified by preparative HPLC to furnish off-white solid Compound 251, 3-[4-[4-[1-[[2,6-dimethoxy-4-(1,4,5-trimethyl-6-oxo-3-pyridyl)phenyl]methyl]-3,3-difluoro-4-piperidyl]piperazin-1-yl]-3-fluoro-phenoxy]piperidine-2,6-dione (331.87 mg, 43% yield).

Preparative HPLC Method:
Column/dimensions: SUNFIRE C18 (19*250 mm),
Mobile phase A: 0.1% TFA in water, Mobile phase B: MeCN (100%)
Gradient (Time/% B): 0/10, 3/10, 10/30, 14/30, 15/95, 20/95, 20.10/10, 22/10,
Flow rate: 18 ml/min.
Solubility: WATER+THF+CAN $^1$H NMR (400 MHz, DMSO-$d_6$) δ 10.92 (s, 1H), 7.52 (s, 1H), 6.99-6.89 (m, 2H), 6.79-6.76 (m, 1H), 6.76 (s, 2H), 5.15-5.11 (m, 1H), 4.69 (bs, 2H), 3.86 (s, 7H), 3.47 (s, 6H), 2.95-2.57 (m, 11H), 2.19-2.09 (m, 10H). LCMS (ES$^+$): m/z 712.49 [M+H]$^+$ Synthesis of Compound 252

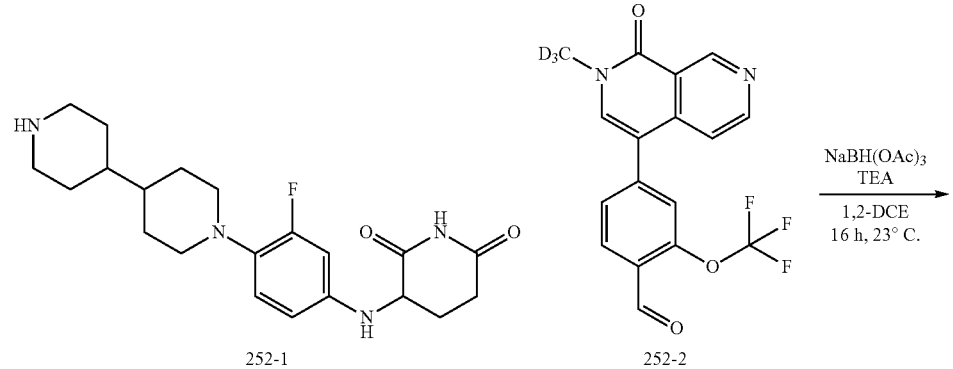

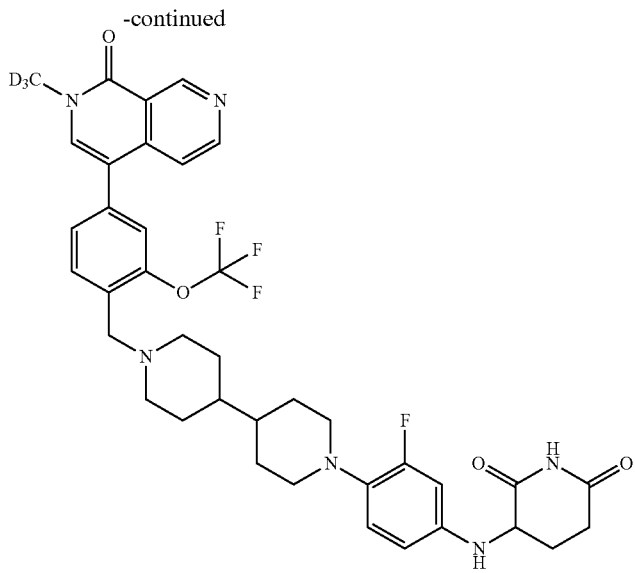

Compound 252

Initially 3-[3-fluoro-4-[4-(4-piperidyl)-1-piperidyl]anilino]piperidine-2,6-dione hydrochloride (96.77 mg, 227.73 μmol), 4-[1-oxo-2-(trideuteriomethyl)-2,7-naphthyridin-4-yl]-2-(trifluoromethoxy)benzaldehyde (80 mg, 227.73 μmol) and TEA (46.09 mg, 455.46 μmol, 63.48 μL) were charged into a reaction vial and dissolved in 1,2-DCE (2.99 mL) before Sodium triacetoxyborohydride, 95% (72.40 mg, 341.59 μmol) was added in one portion and the mixture was allowed to stir overnight. Upon reaction completion the mixture was concentrated to dryness before being purified via Isco RP FCC (0.1% TFA in water/MeCN) to afford the product Compound 252 3-[3-fluoro-4-[4-[1-[[4-[1-oxo-2-(trideuteriomethyl)-2,7-naphthyridin-4-yl]-2-(trifluoromethoxy)phenyl]methyl]-4-piperidyl]-1-piperidyl]anilino]piperidine-2,6-dione trifluoroacetate (32.3 mg, 36.63 μmol, yield 16%)

$^1$H NMR (400 MHz, DMSO-d$_6$) δ 10.83 (s, 1H), 10.04 (s, 1H), 9.49 (s, 1H), 8.76 (d, J=5.8 Hz, 1H), 7.99 (s, 1H), 7.90 (d, J=8.0 Hz, 1H), 7.65 (dd, J=8.0, 1.7 Hz, 1H), 7.60 (q, J=1.8 Hz, 1H), 7.51 (d, J=5.8 Hz, 1H), 7.23 (s, 1H), 6.63 (dd, J=15.0, 2.4 Hz, 1H), 6.54 (dd, J=8.9, 2.5 Hz, 1H), 4.46 (s, 2H), 4.36 (dd, J=11.8, 4.8 Hz, 1H), 3.57-3.36 (m, 4H), 3.10 (s, 4H), 2.73 (ddd, J=17.5, 12.3, 5.4 Hz, 1H), 2.64-2.54 (m, 1H), 2.19-2.00 (m, 1H), 2.00-1.74 (m, 6H), 1.52 (d, J=40.0 Hz, 5H). LCMS (ES$^+$): m/z 724.5 [M+H]$^+$.

Synthesis of Compound 253

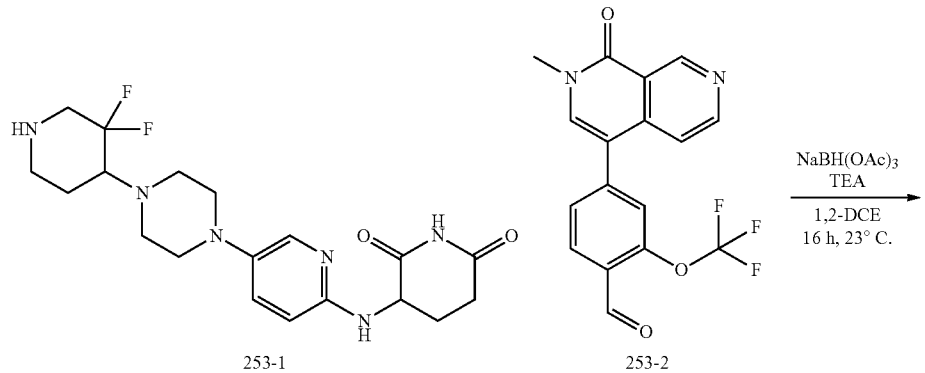

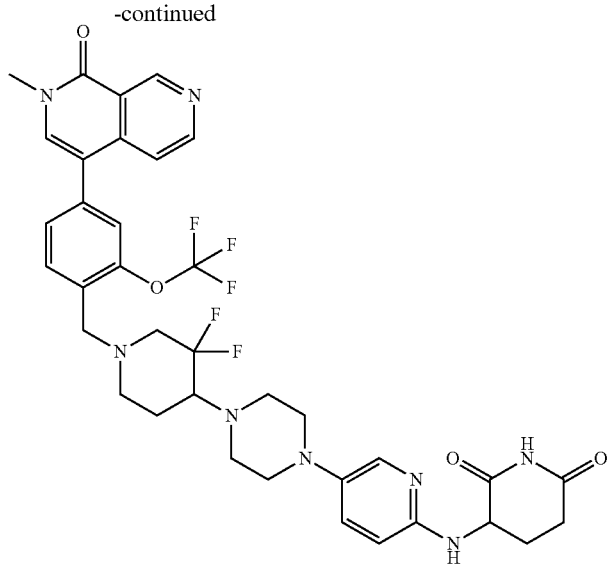

Compound 253

Initially 3-[[5-[4-(3,3-difluoro-4-piperidyl)piperazin-1-yl]-2-pyridyl]amino]piperidine-2,6-dione trifluoroacetate (130 mg, 248.82 μmol), 4-(2-methyl-1-oxo-2,7-naphthyridin-4-yl)-2-(trifluoromethoxy)benzaldehyde (86.66 mg, 248.82 μmol) and TEA (50.36 mg, 497.64 μmol, 69.36 μL) were charged into a reaction vial and dissolved in 1,2-DCE (2.99 mL) before Sodium triacetoxyborohydride, 95% (79.10 mg, 373.23 μmol) was added in one portion and the mixture was allowed to stir overnight. Upon reaction completion the mixture was concentrated to dryness and purified via Isco RP FCC (0.1% TFA in water/MeCN) to afford the product Compound 253 3-[[5-[4-[3,3-difluoro-1-[[4-(2-methyl-1-oxo-2,7-naphthyridin-4-yl)-2-(trifluoromethoxy)phenyl]methyl]-4-piperidyl]piperazin-1-yl]-2-pyridyl]amino]piperidine-2,6-dione trifluoroacetate (39 mg, 43.35 μmol Yield—18%). $^1$H NMR (400 MHz, DMSO-$d_6$) δ 11.08 (s, 1H), 9.50 (s, 1H), 8.75 (d, J=5.9 Hz, 1H), 8.46 (s, 1H), 7.98 (d, J=16.3 Hz, 2H), 7.73 (d, J=7.9 Hz, 1H), 7.56 (dd, J=7.9, 1.7 Hz, 1H), 7.53-7.44 (m, 2H), 7.38 (d, J=2.7 Hz, 1H), 7.12 (d, J=9.7 Hz, 1H), 4.69 (dd, J=11.9, 5.8 Hz, 1H), 3.82 (s, 2H), 3.61 (s, 3H), 3.38 (d, J=36.2 Hz, 2H), 3.14 (d, J=20.7 Hz, 7H), 3.02 (d, J=11.2 Hz, 1H), 2.81-2.52 (m, 3H), 2.37 (t, J=11.3 Hz, 1H), 2.22-1.97 (m, 3H), 1.90 (q, J=12.1, 10.9 Hz, 1H). LCMS (ES$^+$): m/z 741.5 (M+H)$^+$.

Synthesis of Compound 254

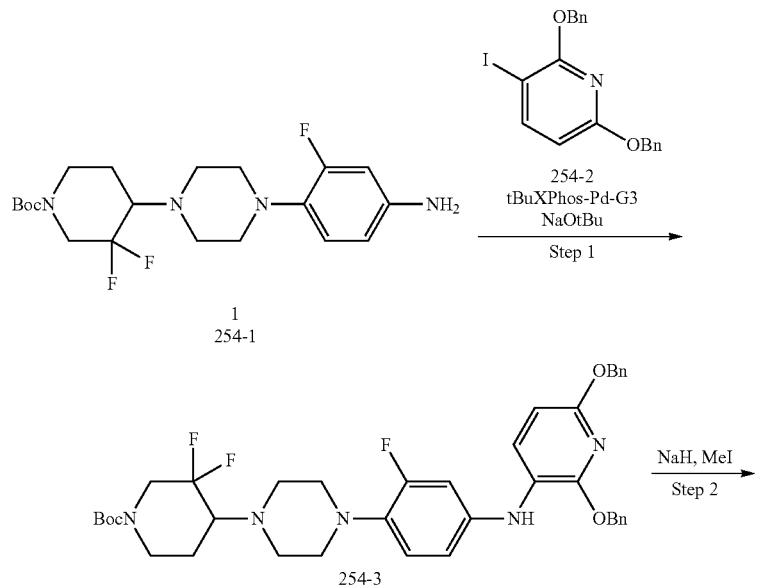

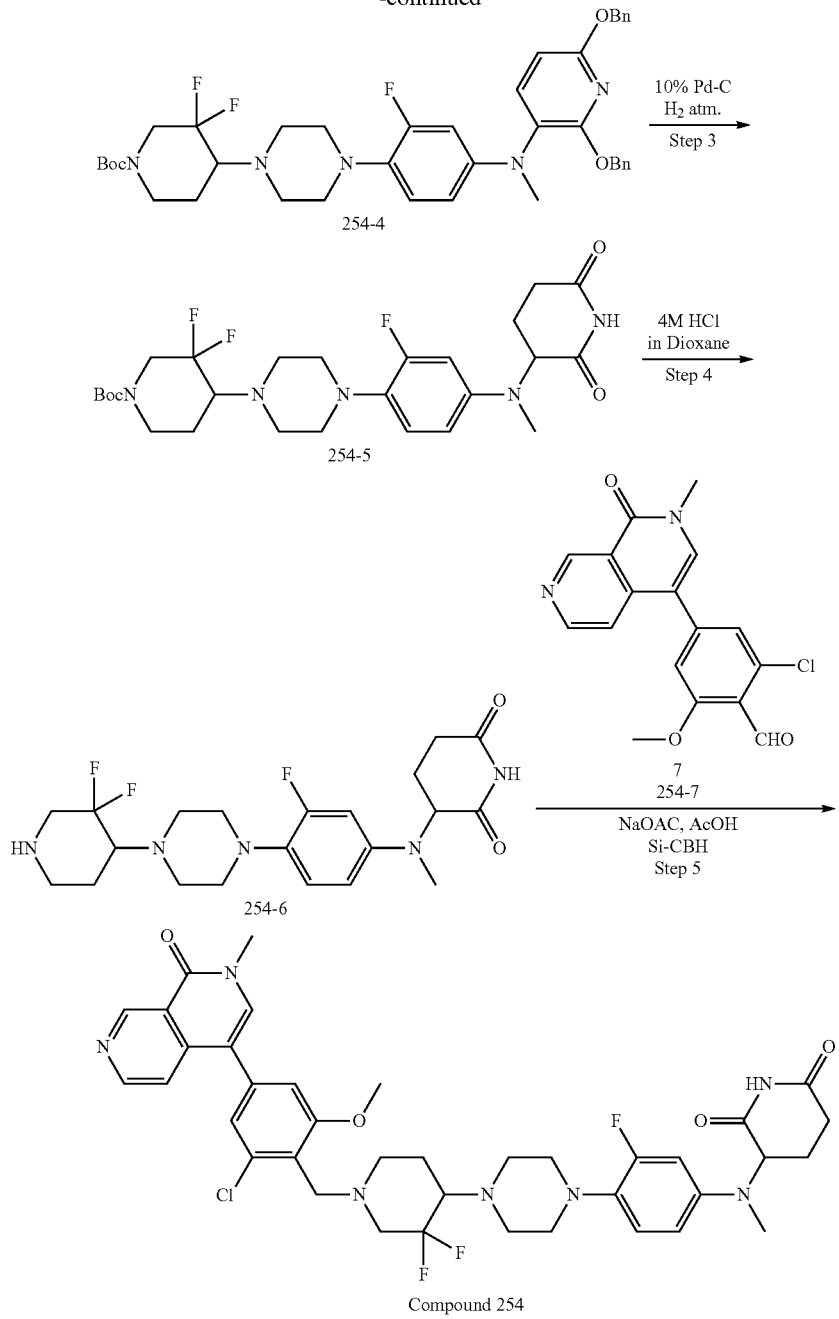

Compound 254

Step-1: To a stirred solution of tert-butyl 4-[4-(4-amino-2-fluoro-phenyl)piperazin-1-yl]-3,3-difluoro-piperidine-1-carboxylate (1 g, 2.41 mmol) in dioxane (20 mL) was added 2,6-dibenzyloxy-3-iodo-pyridine (1.21 g, 2.90 mmol) and Sodium tert-butoxide (347.81 mg, 3.62 mmol) at rt. The reaction mixture was purged with argon for 20 minutes and added t-Bu-XPhos-Pd-G3 (191.57 mg, 241.28 umol) and heated to 90° C. for 6 h. Reaction was monitored by TLC. The reaction mixture was cooled to ambient temperature and diluted with water (100 mL) and extracted with ethyl acetate (2×100 mL). The combined organic extracts were dried over anhydrous sodium sulfate, filtered and evaporated under reduce pressure. The resulting crude was purified by column chromatography on silica gel eluted with 0-15% gradient elution of ethyl acetate in hexanes to afford tert-butyl 4-[4-[4-[(2,6-dibenzyloxy-3-pyridyl)amino]-2-fluoro-phenyl]piperazin-1-yl]-3,3-difluoro-piperidine-1-carboxylate (1.2 g, 1.69 mmol, 70% yield) as pale brown gummy solid. LCMS (ES$^+$): m/z 704.09 [M+H]$^+$ Step-2: To a stirred solution of tert-butyl 4-(4-(4-((2,6-bis(benzyloxy)pyridin-3-yl)amino)-2-fluorophenyl)piperazin-1-yl)-3,3-difluoropiperidine-1-carboxylate (1.6 g, 2.27 mmol) in DMF (10 mL), Sodium hydride (in oil dispersion) 60% dispersion in mineral oil (120.21 mg, 5.23 mmol) was added, stirred at RT for 10 mins. Reaction mixture was cooled to 0° C. and Iodomethane (742.17 mg, 5.23 mmol) was added and stirred at RT for 1 h while monitoring by TLC. The reaction mixture was quenched with saturated NH₄Cl and extracted with ethyl acetate. The combined organic layer was dried over sodium sulphate, filtered and concentrated under reduced pressure. The crude obtained was purified by column chromatography (100-200 mesh silica, 0-15% EtOAc:Pet-ether solvent gradient) to obtain tert-butyl 4-(4-(4-((2,6-bis(benzyloxy)pyridin-3-yl)(methyl)amino)-2-fluorophenyl)piperazin-1-yl)-3,3-difluoropiperidine-1-carboxylate (1.5 g, 2.02 mmol, 89% yield) as pale brown gummy solid. LCMS (ES⁺): m/z 718.41 [M+H]⁺

Step-3: To the stirred solution of tert-butyl 4-(4-(4-((2,6-bis(benzyloxy)piperidin-3-yl)(methyl)amino)-2-fluorophenyl)piperazin-1-yl)-3,3-difluoropiperidine-1-carboxylate (1.2 g, 1.66 mmol) in Ethyl acetate (25 mL) and Ethanol (25 mL) was added 10% Palladium on carbon wet (1.23 g, 11.60 mmol) at RT. The reaction mixture was stirred at RT under H₂ balloon pressure for 12 h. After the completion of the reaction, the reaction mixture was filtered-off through celite and washed with ethyl acetate (50 mL). The filtrate was concentrated to get the crude product. The crude product was triturated with pentane/diethyl ether to afford tert-butyl 4-(4-(4-((2,6-dioxopiperidin-3-yl)(methyl)amino)-2-fluorophenyl)piperazin-1-yl)-3,3-difluoropiperidine-1-carboxylate (0.58 g, 999.65 µmol, 60% yield,) as pale green solid. LCMS (ES⁺): m/z 540.75[M+H]⁺

Step-4: To the stirred solution of tert-butyl 4-[4-[4-[(2,6-dioxo-3-piperidyl)-methyl-amino]-2-fluoro-phenyl]piperazin-1-yl]-3,3-difluoro-piperidine-1-carboxylate (0.58 g, 1.07 mmol) in 1,4-Dioxane (5 mL) was added 4M HCl in dioxane (1.96 g, 53.74 mmol) at 0° C. The reaction mixture was stirred at 0° C. for 30 minutes, slowly warmed to room temperature and stirred at room temperature for 3 h. After the completion of the reaction, the reaction mixture was concentrated and crude was triturated with diethyl ether (3×30 mL) to afford solid precipitate. The solid precipitate was filtered and dried under vacuum to obtain 3-[4-[4-(3,3-difluoro-4-piperidyl)piperazin-1-yl]-3-fluoro-N-methyl-anilino]piperidine-2,6-dione (0.50 g, 966.52 µmol, 90% yield, 92% purity) as white solid. LCMS (ES⁺): m/z 440.35[M+H]⁺

Step-5: To the stirred solution of 3-[4-[4-(3,3-difluoro-4-piperidyl)piperazin-1-yl]-3-fluoro-N-methyl-anilino]piperidine-2,6-dione (250.45 mg, 526.24 µmol) in Methanol (20 mL) and 1,2-Dichloroethane (20 mL) was added Molecular sieves (250 mg, 2.63 mmol), sodium acetate (86.34 mg, 1.05 mmol, 56.43 µL) at RT under N₂ atm. followed by the addition of acetic acid (158.01 mg, 2.63 mmol, 150.48 µL). The reaction mixture was stirred at room temperature for 10 minutes and 2-chloro-6-methoxy-4-(2-methyl-1-oxo-2,7-naphthyridin-4-yl)benzaldehyde (110.34 mg, 335.65 umol) was added to it. The reaction mixture was stirred at 90° C. for 6 h. The reaction mixture was cooled to room temperature and Si-CBH (184.97 mg, 4.21 mmol) was added to it. The reaction mixture was stirred for 12 h at room temperature. After the completion of reaction, the reaction mixture was filtered-off through celite, washed with DCM (50 mL). The filtrate was concentrated under reduced pressure to obtain the crude product. The crude product was purified by Prep HPLC to afford Compound 254 3-[4-[4-[1-[[2-chloro-6-methoxy-4-(2-methyl-1-oxo-2,7-naphthyridin-4-yl)phenyl]methyl]-3,3-difluoro-4-piperidyl]piperazin-1-yl]-3-fluoro-N-methyl-anilino]piperidine-2,6-dione (76.6 mg, 96.27 µmol, 29% yield) as off white solid.

¹H NMR (400 MHz, DMSO-d₆) δ 10.76 (s, 1H), 9.44 (s, 1H), 8.74 (d, J=5.6 Hz, 1H), 7.94 (s, 1H), 7.54 (d, J=5.6 Hz, 1H), 7.14 (d, J=23.3 Hz, 2H), 6.88-6.85 (t, J=9.2 Hz, 1H), 6.68-6.51 (m, 2H), 4.81-4.62 (m, 1H), 3.87 (s, 3H), 3.72 (s, 2H), 3.59 (s, 3H), 3.01-2.79 (m, 11H), 2.67 (s, 3H), 2.55-2.50 (m, 2H), 2.49-2.42 (m, 1H), 2.39-2.31 (m, 2H), 1.86-1.75 (m, 3H). LCMS (ES⁺): m/z 752.43 [M+H]⁺

Compound 255 was prepared following the synthesis of Compound 244.

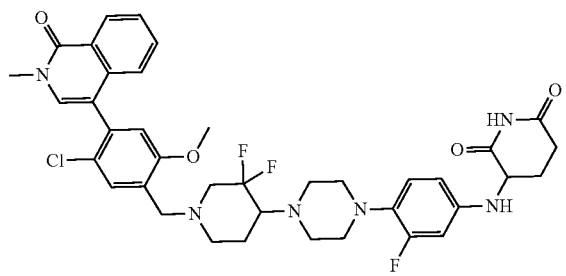 [SMILES: COc1cc(-c2cn(C)c(=O)c3ccccc23)c(Cl)cc1CN1CCC(N2CCN(c3ccc(NC4CCC(=O)NC4=O)cc3F)CC2)C(F)(F)C1]

¹H NMR (400 MHz, DMSO-d₆) δ 10.78 (s, 1H), 9.47 (s, 1H), 8.71 (d, J=5.6 Hz, 1H), 7.90 (s, 1H), 7.60 (s, 1H), 7.19 (s, 1H), 7.10-7.07 (m, 1H), 6.89 (t, J=9.2 Hz, 1H), 6.53 (d, J=15.2 Hz, 1H), 6.45 (d, J=8.8 Hz, 1H), 4.29-4.25 (m, 1H), 3.83 (s, 5H), 3.60 (s, 3H), 3.42-3.05 (m, 11H), 2.77-2.55 (m, 4H), 2.18-1.94 (m, 4H). LCMS (ES⁺): m/z 738.35 [M+H]⁺.

Synthesis of Peak-1-Int-256-7 and Peak-2-Int-256-7-D1-D4

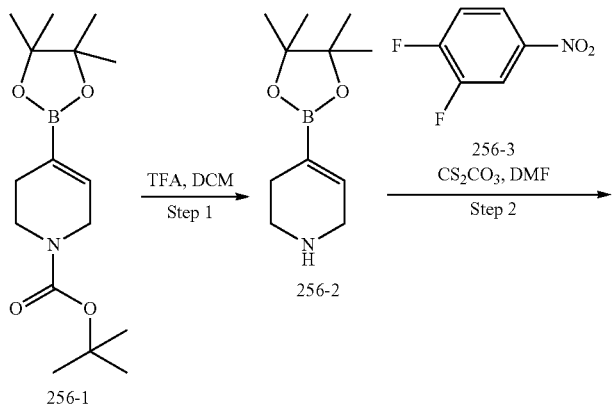

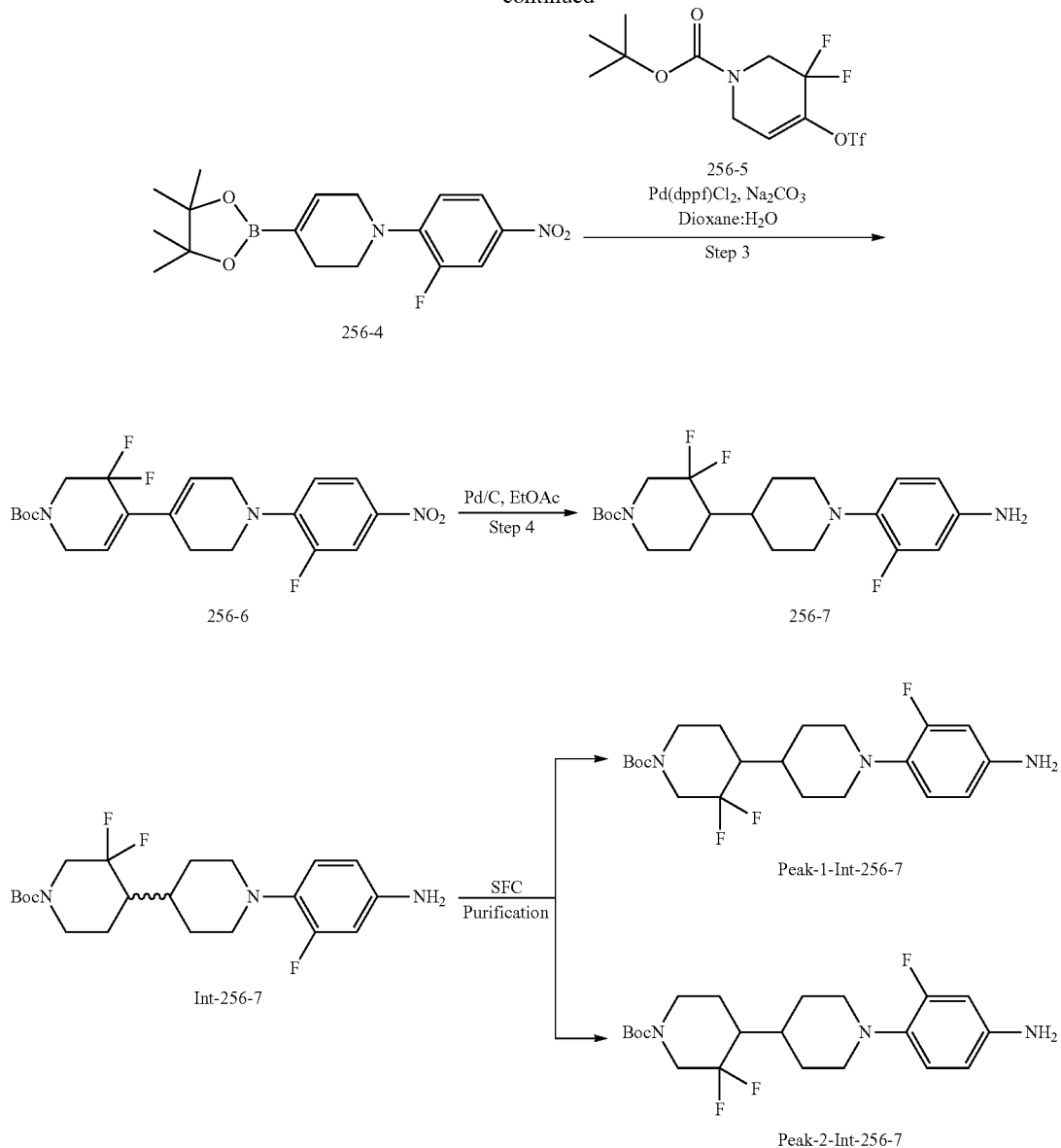
Synthesis of Compound 256 and Compound 267
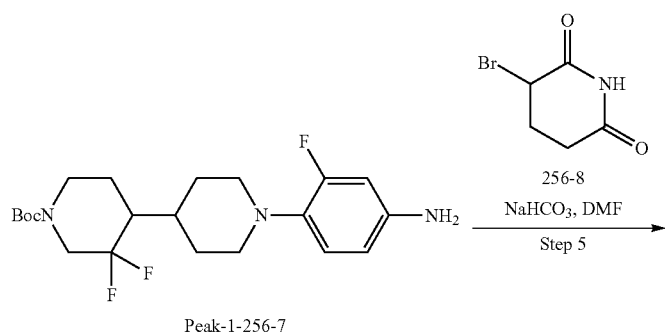

-continued
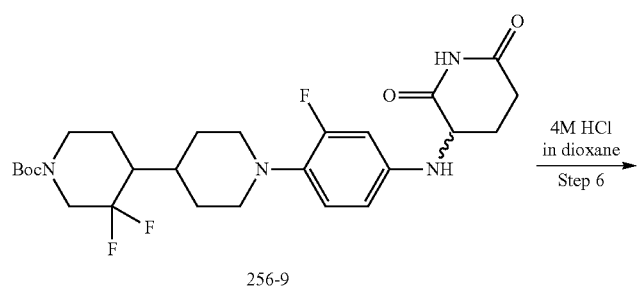
256-9
4M HCl
in dioxane
Step 6
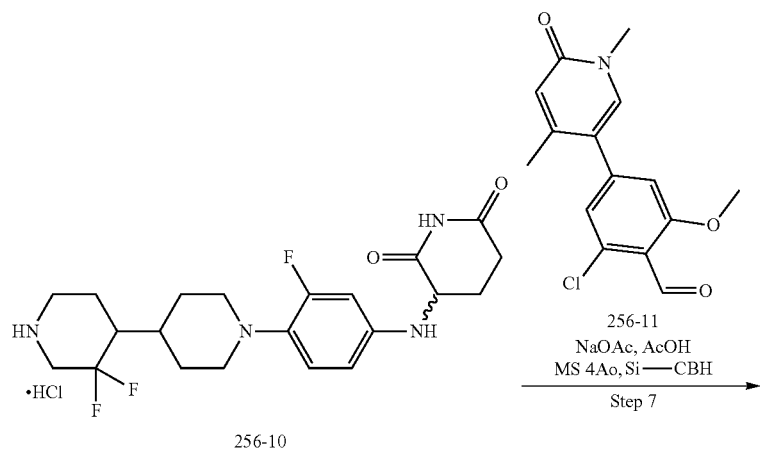
256-10
256-11
NaOAc, AcOH
MS 4Ao, Si—CBH
Step 7
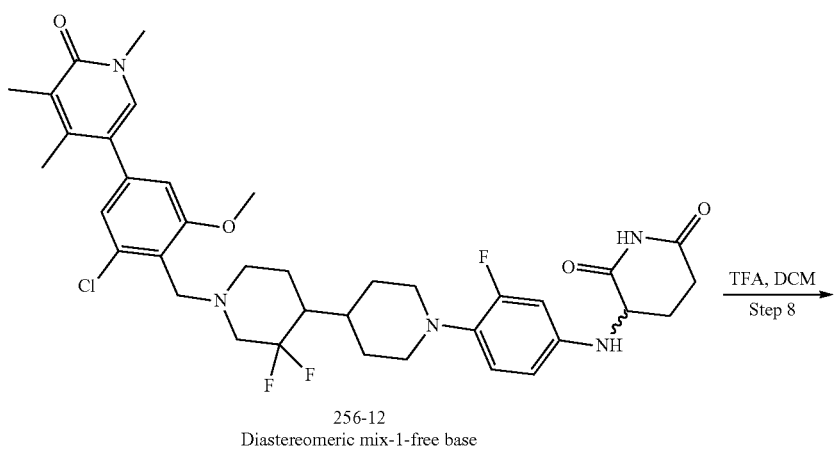
256-12
Diastereomeric mix-1-free base
TFA, DCM
Step 8

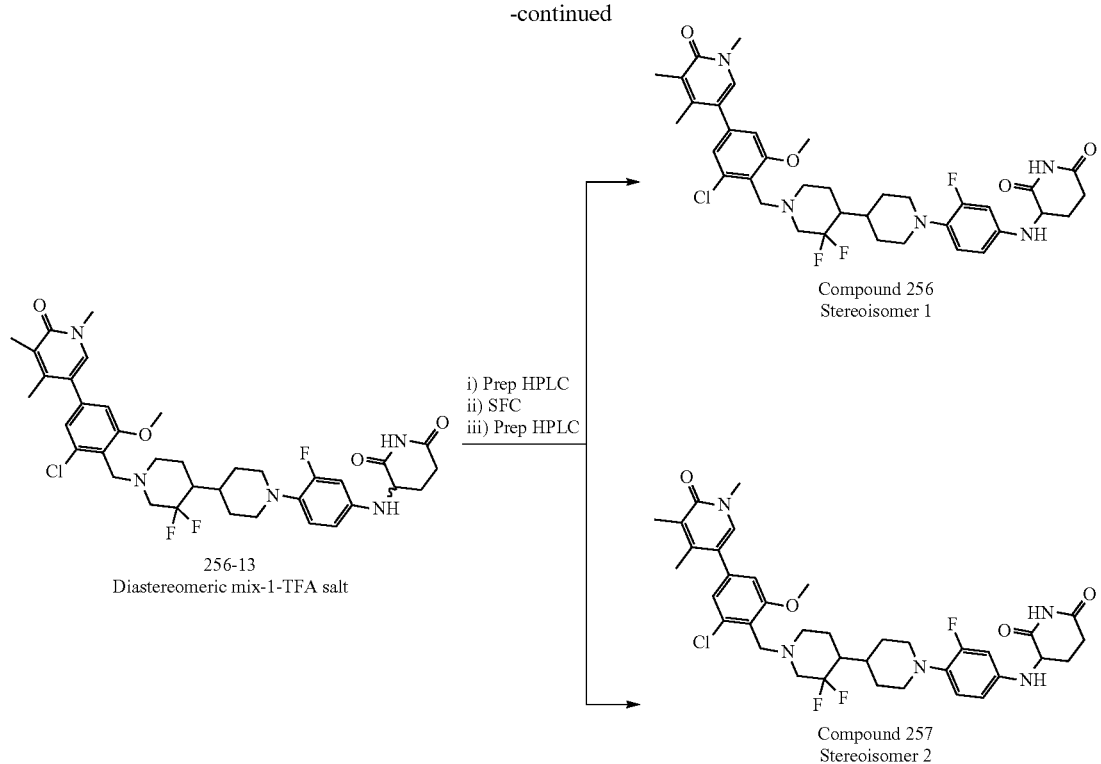

256-13
Diastereomeric mix-1-TFA salt i) Prep HPLC
ii) SFC
iii) Prep HPLC

Compound 256
Stereoisomer 1

Compound 257
Stereoisomer 2

Step-1: To a stirred solution of tert-butyl 4-(4,4,5,5-tetramethyl-1,3,2-dioxaborolan-2-yl)-3,6-dihydro-2H-pyridine-1-carboxylate (5 g, 16.17 mmol) in DCM (10 mL) was added TFA (20 mL) at 0° C. and then reaction mixture was allowed to stir at room temperature for 2 hours while monitoring by TLC. After completion of reaction, the reaction mixture was evaporated to dryness under reduced pressure and crude mixture was co-distilled with toluene (50 mL) to afford 4-(4,4,5,5-tetramethyl-1,3,2-dioxaborolan-2-yl)-1,2,3,6-tetrahydropyridine (5 g) as a colorless liquid. $^1$H NMR (400 MHz, DMSO-d6) δ=8.80 (s, 2H), 6.36 (t, J=1.6 Hz, 1H), 3.63 (s, 2H), 3.15-3.10 (m, 2H), 2.28-2.25 (m, 2H), 1.21 (s, 12H)

Step-2: To a stirred solution of Compound-2 (2 g, 6.19 mmol) in DMF (15 mL) was added CsCO$_3$ (6.05 g, 18.57 mmol) under nitrogen atmosphere. Compound-3 (1.18 g, 7.43 mmol, 820.61 µL) was added through syringe in the reaction mixture. The reaction mixture was stirred for 6 hours at room temperature. After completion of the reaction by TLC, reaction mixture was quenched with ice cold water and the resulting precipitate was filtered and dried completely to afford 1-(2-fluoro-4-nitro-phenyl)-4-(4,4,5,5-tetramethyl-1,3,2-dioxaborolan-2-yl)-3,6-dihydro-2H-pyridine (2 g, 5.17 mmol, 84% yield, 90% purity) as a yellow color solid. $^1$H NMR (400 MHz, CDCl$_3$) δ=7.98-7.94 (d, 1H), 7.91-7.87 (d, 1H), 6.89-6.84 (t, J-8.8 Hz, 1H), 6.56 (m, 1H), 3.92-3.90 (m, 2H), 3.48-3.45 (t, J-5.6 Hz, 2H), 2.44-2.41 (m, 2H), 1.28 (s, 12H).

Step-3: To a stirred solution of compound-5 (1 g, 2.72 mmol) and compound-4 (947.96 mg, 2.72 mmol) in 1,4-dioxane (15 mL) was purged argon for 20 mins. Then, Sodium carbonate (721.43 mg, 6.81 mmol) in water (5 mL) was added to the above mixture and again continue purging for another 10 mins. Finally, Pd(dppf)Cl$_2$ (0.1 g, 136.13 µmol) was added and degassed. Heated the mixture to 55° C. and maintained for 2 hr. The reaction was monitored by TLC. After completion, reaction mixture was cooled to room temperature and diluted with ethyl acetate (50 mL) and washed the organic layer with water and brine solution. It was concentrated under reduced pressure to obtain crude. The crude product was purified by biotage using 0-20% to afford tert-butyl 3,3-difluoro-4-[1-(2-fluoro-4-nitro-phenyl)-3,6-dihydro-2H-pyridin-4-yl]-2,6-dihydropyridine-1-carboxylate (0.74 g, 53% yield, 85% purity) as Yellow solid. $^1$H NMR (400 MHz, CDCl$_3$) δ=8.02-8.00 (m, 1H), 7.99-7.91 (m, 1H), 6.93-6.89 (t, J-8.8 Hz, 1H), 6.17 (m, 1H), 4.13 (m, 2H), 3.97 (m, 2H), 3.89-3.83 (t, J-11.6 Hz, 2H), 3.60-3.57 (t, J-5.6 Hz, 2H), 2.47 (m, 2H), 1.49 (s, 9H).

Step-4: To a stirred solution of tert-butyl 3,3-difluoro-4-[1-(2-fluoro-4-nitro-phenyl)-3,6-dihydro-2H-pyridin-4-yl]-2,6-dihydropyridine-1-carboxylate (4.5 g, 10.24 mmol) in Ethyl acetate (50 mL) and Methanol (25.00 mL) mixture was added Palladium, 10% on carbon (2.18 g, 20.48 mmol) under nitrogen atmosphere. Then, Hydrogen gas (Balloon pressure) was kept for 16 hr at 28° C. while monitoring by TLC. After completion of reaction, it was filtered through celite pad and washed with ethyl acetate. The filtrate was concentrated to dryness under reduced pressure. The crude mixture was purified by silica gel column chromatography (100-200) using 0-35% EA in PE to afford tert-butyl 4-[1-(4-amino-2-fluoro-phenyl)-4-piperidyl]-3,3-difluoro-piperidine-1-carboxylate (3.1 g, 6.60 mmol, 64% yield, 88% purity) as pale brown solid. LCMS [M+H$^+$] 414.76.

SFC separation for Int-256-7 to afford Peak-1-Int-256-7 & Peak-2-Int-256-7:

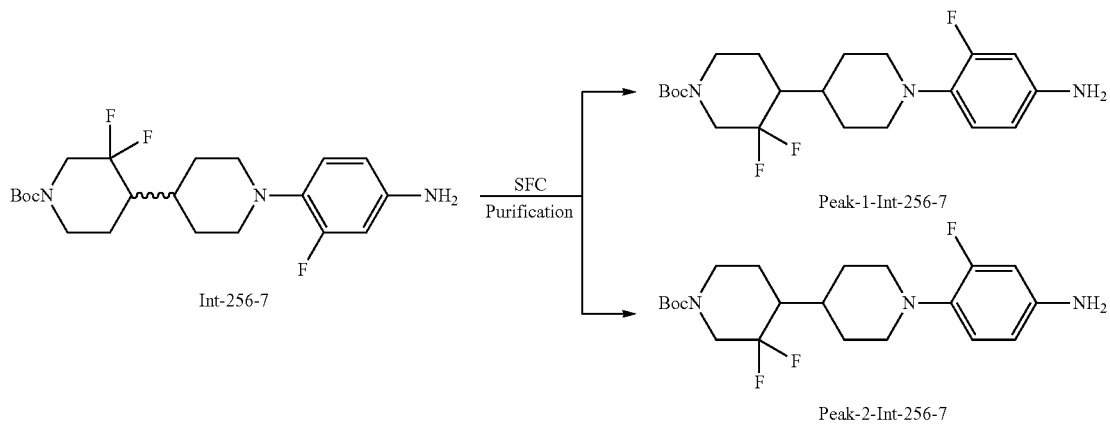

Int-256-7

Peak-1-Int-256-7

Peak-2-Int-256-7

0.1 g of tert-butyl 4-[1-(4-amino-2-fluoro-phenyl)-4-piperidyl]-3,3-difluoro-piperidine-1-carboxylate Int-256-7 was separated by SFC to obtain tert-butyl (4S)-4-[1-(4-amino-2-fluoro-phenyl)-4-piperidyl]-3,3-difluoro-piperidine-1-carboxylate Peak-1-Int-256-7 (0.042 g, 101.37 μmol, 41.92% yield, 99.8% purity, 000) and tert-butyl (4R)-4-[1-(4-amino-2-fluoro-phenyl)-4-piperidyl]-3,3-difluoro-piperidine-1-carboxylate Peak-2-Int-256-7 (0.043 g, 103.68 μmol, 42.87% yield, 99.7% purity) as pale brown solid.

| Preparative SFC Conditions: | |
|---|---|
| Column/dimensions: | Chromega Chiral CCO (30 × 250) mm, 5μ |
| % CO₂: | 60% |
| % Co solvent: | 40% (ACN:IPA(1:1)) |
| Total Flow: | 100.0 g/min |
| Back Pressure: | 100 bar |
| Temperature: | 300° C. |
| UV: | 254 nm |

Step-5: Tert-butyl 4-[1-(4-amino-2-fluoro-phenyl)-4-piperidyl]-3,3-difluoro-piperidine-1-carboxylate Peak-1-Int-7 (0.8 g, 1.93 mmol) was taken in DMF (10 mL) and added sodium bicarbonate (975.22 mg, 11.61 mmol). Reaction mixture was purged nitrogen for 10 mins. Then, added 3-bromopiperidine-2,6-dione (1.11 g, 5.80 mmol) and heated the mixture to 80° C. and maintained for 16 h while monitoring by TLC and LCMS analysis. After completion of reaction, it was quenched with ice-cold water and filtered through celite pad and washed with ethyl acetate. The organic layer was separated and washed with brine solution, dried over Na₂SO₄. It was concentrated under reduced pressure to obtain crude product.

The crude product was purified by biotage using 0-40% EA in PE afforded tert-butyl 4-[1-[4-[(2,6-dioxo-3-piperidyl)amino]-2-fluoro-phenyl]-4-piperidyl]-3,3-difluoro-piperidine-1-carboxylate (0.65 g, 1.21 mmol, 62% yield) as pale green solid, LCMS (ES⁺): m/z 525.84 [M+H]⁺

Step-6: Tert-butyl 4-[1-[4-[(2,6-dioxo-3-piperidyl)amino]-2-fluoro-phenyl]-4-piperidyl]-3,3-difluoro-piperidine-1-carboxylate (0.65 g, 1.24 mmol) was taken in 1,4-dioxane (2 mL) under nitrogen atmosphere at 0° C. was added 4M HCl in dioxane (903.57 mg, 24.78 mmol, 1.13 mL). The reaction mixture was stirred for 3 h at RT while monitoring by TLC. After completion of reaction, it was concentrated to dryness under reduced pressure. The resulting solid was washed with diethyl ether and dried over vacuum to afford 3-[4-[4-(3,3-difluoro-4-piperidyl)-1-piperidyl]-3-fluoro-anilino]piperidine-2,6-dione (0.55 g, 72% yield) as pale green solid. LCMS (ES⁺): m/z 425.22 [M+H]⁺.

Step-7: To a stirred solution of 3-[4-[4-(3,3-difluoro-4-piperidyl)-1-piperidyl]-3-fluoro-anilino]piperidine-2,6-dione (542.69 mg, 1.18 mmol, 021) in DCE (5 mL) and Methanol (5 mL), sodium acetate, anhydrous (241.47 mg, 2.94 mmol, 157.82 μL) was added. To the reaction mixture acetic acid (68.35 uL, 2.94 mmol, 1) and molecular sieves (0.3 g, 981.18 μmol) were added and allowed to stir for 10 mins. Then, 2-chloro-6-methoxy-4-(1, 4, 5-trimethyl-6-oxo-3-pyridyl) benzaldehyde (0.3 g, 981.18 μmol, 000) was added and heated the mixture to 75° C. for 5 hrs. Then, the reaction mixture was cooled to room temperature and added Si-CBH (586.35 mg, 9.81 mmol). It was stirred at room temperature for 16 hours. The reaction was monitored by TLC and LCMS analysis. After completion of reaction, it was filtered through celite pad and washed with methanol then concentrated to dryness.

The crude mixture was purified by column chromatography using 0-10% MeOH in DCM to afford 3-[4-[4-[1-[[2-chloro-6-methoxy-4-(1,4,5-trimethyl-6-oxo-3-pyridyl)phenyl]methyl]-3,3-difluoro-4-piperidyl]-1-piperidyl]-3-fluoro-anilino]piperidine-2,6-dione Compound 256-12-Diastereomeric mix-1-free base (0.35 g, 33.46% yield, 67% purity) as pale green solid.

Step-8: To a stirred solution of 3-[4-[4-[1-[[2-chloro-6-methoxy-4-(1,4,5-trimethyl-6-oxo-3-pyridyl)phenyl]methyl]-3,3-difluoro-4-piperidyl]-1-piperidyl]-3-fluoro-anilino]piperidine-2,6-dione (0.35 g, 490.05 μmol, 000) in DCM (2 mL) was added TFA (2.79 g, 24.50 mmol, 1.89 mL) at 0° C. The reaction mixture was stirred for 2 h at room temperature. Then, it was concentrated under reduced pressure and the resulting residue was washed with diethyl ether (2 times) to afford N-[4-[4-[1-[[2-chloro-6-methoxy-4-(1,4,5-trimethyl-6-oxo-3-pyridyl)phenyl]methyl]-3,3-difluoro-4-piperidyl]-1-piperidyl]-3-fluoro-phenyl]-N-(2,6-dioxo-3-piperidyl)-2,2,2-trifluoro-acetamide Compound 256-13-Diastereomeric mix-1-TFA salt (0.36 g, 268.76 μmol, 54.84% yield, 69% purity) as pale green solid.

SFC separation for Compound 256-13-Diastereomeric mix-1-TFA salt to afford Compound 256 and Compound 257:

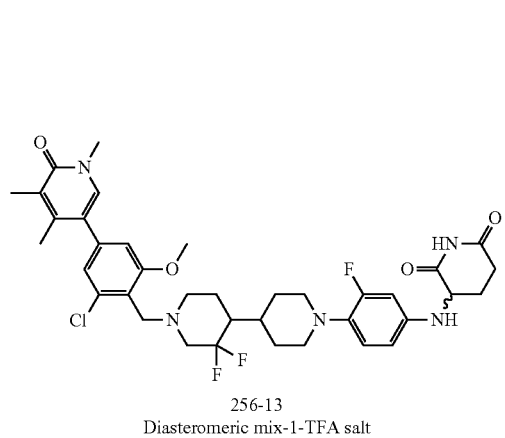

256-13
Diasteromeric mix-1-TFA salt i) Prep HPLC
ii) SFC
iii) Prep HPLC

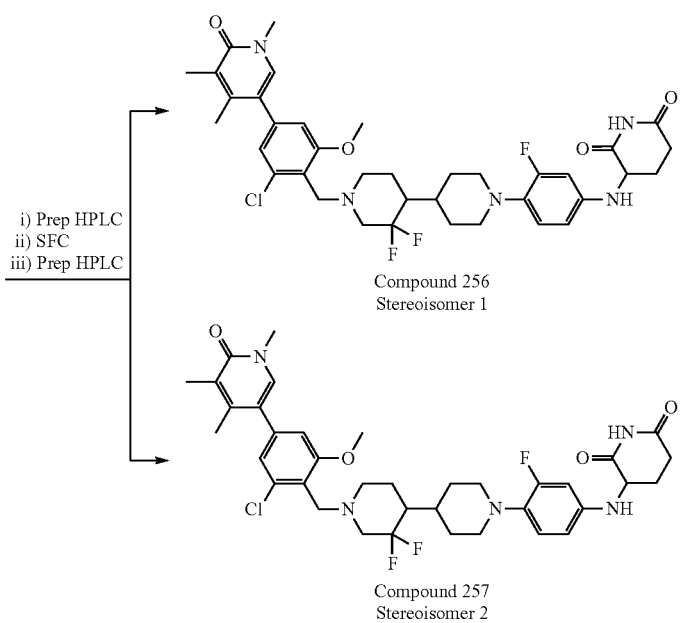

Compound 256
Stereoisomer 1

Compound 257
Stereoisomer 2

Procedure:
0.350 g of TFA salt (Compound 256-13-Diasteromixture-1) was separated by SFC to obtain single stereoisomer.

During SFC separation fractions were collected in TFA buffer to avoid Glutarimide ring opening; as SFC separation method involved use of basic additive. Hence the obtain fractions were submitted again for prep HPLC purification to remove the salt.

| Preparative SFC Conditions: | |
|---|---|
| Column/dimensions: | Chiralpak-AS-H (30 × 250) mm, 5μ |
| % CO$_2$: | 60% |
| % Co solvent: | 40% (0.2% 7M methanolic ammonia in ACN:MEOH (1:1)) |
| Total Flow: | 100.0 g/min |
| Back Pressure: | 100 bar |

-continued

| Preparative SFC Conditions: | |
|---|---|
| Temperature: | 30° C. |
| UV: | 250 nm |
| Solubility: | MeOH + MeCN |
| No of injections: | 12 |
| Total purification time: | 2.5 hrs |
| Instrument details: Make/Model: | SFC-150-I |

Prep condition:
Mobile phase A—0.05% TFA in water
Mobile phase B—acetonitrile
Column—x select-C18
(Note: the first eluted peak during SFC separation was assigned as Compound 256 and second eluted peak was assigned as Compound 257)

| Structure | Spectral data |
|---|---|
| 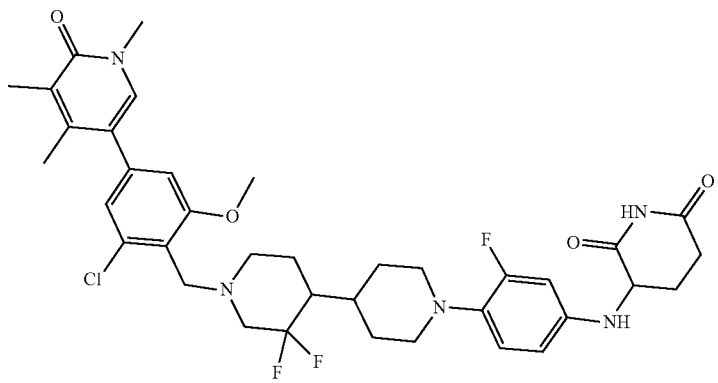  Compound 256 Stereoisomer 1 | $^1$H NMR (400 MHz, DMSO-d$_6$) δ = 10.81 (s, 1H), 7.57 (s, 1H), 7.08 – 6.96 (m, 3H), 6.60 – 6.49 (m, 2H), 4.34 – 4.32 (m, 3H), 3.93 (s, 4H), 3.46 – 3.12 (m, 10H), 2.77 – 2.67 (m, 1H), 2.59 – 2.55 (m, 1H), 2.07 – 1.56 (m, 16H). LCMS (ES$^+$): m/z 714.2 [M + H] [a]$^{25}_D$: +32.90 |

-continued
| Structure | Spectral data |
|---|---|
| 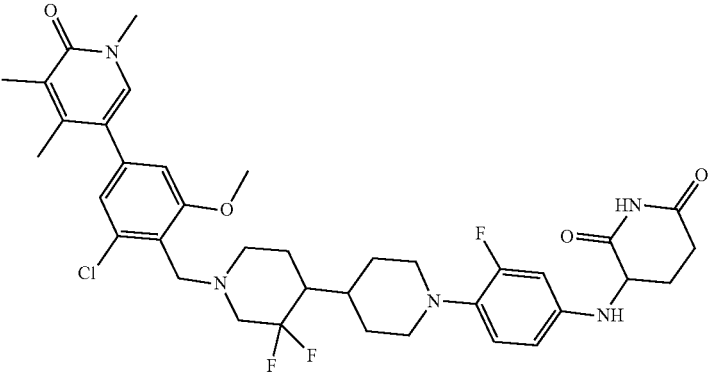
Compound 257
Stereoisomer 2 | $^1$H NMR (400 MHz, DMSO-$d_6$) δ = 10.81 (s, 1H), 7.57 (s, 1H), 7.08 – 6.86 (m, 3H), 6.60 – 6.49 (m, 2H), 4.34 (m, 3H), 3.87 (s, 4H), 3.46 – 2.91 (m, 10H), 2.77 – 2.67 (m, 1H), 2.59 – 2.55 (m, 1H), 2.07 – 1.57 (m, 16H). ). LCMS (ES$^+$): m/z 714.0 [M + H] [a]$^{25}_D$: – 22.18 |
Synthesis of Compound 258 and Compound 259
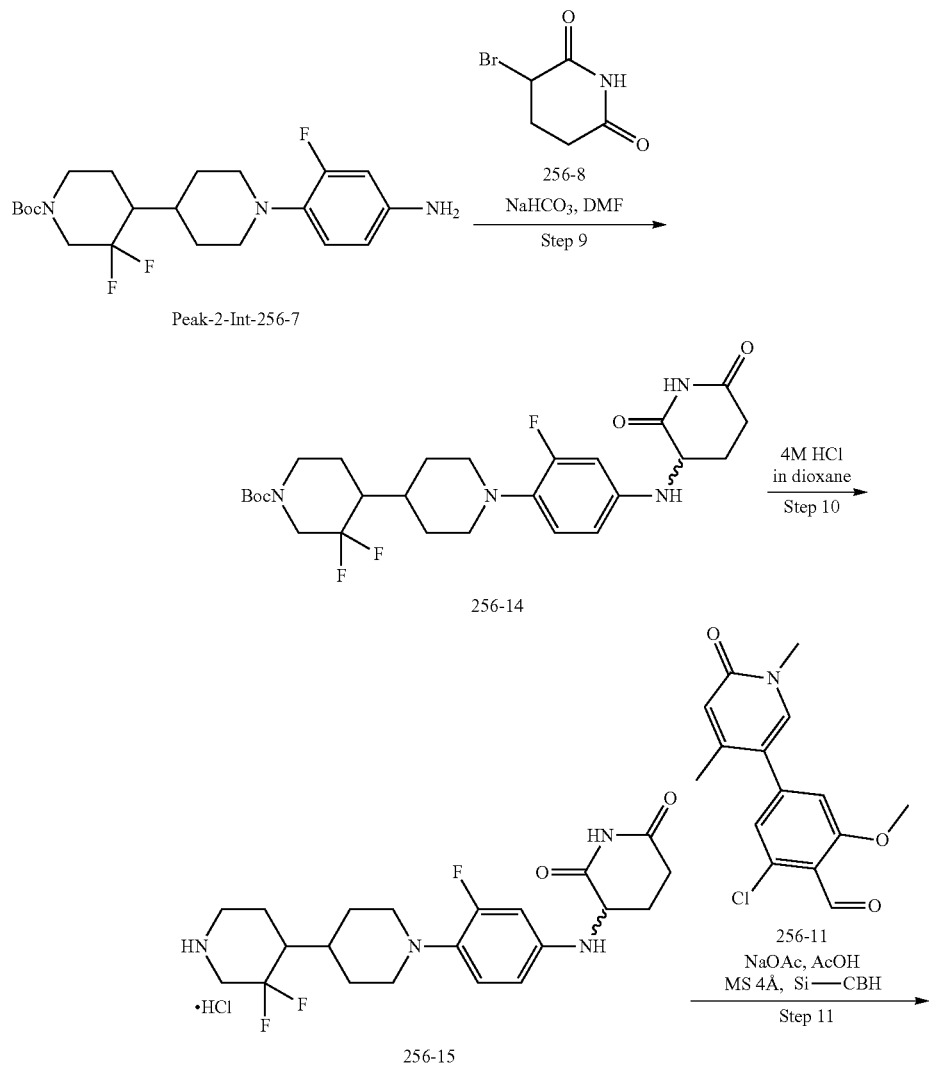

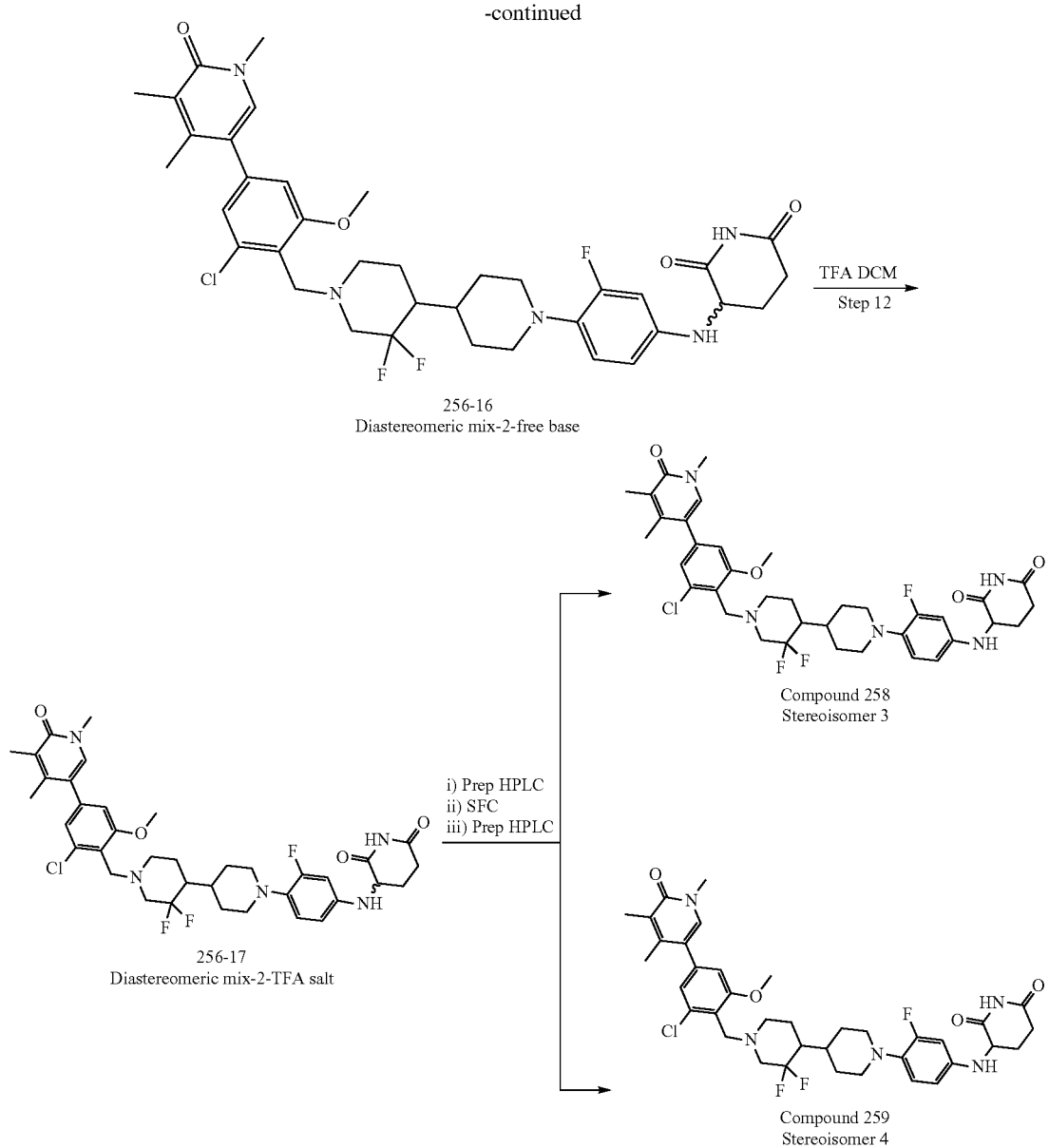

Step-9: tert-butyl 4-[1-(4-amino-2-fluoro-phenyl)-4-piperidyl]-3,3-difluoro-piperidine-1-carboxylate Peak-2-Int-256-7 (780.00 mg, 1.89 mmol) was taken in DMF (10 mL) and added sodium bicarbonate (950.84 mg, 11.32 mmol) purged nitrogen for 10 mins. Then, added 3-bromopiperidine-2, 6-dione (1.09 g, 5.66 mmol) and heated the mixture to 80° C. and maintained for 16 h while monitoring by TLC and LCMS analysis. After completion for reaction, it was quenched with ice-cold water and filtered through celite pad and washed with ethyl acetate. The organic layer separated and washed with brine solution, dried over $Na_2SO_4$. Concentrated under reduced pressure. The crude product was purified by biotage using 0-40% EA in PE to afford tert-butyl 4-[1-[4-[(2,6-dioxo-3-piperidyl)amino]-2-fluoro-phenyl]-4-piperidyl]-3,3-difluoro-piperidine-1-carboxylate (0.58 g, 884.53 μmol, 47% yield) as pale green solid. LCMS (ES⁺): m/z 525.5 [M+H]⁺.

Step-10: Tert-butyl 4-[1-[4-[(2,6-dioxo-3-piperidyl)amino]-2-fluoro-phenyl]-4-piperidyl]-3,3-difluoro-piperidine-1-carboxylate (0.58 g, 1.11 mmol, 000) was taken in 1,4-dioxane (2 mL) under nitrogen atmosphere at 0° C. was added 4M HCl in dioxane (2 mL). The reaction mixture was stirred for 3 h at RT while monitoring by TLC. After completion of reaction, it was concentrated to dryness under reduced pressure. The resulting solid was washed with diethyl ether and dried over vacuum afforded 3-[4-[4-(3,3-difluoro-4-piperidyl)-1-piperidyl]-3-fluoro-anilino]piperidine-2,6-dione; hydrochloride (0.5 g, 79% yield) as pale green solid. LCMS (ES⁺): m/z 425.41 [M+H]⁺.

Step-11: To a stirred Mixture of 2-chloro-6-methoxy-4-(1,4,5-trimethyl-6-oxo-3-pyridyl)benzaldehyde (0.3 g, 981.18 μmol, 000) in DCE (5 mL) and Methanol (5 mL) was added Acetic acid (176.76 mg, 2.94 mmol, 168.35 μL), Sodium acetate, anhydrous (241.47 mg, 2.94 mmol, 157.82 uL) and Molecular sieves (0.3 g, 981.18 μmol) and resulting solution was stirred for 10 min at room temperature. After that, 3-[4-[4-(3,3-difluoro-4-piperidyl)-1-piperidyl]-3-fluoro-anilino]piperidine-2,6-dione (542.69 mg, 1.18 mmol, 021) was added and resulting mixture was heated to reflux at 70° C. for 4 hrs. After that the RM was cooled to room temperature and Si-CBH (568.71 mg, 9.81 mmol) was added and allowed to stir at room temperature for 16 hrs. Reaction was monitored by TLC and LCMS analysis. after completion resulting material was filtered through celite-bed and washed with methanol (100 mL) to get crude material which was purified by Column chromatography (using 2.5% methanol in DCM) to afford 3-[4-[4-[1-[[2-chloro-6-methoxy-4-(1,4,5-trimethyl-6-oxo-3-pyridyl)phenyl]methyl]-3,3-difluoro-4-piperidyl]-1-piperidyl]-3-fluoro-anilino]piperidine-2,6-dione Compound 256-16-Diastereomeric mix-2-free base (0.260 g, 305.79 μmol, 31% yield) as a brown color solid.

Step-12: To a Stirred solution of 3-[4-[4-[1-[[2-chloro-6-methoxy-4-(1,4,5-trimethyl-6-oxo-3-pyridyl)phenyl]methyl]-3,3-difluoro-4-piperidyl]-1-piperidyl]-3-fluoro-anilino]piperidine-2,6-dione (0.250 g, 350.03 μmol, 000) in DCM (5 mL), Trifluoroacetic acid (296.00 mg, 2.60 mmol, 0.2 mL) was added at 0° C. The reaction mixture was stirred at room temperature for 2 h. Reaction was monitored by TLC. After completion the resulting mixture was concentrated under high vacuo to get crude which was triturated by diethyl ether to afford 3-[4-[4-[1-[[2-chloro-6-methoxy-4-(1,4,5-trimethyl-6-oxo-3-pyridyl)phenyl]methyl]-3,3-difluoro-4-piperidyl]-1-piperidyl]-3-fluoro-anilino]piperidine-2,6-dione Diasteromeric mix-2-TFA salt (0.290 g, 329.13 umol, 94% yield) as a light green solid.

SFC separation for Compound 256-17-Diastereomeric mix-2-TFA salt to afford Compound 258 & Compound 259 0.290 g of TFA salt (Compound 256-17-Diasteromixture-2) was separated by SFC to obtain single stereoisomer.

During SFC separation fractions were collected in TFA buffer to avoid Glutarimide ring opening. As SFC separation method involved use of basic additive, the obtain fractions were submitted again for prep HPLC purification to remove the salt.

Preparative SFC Conditions
Column/dimensions: Chiralpak-AS-H (30×250) mm, 5
% $CO_2$: 60%
% Co solvent: 40% (0.2% 7M Methanolic ammonia in ACN: MEOH)
Total Flow: 100.0 g/min
Back Pressure: 100 bar
Temperature: 30° C.
UV: 250 nm
Solubility: MEOH+ACN
No of injections: 12
Total purification time: 2.5 Hrs
Instrument details: Make/Model: SFC-150-I
Prep condition for Compound 256-17-Peak-2-D3 & D4
Mobile phase A: 0.05% TFA in water (aq.)
Mobile phase B: Acetonitrile
Column/dimensions: SUNFIRE-C18 (19*150*5 um)
Flow rate: 15 ml/min
Solubility: MEOH+WATER
(Note: the first eluted peak during SFC separation was assigned as Compound 258 and second eluted peak was assigned as Compound 259)

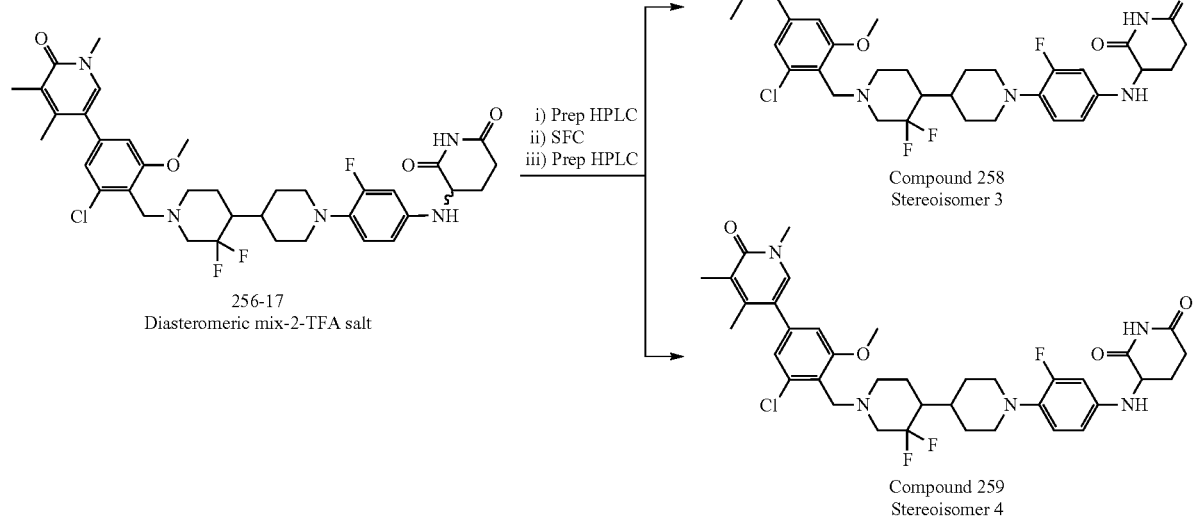

| Structure | Spectral data |
|---|---|
| 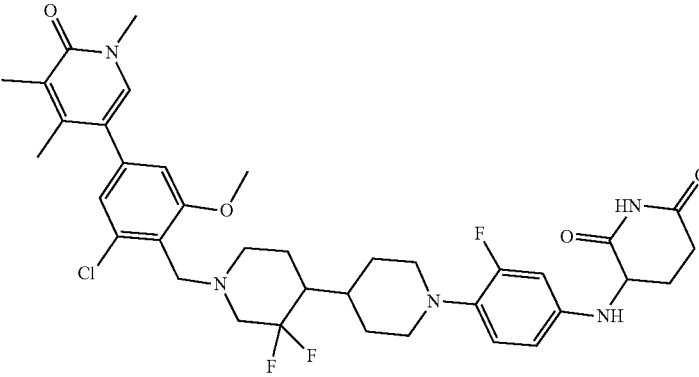<br>Compound 258<br>Stereoisomer 3 | $^1$H NMR (400 MHz, dmso d6) δ = 10.80 (s, 1H), 7.57 (s, 1H), 7.05 – 6.99 (m, 3H), 6.60 – 6.50 (m, 2H), 4.47 – 4.27 (m, 3H), 3.87(m, 4H), 3.46 – 2.67 (m, 11H), 2.59 – 2.55 (m, 1H), 2.07 (d, J = 5.2 Hz, 7H), 1.89 – 1.23 (m, 10H), LCMS (ES$^+$): m/z 714.0 [M + H]$^+$ [a]$^{25}_D$: +16.15 |
| 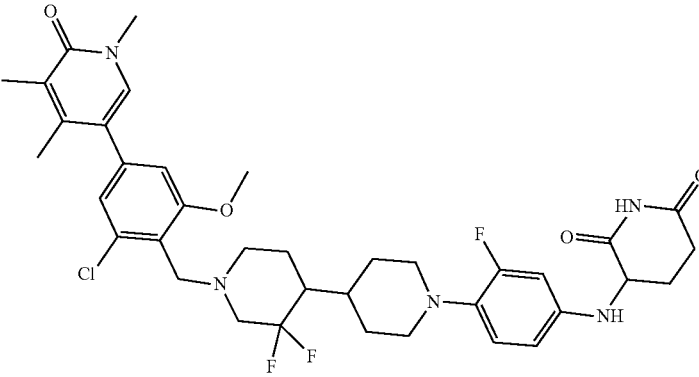<br>Compound 259<br>Stereoisomer 4 | $^1$H NMR (400 MHz, dmso d6) δ = 10.80 (s, 1H), 7.57 (s, 1H), 7.22 – 6.97 (m, 4H), 6.59 – 6.48 (m, 2H), 4.33 – 4.31 (m, 3H), 3.87 (m, 4H), 3.45 – 3.10 (m, 10H), 2.77 – 2.55 (m, 2H), 2.06 (d, J = 4.8 Hz, 7H), 1.89 – 1.55 (m, 9H), LCMS (ES$^+$): m/z 714.0 [M + H]$^+$ [a]$^{25}_D$: – 21.70 |
Synthesis of Compound 260
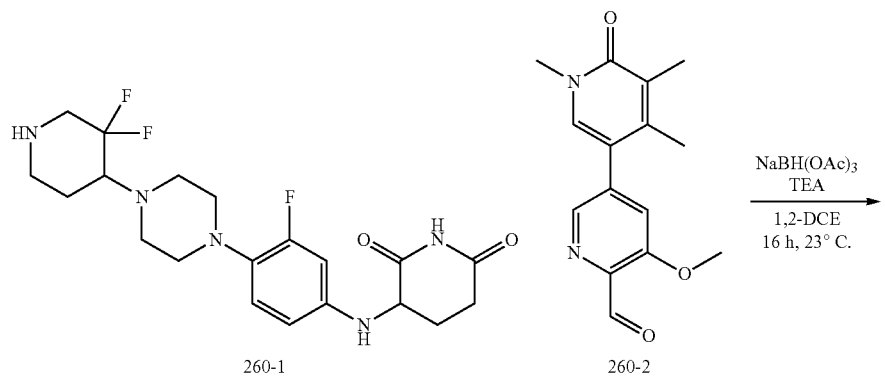

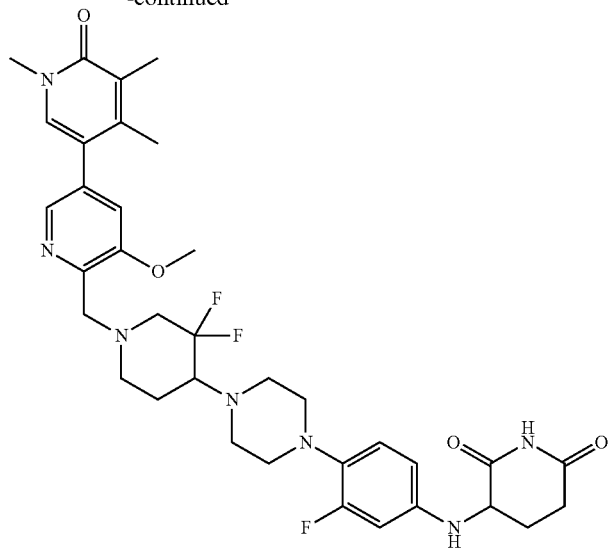

Compound 260

Initially 3-[4-[4-(3,3-difluoro-4-piperidyl)piperazin-1-yl]-3-fluoro-anilino]piperidine-2,6-dione hydrochloride (84.82 mg, 183.62 μmol), 3-methoxy-5-(1,4,5-trimethyl-6-oxo-3-pyridyl)pyridine-2-carbaldehyde (50 mg, 183.62 μmol) and TEA (37.16 mg, 367.24 μmol, 51.19 μL) were charged into a reaction vial and dissolved in 1,2-DCE (13.65 mL) before Sodium triacetoxyborohydride, 95% (58.38 mg, 275.43 μmol) was added in one portion and the mixture was allowed to stir overnight. Upon reaction completion the mixture was concentrated to dryness and purified via Isco RP FCC (0.1% TFA in water/MeCN) to afford the product Compound 260 3-[4-[4-[3,3-difluoro-1-[[3-methoxy-5-(1,4,5-trimethyl-6-oxo-3-pyridyl)-2-pyridyl]methyl]-4-piperidyl]piperazin-1-yl]-3-fluoro-anilino]piperidine-2,6-dione trifluoroacetate (103 mg, 122.96 μmol, yield=66.97%). $^1$H NMR (400 MHz, DMSO-$d_6$) δ 10.79 (s, 1H), 8.18 (d, J=1.7 Hz, 1H), 7.73-7.40 (m, 2H), 6.92 (t, J=9.3 Hz, 1H), 6.55 (dd, J=15.0, 2.5 Hz, 1H), 6.45 (dd, J=8.7, 2.6 Hz, 1H), 4.50-4.18 (m, 3H), 3.91 (s, 3H), 3.74 (d, J=9.4 Hz, 1H), 3.48 (s, 4H), 3.08-2.89 (m, 7H), 2.81-2.66 (m, 1H), 2.57 (dt, J=17.5, 4.3 Hz, 1H), 2.50 (p, J=1.8 Hz, 5H), 2.07 (s, 9H), 1.97-1.76 (m, 1H). LCMS (ES$^+$): m/z 682.5 (M+H)$^+$.

Synthesis of Compound 261

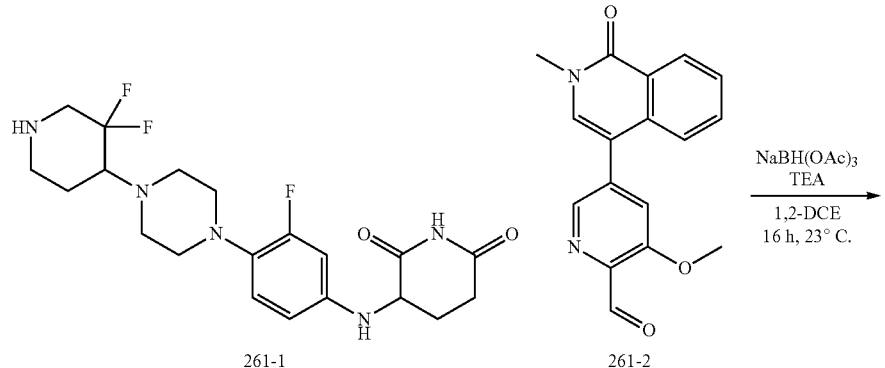

261-1     261-2

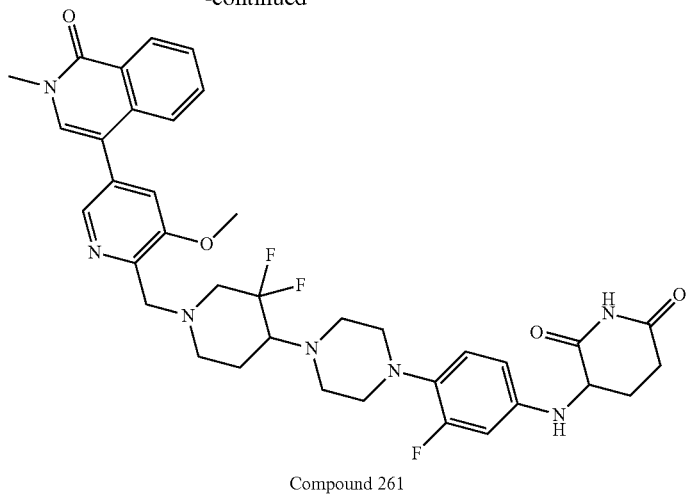

Compound 261

Initially 3-[4-[4-(3,3-difluoro-4-piperidyl)piperazin-1-yl]-3-fluoro-anilino]piperidine-2,6-dione hydrochloride (83.18 mg, 180.09 μmol), 3-methoxy-5-(2-methyl-1-oxo-4-isoquinolyl)pyridine-2-carbaldehyde (53 mg, 180.09 μmol) and TEA (36.45 mg, 360.17 μmol, 50.20 μL) were charged into a reaction vial and dissolved in 1,2-DCE (13.65 mL) before Sodium triacetoxyborohydride, 95% (57.25 mg, 270.13 μmol) was added in one portion and the mixture was allowed to stir overnight. Upon reaction completion the mixture was concentrated to dryness before being purified via Isco RP FCC (0.1% TFA in water/MeCN) to afford the product 3-[4-[4-[3,3-difluoro-1-[[3-methoxy-5-(2-methyl-1-oxo-4-isoquinolyl)-2-pyridyl]methyl]-4-piperidyl]piperazin-1-yl]-3-fluoro-anilino]piperidine-2,6-dione trifluoroacetate (76 mg, 88.29 μmol Yield—49%). $^1$H NMR (400 MHz, DMSO-$d_6$) δ 10.79 (s, 1H), 8.36 (dd, J=8.3, 1.4 Hz, 1H), 8.32 (d, J=1.7 Hz, 1H), 7.75 (ddd, J=8.5, 7.1, 1.5 Hz, 1H), 7.70-7.64 (m, 2H), 7.64-7.53 (m, 2H), 6.89 (t, J=9.3 Hz, 1H), 6.54 (dd, J=15.0, 2.5 Hz, 1H), 6.44 (dd, J=8.7, 2.5 Hz, 1H), 4.54-4.17 (m, 3H), 3.94 (s, 3H), 3.77 (s, 1H), 3.60 (s, 3H), 3.48 (s, 1H), 3.01 (s, 5H), 2.73 (ddd, J=17.4, 12.1, 5.4 Hz, 1H), 2.57 (dt, J=17.5, 4.3 Hz, 1H), 2.50 (p, J=1.8 Hz, 7H), 2.25-2.02 (m, 3H), 1.87 (td, J=12.2, 4.6 Hz, 1H). LCMS (ES$^+$): m/z 704.5 (M+H)$^+$.

Compound 262 was prepared following the synthesis of Compound 177

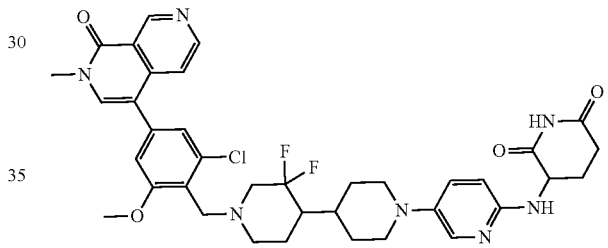

$^1$H NMR (400 MHz, DMSO-$d_6$) δ 1.32-1.48 (m, 2H); 1.50-1.60 (m, 1H); 1.62-1.82 (m, 5H); 1.90-2.24 (m, 3H); 2.30-2.50 (m, 3H); 2.56-2.58 (m, 1H); 2.66-2.80 (m, 1H); 2.90-3.10 (m, 2H); 3.36-3.42 (m, 2H); 3.59 (s, 3H); 3.72 (s, 2H); 3.87 (s, 3H); 4.60-4.70 (m, 1H); 6.39 (d, J=7.6 Hz, 1H); 6.53 (d, J=9.2 Hz, 1H); 7.11 (s, 1H); 7.17 (s, 1H); 7.17-7.22 (m, 1H); 7.54 (d, J=5.6 Hz, 1H); 7.63 (d, J=2.4 Hz, 1H); 7.94 (s, 1H); 8.74 (d, J=5.6 Hz, 1H); 9.44 (s, 1H); 10.73 (s, 1H). LCMS: m/z: 720.37 [M+H]$^+$

Compound 263 was prepared following the synthesis of Compound 151

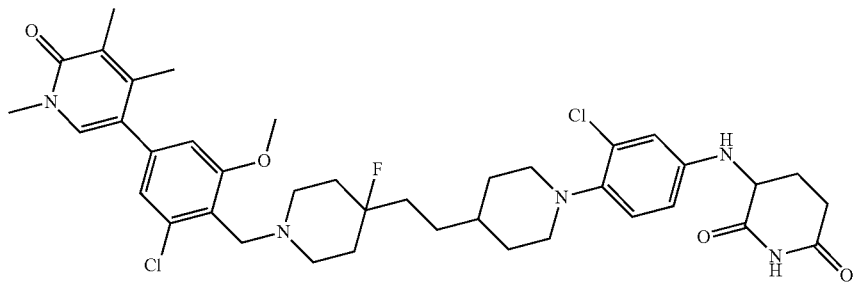 [SMILES: COc1cc(-c2cn(C)c(=O)c(C)c2C)cc(Cl)c1CN1CCC(F)(CCC2CCN(c3ccc(NC4CCC(=O)NC4=O)cc3Cl)CC2)CC1]

1019
¹H NMR (400 MHz, DMSO-d₆) δ 1.20-1.38 (m, 5H); 1.50-1.78 (m, 8H); 1.80-1.91 (m, 1H); 2.05 (s, 6H); 2.05-2.10 (m, 1H); 2.30-2.40 (m, 2H); 2.52-2.72 (m, 6H); 3.00-3.10 (m, 2H); 3.45 (s, 3H); 3.59 (s, 2H); 3.82 (s, 3H); 4.25-4.32 (m, 1H); 5.82 (d, J=7.6 Hz, 1H); 6.59 (dd, J₁=2.4
1020
Hz, J₂=8.8 Hz, 1H); 6.74 (d, J=2.8 Hz, 1H); 6.89-6.96 (m, 3H); 7.56 (s, 1H); 10.76 (s, 1H). LCMS: m/z: 740.37 [M+H]⁺
Compound 264
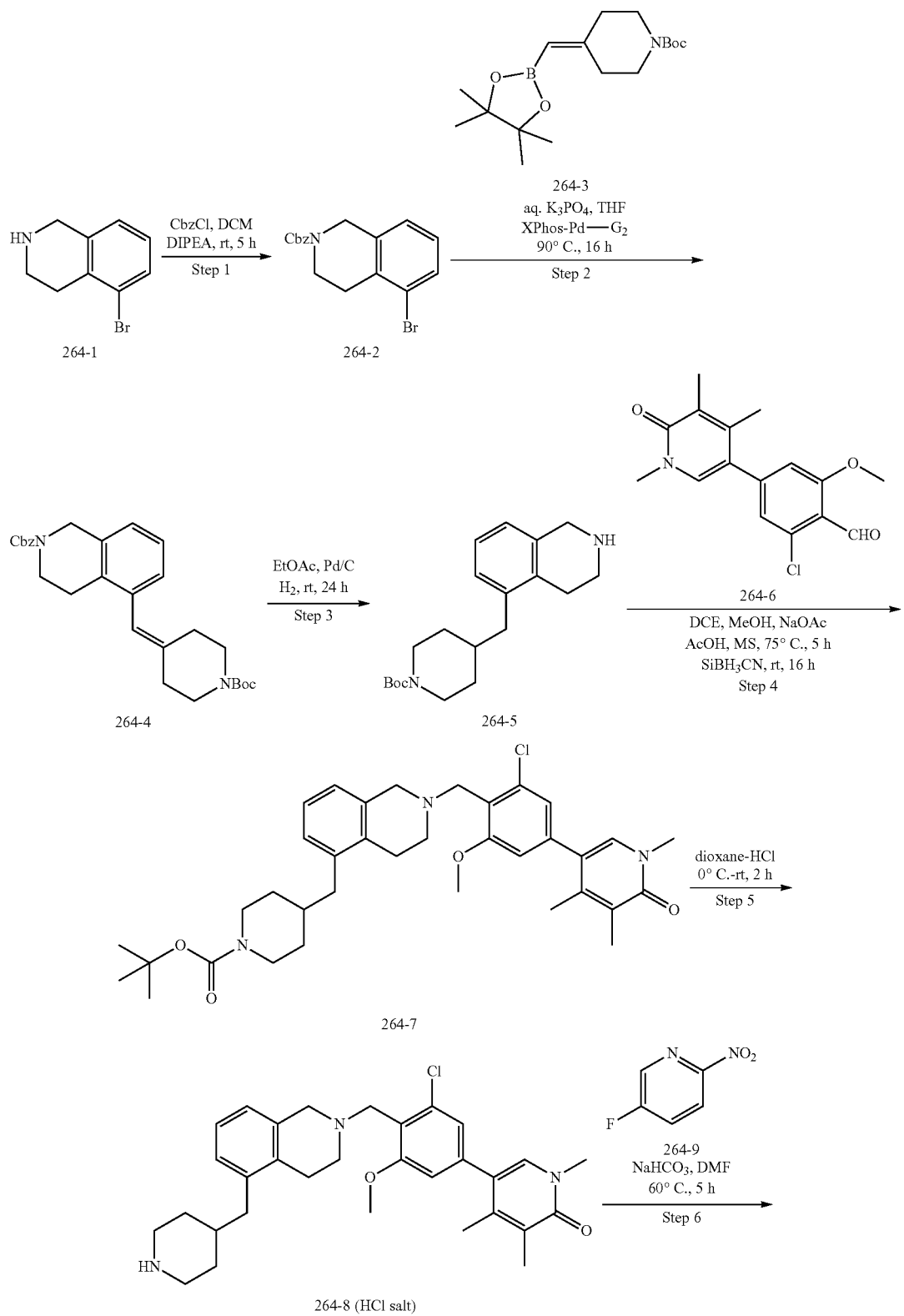

-continued

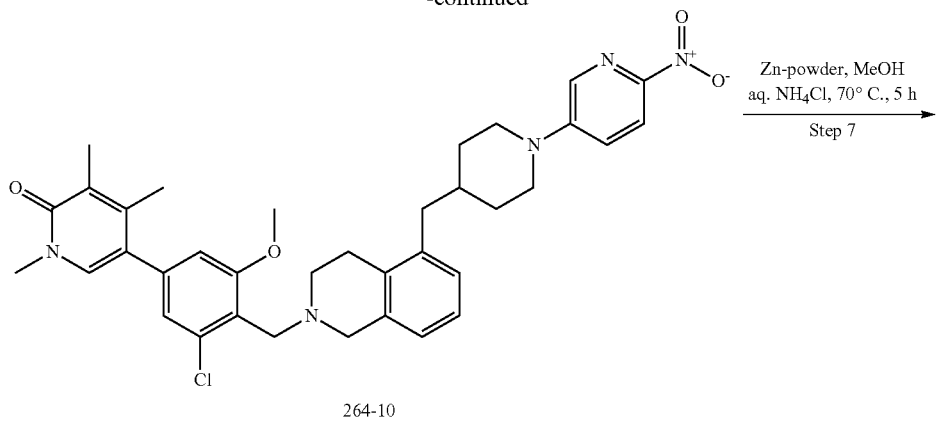

264-10

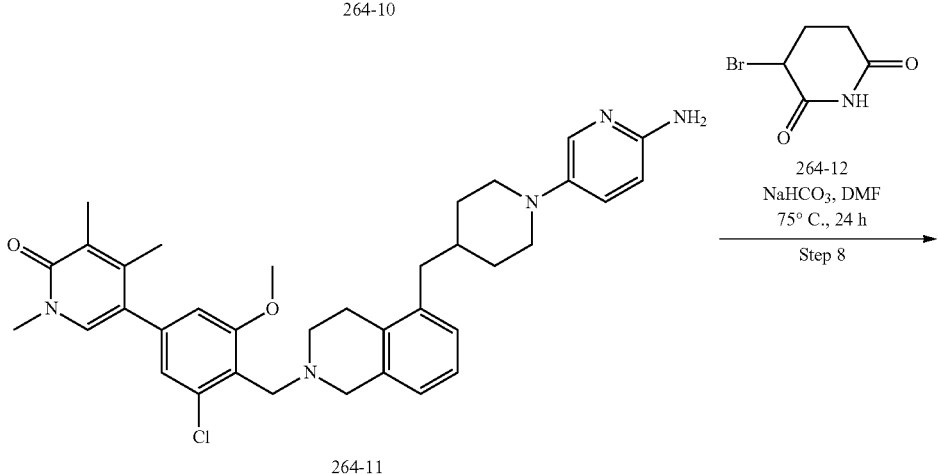

264-11

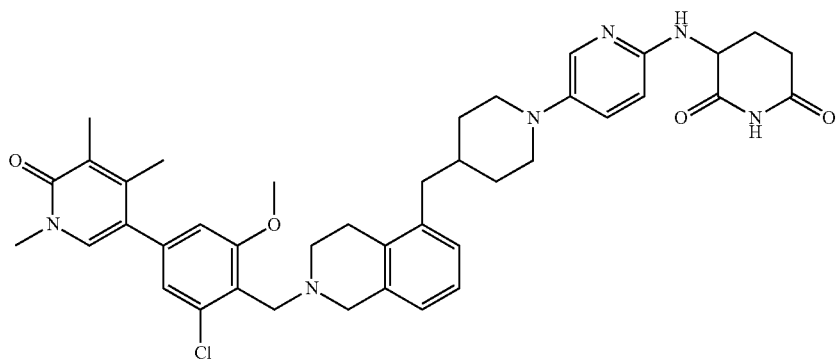

Compound 264

Step-1: To solution of 264-1 (1.5 g, 7.07 mmol) in ACN (15 mL) was added DIPEA (4.57 g, 35.36 mmol), followed by benzyl chloroformate (50% in toluene) (2.41 g, 14.15 mmol) at around 10° C. The reaction mixture was allowed to stir for 5 hours at room temperature. After completion of the reaction, volatiles were removed under reduced pressure and water (50 mL) was added to the residue. Extraction was carried out using EtOAc (3×50 mL); the combined organic layers were dried over anhydrous $Na_2SO_4$, filtered and concentrated under reduced pressure. The residue was purified by silica gel column chromatography (230-400 mesh silica gel, 0-100% gradient elution of ethyl acetate in pet-ether) to afford desired compound benzyl 5-bromo-3,4-dihydro-1H-isoquinoline-2-carboxylate 264-2 (2.0 g, 5.78 mmol, 82% yield) as a light yellow liquid. LCMS (ES$^+$): m/z 346.24 [M+H]$^+$ Step-2: Argon gas was purged through a solution of benzyl 5-bromo-3,4-dihydro-1H-isoquinoline-2-carboxylate 264-1 (0.7 g, 2.02 mmol), 264-3 (653.53 mg, 2.02 mmol) and potassium phosphate (0.944 g, 4.45 mmol) in THF (8 mL) and water (2 mL) for 10 min before addition of XPhos-Pd-G2 (0.159 g, 0.202 mmol). The reaction mixture was then stirred at 90° C. for 16 h. The progress of the reaction monitored by TLC. After completion, it was cooled to ambient temperature and water (20 mL) was added to it. Extraction was carried out using EtOAc (3×30 mL); the combined organic extracts were washed with brine (50 mL), dried over anhydrous sodium sulphate, filtered and evaporated under reduced pressure. The residue was purified by silica gel column chromatography (using 230-400 mesh silica gel and 0-100% gradient elution of ethyl acetate in pet-ether) to afford compound benzyl 5-[(1-tert-butoxycarbonyl-4-piperidylidene)methyl]-3,4-dihydro-1H-isoquinoline-2-carboxylate 264-4 (0.650 g, 1.26 mmol, 63% yield) as a yellow solid. LCMS (ES+): m/z 363.42 (Deboc mass) [M+H]+

Step-3: To a stirred solution of 5-[(1-tert-butoxycarbonyl-4-piperidylidene)methyl]-3,4-dihydro-1H-isoquinoline-2-carboxylate 264-4 (0.650 g, 1.41 mmol) in EtOAc (10 mL) was added 10% Pd/C (0.600 g, 5.64 mmol) and the resulting reaction mixture was stirred under hydrogen atmosphere (100 psi, in a steel-bomb reactor) at room temperature for 24 h. The progress of reaction was monitored by TLC. After completion of the reaction, the catalyst was filtered off and washed with 20% MeOH in DCM (3×10 mL). The filtrate was evaporated under reduced pressure to afford tert-butyl 4-(1,2,3,4-tetrahydroisoquinolin-5-ylmethyl)piperidine-1-carboxylate 264-5 (0.4 g, 0.883 mmol, 63% yield) as a brown liquid. LCMS (ES+): m/z 331.29 [M+H]+

Step-4: To a stirred solution of tert-butyl 4-(1,2,3,4-tetrahydroisoquinolin-5-ylmethyl)piperidine-1-carboxylate 264-5 (0.4 g, 1.21 mmol) and 2-chloro-6-methoxy-4-(1,4,5-trimethyl-6-oxo-1,6-dihydropyridin-3-yl)benzaldehyde 264-6 (0.370 g, 1.21 mmol) in MeOH (3 mL) and DCE (3 mL) was added sodium acetate (0.297 g, 3.63 mmol), acetic acid (181.72 mg, 3.03 mmol) and MS (0.3 g). It was stirred at 75° C. for 5 h. It was then cooled to 0° C. and SiBH$_3$CN (0.432 g, 6.05 mmol) was added to it. The reaction mixture was stirred at room temperature for 16 h. It was then filtered through a pad of celite and washed with DCE-MeOH (1:1; 3×15 mL). The filtrate was concentrated under reduced pressure. The residue was purified by silica gel column chromatography (using 230-400 mesh silica gel and 0-100% gradient elution of ethyl acetate in pet-ether) to afford tert-butyl 4-[[2-[[2-chloro-6-methoxy-4-(1,4,5-trimethyl-6-oxo-3-pyridyl)phenyl]methyl]-3,4-dihydro-1H-isoquinolin-5-yl]methyl]piperidine-1-carboxylate 264-7 (0.6 g, 0.628 mmol, 52% yield) as a light yellow solid LCMS (ES+): m/z 620.95 [M+H]+

Step-5: To a stirred solution of tert-butyl 4-[[2-[[2-chloro-6-methoxy-4-(1,4,5-trimethyl-6-oxo-3-pyridyl)phenyl]methyl]-3,4-dihydro-1H-isoquinolin-5-yl]methyl]piperidine-1-carboxylate 264-7 (0.6 g, 967.40 µmol) in 1,4-diaxone (10 mL) was added 4M HCl in dioxane (6 mL) at 0° C. and the reaction mixture was allowed to warm to room temperature over 2 h, while monitoring progress of the reaction by TLC. After completion of the reaction, volatiles were removed under reduced pressure, the solid obtained was washed with diethyl ether (5 mL×2) and dried to afforded 5-[3-chloro-5-methoxy-4-[[5-(4-piperidylmethyl)-3,4-dihydro-1H-isoquinolin-2-yl]methyl]phenyl]-1,3,4-trimethyl-pyridin-2-one 264-8 (0.6 g, HCl salt, 0.754 mmol, 78% yield) as a yellow solid. LCMS: [M+H]+ 520.41

Step-6: To a stirred solution of 5-[3-chloro-5-methoxy-4-[[5-(4-piperidylmethyl)-3,4-dihydro-1H-isoquinolin-2-yl]methyl]phenyl]-1,3,4-trimethyl-pyridin-2-one 264-8 (0.6 g, 1.08 mmol) in DMF (5 mL) was added DIPEA (0.139 g, 1.08 mmol) and 5-fluoro-2-nitro-pyridine (0.168 g, 1.19 mmol) at room temperature. The reaction mixture was stirred at 60° C. for 5 h. After completion, it was cooled to room temperature and water (20 mL) was added to it. Extraction was carried out using EtOAc (25 mL×2); the combined organic layers were washed with brine solution (20 mL), dried over anhydrous sodium sulphate, filtered and concentrated under reduced pressure. The residue was purified by column chromatography (230-400 silica gel, 0-100% gradient elution of ethyl acetate in pet-ether) to afford compound 5-[3-chloro-5-methoxy-4-[[5-[[1-(6-nitro-3-pyridyl)-4-piperidyl]methyl]-3,4-dihydro-1H-isoquinolin-2-yl]methyl]phenyl]-1,3,4-trimethyl-pyridin-2-one 264-10 (0.4 g, 0.541 mmol, 50% yield). LCMS (ES+): m/z 642.92 [M+H]+

Step-7: To a stirred solution of 5-[3-chloro-5-methoxy-4-[[5-[[1-(6-nitro-3-pyridyl)-4-piperidyl]methyl]-3,4-dihydro-1H-isoquinolin-2-yl]methyl]phenyl]-1,3,4-trimethyl-pyridin-2-one 264-10 (0.4 g, 0.622 mmol) in MeOH (8 mL) was added an aqueous solution of ammonium chloride (0.333 g, 6.23 mmol, in 2 mL water) and zinc-dust (0.407 g, 6.23 mmol). The reaction mixture was stirred at 75° C. for 5 h, while monitoring reaction progress by TLC. After completion, it was cooled to room temperature, filtered through celite bed and washed with MeOH (5 mL×2). The filtrate was concentrated under reduced pressure and water (20 mL) was added to the residue. Extraction was carried out using EtOAc (25 mL×2); the combined organic layers were washed with brine solution (25 mL), dried over anhydrous sodium sulfate, filtered and concentrated under reduced pressure. The residue was purified by column chromatography (over 230-400 silica, using 0-10% Methanol in DCM as an eluent) to afford 5-[4-[[5-[[1-(6-amino-3-pyridyl)-4-piperidyl]methyl]-3,4-dihydro-1H-isoquinolin-2-yl]methyl]-3-chloro-5-methoxy-phenyl]-1,3,4-trimethyl-pyridin-2-one 264-11 (0.350 g, 0.491, 79% yield). LCMS (ES+): m/z 612.43 [M+H]+

Step-8: To a stirred solution of 5-[4-[[5-[[1-(6-amino-3-pyridyl)-4-piperidyl]methyl]-3,4-dihydro-1H-isoquinolin-2-yl]methyl]-3-chloro-5-methoxy-phenyl]-1,3,4-trimethyl-pyridin-2-one 264-11 (0.350 g, 0.571 mmol) in DMF (5 mL) was added sodium bicarbonate (0.480 g, 5.72 mmol) and 264-12 (1.10 g, 5.72 mmol). The reaction mixture was stirred at 75° C. for 24 h, while monitoring reaction progress by TLC. After completion of the reaction, it was cooled to room temperature and saturated sodium bicarbonate solution (15 mL) was added to it. Extraction was carried out using EtOAc (3×300 mL); the combined organic layers were washed with water (30 mL×2), brine (30 mL), dried over anhydrous Na$_2$SO$_4$, filtered and concentrated under reduced pressure. The residue was purified by reverse phase preparative HPLC to afford 3-[[5-[4-[[2-[[2-chloro-6-methoxy-4-(1,4,5-trimethyl-6-oxo-3-pyridyl)phenyl] methyl]-3,4-dihydro-1H-isoquinolin-5-yl]methyl]-1-piperidyl]-2-pyridyl]amino]piperidine-2,6-dione Compound 264 (0.052 g, 0.061 mmol, 11% yield). $^1$H NMR (400 MHz, DMSO-d$_6$) δ 1.32-1.50 (m, 2H); 1.60-1.80 (m, 3H); 2.06 (s, 3H); 2.08 (s, 3H); 2.00-2.15 (m, 2H); 2.50-2.74 (m, 6H); 3.00-3.20 (m, 2H); 3.47 (s, 3H); 3.30-3.50 (m, 4H); 3.92 (s, 3H); 4.48-4.72 (m, 5H); 6.96-7.30 (m, 6H); 7.45-7.60 (m, 2H); 7.80-7.90 (m, 1H); 9.82 (s, 1H); 10.99 (s, 1H). LCMS: m z; 723.40 (M+H)+

Synthesis of Compound 265

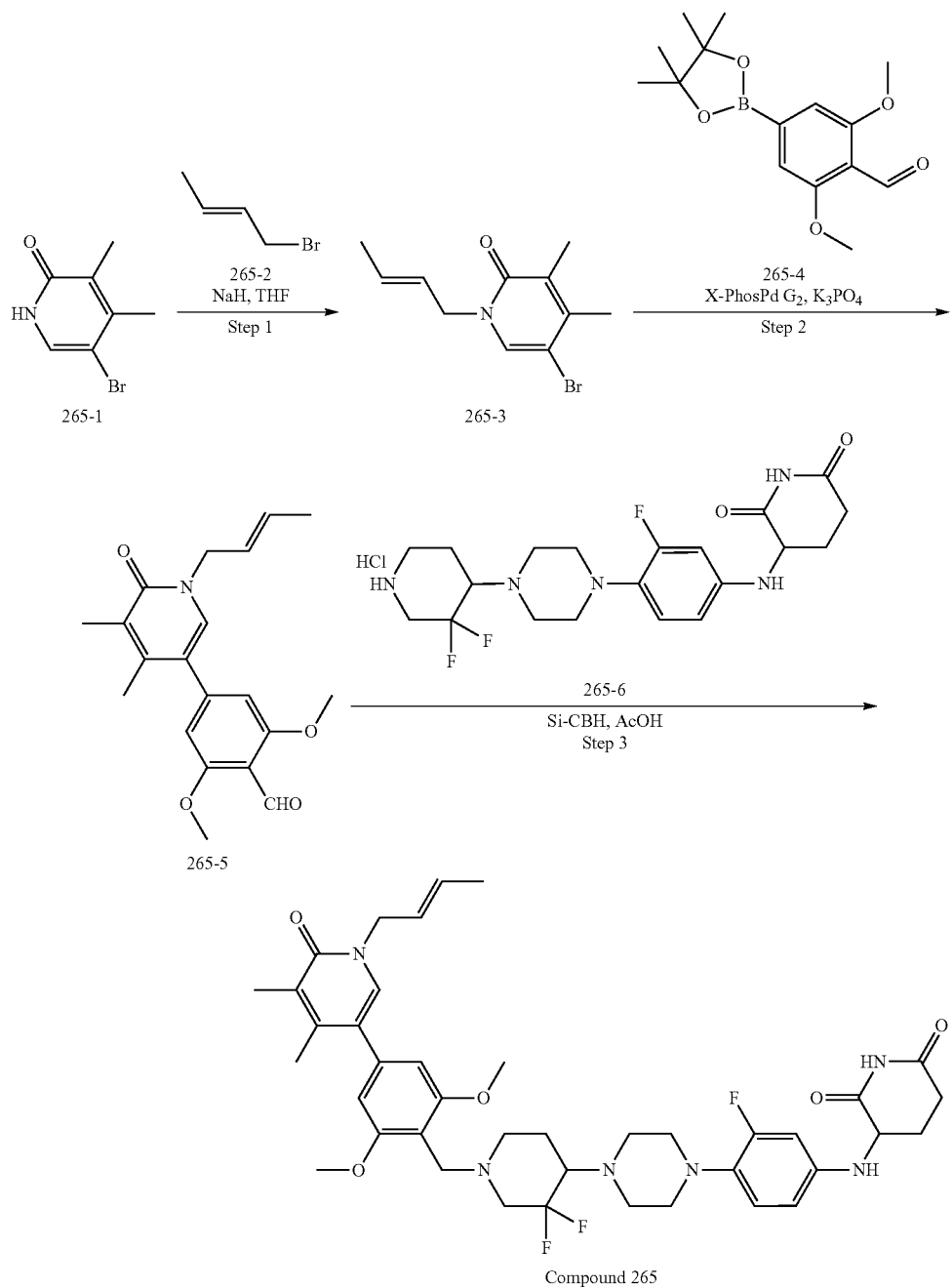

Step-1: To a stirred solution of 5-bromo-3,4-dimethyl-1H-pyridin-2-one (1 g, 4.95 mmol) in DMF (15 mL) was added (E)-1-bromobut-2-ene (668.17 mg, 4.95 mmol, 506.19 uL) drop wise with addition funnel and the reaction mixture was stirred at 0° C. Then Sodium hydride (in oil dispersion) 60% dispersion in mineral oil (227.57 mg, 9.90 mmol) was added slowly into the reaction mixture and stirred at room temperature for 12 h while monitoring by TLC and LCMS. On completion of reaction, the reaction mass was diluted with water, extracted with ethyl acetate. The combined organic layer was dried over $Na_2SO_4$, concentrated to get crude compound which was purified by silica gel column chromatography using 60% ethyl acetate in pet ether, to afford 5-bromo-1-[(E)-but-2-enyl]-3,4-dimethyl-pyridin-2-one (0.7 g, 2.46 mmol, 50% yield) as a brown solid.

Step-2: In a sealed tube, 5-bromo-1-[(E)-but-2-enyl]-3,4-dimethyl-pyridin-2-one (0.5 g, 1.95 mmol) was taken in dry THF (25 mL). 2,6-dimethoxy-4-(4,4,5,5-tetramethyl-1,3,2-dioxaborolan-2-yl)benzaldehyde (570.27 mg, 1.95 mmol) and tripotassium; phosphate (621.54 mg, 2.93 mmol) in Water (5 mL) were added to reaction mixture at room temperature. The reaction mixture was purged with argon for 10 min before XPhos-Pd-G2 (76.79 mg, 97.60 umol) was added to it. The reaction mixture again degassed with Argon and stirred at 85° C. for 5 h while monitoring by TLC and LCMS. After completion, the reaction mixture was cooled to room temperature and filtered-off through celite, washed with ethyl acetate (100 mL). The combined organic layer distilled under reduced pressure. The resultant crude product was purified by reverse phase column chromatography using 0.1% FA in water and Acetonitrile as the eluent gradient to afford 4-[1-[(E)-but-2-enyl]-4,5-dimethyl-6-oxo-3-pyridyl]-2,6-dimethoxy-benzaldehyde (0.35 g, 973.93 µmol, 50% yield,) as brown solid. LCMS (ES+): m/z 342.34 [M+H]+

Step-3: To a stirred solution of 3-[4-[4-(3,3-difluoro-4-piperidyl)piperazin-1-yl]-3-fluoro-anilino]piperidine-2,6-dione (124.62 mg, 269.79 µmol, 021) in DCE (10 mL) and Methanol (10 mL) were added molecular sieve (100 mg), sodium acetate, anhydrous (48.06 mg, 585.82 µmol, 31.41 µL) and acetic acid (52.77 mg, 878.73 µmol, 50.26 µL). The resulting solution was stirred for 10 min, then added 4-[1-[(E)-but-2-enyl]-4,5-dimethyl-6-oxo-3-pyridyl]-2,6-dimethoxy-benzaldehyde (0.1 g, 292.91 µmol, 000) and heated the reaction mixture at 70° C. for 5 hr, Subsequently, the reaction mixture was cooled to room temperature and Si-CBH (110.04 mg, 585.82 µmol) was added and stirred the reaction at room temperature for 8 hr. Reaction progress was monitored by LCMS and TLC. After Completion the reaction mixture was filtered through celite bed to obtain crude. The crude was purified by Prep-HPLC to afford 3-[4-[4-[1-[[4-[1-[(E)-but-2-enyl]-4,5-dimethyl-6-oxo-3-pyridyl]-2,6-dimethoxy-phenyl]methyl]-3,3-difluoro-4-piperidyl]piperazin-1-yl]-3-fluoro-anilino]piperidine-2,6-dione (23 mg, 25.74 µmol, 9% yield) as a grey solid. LCMS (ES+): m/z 751.46 [M+H]+ H NMR (401 MHz, DMSO) δ 10.77 (s, 1H), 7.42 (s, 1H), 6.84-6.80 (t, J=9.2 Hz, 1H), 6.61-6.40 (m, 4H), 5.83-5.50 (m, 3H), 4.59-4.46 (m, 2H), 4.25 (d, J=7.2 Hz, 1H), 3.82 (s, 8H), 2.85-2.57 (m, 14H), 2.54-2.50 (m, 1H), 2.07-1.80 (m, 10H), 1.79-1.64 (m, 3H).

Compound 266 was prepared following the synthesis of Compound 265

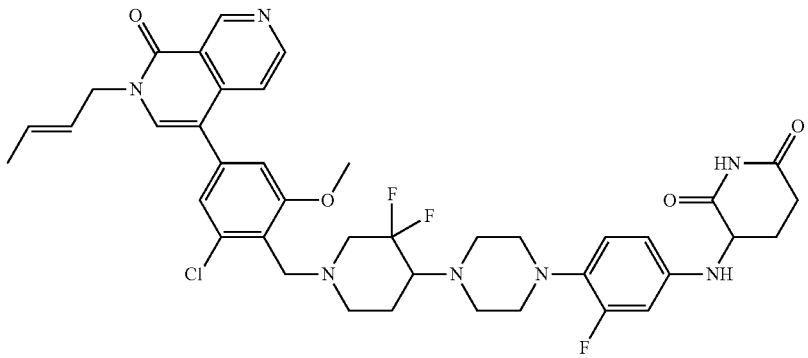 [SMILES: C/C=C/Cn1cc(-c2cc(Cl)c(CN3CCC(N4CCN(c5ccc(NC6CCC(=O)NC6=O)cc5F)CC4)C(F)(F)C3)c(OC)c2)c2ccncc2c1=O]

$^{1}$H NMR (401 MHz, DMSO):S 1H NMR (401 MHz, DMSO) δ 10.78 (s, 1H), 9.46 (s, 1H), 8.75 (d, J=5.6 Hz, 1H), 7.91-7.88 (m, 1H), 7.57 (d, J=5.6 Hz, 1H), 7.21-6.96 (m, 3H), 6.90-6.858 (t, J=9.2 Hz, 1H), 6.55-6.43 (m, 2H), 5.81-5.65 (m, 3H), 4.71-4.59 (m, 2H), 4.29-4.25 (m, 1H), 3.89 (s, 3H), 3.27-2.88 (m, 15H), 2.77-2.59 (m, 2H), 2.09-2.05 (m, 2H), 1.90-1.80 (m, 2H), 1.78-1.65 (m, 3H). LCMS (ES+): m/z 778.35 [M+H]+

Synthetic Scheme of Compound 267 and Compound 268

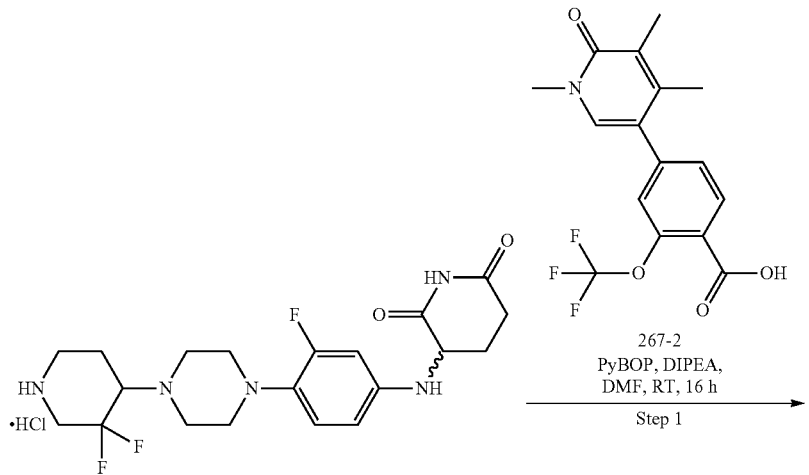

-continued
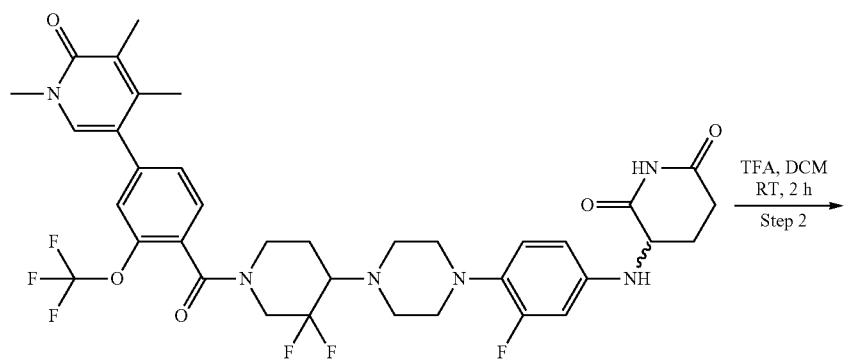
267-3-Diastereomeric mix-1-free base
TFA, DCM
RT, 2 h
Step 2
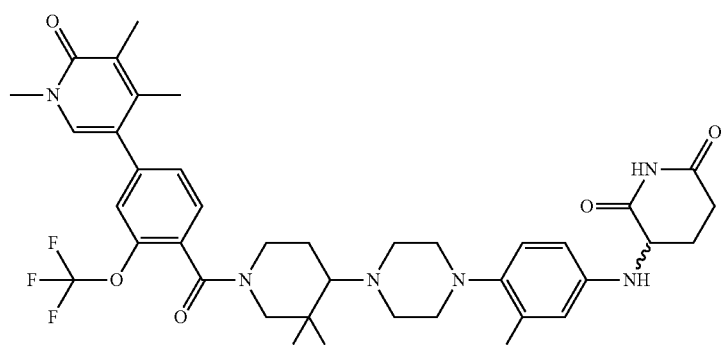
267-4-Diastereomeric mix-1- TFA salt
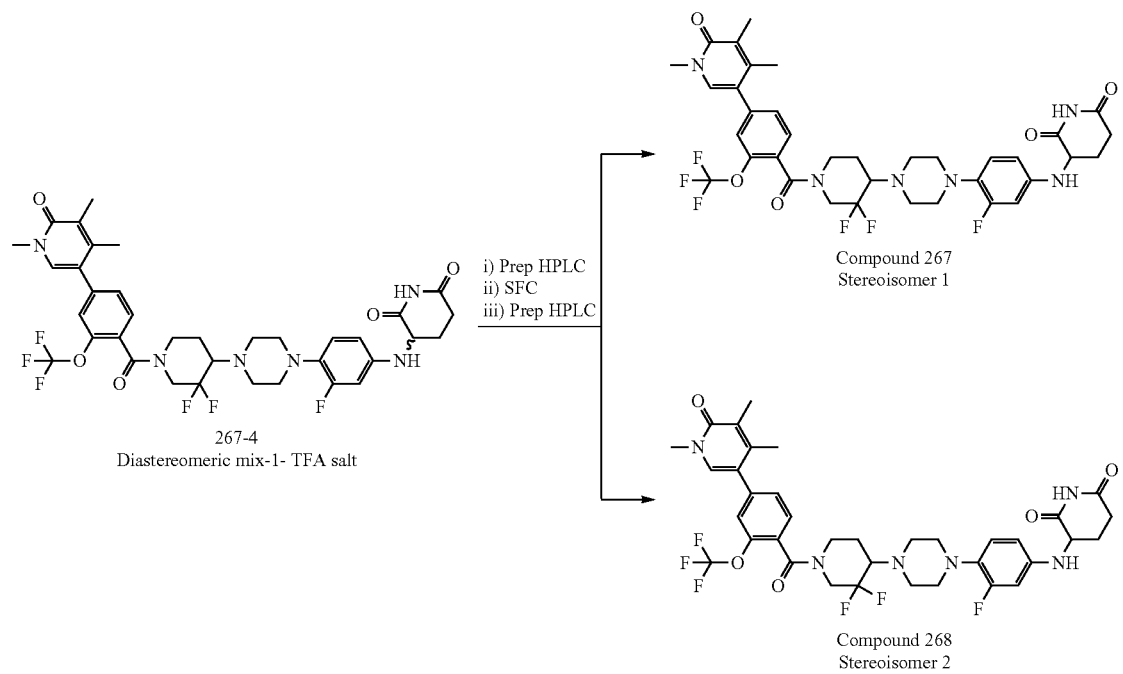 [SMILES: Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C ; Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C ; Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C]
267-4
Diastereomeric mix-1- TFA salt
i) Prep HPLC
ii) SFC
iii) Prep HPLC
Compound 267
Stereoisomer 1
Compound 268
Stereoisomer 2

Step-1: To a stirred solution of 3-[4-[4-[(4S)-3,3-difluoro-4-piperidyl]piperazin-1-yl]-3-fluoro-anilino]piperidine-2,6-dione. HCl 267-2 (0.676 g, 1.47 mmol) in dry DMF (10 mL) were added DIPEA (1.14 g, 8.79 mmol) and 2-(trifluoromethoxy)-4-(1,4,5-trimethyl-6-oxo-1,6-dihydropyridin-3-yl)benzoic acid 267-1 (0.5 g, 1.47 mmol) at 0° C. under $N_2$. The reaction mixture was allowed to warm at RT and added PyBOP (1.14 g, 2.20 mmol) after addition of PyBOP reaction mixture was stirred at RT for 16 h, while monitoring by TLC and LCMS. The reaction mixture was quenched with ice flakes to obtain solid. The solid was filtered to obtain crude product. The crude was purified by (Devisil silica gel, product eluted with 3% to 5% MeOH in $CH_2Cl_2$) column flash chromatography to afford 3-[4-[4-[(4S)-3,3-difluoro-1-[2-(trifluoromethoxy)-4-(1,4,5-trimethyl-6-oxo-3-pyridyl)benzoyl]-4-piperidyl]piperazin-1-yl]-3-fluoro-anilino]piperidine-2,6-dione 267-3-diastermeric mixture-1-Free base (0.450 g, 0.437 mmol, 35% yield, 84.92% purity) as a brown solid. LCMS ($ES^+$): m/z 749.74 $[M+H]^+$ Step-2: To a stirred solution of 3-[4-[4-[(4R)-3,3-difluoro-1-[2-(trifluoromethoxy)-4-(1,4,5-trimethyl-6-oxo-3-pyridyl)benzoyl]-4-piperidyl]piperazin-1-yl]-3-fluoro-anilino]piperidine-2,6-dione 267-3-Diasteromeric mix-1-free base (0.45 g, 0.601 mmol) in dry $CH_2Cl_2$ (2 mL) was added TFA (0.5 mL) at 0° C. and allowed to stirred at RT for 1 h. After 1 h the reaction mass was concentrated to dryness and triturated with diethyl ether (2×100 ml) to afford 3-[4-[4-[(4R)-3,3-difluoro-1-[2-(trifluoromethoxy)-4-(1,4,5-trimethyl-6-oxo-3-pyridyl)benzoyl]-4-piperidyl]piperazin-1-yl]-3-fluoro-anilino]piperidine-2,6-dione.267-4-Diasteromeric mix-1-TFA salt (0.5 g, 84% yield, 87.14% purity) as a light green solid.

SFC separation for 267-4-Diastereomeric mix-1-TFA salt to afford Compound 267 and Compound 268

0.5 g of 267-4-Diasteromixture-1 was separated by SFC to obtain single stereoisomer. During SFC separation fractios were collected in TFA buffer to avoid Glutarimide ring opening. As SFC separation method involved use of basic additive, the obtain fractions were submitted again for prep HPLC purification to remove the salt.

| Preparative SFC Conditions: | |
|---|---|
| Column/dimensions: | Chiralpak AS-H (30 × 250) mm, 5μ |
| % $CO_2$: | 50% |
| % Co solvent: | 50% (0.2% 7MM Methanolic ammonia in Methanol) |
| Total Flow: | 120.0 g/min |
| Back Pressure: | 100 bar |
| Temperature: | 30° C. |
| UV: | 220 nm |
| Solubility: | MeOH |

| Preparative HPLC Conditions: | |
|---|---|
| Column/dimensions: | SUNFIRE C18 (19*150 mm) |
| Mobile phase A: | 0.05% TFA in water |
| Mobile phase B: | Acetonitrile |
| Gradient (Time/% B): | 0/10, 3/10, 10/35, 15/35 |
| Flow rate: | 17 ml/min |
| Solubility: | THF + ACN |

(Note: the first eluted peak during SFC separation was assigned as Compound 267 and second eluted peak was assigned as Compound 268)

267-4-Peak-1-D1-Chiral HPLC RT: 17.457 min
267-4-Peak-1-D2-Chiral HPLC RT: 14.018 min

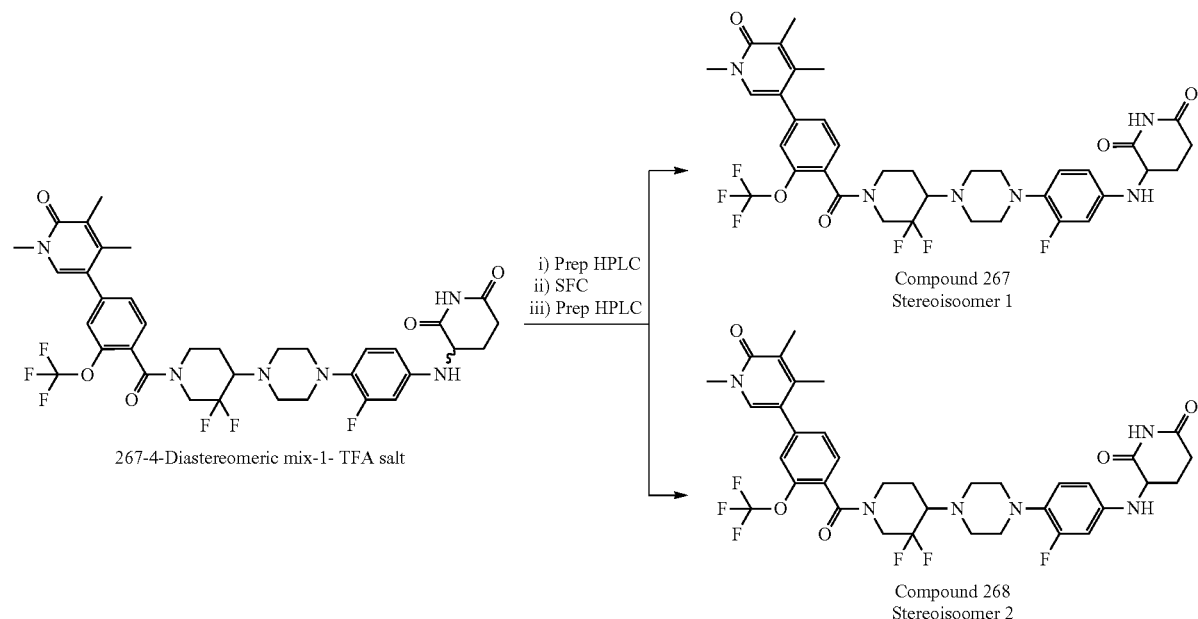 [SMILES: Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C ; Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C ; Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C]

| Structure | Spectral data |
|---|---|
| 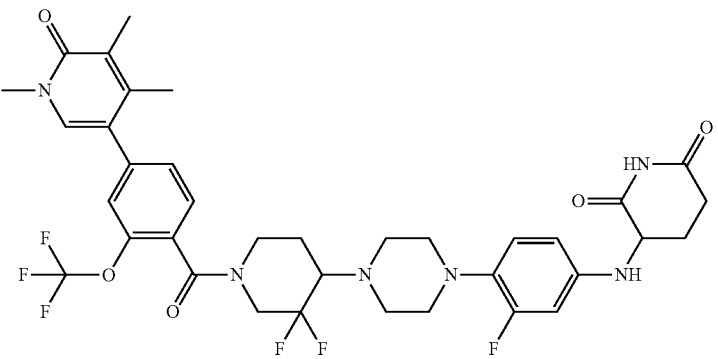<br>Compound 267<br>Stereoisomer 1 | ¹H NMR (401 MHz, DMSO) δ 10.78 (s, 1H), 7.62 – 7.60 (m, 1H), 7.54 – 7.39 (m, 3H), 6.88 – 6.84 (t, J = 8.8 Hz, 1H), 6.53 – 6.42 (m, 2H), 4.72 – 4.61 (m, 1H), 4.28 – 4.24 (m, 1H), 3.46 – 3.26 (m, 5H), 2.91 – 2.72 (m, 10H), 2.67 – 2.57 (m, 2H), 2.07 – 2.05 (m, 10H), 1.23 – 1.15 (m, 1H).<br>$[\alpha]^{25}_D$: = +12.95 |
| 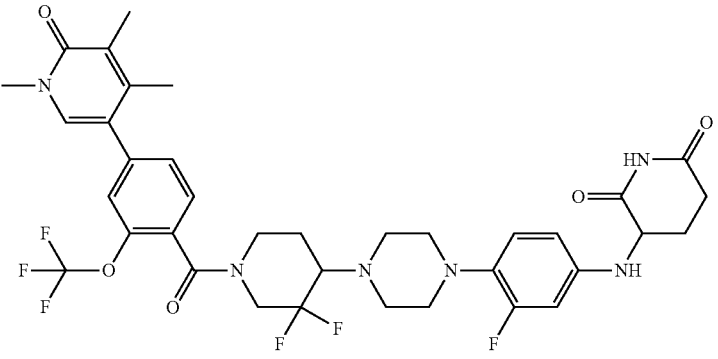<br>Compound 268<br>Stereoisomer 2 | ¹H NMR (401 MHz, DMSO) δ 10.78 (s, 1H), 7.62 – 7.39 (m, 4H), 6.96 – 6.90 (m, 1H), 6.55 – 6.43 (m, 2H), 4.74 – 4.62 (m, 1H), 4.29 – 4.25 (m, 2H), 3.67 – 2.99 (m, 15H), 2.72 – 2.54 (m, 2H), 2.09 – 1.81 (m, 10H).<br>$[\alpha]^{25}_D$: = – 8.99 |
Synthetic Scheme of Compound 269 and Compound 270
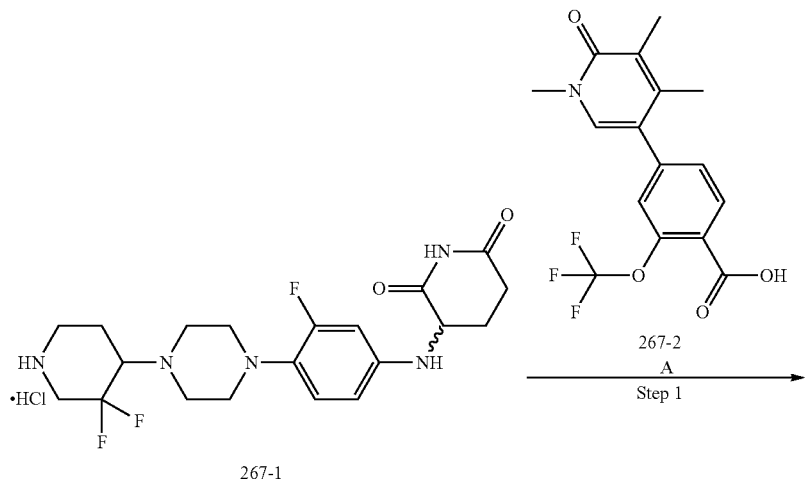

-continued
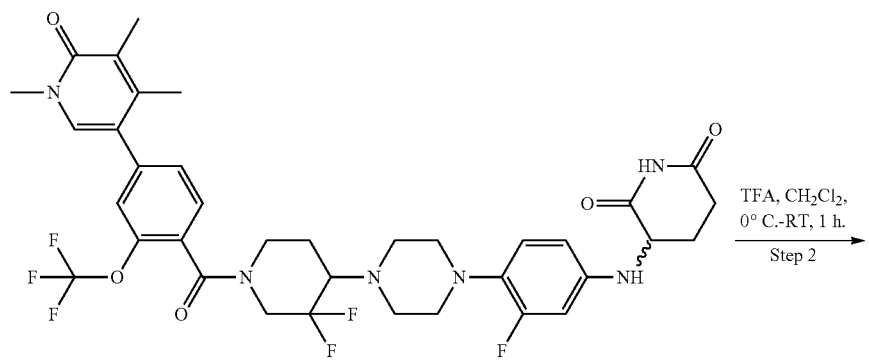
269-3
Diastereomeric mix-2-Free base
TFA, CH$_2$Cl$_2$,
0° C.-RT, 1 h.
Step 2
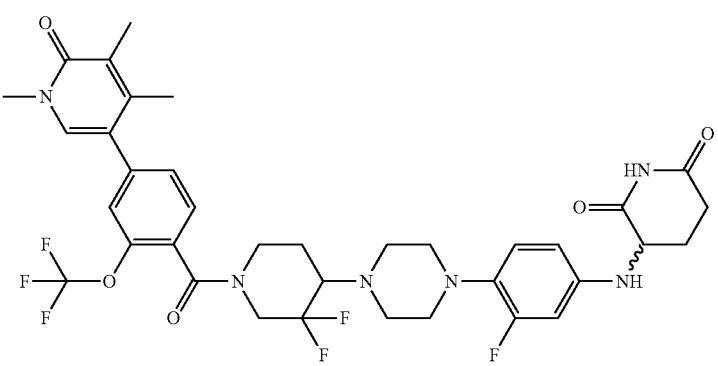
269-4-Diastereomeric mix-2-TFA salt
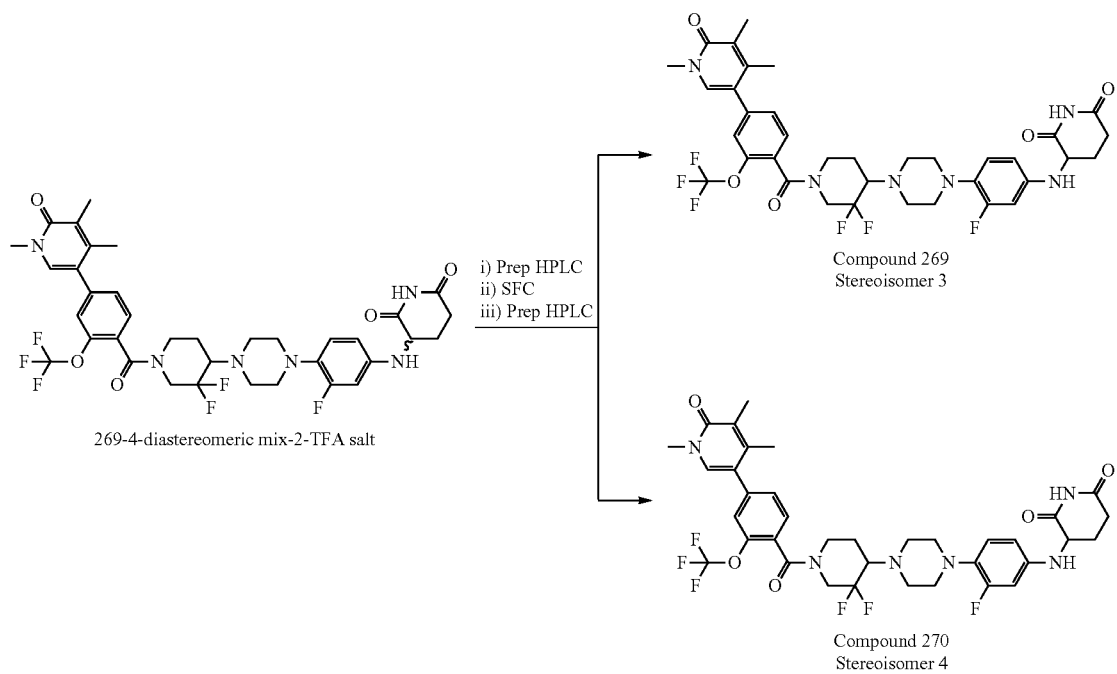 [SMILES: Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C ; Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C ; Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C]
269-4-diastereomeric mix-2-TFA salt
i) Prep HPLC
ii) SFC
iii) Prep HPLC
Compound 269
Stereoisomer 3
Compound 270
Stereoisomer 4

Step-1: To a stirred solution of 3-[4-[4-[(4S)-3,3-difluoro-4-piperidyl]piperazin-1-yl]-3-fluoro-anilino]piperidine-2,6-dione.HCl salt (0.6 g, 1.30 mmol) in dry DMF (3 mL) were added DIPEA (0.504 g, 3.90 mmol) and 2-(trifluoromethoxy)-4-(1,4,5-trimethyl-6-oxo-1,6-dihydropyridin-3-yl)benzoic acid (0.443 g, 1.30 mmol) at 0° C. under $N_2$. The reaction mixture was allowed to warm at RT and added PyBOP (0.811 g, 1.56 mmol) after addition of PyBOP reaction mixture was stirred at RT for 16 h, while monitoring by TLC and LCMS. The reaction mixture was concentrated under reduced pressure to obtain the crude product. The crude was purified by (Devisil silica gel, and product eluted with 1% to 5% MeOH in $CH_2Cl_2$) column flash chromatography to afford 3-[4-[4-[(4S)-3,3-difluoro-1-[2-(trifluoromethoxy)-4-(1,4,5-trimethyl-6-oxo-3-pyridyl)benzoyl]-4-piperidyl]piperazin-1-yl]-3-fluoro-anilino]piperidine-2,6-dione 269-3-diastermeric mixture-2-Free base (0.450 g, 0.437 mmol, 34% yield, 72.70% purity) as a brown solid. LCMS (ES$^+$): m/z 749.70 [M+H]$^+$.

Step-2: To a stirred solution of 3-[4-[4-[(4S)-3,3-difluoro-1-[2-(trifluoromethoxy)-4-(1,4,5-trimethyl-6-oxo-3-pyridyl)benzoyl]-4-piperidyl]piperazin-1-yl]-3-fluoro-anilino]piperidine-2,6-dione 269-3-Diasteromeric mix-2-free base (0.45 g, 0.601 mmol) in dry $CH_2Cl_2$ (2 mL) was added TFA (0.5 mL) at 0° C. and allowed to stirred at RT for 1 h. After 1 h the reaction mass was concentrated to dryness and triturated with diethyl ether (2×100 ml) to afford 3-[4-[4-[(4S)-3,3-difluoro-1-[2-(trifluoromethoxy)-4-(1,4,5-trimethyl-6-oxo-3-pyridyl)benzoyl]-4-piperidyl]piperazin-1-yl]-3-fluoro-anilino]piperidine-2,6-dione.TFA salt 269-4-Diasteromeric mix-2-TFA salt (0.5 g, 0.438 mmol, 73% yield, 75.65% purity) as a light green solid. LCMS (ES$^+$): m/z 749.46 [M+H]$^+$ SFC separation for 269-4-Diastereomeric mix-2-TFA salt to obtain Compound 269 and Compound 270

269-4-Diasteromixture-2-TFA salt was separated by SFC to obtain single stereoisomer.

During SFC separation fractions were collected in TFA buffer to avoid Glutarimide ring opening; As SFC separation method involved use of basic additive, the obtain fractions of Compound 269 and of Compound 270 were submitted again for prep-HPLC purification to remove the salt. (Note: the first eluted peak during SFC separation was assigned as Compound 269 and second eluted peak was assigned as Compound 270.

| Preparative SFC Conditions: | |
|---|---|
| Column/dimensions: | Chiralpak AS-H (30 × 250) mm, 5µ |
| % CO$_2$: | 50% |
| % Co solvent: | 50% (0.2% 7M Methanolic Ammonia in Methanol |
| Total Flow: | 120.0 g/min |
| Back Pressure: | 100 bar |
| Temperature: | 30° C. |
| UV: | 220 nm |
| Solubility: | MeOH |

| Preparative HPLC Conditions: | |
|---|---|
| Column/dimensions: | SUNFIRE C18 (19*150*5µ) |
| Mobile phase A: | 0.05% TFA in water (PH) |
| Mobile phase B: | Acetonitrile |
| Gradient (Time/% B): | 0/10, 5/10, 10/50, 13/50, 13.1/98, 17/98, 17.1/10, 20/10 |
| Flow rate: | 18 ml/min |
| Solubility: | ACN ++ WATER |

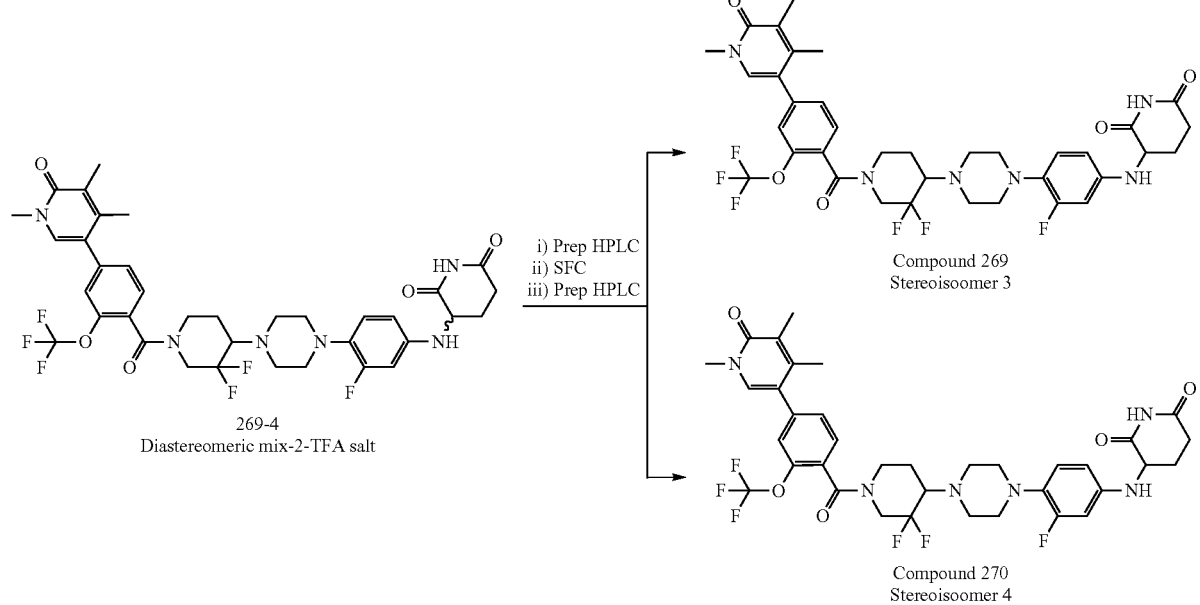 [SMILES: Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C ; Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C ; Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C]

269-4
Diastereomeric mix-2-TFA salt i) Prep HPLC
ii) SFC
iii) Prep HPLC

Compound 269
Stereoisoomer 3

Compound 270
Stereoisoomer 4

| Structure | Spectral data |
|---|---|
| 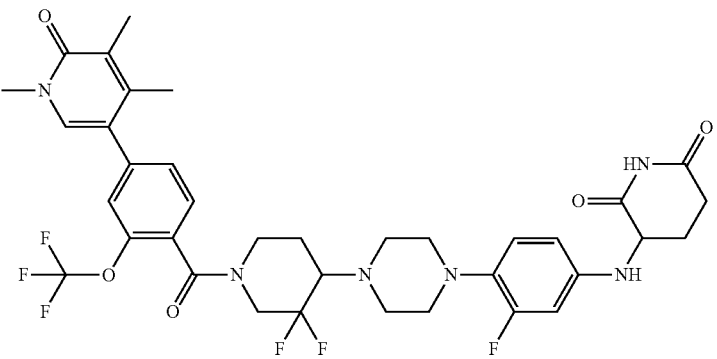

Compound 269
Stereoisomer 3 | ¹H NMR (400 MHz, DMSO-d6) δ 10.79 (s, 1H), 7.62 – 7.60 (m, 1H), 7.55 – 7.39 (m, 3H), 6.96 – 6.92 (m, 1H), 6.56 – 6.44 (m, 2H), 4.75 – 4.62 (m, 1H), 4.30 – 4.26 (m, 1H), 3.57 – 3.03 (m, 16H), 2.72 – 2.53 (m, 2H), 2.09 – 1.84 (m, 10H) [a]²⁵_D: = +16.86 |
| 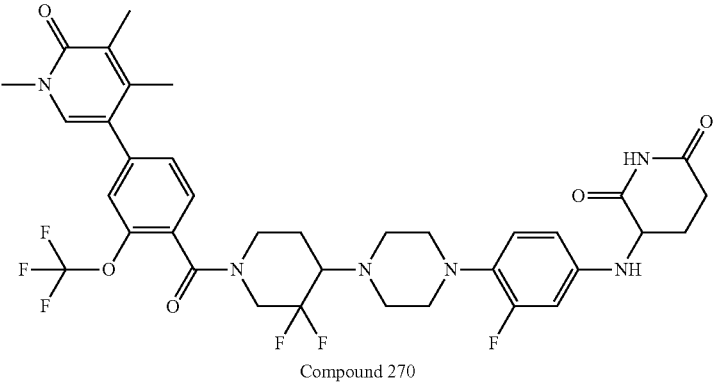

Compound 270
Stereoisomer 4 | ¹H NMR (400 MHz, DMSO-d6) δ 10.79 (s, 1H), 7.62 – 7.60 (m, 1H), 7.54 – 7.39 (m, 3H), 6.96 – 6.88 (m, 1H), 6.55 – 6.43 (m, 2H), 4.74 – 4.62 (m, 1H), 4.29 – 4.25 (m, 1H), 3.56 – 2.99 (m, 16H), 2.72 – 2.53 (m, 2H), 2.10 – 1.81 (m, 10H). [a]²⁵_D: = – 19.77 |

Compound 271 was prepared following the synthesis of Compound 49

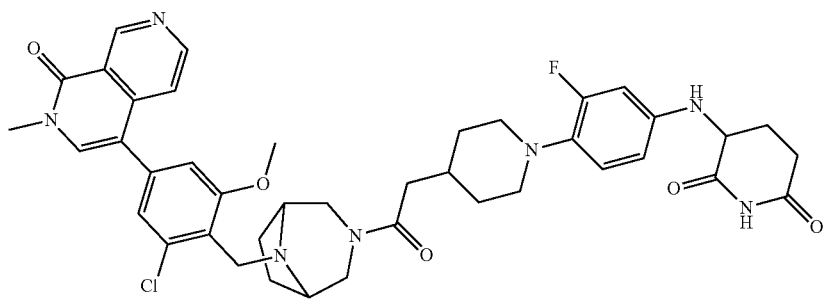 [SMILES: COc1cc(-c2cn(C)c(=O)c3cnccc23)cc(Cl)c1CN1C2CCC1CN(C(=O)CC1CCN(c3ccc(NC4CCC(=O)NC4=O)cc3F)CC1)C2]

¹HMR (400 MHz, DMSO-d6): 1H NMR (401 MHz, DMSO) δ 10.80 (s, 1H), 9.62 (s, 1H), 9.48 (s, 1H), 8.78 (d, J=5.6 Hz, 1H), 7.95 (s, 1H), 7.53 (d, J=5.6 Hz, 1H), 7.36 (s 1H), 7.29 (s, 1H), 6.58-6.49 (m, 3H), 4.37-3.98 (in, 10H), 3.62 (s, 4H), 3.40-3.15 (m, 5H), 2.84-2.60 (m, 2H), 2.40-2.30 (m, 2H), 2.07-1.85 (m, 9H), 1.78-1.47 (in, 2H).

LCMS (ES⁺): m/z 770.45 [M+H]⁺

Compound 272 was prepared following the synthesis of Compound 49

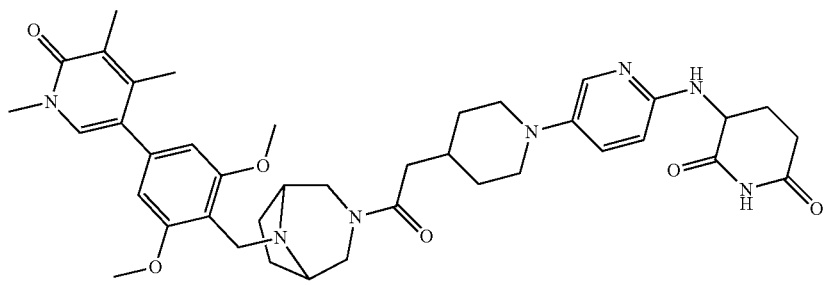 [SMILES: COc1cc(-c2cn(C)c(=O)c(C)c2C)cc(OC)c1CN1C2CCC1CN(C(=O)CC1CCN(c3ccc(NC4CCC(=O)NC4=O)nc3)CC1)C2]

¹H NMR (400 MHz, DMSO-d6): δ 11.03 (s, 1H), 9.41 (s, 1H), 7.91 (s, 1H), 7.52 (m, 2H), 7.00 (s, 1H) 6.70-6.69 (m, 2H), 4.66 (s, 1H), 4.29 (s, 1H), 4.26-3.89 (m, 14H), 3.6-3.47 (m, 6H), 3.14-3.11 (m, 1H), 2.77-2.60 (m, 2H), 2.50-2.30 (m, 4H), 2.26-2.07 (m, 7H), 1.96-1.67 (m, 5H), 1.34-1.23 (m, 2H). LCMS (ES⁺): m/z 726.32 [M+H]⁺

Compound 273 was prepared following the synthesis of Compound 262

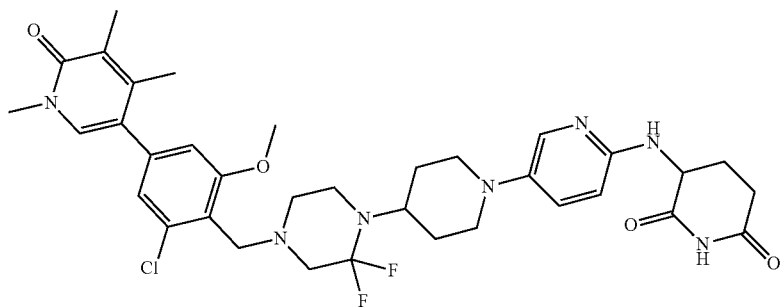 [SMILES: COc1cc(-c2cn(C)c(=O)c(C)c2C)cc(Cl)c1CN1CCN(C2CCN(c3ccc(NC4CCC(=O)NC4=O)nc3)CC2)C(F)(F)C1]

¹H NMR (400 MHz, DMSO-d₆) δ 1.30-1.42 (m, 2H); 1.50-1.80 (m, 6H); 1.90-2.20 (m, 3H); 2.05 (s, 6H); 2.30-2.60 (m, 4H); 2.64-3.05 (m, 3H); 3.36-3.42 (m, 2H); 3.45 (s, 3H); 3.65 (s, 2H); 3.84 (s, 3H); 4.60-4.70 (m, 1H); 6.39 (d, J=7.6 Hz, 1H); 6.53 (d, J=8.8 Hz, 1H); 6.92 (s, 1H); 6.98 (s, 1H); 7.20 (dd, J₁=2.8 Hz, J₂=8.8 Hz, 1H); 7.58 (s, 1H); 7.62 (d, J=2.4 Hz, 1H); 10.73 (s, 1H). LCMS (ES⁺) m/z: 697.17 [M+H]⁺

Compound 274 was prepared following the synthesis of

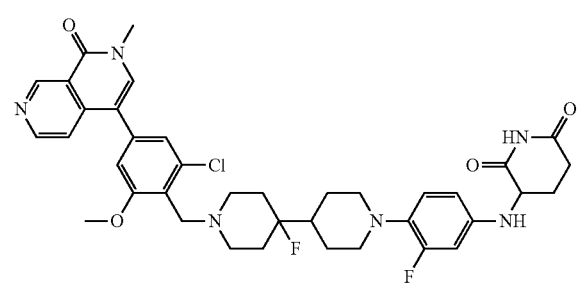 [SMILES: COc1cc(-c2cn(C)c(=O)c3cnccc23)cc(Cl)c1CN1CCC(F)(C2CCN(c3ccc(NC4CCC(=O)NC4=O)cc3F)CC2)CC1]

¹H NMR (400 MHz, DMSO-d₆) δ 1.50-1.90 (m, 6H); 2.00-2.18 (m, 5H); 2.52-2.62 (m, 1H); 2.66-2.90 (m, 3H); 3.22-3.42 (m, 4H); 2.46-3.56 (m, 2H); 3.62 (s, 3H); 3.97 (s, 3H); 4.24-4.32 (m, 1H); 4.49-4.55 (m, 2H); 6.46 (d, J=8.8 Hz, 1H); 6.54 (d, J=14.8 Hz, 1H); 6.96 (bs, 1H); 7.28 (s, 1H); 7.35 (s, 1H); 7.55 (d, J=6.0 Hz, 1H); 7.96 (s, 1H); 8.77 (d, J=6.0 Hz, 1H); 9.23 (bs, 1H); 9.48 (s, 1H); 10.79 (s, 1H). LCMS (ES⁺): m/z 719.11 [M+H]⁺

Compound 275 was prepared following the synthesis of Compound 244

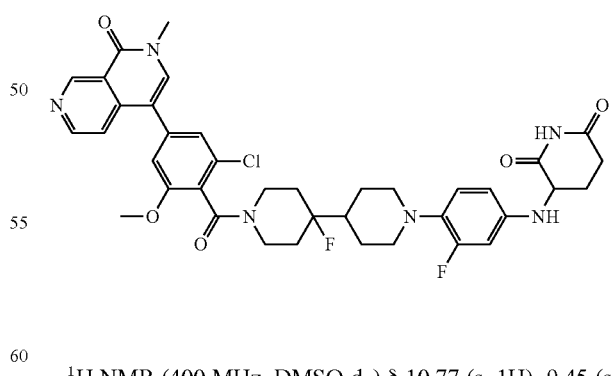

¹H NMR (400 MHz, DMSO-d₆) δ 10.77 (s, 1H), 9.45 (s, 1H), 8.74 (d, J=6 Hz, 1H), 7.95 (s, 1H), 7.57 (d, J=5.6 Hz, 1H), 7.22-7.18 (m, 2H), 6.85-6.80 (m, 1H), 6.52-6.40 (m, 2H), 5.79 (d, J=7.6 Hz, 1H), 4.51 (d, J=11.6 Hz, 1H), 4.26-4.23 (m, 1H), 3.86-3.85 (d, J=3.6 Hz, 3H), 3.59 (s, 3H), 3.19-3.00 (m, 5H), 2.72-2.54 (m, 4H), 2.10-2.05 (m, 1H), 1.92-1.60 (m, 10H). LCMS (ES⁺): m/z 733.15 [M+H]⁺

TABLE 1

XII. DATA
BRD9 Degradation Data.

| Cmpd # | Structure | HiBiT-Degradation 293T.166 BRD9 2.0 hours (DC50) [nM] |
|---|---|---|
| 1 | 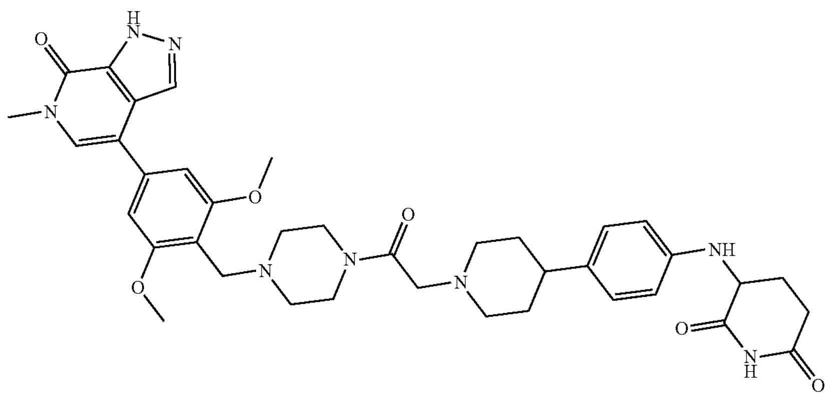 [SMILES: COc1cc(-c2cn(C)c(=O)c3[nH]ncc23)cc(OC)c1CN1CCN(C(=O)CN2CCC(c3ccc(NC4CCC(=O)NC4=O)cc3)CC2)CC1] | +++ |
| 2 | Enantiomer 1 | +++ |
| 3 | Enantiomer 2 | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 4 | 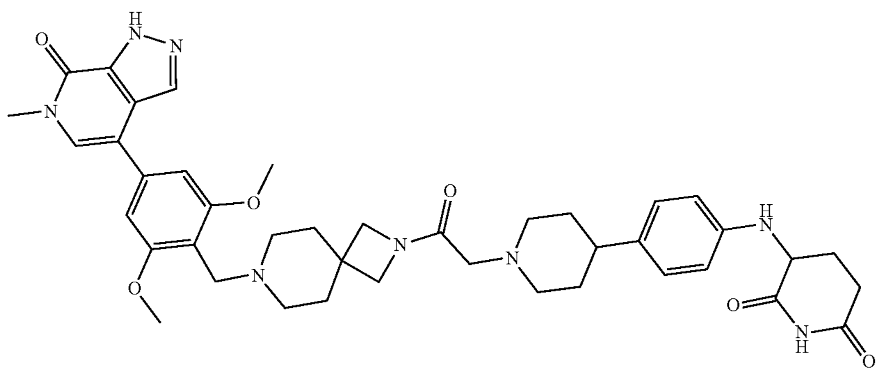 [SMILES: COc1cc(-c2cn(C)c(=O)c3[nH]ncc23)cc(OC)c1CN1CCC2(CC1)CN(C(=O)CN1CCC(c3ccc(NC4CCC(=O)NC4=O)cc3)CC1)C2] | +++ |
| 5 | 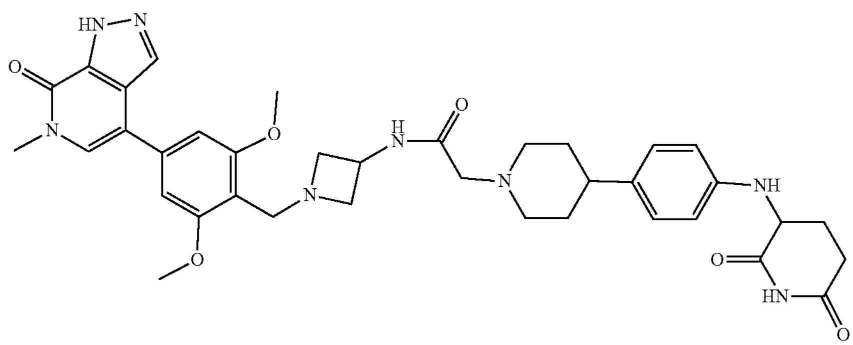 [SMILES: COc1cc(-c2cn(C)c(=O)c3[nH]ncc23)cc(OC)c1CN1CC(NC(=O)CN2CCC(c3ccc(NC4CCC(=O)NC4=O)cc3)CC2)C1] | +++ |
| 6 | 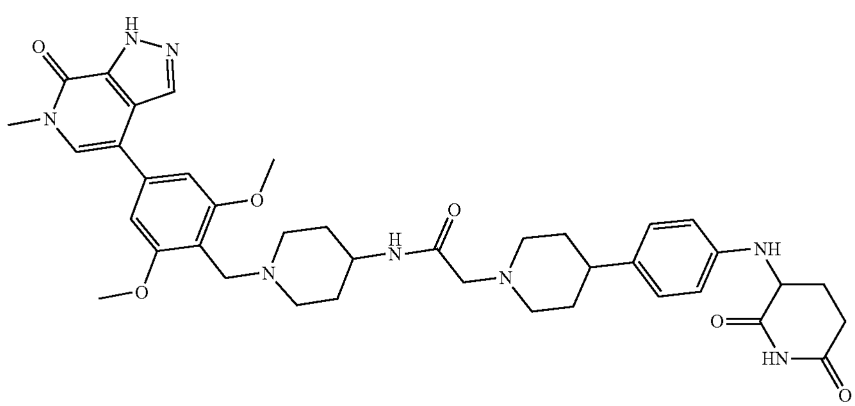 [SMILES: COc1cc(-c2cn(C)c(=O)c3[nH]ncc23)cc(OC)c1CN1CCC(NC(=O)CN2CCC(c3ccc(NC4CCC(=O)NC4=O)cc3)CC2)CC1] | +++ |
| 7 | 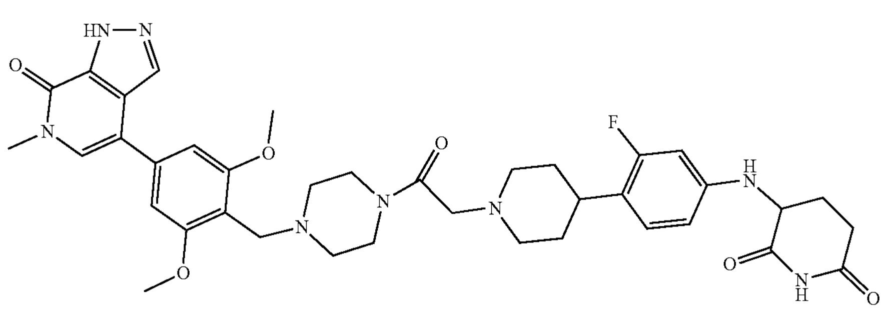 [SMILES: COc1cc(-c2cn(C)c(=O)c3[nH]ncc23)cc(OC)c1CN1CCN(C(=O)CN2CCC(c3ccc(NC4CCC(=O)NC4=O)cc3F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 8 | 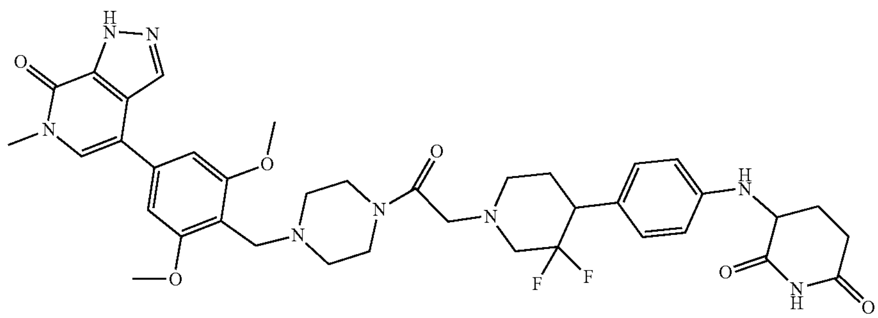 [SMILES: COc1cc(-c2cn(C)c(=O)c3[nH]ncc23)cc(OC)c1CN1CCN(C(=O)CN2CCC(c3ccc(NC4CCC(=O)NC4=O)cc3)C(F)(F)C2)CC1] | +++ |
| 9 | 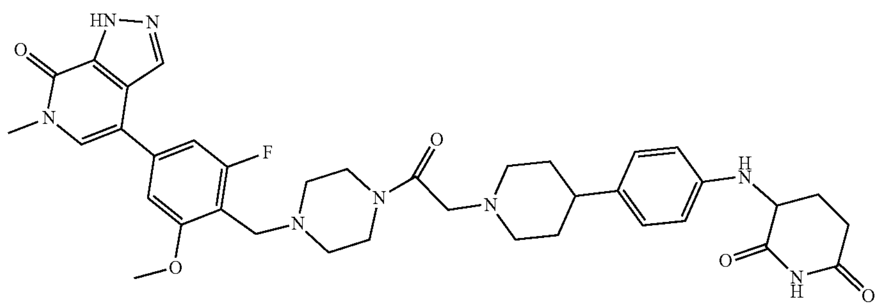 [SMILES: COc1cc(-c2cn(C)c(=O)c3[nH]ncc23)cc(F)c1CN1CCN(C(=O)CN2CCC(c3ccc(NC4CCC(=O)NC4=O)cc3)CC2)CC1] | +++ |
| 10 | 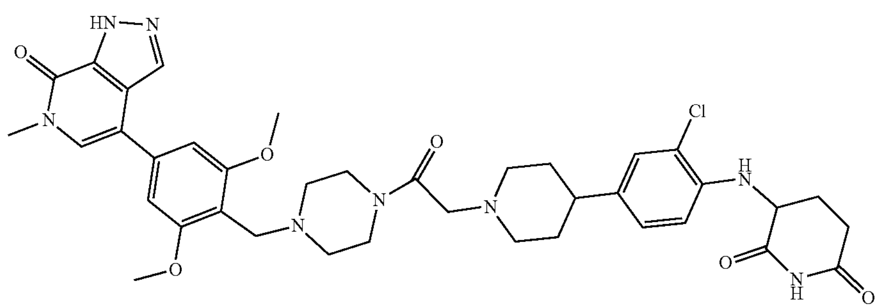 [SMILES: COc1cc(-c2cn(C)c(=O)c3[nH]ncc23)cc(OC)c1CN1CCN(C(=O)CN2CCC(c3ccc(NC4CCC(=O)NC4=O)c(Cl)c3)CC2)CC1] | +++ |
| 11 | 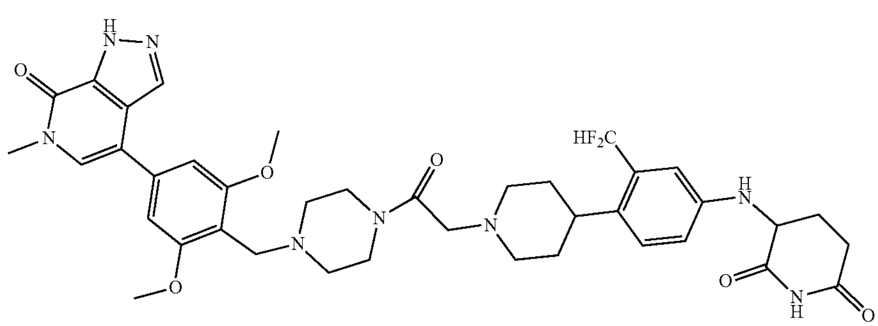 | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 12 | 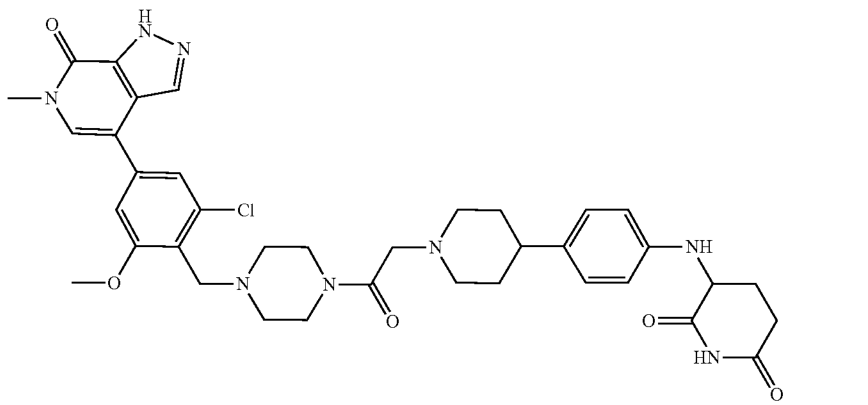 [SMILES: COc1cc(-c2cn(C)c(=O)c3[nH]ncc23)cc(Cl)c1CN1CCN(C(=O)CN2CCC(c3ccc(NC4CCC(=O)NC4=O)cc3)CC2)CC1] | +++ |
| 13 | 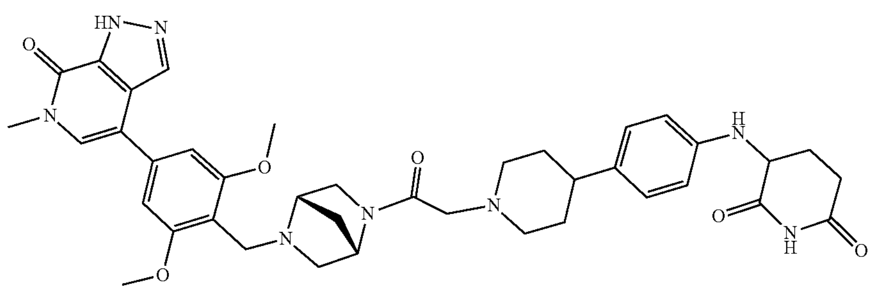 [SMILES: COc1cc(-c2cn(C)c(=O)c3[nH]ncc23)cc(OC)c1CN1C[C@@H]2C[C@H]1CN2C(=O)CN1CCC(c2ccc(NC3CCC(=O)NC3=O)cc2)CC1] | +++ |
| 14 | 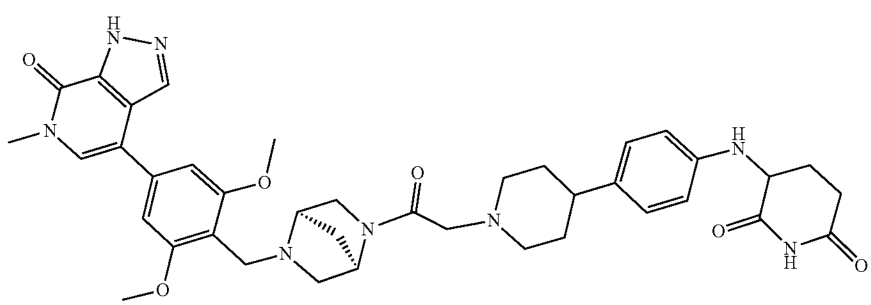 [SMILES: COc1cc(-c2cn(C)c(=O)c3[nH]ncc23)cc(OC)c1CN1C[C@H]2C[C@@H]1CN2C(=O)CN1CCC(c2ccc(NC3CCC(=O)NC3=O)cc2)CC1] | +++ |
| 15 | 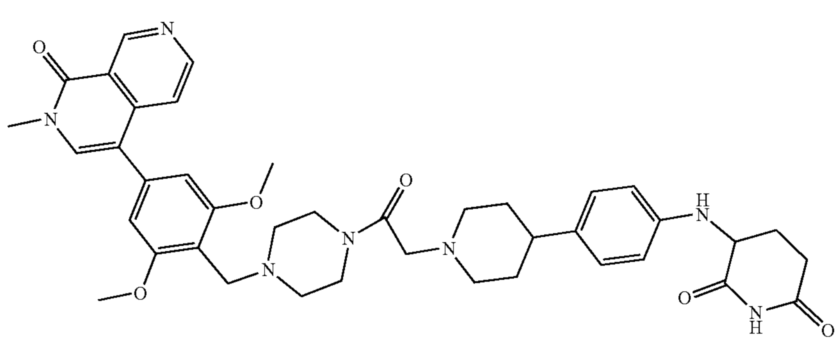 [SMILES: COc1cc(-c2cn(C)c(=O)c3cnccc23)cc(OC)c1CN1CCN(C(=O)CN2CCC(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 16 | 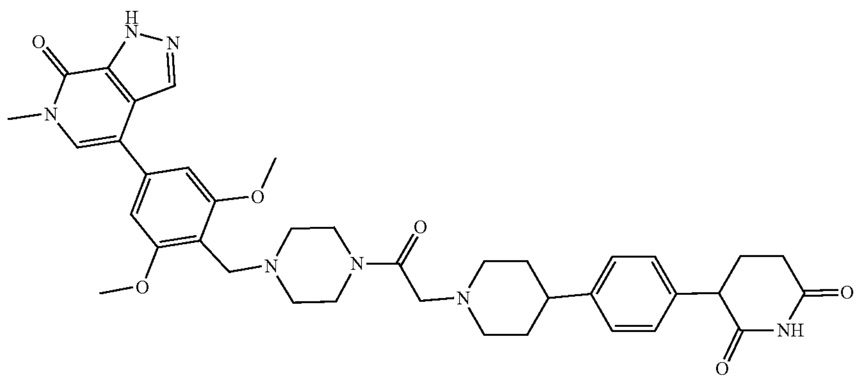 [SMILES: COc1cc(-c2cn(C)c(=O)c3[nH]ncc23)cc(OC)c1CN1CCN(C(=O)CN2CCC(c3ccc(C4CCC(=O)NC4=O)cc3)CC2)CC1] | +++ |
| 17 | 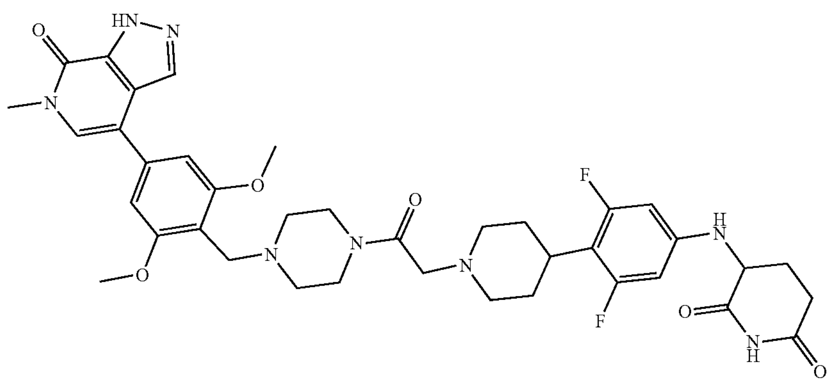 [SMILES: COc1cc(-c2cn(C)c(=O)c3[nH]ncc23)cc(OC)c1CN1CCN(C(=O)CN2CCC(c3c(F)cc(NC4CCC(=O)NC4=O)cc3F)CC2)CC1] | +++ |
| 18 | 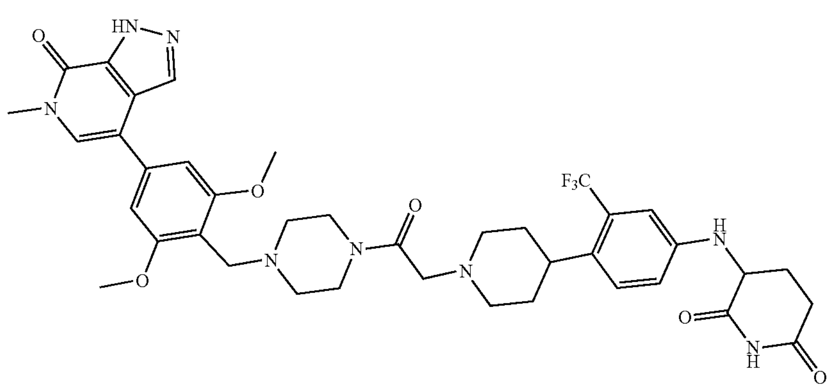 [SMILES: COc1cc(-c2cn(C)c(=O)c3[nH]ncc23)cc(OC)c1CN1CCN(C(=O)CN2CCC(c3ccc(NC4CCC(=O)NC4=O)cc3C(F)(F)F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 19 | 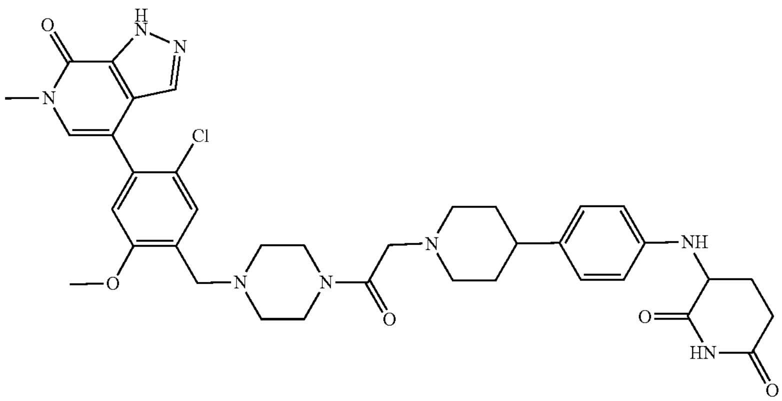 [SMILES: COc1cc(-c2cn(C)c(=O)c3[nH]ncc23)c(Cl)cc1CN1CCN(C(=O)CN2CCC(c3ccc(NC4CCC(=O)NC4=O)cc3)CC2)CC1] | +++ |
| 20 | 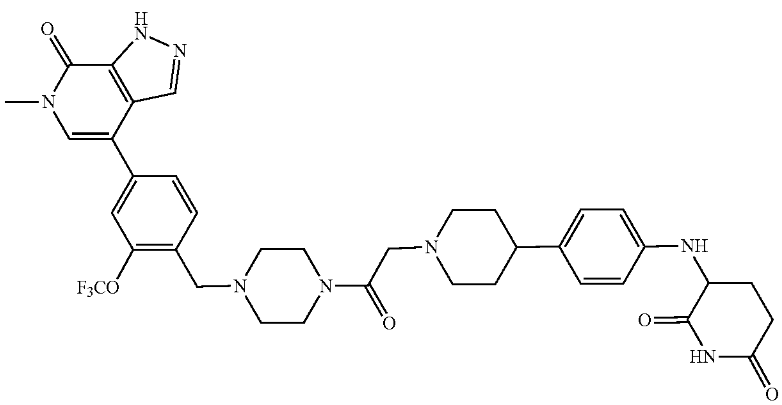 [SMILES: Cn1cc(-c2ccc(CN3CCN(C(=O)CN4CCC(c5ccc(NC6CCC(=O)NC6=O)cc5)CC4)CC3)c(OC(F)(F)F)c2)c2cn[nH]c2c1=O] | +++ |
| 21 | 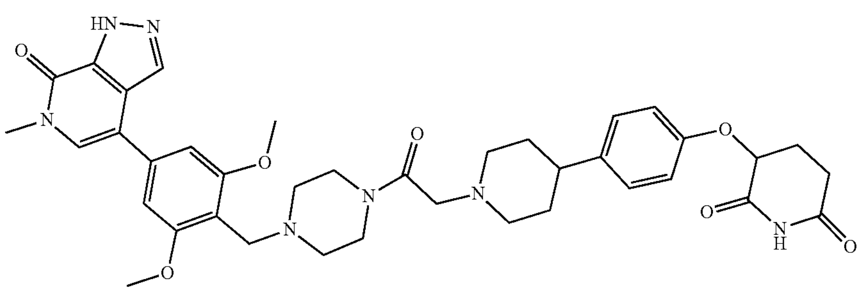 [SMILES: COc1cc(-c2cn(C)c(=O)c3[nH]ncc23)cc(OC)c1CN1CCN(C(=O)CN2CCC(c3ccc(OC4CCC(=O)NC4=O)cc3)CC2)CC1] | +++ |
| 22 | 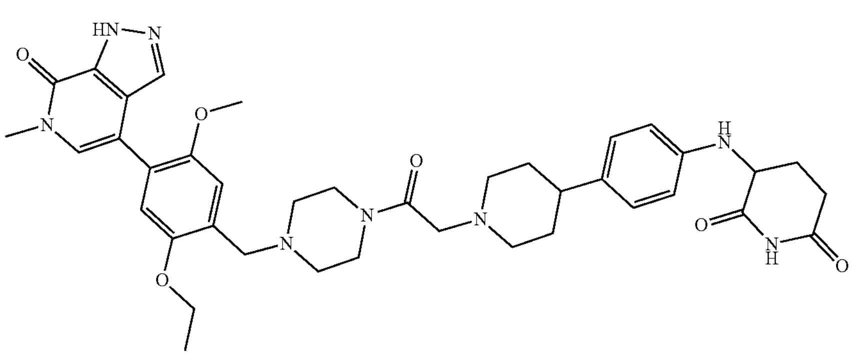 [SMILES: CCOc1cc(-c2cn(C)c(=O)c3[nH]ncc23)c(OC)cc1CN1CCN(C(=O)CN2CCC(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 23 | 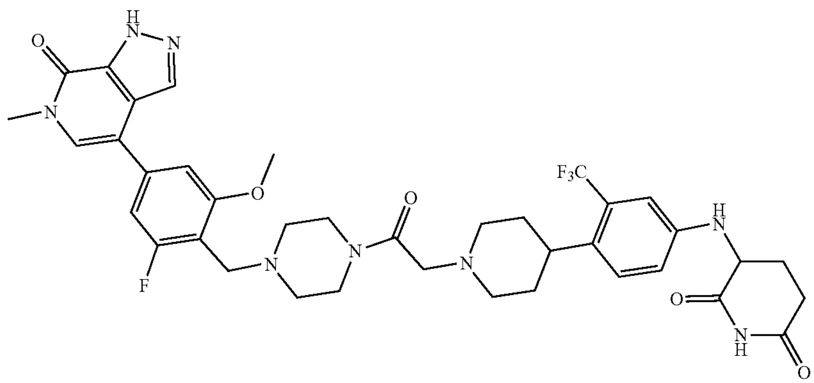 [SMILES: COc1cc(-c2cn(C)c(=O)c3[nH]ncc23)cc(F)c1CN1CCN(C(=O)CN2CCC(c3ccc(NC4CCC(=O)NC4=O)cc3C(F)(F)F)CC2)CC1] | +++ |
| 24 | 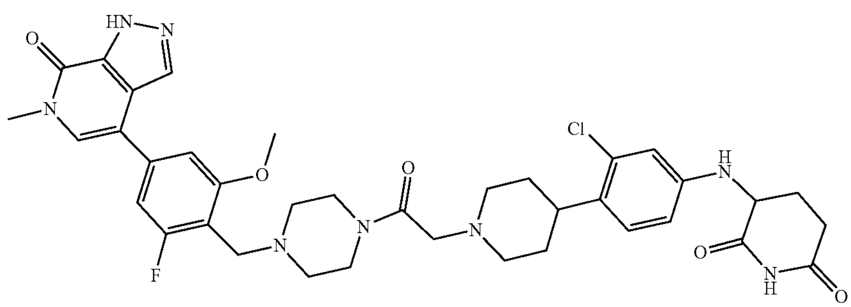 [SMILES: COc1cc(-c2cn(C)c(=O)c3[nH]ncc23)cc(F)c1CN1CCN(C(=O)CN2CCC(c3ccc(NC4CCC(=O)NC4=O)cc3Cl)CC2)CC1] | +++ |
| 25 | 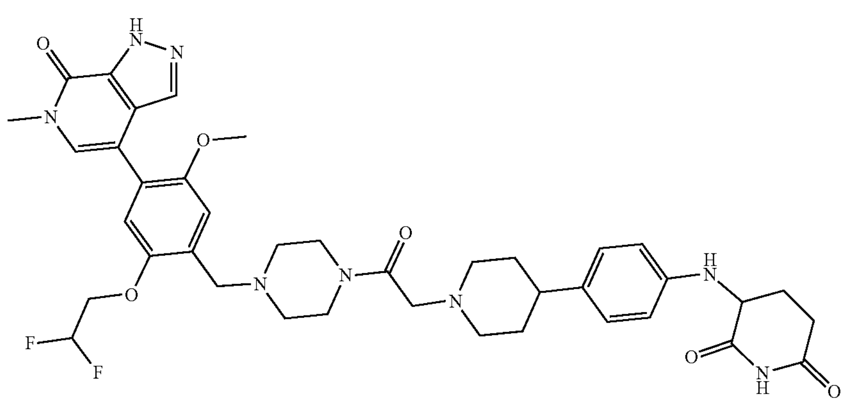 [SMILES: COc1cc(CN2CCN(C(=O)CN3CCC(c4ccc(NC5CCC(=O)NC5=O)cc4)CC3)CC2)c(OCC(F)F)cc1-c1cn(C)c(=O)c2[nH]ncc12] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 26 | 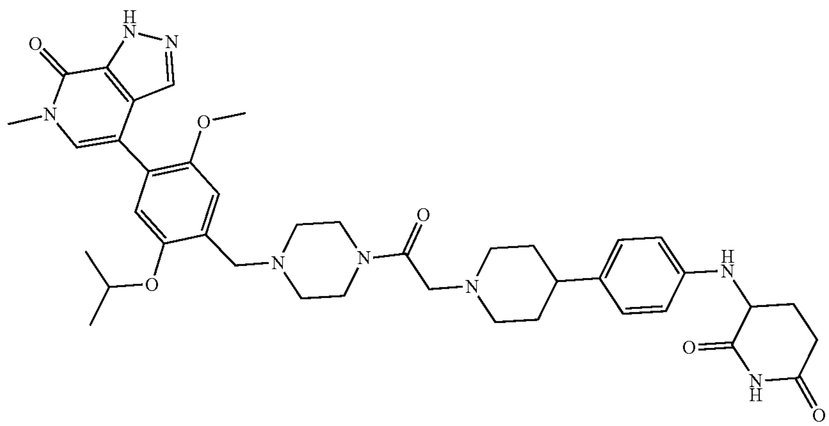 [SMILES: COc1cc(CN2CCN(C(=O)CN3CCC(c4ccc(NC5CCC(=O)NC5=O)cc4)CC3)CC2)c(OC(C)C)cc1-c1cn(C)c(=O)c2[nH]ncc12] | +++ |
| 27 | 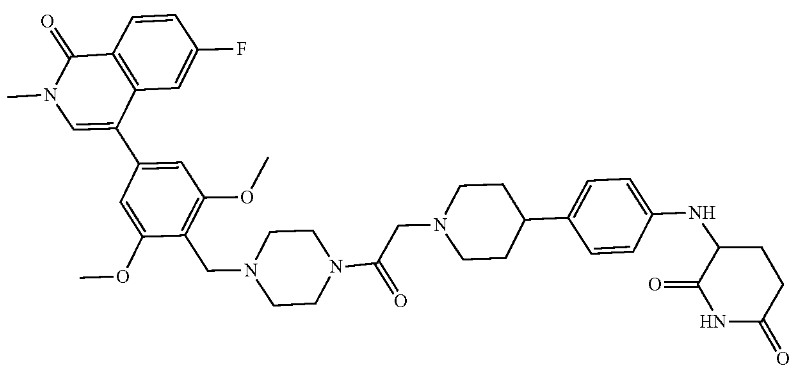 [SMILES: COc1cc(-c2cn(C)c(=O)c3ccc(F)cc23)cc(OC)c1CN1CCN(C(=O)CN2CCC(c3ccc(NC4CCC(=O)NC4=O)cc3)CC2)CC1] | +++ |
| 28 | 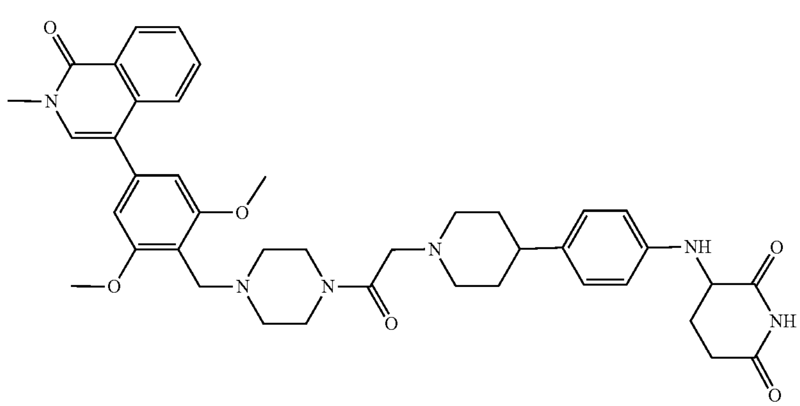 [SMILES: COc1cc(-c2cn(C)c(=O)c3ccccc23)cc(OC)c1CN1CCN(C(=O)CN2CCC(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 29 | 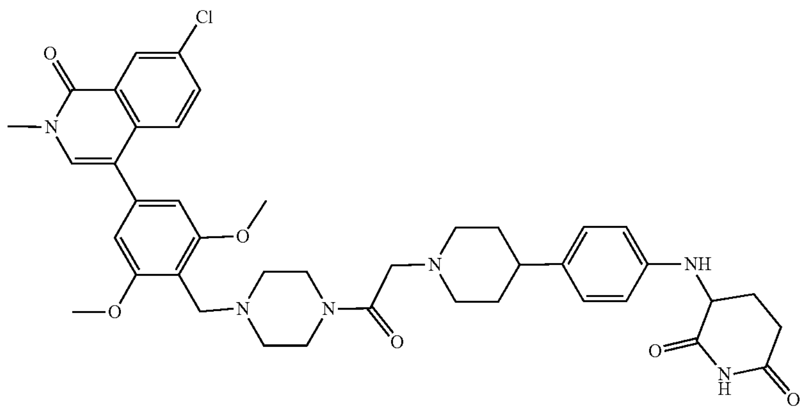 [SMILES: COc1cc(-c2cn(C)c(=O)c3cc(Cl)ccc23)cc(OC)c1CN1CCN(C(=O)CN2CCC(c3ccc(NC4CCC(=O)NC4=O)cc3)CC2)CC1] | +++ |
| 30 | 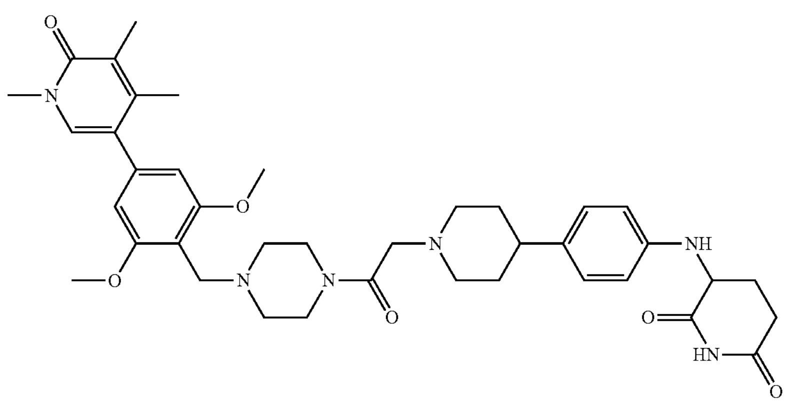 [SMILES: COc1cc(-c2cn(C)c(=O)c(C)c2C)cc(OC)c1CN1CCN(C(=O)CN2CCC(c3ccc(NC4CCC(=O)NC4=O)cc3)CC2)CC1] | +++ |
| 31 | 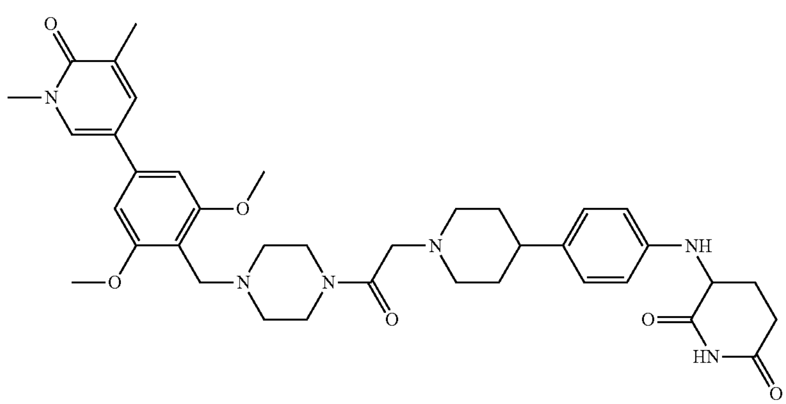 [SMILES: COc1cc(-c2cc(C)c(=O)n(C)c2)cc(OC)c1CN1CCN(C(=O)CN2CCC(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 32 | 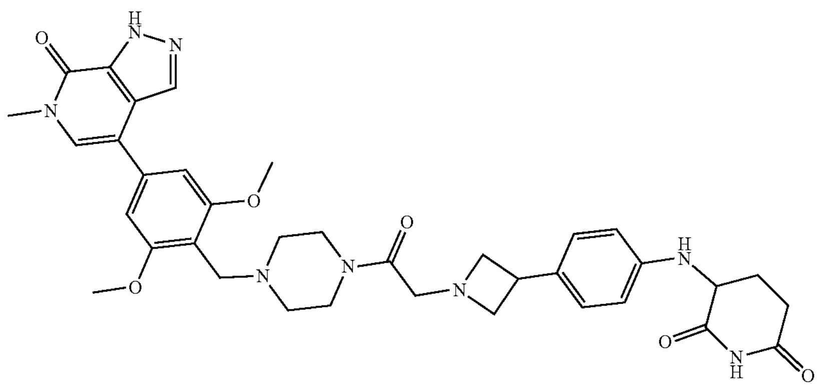 [SMILES: COc1cc(-c2cn(C)c(=O)c3[nH]ncc23)cc(OC)c1CN1CCN(C(=O)CN2CC(c3ccc(NC4CCC(=O)NC4=O)cc3)C2)CC1] | +++ |
| 33 | 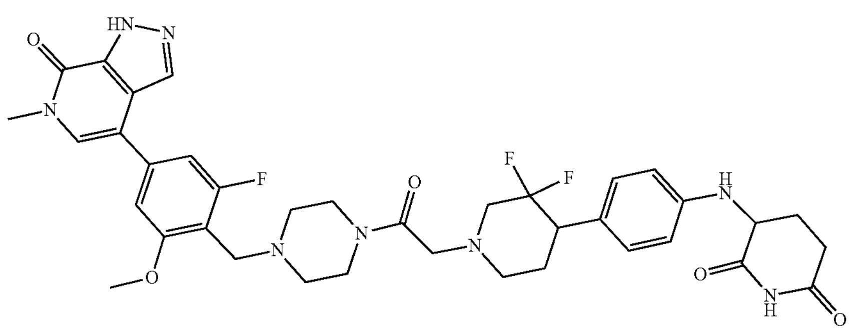 [SMILES: COc1cc(-c2cn(C)c(=O)c3[nH]ncc23)cc(F)c1CN1CCN(C(=O)CN2CCC(c3ccc(NC4CCC(=O)NC4=O)cc3)C(F)(F)C2)CC1] | +++ |
| 34 | 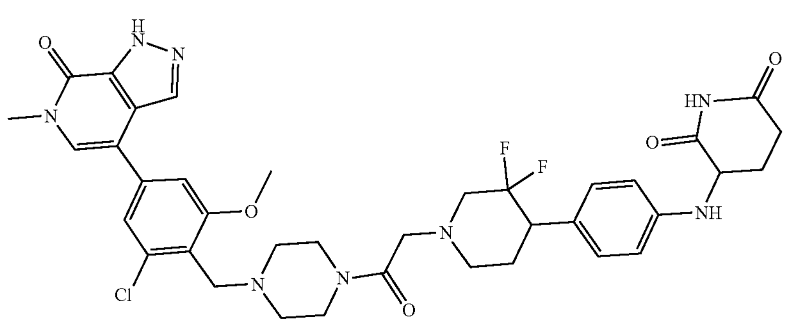 [SMILES: COc1cc(-c2cn(C)c(=O)c3[nH]ncc23)cc(Cl)c1CN1CCN(C(=O)CN2CCC(c3ccc(NC4CCC(=O)NC4=O)cc3)C(F)(F)C2)CC1] | +++ |
| 35 | 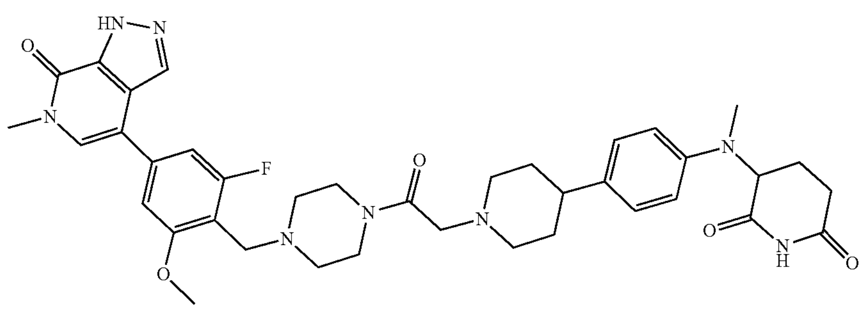 [SMILES: COc1cc(-c2cn(C)c(=O)c3[nH]ncc23)cc(F)c1CN1CCN(C(=O)CN2CCC(c3ccc(N(C)C4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 36 | 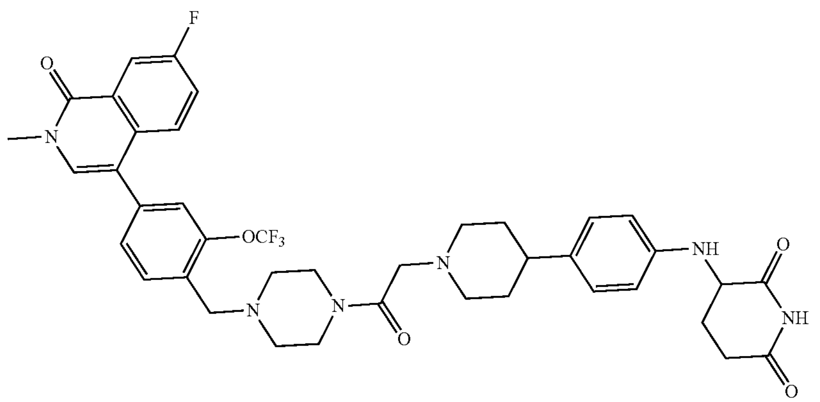 [SMILES: Cn1cc(-c2ccc(CN3CCN(C(=O)CN4CCC(c5ccc(NC6CCC(=O)NC6=O)cc5)CC4)CC3)c(OC(F)(F)F)c2)c2ccc(F)cc2c1=O] | +++ |
| 37 | 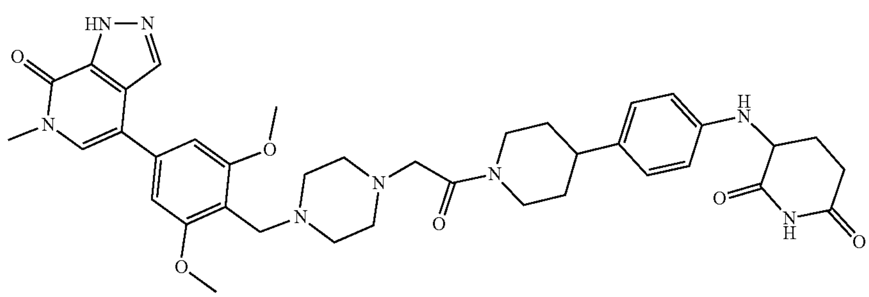 [SMILES: COc1cc(-c2cn(C)c(=O)c3[nH]ncc23)cc(OC)c1CN1CCN(CC(=O)N2CCC(c3ccc(NC4CCC(=O)NC4=O)cc3)CC2)CC1] | +++ |
| 38 | 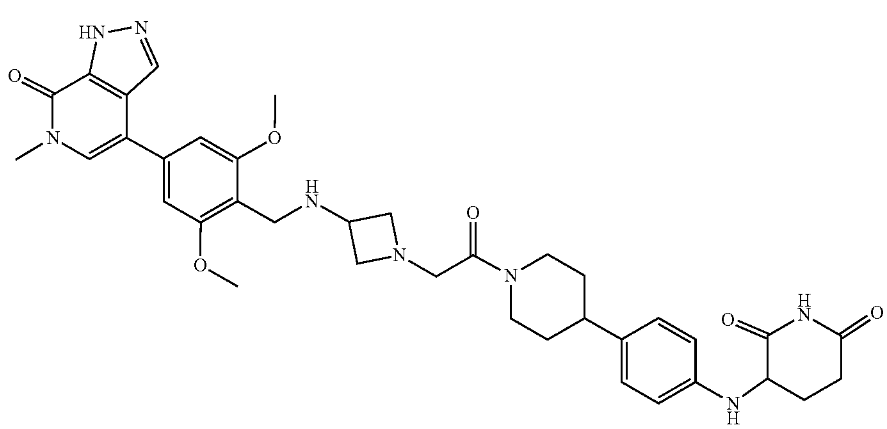 [SMILES: COc1cc(-c2cn(C)c(=O)c3[nH]ncc23)cc(OC)c1CNC1CN(CC(=O)N2CCC(c3ccc(NC4CCC(=O)NC4=O)cc3)CC2)C1] | ++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 39 | 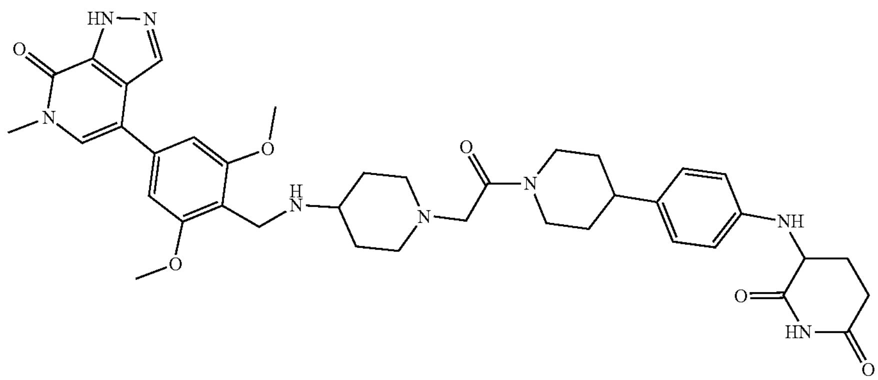 [SMILES: COc1cc(-c2cn(C)c(=O)c3[nH]ncc23)cc(OC)c1CNC1CCN(CC(=O)N2CCC(c3ccc(NC4CCC(=O)NC4=O)cc3)CC2)CC1] | +++ |
| 40 | 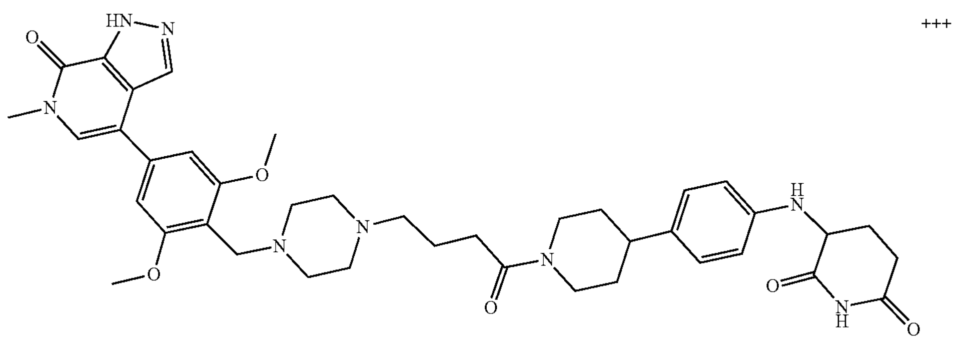 | +++ |
| 41 | 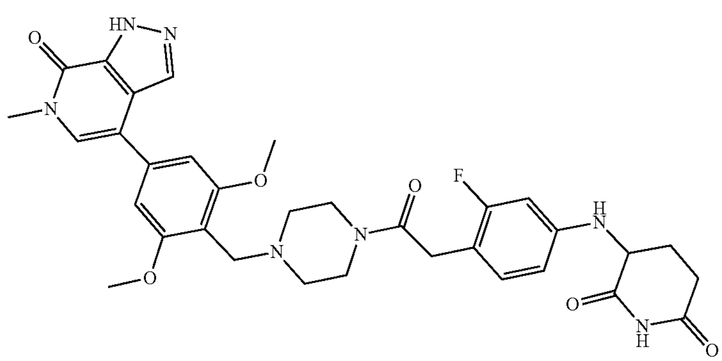 [SMILES: COc1cc(-c2cn(C)c(=O)c3[nH]ncc23)cc(OC)c1CN1CCN(C(=O)Cc2ccc(NC3CCC(=O)NC3=O)cc2F)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 42 | 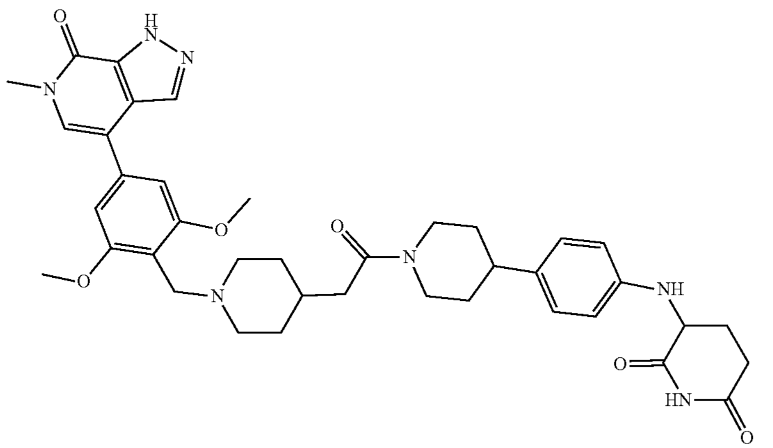 [SMILES: COc1cc(-c2cn(C)c(=O)c3[nH]ncc23)cc(OC)c1CN1CCC(CC(=O)N2CCC(c3ccc(NC4CCC(=O)NC4=O)cc3)CC2)CC1] | +++ |
| 43 | 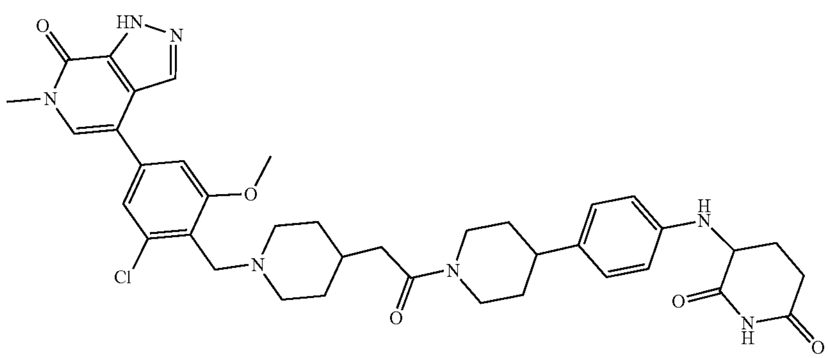 [SMILES: COc1cc(-c2cn(C)c(=O)c3[nH]ncc23)cc(Cl)c1CN1CCC(CC(=O)N2CCC(c3ccc(NC4CCC(=O)NC4=O)cc3)CC2)CC1] | +++ |
| 44 | 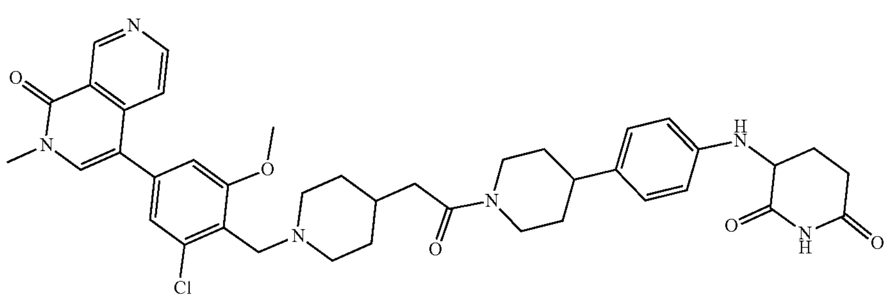 [SMILES: COc1cc(-c2cn(C)c(=O)c3cnccc23)cc(Cl)c1CN1CCC(CC(=O)N2CCC(c3ccc(NC4CCC(=O)NC4=O)cc3)CC2)CC1] | +++ |
| 45 | 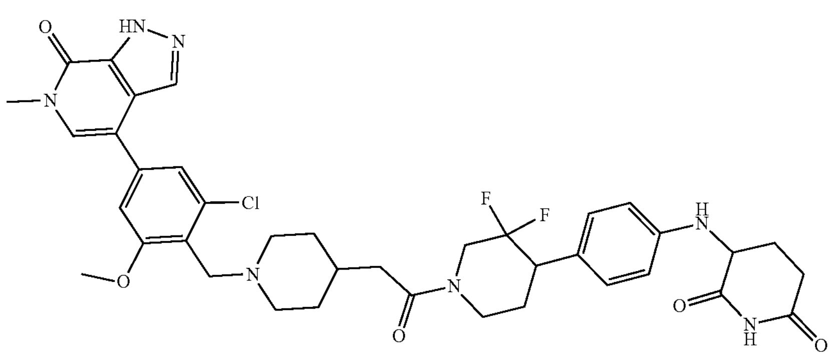 [SMILES: COc1cc(-c2cn(C)c(=O)c3[nH]ncc23)cc(Cl)c1CN1CCC(CC(=O)N2CCC(c3ccc(NC4CCC(=O)NC4=O)cc3)C(F)(F)C2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 46 | 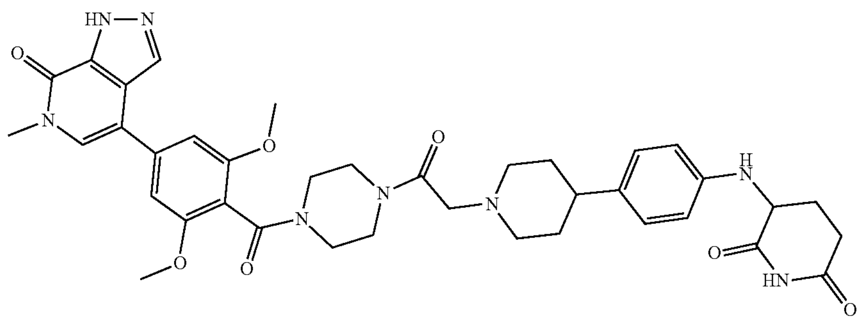 [SMILES: COc1cc(-c2cn(C)c(=O)c3[nH]ncc23)cc(OC)c1C(=O)N1CCN(C(=O)CN2CCC(c3ccc(NC4CCC(=O)NC4=O)cc3)CC2)CC1] | +++ |
| 47 | 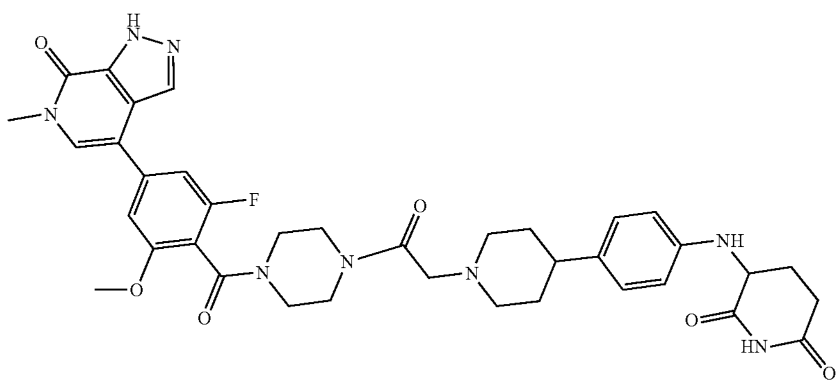 [SMILES: COc1cc(-c2cn(C)c(=O)c3[nH]ncc23)cc(F)c1C(=O)N1CCN(C(=O)CN2CCC(c3ccc(NC4CCC(=O)NC4=O)cc3)CC2)CC1] | +++ |
| 48 | 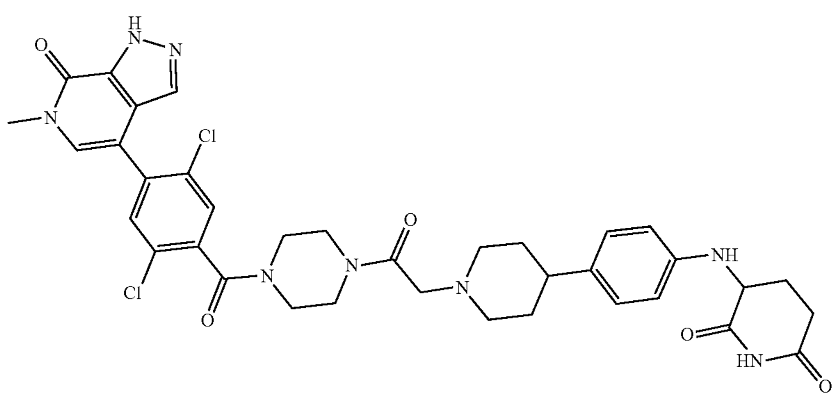 [SMILES: Cn1cc(-c2cc(Cl)c(C(=O)N3CCN(C(=O)CN4CCC(c5ccc(NC6CCC(=O)NC6=O)cc5)CC4)CC3)cc2Cl)c2cn[nH]c2c1=O] | ++ |
| 49 | 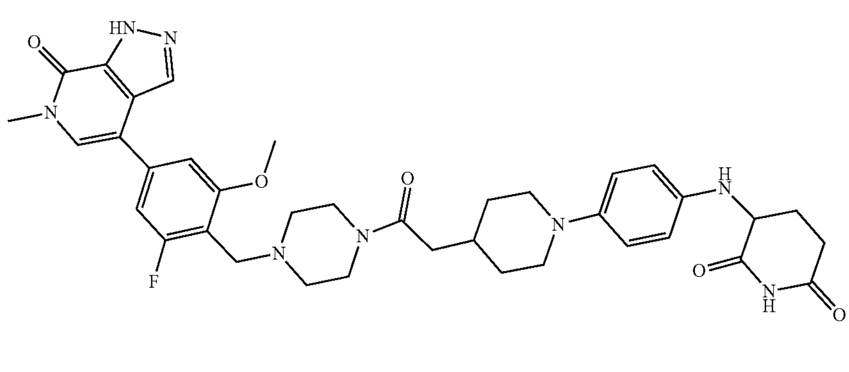 [SMILES: COc1cc(-c2cn(C)c(=O)c3[nH]ncc23)cc(F)c1CN1CCN(C(=O)CC2CCN(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 50 | 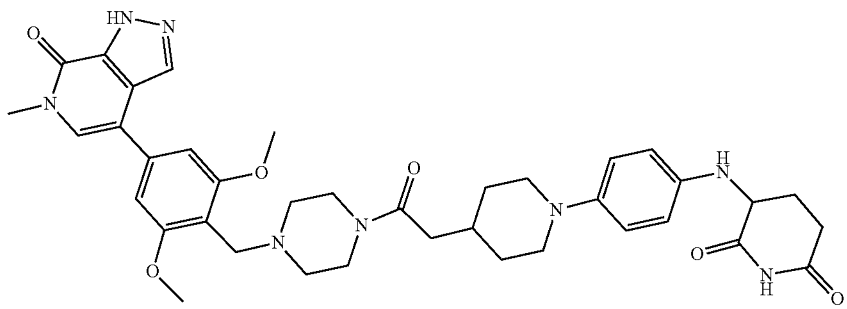 [SMILES: COc1cc(-c2cn(C)c(=O)c3[nH]ncc23)cc(OC)c1CN1CCN(C(=O)CC2CCN(c3ccc(NC4CCC(=O)NC4=O)cc3)CC2)CC1] | +++ |
| 51 | 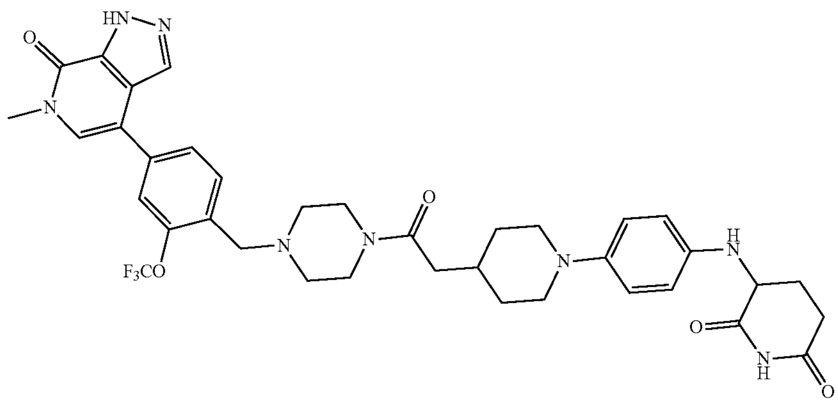 [SMILES: Cn1cc(-c2ccc(CN3CCN(C(=O)CC4CCN(c5ccc(NC6CCC(=O)NC6=O)cc5)CC4)CC3)c(OC(F)(F)F)c2)c2cn[nH]c2c1=O] | +++ |
| 52 | 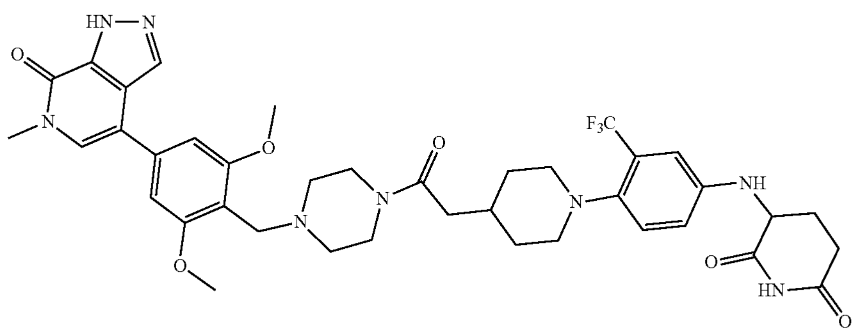 [SMILES: COc1cc(-c2cn(C)c(=O)c3[nH]ncc23)cc(OC)c1CN1CCN(C(=O)CC2CCN(c3ccc(NC4CCC(=O)NC4=O)cc3C(F)(F)F)CC2)CC1] | +++ |
| 53 | 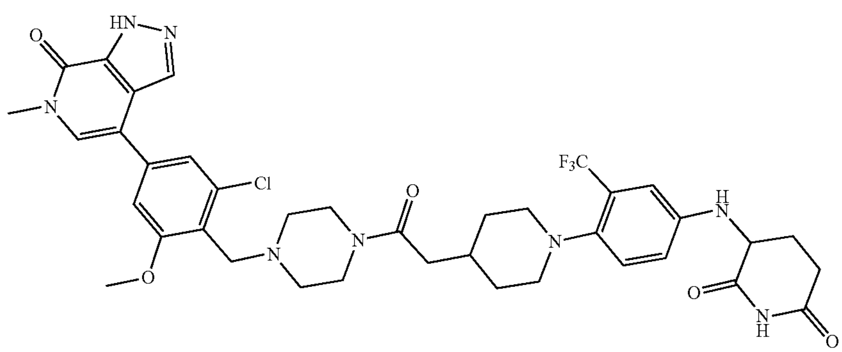 [SMILES: COc1cc(-c2cn(C)c(=O)c3[nH]ncc23)cc(Cl)c1CN1CCN(C(=O)CC2CCN(c3ccc(NC4CCC(=O)NC4=O)cc3C(F)(F)F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 54 | 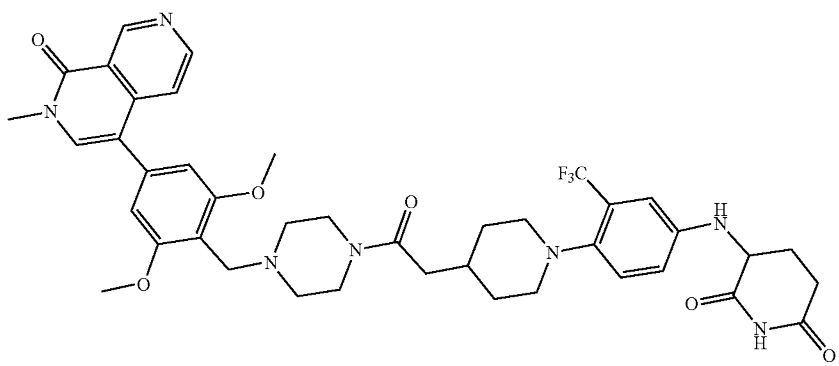 [SMILES: COc1cc(-c2cn(C)c(=O)c3cnccc23)cc(OC)c1CN1CCN(C(=O)CC2CCN(c3ccc(NC4CCC(=O)NC4=O)cc3C(F)(F)F)CC2)CC1] | +++ |
| 55 | Enantiomer 1 | +++ |
| 56 | Enantiomer 2 | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 57 | 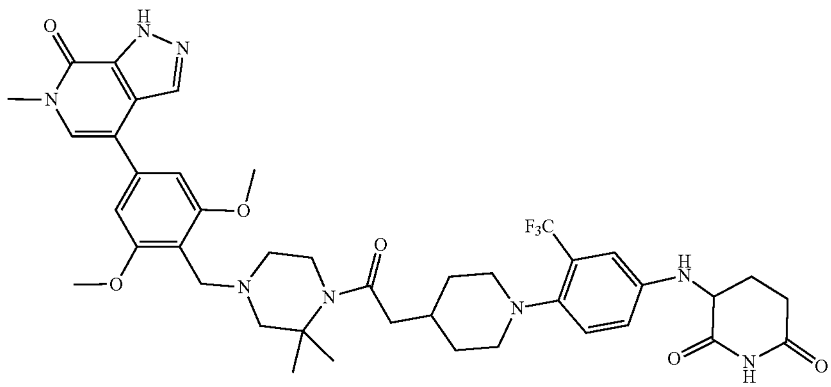 [SMILES: COc1cc(-c2cn(C)c(=O)c3[nH]ncc23)cc(OC)c1CN1CCN(C(=O)CC2CCN(c3ccc(NC4CCC(=O)NC4=O)cc3C(F)(F)F)CC2)C(C)(C)C1] | +++ |
| 58 | 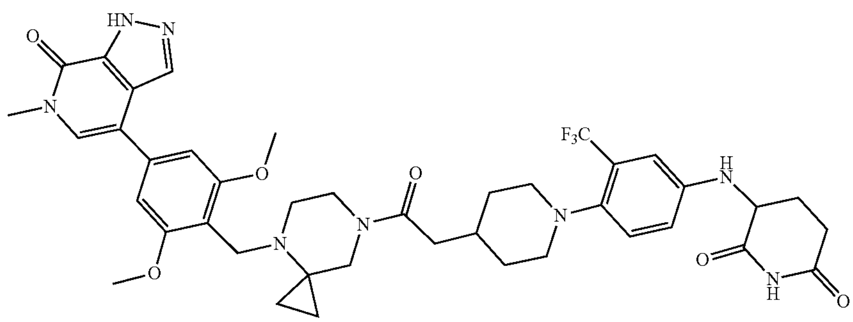 [SMILES: COc1cc(-c2cn(C)c(=O)c3[nH]ncc23)cc(OC)c1CN1CCN(C(=O)CC2CCN(c3ccc(NC4CCC(=O)NC4=O)cc3C(F)(F)F)CC2)CC12CC2] | +++ |
| 59 | 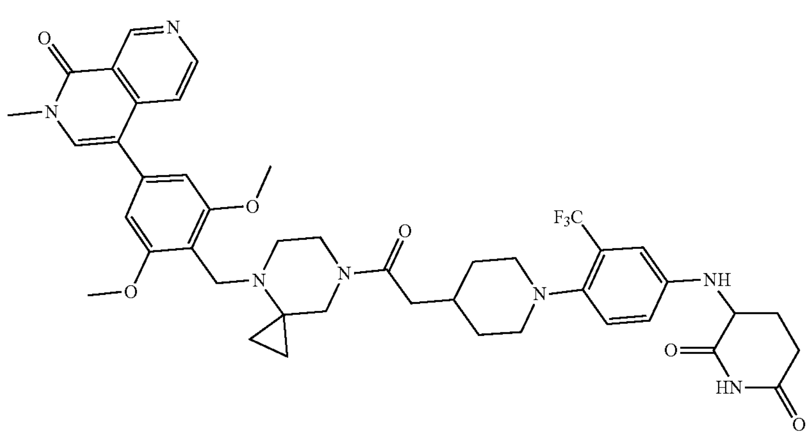 [SMILES: COc1cc(-c2cn(C)c(=O)c3cnccc23)cc(OC)c1CN1CCN(C(=O)CC2CCN(c3ccc(NC4CCC(=O)NC4=O)cc3C(F)(F)F)CC2)CC12CC2] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 60 | 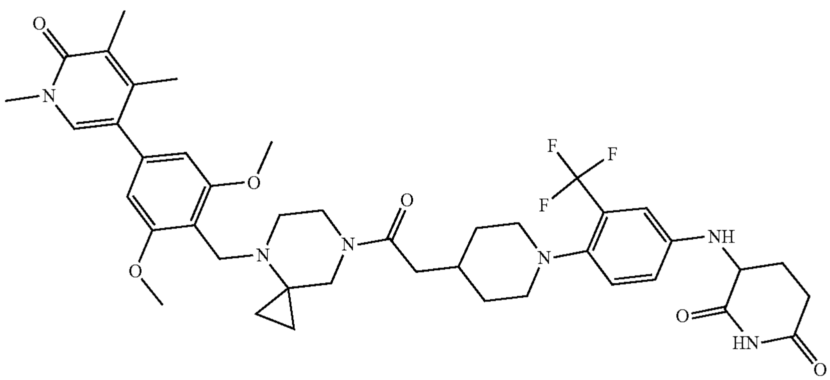 [SMILES: COc1cc(-c2cn(C)c(=O)c(C)c2C)cc(OC)c1CN1CCN(C(=O)CC2CCN(c3ccc(NC4CCC(=O)NC4=O)cc3C(F)(F)F)CC2)CC12CC2] | +++ |
| 61 | 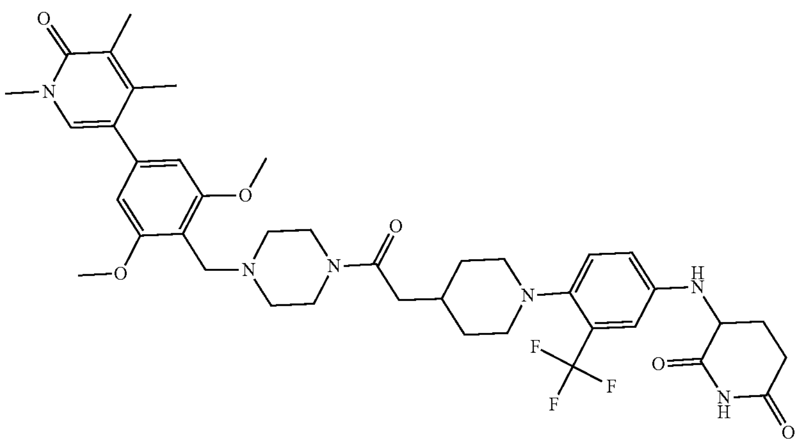 [SMILES: COc1cc(-c2cn(C)c(=O)c(C)c2C)cc(OC)c1CN1CCN(C(=O)CC2CCN(c3ccc(NC4CCC(=O)NC4=O)cc3C(F)(F)F)CC2)CC1] | +++ |
| 62 | 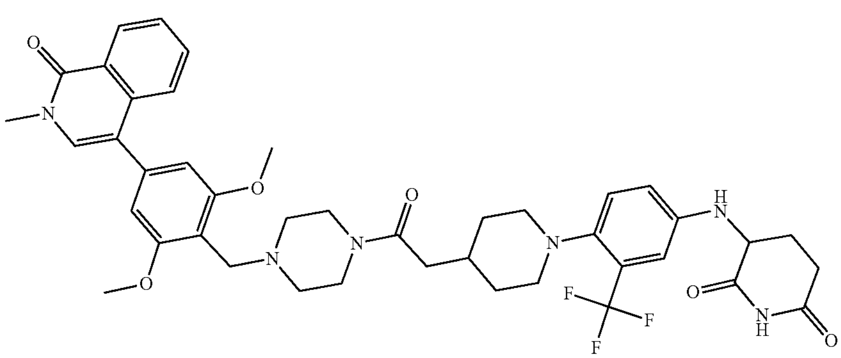 [SMILES: COc1cc(-c2cn(C)c(=O)c3ccccc23)cc(OC)c1CN1CCN(C(=O)CC2CCN(c3ccc(NC4CCC(=O)NC4=O)cc3C(F)(F)F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 63 | 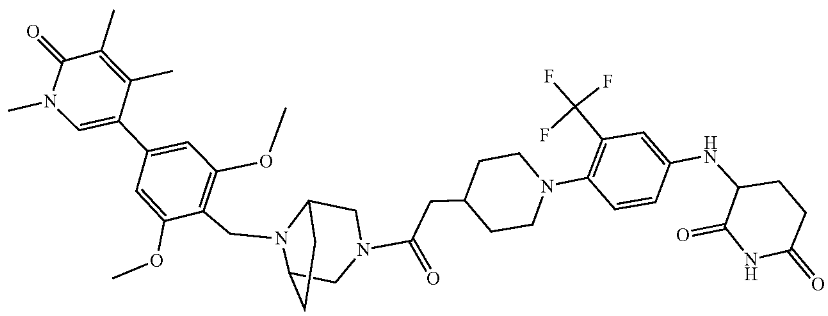 [SMILES: COc1cc(-c2cn(C)c(=O)c(C)c2C)cc(OC)c1CN1C2CCC1CN(C(=O)CC1CCN(c3ccc(NC4CCC(=O)NC4=O)cc3C(F)(F)F)CC1)C2] | +++ |
| 64 | 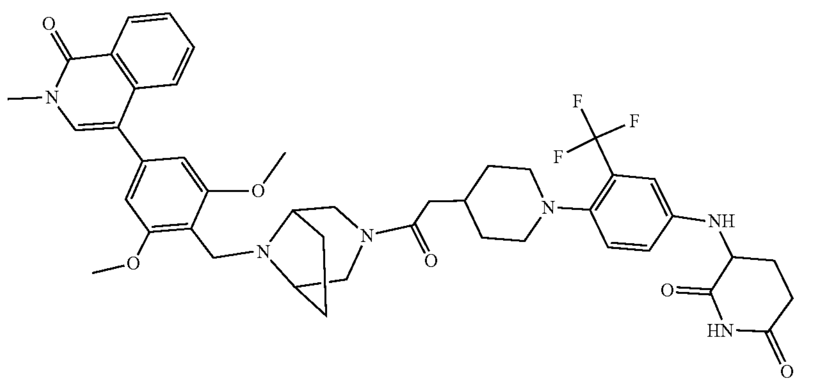 [SMILES: COc1cc(-c2cn(C)c(=O)c3ccccc23)cc(OC)c1CN1C2CCC1CN(C(=O)CC1CCN(c3ccc(NC4CCC(=O)NC4=O)cc3C(F)(F)F)CC1)C2] | +++ |
| 65 | 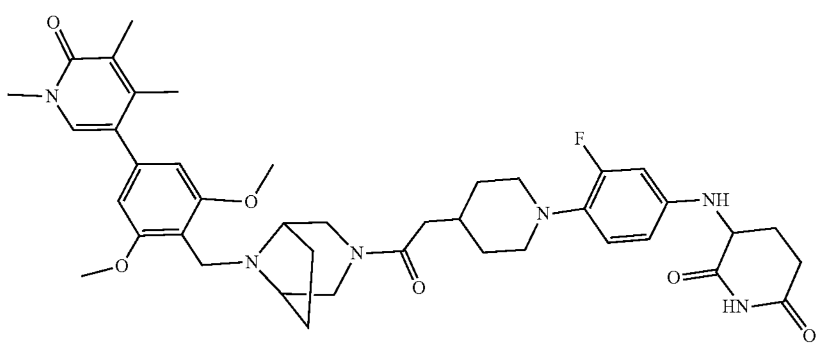 [SMILES: COc1cc(-c2cn(C)c(=O)c(C)c2C)cc(OC)c1CN1C2CCC1CN(C(=O)CC1CCN(c3ccc(NC4CCC(=O)NC4=O)cc3F)CC1)C2] | +++ |
| 66 | 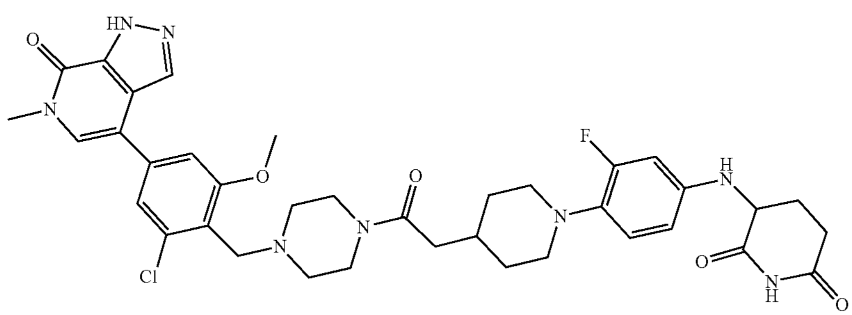 [SMILES: COc1cc(-c2cn(C)c(=O)c3[nH]ncc23)cc(Cl)c1CN1CCN(C(=O)CC2CCN(c3ccc(NC4CCC(=O)NC4=O)cc3F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 67 | 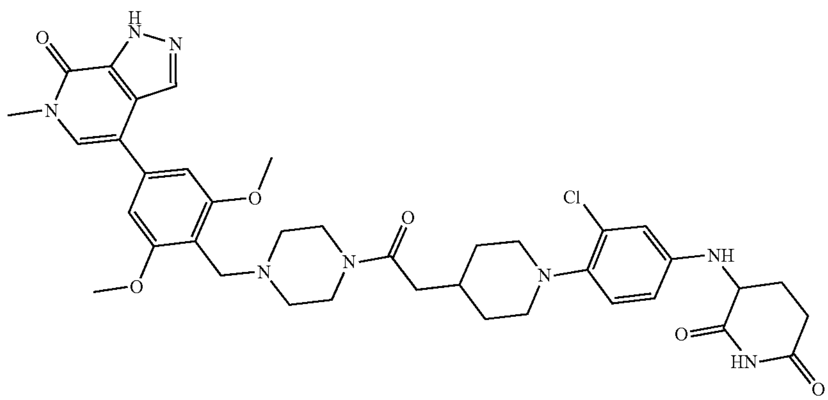 [SMILES: COc1cc(-c2cn(C)c(=O)c3[nH]ncc23)cc(OC)c1CN1CCN(C(=O)CC2CCN(c3ccc(NC4CCC(=O)NC4=O)cc3Cl)CC2)CC1] | +++ |
| 68 | 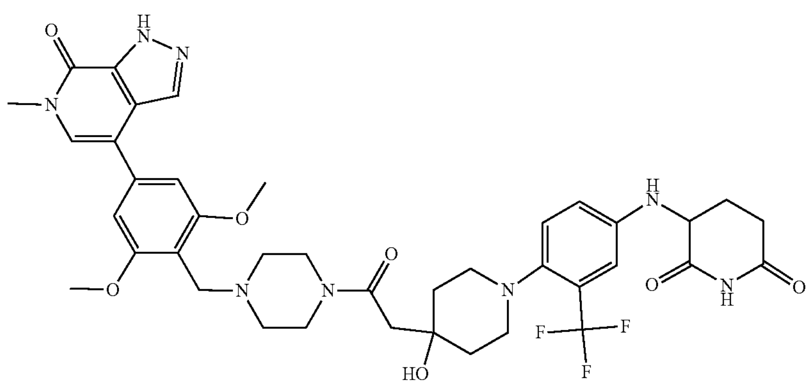 [SMILES: COc1cc(-c2cn(C)c(=O)c3[nH]ncc23)cc(OC)c1CN1CCN(C(=O)CC2(O)CCN(c3ccc(NC4CCC(=O)NC4=O)cc3C(F)(F)F)CC2)CC1] | +++ |
| 69 | 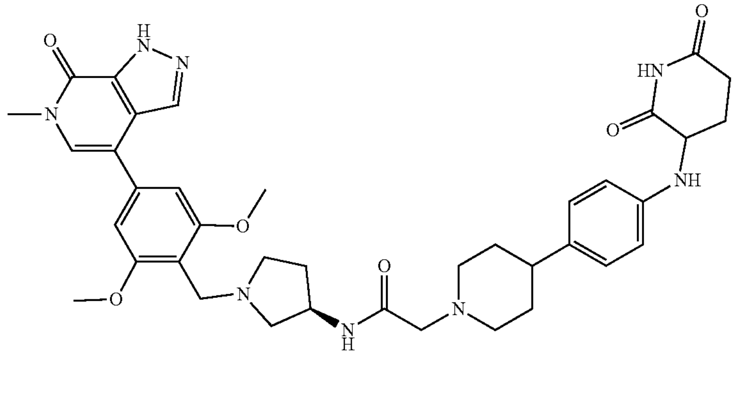 [SMILES: COc1cc(-c2cn(C)c(=O)c3[nH]ncc23)cc(OC)c1CN1CC[C@@H](NC(=O)CN2CCC(c3ccc(NC4CCC(=O)NC4=O)cc3)CC2)C1] | ++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 70 | 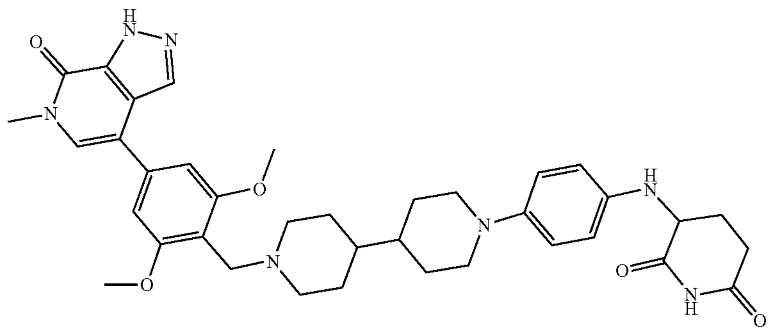 [SMILES: COc1cc(-c2cn(C)c(=O)c3[nH]ncc23)cc(OC)c1CN1CCC(C2CCN(c3ccc(NC4CCC(=O)NC4=O)cc3)CC2)CC1] | +++ |
| 71 | 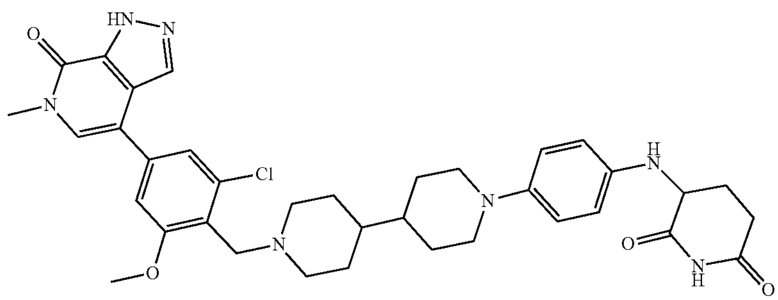 [SMILES: COc1cc(-c2cn(C)c(=O)c3[nH]ncc23)cc(Cl)c1CN1CCC(C2CCN(c3ccc(NC4CCC(=O)NC4=O)cc3)CC2)CC1] | +++ |
| 72 | 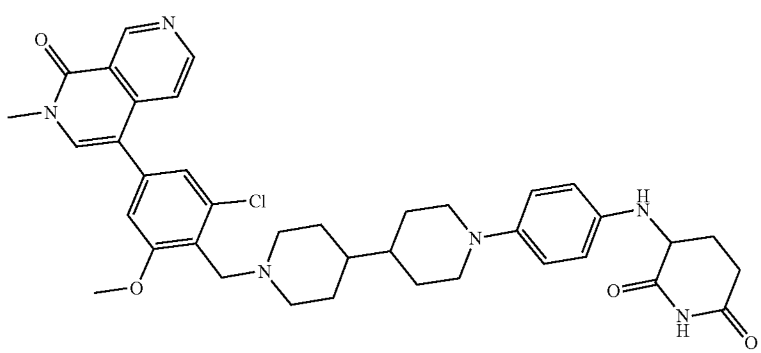 [SMILES: COc1cc(-c2cn(C)c(=O)c3cnccc23)cc(Cl)c1CN1CCC(C2CCN(c3ccc(NC4CCC(=O)NC4=O)cc3)CC2)CC1] | +++ |
| 73 | 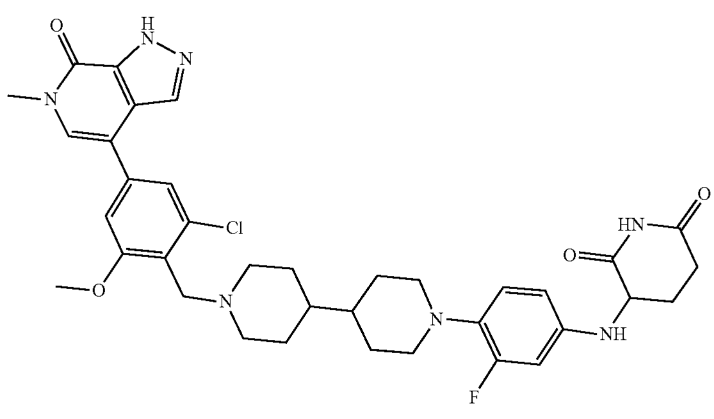 [SMILES: COc1cc(-c2cn(C)c(=O)c3[nH]ncc23)cc(Cl)c1CN1CCC(C2CCN(c3ccc(NC4CCC(=O)NC4=O)cc3F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 74 | 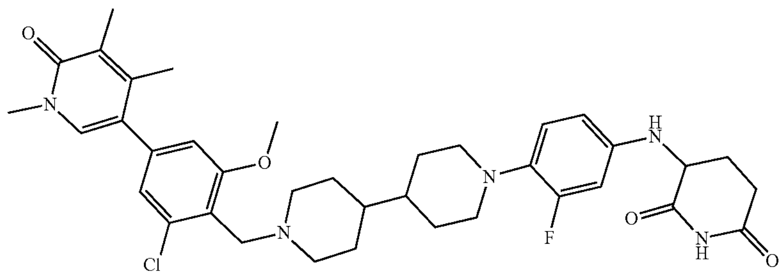 [SMILES: COc1cc(-c2cn(C)c(=O)c(C)c2C)cc(Cl)c1CN1CCC(C2CCN(c3ccc(NC4CCC(=O)NC4=O)cc3F)CC2)CC1] | +++ |
| 75 | 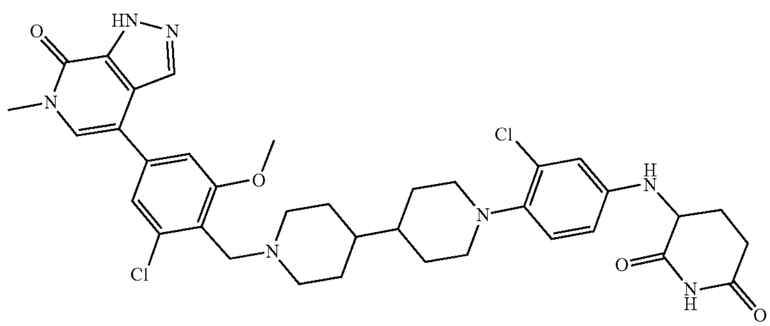 [SMILES: COc1cc(-c2cn(C)c(=O)c3[nH]ncc23)cc(Cl)c1CN1CCC(C2CCN(c3ccc(NC4CCC(=O)NC4=O)cc3Cl)CC2)CC1] | +++ |
| 76 | 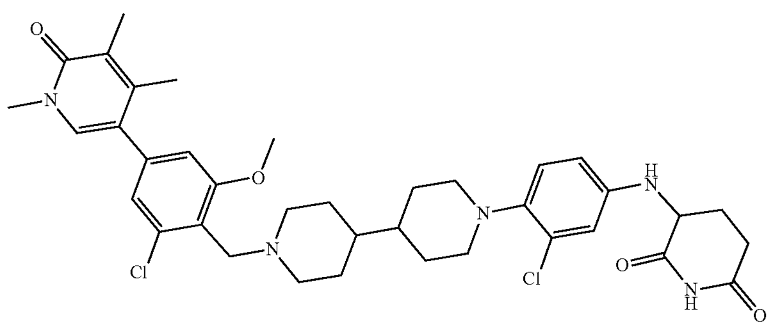 [SMILES: COc1cc(-c2cn(C)c(=O)c(C)c2C)cc(Cl)c1CN1CCC(C2CCN(c3ccc(NC4CCC(=O)NC4=O)cc3Cl)CC2)CC1] | +++ |
| 77 | 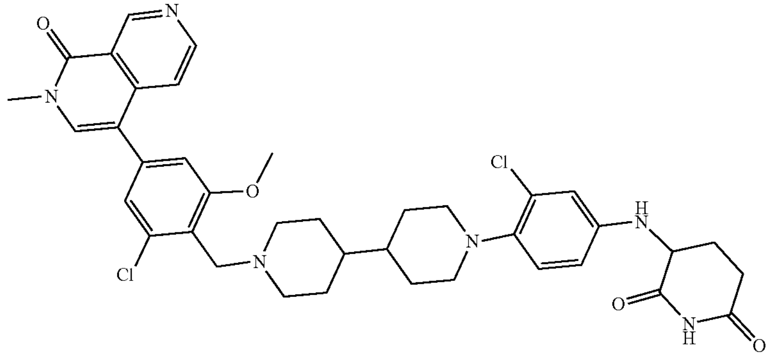 [SMILES: COc1cc(-c2cn(C)c(=O)c3cnccc23)cc(Cl)c1CN1CCC(C2CCN(c3ccc(NC4CCC(=O)NC4=O)cc3Cl)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 78 | 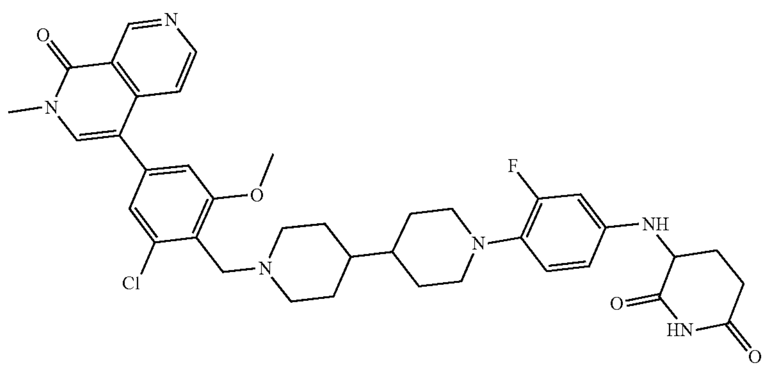 [SMILES: COc1cc(-c2cn(C)c(=O)c3cnccc23)cc(Cl)c1CN1CCC(C2CCN(c3ccc(NC4CCC(=O)NC4=O)cc3F)CC2)CC1] | +++ |
| 79 | 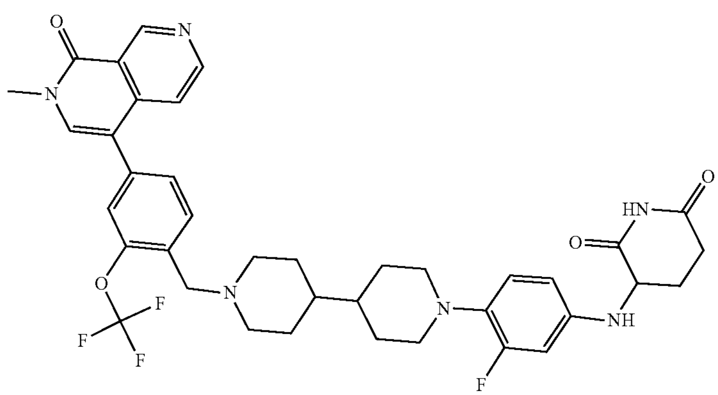 [SMILES: Cn1cc(-c2ccc(CN3CCC(C4CCN(c5ccc(NC6CCC(=O)NC6=O)cc5F)CC4)CC3)c(OC(F)(F)F)c2)c2ccncc2c1=O] | +++ |
| 80 | 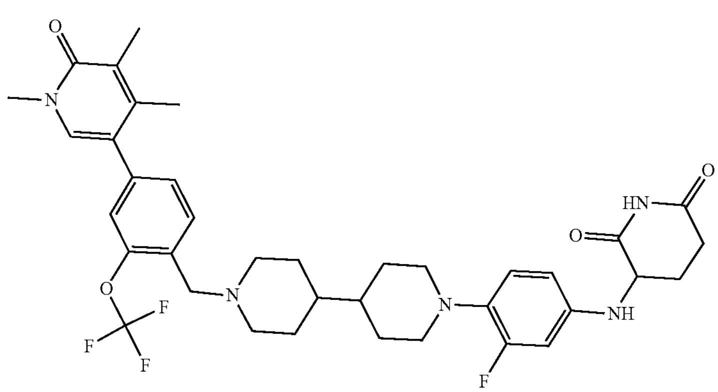 [SMILES: Cc1c(-c2ccc(CN3CCC(C4CCN(c5ccc(NC6CCC(=O)NC6=O)cc5F)CC4)CC3)c(OC(F)(F)F)c2)cn(C)c(=O)c1C] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 81 | 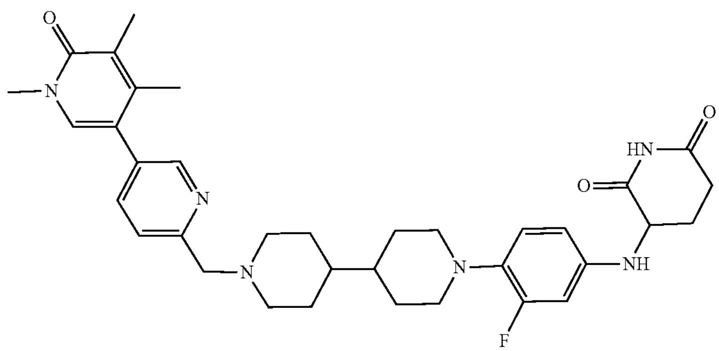 [SMILES: Cc1c(-c2ccc(CN3CCC(C4CCN(c5ccc(NC6CCC(=O)NC6=O)cc5F)CC4)CC3)nc2)cn(C)c(=O)c1C] | +++ |
| 82 | 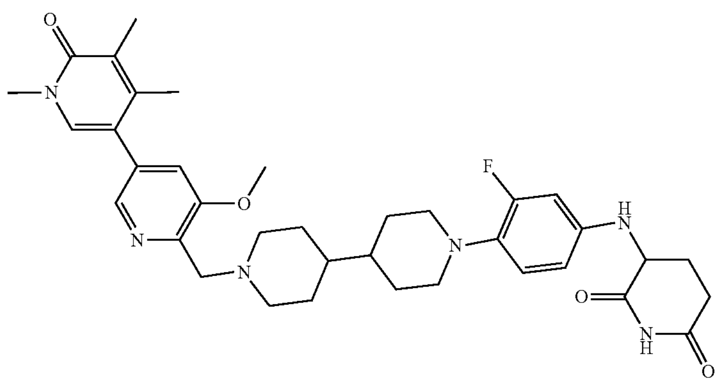 [SMILES: COc1cc(-c2cn(C)c(=O)c(C)c2C)cnc1CN1CCC(C2CCN(c3ccc(NC4CCC(=O)NC4=O)cc3F)CC2)CC1] | +++ |
| 83 | 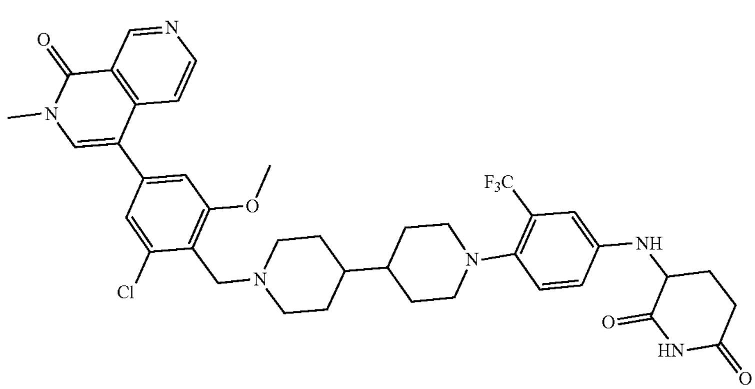 [SMILES: COc1cc(-c2cn(C)c(=O)c3cnccc23)cc(Cl)c1CN1CCC(C2CCN(c3ccc(NC4CCC(=O)NC4=O)cc3C(F)(F)F)CC2)CC1] | +++ |

TABLE 1-continued
XII. DATA
BRD9 Degradation Data.
| Cmpd # | Structure | HiBiT-Degradation 293T.166 BRD9 2.0 hours (DC50) [nM] |
|---|---|---|
| 84 | 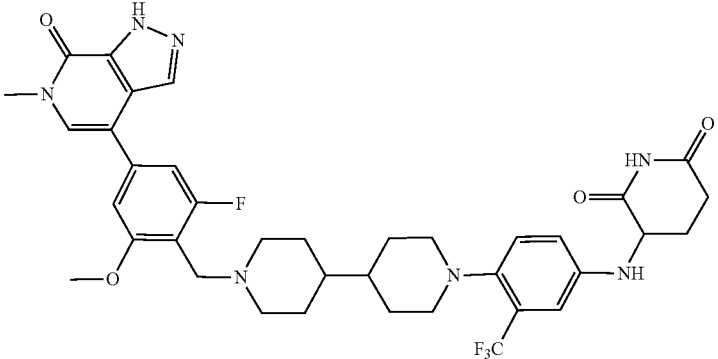 [SMILES: COc1cc(-c2cn(C)c(=O)c3[nH]ncc23)cc(F)c1CN1CCC(C2CCN(c3ccc(NC4CCC(=O)NC4=O)cc3C(F)(F)F)CC2)CC1] | +++ |
| 85 | 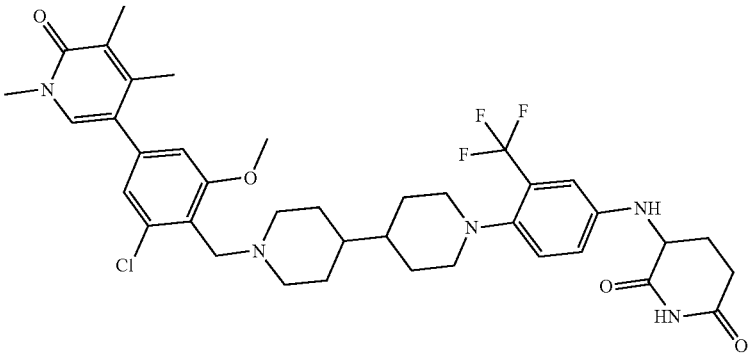 [SMILES: COc1cc(-c2cn(C)c(=O)c(C)c2C)cc(Cl)c1CN1CCC(C2CCN(c3ccc(NC4CCC(=O)NC4=O)cc3C(F)(F)F)CC2)CC1] | +++ |
| 86 | 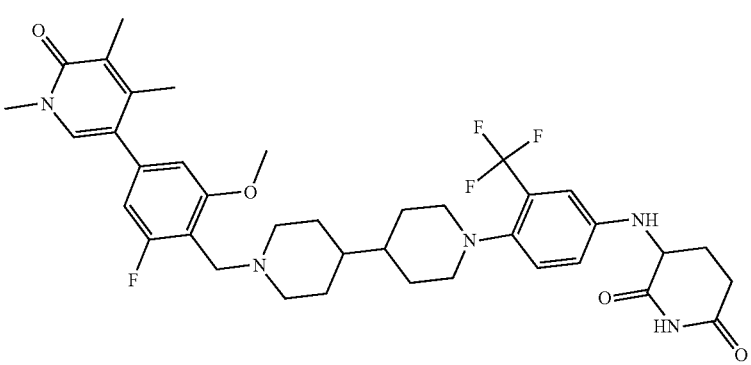 [SMILES: COc1cc(-c2cn(C)c(=O)c(C)c2C)cc(F)c1CN1CCC(C2CCN(c3ccc(NC4CCC(=O)NC4=O)cc3C(F)(F)F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 87 | 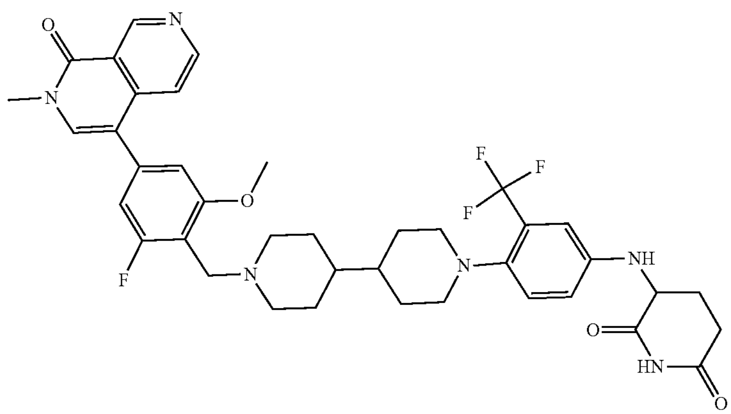 [SMILES: COc1cc(-c2cn(C)c(=O)c3cnccc23)cc(F)c1CN1CCC(C2CCN(c3ccc(NC4CCC(=O)NC4=O)cc3C(F)(F)F)CC2)CC1] | +++ |
| 88 | 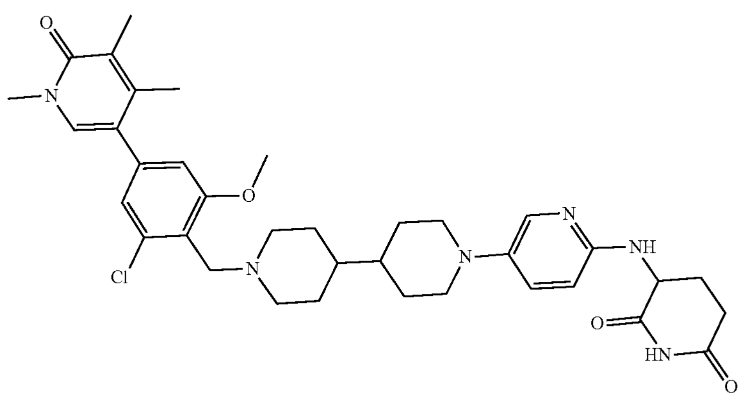 [SMILES: COc1cc(-c2cn(C)c(=O)c(C)c2C)cc(Cl)c1CN1CCC(C2CCN(c3ccc(NC4CCC(=O)NC4=O)nc3)CC2)CC1] | +++ |
| 89 | 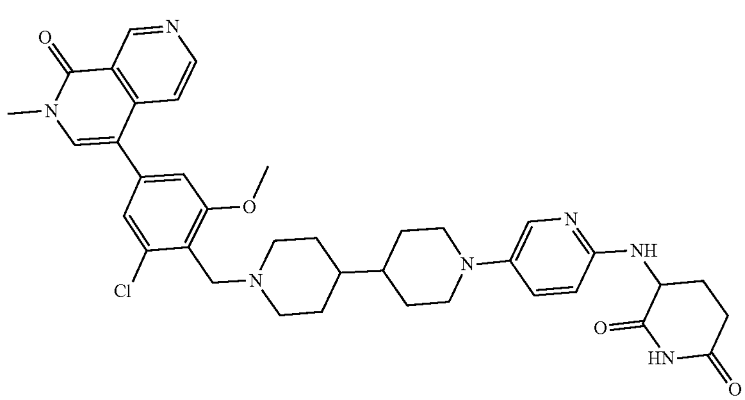 [SMILES: COc1cc(-c2cn(C)c(=O)c3cnccc23)cc(Cl)c1CN1CCC(C2CCN(c3ccc(NC4CCC(=O)NC4=O)nc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 90 | 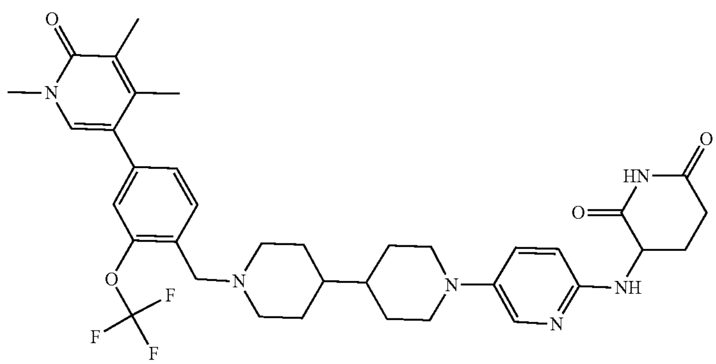 [SMILES: Cc1c(-c2ccc(CN3CCC(C4CCN(c5ccc(NC6CCC(=O)NC6=O)nc5)CC4)CC3)c(OC(F)(F)F)c2)cn(C)c(=O)c1C] | +++ |
| 91 | 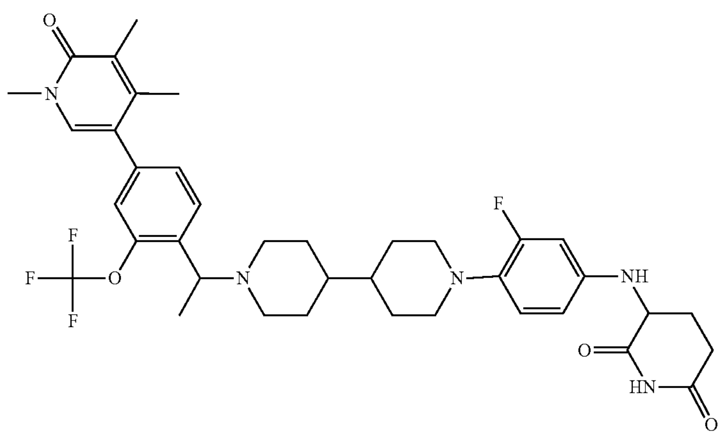 [SMILES: Cc1c(-c2ccc(C(C)N3CCC(C4CCN(c5ccc(NC6CCC(=O)NC6=O)cc5F)CC4)CC3)c(OC(F)(F)F)c2)cn(C)c(=O)c1C] | +++ |
| 92 | 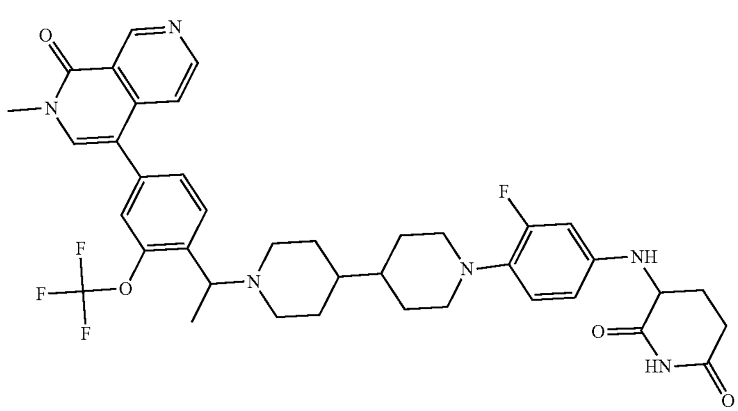 [SMILES: CC(c1ccc(-c2cn(C)c(=O)c3cnccc23)cc1OC(F)(F)F)N1CCC(C2CCN(c3ccc(NC4CCC(=O)NC4=O)cc3F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 93 | 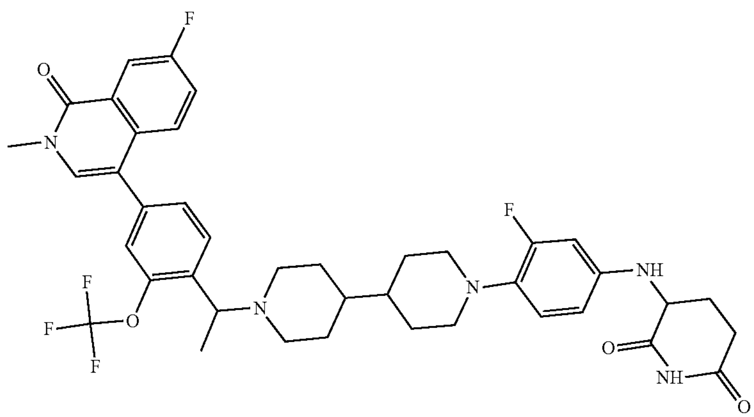 [SMILES: CC(c1ccc(-c2cn(C)c(=O)c3cc(F)ccc23)cc1OC(F)(F)F)N1CCC(C2CCN(c3ccc(NC4CCC(=O)NC4=O)cc3F)CC2)CC1] | +++ |
| 94 | 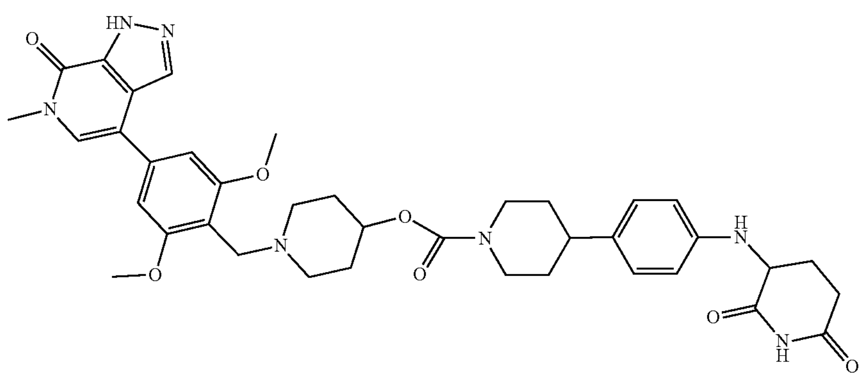 [SMILES: COc1cc(-c2cn(C)c(=O)c3[nH]ncc23)cc(OC)c1CN1CCC(OC(=O)N2CCC(c3ccc(NC4CCC(=O)NC4=O)cc3)CC2)CC1] | +++ |
| 95 | 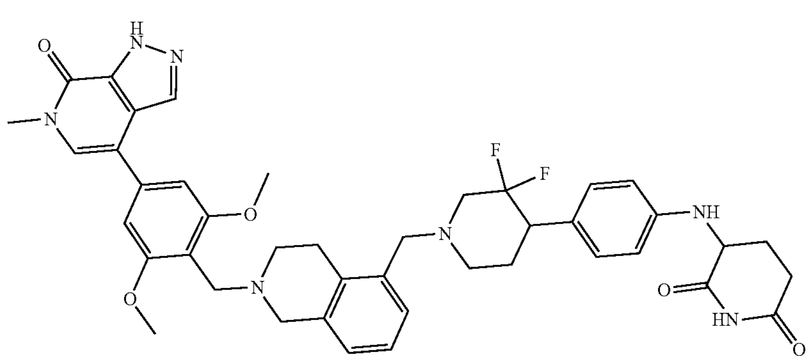 [SMILES: COc1cc(-c2cn(C)c(=O)c3[nH]ncc23)cc(OC)c1CN1CCc2c(cccc2CN2CCC(c3ccc(NC4CCC(=O)NC4=O)cc3)C(F)(F)C2)C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 96 | 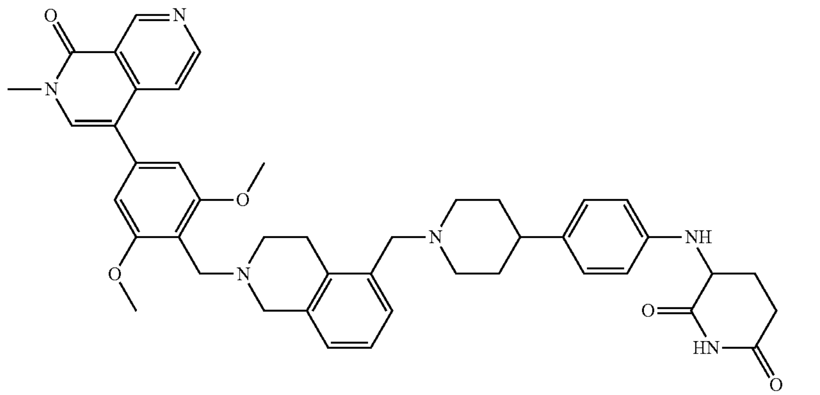 [SMILES: COc1cc(-c2cn(C)c(=O)c3cnccc23)cc(OC)c1CN1CCc2c(CN3CCC(c4ccc(NC5CCC(=O)NC5=O)cc4)CC3)cccc2C1] | +++ |
| 97 | 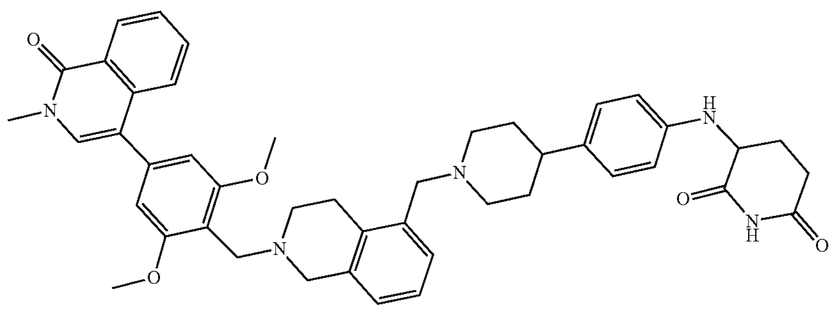 [SMILES: COc1cc(-c2cn(C)c(=O)c3ccccc23)cc(OC)c1CN1CCc2c(CN3CCC(c4ccc(NC5CCC(=O)NC5=O)cc4)CC3)cccc2C1] | +++ |
| 98 | 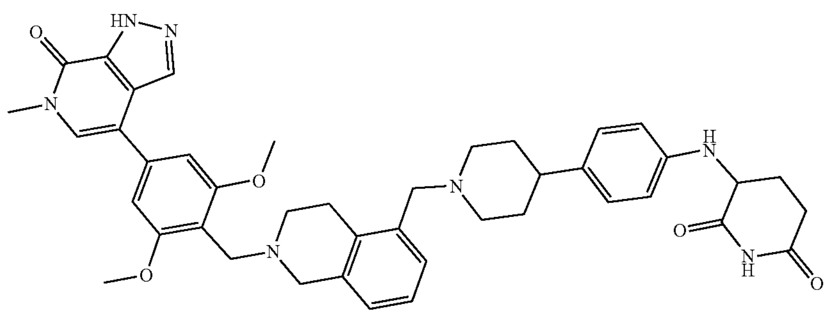 [SMILES: COc1cc(-c2cn(C)c(=O)c3[nH]ncc23)cc(OC)c1CN1CCc2c(CN3CCC(c4ccc(NC5CCC(=O)NC5=O)cc4)CC3)cccc2C1] | +++ |
| 99 | 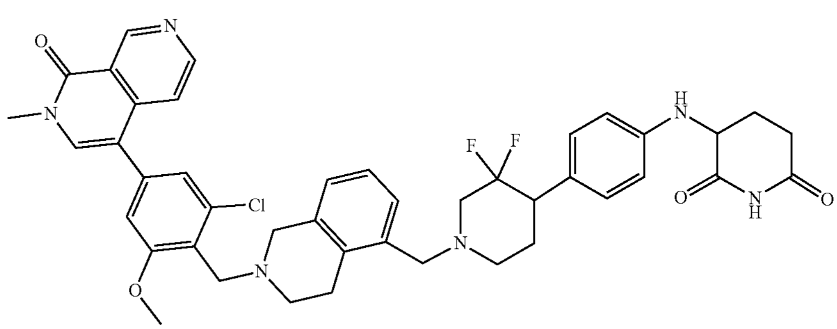 [SMILES: COc1cc(-c2cn(C)c(=O)c3cnccc23)cc(Cl)c1CN1CCc2c(cccc2CN2CCC(c3ccc(NC4CCC(=O)NC4=O)cc3)C(F)(F)C2)C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 100 | 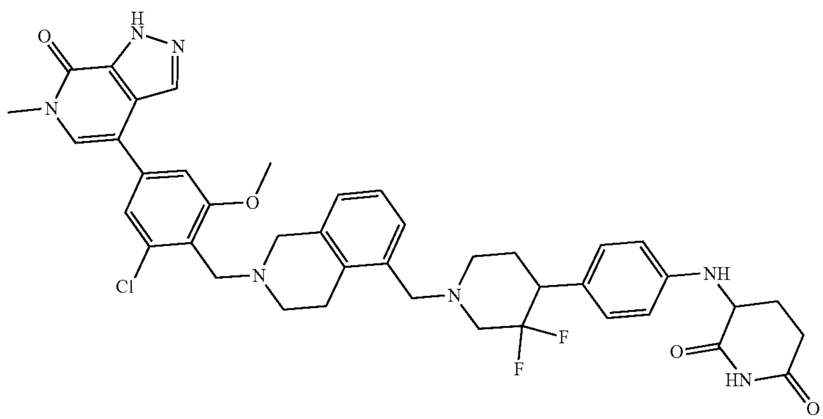 [SMILES: COc1cc(-c2cn(C)c(=O)c3[nH]ncc23)cc(Cl)c1CN1CCc2c(cccc2CN2CCC(c3ccc(NC4CCC(=O)NC4=O)cc3)C(F)(F)C2)C1] | +++ |
| 101 | 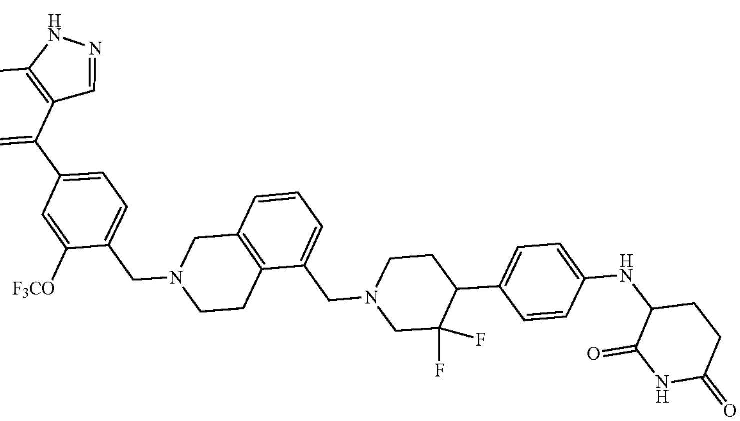 | +++ |
| 102 | 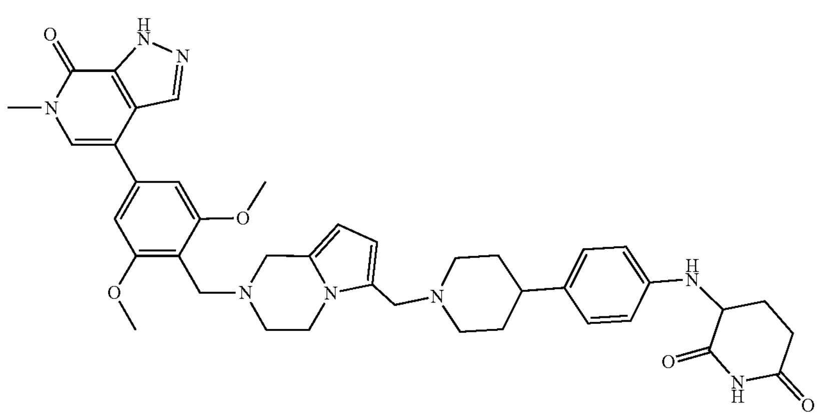 [SMILES: COc1cc(-c2cn(C)c(=O)c3[nH]ncc23)cc(OC)c1CN1CCn2c(CN3CCC(c4ccc(NC5CCC(=O)NC5=O)cc4)CC3)ccc2C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 103 | 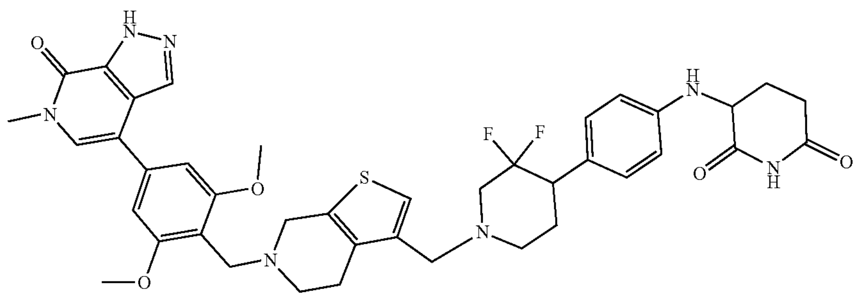 [SMILES: COc1cc(-c2cn(C)c(=O)c3[nH]ncc23)cc(OC)c1CN1CCc2c(CN3CCC(c4ccc(NC5CCC(=O)NC5=O)cc4)C(F)(F)C3)csc2C1] | +++ |
| 104 | 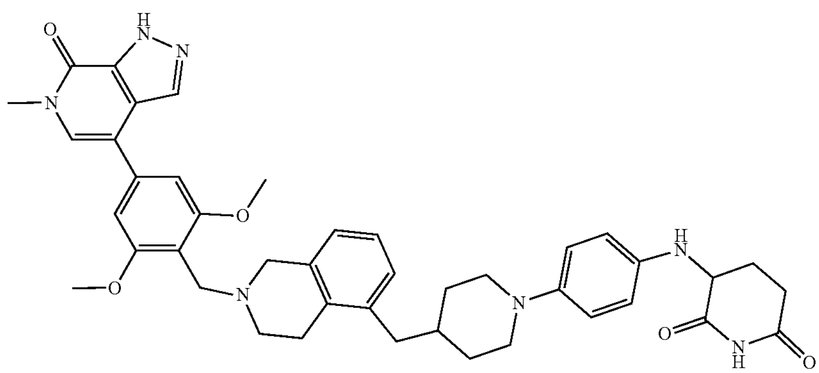 [SMILES: COc1cc(-c2cn(C)c(=O)c3[nH]ncc23)cc(OC)c1CN1CCc2c(CC3CCN(c4ccc(NC5CCC(=O)NC5=O)cc4)CC3)cccc2C1] | +++ |
| 105 | 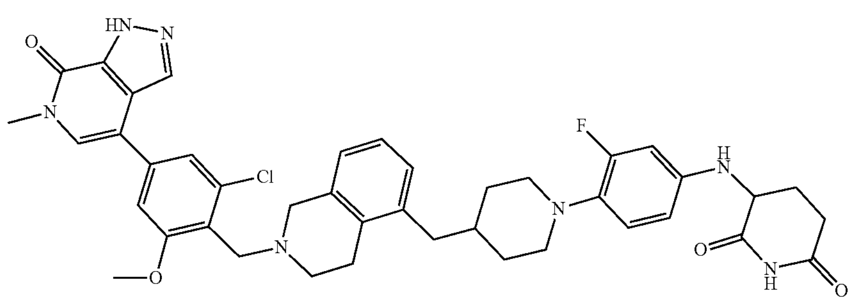 [SMILES: COc1cc(-c2cn(C)c(=O)c3[nH]ncc23)cc(Cl)c1CN1CCc2c(CC3CCN(c4ccc(NC5CCC(=O)NC5=O)cc4F)CC3)cccc2C1] | +++ |
| 106 | 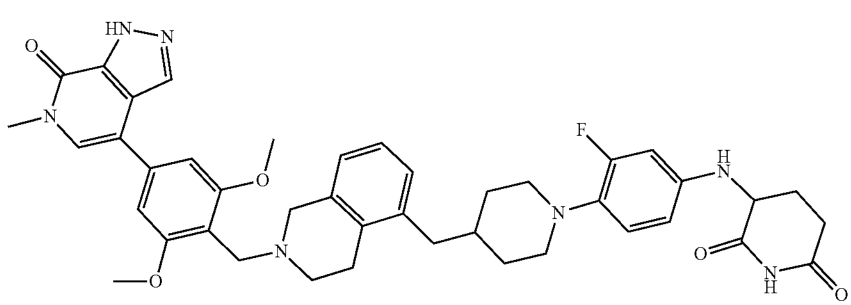 [SMILES: COc1cc(-c2cn(C)c(=O)c3[nH]ncc23)cc(OC)c1CN1CCc2c(CC3CCN(c4ccc(NC5CCC(=O)NC5=O)cc4F)CC3)cccc2C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 107 | 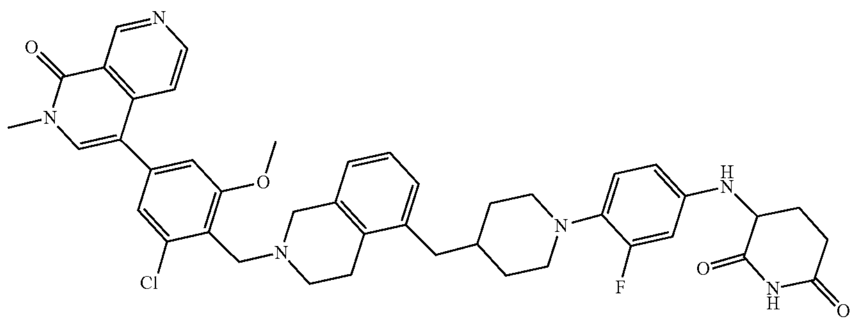 [SMILES: COc1cc(-c2cn(C)c(=O)c3cnccc23)cc(Cl)c1CN1CCc2c(CC3CCN(c4ccc(NC5CCC(=O)NC5=O)cc4F)CC3)cccc2C1] | +++ |
| 108 | 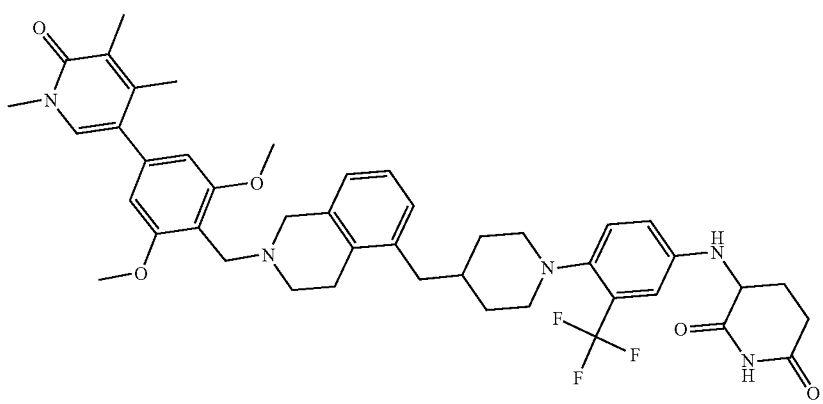 [SMILES: COc1cc(-c2cn(C)c(=O)c(C)c2C)cc(OC)c1CN1CCc2c(CC3CCN(c4ccc(NC5CCC(=O)NC5=O)cc4C(F)(F)F)CC3)cccc2C1] | +++ |
| 109 | 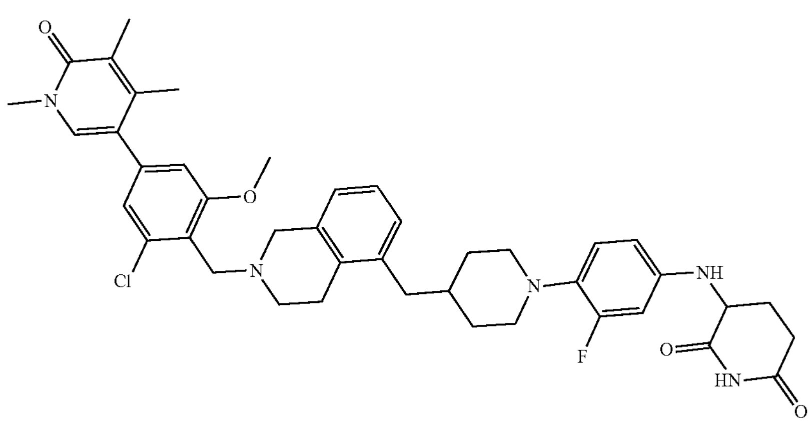 [SMILES: COc1cc(-c2cn(C)c(=O)c(C)c2C)cc(Cl)c1CN1CCc2c(CC3CCN(c4ccc(NC5CCC(=O)NC5=O)cc4F)CC3)cccc2C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 110 | 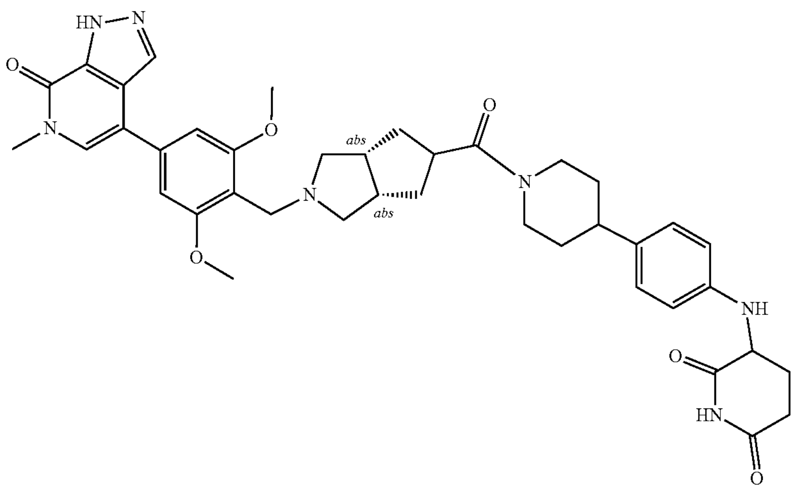 | +++ |
| 111 | 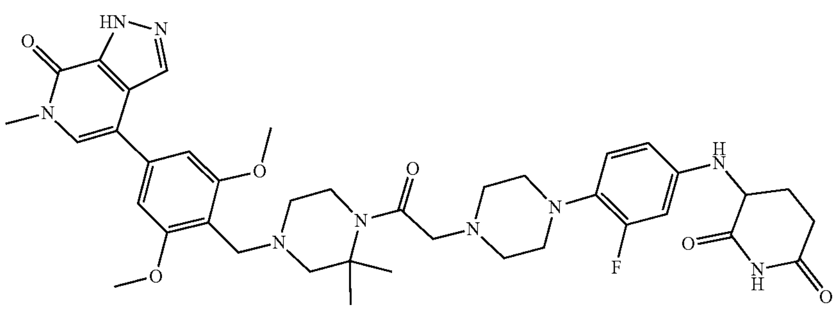 [SMILES: COc1cc(-c2cn(C)c(=O)c3[nH]ncc23)cc(OC)c1CN1CCN(C(=O)CN2CCN(c3ccc(NC4CCC(=O)NC4=O)cc3F)CC2)C(C)(C)C1] | +++ |
| 112 | 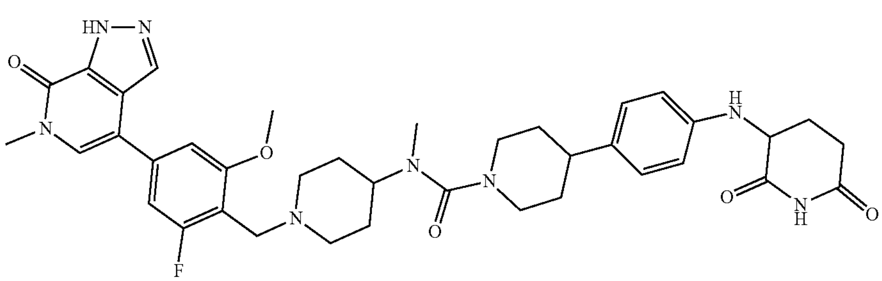 [SMILES: COc1cc(-c2cn(C)c(=O)c3[nH]ncc23)cc(F)c1CN1CCC(N(C)C(=O)N2CCC(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 113 | 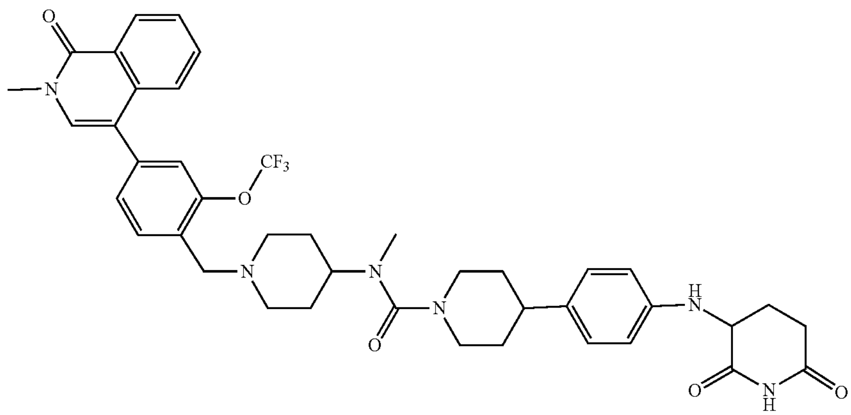 [SMILES: CN(C(=O)N1CCC(c2ccc(NC3CCC(=O)NC3=O)cc2)CC1)C1CCN(Cc2ccc(-c3cn(C)c(=O)c4ccccc34)cc2OC(F)(F)F)CC1] | +++ |
| 114 | 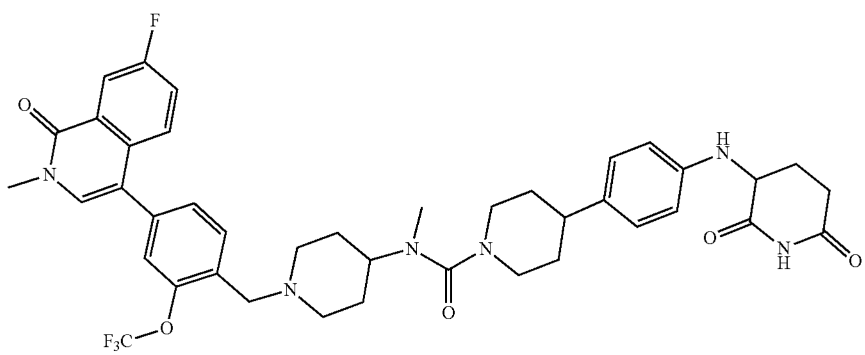 [SMILES: CN(C(=O)N1CCC(c2ccc(NC3CCC(=O)NC3=O)cc2)CC1)C1CCN(Cc2ccc(-c3cn(C)c(=O)c4cc(F)ccc34)cc2OC(F)(F)F)CC1] | +++ |
| 115 | 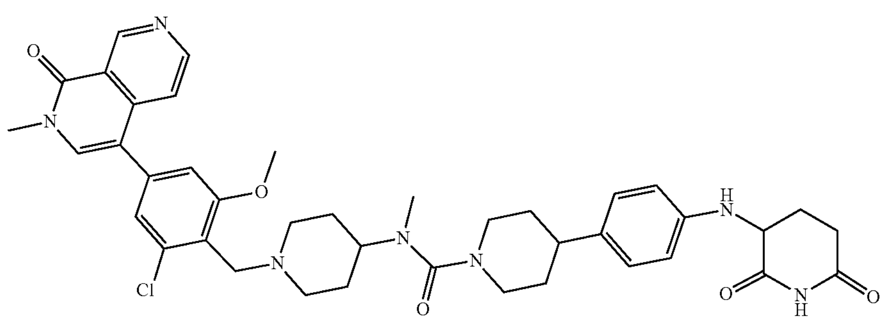 [SMILES: COc1cc(-c2cn(C)c(=O)c3cnccc23)cc(Cl)c1CN1CCC(N(C)C(=O)N2CCC(c3ccc(NC4CCC(=O)NC4=O)cc3)CC2)CC1] | +++ |
| 116 | 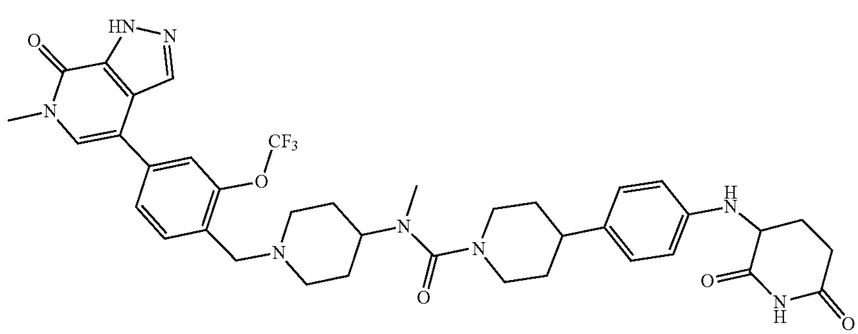 [SMILES: CN(C(=O)N1CCC(c2ccc(NC3CCC(=O)NC3=O)cc2)CC1)C1CCN(Cc2ccc(-c3cn(C)c(=O)c4[nH]ncc34)cc2OC(F)(F)F)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 117 | 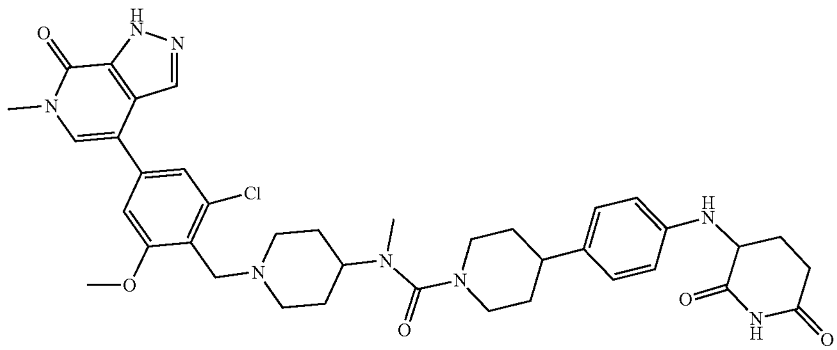 [SMILES: COc1cc(-c2cn(C)c(=O)c3[nH]ncc23)cc(Cl)c1CN1CCC(N(C)C(=O)N2CCC(c3ccc(NC4CCC(=O)NC4=O)cc3)CC2)CC1] | +++ |
| 118 | 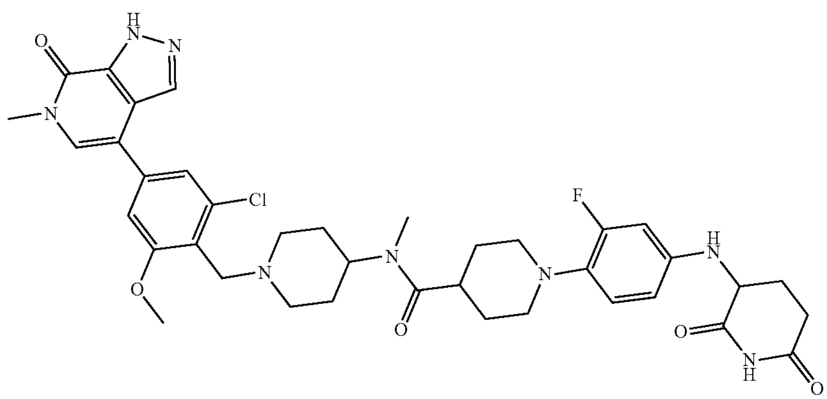 [SMILES: COc1cc(-c2cn(C)c(=O)c3[nH]ncc23)cc(Cl)c1CN1CCC(N(C)C(=O)C2CCN(c3ccc(NC4CCC(=O)NC4=O)cc3F)CC2)CC1] | +++ |
| 119 | 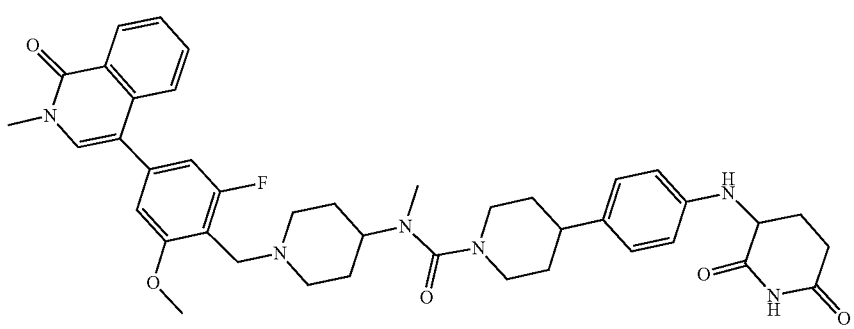 [SMILES: COc1cc(-c2cn(C)c(=O)c3ccccc23)cc(F)c1CN1CCC(N(C)C(=O)N2CCC(c3ccc(NC4CCC(=O)NC4=O)cc3)CC2)CC1] | +++ |
| 120 | 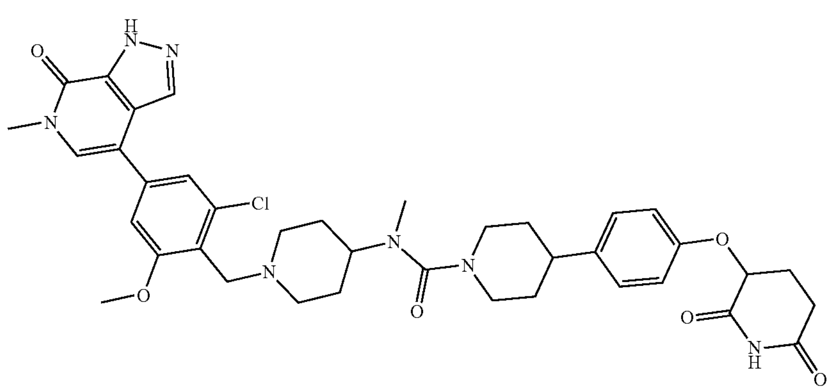 [SMILES: COc1cc(-c2cn(C)c(=O)c3[nH]ncc23)cc(Cl)c1CN1CCC(N(C)C(=O)N2CCC(c3ccc(OC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 121 | 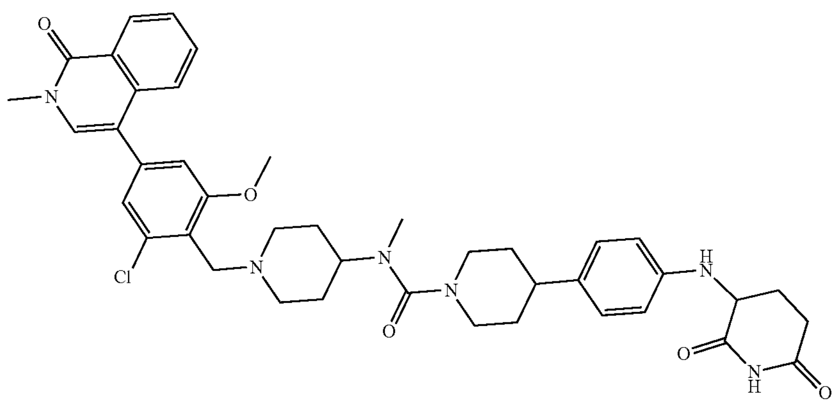 [SMILES: COc1cc(-c2cn(C)c(=O)c3ccccc23)cc(Cl)c1CN1CCC(N(C)C(=O)N2CCC(c3ccc(NC4CCC(=O)NC4=O)cc3)CC2)CC1] | +++ |
| 122 | 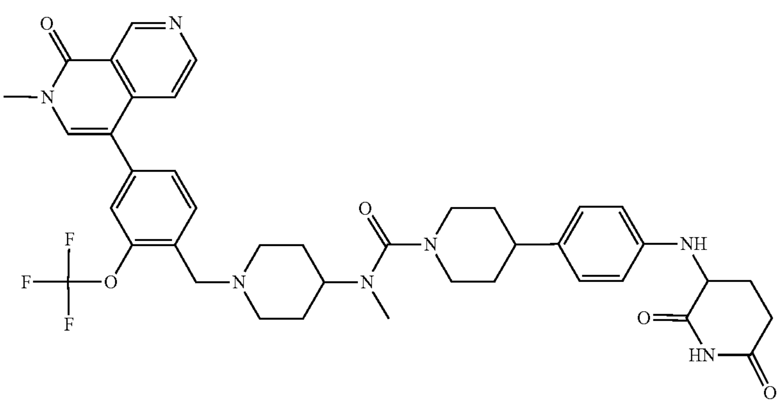 [SMILES: CN(C(=O)N1CCC(c2ccc(NC3CCC(=O)NC3=O)cc2)CC1)C1CCN(Cc2ccc(-c3cn(C)c(=O)c4cnccc34)cc2OC(F)(F)F)CC1] | +++ |
| 123 | 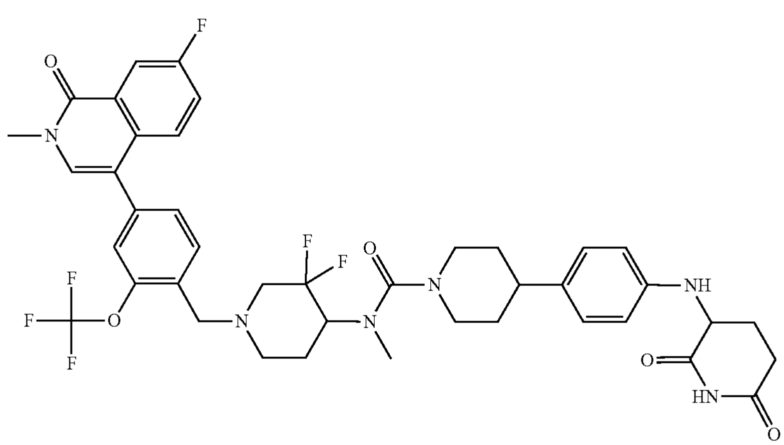 [SMILES: CN(C(=O)N1CCC(c2ccc(NC3CCC(=O)NC3=O)cc2)CC1)C1CCN(Cc2ccc(-c3cn(C)c(=O)c4cc(F)ccc34)cc2OC(F)(F)F)CC1(F)F] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 124 | 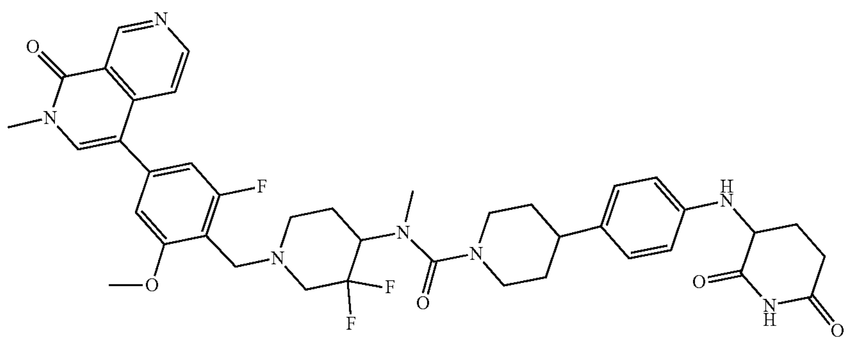 [SMILES: COc1cc(-c2cn(C)c(=O)c3cnccc23)cc(F)c1CN1CCC(N(C)C(=O)N2CCC(c3ccc(NC4CCC(=O)NC4=O)cc3)CC2)C(F)(F)C1] | +++ |
| 125 | 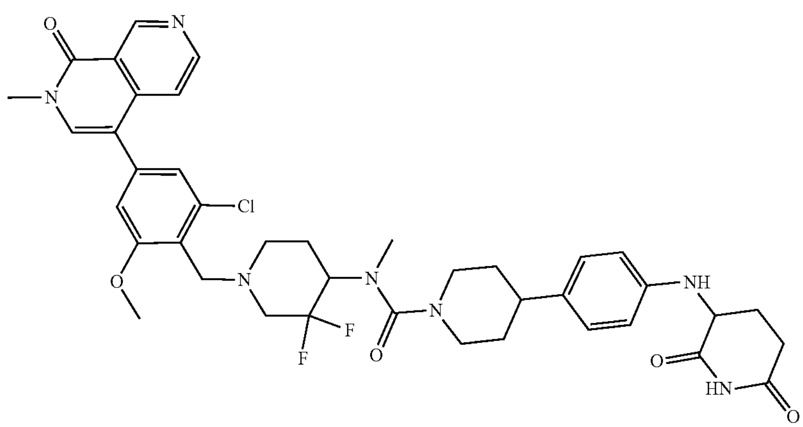 [SMILES: COc1cc(-c2cn(C)c(=O)c3cnccc23)cc(Cl)c1CN1CCC(N(C)C(=O)N2CCC(c3ccc(NC4CCC(=O)NC4=O)cc3)CC2)C(F)(F)C1] | +++ |
| 126 | 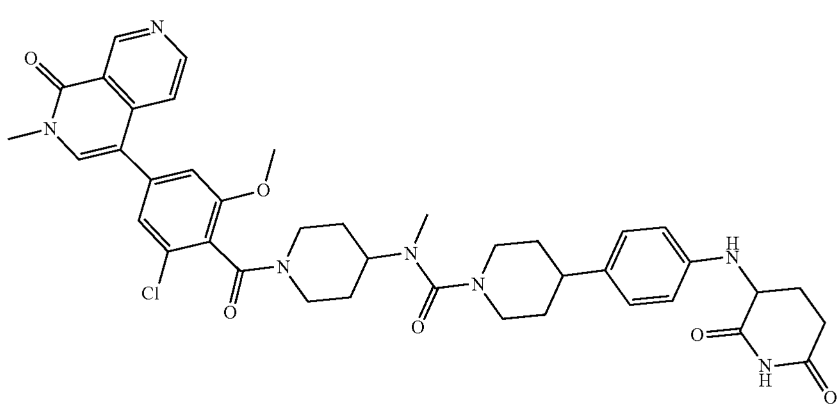 [SMILES: COc1cc(-c2cn(C)c(=O)c3cnccc23)cc(Cl)c1C(=O)N1CCC(N(C)C(=O)N2CCC(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 127 | 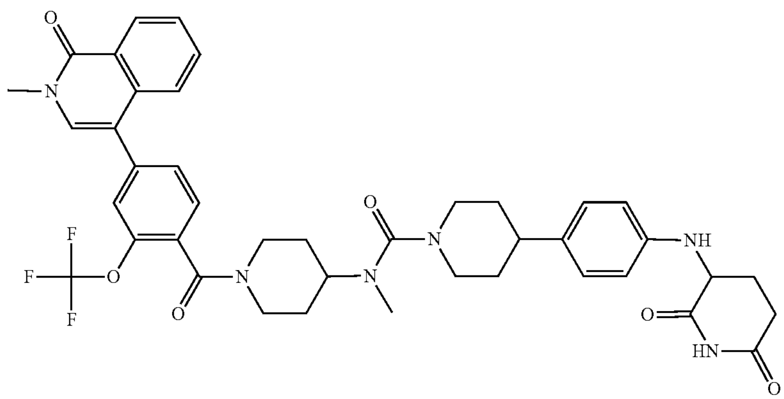 [SMILES: CN(C(=O)N1CCC(c2ccc(NC3CCC(=O)NC3=O)cc2)CC1)C1CCN(C(=O)c2ccc(-c3cn(C)c(=O)c4ccccc34)cc2OC(F)(F)F)CC1] | +++ |
| 128 | 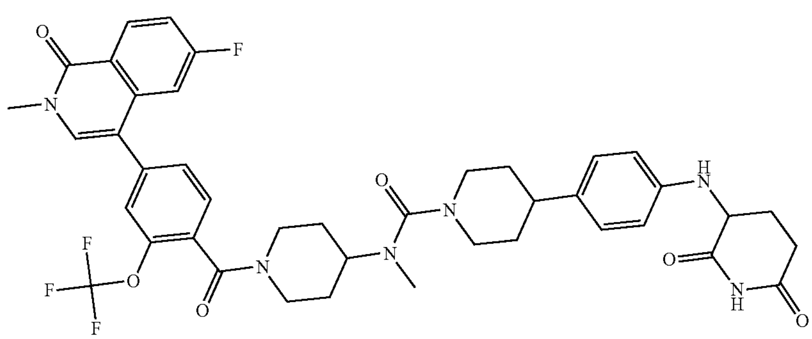 [SMILES: CN(C(=O)N1CCC(c2ccc(NC3CCC(=O)NC3=O)cc2)CC1)C1CCN(C(=O)c2ccc(-c3cn(C)c(=O)c4ccc(F)cc34)cc2OC(F)(F)F)CC1] | +++ |
| 129 | 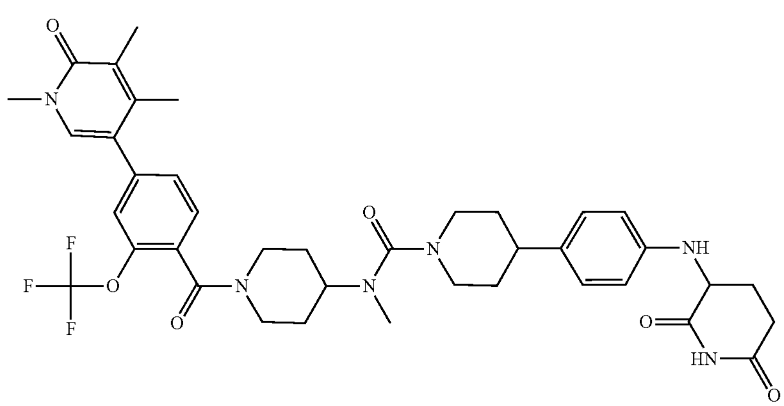 [SMILES: Cc1c(-c2ccc(C(=O)N3CCC(N(C)C(=O)N4CCC(c5ccc(NC6CCC(=O)NC6=O)cc5)CC4)CC3)c(OC(F)(F)F)c2)cn(C)c(=O)c1C] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 130 | 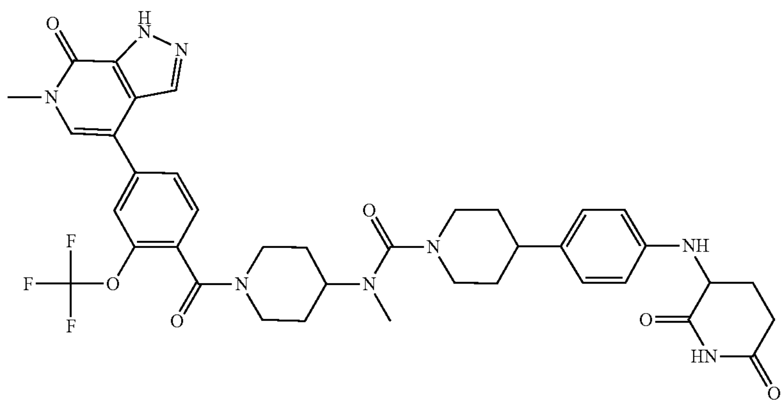 [SMILES: CN(C(=O)N1CCC(c2ccc(NC3CCC(=O)NC3=O)cc2)CC1)C1CCN(C(=O)c2ccc(-c3cn(C)c(=O)c4[nH]ncc34)cc2OC(F)(F)F)CC1] | +++ |
| 131 | 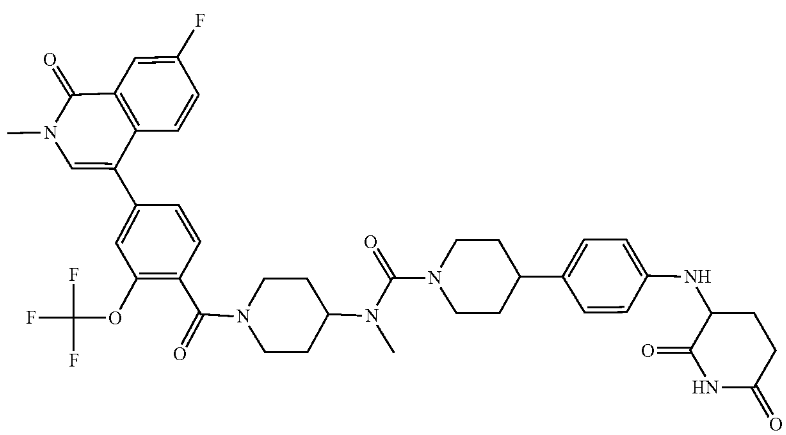 [SMILES: CN(C(=O)N1CCC(c2ccc(NC3CCC(=O)NC3=O)cc2)CC1)C1CCN(C(=O)c2ccc(-c3cn(C)c(=O)c4cc(F)ccc34)cc2OC(F)(F)F)CC1] | +++ |
| 132 | 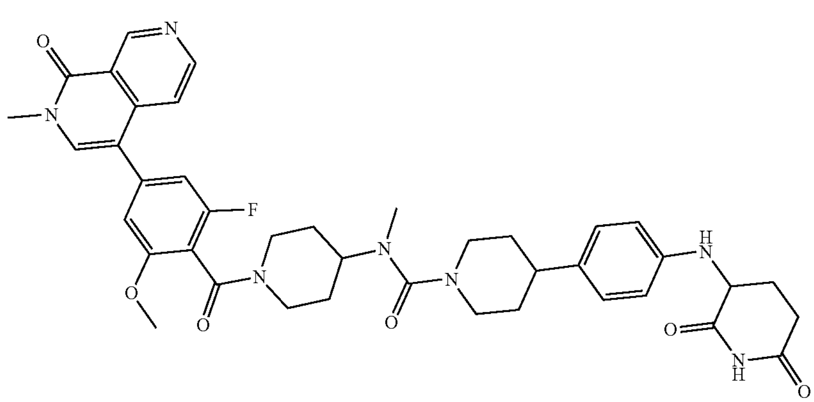 [SMILES: COc1cc(-c2cn(C)c(=O)c3cnccc23)cc(F)c1C(=O)N1CCC(N(C)C(=O)N2CCC(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 133 | 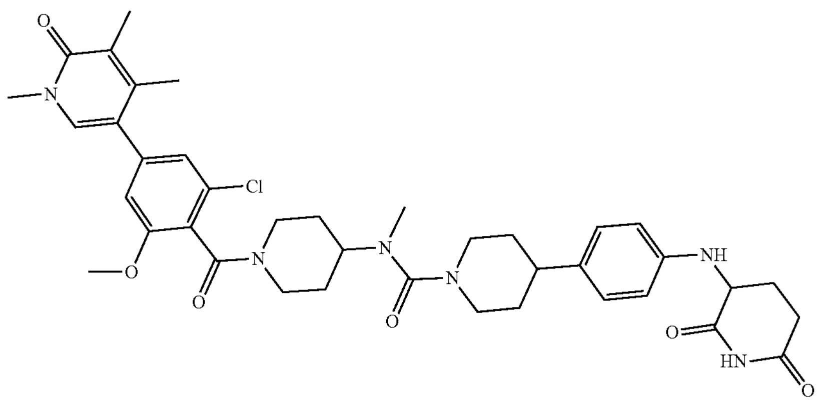 [SMILES: COc1cc(-c2cn(C)c(=O)c(C)c2C)cc(Cl)c1C(=O)N1CCC(N(C)C(=O)N2CCC(c3ccc(NC4CCC(=O)NC4=O)cc3)CC2)CC1] | +++ |
| 134 | 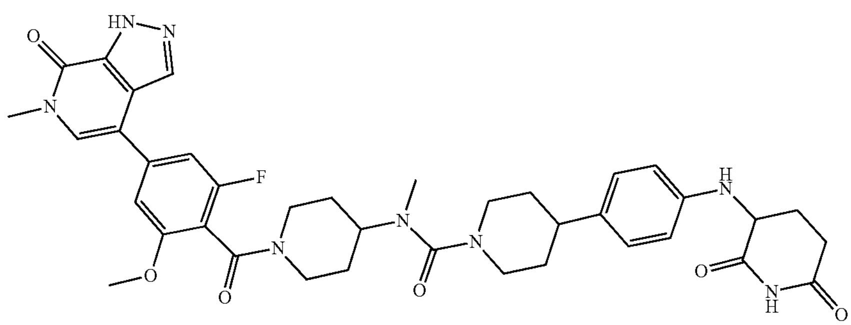 [SMILES: COc1cc(-c2cn(C)c(=O)c3[nH]ncc23)cc(F)c1C(=O)N1CCC(N(C)C(=O)N2CCC(c3ccc(NC4CCC(=O)NC4=O)cc3)CC2)CC1] | +++ |
| 135 | 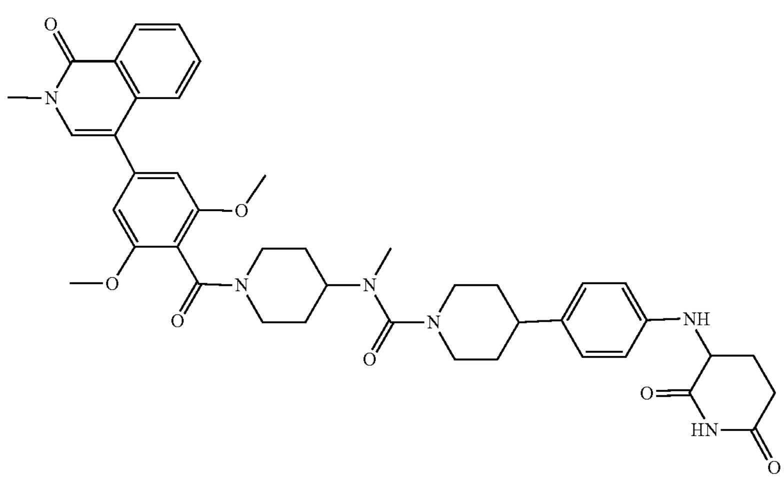 [SMILES: COc1cc(-c2cn(C)c(=O)c3ccccc23)cc(OC)c1C(=O)N1CCC(N(C)C(=O)N2CCC(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 136 | 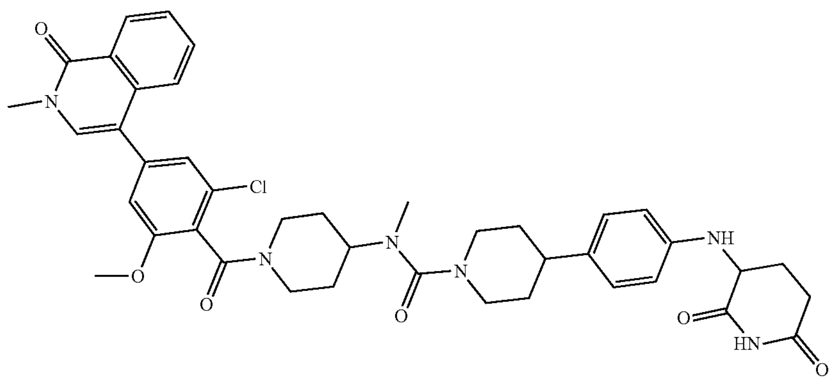 [SMILES: COc1cc(-c2cn(C)c(=O)c3ccccc23)cc(Cl)c1C(=O)N1CCC(N(C)C(=O)N2CCC(c3ccc(NC4CCC(=O)NC4=O)cc3)CC2)CC1] | +++ |
| 137 | 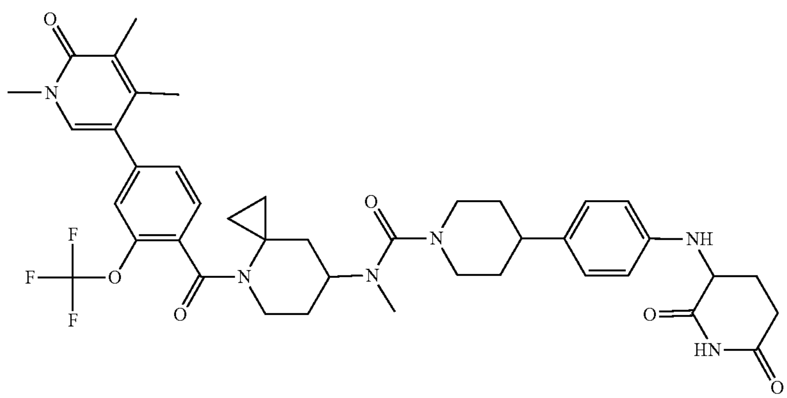 [SMILES: Cc1c(-c2ccc(C(=O)N3CCC(N(C)C(=O)N4CCC(c5ccc(NC6CCC(=O)NC6=O)cc5)CC4)CC34CC4)c(OC(F)(F)F)c2)cn(C)c(=O)c1C] | +++ |
| 138 | 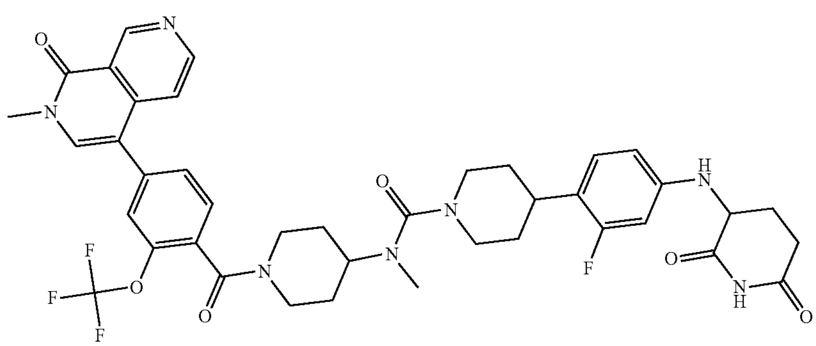 [SMILES: CN(C(=O)N1CCC(c2ccc(NC3CCC(=O)NC3=O)cc2F)CC1)C1CCN(C(=O)c2ccc(-c3cn(C)c(=O)c4cnccc34)cc2OC(F)(F)F)CC1] | +++ |
| 139 | 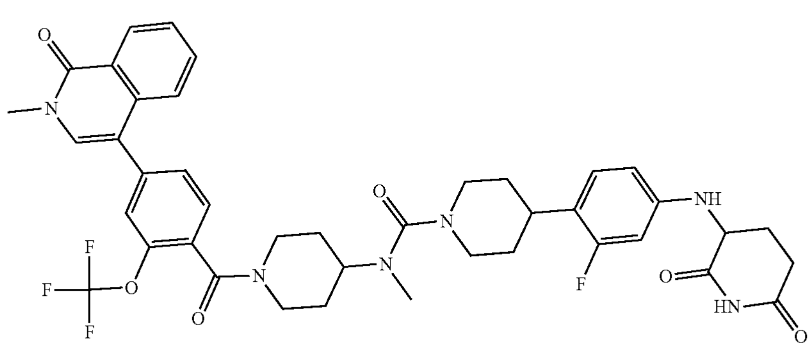 [SMILES: CN(C(=O)N1CCC(c2ccc(NC3CCC(=O)NC3=O)cc2F)CC1)C1CCN(C(=O)c2ccc(-c3cn(C)c(=O)c4ccccc34)cc2OC(F)(F)F)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 140 | 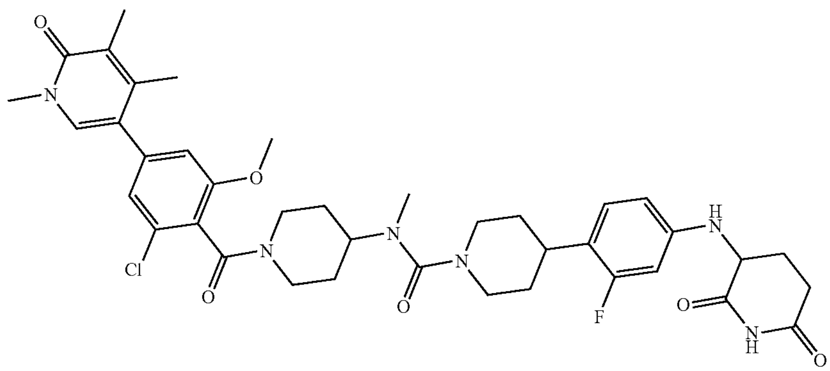 [SMILES: COc1cc(-c2cn(C)c(=O)c(C)c2C)cc(Cl)c1C(=O)N1CCC(N(C)C(=O)N2CCC(c3ccc(NC4CCC(=O)NC4=O)cc3F)CC2)CC1] | +++ |
| 141 | 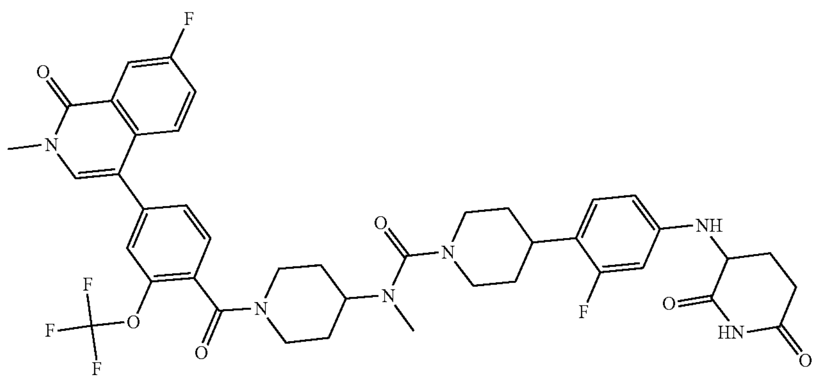 [SMILES: CN(C(=O)N1CCC(c2ccc(NC3CCC(=O)NC3=O)cc2F)CC1)C1CCN(C(=O)c2ccc(-c3cn(C)c(=O)c4cc(F)ccc34)cc2OC(F)(F)F)CC1] | +++ |
| 142 | 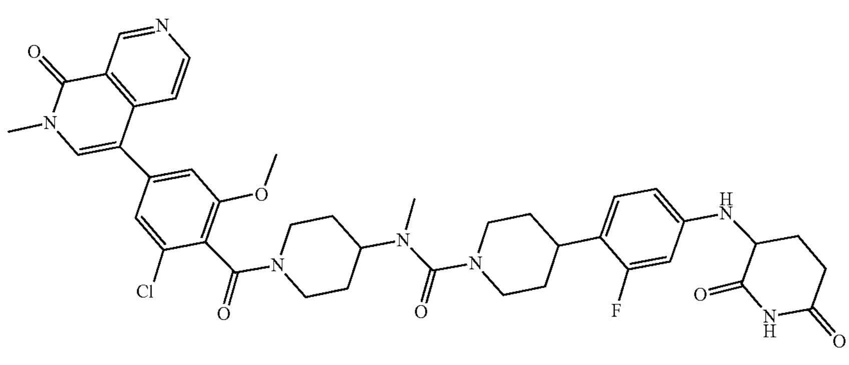 [SMILES: COc1cc(-c2cn(C)c(=O)c3cnccc23)cc(Cl)c1C(=O)N1CCC(N(C)C(=O)N2CCC(c3ccc(NC4CCC(=O)NC4=O)cc3F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 143 | 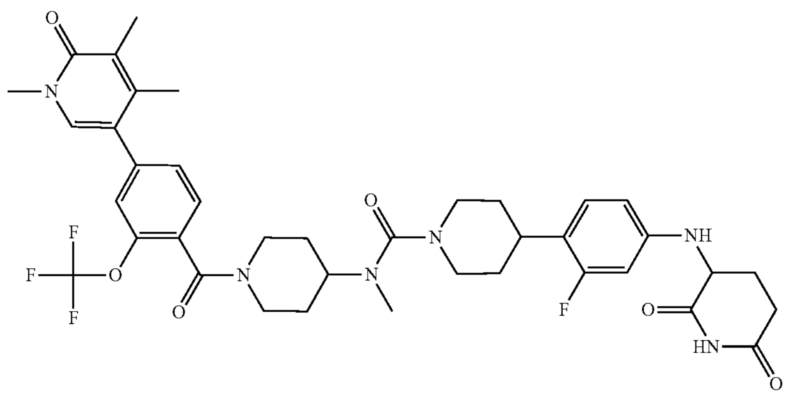 [SMILES: Cc1c(-c2ccc(C(=O)N3CCC(N(C)C(=O)N4CCC(c5ccc(NC6CCC(=O)NC6=O)cc5F)CC4)CC3)c(OC(F)(F)F)c2)cn(C)c(=O)c1C] | +++ |
| 144 | 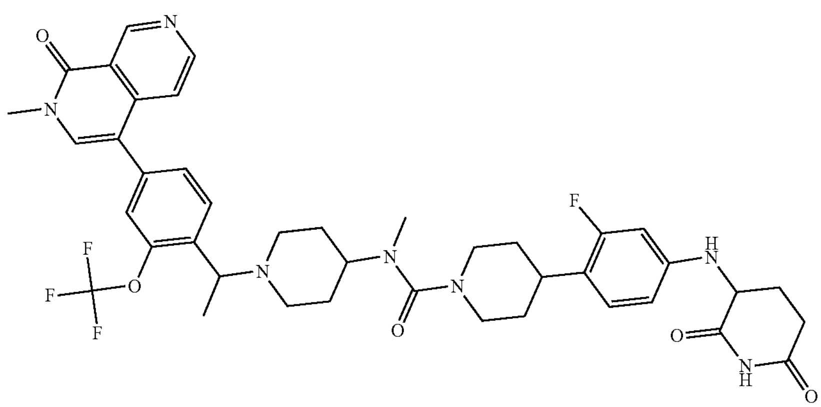 [SMILES: CC(c1ccc(-c2cn(C)c(=O)c3cnccc23)cc1OC(F)(F)F)N1CCC(N(C)C(=O)N2CCC(c3ccc(NC4CCC(=O)NC4=O)cc3F)CC2)CC1] | +++ |
| 145 | 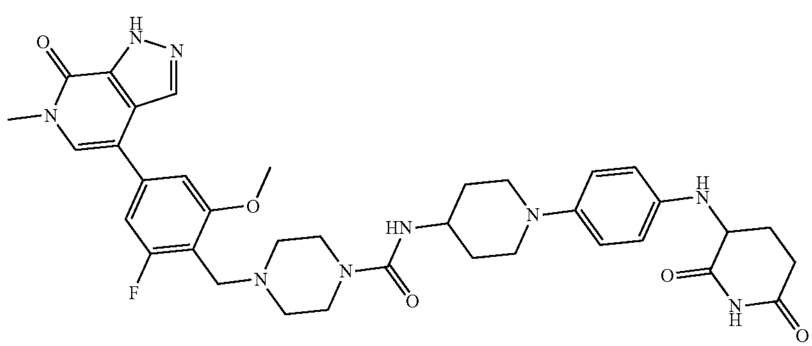 [SMILES: COc1cc(-c2cn(C)c(=O)c3[nH]ncc23)cc(F)c1CN1CCN(C(=O)NC2CCN(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 146 | 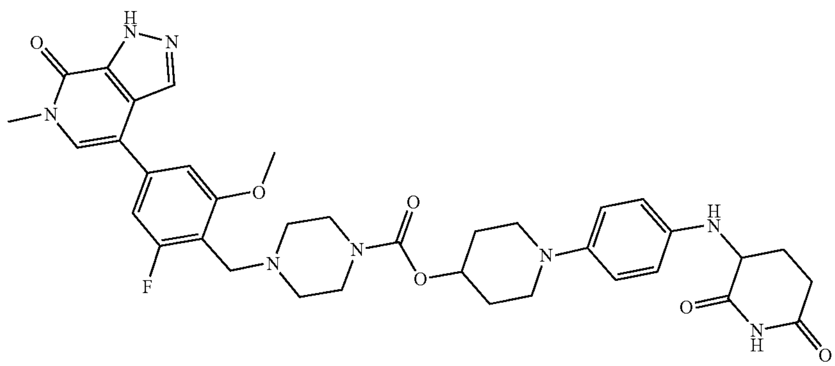 [SMILES: COc1cc(-c2cn(C)c(=O)c3[nH]ncc23)cc(F)c1CN1CCN(C(=O)OC2CCN(c3ccc(NC4CCC(=O)NC4=O)cc3)CC2)CC1] | +++ |
| 147 | 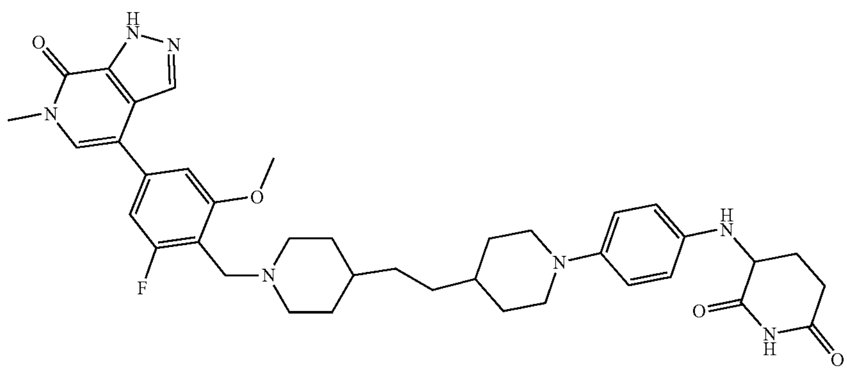 [SMILES: COc1cc(-c2cn(C)c(=O)c3[nH]ncc23)cc(F)c1CN1CCC(CCC2CCN(c3ccc(NC4CCC(=O)NC4=O)cc3)CC2)CC1] | +++ |
| 148 | 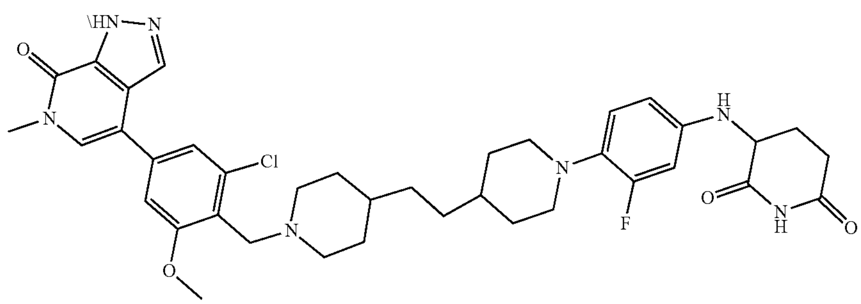 | +++ |
| 149 | 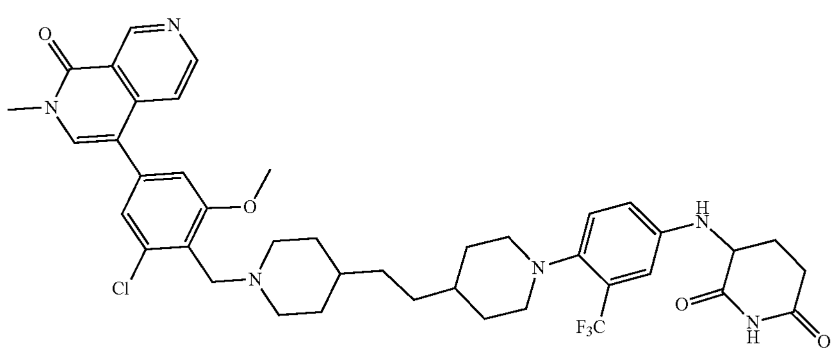 [SMILES: COc1cc(-c2cn(C)c(=O)c3cnccc23)cc(Cl)c1CN1CCC(CCC2CCN(c3ccc(NC4CCC(=O)NC4=O)cc3C(F)(F)F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 150 | 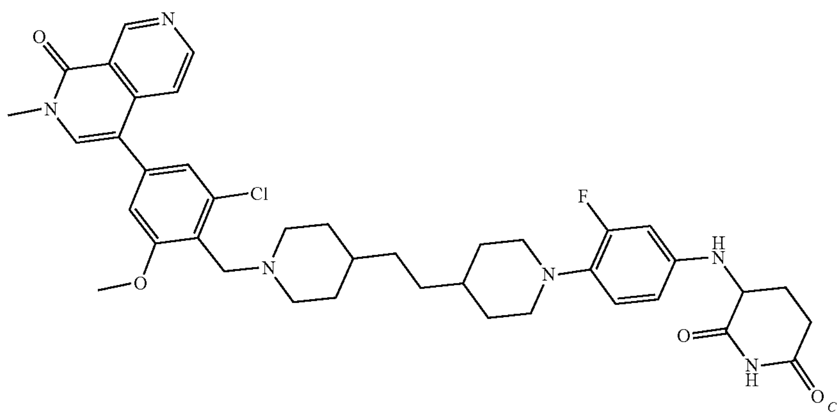 | +++ |
| 151 | 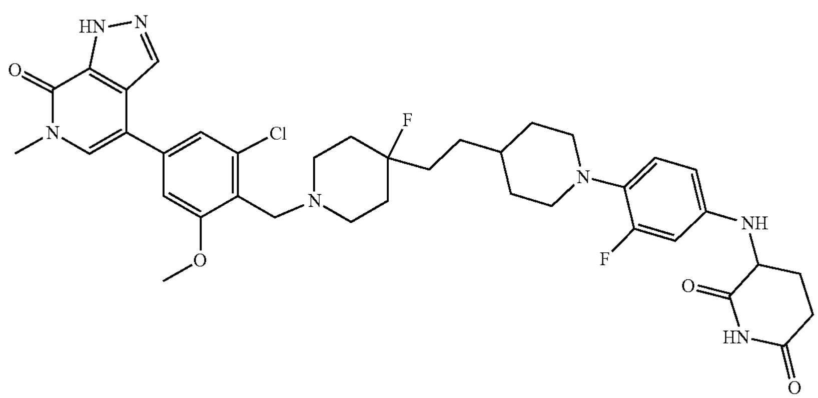 [SMILES: COc1cc(-c2cn(C)c(=O)c3[nH]ncc23)cc(Cl)c1CN1CCC(F)(CCC2CCN(c3ccc(NC4CCC(=O)NC4=O)cc3F)CC2)CC1] | +++ |
| 152 | 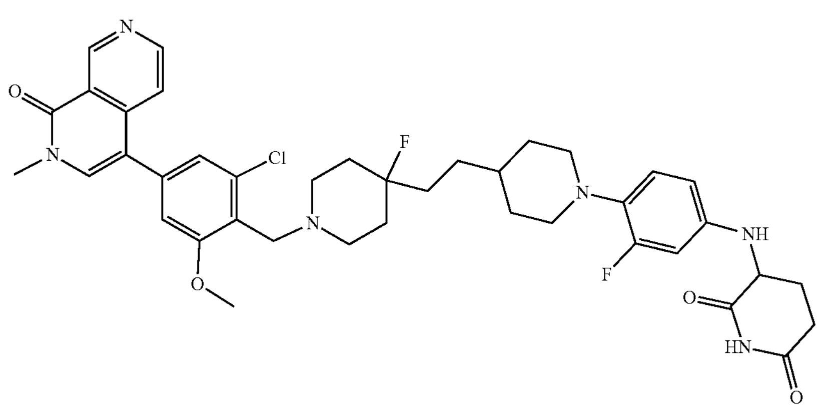 [SMILES: COc1cc(-c2cn(C)c(=O)c3cnccc23)cc(Cl)c1CN1CCC(F)(CCC2CCN(c3ccc(NC4CCC(=O)NC4=O)cc3F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 153 | 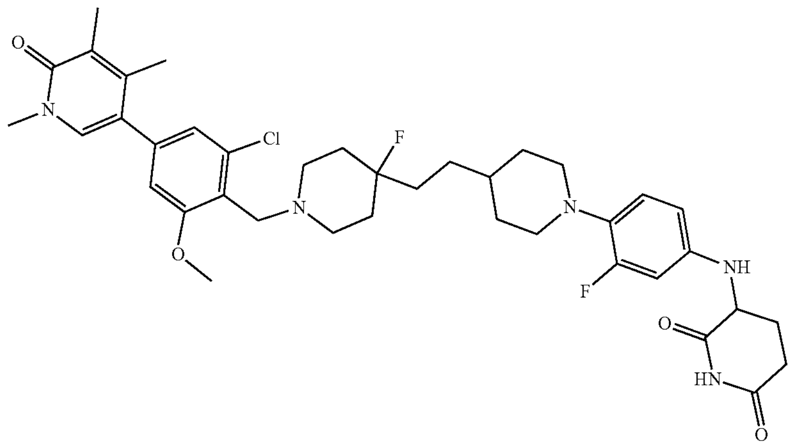 [SMILES: COc1cc(-c2cn(C)c(=O)c(C)c2C)cc(Cl)c1CN1CCC(F)(CCC2CCN(c3ccc(NC4CCC(=O)NC4=O)cc3F)CC2)CC1] | +++ |
| 154 | 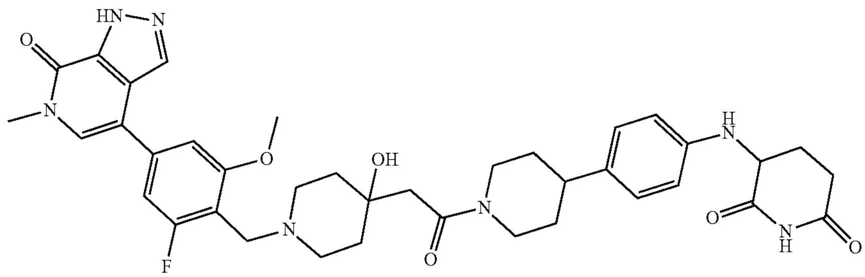 [SMILES: COc1cc(-c2cn(C)c(=O)c3[nH]ncc23)cc(F)c1CN1CCC(O)(CC(=O)N2CCC(c3ccc(NC4CCC(=O)NC4=O)cc3)CC2)CC1] | +++ |
| 155 | 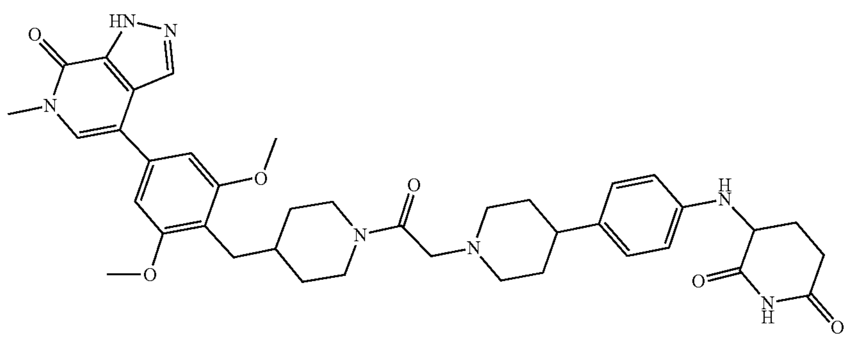 [SMILES: COc1cc(-c2cn(C)c(=O)c3[nH]ncc23)cc(OC)c1CC1CCN(C(=O)CN2CCC(c3ccc(NC4CCC(=O)NC4=O)cc3)CC2)CC1] | +++ |
| 156 | 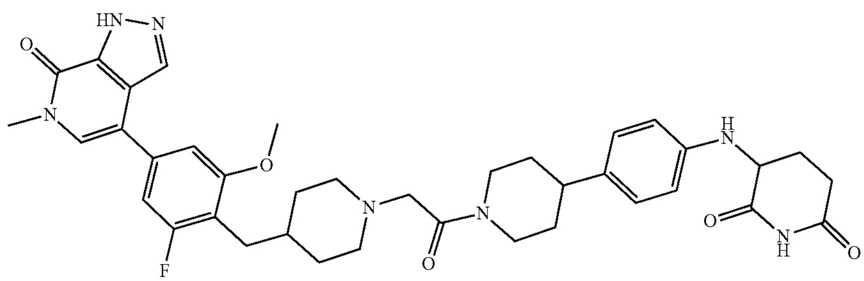 [SMILES: COc1cc(-c2cn(C)c(=O)c3[nH]ncc23)cc(F)c1CC1CCN(CC(=O)N2CCC(c3ccc(NC4CCC(=O)NC4=O)cc3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 157 | 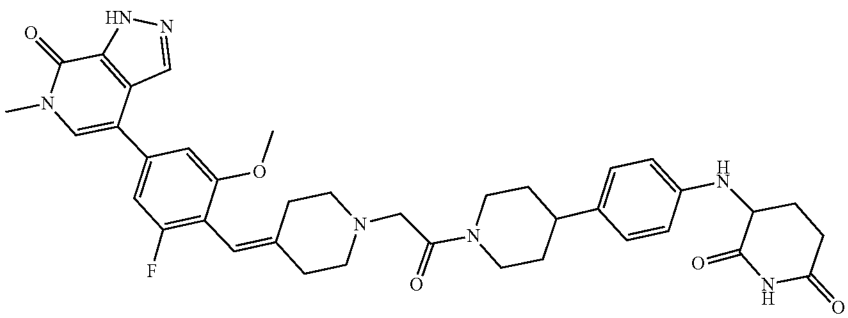 [SMILES: COc1cc(-c2cn(C)c(=O)c3[nH]ncc23)cc(F)c1C=C1CCN(CC(=O)N2CCC(c3ccc(NC4CCC(=O)NC4=O)cc3)CC2)CC1] | +++ |
| 158 | 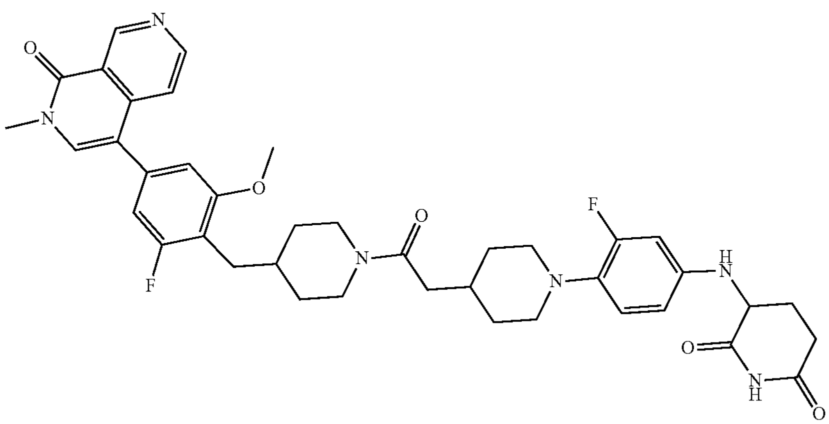 [SMILES: COc1cc(-c2cn(C)c(=O)c3cnccc23)cc(F)c1CC1CCN(C(=O)CC2CCN(c3ccc(NC4CCC(=O)NC4=O)cc3F)CC2)CC1] | +++ |
| 159 | 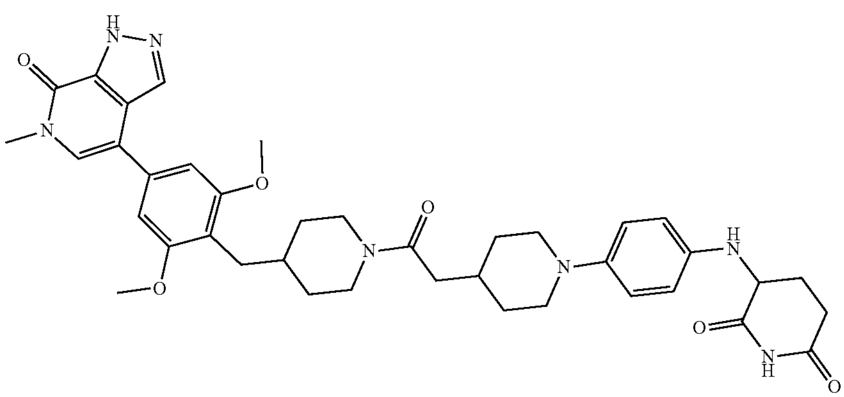 [SMILES: COc1cc(-c2cn(C)c(=O)c3[nH]ncc23)cc(OC)c1CC1CCN(C(=O)CC2CCN(c3ccc(NC4CCC(=O)NC4=O)cc3)CC2)CC1] | +++ |
| 160 | 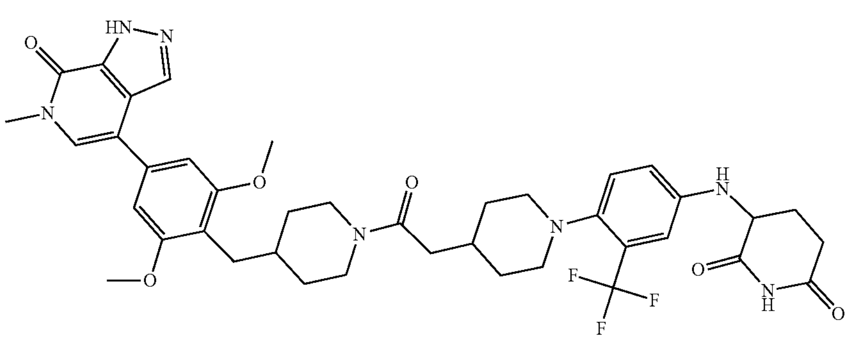 [SMILES: COc1cc(-c2cn(C)c(=O)c3[nH]ncc23)cc(OC)c1CC1CCN(C(=O)CC2CCN(c3ccc(NC4CCC(=O)NC4=O)cc3C(F)(F)F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 161 | 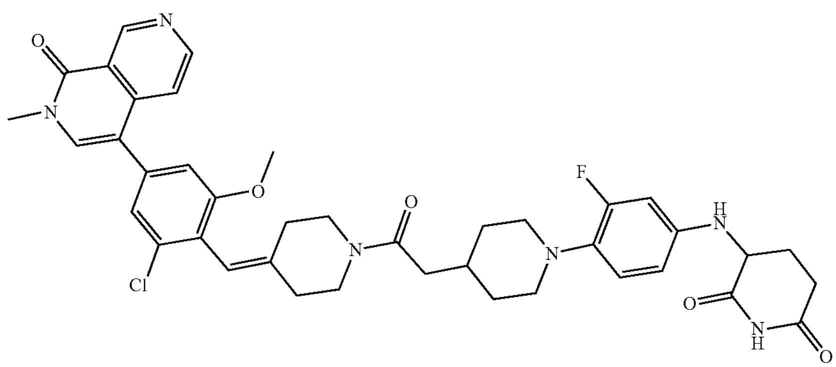 [SMILES: COc1cc(-c2cn(C)c(=O)c3cnccc23)cc(Cl)c1C=C1CCN(C(=O)CC2CCN(c3ccc(NC4CCC(=O)NC4=O)cc3F)CC2)CC1] | +++ |
| 162 | 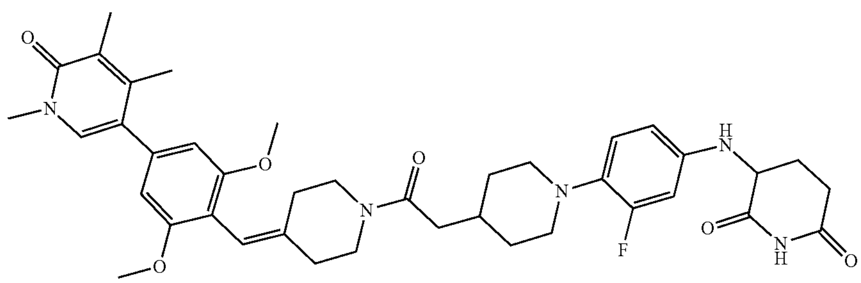 [SMILES: COc1cc(-c2cn(C)c(=O)c(C)c2C)cc(OC)c1C=C1CCN(C(=O)CC2CCN(c3ccc(NC4CCC(=O)NC4=O)cc3F)CC2)CC1] | +++ |
| 163 | 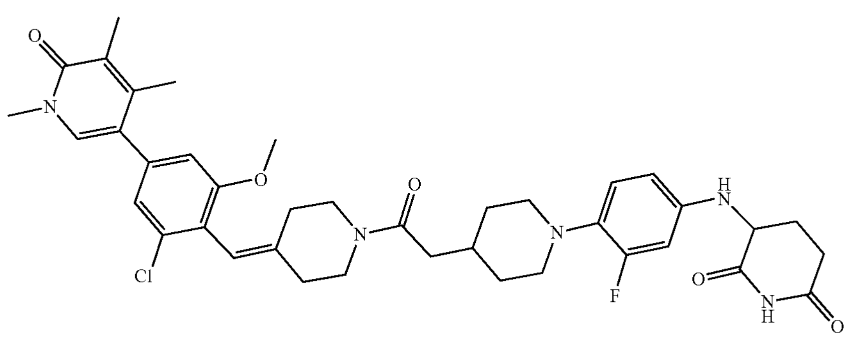 [SMILES: COc1cc(-c2cn(C)c(=O)c(C)c2C)cc(Cl)c1C=C1CCN(C(=O)CC2CCN(c3ccc(NC4CCC(=O)NC4=O)cc3F)CC2)CC1] | +++ |
| 164 | 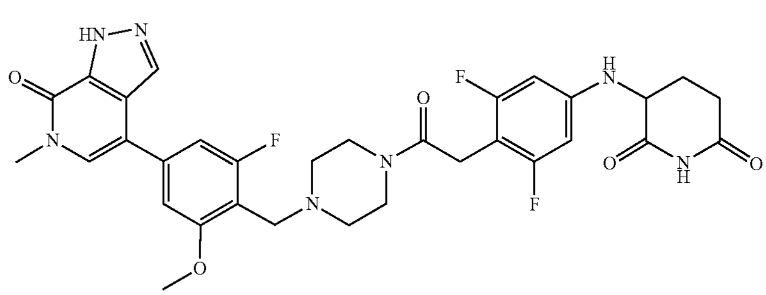 [SMILES: COc1cc(-c2cn(C)c(=O)c3[nH]ncc23)cc(F)c1CN1CCN(C(=O)Cc2c(F)cc(NC3CCC(=O)NC3=O)cc2F)CC1] | ++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 165 | 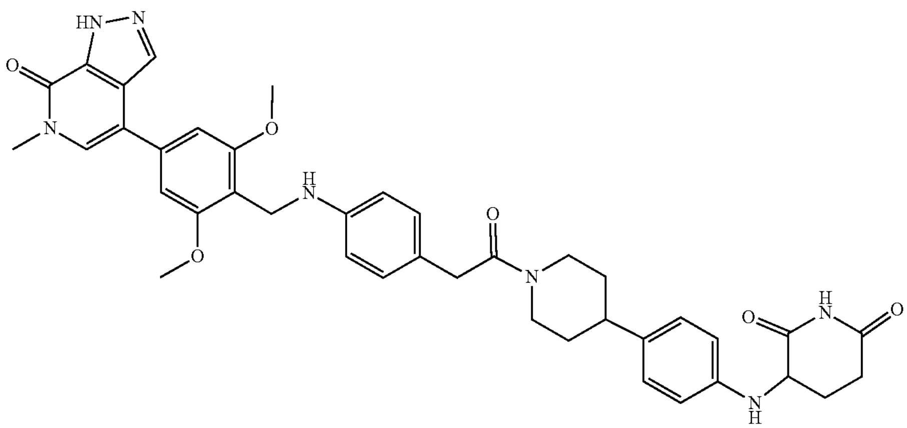 [SMILES: COc1cc(-c2cn(C)c(=O)c3[nH]ncc23)cc(OC)c1CNc1ccc(CC(=O)N2CCC(c3ccc(NC4CCC(=O)NC4=O)cc3)CC2)cc1] | +++ |
| 166 | 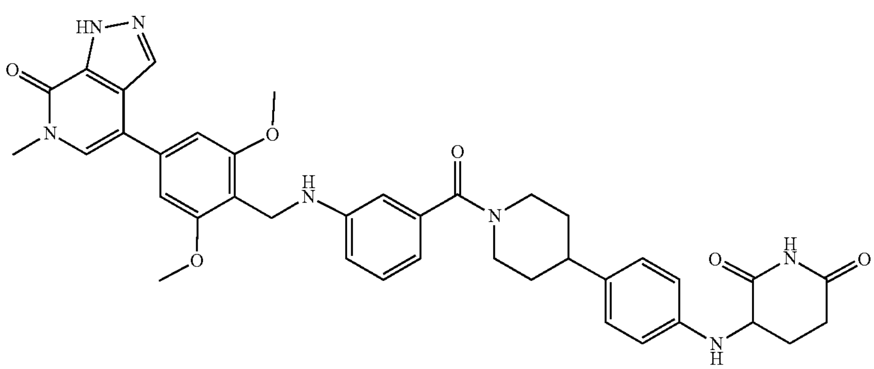 [SMILES: COc1cc(-c2cn(C)c(=O)c3[nH]ncc23)cc(OC)c1CNc1cccc(C(=O)N2CCC(c3ccc(NC4CCC(=O)NC4=O)cc3)CC2)c1] | +++ |
| 167 | 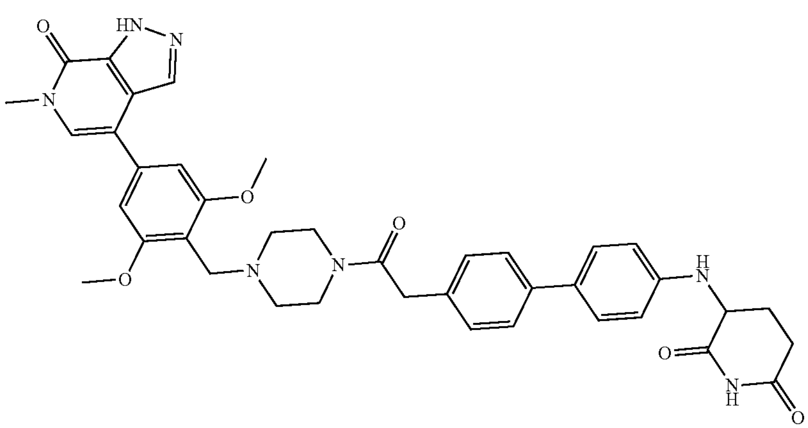 [SMILES: COc1cc(-c2cn(C)c(=O)c3[nH]ncc23)cc(OC)c1CN1CCN(C(=O)Cc2ccc(-c3ccc(NC4CCC(=O)NC4=O)cc3)cc2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 168 | 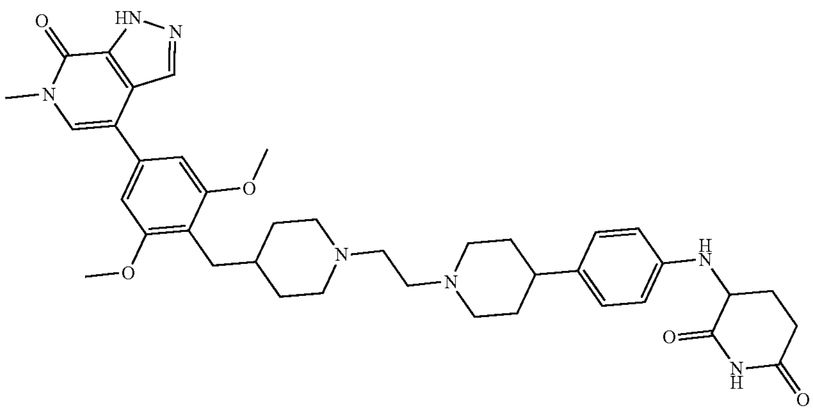 [SMILES: COc1cc(-c2cn(C)c(=O)c3[nH]ncc23)cc(OC)c1CC1CCN(CCN2CCC(c3ccc(NC4CCC(=O)NC4=O)cc3)CC2)CC1] | +++ |
| 169 | 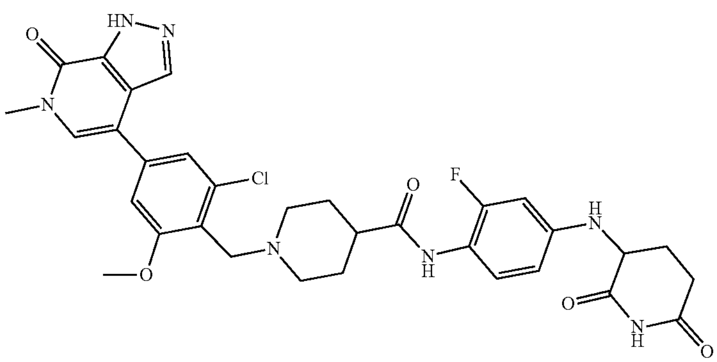 [SMILES: COc1cc(-c2cn(C)c(=O)c3[nH]ncc23)cc(Cl)c1CN1CCC(C(=O)Nc2ccc(NC3CCC(=O)NC3=O)cc2F)CC1] | +++ |
| 170 | 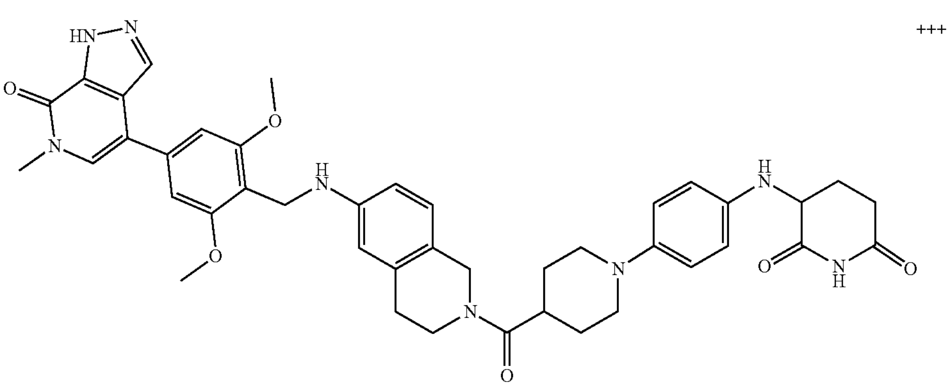 | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 171 | 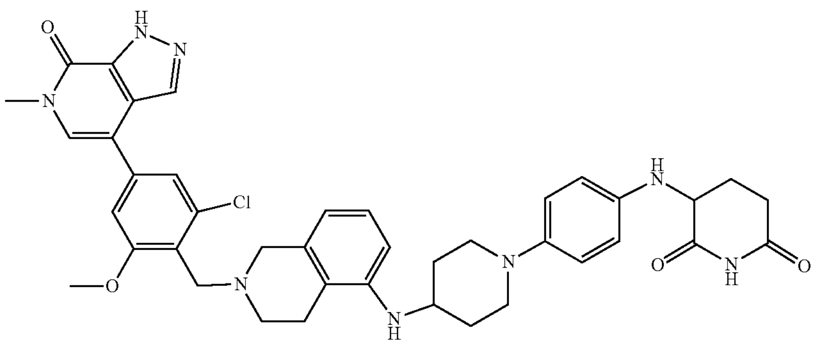 [SMILES: COc1cc(-c2cn(C)c(=O)c3[nH]ncc23)cc(Cl)c1CN1CCc2c(cccc2NC2CCN(c3ccc(NC4CCC(=O)NC4=O)cc3)CC2)C1] | +++ |
| 172 | 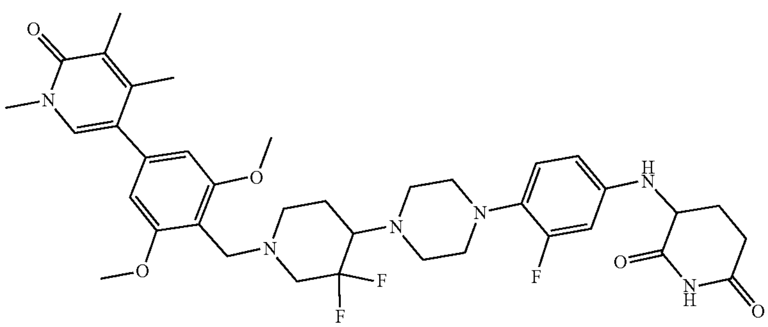 [SMILES: COc1cc(-c2cn(C)c(=O)c(C)c2C)cc(OC)c1CN1CCC(N2CCN(c3ccc(NC4CCC(=O)NC4=O)cc3F)CC2)C(F)(F)C1] | +++ |
| 173 | Stereoisomer 1 | +++ |
| 174 | Stereoisomer 2 | +++ |

TABLE 1-continued
XII. DATA
BRD9 Degradation Data.
| Cmpd # | Structure | HiBiT-Degradation 293T.166 BRD9 2.0 hours (DC50) [nM] |
|---|---|---|
| 175 | 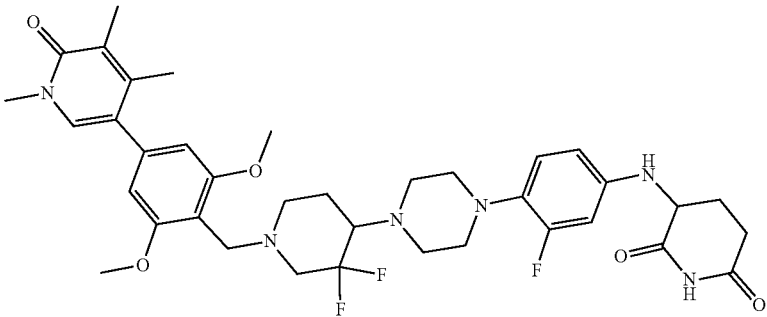 Stereoisomer 3 | +++ |
| 176 | 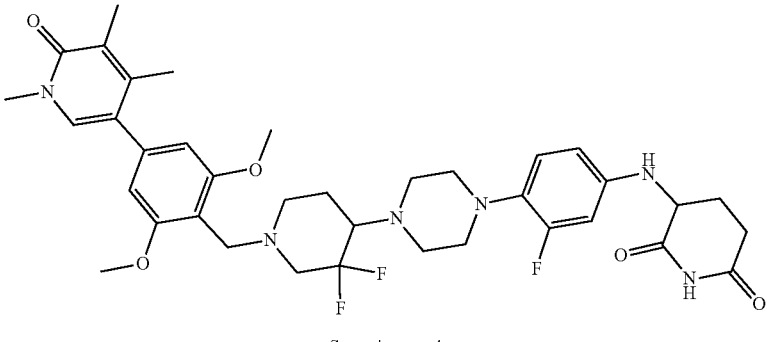 Stereoisomer 4 | +++ |
| 177 | 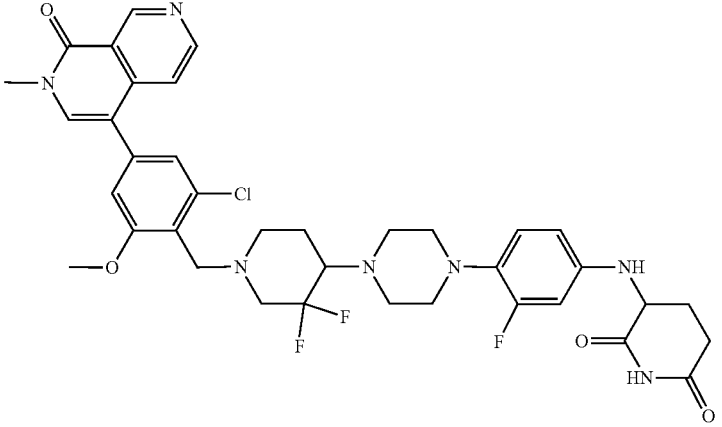 [SMILES: COc1cc(-c2cn(C)c(=O)c3cnccc23)cc(Cl)c1CN1CCC(N2CCN(c3ccc(NC4CCC(=O)NC4=O)cc3F)CC2)C(F)(F)C1] | +++ |

TABLE 1-continued
XII. DATA
BRD9 Degradation Data.
| Cmpd # | Structure | HiBiT-Degradation 293T.166 BRD9 2.0 hours (DC50) [nM] |
|---|---|---|
| 178 | 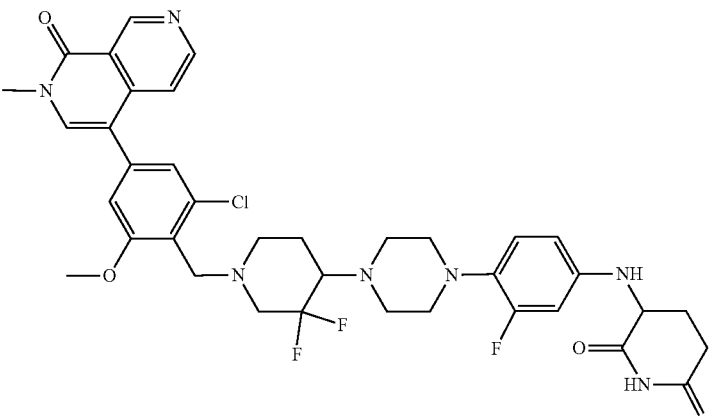<br>Stereoisomer 1 | +++ |
| 179 | 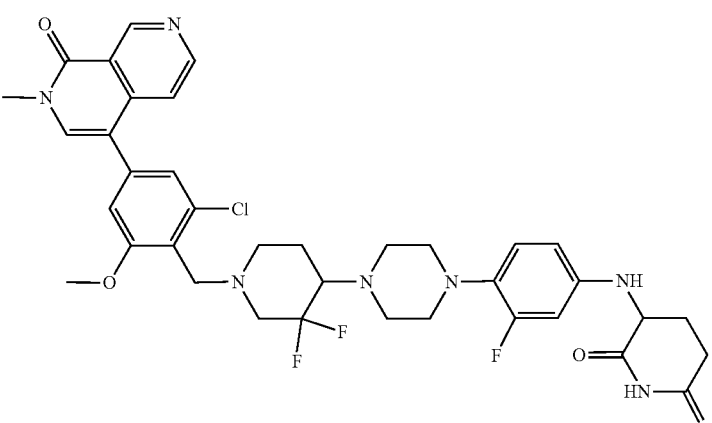<br>Stereoisomer 2 | +++ |
| 180 | 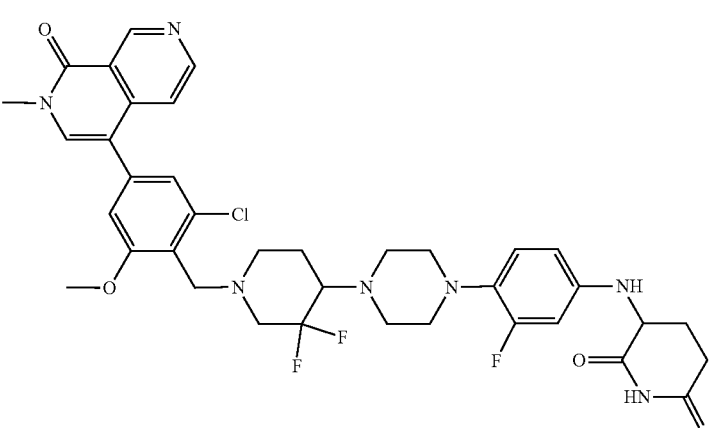<br>Stereoisomer 3 | +++ |

TABLE 1-continued
XII. DATA
BRD9 Degradation Data.
| Cmpd # | Structure | HiBiT-Degradation 293T.166 BRD9 2.0 hours (DC50) [nM] |
|---|---|---|
| 181 | 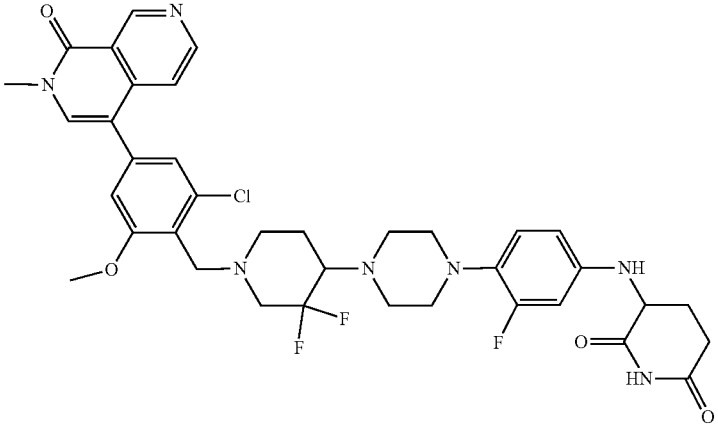<br>Stereoisomer 4 | +++ |
| 182 | 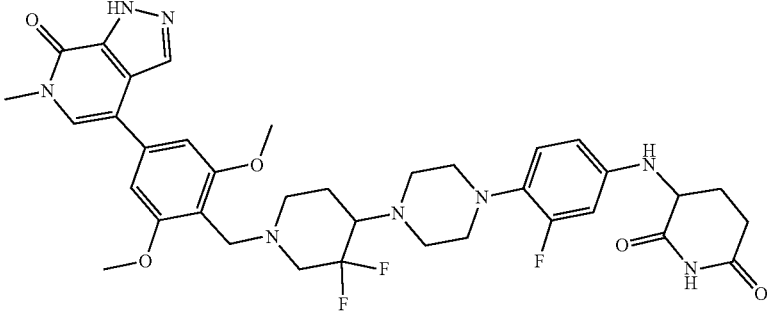 [SMILES: COc1cc(-c2cn(C)c(=O)c3[nH]ncc23)cc(OC)c1CN1CCC(N2CCN(c3ccc(NC4CCC(=O)NC4=O)cc3F)CC2)C(F)(F)C1] | +++ |
| 183 | 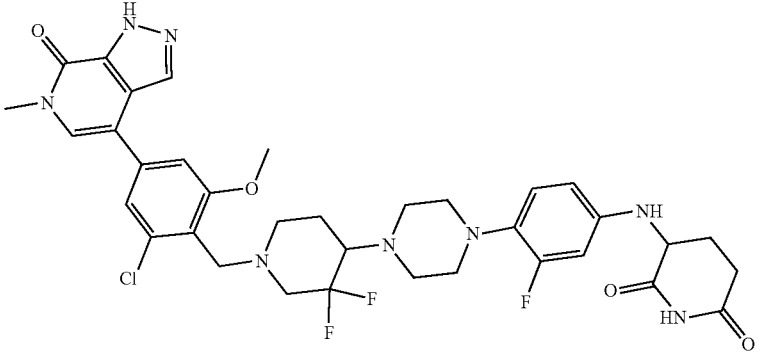 [SMILES: COc1cc(-c2cn(C)c(=O)c3[nH]ncc23)cc(Cl)c1CN1CCC(N2CCN(c3ccc(NC4CCC(=O)NC4=O)cc3F)CC2)C(F)(F)C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 184 | 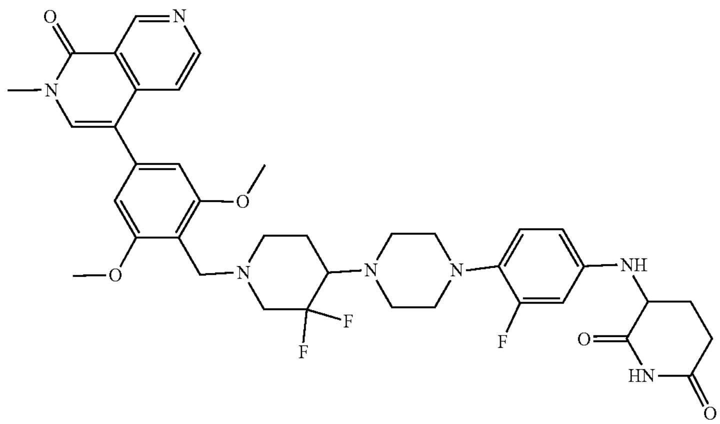 [SMILES: COc1cc(-c2cn(C)c(=O)c3cnccc23)cc(OC)c1CN1CCC(N2CCN(c3ccc(NC4CCC(=O)NC4=O)cc3F)CC2)C(F)(F)C1] | +++ |
| 185 | 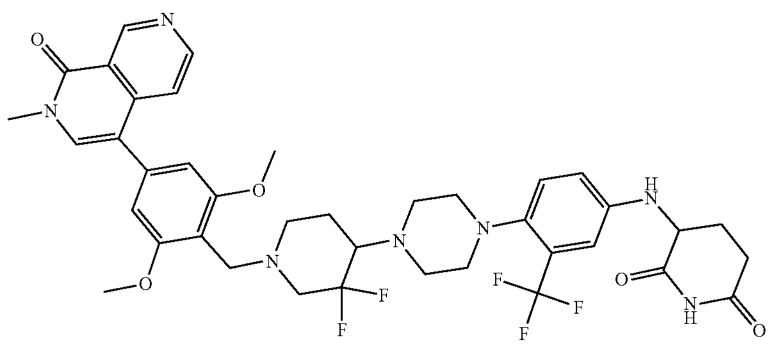 [SMILES: COc1cc(-c2cn(C)c(=O)c3cnccc23)cc(OC)c1CN1CCC(N2CCN(c3ccc(NC4CCC(=O)NC4=O)cc3C(F)(F)F)CC2)C(F)(F)C1] | +++ |
| 186 | 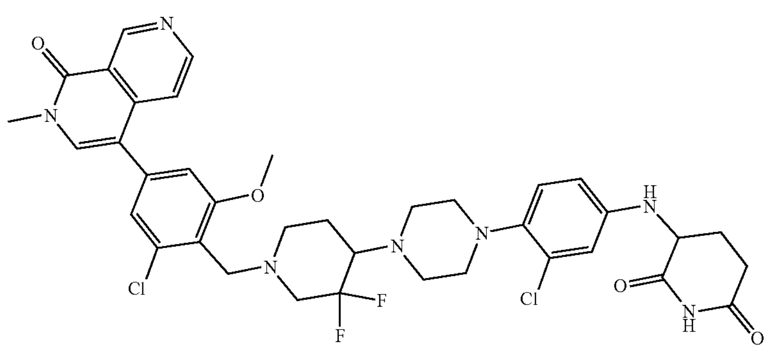 [SMILES: COc1cc(-c2cn(C)c(=O)c3cnccc23)cc(Cl)c1CN1CCC(N2CCN(c3ccc(NC4CCC(=O)NC4=O)cc3Cl)CC2)C(F)(F)C1] | +++ |
| 187 | 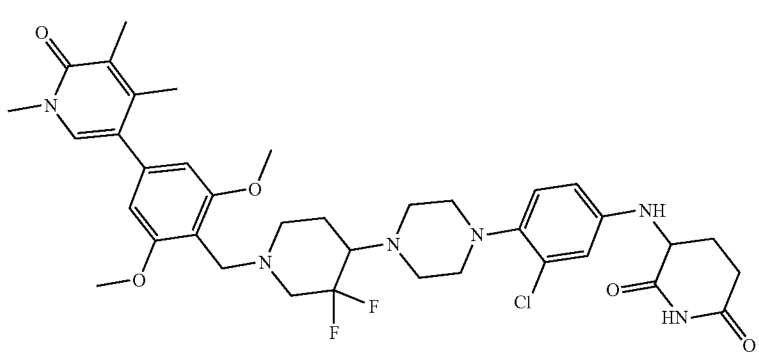 [SMILES: COc1cc(-c2cn(C)c(=O)c(C)c2C)cc(OC)c1CN1CCC(N2CCN(c3ccc(NC4CCC(=O)NC4=O)cc3Cl)CC2)C(F)(F)C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 188 | 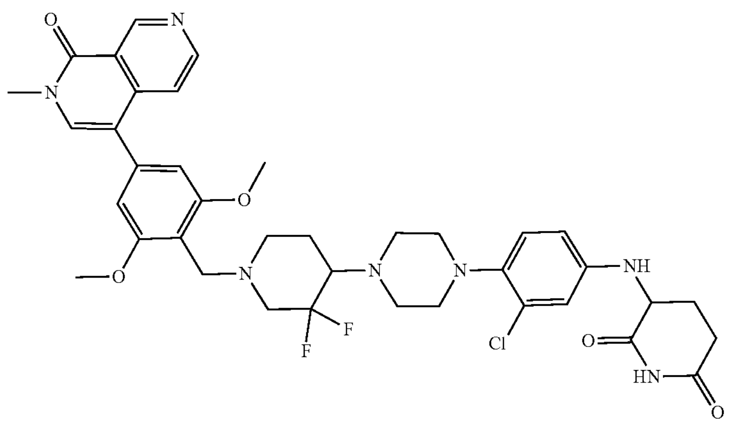 [SMILES: COc1cc(-c2cn(C)c(=O)c3cnccc23)cc(OC)c1CN1CCC(N2CCN(c3ccc(NC4CCC(=O)NC4=O)cc3Cl)CC2)C(F)(F)C1] | +++ |
| 189 | 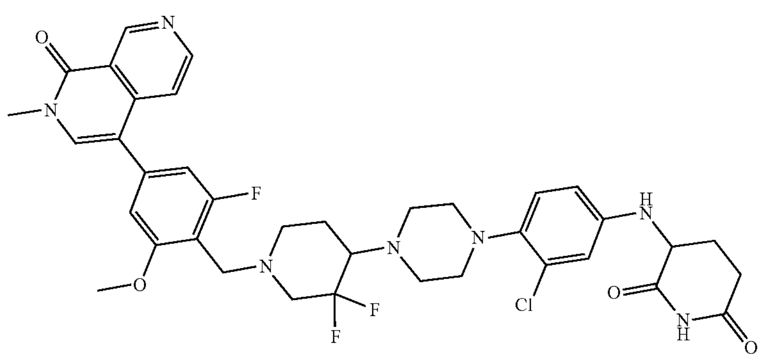 [SMILES: COc1cc(-c2cn(C)c(=O)c3cnccc23)cc(F)c1CN1CCC(N2CCN(c3ccc(NC4CCC(=O)NC4=O)cc3Cl)CC2)C(F)(F)C1] | +++ |
| 190 | 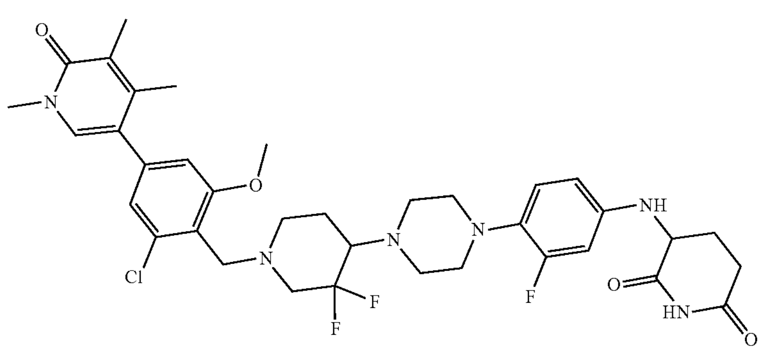 [SMILES: COc1cc(-c2cn(C)c(=O)c(C)c2C)cc(Cl)c1CN1CCC(N2CCN(c3ccc(NC4CCC(=O)NC4=O)cc3F)CC2)C(F)(F)C1] | +++ |
| 191 | 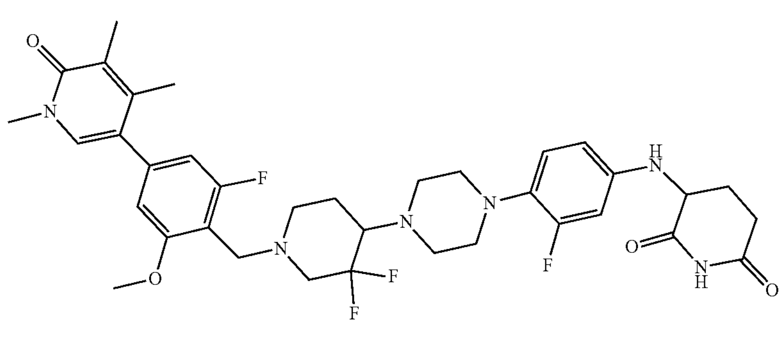 [SMILES: COc1cc(-c2cn(C)c(=O)c(C)c2C)cc(F)c1CN1CCC(N2CCN(c3ccc(NC4CCC(=O)NC4=O)cc3F)CC2)C(F)(F)C1] | +++ |

TABLE 1-continued
XII. DATA
BRD9 Degradation Data.
| Cmpd # | Structure | HiBiT-Degradation 293T.166 BRD9 2.0 hours (DC50) [nM] |
|---|---|---|
| 192 | 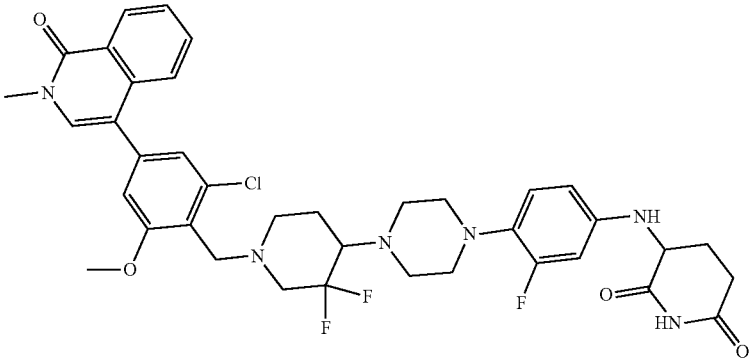 [SMILES: COc1cc(-c2cn(C)c(=O)c3ccccc23)cc(Cl)c1CN1CCC(N2CCN(c3ccc(NC4CCC(=O)NC4=O)cc3F)CC2)C(F)(F)C1] | +++ |
| 193 | 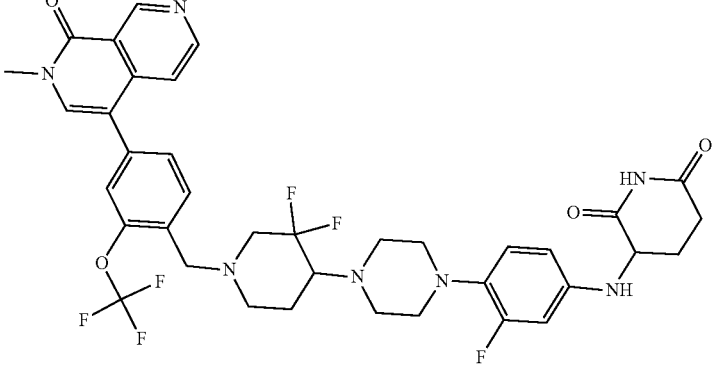 | +++ |
| 194 | 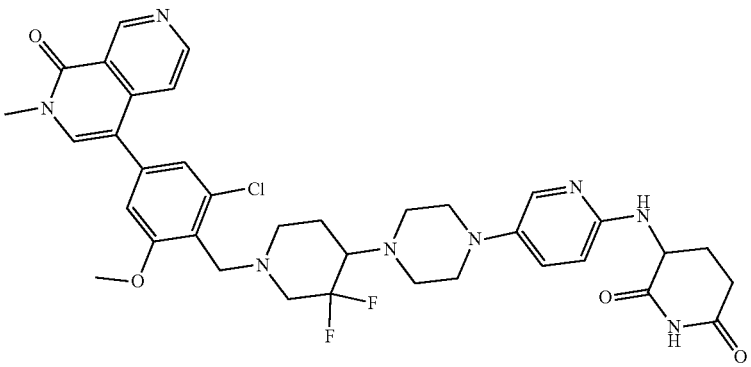 [SMILES: COc1cc(-c2cn(C)c(=O)c3cnccc23)cc(Cl)c1CN1CCC(N2CCN(c3ccc(NC4CCC(=O)NC4=O)nc3)CC2)C(F)(F)C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 195 | 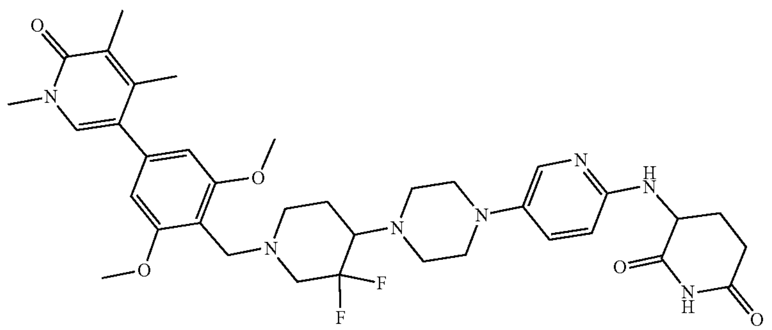 [SMILES: COc1cc(-c2cn(C)c(=O)c(C)c2C)cc(OC)c1CN1CCC(N2CCN(c3ccc(NC4CCC(=O)NC4=O)nc3)CC2)C(F)(F)C1] | +++ |
| 196 | 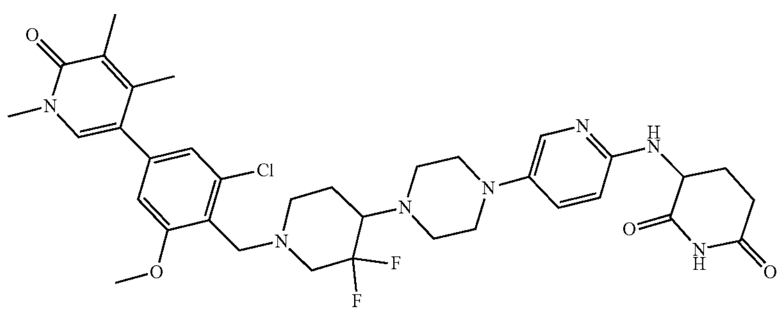 [SMILES: COc1cc(-c2cn(C)c(=O)c(C)c2C)cc(Cl)c1CN1CCC(N2CCN(c3ccc(NC4CCC(=O)NC4=O)nc3)CC2)C(F)(F)C1] | +++ |
| 197 | 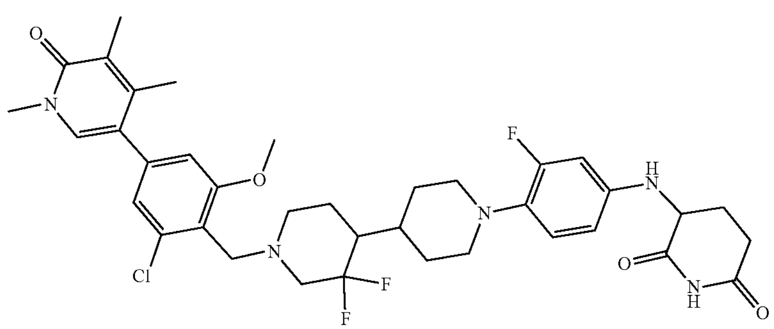 [SMILES: COc1cc(-c2cn(C)c(=O)c(C)c2C)cc(Cl)c1CN1CCC(C2CCN(c3ccc(NC4CCC(=O)NC4=O)cc3F)CC2)C(F)(F)C1] | +++ |
| 198 | 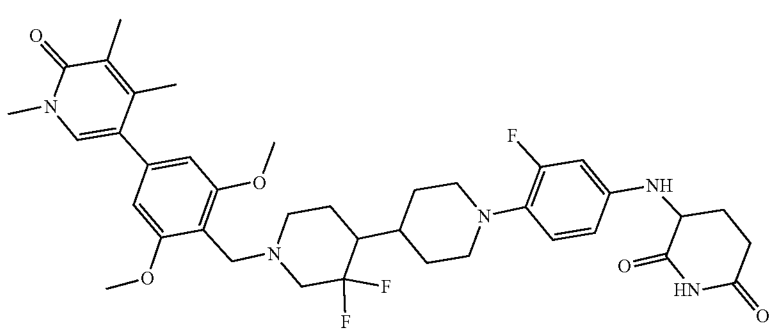 [SMILES: COc1cc(-c2cn(C)c(=O)c(C)c2C)cc(OC)c1CN1CCC(C2CCN(c3ccc(NC4CCC(=O)NC4=O)cc3F)CC2)C(F)(F)C1] | +++ |

TABLE 1-continued
XII. DATA
BRD9 Degradation Data.
| Cmpd # | Structure | HiBiT-Degradation 293T.166 BRD9 2.0 hours (DC50) [nM] |
|---|---|---|
| 199 | 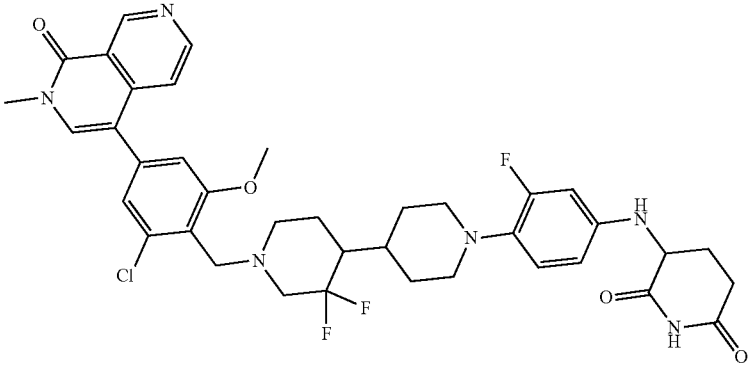 [SMILES: COc1cc(-c2cn(C)c(=O)c3cnccc23)cc(Cl)c1CN1CCC(C2CCN(c3ccc(NC4CCC(=O)NC4=O)cc3F)CC2)C(F)(F)C1] | +++ |
| 200 | 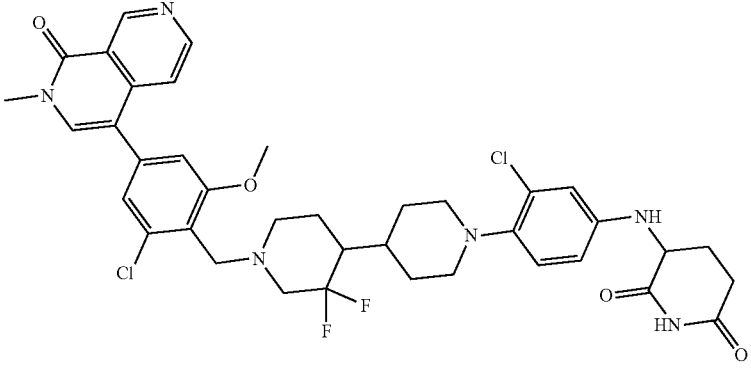 [SMILES: COc1cc(-c2cn(C)c(=O)c3cnccc23)cc(Cl)c1CN1CCC(C2CCN(c3ccc(NC4CCC(=O)NC4=O)cc3Cl)CC2)C(F)(F)C1] | +++ |
| 201 | 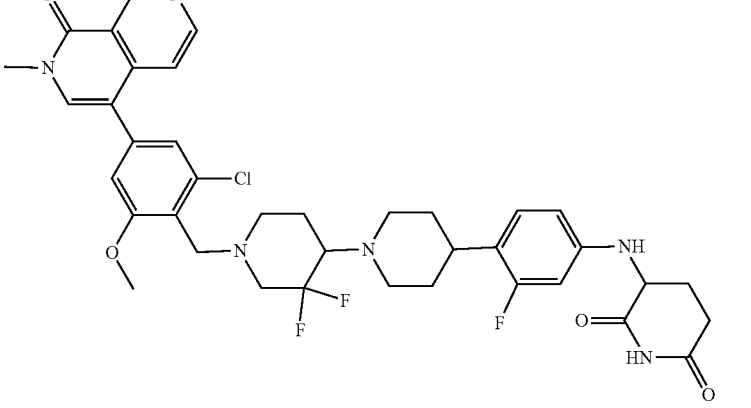 | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 202 | 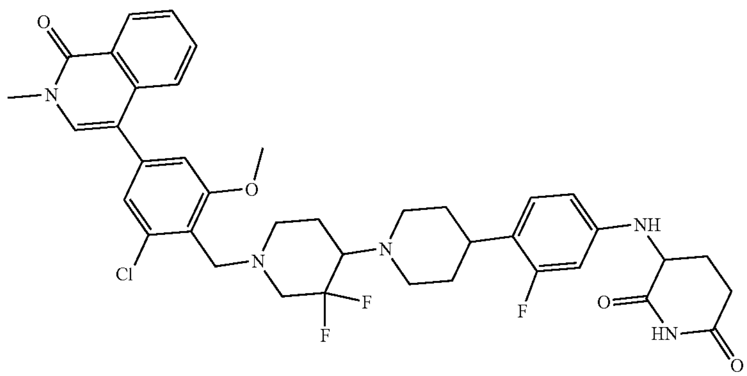 [SMILES: COc1cc(-c2cn(C)c(=O)c3ccccc23)cc(Cl)c1CN1CCC(N2CCC(c3ccc(NC4CCC(=O)NC4=O)cc3F)CC2)C(F)(F)C1] | +++ |
| 203 | Diastereomer 1 | +++ |
| 204 | Diastereomer 2 | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 205 | 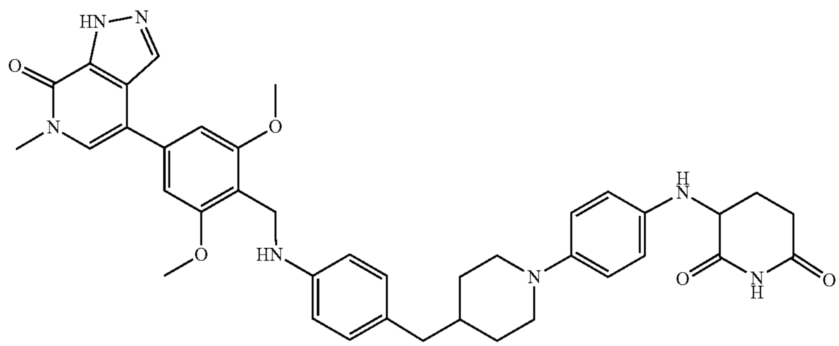 [SMILES: COc1cc(-c2cn(C)c(=O)c3[nH]ncc23)cc(OC)c1CNc1ccc(CC2CCN(c3ccc(NC4CCC(=O)NC4=O)cc3)CC2)cc1] | +++ |
| 206 | 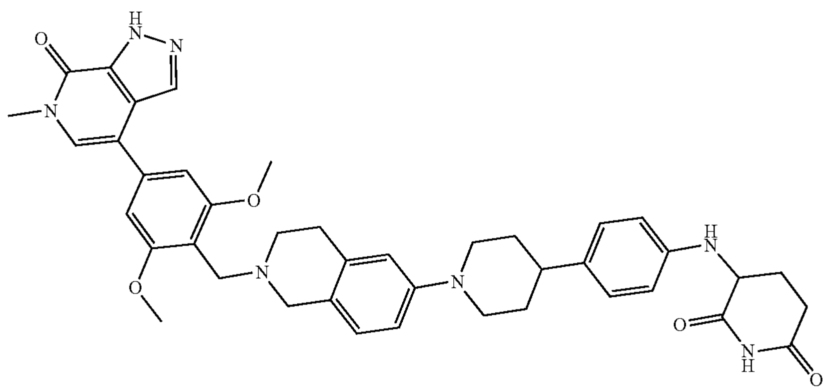 [SMILES: COc1cc(-c2cn(C)c(=O)c3[nH]ncc23)cc(OC)c1CN1CCc2cc(N3CCC(c4ccc(NC5CCC(=O)NC5=O)cc4)CC3)ccc2C1] | +++ |
| 207 | 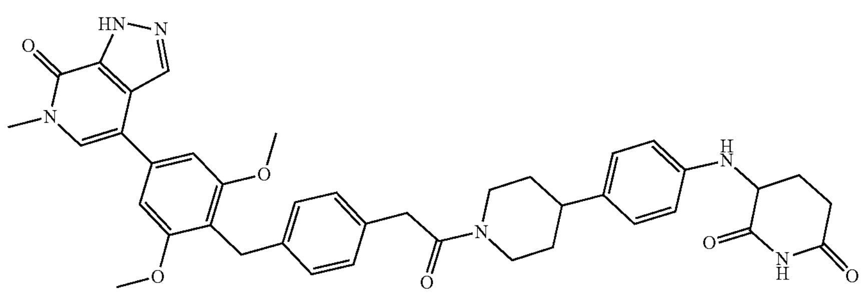 [SMILES: COc1cc(-c2cn(C)c(=O)c3[nH]ncc23)cc(OC)c1Cc1ccc(CC(=O)N2CCC(c3ccc(NC4CCC(=O)NC4=O)cc3)CC2)cc1] | +++ |
| 208 | 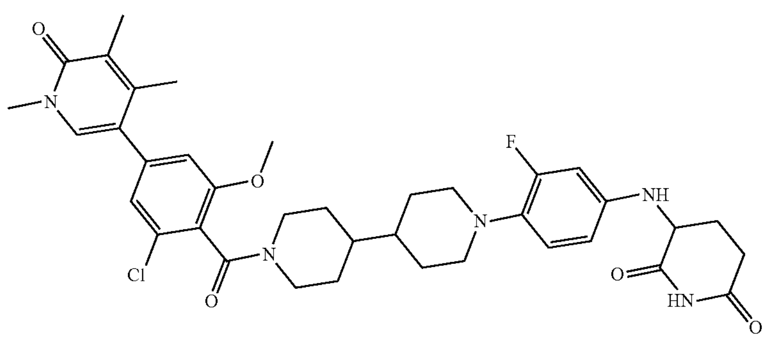 [SMILES: COc1cc(-c2cn(C)c(=O)c(C)c2C)cc(Cl)c1C(=O)N1CCC(C2CCN(c3ccc(NC4CCC(=O)NC4=O)cc3F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 209 | 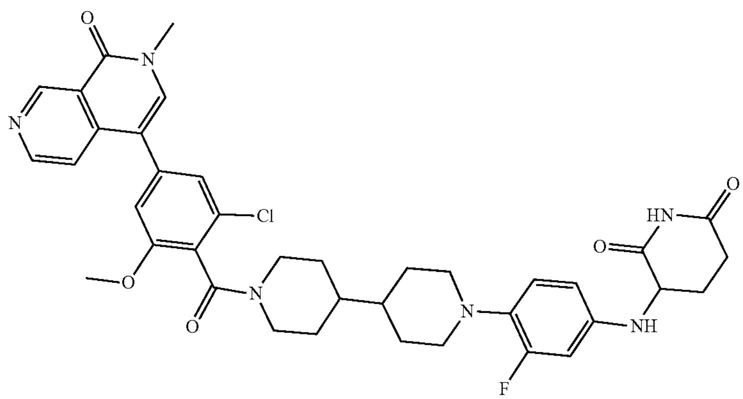 [SMILES: COc1cc(-c2cn(C)c(=O)c3cnccc23)cc(Cl)c1C(=O)N1CCC(C2CCN(c3ccc(NC4CCC(=O)NC4=O)cc3F)CC2)CC1] | +++ |
| 210 | 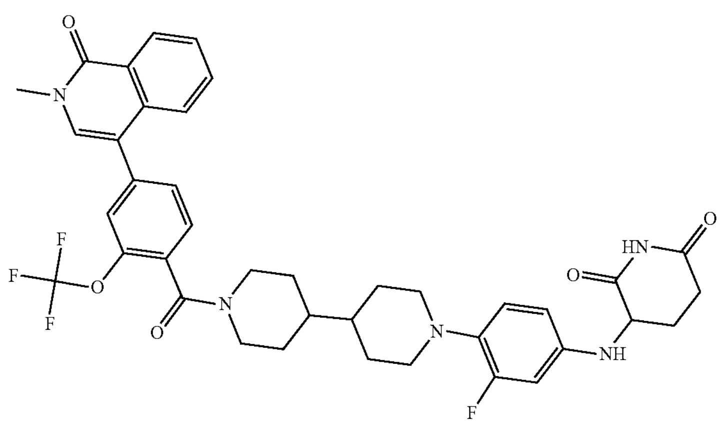 [SMILES: Cn1cc(-c2ccc(C(=O)N3CCC(C4CCN(c5ccc(NC6CCC(=O)NC6=O)cc5F)CC4)CC3)c(OC(F)(F)F)c2)c2ccccc2c1=O] | +++ |
| 211 | 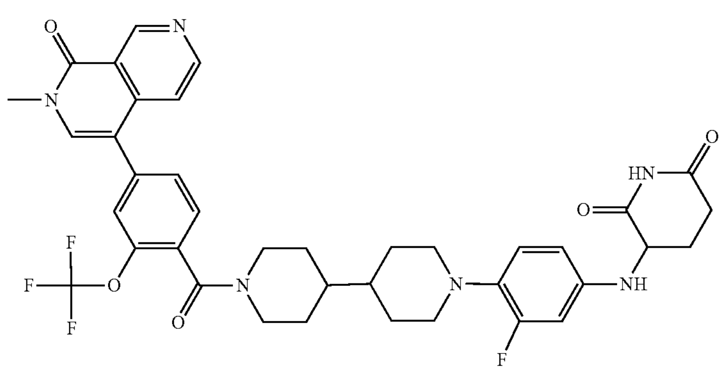 [SMILES: Cn1cc(-c2ccc(C(=O)N3CCC(C4CCN(c5ccc(NC6CCC(=O)NC6=O)cc5F)CC4)CC3)c(OC(F)(F)F)c2)c2ccncc2c1=O] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 212 | 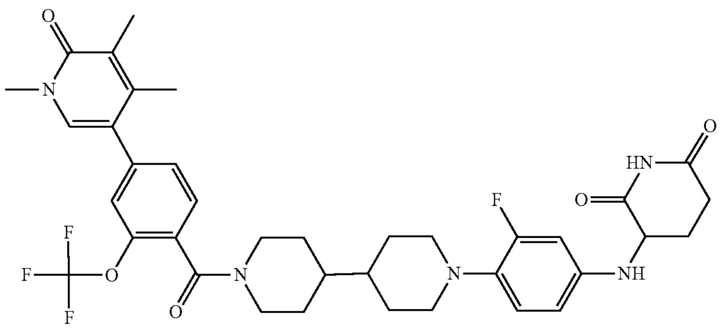 [SMILES: Cc1c(-c2ccc(C(=O)N3CCC(C4CCN(c5ccc(NC6CCC(=O)NC6=O)cc5F)CC4)CC3)c(OC(F)(F)F)c2)cn(C)c(=O)c1C] | +++ |
| 213 | Enantiomer 1 | >800 |
| 214 | Enantiomer 2 | +++ |
| 215 | 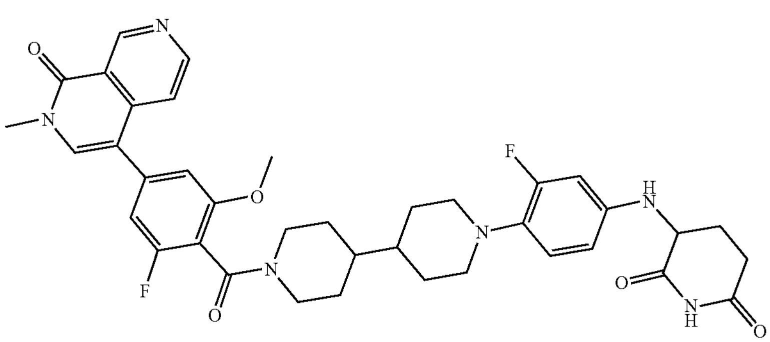 [SMILES: COc1cc(-c2cn(C)c(=O)c3cnccc23)cc(F)c1C(=O)N1CCC(C2CCN(c3ccc(NC4CCC(=O)NC4=O)cc3F)CC2)CC1] | +++ |

TABLE 1-continued
XII. DATA
BRD9 Degradation Data.
| Cmpd # | Structure | HiBiT-Degradation 293T.166 BRD9 2.0 hours (DC50) [nM] |
|---|---|---|
| 216 | 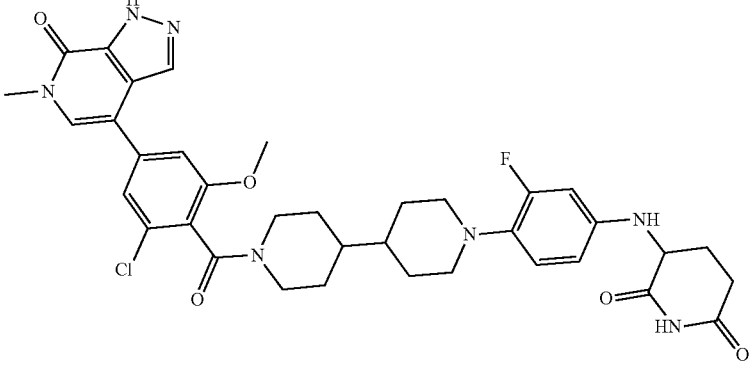 | +++ |
| 217 | 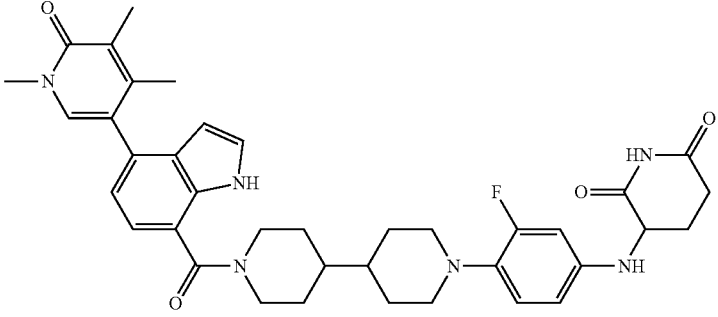 [SMILES: Cc1c(-c2ccc(C(=O)N3CCC(C4CCN(c5ccc(NC6CCC(=O)NC6=O)cc5F)CC4)CC3)c3[nH]ccc23)cn(C)c(=O)c1C] | +++ |
| 218 | 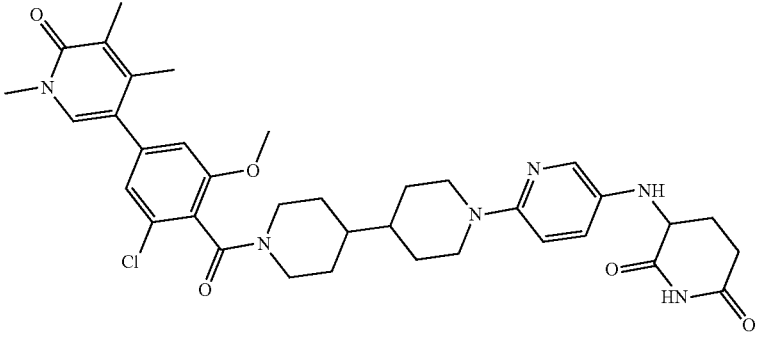 [SMILES: COc1cc(-c2cn(C)c(=O)c(C)c2C)cc(Cl)c1C(=O)N1CCC(C2CCN(c3ccc(NC4CCC(=O)NC4=O)cn3)CC2)CC1] | +++ |
| 219 | 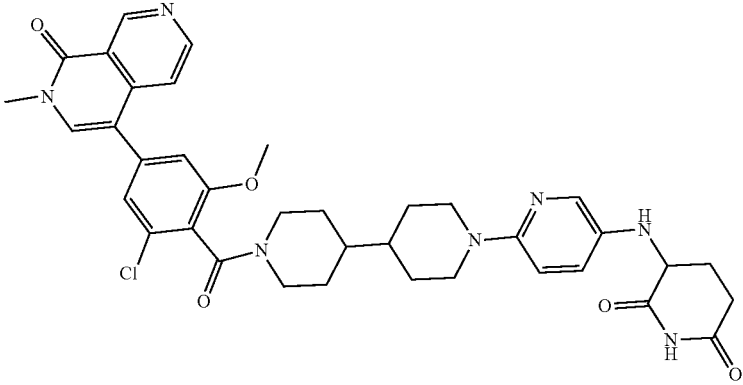 [SMILES: COc1cc(-c2cn(C)c(=O)c3cnccc23)cc(Cl)c1C(=O)N1CCC(C2CCN(c3ccc(NC4CCC(=O)NC4=O)cn3)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
| --- | --- | --- |
| 220 | 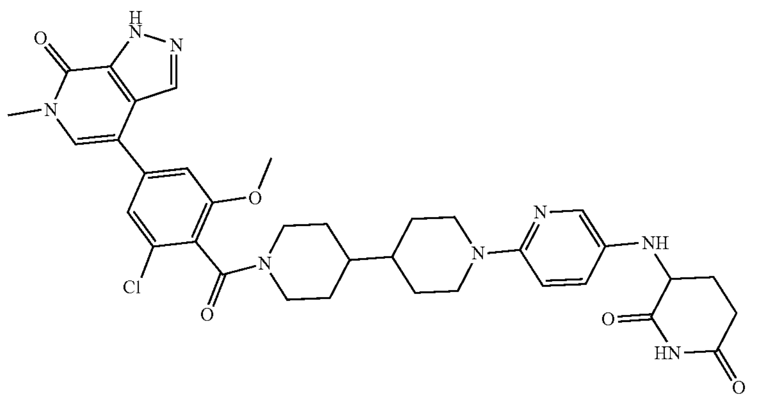 [SMILES: COc1cc(-c2cn(C)c(=O)c3[nH]ncc23)cc(Cl)c1C(=O)N1CCC(C2CCN(c3ccc(NC4CCC(=O)NC4=O)cn3)CC2)CC1] | +++ |
| 221 | 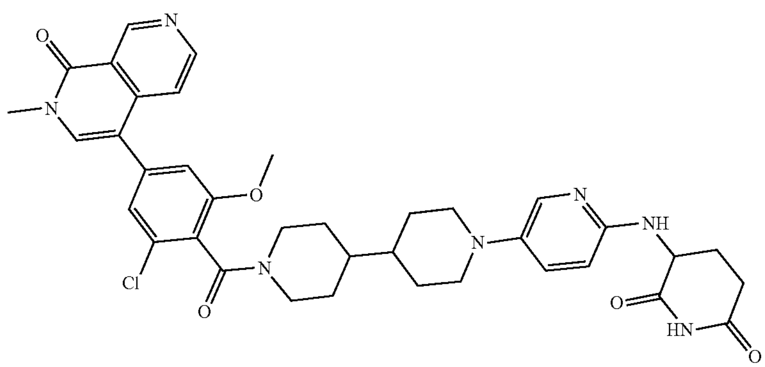 [SMILES: COc1cc(-c2cn(C)c(=O)c3cnccc23)cc(Cl)c1C(=O)N1CCC(C2CCN(c3ccc(NC4CCC(=O)NC4=O)nc3)CC2)CC1] | +++ |
| 222 | 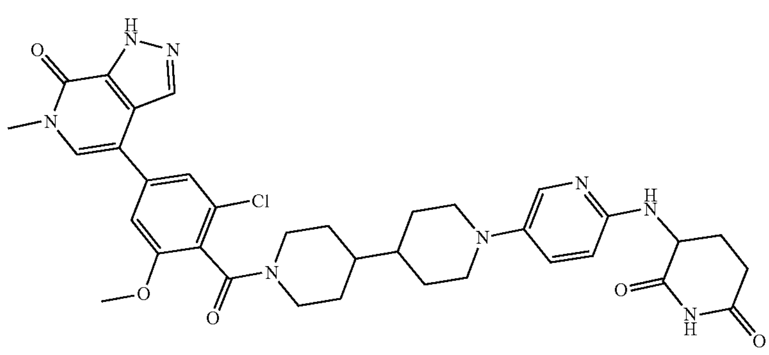 [SMILES: COc1cc(-c2cn(C)c(=O)c3[nH]ncc23)cc(Cl)c1C(=O)N1CCC(C2CCN(c3ccc(NC4CCC(=O)NC4=O)nc3)CC2)CC1] | +++ |
| 223 | 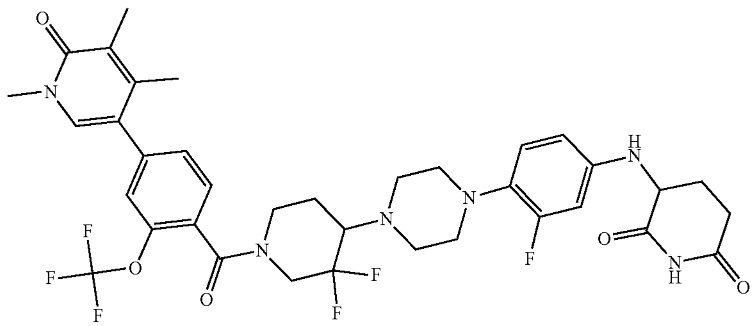 [SMILES: Cc1c(-c2ccc(C(=O)N3CCC(N4CCN(c5ccc(NC6CCC(=O)NC6=O)cc5F)CC4)C(F)(F)C3)c(OC(F)(F)F)c2)cn(C)c(=O)c1C] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 224 | 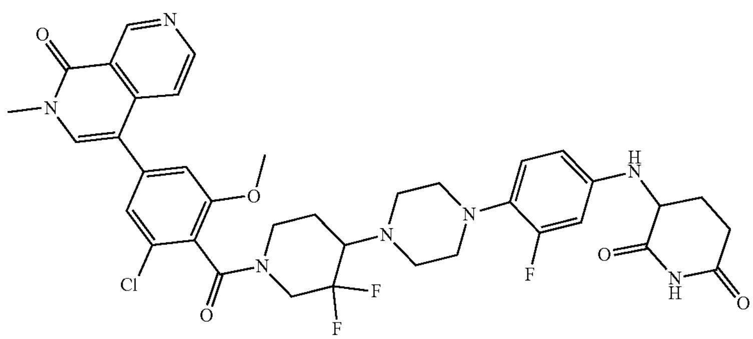 [SMILES: COc1cc(-c2cn(C)c(=O)c3cnccc23)cc(Cl)c1C(=O)N1CCC(N2CCN(c3ccc(NC4CCC(=O)NC4=O)cc3F)CC2)C(F)(F)C1] | +++ |
| 225 | 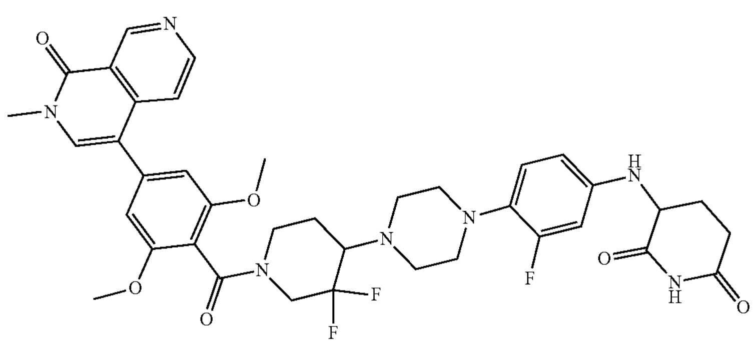 [SMILES: COc1cc(-c2cn(C)c(=O)c3cnccc23)cc(OC)c1C(=O)N1CCC(N2CCN(c3ccc(NC4CCC(=O)NC4=O)cc3F)CC2)C(F)(F)C1] | +++ |
| 226 | 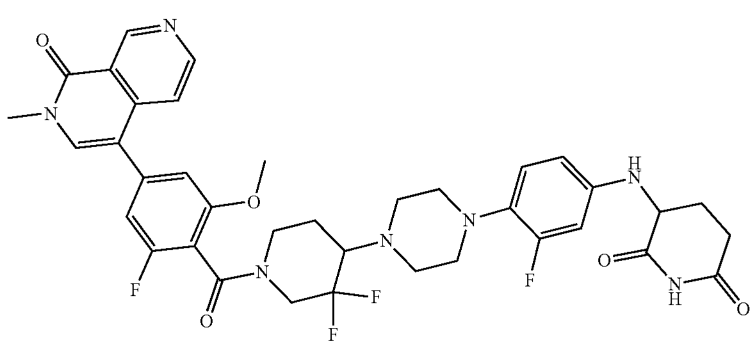 [SMILES: COc1cc(-c2cn(C)c(=O)c3cnccc23)cc(F)c1C(=O)N1CCC(N2CCN(c3ccc(NC4CCC(=O)NC4=O)cc3F)CC2)C(F)(F)C1] | +++ |
| 227 | 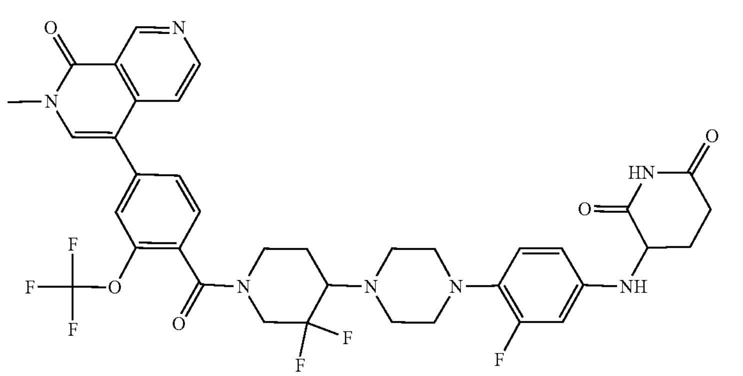 [SMILES: Cn1cc(-c2ccc(C(=O)N3CCC(N4CCN(c5ccc(NC6CCC(=O)NC6=O)cc5F)CC4)C(F)(F)C3)c(OC(F)(F)F)c2)c2ccncc2c1=O] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 228 | 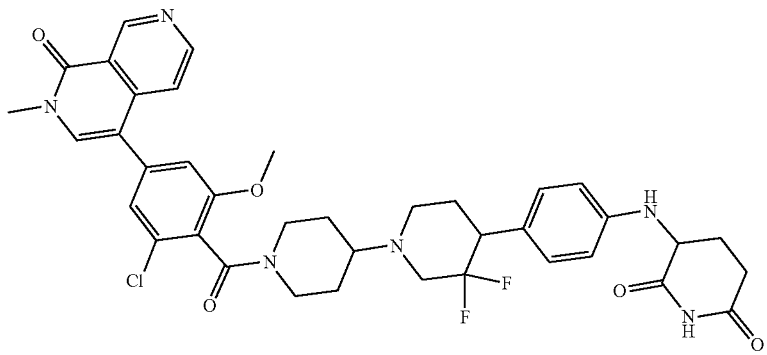 [SMILES: COc1cc(-c2cn(C)c(=O)c3cnccc23)cc(Cl)c1C(=O)N1CCC(N2CCC(c3ccc(NC4CCC(=O)NC4=O)cc3)C(F)(F)C2)CC1] | +++ |
| 229 | 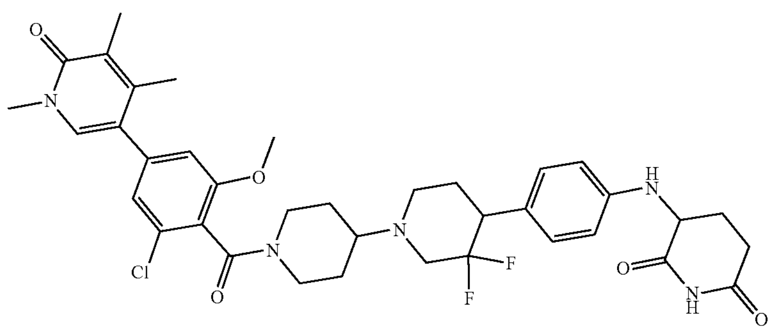 [SMILES: COc1cc(-c2cn(C)c(=O)c(C)c2C)cc(Cl)c1C(=O)N1CCC(N2CCC(c3ccc(NC4CCC(=O)NC4=O)cc3)C(F)(F)C2)CC1] | +++ |
| 230 | 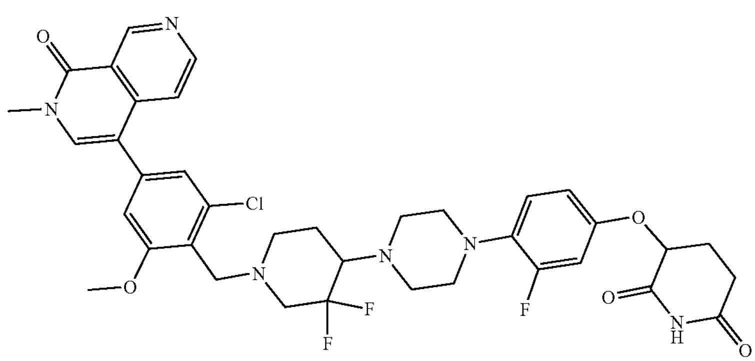 [SMILES: COc1cc(-c2cn(C)c(=O)c3cnccc23)cc(Cl)c1CN1CCC(N2CCN(c3ccc(OC4CCC(=O)NC4=O)cc3F)CC2)C(F)(F)C1] | +++ |
| 231 | 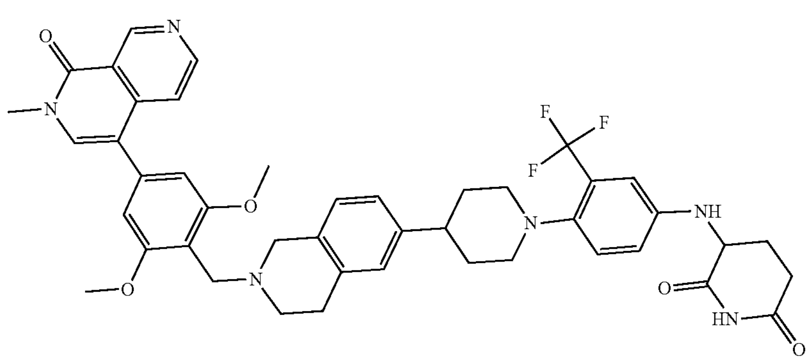 [SMILES: COc1cc(-c2cn(C)c(=O)c3cnccc23)cc(OC)c1CN1CCc2cc(C3CCN(c4ccc(NC5CCC(=O)NC5=O)cc4C(F)(F)F)CC3)ccc2C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 232 | 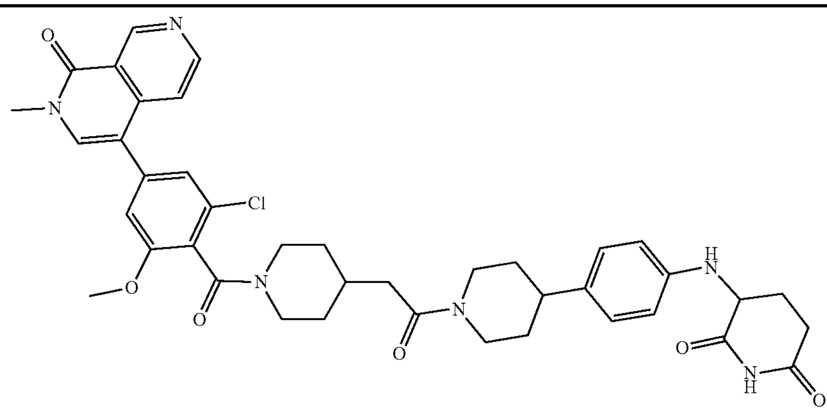 | +++ |
| 233 | 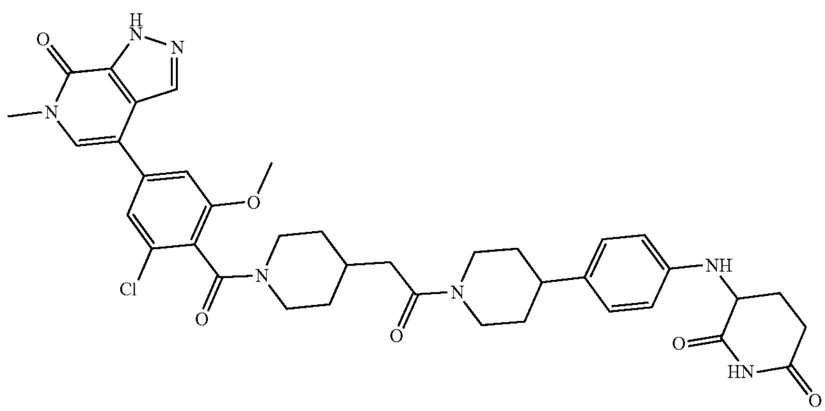 [SMILES: COc1cc(-c2cn(C)c(=O)c3[nH]ncc23)cc(Cl)c1C(=O)N1CCC(CC(=O)N2CCC(c3ccc(NC4CCC(=O)NC4=O)cc3)CC2)CC1] | +++ |
| 234 | 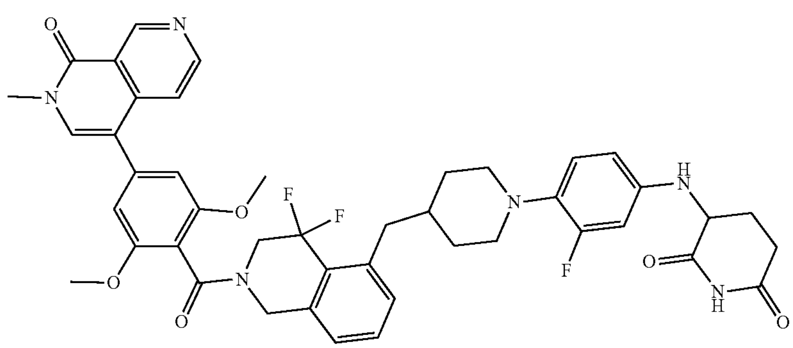 [SMILES: COc1cc(-c2cn(C)c(=O)c3cnccc23)cc(OC)c1C(=O)N1Cc2cccc(CC3CCN(c4ccc(NC5CCC(=O)NC5=O)cc4F)CC3)c2C(F)(F)C1] | +++ |
| 235 | 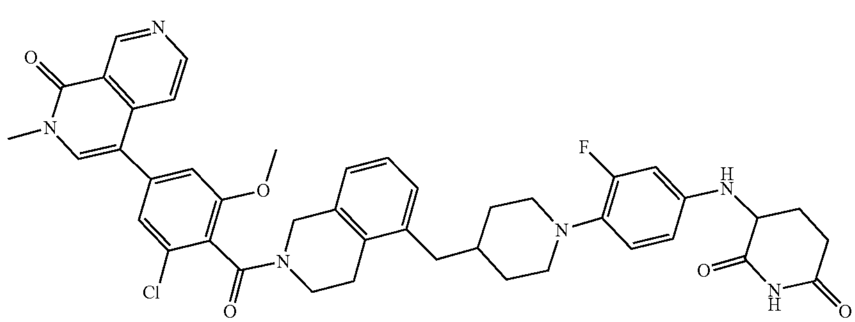 [SMILES: COc1cc(-c2cn(C)c(=O)c3cnccc23)cc(Cl)c1C(=O)N1CCc2c(CC3CCN(c4ccc(NC5CCC(=O)NC5=O)cc4F)CC3)cccc2C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 236 | 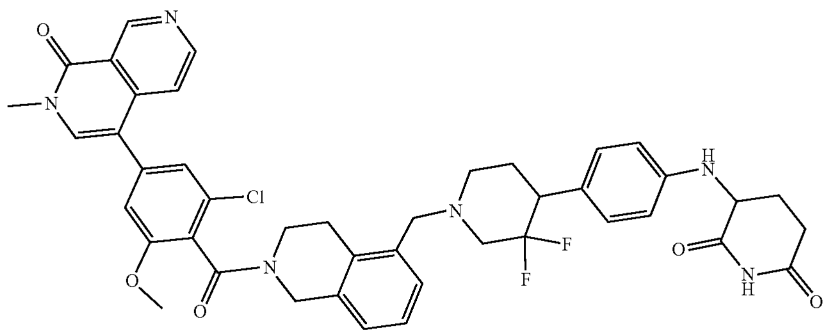 [SMILES: COc1cc(-c2cn(C)c(=O)c3cnccc23)cc(Cl)c1C(=O)N1CCc2c(CN3CCC(c4ccc(NC5CCC(=O)NC5=O)cc4)C(F)(F)C3)cccc2C1] | +++ |
| 237 | 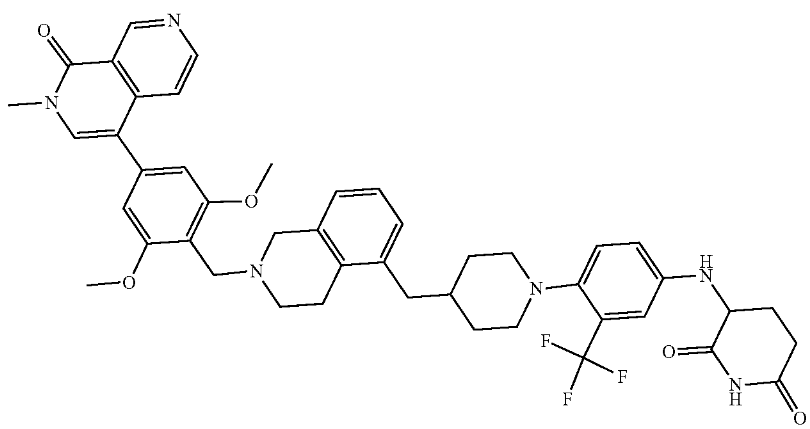 [SMILES: COc1cc(-c2cn(C)c(=O)c3cnccc23)cc(OC)c1CN1CCc2c(CC3CCN(c4ccc(NC5CCC(=O)NC5=O)cc4C(F)(F)F)CC3)cccc2C1] | +++ |
| 238 | 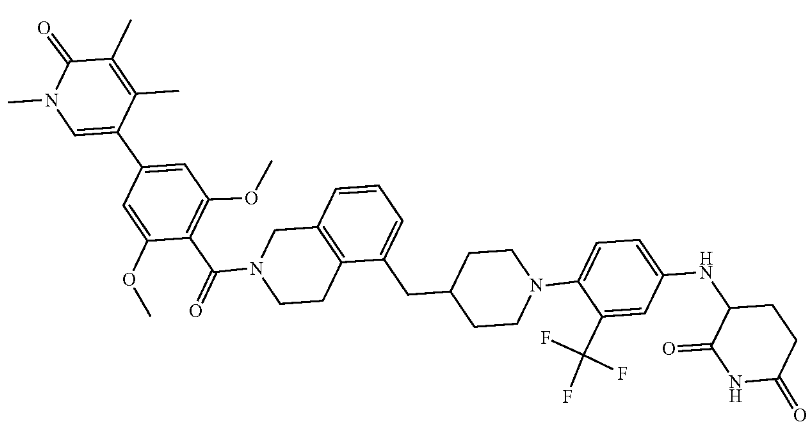 [SMILES: COc1cc(-c2cn(C)c(=O)c(C)c2C)cc(OC)c1C(=O)N1CCc2c(CC3CCN(c4ccc(NC5CCC(=O)NC5=O)cc4C(F)(F)F)CC3)cccc2C1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 239 | 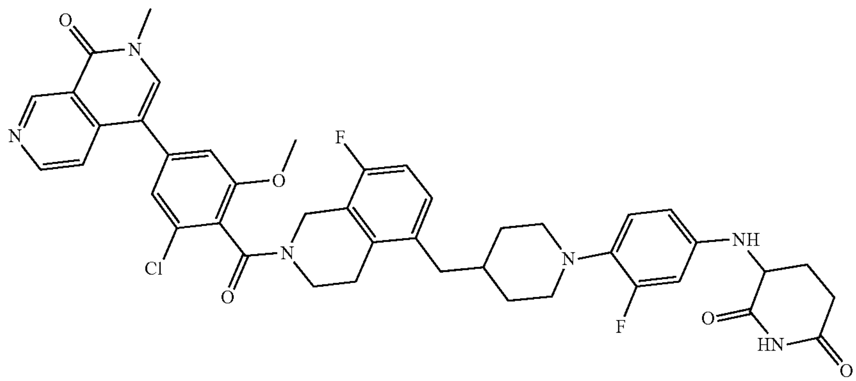 [SMILES: COc1cc(-c2cn(C)c(=O)c3cnccc23)cc(Cl)c1C(=O)N1CCc2c(CC3CCN(c4ccc(NC5CCC(=O)NC5=O)cc4F)CC3)ccc(F)c2C1] | +++ |
| 240 | 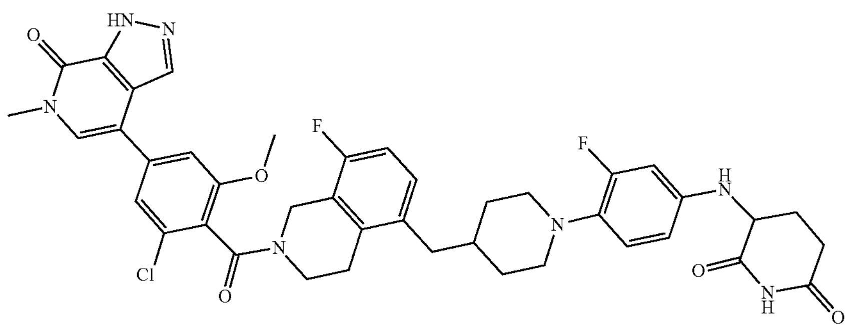 [SMILES: COc1cc(-c2cn(C)c(=O)c3[nH]ncc23)cc(Cl)c1C(=O)N1CCc2c(CC3CCN(c4ccc(NC5CCC(=O)NC5=O)cc4F)CC3)ccc(F)c2C1] | +++ |
| 241 | 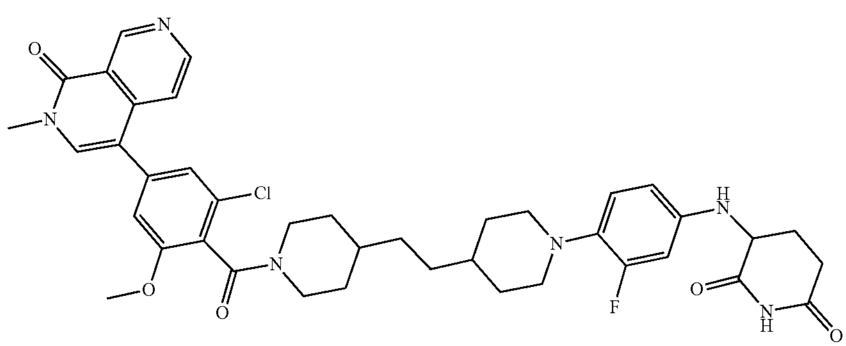 [SMILES: COc1cc(-c2cn(C)c(=O)c3cnccc23)cc(Cl)c1C(=O)N1CCC(CCC2CCN(c3ccc(NC4CCC(=O)NC4=O)cc3F)CC2)CC1] | +++ |
| 242 | 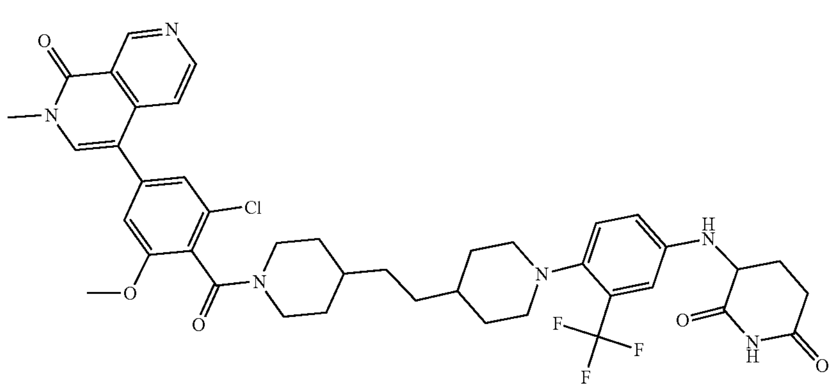 [SMILES: COc1cc(-c2cn(C)c(=O)c3cnccc23)cc(Cl)c1C(=O)N1CCC(CCC2CCN(c3ccc(NC4CCC(=O)NC4=O)cc3C(F)(F)F)CC2)CC1] | +++ |

TABLE 1-continued

XII. DATA
BRD9 Degradation Data.

| Cmpd # | Structure | HiBiT-Degradation 293T.166 BRD9 2.0 hours (DC50) [nM] |
|---|---|---|
| 243 | 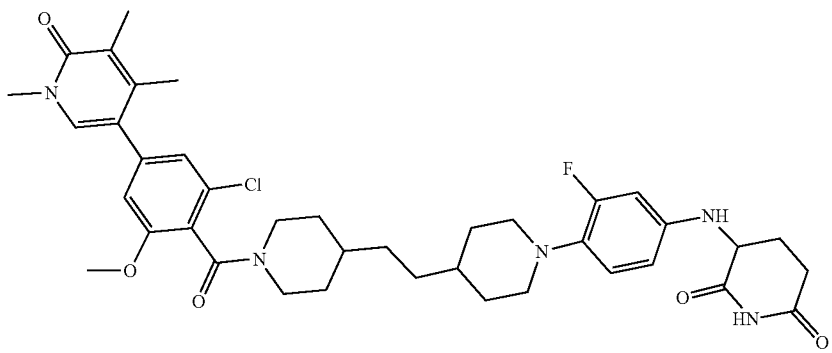 [SMILES: COc1cc(-c2cn(C)c(=O)c(C)c2C)cc(Cl)c1C(=O)N1CCC(CCC2CCN(c3ccc(NC4CCC(=O)NC4=O)cc3F)CC2)CC1] | +++ |
| 244 | 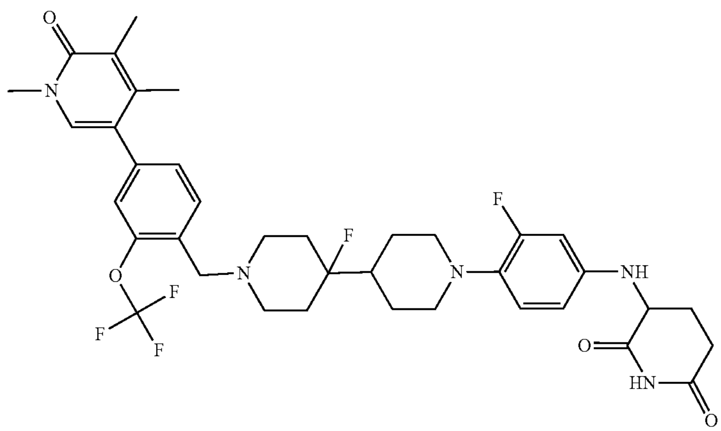 [SMILES: Cc1c(-c2ccc(CN3CCC(F)(C4CCN(c5ccc(NC6CCC(=O)NC6=O)cc5F)CC4)CC3)c(OC(F)(F)F)c2)cn(C)c(=O)c1C] | +++ |
| 245 | 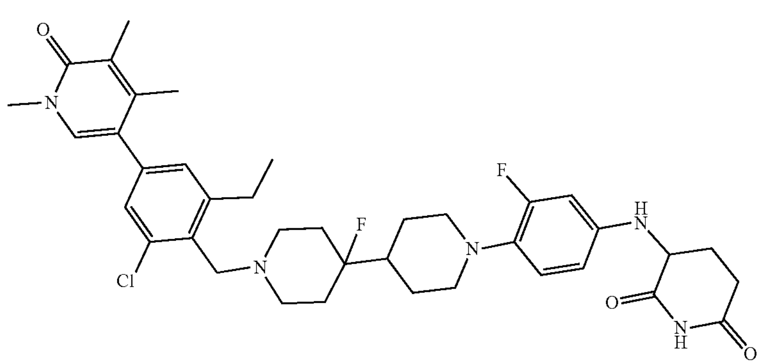 [SMILES: CCc1cc(-c2cn(C)c(=O)c(C)c2C)cc(Cl)c1CN1CCC(F)(C2CCN(c3ccc(NC4CCC(=O)NC4=O)cc3F)CC2)CC1] | +++ |

In Table 1 <100 nM = +++, 100-500 nM = ++, and 500-800 nM = +

TABLE 2
| Cmpd # | Structure | HiBiT-Degradation 293T.166 BRD9 2.0 hours (DC50) [nM] |
|---|---|---|
| 246 | 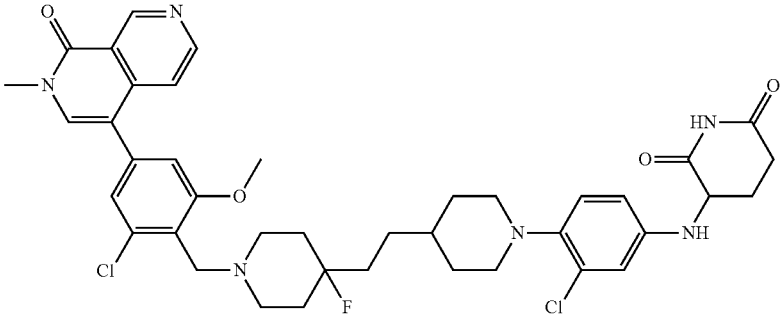 [SMILES: COc1cc(-c2cn(C)c(=O)c3cnccc23)cc(Cl)c1CN1CCC(F)(CCC2CCN(c3ccc(NC4CCC(=O)NC4=O)cc3Cl)CC2)CC1] | +++ |
| 247 | 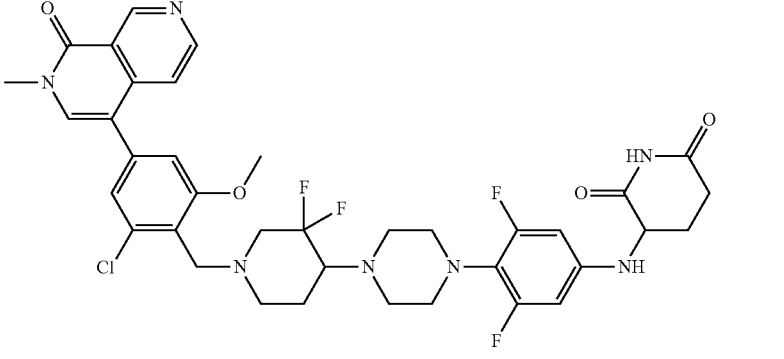 [SMILES: COc1cc(-c2cn(C)c(=O)c3cnccc23)cc(Cl)c1CN1CCC(N2CCN(c3c(F)cc(NC4CCC(=O)NC4=O)cc3F)CC2)C(F)(F)C1] | +++ |
| 248 | 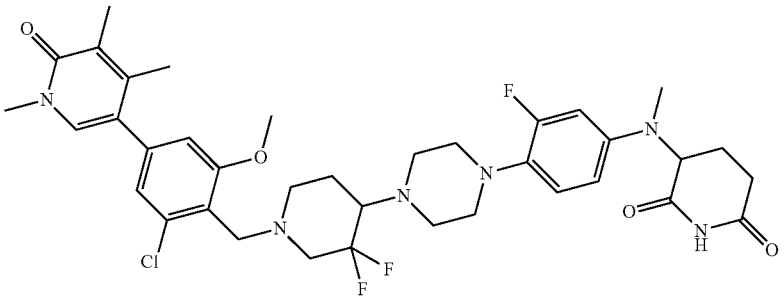 [SMILES: COc1cc(-c2cn(C)c(=O)c(C)c2C)cc(Cl)c1CN1CCC(N2CCN(c3ccc(N(C)C4CCC(=O)NC4=O)cc3F)CC2)C(F)(F)C1] | +++ |
| 249 | 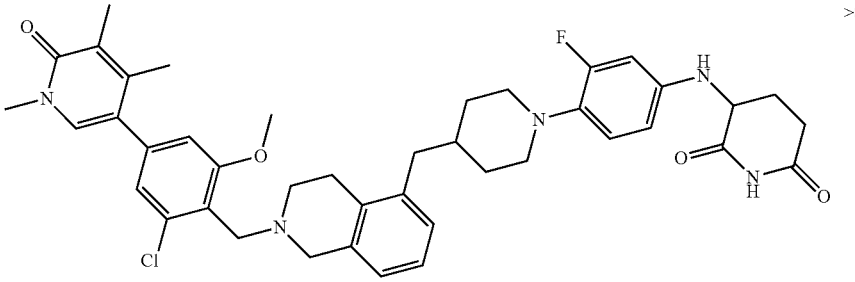<br>Enantiomer 1 | >800 |

TABLE 2-continued
| Cmpd # | Structure | HiBiT-Degradation 293T.166 BRD9 2.0 hours (DC50) [nM] |
|---|---|---|
| 250 | 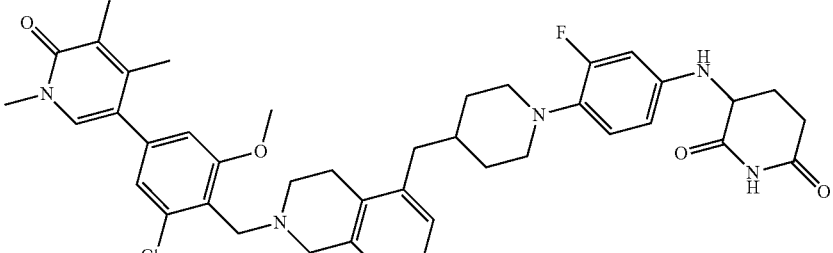 Enantiomer 2 | +++ |
| 251 | 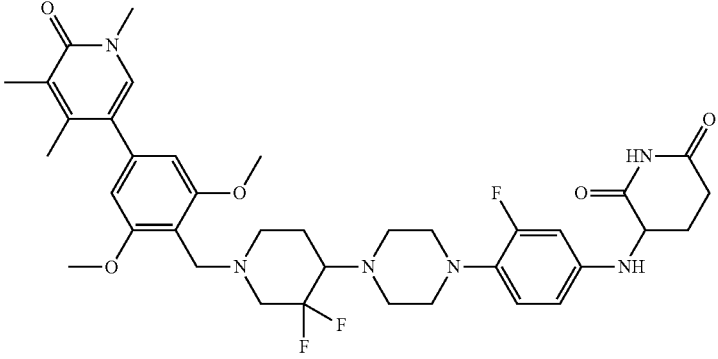 [SMILES: COc1cc(-c2cn(C)c(=O)c(C)c2C)cc(OC)c1CN1CCC(N2CCN(c3ccc(NC4CCC(=O)NC4=O)cc3F)CC2)C(F)(F)C1] | +++ |
| 252 | 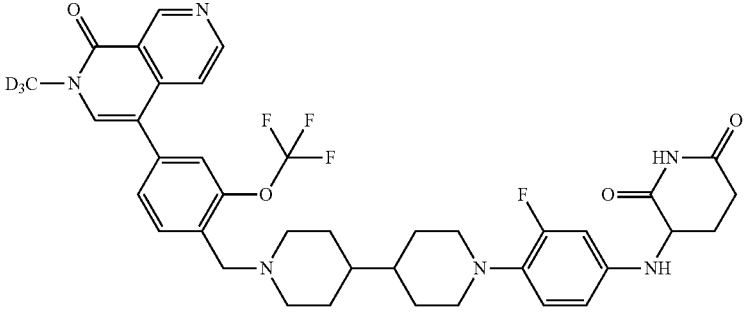 [SMILES: [2H]C([2H])([2H])n1cc(-c2ccc(CN3CCC(C4CCN(c5ccc(NC6CCC(=O)NC6=O)cc5F)CC4)CC3)c(OC(F)(F)F)c2)c2ccncc2c1=O] | +++ |
| 253 | 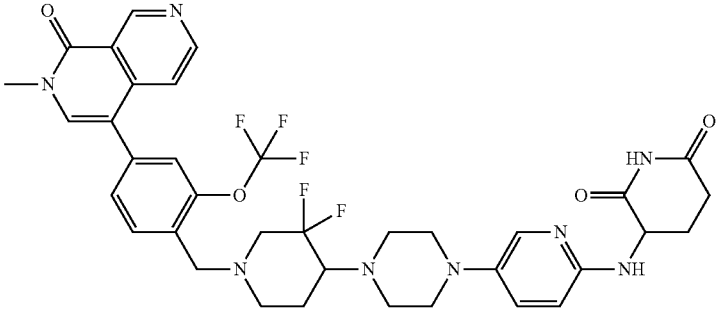 [SMILES: Cn1cc(-c2ccc(CN3CCC(N4CCN(c5ccc(NC6CCC(=O)NC6=O)nc5)CC4)C(F)(F)C3)c(OC(F)(F)F)c2)c2ccncc2c1=O] | +++ |

TABLE 2-continued

| Cmpd # | Structure | HiBiT-Degradation 293T.166 BRD9 2.0 hours (DC50) [nM] |
|---|---|---|
| 254 | 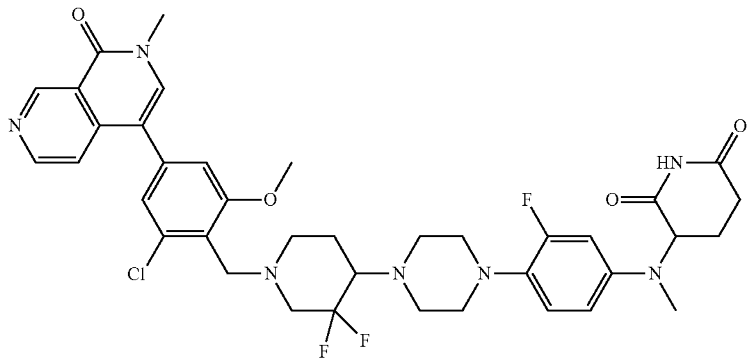 [SMILES: COc1cc(-c2cn(C)c(=O)c3cnccc23)cc(Cl)c1CN1CCC(N2CCN(c3ccc(N(C)C4CCC(=O)NC4=O)cc3F)CC2)C(F)(F)C1] | +++ |
| 255 | 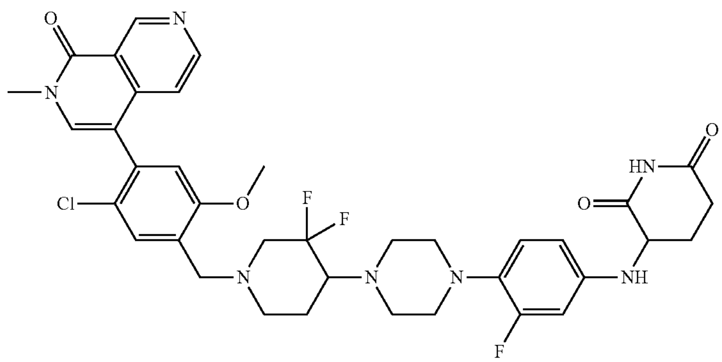 [SMILES: COc1cc(-c2cn(C)c(=O)c3cnccc23)c(Cl)cc1CN1CCC(N2CCN(c3ccc(NC4CCC(=O)NC4=O)cc3F)CC2)C(F)(F)C1] | +++ |
| 256 | Stereoisomer 1 | +++ |
| 257 | Stereoisomer 2 | +++ |

| Cmpd # | Structure | HiBiT-Degradation 293T.166 BRD9 2.0 hours (DC50) [nM] |
|---|---|---|
| 258 | 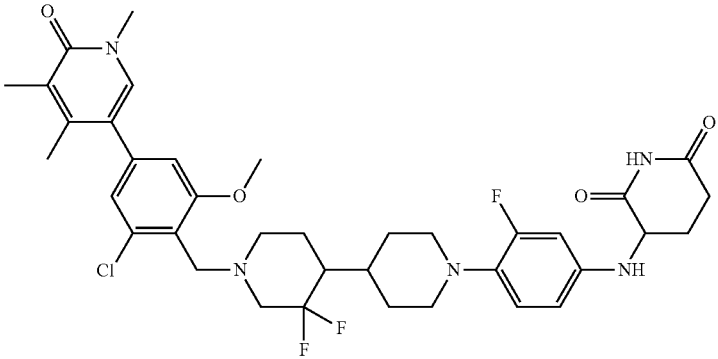Stereoisomer 3 | ++ |
| 259 | 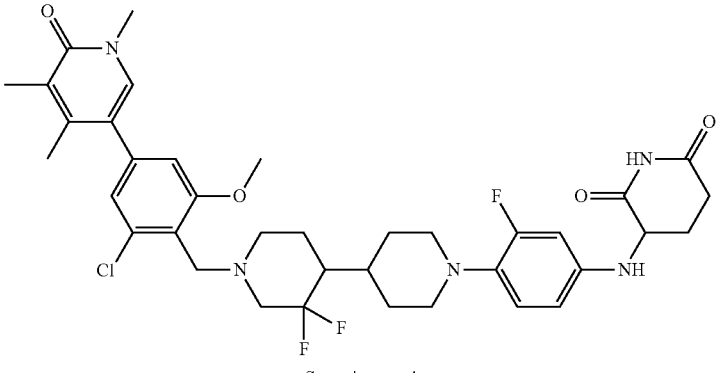Stereoisomer 4 | +++ |
| 260 | 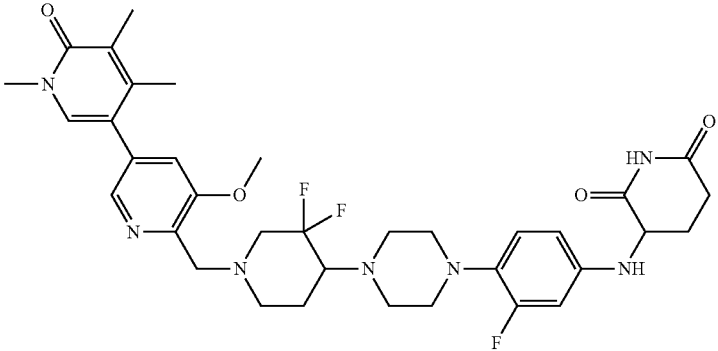 [SMILES: COc1cc(-c2cn(C)c(=O)c(C)c2C)cnc1CN1CCC(N2CCN(c3ccc(NC4CCC(=O)NC4=O)cc3F)CC2)C(F)(F)C1] | +++ |

TABLE 2-continued
| Cmpd # | Structure | HiBiT-Degradation 293T.166 BRD9 2.0 hours (DC50) [nM] |
|---|---|---|
| 261 | 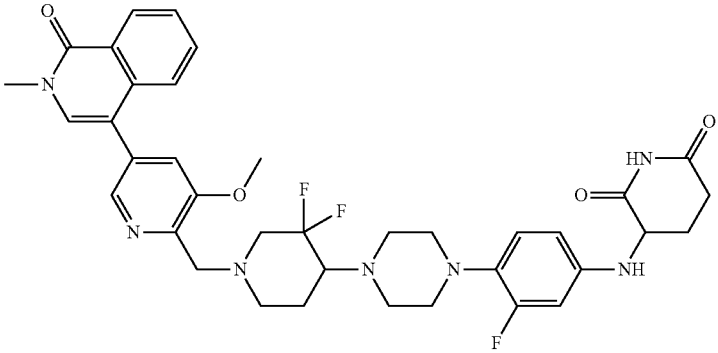 [SMILES: COc1cc(-c2cn(C)c(=O)c3ccccc23)cnc1CN1CCC(N2CCN(c3ccc(NC4CCC(=O)NC4=O)cc3F)CC2)C(F)(F)C1] | +++ |
| 262 | 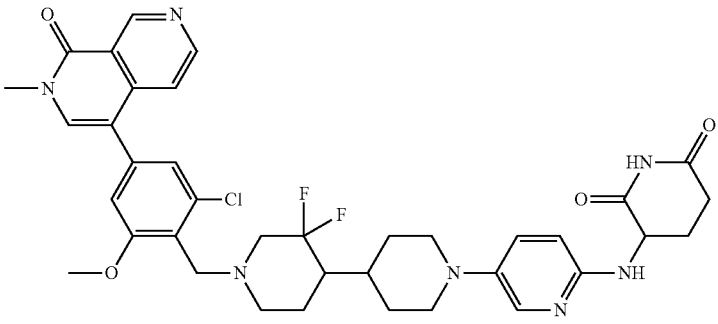 [SMILES: COc1cc(-c2cn(C)c(=O)c3cnccc23)cc(Cl)c1CN1CCC(C2CCN(c3ccc(NC4CCC(=O)NC4=O)nc3)CC2)C(F)(F)C1] | +++ |
| 263 | 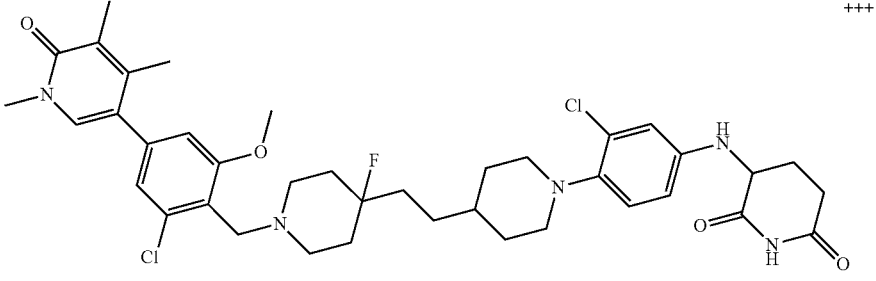 | +++ |
| 264 | 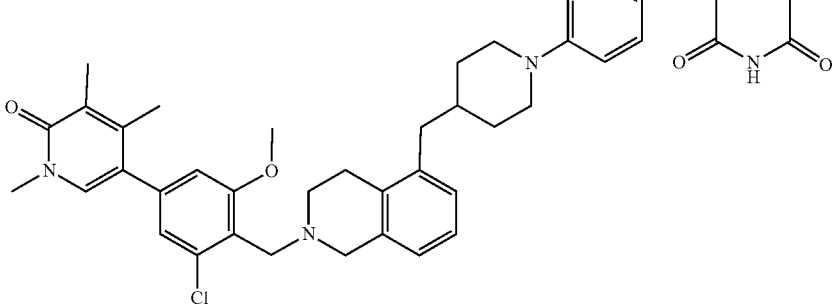 | +++ |

TABLE 2-continued

| Cmpd # | Structure | HiBiT-Degradation 293T.166 BRD9 2.0 hours (DC50) [nM] |
|---|---|---|
| 265 | 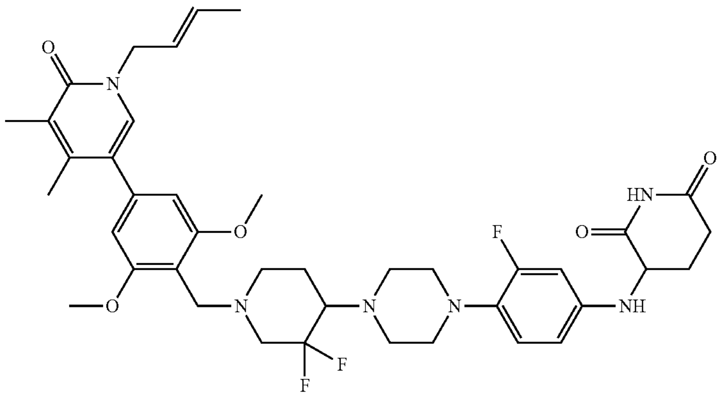 [SMILES: C/C=C/Cn1cc(-c2cc(OC)c(CN3CCC(N4CCN(c5ccc(NC6CCC(=O)NC6=O)cc5F)CC4)C(F)(F)C3)c(OC)c2)c(C)c(C)c1=O] | +++ |
| 266 | 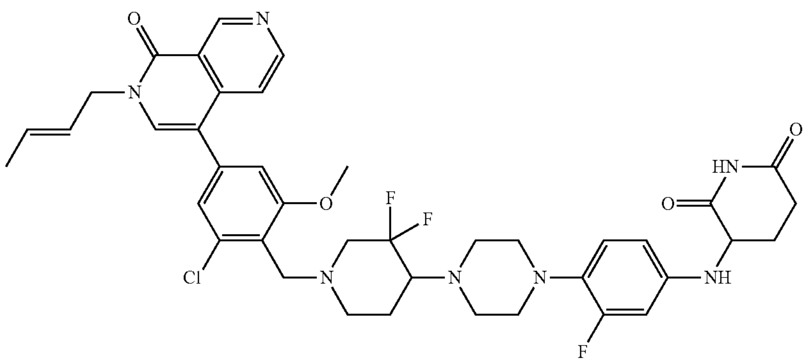 [SMILES: C/C=C/Cn1cc(-c2cc(Cl)c(CN3CCC(N4CCN(c5ccc(NC6CCC(=O)NC6=O)cc5F)CC4)C(F)(F)C3)c(OC)c2)c2ccncc2c1=O] | +++ |
| 267 | Stereoisomer 1 | >800 |

TABLE 2-continued
| Cmpd # | Structure | HiBiT-Degradation 293T.166 BRD9 2.0 hours (DC50) [nM] |
|---|---|---|
| 268 | 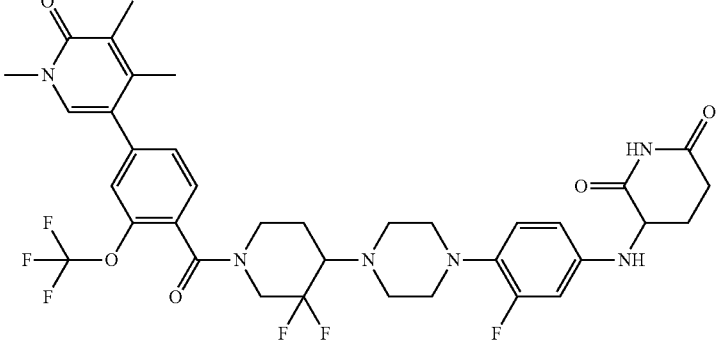 Stereoisomer 2 | >800 |
| 269 | 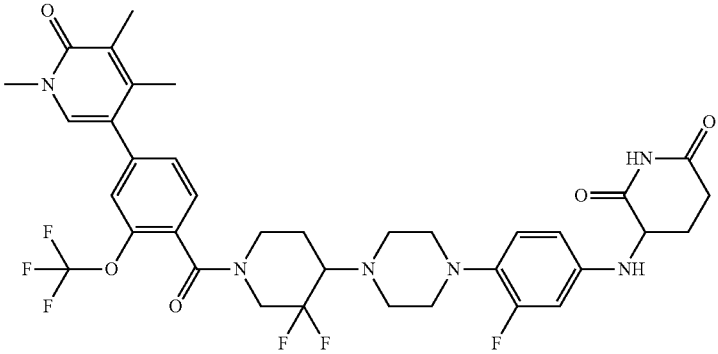 Stereoisomer 3 | +++ |
| 270 | 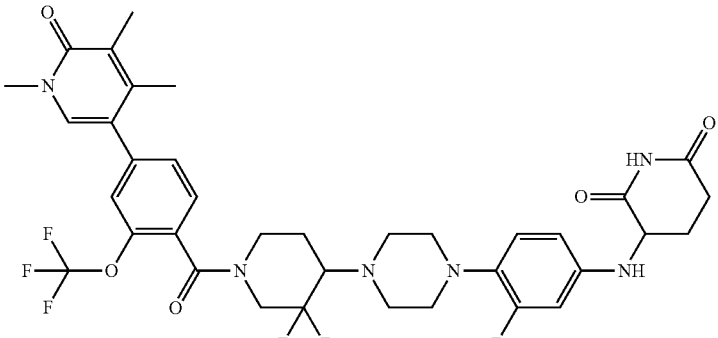 Stereoisomer 4 | +++ |
| 271 | 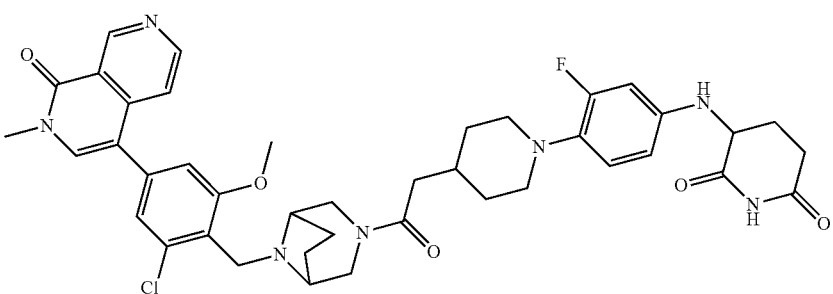 [SMILES: COc1cc(-c2cn(C)c(=O)c3cnccc23)cc(Cl)c1CN1C2CCC1CN(C(=O)CC1CCN(c3ccc(NC4CCC(=O)NC4=O)cc3F)CC1)C2] | +++ |

TABLE 2-continued

| Cmpd # | Structure | HiBiT-Degradation 293T.166 BRD9 2.0 hours (DC50) [nM] |
|---|---|---|
| 272 | 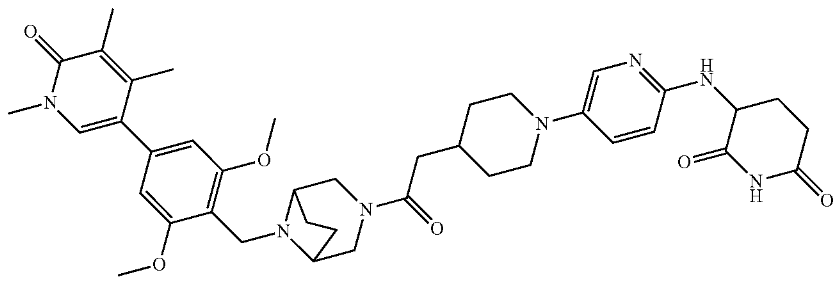 [SMILES: COc1cc(-c2cn(C)c(=O)c(C)c2C)cc(OC)c1CN1C2CCC1CN(C(=O)CC1CCN(c3ccc(NC4CCC(=O)NC4=O)nc3)CC1)C2] | +++ |
| 273 | 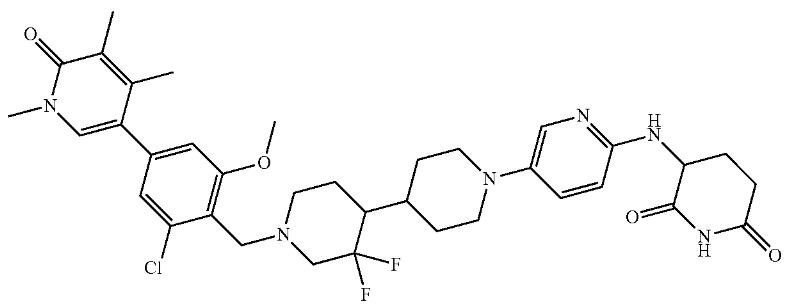 [SMILES: COc1cc(-c2cn(C)c(=O)c(C)c2C)cc(Cl)c1CN1CCC(C2CCN(c3ccc(NC4CCC(=O)NC4=O)nc3)CC2)C(F)(F)C1] | +++ |
| 274 | 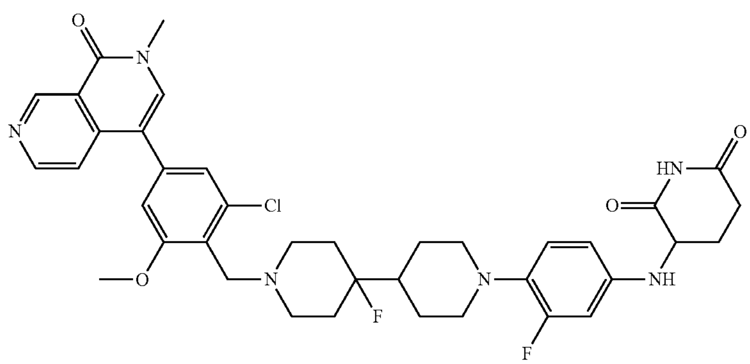 [SMILES: COc1cc(-c2cn(C)c(=O)c3cnccc23)cc(Cl)c1CN1CCC(F)(C2CCN(c3ccc(NC4CCC(=O)NC4=O)cc3F)CC2)CC1] | +++ |
| 275 | 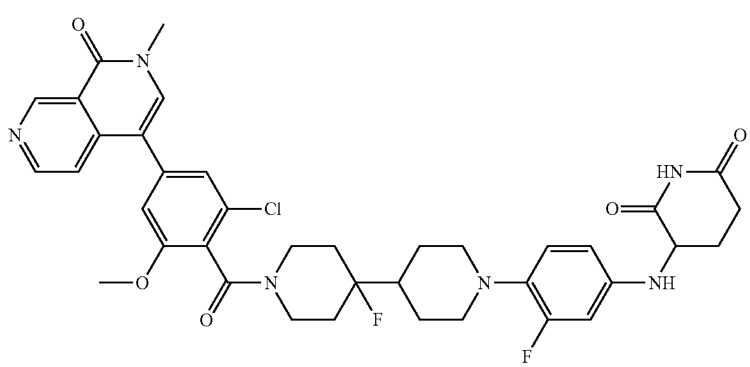 [SMILES: COc1cc(-c2cn(C)c(=O)c3cnccc23)cc(Cl)c1C(=O)N1CCC(F)(C2CCN(c3ccc(NC4CCC(=O)NC4=O)cc3F)CC2)CC1] | +++ |

In Table 2 < 100 nM = +++, 100-500 nM = ++, and 500-800 nM = +

Example 1 HiBIT Ligand Displacement Assay

Selected compounds were tested in a BRD9 degradation assay using the HiBit Method. $DC_{50}$ values at each protein are given in Table 1 and 2.

Materials

Dulbecco's modified Eagle medium (DMEM) without phenol red and fetal bovine serum (FBS) were purchased from Gibco (Grand Island, NY, USA). Nano-Glo® HiBiT Lytic Assay System was purchased from Promega (Madison, WI, USA). 293T.166 (BRD9-HiBiT) cell line, endogenously expressing BRD9 with HiBiT fusion tag via CRISPR and ectopically expressing LgBiT tag, was purchased from Promega (Madison, WI, USA). 293T.167 (BRD7-HiBiT) cell line, endogenously expressing BRD7 with HiBiT fusion tag via CRISPR and ectopically expressing LgBiT tag, was purchased from Promega (Madison, WI, USA). 293T.92 (BRD4-HiBiT) cell line, endogenously expressing BRD4 with HiBiT fusion tag via CRISPR and ectopically expressing LgBiT tag, was generated in-house. Cell culture flasks and 384-well microplates were acquired from VWR (Radnor, PA, USA).

BRD9 Degradation Analysis

BRD9 degradation was determined based on quantification of luminescent signal using Nano-Glo® HiBiT Lytic Assay kit. Test compounds were added to the 384-well plate from a top concentration of 10 μM with 11 points, half log titration in duplicates. 293T.166 cells were added into 384-well plates at a cell density of 10,000 cells per well. The plates were kept at 37° C. with 5% $CO_2$ for 2 hours. BRD7 and BRD4 degradation was similarly determined with 293T.167 cells and 293T.92 cells, respectively. The cells treated in the absence of the test compound were the negative control and the cells without Nano-Glo® HiBiT Lytic reagent were the positive control. After 2-hour incubation, Nano-Glo® HiBiT Lytic Assay reagents were added to the cells. Luminescence was acquired on EnVision™ Multilabel Reader (PerkinElmer, Santa Clara, CA, USA).

Figure 2:
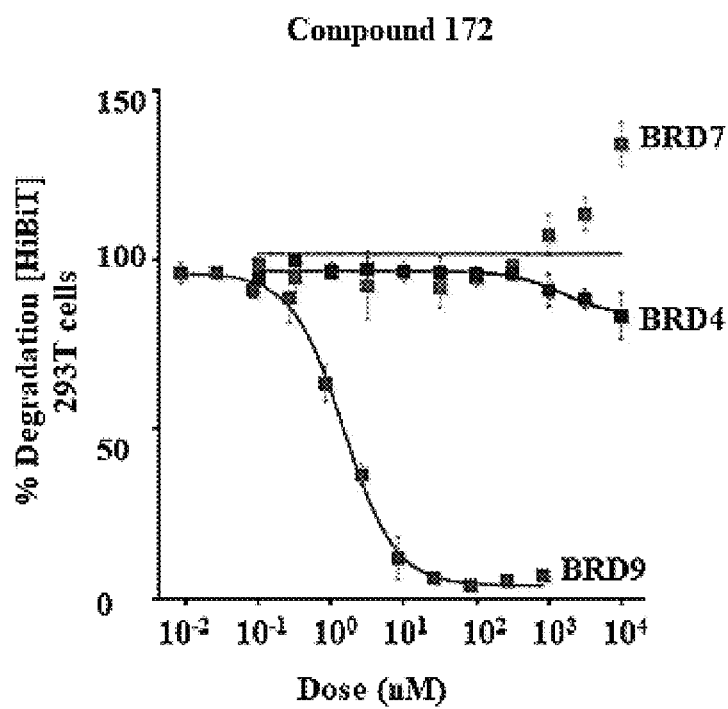
FIG. 2 is a graph of protein degradation by Compound 172. The x-axis is dose measured in nanomolar (nM) and the y-axis is protein degradation levels as measured by HiBiT luminescent readout for each respective protein BRD9, BRD7 and BRD4.
Figure 11:
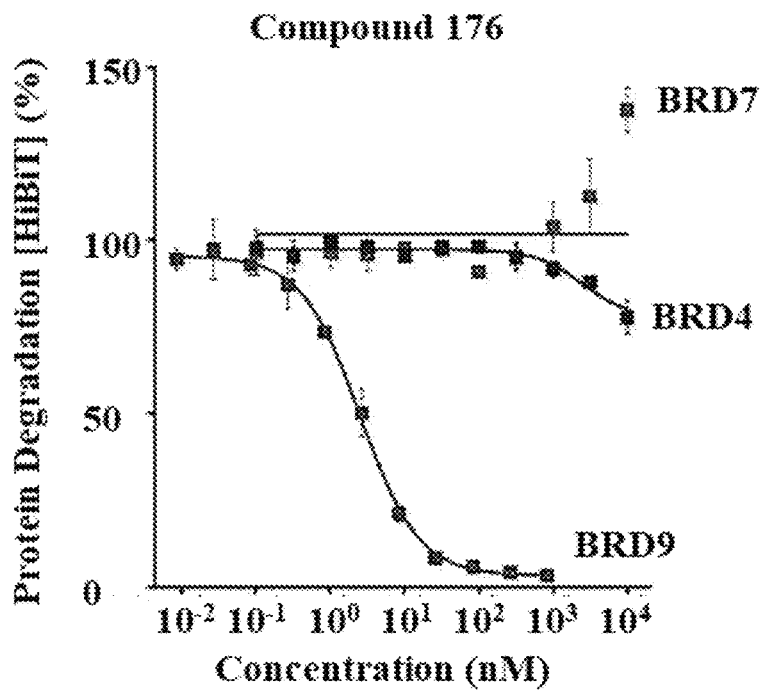
FIG. 11 is a graph demonstrating selective degradation of BRD9 protein by Compound 176. The x-axis is dose measured in nanomolar (nM) and the y-axis is protein degradation levels as measured by HiBiT luminescent readout for each respective protein BRD9, BRD7 and BRD4.

This assay was also used to produce the data shown in FIG. 2 and FIG. 11.

Example 2. Pharmacology and Chemical Properties of Compound 172

| Biochemical and in-vitro pharmacology | |
|---|---|
| BRD9 binding (Ki) | 82 nM |
| FP-E3 binding (Kd) | 950 nM |
| BRD9-E3 dimerization | 120/461 nM/13% |
| BRD9 degradation (2 h), Kendo 17 h | 3.4 nM/5% |
| BRD9 Degradation kinetics | 11 nM/>832 nM/1.81 $h^{-1}$ |
| BRD7 degradation (24 h), IP/Emax | >9990 nM/100% |
| BRD4 degradation (24 h), IP/Emax | 1997 nM/81% |
| SW982 Viability (GI50) | >10000 nM |
| BRD9 degradation mouse/rat/dog cells (24 h) | 99 nM/36%/1000 nM/53%/99 nM/36.4% |
| IKZF1/SALL4/GSPT1 degradation | >9990 nM |
| HEPG2 Viability | >9990 nM |

| In-vitro DMPK and safety pharmacology | |
|---|---|
| Stability (plasma) m/r/d/h % remaining @3 hrs mouse/rat/dog/human | 90.3/97.0/80.2/83.4 |
| PPB mouse/rat/dog/human | 98.2/91.7/96.1/91.2 |
| Hepatocyte stability m/r/d/h Clint scaled ws, mL/min/kg | 38/15/2/9.4 |
| CYP Inhibition (μM) 1A2/2C9/2C19/2D6/3A4/2B6/2C8/2E1 | 30/30/30/30/18.2/0.1/30/30 |
| CYP TDI (Y/N), isoform | Y, 2C19*(>50/24μM) |
| hERG (μM) | >30 |
| Caco-2 Papp (A-B)/(B-A) (10-6, cm/s)/Efflux ratio | 7.1/18.7/2.64 |

| In-vivo DMPK | | |
|---|---|---|
| IV PK mouse/rat/dog | Cmax [ng/mL]/(mg/kg) | 1228/517/767 |
| | CL (mL/min/kg) | 3.4/16/6.2 |
| | T½, [h] | 3.6/9.5/8.8 |
| | Vdss, [L/kg] | 1.1/7.9/4.36 |
| | AUC(0-last) (h*ng/mL)/(mg/kg) | 4942/1230/2343 |
| PO PK mouse/rat | Cmax (ng/mL)/(mg/kg) | 844/92 |
| | T½ [h] | 3.3/4.3 |
| | AUC(0-last) (h*ng/mL)/(mg/kg) | 5947/520 |
| | F % | 122/49 |

Example 3. Pharmacology and Chemical Properties of Compound 176

| In-vitro DMPK and safety pharmacology | |
|---|---|
| Stability (plasma) m/r/d/h % remaining @3 hrs mouse/rat/dog/human | 85/88/100/67 |
| PPB mouse/rat/dog/human | 96.6/90.2/93.5/93.3 |
| Hepatocyte stability mouse/rat/dog/human Clint scaled ws, mL/min/kg | 30/14.2/8.6/9.4 |
| hERG (μM) | >30 |

| In-vivo DMPK | | |
|---|---|---|
| IV PK mouse/rat | Cmax [ng/mL]/(mg/kg) | 720/439 |
| | CL (mL/min/kg) | 6.2/21.6 |
| | t½, [h] | 3.7/4.0 |
| | Vdss, [L/kg] | 2.0/6.7 |
| | AUC(0-last) (h*ng/mL)/(mg/kg) | 2724/771 |
| PO PK mouse/rat | Cmax (ng/mL)/(mg/kg) | 346/75 |
| | $t_{1/2}$ [h] | 3.5/5.1 |
| | AUC(0-last) (h*ng/mL)/(mg/kg) | 1999/656 |
| | F % | 74/83 |

Example 4: Xenographic Studies of Compound 172

FIG. 1 is a graph of tumor volume after treatment with Compound 172 demonstrating strong effect in synovial sarcoma xenograft model Yamato-SS. Yamato-SS cells were maintained in vitro until exponential growth phase and inoculated subcutaneously into BALB/c nude mice at the right flank for tumor development. Treatments of Compound 172 were started at the appropriate tumor volume. Mice were treated with 40 mg/kg PO QD of Compound 172 and tumor volumes (x-axis) were measured twice a week using a caliper. The x-axis is time after start of treatment measured in days and the y-axis is tumor volume measured in mm³.

Example 5: Western Blot Showing Dose Response Degradation by Compound 172

Figure 3:
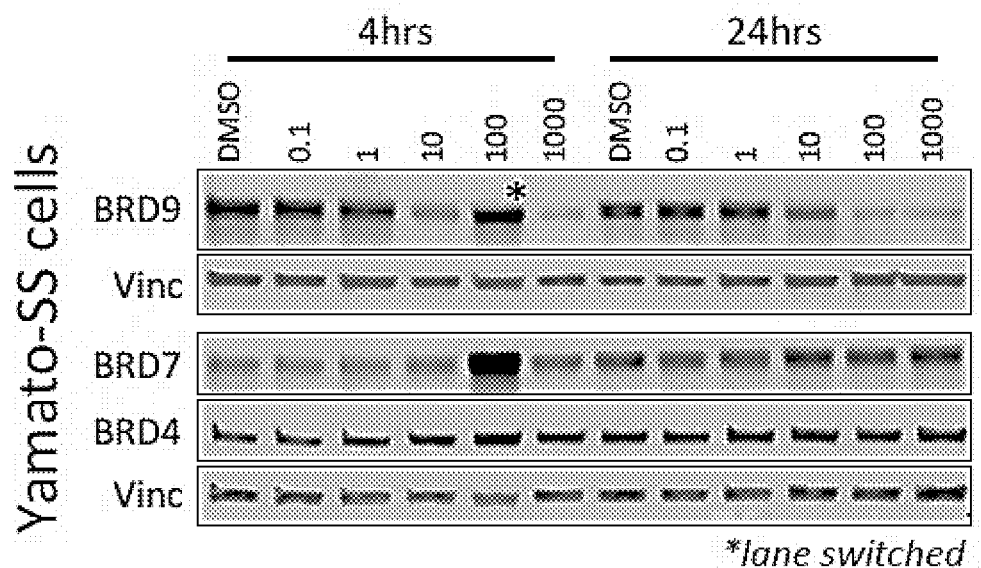
FIG. 3 is a graph illustrating the dose response degradation of various proteins by Compound 172 in Yamato-SS cells, a human cell line derived from synovial sarcoma (Stem Cells 2010; 28:1119-1131) via western blot.

FIG. 3 is a western blot which illustrates the dose response degradation specific to BRD9, and not bromodomain containing proteins BRD4 and BRD7 by Compound 172 in Yamato-SS cells, a human cell line derived from synovial sarcoma (Stem Cells 2010; 28:1119-1131) via western blot. After treatment cells were collected, lysed in RIPA buffer supplemented with 2× proteasome/protease inhibitor, and protein concentrations were determined by Pierce™ BCA Protein Assay Kit. Samples were diluted to appropriate concentrations and run in a western blot.

Figure 12:
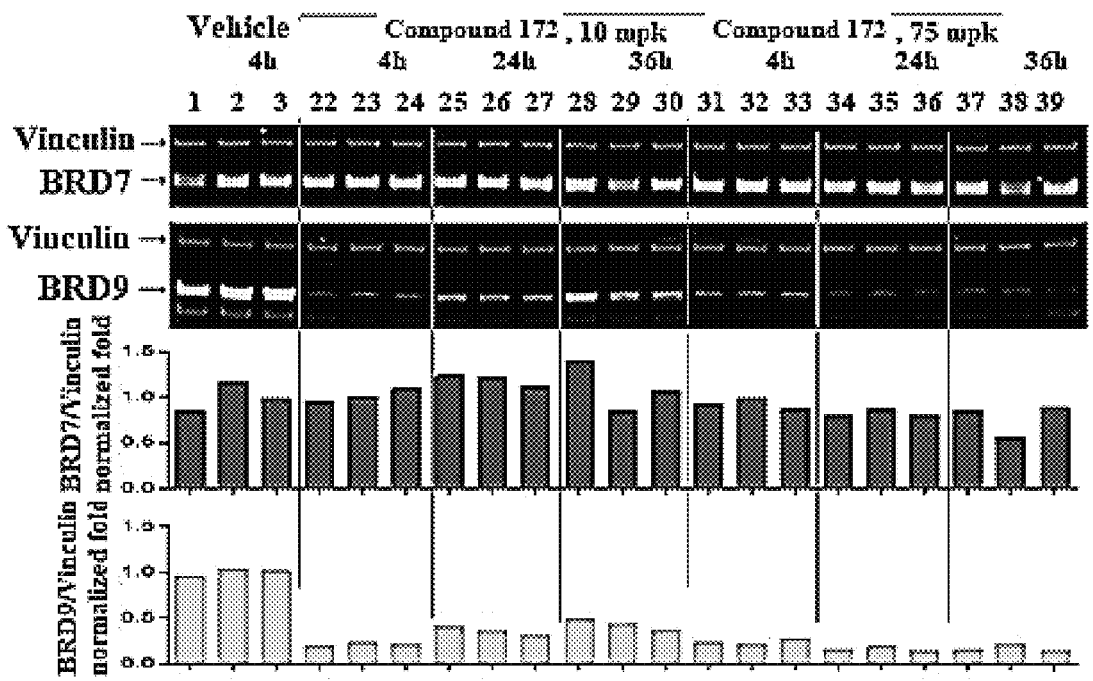
FIG. 12 is a bar graph showing the dose dependent in-vivo BRD9 degradation with Compound 172 at various concentrations in a Yamato-SS xenograph model. The x-axis is concentration and time measured in mg/kg and hours respectively and the y-axis is normalized concentration.

FIG. 12 is a western blot showing the dose dependent in-vivo BRD9 degradation with Compound 172 at 10 mg/ml and 75 mg/ml and not BRD7 in Yamato-SS cells. Yamato-SS cells were maintained in vitro until exponential growth phase and inoculated subcutaneously into BALB/c nude mice at the right flank for tumor development. Mice were treated with single dose of Compound 172 at 10 or 75 mg/kg PO. Tumor were collected at indicated time points and snap frozen until lysis. Tumors were ground and lysed in RIPA Buffer containing 2× protease/phosphatase inhibitor using a freeze grinder at 50 Hz for 5 minutes. Protein concentrations were determined by Pierce™ BCA Protein Assay Kit. Samples were diluted to appropriate concentrations and run in a western blot.

Figure 13:
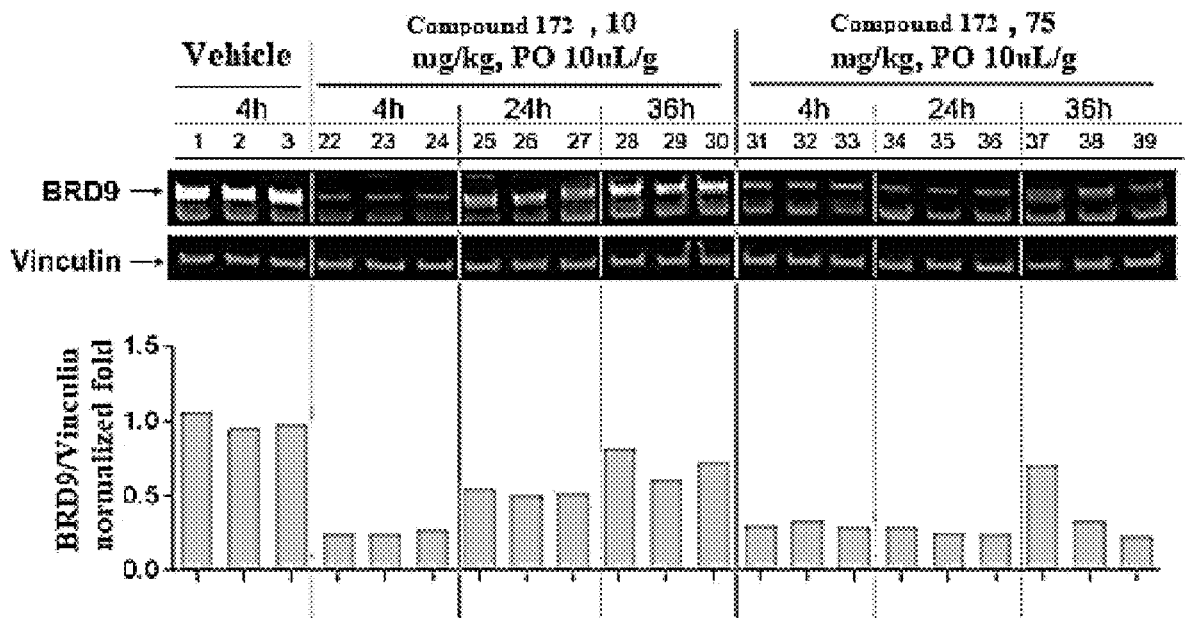
FIG. 13 is a bar graph showing the dose dependent in-vivo BRD9 degradation with Compound 172 at various concentrations in an Aska-SS xenograph model. The x-axis is concentration and time measured in mg/kg and hours respectively and the y-axis is normalized concentration.

FIG. 13 is a western blot showing the dose dependent in-vivo BRD9 degradation with Compound 172 at 10 mg/ml and 75 mg/ml in ASKA-SS cells. ASKA-SS cells were maintained in vitro until exponential growth phase and inoculated subcutaneously into BALB/c nude mice at the right flank for tumor development. Mice were treated with single dose of Compound 172 at 10 or 75 mg/kg PO. Tumor were collected at indicated time points and snap frozen until lysis. Tumors were ground and lysed in RIPA Buffer containing 2× protease/phosphatase inhibitor using a freeze grinder at 50 Hz for 5 minutes. Protein concentrations were determined by Pierce™ BCA Protein Assay Kit. Samples were diluted to appropriate concentrations and run in a western blot.

Example 6: Confluence Perturbation

Figure 4:
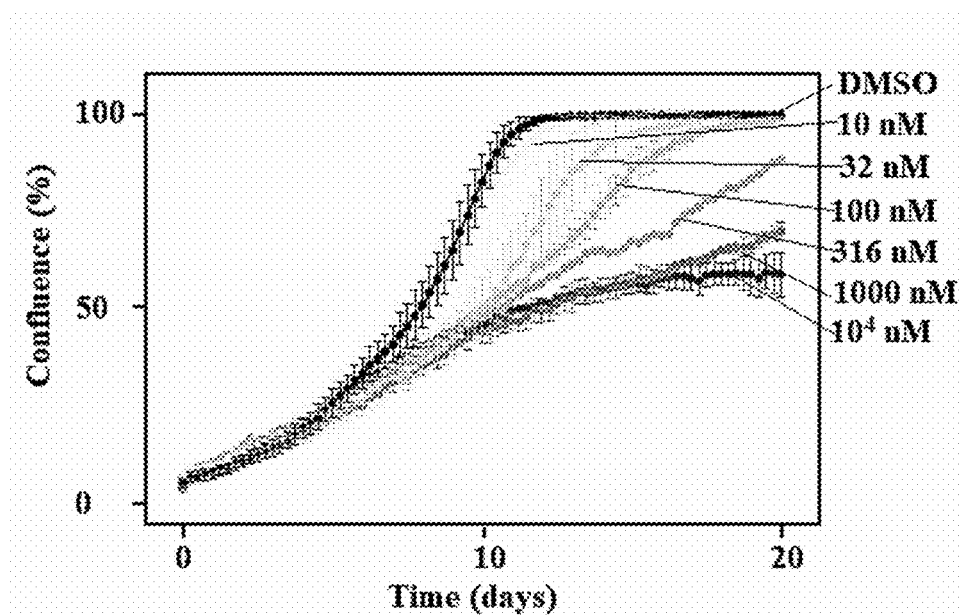
FIG. 4 is a confluence graph demonstrating growth inhibition over time in Yamato-SS cells by Compound 172. The x-axis is time measured in days and the y axis is confluence measured as a percentage of control.
Figure 16:
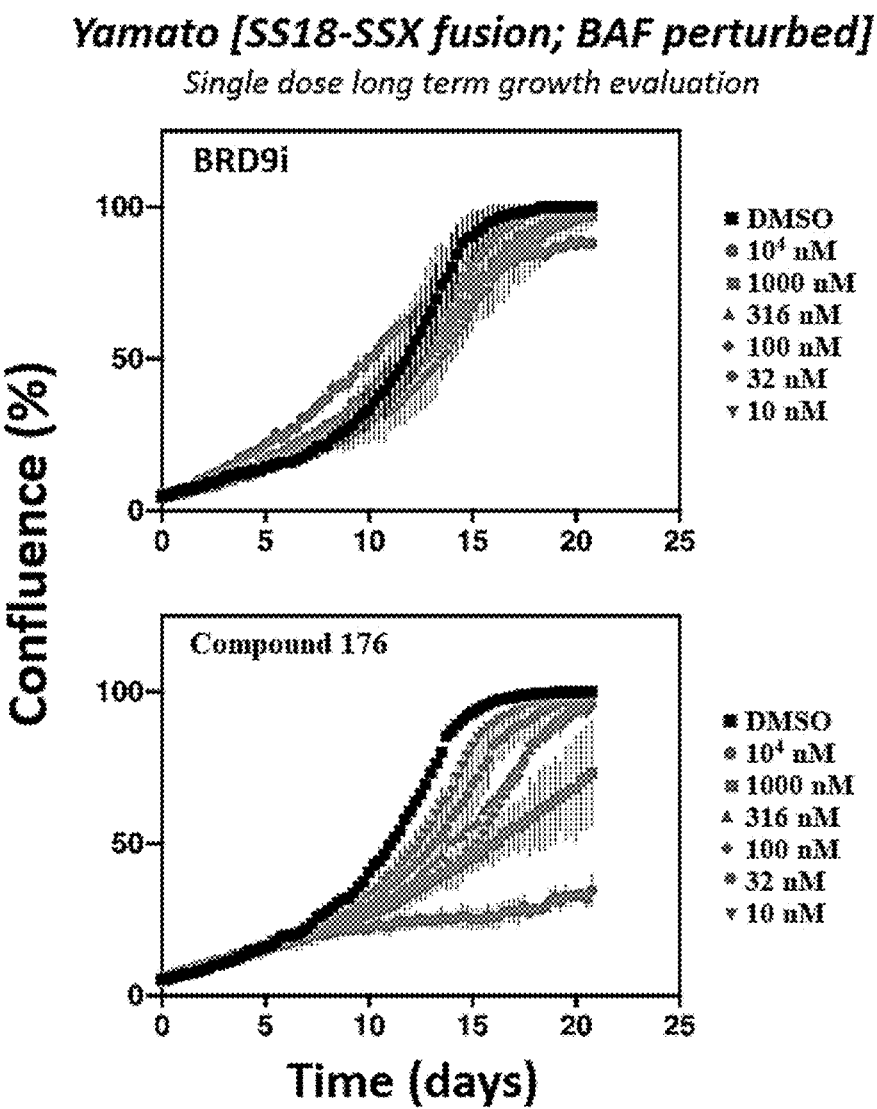
FIG. 16 is a confluence graph for Compound 176 at various concentrations. Single dose long term growth evaluation of the degradation of induced selective growth inhibition in BAF perturbed Yamato-SS model. The x-axis is time measured in days and the y axis is confluence measured as a percentage of control.
Figure 17:
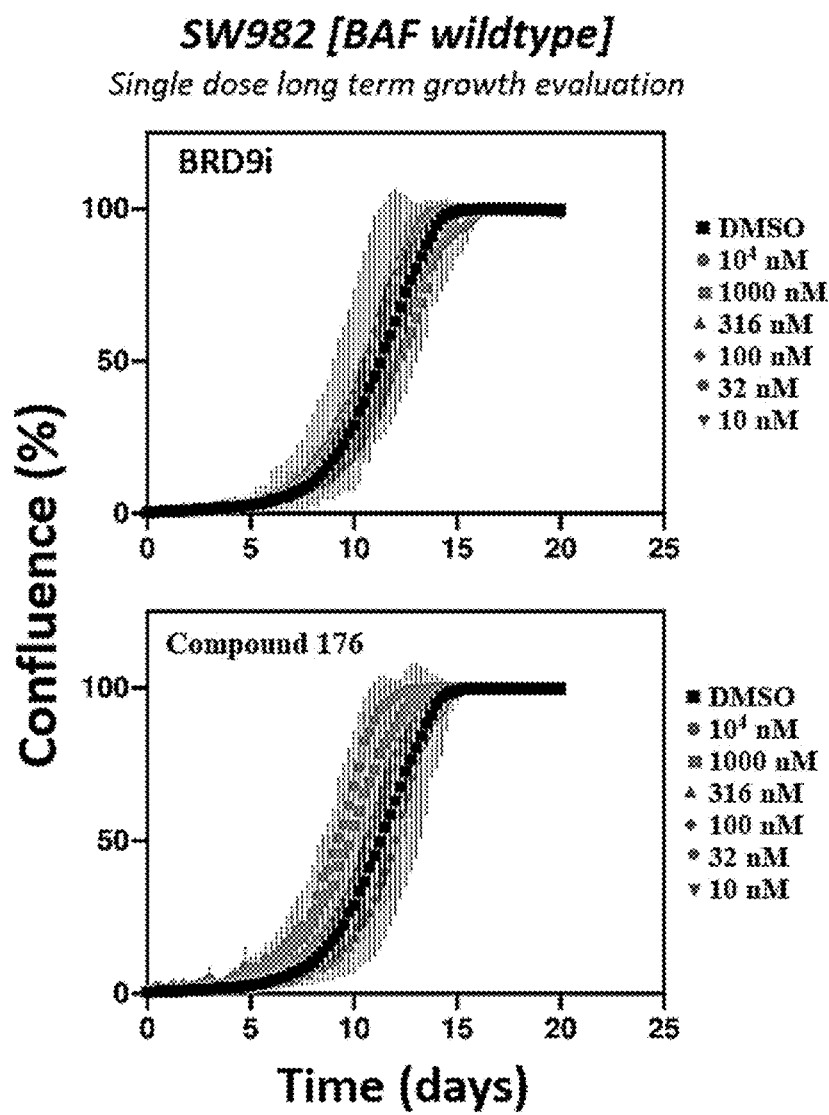
FIG. 17 is a confluence graph for Compound 176 at various concentrations demonstrating the lack of growth inhibition in BAF wildtype synovial sarcoma cells (SW982). The x-axis is time measured in days and the y axis is confluence measured as a percentage of control.

FIG. 4, FIG. 16, and FIG. 17 are line graphs illustrating the confluence caused by Compound 172 and Compound 176 at various concentrations. The x-axis is time measured in days and the y axis is confluence measured as a percentage of control. The compounds were incubated at 10 nM, 32 nM, 100 nM, 316 nM, 1000 nM, and $10^4$ nM concentrations at a single dose. The compounds were tested in a Yamato (SS18-SSX fusion; BAF perturbed) cells and SW982 (BAF wildtype) cells. A dose response is clearly visible.

Compound 172 was serially diluted in DMSO and 200 nL were dispensed into 96 well tissue-culture treated plates by the Echo acoustic liquid handler. Yamato cells were counted and adjusted to 11,000 cells/mL with DMEM media supplemented with 10% heat-inactivated FBS. 200 ul of the cell suspension was dispensed into each well. The plate was sealed with a gas-permeable membrane and confluence was measured in a temperature- and humidity-controlled incubator (37° C., 5% $CO_2$) over a 20-day period at 6-hour intervals by the IncuCyte S3. Analysis was performed using the Incucyte software and data were exported to GraphPad Prism for visualization.

Compound 176 and a comparator BRD9 inhibitor were serially diluted in DMSO and 200 nL were dispensed into 96 well tissue-culture treated plates by the Echo acoustic liquid handler. Yamato cells were counted and adjusted to 11,000 cells/mL with DMEM media supplemented with 10% heat-inactivated FBS. 200 ul of the cell suspension was dispensed into each well. The plate was sealed with a gas-permeable membrane and confluence was measured in a temperature- and humidity-controlled incubator (37° C., 5% $CO_2$) over a 20-day period at 6-hour intervals by the IncuCyte S3. Analysis was performed using the Incucyte software and data were exported to GraphPad Prism for visualization.

Compound 176 and a comparator BRD9 inhibitor were serially diluted in DMSO and 200 nL were dispensed into 96 well tissue-culture treated plates by the Echo acoustic liquid handler. SW982 cells were counted and adjusted to 700 cells/mL with DMEM media supplemented with 10% heat-inactivated FBS. 200 ul of the cell suspension was dispensed into each well. The plate was sealed with a gas-permeable membrane and confluence was measured in a temperature- and humidity-controlled incubator (37° C., 5% $CO_2$) over a 20-day period at 6-hour intervals by the IncuCyte S3. Analysis was performed using the Incucyte software and data were exported to GraphPad Prism for visualization.

Example 7: Pharmacodynamics of Compound 172

Figure 5:
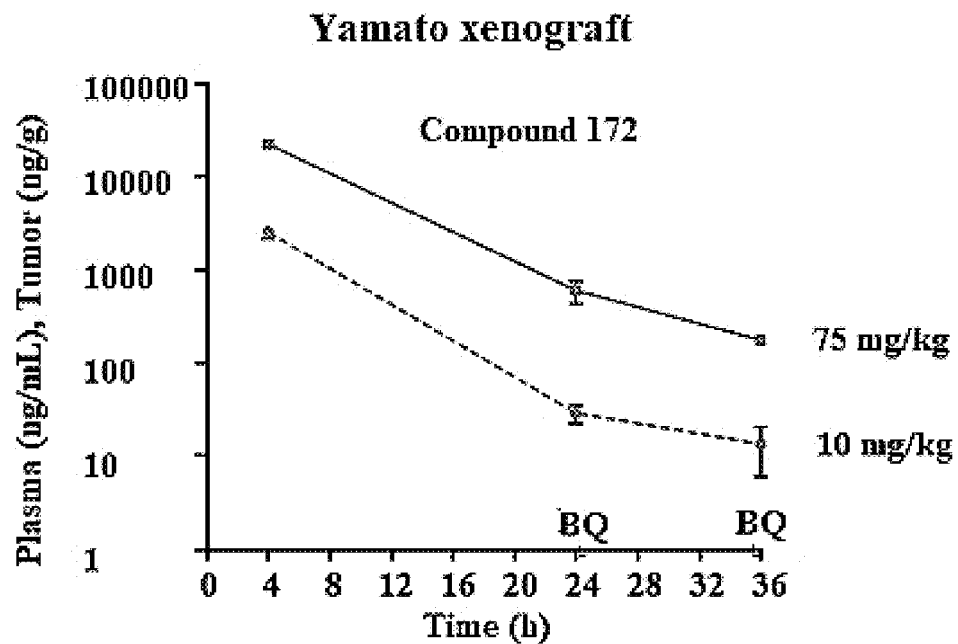
FIG. 5 is a graph demonstrating the pharmacokinetics (PK) of Compound 172 in Yamato-SS xenograft tumor model. The x-axis is time measured in hours and the y-axis is plasma concentration measured in ng/mL.
Figure 6:
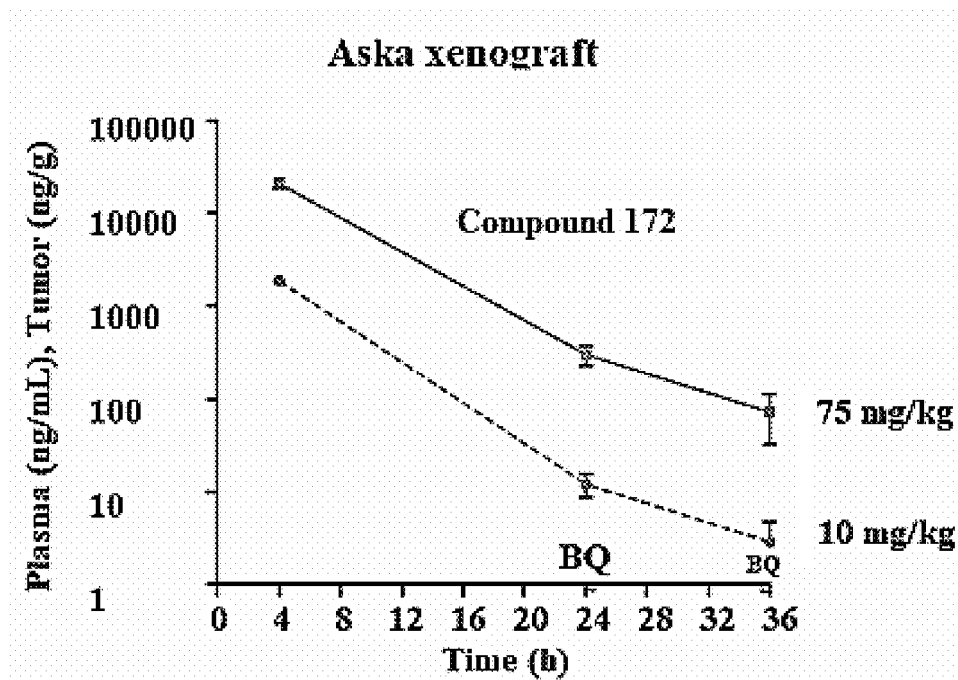
FIG. 6 is a graph demonstrating the pharmacokinetics of Compound 172 in Aska-SS xenograft tumor model. The x-axis is time measured in hours and the y-axis is plasma concentration measured in ng/mL. Aska-SS is a human cell line derived from synovial sarcoma (Stem Cells 2010; 28:1119-1131).
Figure 14:
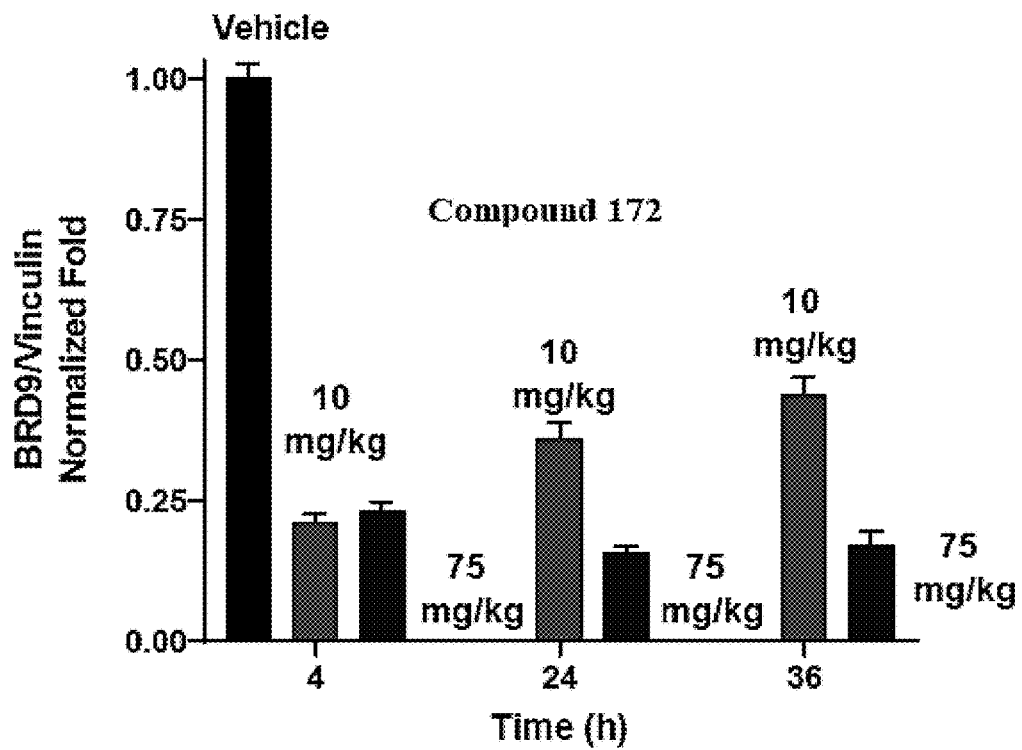
FIG. 14 is a bar graph comparing the levels of BRD9 left in synovial sarcoma tumors at different time points after a single dose of Compound 172. The x-axis is time measured in hours and the y-axis is percent protein remaining.

FIG. 5 and FIG. 6 are concentration over time graphs showing the concentration of Compound 172 in Yamato and Aska cancer cells over time. The x-axis is time measured in hours and the y-axis is plasma concentration measured in ng/mL for plasma and ng/g for tumor. The tumor and animal xenograft host were assayed for Compound 172 concentration at 4, 24, and 36 hours. FIG. 14 shows this data in graphic form.

Example 8: Yamato-SS Xenograft Study

Figure 7:
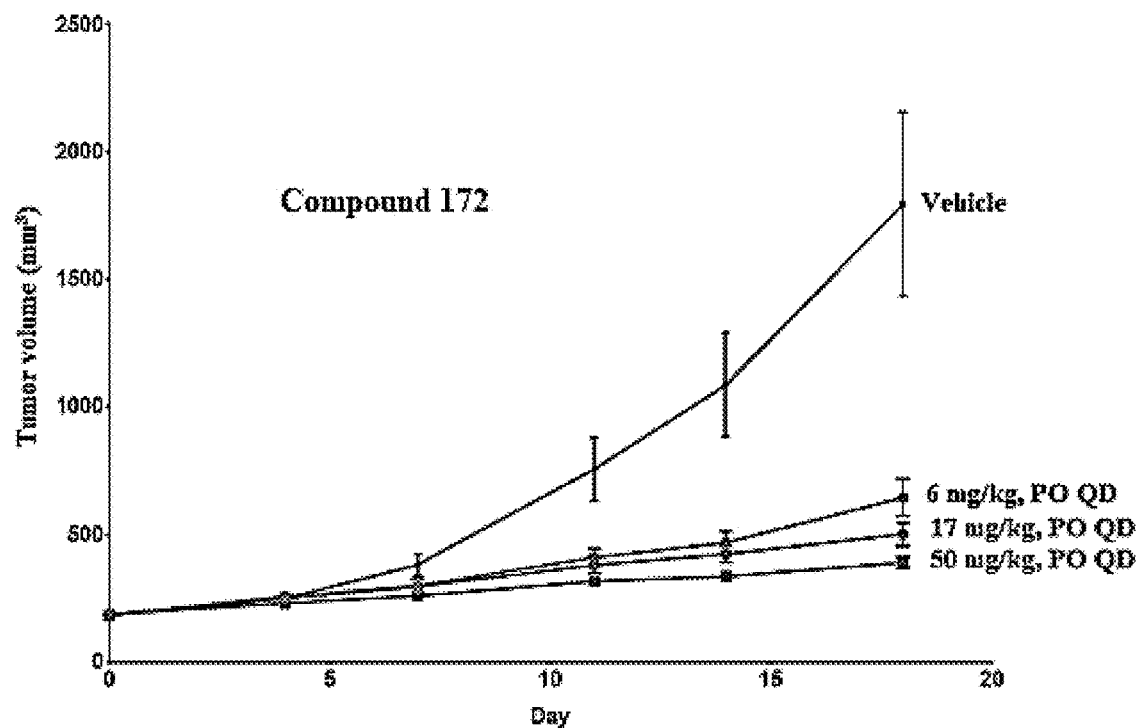
FIG. 7 is a graph showing the dose dependent response of tumor volume to various concentrations of Compound 172 in the Yamato-SS xenograft model, demonstrating its dose dependent efficacy in a synovial sarcoma model. The x-axis is time measured in days and the y-axis is tumor volume measured in $mm^3$.

FIG. 7 is a graph showing the dose dependent response of tumor volume after treatment with Compound 172 demonstrating its dose dependent efficacy in synovial sarcoma xenograft model Yamato-SS. Yamato-SS cells were maintained in vitro until exponential growth phase and inoculated subcutaneously into BALB/c nude mice at the right flank. Treatments of Compound 172 were started at the appropriate tumor volume. Mice were randomized into groups and treated with 6, 17, or 50 mg/kg PO QD of Compound 172 and tumor volumes (x-axis) were measured twice a week using a caliper. The x-axis is time after start of treatment measured in days and the y-axis is tumor volume measured in mm³.

Figure 8:
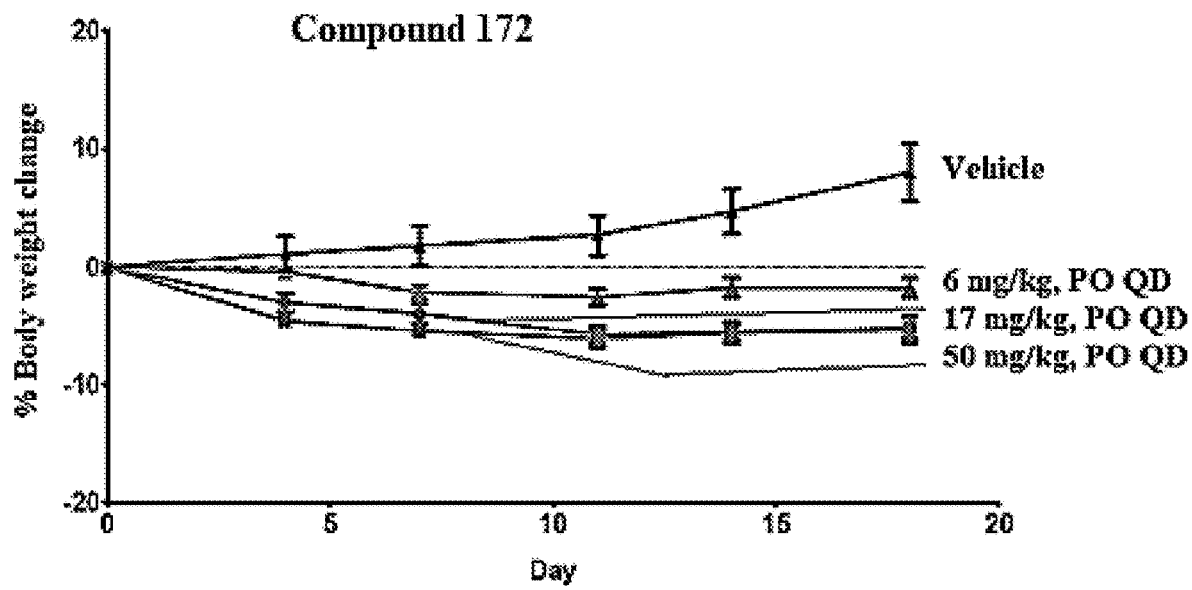
FIG. 8 is a graph showing the dose dependent response of mouse body weight change to various concentrations of Compound 172 in the Yamato-SS xenograft model. The x-axis is time measured in days and the y-axis is body weight change measured in percentage.

FIG. 8 is a graph showing Percent body weight (BW) change of the mice in FIG. 7 over the course of treatment. BW change was calculated based on animal weight on the first day of grouping. Data points represent percent group mean change in BW. Error bars represent standard error of the mean (SEM). The x-axis is time measured in days and the y-axis is body weight change measured in percentage.

Example 9: Patient Derived Xenograft Model

FIG. 1 is a graph demonstrating the efficacy of Compound 172 in a synovial sarcoma patient derived xenograft (PDX) model (SA13412). The x-axis is days after start of treatment measured in days and the y-axis is tumor volume measured in mm$^3$. The mice were dosed with 40 mg/kg of Compound 172 orally once a day. Even after 20 days of treatment there was no appreciable tumor growth.

Figure 9:
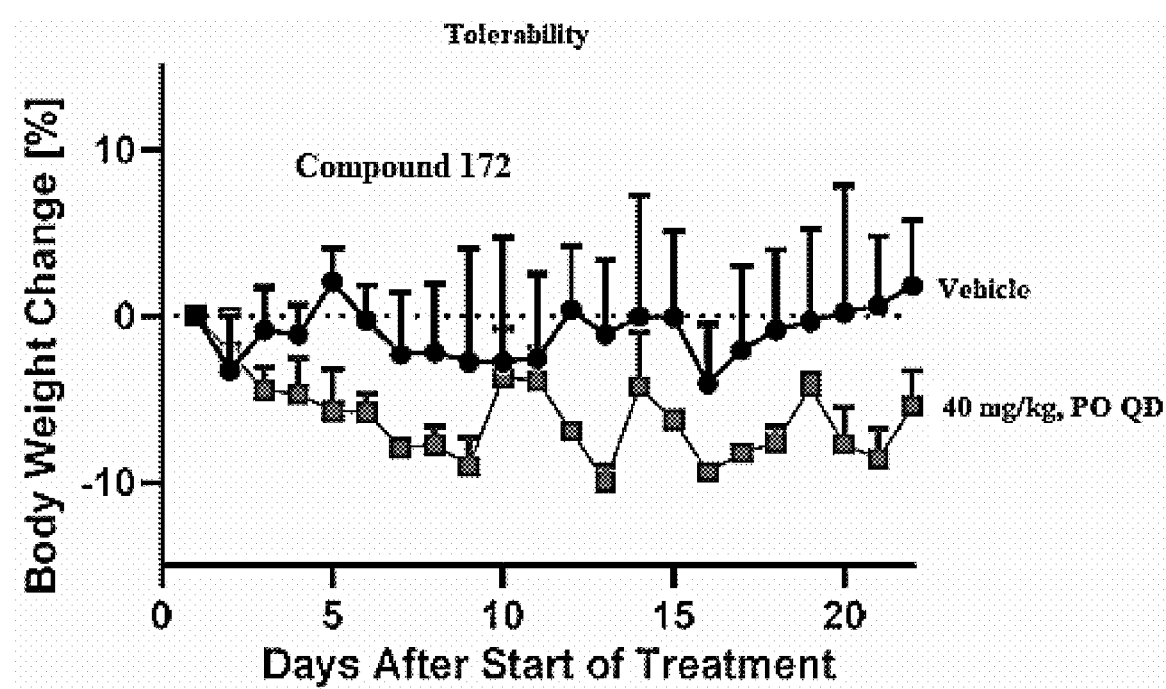
FIG. 9 is a graph demonstrating the tolerability of Compound 172 in the SA13412 synovial sarcoma PDX-model. The x-axis is days after start of treatment measured in days and the y-axis is body weight change measured in percentage.

FIG. 9 is a graph showing Percent body weight (BW) change of the mice in FIG. 1 over the course of treatment. BW change was calculated based on animal weight on the first day of grouping. Data points represent percent group mean change in BW. Error bars represent standard error of the mean (SEM). The x-axis is time measured in days and the y-axis is body weight change measured in percentage.

Example 10: Predicted Human PK/PD

Figure 10A:
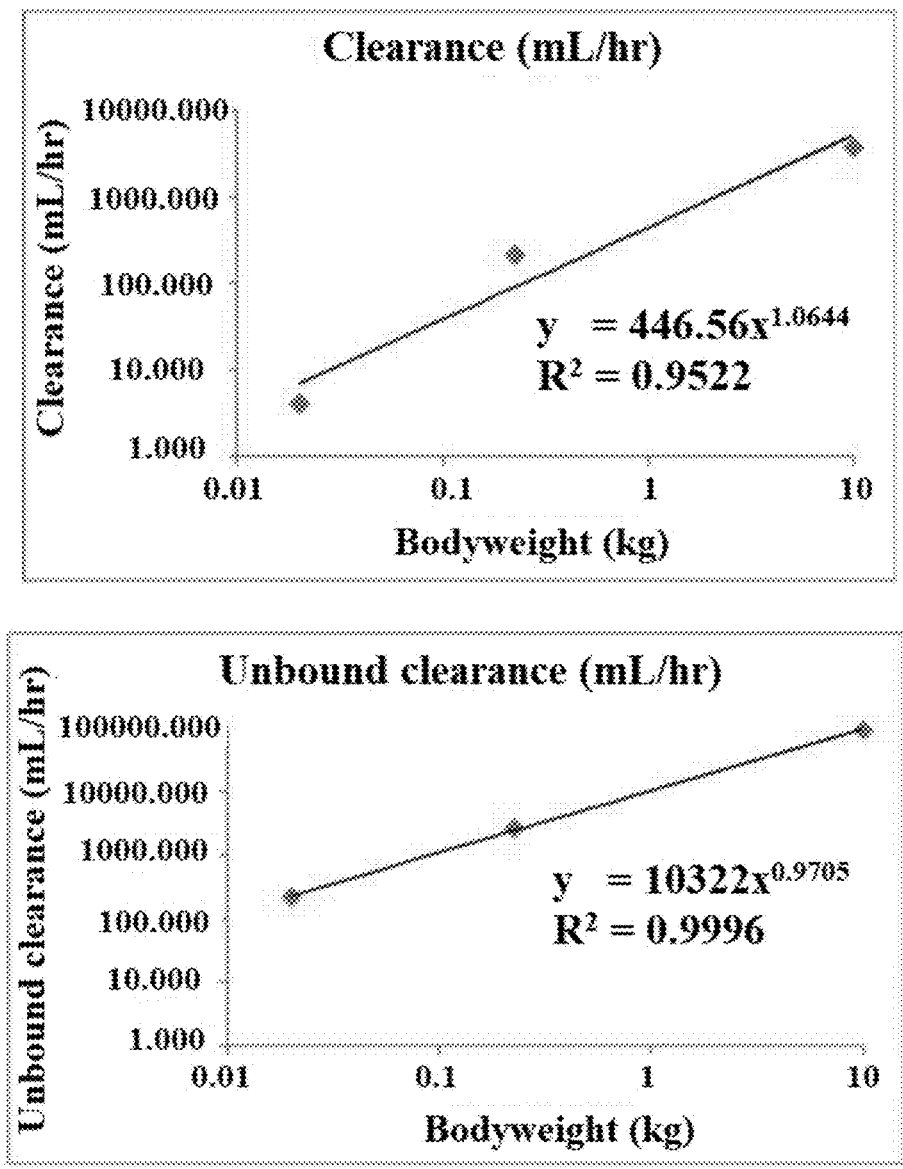
FIGS. 10A and 10B are graphs demonstrating the preclinical scaling dose prediction models of Compound 172 for projected human values of unbound clearance, half-life and degraded volume. The x-axis of each graph is bodyweight measured in kg. The y-axis of top left is clearance measured in mL/hr; the y-axis for top right is unbound clearance measured in mL/hr; y-axis for bottom left is volume measured in mL and the y-axis for bottom right is unbound volume measured in mL.
Figure 10B:
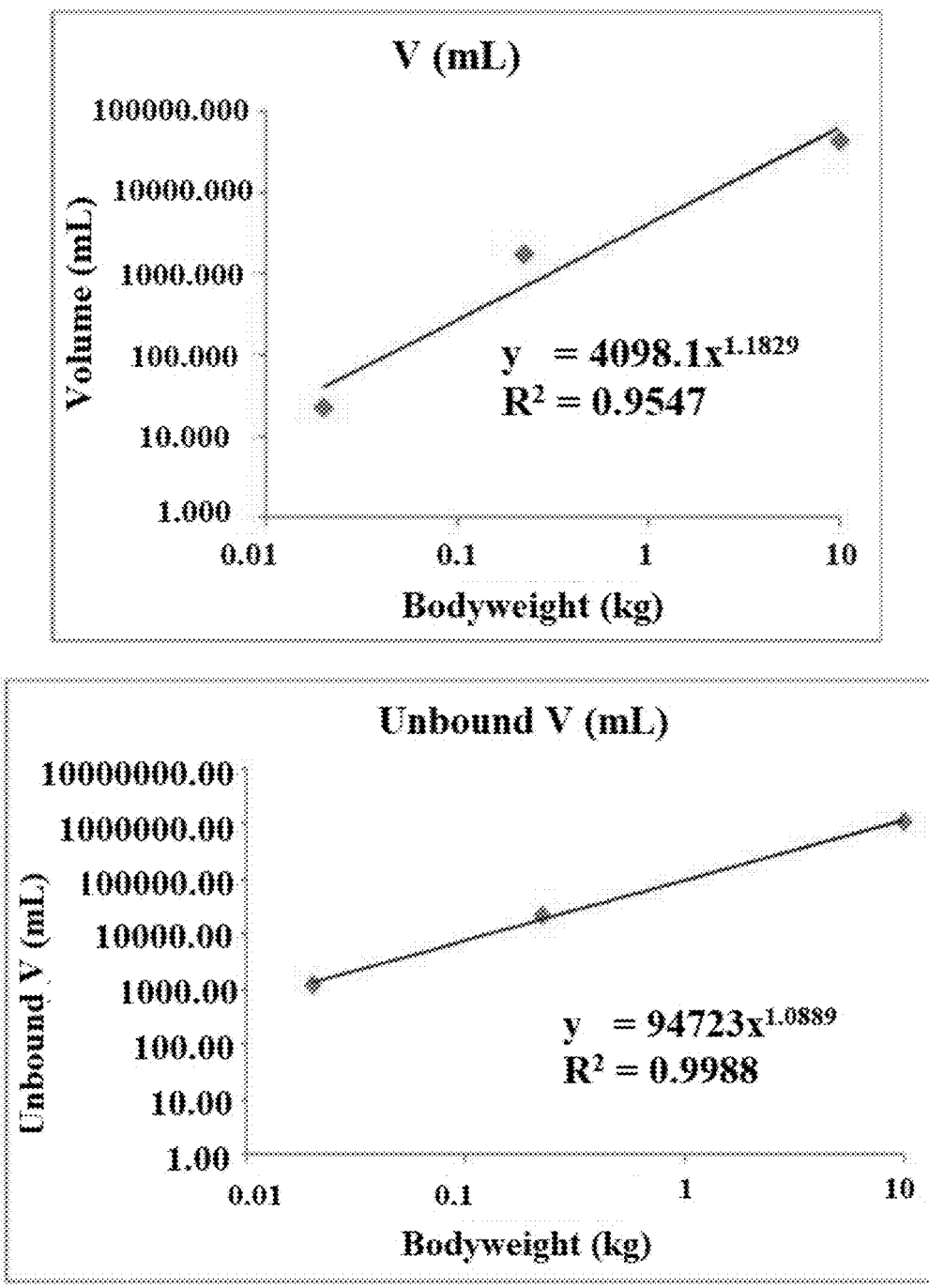

FIGS. 10A and 10B are graphs demonstrating the pre-clinical scaling dose prediction models of Compound 172 for projected human values of unbound clearance, half-life and degraded volume. The x-axis of each graph is body-weight measured in kg. The y-axis of top left is clearance measured in mL/hr; the y-axis for top right is unbound clearance measured in mL/hr; y-axis for bottom left is volume measured in mL and the y-axis for bottom right is unbound volume measured in mL.

Example 11: Alpha BRD9 Degradation

Figure 15:
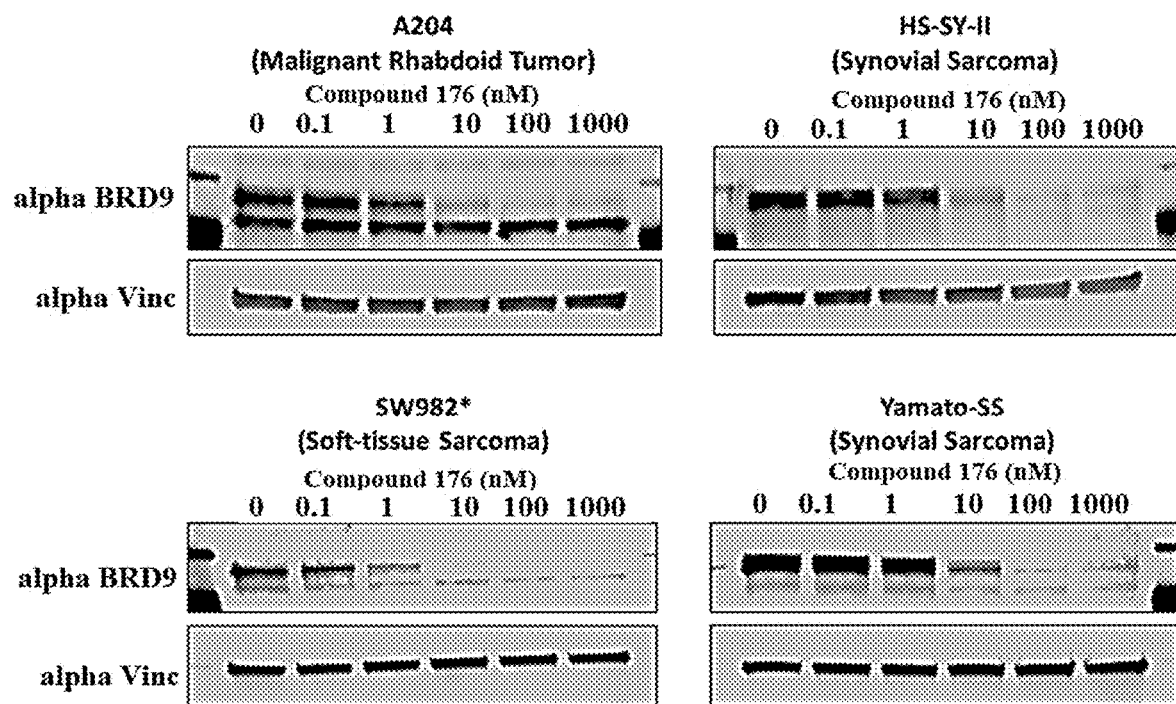
FIG. 15 is a graph illustrating the endogenous dose degradation across representative cellular contexts of Compound 176 at various concentrations. The top left represents the malignant human rhabdoid tumor (A204), top right represents the human synovial sarcoma (HS-SY-II), the bottom left represents human soft tissue sarcoma (SW982, BAF wildtype) and the bottom right represents synovial sarcoma (Yamato SS), all via western blot.

FIG. 15 is western blots demonstrating the endogenous dose degradation across representative cellular contexts of Compound 176 at various concentrations. The top left represents the malignant human rhabdoid tumor (A204), top right represents the human synovial sarcoma (HS-SY-II), the bottom left represents human soft tissue sarcoma (SW982, BAF wildtype) and the bottom right represents synovial sarcoma (Yamato SS), all via western blot. These figures show that Compound 176 has a dose dependent degradation of alpha BRD9 in cancer models that predict activity for malignant rhabdoid tumors, synovial sarcoma, and soft-tissue sarcoma.

Cells were plated at 500,000 cells/well in a 6-well plate and allowed to adhere for 16 hours. Each cell line was treated with Compound 176 serially diluted in DMSO for 6 hours. Cell pellets were collected, lysed with RIPA lysis buffer in the presence of protease inhibitors, and run on a 4-12% acrylamide gel for 45 minutes at 150V. Proteins were transferred to a nitrocellulose membrane and incubated with antibodies against BRD9 (1:1000; Cell Signaling Technology, #71232) or Vinculin (1:10,000; EMD, 05-386) overnight with agitation at 4° C. Blots were thrice washed with tris-buffered saline+0.05% tween-20 and incubated with host-directed fluorescently-conjugated antibodies for 1 hour at room temperature. Blots were thrice washed and imaged on a LiCor Odyssey CLx.

Example 12: Synovial Sarcoma CDX (Yamato-SS) Experiment

Figure 18:
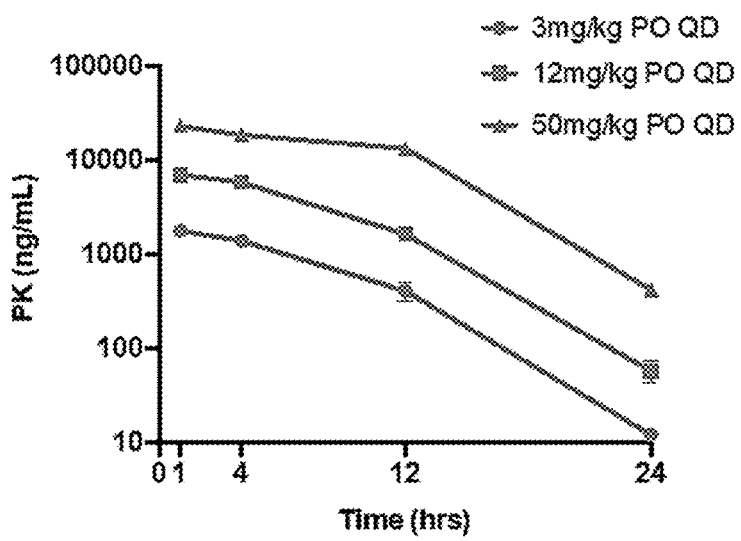
FIG. 18 is a graph illustrating the pharmacokinetics (PK) of Compound 176 at various concentrations (PO QD) in a synovial sarcoma CDX (Yamato-SS) model. The x axis is time measured in hours and the y axis is tumor PK measured in nanograms per milliliter (ng/mL).

FIG. 18 is a graph illustrating the pharmacokinetics (PK) of Compound 176 at various concentrations (PO QD) in a synovial sarcoma CDX (Yamato-SS) model. The x axis is time measured in hours and the y axis is tumor PK measured in nanograms per milliliter (ng/mL). Compound 176 was dosed at 3 mg/kg, 12 mg/kg, or 50 mg/kg once a day orally and measurements were taken at 1 hour, 4 hours, 12 hours, and 24 hours.

Figure 21:
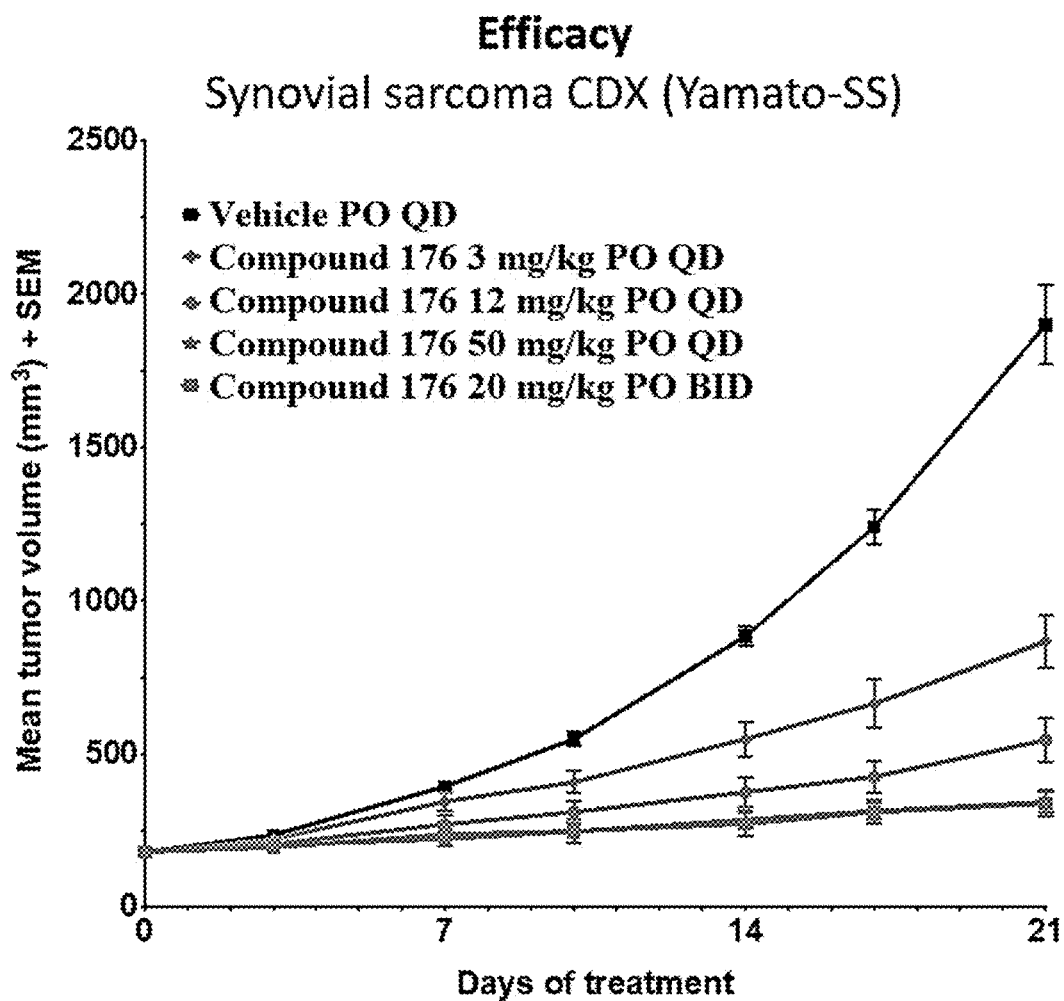
FIG. 21 is a graph demonstrating the efficacy of Compound 176 at various concentrations in a synovial sarcoma CDX model (Yamato SS). The x axis is treatment measured in days and the y axis is mean tumor volume+SEM measured in cubic millimeters ($mm^3$).

FIG. 21 is a graph of tumor volume after treatment with Compound 176 demonstrating strong effect in synovial sarcoma xenograft model Yamato-SS. Yamato-SS cells were maintained in vitro until exponential growth phase and inoculated subcutaneously into BALB/c nude mice at the right flank for tumor development. Treatments of Compound 176 were started at the appropriate tumor volume. Mice were treated as indicated with Compound 176 and tumor volumes (x-axis) were measured twice a week using a caliper. The x-axis is time after start of treatment measured in days and the y-axis is tumor volume measured in mm$^3$.

Figure 22:
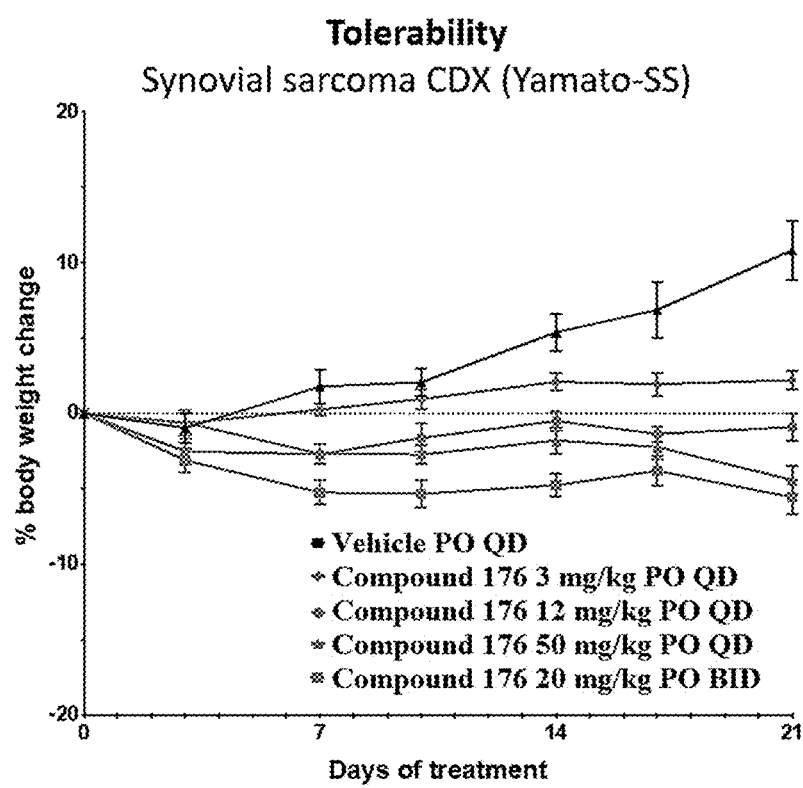
FIG. 22 is a graph demonstrating the tolerability of Compound 176 at various concentrations in a synovial sarcoma CDX model (Yamato SS). The x axis is treatment measured in days and the y axis is body weight change measured in percentage.

FIG. 22 is a graph demonstrating the tolerability of Compound 176 in the synovial sarcoma CDX (Yamato-SS) model. The x axis is treatment measured in days and the y axis is body weight change measured in percentage.

Example 13: Western Blot Showing Dose Response Degradation by Compound 172

Figure 19:
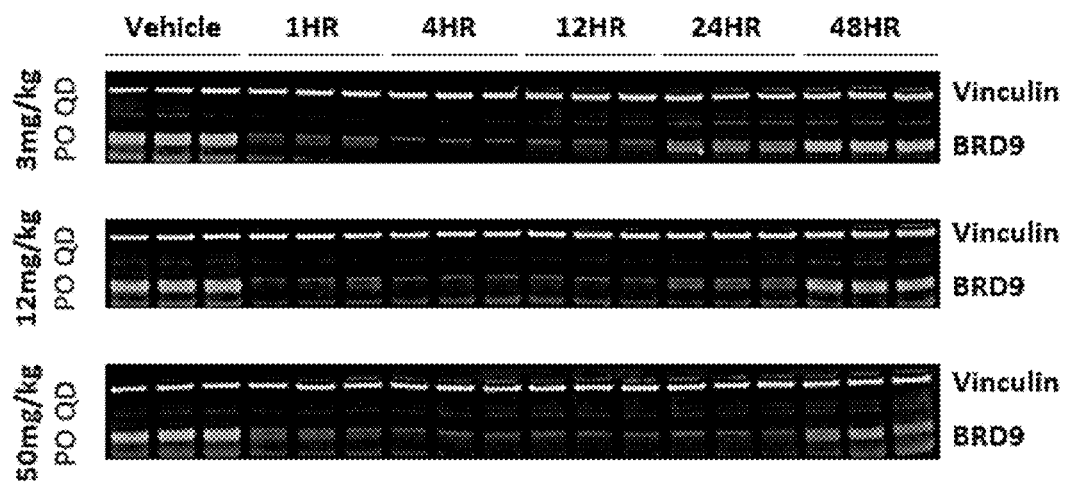
FIG. 19 is a graph illustrating the protein degradation of BRD9 in synovial sarcoma tumors (tumor PD) by Compound 176 at various concentrations (PO QD). The x axis is time measured in hours and the y axis is concentration of Compound 176 measured in mg/kg PO QD.

FIG. 19 is a western blot showing the time dependent in-vivo BRD9 degradation with Compound 176 at 3, 12, or 50 mg/ml collected at 1, 4, 12, 24, 48 hr after dosing in Yamato-SS cells. Yamato-SS were maintained in vitro until exponential growth phase and inoculated subcutaneously into BALB/c nude mice at the right flank. Mice were treated with single dose of Compound 176 at 3, 12 or 50 mg/kg PO. Tumor were collected at indicated time points and snap frozen until lysis. Tumors were ground and lysed in RIPA Buffer containing 2× protease/phosphatase inhibitor using a freeze grinder at 50 Hz for 5 minutes. Protein concentrations were determined by Pierce™ BCA Protein Assay Kit. Samples were diluted to appropriate concentrations and run in a western blot.

Figure 20:
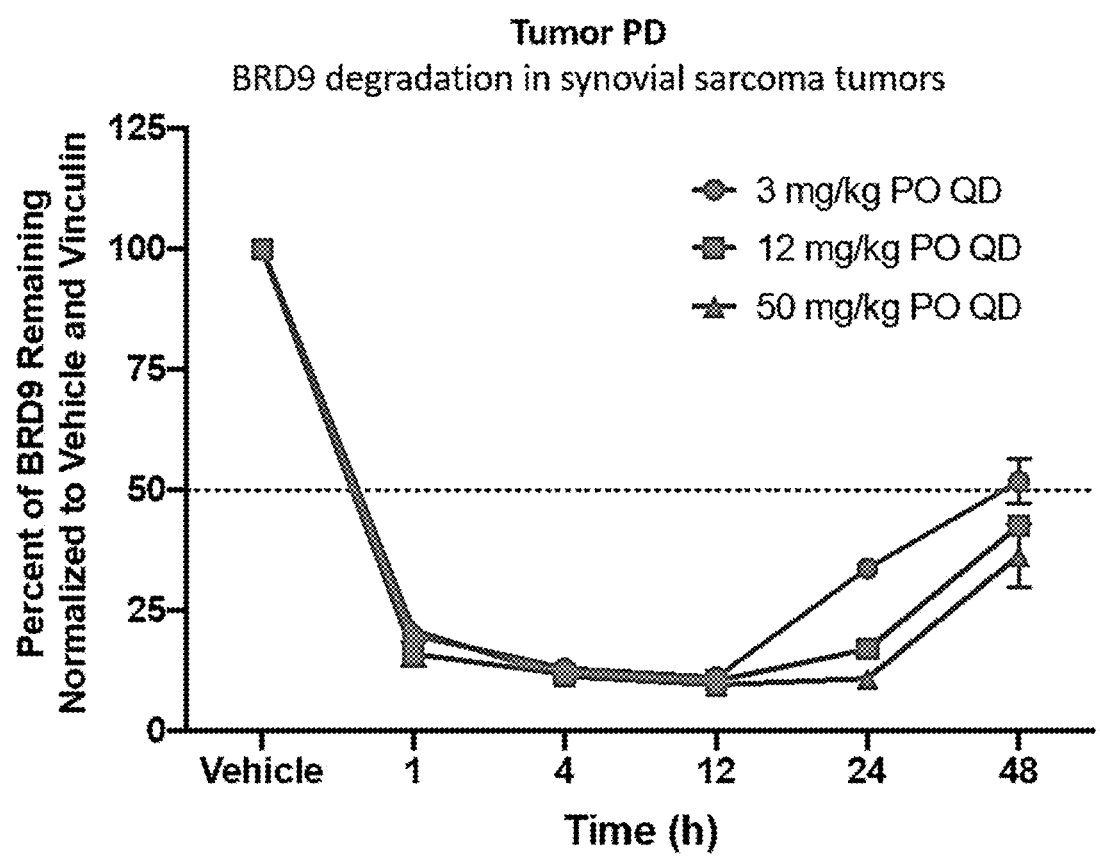
FIG. 20 is a graph illustrating the protein degradation of BRD9 in synovial sarcoma tumors (tumor PD) by Compound 176 at various concentrations PO QD. The x axis is time measured in hours and the y axis is BRD9 remaining normalized to vehicle and vinculin measured in percentage.

FIG. 20 is a histogram reflecting quantitated bands from FIG. 19. The x axis is time measured in hours and the y axis is BRD9 remaining normalized to vehicle and vinculin measured in percentage.

Example 14: Synovial Sarcoma PDX (SA13412) Experiment

Figure 23:
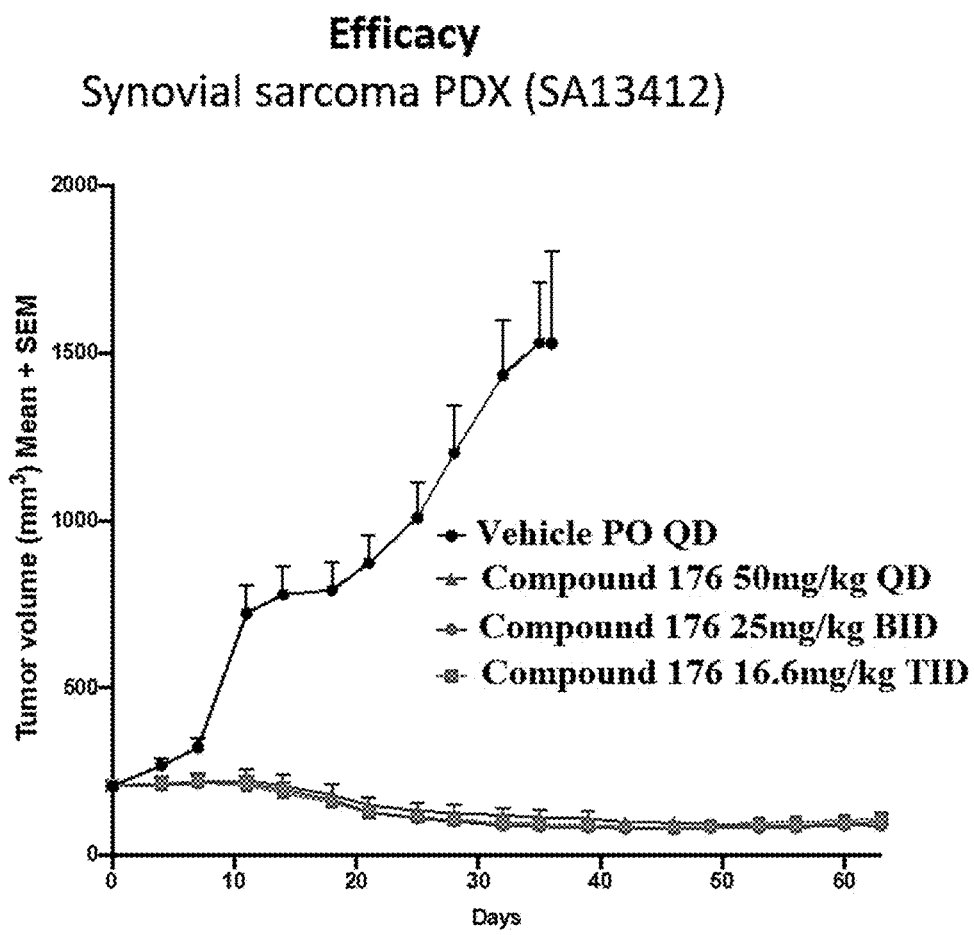
FIG. 23 is a graph demonstrating the efficacy of Compound 176 at various concentrations in a Synovial Sarcoma PDX model (SA13412). The x axis is treatment measured in days and the y axis is mean tumor volume+SEM measured in cubic millimeters ($mm^3$).

FIG. 23 is a graph demonstrating the efficacy of Compound 176 at various concentrations in a Synovial Sarcoma PDX model (SA13412). The x axis is treatment measured in days and the y axis is mean tumor volume+SEM measured in cubic millimeters (mm$^3$). Compound 176 was dosed at 50 mg/kg once a day, 25 mg/kg twice a day, and 16.6 mg/kg three times a day.

Figure 24:
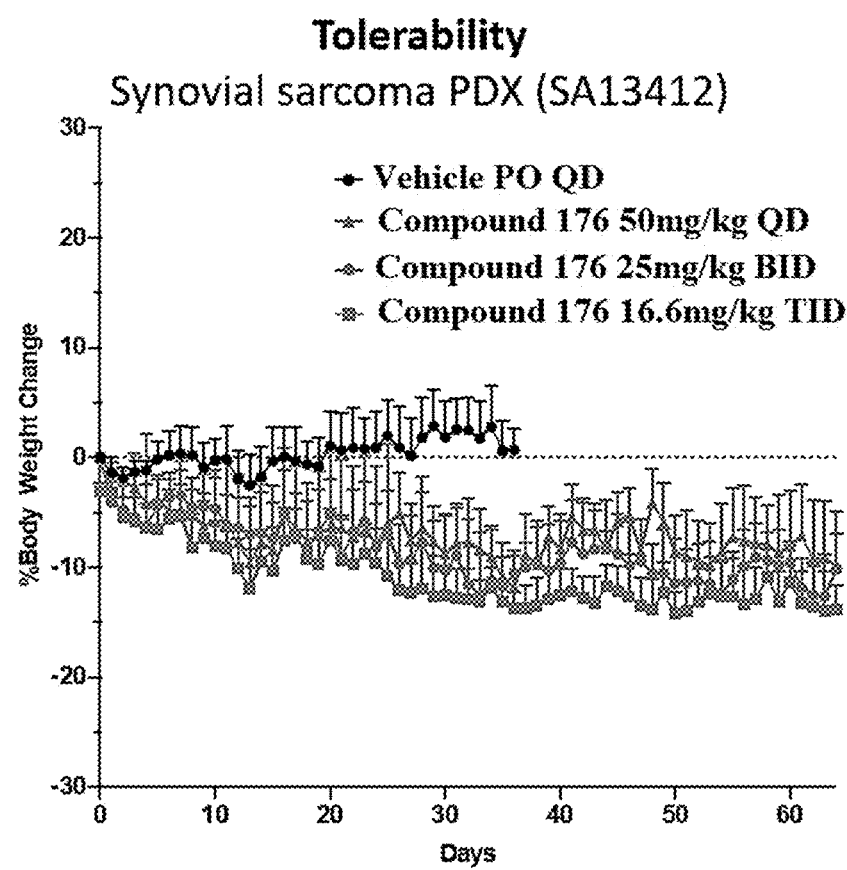
FIG. 24 is a graph demonstrating the tolerability of Compound 176 at various concentrations in a synovial sarcoma PDX model (SA13412). The x axis is treatment measured in days and the y axis is body weight change measured in percentage.
Figure 25:
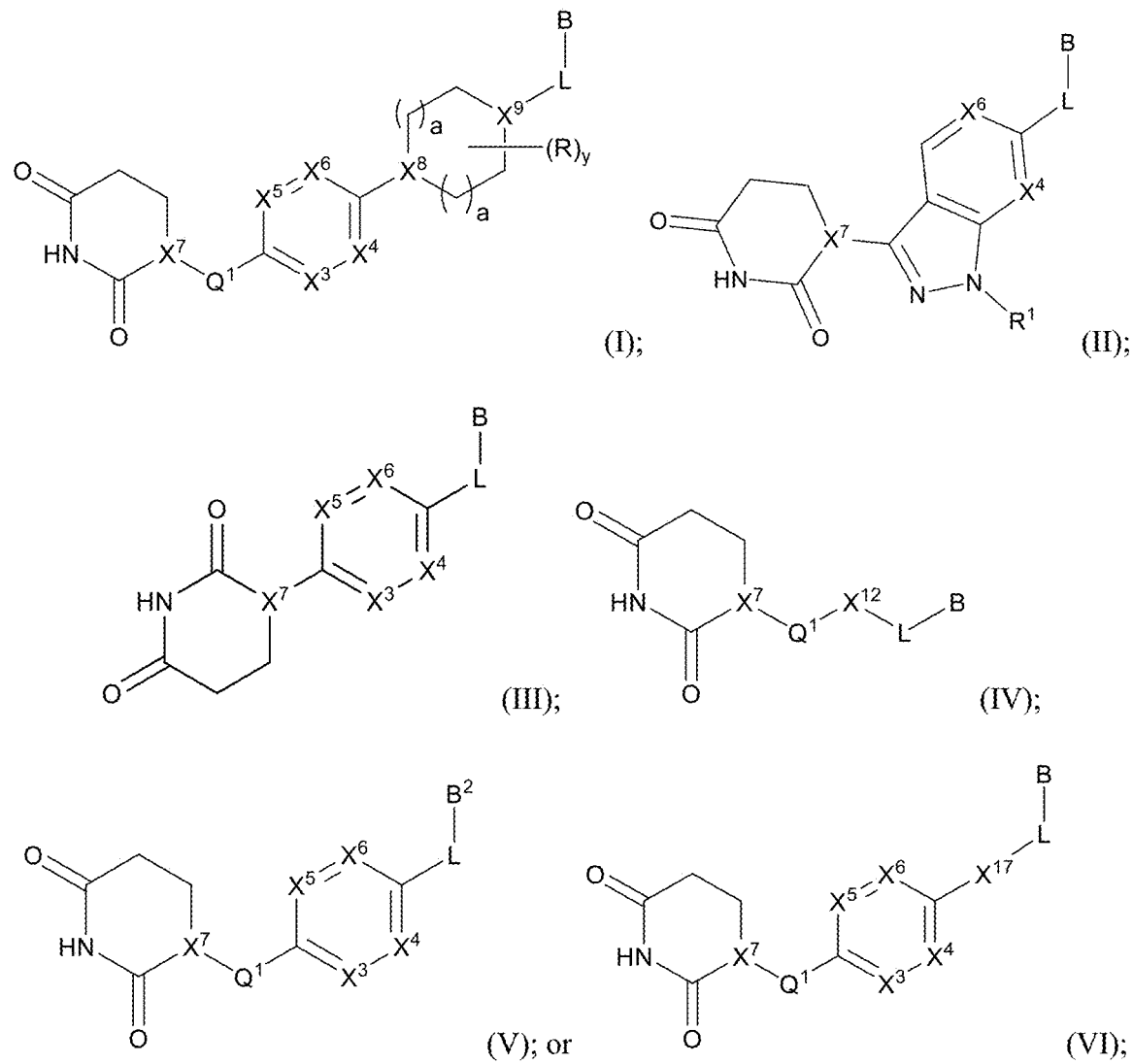
FIG. 25 provides representative Formulas of the present invention.

FIG. 24 is a graph demonstrating the tolerability of Compound 176 at various concentrations in a synovial sarcoma PDX model (SA13412). The x axis is treatment measured in days and the y axis is body weight change measured in percentage. Less than 15% loss of body weight was observed on average.

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the appended claims. Additionally, those skilled in the art will recognize, or be able to ascertain using no more than routine experimentation, many equivalents to the specific embodiments and methods described herein. Such equivalents are intended to be encompassed by the scope of the present application.

We claim:

1. A method of treating a disorder mediated by BRD9 comprising administering an effective amount of a compound of Formula:

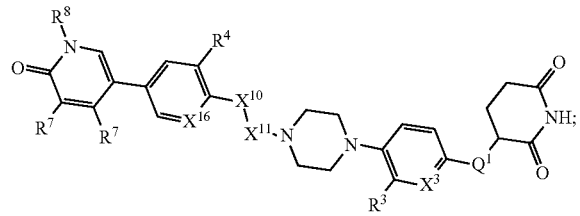

or a pharmaceutically acceptable salt thereof to a human in need thereof;
wherein:
Q$^1$ is selected from the group consisting of NH, N(alkyl), N(haloalkyl), CH$_2$, a, and S;
X$^3$ is N, CH, or CR$^3$;
X$^{10}$ is Cc(R$^7$)$_2$, C(O), or O;
X$^{11}$ is a heterocycle optionally substituted with 1, 2, or 3 groups independently selected from R$^3$;
X$^{16}$ is selected from the group consisting of N, CH, and CR$^4$;
R$^3$ is independently at each occurrence selected from the group consisting of hydrogen, hydroxyl, alkoxy, C$_1$-C$_4$alkyl, C$_1$-C$_4$haloalkyl, cycloalkyl, fluorine, chlorine, bromine, and iodine;
each R$^4$ is independently selected from the group consisting of hydrogen, aryl, heteroaryl, C$_1$-C$_4$alkoxy, C$_1$-C$_4$haloalkyl, C$_1$-C$_4$haloalkoxy, C$_1$-C$_4$alkyl, fluorine, chlorine, bromine, and iodine;
each R$^7$ is independently hydrogen, methyl, or ethyl; and
R$^8$ is hydrogen, C$_1$-C$_4$alkyl, alkenyl, alkynyl, haloalkyl, or cycloalkyl.

2. The method of claim 1, wherein the compound is of Formula:

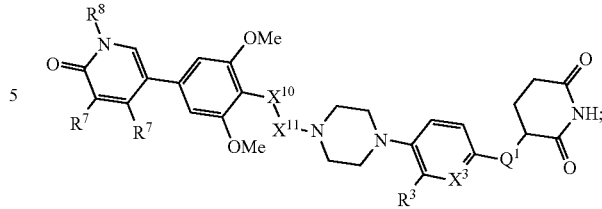

or a pharmaceutically acceptable salt thereof.

3. The method of claim 2, wherein Q$^1$ is NH.
4. The method of claim 3, wherein X$^{10}$ is CH$_2$.
5. The method of claim 4, wherein each R$^7$ is CH$_3$.
6. The method of claim 5, wherein X$^{11}$ is selected from:

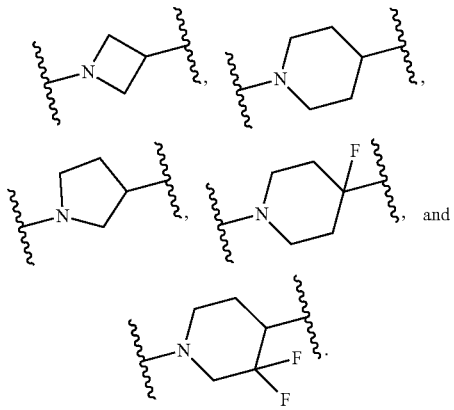

7. The method of claim 6, wherein the BRD9 mediated disorder is synovial sarcoma.
8. The method of claim 6, wherein the BRD9 mediated disorder is a SMARCB1-perturbed cancer.
9. The method of claim 1, wherein the compound is of structure

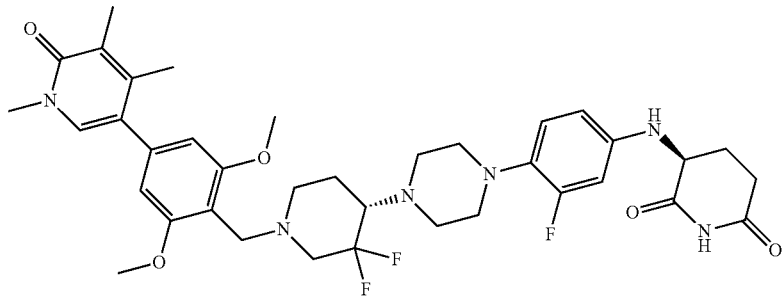 [SMILES: COc1cc(-c2cn(C)c(=O)c(C)c2C)cc(OC)c1CN1CC[C@H](N2CCN(c3ccc(N[C@H]4CCC(=O)NC4=O)cc3F)CC2)C(F)(F)C1]

or a pharmaceutically acceptable salt thereof.
10. The method of claim 9, wherein the BRD9 mediated disorder is synovial sarcoma.
11. The method of claim 9, wherein the BRD9 mediated disorder is a SMARCB1-perturbed cancer.

* * * * *